US012691070B2

(12) United States Patent
Mashiach

(10) Patent No.: US 12,691,070 B2
(45) Date of Patent: Jul. 28, 2026

(54) CATIONIC LIPIDS AND PREPARATION METHOD THEREOF

(71) Applicant: RiboX Therapeutics HK Limited, Hong Kong (CN)

(72) Inventor: Roi Mashiach, Hong Kong (CN)

(73) Assignee: RIBOX THERAPEUTICS HK LIMITED, Hong Kong (CN)

( * ) Notice: Subject to any disclaimer, the term of this patent is extended or adjusted under 35 U.S.C. 154(b) by 0 days.

(21) Appl. No.: 19/214,841

(22) Filed: May 21, 2025

(65) Prior Publication Data

US 2026/0069542 A1 Mar. 12, 2026

Related U.S. Application Data

(63) Continuation of application No. PCT/CN2024/092807, filed on May 13, 2024.

(30) Foreign Application Priority Data

May 11, 2023 (CN) ................. PCT/CN2023/093506
May 22, 2023 (CN) ................. PCT/CN2023/095514
Jun. 9, 2023 (CN) ................. PCT/CN2023/099393
Jul. 14, 2023 (CN) ................. PCT/CN2023/107440
Dec. 21, 2023 (CN) ................. PCT/CN2023/140569
Jan. 4, 2024 (CN) ................. PCT/CN2024/070551
Apr. 11, 2024 (CN) ................. PCT/CN2024/087191

(51) Int. Cl.
*A61K 9/1272* (2025.01)
*A61K 9/51* (2006.01)
*C07C 271/20* (2006.01)

(52) U.S. Cl.
CPC .......... *A61K 9/1272* (2013.01); *A61K 9/5123* (2013.01); *C07C 271/20* (2013.01)

(58) Field of Classification Search
CPC ...... A61K 9/00; A61K 9/1272; A61K 9/5123; C07C 271/20
See application file for complete search history.

(56) References Cited

FOREIGN PATENT DOCUMENTS

| | | | |
|---|---|---|---|
| CN | 113387825 | A | 9/2021 |
| CN | 116675624 | A | 9/2023 |
| WO | 2020061367 | A1 | 3/2020 |

OTHER PUBLICATIONS

International Search Report and Written Opinion issued on Nov. 14, 2024 for International Application No. PCT/ CN2024/092807 (11 pages).

*Primary Examiner* — D. L. Jones
(74) *Attorney, Agent, or Firm* — FOX ROTHSCHILD LLP

(57) ABSTRACT

The present invention provides cationic lipids and lipid nanoparticle formulations comprising these lipids, alone or in combination with other lipids. These lipid nanoparticles may be formulated with nucleic acids to facilitate their intracellular delivery both in vitro and for therapeutic applications. The present invention also provides methods of chemical synthesis of these lipids.

12 Claims, 6 Drawing Sheets

Specification includes a Sequence Listing.

SEQUENCE LISTING

```
Sequence total quantity: 2
SEQ ID NO: 1            moltype = RNA  length = 2367
FEATURE                 Location/Qualifiers
source                  1..2367
                        mol_type = other RNA
                        organism = synthetic construct
SEQUENCE: 1
aacttttagt tatcccacag caagaatgcc atcatctgtc ctcaccccca attttccctt  60
ttcttcccct gcaaccatta cgcttactcg catgtgcatt gagtggtgca tgtgttgaac  120
aaacagctac actcacatgg gggcgggttt tcccgcccta cggcctctcg cgaggcccac  180
cccttccctc cccttataac tacagtgctt tggtaggtaa gcatcctgat cccccgcgga  240
agctgctcac gtggcaactg tggggaccca gacaggttat caaaggcacc cggtctttcc  300
gccttcagga gtatccctac tagtgaattc tagcggggct ctgcttggtg ccaacctccc  360
ccaaatgcgc gctgcgggag tgctcttccc caactcaccc tagtatcctc tcatgtgtgt  420
gcttggtcag catatctgag acgatgttcc gctgtcccag accagtccag taatggacgg  480
gccagtgcgt gtagtcgtct tccggcttgt ccggggcatg tttggtgaac cggtggggta  540
aggttggtgt gcccaacgcc cgtactttgg tgacacctca agaccaccca ggaatgccag  600
ggaggtaccc cacctcacgg tgggatctga ccctgggcta attgtctacg gtggttcttc  660
```

-continued

```
ttgcttccac ttctttcttc tgttcacggc caccatggag gacgccaaga acatcaagaa  720
gggcccggcg cccttctacc cgctggagga cgggaccgcc ggcgagcagc tccacaaggc  780
catgaagcgg tacgccctgg tgccgggcac gatcgccttc accgacgccc acatcgaggt  840
cgacatcacc tacgcggagt acttcgagat gagcgtgcgc ctggccgagg ccatgaagcg  900
gtacggcctg aacaccaacc accggatcgt ggtgtgctcg gagaacagcc tgcagttctt  960
catgccggtg ctgggcgccc tcttcatcgg cgtggccgtc gccccggcga acgacatcta  1020
caacgagcgg gagctgctga acagcatggg gatcagccag ccgaccgtgg tgttcgtgag  1080
caagaagggc ctgcagaaga tcctgaacgt gcagaagaag ctgcccatca tccagaagat  1140
catcatcatg gacagcaaga ccgactacca gggcttccag tcgatgtaca cgttcgtgac  1200
cagccacctc ccgccgggct tcaacgagta cgacttcgtc ccggagagct tcgaccggga  1260
caagaccatc gccctgatca tgaacagcag cggcagcacc ggcctgccga agggggtggc  1320
cctgccgcac cggaccgcct gcgtgcgctt ctcgcacgcc cgggacccca tcttcggcaa  1380
ccagatcatc ccggacaccg ccatcctgag cgtggtgccg ttccaccacg gcttcggcat  1440
gttcacgacc ctgggctacc tcatctgcgg cttccgggtg gtcctgatgt accggttcga  1500
ggaggagctg ttcctgcgga gcctgcagga ctacaagatc cagagcgcgc tgctcgtgcc  1560
gaccctgttc agcttcttcg ccaagagcac cctgatcgac aagtacgacc tgtcgaacct  1620
gcacgagatc gccagcgggg gcgccccgct gagcaaggag gtgggcgagg ccgtggccaa  1680
gcggttccac ctcccgggca tccgccaggg ctacggcctg accgagacca cgagcgcgat  1740
cctgatcacc cccgaggggg acgacaagcc gggcgccgtg ggcaaggtgg tcccgttctt  1800
cgaggccaag gtggtggacc tggacaccgg caagaccctg ggcgtgaacc agcggggcga  1860
gctgtgcgtg cgggggccga tgatcatgag cggctacgtg aacaacccgg aggccaccaa  1920
cgccctcatc gacaaggacg gctggctgca cagcggcgac atcgcctact gggacgagga  1980
cgagcacttc ttcatcgtcg accggctgaa gtcgctgatc aagtacaagg gctaccaggt  2040
ggcgccggcc gagctggaga gcatcctgct ccagcacccc aacatcttcg acgccggcgt  2100
ggccgggctg ccggacgacg acgccggcga gctgccggcc gcggtggtgg tgctggagca  2160
cggcaagacc atgacggaga aggagatcgt cgactacgtg gccagccagg tgaccaccgc  2220
caagaagctg cggggcggcg tggtgttcgt ggacgaggtc ccgaagggcc tgaccgggaa  2280
gctcgacgcc cggaagatcc gcgagatcct gatcaaggcc aagaagggcg gcaagatcgc  2340
cgtgagctga taaactactg aaagcat                                     2367
```

```
SEQ ID NO: 2            moltype = RNA  length = 1919
FEATURE                 Location/Qualifiers
source                  1..1919
                        mol_type = other RNA
                        organism = synthetic construct
SEQUENCE: 2
aaataagaga gaaaagaaga gtaagaagaa atataagagc caccatggag gacgccaaga  60
acatcaagaa gggcccggcg cccttctacc cgctggagga cgggaccgcc ggcgagcagc  120
tccacaaggc catgaagcgg tacgccctgg tgccgggcac gatcgccttc accgacgccc  180
acatcgaggt cgacatcacc tacgcggagt acttcgagat gagcgtgcgc ctggccgagg  240
ccatgaagcg gtacggcctg aacaccaacc accggatcgt ggtgtgctcg gagaacagcc  300
tgcagttctt catgccggtg ctgggcgccc tcttcatcgg cgtggccgtc gccccggcga  360
acgacatcta caacgagcgg gagctgctga acagcatggg gatcagccag ccgaccgtgg  420
tgttcgtgag caagaagggc ctgcagaaga tcctgaacgt gcagaagaag ctgcccatca  480
tccagaagat catcatcatg gacagcaaga ccgactacca gggcttccag tcgatgtaca  540
cgttcgtgac cagccacctc ccgccgggct tcaacgagta cgacttcgtc ccggagagct  600
tcgaccggga caagaccatc gccctgatca tgaacagcag cggcagcacc ggcctgccga  660
agggggtggc cctgccgcac cggaccgcct gcgtgcgctt ctcgcacgcc cgggacccca  720
tcttcggcaa ccagatcatc ccggacaccg ccatcctgag cgtggtgccg ttccaccacg  780
gcttcggcat gttcacgacc ctgggctacc tcatctgcgg cttccgggtg gtcctgatgt  840
accggttcga ggaggagctg ttcctgcgga gcctgcagga ctacaagatc cagagcgcgc  900
tgctcgtgcc gaccctgttc agcttcttcg ccaagagcac cctgatcgac aagtacgacc  960
tgtcgaacct gcacgagatc gccagcgggg gcgccccgct gagcaaggag gtgggcgagg  1020
ccgtggccaa gcggttccac ctcccgggca tccgccaggg ctacggcctg accgagacca  1080
cgagcgcgat cctgatcacc cccgaggggg acgacaagcc gggcgccgtg ggcaaggtgg  1140
tcccgttctt cgaggccaag gtggtggacc tggacaccgg caagaccctg ggcgtgaacc  1200
agcggggcga gctgtgcgtg cgggggccga tgatcatgag cggctacgtg aacaacccgg  1260
aggccaccaa cgccctcatc gacaaggacg gctggctgca cagcggcgac atcgcctact  1320
gggacgagga cgagcacttc ttcatcgtcg accggctgaa gtcgctgatc aagtacaagg  1380
gctaccaggt ggcgccggcc gagctggaga gcatcctgct ccagcacccc aacatcttcg  1440
acgccggcgt ggccgggctg ccggacgacg acgccggcga gctgccggcc gcggtggtgg  1500
tgctggagca cggcaagacc atgacggaga aggagatcgt cgactacgtg gccagccagg  1560
tgaccaccgc caagaagctg cggggcggcg tggtgttcgt ggacgaggtc ccgaagggcc  1620
tgaccgggaa gctcgacgcc cggaagatcc gcgagatcct gatcaaggcc aagaagggcg  1680
gcaagatcgc cgtgagctaa gctgccttct gcggggcttg ccttctggcc atgcccttct  1740
tctctccctt gcacctgtac ctcttggtct ttgaataaag cctgagtagg aagtatccca  1800
atggcgcgcc gagcttggca aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaa   1919
```

CATIONIC LIPIDS AND PREPARATION METHOD THEREOF

REFERENCE TO A SEQUENCE LISTING

This application incorporates by reference the Sequence Listing submitted in Computer Readable Form as a xml file named "Seq Listing (379855.00002).xml" created on May 20, 2025 and containing 6,873 bytes in size.

TECHNICAL FIELD

The present invention provides novel cationic lipids and compositions such as lipid nanoparticles comprising such cationic lipids, which can be used for intracellular delivery of therapeutic agents. These lipid nanoparticles may be formulated with nucleic acids to facilitate their intracellular delivery both in vitro and for in vivo therapeutic applications. The present invention also provides methods of chemical synthesis of the cationic lipids.

BACKGROUND

Research and development of therapeutic nucleic acids including circular RNA (cRNA), small interfering RNA (siRNA), microRNA (miRNA), antisense oligo nucleotides, messenger RNA (mRNA) as pharmaceutical drug have spurred exponential growth in the last decade. Drugs based on nucleic acids, which include large nucleic acid molecules, have to be delivered to the proper cellular compartment in order to be effective.

Cationic lipids have proved to be excellent carriers of nucleic acids to treat varies diseases in gene therapy applications. Lipid nanoparticles (LNPs) formed from cationic lipids and other co-lipids including but not limited to cholesterol, DSPC and PEGylated lipids encapsulated oligonucleotides which protect them from degradation and facilitate the cellular uptake.

Despites these efforts, there remains a need for improved lipid nanoparticle formulations that provide high potency following administration and that allow for the administration of various types of nucleic acids.

SUMMARY OF THE INVENTION

In some aspects, the present invention provides a cationic lipid represented by the structure of formula (I):

(I)

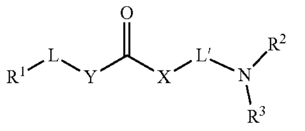

or a salt, hydrate, solvate, polymorph, optical isomer, geometrical isomer, enantiomer, diastereomer, tautomer, isotope labeled compound or mixtures thereof wherein:

X is —O—, —NH— or —S—;

Y is —O—, —NH— or —S—;

L and L', at each occurrence, are each independently selected from the group consisting of a direct bond, —O—, —C(=O)—, —C(=O)O—, —NH—, —NHC(=O)—, —NH(S=O)—, —NHS(=O)$_2$—, —S—, —S=O—, —S(=O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(=O)—, —C(=O)O—, —NH—, —NHC(=O)—, —NH(S=O)—, —NHS(=O)$_2$—, —S—, —S=O—, —S(=O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3- to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring optionally substituted by —$NH_2$, a 3- to 10-membered heterocyclic ring or 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;

(b) $C_{10}$-$C_{22}$ alkenyl;

(c) $C_{10}$-$C_{22}$ alkynyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(=O)—, —C(=O)—O— or —O—.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IA):

(IA)

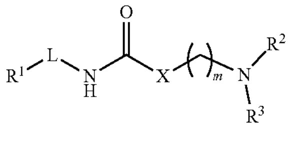

wherein:

X is —O—, —NH— or —S—;

L is selected from the group consisting of a direct bond, —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3- to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring, a 3- to 10-membered heterocyclic ring or 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;

(b) $C_{10}$-$C_{22}$ alkenyl;

(c) $C_{10}$-$C_{22}$ alkynyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(═O)—, —C(═O)—O— or —O—;

m is 0, 1, 2, 3, 4, 5 or 6, preferably is 2, 3 or 4, more preferably 3 or 4.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (II) or (III):

(II)

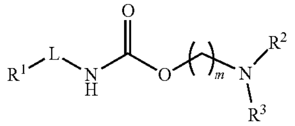

(III)

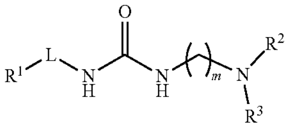

wherein:

L is selected from the group consisting of a direct bond, —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3 to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring, a 3- to 10-membered heterocyclic ring or 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;

(b) $C_{10}$-$C_{22}$ alkenyl;

(c) $C_{10}$-$C_{22}$ alkynyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(═O)—, —C(═O)—O— or —O—;

m is 0, 1, 2, 3, 4, 5 or 6, preferably is 2, 3 or 4.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IV):

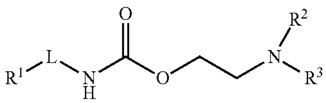

wherein:

L is —$(CH_2)$n-, wherein n=1, 2 or 3;

$R^1$ is —$N(CH_3)_2$,

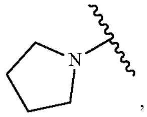,
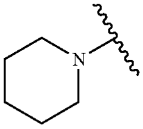, or
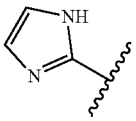;

$R^2$ and $R^3$ are each independently selected from the group consisting of:

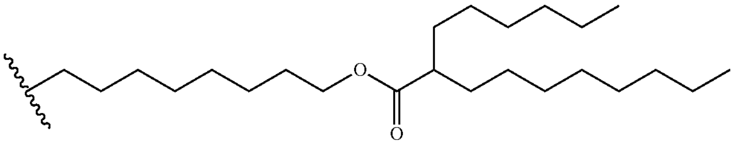 [SMILES: *CCCCCCCCOC(=O)C(CCCCCC)CCCCCCCC]

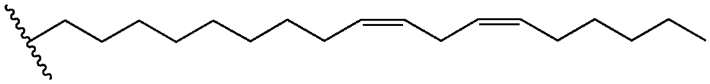

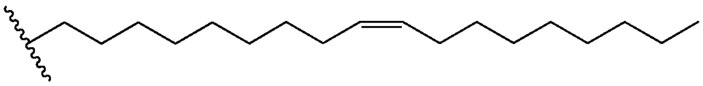 [SMILES: *CCCCCCCC/C=C\CCCCCCCC]

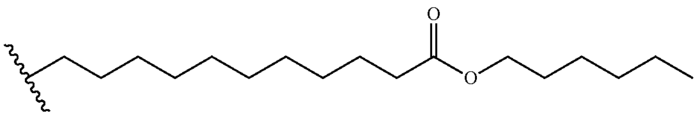 [SMILES: *CCCCCCCCCCC(=O)OCCCCCC]

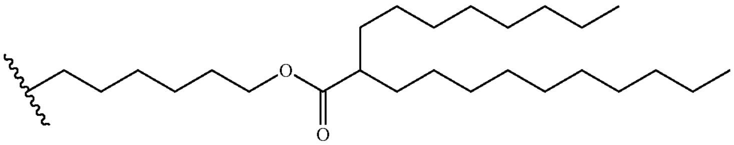 [SMILES: *CCCCCCOC(=O)C(CCCCCCCC)CCCCCCCCCC]

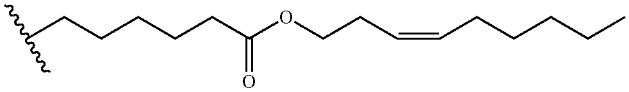 [SMILES: *CCCCCC(=O)OCC/C=C\CCCCC]

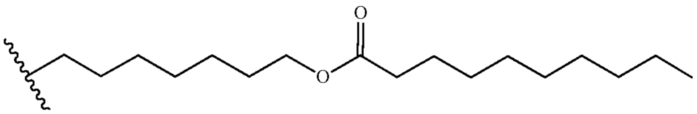 [SMILES: *CCCCCCCOC(=O)CCCCCCCCC]

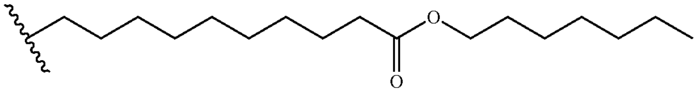 [SMILES: *CCCCCCCCCC(=O)OCCCCCCC]

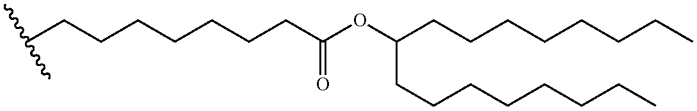 [SMILES: *CCCCCCCC(=O)OC(CCCCCCCC)CCCCCCCC]

-continued

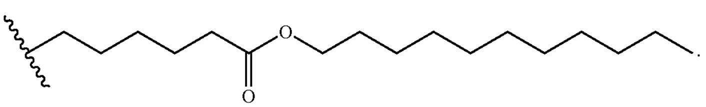 [SMILES: *CCCCCC(=O)OCCCCCCCCCCC]

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IV):

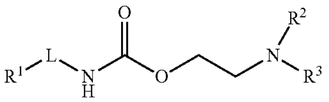

wherein $R^1$-L- is selected from

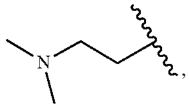,
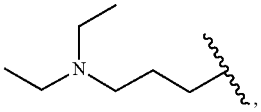,
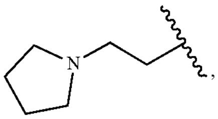,
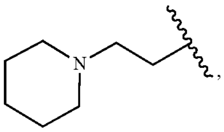, and
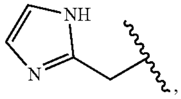, and wherein other groups are defined as above.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (V):

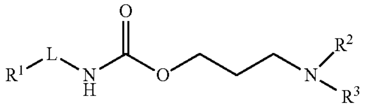

wherein:

L is —$(CH_2)$n-, wherein n=1, 2 or 3;

$R^1$ is —$N(CH_3)_2$,

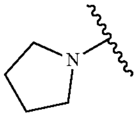,
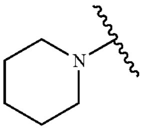, or
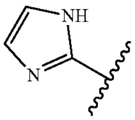;

$R^2$ and $R^3$ are each independently selected from the group consisting of:

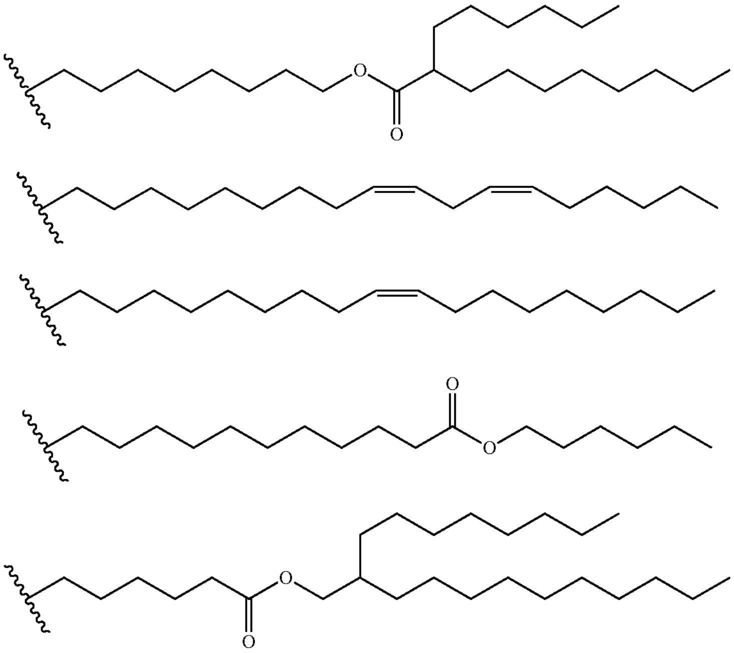

-continued

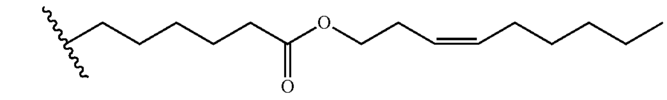 [SMILES: *CCCCCC(=O)OCC/C=C\CCCCC]

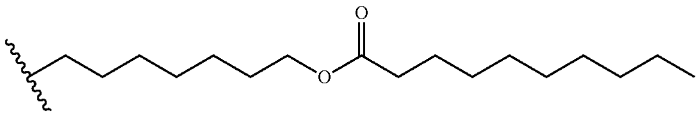 [SMILES: *CCCCCCCOC(=O)CCCCCCCCC]

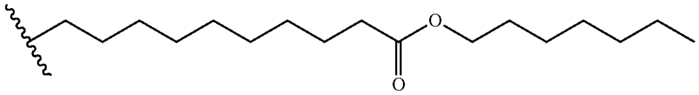 [SMILES: *CCCCCCCCCC(=O)OCCCCCCC]

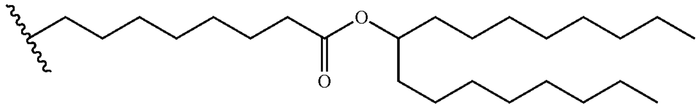 [SMILES: *CCCCCCCC(=O)OC(CCCCCCCC)CCCCCCCC]

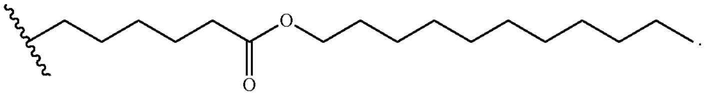 [SMILES: *CCCCCC(=O)OCCCCCCCCCCC]

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (V):

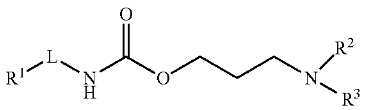

wherein $R^1$-L- is selected from

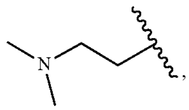,

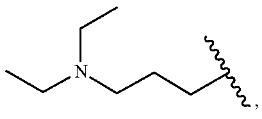,

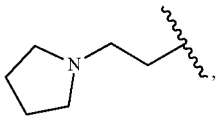,

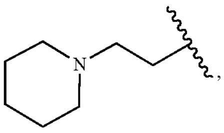, and

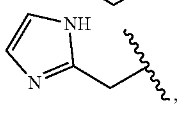, and wherein other groups are defined as above.

In some aspects, the present invention provides an intermediate compound represented by the structure of formula (VI):

(VI)

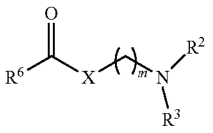

wherein $R^6$ is a leaving group, preferable is

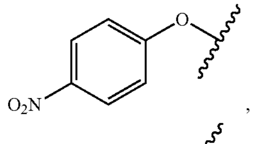,

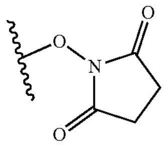, or

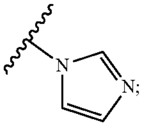;

and the remaining groups are as defined above.

In some aspects, the present invention provides a method of preparing the cationic lipid of the invention, comprising a step of reacting a compound of formula (VI) with a compound of formula (VII), to afford the cationic lipid of formula (IA):

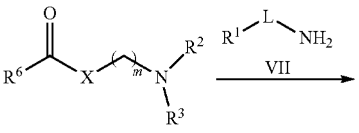

VI

-continued

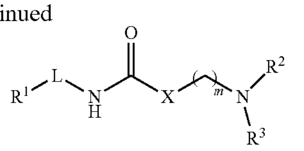

(IA)

wherein each of the groups is as defined in aspects of the invention. In embodiments, the reaction is conducted in the presence of a base, e.g., TEA or DIPEA.

In some aspects, the present invention provides a nanoparticle composition, comprising a cationic lipid of the invention.

In some aspects, the present invention provides a nanoparticle composition, further comprising one or more selected from the group of a phospholipid, a PEG lipid and a structural lipid. In some aspects, the present invention provides a nanoparticle composition, further comprising a phospholipid, a PEG lipid and a structural lipid.

In some aspects, the present invention provides a pharmaceutical composition comprising a nanoparticle composition according to the present invention and a pharmaceutically acceptable carrier.

In some aspects, the present invention provides a method of delivering a therapeutic and/or prophylactic nucleic acid molecule to a cell, including the step of administering to a subject (i) the nanoparticle composition of the invention and (ii) a therapeutic and/or prophylactic nucleic acid molecule, in which administering involves contacting the cell with the nanoparticle composition, whereby the therapeutic and/or prophylactic nucleic acid molecule is delivered to the cell. In embodiment, the therapeutic and/or prophylactic nucleic acid is encapsulated in the nanoparticle composition of the present invention. In embodiment, the therapeutic and/or prophylactic nucleic acid is combined with the nanoparticle composition of the present invention.

In some aspects, the present invention provides a method of delivering a protein-coding nucleic acid molecule to a cell, including the step of administering to a subject (i) the nanoparticle composition of the invention and (ii) a protein-coding nucleic acid molecule, in which administering involves contacting the cell with the nanoparticle composition of the present invention, whereby the nucleic acid is delivered to the cell. In embodiment, the protein-coding nucleic acid is encapsulated in the nanoparticle composition of the present invention. In embodiment, the protein-coding nucleic acid is combined with the nanoparticle composition of the present invention.

In some aspects, the present invention provides a method of producing a polypeptide of interest in a cell, including the step of contacting the cell with a nanoparticle composition of the invention and (ii) a nucleic acid molecule encoding the polypeptide of interest, whereby the nucleic acid molecule is capable of being translated in the cell to produce the polypeptide. In embodiments, the nucleic acid molecule is an mRNA molecule, a siRNA molecule, or a circular RNA molecule. In embodiments, the nucleic acid molecule is a linear RNA. In embodiments, the nucleic acid molecule is a circular RNA.

In some aspects, the present invention provides a nanoparticle composition for use in the manufacture of a medicament for the treatment of a disease or disorder in a mammal in need thereof, wherein the nanoparticle composition includes (i) a lipid component including a phospholipid, a PEG lipid, a structural lipid, and a cationic lipid of the invention and (ii) a therapeutic and/or prophylactic nucleic acid molecule. In embodiments, the nucleic acid molecule is an mRNA, a siRNA or a circular RNA. In embodiments, the nucleic acid molecule is a linear RNA. In embodiments, the nucleic acid molecule is a circular RNA.

In some aspects, the present invention provides a nanoparticle composition for use in the manufacture of a medicament for the treatment of a disease or disorder in a mammal in need thereof, wherein the nanoparticle composition includes (i) a cationic lipid of the invention and (ii) a nucleic acid molecule encoding a therapeutic and/or prophylactic protein. In embodiments, the nucleic acid molecule is an mRNA, a siRNA or a circular RNA. In embodiments, the nucleic acid molecule is a linear RNA. In embodiments, the nucleic acid molecule is a circular RNA.

In some aspects, the present invention provides use of the cationic lipid of the invention, for the manufacture of a nanoparticle composition.

In some aspects, the present invention provides use of the cationic lipid of the invention or use of the nanoparticle composition of the invention for the manufacture of a medicament for the treatment of a disease or disorder in a subject in need thereof.

In some aspects, the present invention provides a method of synthesizing a cationic lipid of Formula (I), (IA), (II), (III), (IV), or (V) and methods of making a nanoparticle composition including a lipid component comprising the cationic lipid of Formula (I), (IA), (II), (III), (IV), or (V).

DETAILED DESCRIPTION OF THE PRESENT INVENTION

Figure 1:
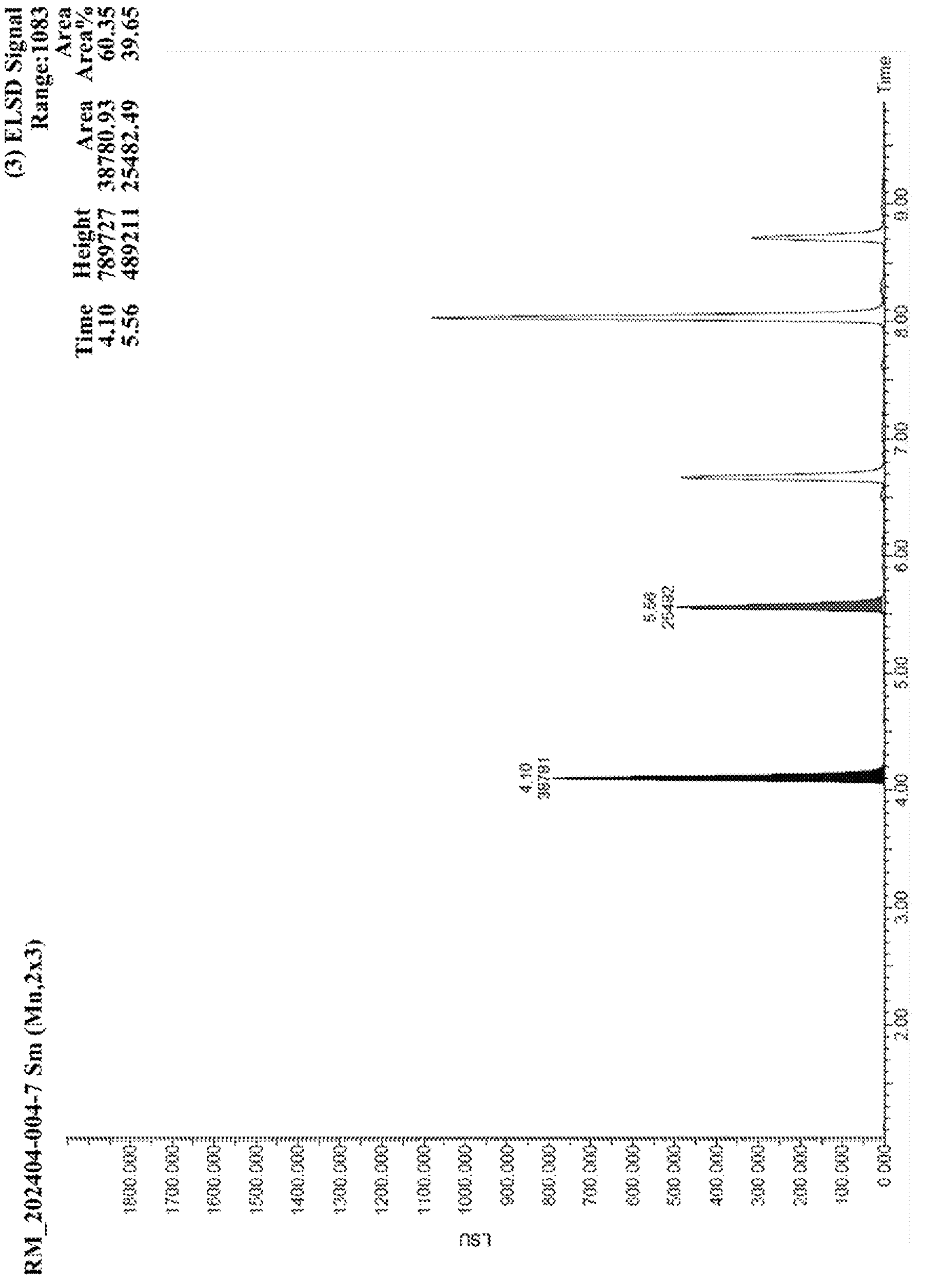
FIG. 1. HPLC-ELSD chromatogram of LNP made from Lipid C showing the parent lipid at Rt 4.10 mins and the hydrolyzed compound at Rt 5.56 mins and the corresponding ratios.

The present invention provides novel lipids and lipid nanoparticle compositions including a novel cationic lipid. The present invention also provides methods of providing a protein-coding nucleic acid molecule to a mammalian cell, specifically delivering said protein-coding nucleic acid molecule to a mammalian organ and producing a polypeptide of interest in a mammalian cell. The present invention also provides methods of delivering a therapeutic and/or prophylactic nucleic acid molecule to a mammalian cell, specifically delivering a therapeutic and/or prophylactic nucleic acid molecule to a mammalian organ, producing a polypeptide of interest in a mammalian cell, and treating a disease or disorder in a mammal in need thereof. For example, a method of producing a polypeptide of interest in a cell involves contacting a nanoparticle composition comprising a linear RNA, e.g. an mRNA, a siRNA, or a circular RNA with a mammalian cell, whereby the mRNA may be translated to produce the polypeptide of interest. A method of delivering a therapeutic and/or prophylactic nucleic acid molecule to a mammalian cell or organ may involve administration of a nanoparticle composition including the therapeutic and/or prophylactic nucleic acid molecule to a subject, in which the administration involves contacting the cell or organ with the composition, whereby the therapeutic and/or prophylactic nucleic acid molecule is delivered to the cell or organ.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The term "C1-14 alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The term "$C_{2-14}$ alkenyl" means an optionally substituted linear or branched hydrocarbon including 2-14 carbon atoms and at least one carbon-carbon double bond. For example, an alkenyl group may include one, two, three, four, or more carbon-carbon double bonds. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The term "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, an alkynyl group may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The term "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means anon-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, alkyl, alkenyl, alkylene, alkenylene, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R$. in which each OR are alkoxy groups that can be the same or different and R is an alkyl or alkenyl group), a phosphate, a thiol (e.g., —SH), a sulfoxide (e.g., —S(O)R), a sulfmic acid (e.g., —S(O)OH), a sulfonic acid (e.g., $—S(O)_2OH$), a thial (e.g., —C(S)H), a sulfate, a sulfonyl, an amide (e.g., $—C(O)NR_2$, or —N(R)C(O)R), an azido (e.g., —N3), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C1-6 alkyl group may be further substituted with one, two, three, four, five, or six substituents as described herein.

As used herein, the term "compound" is meant to include all isomers and isotope labeled compounds of the structure depicted. "Isotope" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Compounds of the present invention that contain nitrogens can be converted to N-oxides by treatment with an oxidizing agent (e.g., 3-chloroperoxy benzoic acid and/or hydrogen peroxides) to afford other compounds of the disclosure. Thus, all shown and claimed nitrogen-containing compounds are considered, when allowed by valency and structure, to include both the compound as shown and its N-oxide derivative. Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

As used herein, the term "delivering" means providing an entity to a destination. For example, delivering a therapeutic and/or prophylactic nucleic acid molecule to a subject may involve administering a nanoparticle composition including the therapeutic and/or prophylactic nucleic acid molecule to the subject (e.g., by an intravenous, intramuscular, intradermal, or subcutaneous route). Administration of a nanoparticle composition to a mammal or mammalian cell may involve contacting one or more cells with the nanoparticle composition.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerization is called tautomerism.

It is to be understood that the compounds of the present invention may be depicted as different tautomers. It should also be understood that when compounds have tautomeric forms, all tautomeric forms are intended to be included in the scope of the disclosure, and the naming of the compounds does not exclude any tautomer form.

As used herein, a "lipid component" is that component of a nanoparticle composition that includes one or more lipids. For example, the lipid component may include one or more cationic/ionizable, PEGylated, structural, or other lipids, such as phospholipids.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17* ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al, Journal of Pharmaceutical Science, 66, 1-19 (1977), each of which is incorporated herein by reference in its entirety.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides (PEG-CER), PEG-modified dialkylamines, PEG-modified diacylglycerols (PEG-DEG), PEG-modified dialkylglycerols, and mixtures thereof.

For example, a PEG lipid may be PEG-c-DOMG, PEG-DMG, PEG-DLPE, PEG-DMPE, PEG-DPPC, or a PEG-DSPE lipid.

As used herein, the lipid component of a nanoparticle composition may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the structural lipid includes cholesterol and a corticosteroid (such as prednisolone, dexamethasone, prednisone, and hydrocortisone), or a combination thereof.

As used herein, the lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties. For example, a phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated.

For example, a phospholipid may be functionalized with or cross-linked to one or more alkynes (e.g., an alkenyl group in which one or more double bonds is replaced with a triple bond).

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA), a small interference RNA (siRNA), or a circular RNA (cRNA). Translation of an mRNA or a circular RNA encoding a particular polypeptide, for example, in vivo translation thereof inside a mammalian cell, may produce the encoded polypeptide.

In some aspects, the present invention provides a cationic lipid represented by the structure of formula (I):

(I)

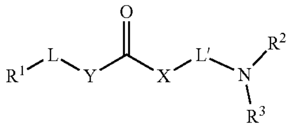

or a salt, hydrate, solvate, polymorph, optical isomer, geometrical isomer, enantiomer, diastereomer, tautomer, isotope labeled compound or mixtures thereof wherein:

X is —O—, —NH— or —S—;

Y is —O—, —NH— or —S—;

L and L', at each occurrence, are each independently selected from the group consisting of a direct bond, —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(═O)—, —C(═O)O—, —NH—, —NHC (=O)—, —NH(S=O)—, —NHS(=O)$_2$—, —S—, —S=O—, —S(=O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3- to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring, a 3- to 10-membered heterocyclic ring, a 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;
(b) $C_{10}$-$C_{22}$ alkenyl;
(c) $C_{10}$-$C_{22}$ alkynyl;
(d) $C_4$-$C_{15}$ alkylene-Z—$C_4$-$C_{22}$ alkyl; and
(e) $C_4$-$C_{15}$ alkylene-Z—$C_4$-$C_{22}$ alkenyl;

Z is —O—C(=O)—, —C(=O)—O— or —O—.

In embodiments, $R^1$ is selected from the group consisting of:

(a) $NR^4R^5$ wherein $R^4$ and $R^5$ are each independently H, $C_1$-$C_6$ alkyl or $C_{6-12}$ aralkyl optionally substituted with —$NH_2$; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered heterocyclic ring or 5- to 10-membered heteroaromatic ring containing one or more heteroatoms selected from the group consisting of O, N and S; and (d) —OH or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;
(b) $C_{10}$-$C_{22}$ alkenyl;
(c) $C_{10}$-$C_{22}$ alkynyl;
(d) $C_4$-$C_{15}$ alkylene-Z—$C_4$-$C_{22}$ alkyl; and
(e) $C_4$-$C_{15}$ alkylene-Z—$C_4$-$C_{22}$ alkenyl;

Z is —O—C(=O)—, —C(=O)—O— or —O—.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IA):

(IA)

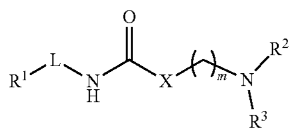

wherein:

X is —O—, —NH— or —S—;

L is selected from the group consisting of a direct bond, —O—, —C(=O)—, —C(=O)O—, —NH—, —NHC(=O)—, —NH(S=O)—, —NHS(=O)$_2$—, —S—, —S=O—, —S(=O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(=O)—, —C(=O)O—, —NH—, —NHC(=O)—, —NH(S=O)—, —NHS(=O)$_2$—, —S—, —S=O—, —S(=O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3- to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring, a 3- to 10-membered heterocyclic ring, a 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;
(b) $C_{10}$-$C_{22}$ alkenyl;

(c) $C_{10}$-$C_{22}$ alkynyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(═O)—, —C(═O)—O— or —O—;

m is 0, 1, 2, 3, 4, 5 or 6, preferably is 2, 3 or 4, more preferably 3 or 4.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (II) or (III):

(II)

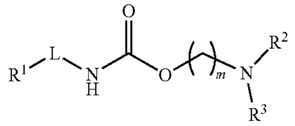

(III)

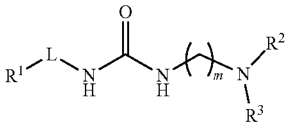

wherein:

L is selected from the group consisting of a direct bond, —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—, wherein the alkylene and alkenylene are optionally further interrupted by one or more W;

W and W', at each occurrence, are each independently selected from the group consisting of —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, and —$C_{2-6}$ alkenylene-;

$R^1$ is selected from the group consisting of:

(a) $NR^4R^5$ wherein $R^4$ and $R^5$ are each independently H, $C_1$-$C_6$ alkyl, —$NH_2$, halogen, —OH, a 3- to 10-membered cyclic ring or $C_{6-12}$ aralkyl, wherein the $C_1$-$C_6$ alkyl, 3- to 10-membered cyclic ring or $C_{6-12}$ aralkyl is optionally substituted with one or more substituents selected from the group consisting of —$NH_2$, halogen, —OH, —$C_{1-6}$ alkyl and a 3- to 4-membered cyclic ring; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered cyclic ring, for example a $C_{6-12}$ aromatic ring, a 3- to 10-membered heterocyclic ring, a 5- to 10-membered heteroaromatic ring containing one or more heteroatoms selected from the group consisting of O, N and S, or a fused ring (e.g., a 4- to 10-membered fused ring), wherein the above cyclic ring is optionally substituted with one or more substituents selected from the group consisting of —$NH_2$, halogen, —OH, —$C_{1-6}$ alkyl and a 3- to 4-membered cyclic ring; and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring;

$R^2$ and $R^3$ are each independently selected from the group consisting of:

(a) $C_{10}$-$C_{22}$ alkyl;

(b) $C_{10}$-$C_{22}$ alkenyl;

(c) $C_{10}$-$C_{22}$ alkynyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(═O)—, —C(═O)—O— or —O—;

m is 0, 1, 2, 3, 4, 5 or 6, preferably is 2, 3 or 4.

In embodiments, m is 2. In embodiments, m is 3. In embodiments, m is 4.

In embodiments, $R^1$ is selected from the group consisting of:

(a) $NR^4R^5$ wherein $R^4$ and $R^5$ are each independently H, $C_1$-$C_6$ alkyl, or $C_{6-12}$ aralkyl optionally substituted with —$NH_2$; or $R^4$ and $R^5$ together with the nitrogen to which they are attached form a 4- to 10-membered heterocyclic ring or 5- to 10-membered heteroaromatic ring, optionally containing one or more additional heteroatoms selected from the group consisting of O, N and S;

(b) the side chain of a natural or unnatural amino acid;

(c) a 3- to 10-membered heterocyclic ring or 5- to 10-membered heteroaromatic ring containing one or more heteroatoms selected from the group consisting of O, N and S, or a fused ring (e.g., a 4- to 10-membered fused ring); and (d) —OH, or —$C_{1-10}$ alkyl optionally substituted with one or more substituents selected from the group consisting of —$NH_2$, halogen, —OH, —$C_{1-6}$ alkyl and a 3- to 4-membered cyclic ring.

In embodiments, the present invention provides a cationic lipid, or a salt, hydrate, solvate, polymorph, optical isomer, geometrical isomer, enantiomer, diastereomer, tautomer, isotope labeled compound or mixtures thereof, wherein L is selected from the group consisting of —$C_{1-6}$ alkylene-, —$C_{2-6}$ alkenylene-, —W—$C_{1-6}$ alkylene-, —W—$C_{2-6}$ alkenylene-, —$C_{1-6}$ alkylene-W—, —$C_{2-6}$ alkenylene-W—, —W—W'—$C_{1-6}$ alkylene-, —$C_{1-6}$ alkylene-W—W'—, —W—W'—$C_{1-6}$ alkenylene-, —$C_{2-6}$ alkenylene-W—W'—, —W—$C_{1-6}$ alkylene-W'— and —W—$C_{2-6}$ alkenylene-W'—;

W and W', at each occurrence, are each independently selected from the group consisting of —O—, —C(═O)—, —C(═O)O—, —NH—, —NHC(═O)—, —NH(S═O)—, —NHS(═O)$_2$—, —S—, —S═O—, —S(═O)$_2$—, —$C_{1-6}$ alkylene-, and —$C_{2-6}$ alkenylene-.

In embodiments, the present invention provides a cationic lipid, or a salt, hydrate, solvate, polymorph, optical isomer, geometrical isomer, enantiomer, diastereomer, tautomer, isotope labeled compound or mixtures thereof, wherein L is —$C_{1-6}$ alkylene-, —W—$C_{1-6}$ alkylene-, —$C_{1-6}$ alkylene-W—, —W—W'—$C_{1-6}$ alkylene-, or —W—$C_{1-6}$ alkylene-W'—;

W and W', at each occurrence, are each independently selected from the group consisting of —O—, —C(═O)—, —C(═O)O—, —NH—, —NHC (=O)—, —NH(S=O)—, —NHS(=O)$_2$—, —S—, —S=O—, —S(=O)$_2$—, —$C_{1-6}$ alkylene-, and —$C_{2-6}$ alkenylene.

In embodiments, the present invention provides a cationic lipid, or a salt, hydrate, solvate, polymorph, optical isomer, geometrical isomer, enantiomer, diastereomer, tautomer, isotope labeled compound or mixtures thereof, wherein L is —$C_{1-6}$ alkylene-, —W—$C_{1-6}$ alkylene-, —$C_{1-6}$ alkylene-W—, —W—W'—$C_{1-6}$ alkylene-, or —W—$C_{1-6}$ alkylene-W'—;

W and W', at each occurrence, are each independently selected from the group consisting of —O—, —C(=O)—, —C(=O)O—, —$C_{1-6}$ alkylene- or —$C_{2-6}$ alkenylene.

In embodiments, L is —$C_{1-6}$ alkylene-.

In embodiments, L is —$(CH_2)$n-, wherein n=1, 2 or 3.

In embodiments, L is —$(CH_2)$n-, wherein n=1. In embodiments, L is —$(CH_2)$n-, wherein n=2. In embodiments, L is —$(CH_2)$n-, wherein n=3.

In embodiments, $R^1$ is selected from the group consisting of:

(a) $NR^4R^5$ wherein $R^4$ and $R^5$ are each independently H, $C_1$-$C_3$ alkyl or $C_{6-12}$ aralkyl optionally substituted with —$NH_2$; or $R^4$ and $R^5$ together with the nitrogen to which they are attached form a 5- to 6-membered heterocyclic ring or 5- to 6-membered heteroaromatic ring, optionally containing one or more additional heteroatoms selected from the group consisting of O, N and S; and (b) a 5- to 6-membered heterocyclic ring or 5- to 6-membered heteroaromatic ring containing one or more heteroatoms selected from the group consisting of O, N and S.

In embodiments, $R^1$ is $NR^4R^5$, wherein $R^4$ and $R^5$ are each independently H, $C_1$-$C_3$ alkyl or benzyl optionally substituted with —$NH_2$.

In embodiments, $R^1$ is $NR^4R^5$, $R^4$ and $R^5$ together with the nitrogen to which they are attached form a 5- to 6-membered heterocyclic ring or 5- to 6-membered heteroaromatic ring, optionally containing one or more additional heteroatoms selected from the group consisting of O, N and S.

In embodiments, $R^1$ is a 5- to 6-membered heterocyclic ring or 5- to 6-membered heteroaromatic ring containing one or more heteroatoms selected from the group consisting of: O, N and S.

In embodiments, $R^1$ is —OH.

In embodiments, $R^1$ is —$C_{1-10}$ alkyl optionally substituted with one or more substituents selected from the group consisting of —$NH_2$, halogen, —OH, —$C_{1-6}$ alkyl and a 3- to 4-membered cyclic ring.

In embodiments, $R^1$ is —OH, —$C(CH_3)_3$, —$NH_2$, —$N(CH_3)_2$, —$N(C_2H_5)_2$,

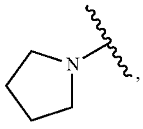, 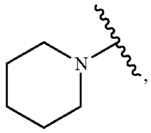, 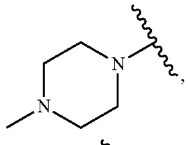,

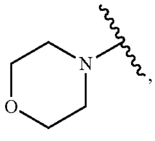, 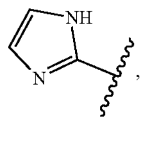, 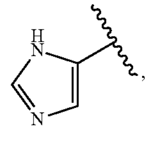,

-continued

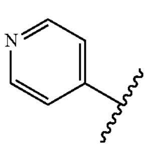 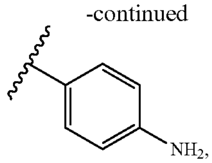, or 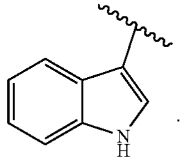.

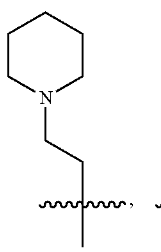, 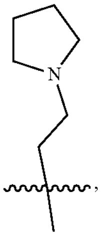, 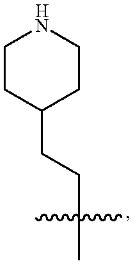, 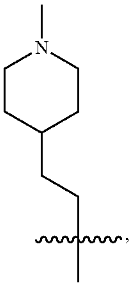,

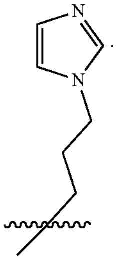.

In embodiments, $R^2$ and $R^3$ are each independently selected from the group consisting of:

(a) $C_{10}$-$C_{22}$ alkyl;

(b) $C_{10}$-$C_{22}$ alkenyl;

(d) $C_4$-$C_{15}$ alkylene-Z—$C_4$-$C_{22}$ alkyl; and (e) $C_4$-$C_{15}$ alkylene-Z—$C_4$-$C_{22}$ alkenyl;

Z is —O—C(=O)—, —C(=O)—O— or —O—.

In embodiments, $R^2$ and $R^3$ are each independently selected from the group consisting of:

(a) $C_{10}$-$C_{22}$ alkyl, for example $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkyl;

(b) $C_{10}$-$C_{22}$ alkenyl, for example $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkenyl;

(d) $C_p$ alkylene-Z—$C_q$ alkyl; and (e) $C_p$ alkylene-Z—$C_q$ alkenyl;

Z is —O—C(=O)—, —C(=O)—O— or —O—, p is any integer between 4 to 15, for example 4, 5, 6, 7, 8, 9, 10, 11, 12, 13, 14 or 15, q is any integer between 4 to 22, for example 4, 5, 6, 7, 8, 9, 10, 11, 12, 13, 14, 15, 16, 17, 18, 19, 20, 21 or 22.

In embodiments, $R^2$ and $R^3$ are each independently selected from the group consisting of:

(b) $C_{10}$-$C_{22}$ alkenyl, for example $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkenyl; and (c) $C_p$ alkylene-Z—$C_q$ alkyl;

Z is —O—C(=O)— or —C(=O)—O—, p is any integer between 4 to 15, for example 4, 5, 6, 7, 8, 9, 10, 11, 12, 13, 14 or 15;

q is any integer between 4 to 22, for example 4, 5, 6, 7, 8, 9, 10, 11, 12, 13, 14, 15, 16, 17, 18, 19, 20, 21 or 22.

In embodiments, $R^2$ and $R^3$ are each independently selected from the group consisting of:

(c) $C_p$ alkylene-Z—$C_q$ alkyl;

Z is —O—C(=O)— or —C(=O)—O—, p is any integer between 4 to 15, for example 4, 5, 6, 7, 8, 9, 10, 11, 12, 13, 14 or 15;

q is any integer between 4 to 22, for example 4, 5, 6, 7, 8, 9, 10, 11, 12, 13, 14, 15, 16, 17, 18, 19, 20, 21 or 22, Z in $R^2$ and $R^3$ are different.

In embodiments, $R^2$ is (b) $C_{10}$-$C_{22}$ alkenyl, for example $C_{10}$, $C_{11}$, $C_{12}$, $C_{13}$, $C_{14}$, $C_{15}$, $C_{16}$, $C_{17}$, $C_{18}$, $C_{19}$ or $C_{20}$ alkenyl, and $R^3$ is (c) $C_p$ alkylene-Z—$C_q$ alkyl, Z is —O—C(═O)— or —C(═O)—O—, p is any integer between 4 to 15, for example 4, 5, 6, 7, 8, 9, 10, 11, 12, 13, 14 or 15;

q is any integer between 4 to 22, for example 4, 5, 6, 7, 8, 9, 10, 11, 12, 13, 14, 15, 16, 17, 18, 19, 20, 21 or 22.

In embodiments, $R^2$ and $R^3$ are (c) $C_p$ alkylene-Z—$C_q$ alkyl,

Z is —O—C(═O)— or —C(═O)—O—, p is any integer between 4 to 15, for example 4, 5, 6, 7, 8, 9, 10, 11, 12, 13, 14 or 15;

q is any integer between 4 to 22, for example 4, 5, 6, 7, 8, 9, 10, 11, 12, 13, 14, 15, 16, 17, 18, 19, 20, 21 or 22;

Z in $R^2$ and $R^3$ are the same, for example, Z in $R^2$ and $R^3$ is —O—C(═O)—.

In embodiments, $R^2$ and $R^3$ are each independently selected from the group consisting of:

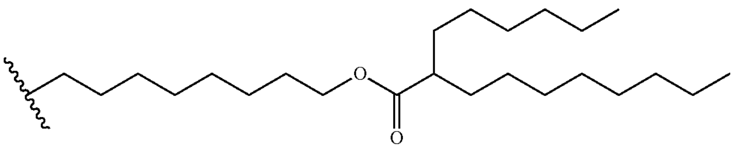 [SMILES: *CCCCCCCCOC(=O)C(CCCCCC)CCCCCCCC]

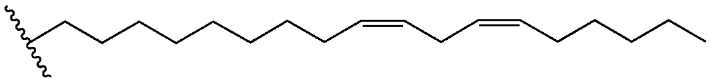

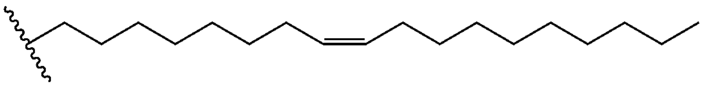 [SMILES: *CCCCCCC/C=C\CCCCCCCCC]

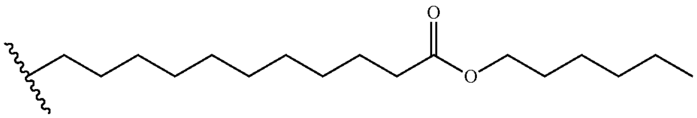 [SMILES: *CCCCCCCCCCC(=O)OCCCCCC]

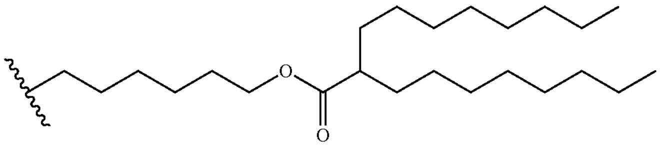 [SMILES: *CCCCCCOC(=O)C(CCCCCCCC)CCCCCCCC]

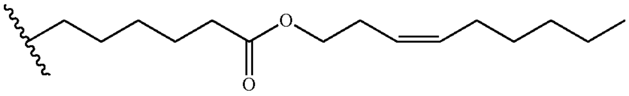 [SMILES: *CCCCCC(=O)OCC/C=C\CCCCC]

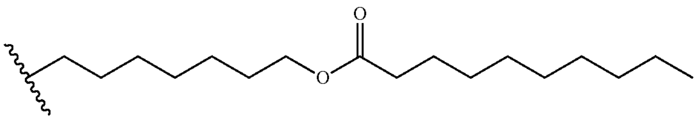 [SMILES: *CCCCCCCOC(=O)CCCCCCCCC]

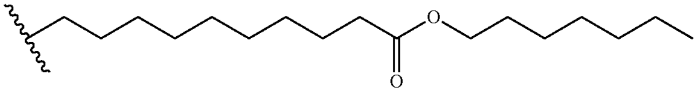 [SMILES: *CCCCCCCCCC(=O)OCCCCCCC]

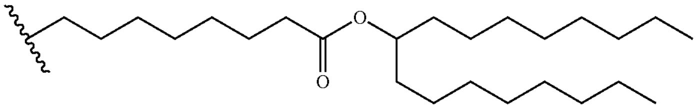 [SMILES: *CCCCCCCC(=O)OC(CCCCCCCC)CCCCCCCC]

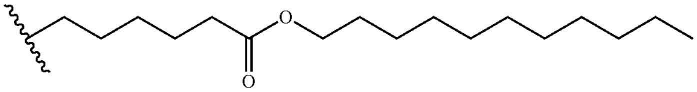 [SMILES: *CCCCCC(=O)OCCCCCCCCCCC]

-continued

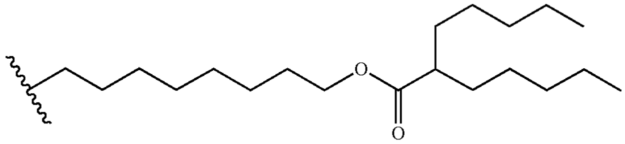 [SMILES: *CCCCCCCCOC(=O)C(CCCCC)CCCCC]

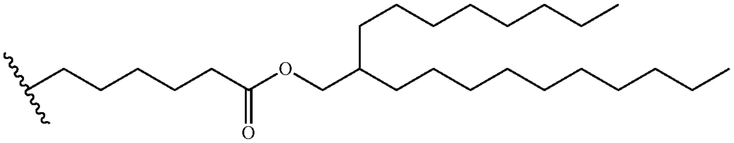 [SMILES: *CCCCCC(=O)OCC(CCCCCCCC)CCCCCCCCCC]

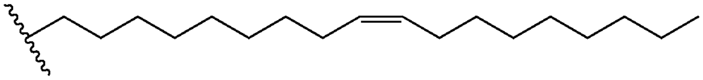 [SMILES: *CCCCCCCC/C=C\CCCCCCCC]

In embodiments, $R^Z$ and Rare the same or different groups.

In embodiments, $R^2$ and $R^3$ are the same group and are

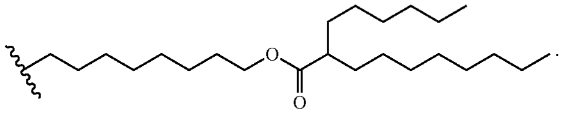 [SMILES: *CCCCCCCCOC(=O)C(CCCCCC)CCCCCCCC]

In embodiments, $R^2$ and $R^3$ are the same group and are

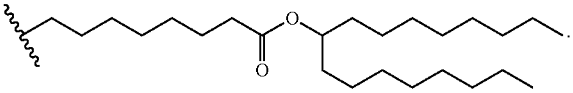 [SMILES: *CCCCCCCC(=O)OC(CCCCCCCC)CCCCCCCC]

In embodiments, $R^2$ and $R^3$ are the same group and are

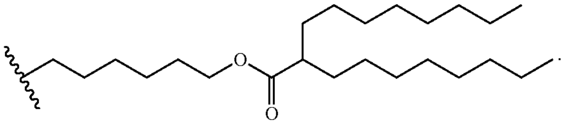 [SMILES: *CCCCCCOC(=O)C(CCCCCCCC)CCCCCCCC]

In embodiments, $R^2$ and $R^3$ are the same group and are

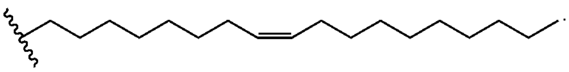 [SMILES: *CCCCCCC/C=C\CCCCCCCCC]

In embodiments. $R^2$ and $R^3$ are the same group and are

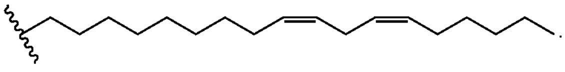 [SMILES: *CCCCCCCC/C=C\C/C=C\CCCCC]

In embodiments, $R^2$ and $R^3$ are different groups and respectively are

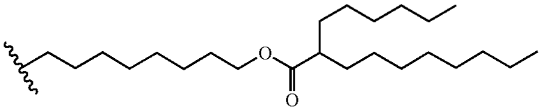

or

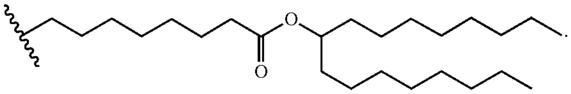

In embodiments, $R^2$ and $R^3$ are different groups and respectively are

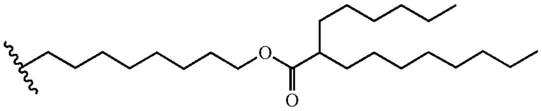

or

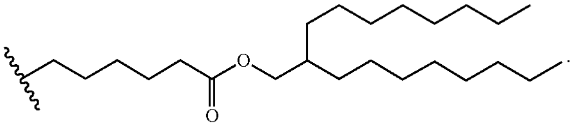

In embodiments $R^2$ and $R^3$ are different groups and respectively are

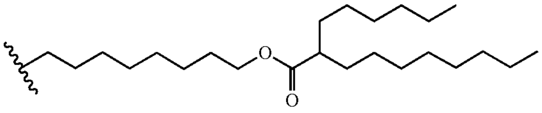

or

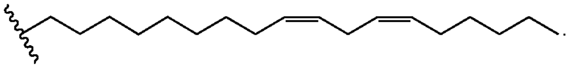

In embodiments, $R^2$ and $R^3$ are different groups and respectively are

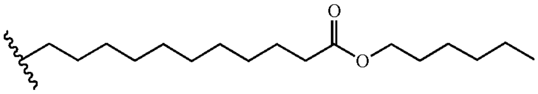

or

-continued

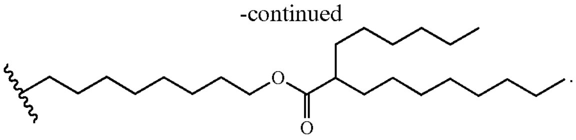

.

In embodiments, the cationic lipid of the present invention is a deuterated compound.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IV):

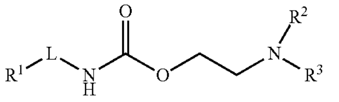

wherein:

L is —$(CH_2)$n-, wherein n=1, 2 or 3;

$R^1$ is —$N(CH_3)_2$, —$N(C_2H_5)_2$,

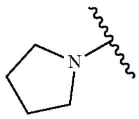
,
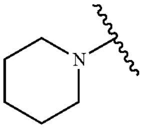
, or
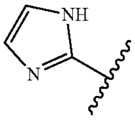
;

$R^2$ and $R^3$ are each independently selected from the group consisting of:

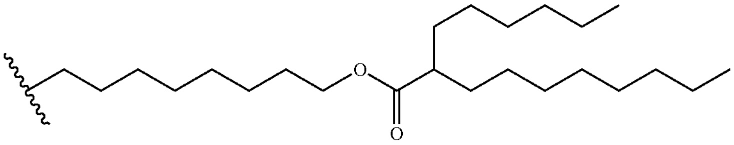 [SMILES: *CCCCCCCCOC(=O)C(CCCCCC)CCCCCCCC]

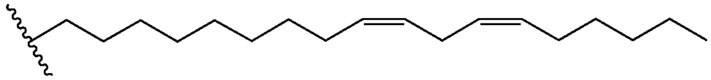 [SMILES: *CCCCCCCC/C=C\C/C=C\CCCCC]

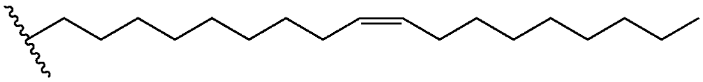 [SMILES: *CCCCCCCC/C=C\CCCCCCCC]

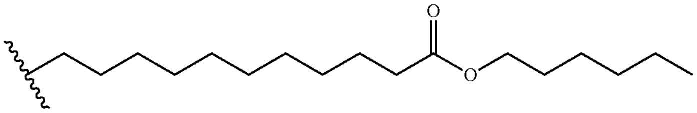 [SMILES: *CCCCCCCCCCC(=O)OCCCCCC]

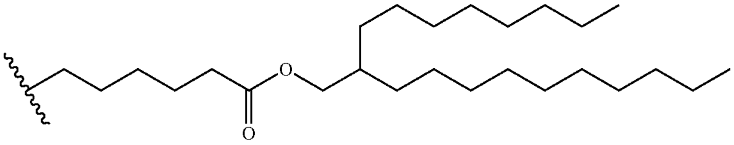 [SMILES: *CCCCCC(=O)OCC(CCCCCCCC)CCCCCCCCCC]

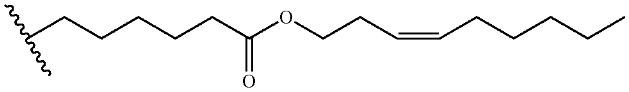 [SMILES: *CCCCCC(=O)OCC/C=C\CCCCC]

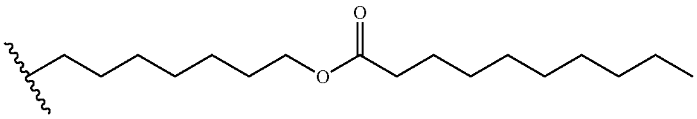 [SMILES: *CCCCCCCOC(=O)CCCCCCCCC]

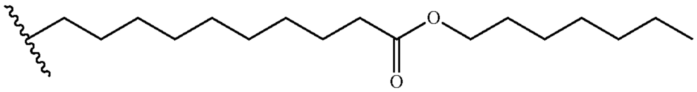 [SMILES: *CCCCCCCCCC(=O)OCCCCCCC]

-continued

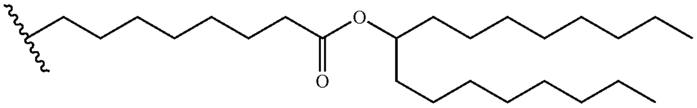 [SMILES: *CCCCCCCC(=O)OC(CCCCCCCC)CCCCCCCC]

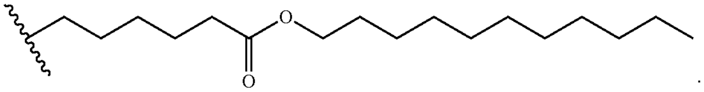 [SMILES: *CCCCCC(=O)OCCCCCCCCCCC]

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IV):

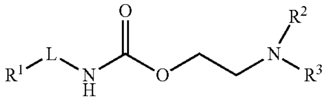

wherein $R^1$-L- is selected from

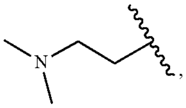,

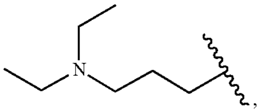,

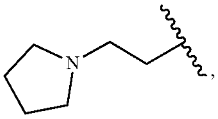,

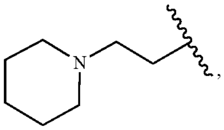, and

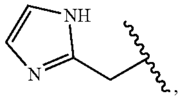, and wherein other groups are defined as above.

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (V):

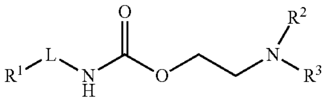

wherein:

L is —$(CH_2)n$-, wherein n=1, 2 or 3; R is —$N(CH_3)_2$, —$N(C_2H_5)_2$,

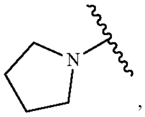,

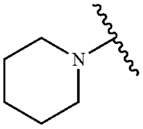, or

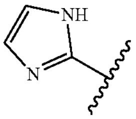;

$R^2$ and $R^3$ are each independently selected from the group consisting of:

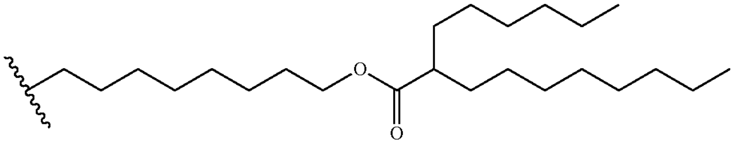 [SMILES: *CCCCCCCCOC(=O)C(CCCCCC)CCCCCCCC]

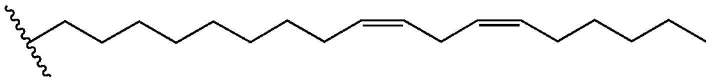 [SMILES: *CCCCCCCC/C=C\C/C=C\CCCCC]

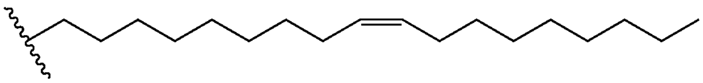 [SMILES: *CCCCCCCC/C=C\CCCCCCCC]

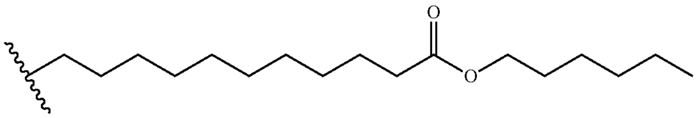 [SMILES: *CCCCCCCCCCC(=O)OCCCCCC]

-continued

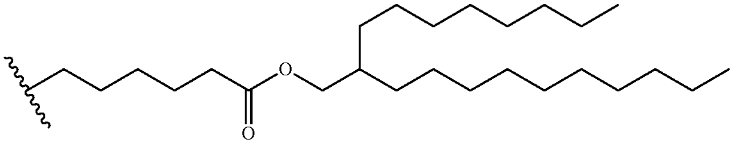 [SMILES: *CCCCCC(=O)OCC(CCCCCCCC)CCCCCCCCCC]

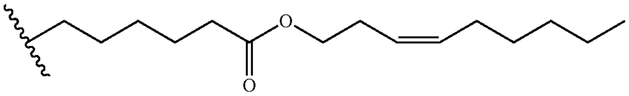 [SMILES: *CCCCCC(=O)OCC/C=C\CCCCC]

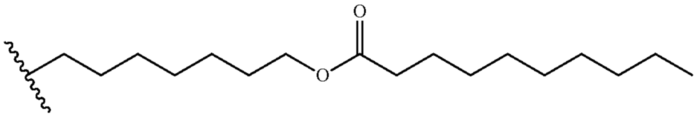 [SMILES: *CCCCCCCOC(=O)CCCCCCCCC]

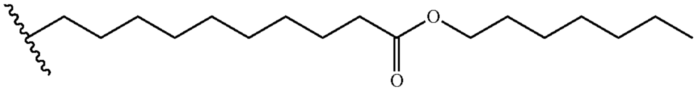 [SMILES: *CCCCCCCCCC(=O)OCCCCCCC]

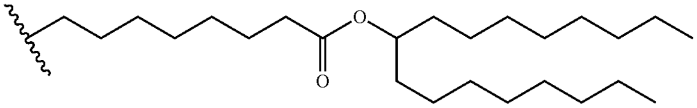 [SMILES: *CCCCCCCC(=O)OC(CCCCCCCC)CCCCCCCC]

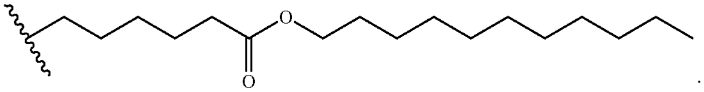 [SMILES: *CCCCCC(=O)OCCCCCCCCCCC]

In some aspects, the present invention provides a cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (V):

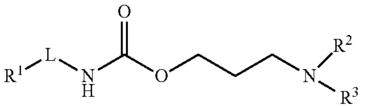

wherein $R^1$-L- is selected from

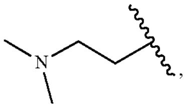,

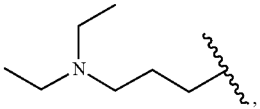,

-continued

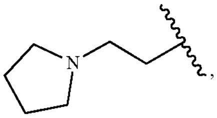,

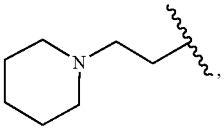, and

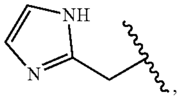, and wherein other groups are defined as above.

In embodiments, the cationic lipid of the present invention is selected from the group consisting of:

TABLE 1
| # | Structure | Mw |
|---|---|---|
| 1. | 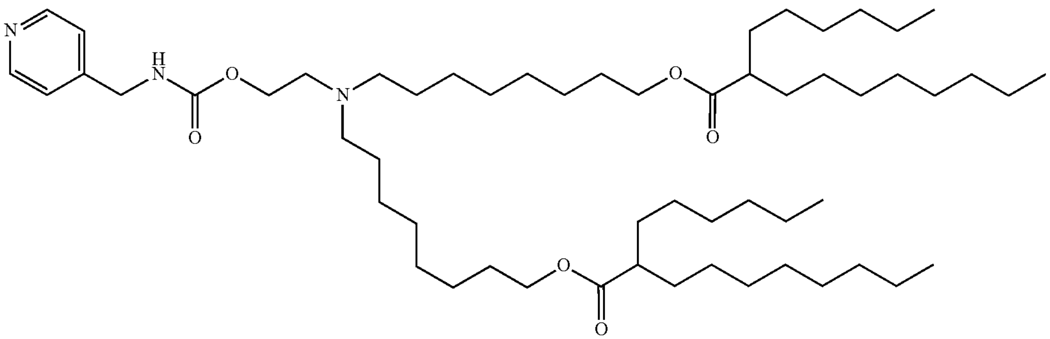 [SMILES: CCCCCCCCC(CCCCCC)C(=O)OCCCCCCCCN(CCCCCCCCOC(=O)C(CCCCCC)CCCCCCCC)CCOC(=O)NCc1ccncc1] | 928.5 |
| 2. | 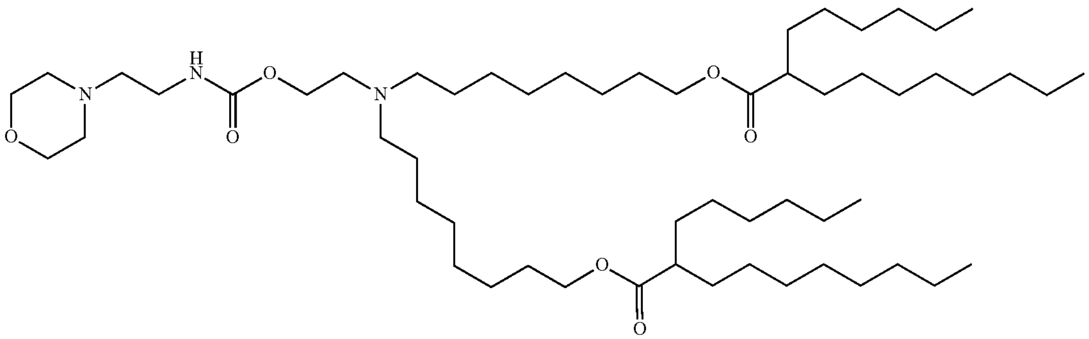 [SMILES: CCCCCCCCC(CCCCCC)C(=O)OCCCCCCCCN(CCCCCCCCOC(=O)C(CCCCCC)CCCCCCCC)CCOC(=O)NCCN1CCOCC1] | 950.5 |
| 3. | 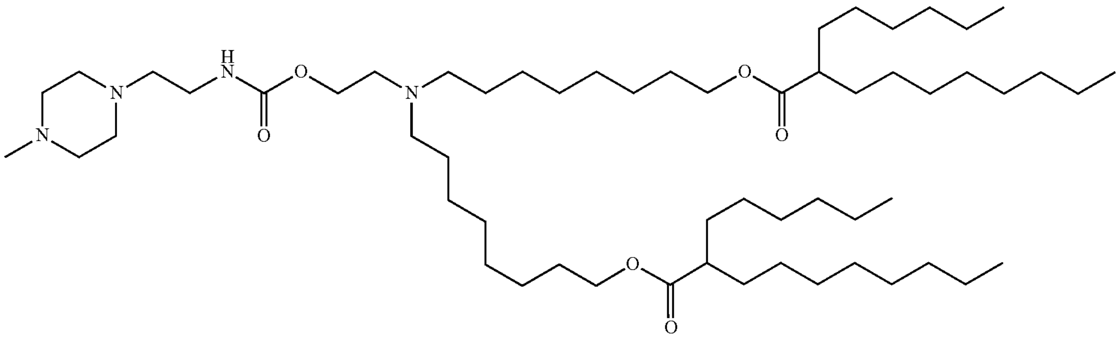 [SMILES: CCCCCCCCC(CCCCCC)C(=O)OCCCCCCCCN(CCCCCCCCOC(=O)C(CCCCCC)CCCCCCCC)CCOC(=O)NCCN1CCN(C)CC1] | 963.6 |

TABLE 1-continued
| # | Structure | Mw |
|---|---|---|
| 4. | 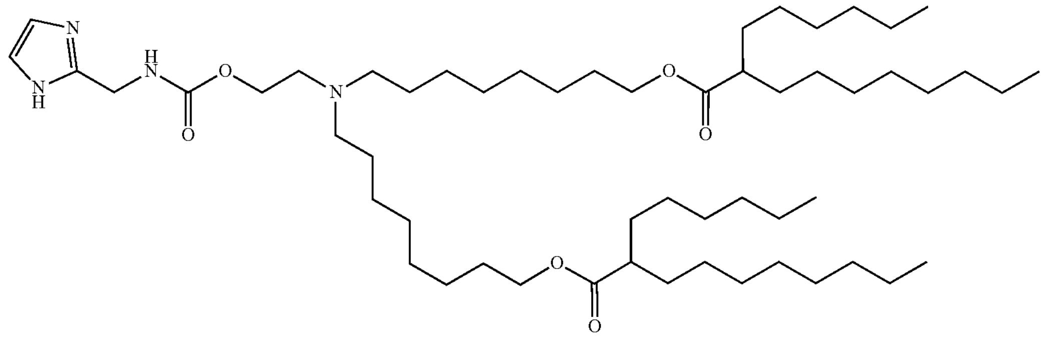 [SMILES: CCCCCCCCC(CCCCCC)C(=O)OCCCCCCCCN(CCCCCCCCOC(=O)C(CCCCCC)CCCCCCCC)CCOC(=O)NCc1ncc[nH]1] | 917.5 |
| 5. | 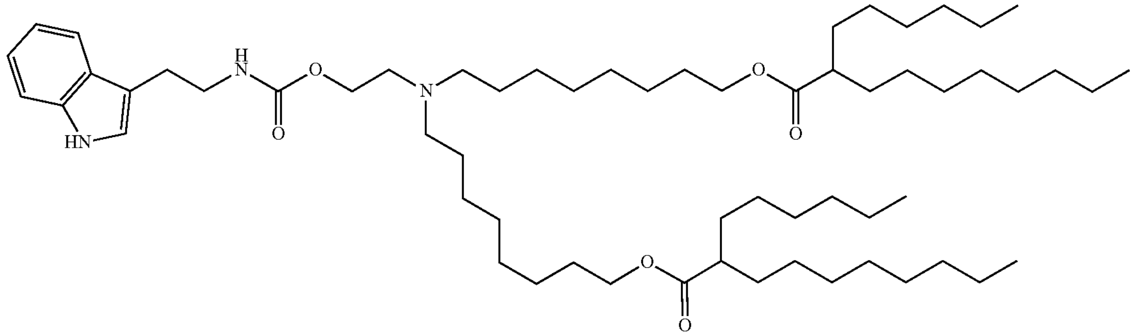 [SMILES: CCCCCCCCC(CCCCCC)C(=O)OCCCCCCCCN(CCCCCCCCOC(=O)C(CCCCCC)CCCCCCCC)CCOC(=O)NCCc1c[nH]c2ccccc12] | 980.6 |
| 6. | 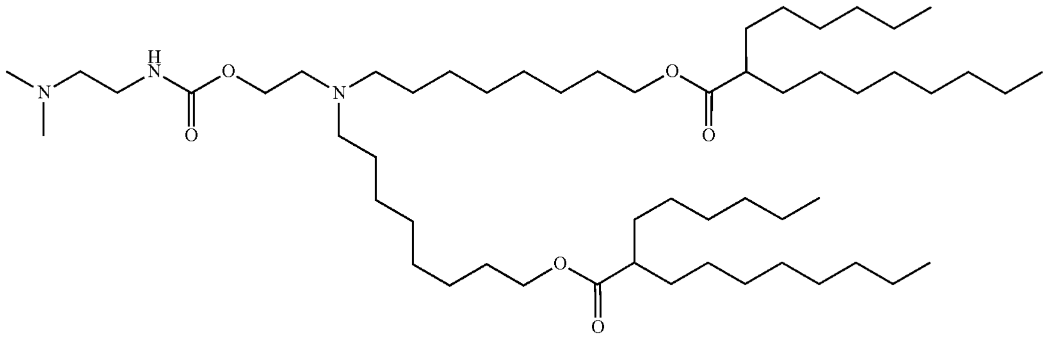 [SMILES: CCCCCCCCC(CCCCCC)C(=O)OCCCCCCCCN(CCCCCCCCOC(=O)C(CCCCCC)CCCCCCCC)CCOC(=O)NCCN(C)C] | 908.5 |

TABLE 1-continued
| # | Structure | Mw |
|---|---|---|
| 7. | 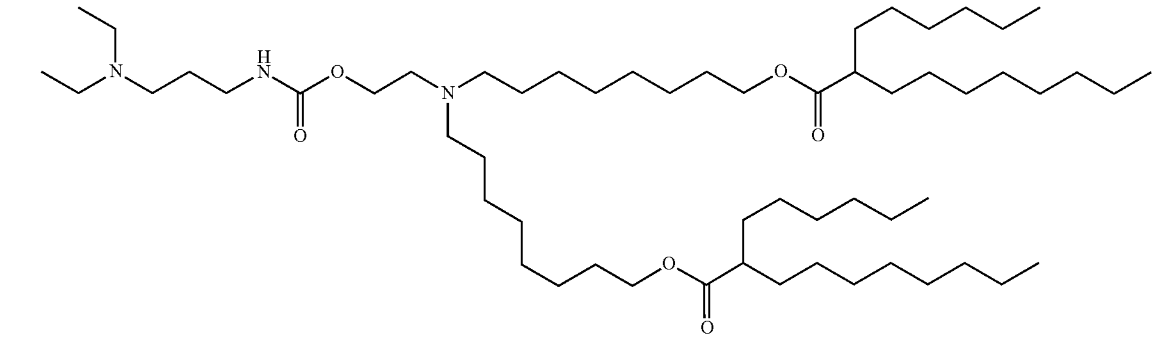 [SMILES: CCCCCCCCC(CCCCCC)C(=O)OCCCCCCCCN(CCCCCCCCOC(=O)C(CCCCCC)CCCCCCCC)CCOC(=O)NCCCN(CC)CC] | 950.6 |
| 8. | 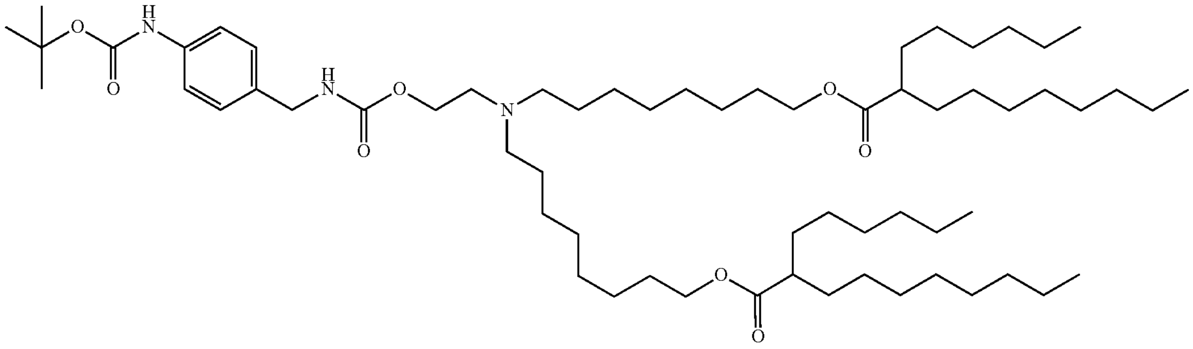 [SMILES: CCCCCCCCC(CCCCCC)C(=O)OCCCCCCCCN(CCCCCCCCOC(=O)C(CCCCCC)CCCCCCCC)CCOC(=O)NCc1ccc(NC(=O)OC(C)(C)C)cc1] | 1042.6 |
| 9. | 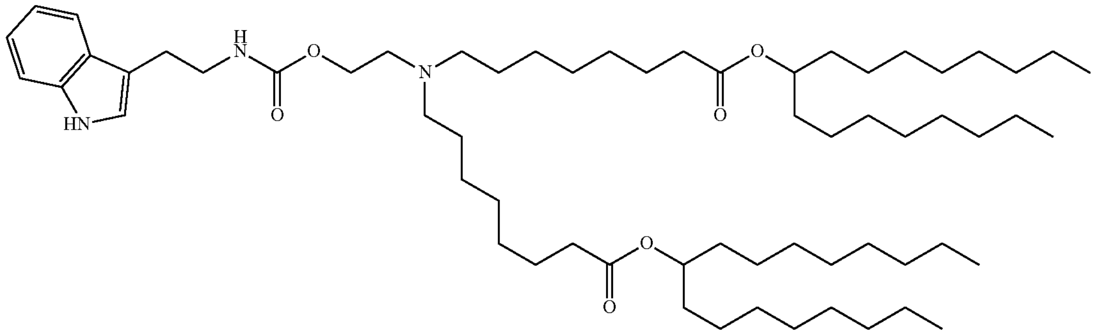 [SMILES: CCCCCCCCC(CCCCCCCC)OC(=O)CCCCCCCN(CCCCCCCC(=O)OC(CCCCCCCC)CCCCCCCC)CCOC(=O)NCCc1c[nH]c2ccccc12] | 1008.6 |

TABLE 1-continued
| # | Structure | Mw |
|---|---|---|
| 10. | 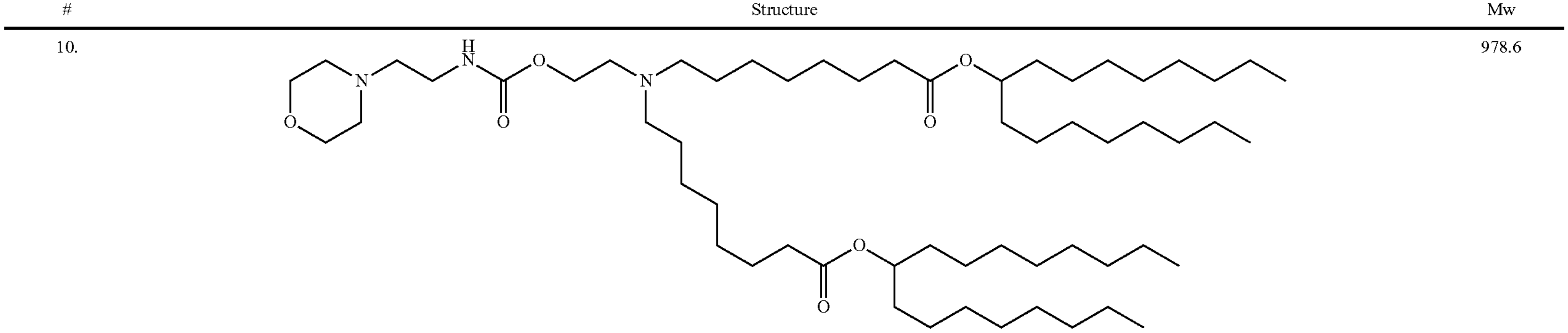 | 978.6 |
| 11. | 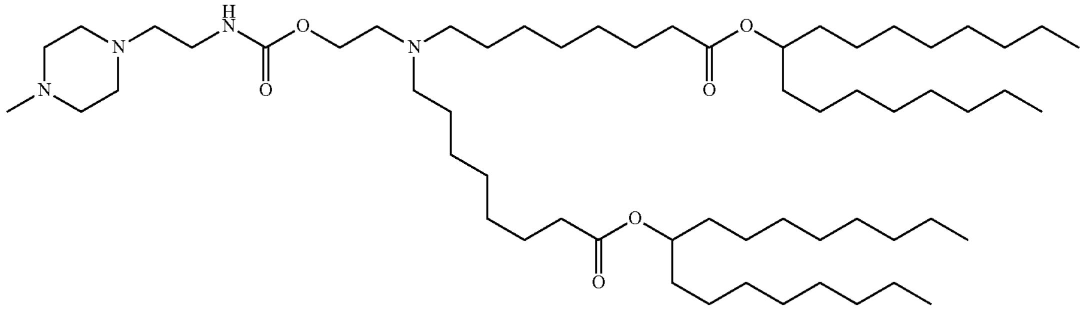 [SMILES: CCCCCCCCC(CCCCCCCC)OC(=O)CCCCCCCN(CCCCCCCC(=O)OC(CCCCCCCC)CCCCCCCC)CCOC(=O)NCCN1CCN(C)CC1] | 991.6 |
| 12. | 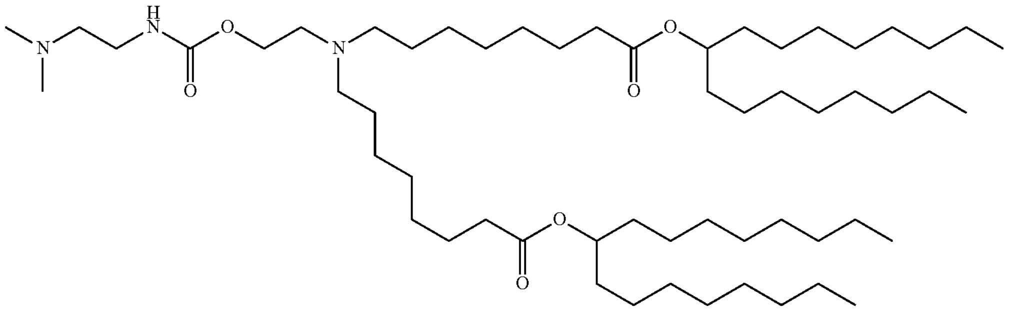 [SMILES: CCCCCCCCC(CCCCCCCC)OC(=O)CCCCCCCN(CCCCCCCC(=O)OC(CCCCCCCC)CCCCCCCC)CCOC(=O)NCCN(C)C] | 936.5 |

TABLE 1-continued
| # | Structure | Mw |
| --- | --- | --- |
| 13. | 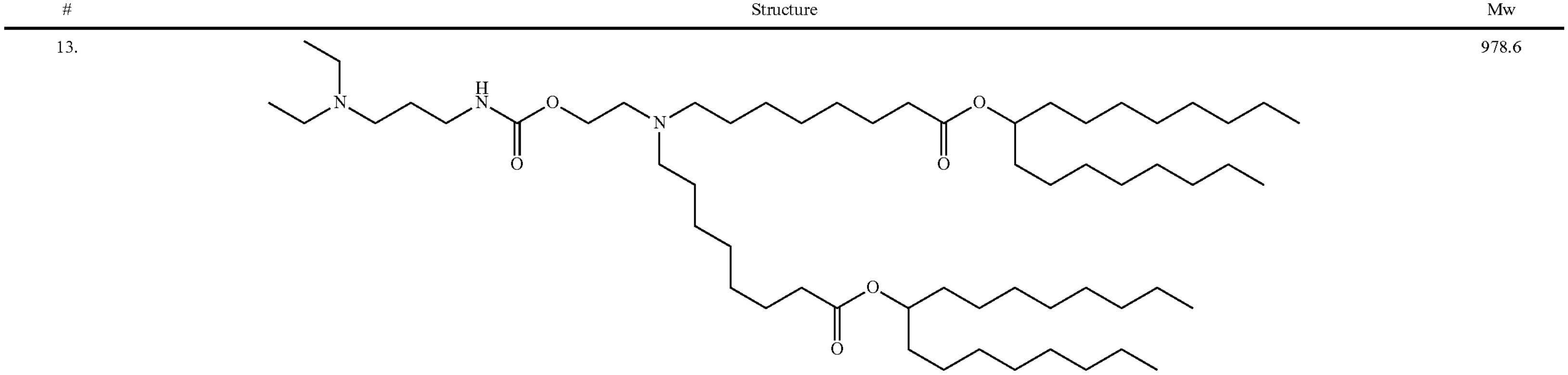 | 978.6 |
| 14. | 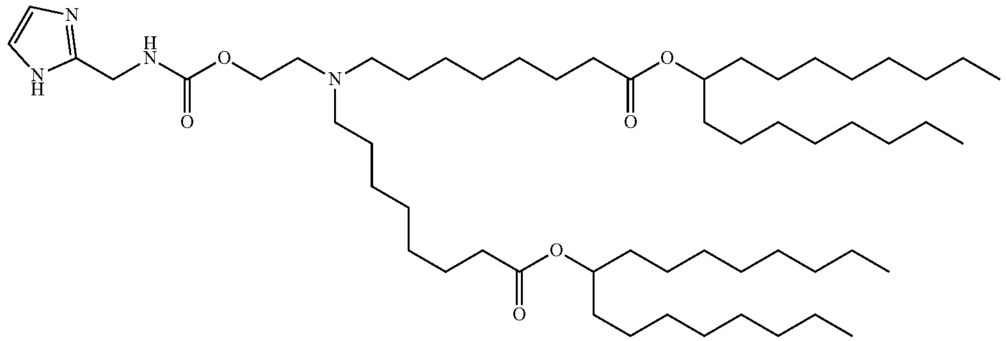 [SMILES: CCCCCCCCC(CCCCCCCC)OC(=O)CCCCCCCN(CCCCCCCC(=O)OC(CCCCCCCC)CCCCCCCC)CCOC(=O)NCc1ncc[nH]1] | 945.5 |
| 15. | 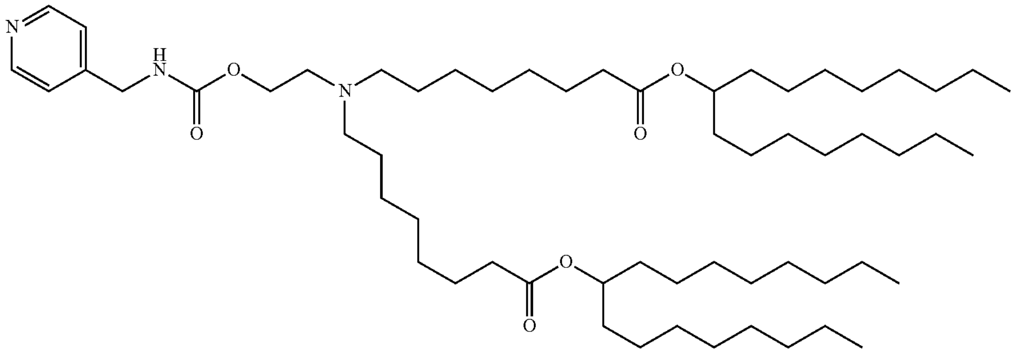 [SMILES: CCCCCCCCC(CCCCCCCC)OC(=O)CCCCCCCN(CCCCCCCC(=O)OC(CCCCCCCC)CCCCCCCC)CCOC(=O)NCc1ccncc1] | 956.5 |

TABLE 1-continued
| # | Structure | Mw |
|---|---|---|
| 16. | 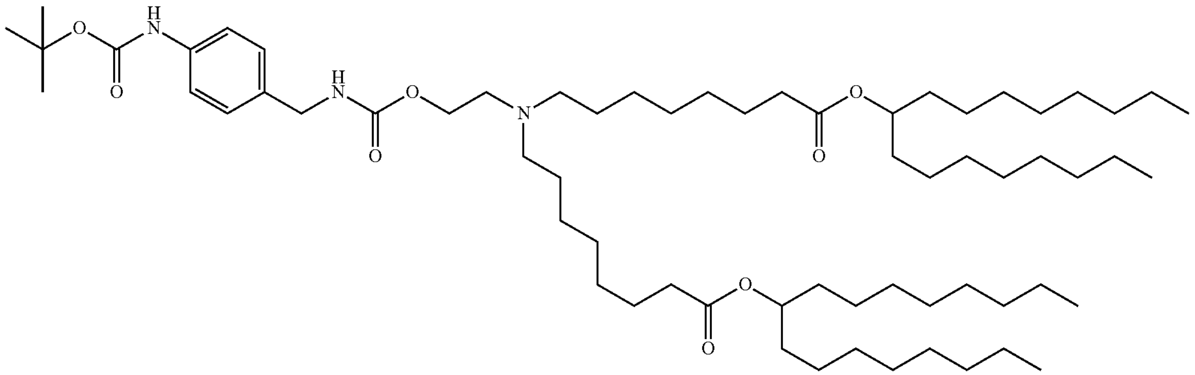 [SMILES: CCCCCCCCC(CCCCCCCC)OC(=O)CCCCCCCN(CCCCCCCC(=O)OC(CCCCCCCC)CCCCCCCC)CCOC(=O)NCc1ccc(NC(=O)OC(C)(C)C)cc1] | 1070.7 |
| 17. | 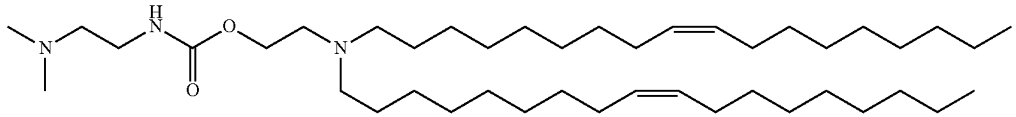 | 676.2 |
| 18. | 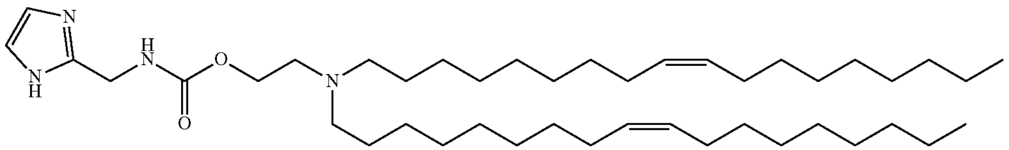 [SMILES: CCCCCCCC/C=C\CCCCCCCCN(CCCCCCCC/C=C\CCCCCCCC)CCOC(=O)NCc1ncc[nH]1] | 685.1 |
| 19. | 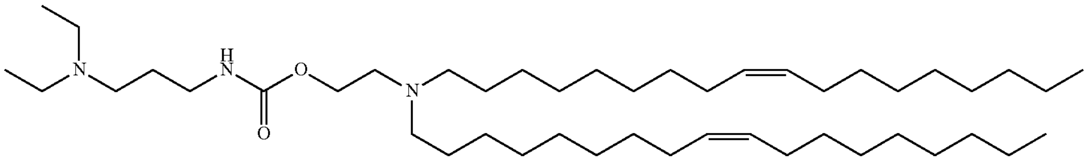 [SMILES: CCCCCCCC/C=C\CCCCCCCCN(CCCCCCCC/C=C\CCCCCCCC)CCOC(=O)NCCCN(CC)CC] | 718.3 |
| 20. | 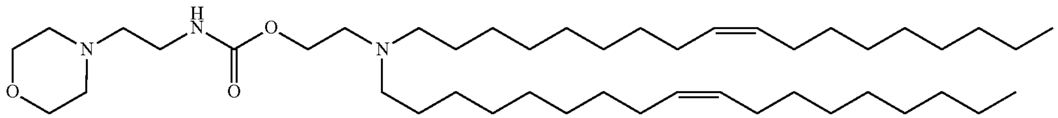 [SMILES: CCCCCCCC/C=C\CCCCCCCCN(CCCCCCCC/C=C\CCCCCCCC)CCOC(=O)NCCN1CCOCC1] | 718.2 |

TABLE 1-continued
| # | Structure | Mw |
| --- | --- | --- |
| 21. | 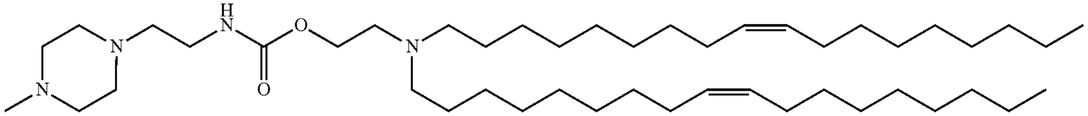 [SMILES: CCCCCCCC/C=C\CCCCCCCCN(CCCCCCCC/C=C\CCCCCCCC)CCOC(=O)NCCN1CCN(C)CC1] | 731.3 |
| 22. | 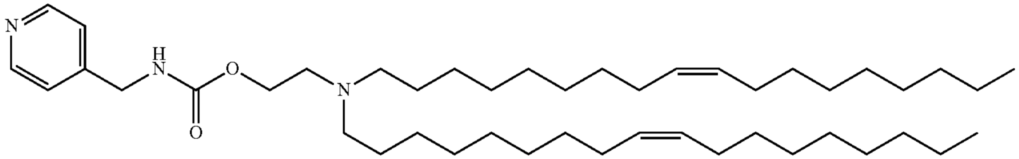 [SMILES: CCCCCCCC/C=C\CCCCCCCCN(CCCCCCCC/C=C\CCCCCCCC)CCOC(=O)NCc1ccncc1] | 696.2 |
| 23. | 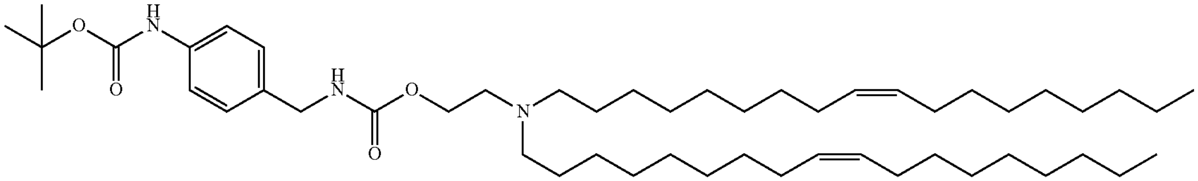 [SMILES: CCCCCCCC/C=C\CCCCCCCCN(CCCCCCCC/C=C\CCCCCCCC)CCOC(=O)NCc1ccc(NC(=O)OC(C)(C)C)cc1] | 810.3 |
| 24. | 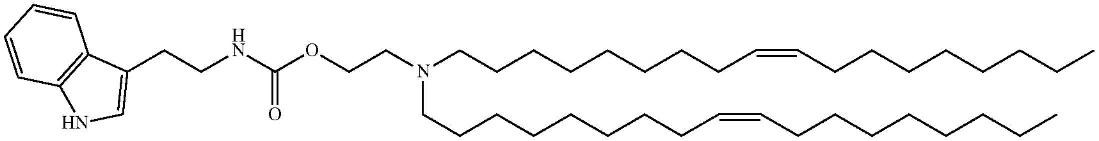 [SMILES: CCCCCCCC/C=C\CCCCCCCCN(CCCCCCCC/C=C\CCCCCCCC)CCOC(=O)NCCc1c[nH]c2ccccc12] | 748.2 |
| 25. | 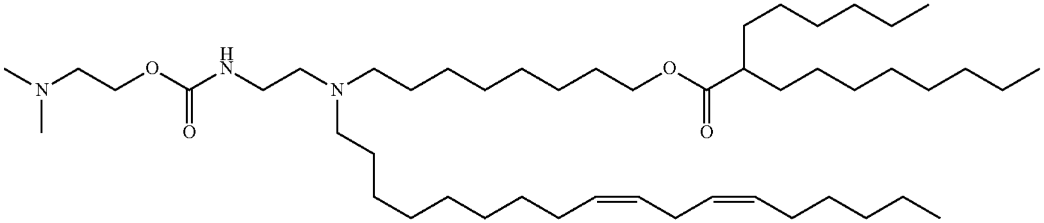 [SMILES: CCCCC/C=C\C/C=C\CCCCCCCCN(CCCCCCCCOC(=O)C(CCCCCC)CCCCCCCC)CCNC(=O)OCCN(C)C] | 790.3 |

TABLE 1-continued
| # | Structure | Mw |
|---|---|---|
| 26. | 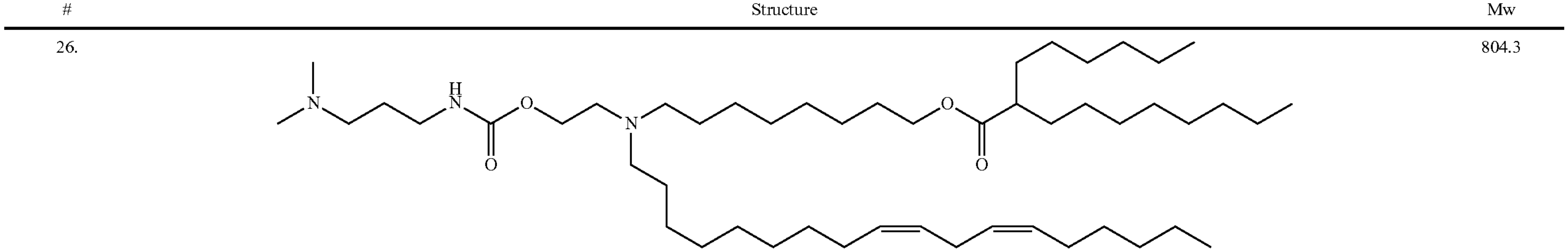 | 804.3 |
| 27. | 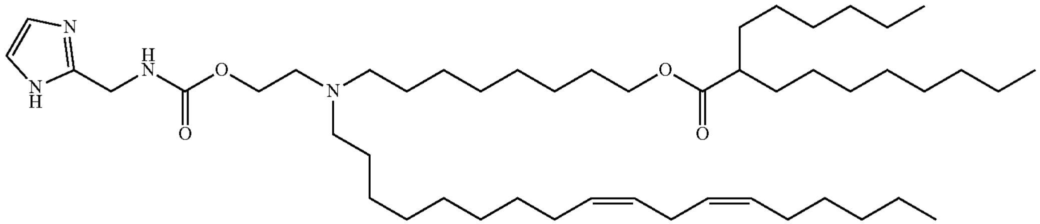 [SMILES: CCCCC/C=C\C/C=C\CCCCCCCCN(CCCCCCCCOC(=O)C(CCCCCC)CCCCCCCC)CCOC(=O)NCc1ncc[nH]1] | 799.3 |
| 28. | 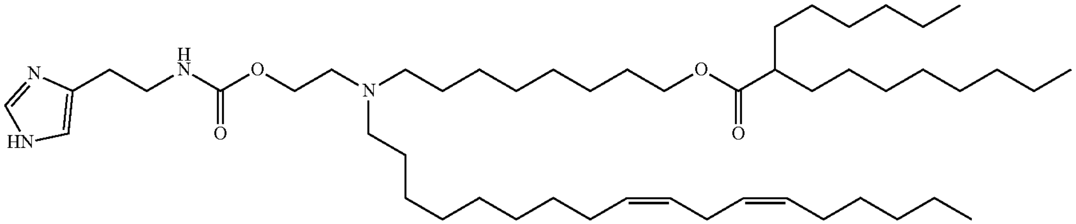 [SMILES: CCCCC/C=C\C/C=C\CCCCCCCCN(CCCCCCCCOC(=O)C(CCCCCC)CCCCCCCC)CCOC(=O)NCCc1c[nH]cn1] | 813.3 |
| 29. | 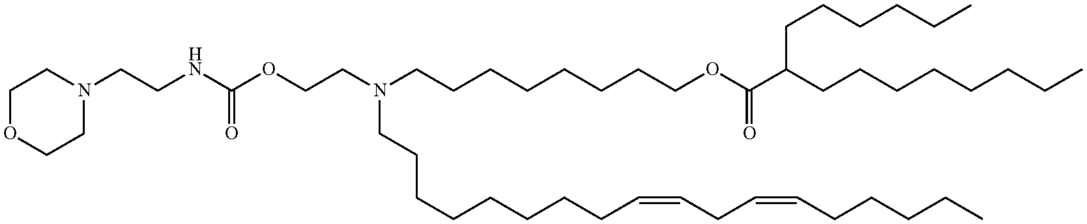 [SMILES: CCCCC/C=C\C/C=C\CCCCCCCCN(CCCCCCCCOC(=O)C(CCCCCC)CCCCCCCC)CCOC(=O)NCCN1CCOCC1] | 832.4 |

TABLE 1-continued
| # | Structure | Mw |
| --- | --- | --- |
| 30. | 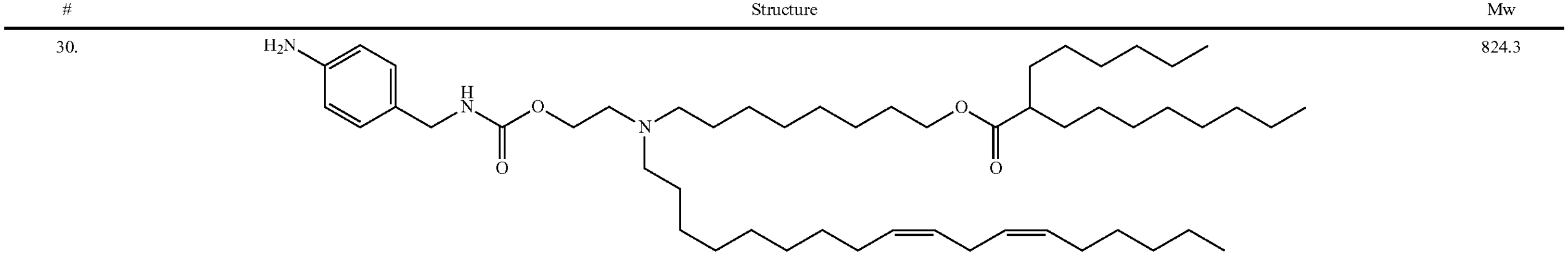 | 824.3 |
| 31. | 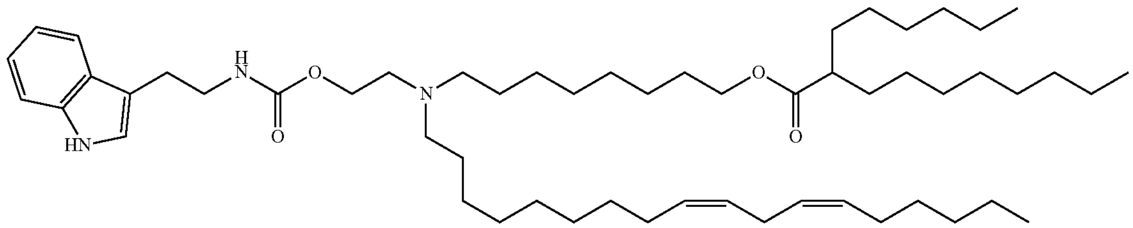 [SMILES: CCCCC/C=C\C/C=C\CCCCCCCCN(CCCCCCCCOC(=O)C(CCCCCC)CCCCCCCC)CCOC(=O)NCCc1c[nH]c2ccccc12] | 862.4 |
| 32. | 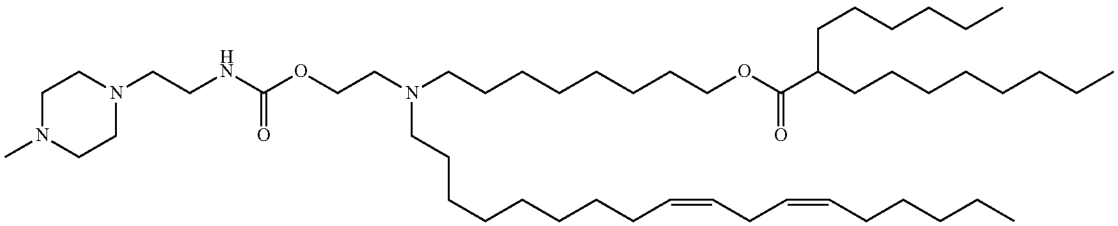 [SMILES: CCCCC/C=C\C/C=C\CCCCCCCCN(CCCCCCCCOC(=O)C(CCCCCC)CCCCCCCC)CCOC(=O)NCCN1CCN(C)CC1] | 845.4 |
| 33. | 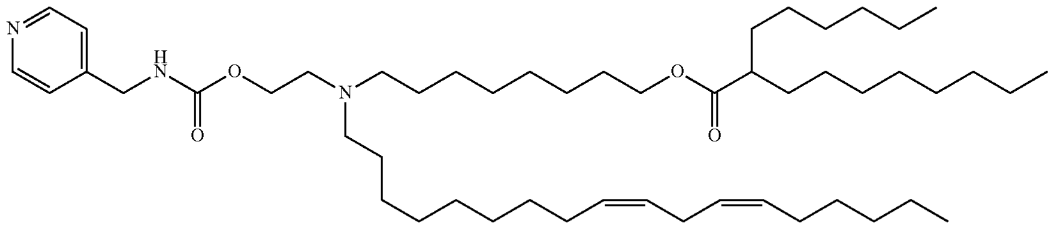 [SMILES: CCCCC/C=C\C/C=C\CCCCCCCCN(CCCCCCCCOC(=O)C(CCCCCC)CCCCCCCC)CCOC(=O)NCc1ccncc1] | 810.3 |

TABLE 1-continued
| # | Structure | Mw |
| --- | --- | --- |
| 34. | 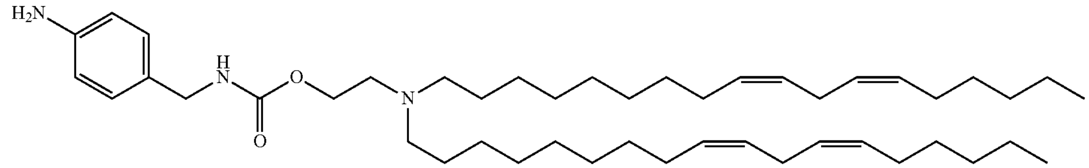 [SMILES: CCCCC/C=C\C/C=C\CCCCCCCCN(CCCCCCCC/C=C\C/C=C\CCCCC)CCOC(=O)NCc1ccc(N)cc1] | 706.2 |
| 35. | 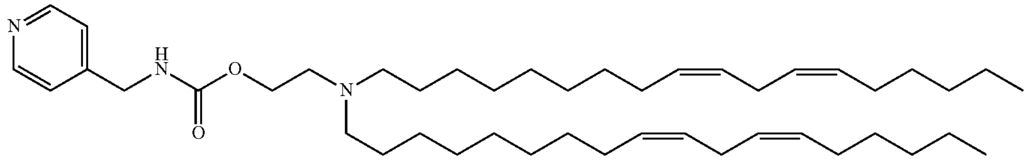 [SMILES: CCCCC/C=C\C/C=C\CCCCCCCCN(CCCCCCCC/C=C\C/C=C\CCCCC)CCOC(=O)NCc1ccncc1] | 692.1 |
| 36. | 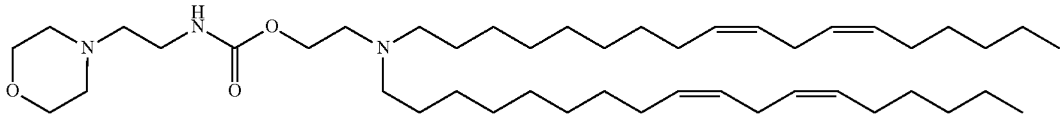 [SMILES: CCCCC/C=C\C/C=C\CCCCCCCCN(CCCCCCCC/C=C\C/C=C\CCCCC)CCOC(=O)NCCN1CCOCC1] | 714.2 |
| 37. | 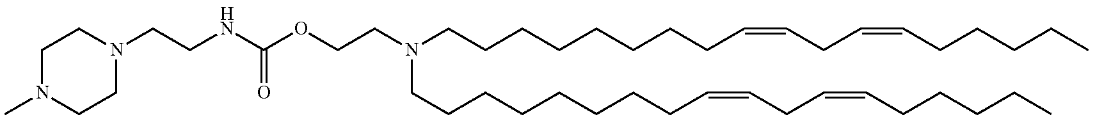 | 727.2 |
| 38. | 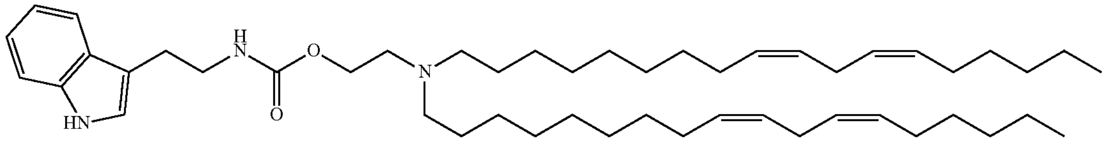 [SMILES: CCCCC/C=C\C/C=C\CCCCCCCCN(CCCCCCCC/C=C\C/C=C\CCCCC)CCOC(=O)NCCc1c[nH]c2ccccc12] | 744.2 |
| 39. | 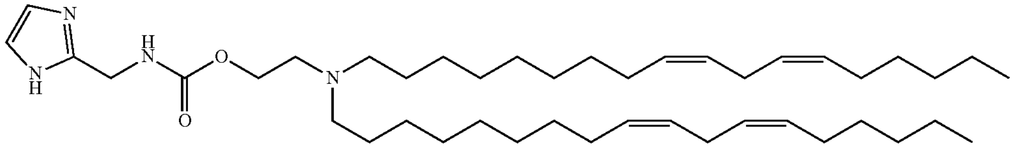 [SMILES: CCCCC/C=C\C/C=C\CCCCCCCCN(CCCCCCCC/C=C\C/C=C\CCCCC)CCOC(=O)NCc1ncc[nH]1] | 681.1 |
| 40. | 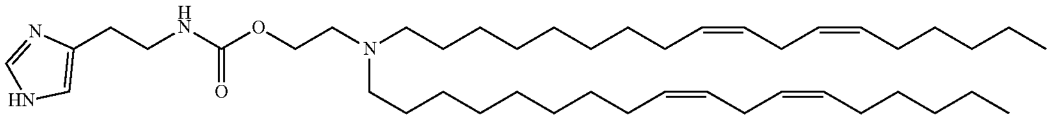 [SMILES: CCCCC/C=C\C/C=C\CCCCCCCCN(CCCCCCCC/C=C\C/C=C\CCCCC)CCOC(=O)NCCc1c[nH]cn1] | 695.1 |

TABLE 1-continued
| # | Structure | Mw |
| --- | --- | --- |
| 41. | 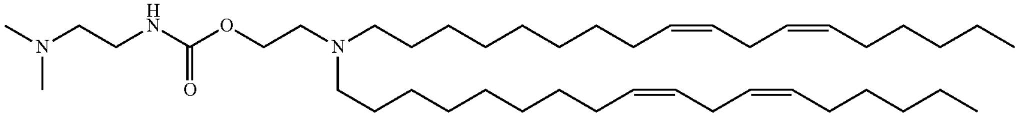 [SMILES: CCCCC/C=C\C/C=C\CCCCCCCCN(CCCCCCCC/C=C\C/C=C\CCCCC)CCOC(=O)NCCN(C)C] | 672.1 |
| 42. | 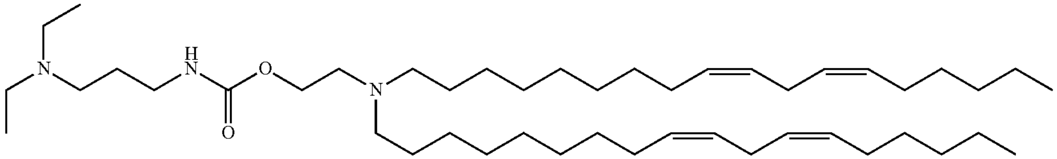 [SMILES: CCCCC/C=C\C/C=C\CCCCCCCCN(CCCCCCCC/C=C\C/C=C\CCCCC)CCOC(=O)NCCCN(CC)CC] | 714.2 |
| 43. | 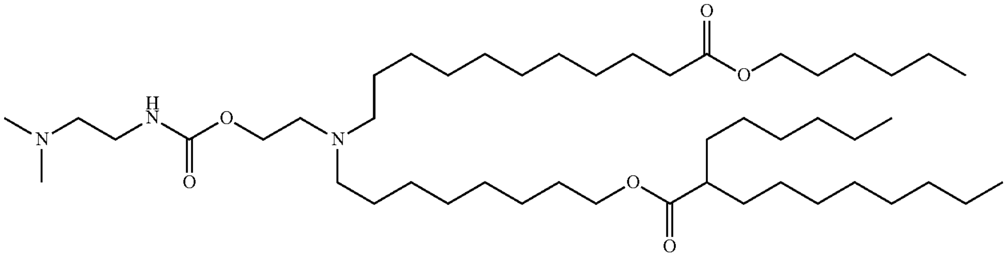 [SMILES: CCCCCCCCC(CCCCCC)C(=O)OCCCCCCCCN(CCCCCCCCCCC(=O)OCCCCCC)CCOC(=O)NCCN(C)C] | 810.3 |
| 44. | 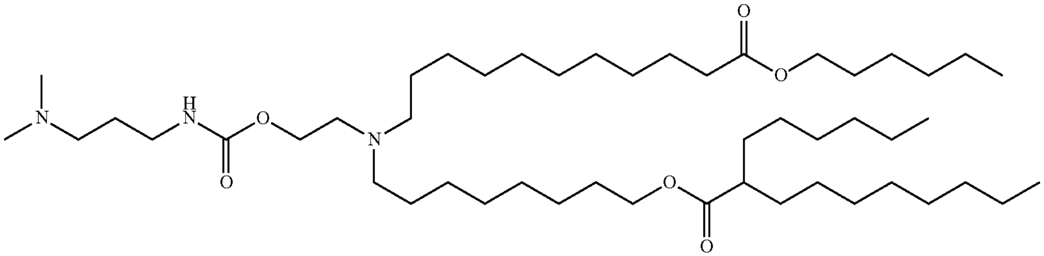 [SMILES: CCCCCCCCC(CCCCCC)C(=O)OCCCCCCCCN(CCCCCCCCCCC(=O)OCCCCCC)CCOC(=O)NCCCN(C)C] | 824.3 |

TABLE 1-continued
| # | Structure | Mw |
|---|---|---|
| 45. | 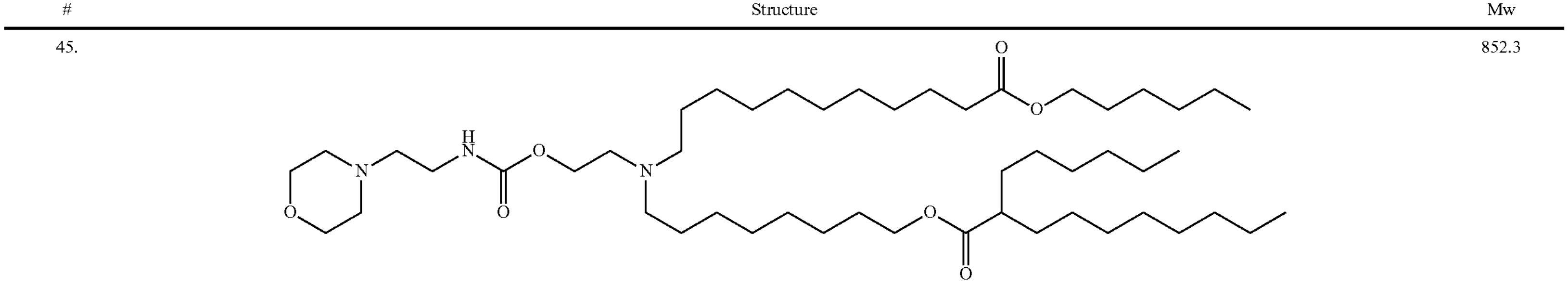 | 852.3 |
| 46. | 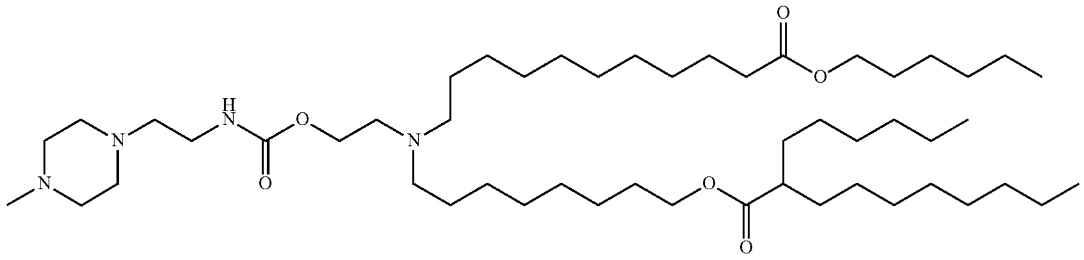 [SMILES: CCCCCCCCC(CCCCCC)C(=O)OCCCCCCCCN(CCCCCCCCCCC(=O)OCCCCCC)CCOC(=O)NCCN1CCN(C)CC1] | 865.4 |
| 47. | 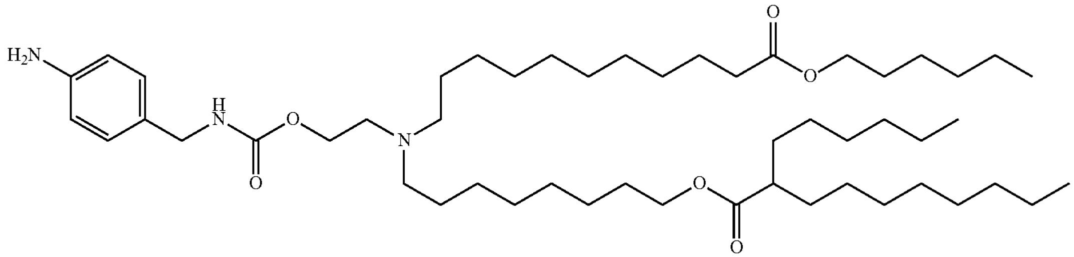 [SMILES: CCCCCCCCC(CCCCCC)C(=O)OCCCCCCCCN(CCCCCCCCCCC(=O)OCCCCCC)CCOC(=O)NCc1ccc(N)cc1] | 844.3 |
| 48. | 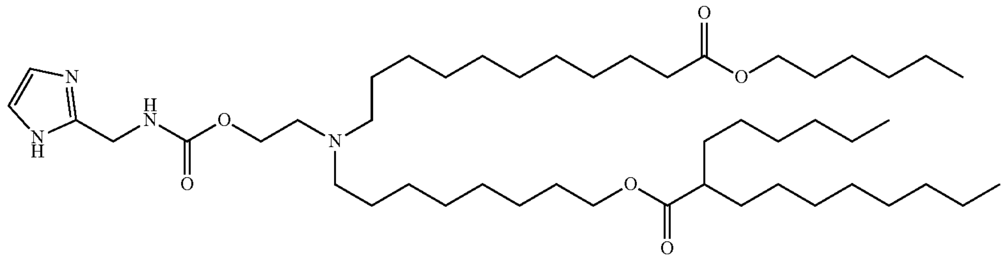 [SMILES: CCCCCCCCC(CCCCCC)C(=O)OCCCCCCCCN(CCCCCCCCCCC(=O)OCCCCCC)CCOC(=O)NCc1ncc[nH]1] | 819.3 |

TABLE 1-continued
| # | Structure | Mw |
| --- | --- | --- |
| 49. | 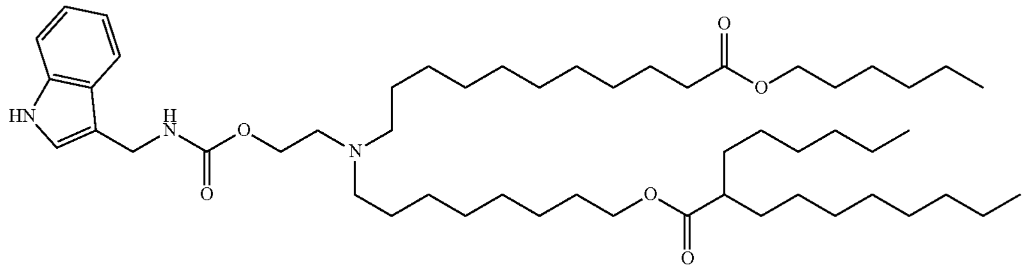 [SMILES: CCCCCCCCC(CCCCCC)C(=O)OCCCCCCCCN(CCCCCCCCCCC(=O)OCCCCCC)CCOC(=O)NCc1c[nH]c2ccccc12] | 868.3 |
| 50. | 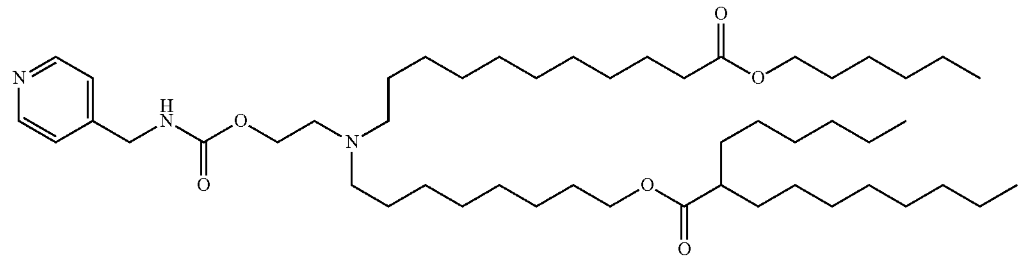 [SMILES: CCCCCCCCC(CCCCCC)C(=O)OCCCCCCCCN(CCCCCCCCCCC(=O)OCCCCCC)CCOC(=O)NCc1ccncc1] | 830.3 |
| 51. | 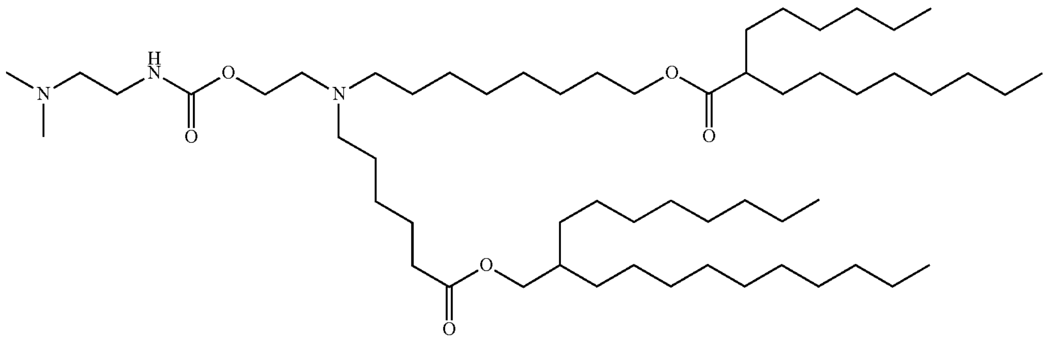 [SMILES: CCCCCCCCCCC(CCCCCCCC)COC(=O)CCCCCN(CCCCCCCCOC(=O)C(CCCCCC)CCCCCCCC)CCOC(=O)NCCN(C)C] | 936.5 |

TABLE 1-continued
| # | Structure | Mw |
|---|---|---|
| 52. | 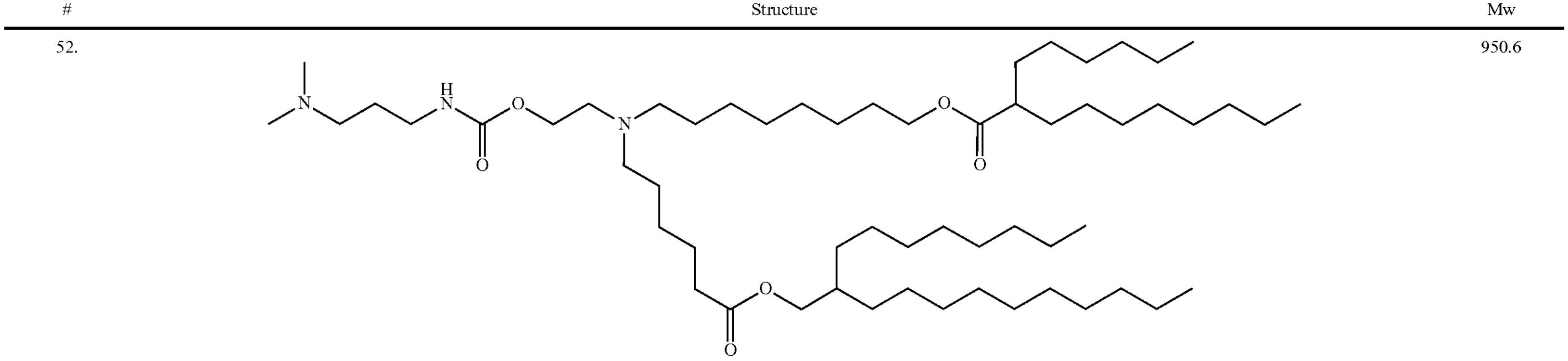 | 950.6 |
| 53. | 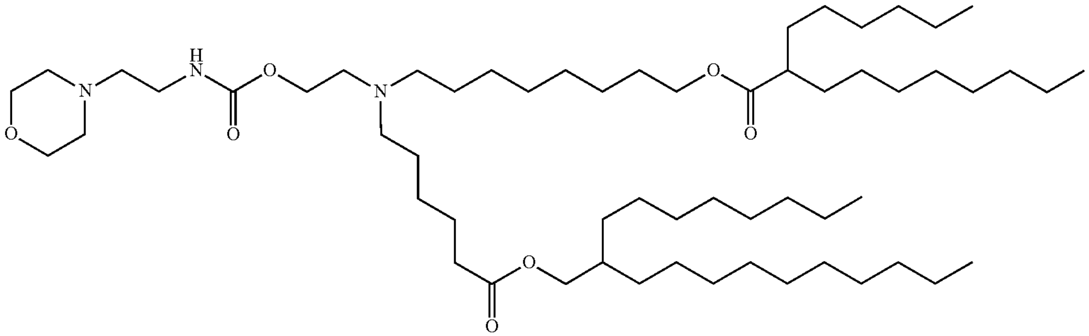 [SMILES: CCCCCCCCCCC(CCCCCCCC)COC(=O)CCCCCN(CCCCCCCCOC(=O)C(CCCCCC)CCCCCCCC)CCOC(=O)NCCN1CCOCC1] | 978.6 |
| 54. | 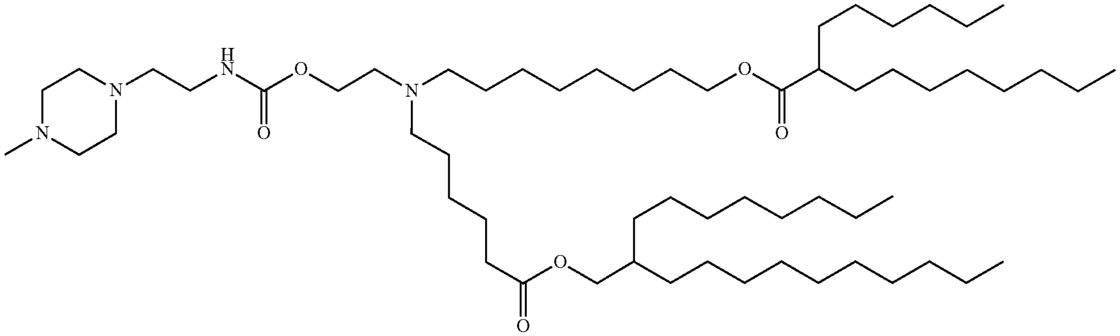 [SMILES: CCCCCCCCCCC(CCCCCCCC)COC(=O)CCCCCN(CCCCCCCCOC(=O)C(CCCCCC)CCCCCCCC)CCOC(=O)NCCN1CCN(C)CC1] | 991.6 |

TABLE 1-continued
| # | Structure | Mw |
| --- | --- | --- |
| 55. | 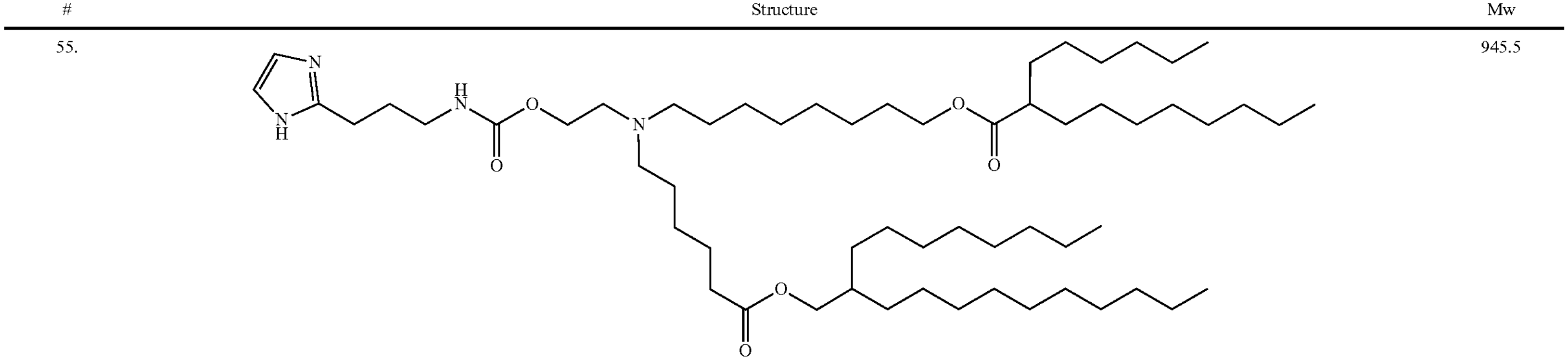 | 945.5 |
| 56. | 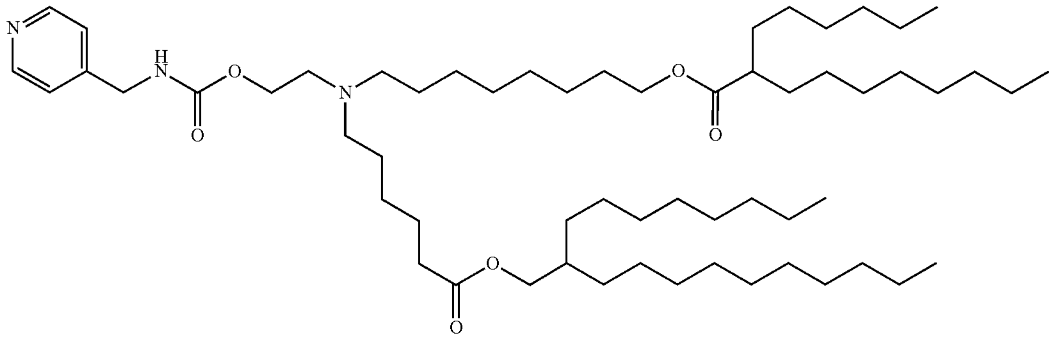 [SMILES: CCCCCCCCCCC(CCCCCCCC)COC(=O)CCCCCN(CCCCCCCCOC(=O)C(CCCCCC)CCCCCCCC)CCOC(=O)NCc1ccncc1] | 956.5 |
| 57. | 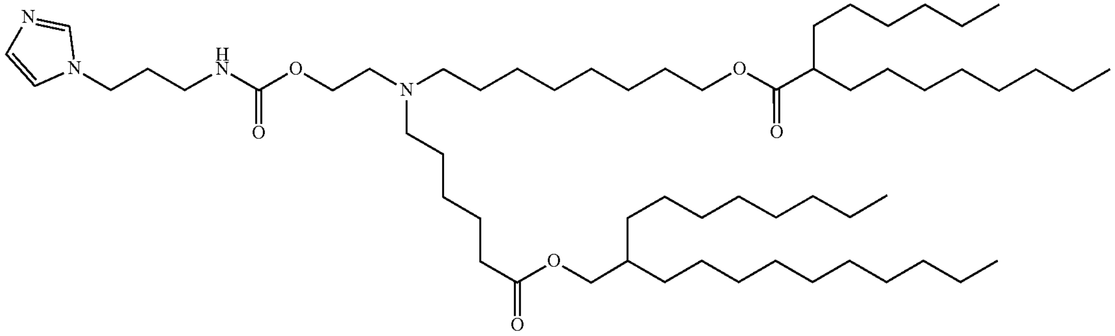 [SMILES: CCCCCCCCCCC(CCCCCCCC)COC(=O)CCCCCN(CCCCCCCCOC(=O)C(CCCCCC)CCCCCCCC)CCOC(=O)NCCCn1ccnc1] | 973.6 |

TABLE 1-continued
| # | Structure | Mw |
|---|---|---|
| 58. | 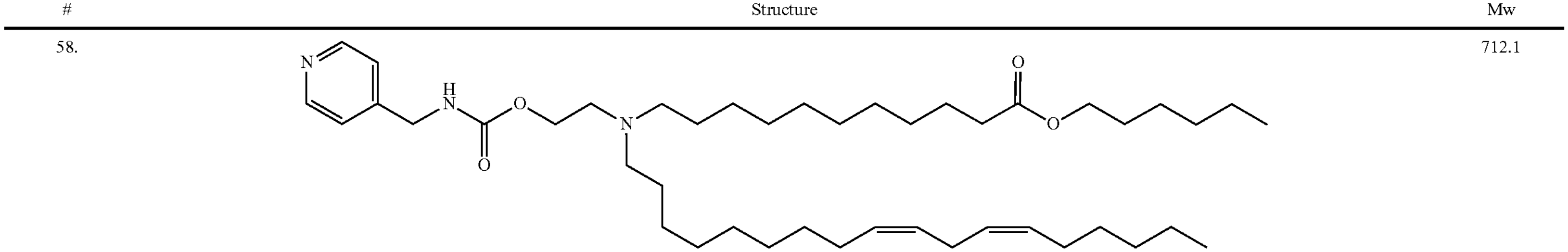 | 712.1 |
| 59. | 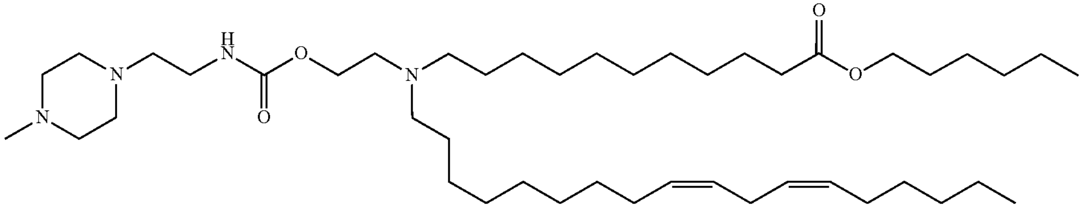 [SMILES: CCCCC/C=C\C/C=C\CCCCCCCCN(CCCCCCCCCCC(=O)OCCCCCC)CCOC(=O)NCCN1CCN(C)CC1] | 747.2 |
| 60. | 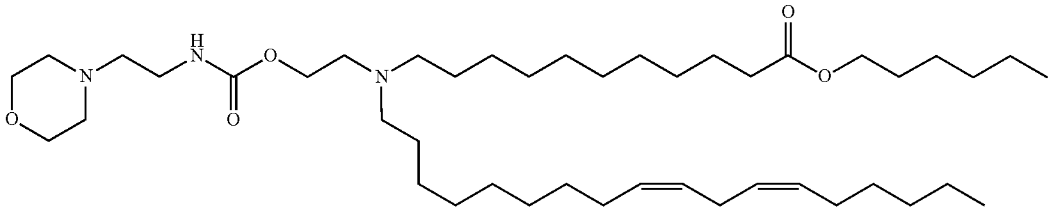 [SMILES: CCCCC/C=C\C/C=C\CCCCCCCCN(CCCCCCCCCCC(=O)OCCCCCC)CCOC(=O)NCCN1CCOCC1] | 734.2 |
| 61. | 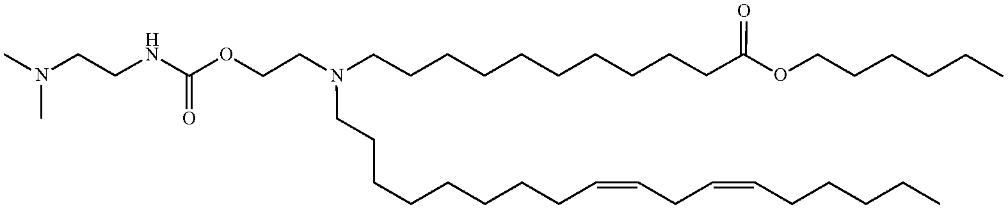 | 692.1 |

TABLE 1-continued
| # | Structure | Mw |
|---|---|---|
| 62. | 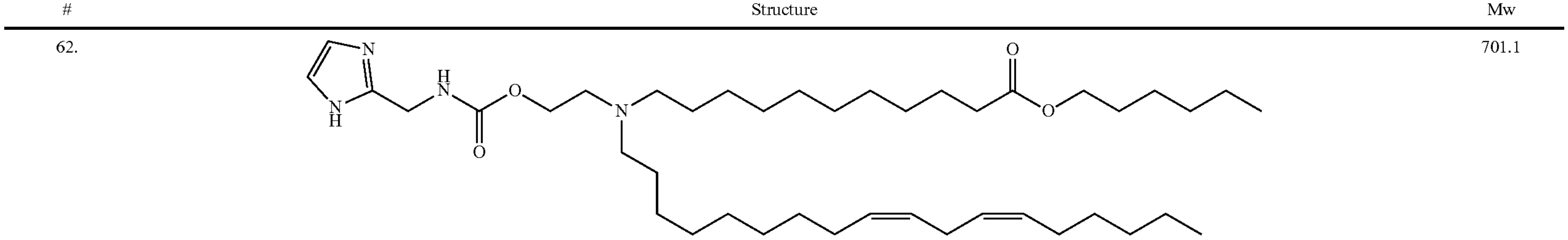 | 701.1 |
| 63. | 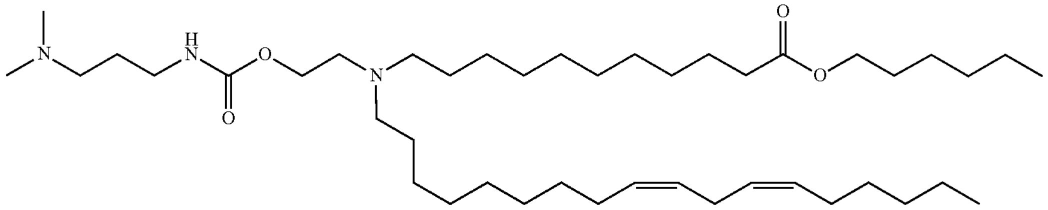 [SMILES: CCCCC/C=C\C/C=C\CCCCCCCCN(CCCCCCCCCCC(=O)OCCCCCC)CCOC(=O)NCCCN(C)C] | 706.2 |
| 64. | 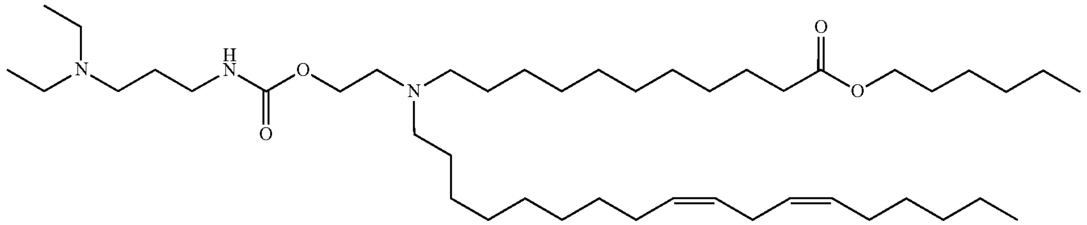 [SMILES: CCCCC/C=C\C/C=C\CCCCCCCCN(CCCCCCCCCCC(=O)OCCCCCC)CCOC(=O)NCCCN(CC)CC] | 734.2 |
| 65. | 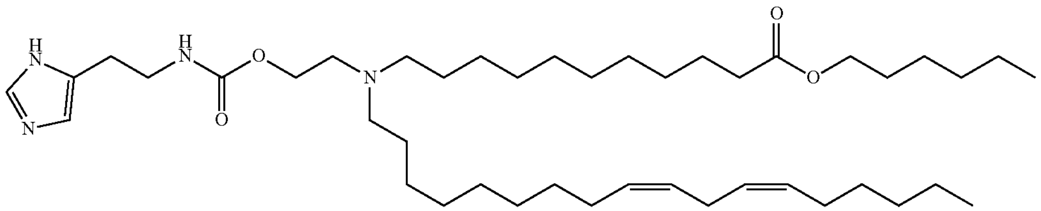 [SMILES: CCCCC/C=C\C/C=C\CCCCCCCCN(CCCCCCCCCCC(=O)OCCCCCC)CCOC(=O)NCCc1cnc[nH]1] | 715.1 |

TABLE 1-continued
| # | Structure | Mw |
| --- | --- | --- |
| 66. | 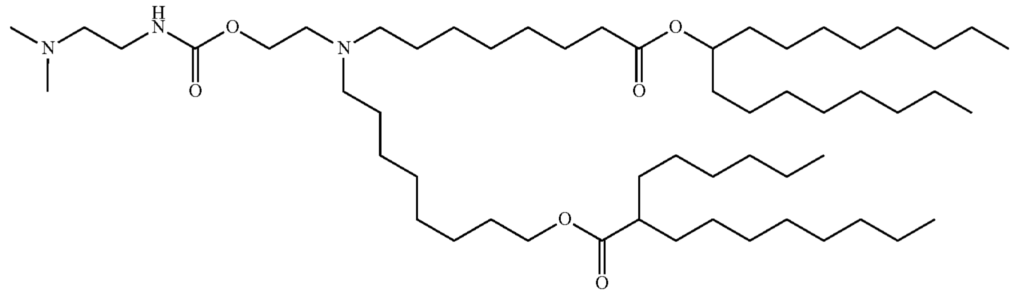 [SMILES: CCCCCCCCC(CCCCCCCC)OC(=O)CCCCCCCN(CCCCCCCCOC(=O)C(CCCCCC)CCCCCCCC)CCOC(=O)NCCN(C)C] | 922.2 |
| 67. | 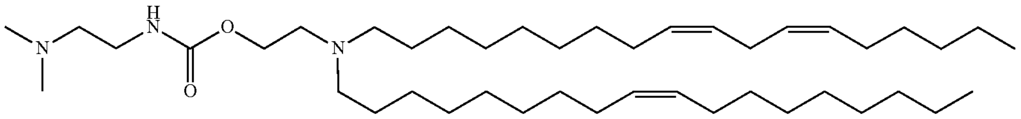 | 674.2 |
| 68. | 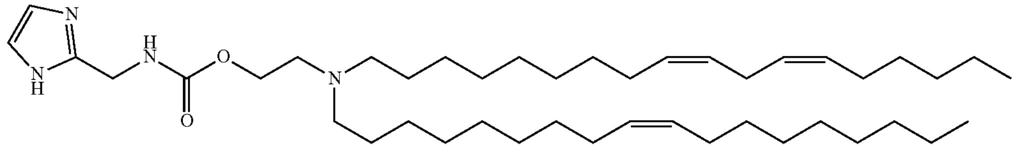 [SMILES: CCCCC/C=C\C/C=C\CCCCCCCCN(CCCCCCCC/C=C\CCCCCCCC)CCOC(=O)NCc1ncc[nH]1] | 683.1 |
| 69 | 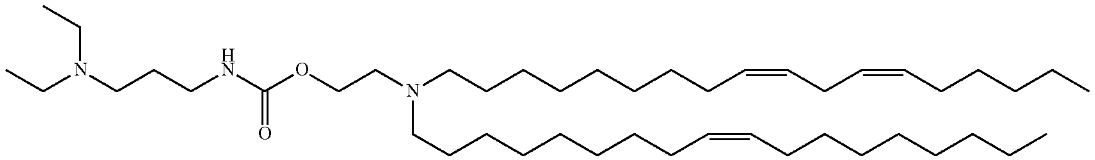 [SMILES: CCCCC/C=C\C/C=C\CCCCCCCCN(CCCCCCCC/C=C\CCCCCCCC)CCOC(=O)NCCCN(CC)CC] | 716.2 |
| 70. | 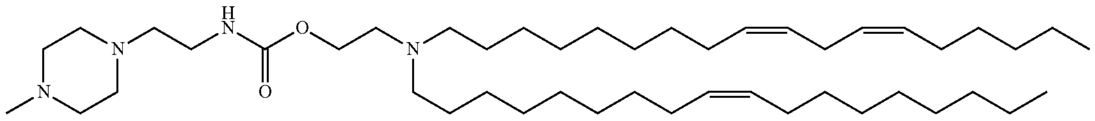 [SMILES: CCCCC/C=C\C/C=C\CCCCCCCCN(CCCCCCCC/C=C\CCCCCCCC)CCOC(=O)NCCN1CCN(C)CC1] | 729.2 |
| 71. | 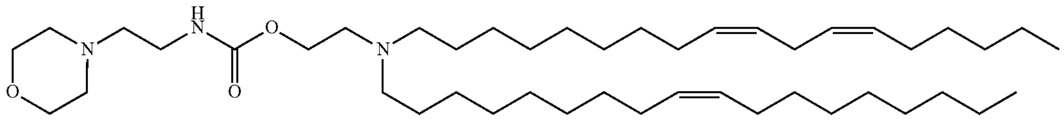 [SMILES: CCCCC/C=C\C/C=C\CCCCCCCCN(CCCCCCCC/C=C\CCCCCCCC)CCOC(=O)NCCN1CCOCC1] | 716.2 |

TABLE 1-continued
| # | Structure | Mw |
| --- | --- | --- |
| 72. | 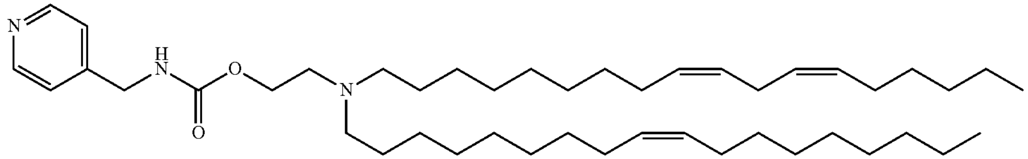 [SMILES: CCCCC/C=C\C/C=C\CCCCCCCCN(CCCCCCCC/C=C\CCCCCCCC)CCOC(=O)NCc1ccncc1] | 694.1 |
| 73. | 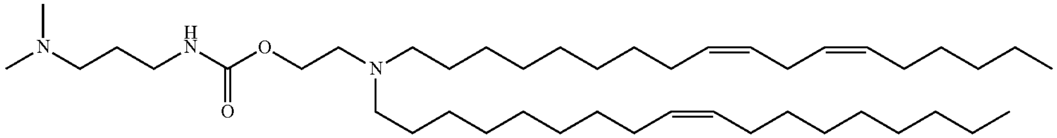 [SMILES: CCCCC/C=C\C/C=C\CCCCCCCCN(CCCCCCCC/C=C\CCCCCCCC)CCOC(=O)NCCCN(C)C] | 688.2 |
| 74. | 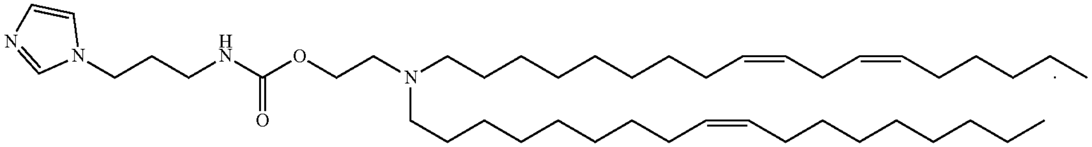 [SMILES: CCCCC/C=C\C/C=C\CCCCCCCCN(CCCCCCCC/C=C\CCCCCCCC)CCOC(=O)NCCCn1ccnc1] | 711.2 |
| 75. | 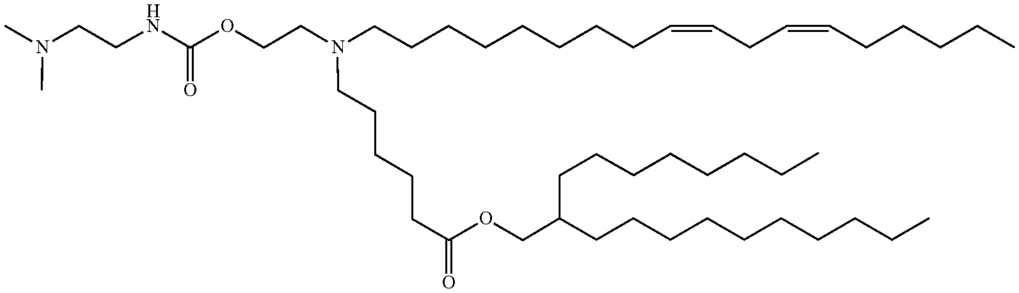 [SMILES: CCCCC/C=C\C/C=C\CCCCCCCCN(CCCCCC(=O)OCC(CCCCCCCC)CCCCCCCCCC)CCOC(=O)NCCN(C)C] | 818.4 |

TABLE 1-continued
| # | Structure | Mw |
| --- | --- | --- |
| 76. | 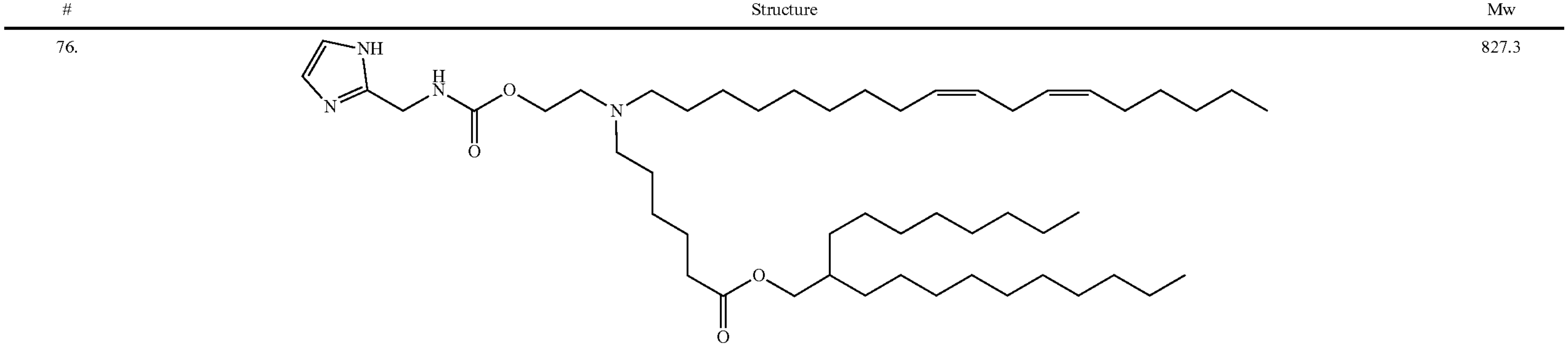 | 827.3 |
| 77. | 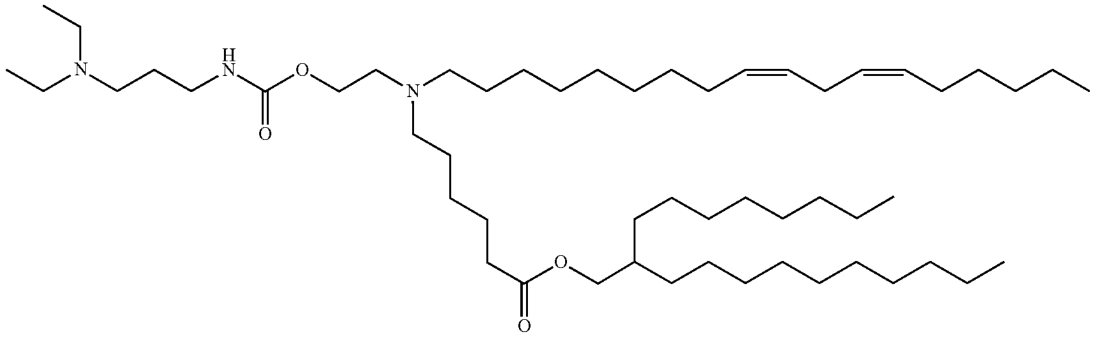 [SMILES: CCCCC/C=C\C/C=C\CCCCCCCCN(CCCCCC(=O)OCC(CCCCCCCC)CCCCCCCCCC)CCOC(=O)NCCCN(CC)CC] | 860.5 |
| 78. | 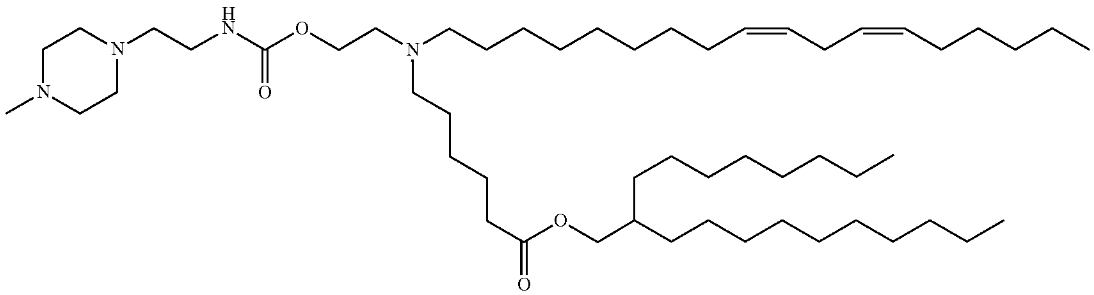 [SMILES: CCCCC/C=C\C/C=C\CCCCCCCCN(CCCCCC(=O)OCC(CCCCCCCC)CCCCCCCCCC)CCOC(=O)NCCN1CCN(C)CC1] | 873.5 |

TABLE 1-continued
| # | Structure | Mw |
|---|---|---|
| 79. | 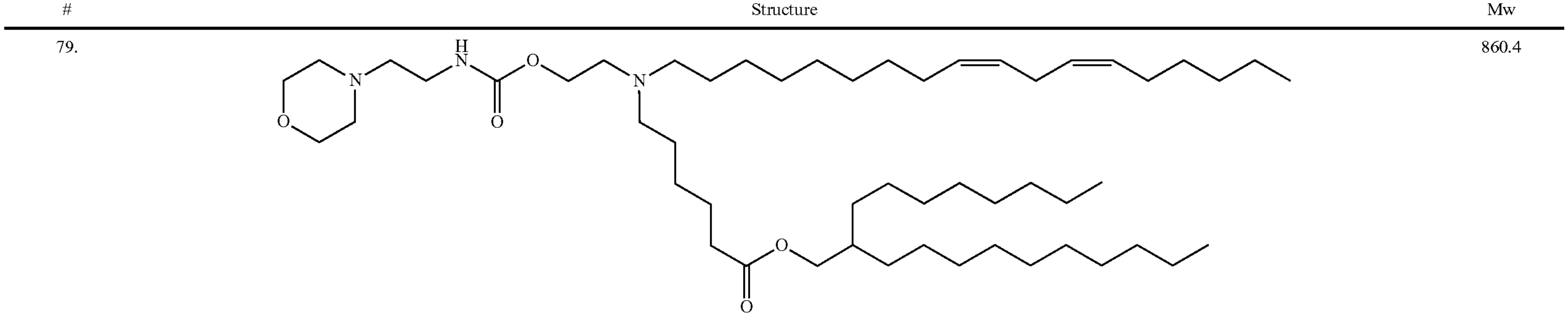 | 860.4 |
| 80 | 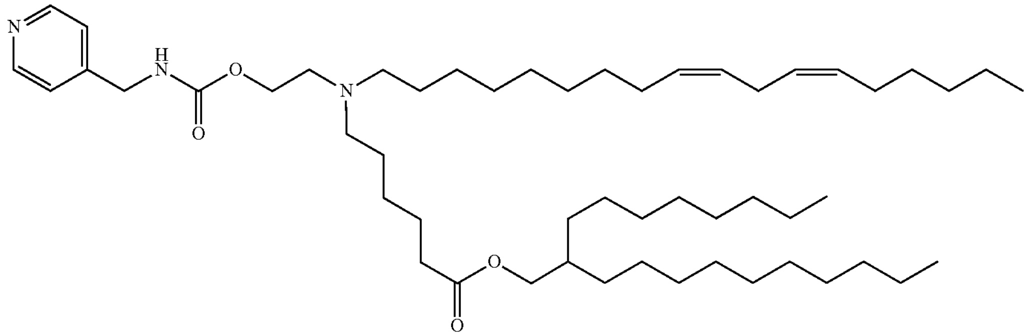 [SMILES: CCCCC/C=C\C/C=C\CCCCCCCCN(CCCCCC(=O)OCC(CCCCCCCC)CCCCCCCCCC)CCOC(=O)NCc1ccncc1] | 838.4 |
| 81. | 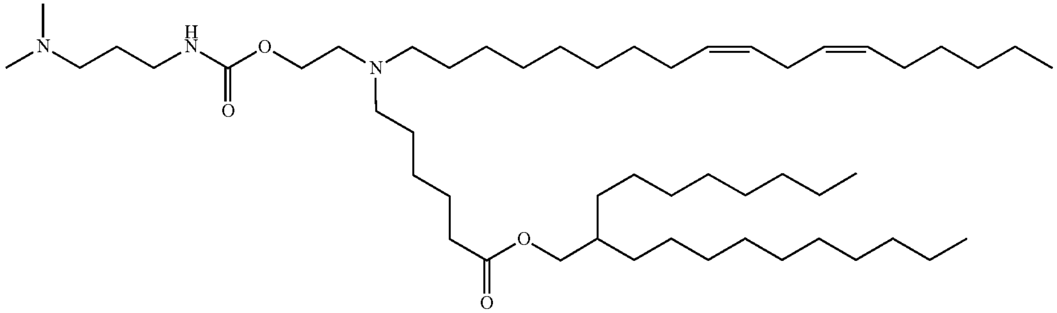 [SMILES: CCCCC/C=C\C/C=C\CCCCCCCCN(CCCCCC(=O)OCC(CCCCCCCC)CCCCCCCCCC)CCOC(=O)NCCCN(C)C] | 832.4 |

TABLE 1-continued
| # | Structure | Mw |
|---|---|---|
| 82. | 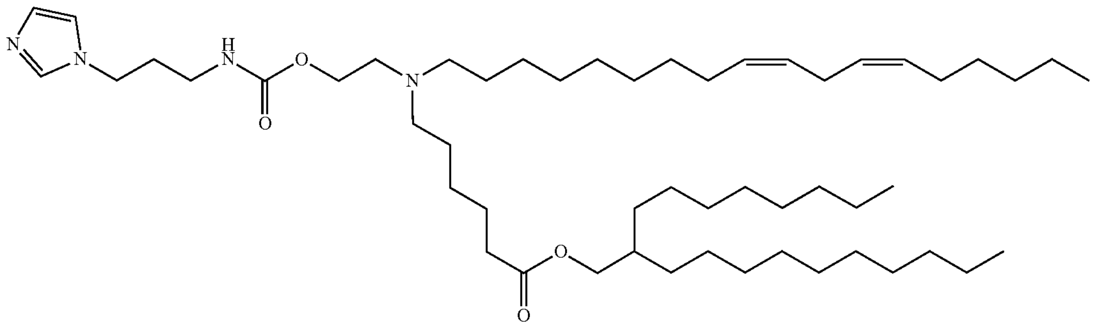 [SMILES: CCCCC/C=C\C/C=C\CCCCCCCCN(CCCCCC(=O)OCC(CCCCCCCC)CCCCCCCCCC)CCOC(=O)NCCCn1ccnc1] | 855.4 |
| 83. | 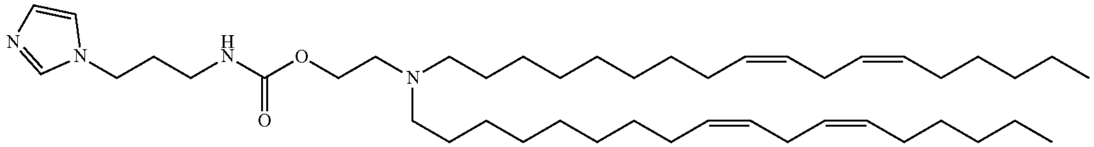 [SMILES: CCCCC/C=C\C/C=C\CCCCCCCCN(CCCCCCCC/C=C\C/C=C\CCCCC)CCOC(=O)NCCCn1ccnc1] | 709.2 |
| 84. | 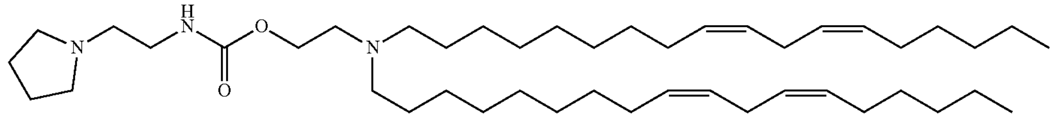 | 698.2 |
| 85. | 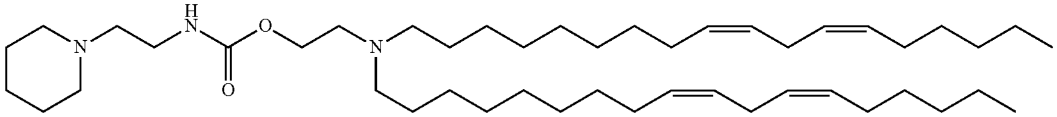 | 712.2 |
| 86. | 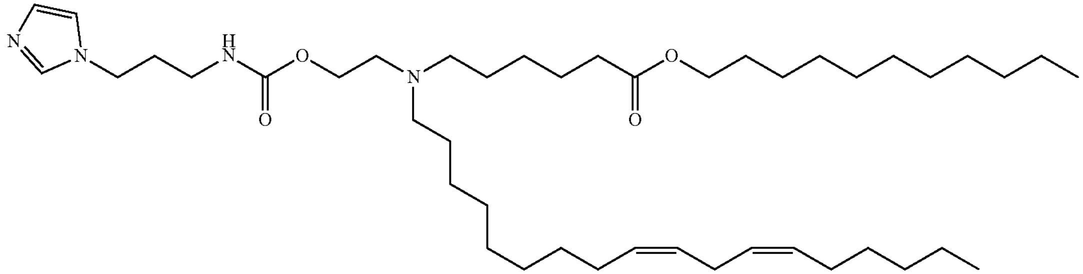 [SMILES: CCCCC/C=C\C/C=C\CCCCCCCCN(CCCCCC(=O)OCCCCCCCCCCC)CCOC(=O)NCCCn1ccnc1] | 729.1 |

TABLE 1-continued
| # | Structure | Mw |
|---|---|---|
| 87. | 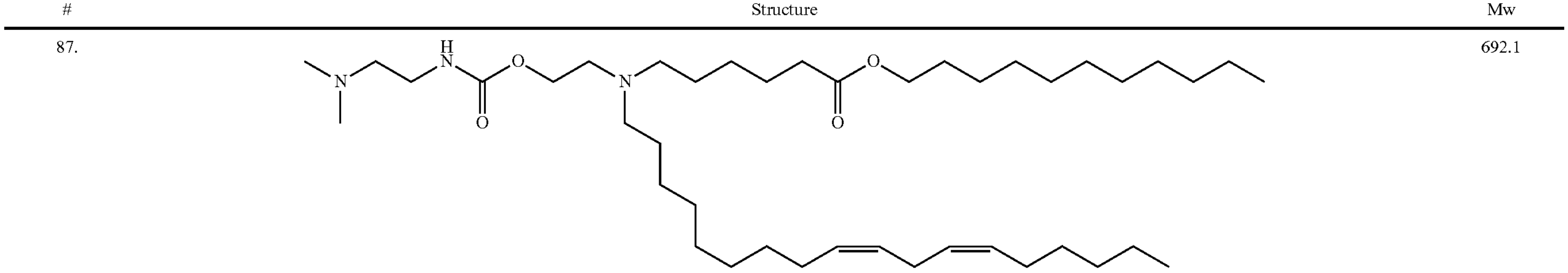 | 692.1 |
| 88. | 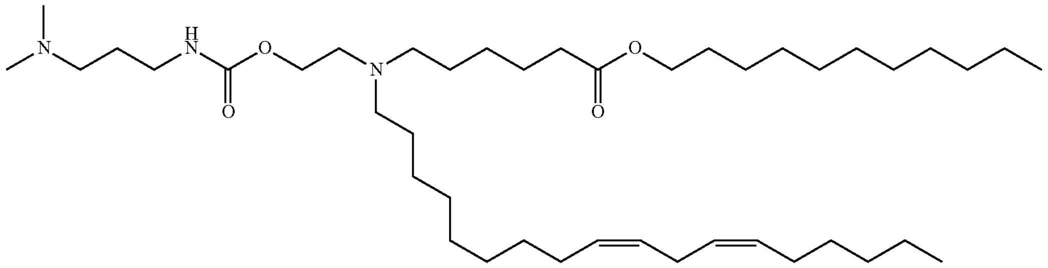 [SMILES: CCCCC/C=C\C/C=C\CCCCCCCCN(CCCCCC(=O)OCCCCCCCCCCC)CCOC(=O)NCCCN(C)C] | 706.2 |
| 89. | 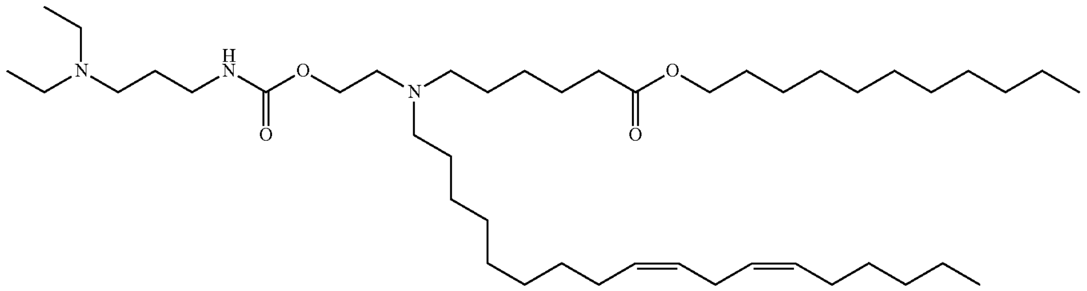 [SMILES: CCCCC/C=C\C/C=C\CCCCCCCCN(CCCCCC(=O)OCCCCCCCCCCC)CCOC(=O)NCCCN(CC)CC] | 734.2 |

TABLE 1-continued
| # | Structure | Mw |
|---|---|---|
| 90. | 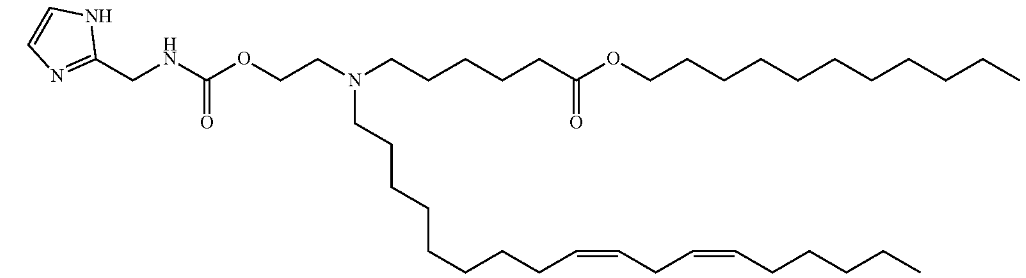 [SMILES: CCCCC/C=C\C/C=C\CCCCCCCCN(CCCCCC(=O)OCCCCCCCCCCC)CCOC(=O)NCc1ncc[nH]1] | 701.1 |
| 91. | 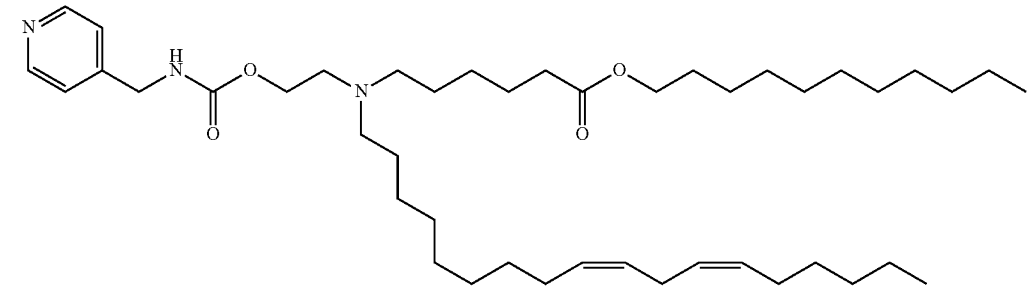 [SMILES: CCCCC/C=C\C/C=C\CCCCCCCCN(CCCCCC(=O)OCCCCCCCCCCC)CCOC(=O)NCc1ccncc1] | 712.1 |
| 92. | 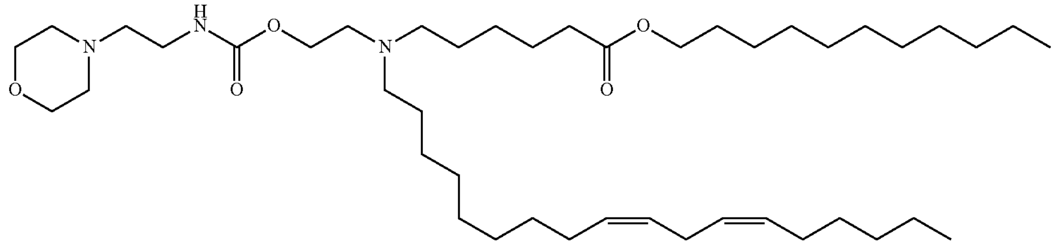 [SMILES: CCCCC/C=C\C/C=C\CCCCCCCCN(CCCCCC(=O)OCCCCCCCCCCC)CCOC(=O)NCCN1CCOCC1] | 734.2 |

TABLE 1-continued
| # | Structure | Mw |
| --- | --- | --- |
| 93. | 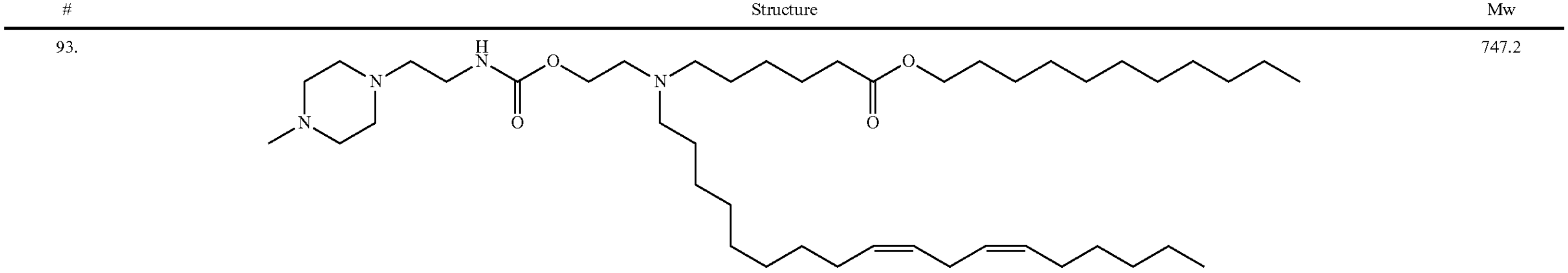 | 747.2 |
| 94. | 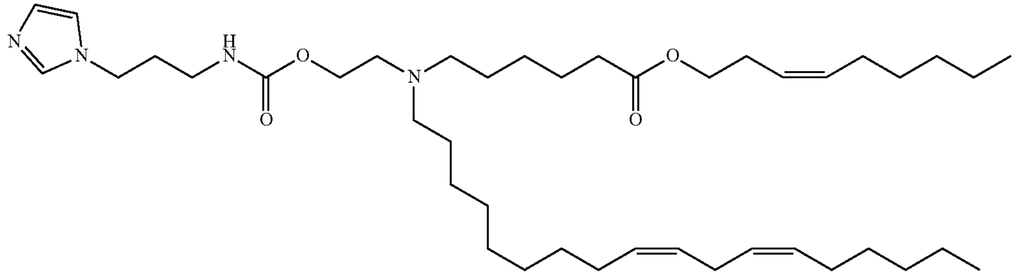 | 699.1 |
| 95. | 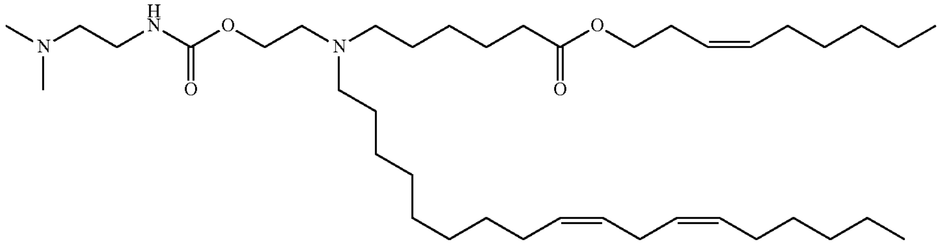 [SMILES: CCCCC/C=C\C/C=C\CCCCCCCCN(CCCCCC(=O)OCC/C=C\CCCCC)CCOC(=O)NCCN(C)C] | 662.1 |
| 96. | 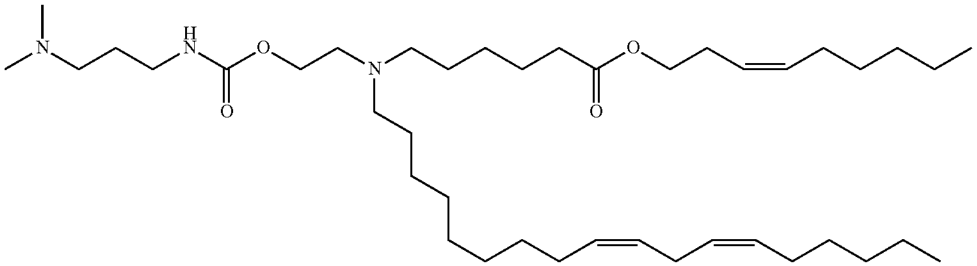 [SMILES: CCCCC/C=C\C/C=C\CCCCCCCCN(CCCCCC(=O)OCC/C=C\CCCCC)CCOC(=O)NCCCN(C)C] | 676.1 |

TABLE 1-continued
| # | Structure | Mw |
| --- | --- | --- |
| 97. | 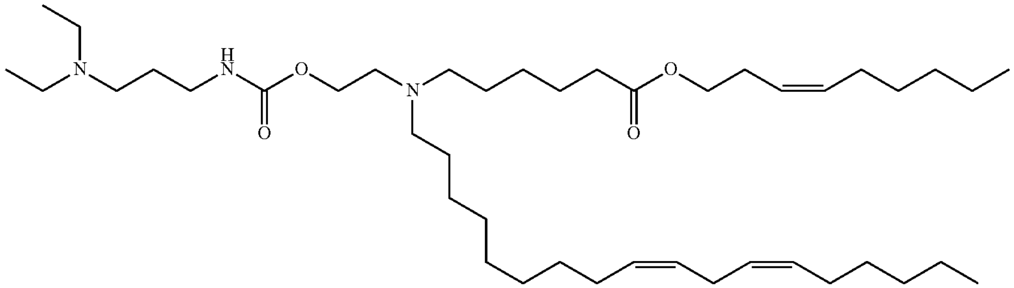 | 704.1 |
| 98. | 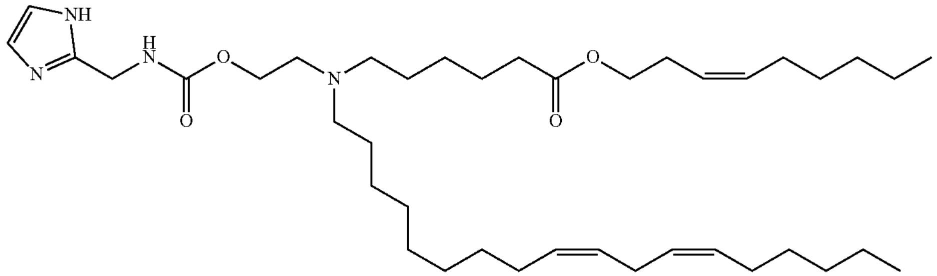 [SMILES: CCCCC/C=C\C/C=C\CCCCCCCCN(CCCCCC(=O)OCC/C=C\CCCCC)CCOC(=O)NCc1ncc[nH]1] | 671.0 |
| 99. | 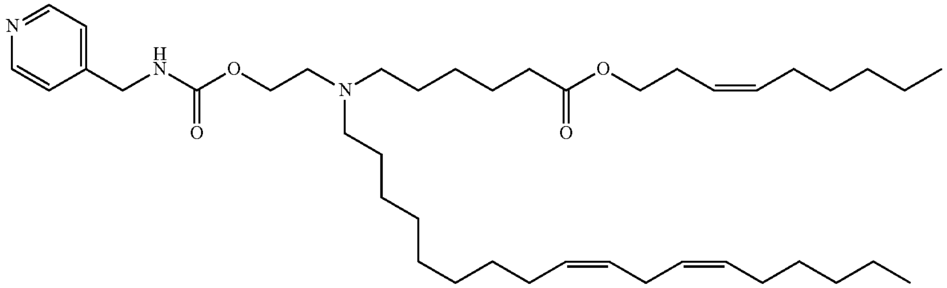 [SMILES: CCCCC/C=C\C/C=C\CCCCCCCCN(CCCCCC(=O)OCC/C=C\CCCCC)CCOC(=O)NCc1ccncc1] | 682.0 |

TABLE 1-continued
| # | Structure | Mw |
| --- | --- | --- |
| 100. | 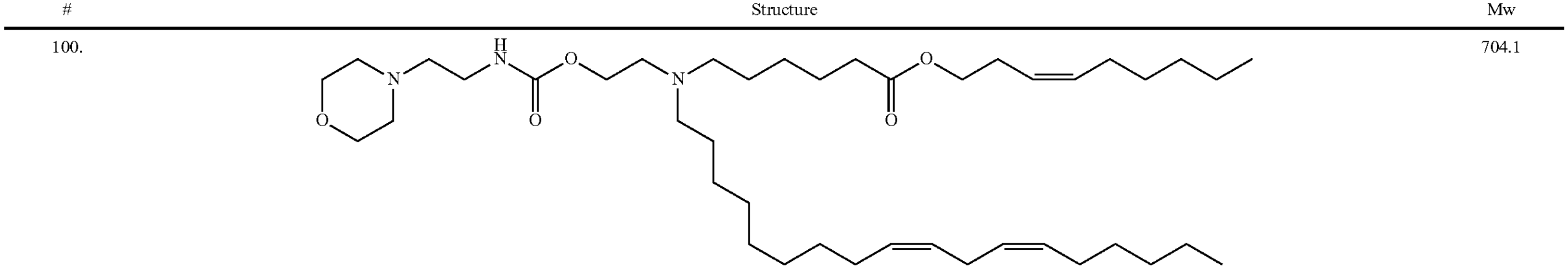 | 704.1 |
| 101. | 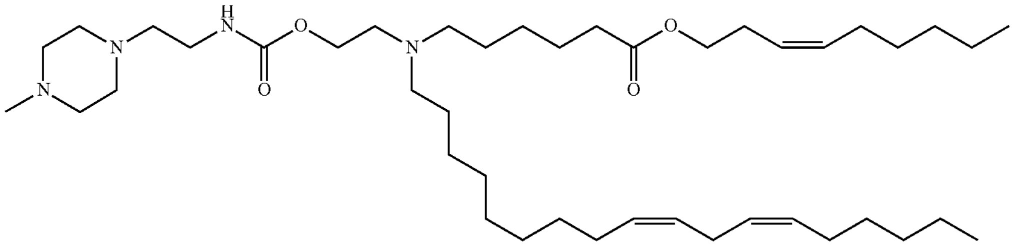 [SMILES: CCCCC/C=C\C/C=C\CCCCCCCCN(CCCCCC(=O)OCC/C=C\CCCCC)CCOC(=O)NCCN1CCN(C)CC1] | 717.1 |
| 102. | 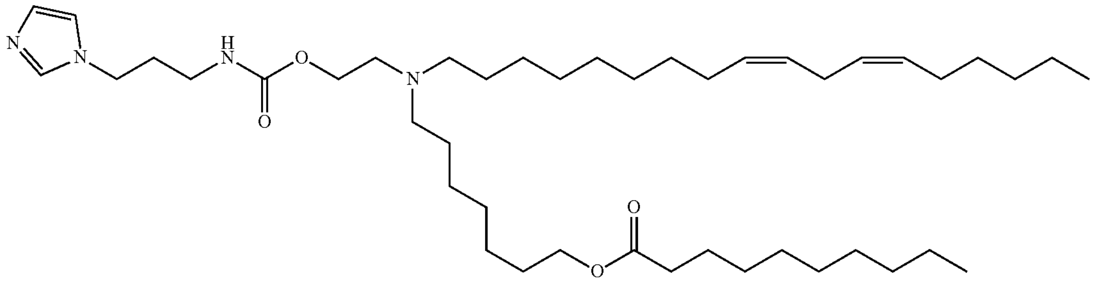 [SMILES: CCCCC/C=C\C/C=C\CCCCCCCCN(CCCCCCCOC(=O)CCCCCCCCC)CCOC(=O)NCCCn1ccnc1] | 729.1 |

TABLE 1-continued
| # | Structure | Mw |
|---|---|---|
| 103. | 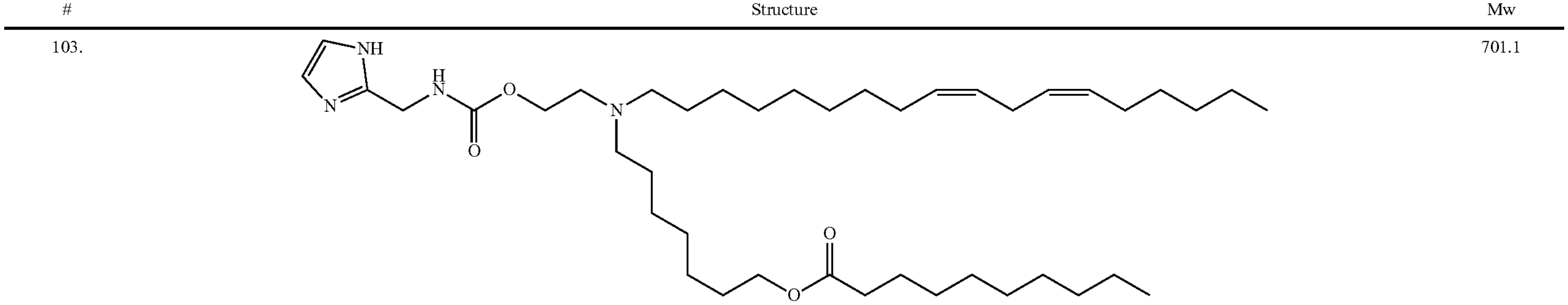 | 701.1 |
| 104. | 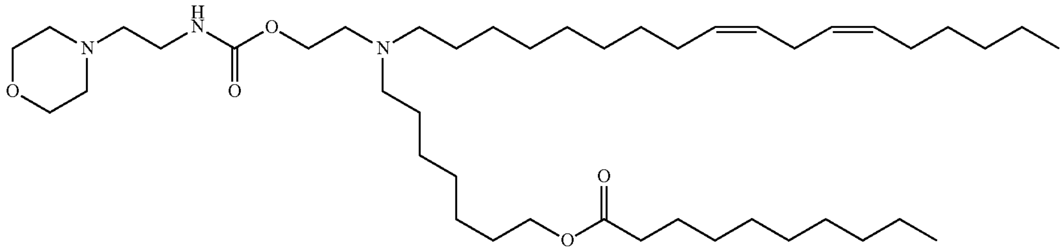 [SMILES: CCCCC/C=C\C/C=C\CCCCCCCCN(CCCCCCCOC(=O)CCCCCCCCC)CCOC(=O)NCCN1CCOCC1] | 734.2 |
| 105. | 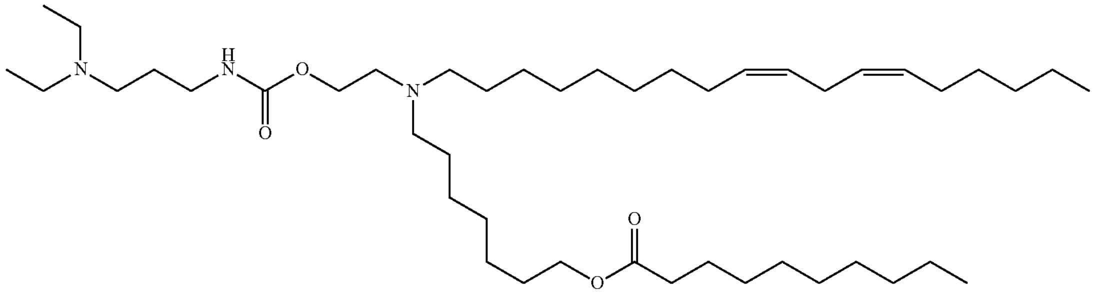 [SMILES: CCCCC/C=C\C/C=C\CCCCCCCCN(CCCCCCCOC(=O)CCCCCCCCC)CCOC(=O)NCCCN(CC)CC] | 734.2 |

TABLE 1-continued
| # | Structure | Mw |
| --- | --- | --- |
| 106. | 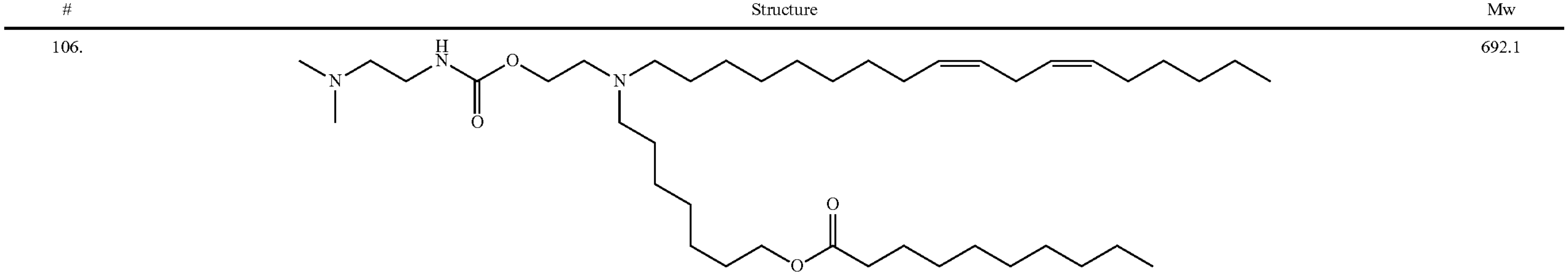 | 692.1 |
| 107. | 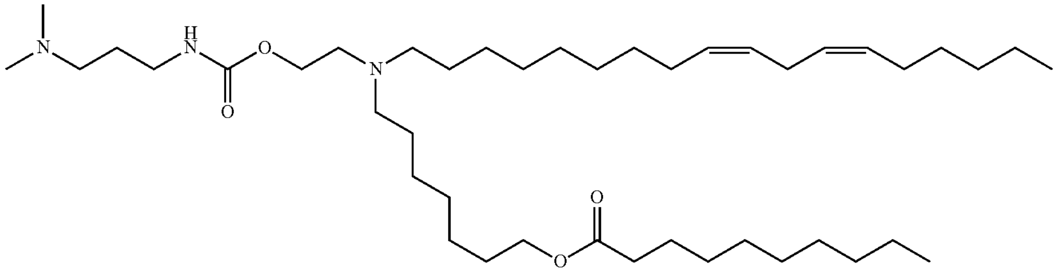 [SMILES: CCCCC/C=C\C/C=C\CCCCCCCCN(CCCCCCCOC(=O)CCCCCCCCC)CCOC(=O)NCCCN(C)C] | 706.2 |
| 108. | 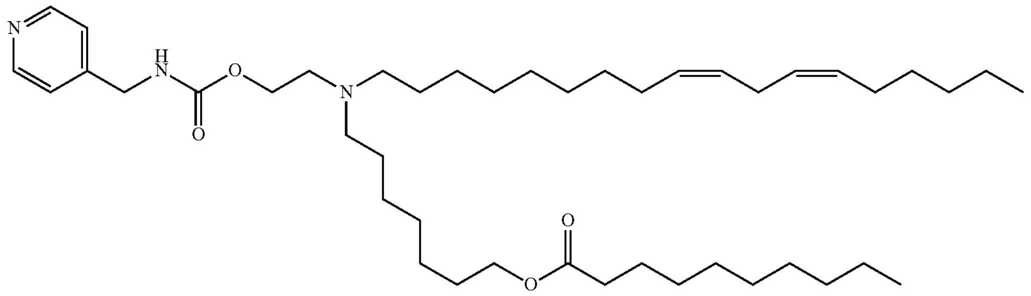 [SMILES: CCCCC/C=C\C/C=C\CCCCCCCCN(CCCCCCCOC(=O)CCCCCCCCC)CCOC(=O)NCc1ccncc1] | 712.1 |

TABLE 1-continued
| # | Structure | Mw |
|---|---|---|
| 109. | 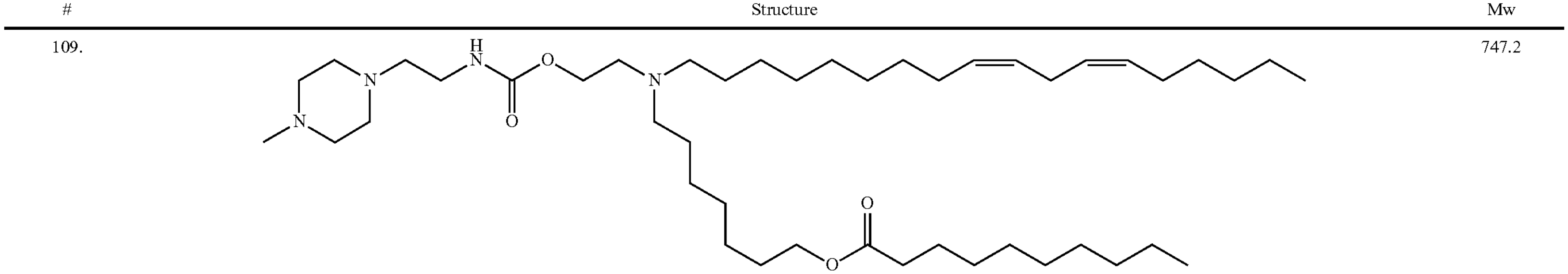 | 747.2 |
| 110. | 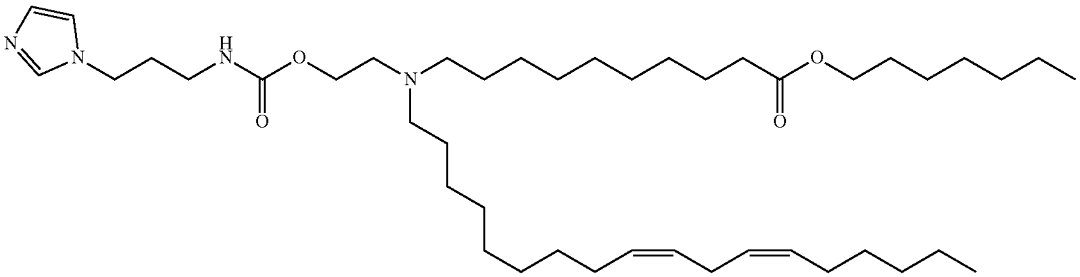 | 729.1 |
| 111. | 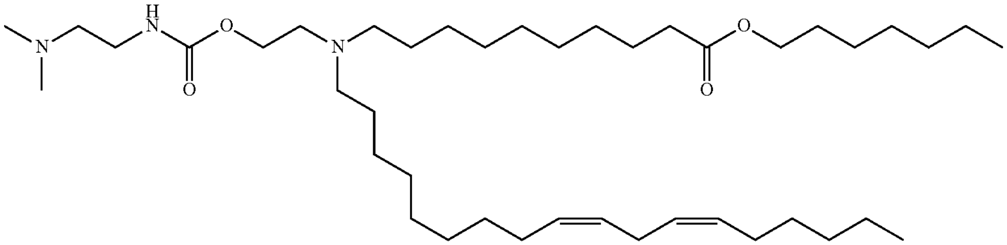 | 692.1 |
| 112. | 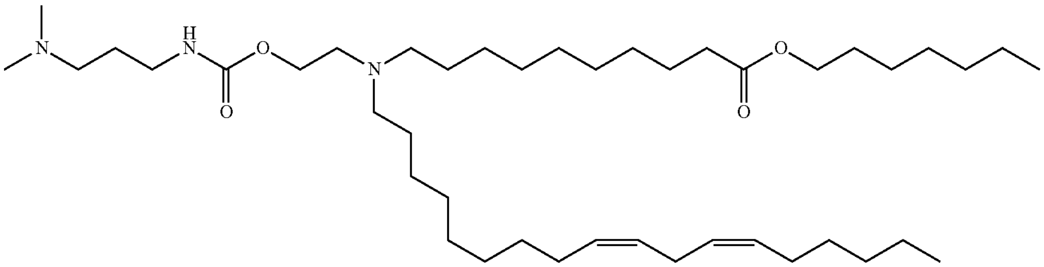 [SMILES: CCCCC/C=C\C/C=C\CCCCCCCCN(CCCCCCCCCC(=O)OCCCCCCC)CCOC(=O)NCCCN(C)C] | 706.2 |

TABLE 1-continued
| # | Structure | Mw |
| --- | --- | --- |
| 113. | 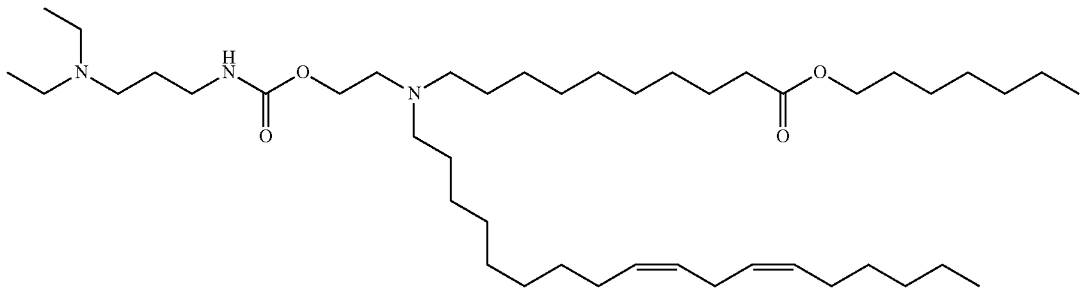 [SMILES: CCCCC/C=C\C/C=C\CCCCCCCCN(CCCCCCCCCC(=O)OCCCCCCC)CCOC(=O)NCCCN(CC)CC] | 734.2 |
| 114. | 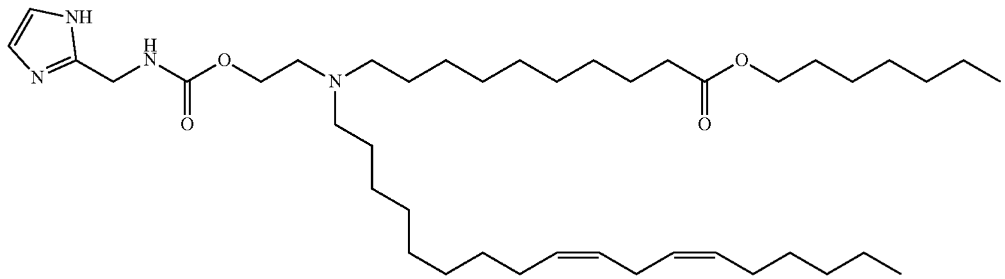 [SMILES: CCCCC/C=C\C/C=C\CCCCCCCCN(CCCCCCCCCC(=O)OCCCCCCC)CCOC(=O)NCc1ncc[nH]1] | 701.1 |
| 115. | 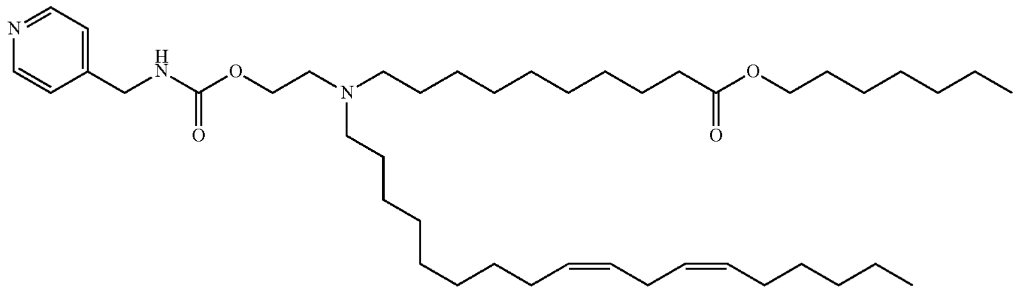 [SMILES: CCCCC/C=C\C/C=C\CCCCCCCCN(CCCCCCCCCC(=O)OCCCCCCC)CCOC(=O)NCc1ccncc1] | 712.1 |

TABLE 1-continued
| # | Structure | Mw |
| --- | --- | --- |
| 116. | 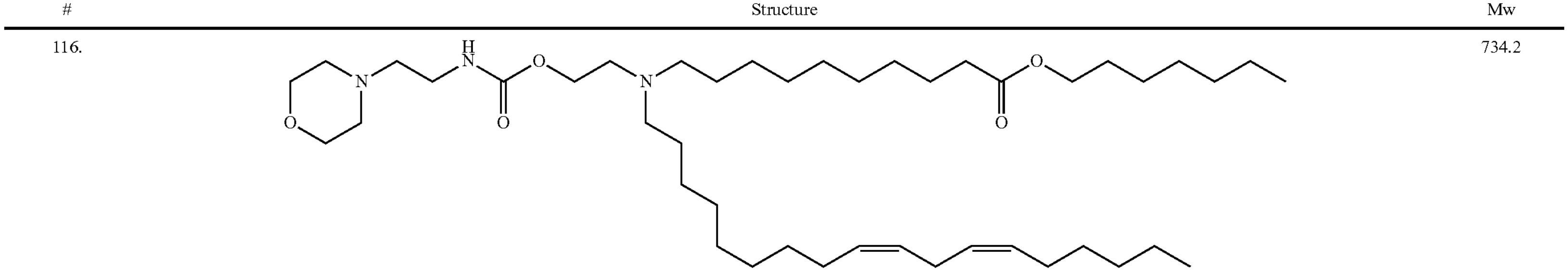 | 734.2 |
| 117. | 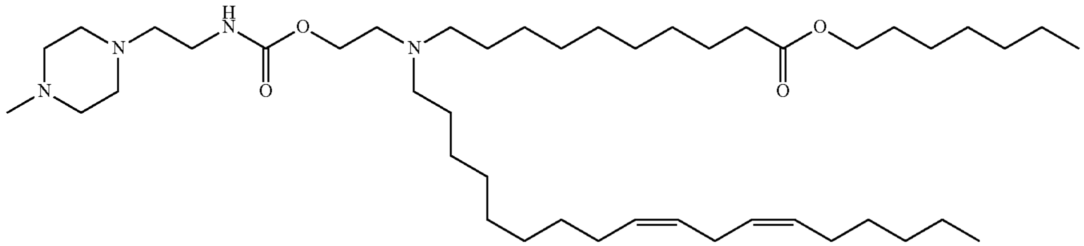 [SMILES: CCCCC/C=C\C/C=C\CCCCCCCCN(CCCCCCCCCC(=O)OCCCCCCC)CCOC(=O)NCCN1CCN(C)CC1] | 747.2 |
| 118. | 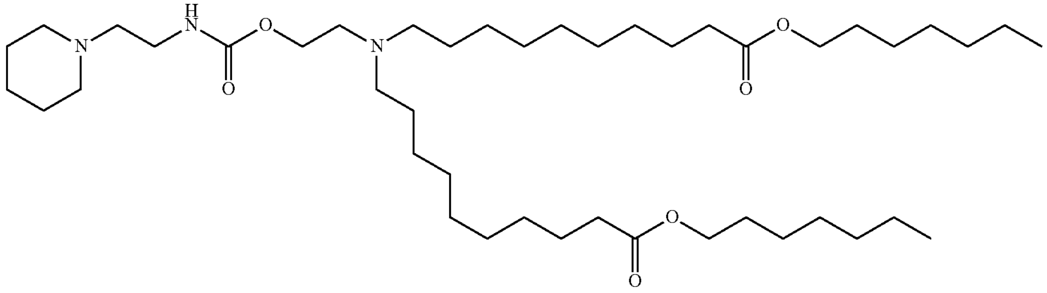 [SMILES: CCCCCCCOC(=O)CCCCCCCCCN(CCCCCCCCCC(=O)OCCCCCCC)CCOC(=O)NCCN1CCCCC1] | 752.2 |

TABLE 1-continued
| # | Structure | Mw |
| --- | --- | --- |
| 119. | 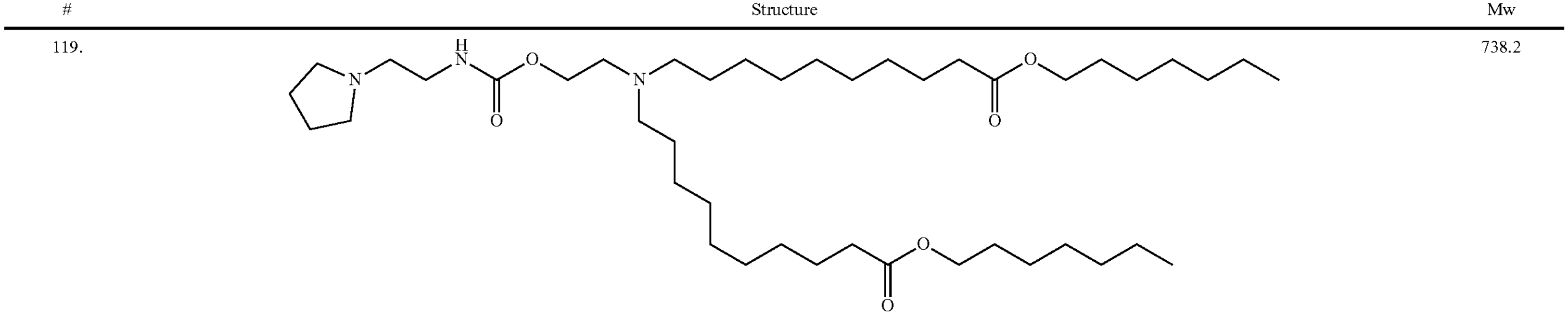 | 738.2 |
| 120. | 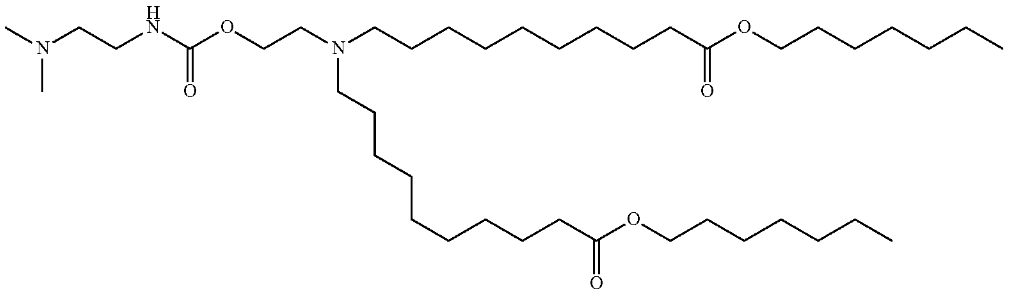 [SMILES: CCCCCCCOC(=O)CCCCCCCCCN(CCCCCCCCCC(=O)OCCCCCCC)CCOC(=O)NCCN(C)C] | 712.1 |
| 121. | 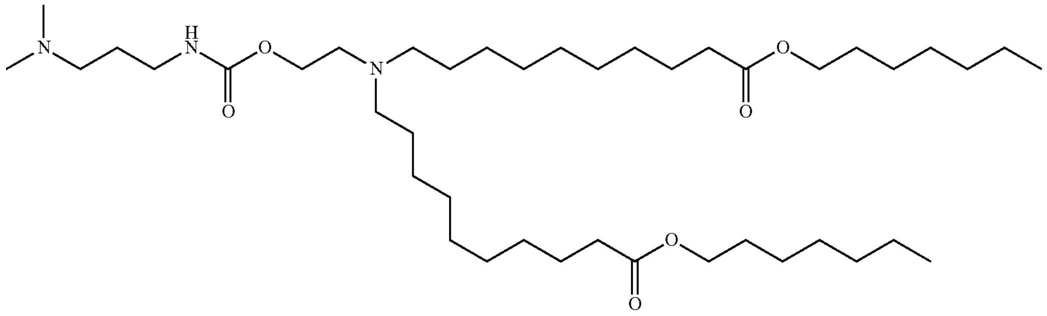 [SMILES: CCCCCCCOC(=O)CCCCCCCCCN(CCCCCCCCCC(=O)OCCCCCCC)CCOC(=O)NCCCN(C)C] | 726.1 |

TABLE 1-continued
| # | Structure | Mw |
|---|---|---|
| 122. | 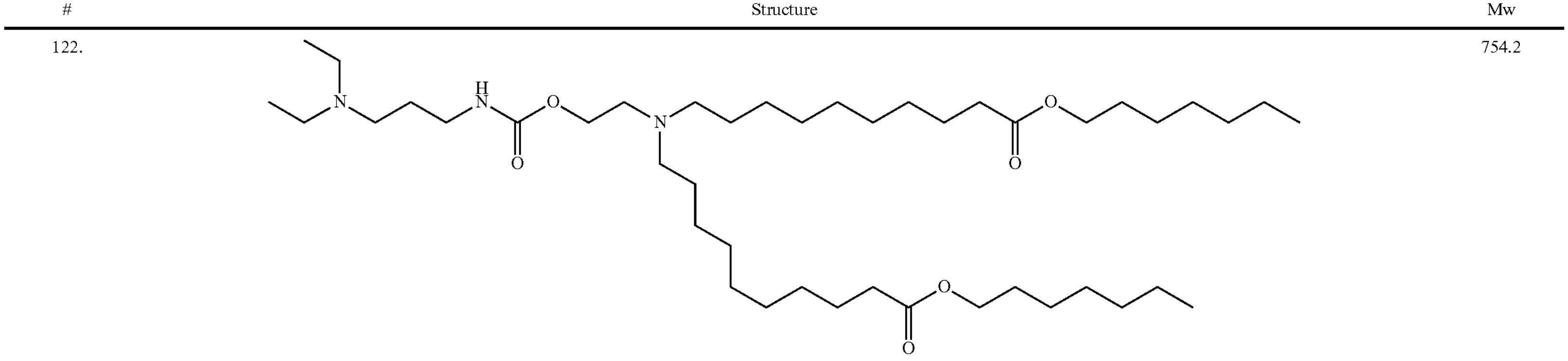 | 754.2 |
| 123. | 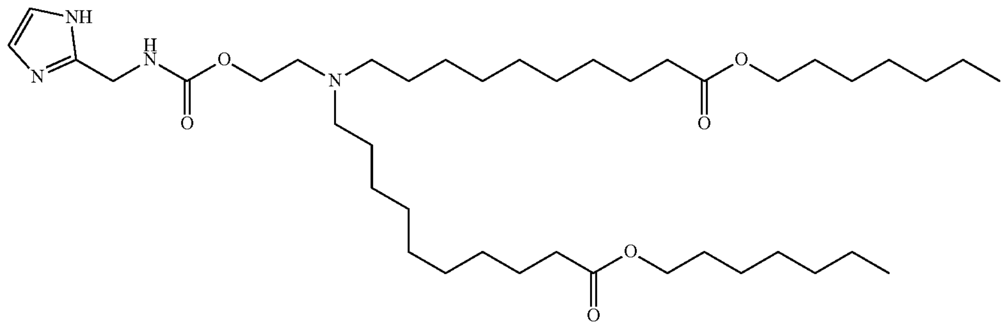 [SMILES: CCCCCCCOC(=O)CCCCCCCCCN(CCCCCCCCCC(=O)OCCCCCCC)CCOC(=O)NCc1ncc[nH]1] | 721.1 |
| 124. | 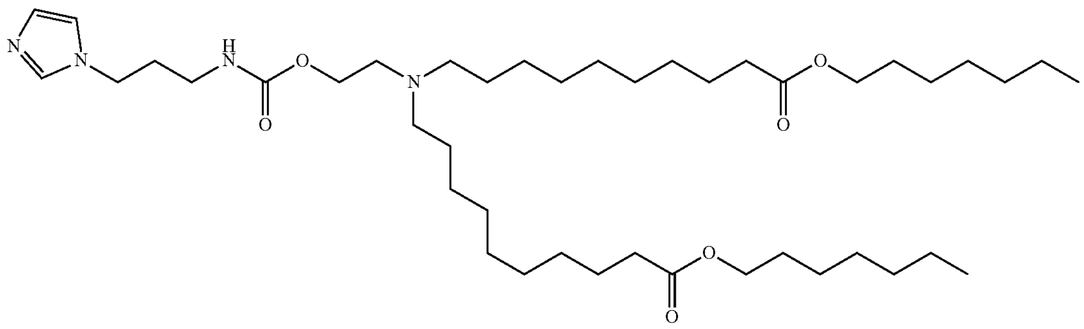 [SMILES: CCCCCCCOC(=O)CCCCCCCCCN(CCCCCCCCCC(=O)OCCCCCCC)CCOC(=O)NCCCn1ccnc1] | 749.1 |

TABLE 1-continued
| # | Structure | Mw |
| --- | --- | --- |
| 125. | 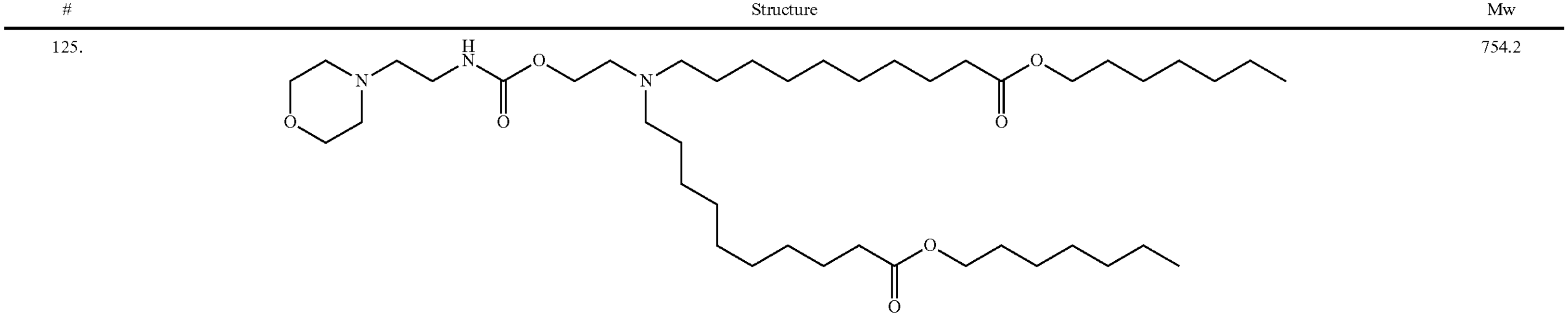 | 754.2 |
| 126. | 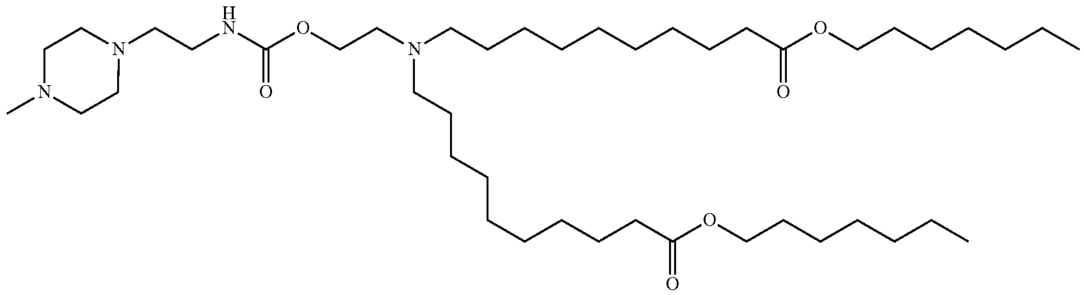 [SMILES: CCCCCCCOC(=O)CCCCCCCCCN(CCCCCCCCCC(=O)OCCCCCCC)CCOC(=O)NCCN1CCN(C)CC1] | 767.2 |
| 127. | 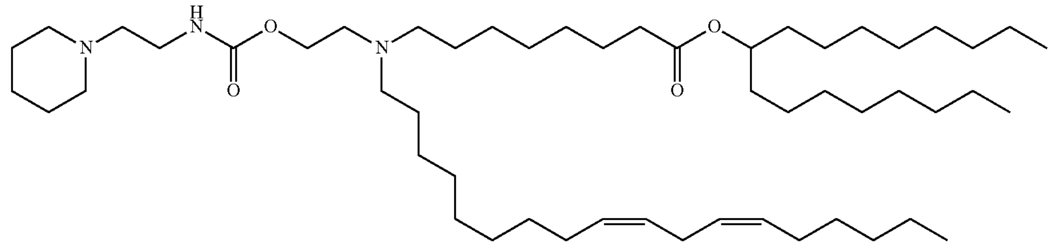 [SMILES: CCCCC/C=C\C/C=C\CCCCCCCCN(CCCCCCCC(=O)OC(CCCCCCCC)CCCCCCCC)CCOC(=O)NCCN1CCCCC1] | 844.4 |

TABLE 1-continued
| # | Structure | Mw |
|---|---|---|
| 128. | 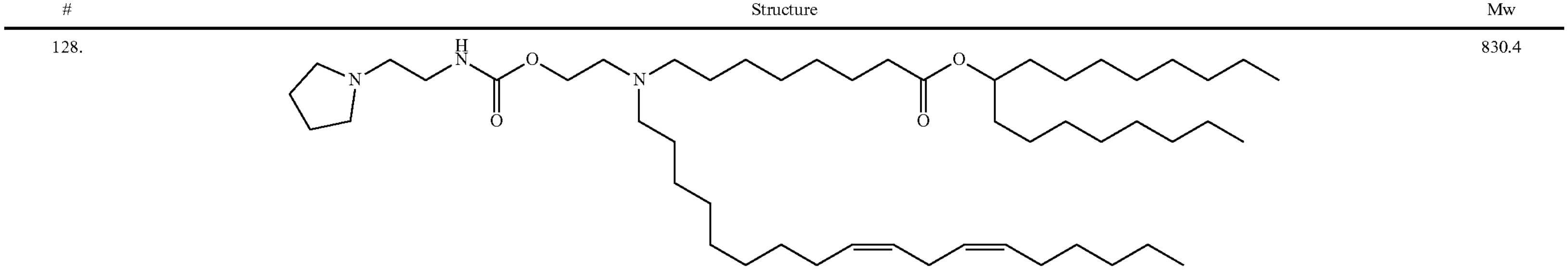 | 830.4 |
| 129. | 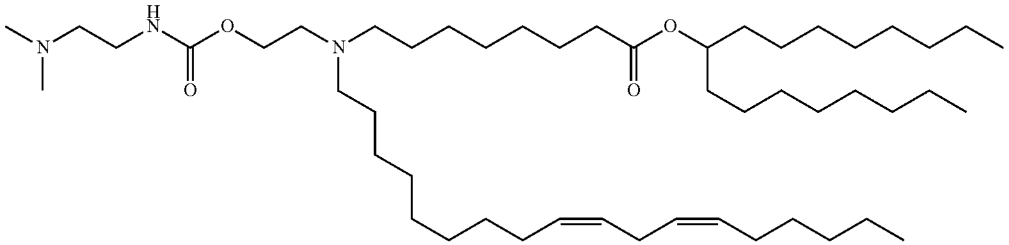 [SMILES: CCCCC/C=C\C/C=C\CCCCCCCCN(CCCCCCCC(=O)OC(CCCCCCCC)CCCCCCCC)CCOC(=O)NCCN(C)C] | 804.3 |
| 130. | 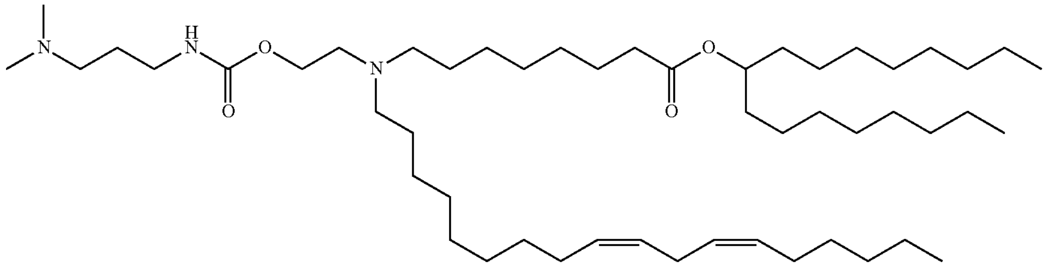 [SMILES: CCCCC/C=C\C/C=C\CCCCCCCCN(CCCCCCCC(=O)OC(CCCCCCCC)CCCCCCCC)CCOC(=O)NCCCN(C)C] | 818.4 |
| 131. | 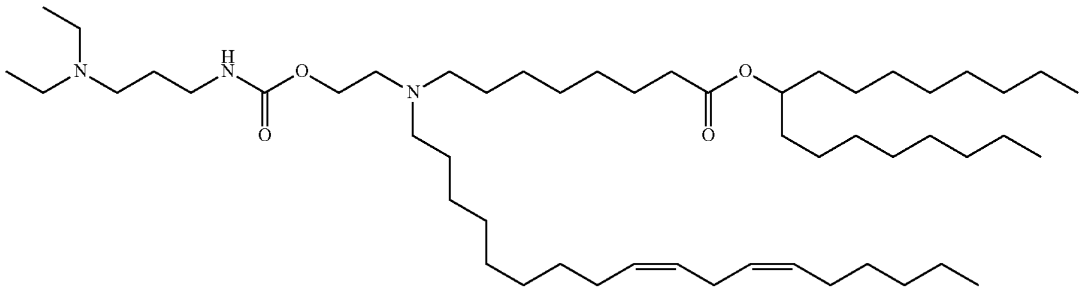 [SMILES: CCCCC/C=C\C/C=C\CCCCCCCCN(CCCCCCCC(=O)OC(CCCCCCCC)CCCCCCCC)CCOC(=O)NCCCN(CC)CC] | 846.4 |

TABLE 1-continued
| # | Structure | Mw |
|---|---|---|
| 132. | 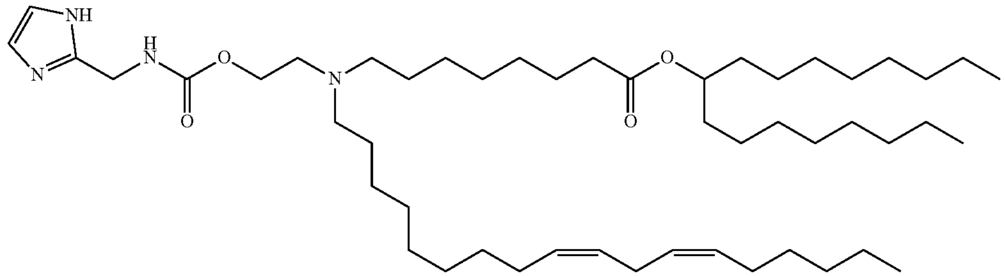 [SMILES: CCCCC/C=C\C/C=C\CCCCCCCCN(CCCCCCCC(=O)OC(CCCCCCCC)CCCCCCCC)CCOC(=O)NCc1ncc[nH]1] | 813.3 |
| 133. | 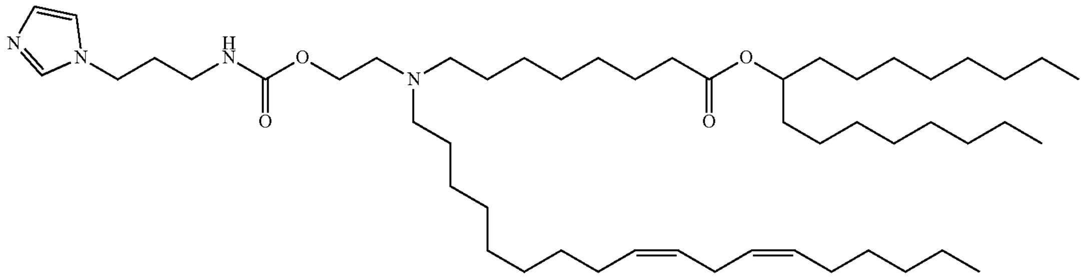 [SMILES: CCCCC/C=C\C/C=C\CCCCCCCCN(CCCCCCCC(=O)OC(CCCCCCCC)CCCCCCCC)CCOC(=O)NCCCn1ccnc1] | 841.4 |
| 134. | 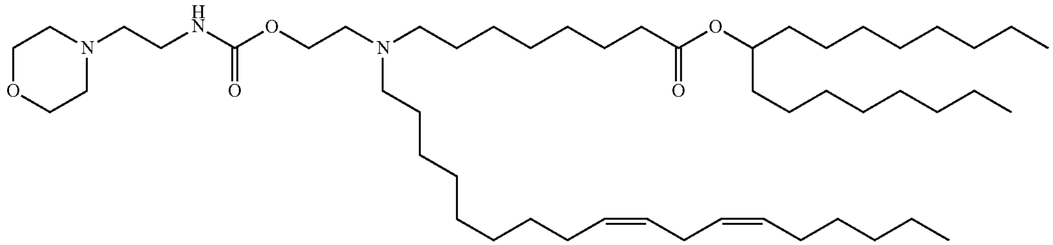 [SMILES: CCCCC/C=C\C/C=C\CCCCCCCCN(CCCCCCCC(=O)OC(CCCCCCCC)CCCCCCCC)CCOC(=O)NCCN1CCOCC1] | 846.4 |

TABLE 1-continued
| # | Structure | Mw |
| --- | --- | --- |
| 135. | 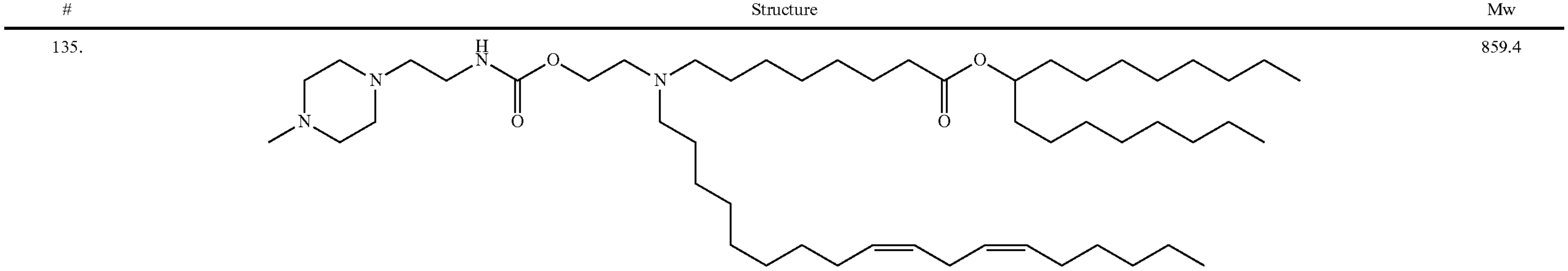 | 859.4 |
| 136. | 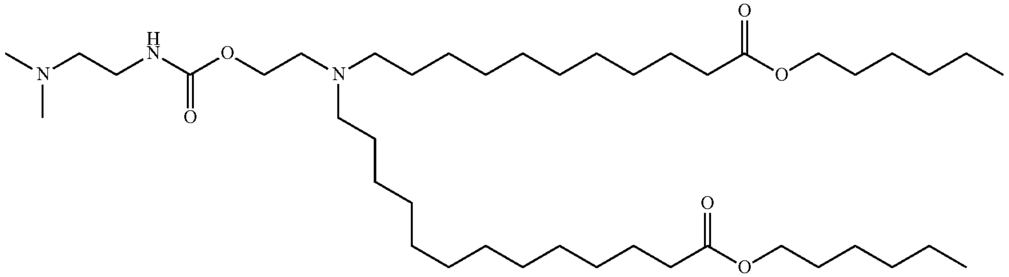 [SMILES: CCCCCCOC(=O)CCCCCCCCCCCCN(CCCCCCCCCCC(=O)OCCCCCC)CCOC(=O)NCCN(C)C] | 712.1 |
| 137. | 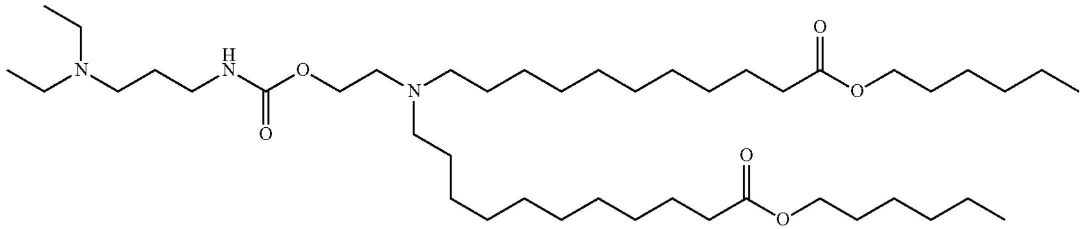 [SMILES: CCCCCCOC(=O)CCCCCCCCCCN(CCCCCCCCCCC(=O)OCCCCCC)CCOC(=O)NCCCN(CC)CC] | 754.2 |
| 138. | 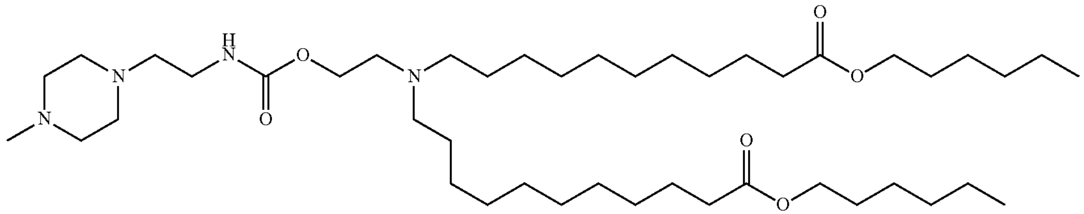 [SMILES: CCCCCCOC(=O)CCCCCCCCCCN(CCCCCCCCCCC(=O)OCCCCCC)CCOC(=O)NCCN1CCN(C)CC1] | 767.2 |

TABLE 1-continued
| # | Structure | Mw |
|---|---|---|
| 139. | 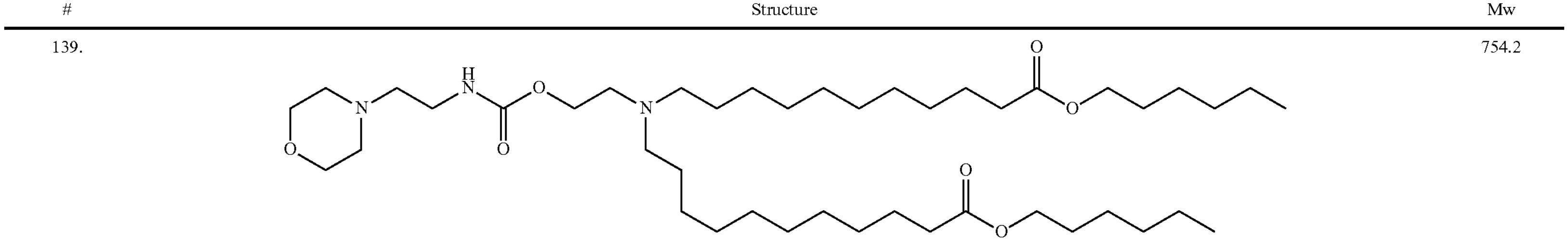 | 754.2 |
| 140. | 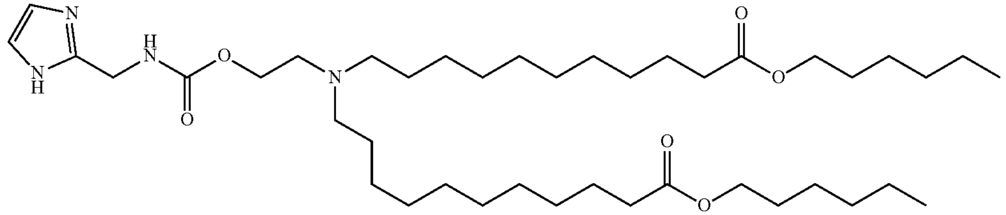 [SMILES: CCCCCCOC(=O)CCCCCCCCCCN(CCCCCCCCCCC(=O)OCCCCCC)CCOC(=O)NCc1ncc[nH]1] | 721.1 |
| 141. | 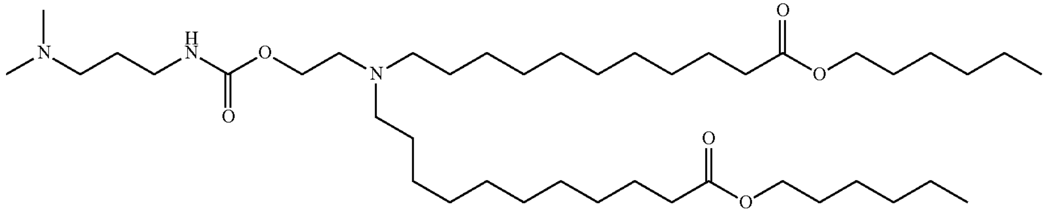 [SMILES: CCCCCCOC(=O)CCCCCCCCCCN(CCCCCCCCCCC(=O)OCCCCCC)CCOC(=O)NCCCN(C)C] | 726.1 |
| 142. | 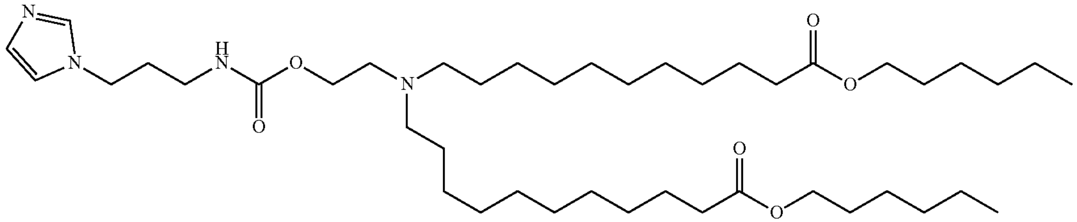 [SMILES: CCCCCCOC(=O)CCCCCCCCCCN(CCCCCCCCCCC(=O)OCCCCCC)CCOC(=O)NCCCn1ccnc1] | 749.1 |

TABLE 1-continued
| # | Structure | Mw |
| --- | --- | --- |
| 143. | 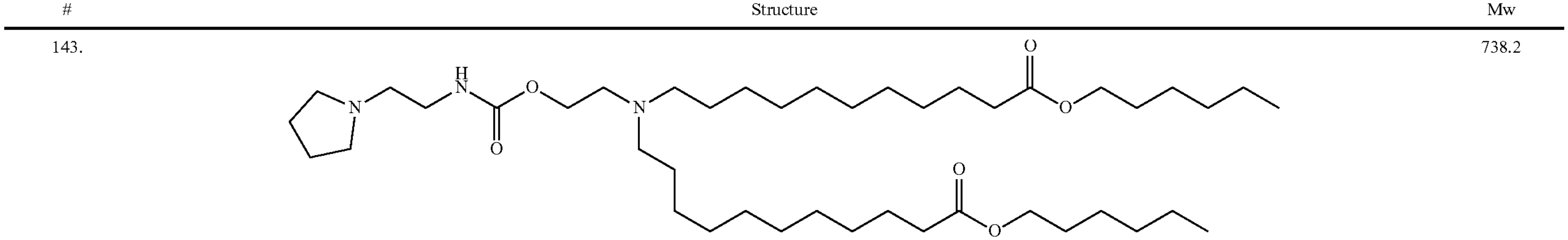 | 738.2 |
| 144. | 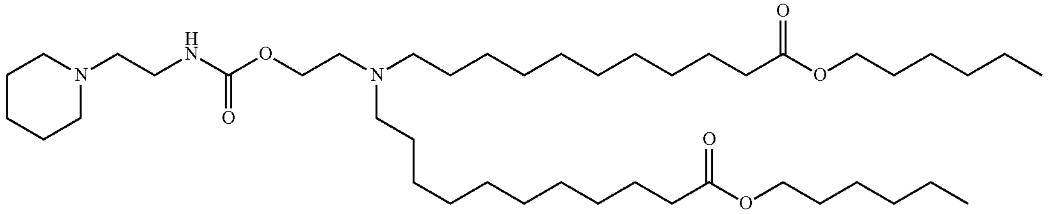 | 752.2 |
| 145. | 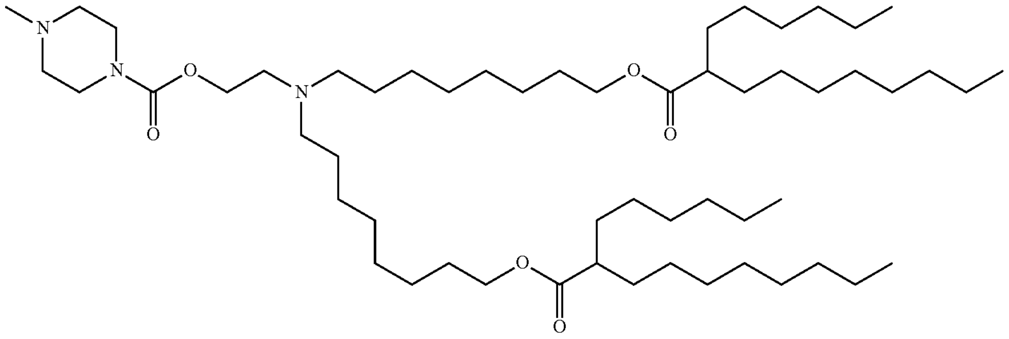 [SMILES: CCCCCCCCC(CCCCCC)C(=O)OCCCCCCCCN(CCCCCCCCOC(=O)C(CCCCCC)CCCCCCCC)CCOC(=O)N1CCN(C)CC1] | 920.5 |

TABLE 1-continued
| # | Structure | Mw |
| --- | --- | --- |
| 146. | 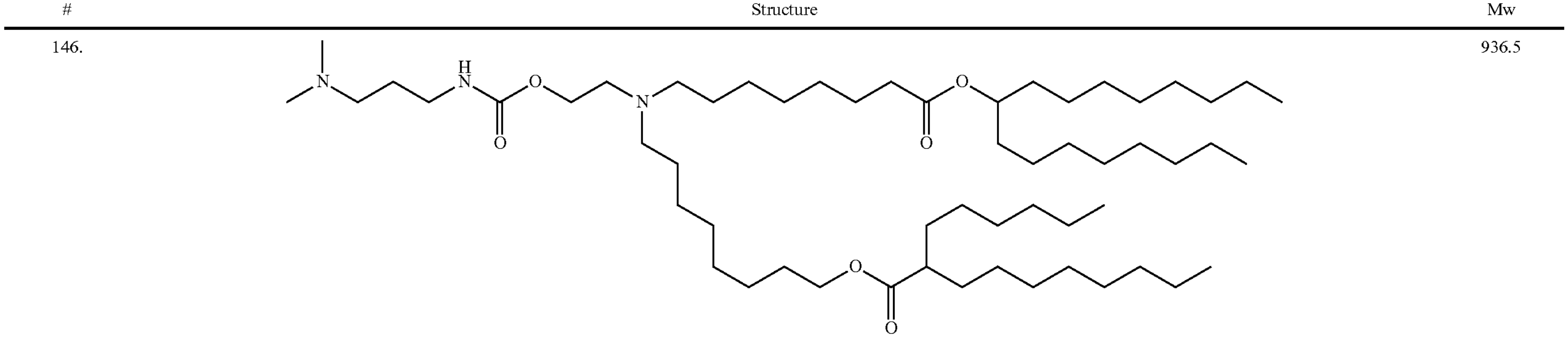 | 936.5 |
| 147. | 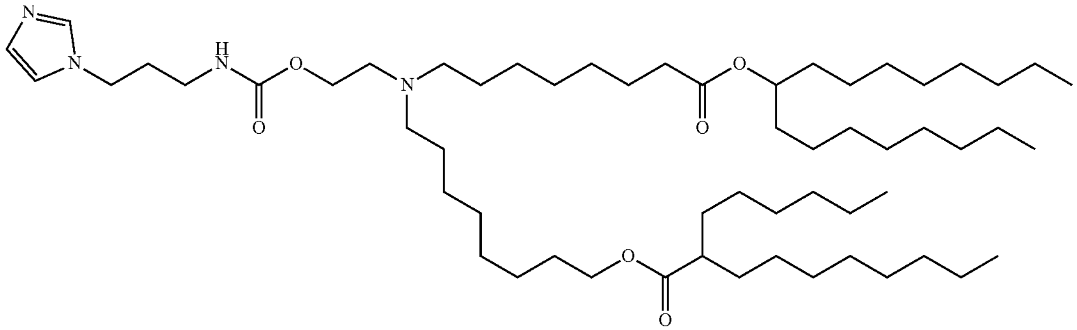 [SMILES: CCCCCCCCC(CCCCCCCC)OC(=O)CCCCCCCN(CCCCCCCCOC(=O)C(CCCCCC)CCCCCCCC)CCOC(=O)NCCCn1ccnc1] | 959.5 |
| 148. | 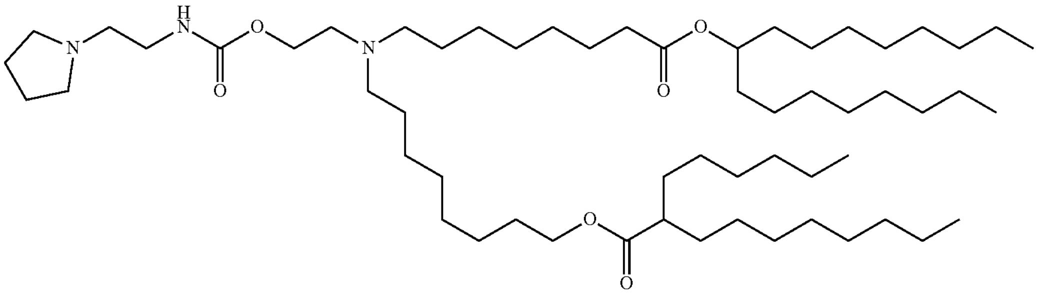 [SMILES: CCCCCCCCC(CCCCCCCC)OC(=O)CCCCCCCN(CCCCCCCCOC(=O)C(CCCCCC)CCCCCCCC)CCOC(=O)NCCN1CCCC1] | 948.6 |

TABLE 1-continued
| # | Structure | Mw |
| --- | --- | --- |
| 149. | 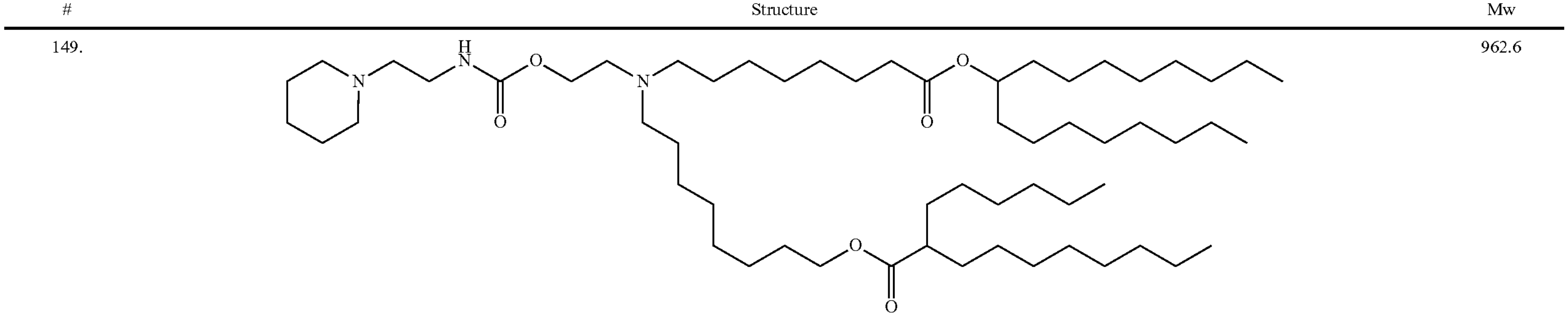 | 962.6 |
| 150. | 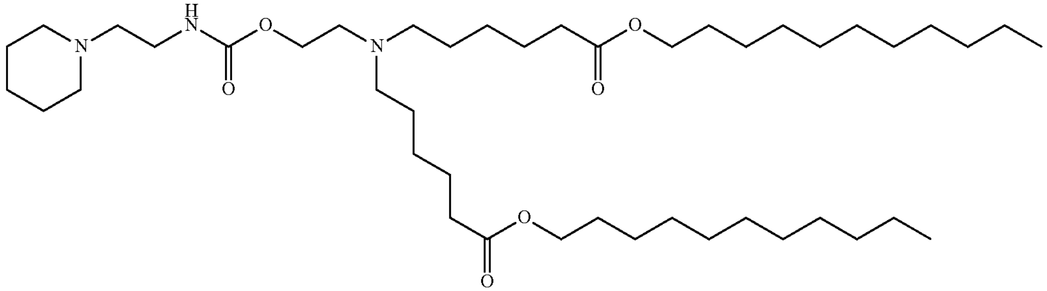 [SMILES: CCCCCCCCCCCOC(=O)CCCCCN(CCCCCC(=O)OCCCCCCCCCCC)CCOC(=O)NCCN1CCCCC1] | 752.2 |
| 151. | 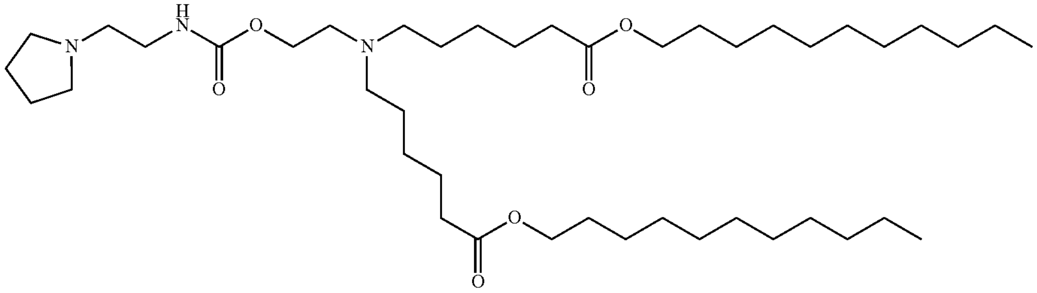 [SMILES: CCCCCCCCCCCOC(=O)CCCCCN(CCCCCC(=O)OCCCCCCCCCCC)CCOC(=O)NCCN1CCCC1] | 738.2 |

TABLE 1-continued
| # | Structure | Mw |
|---|---|---|
| 152. | 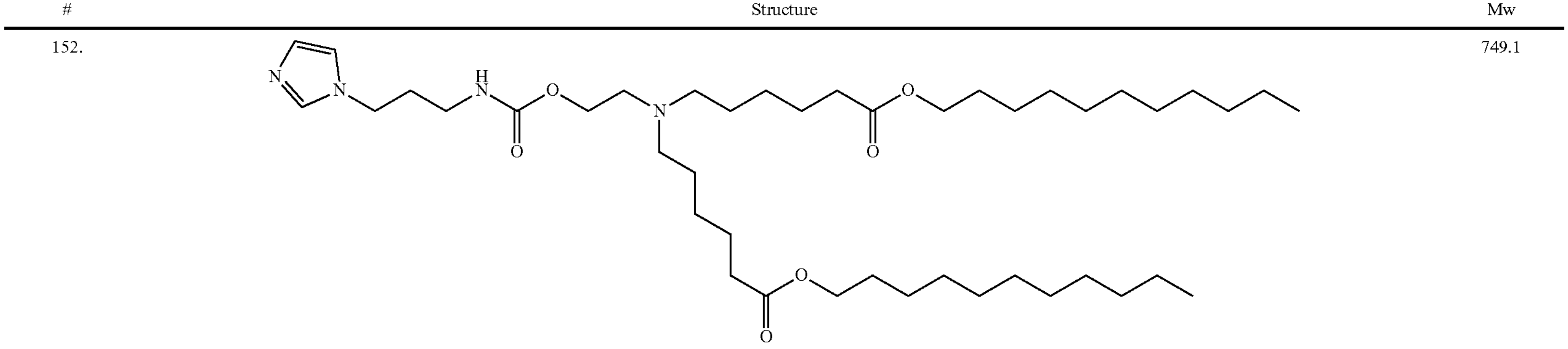 | 749.1 |
| 153. | 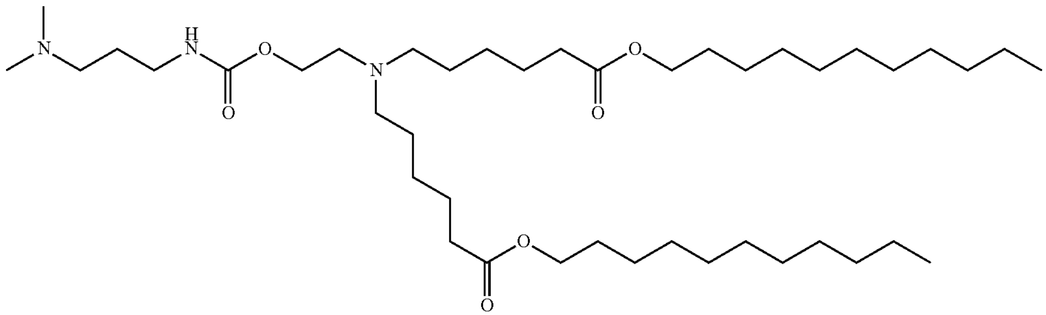 [SMILES: CCCCCCCCCCCOC(=O)CCCCCN(CCCCCC(=O)OCCCCCCCCCCC)CCOC(=O)NCCCN(C)C] | 726.1 |
| 154. | 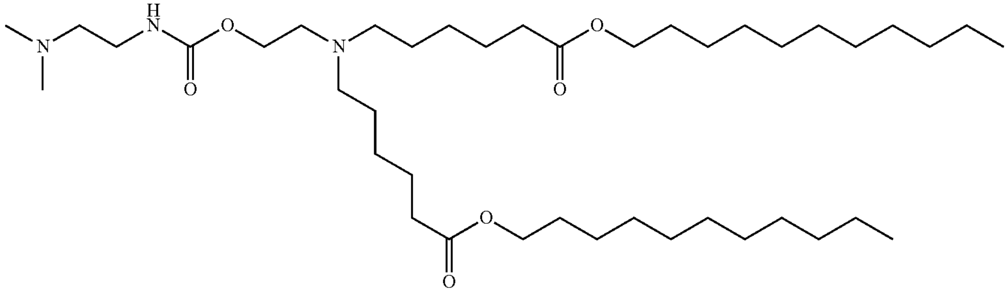 [SMILES: CCCCCCCCCCCOC(=O)CCCCCN(CCCCCC(=O)OCCCCCCCCCCC)CCOC(=O)NCCN(C)C] | 712.1 |

TABLE 1-continued
| # | Structure | Mw |
|---|---|---|
| 155. | 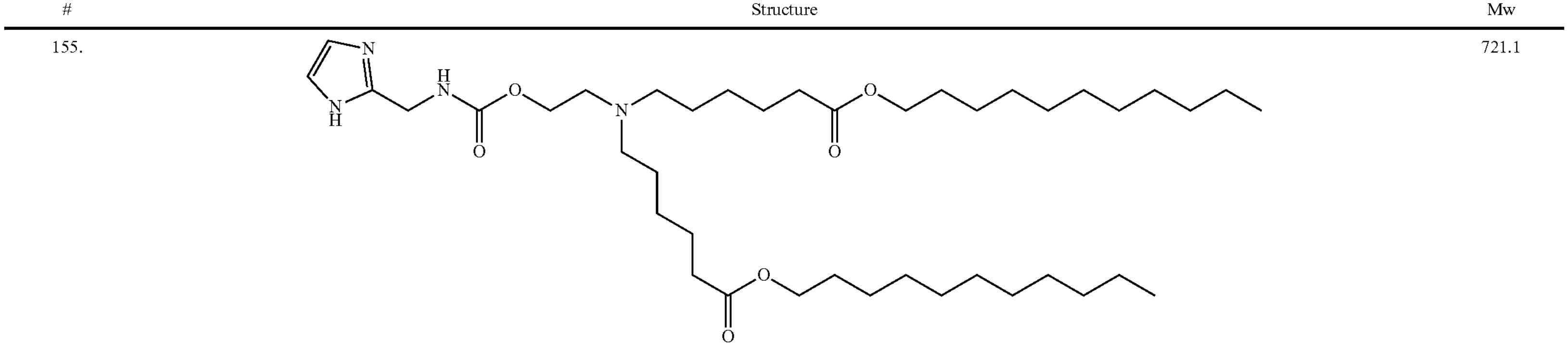 | 721.1 |
| 156. | 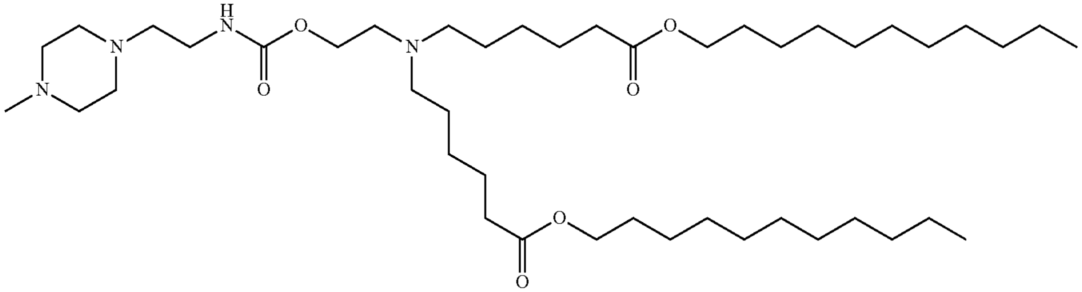 [SMILES: CCCCCCCCCCCOC(=O)CCCCCN(CCCCCC(=O)OCCCCCCCCCCC)CCOC(=O)NCCN1CCN(C)CC1] | 767.2 |
| 157. | 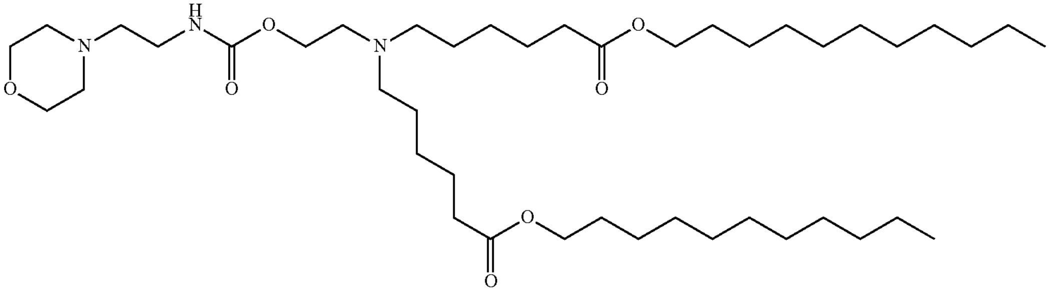 [SMILES: CCCCCCCCCCCOC(=O)CCCCCN(CCCCCC(=O)OCCCCCCCCCCC)CCOC(=O)NCCN1CCOCC1] | 754.2 |

TABLE 1-continued
| # | Structure | Mw |
|---|---|---|
| 158. | 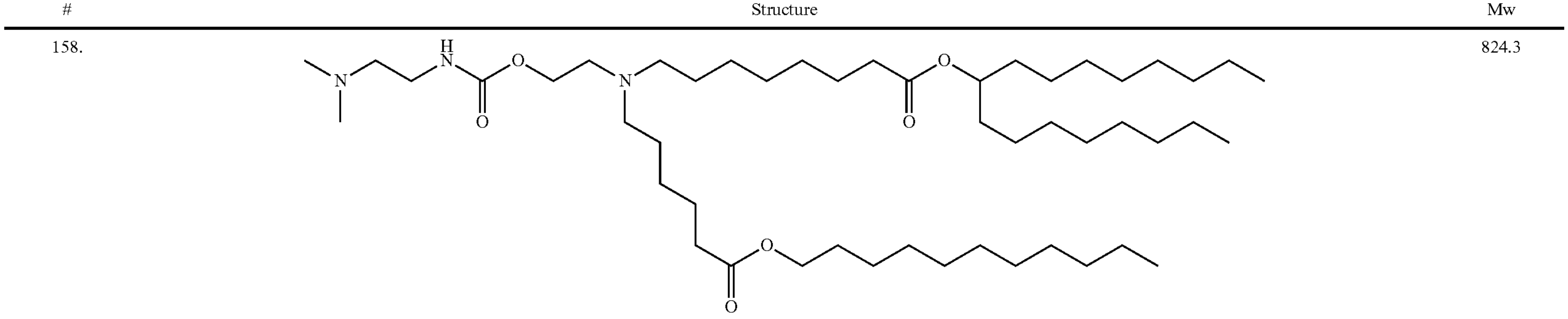 | 824.3 |
| 159. | 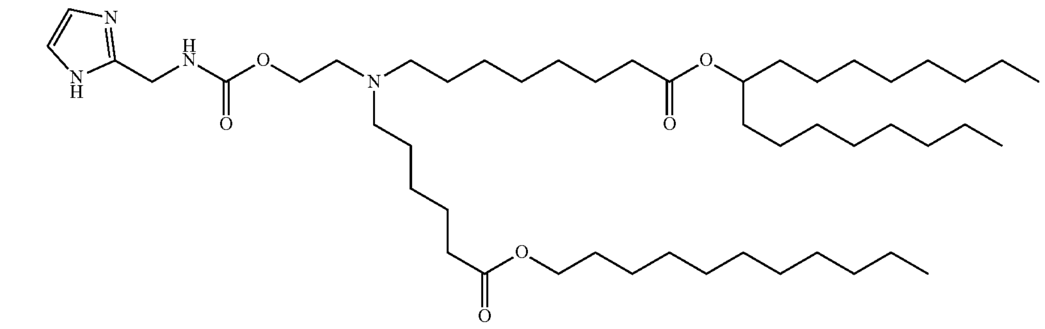 [SMILES: CCCCCCCCCCCOC(=O)CCCCCN(CCCCCCCC(=O)OC(CCCCCCCC)CCCCCCCC)CCOC(=O)NCc1ncc[nH]1] | 833.3 |
| 160. | 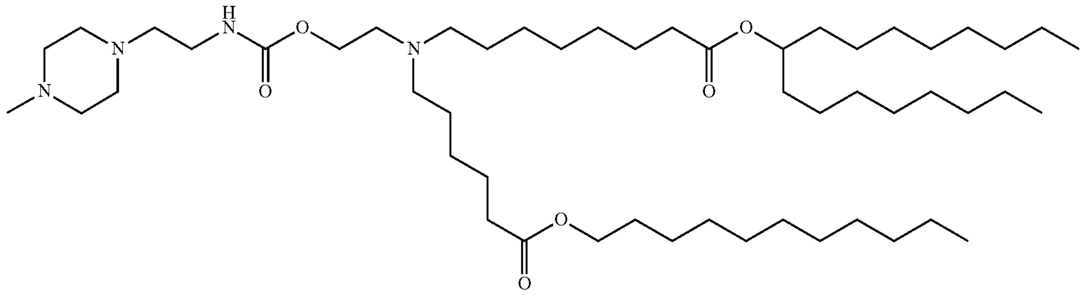 [SMILES: CCCCCCCCCCCOC(=O)CCCCCN(CCCCCCCC(=O)OC(CCCCCCCC)CCCCCCCC)CCOC(=O)NCCN1CCN(C)CC1] | 879.4 |

TABLE 1-continued
| # | Structure | Mw |
|---|---|---|
| 161. | 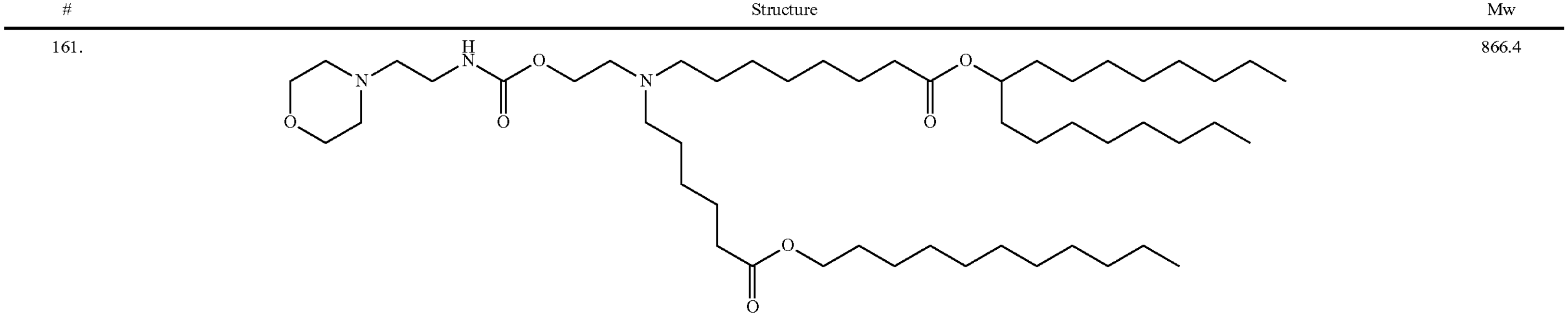 | 866.4 |
| 162. | 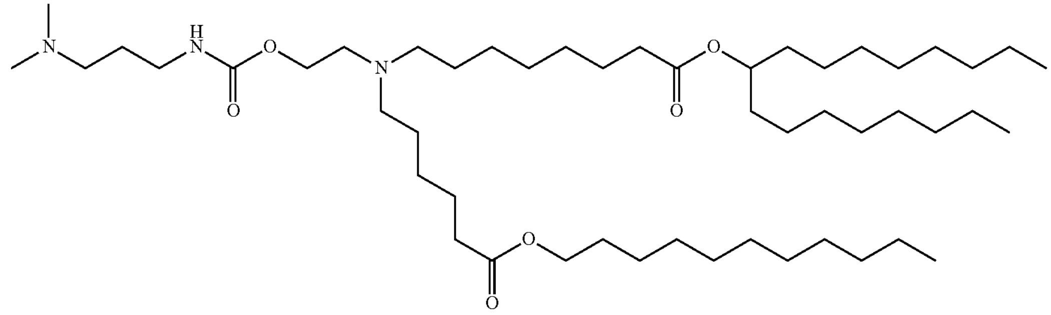 [SMILES: CCCCCCCCCCCOC(=O)CCCCCN(CCCCCCCC(=O)OC(CCCCCCCC)CCCCCCCC)CCOC(=O)NCCCN(C)C] | 838.4 |
| 163. | 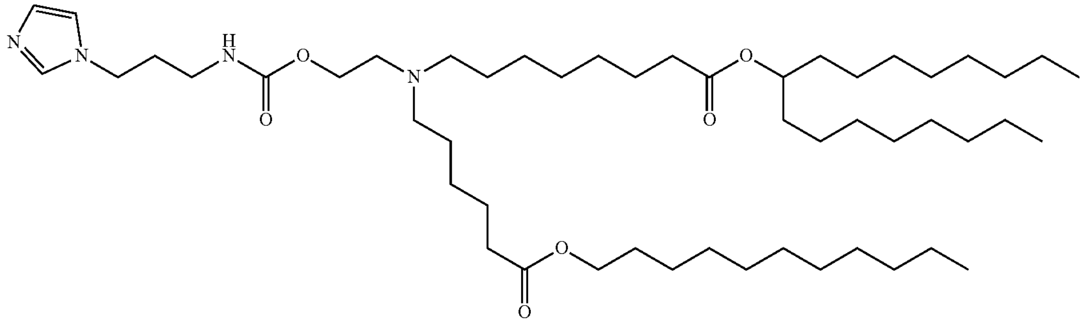 [SMILES: CCCCCCCCCCCOC(=O)CCCCCN(CCCCCCCC(=O)OC(CCCCCCCC)CCCCCCCC)CCOC(=O)NCCCn1ccnc1] | 861.4 |

TABLE 1-continued
| # | Structure | Mw |
|---|---|---|
| 164. | 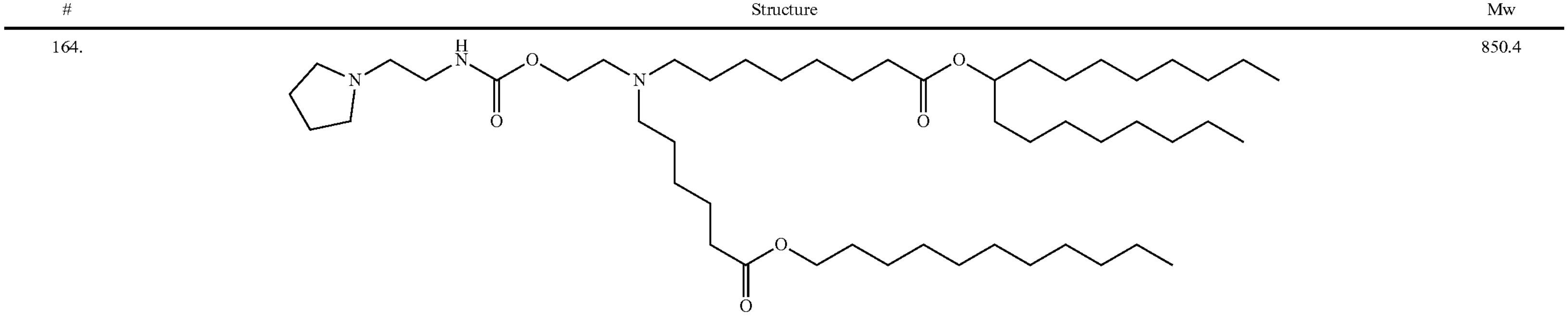 | 850.4 |
| 165. | 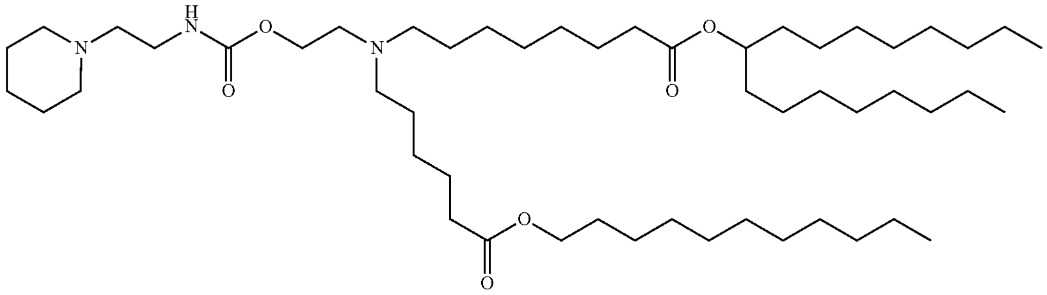 [SMILES: CCCCCCCCCCCOC(=O)CCCCCN(CCCCCCCC(=O)OC(CCCCCCCC)CCCCCCCC)CCOC(=O)NCCN1CCCCC1] | 864.4 |
| 166. | 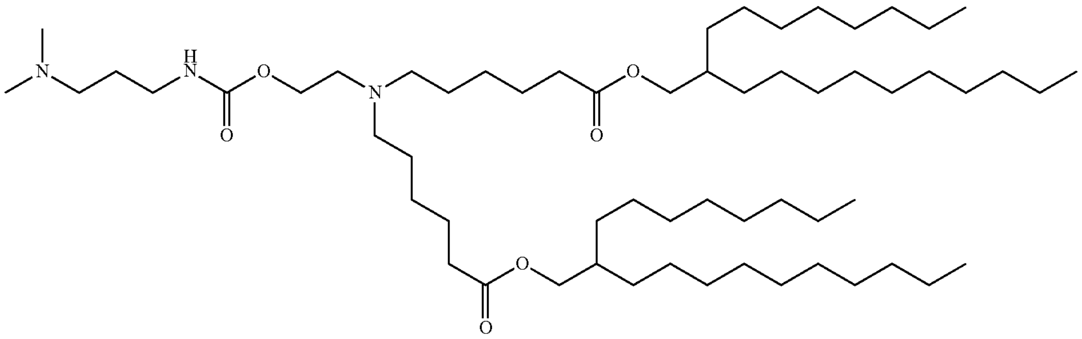 [SMILES: CCCCCCCCCCC(CCCCCCCC)COC(=O)CCCCCN(CCCCCC(=O)OCC(CCCCCCCC)CCCCCCCCCC)CCOC(=O)NCCCN(C)C] | 978.6 |

TABLE 1-continued
| # | Structure | Mw |
|---|---|---|
| 167. | 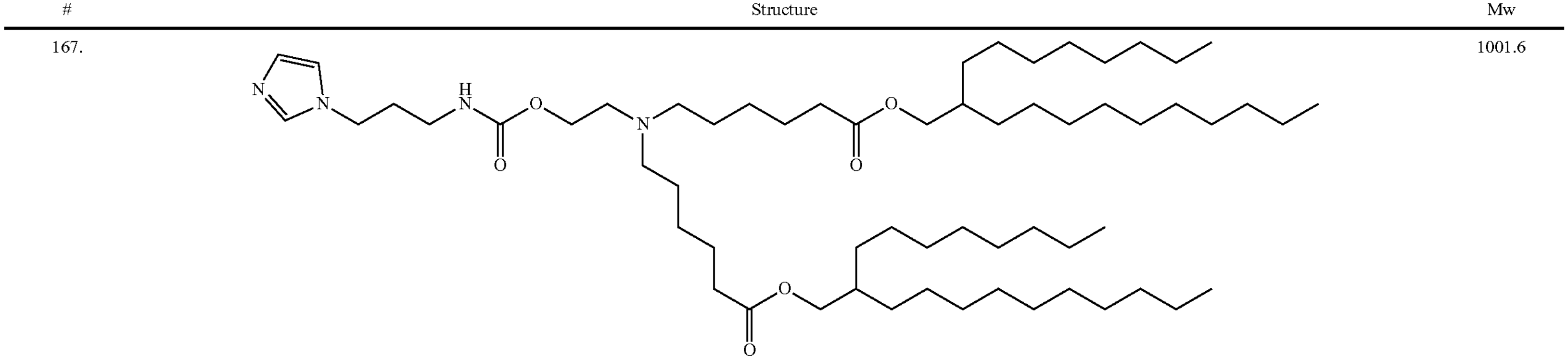 | 1001.6 |
| 168. | 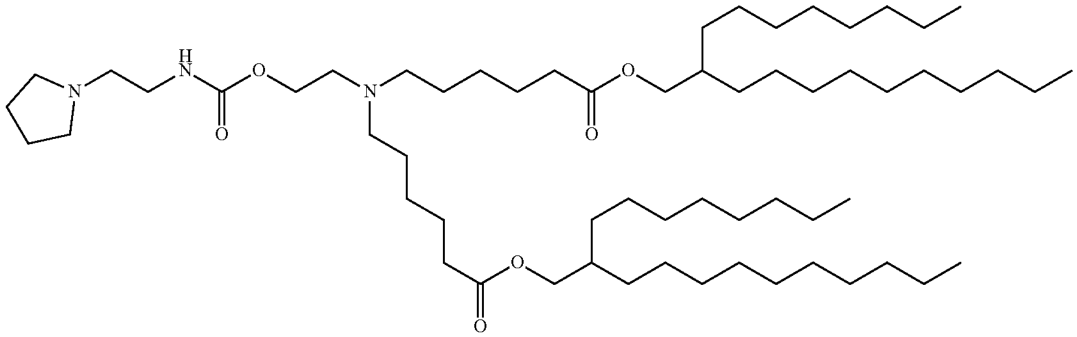 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCC1] | 990.6 |
| 169. | 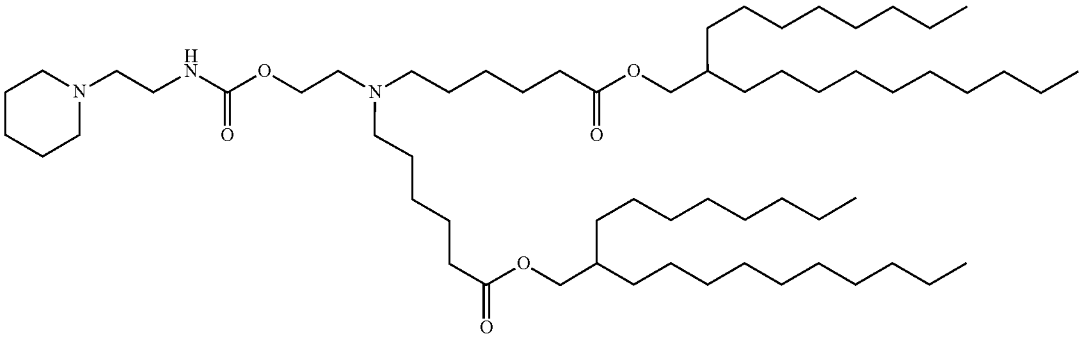 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCCC1] | 1004.7 |

TABLE 1-continued
| # | Structure | Mw |
|---|---|---|
| 170. | 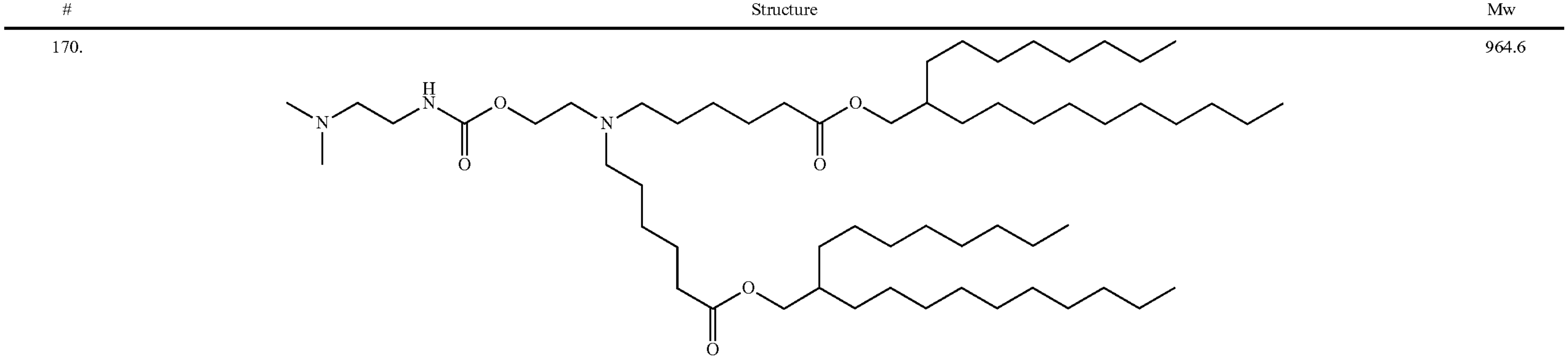 | 964.6 |
| 171. | 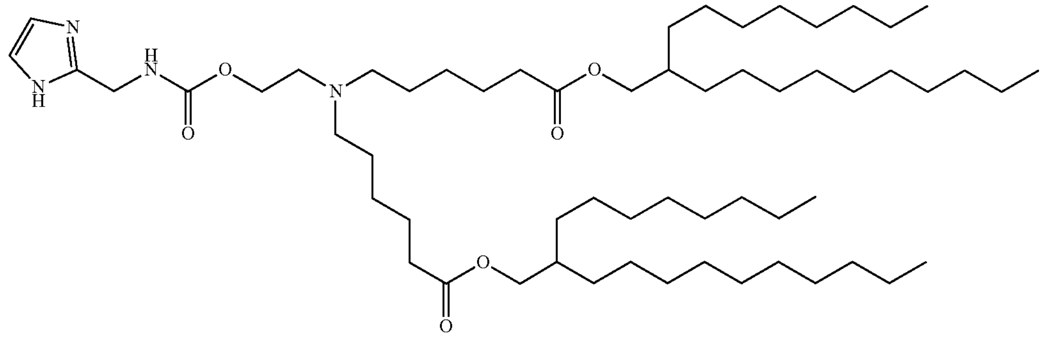 [SMILES: CCCCCCCCCCC(CCCCCCCC)COC(=O)CCCCCN(CCCCCC(=O)OCC(CCCCCCCC)CCCCCCCCCC)CCOC(=O)NCc1ncc[nH]1] | 973.6 |
| 172. | 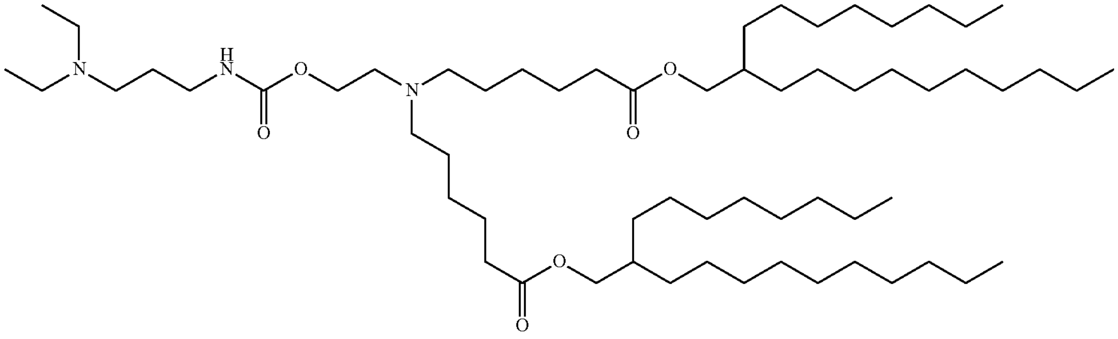 [SMILES: CCCCCCCCCCC(CCCCCCCC)COC(=O)CCCCCN(CCCCCC(=O)OCC(CCCCCCCC)CCCCCCCCCC)CCOC(=O)NCCCN(CC)CC] | 1006.7 |

TABLE 1-continued
| # | Structure | Mw |
| --- | --- | --- |
| 173. | 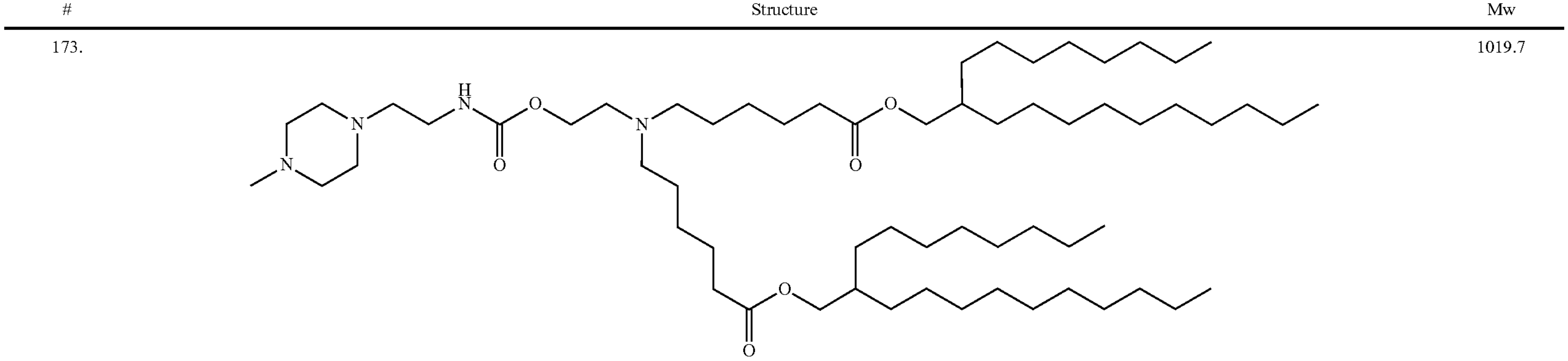 | 1019.7 |
| 174. | 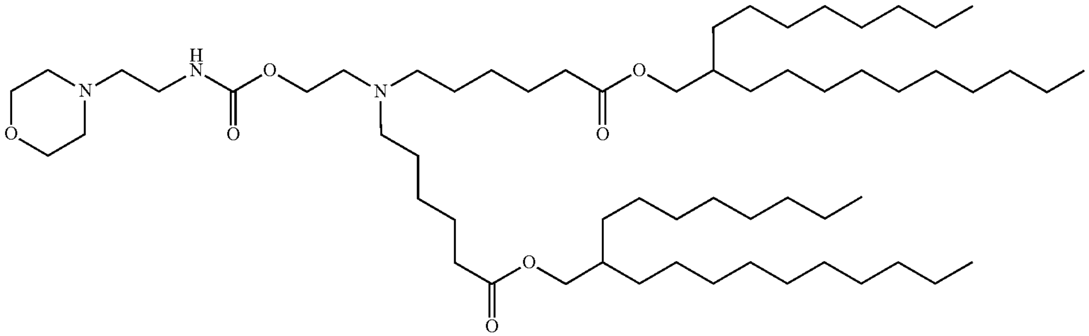 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCOCC1] | 1006.6 |
| 175. | 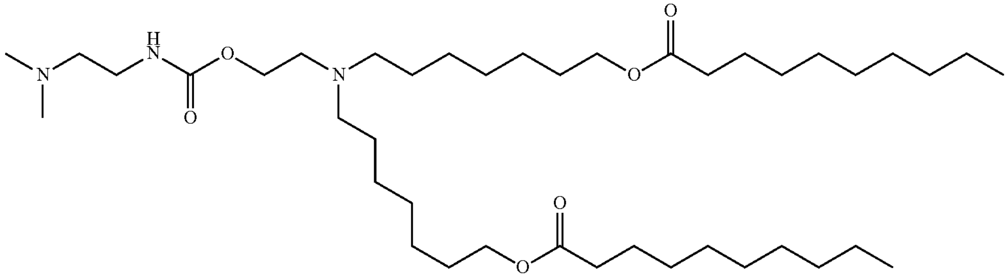 [SMILES: CCCCCCCCCC(=O)OCCCCCCCN(CCCCCCCOC(=O)CCCCCCCCC)CCOC(=O)NCCN(C)C] | 712.1 |

TABLE 1-continued
| # | Structure | Mw |
| --- | --- | --- |
| 176. | 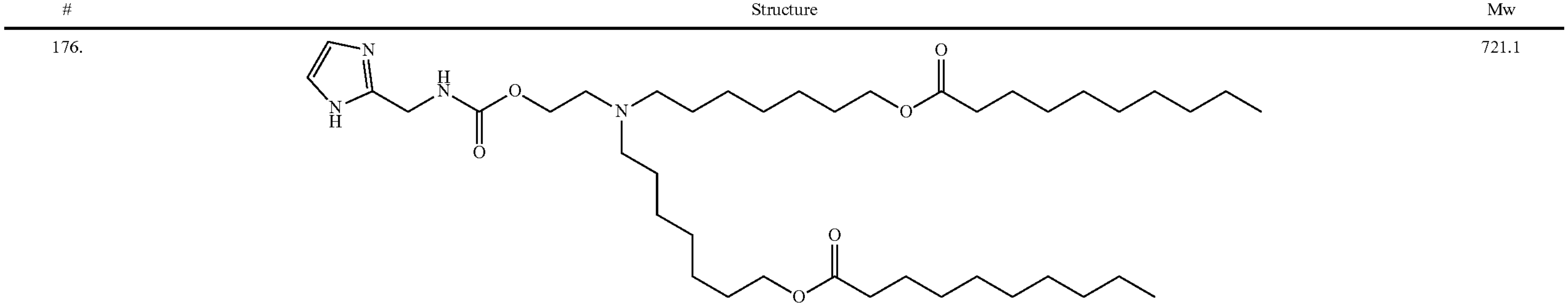 | 721.1 |
| 177. | 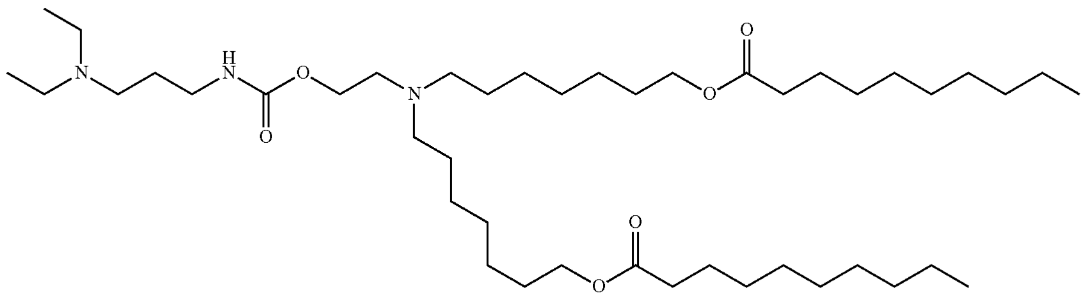 [SMILES: CCCCCCCCCC(=O)OCCCCCCCN(CCCCCCCOC(=O)CCCCCCCCC)CCOC(=O)NCCCN(CC)CC] | 754.2 |
| 178. | 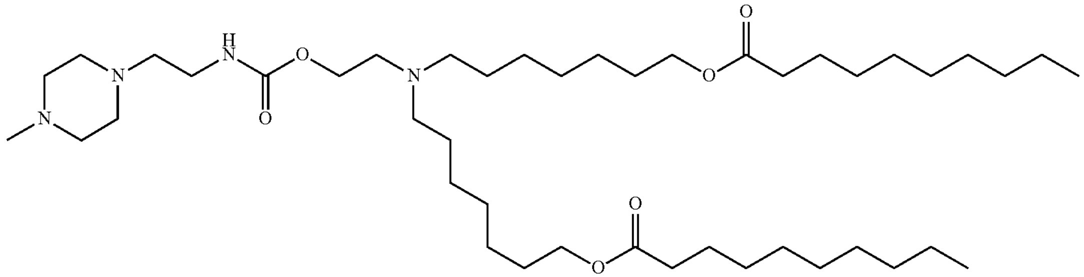 [SMILES: CCCCCCCCCC(=O)OCCCCCCCN(CCCCCCCOC(=O)CCCCCCCCC)CCOC(=O)NCCN1CCN(C)CC1] | 767.2 |

TABLE 1-continued
| # | Structure | Mw |
|---|---|---|
| 179. | 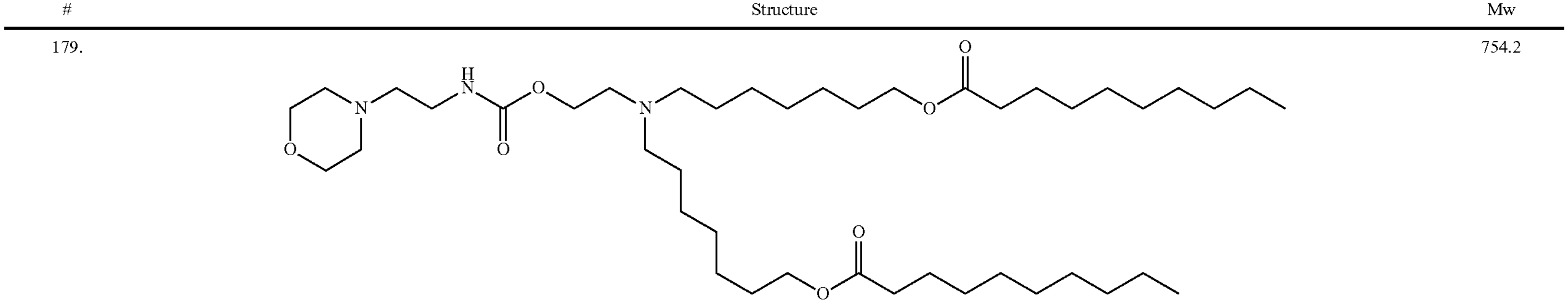 | 754.2 |
| 180. | 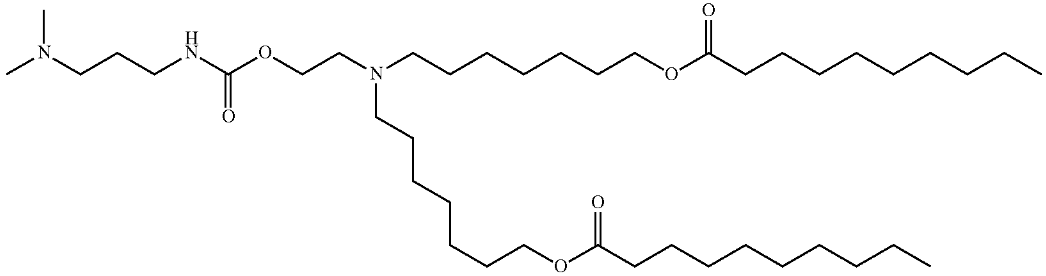 [SMILES: CCCCCCCCCC(=O)OCCCCCCCN(CCCCCCCOC(=O)CCCCCCCCC)CCOC(=O)NCCCN(C)C] | 726.1 |
| 181. | 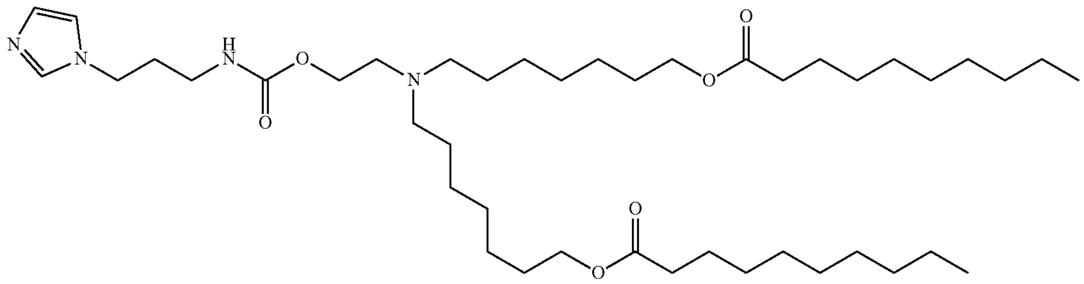 [SMILES: CCCCCCCCCC(=O)OCCCCCCCN(CCCCCCCOC(=O)CCCCCCCCC)CCOC(=O)NCCCn1ccnc1] | 749.1 |

TABLE 1-continued
| # | Structure | Mw |
|---|---|---|
| 182. | 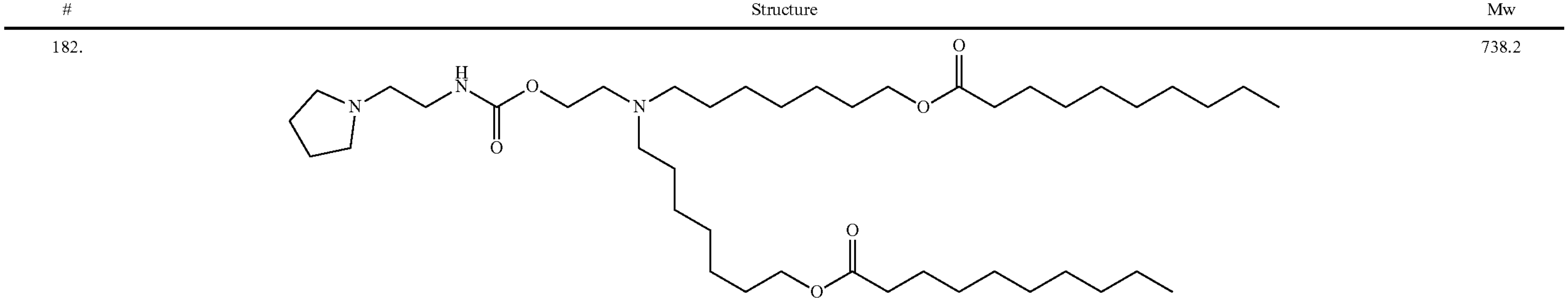 | 738.2 |
| 183. | 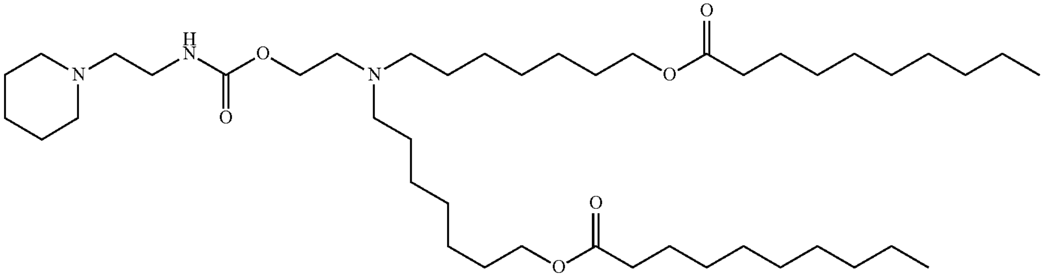 [SMILES: CCCCCCCCCC(=O)OCCCCCCCN(CCCCCCCOC(=O)CCCCCCCCC)CCOC(=O)NCCN1CCCCC1] | 752.2 |
| 184. | 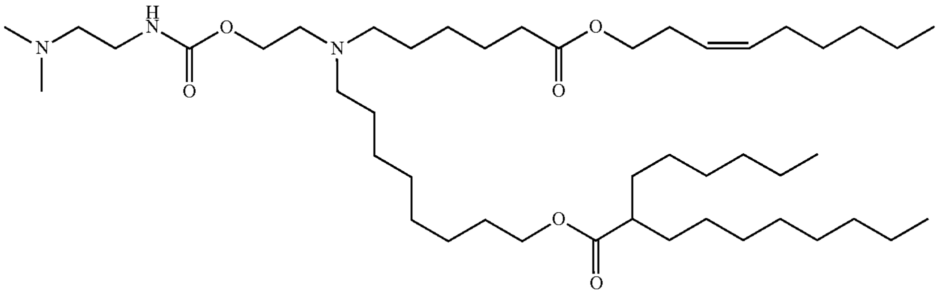 | 780.2 |

TABLE 1-continued
| # | Structure | Mw |
|---|---|---|
| 185. | 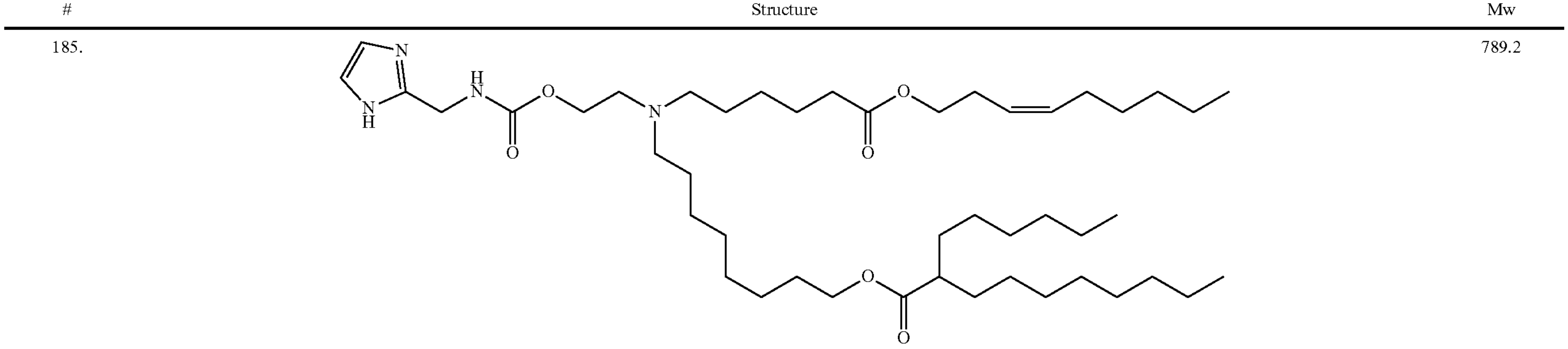 | 789.2 |
| 186. | 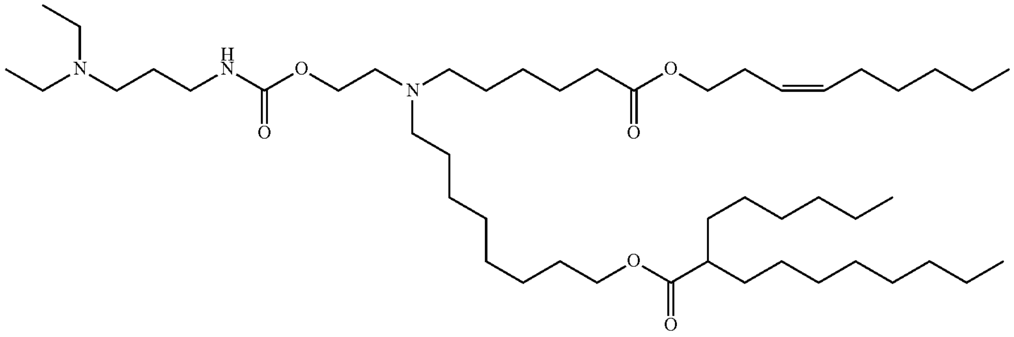 [SMILES: CCCCC/C=C\CCOC(=O)CCCCCN(CCCCCCCCOC(=O)C(CCCCCC)CCCCCCCC)CCOC(=O)NCCCN(CC)CC] | 822.3 |
| 187. | 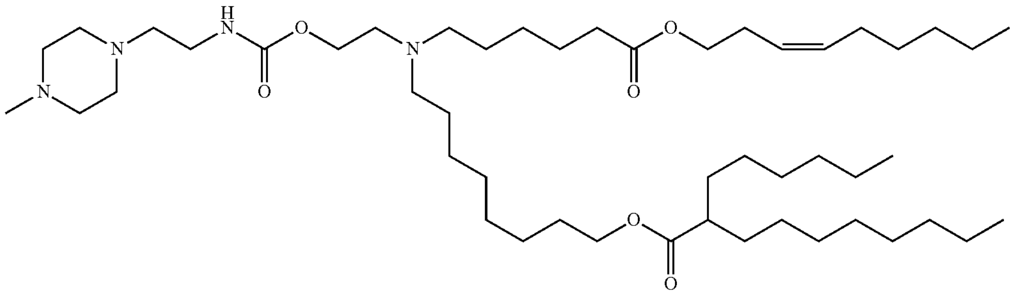 [SMILES: CCCCC/C=C\CCOC(=O)CCCCCN(CCCCCCCCOC(=O)C(CCCCCC)CCCCCCCC)CCOC(=O)NCCN1CCN(C)CC1] | 835.3 |

TABLE 1-continued
| # | Structure | Mw |
| --- | --- | --- |
| 188. | 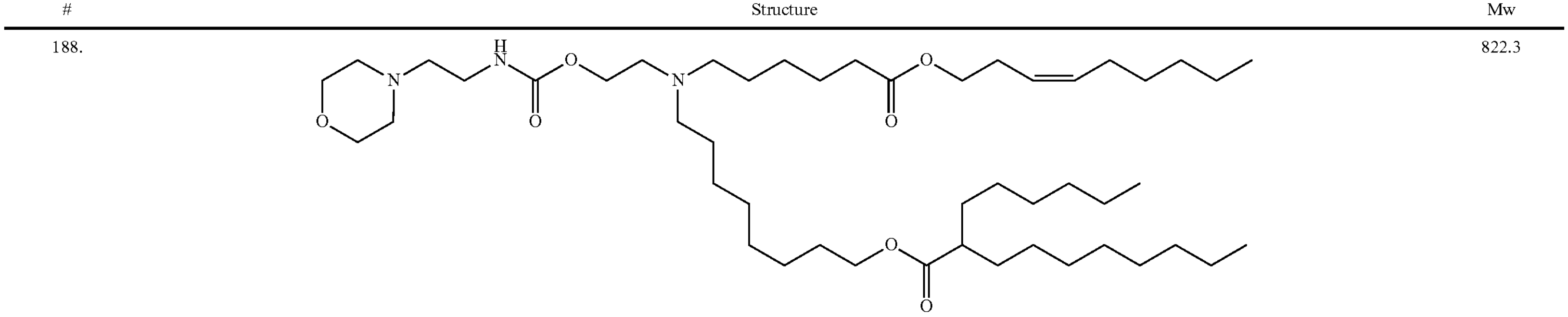 | 822.3 |
| 189. | 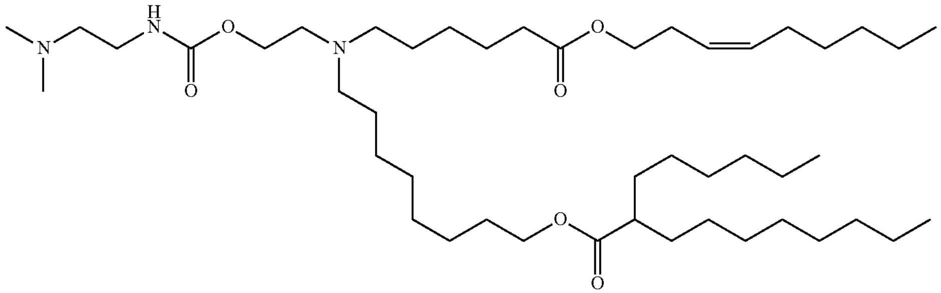 [SMILES: CCCCC/C=C\CCOC(=O)CCCCCN(CCCCCCCCOC(=O)C(CCCCCC)CCCCCCCC)CCOC(=O)NCCN(C)C] | 794.3 |
| 190. | 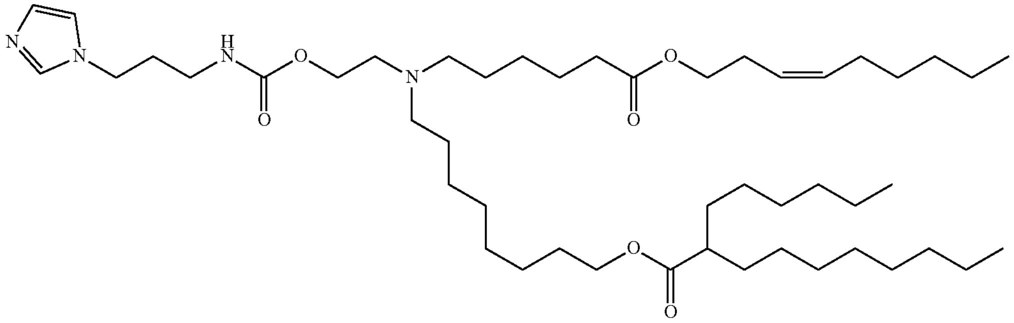 [SMILES: CCCCC/C=C\CCOC(=O)CCCCCN(CCCCCCCCOC(=O)C(CCCCCC)CCCCCCCC)CCOC(=O)NCCCn1ccnc1] | 817.3 |

TABLE 1-continued
| # | Structure | Mw |
|---|---|---|
| 191. | 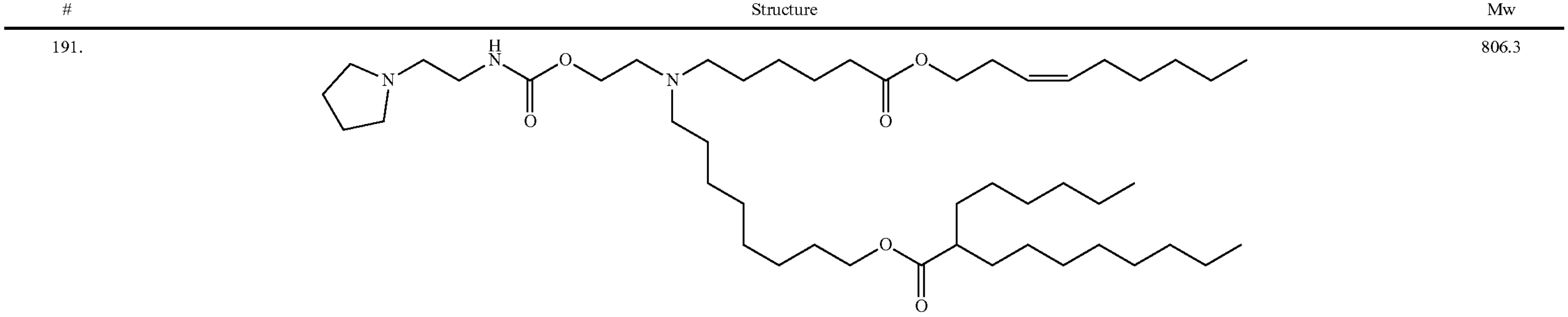 | 806.3 |
| 192. | 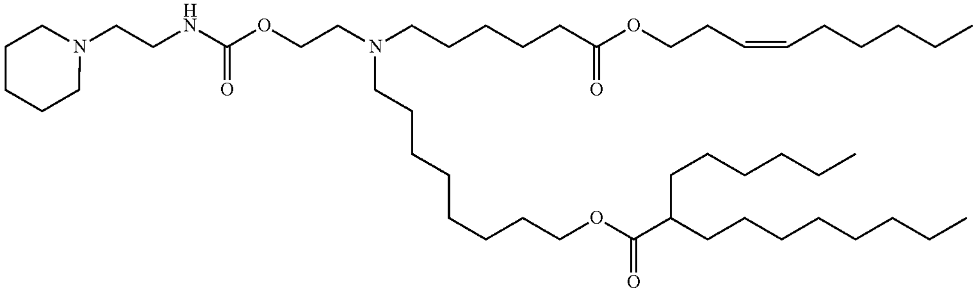 [SMILES: CCCCC/C=C\CCOC(=O)CCCCCN(CCCCCCCCOC(=O)C(CCCCCC)CCCCCCCC)CCOC(=O)NCCN1CCCCC1] | 820.3 |
| 193. | 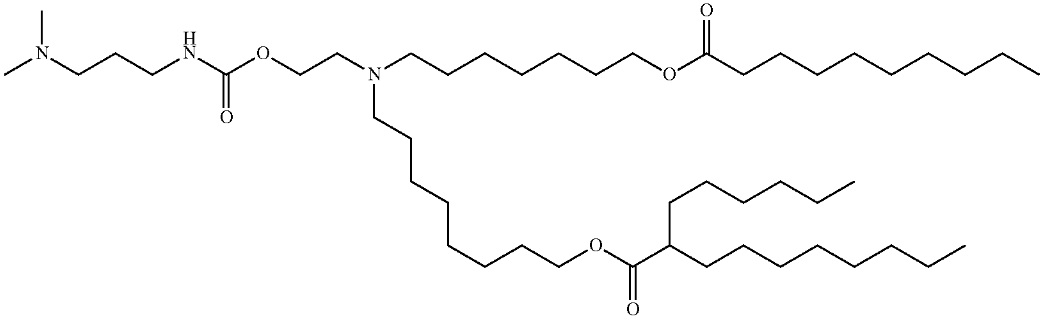 [SMILES: CCCCCCCCCC(=O)OCCCCCCCN(CCCCCCCCOC(=O)C(CCCCCC)CCCCCCCC)CCOC(=O)NCCCN(C)C] | 824.3 |

TABLE 1-continued
| # | Structure | Mw |
|---|---|---|
| 194. | 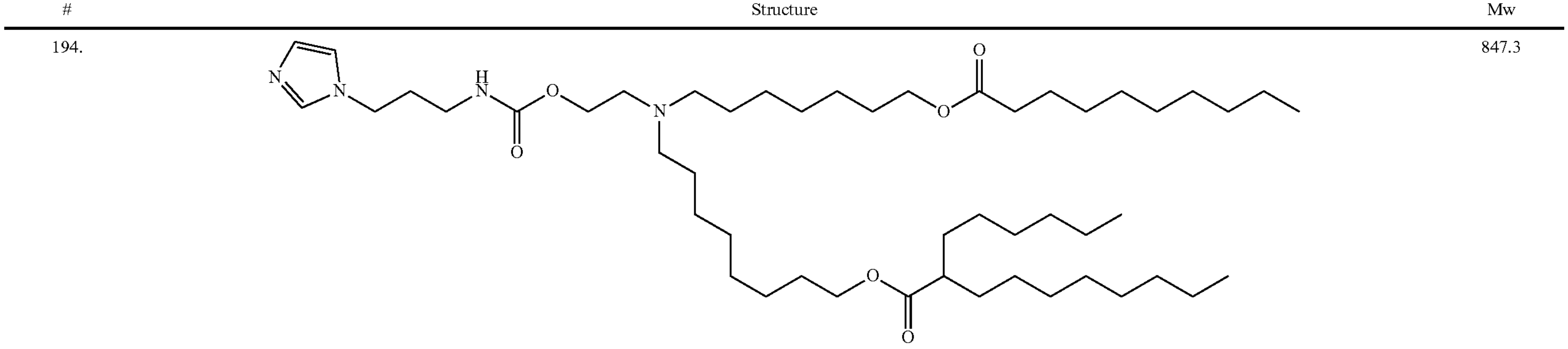 | 847.3 |
| 195. | 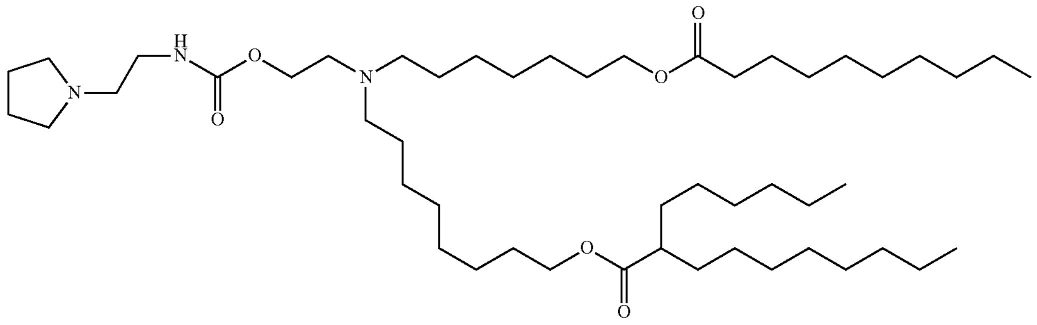 [SMILES: CCCCCCCCCC(=O)OCCCCCCCN(CCCCCCCCOC(=O)C(CCCCCC)CCCCCCCC)CCOC(=O)NCCN1CCCC1] | 836.3 |
| 196. | 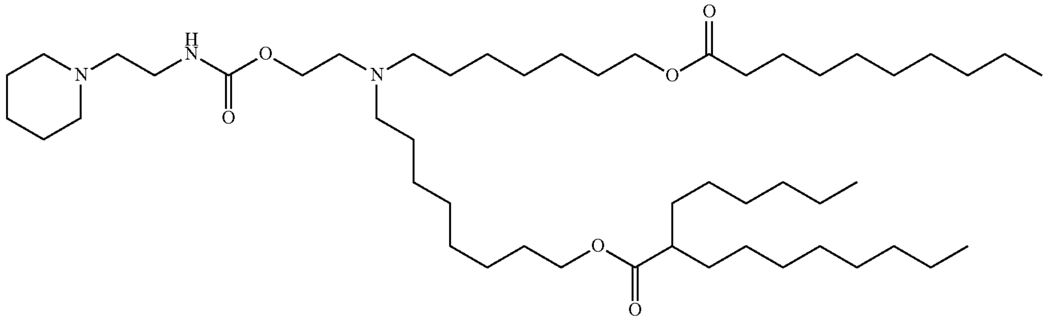 [SMILES: CCCCCCCCCC(=O)OCCCCCCCN(CCCCCCCCOC(=O)C(CCCCCC)CCCCCCCC)CCOC(=O)NCCN1CCCCC1] | 850.4 |

TABLE 1-continued
| # | Structure | Mw |
| --- | --- | --- |
| 197. | 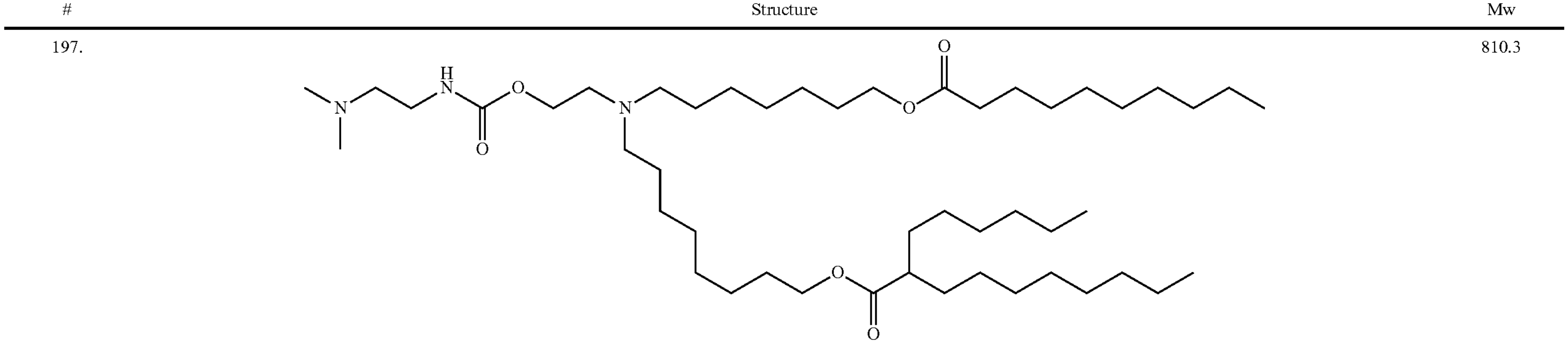 | 810.3 |
| 198. | 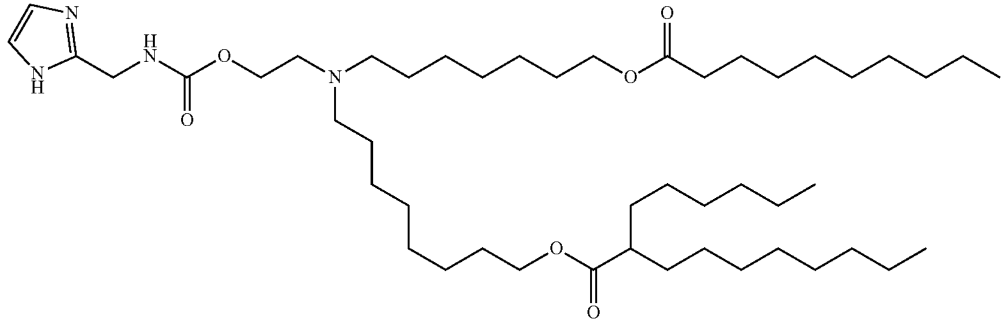 [SMILES: CCCCCCCCCC(=O)OCCCCCCCN(CCCCCCCCOC(=O)C(CCCCCC)CCCCCCCC)CCOC(=O)NCc1ncc[nH]1] | 819.3 |
| 199. | 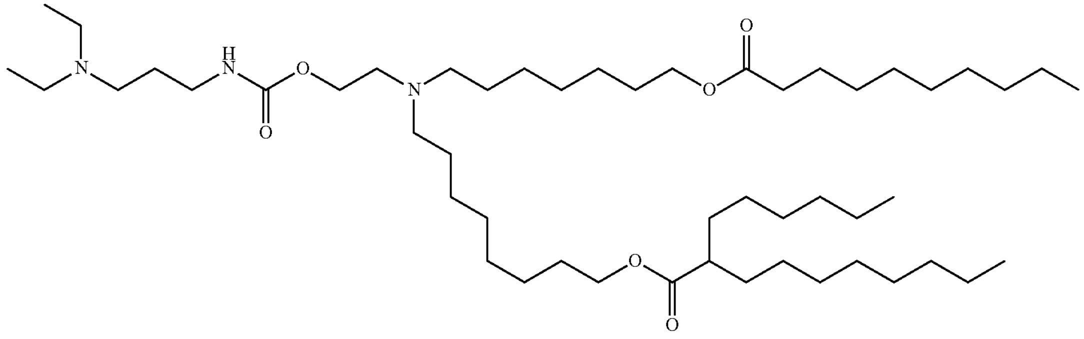 [SMILES: CCCCCCCCCC(=O)OCCCCCCCN(CCCCCCCCOC(=O)C(CCCCCC)CCCCCCCC)CCOC(=O)NCCCN(CC)CC] | 852.4 |

TABLE 1-continued
| # | Structure | Mw |
|---|---|---|
| 200. | 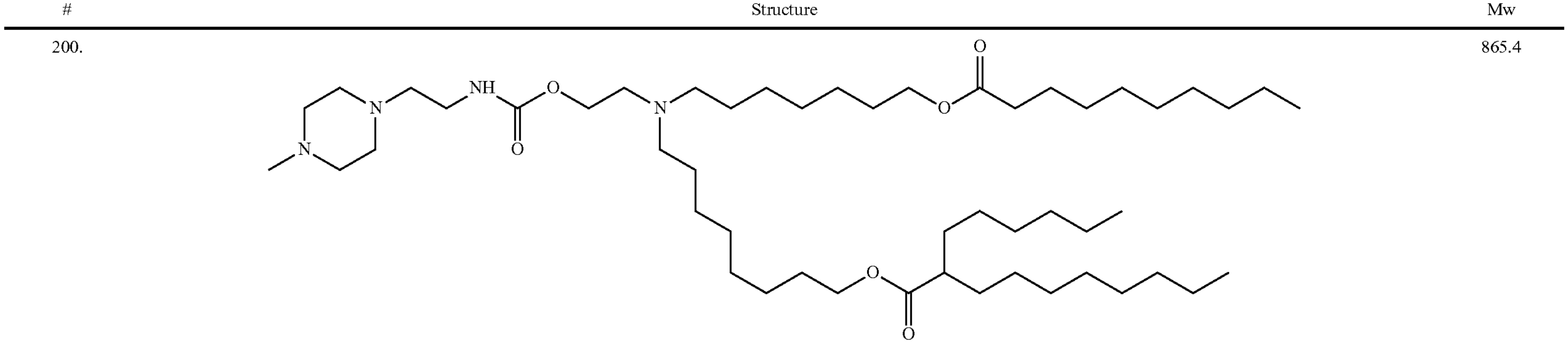 | 865.4 |
| 201. | 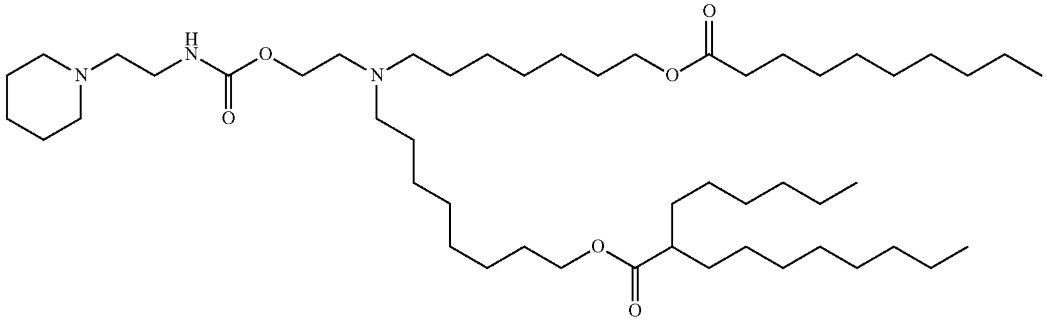 [SMILES: CCCCCCCCCC(=O)OCCCCCCCN(CCCCCCCCOC(=O)C(CCCCCC)CCCCCCCC)CCOC(=O)NCCN1CCCCC1] | 852.3 |
| 202. | 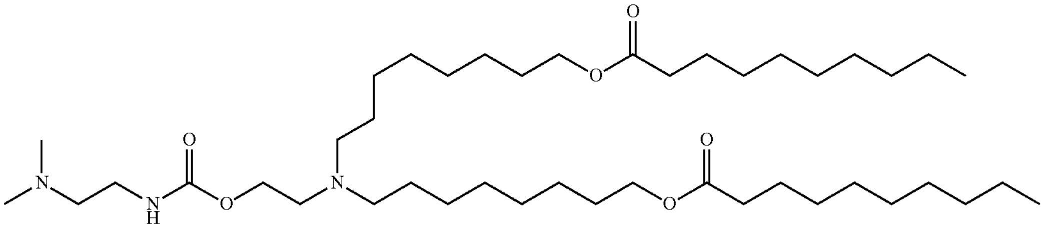 [SMILES: CCCCCCCCCC(=O)OCCCCCCCCN(CCCCCCCCOC(=O)CCCCCCCCC)CCOC(=O)NCCN(C)C] | 740.2 |

TABLE 1-continued
| # | Structure | Mw |
| --- | --- | --- |
| 203. | 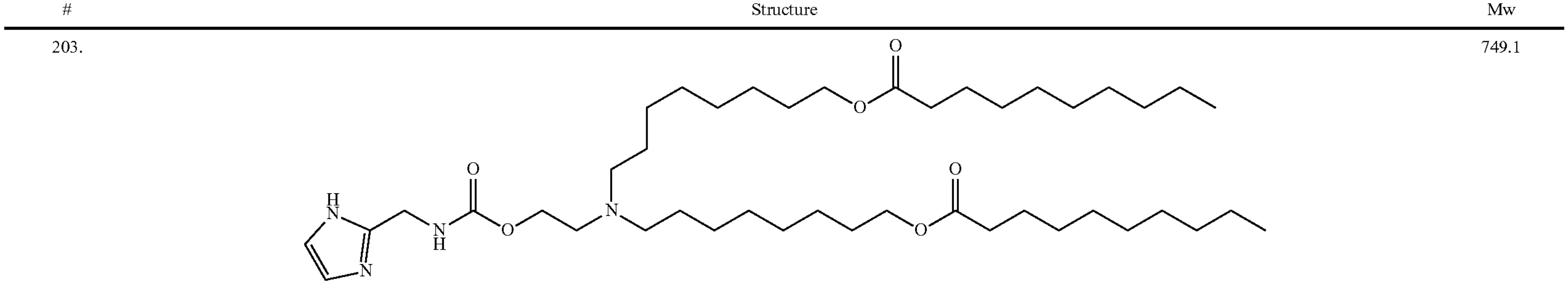 | 749.1 |
| 204. | 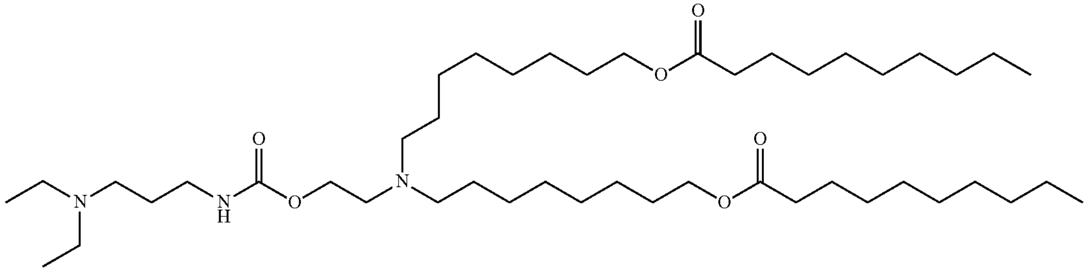 [SMILES: CCCCCCCCCC(=O)OCCCCCCCCN(CCCCCCCCOC(=O)CCCCCCCCC)CCOC(=O)NCCCN(CC)CC] | 782.2 |
| 205. | 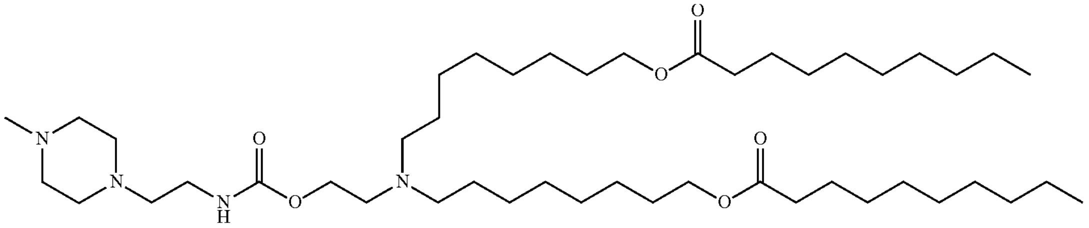 [SMILES: CCCCCCCCCC(=O)OCCCCCCCCN(CCCCCCCCOC(=O)CCCCCCCCC)CCOC(=O)NCCN1CCN(C)CC1] | 795.2 |
| 206. | 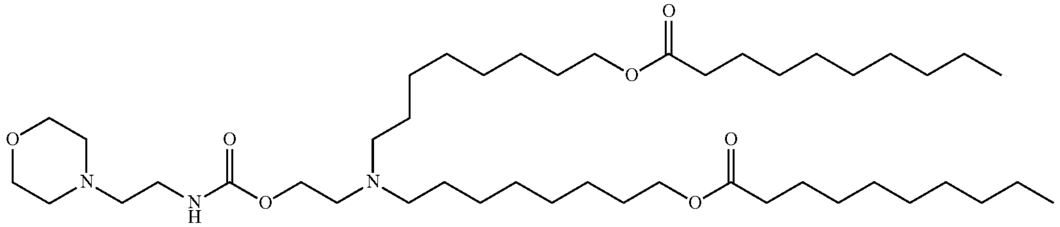 [SMILES: CCCCCCCCCC(=O)OCCCCCCCCN(CCCCCCCCOC(=O)CCCCCCCCC)CCOC(=O)NCCN1CCOCC1] | 782.2 |

TABLE 1-continued
| # | Structure | Mw |
| --- | --- | --- |
| 207. | 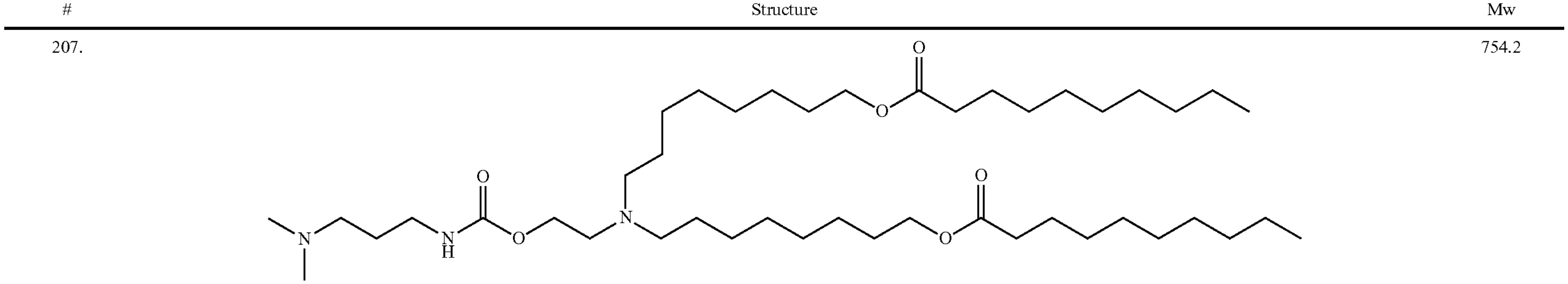 | 754.2 |
| 208. | 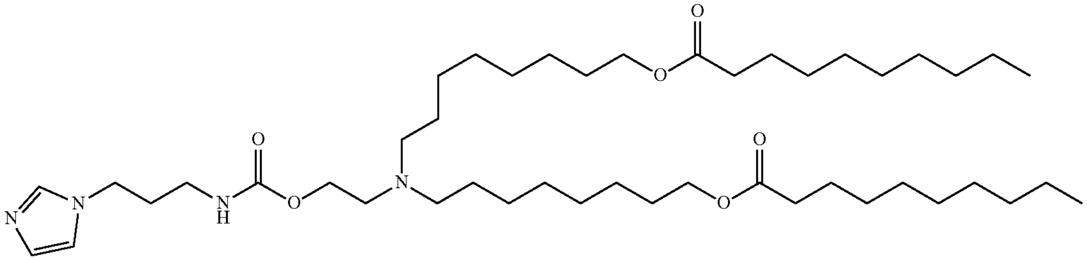 [SMILES: CCCCCCCCCC(=O)OCCCCCCCCN(CCCCCCCCOC(=O)CCCCCCCCC)CCOC(=O)NCCCn1ccnc1] | 777.2 |
| 209. | 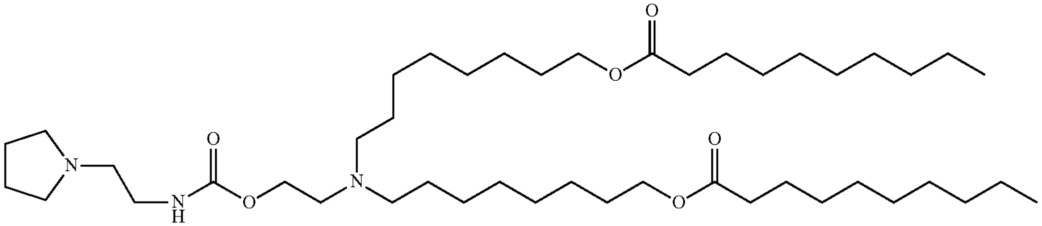 [SMILES: CCCCCCCCCC(=O)OCCCCCCCCN(CCCCCCCCOC(=O)CCCCCCCCC)CCOC(=O)NCCN1CCCC1] | 766.2 |
| 210. | 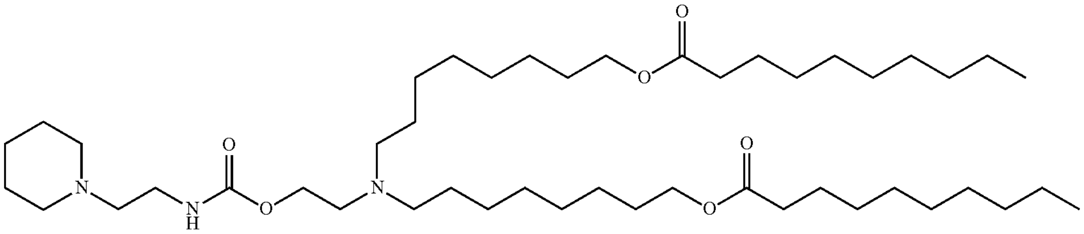 [SMILES: CCCCCCCCCC(=O)OCCCCCCCCN(CCCCCCCCOC(=O)CCCCCCCCC)CCOC(=O)NCCN1CCCCC1] | 780.2 |

TABLE 1-continued
| # | Structure | Mw |
|---|---|---|
| 211. | 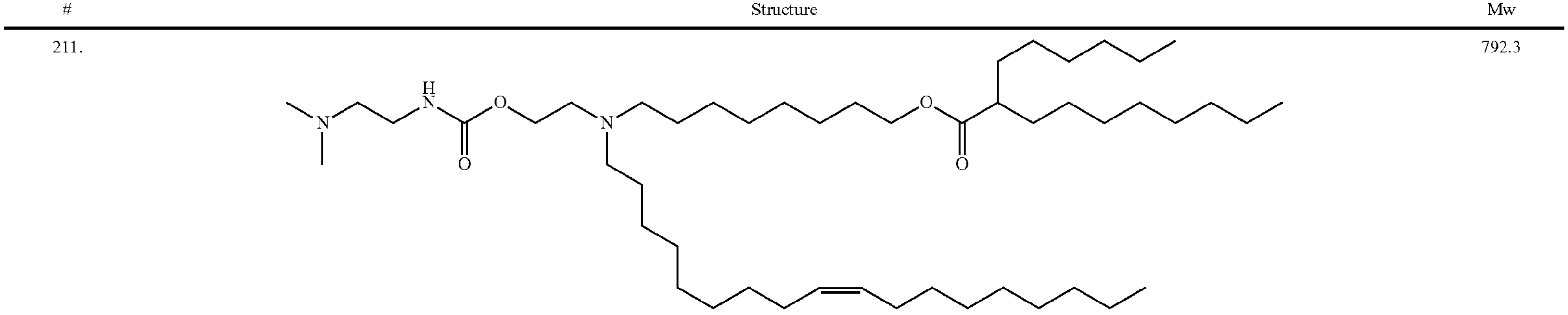 | 792.3 |
| 212. | 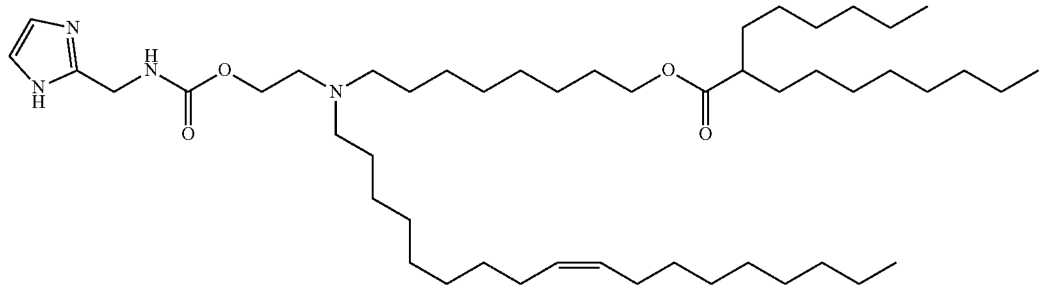 [SMILES: CCCCCCCC/C=C\CCCCCCCCN(CCCCCCCCOC(=O)C(CCCCCC)CCCCCCCC)CCOC(=O)NCc1ncc[nH]1] | 801.3 |
| 213. | 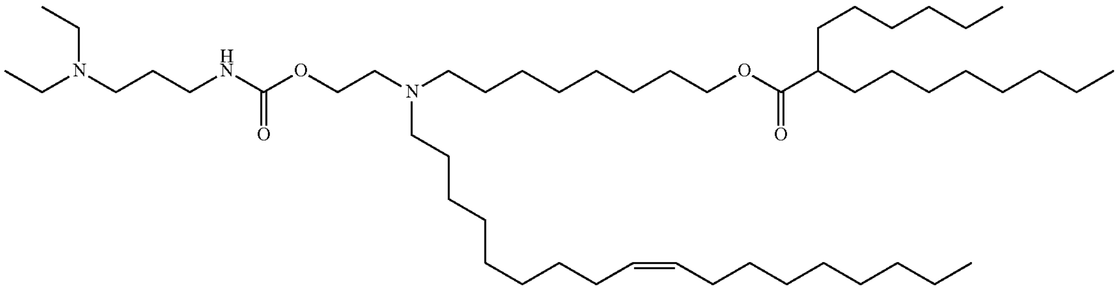 [SMILES: CCCCCCCC/C=C\CCCCCCCCN(CCCCCCCCOC(=O)C(CCCCCC)CCCCCCCC)CCOC(=O)NCCCN(CC)CC] | 834.4 |

TABLE 1-continued
| # | Structure | Mw |
|---|---|---|
| 214. | 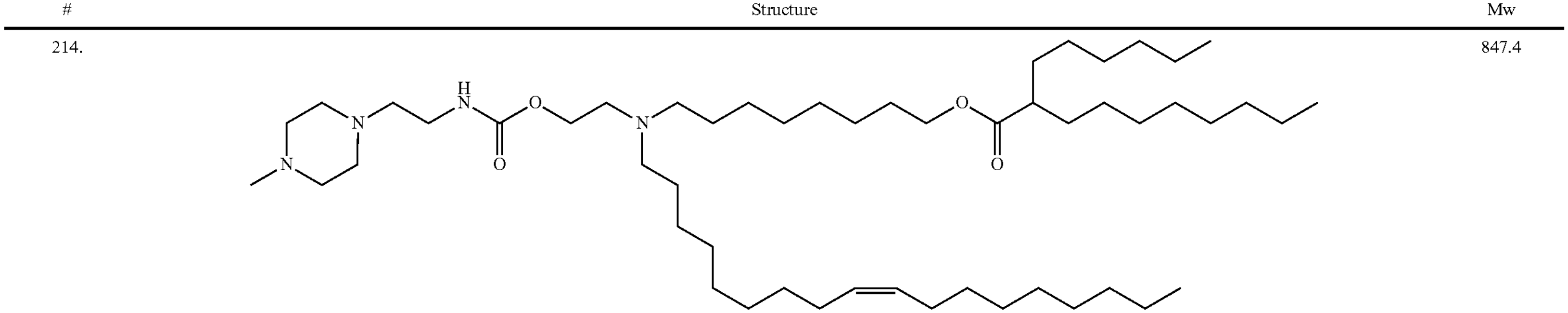 | 847.4 |
| 215. | 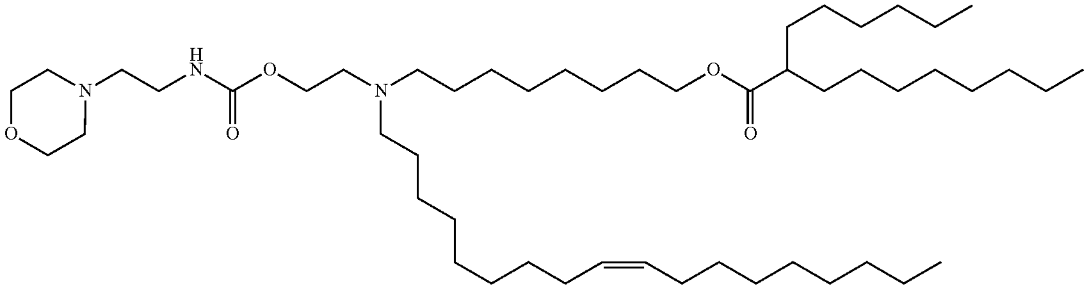 [SMILES: CCCCCCCC/C=C\CCCCCCCCN(CCCCCCCCOC(=O)C(CCCCCC)CCCCCCCC)CCOC(=O)NCCN1CCOCC1] | 834.4 |
| 216. | 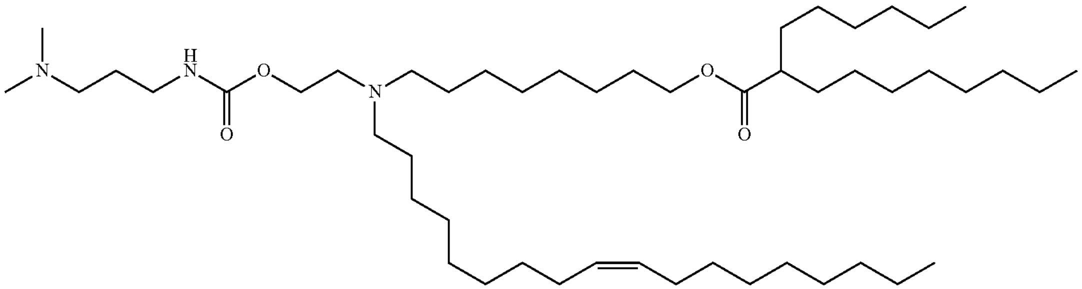 | 806.4 |

TABLE 1-continued
| # | Structure | Mw |
|---|---|---|
| 217. | 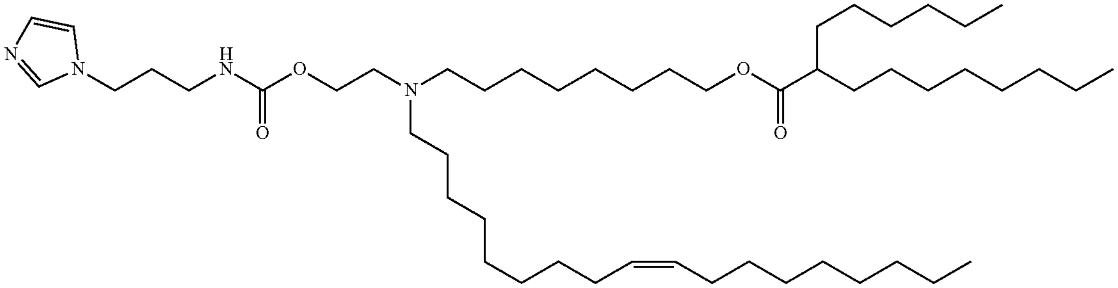 [SMILES: CCCCCCCC/C=C\CCCCCCCCN(CCCCCCCCOC(=O)C(CCCCCC)CCCCCCCC)CCOC(=O)NCCCn1ccnc1] | 829.4 |
| 218. | 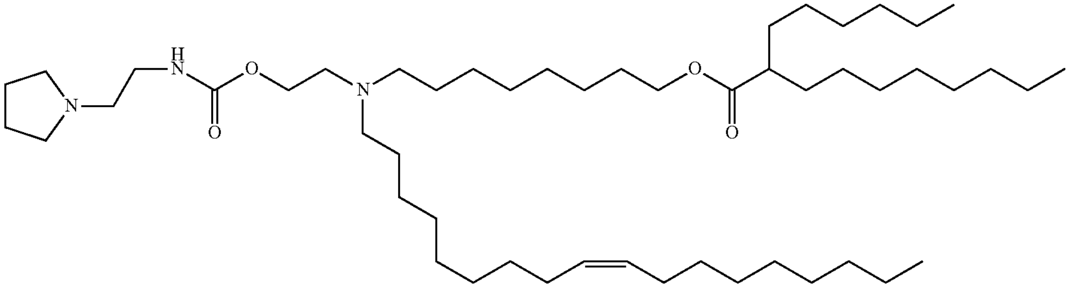 [SMILES: CCCCCCCC/C=C\CCCCCCCCN(CCCCCCCCOC(=O)C(CCCCCC)CCCCCCCC)CCOC(=O)NCCN1CCCC1] | 818.4 |
| 219. | 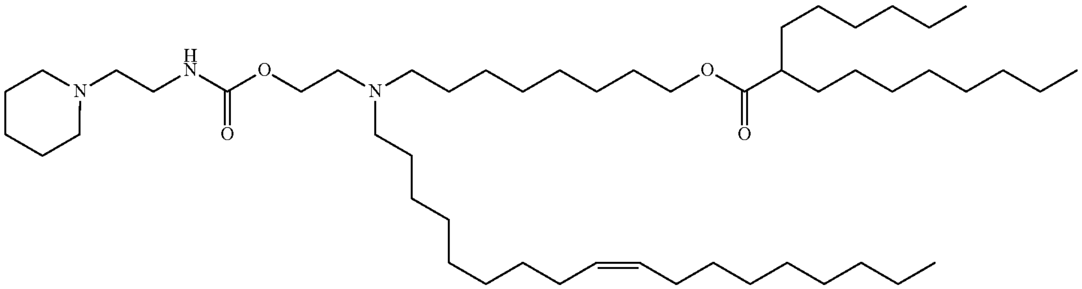 [SMILES: CCCCCCCC/C=C\CCCCCCCCN(CCCCCCCCOC(=O)C(CCCCCC)CCCCCCCC)CCOC(=O)NCCN1CCCCC1] | 832.4 |

TABLE 1-continued
| # | Structure | Mw |
| --- | --- | --- |
| 220. | 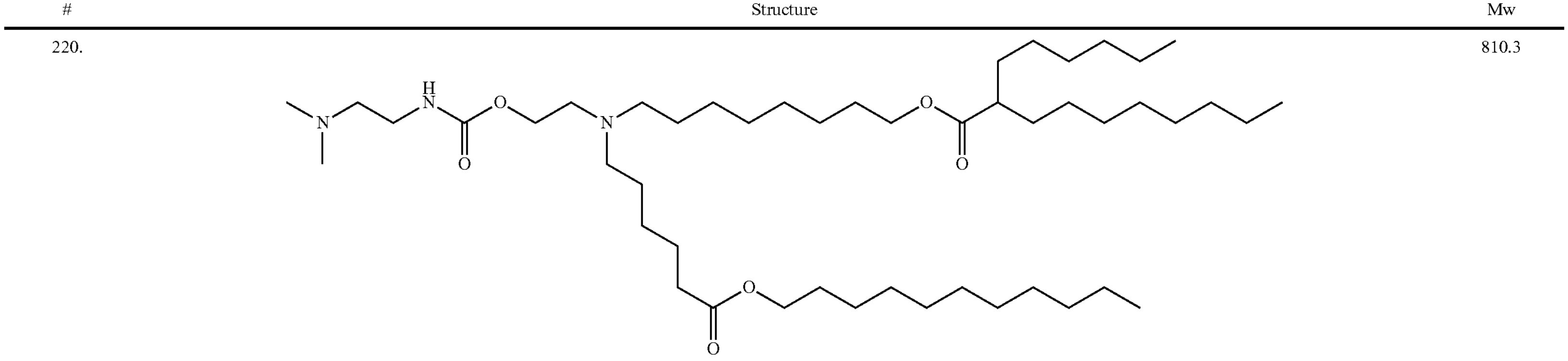 | 810.3 |
| 221. | 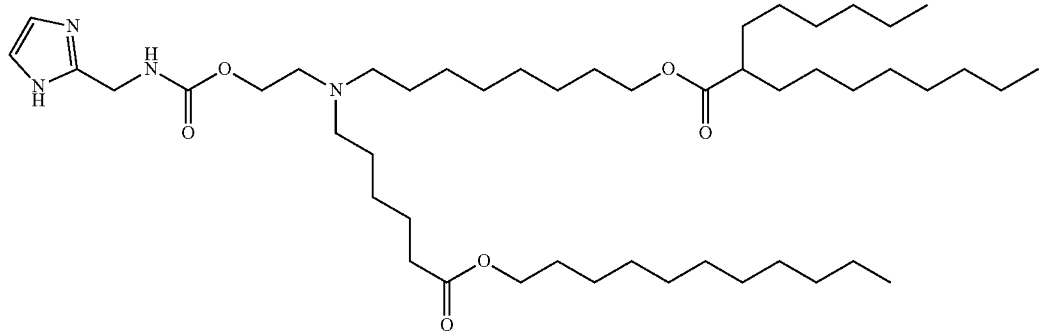 [SMILES: CCCCCCCCCCCOC(=O)CCCCCN(CCCCCCCCOC(=O)C(CCCCCC)CCCCCCCC)CCOC(=O)NCc1ncc[nH]1] | 819.3 |
| 222. | 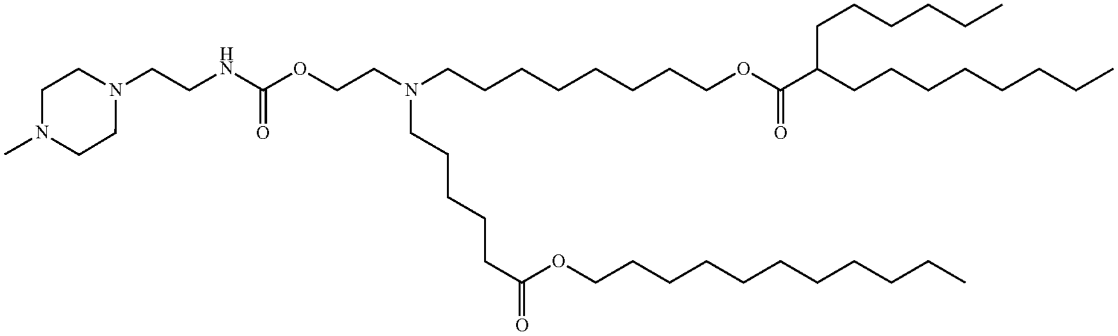 [SMILES: CCCCCCCCCCCOC(=O)CCCCCN(CCCCCCCCOC(=O)C(CCCCCC)CCCCCCCC)CCOC(=O)NCCN1CCN(C)CC1] | 865.4 |

TABLE 1-continued
| # | Structure | Mw |
|---|---|---|
| 223. | 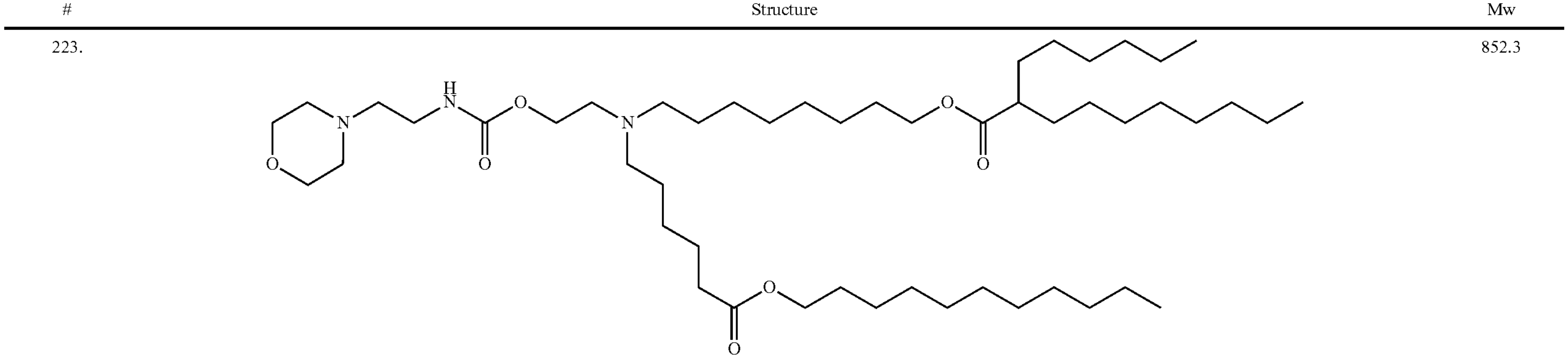 | 852.3 |
| 224. | 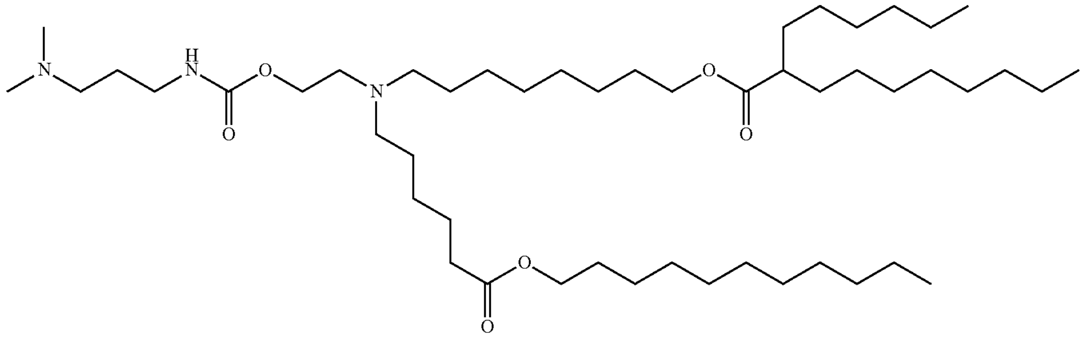 [SMILES: CCCCCCCCCCCOC(=O)CCCCCN(CCCCCCCCOC(=O)C(CCCCCC)CCCCCCCC)CCOC(=O)NCCCN(C)C] | 824.3 |
| 225. | 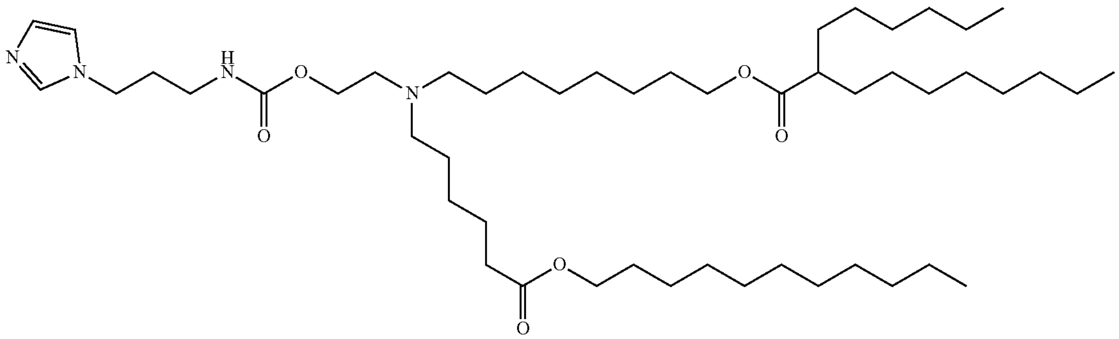 [SMILES: CCCCCCCCCCCOC(=O)CCCCCN(CCCCCCCCOC(=O)C(CCCCCC)CCCCCCCC)CCOC(=O)NCCCn1ccnc1] | 847.3 |

TABLE 1-continued
| # | Structure | Mw |
|---|---|---|
| 226. | 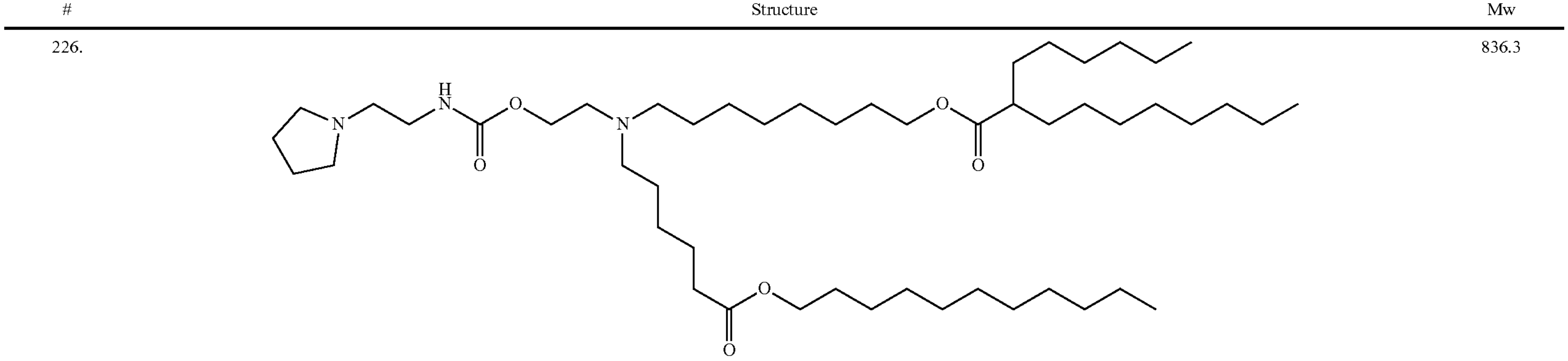 | 836.3 |
| 227. | 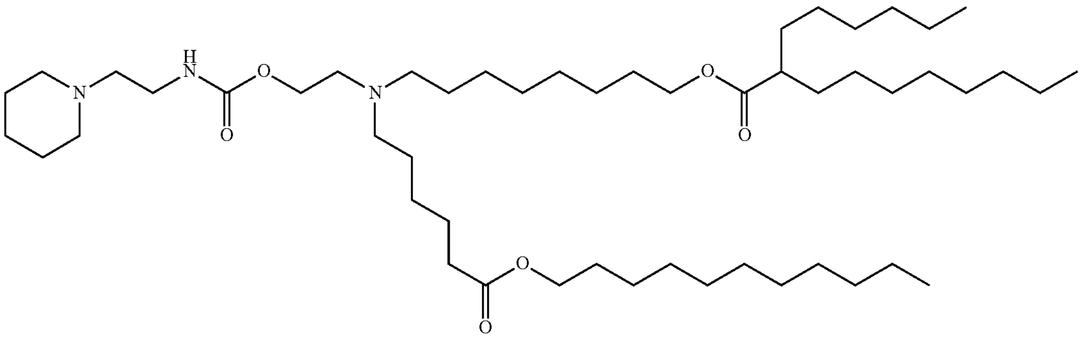 [SMILES: CCCCCCCCCCCOC(=O)CCCCCN(CCCCCCCCOC(=O)C(CCCCCC)CCCCCCCC)CCOC(=O)NCCN1CCCCC1] | 850.4 |
| 228. | 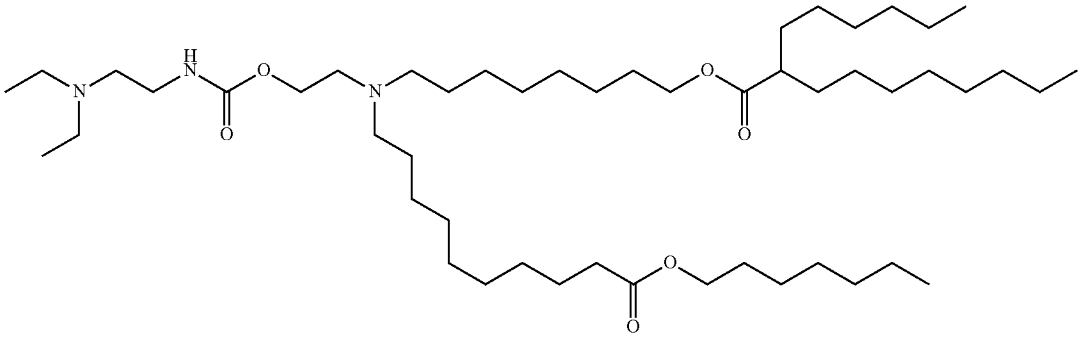 [SMILES: CCCCCCCCC(CCCCCC)C(=O)OCCCCCCCCN(CCCCCCCCCC(=O)OCCCCCCC)CCOC(=O)NCCN(CC)CC] | 838.4 |

TABLE 1-continued
| # | Structure | Mw |
| --- | --- | --- |
| 229. | 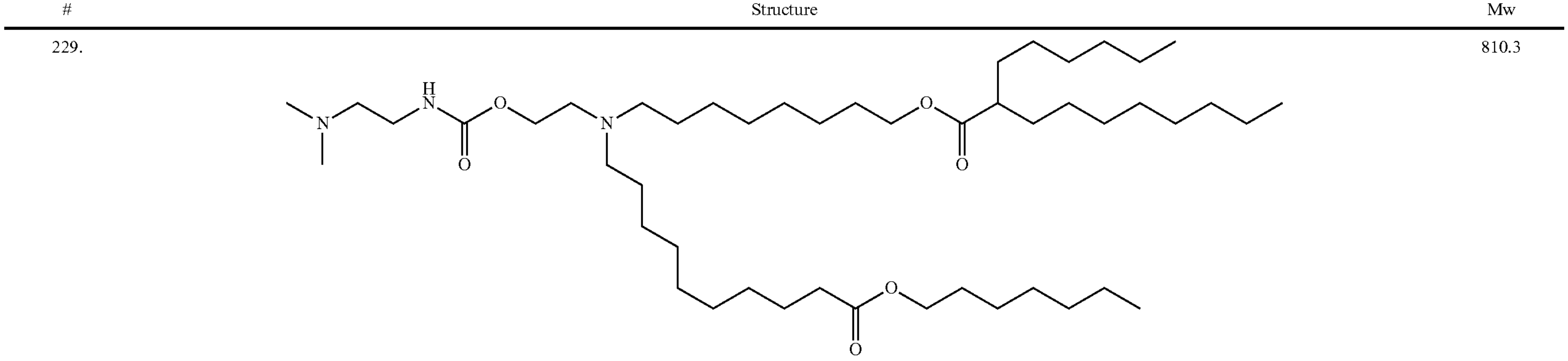 | 810.3 |
| 230. | 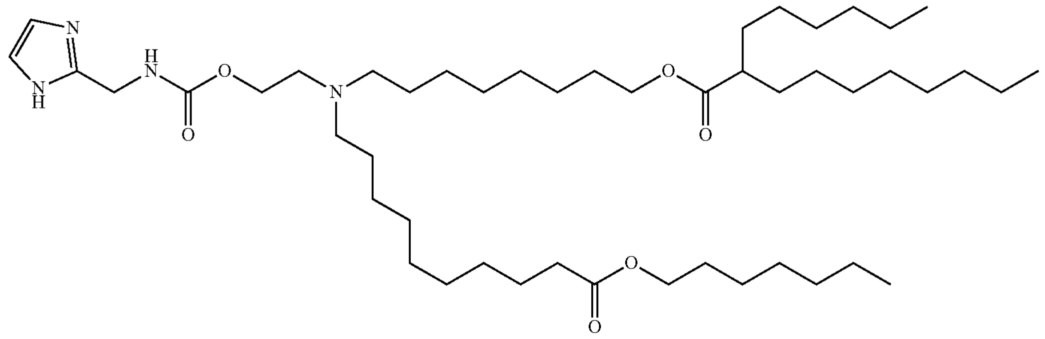 [SMILES: CCCCCCCCC(CCCCCC)C(=O)OCCCCCCCCN(CCCCCCCCCC(=O)OCCCCCCC)CCOC(=O)NCc1ncc[nH]1] | 819.3 |
| 231. | 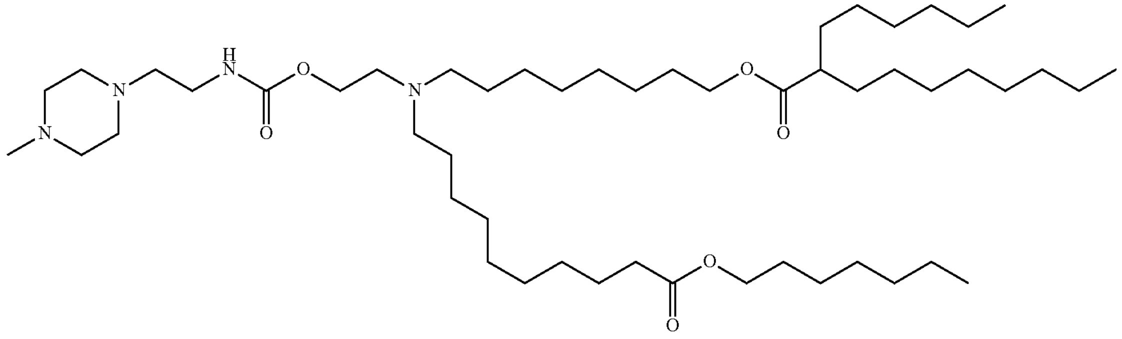 [SMILES: CCCCCCCCC(CCCCCC)C(=O)OCCCCCCCCN(CCCCCCCCCC(=O)OCCCCCCC)CCOC(=O)NCCN1CCN(C)CC1] | 865.4 |

TABLE 1-continued
| # | Structure | Mw |
|---|---|---|
| 232. | 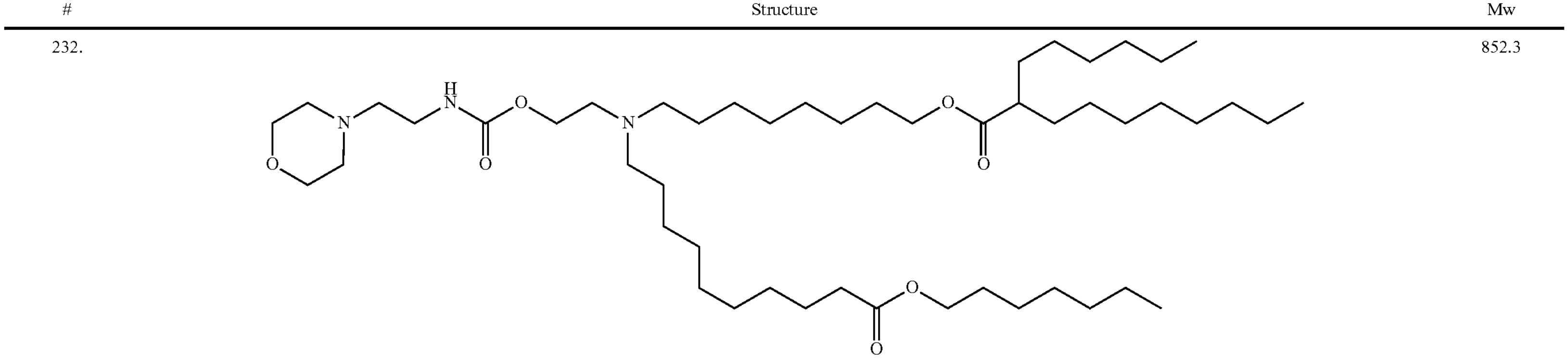 | 852.3 |
| 233. | 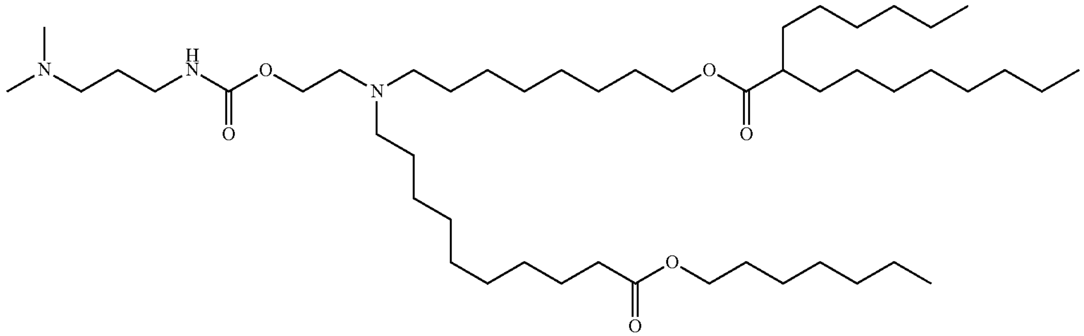 [SMILES: CCCCCCCCC(CCCCCC)C(=O)OCCCCCCCCN(CCCCCCCCCC(=O)OCCCCCCC)CCOC(=O)NCCCN(C)C] | 824.3 |
| 234. | 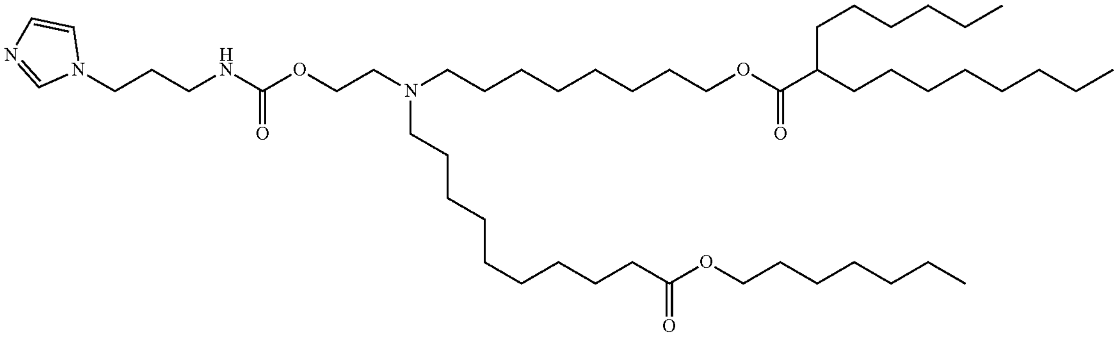 [SMILES: CCCCCCCCC(CCCCCC)C(=O)OCCCCCCCCN(CCCCCCCCCC(=O)OCCCCCCC)CCOC(=O)NCCCn1ccnc1] | 847.3 |

TABLE 1-continued
| # | Structure | Mw |
|---|---|---|
| 235. | 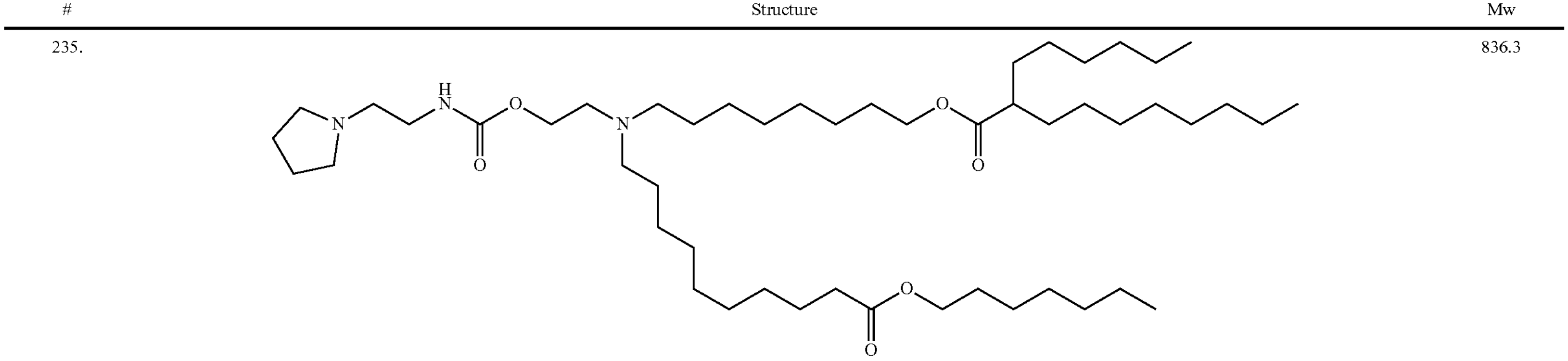 | 836.3 |
| 236. | 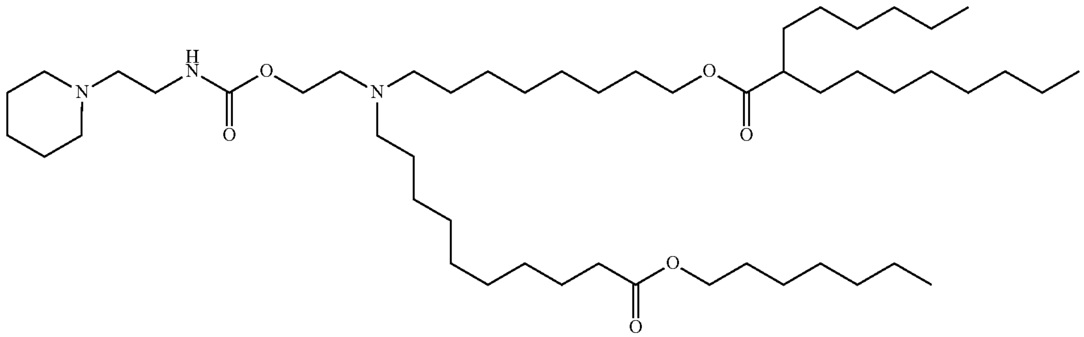 [SMILES: CCCCCCCCC(CCCCCC)C(=O)OCCCCCCCCN(CCCCCCCCCC(=O)OCCCCCCC)CCOC(=O)NCCN1CCCCC1] | 850.4 |
| 237. | 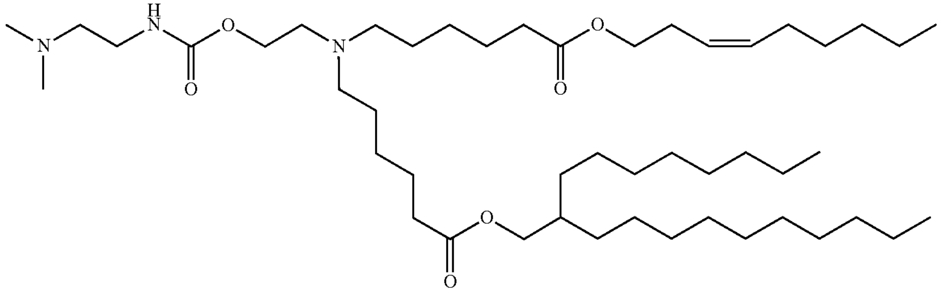 [SMILES: CCCCC/C=C\CCOC(=O)CCCCCN(CCCCCC(=O)OCC(CCCCCCCC)CCCCCCCCCC)CCOC(=O)NCCN(C)C] | 808.3 |

TABLE 1-continued
| # | Structure | Mw |
|---|---|---|
| 238. | 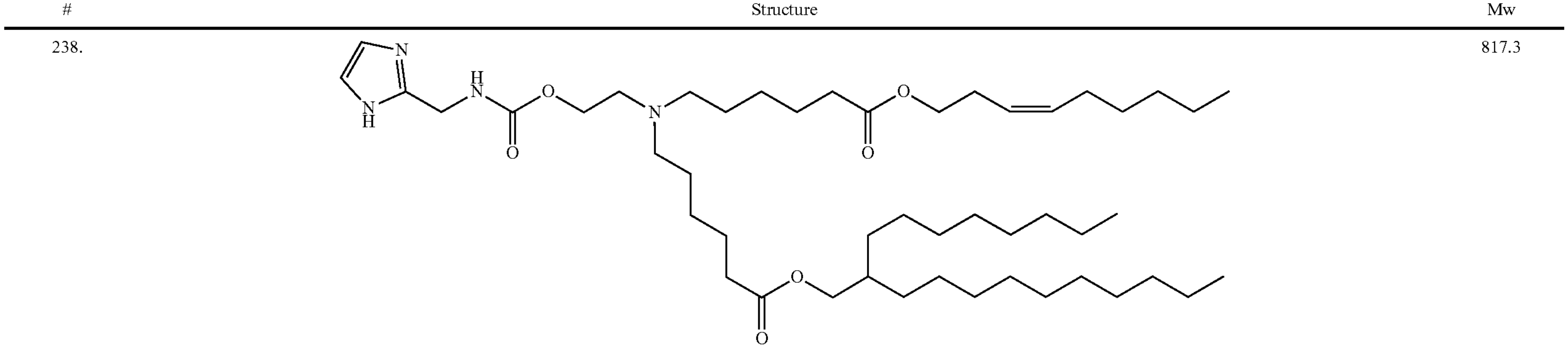 | 817.3 |
| 239. | 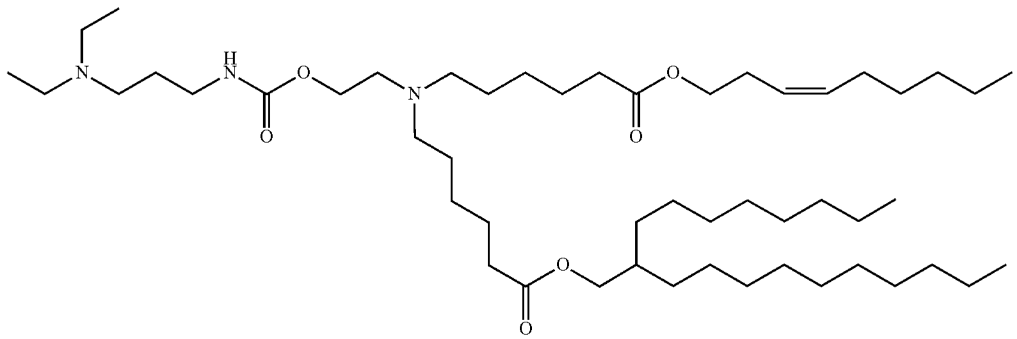 [SMILES: CCCCC/C=C\CCOC(=O)CCCCCN(CCCCCC(=O)OCC(CCCCCCCC)CCCCCCCCCC)CCOC(=O)NCCCN(CC)CC] | 850.4 |
| 240. | 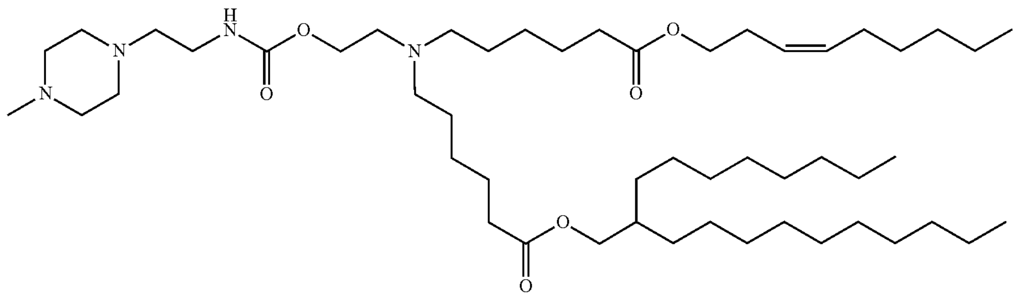 [SMILES: CCCCC/C=C\CCOC(=O)CCCCCN(CCCCCC(=O)OCC(CCCCCCCC)CCCCCCCCCC)CCOC(=O)NCCN1CCN(C)CC1] | 863.4 |

TABLE 1-continued
| # | Structure | Mw |
|---|---|---|
| 241. | 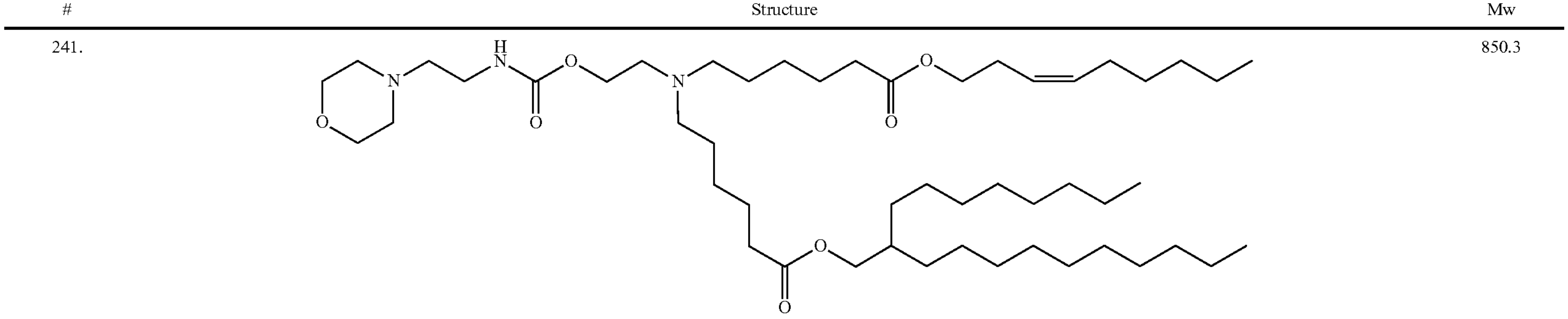 | 850.3 |
| 242. | 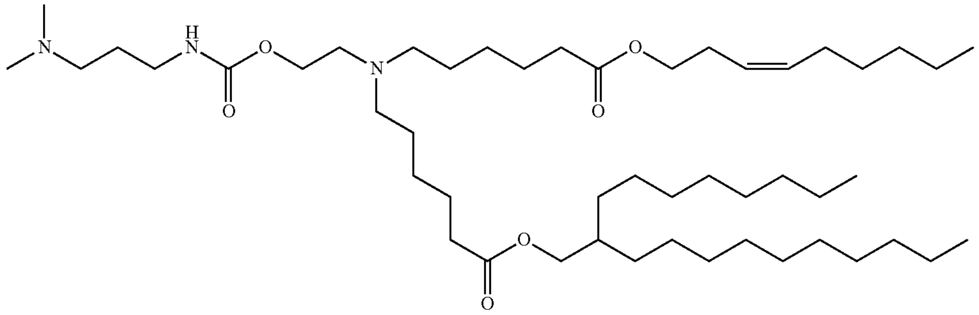 [SMILES: CCCCC/C=C\CCOC(=O)CCCCCN(CCCCCC(=O)OCC(CCCCCCCC)CCCCCCCCCC)CCOC(=O)NCCCN(C)C] | 822.3 |
| 243. | 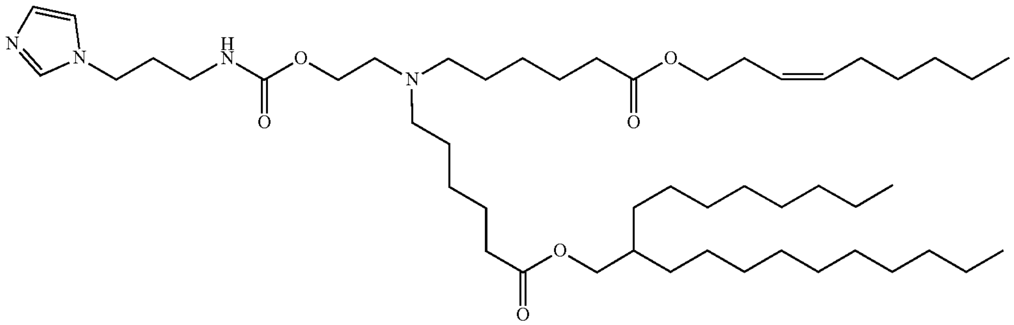 [SMILES: CCCCC/C=C\CCOC(=O)CCCCCN(CCCCCC(=O)OCC(CCCCCCCC)CCCCCCCCCC)CCOC(=O)NCCCn1ccnc1] | 845.3 |

TABLE 1-continued
| # | Structure | Mw |
| --- | --- | --- |
| 244. | 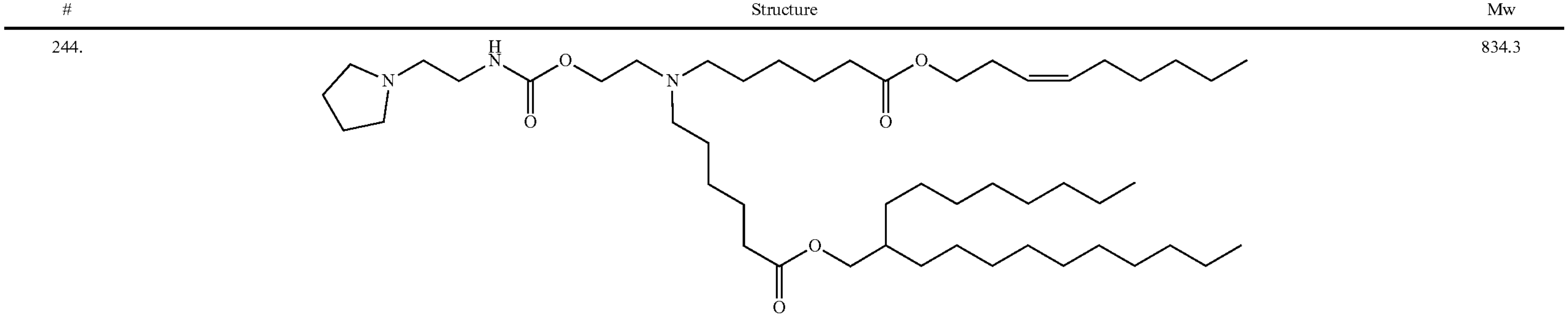 | 834.3 |
| 245. | 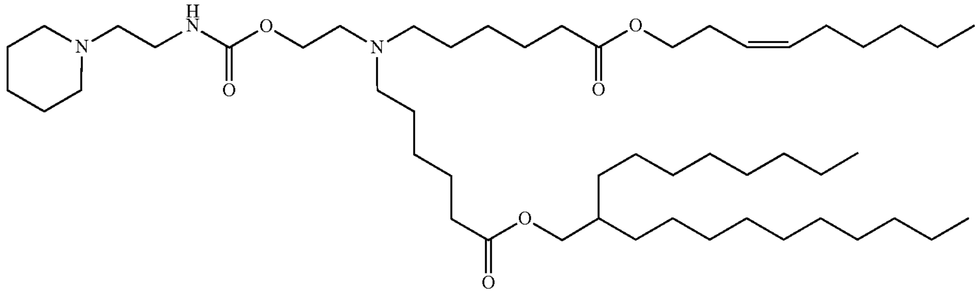 [SMILES: CCCCC/C=C\CCOC(=O)CCCCCN(CCCCCC(=O)OCC(CCCCCCCC)CCCCCCCCCC)CCOC(=O)NCCN1CCCCC1] | 848.4 |
| 246. | 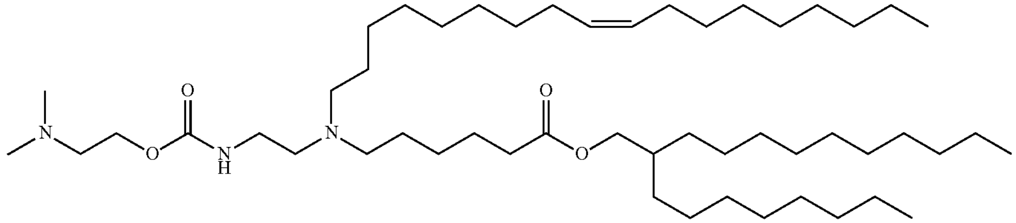 [SMILES: CCCCCCCC/C=C\CCCCCCCCN(CCCCCC(=O)OCC(CCCCCCCC)CCCCCCCCCC)CCNC(=O)OCCN(C)C] | 820.4 |
| 247. | 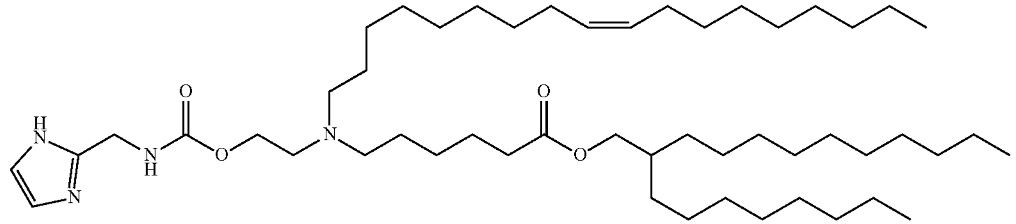 [SMILES: CCCCCCCC/C=C\CCCCCCCCN(CCCCCC(=O)OCC(CCCCCCCC)CCCCCCCCCC)CCOC(=O)NCc1ncc[nH]1] | 829.4 |

TABLE 1-continued
| # | Structure | Mw |
|---|---|---|
| 248. | 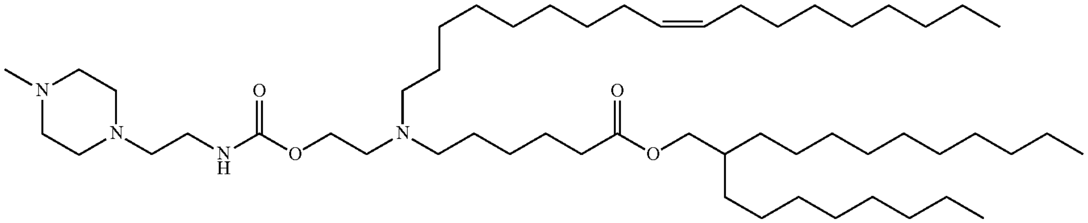 [SMILES: CCCCCCCC/C=C\CCCCCCCCN(CCCCCC(=O)OCC(CCCCCCCC)CCCCCCCCCC)CCOC(=O)NCCN1CCN(C)CC1] | 875.5 |
| 249. | 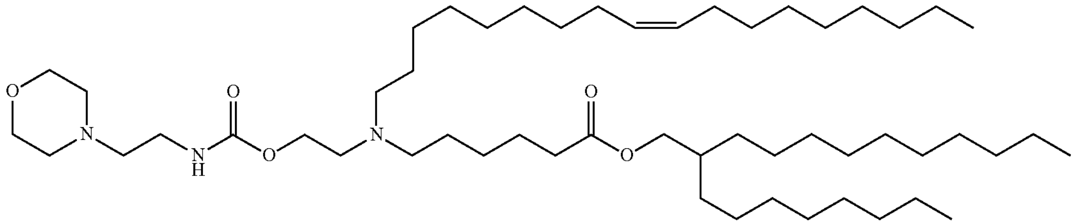 [SMILES: CCCCCCCC/C=C\CCCCCCCCN(CCCCCC(=O)OCC(CCCCCCCC)CCCCCCCCCC)CCOC(=O)NCCN1CCOCC1] | 862.4 |
| 250. | 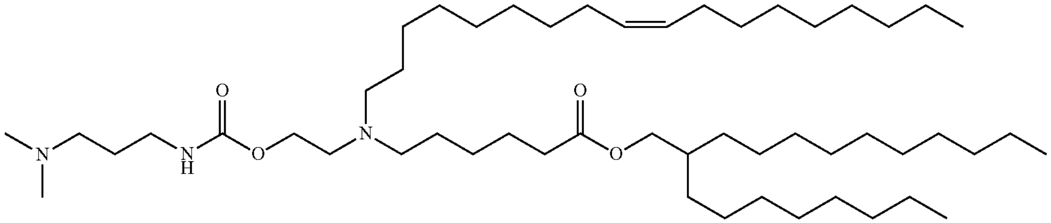 [SMILES: CCCCCCCC/C=C\CCCCCCCCN(CCCCCC(=O)OCC(CCCCCCCC)CCCCCCCCCC)CCOC(=O)NCCCN(C)C] | 834.4 |
| 251. | 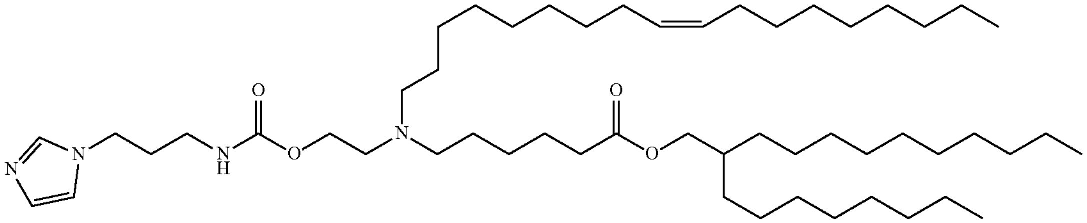 [SMILES: CCCCCCCC/C=C\CCCCCCCCN(CCCCCC(=O)OCC(CCCCCCCC)CCCCCCCCCC)CCOC(=O)NCCCn1ccnc1] | 857.4 |

TABLE 1-continued
| # | Structure | Mw |
|---|---|---|
| 252. | 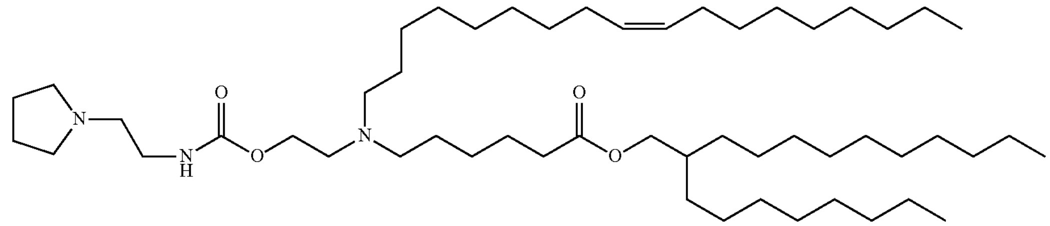 | 846.4 |
| 253. | 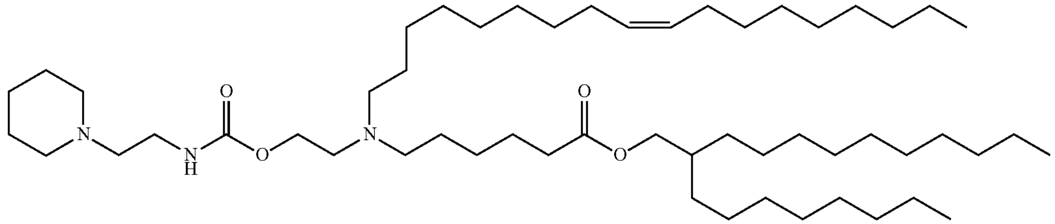 [SMILES: CCCCCCCC/C=C\CCCCCCCCN(CCCCCC(=O)OCC(CCCCCCCC)CCCCCCCCCC)CCOC(=O)NCCN1CCCCC1] | 860.5 |
| 254. | 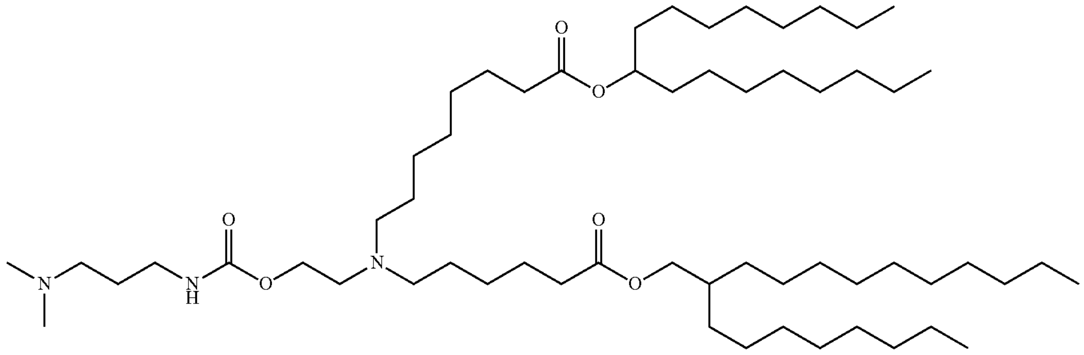 [SMILES: CCCCCCCCCCC(CCCCCCCC)COC(=O)CCCCCN(CCCCCCCC(=O)OC(CCCCCCCC)CCCCCCCC)CCOC(=O)NCCCN(C)C] | 964.6 |

TABLE 1-continued
| # | Structure | Mw |
| --- | --- | --- |
| 255. | 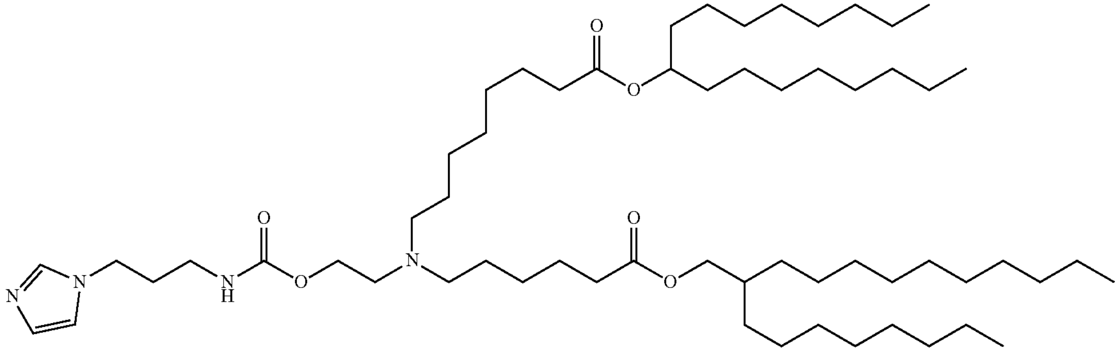 [SMILES: CCCCCCCCCCC(CCCCCCCC)COC(=O)CCCCCN(CCCCCCCC(=O)OC(CCCCCCCC)CCCCCCCC)CCOC(=O)NCCCn1ccnc1] | 987.6 |
| 256. | 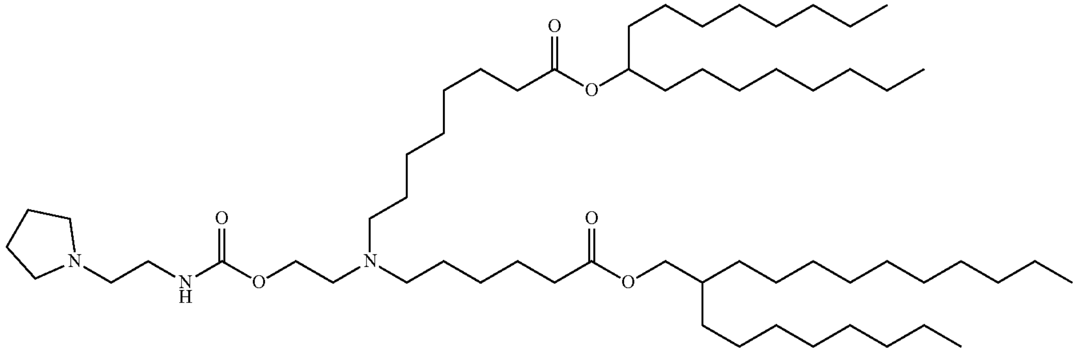 [SMILES: CCCCCCCCCCC(CCCCCCCC)COC(=O)CCCCCN(CCCCCCCC(=O)OC(CCCCCCCC)CCCCCCCC)CCOC(=O)NCCN1CCCC1] | 976.6 |
| 257. | 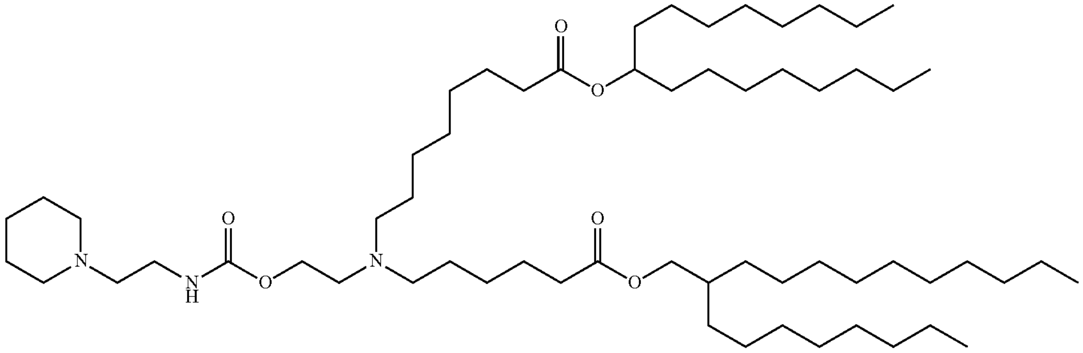 [SMILES: CCCCCCCCCCC(CCCCCCCC)COC(=O)CCCCCN(CCCCCCCC(=O)OC(CCCCCCCC)CCCCCCCC)CCOC(=O)NCCN1CCCCC1] | 990.6 |

TABLE 1-continued
| # | Structure | Mw |
| --- | --- | --- |
| 258. | 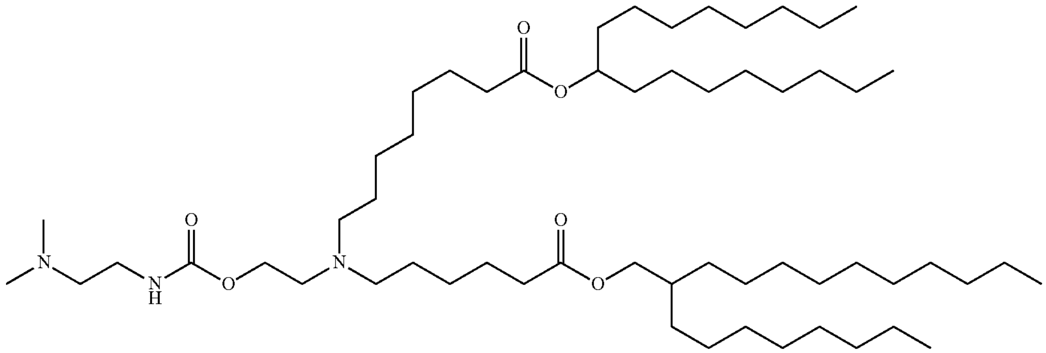 [SMILES: CCCCCCCCCCC(CCCCCCCC)COC(=O)CCCCCN(CCCCCCCC(=O)OC(CCCCCCCC)CCCCCCCC)CCOC(=O)NCCN(C)C] | 950.6 |
| 259. | 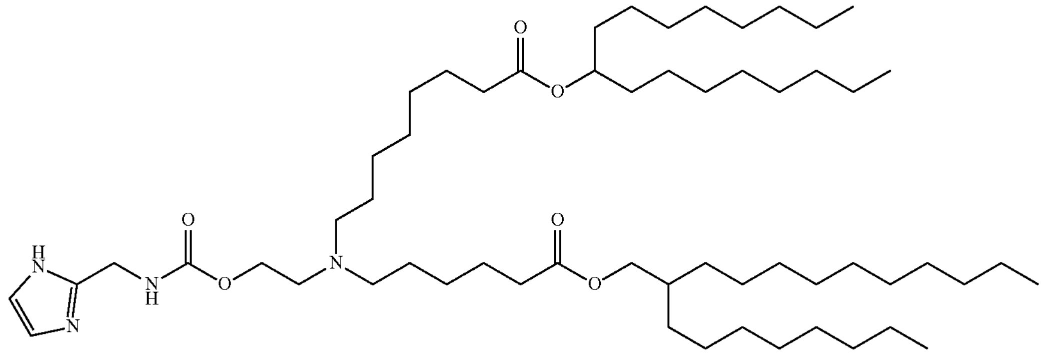 [SMILES: CCCCCCCCCCC(CCCCCCCC)COC(=O)CCCCCN(CCCCCCCC(=O)OC(CCCCCCCC)CCCCCCCC)CCOC(=O)NCc1ncc[nH]1] | 959.5 |

TABLE 1-continued
| # | Structure | Mw |
|---|---|---|
| 260. | 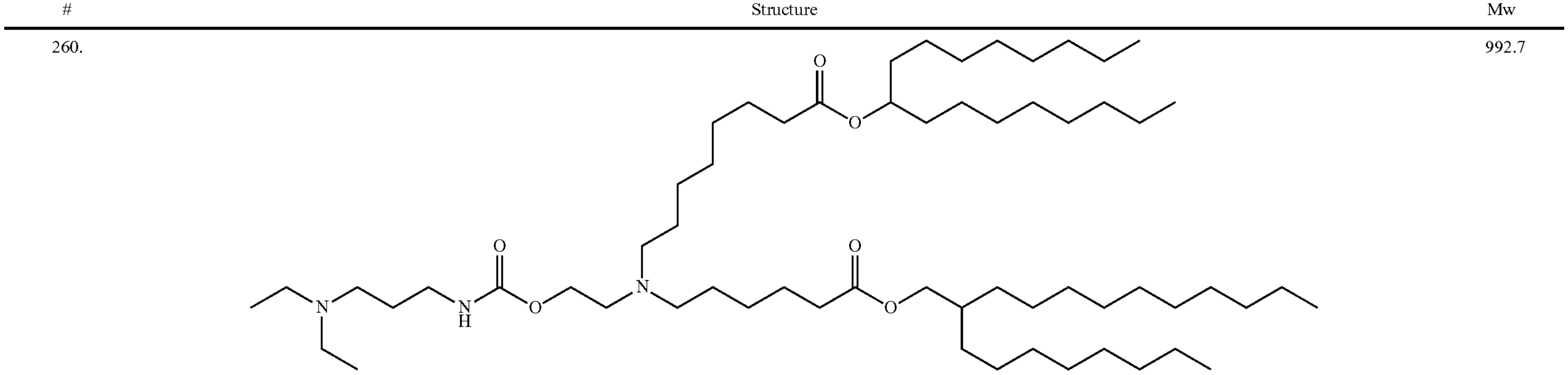 | 992.7 |
| 261. | 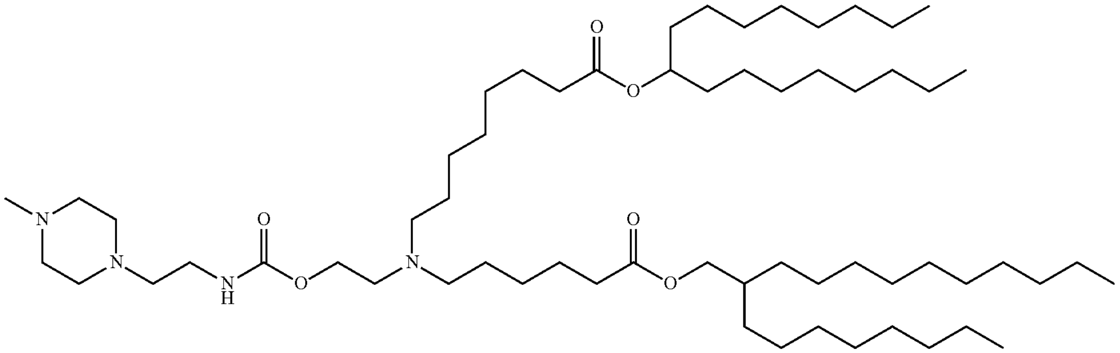 [SMILES: CCCCCCCCCCC(CCCCCCCC)COC(=O)CCCCCN(CCCCCCCC(=O)OC(CCCCCCCC)CCCCCCCC)CCOC(=O)NCCN1CCN(C)CC1] | 1005.7 |
| 262. | 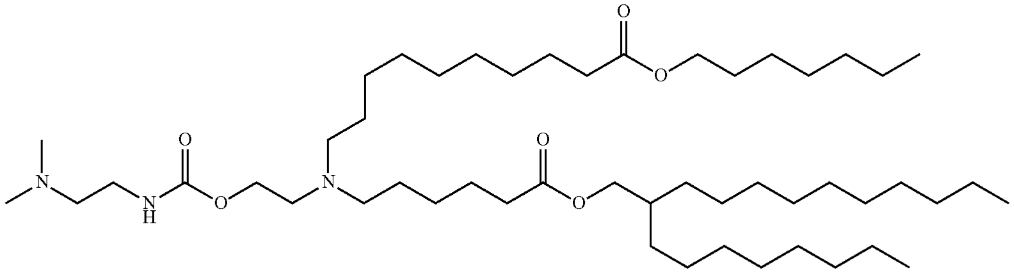 [SMILES: CCCCCCCCCCC(CCCCCCCC)COC(=O)CCCCCN(CCCCCCCCCC(=O)OCCCCCCC)CCOC(=O)NCCN(C)C] | 838.4 |

TABLE 1-continued
| # | Structure | Mw |
| --- | --- | --- |
| 263. | 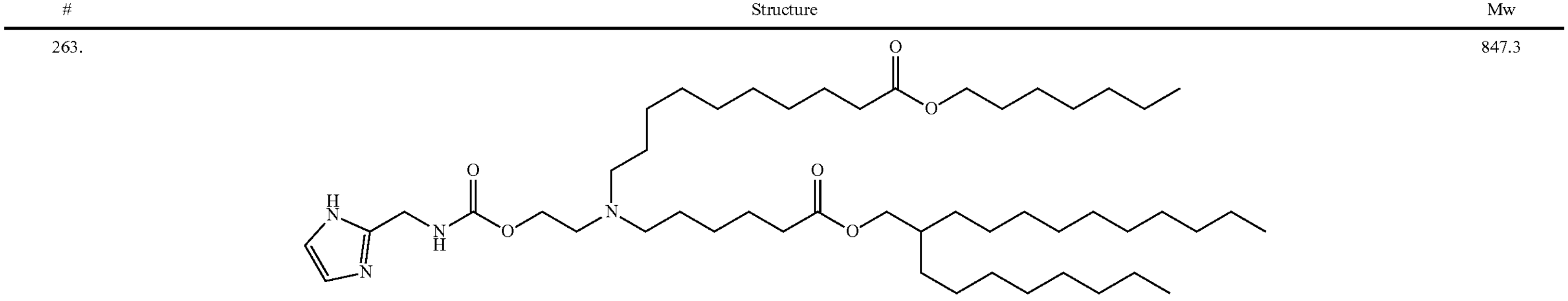 | 847.3 |
| 264. | 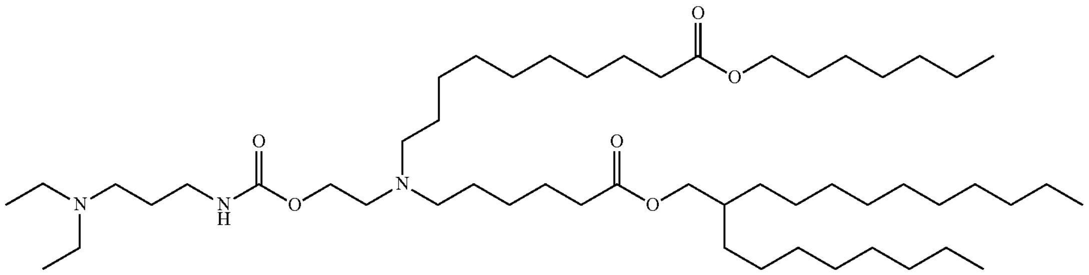 [SMILES: CCCCCCCCCCC(CCCCCCCC)COC(=O)CCCCCN(CCCCCCCCCC(=O)OCCCCCCC)CCOC(=O)NCCCN(CC)CC] | 880.4 |
| 265. | 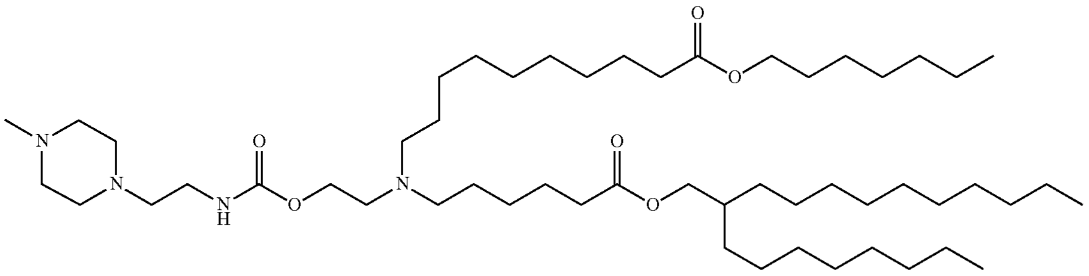 [SMILES: CCCCCCCCCCC(CCCCCCCC)COC(=O)CCCCCN(CCCCCCCCCC(=O)OCCCCCCC)CCOC(=O)NCCN1CCN(C)CC1] | 893.4 |

TABLE 1-continued
| # | Structure | Mw |
|---|---|---|
| 266. | 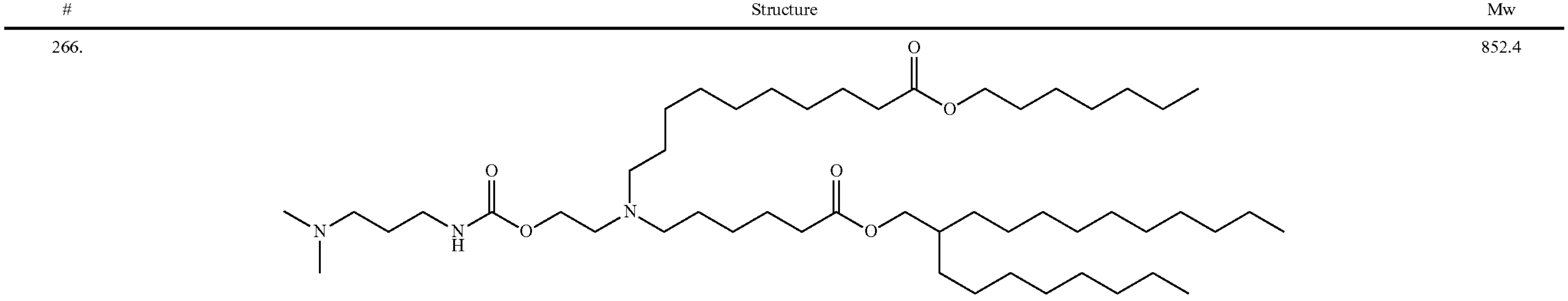 | 852.4 |
| 267. | 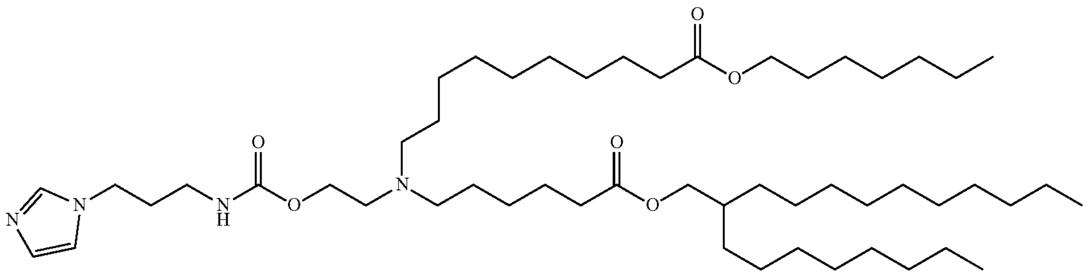 [SMILES: CCCCCCCCCCC(CCCCCCCC)COC(=O)CCCCCN(CCCCCCCCCC(=O)OCCCCCCC)CCOC(=O)NCCCn1ccnc1] | 875.4 |
| 268. | 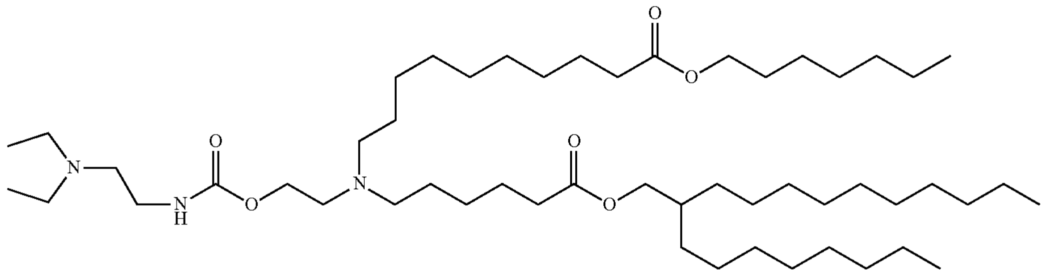 [SMILES: CCCCCCCCCCC(CCCCCCCC)COC(=O)CCCCCN(CCCCCCCCCC(=O)OCCCCCCC)CCOC(=O)NCCN(CC)CC] | 864.4 |

TABLE 1-continued
| # | Structure | Mw |
|---|---|---|
| 269. | 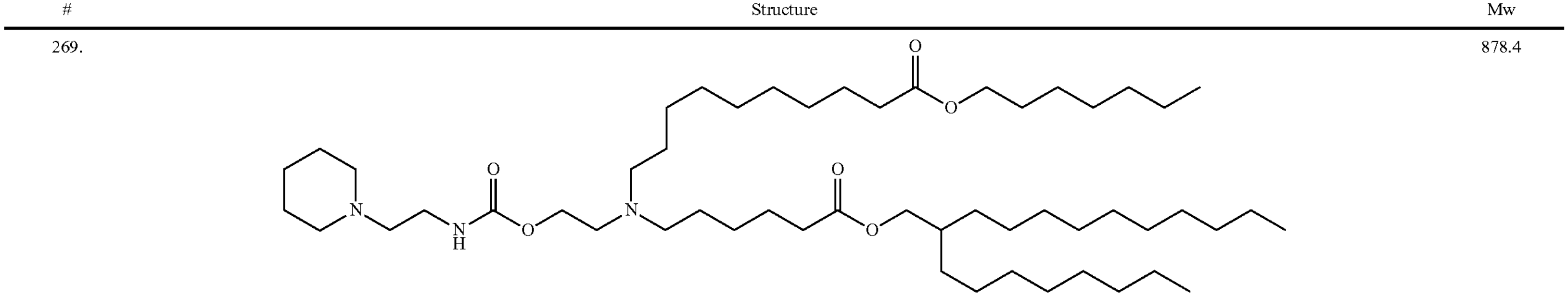 | 878.4 |
| 270. | 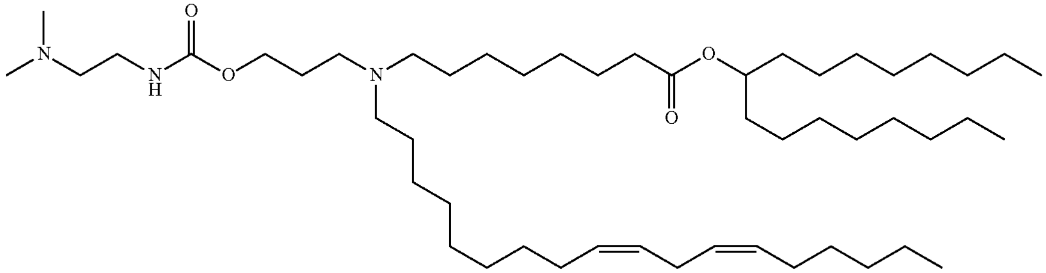 [SMILES: CCCCC/C=C\C/C=C\CCCCCCCCN(CCCCCCCC(=O)OC(CCCCCCCC)CCCCCCCC)CCCOC(=O)NCCN(C)C] | 818.4 |
| 271. | 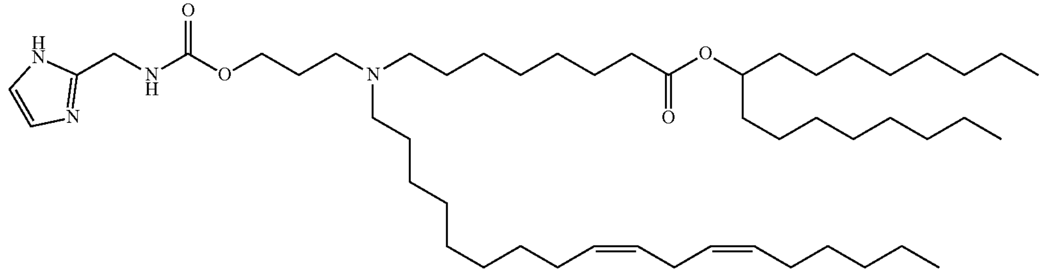 [SMILES: CCCCC/C=C\C/C=C\CCCCCCCCN(CCCCCCCC(=O)OC(CCCCCCCC)CCCCCCCC)CCCOC(=O)NCc1ncc[nH]1] | 827.3 |

TABLE 1-continued
| # | Structure | Mw |
|---|---|---|
| 272. | 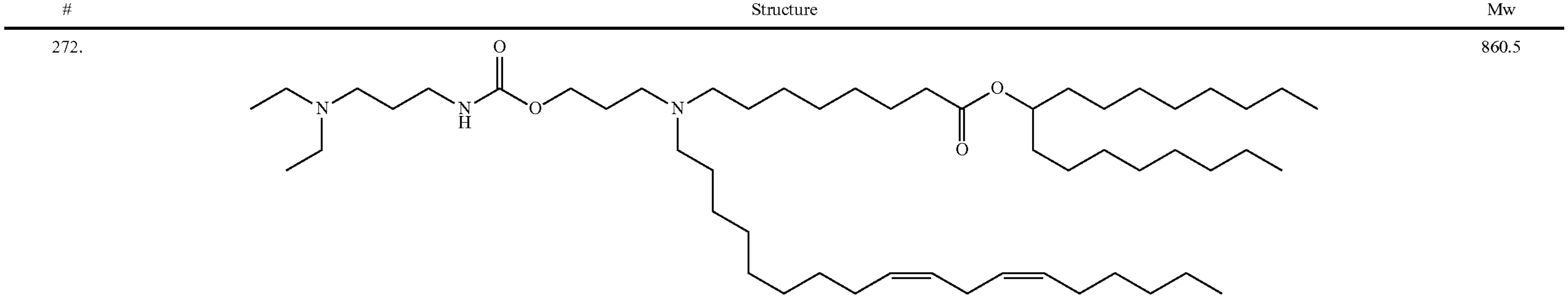 | 860.5 |
| 273. | 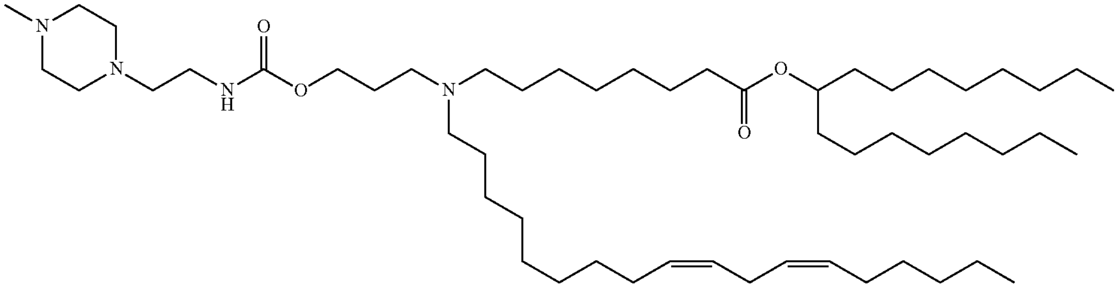 [SMILES: CCCCC/C=C\C/C=C\CCCCCCCCN(CCCCCCCC(=O)OC(CCCCCCCC)CCCCCCCC)CCCOC(=O)NCCN1CCN(C)CC1] | 873.5 |
| 274. | 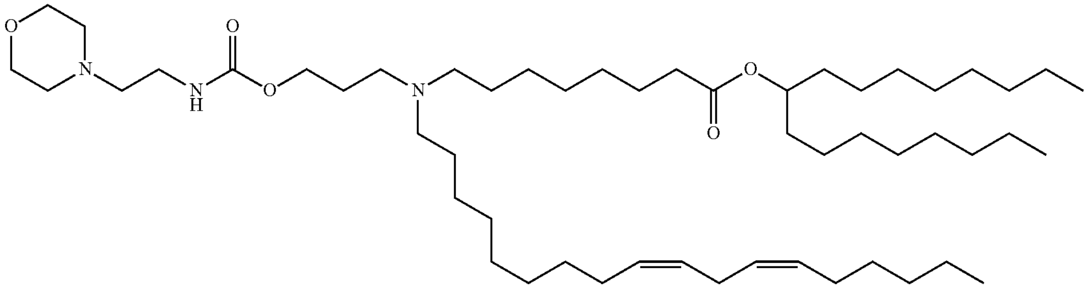 [SMILES: CCCCC/C=C\C/C=C\CCCCCCCCN(CCCCCCCC(=O)OC(CCCCCCCC)CCCCCCCC)CCCOC(=O)NCCN1CCOCC1] | 860.4 |

TABLE 1-continued
| # | Structure | Mw |
| --- | --- | --- |
| 275. | 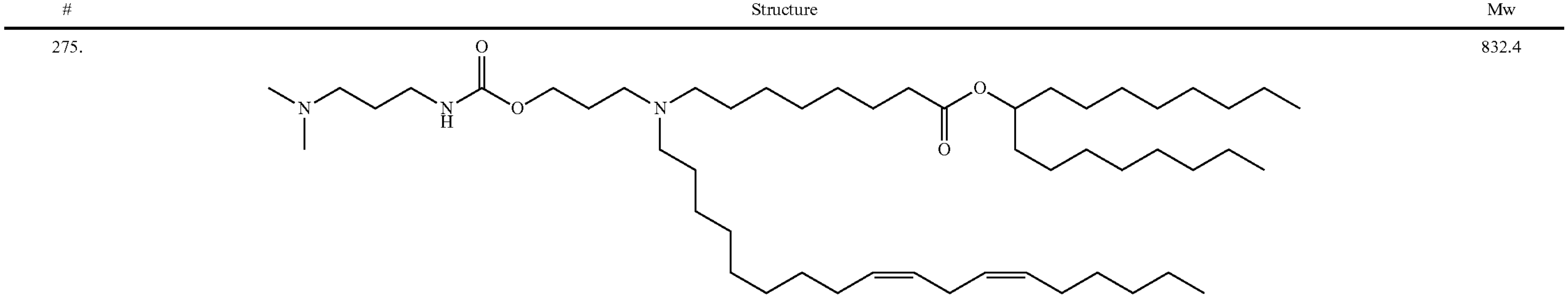 | 832.4 |
| 276. | 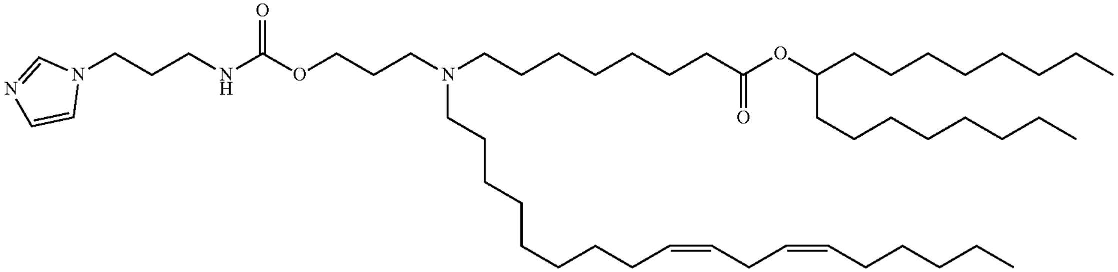 [SMILES: CCCCC/C=C\C/C=C\CCCCCCCCN(CCCCCCCC(=O)OC(CCCCCCCC)CCCCCCCC)CCCOC(=O)NCCCn1ccnc1] | 855.4 |
| 277. | 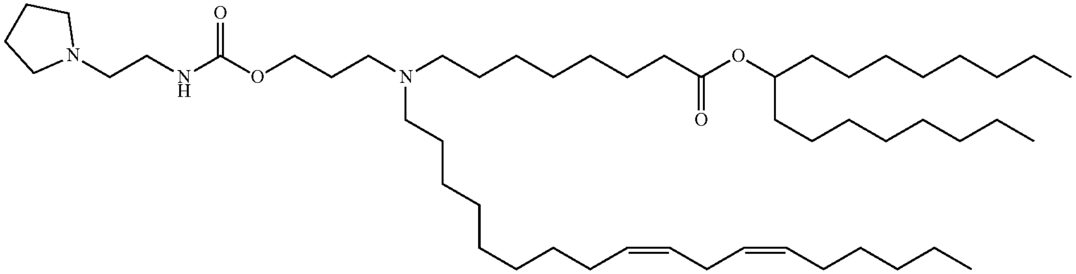 [SMILES: CCCCC/C=C\C/C=C\CCCCCCCCN(CCCCCCCC(=O)OC(CCCCCCCC)CCCCCCCC)CCCOC(=O)NCCN1CCCC1] | 844.4 |

TABLE 1-continued
| # | Structure | Mw |
|---|---|---|
| 278. | 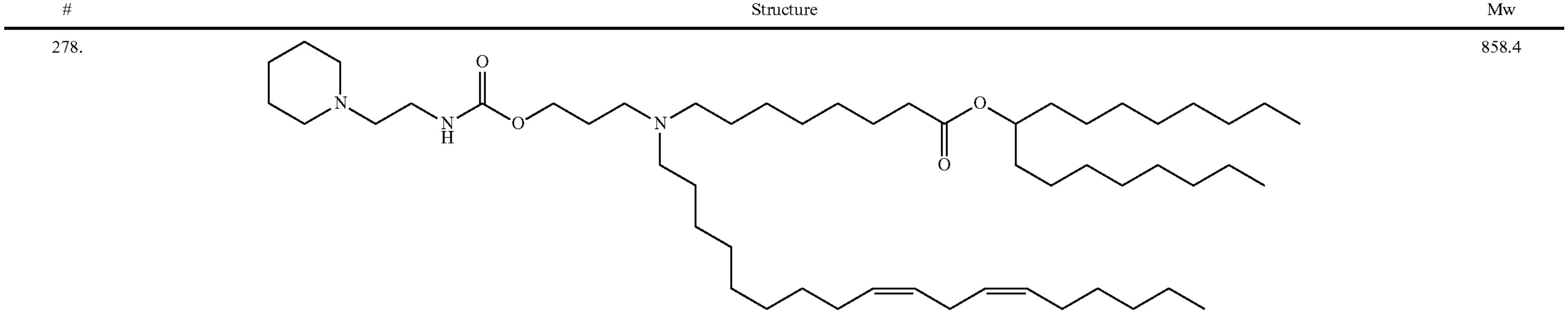 | 858.4 |
| 279. | 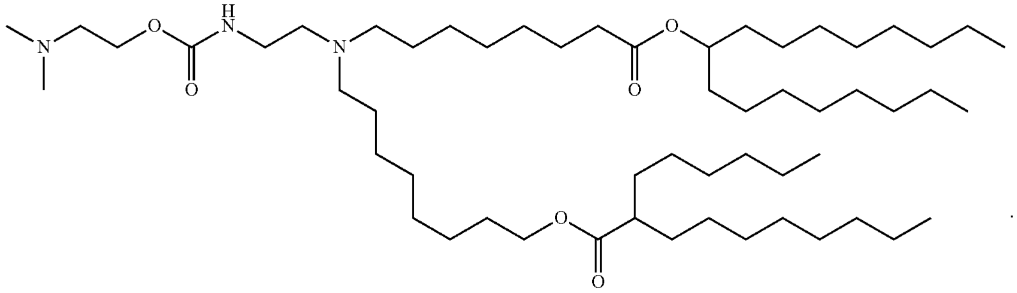 | 922.2 |
| 280. | 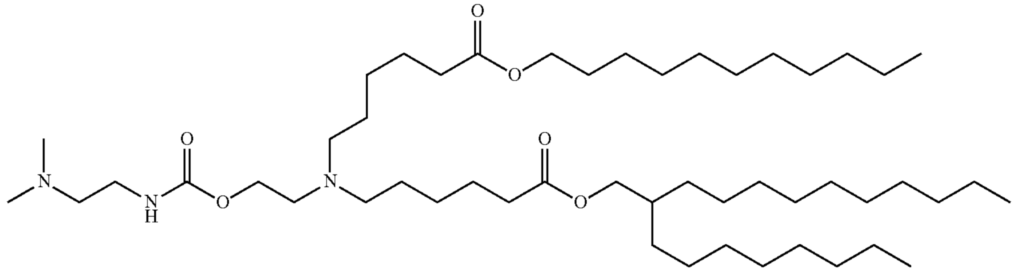 [SMILES: CCCCCCCCCCCOC(=O)CCCCCN(CCCCCC(=O)OCC(CCCCCCCC)CCCCCCCCCC)CCOC(=O)NCCN(C)C] | 838.4 |

TABLE 1-continued
| # | Structure | Mw |
|---|---|---|
| 281. | 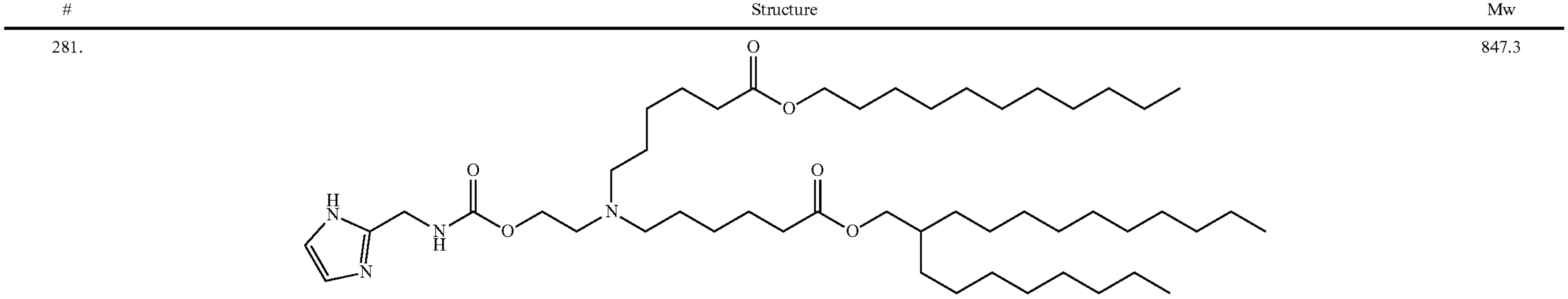 | 847.3 |
| 282. | 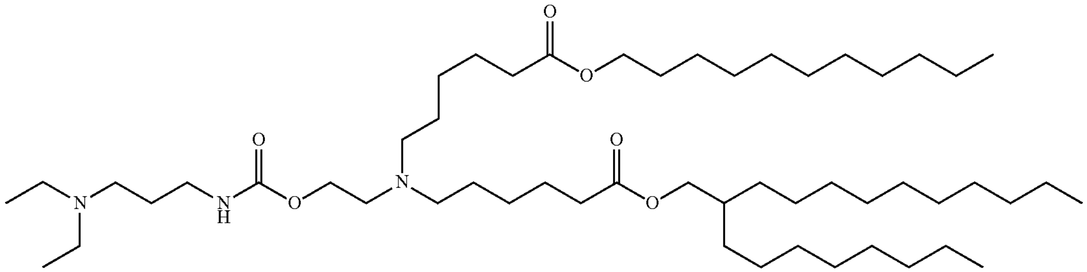 [SMILES: CCCCCCCCCCCOC(=O)CCCCCN(CCCCCC(=O)OCC(CCCCCCCC)CCCCCCCCCC)CCOC(=O)NCCCN(CC)CC] | 880.4 |
| 283. | 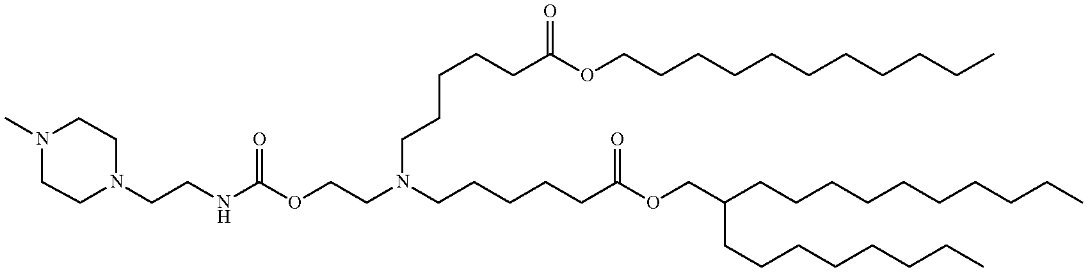 [SMILES: CCCCCCCCCCCOC(=O)CCCCCN(CCCCCC(=O)OCC(CCCCCCCC)CCCCCCCCCC)CCOC(=O)NCCN1CCN(C)CC1] | 893.4 |

TABLE 1-continued
| # | Structure | Mw |
| --- | --- | --- |
| 284. | 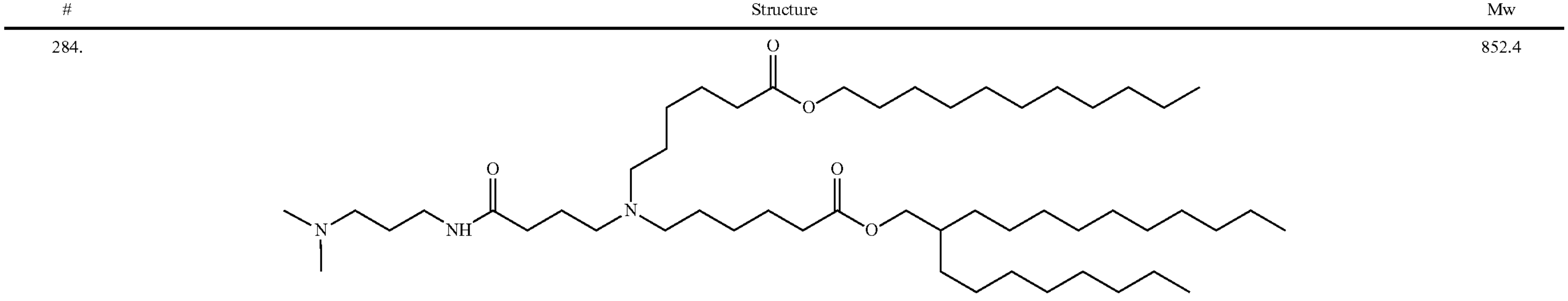 | 852.4 |
| 285. | 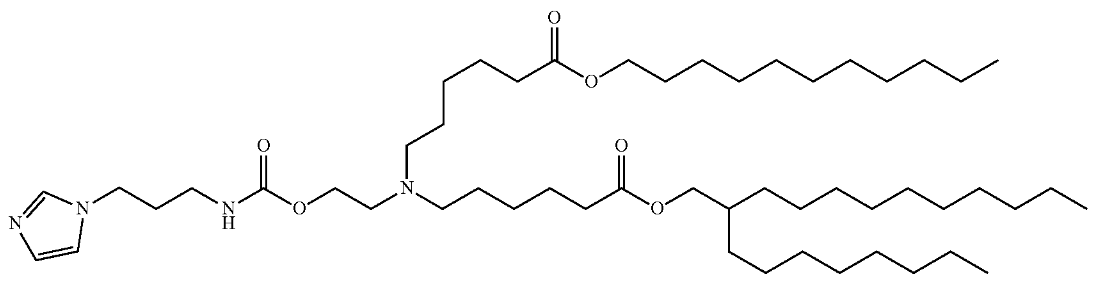 [SMILES: CCCCCCCCCCCOC(=O)CCCCCN(CCCCCC(=O)OCC(CCCCCCCC)CCCCCCCCCC)CCOC(=O)NCCCn1ccnc1] | 875.4 |
| 286. | 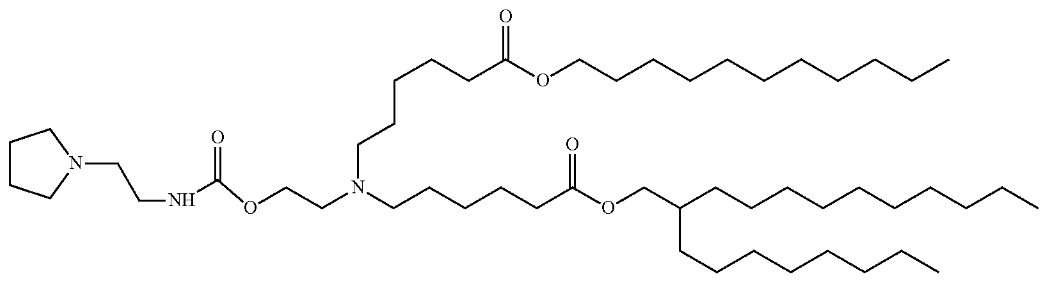 [SMILES: CCCCCCCCCCCOC(=O)CCCCCN(CCCCCC(=O)OCC(CCCCCCCC)CCCCCCCCCC)CCOC(=O)NCCN1CCCC1] | 864.4 |

TABLE 1-continued
| # | Structure | Mw |
|---|---|---|
| 287. | 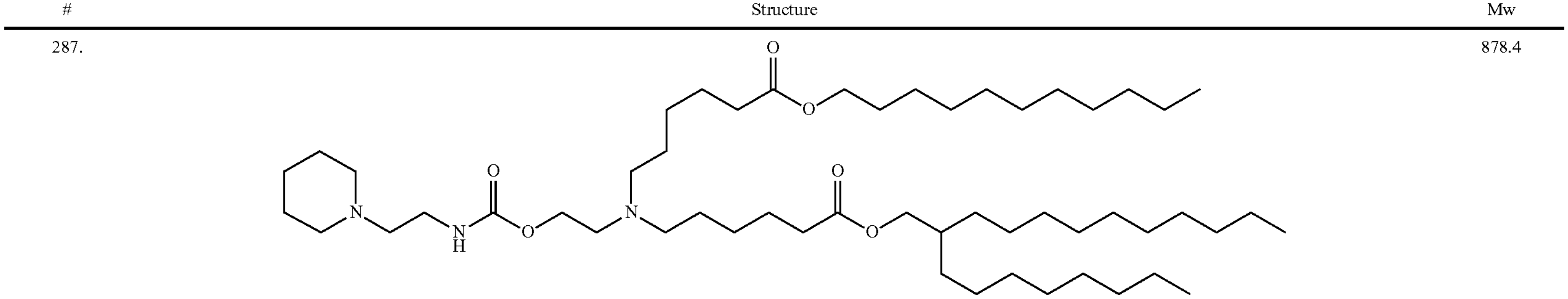 | 878.4 |
| 288. | 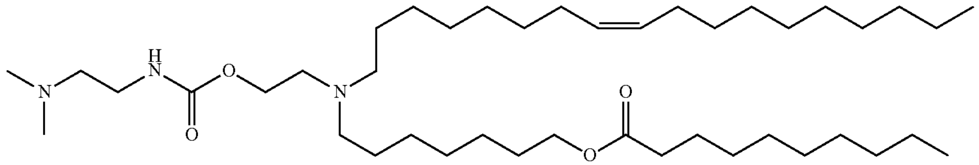 [SMILES: CCCCCCCCC/C=C\CCCCCCCN(CCCCCCCOC(=O)CCCCCCCCC)CCOC(=O)NCCN(C)C] | 694.1 |
| 289. | 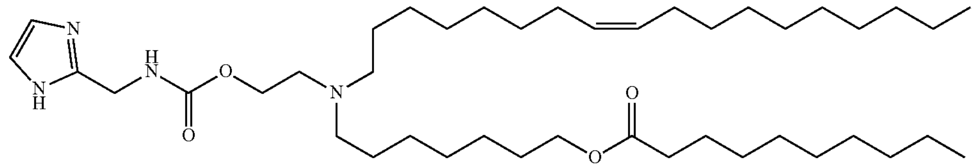 [SMILES: CCCCCCCCC/C=C\CCCCCCCN(CCCCCCCOC(=O)CCCCCCCCC)CCOC(=O)NCc1ncc[nH]1] | 703.1 |
| 290. | 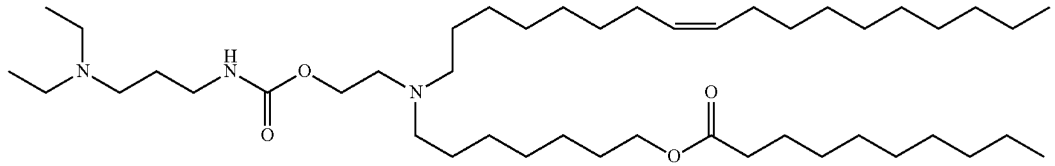 [SMILES: CCCCCCCCC/C=C\CCCCCCCN(CCCCCCCOC(=O)CCCCCCCCC)CCOC(=O)NCCCN(CC)CC] | 736.2 |
| 291. | 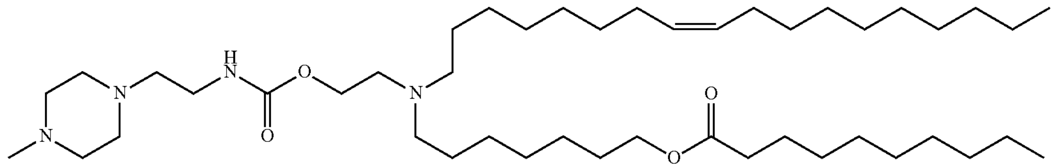 [SMILES: CCCCCCCCC/C=C\CCCCCCCN(CCCCCCCOC(=O)CCCCCCCCC)CCOC(=O)NCCN1CCN(C)CC1] | 749.2 |

TABLE 1-continued
| # | Structure | Mw |
|---|---|---|
| 292. | 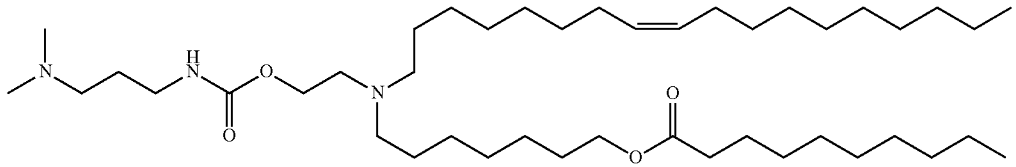 [SMILES: CCCCCCCCC/C=C\CCCCCCCN(CCCCCCCOC(=O)CCCCCCCCC)CCOC(=O)NCCCN(C)C] | 708.2 |
| 293. | 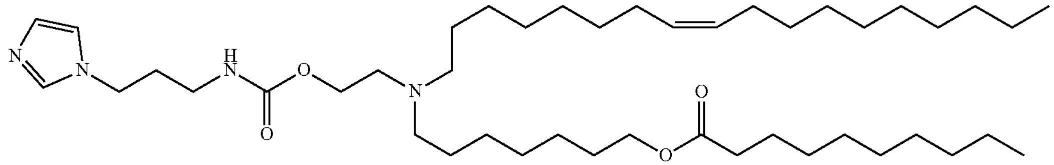 [SMILES: CCCCCCCCC/C=C\CCCCCCCN(CCCCCCCOC(=O)CCCCCCCCC)CCOC(=O)NCCCn1ccnc1] | 731.2 |
| 294. | 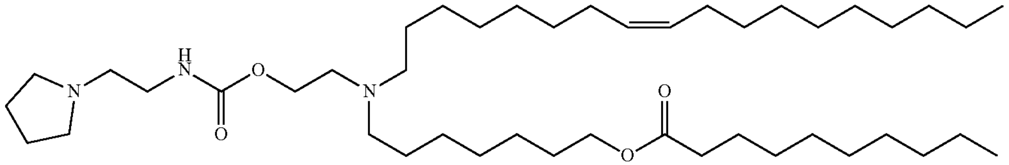 [SMILES: CCCCCCCCC/C=C\CCCCCCCN(CCCCCCCOC(=O)CCCCCCCCC)CCOC(=O)NCCN1CCCC1] | 720.2 |
| 295. | 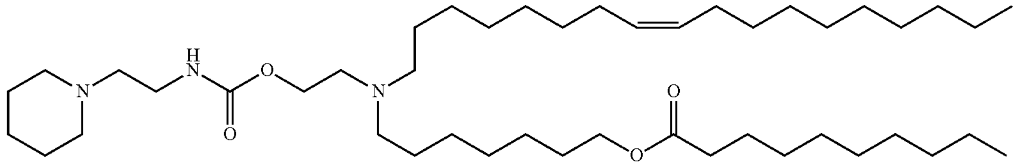 [SMILES: CCCCCCCCC/C=C\CCCCCCCN(CCCCCCCOC(=O)CCCCCCCCC)CCOC(=O)NCCN1CCCCC1] | 734.2 |
| 296. | 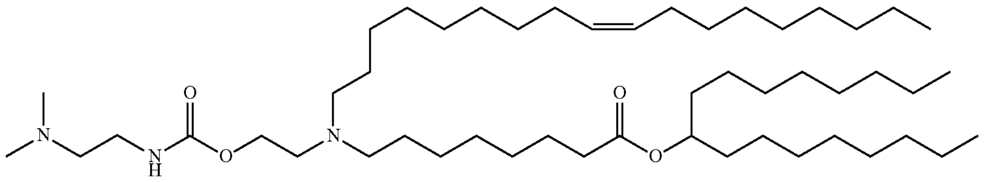 [SMILES: CCCCCCCC/C=C\CCCCCCCCN(CCCCCCCC(=O)OC(CCCCCCCC)CCCCCCCC)CCOC(=O)NCCN(C)C] | 806.4 |

TABLE 1-continued
| # | Structure | Mw |
|---|---|---|
| 297. | 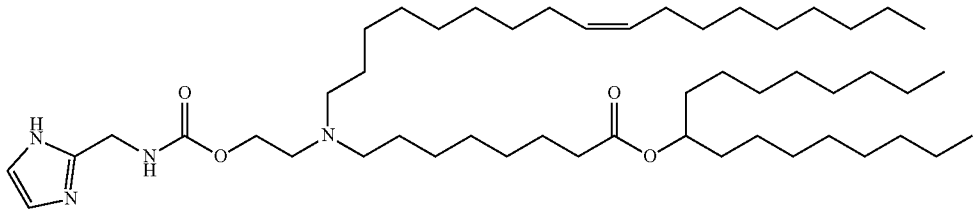 [SMILES: CCCCCCCC/C=C\CCCCCCCCN(CCCCCCCC(=O)OC(CCCCCCCC)CCCCCCCC)CCOC(=O)NCc1ncc[nH]1] | 815.3 |
| 298. | 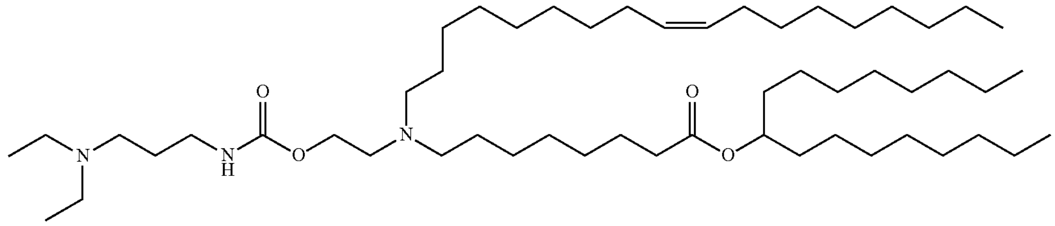 [SMILES: CCCCCCCC/C=C\CCCCCCCCN(CCCCCCCC(=O)OC(CCCCCCCC)CCCCCCCC)CCOC(=O)NCCCN(CC)CC] | 848.4 |
| 299. | 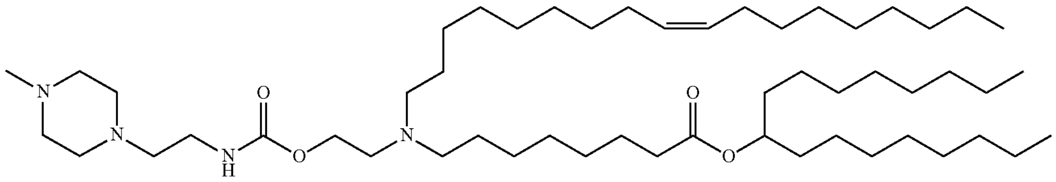 [SMILES: CCCCCCCC/C=C\CCCCCCCCN(CCCCCCCC(=O)OC(CCCCCCCC)CCCCCCCC)CCOC(=O)NCCN1CCN(C)CC1] | 861.4 |
| 300. | 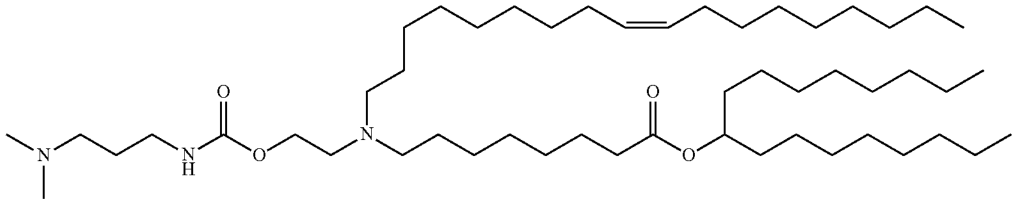 [SMILES: CCCCCCCC/C=C\CCCCCCCCN(CCCCCCCC(=O)OC(CCCCCCCC)CCCCCCCC)CCOC(=O)NCCCN(C)C] | 820.4 |

TABLE 1-continued
| # | Structure | Mw |
|---|---|---|
| 301. | 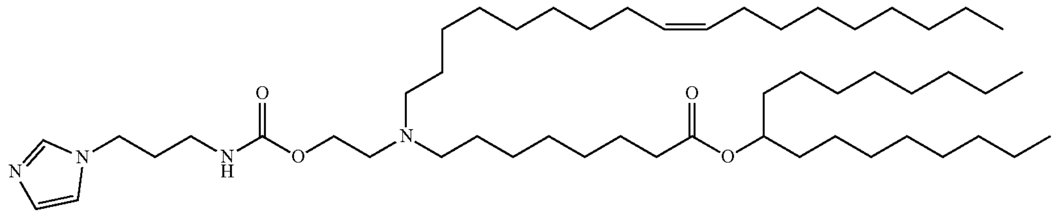 [SMILES: CCCCCCCC/C=C\CCCCCCCCN(CCCCCCCC(=O)OC(CCCCCCCC)CCCCCCCC)CCOC(=O)NCCCn1ccnc1] | 843.4 |
| 302. | 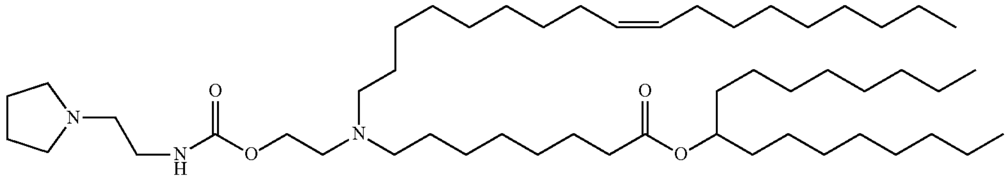 [SMILES: CCCCCCCC/C=C\CCCCCCCCN(CCCCCCCC(=O)OC(CCCCCCCC)CCCCCCCC)CCOC(=O)NCCN1CCCC1] | 832.4 |
| 303. | 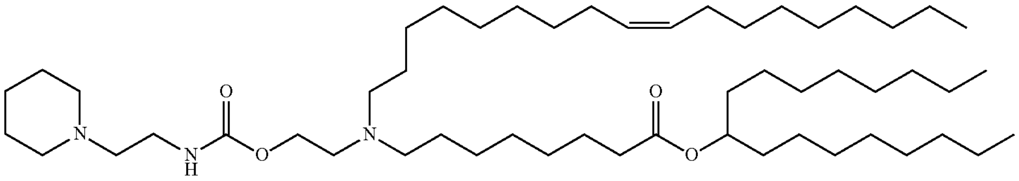 [SMILES: CCCCCCCC/C=C\CCCCCCCCN(CCCCCCCC(=O)OC(CCCCCCCC)CCCCCCCC)CCOC(=O)NCCN1CCCCC1] | 846.4 |
| 304. | 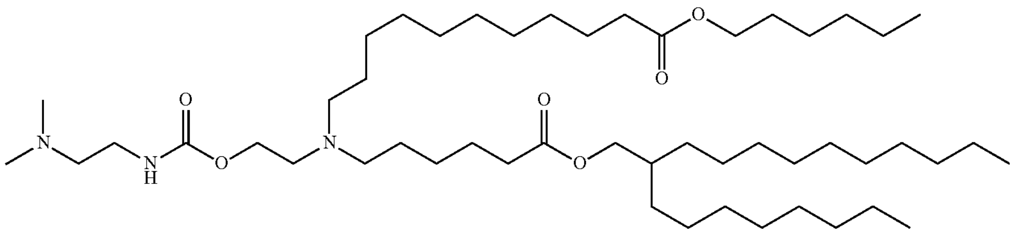 [SMILES: CCCCCCCCCCC(CCCCCCCC)COC(=O)CCCCCN(CCCCCCCCCCC(=O)OCCCCCC)CCOC(=O)NCCN(C)C] | 838.4 |
| 305. | 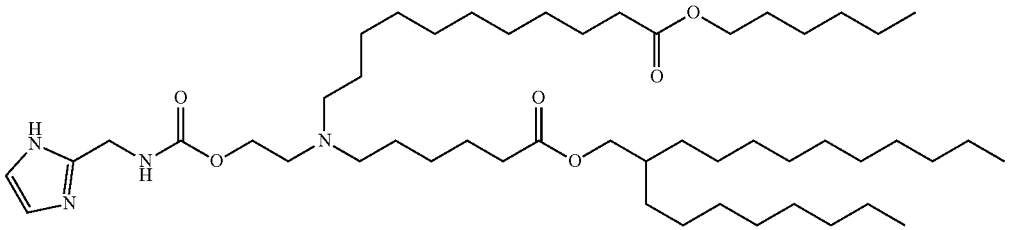 [SMILES: CCCCCCCCCCC(CCCCCCCC)COC(=O)CCCCCN(CCCCCCCCCCC(=O)OCCCCCC)CCOC(=O)NCc1ncc[nH]1] | 847.3 |

TABLE 1-continued
| # | Structure | Mw |
| --- | --- | --- |
| 306. | 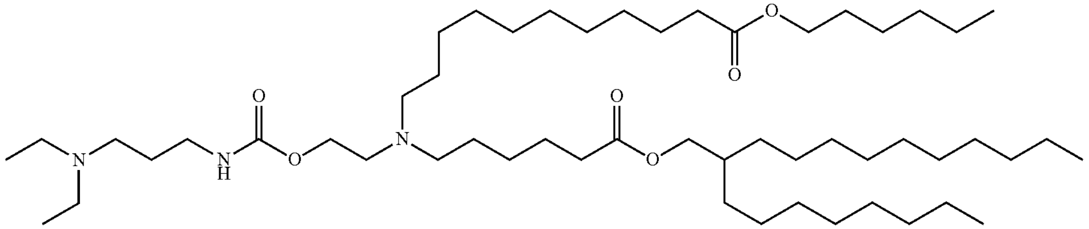 [SMILES: CCCCCCCCCCC(CCCCCCCC)COC(=O)CCCCCN(CCCCCCCCCCC(=O)OCCCCCC)CCOC(=O)NCCCN(CC)CC] | 880.4 |
| 307. | 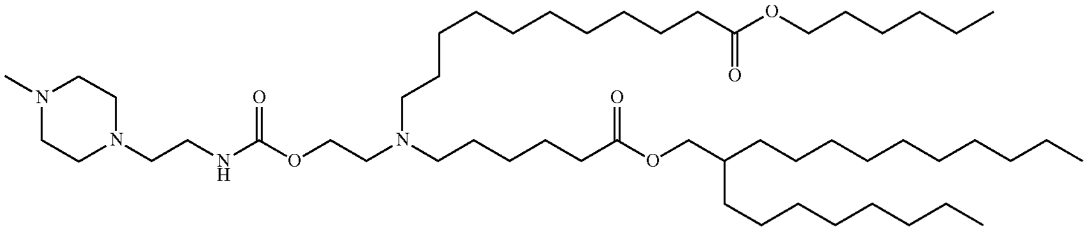 [SMILES: CCCCCCCCCCC(CCCCCCCC)COC(=O)CCCCCN(CCCCCCCCCCC(=O)OCCCCCC)CCOC(=O)NCCN1CCN(C)CC1] | 893.4 |
| 308. | 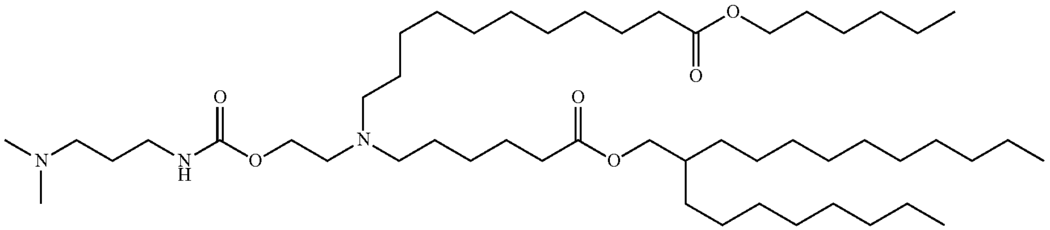 [SMILES: CCCCCCCCCCC(CCCCCCCC)COC(=O)CCCCCN(CCCCCCCCCCC(=O)OCCCCCC)CCOC(=O)NCCCN(C)C] | 852.4 |
| 309. | 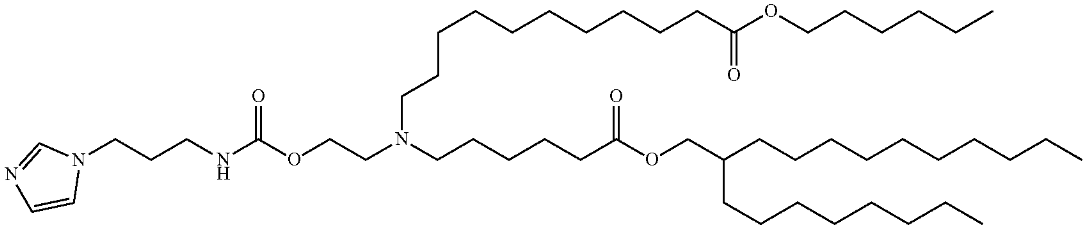 [SMILES: CCCCCCCCCCC(CCCCCCCC)COC(=O)CCCCCN(CCCCCCCCCCC(=O)OCCCCCC)CCOC(=O)NCCCn1ccnc1] | 875.4 |

TABLE 1-continued
| # | Structure | Mw |
| --- | --- | --- |
| 310. | 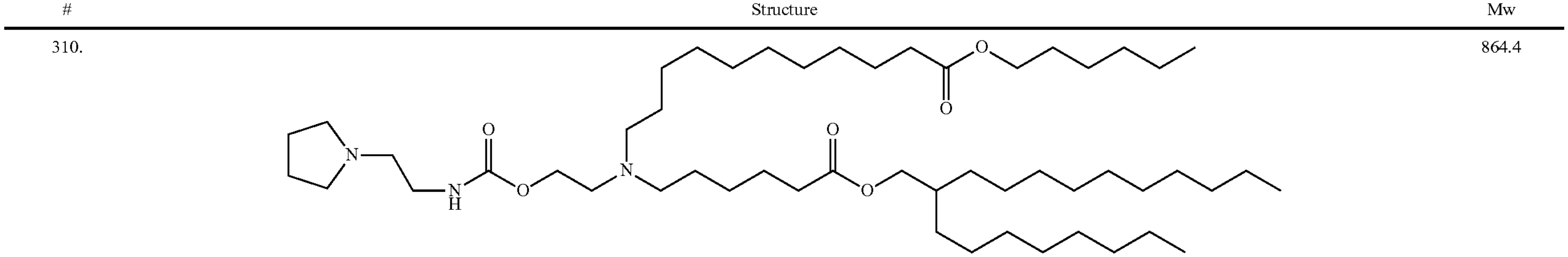 | 864.4 |
| 311. | 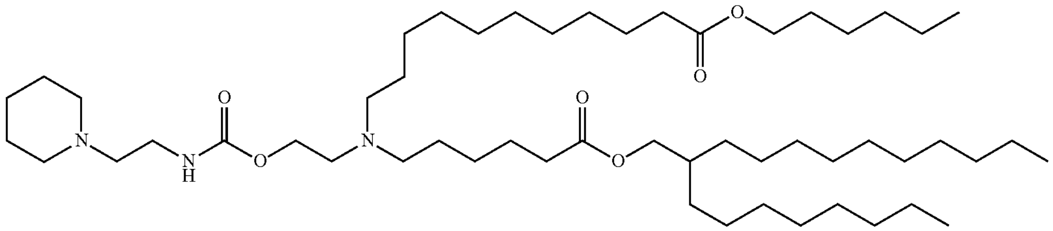 [SMILES: CCCCCCCCCCC(CCCCCCCC)COC(=O)CCCCCN(CCCCCCCCCCC(=O)OCCCCCC)CCOC(=O)NCCN1CCCCC1] | 878.4 |
| 312. | 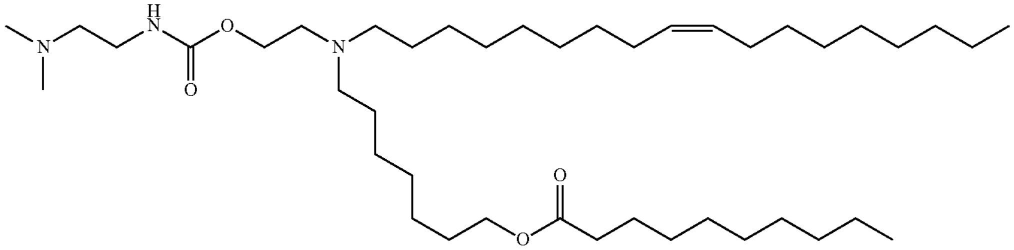 [SMILES: CCCCCCCC/C=C\CCCCCCCCN(CCCCCCCOC(=O)CCCCCCCCC)CCOC(=O)NCCN(C)C] | 694.1 |
| 313. | 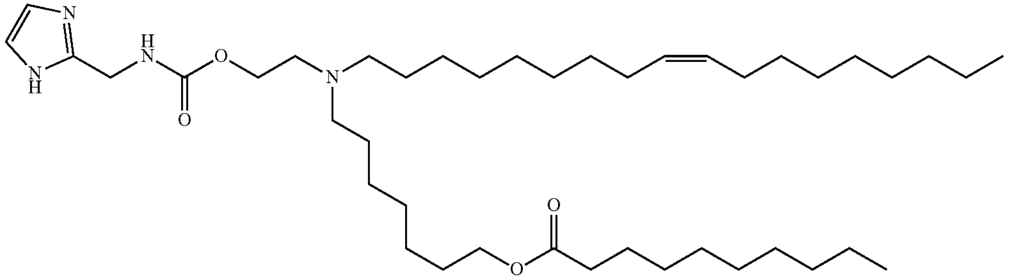 [SMILES: CCCCCCCC/C=C\CCCCCCCCN(CCCCCCCOC(=O)CCCCCCCCC)CCOC(=O)NCc1ncc[nH]1] | 703.1 |

TABLE 1-continued
| # | Structure | Mw |
|---|---|---|
| 314. | 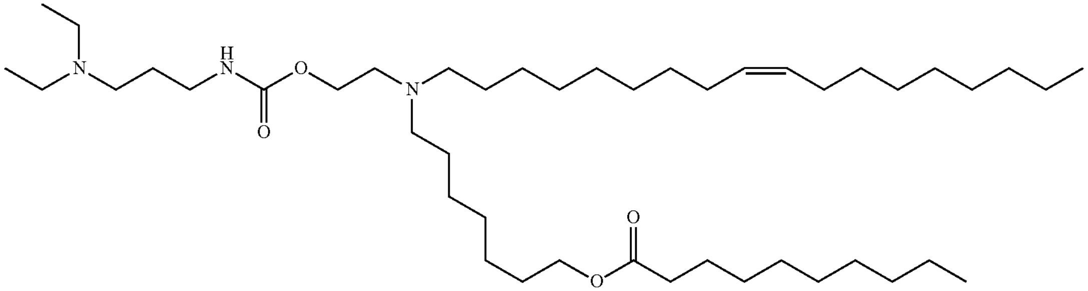 [SMILES: CCCCCCCC/C=C\CCCCCCCCN(CCCCCCCOC(=O)CCCCCCCCC)CCOC(=O)NCCCN(CC)CC] | 736.2 |
| 315. | 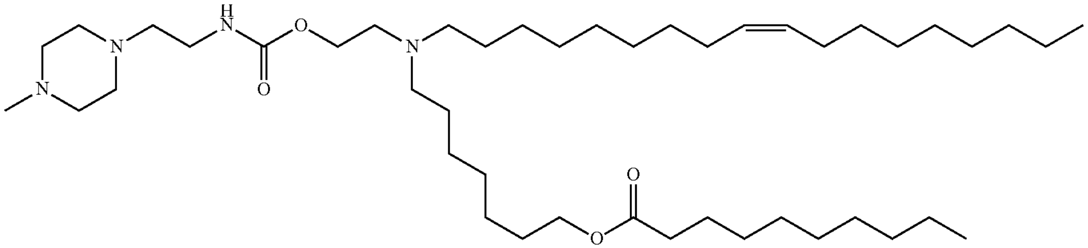 [SMILES: CCCCCCCC/C=C\CCCCCCCCN(CCCCCCCOC(=O)CCCCCCCCC)CCOC(=O)NCCN1CCN(C)CC1] | 749.2 |
| 316. | 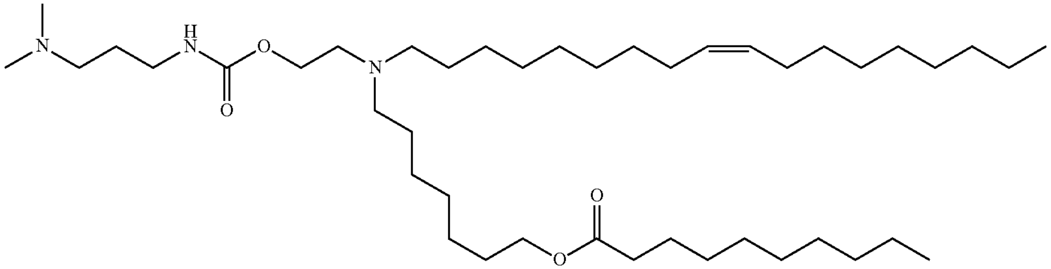 [SMILES: CCCCCCCC/C=C\CCCCCCCCN(CCCCCCCOC(=O)CCCCCCCCC)CCOC(=O)NCCCN(C)C] | 708.2 |

TABLE 1-continued
| # | Structure | Mw |
| --- | --- | --- |
| 317. | 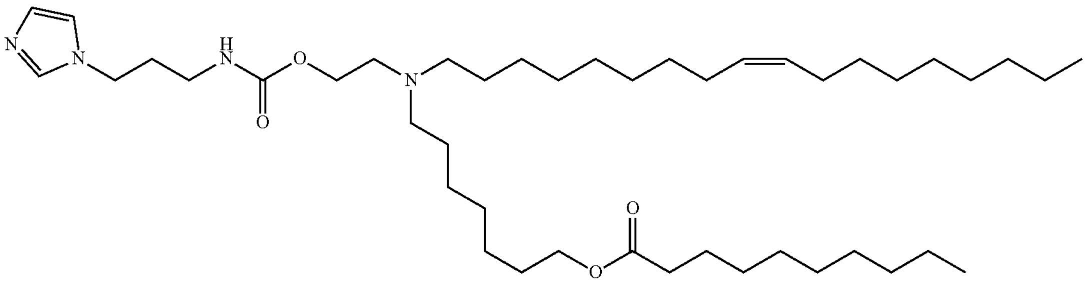 [SMILES: CCCCCCCC/C=C\CCCCCCCCN(CCCCCCCOC(=O)CCCCCCCCC)CCOC(=O)NCCCn1ccnc1] | 731.2 |
| 318. | 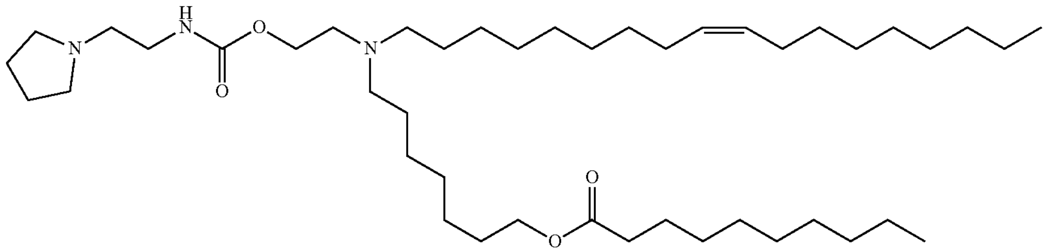 [SMILES: CCCCCCCC/C=C\CCCCCCCCN(CCCCCCCOC(=O)CCCCCCCCC)CCOC(=O)NCCN1CCCC1] | 720.2 |
| 319. | 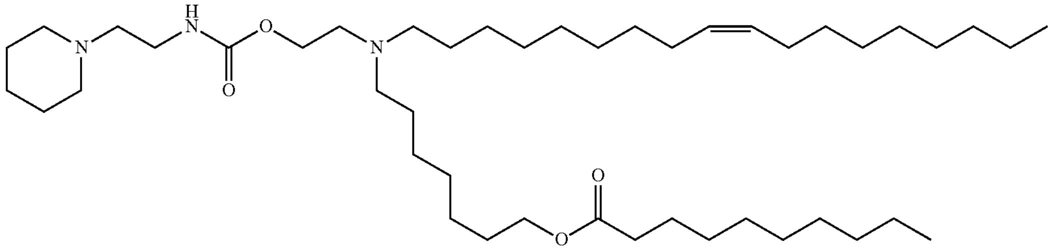 [SMILES: CCCCCCCC/C=C\CCCCCCCCN(CCCCCCCOC(=O)CCCCCCCCC)CCOC(=O)NCCN1CCCCC1] | 734.2 |

TABLE 1-continued
| # | Structure | Mw |
|---|---|---|
| 320. | 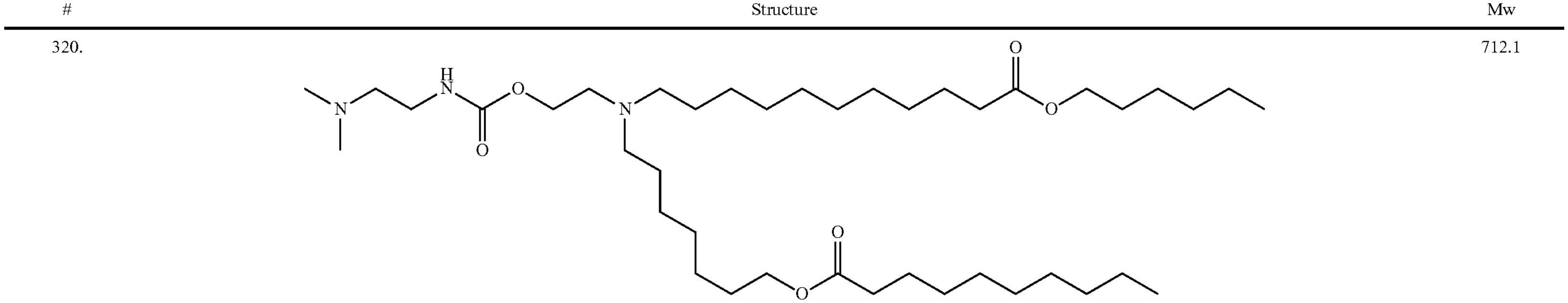 | 712.1 |
| 321. | 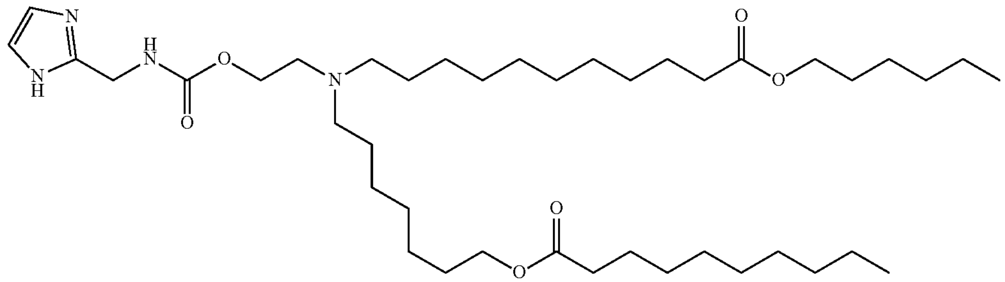 [SMILES: CCCCCCCCCC(=O)OCCCCCCCN(CCCCCCCCCCC(=O)OCCCCCC)CCOC(=O)NCc1ncc[nH]1] | 721.1 |
| 322. | 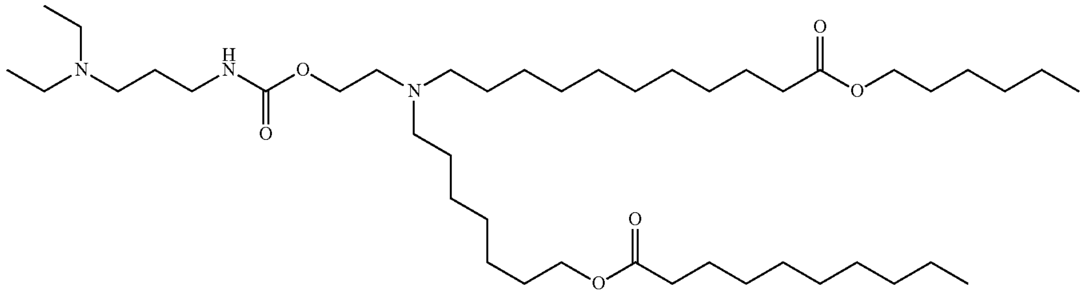 [SMILES: CCCCCCCCCC(=O)OCCCCCCCN(CCCCCCCCCCC(=O)OCCCCCC)CCOC(=O)NCCCN(CC)CC] | 754.2 |

TABLE 1-continued
| # | Structure | Mw |
| --- | --- | --- |
| 323. | 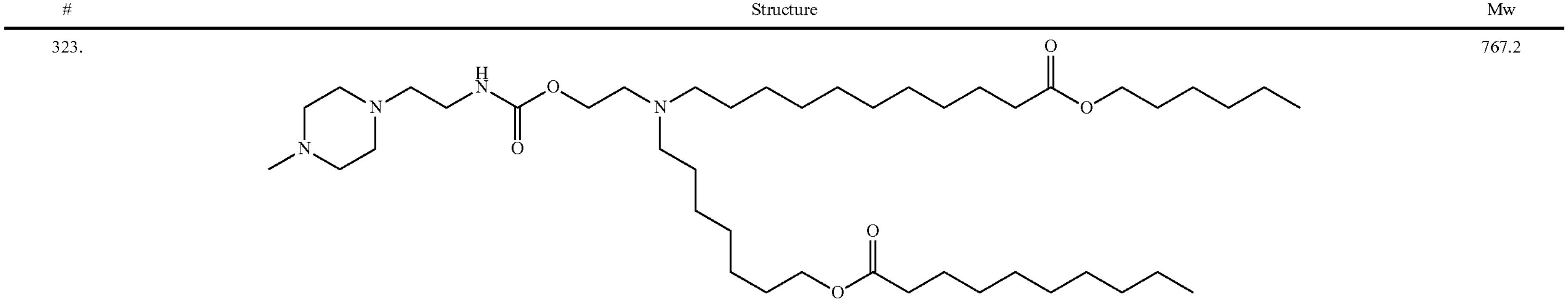 | 767.2 |
| 324. | 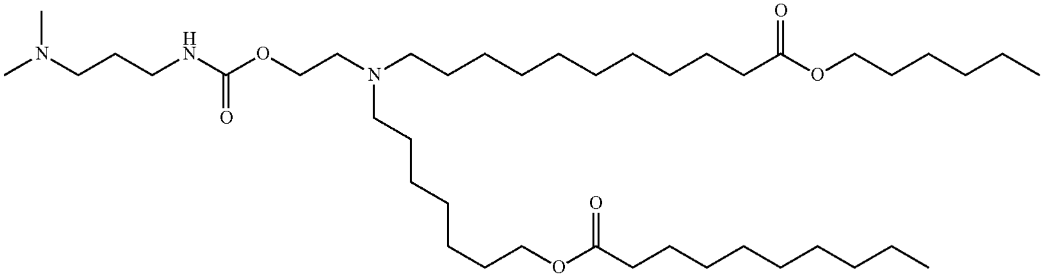 [SMILES: CCCCCCCCCC(=O)OCCCCCCCN(CCCCCCCCCCC(=O)OCCCCCC)CCOC(=O)NCCCN(C)C] | 726.1 |
| 325. | 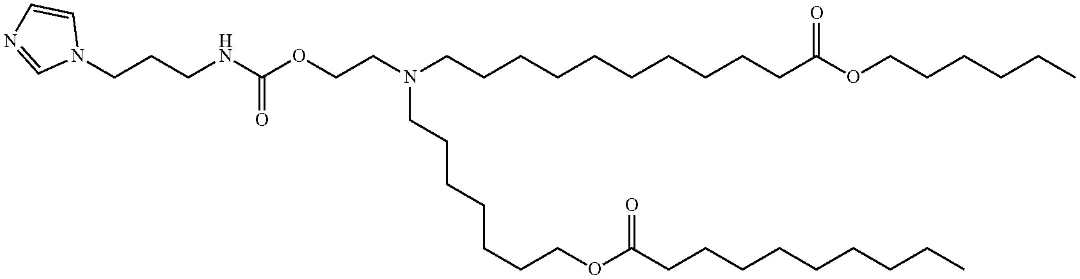 [SMILES: CCCCCCCCCC(=O)OCCCCCCCN(CCCCCCCCCCC(=O)OCCCCCC)CCOC(=O)NCCCn1ccnc1] | 749.1 |

TABLE 1-continued
| # | Structure | Mw |
|---|---|---|
| 326. | 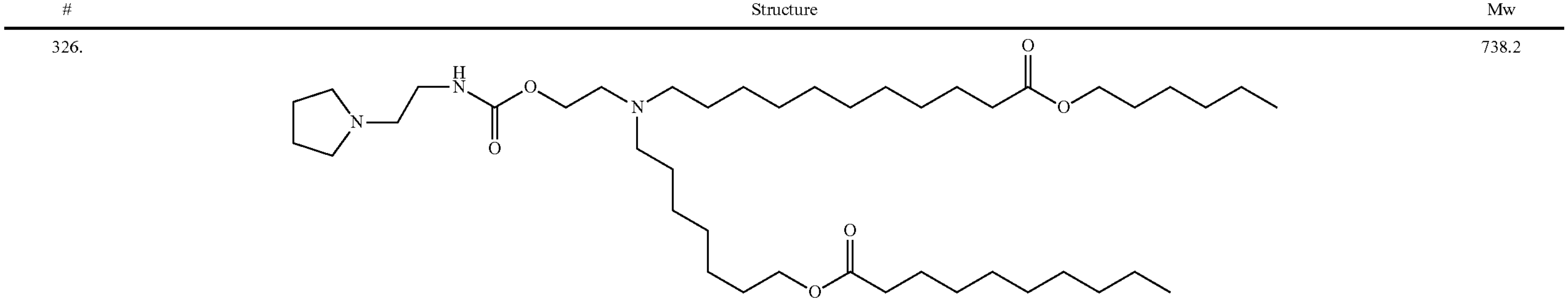 | 738.2 |
| 327. | 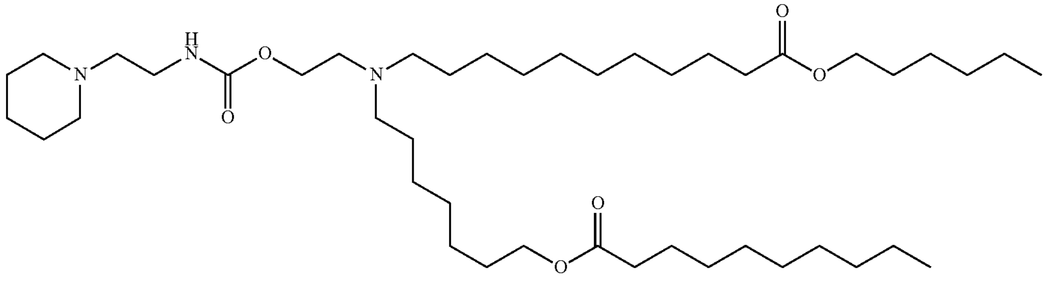 [SMILES: CCCCCCCCCC(=O)OCCCCCCCN(CCCCCCCCCCC(=O)OCCCCCC)CCOC(=O)NCCN1CCCCC1] | 752.2 |
| 328. | 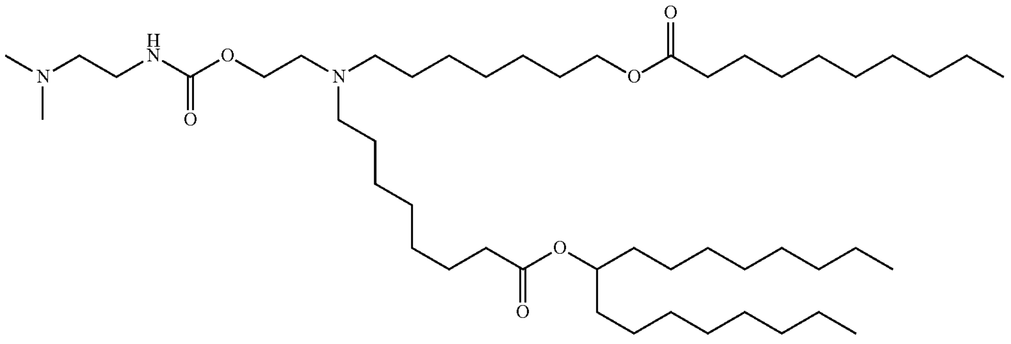 [SMILES: CCCCCCCCCC(=O)OCCCCCCCN(CCCCCCCC(=O)OC(CCCCCCCC)CCCCCCCC)CCOC(=O)NCCN(C)C] | 838.4 |

TABLE 1-continued
| # | Structure | Mw |
|---|---|---|
| 329. | 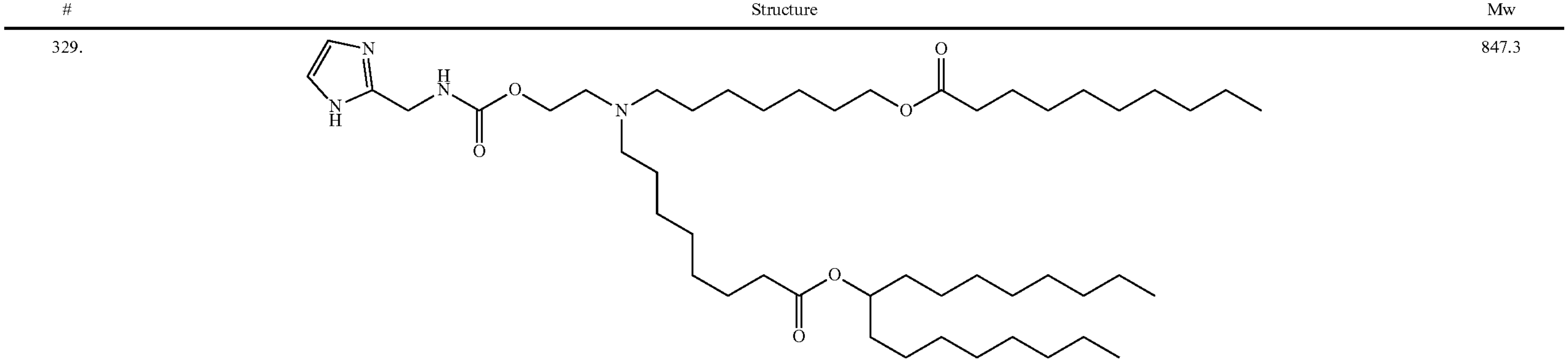 | 847.3 |
| 330. | 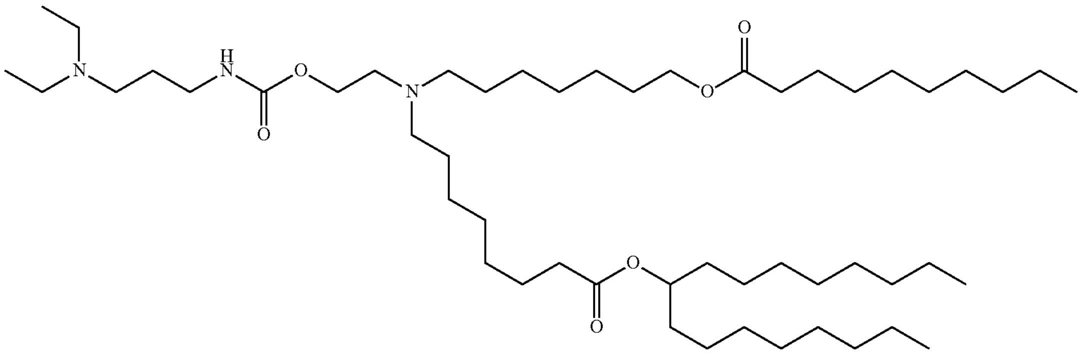 [SMILES: CCCCCCCCCC(=O)OCCCCCCCN(CCCCCCCC(=O)OC(CCCCCCCC)CCCCCCCC)CCOC(=O)NCCCN(CC)CC] | 880.4 |
| 331. | 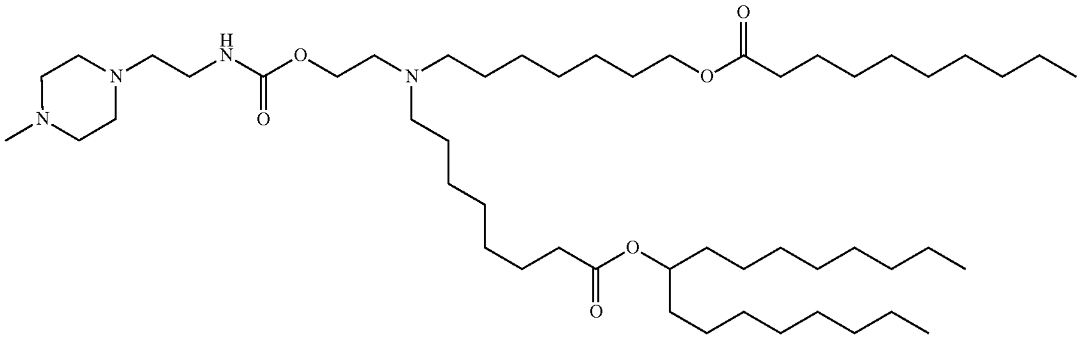 [SMILES: CCCCCCCCCC(=O)OCCCCCCCN(CCCCCCCC(=O)OC(CCCCCCCC)CCCCCCCC)CCOC(=O)NCCN1CCN(C)CC1] | 893.4 |

TABLE 1-continued
| # | Structure | Mw |
|---|---|---|
| 332. | 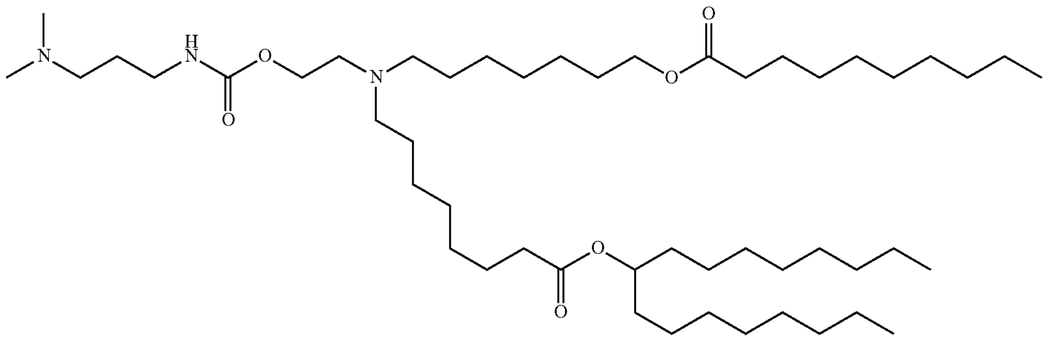 [SMILES: CCCCCCCCCC(=O)OCCCCCCCN(CCCCCCCC(=O)OC(CCCCCCCC)CCCCCCCC)CCOC(=O)NCCCN(C)C] | 852.4 |
| 333. | 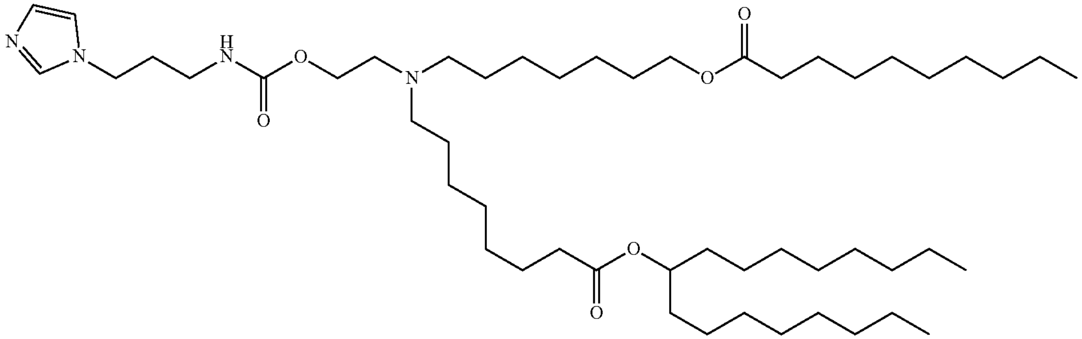 [SMILES: CCCCCCCCCC(=O)OCCCCCCCN(CCCCCCCC(=O)OC(CCCCCCCC)CCCCCCCC)CCOC(=O)NCCCn1ccnc1] | 875.4 |
| 334. | 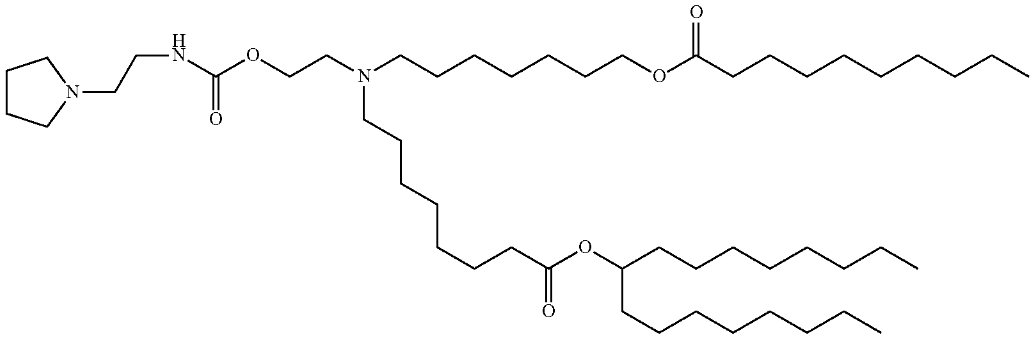 [SMILES: CCCCCCCCCC(=O)OCCCCCCCN(CCCCCCCC(=O)OC(CCCCCCCC)CCCCCCCC)CCOC(=O)NCCN1CCCC1] | 864.4 |

TABLE 1-continued
| # | Structure | Mw |
| --- | --- | --- |
| 335. | 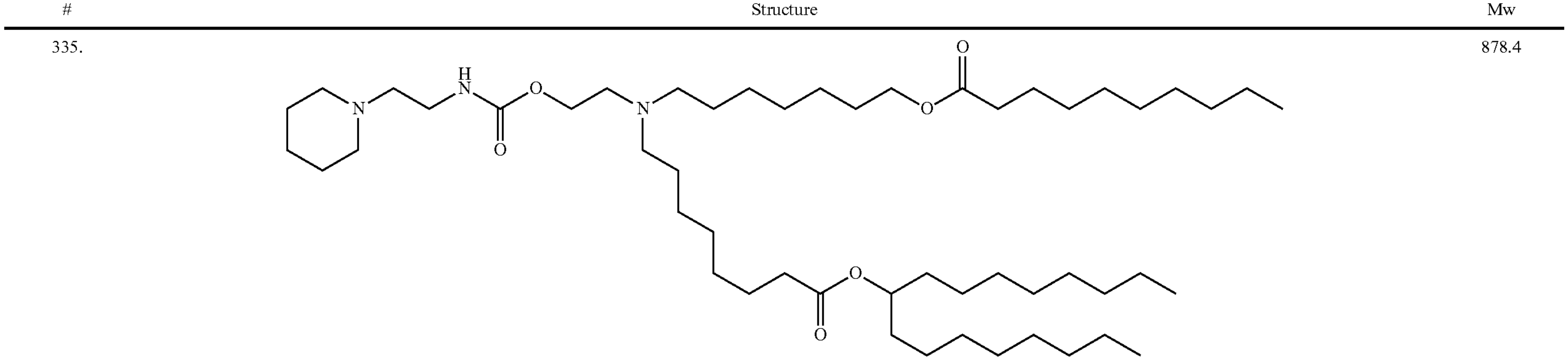 | 878.4 |
| 336. | 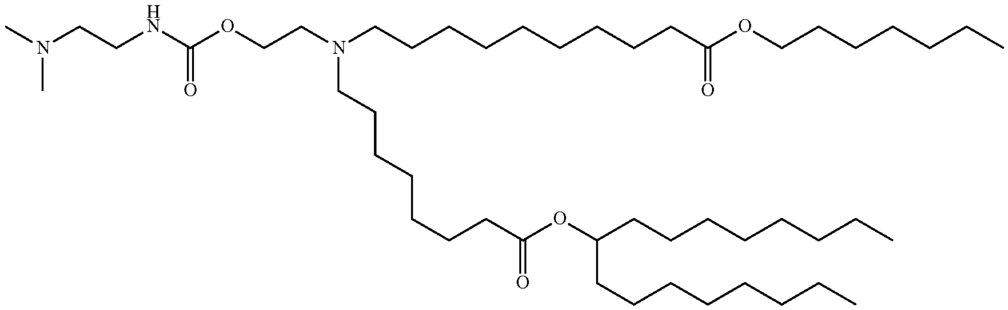 [SMILES: CCCCCCCCC(CCCCCCCC)OC(=O)CCCCCCCN(CCCCCCCCCC(=O)OCCCCCCC)CCOC(=O)NCCN(C)C] | 824.3 |
| 337. | 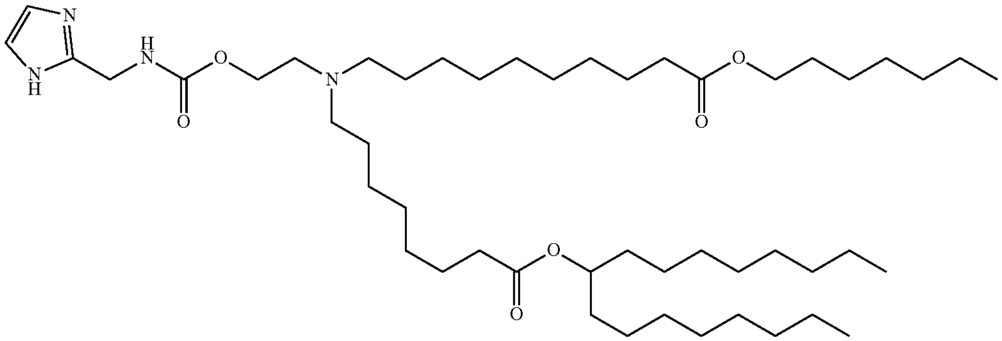 [SMILES: CCCCCCCCC(CCCCCCCC)OC(=O)CCCCCCCN(CCCCCCCCCC(=O)OCCCCCCC)CCOC(=O)NCc1ncc[nH]1] | 833.3 |

TABLE 1-continued
| # | Structure | Mw |
| --- | --- | --- |
| 338. | 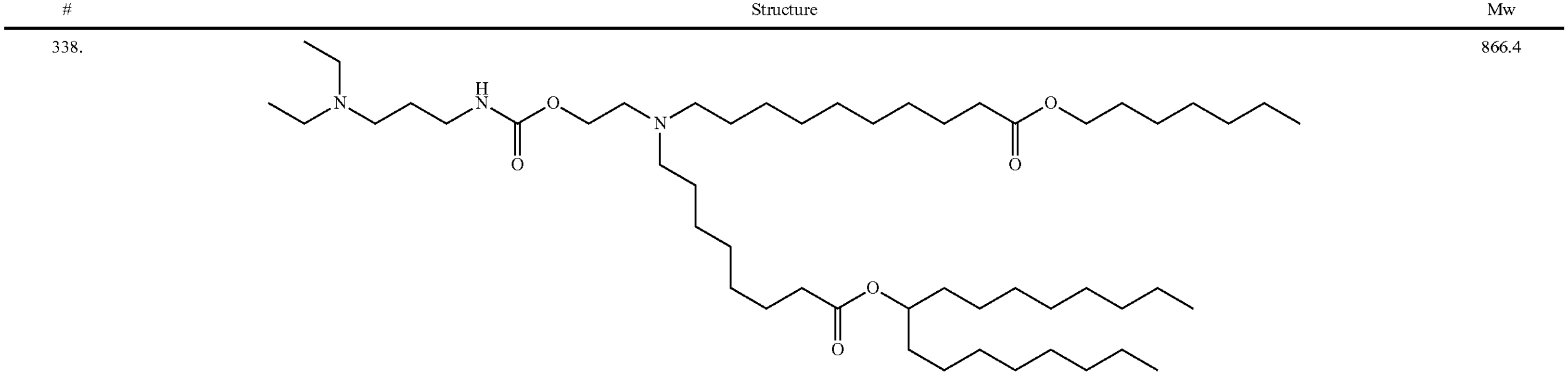 | 866.4 |
| 339. | 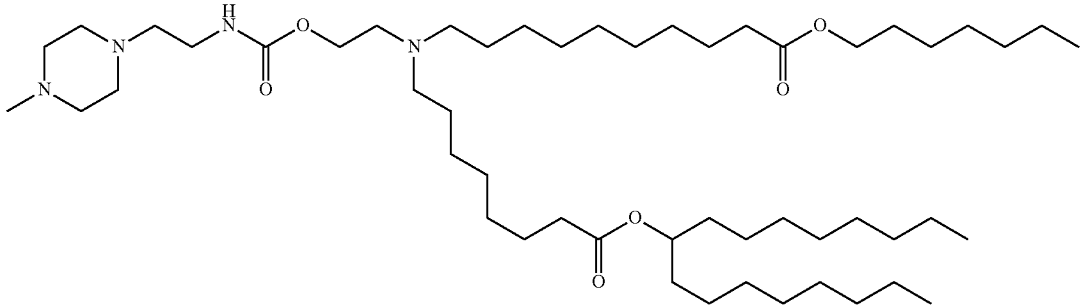 [SMILES: CCCCCCCCC(CCCCCCCC)OC(=O)CCCCCCCN(CCCCCCCCCC(=O)OCCCCCCC)CCOC(=O)NCCN1CCN(C)CC1] | 879.4 |
| 340. | 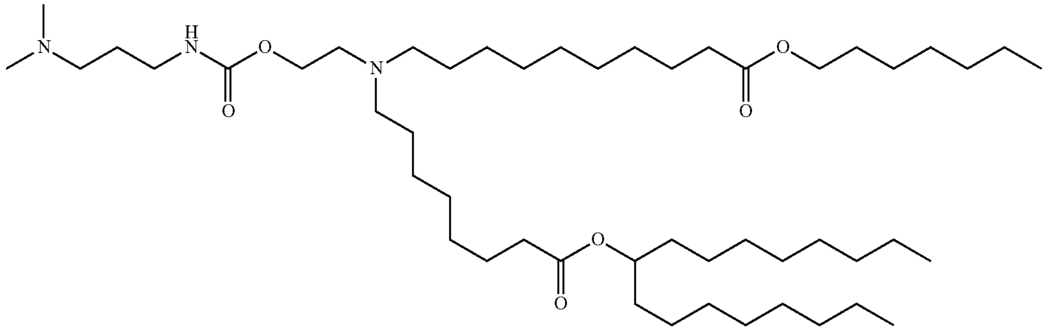 [SMILES: CCCCCCCCC(CCCCCCCC)OC(=O)CCCCCCCN(CCCCCCCCCC(=O)OCCCCCCC)CCOC(=O)NCCCN(C)C] | 838.4 |

TABLE 1-continued
| # | Structure | Mw |
|---|---|---|
| 341. | 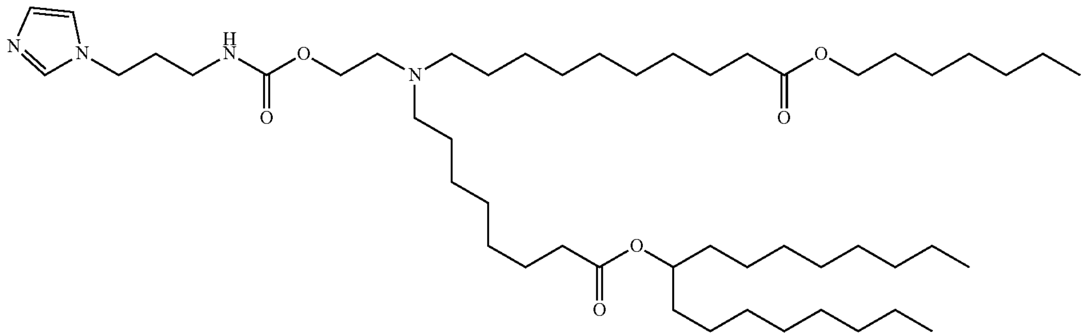 [SMILES: CCCCCCCCC(CCCCCCCC)OC(=O)CCCCCCCN(CCCCCCCCCC(=O)OCCCCCCC)CCOC(=O)NCCCn1ccnc1] | 861.4 |
| 342. | 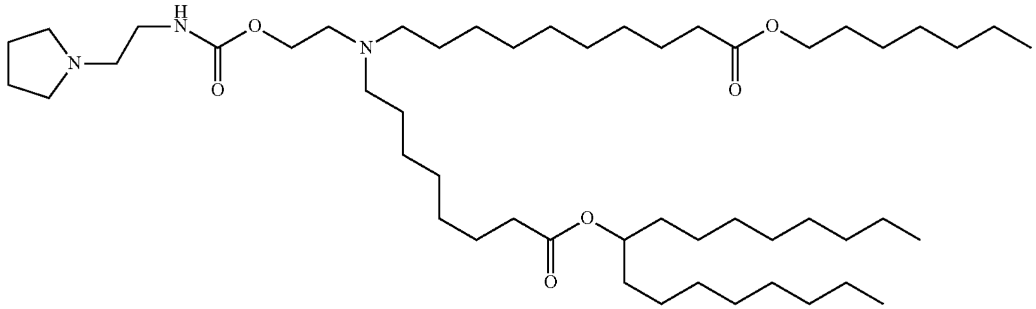 [SMILES: CCCCCCCCC(CCCCCCCC)OC(=O)CCCCCCCN(CCCCCCCCCC(=O)OCCCCCCC)CCOC(=O)NCCN1CCCC1] | 850.4 |
| 343. | 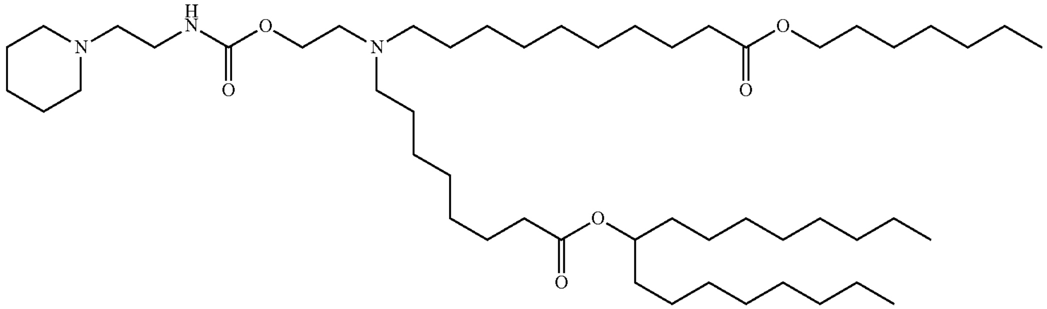 [SMILES: CCCCCCCCC(CCCCCCCC)OC(=O)CCCCCCCN(CCCCCCCCCC(=O)OCCCCCCC)CCOC(=O)NCCN1CCCCC1] | 864.4 |

TABLE 1-continued
| # | Structure | Mw |
|---|---|---|
| 344. | 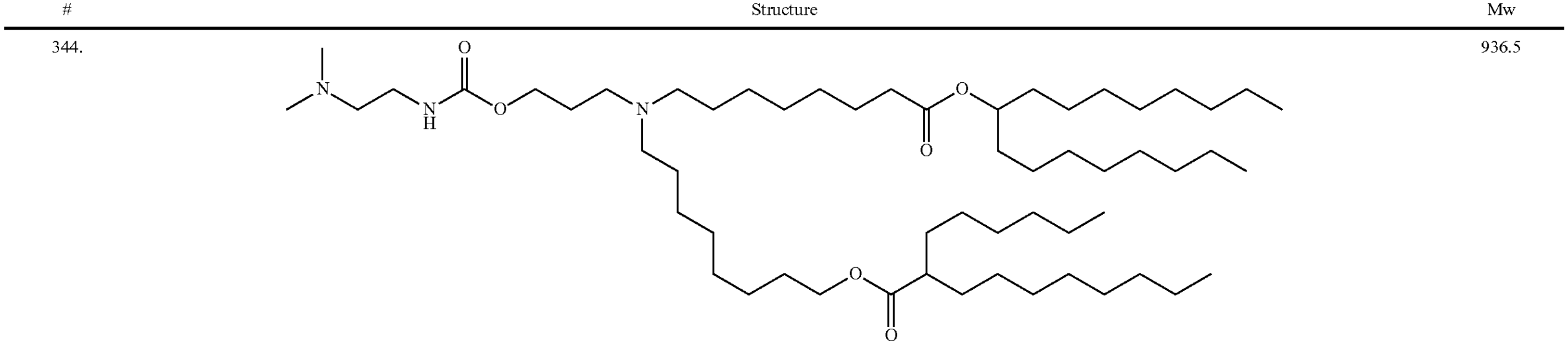 | 936.5 |
| 345. | 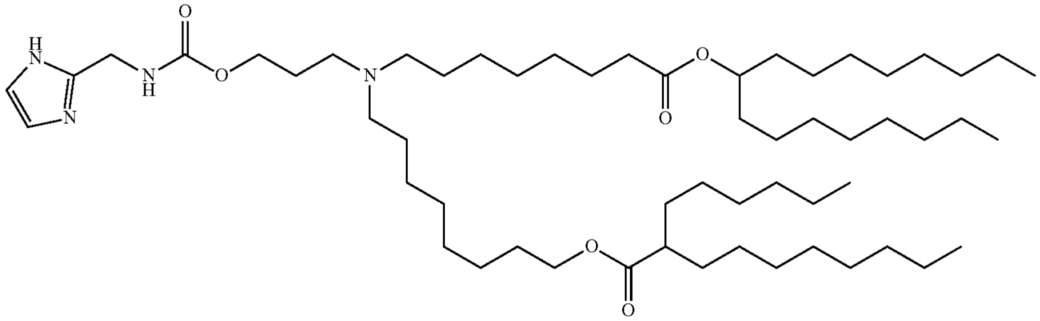 [SMILES: CCCCCCCCC(CCCCCCCC)OC(=O)CCCCCCCN(CCCCCCCCOC(=O)C(CCCCCC)CCCCCCCC)CCCOC(=O)NCc1ncc[nH]1] | 945.5 |
| 346. | 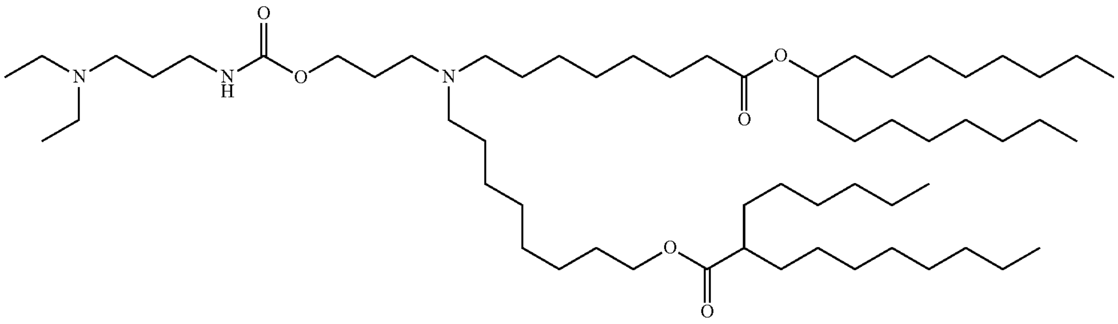 [SMILES: CCCCCCCCC(CCCCCCCC)OC(=O)CCCCCCCN(CCCCCCCCOC(=O)C(CCCCCC)CCCCCCCC)CCCOC(=O)NCCCN(CC)CC] | 978.6 |

TABLE 1-continued
| # | Structure | Mw |
| --- | --- | --- |
| 347. | 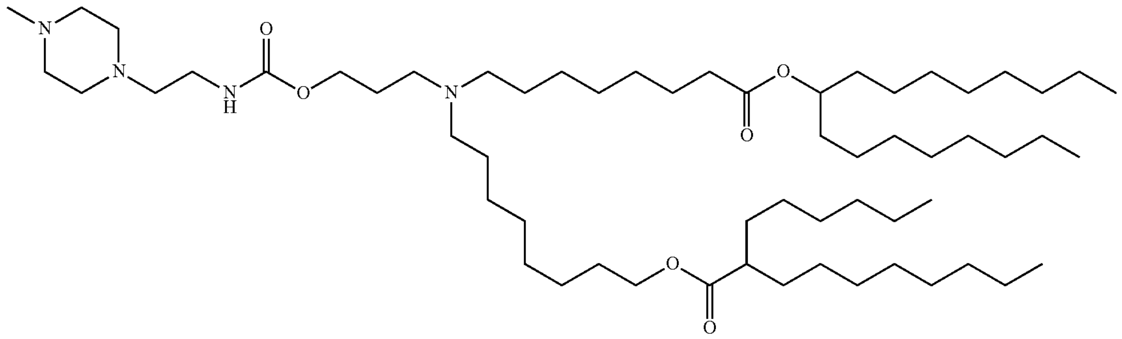 [SMILES: CCCCCCCCC(CCCCCCCC)OC(=O)CCCCCCCN(CCCCCCCCOC(=O)C(CCCCCC)CCCCCCCC)CCCOC(=O)NCCN1CCN(C)CC1] | 991.6 |
| 348. | 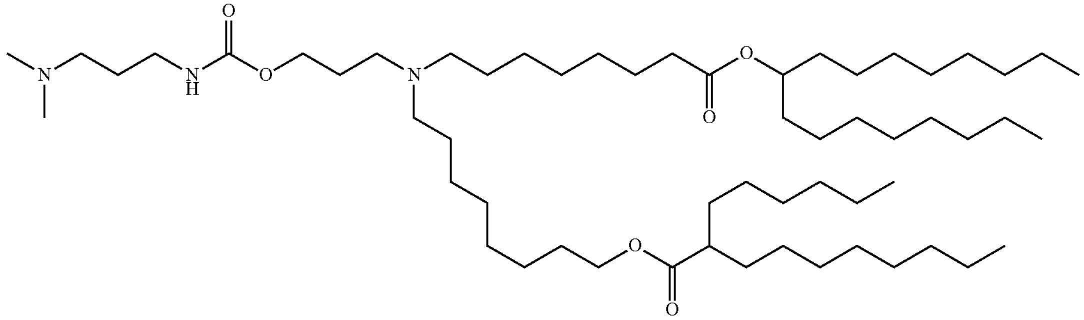 [SMILES: CCCCCCCCC(CCCCCCCC)OC(=O)CCCCCCCN(CCCCCCCCOC(=O)C(CCCCCC)CCCCCCCC)CCCOC(=O)NCCCN(C)C] | 950.5 |
| 349. | 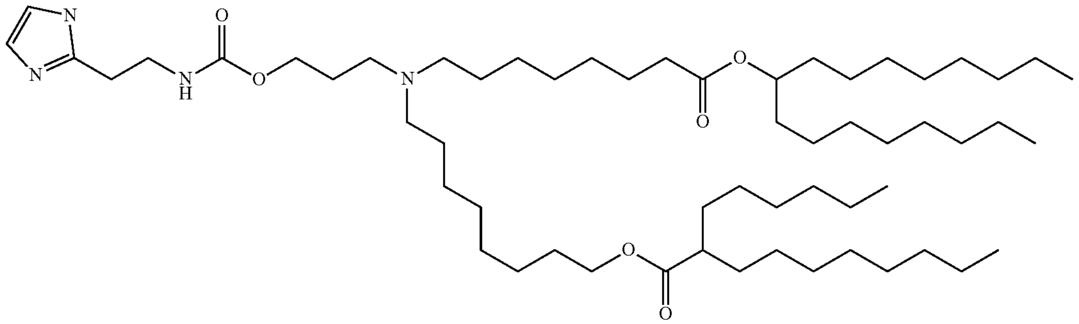 [SMILES: CCCCCCCCC(CCCCCCCC)OC(=O)CCCCCCCN(CCCCCCCCOC(=O)C(CCCCCC)CCCCCCCC)CCCOC(=O)NCCc1ncc[nH]1] | 973.5 |

TABLE 1-continued
| # | Structure | Mw |
|---|---|---|
| 350. | 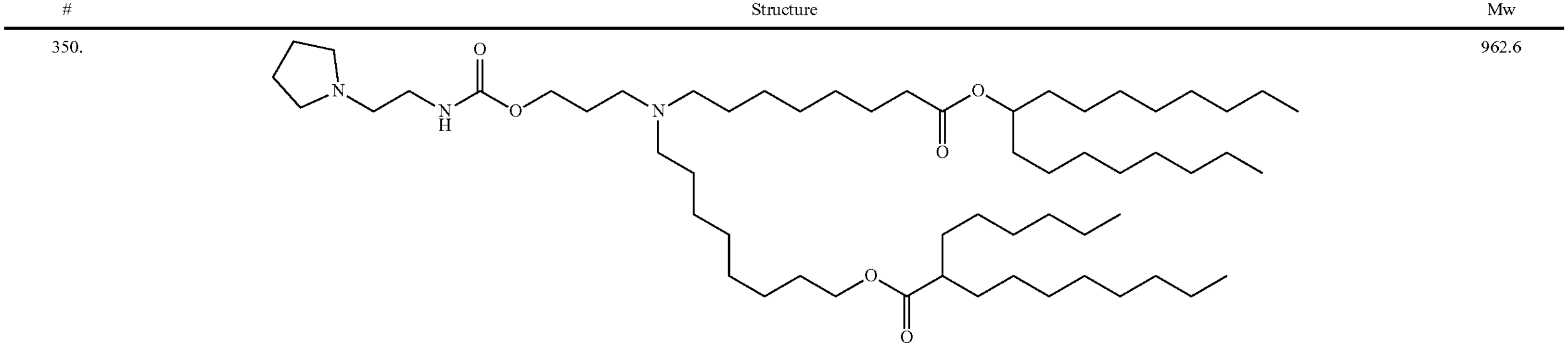 | 962.6 |
| 351. | 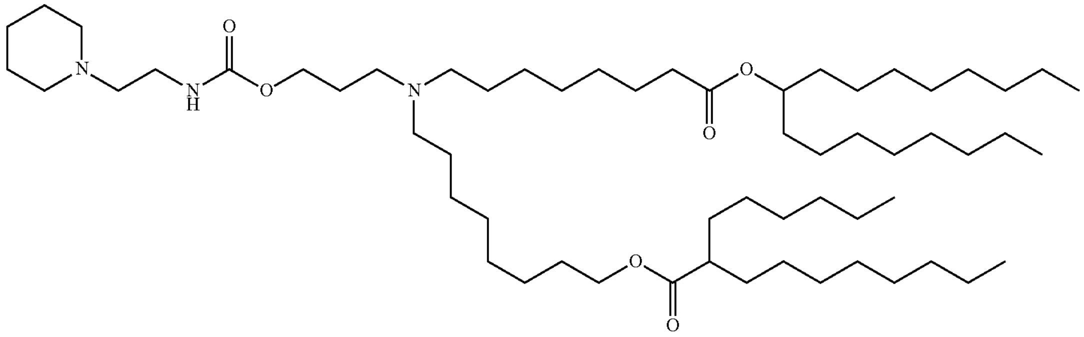 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCCC1] | 976.6 |
| 352. | 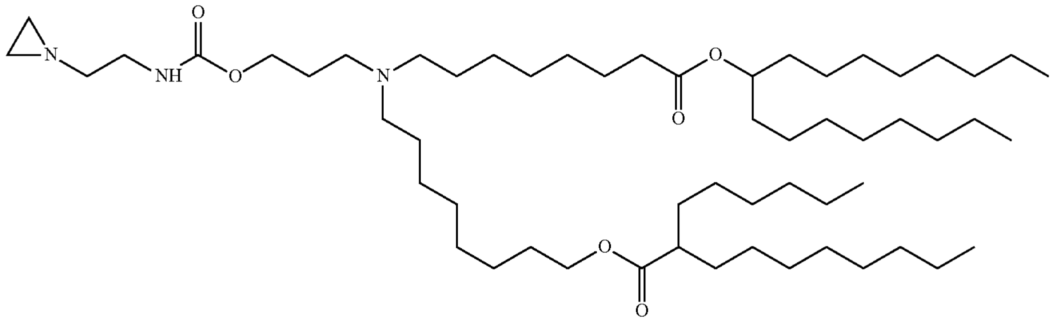 [SMILES: CCCCCCCCC(CCCCCCCC)OC(=O)CCCCCCCN(CCCCCCCCOC(=O)C(CCCCCC)CCCCCCCC)CCCOC(=O)NCCN1CC1] | 934.5 |

TABLE 1-continued
| # | Structure | Mw |
| --- | --- | --- |
| 353. | 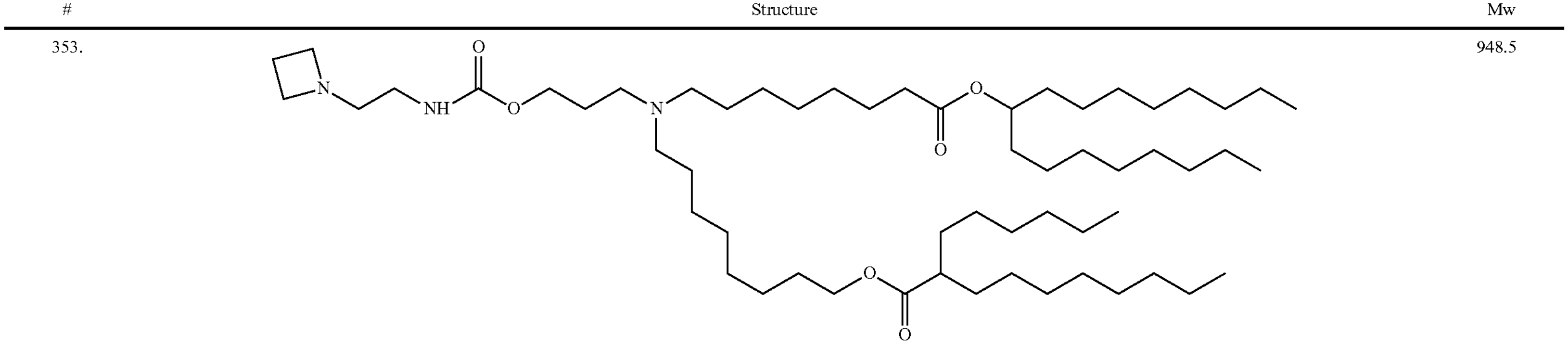 | 948.5 |
| 354. | 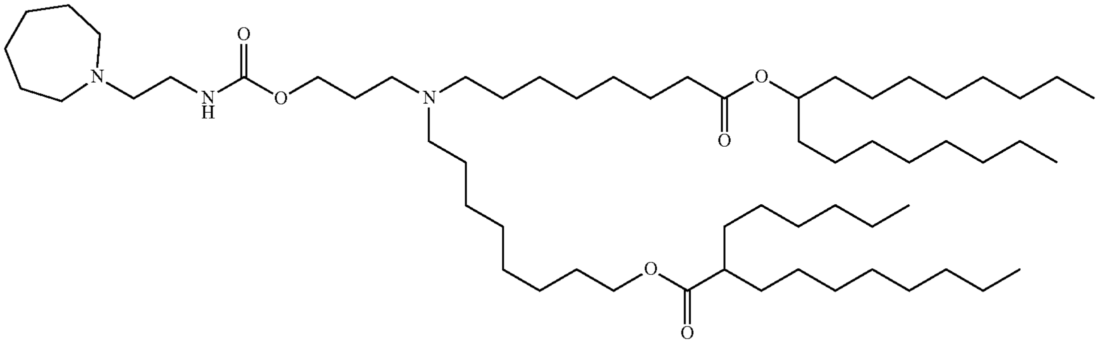 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCCCC1] | 990.63 |
| 355. | 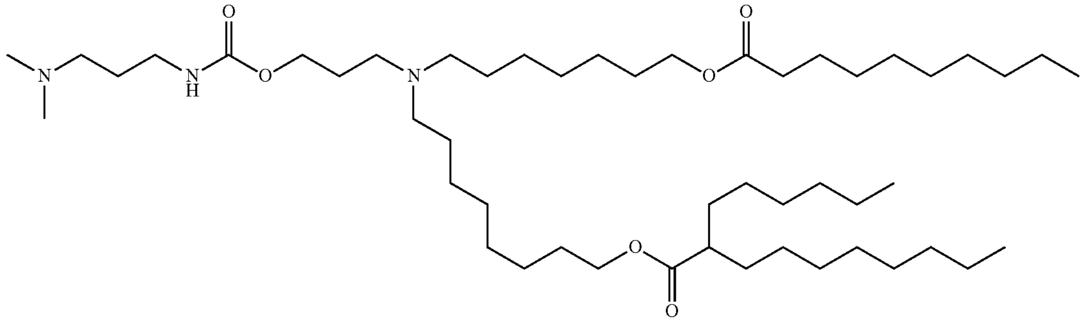 [SMILES: CCCCCCCCCC(=O)OCCCCCCCN(CCCCCCCCOC(=O)C(CCCCCC)CCCCCCCC)CCCOC(=O)NCCCN(C)C] | 838.3 |

TABLE 1-continued
| # | Structure | Mw |
| --- | --- | --- |
| 356. | 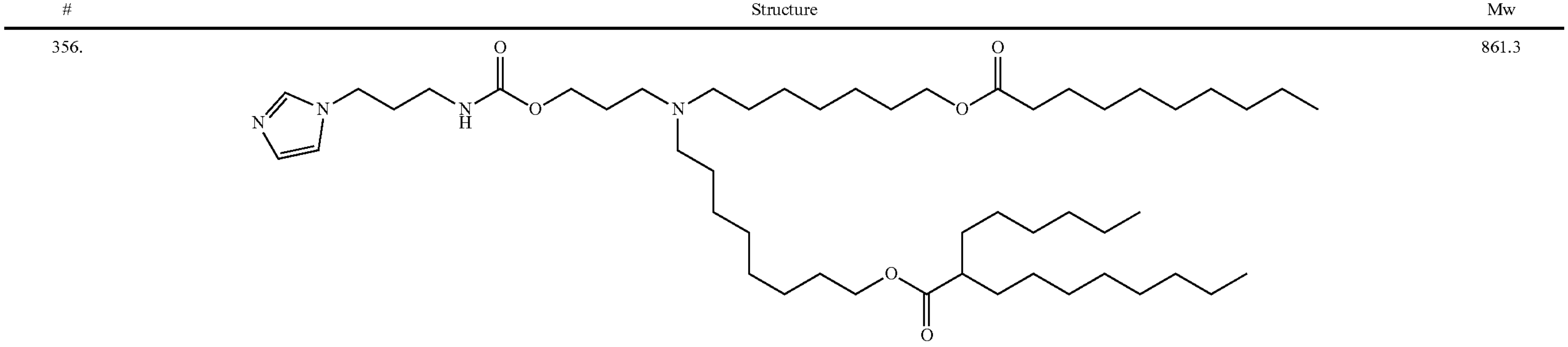 | 861.3 |
| 357. | 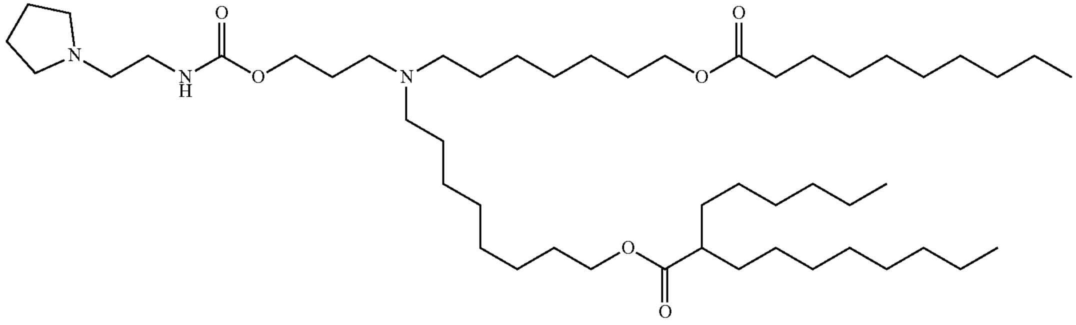 [SMILES: CCCCCCCCCC(=O)OCCCCCCCN(CCCCCCCCOC(=O)C(CCCCCC)CCCCCCCC)CCCOC(=O)NCCN1CCCC1] | 850.3 |
| 358. | 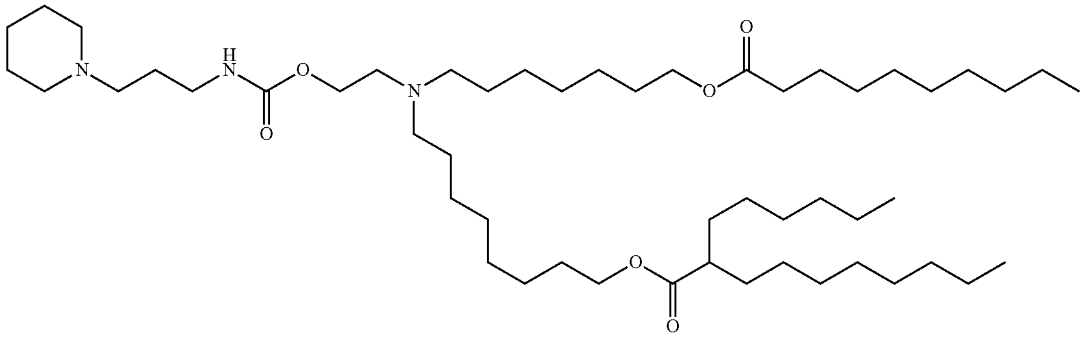 [SMILES: CCCCCCCCCC(=O)OCCCCCCCN(CCCCCCCCOC(=O)C(CCCCCC)CCCCCCCC)CCOC(=O)NCCCN1CCCCC1] | 864.4 |

TABLE 1-continued
| # | Structure | Mw |
|---|---|---|
| 359. | 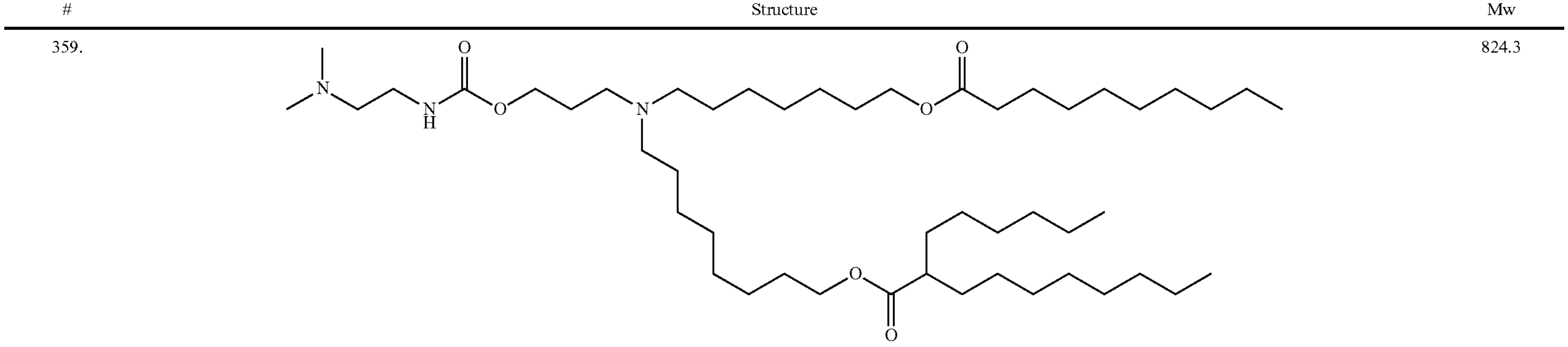 | 824.3 |
| 360. | 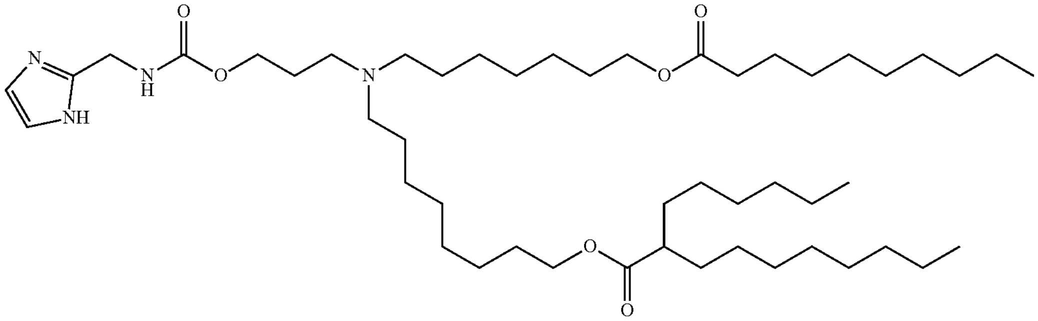 [SMILES: CCCCCCCCCC(=O)OCCCCCCCN(CCCCCCCCOC(=O)C(CCCCCC)CCCCCCCC)CCCOC(=O)NCc1ncc[nH]1] | 833.3 |
| 361. | 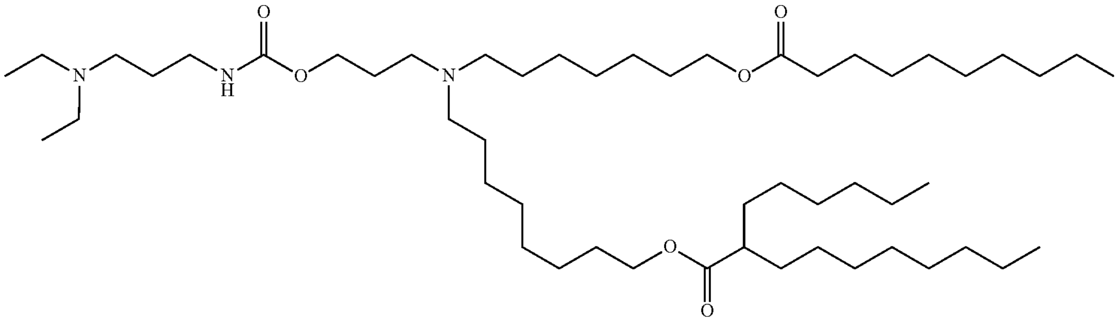 [SMILES: CCCCCCCCCC(=O)OCCCCCCCN(CCCCCCCCOC(=O)C(CCCCCC)CCCCCCCC)CCCOC(=O)NCCCN(CC)CC] | 866.4 |

TABLE 1-continued
| # | Structure | Mw |
|---|---|---|
| 362. | 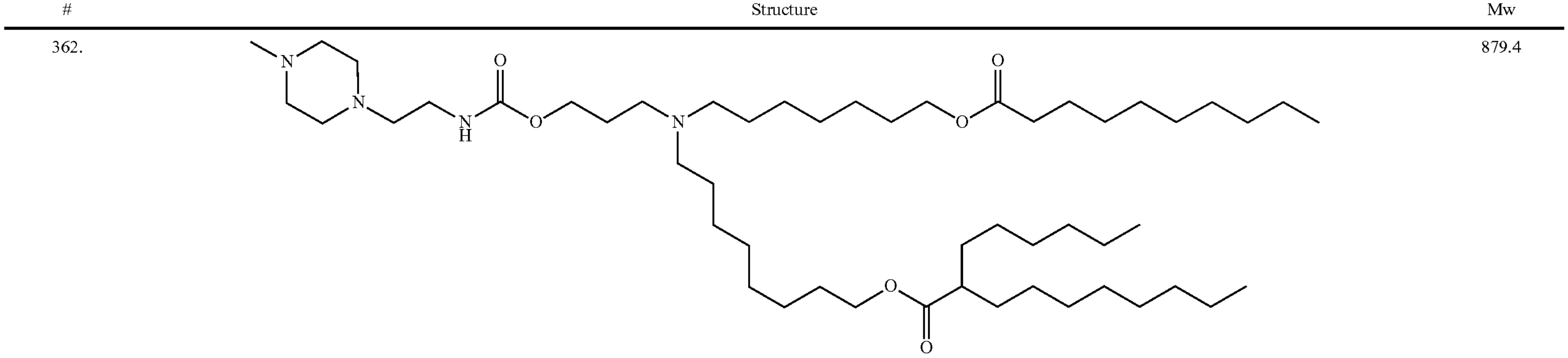 | 879.4 |
| 363. | 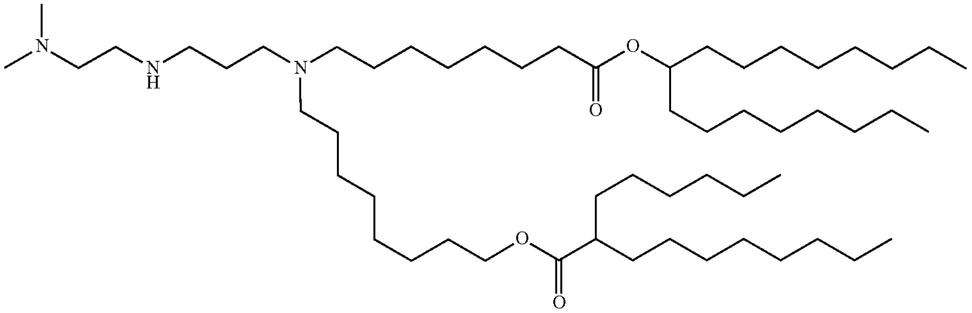 [SMILES: CCCCCCCCC(CCCCCCCC)OC(=O)CCCCCCCN(CCCCCCCCOC(=O)C(CCCCCC)CCCCCCCC)CCCNCCN(C)C] | 892.5 |
| 364. | 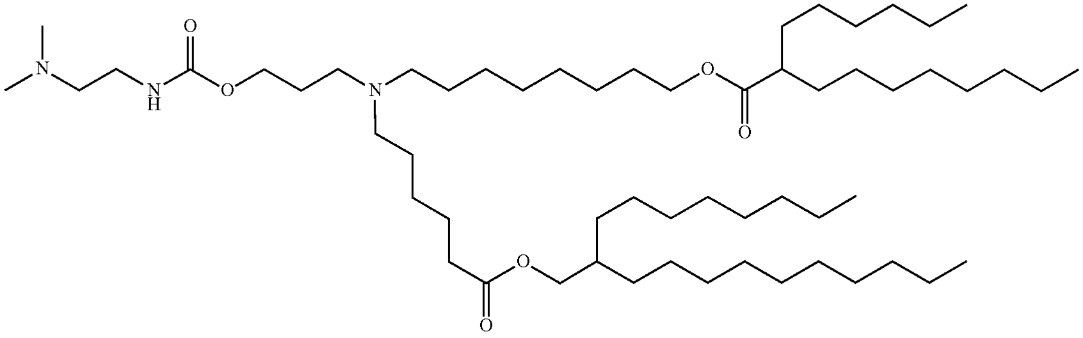 [SMILES: CCCCCCCCCCC(CCCCCCCC)COC(=O)CCCCCN(CCCCCCCCOC(=O)C(CCCCCC)CCCCCCCC)CCCOC(=O)NCCN(C)C] | 978.6 |

TABLE 1-continued
| # | Structure | Mw |
| --- | --- | --- |
| 365. | 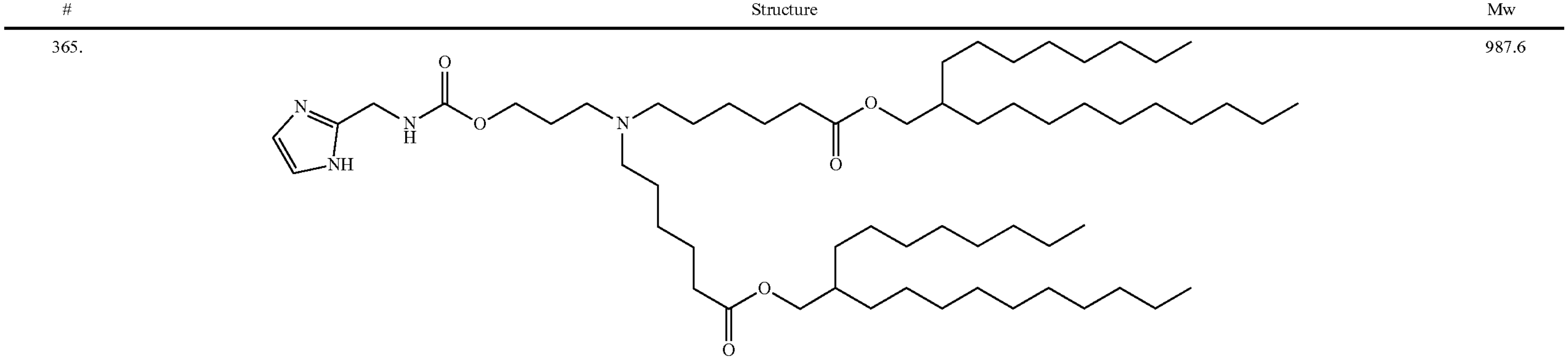 | 987.6 |
| 366. | 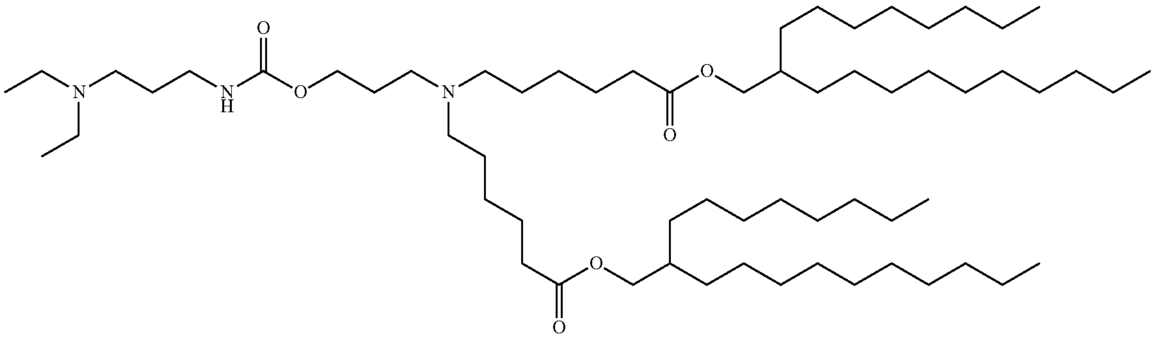 [SMILES: CCCCCCCCCCC(CCCCCCCC)COC(=O)CCCCCN(CCCCCC(=O)OCC(CCCCCCCC)CCCCCCCCCC)CCCOC(=O)NCCCN(CC)CC] | 1020.7 |
| 367. | 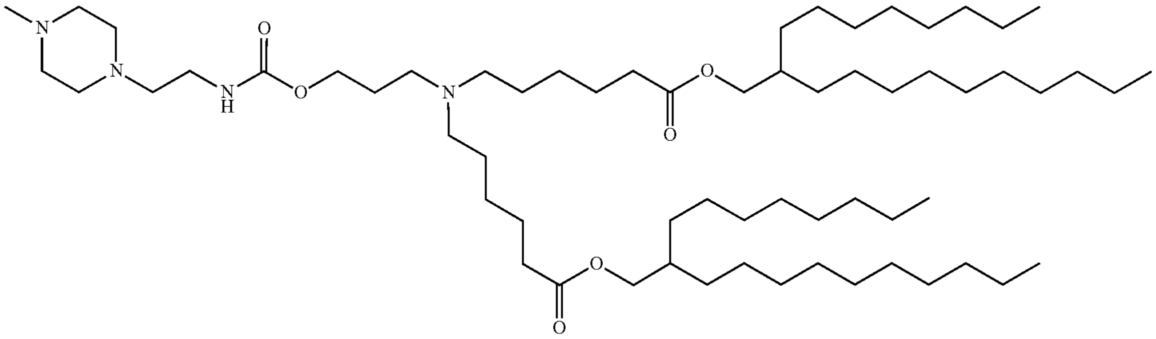 | 1033.7 |

TABLE 1-continued
| # | Structure | Mw |
| --- | --- | --- |
| 368. | 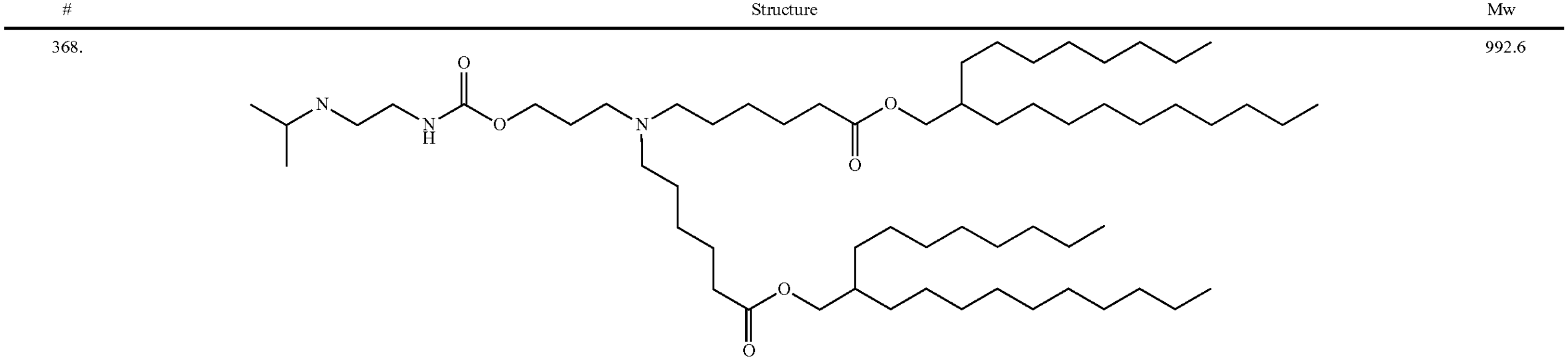 | 992.6 |
| 369. | 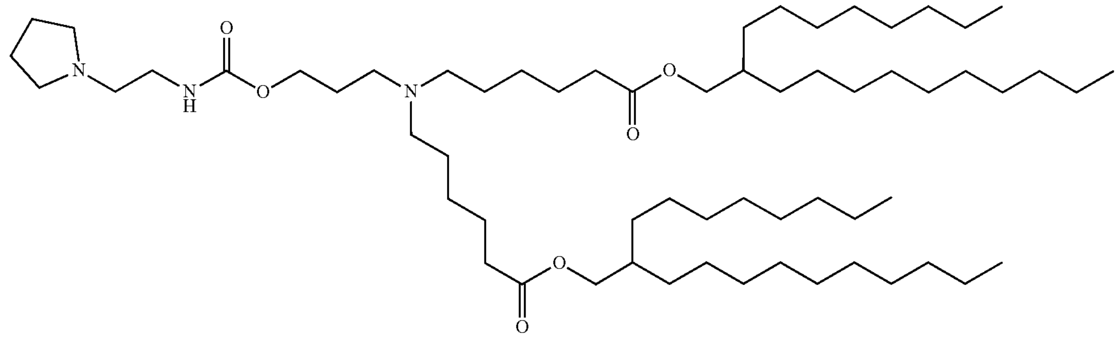 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCC1] | 1004.6 |
| 370. | 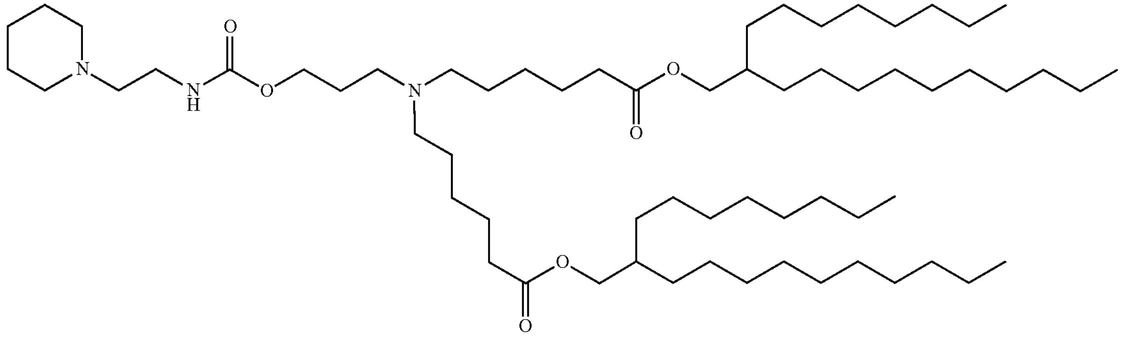 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCCC1] | 1018.9 |

TABLE 1-continued
| # | Structure | Mw |
|---|---|---|
| 371. | 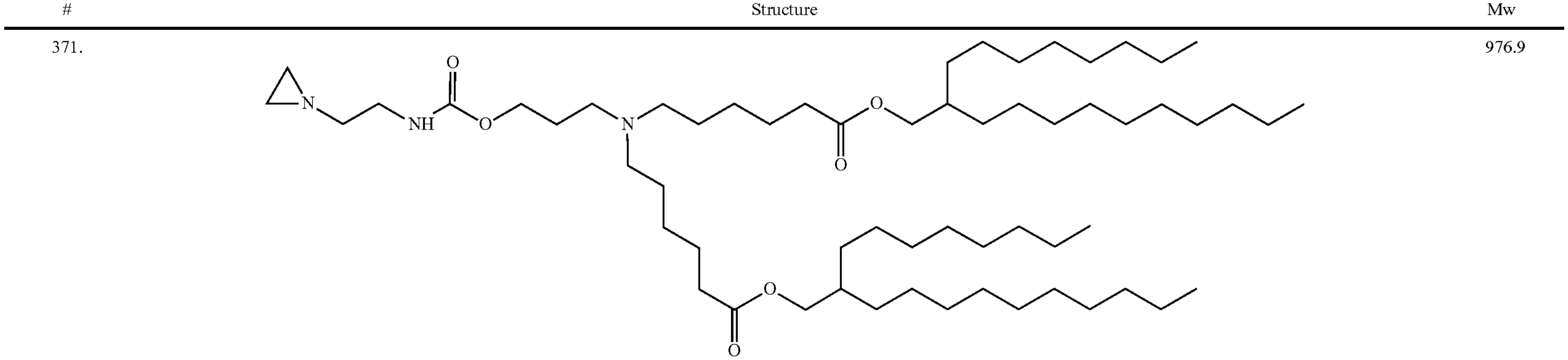 | 976.9 |
| 372. | 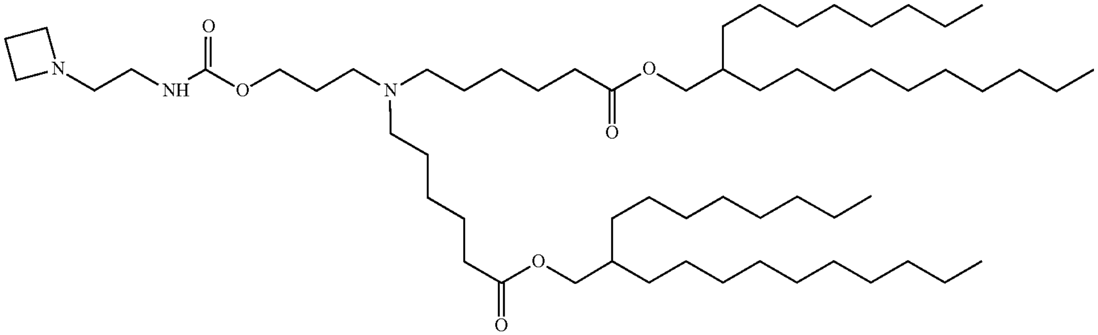 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCC1] | 990.9 |
| 373. | 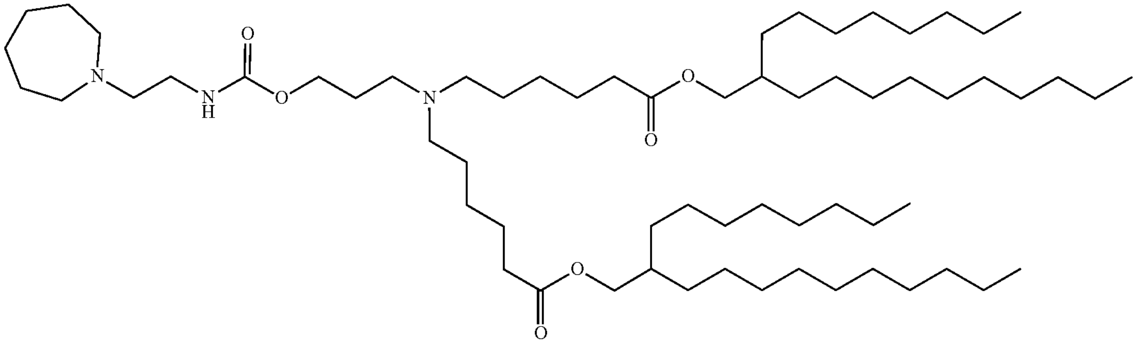 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCCCC1] | 1033.0 |

TABLE 1-continued
| # | Structure | Mw |
|---|---|---|
| 374. | 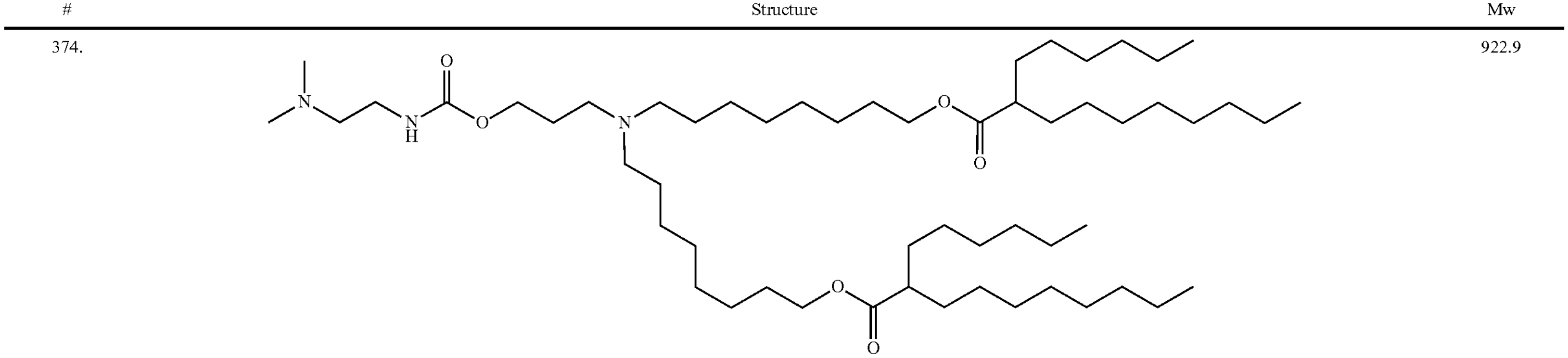 | 922.9 |
| 375. | 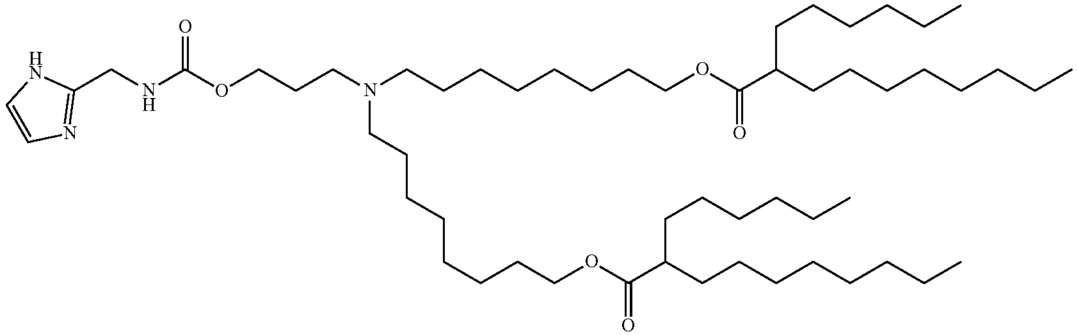 [SMILES: CCCCCCCCC(CCCCCC)C(=O)OCCCCCCCCN(CCCCCCCCOC(=O)C(CCCCCC)CCCCCCCC)CCCOC(=O)NCc1ncc[nH]1] | 932.2 |
| 376. | 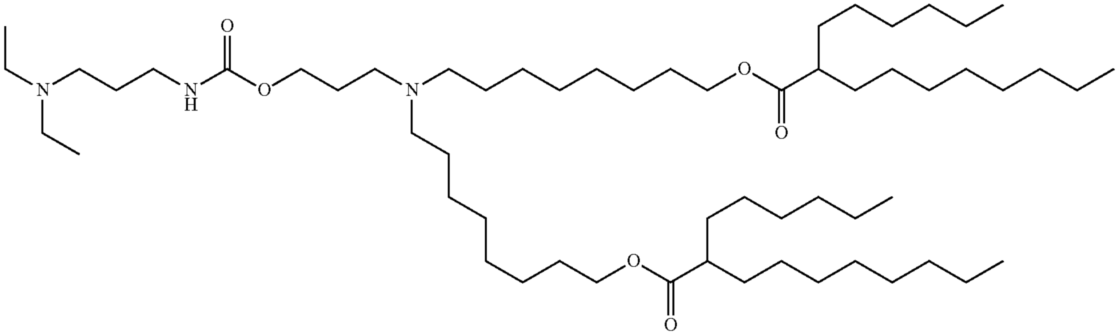 [SMILES: CCCCCCCCC(CCCCCC)C(=O)OCCCCCCCCN(CCCCCCCCOC(=O)C(CCCCCC)CCCCCCCC)CCCOC(=O)NCCCN(CC)CC] | 964.9 |

TABLE 1-continued
| # | Structure | Mw |
|---|---|---|
| 377. | 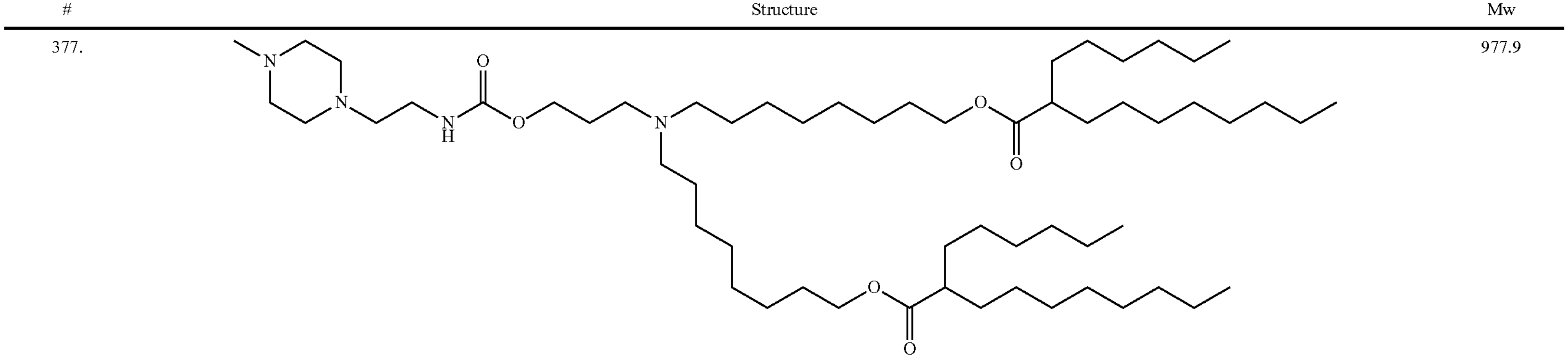 | 977.9 |
| 378. | 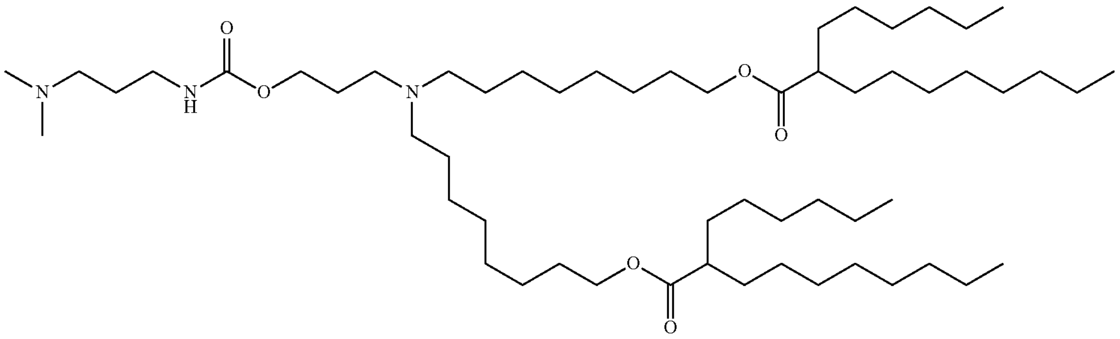 [SMILES: CCCCCCCCC(CCCCCC)C(=O)OCCCCCCCCN(CCCCCCCCOC(=O)C(CCCCCC)CCCCCCCC)CCCOC(=O)NCCCN(C)C] | 936.9 |
| 379. | 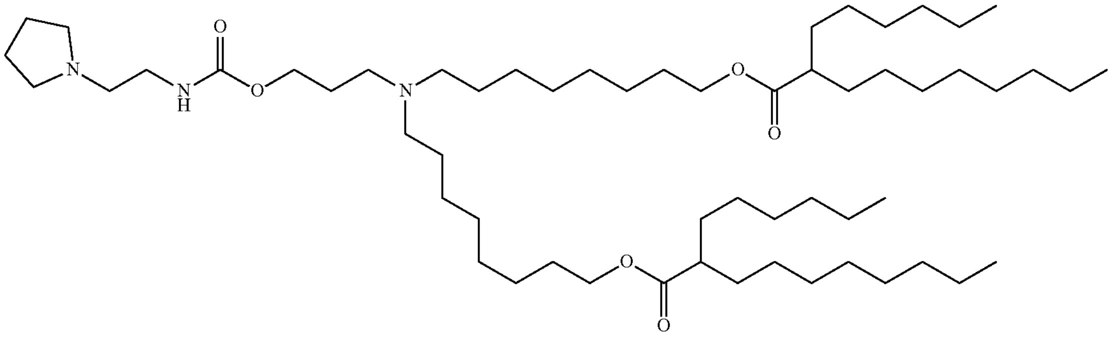 [SMILES: CCCCCCCCC(CCCCCC)C(=O)OCCCCCCCCN(CCCCCCCCOC(=O)C(CCCCCC)CCCCCCCC)CCCOC(=O)NCCN1CCCC1] | 948.9 |

TABLE 1-continued
| # | Structure | Mw |
|---|---|---|
| 380. | 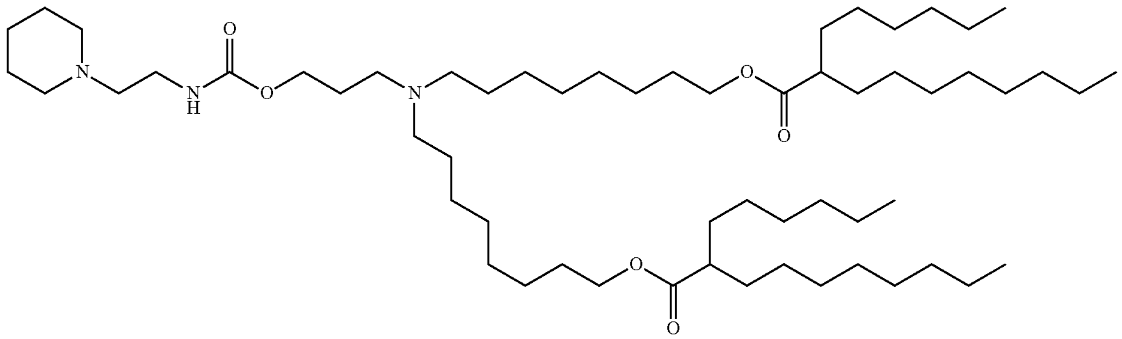 [SMILES: CCCCCCCCC(CCCCCC)C(=O)OCCCCCCCCN(CCCCCCCCOC(=O)C(CCCCCC)CCCCCCCC)CCCOC(=O)NCCN1CCCCC1] | 962.9 |
| 381. | 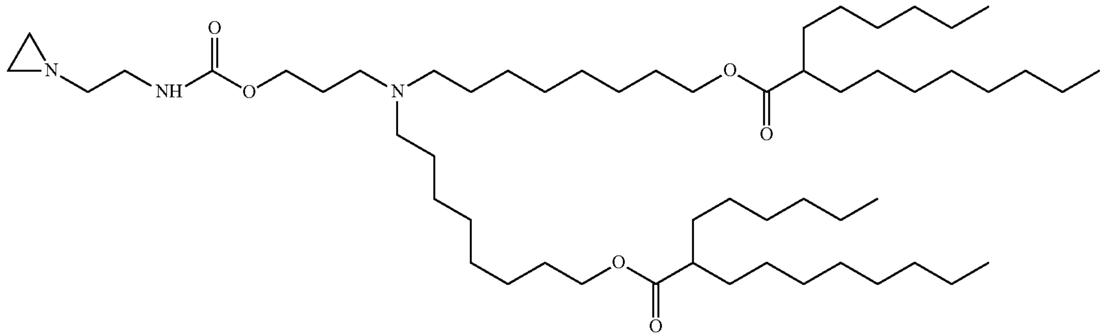 [SMILES: CCCCCCCCC(CCCCCC)C(=O)OCCCCCCCCN(CCCCCCCCOC(=O)C(CCCCCC)CCCCCCCC)CCCOC(=O)NCCN1CC1] | 920.8 |
| 382. | 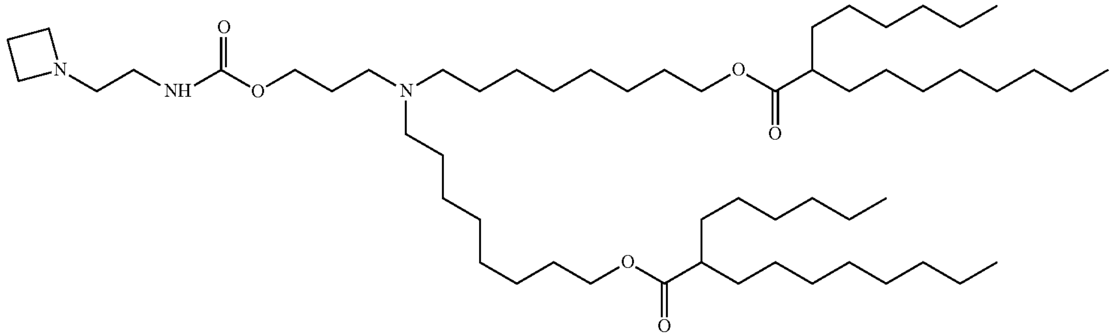 [SMILES: CCCCCCCCC(CCCCCC)C(=O)OCCCCCCCCN(CCCCCCCCOC(=O)C(CCCCCC)CCCCCCCC)CCCOC(=O)NCCN1CCC1] | 934.9 |

TABLE 1-continued
| # | Structure | Mw |
| --- | --- | --- |
| 383. | 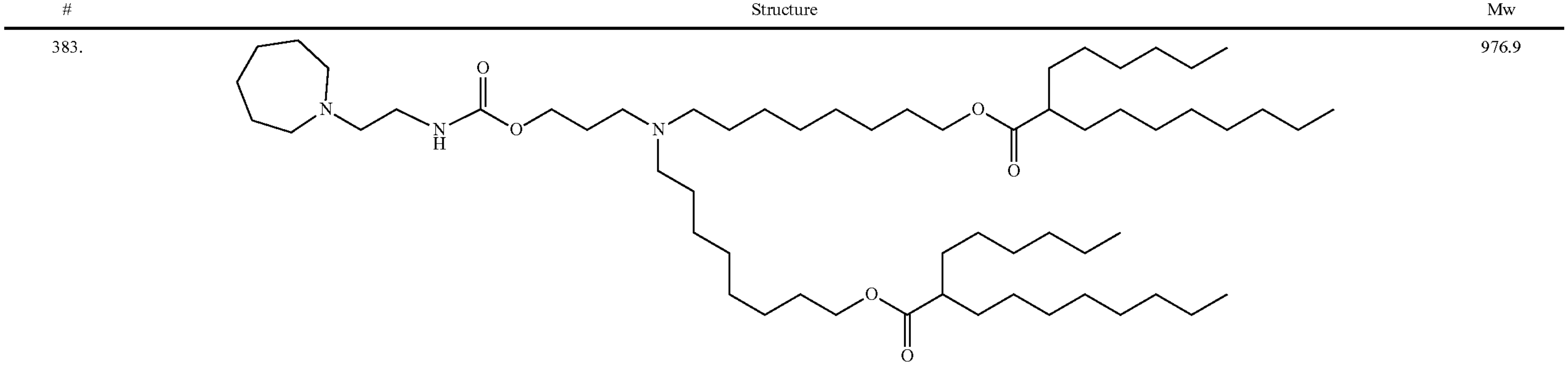 | 976.9 |
| 384. | 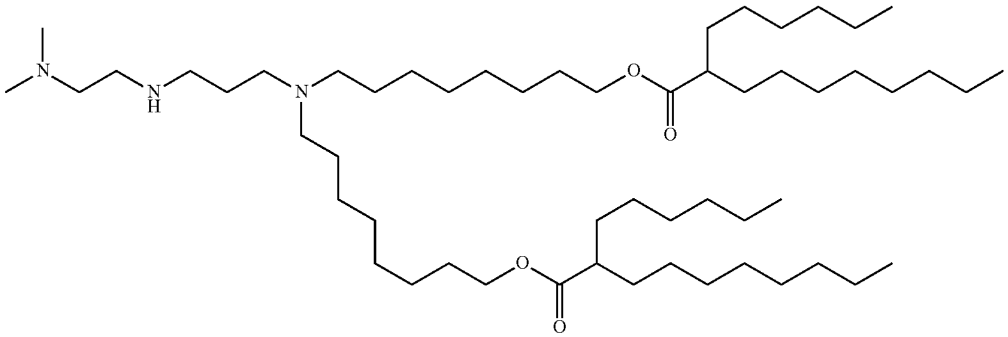 [SMILES: CCCCCCCCC(CCCCCC)C(=O)OCCCCCCCCN(CCCCCCCCOC(=O)C(CCCCCC)CCCCCCCC)CCCNCCN(C)C] | 878.9 |
| 385. | 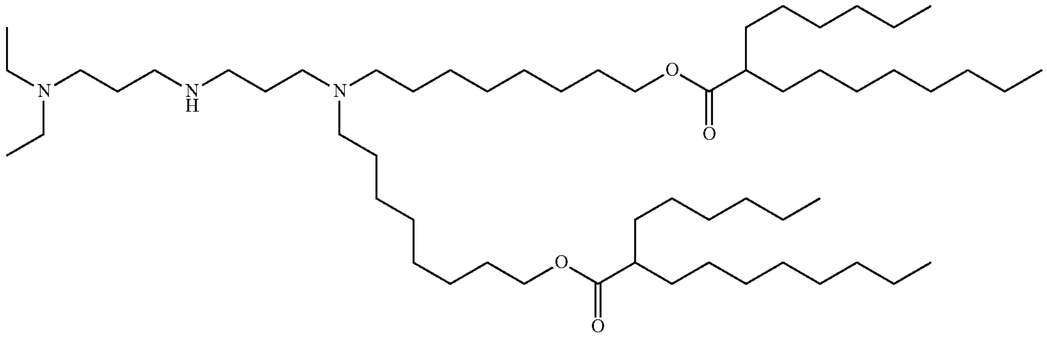 [SMILES: CCCCCCCCC(CCCCCC)C(=O)OCCCCCCCCN(CCCCCCCCOC(=O)C(CCCCCC)CCCCCCCC)CCCNCCCN(CC)CC] | 920.9 |

TABLE 1-continued
| # | Structure | Mw |
|---|---|---|
| 386. | 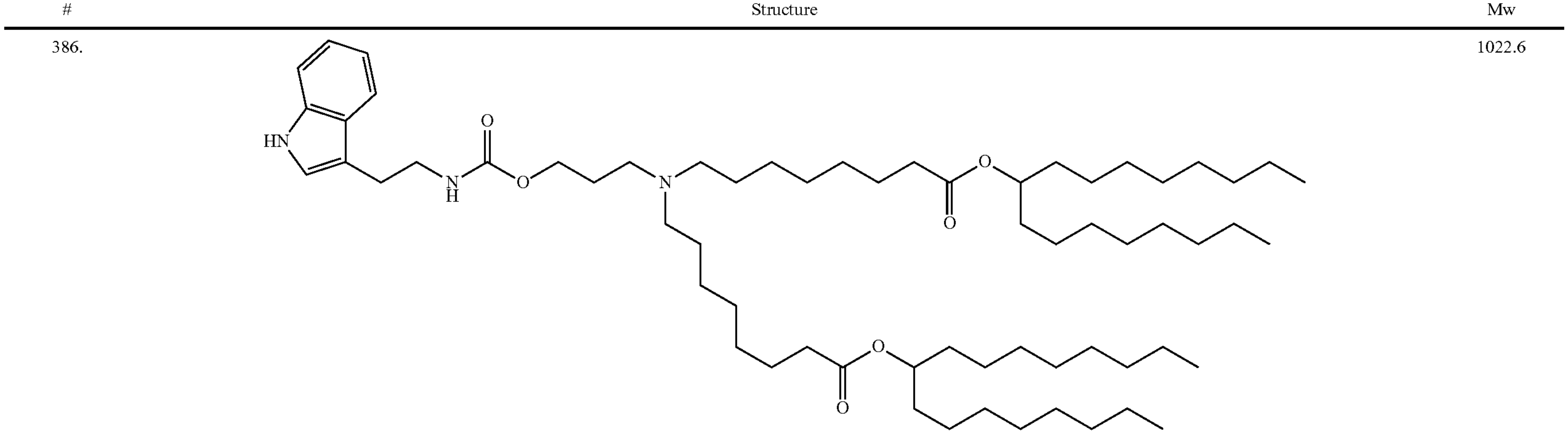 | 1022.6 |
| 387. | 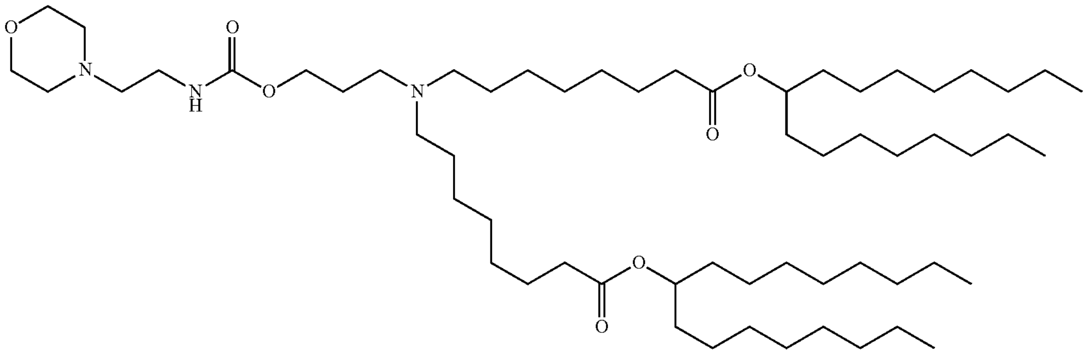 [SMILES: CCCCCCCCC(CCCCCCCC)OC(=O)CCCCCCCN(CCCCCCCC(=O)OC(CCCCCCCC)CCCCCCCC)CCCOC(=O)NCCN1CCOCC1] | 992.6 |

TABLE 1-continued
| # | Structure | Mw |
| --- | --- | --- |
| 388. | 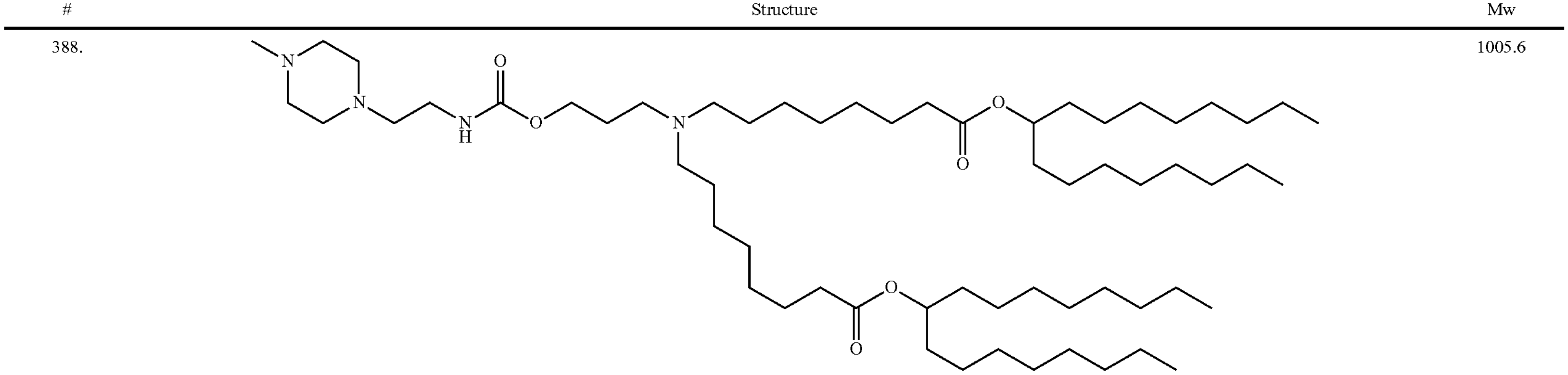 | 1005.6 |
| 389. | 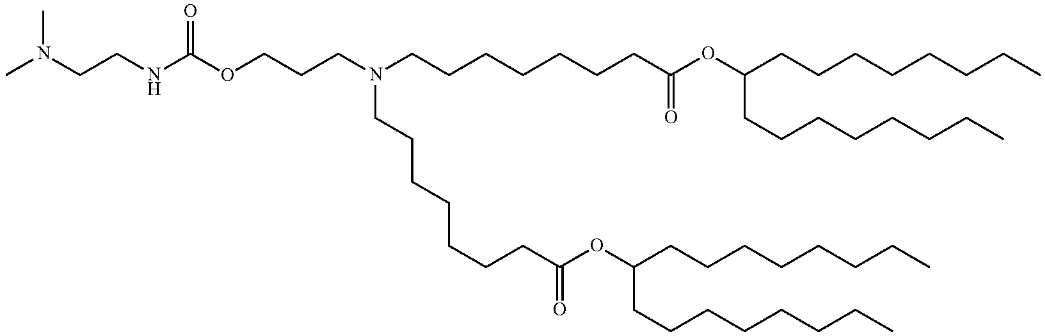 [SMILES: CCCCCCCCC(CCCCCCCC)OC(=O)CCCCCCCN(CCCCCCCC(=O)OC(CCCCCCCC)CCCCCCCC)CCCOC(=O)NCCN(C)C] | 950.7 |
| 390. | 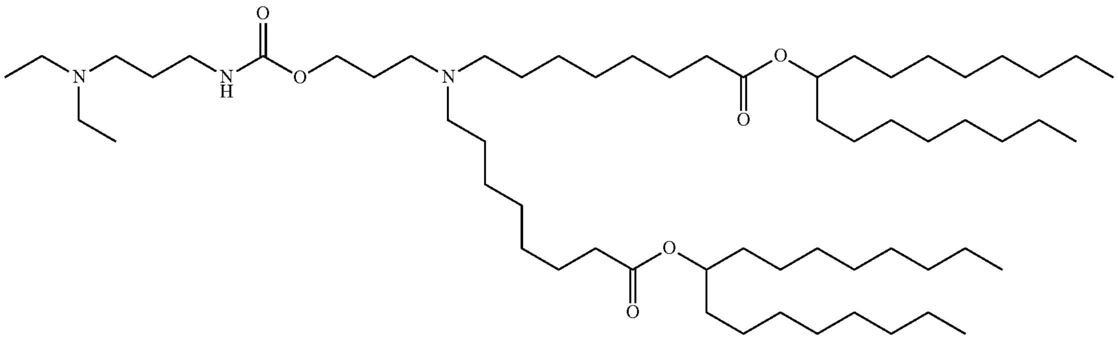 [SMILES: CCCCCCCCC(CCCCCCCC)OC(=O)CCCCCCCN(CCCCCCCC(=O)OC(CCCCCCCC)CCCCCCCC)CCCOC(=O)NCCCN(CC)CC] | 992.6 |

TABLE 1-continued
| # | Structure | Mw |
| --- | --- | --- |
| 391. | 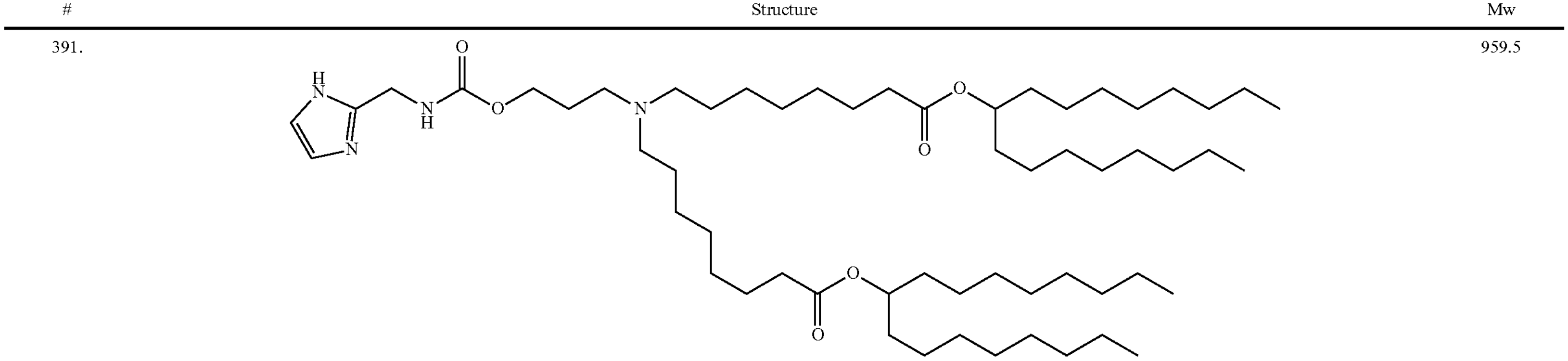 | 959.5 |
| 392. | 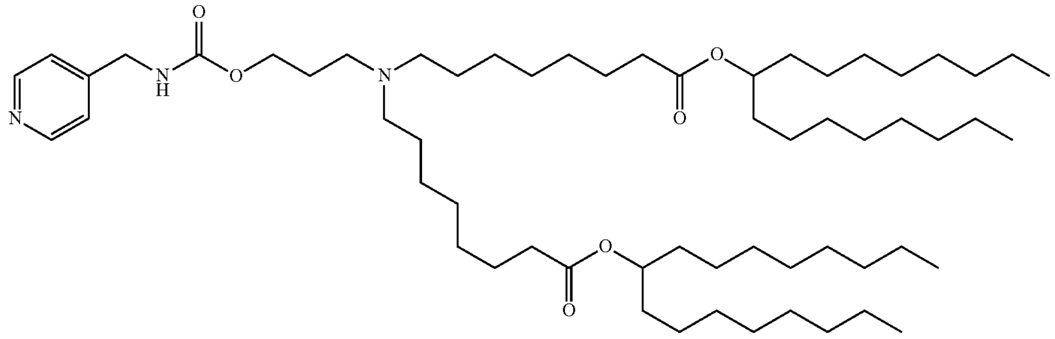 [SMILES: CCCCCCCCC(CCCCCCCC)OC(=O)CCCCCCCN(CCCCCCCC(=O)OC(CCCCCCCC)CCCCCCCC)CCCOC(=O)NCc1ccncc1] | 970.5 |
| 393. | 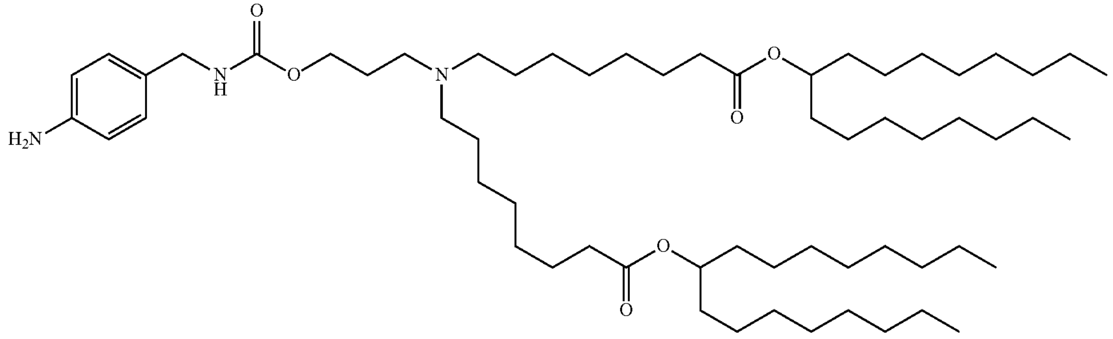 [SMILES: CCCCCCCCC(CCCCCCCC)OC(=O)CCCCCCCN(CCCCCCCC(=O)OC(CCCCCCCC)CCCCCCCC)CCCOC(=O)NCc1ccc(N)cc1] | 984.6 |

TABLE 1-continued
| # | Structure | Mw |
|---|---|---|
| 394. | 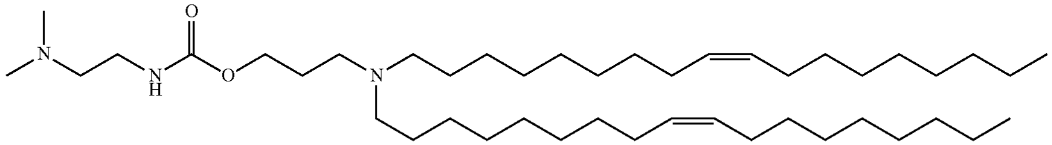 [SMILES: CCCCCCCC/C=C\CCCCCCCCN(CCCCCCCC/C=C\CCCCCCCC)CCCOC(=O)NCCN(C)C] | 690.2 |
| 395. | 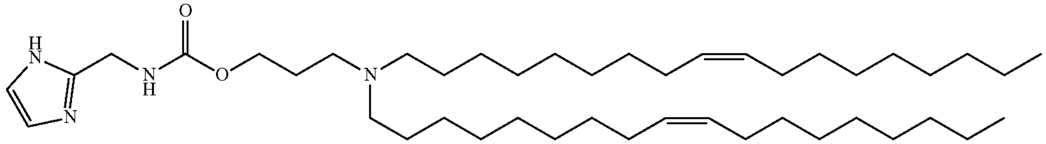 [SMILES: CCCCCCCC/C=C\CCCCCCCCN(CCCCCCCC/C=C\CCCCCCCC)CCCOC(=O)NCc1ncc[nH]1] | 699.1 |
| 396. | 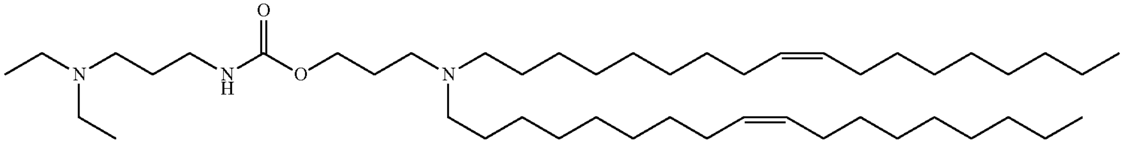 [SMILES: CCCCCCCC/C=C\CCCCCCCCN(CCCCCCCC/C=C\CCCCCCCC)CCCOC(=O)NCCCN(CC)CC] | 732.3 |
| 397. | 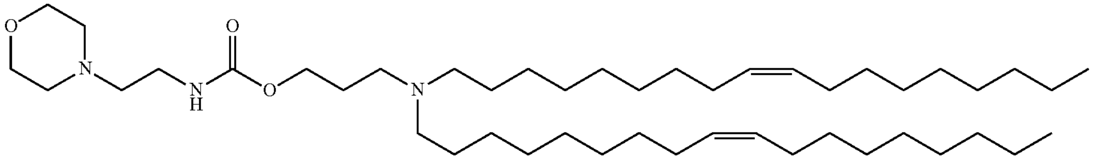 [SMILES: CCCCCCCC/C=C\CCCCCCCCN(CCCCCCCC/C=C\CCCCCCCC)CCCOC(=O)NCCN1CCOCC1] | 732.2 |
| 398. | 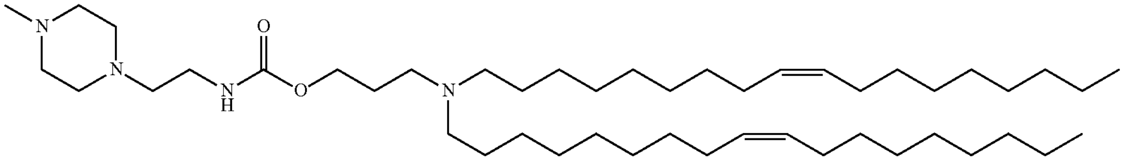 [SMILES: CCCCCCCC/C=C\CCCCCCCCN(CCCCCCCC/C=C\CCCCCCCC)CCCOC(=O)NCCN1CCN(C)CC1] | 745.3 |
| 399. | 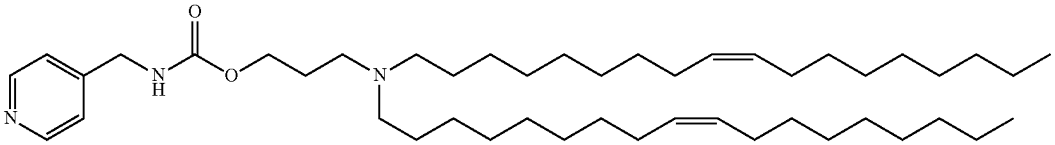 [SMILES: CCCCCCCC/C=C\CCCCCCCCN(CCCCCCCC/C=C\CCCCCCCC)CCCOC(=O)NCc1ccncc1] | 710.2 |

TABLE 1-continued
| # | Structure | Mw |
| --- | --- | --- |
| 400. | 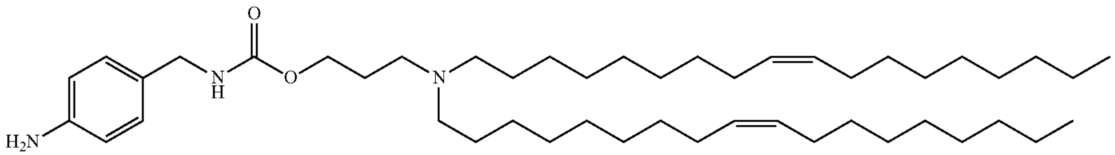 | 724.2 |
| 401. | 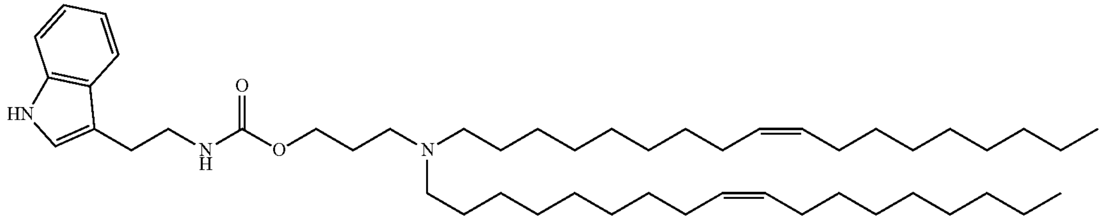 [SMILES: CCCCCCCC/C=C\CCCCCCCCN(CCCCCCCC/C=C\CCCCCCCC)CCCOC(=O)NCCc1c[nH]c2ccccc12] | 762.2 |
| 402. | 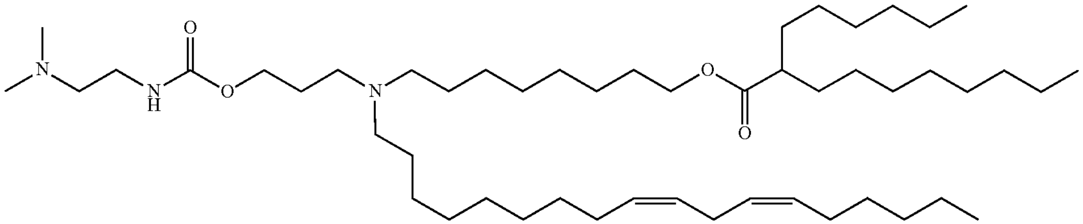 [SMILES: CCCCC/C=C\C/C=C\CCCCCCCCN(CCCCCCCCOC(=O)C(CCCCCC)CCCCCCCC)CCCOC(=O)NCCN(C)C] | 804.3 |
| 403. | 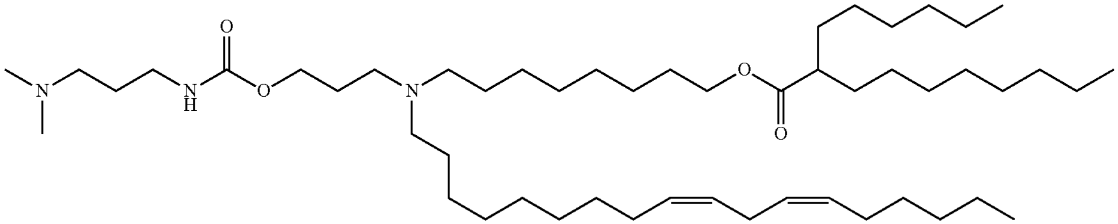 [SMILES: CCCCC/C=C\C/C=C\CCCCCCCCN(CCCCCCCCOC(=O)C(CCCCCC)CCCCCCCC)CCCOC(=O)NCCCN(C)C] | 818.4 |

TABLE 1-continued
| # | Structure | Mw |
|---|---|---|
| 404. | 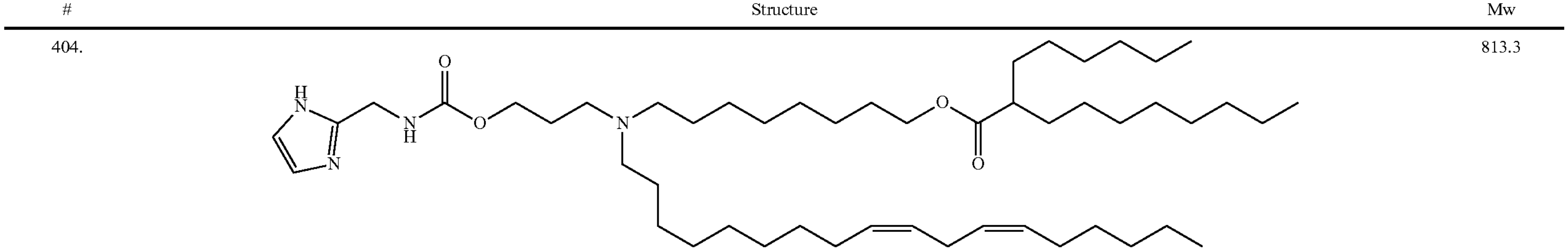 | 813.3 |
| 405. | 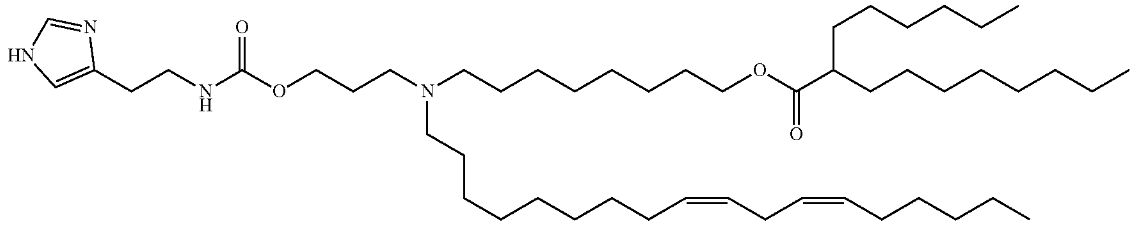 [SMILES: CCCCC/C=C\C/C=C\CCCCCCCCN(CCCCCCCCOC(=O)C(CCCCCC)CCCCCCCC)CCCOC(=O)NCCc1c[nH]cn1] | 827.3 |
| 406. | 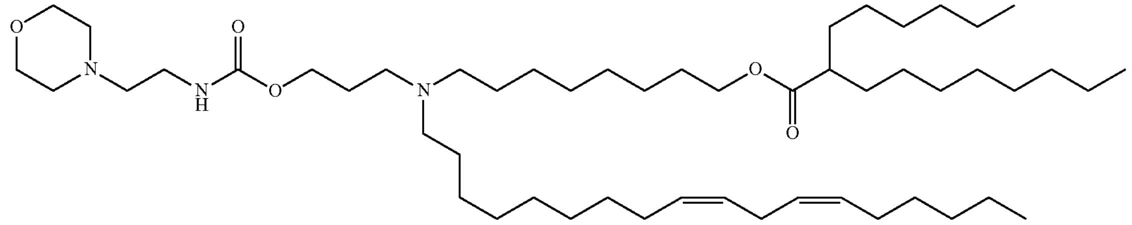 [SMILES: CCCCC/C=C\C/C=C\CCCCCCCCN(CCCCCCCCOC(=O)C(CCCCCC)CCCCCCCC)CCCOC(=O)NCCN1CCOCC1] | 846.4 |
| 407. | 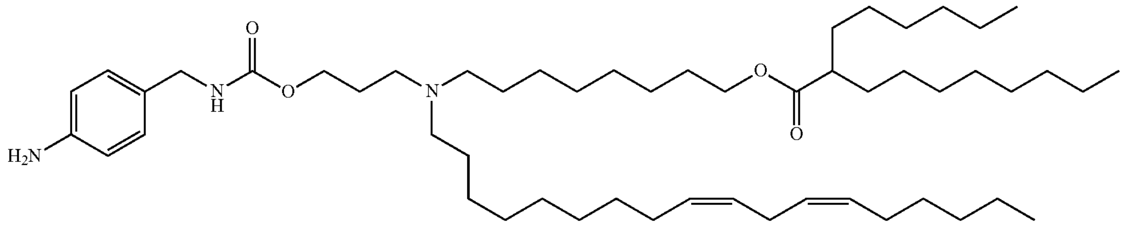 [SMILES: CCCCC/C=C\C/C=C\CCCCCCCCN(CCCCCCCCOC(=O)C(CCCCCC)CCCCCCCC)CCCOC(=O)NCc1ccc(N)cc1] | 838.4 |

TABLE 1-continued
| # | Structure | Mw |
|---|---|---|
| 408. | 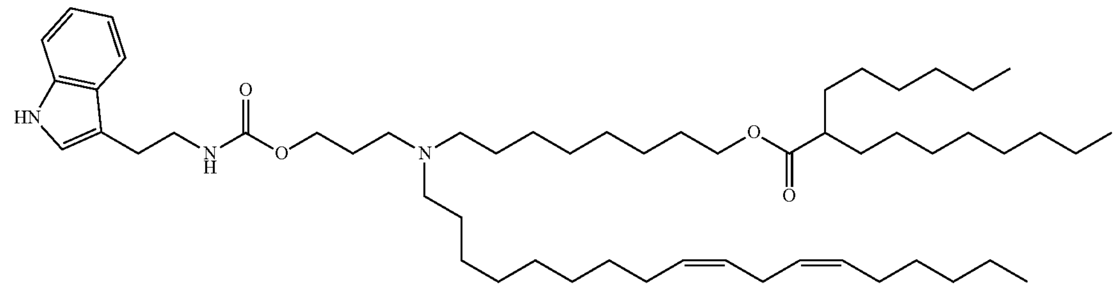 [SMILES: CCCCC/C=C\C/C=C\CCCCCCCCN(CCCCCCCCOC(=O)C(CCCCCC)CCCCCCCC)CCCOC(=O)NCCc1c[nH]c2ccccc12] | 876.4 |
| 409. | 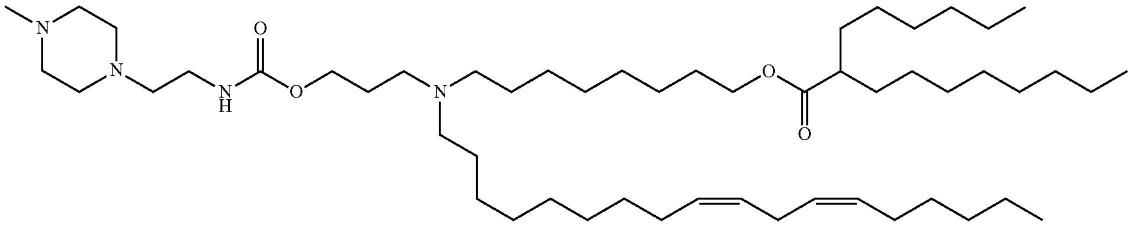 [SMILES: CCCCC/C=C\C/C=C\CCCCCCCCN(CCCCCCCCOC(=O)C(CCCCCC)CCCCCCCC)CCCOC(=O)NCCN1CCN(C)CC1] | 859.4 |
| 410. | 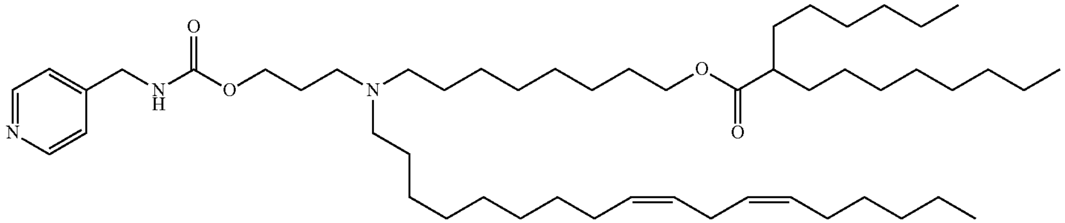 [SMILES: CCCCC/C=C\C/C=C\CCCCCCCCN(CCCCCCCCOC(=O)C(CCCCCC)CCCCCCCC)CCCOC(=O)NCc1ccncc1] | 824.3 |
| 411. | 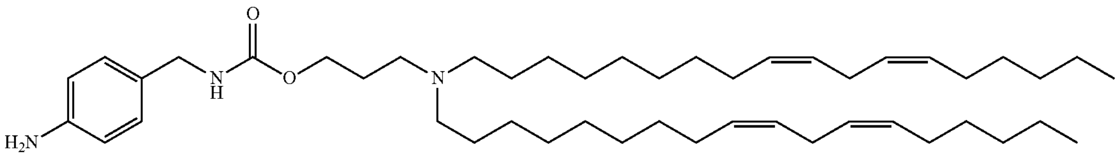 | 720.2 |

TABLE 1-continued
| # | Structure | Mw |
| --- | --- | --- |
| 412. | 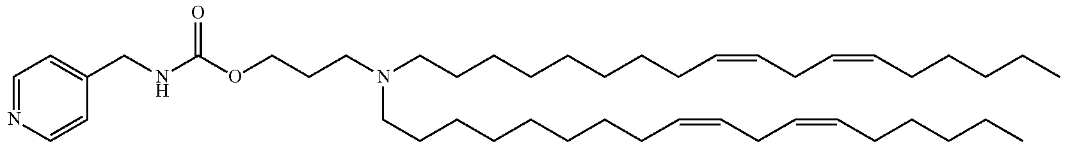 [SMILES: CCCCC/C=C\C/C=C\CCCCCCCCN(CCCCCCCC/C=C\C/C=C\CCCCC)CCCOC(=O)NCc1ccncc1] | 706.1 |
| 413. | 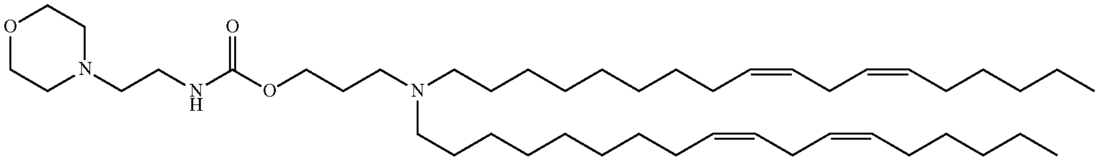 [SMILES: CCCCC/C=C\C/C=C\CCCCCCCCN(CCCCCCCC/C=C\C/C=C\CCCCC)CCCOC(=O)NCCN1CCOCC1] | 728.2 |
| 414. | 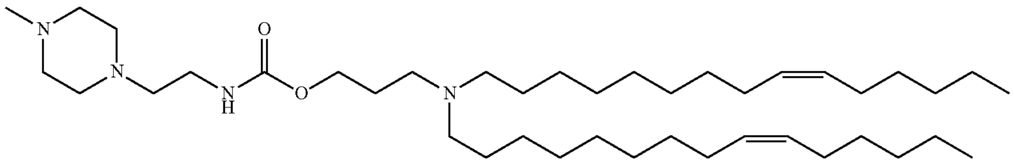 [SMILES: CCCCC/C=C\CCCCCCCCN(CCCCCCCC/C=C\CCCCC)CCCOC(=O)NCCN1CCN(C)CC1] | 741.2 |
| 415. | 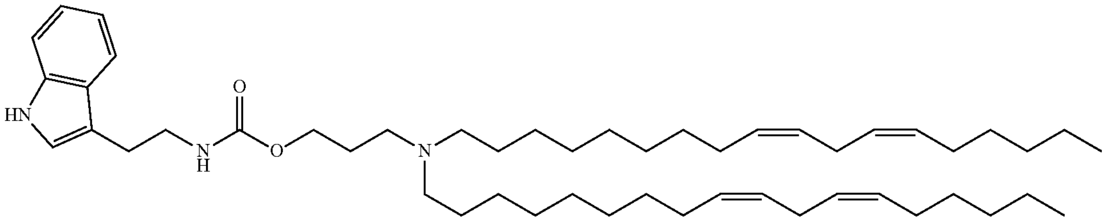 [SMILES: CCCCC/C=C\C/C=C\CCCCCCCCN(CCCCCCCC/C=C\C/C=C\CCCCC)CCCOC(=O)NCCc1c[nH]c2ccccc12] | 758.2 |
| 416. | 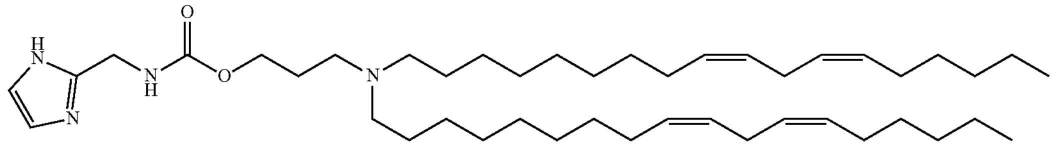 [SMILES: CCCCC/C=C\C/C=C\CCCCCCCCN(CCCCCCCC/C=C\C/C=C\CCCCC)CCCOC(=O)NCc1ncc[nH]1] | 695.1 |
| 417. | 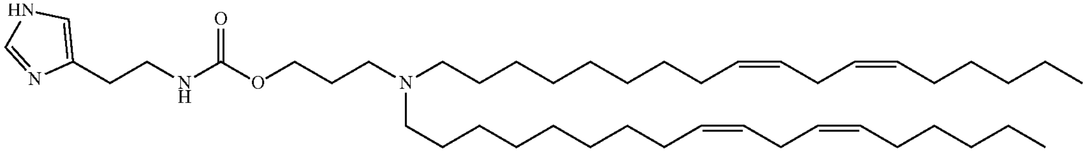 [SMILES: CCCCC/C=C\C/C=C\CCCCCCCCN(CCCCCCCC/C=C\C/C=C\CCCCC)CCCOC(=O)NCCc1c[nH]cn1] | 709.1 |

TABLE 1-continued
| # | Structure | Mw |
| --- | --- | --- |
| 418. | 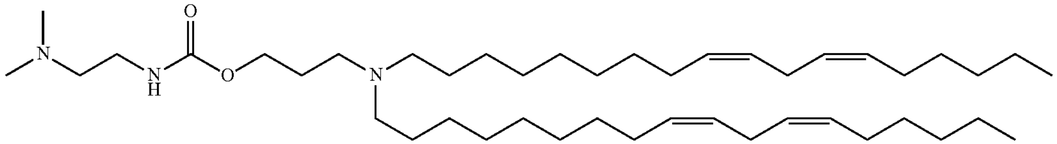 [SMILES: CCCCC/C=C\C/C=C\CCCCCCCCN(CCCCCCCC/C=C\C/C=C\CCCCC)CCCOC(=O)NCCN(C)C] | 686.1 |
| 419. | 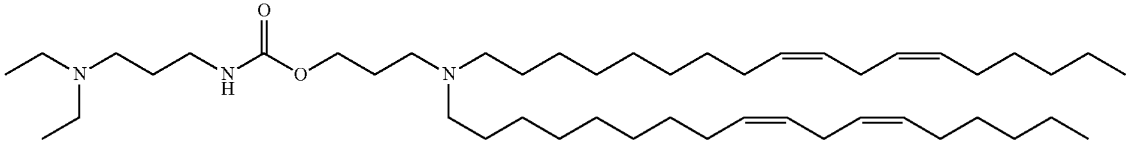 [SMILES: CCCCC/C=C\C/C=C\CCCCCCCCN(CCCCCCCC/C=C\C/C=C\CCCCC)CCCOC(=O)NCCCN(CC)CC] | 728.2 |
| 420. | 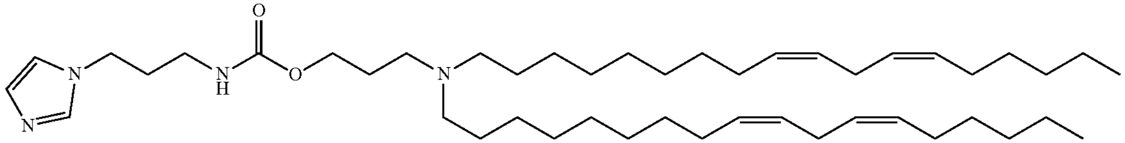 [SMILES: CCCCC/C=C\C/C=C\CCCCCCCCN(CCCCCCCC/C=C\C/C=C\CCCCC)CCCOC(=O)NCCCn1ccnc1] | 723.2 |
| 421. | 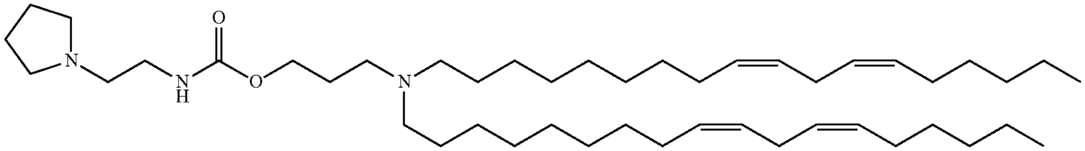 [SMILES: CCCCC/C=C\C/C=C\CCCCCCCCN(CCCCCCCC/C=C\C/C=C\CCCCC)CCCOC(=O)NCCN1CCCC1] | 712.2 |
| 422. | 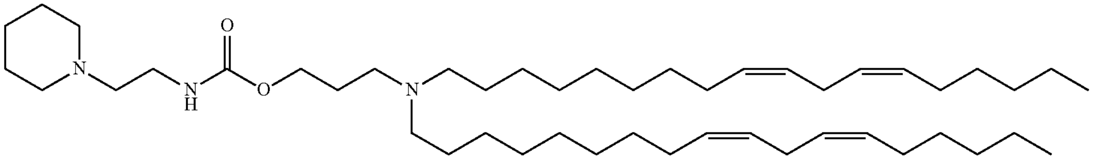 [SMILES: CCCCC/C=C\C/C=C\CCCCCCCCN(CCCCCCCC/C=C\C/C=C\CCCCC)CCCOC(=O)NCCN1CCCCC1] | 726.2 |
| 423. | 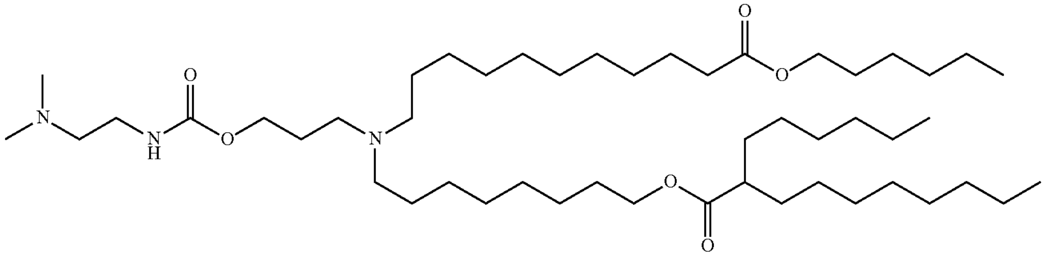 [SMILES: CCCCCCCCC(CCCCCC)C(=O)OCCCCCCCCN(CCCCCCCCCCC(=O)OCCCCCC)CCCOC(=O)NCCN(C)C] | 824.3 |

TABLE 1-continued
| # | Structure | Mw |
| --- | --- | --- |
| 424. | 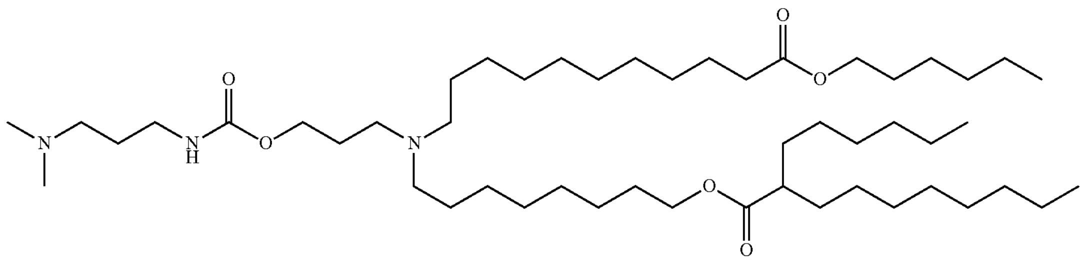 [SMILES: CCCCCCCCC(CCCCCC)C(=O)OCCCCCCCCN(CCCCCCCCCCC(=O)OCCCCCC)CCCOC(=O)NCCCN(C)C] | 838.3 |
| 425. | 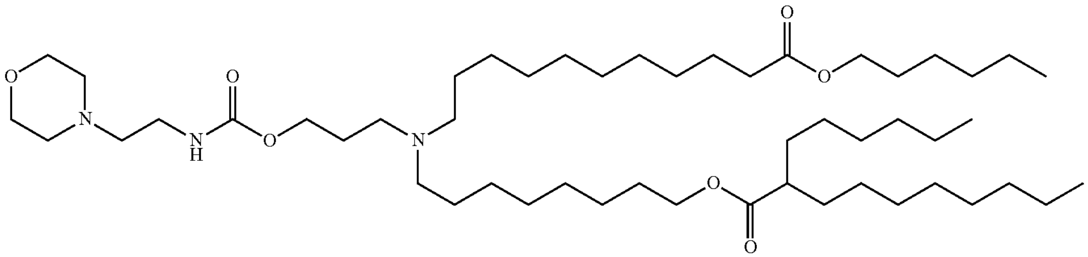 [SMILES: CCCCCCCCC(CCCCCC)C(=O)OCCCCCCCCN(CCCCCCCCCCC(=O)OCCCCCC)CCCOC(=O)NCCN1CCOCC1] | 866.4 |
| 426. | 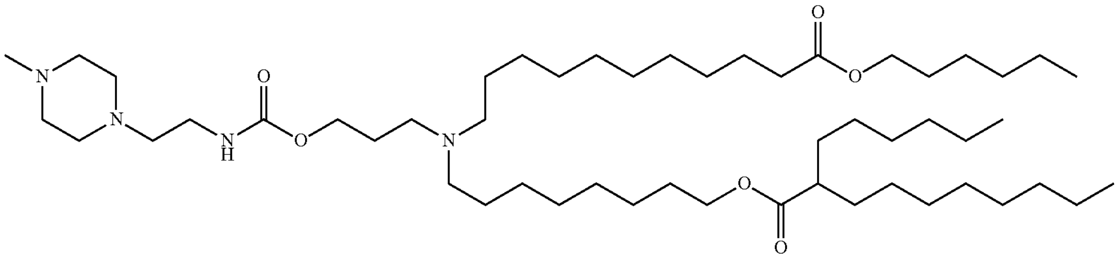 [SMILES: CCCCCCCCC(CCCCCC)C(=O)OCCCCCCCCN(CCCCCCCCCCC(=O)OCCCCCC)CCCOC(=O)NCCN1CCN(C)CC1] | 879.4 |

TABLE 1-continued
| # | Structure | Mw |
|---|---|---|
| 427. | 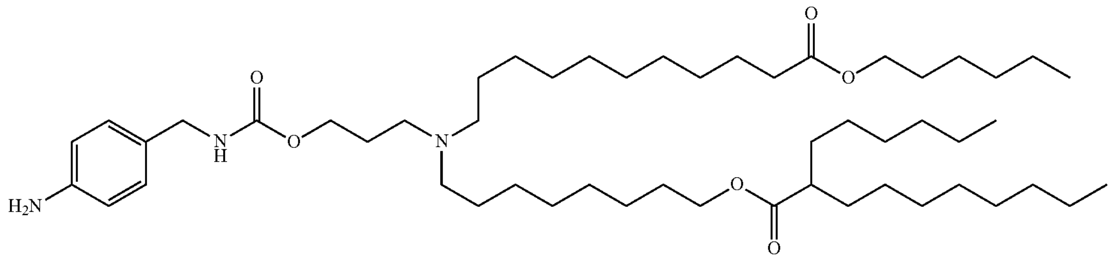 [SMILES: CCCCCCCCC(CCCCCC)C(=O)OCCCCCCCCN(CCCCCCCCCCC(=O)OCCCCCC)CCCOC(=O)NCc1ccc(N)cc1] | 858.4 |
| 428. | 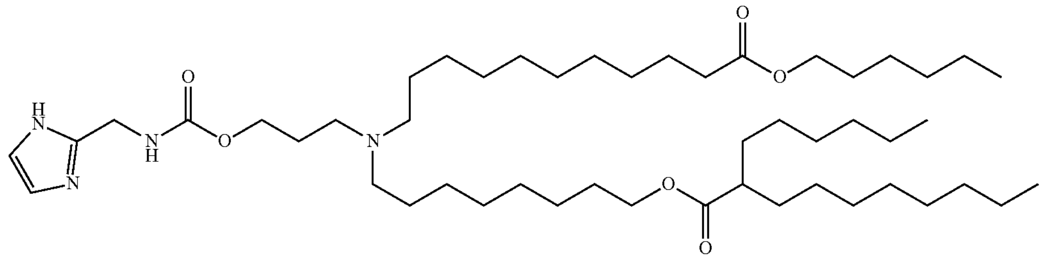 [SMILES: CCCCCCCCC(CCCCCC)C(=O)OCCCCCCCCN(CCCCCCCCCCC(=O)OCCCCCC)CCCOC(=O)NCc1ncc[nH]1] | 833.3 |
| 429. | 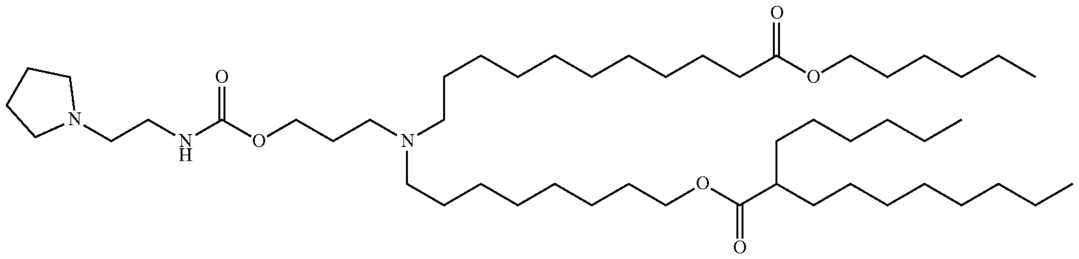 [SMILES: CCCCCCCCC(CCCCCC)C(=O)OCCCCCCCCN(CCCCCCCCCCC(=O)OCCCCCC)CCCOC(=O)NCCN1CCCC1] | 850.3 |
| 430. | 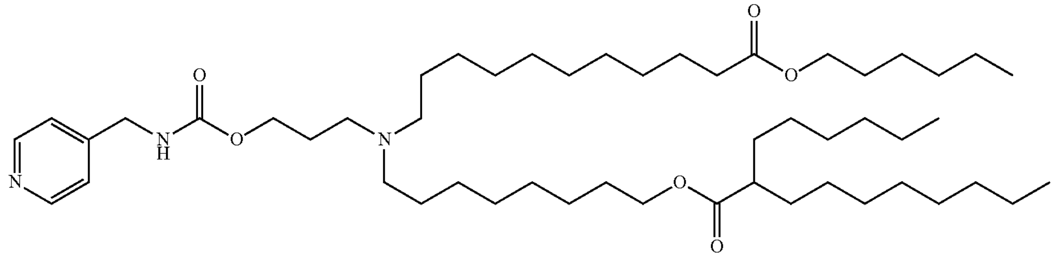 [SMILES: CCCCCCCCC(CCCCCC)C(=O)OCCCCCCCCN(CCCCCCCCCCC(=O)OCCCCCC)CCCOC(=O)NCc1ccncc1] | 844.3 |

TABLE 1-continued
| # | Structure | Mw |
| --- | --- | --- |
| 431. | 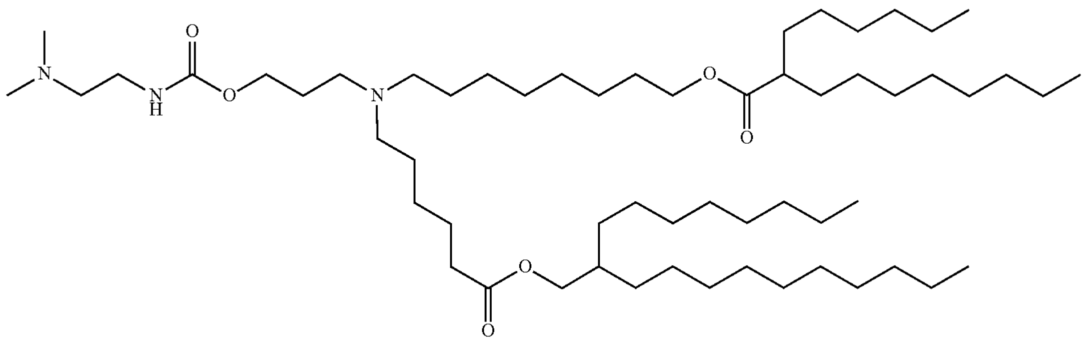 [SMILES: CCCCCCCCCCC(CCCCCCCC)COC(=O)CCCCCN(CCCCCCCCOC(=O)C(CCCCCC)CCCCCCCC)CCCOC(=O)NCCN(C)C] | 950.6 |
| 432. | 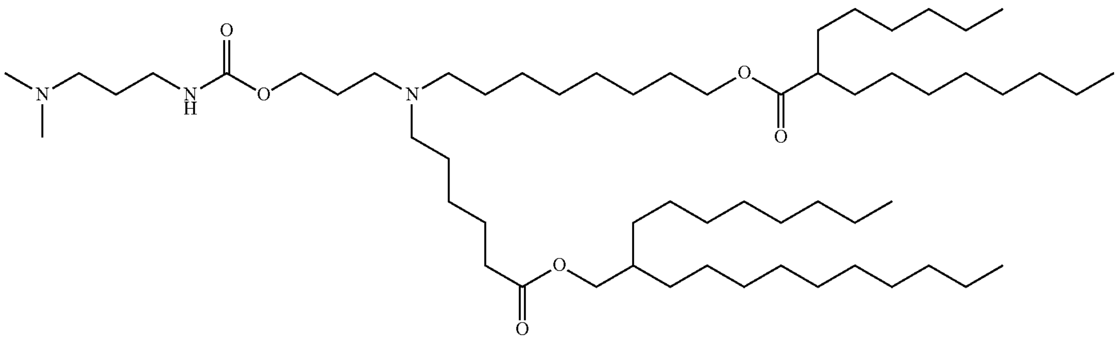 [SMILES: CCCCCCCCCCC(CCCCCCCC)COC(=O)CCCCCN(CCCCCCCCOC(=O)C(CCCCCC)CCCCCCCC)CCCOC(=O)NCCCN(C)C] | 964.6 |
| 433. | 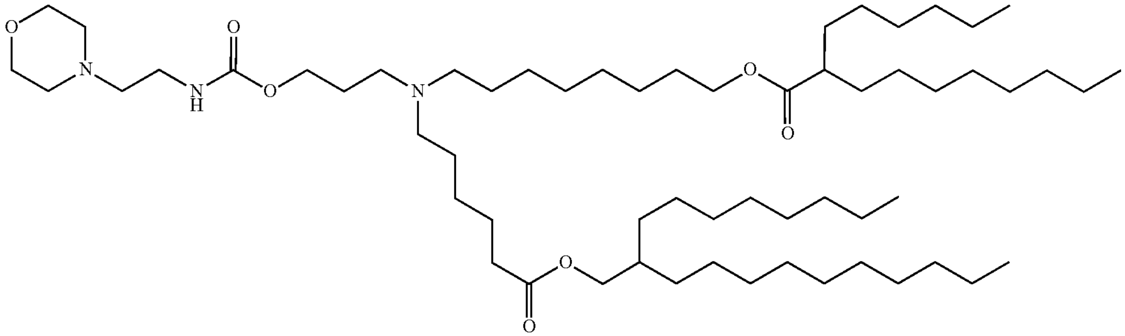 [SMILES: CCCCCCCCCCC(CCCCCCCC)COC(=O)CCCCCN(CCCCCCCCOC(=O)C(CCCCCC)CCCCCCCC)CCCOC(=O)NCCN1CCOCC1] | 992.6 |

TABLE 1-continued
| # | Structure | Mw |
| --- | --- | --- |
| 434. | 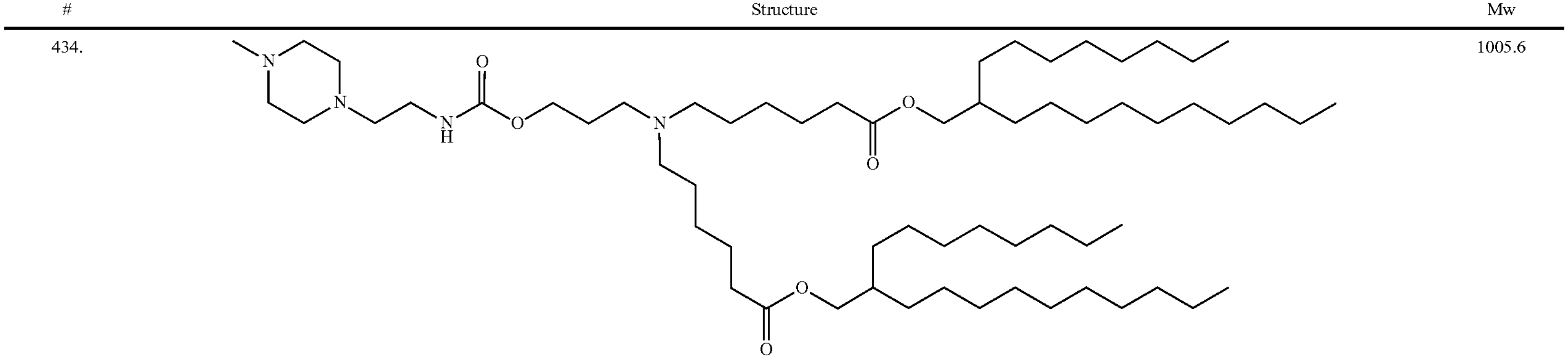 | 1005.6 |
| 435. | 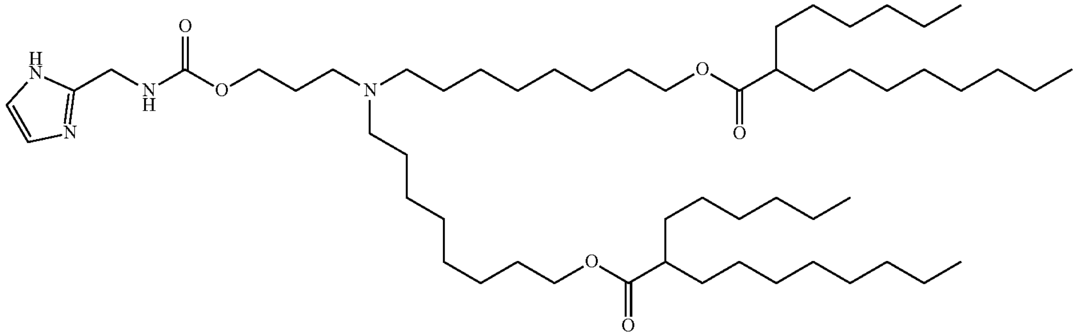 [SMILES: CCCCCCCCC(CCCCCC)C(=O)OCCCCCCCCN(CCCCCCCCOC(=O)C(CCCCCC)CCCCCCCC)CCCOC(=O)NCc1ncc[nH]1] | 959.5 |
| 436. | 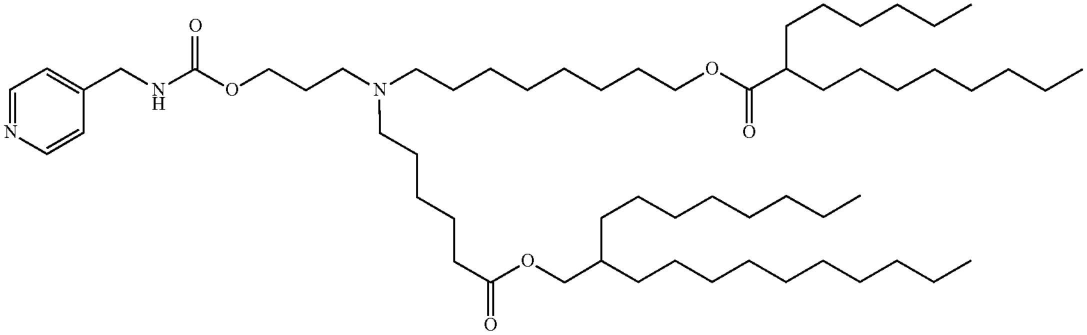 [SMILES: CCCCCCCCCCC(CCCCCCCC)COC(=O)CCCCCN(CCCCCCCCOC(=O)C(CCCCCC)CCCCCCCC)CCCOC(=O)NCc1ccncc1] | 970.6 |

TABLE 1-continued
| # | Structure | Mw |
| --- | --- | --- |
| 437. | 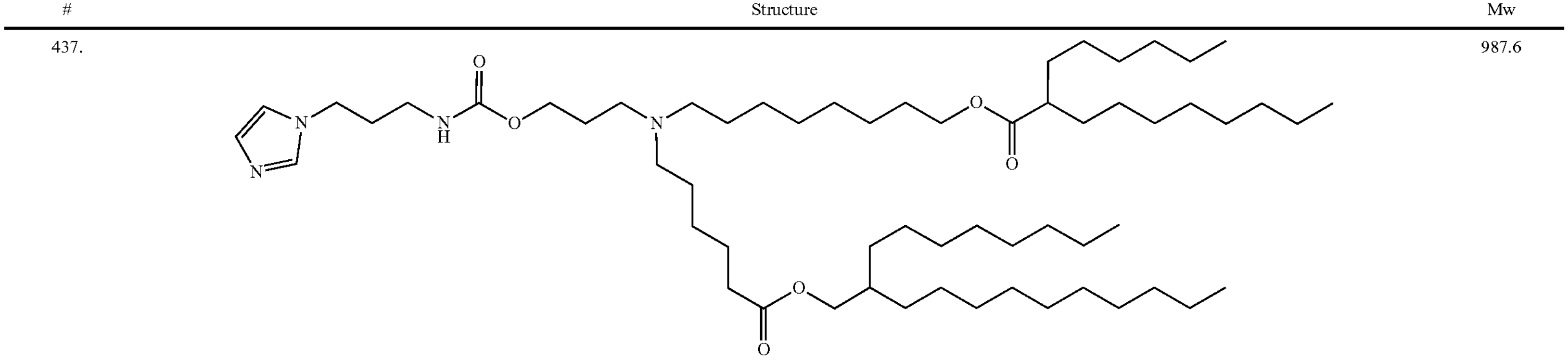 | 987.6 |
| 438. | 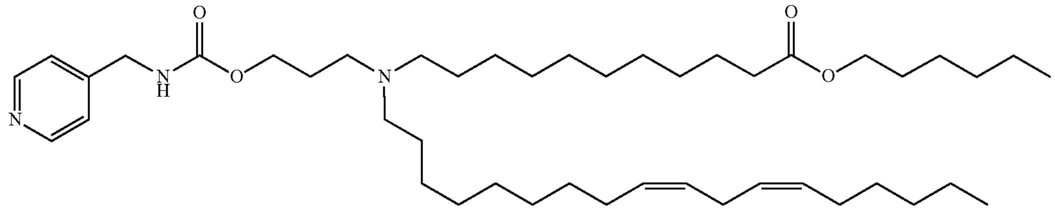 [SMILES: CCCCC/C=C\C/C=C\CCCCCCCCN(CCCCCCCCCCC(=O)OCCCCCC)CCCOC(=O)NCc1ccncc1] | 726.1 |
| 439. | 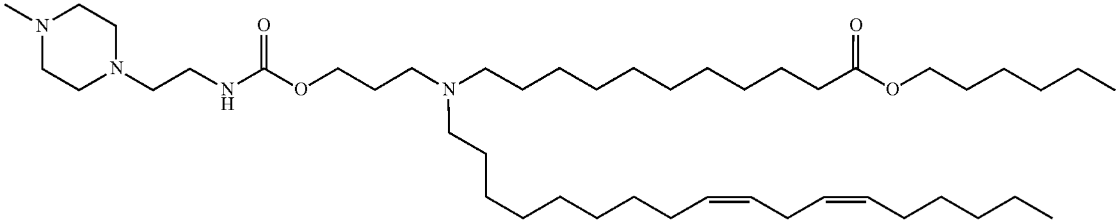 [SMILES: CCCCC/C=C\C/C=C\CCCCCCCCN(CCCCCCCCCCC(=O)OCCCCCC)CCCOC(=O)NCCN1CCN(C)CC1] | 761.2 |
| 440. | 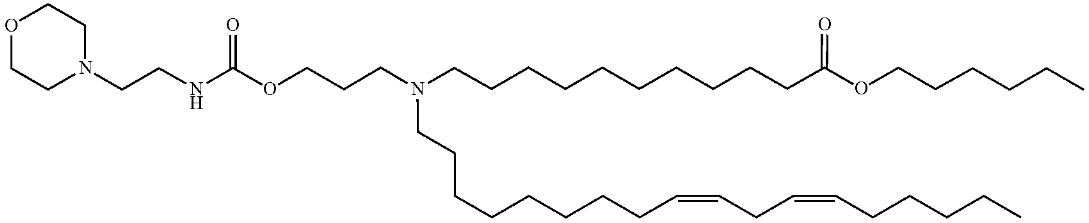 [SMILES: CCCCC/C=C\C/C=C\CCCCCCCCN(CCCCCCCCCCC(=O)OCCCCCC)CCCOC(=O)NCCN1CCOCC1] | 748.2 |

TABLE 1-continued
| # | Structure | Mw |
| --- | --- | --- |
| 441. | 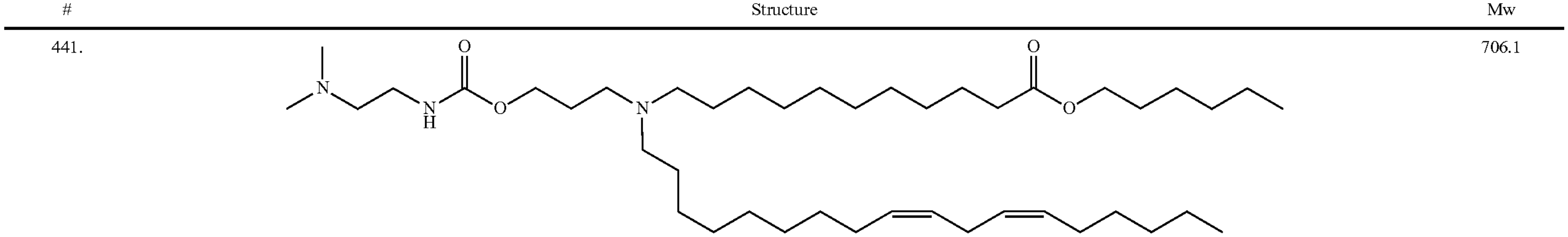 | 706.1 |
| 442. | 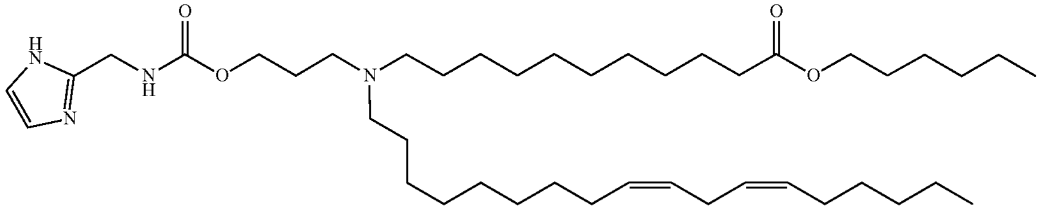 [SMILES: CCCCC/C=C\C/C=C\CCCCCCCCN(CCCCCCCCCCC(=O)OCCCCCC)CCCOC(=O)NCc1ncc[nH]1] | 715.1 |
| 443. | 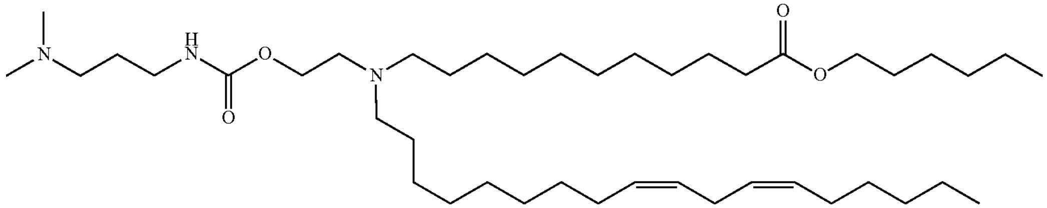 [SMILES: CCCCC/C=C\C/C=C\CCCCCCCCN(CCCCCCCCCCC(=O)OCCCCCC)CCOC(=O)NCCCN(C)C] | 706.2 |
| 444. | 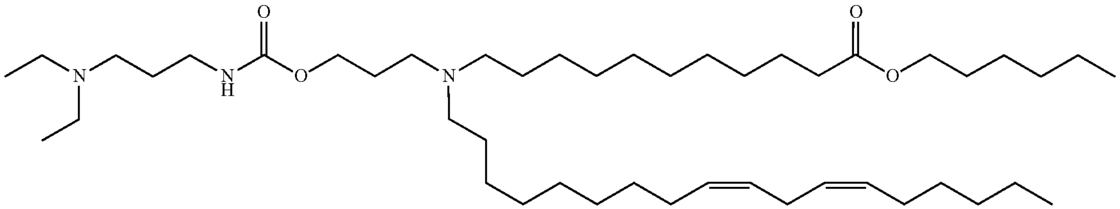 [SMILES: CCCCC/C=C\C/C=C\CCCCCCCCN(CCCCCCCCCCC(=O)OCCCCCC)CCCOC(=O)NCCCN(CC)CC] | 748.2 |
| 445. | 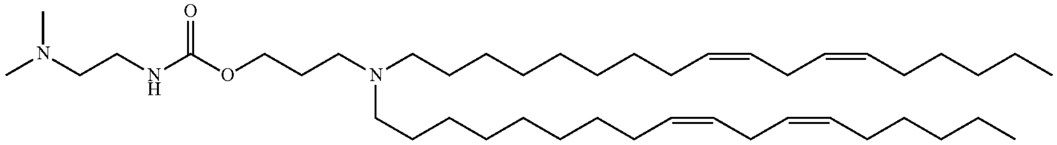 [SMILES: CCCCC/C=C\C/C=C\CCCCCCCCN(CCCCCCCC/C=C\C/C=C\CCCCC)CCCOC(=O)NCCN(C)C] | 688.2 |

TABLE 1-continued
| # | Structure | Mw |
|---|---|---|
| 446. | 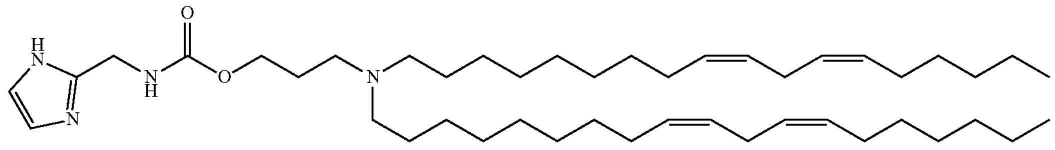 [SMILES: CCCCC/C=C\C/C=C\CCCCCCCCN(CCCCCCCC/C=C\C/C=C\CCCCCC)CCCOC(=O)NCc1ncc[nH]1] | 697.1 |
| 447. | 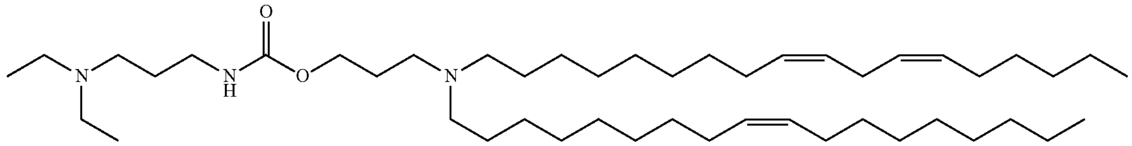 [SMILES: CCCCC/C=C\C/C=C\CCCCCCCCN(CCCCCCCC/C=C\CCCCCCCC)CCCOC(=O)NCCCN(CC)CC] | 730.2 |
| 448. | 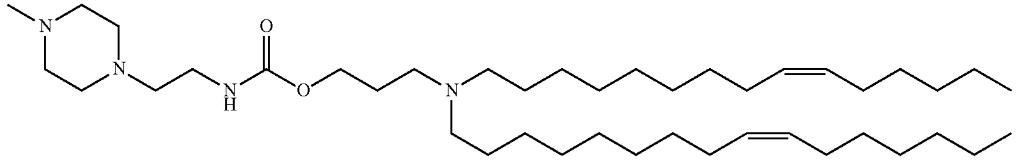 [SMILES: CCCCC/C=C\CCCCCCCCN(CCCCCCCC/C=C\CCCCCC)CCCOC(=O)NCCN1CCN(C)CC1] | 729.2 |
| 449. | 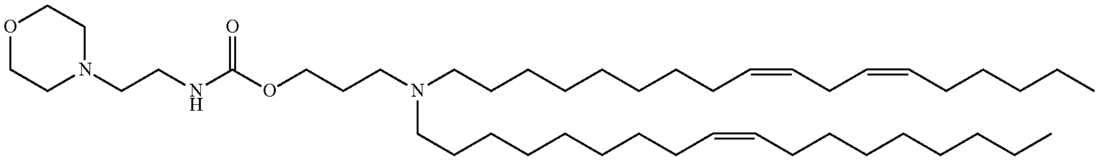 [SMILES: CCCCC/C=C\C/C=C\CCCCCCCCN(CCCCCCCC/C=C\CCCCCCCC)CCCOC(=O)NCCN1CCOCC1] | 730.2 |
| 450. | 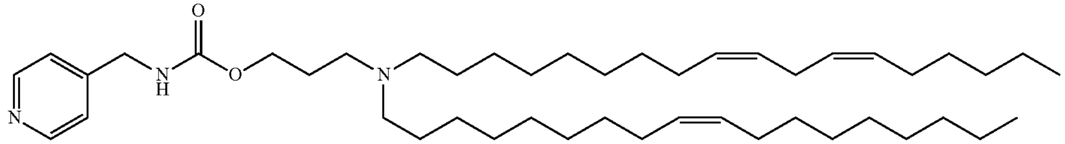 [SMILES: CCCCC/C=C\C/C=C\CCCCCCCCN(CCCCCCCC/C=C\CCCCCCCC)CCCOC(=O)NCc1ccncc1] | 708.1 |
| 451. | 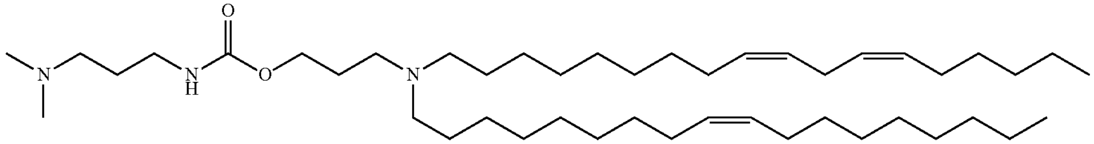 [SMILES: CCCCC/C=C\C/C=C\CCCCCCCCN(CCCCCCCC/C=C\CCCCCCCC)CCCOC(=O)NCCCN(C)C] | 702.2 |

TABLE 1-continued
| # | Structure | Mw |
| --- | --- | --- |
| 452. | 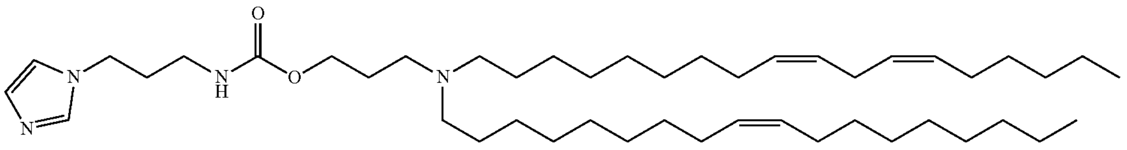 [SMILES: CCCCC/C=C\C/C=C\CCCCCCCCN(CCCCCCCC/C=C\CCCCCCCC)CCCOC(=O)NCCCn1ccnc1] | 725.2 |
| 453. | 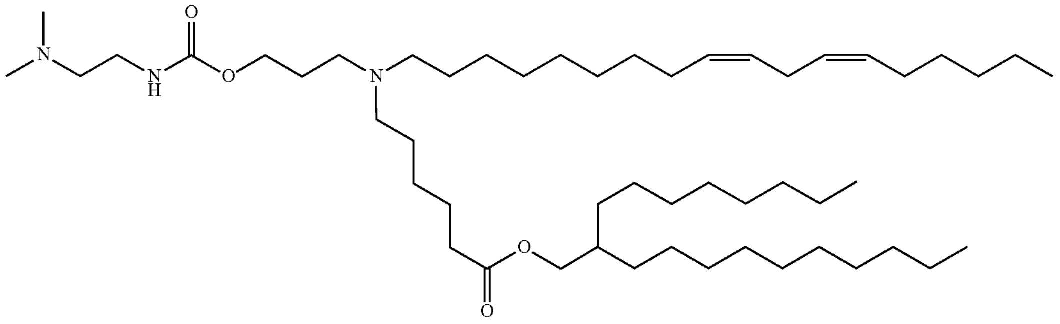 [SMILES: CCCCC/C=C\C/C=C\CCCCCCCCN(CCCCCC(=O)OCC(CCCCCCCC)CCCCCCCCCC)CCCOC(=O)NCCN(C)C] | 832.4 |
| 454. | 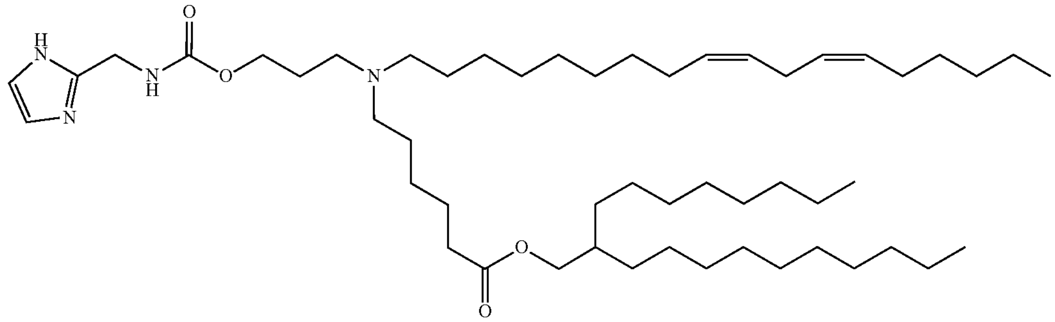 [SMILES: CCCCC/C=C\C/C=C\CCCCCCCCN(CCCCCC(=O)OCC(CCCCCCCC)CCCCCCCCCC)CCCOC(=O)NCc1ncc[nH]1] | 841.3 |

TABLE 1-continued
| # | Structure | Mw |
|---|---|---|
| 455. | 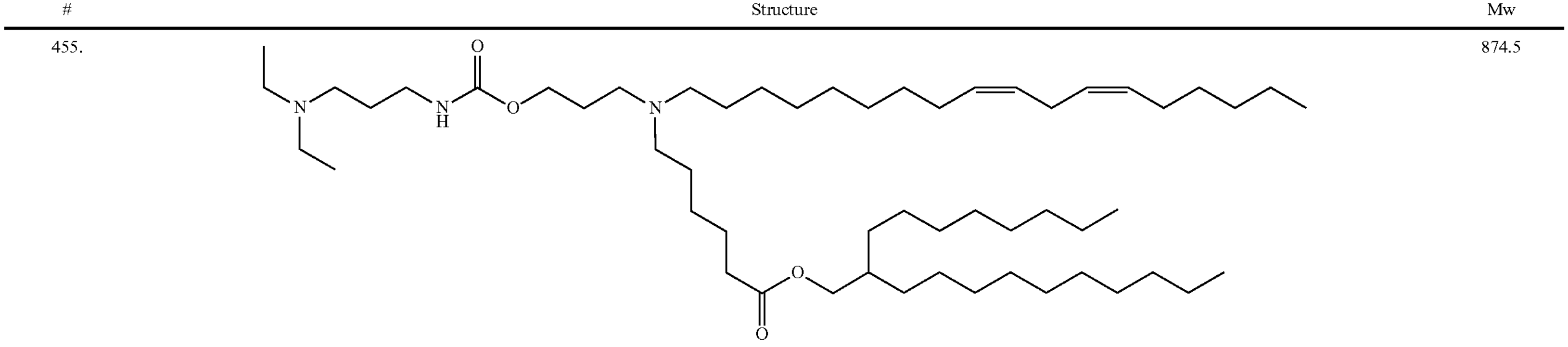 | 874.5 |
| 456. | 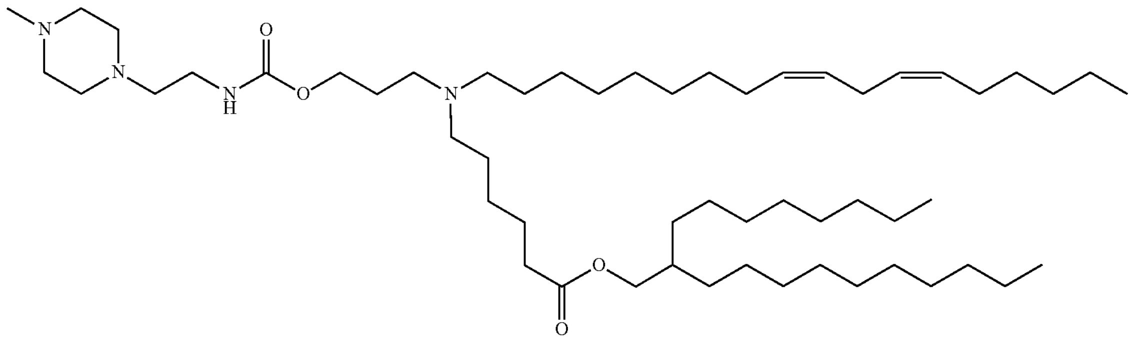 [SMILES: CCCCC/C=C\C/C=C\CCCCCCCCN(CCCCCC(=O)OCC(CCCCCCCC)CCCCCCCCCC)CCCOC(=O)NCCN1CCN(C)CC1] | 887.5 |
| 457. | 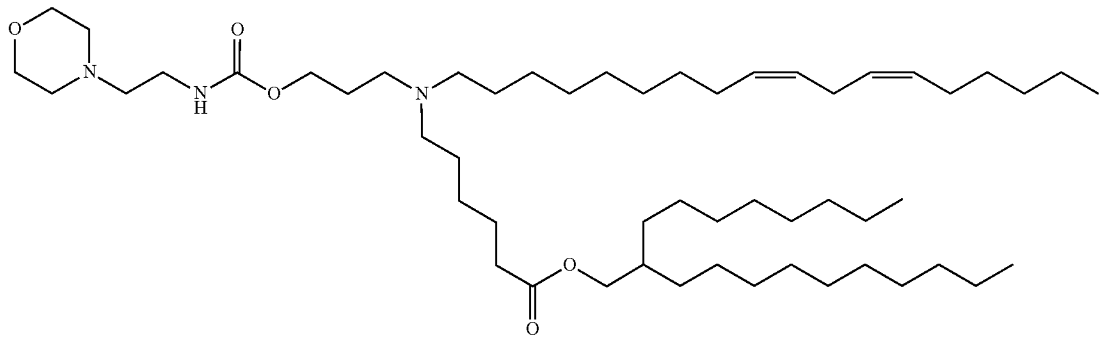 [SMILES: CCCCC/C=C\C/C=C\CCCCCCCCN(CCCCCC(=O)OCC(CCCCCCCC)CCCCCCCCCC)CCCOC(=O)NCCN1CCOCC1] | 874.4 |

TABLE 1-continued
| # | Structure | Mw |
|---|---|---|
| 458. | 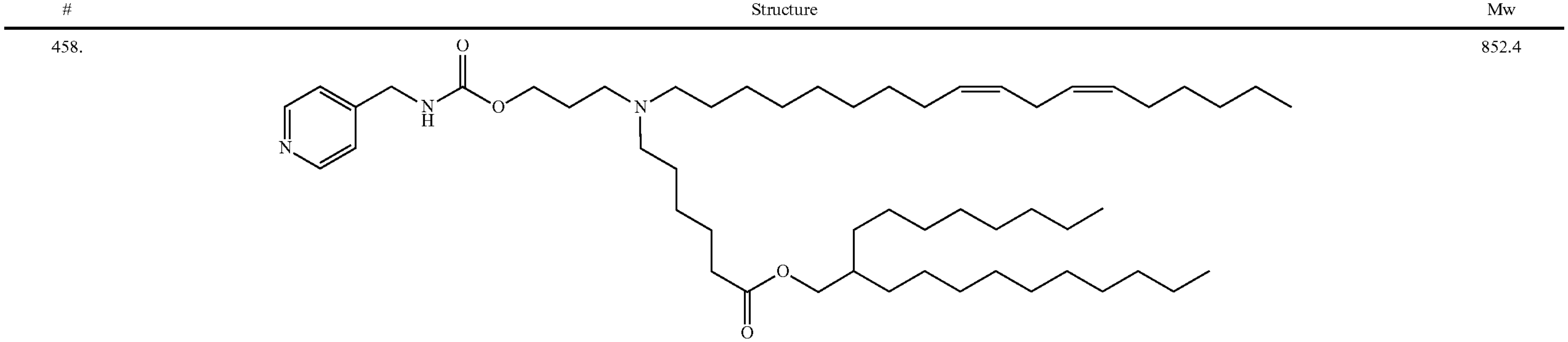 | 852.4 |
| 459. | 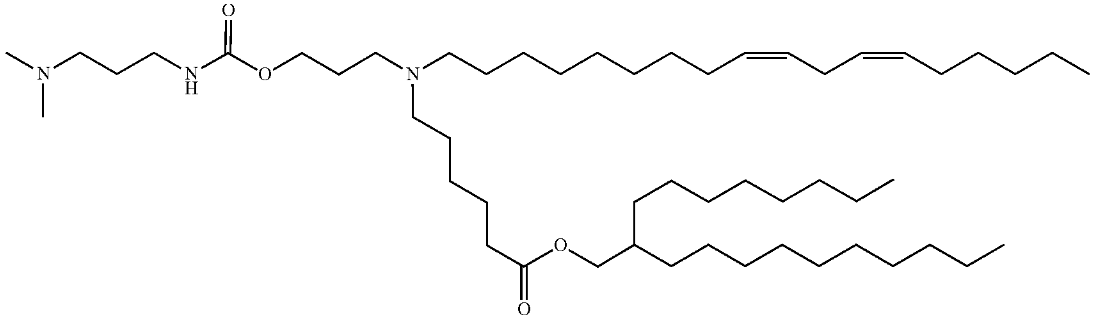 [SMILES: CCCCC/C=C\C/C=C\CCCCCCCCN(CCCCCC(=O)OCC(CCCCCCCC)CCCCCCCCCC)CCCOC(=O)NCCCN(C)C] | 846.4 |
| 460. | 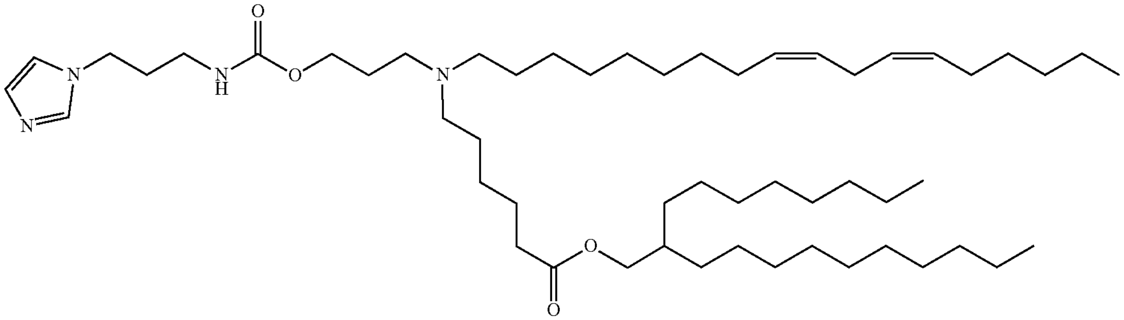 [SMILES: CCCCC/C=C\C/C=C\CCCCCCCCN(CCCCCC(=O)OCC(CCCCCCCC)CCCCCCCCCC)CCCOC(=O)NCCCn1ccnc1] | 869.4 |

TABLE 1-continued
| # | Structure | Mw |
|---|---|---|
| 461. | 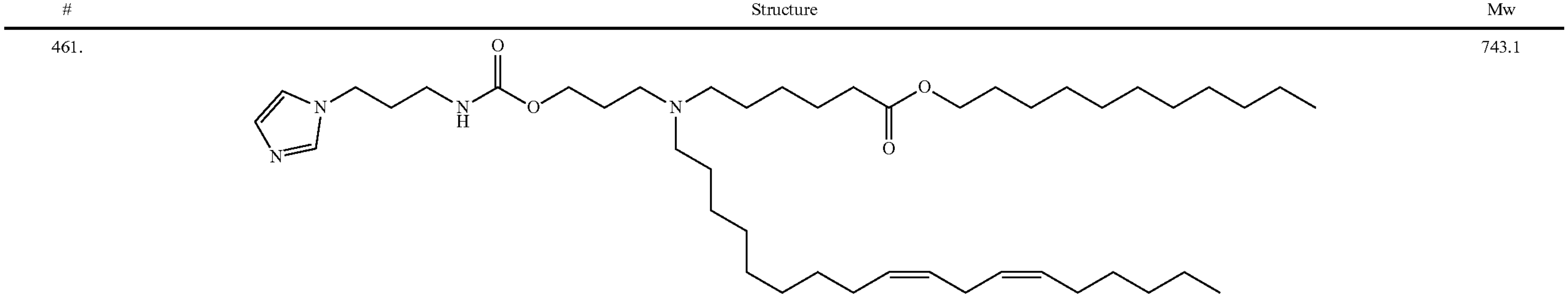 | 743.1 |
| 462. | 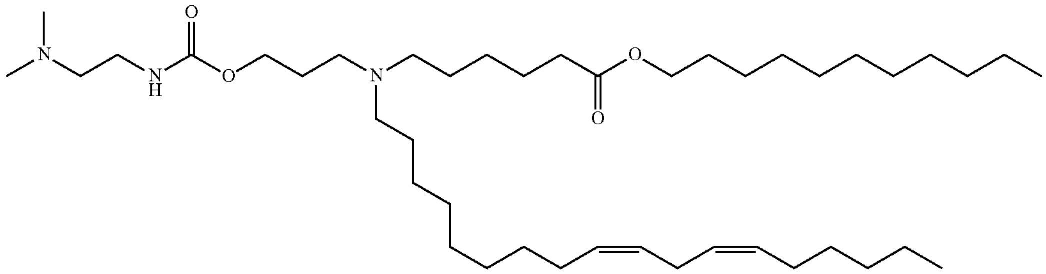 [SMILES: CCCCC/C=C\C/C=C\CCCCCCCCN(CCCCCC(=O)OCCCCCCCCCCC)CCCOC(=O)NCCN(C)C] | 706.1 |
| 463. | 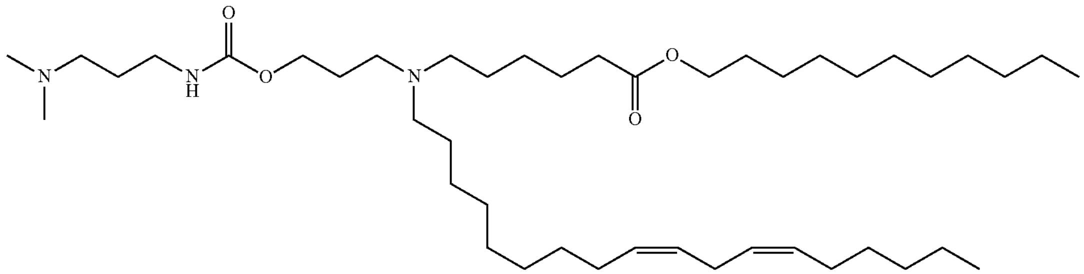 [SMILES: CCCCC/C=C\C/C=C\CCCCCCCCN(CCCCCC(=O)OCCCCCCCCCCC)CCCOC(=O)NCCCN(C)C] | 720.2 |

TABLE 1-continued
| # | Structure | Mw |
|---|---|---|
| 464. | 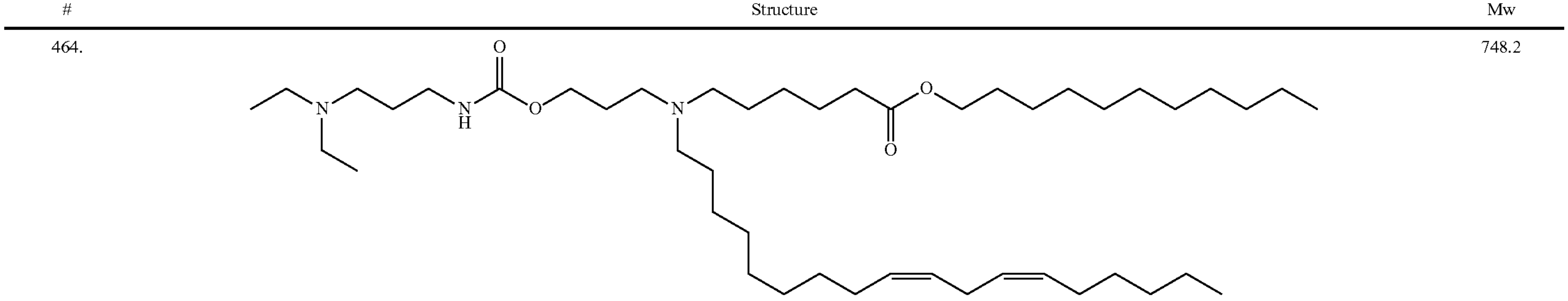 | 748.2 |
| 465. | 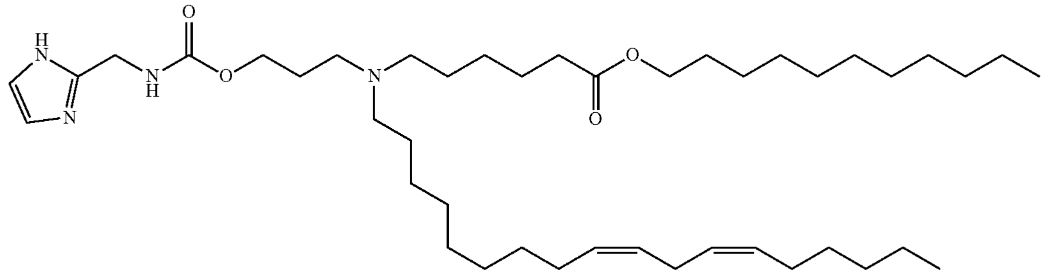 [SMILES: CCCCC/C=C\C/C=C\CCCCCCCCN(CCCCCC(=O)OCCCCCCCCCCC)CCCOC(=O)NCc1ncc[nH]1] | 715.1 |
| 466. | 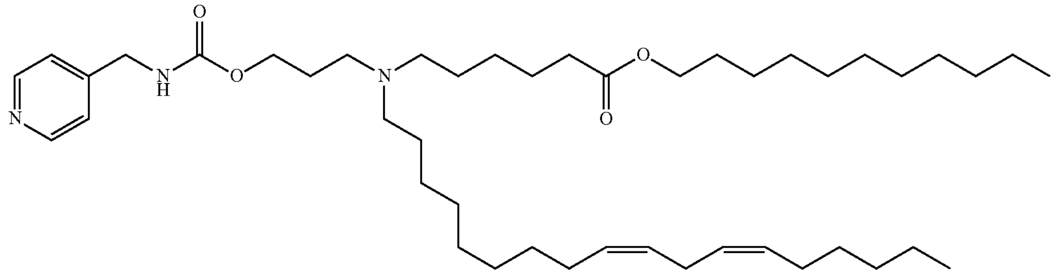 [SMILES: CCCCC/C=C\C/C=C\CCCCCCCCN(CCCCCC(=O)OCCCCCCCCCCC)CCCOC(=O)NCc1ccncc1] | 726.1 |

TABLE 1-continued
| # | Structure | Mw |
|---|---|---|
| 467. | 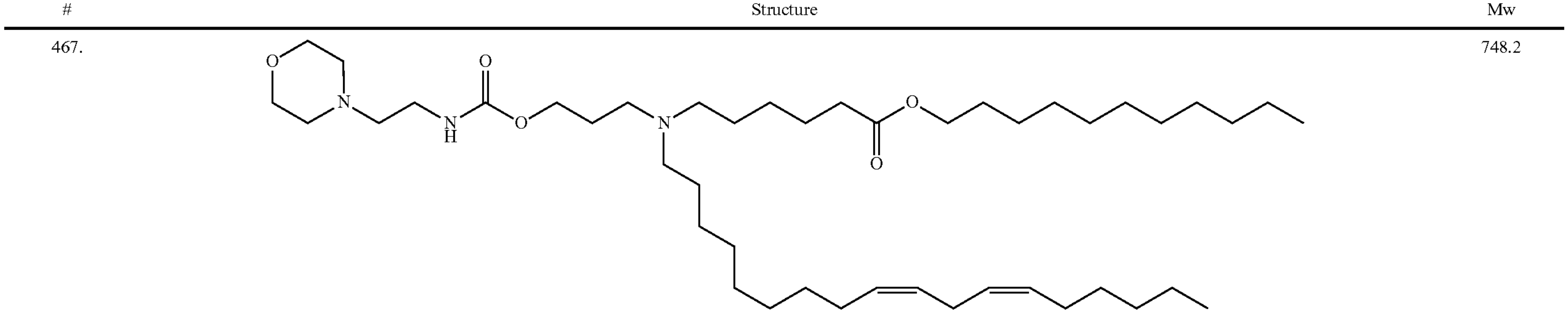 | 748.2 |
| 468. | 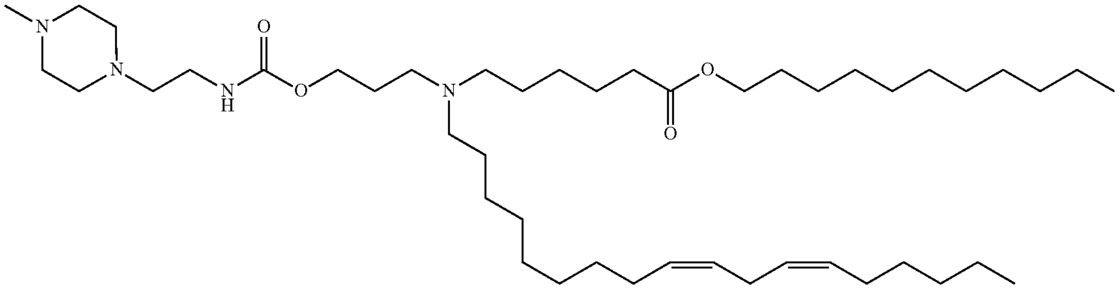 [SMILES: CCCCC/C=C\C/C=C\CCCCCCCCN(CCCCCC(=O)OCCCCCCCCCCC)CCCOC(=O)NCCN1CCN(C)CC1] | 761.2 |
| 469. | 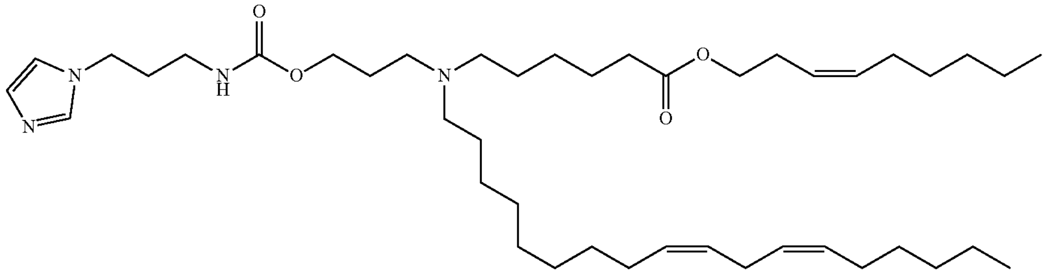 [SMILES: CCCCC/C=C\C/C=C\CCCCCCCCN(CCCCCC(=O)OCC/C=C\CCCCC)CCCOC(=O)NCCCn1ccnc1] | 713.1 |

TABLE 1-continued
| # | Structure | Mw |
| --- | --- | --- |
| 470. | 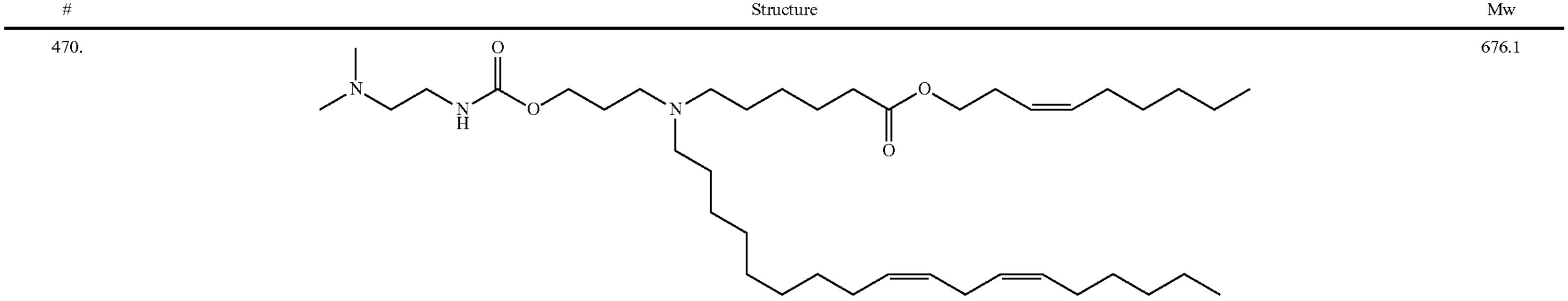 | 676.1 |
| 471. | 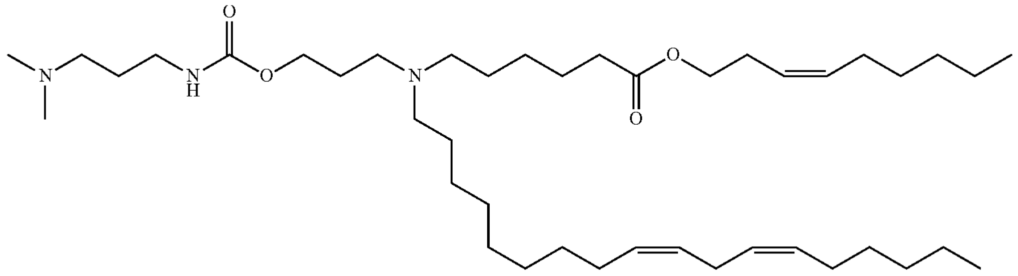 [SMILES: CCCCC/C=C\C/C=C\CCCCCCCCN(CCCCCC(=O)OCC/C=C\CCCCC)CCCOC(=O)NCCCN(C)C] | 690.1 |
| 472. | 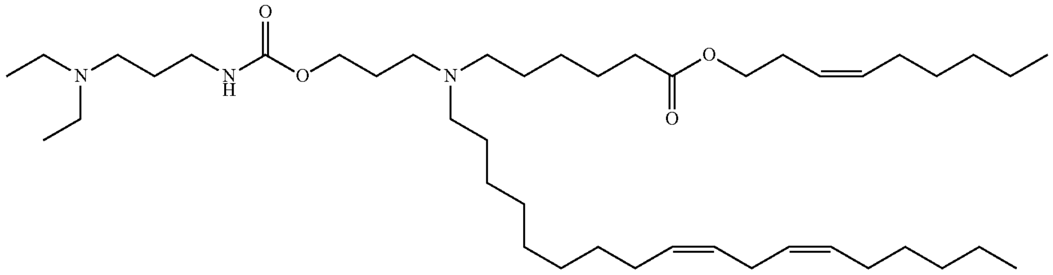 [SMILES: CCCCC/C=C\C/C=C\CCCCCCCCN(CCCCCC(=O)OCC/C=C\CCCCC)CCCOC(=O)NCCCN(CC)CC] | 718.1 |

TABLE 1-continued
| # | Structure | Mw |
|---|---|---|
| 473. | 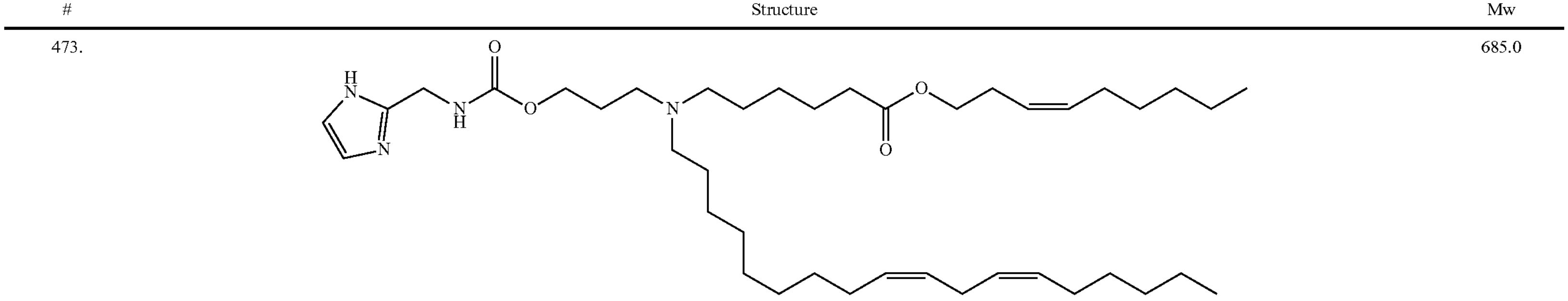 | 685.0 |
| 474. | 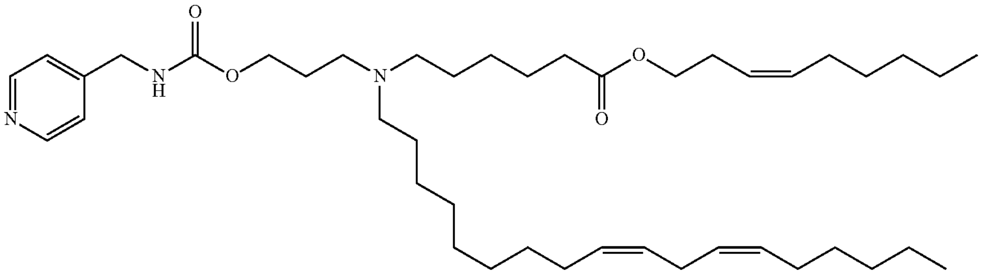 [SMILES: CCCCC/C=C\C/C=C\CCCCCCCCN(CCCCCC(=O)OCC/C=C\CCCCC)CCCOC(=O)NCc1ccncc1] | 696.0 |
| 475. | 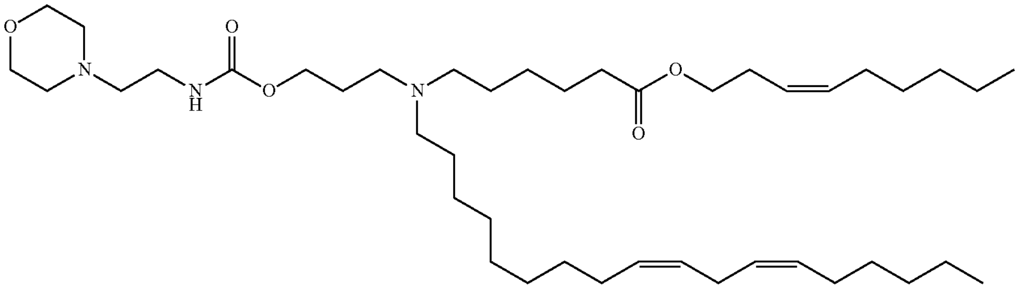 [SMILES: CCCCC/C=C\C/C=C\CCCCCCCCN(CCCCCC(=O)OCC/C=C\CCCCC)CCCOC(=O)NCCN1CCOCC1] | 718.1 |

TABLE 1-continued
| # | Structure | Mw |
|---|---|---|
| 476. | 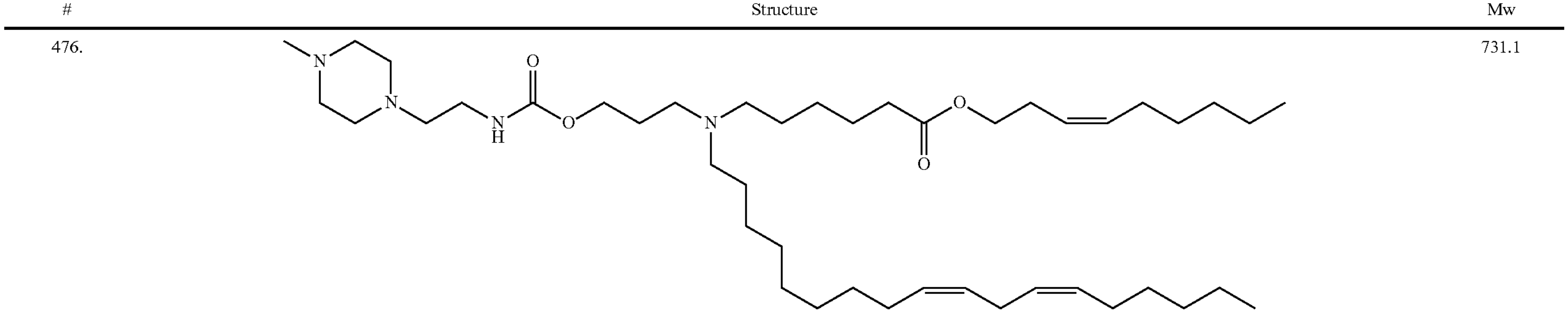 | 731.1 |
| 477. | 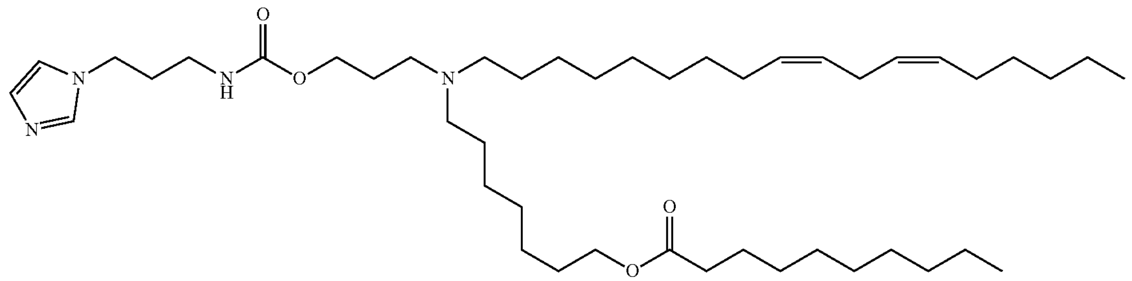 [SMILES: CCCCC/C=C\C/C=C\CCCCCCCCN(CCCCCCCOC(=O)CCCCCCCCC)CCCOC(=O)NCCCn1ccnc1] | 743.1 |
| 478. | 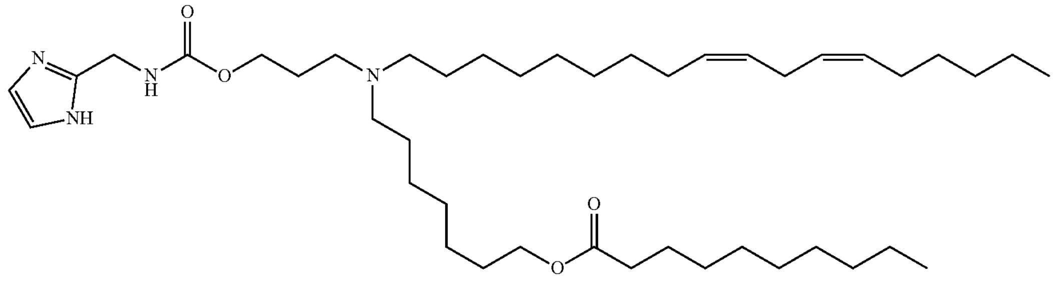 [SMILES: CCCCC/C=C\C/C=C\CCCCCCCCN(CCCCCCCOC(=O)CCCCCCCCC)CCCOC(=O)NCc1ncc[nH]1] | 715.1 |

TABLE 1-continued
| # | Structure | Mw |
| --- | --- | --- |
| 479. | 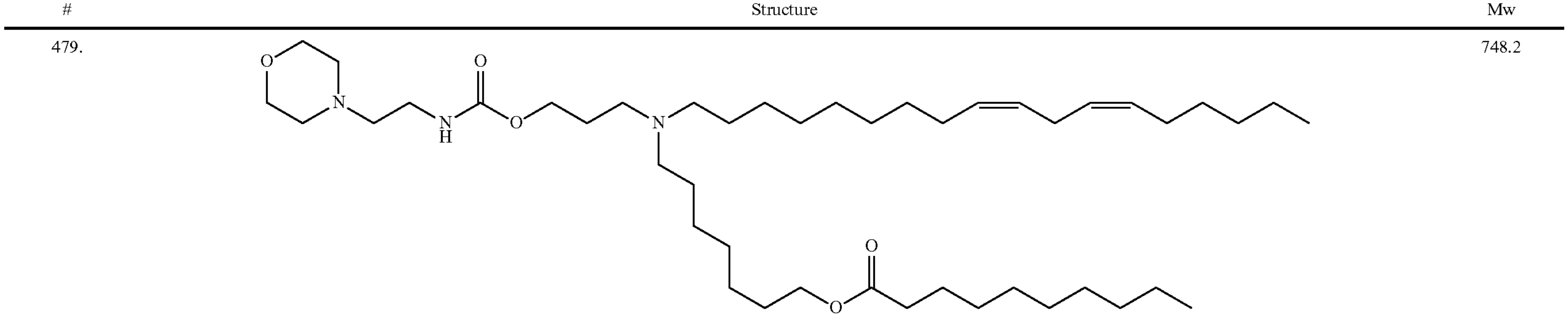 | 748.2 |
| 480. | 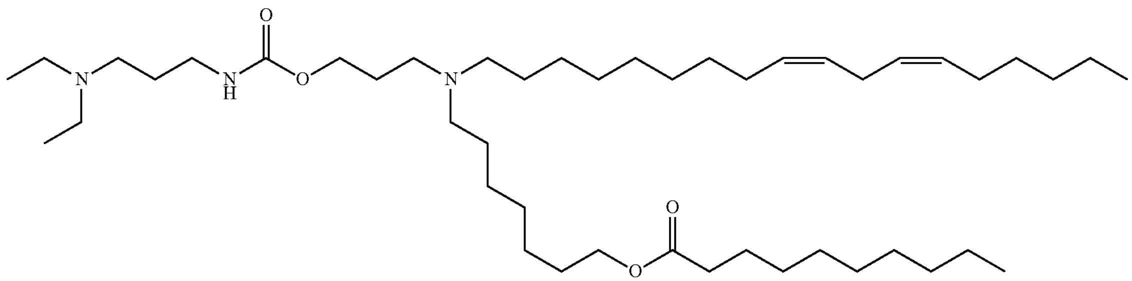 [SMILES: CCCCC/C=C\C/C=C\CCCCCCCCN(CCCCCCCOC(=O)CCCCCCCCC)CCCOC(=O)NCCCN(CC)CC] | 748.2 |
| 481. | 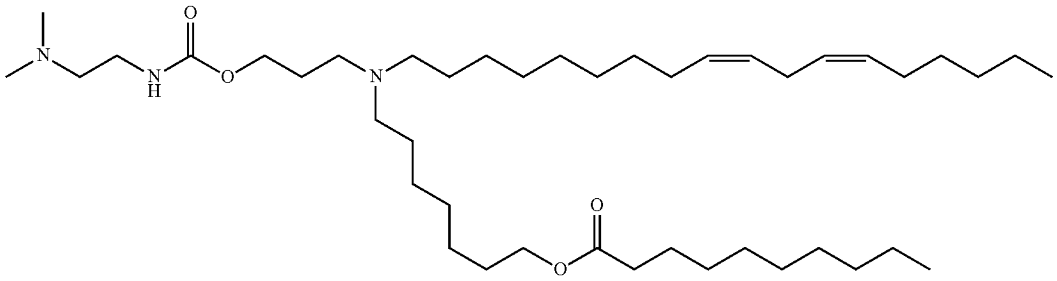 [SMILES: CCCCC/C=C\C/C=C\CCCCCCCCN(CCCCCCCOC(=O)CCCCCCCCC)CCCOC(=O)NCCN(C)C] | 706.1 |

TABLE 1-continued
| # | Structure | Mw |
|---|---|---|
| 482. | 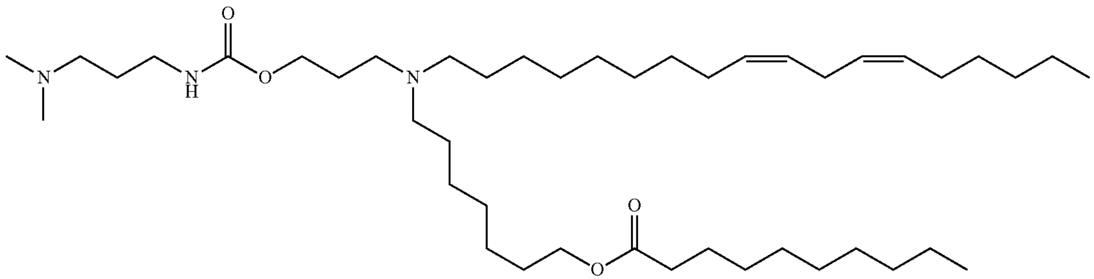 [SMILES: CCCCC/C=C\C/C=C\CCCCCCCCN(CCCCCCCOC(=O)CCCCCCCCC)CCCOC(=O)NCCCN(C)C] | 720.2 |
| 483. | 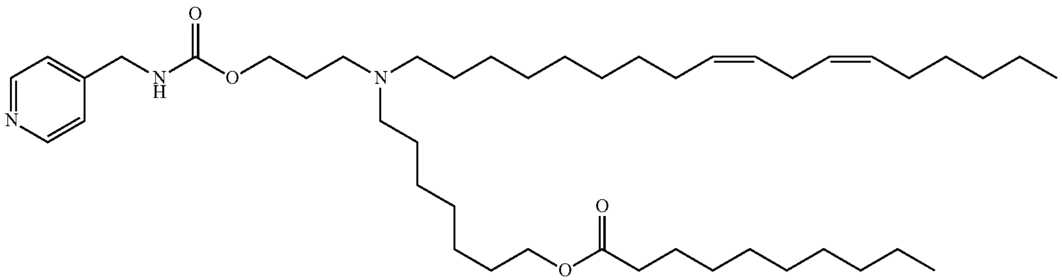 [SMILES: CCCCC/C=C\C/C=C\CCCCCCCCN(CCCCCCCOC(=O)CCCCCCCCC)CCCOC(=O)NCc1ccncc1] | 726.1 |
| 484. | 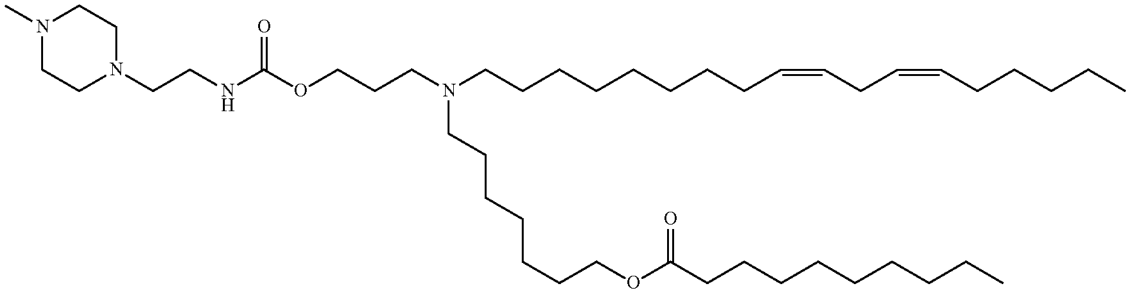 [SMILES: CCCCC/C=C\C/C=C\CCCCCCCCN(CCCCCCCOC(=O)CCCCCCCCC)CCCOC(=O)NCCN1CCN(C)CC1] | 761.2 |

TABLE 1-continued
| # | Structure | Mw |
| --- | --- | --- |
| 485. | 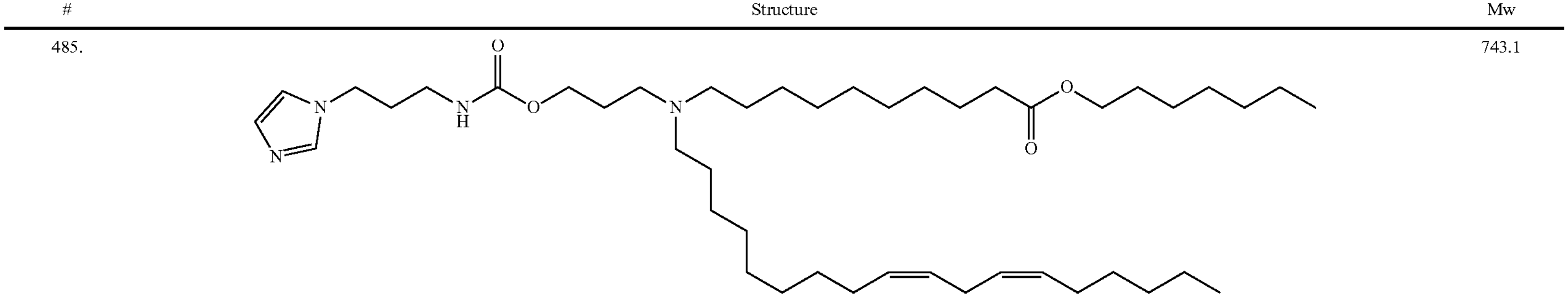 | 743.1 |
| 486. | 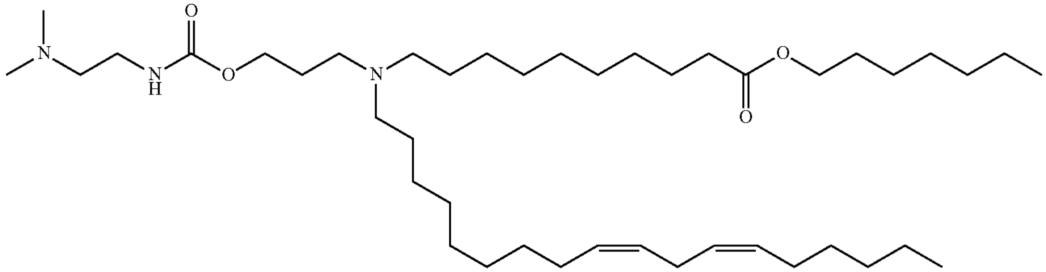 [SMILES: CCCCC/C=C\C/C=C\CCCCCCCCN(CCCCCCCCCC(=O)OCCCCCCC)CCCOC(=O)NCCN(C)C] | 706.1 |
| 487. | 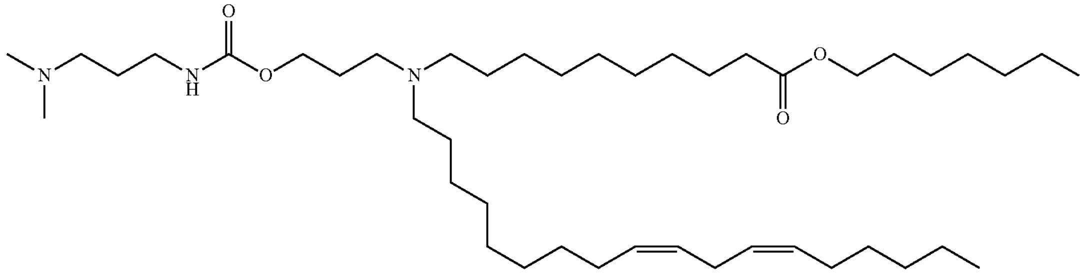 [SMILES: CCCCC/C=C\C/C=C\CCCCCCCCN(CCCCCCCCCC(=O)OCCCCCCC)CCCOC(=O)NCCCN(C)C] | 720.2 |

TABLE 1-continued
| # | Structure | Mw |
| --- | --- | --- |
| 488. | 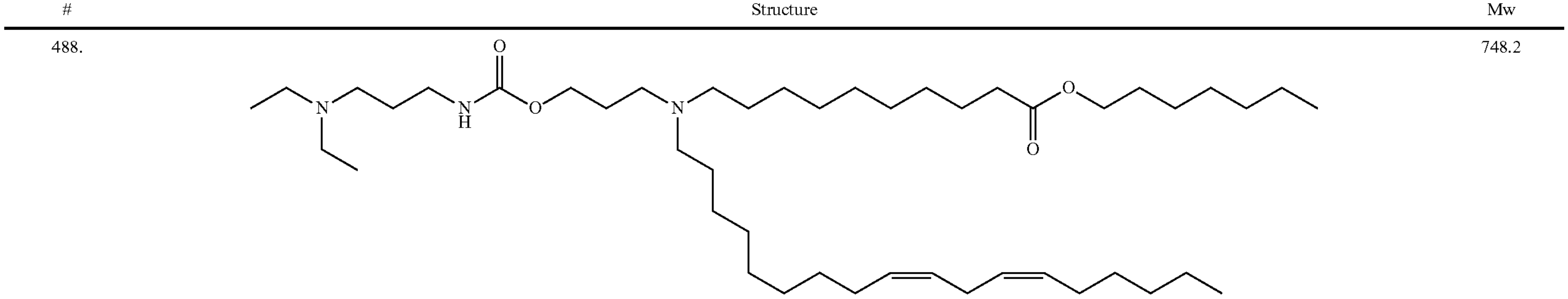 | 748.2 |
| 489. | 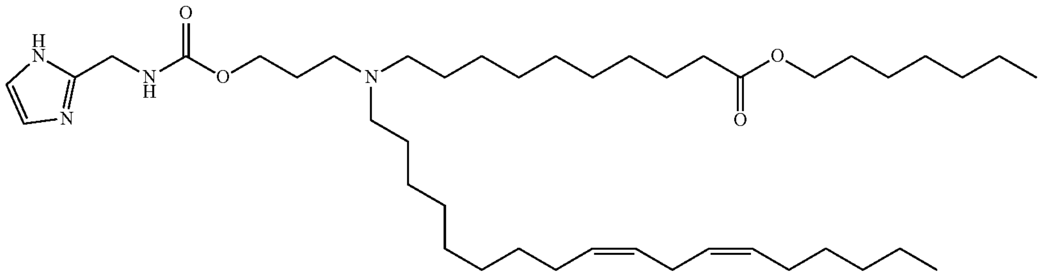 [SMILES: CCCCC/C=C\C/C=C\CCCCCCCCN(CCCCCCCCCC(=O)OCCCCCCC)CCCOC(=O)NCc1ncc[nH]1] | 715.1 |
| 490. | 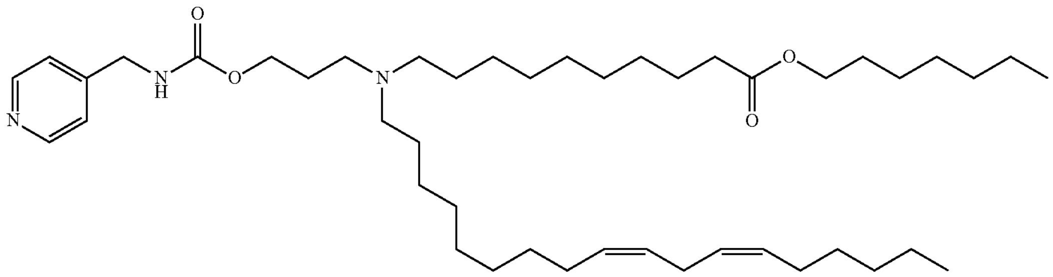 [SMILES: CCCCC/C=C\C/C=C\CCCCCCCCN(CCCCCCCCCC(=O)OCCCCCCC)CCCOC(=O)NCc1ccncc1] | 726.1 |

TABLE 1-continued
| # | Structure | Mw |
| --- | --- | --- |
| 491. | 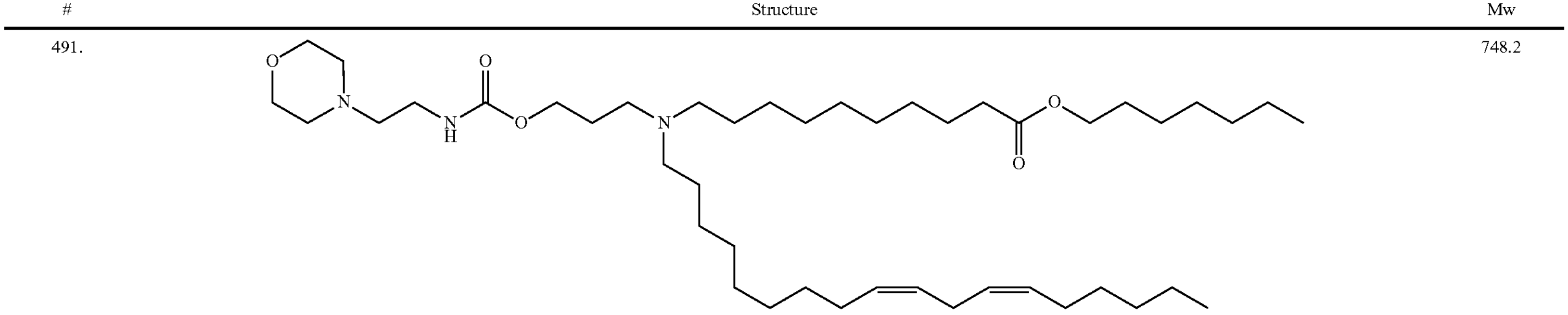 | 748.2 |
| 492. | 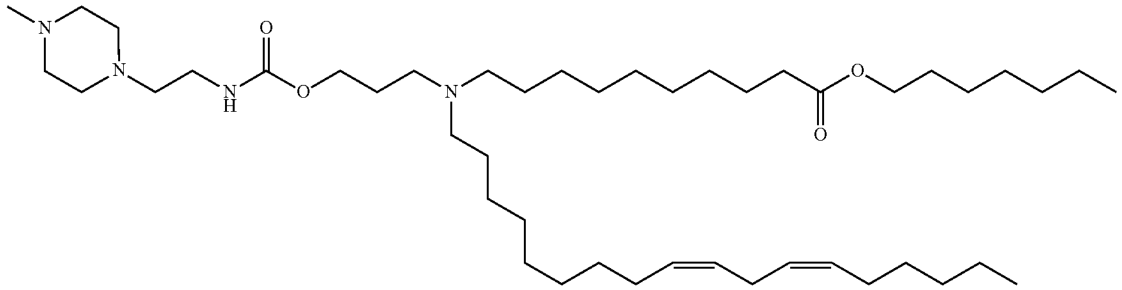 [SMILES: CCCCC/C=C\C/C=C\CCCCCCCCN(CCCCCCCCCC(=O)OCCCCCCC)CCCOC(=O)NCCN1CCN(C)CC1] | 761.2 |
| 493. | 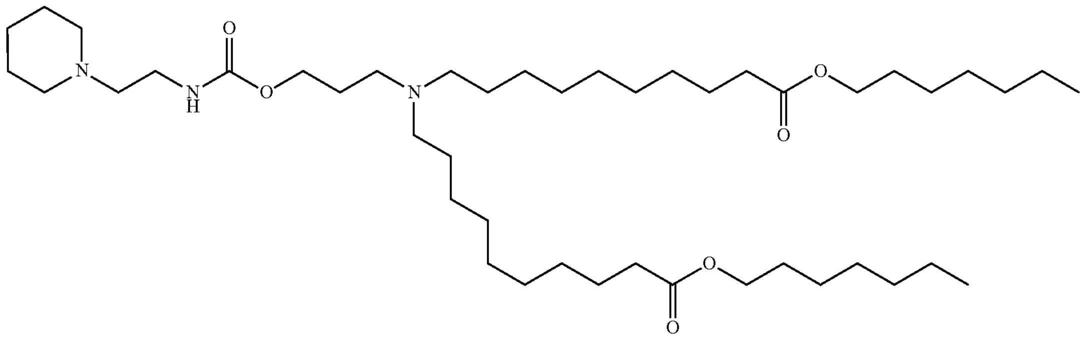 [SMILES: CCCCCCCOC(=O)CCCCCCCCCN(CCCCCCCCCC(=O)OCCCCCCC)CCCOC(=O)NCCN1CCCCC1] | 766.2 |

TABLE 1-continued
| # | Structure | Mw |
| --- | --- | --- |
| 494. | 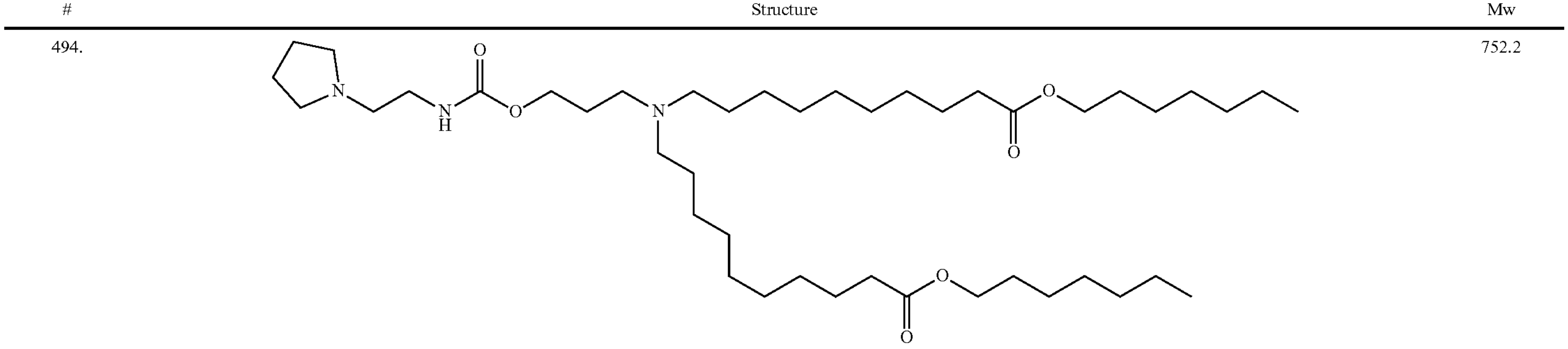 | 752.2 |
| 495. | 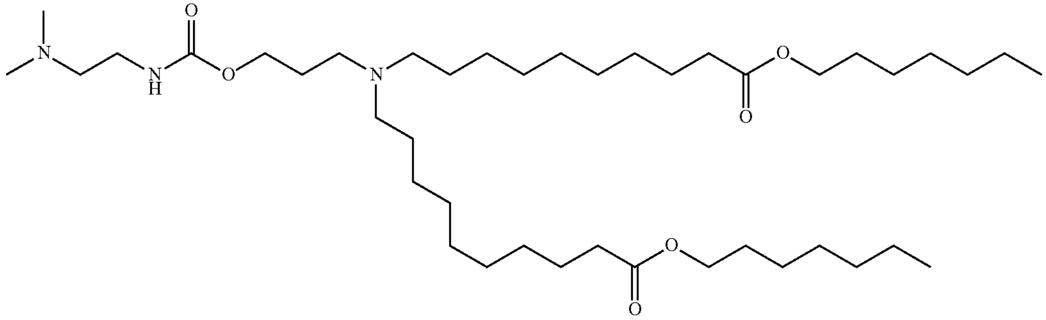 [SMILES: CCCCCCCOC(=O)CCCCCCCCCN(CCCCCCCCCC(=O)OCCCCCCC)CCCOC(=O)NCCN(C)C] | 726.1 |
| 496. | 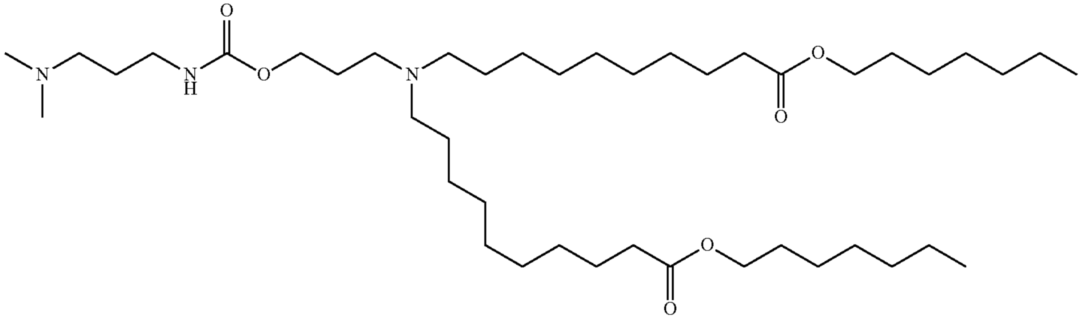 [SMILES: CCCCCCCOC(=O)CCCCCCCCCN(CCCCCCCCCC(=O)OCCCCCCC)CCCOC(=O)NCCCN(C)C] | 740.1 |

TABLE 1-continued
| # | Structure | Mw |
| --- | --- | --- |
| 497. | 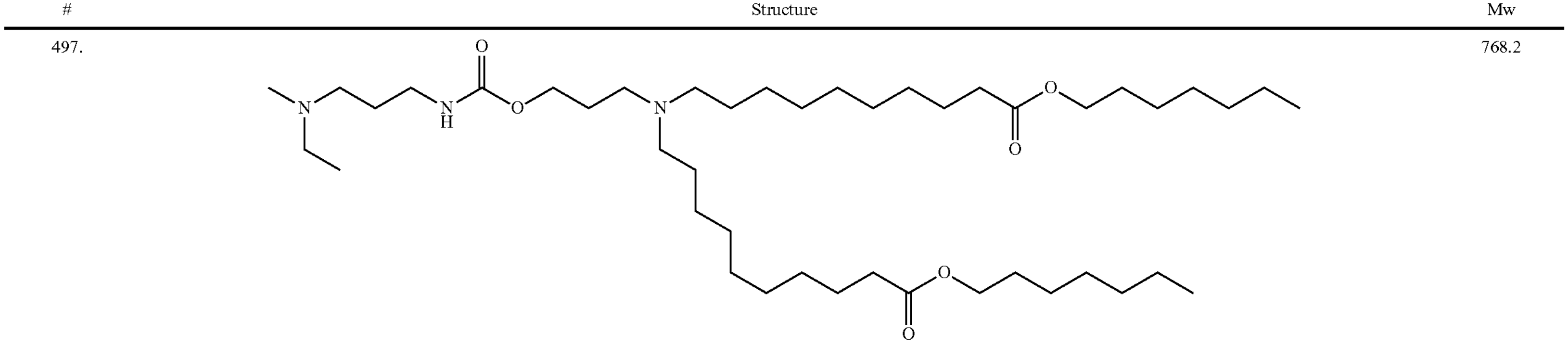 | 768.2 |
| 498. | 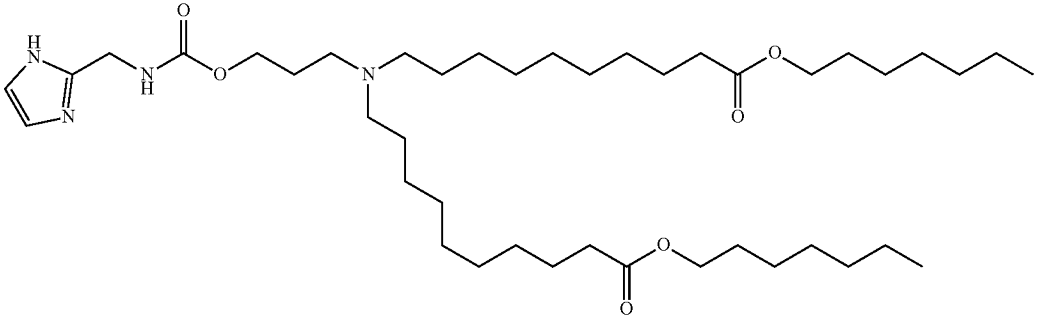 [SMILES: CCCCCCCOC(=O)CCCCCCCCCN(CCCCCCCCCC(=O)OCCCCCCC)CCCOC(=O)NCc1ncc[nH]1] | 735.1 |
| 499. | 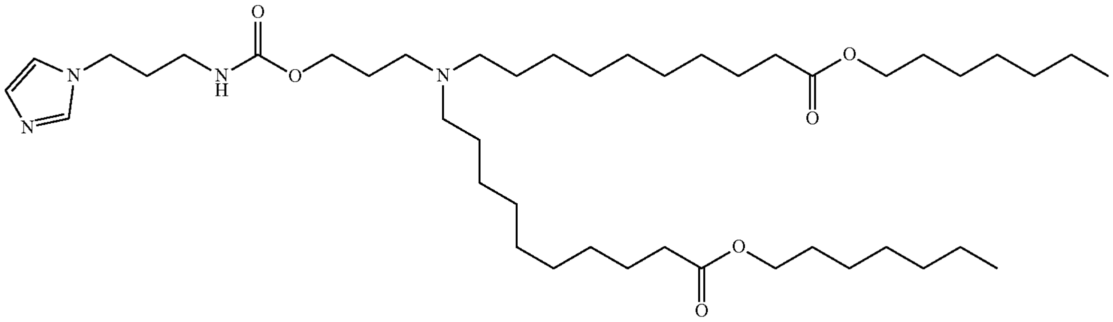 [SMILES: CCCCCCCOC(=O)CCCCCCCCCN(CCCCCCCCCC(=O)OCCCCCCC)CCCOC(=O)NCCCn1ccnc1] | 763.1 |

TABLE 1-continued
| # | Structure | Mw |
| --- | --- | --- |
| 500. | 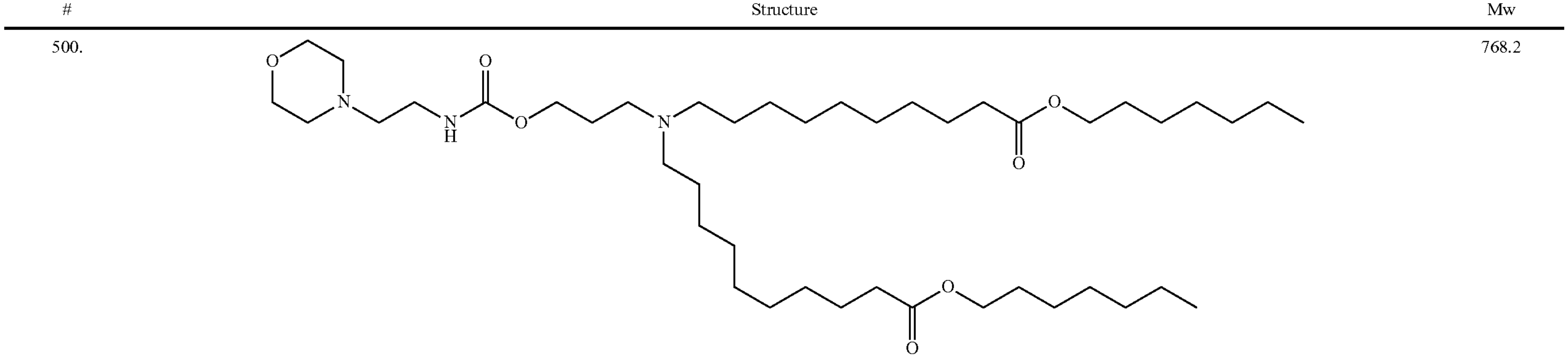 | 768.2 |
| 501. | 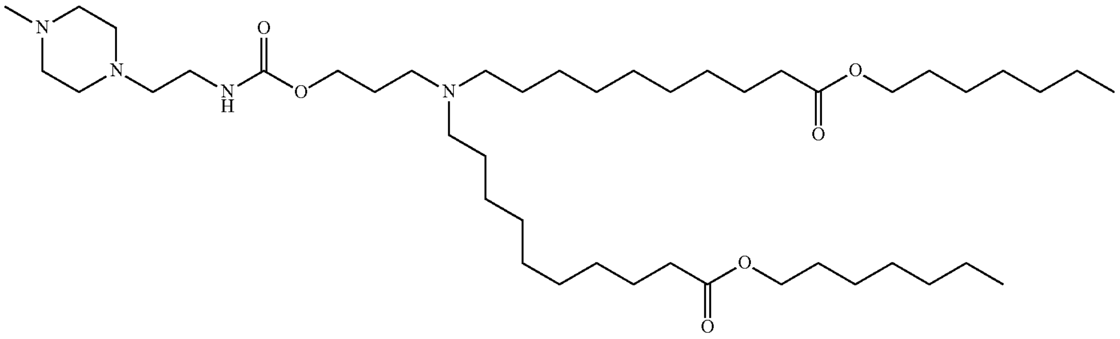 [SMILES: CCCCCCCOC(=O)CCCCCCCCCN(CCCCCCCCCC(=O)OCCCCCCC)CCCOC(=O)NCCN1CCN(C)CC1] | 781.2 |
| 502. | 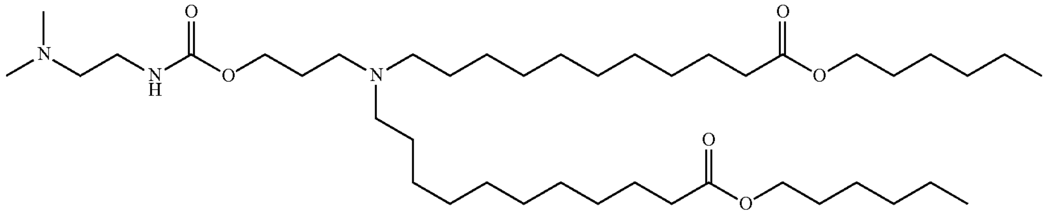 [SMILES: CCCCCCOC(=O)CCCCCCCCCCN(CCCCCCCCCCC(=O)OCCCCCC)CCCOC(=O)NCCN(C)C] | 712.1 |

TABLE 1-continued
| # | Structure | Mw |
|---|---|---|
| 503. | 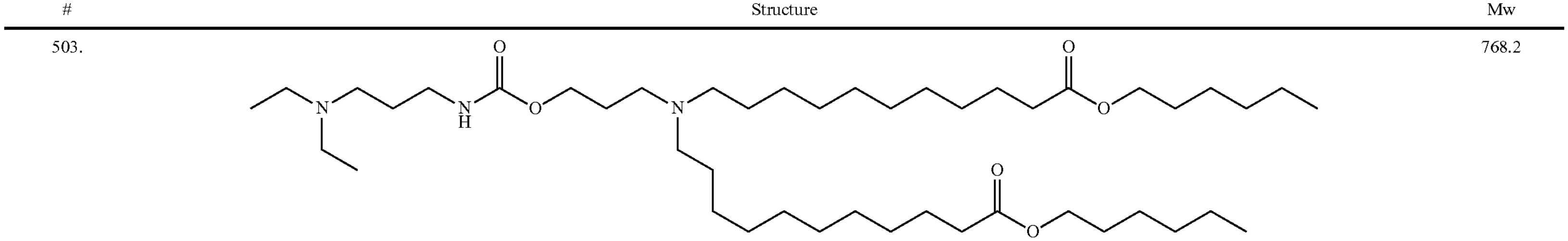 | 768.2 |
| 504. | 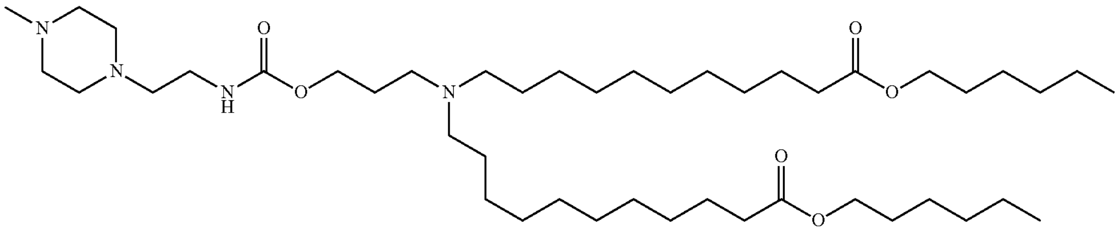 [SMILES: CCCCCCOC(=O)CCCCCCCCCCN(CCCCCCCCCCC(=O)OCCCCCC)CCCOC(=O)NCCN1CCN(C)CC1] | 781.2 |
| 505. | 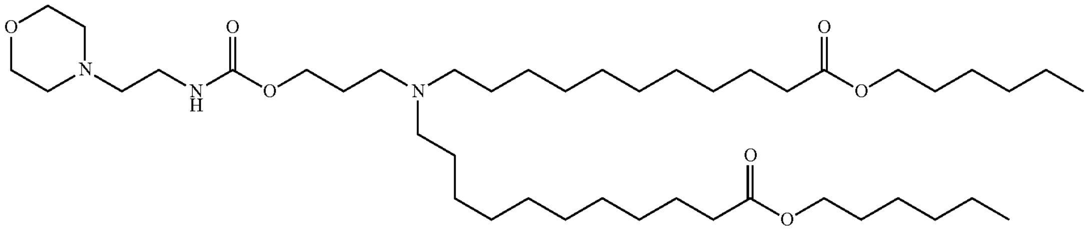 [SMILES: CCCCCCOC(=O)CCCCCCCCCCN(CCCCCCCCCCC(=O)OCCCCCC)CCCOC(=O)NCCN1CCOCC1] | 768.2 |
| 506. | 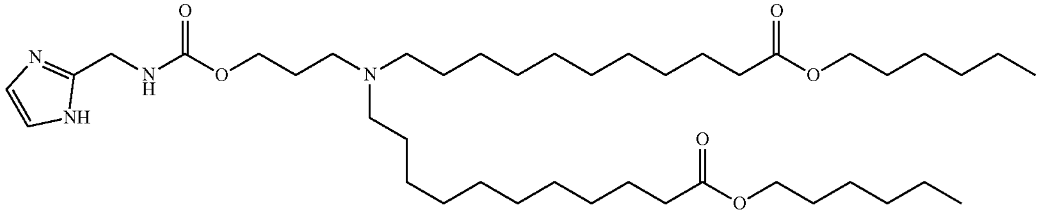 [SMILES: CCCCCCOC(=O)CCCCCCCCCCN(CCCCCCCCCCC(=O)OCCCCCC)CCCOC(=O)NCc1ncc[nH]1] | 735.1 |

TABLE 1-continued
| # | Structure | Mw |
|---|---|---|
| 507. | 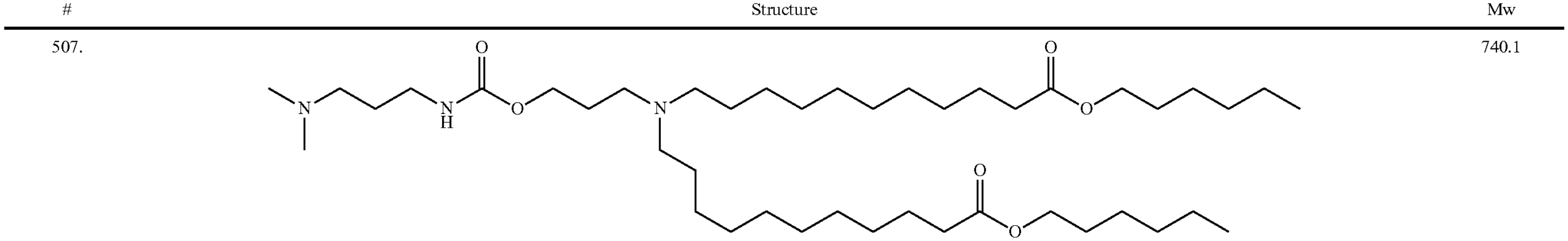 | 740.1 |
| 508. | 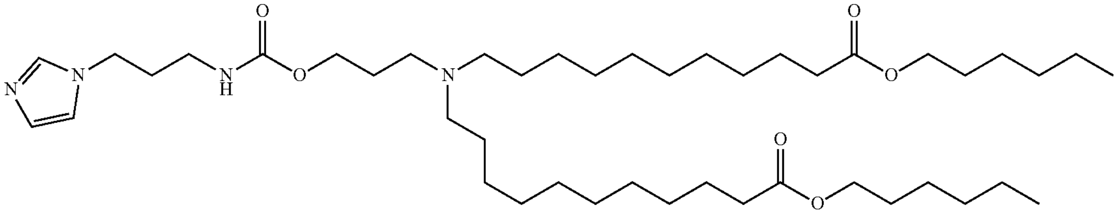 [SMILES: CCCCCCOC(=O)CCCCCCCCCCN(CCCCCCCCCCC(=O)OCCCCCC)CCCOC(=O)NCCCn1ccnc1] | 763.1 |
| 509. | 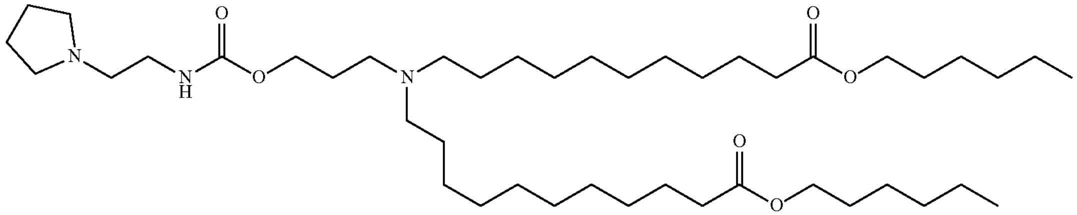 [SMILES: CCCCCCOC(=O)CCCCCCCCCCN(CCCCCCCCCCC(=O)OCCCCCC)CCCOC(=O)NCCN1CCCC1] | 752.2 |
| 510. | 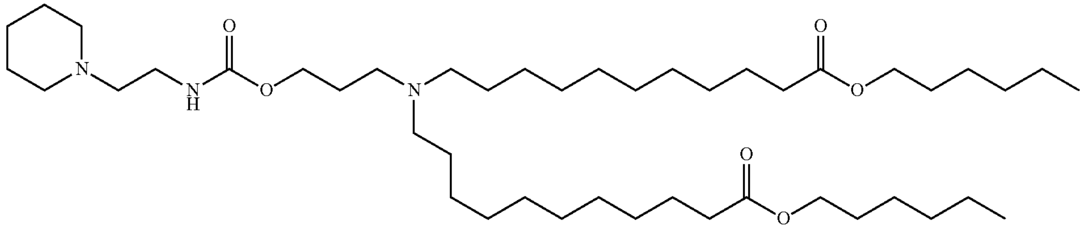 [SMILES: CCCCCCOC(=O)CCCCCCCCCCN(CCCCCCCCCCC(=O)OCCCCCC)CCCOC(=O)NCCN1CCCCC1] | 766.2 |

TABLE 1-continued
| # | Structure | Mw |
|---|---|---|
| 511. | 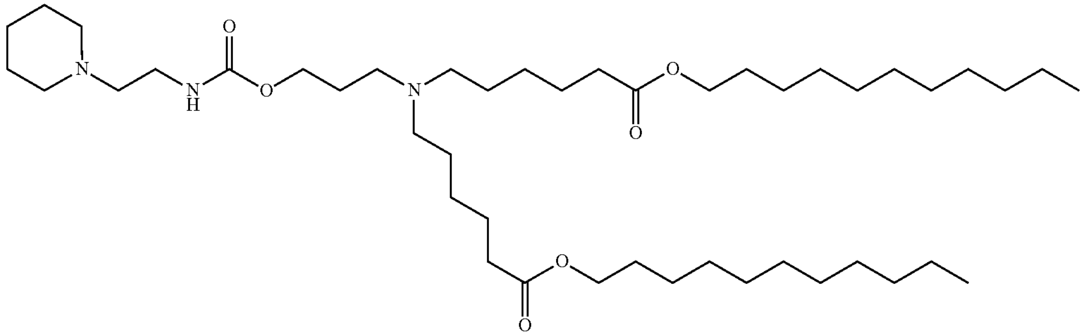 [SMILES: CCCCCCCCCCCOC(=O)CCCCCN(CCCCCC(=O)OCCCCCCCCCCC)CCCOC(=O)NCCN1CCCCC1] | 766.2 |
| 512. | 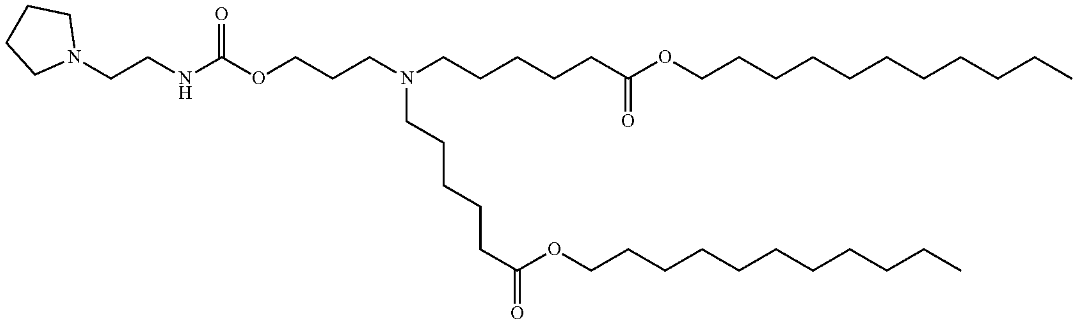 [SMILES: CCCCCCCCCCCOC(=O)CCCCCN(CCCCCC(=O)OCCCCCCCCCCC)CCCOC(=O)NCCN1CCCC1] | 752.2 |
| 513. | 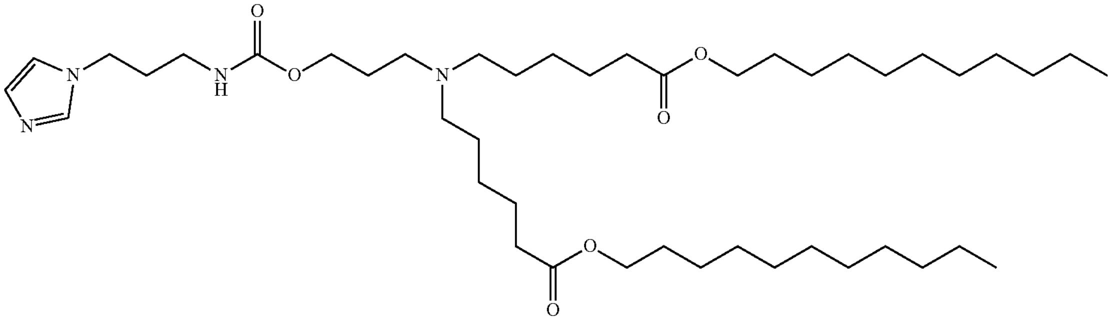 [SMILES: CCCCCCCCCCCOC(=O)CCCCCN(CCCCCC(=O)OCCCCCCCCCCC)CCCOC(=O)NCCCn1ccnc1] | 763.1 |

TABLE 1-continued
| # | Structure | Mw |
|---|---|---|
| 514. | 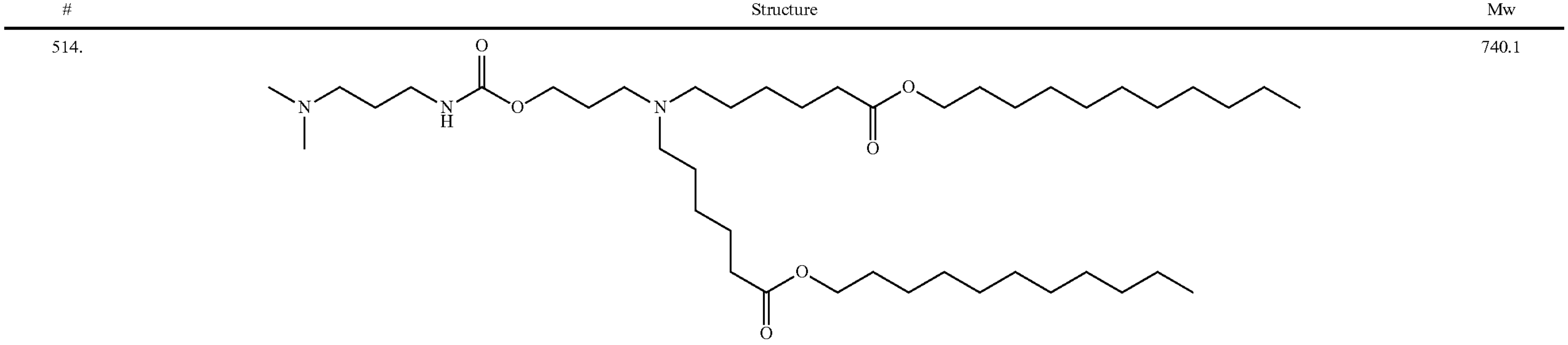 | 740.1 |
| 515. | 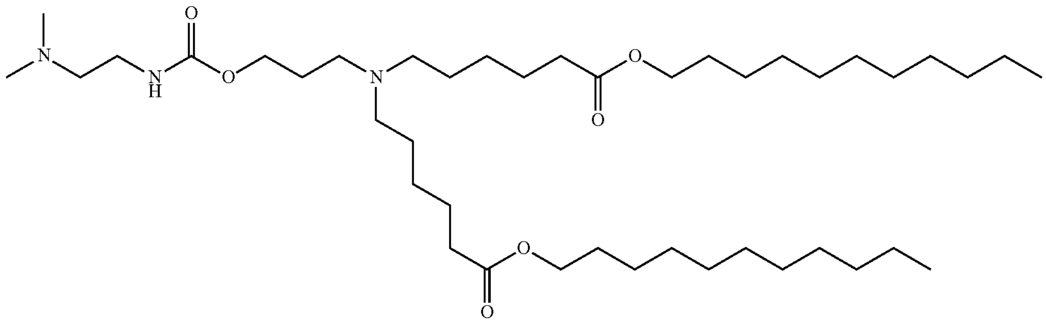 [SMILES: CCCCCCCCCCCOC(=O)CCCCCN(CCCCCC(=O)OCCCCCCCCCCC)CCCOC(=O)NCCN(C)C] | 726.1 |
| 516. | 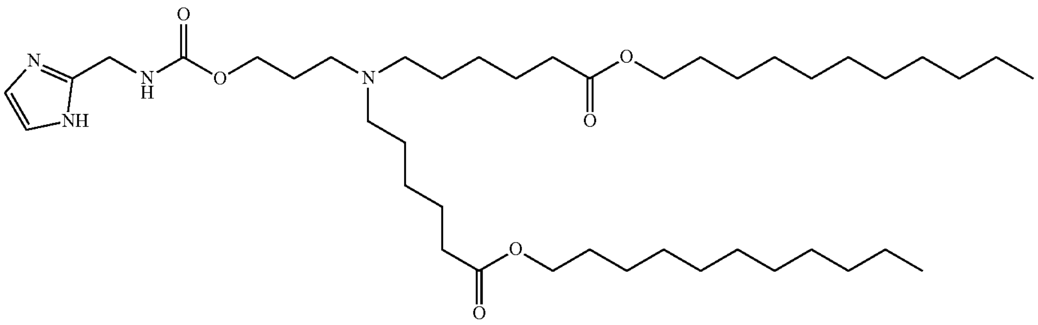 [SMILES: CCCCCCCCCCCOC(=O)CCCCCN(CCCCCC(=O)OCCCCCCCCCCC)CCCOC(=O)NCc1ncc[nH]1] | 735.1 |

TABLE 1-continued
| # | Structure | Mw |
|---|---|---|
| 517. | 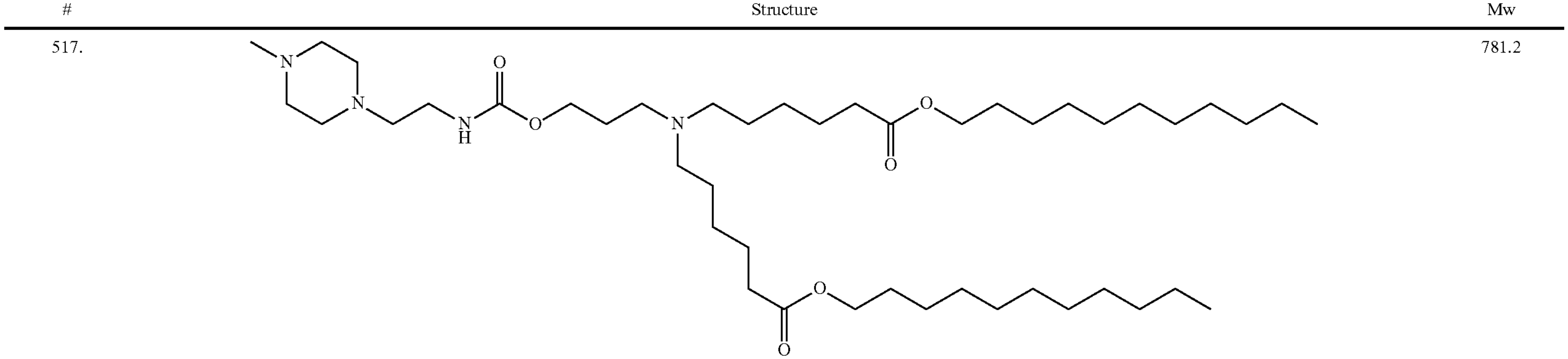 | 781.2 |
| 518. | 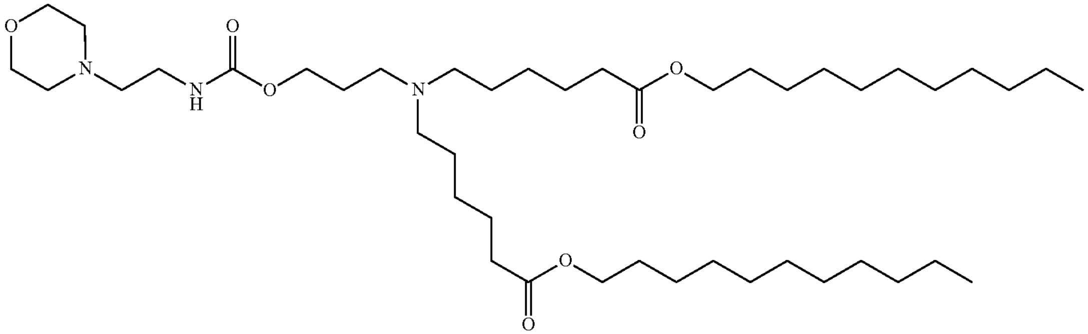 [SMILES: CCCCCCCCCCCOC(=O)CCCCCN(CCCCCC(=O)OCCCCCCCCCCC)CCCOC(=O)NCCN1CCOCC1] | 768.2 |
| 519. | 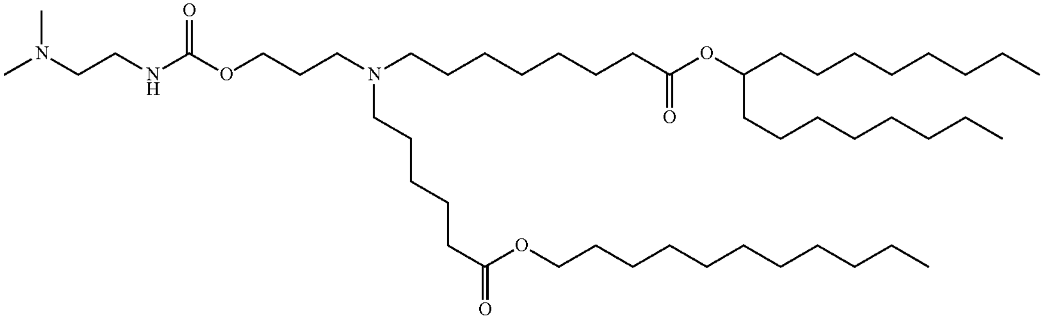 [SMILES: CCCCCCCCCCCOC(=O)CCCCCN(CCCCCCCC(=O)OC(CCCCCCCC)CCCCCCCC)CCCOC(=O)NCCN(C)C] | 838.3 |

TABLE 1-continued
| # | Structure | Mw |
| --- | --- | --- |
| 520. | 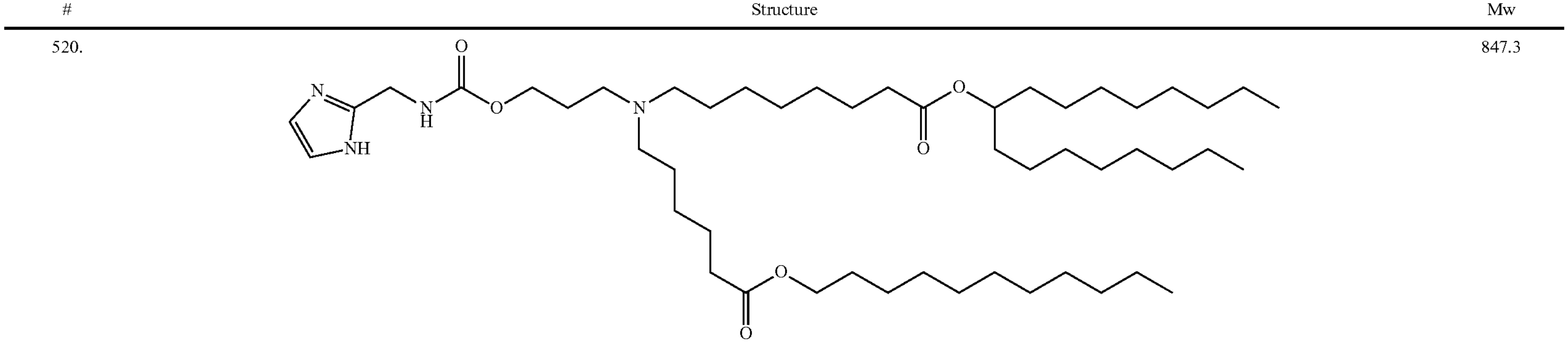 | 847.3 |
| 521. | 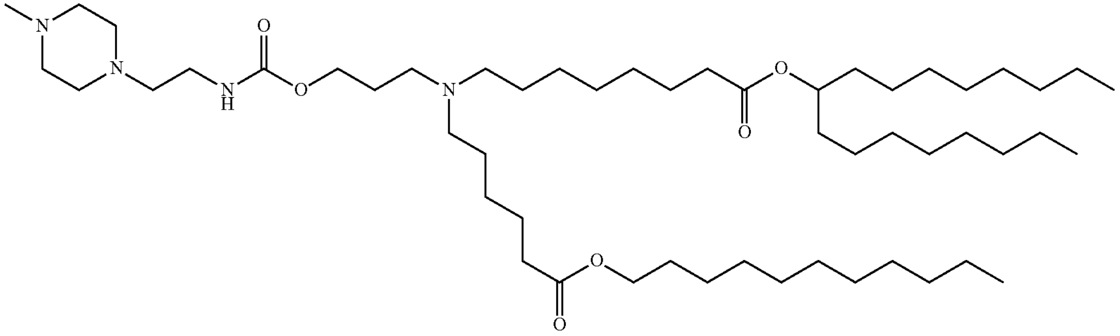 [SMILES: CCCCCCCCCCCOC(=O)CCCCCN(CCCCCCCC(=O)OC(CCCCCCCC)CCCCCCCC)CCCOC(=O)NCCN1CCN(C)CC1] | 893.4 |
| 522. | 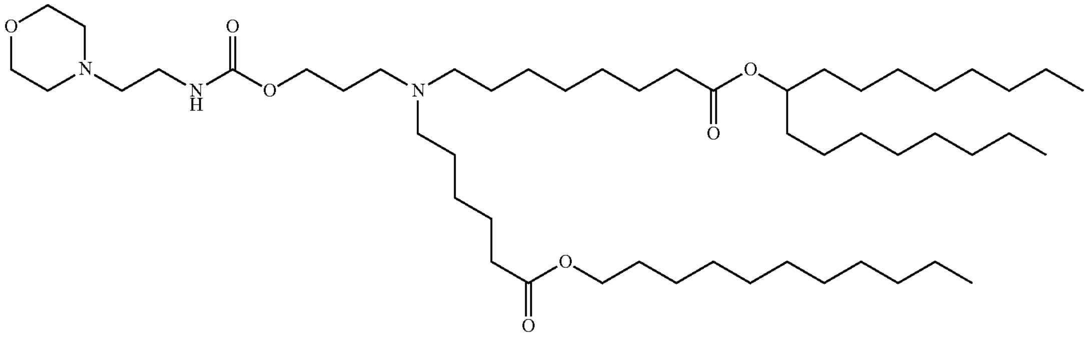 [SMILES: CCCCCCCCCCCOC(=O)CCCCCN(CCCCCCCC(=O)OC(CCCCCCCC)CCCCCCCC)CCCOC(=O)NCCN1CCOCC1] | 880.4 |

TABLE 1-continued
| # | Structure | Mw |
|---|---|---|
| 523. | 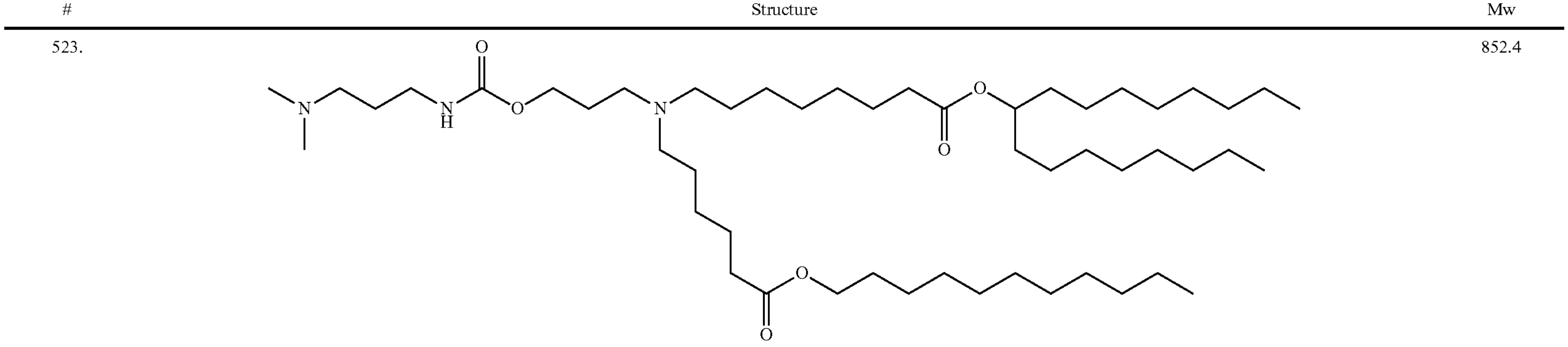 | 852.4 |
| 524. | 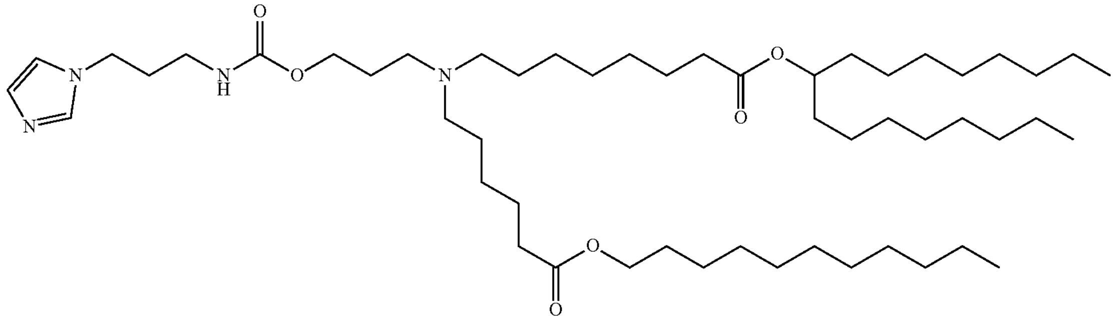 [SMILES: CCCCCCCCCCCOC(=O)CCCCCN(CCCCCCCC(=O)OC(CCCCCCCC)CCCCCCCC)CCCOC(=O)NCCCn1ccnc1] | 875.4 |
| 525. | 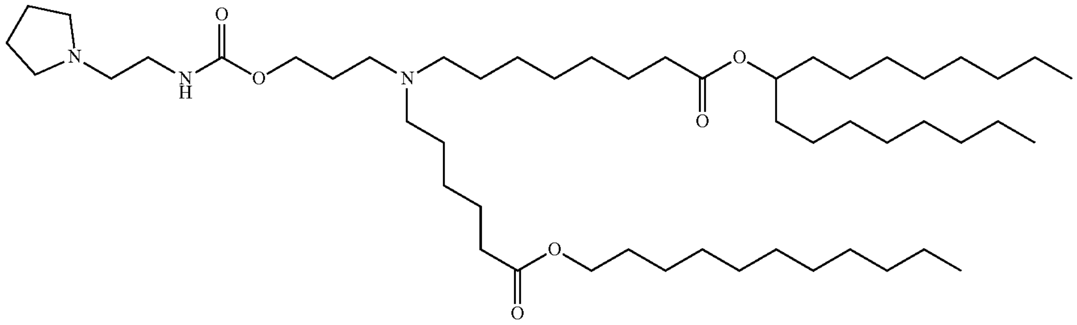 [SMILES: CCCCCCCCCCCOC(=O)CCCCCN(CCCCCCCC(=O)OC(CCCCCCCC)CCCCCCCC)CCCOC(=O)NCCN1CCCC1] | 864.4 |

TABLE 1-continued
| # | Structure | Mw |
| --- | --- | --- |
| 526. | 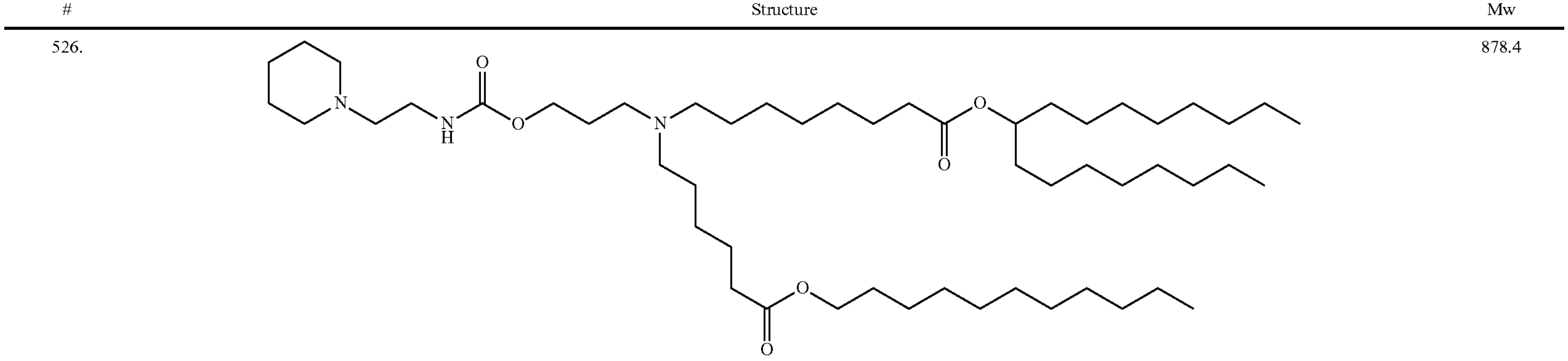 | 878.4 |
| 527. | 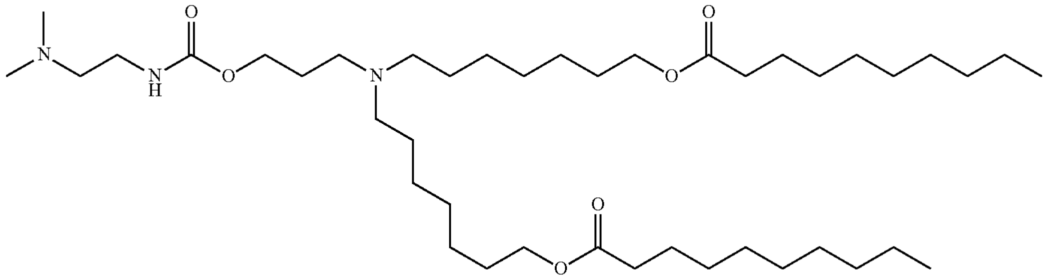 [SMILES: CCCCCCCCCC(=O)OCCCCCCCN(CCCCCCCOC(=O)CCCCCCCCC)CCCOC(=O)NCCN(C)C] | 726.1 |
| 528. | 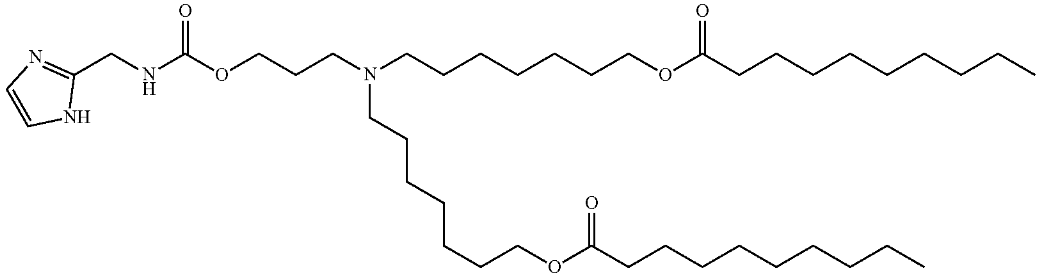 [SMILES: CCCCCCCCCC(=O)OCCCCCCCN(CCCCCCCOC(=O)CCCCCCCCC)CCCOC(=O)NCc1ncc[nH]1] | 735.1 |

TABLE 1-continued
| # | Structure | Mw |
|---|---|---|
| 529. | 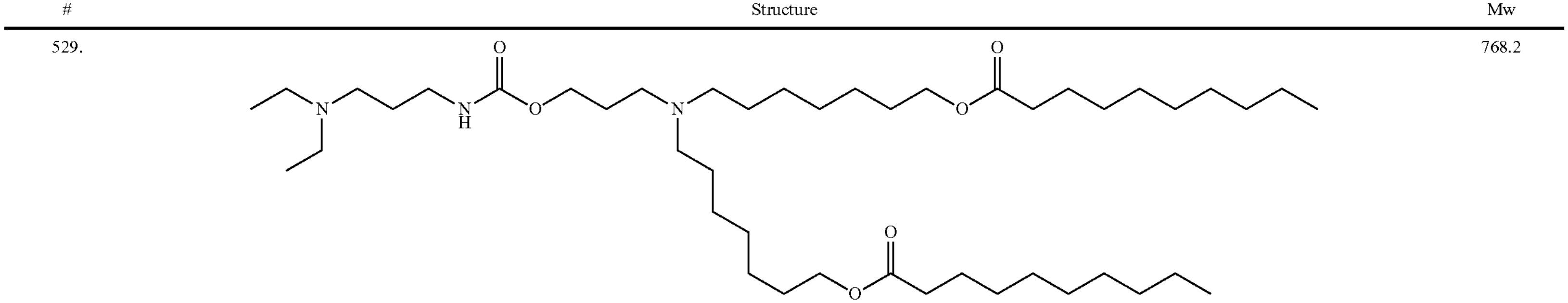 | 768.2 |
| 530. | 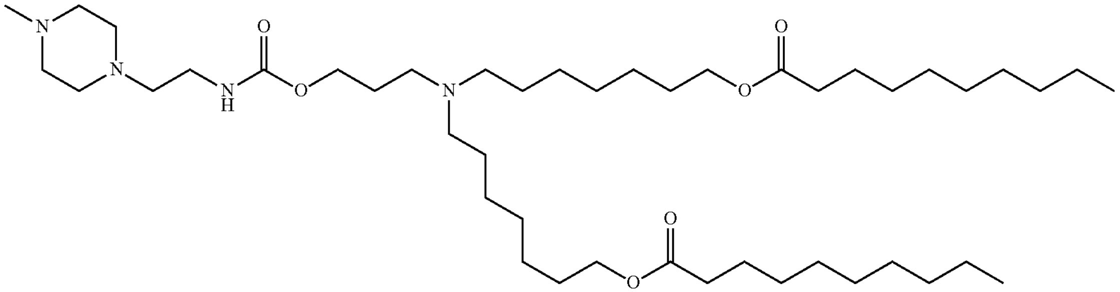 [SMILES: CCCCCCCCCC(=O)OCCCCCCCN(CCCCCCCOC(=O)CCCCCCCCC)CCCOC(=O)NCCN1CCN(C)CC1] | 781.2 |
| 531. | 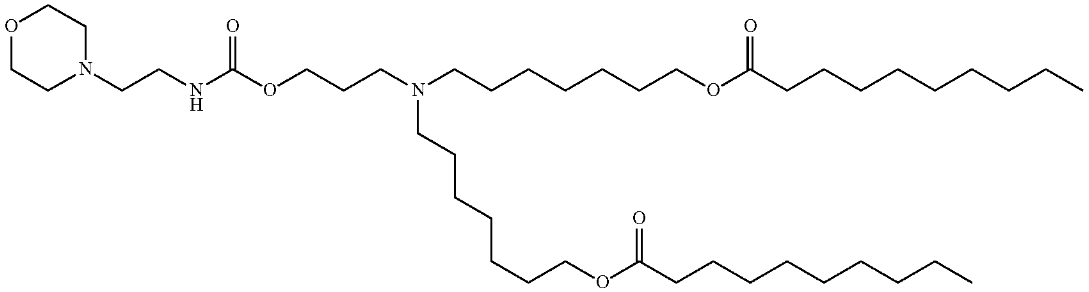 [SMILES: CCCCCCCCCC(=O)OCCCCCCCN(CCCCCCCOC(=O)CCCCCCCCC)CCCOC(=O)NCCN1CCOCC1] | 768.2 |

TABLE 1-continued
| # | Structure | Mw |
| --- | --- | --- |
| 532. | 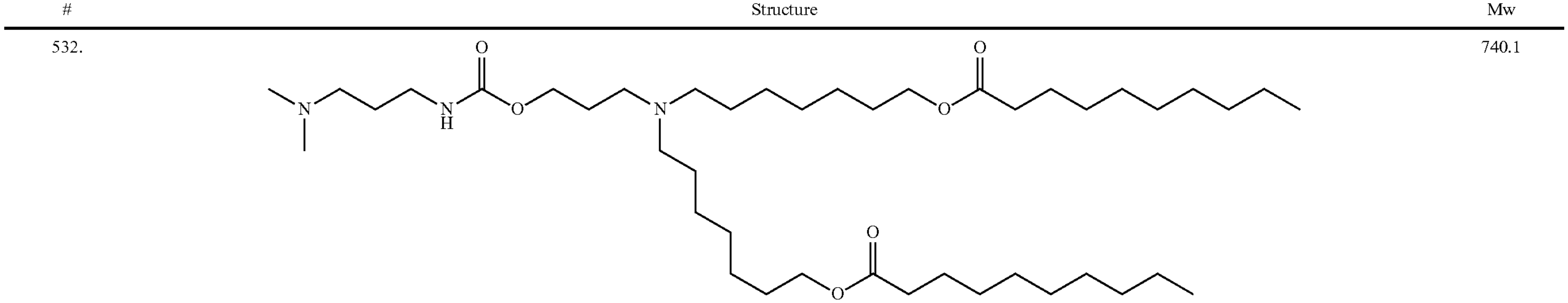 | 740.1 |
| 533. | 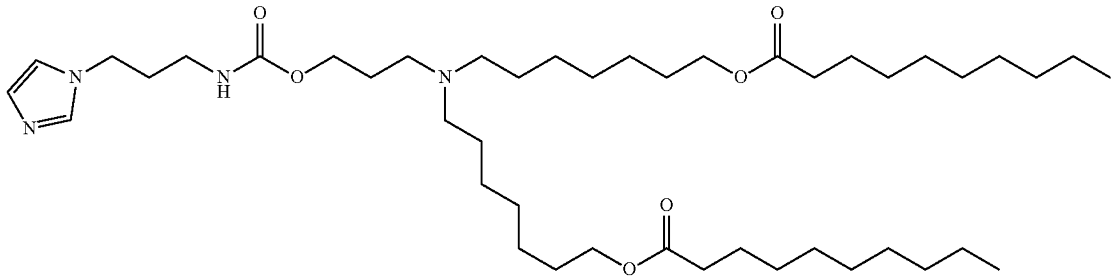 [SMILES: CCCCCCCCCC(=O)OCCCCCCCN(CCCCCCCOC(=O)CCCCCCCCC)CCCOC(=O)NCCCn1ccnc1] | 763.1 |
| 534. | 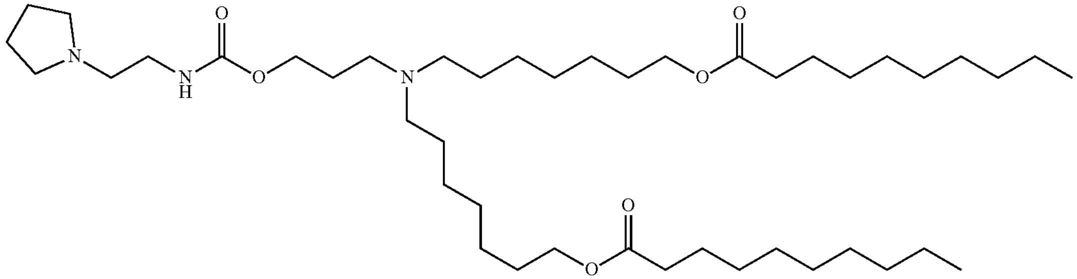 [SMILES: CCCCCCCCCC(=O)OCCCCCCCN(CCCCCCCOC(=O)CCCCCCCCC)CCCOC(=O)NCCN1CCCC1] | 752.2 |

TABLE 1-continued
| # | Structure | Mw |
|---|---|---|
| 535. | 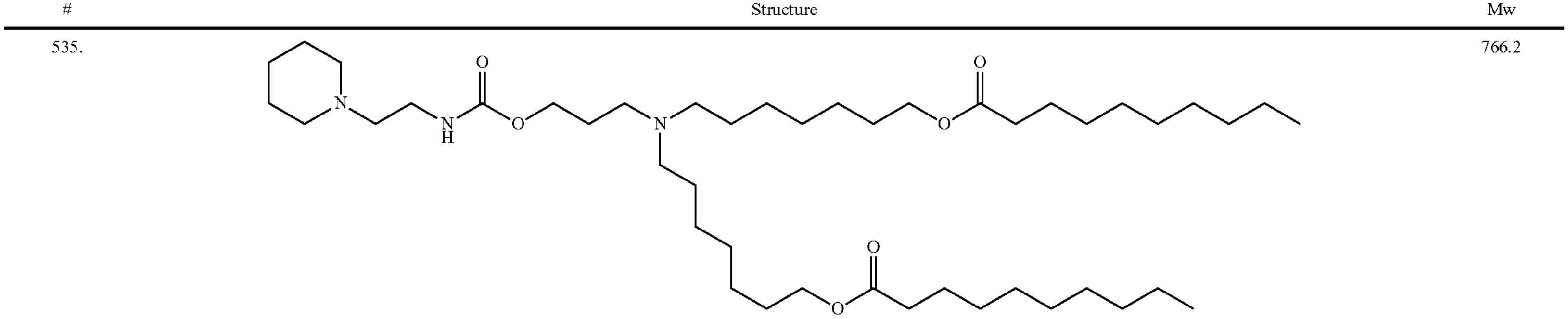 | 766.2 |
| 536. | 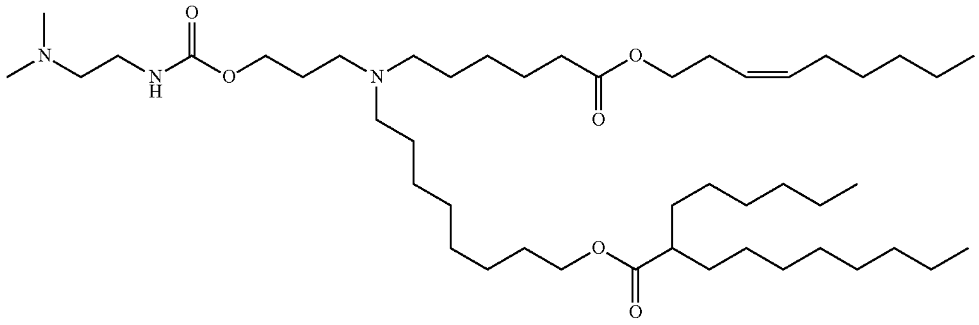 [SMILES: CCCCC/C=C\CCOC(=O)CCCCCN(CCCCCCCCOC(=O)C(CCCCCC)CCCCCCCC)CCCOC(=O)NCCN(C)C] | 794.2 |
| 537. | 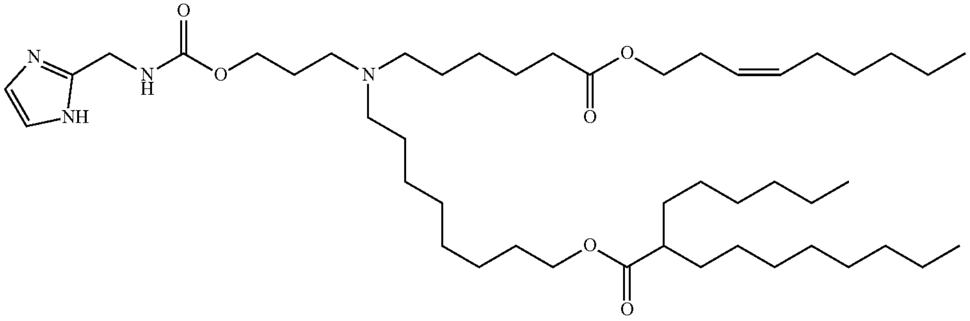 [SMILES: CCCCC/C=C\CCOC(=O)CCCCCN(CCCCCCCCOC(=O)C(CCCCCC)CCCCCCCC)CCCOC(=O)NCc1ncc[nH]1] | 803.2 |

TABLE 1-continued
| # | Structure | Mw |
| --- | --- | --- |
| 538. | 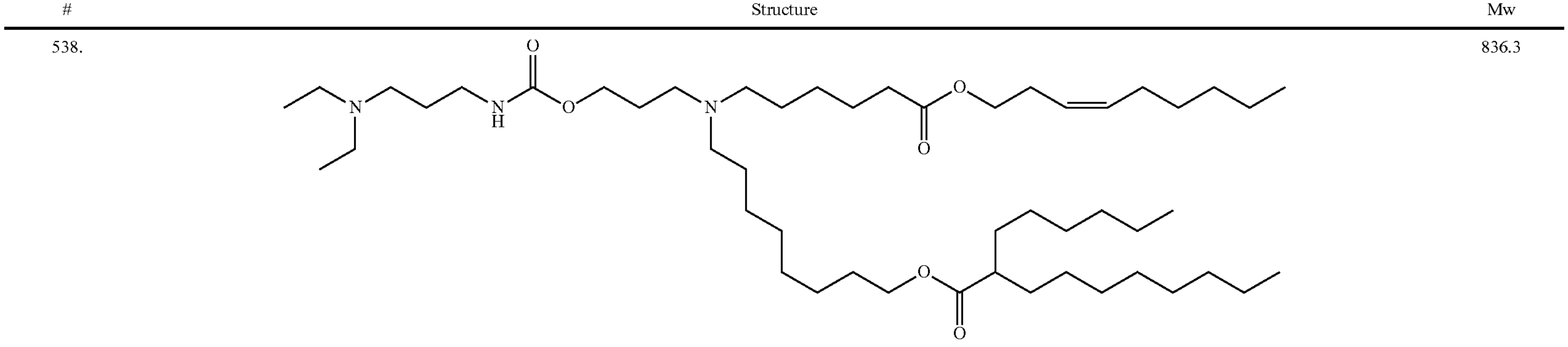 | 836.3 |
| 539. | 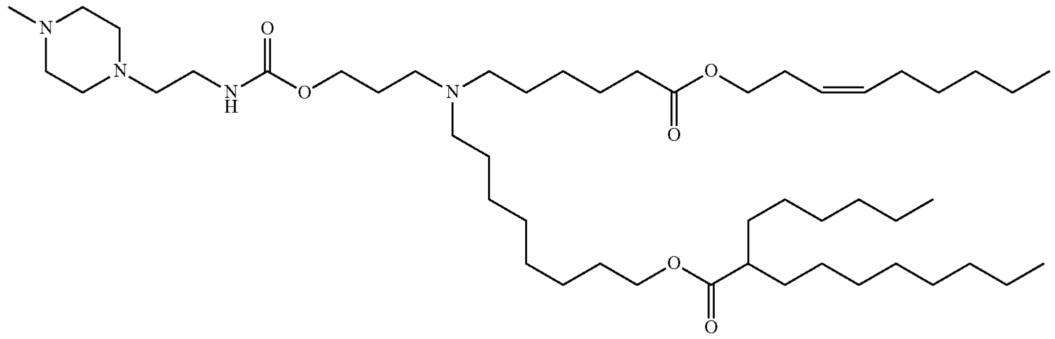 [SMILES: CCCCC/C=C\CCOC(=O)CCCCCN(CCCCCCCCOC(=O)C(CCCCCC)CCCCCCCC)CCCOC(=O)NCCN1CCN(C)CC1] | 849.3 |
| 540. | 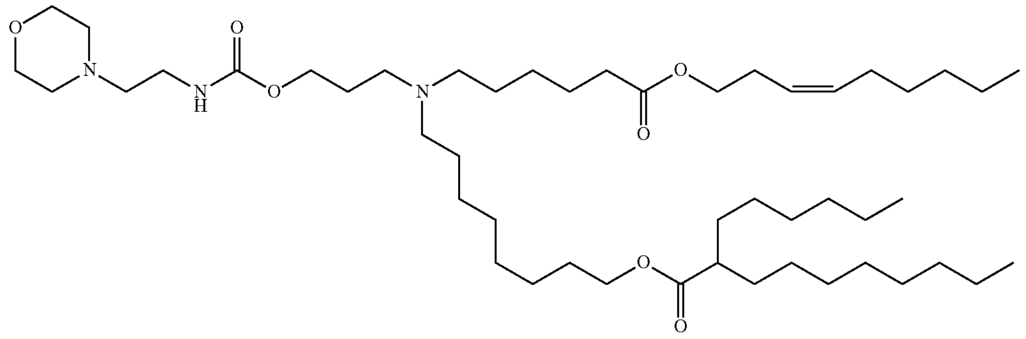 [SMILES: CCCCC/C=C\CCOC(=O)CCCCCN(CCCCCCCCOC(=O)C(CCCCCC)CCCCCCCC)CCCOC(=O)NCCN1CCOCC1] | 836.3 |

TABLE 1-continued
| # | Structure | Mw |
|---|---|---|
| 541. | 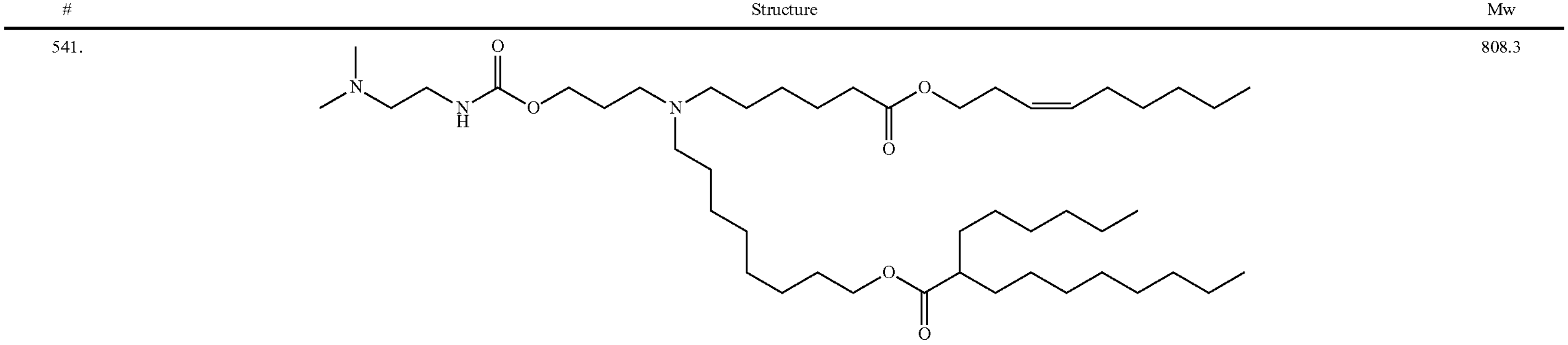 | 808.3 |
| 542. | 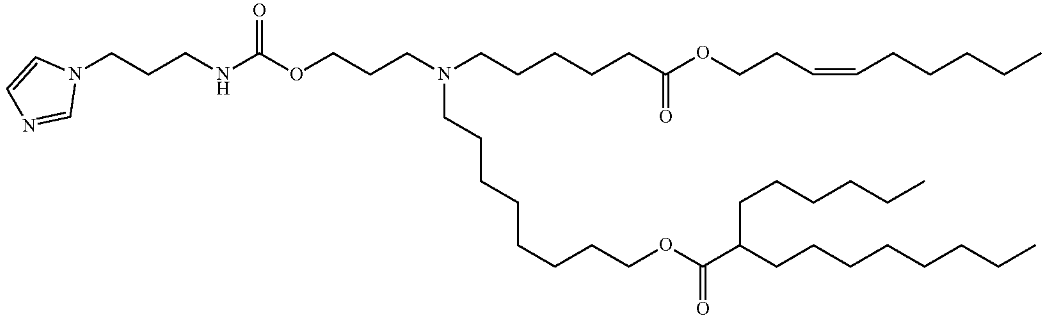 [SMILES: CCCCC/C=C\CCOC(=O)CCCCCN(CCCCCCCCOC(=O)C(CCCCCC)CCCCCCCC)CCCOC(=O)NCCCn1ccnc1] | 831.3 |
| 543. | 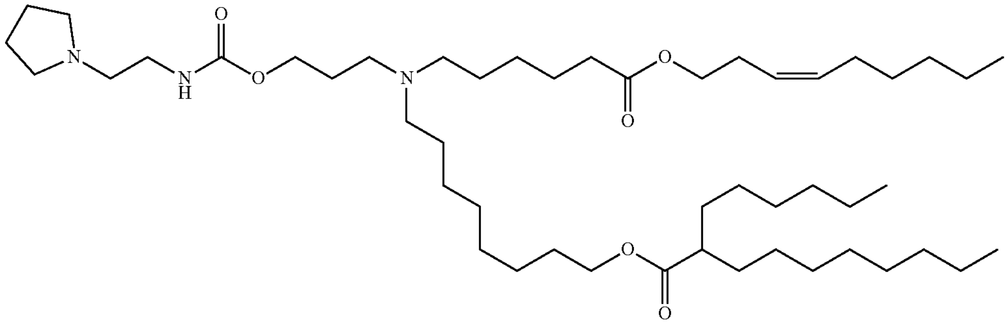 [SMILES: CCCCC/C=C\CCOC(=O)CCCCCN(CCCCCCCCOC(=O)C(CCCCCC)CCCCCCCC)CCCOC(=O)NCCN1CCCC1] | 820.3 |

TABLE 1-continued
| # | Structure | Mw |
| --- | --- | --- |
| 544. | 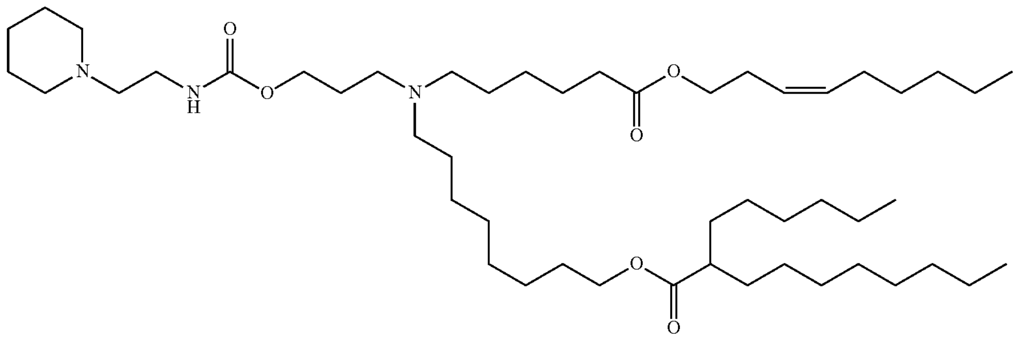 [SMILES: CCCCC/C=C\CCOC(=O)CCCCCN(CCCCCCCCOC(=O)C(CCCCCC)CCCCCCCC)CCCOC(=O)NCCN1CCCCC1] | 834.3 |
| 545. | 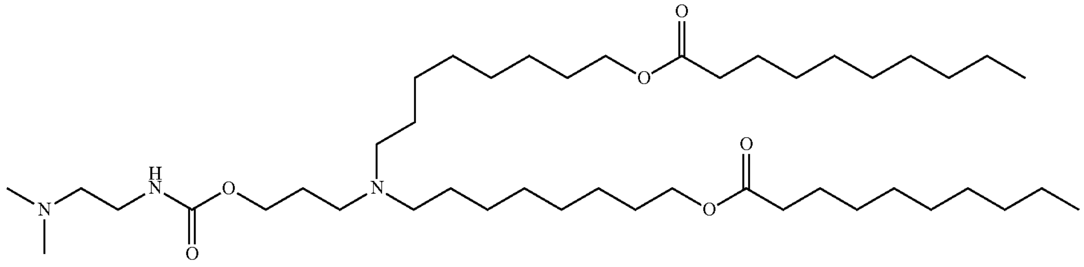 [SMILES: CCCCCCCCCC(=O)OCCCCCCCCN(CCCCCCCCOC(=O)CCCCCCCCC)CCCOC(=O)NCCN(C)C] | 754.2 |
| 546. | 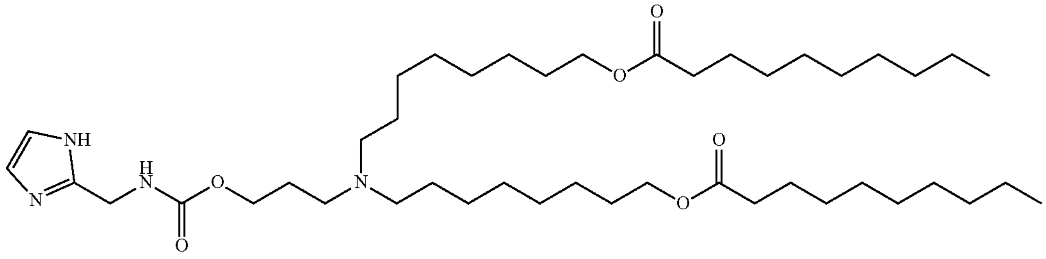 [SMILES: CCCCCCCCCC(=O)OCCCCCCCCN(CCCCCCCCOC(=O)CCCCCCCCC)CCCOC(=O)NCc1ncc[nH]1] | 763.1 |

TABLE 1-continued
| # | Structure | Mw |
| --- | --- | --- |
| 547. | 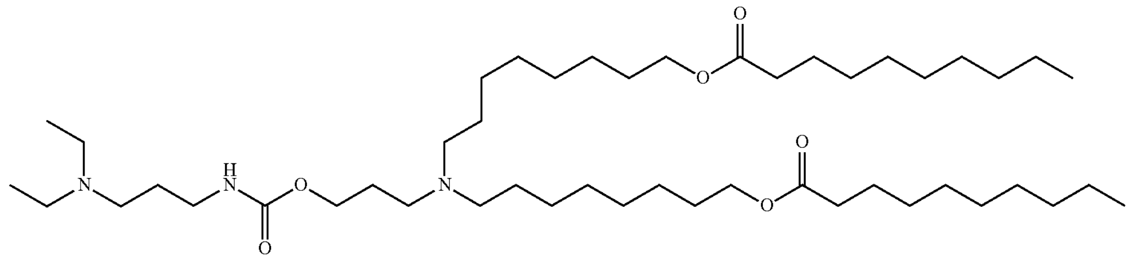 [SMILES: CCCCCCCCCC(=O)OCCCCCCCCN(CCCCCCCCOC(=O)CCCCCCCCC)CCCOC(=O)NCCCN(CC)CC] | 796.2 |
| 548. | 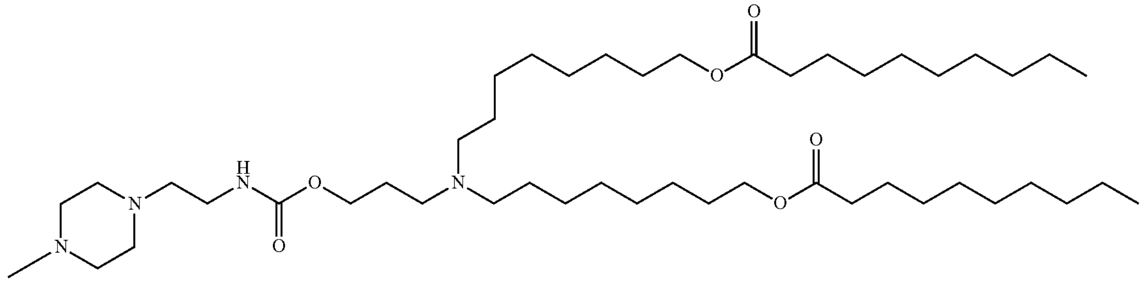 [SMILES: CCCCCCCCCC(=O)OCCCCCCCCN(CCCCCCCCOC(=O)CCCCCCCCC)CCCOC(=O)NCCN1CCN(C)CC1] | 809.3 |
| 549. | 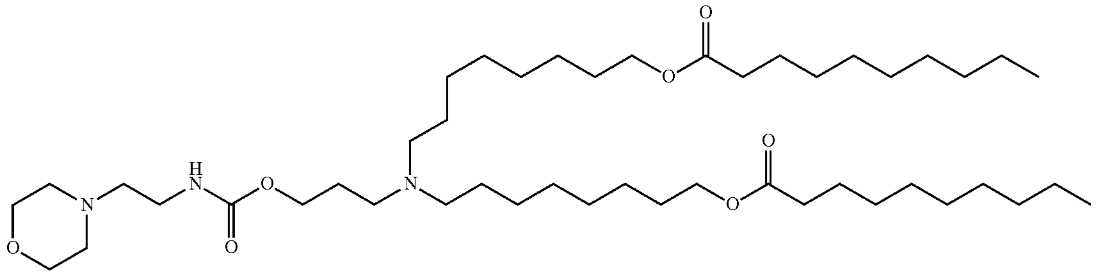 [SMILES: CCCCCCCCCC(=O)OCCCCCCCCN(CCCCCCCCOC(=O)CCCCCCCCC)CCCOC(=O)NCCN1CCOCC1] | 796.2 |

TABLE 1-continued
| # | Structure | Mw |
| --- | --- | --- |
| 550. | 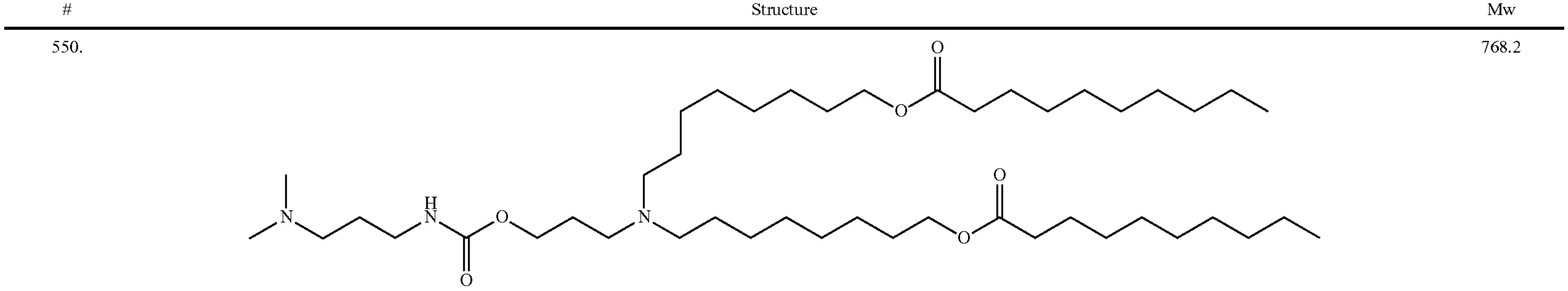 | 768.2 |
| 551. | 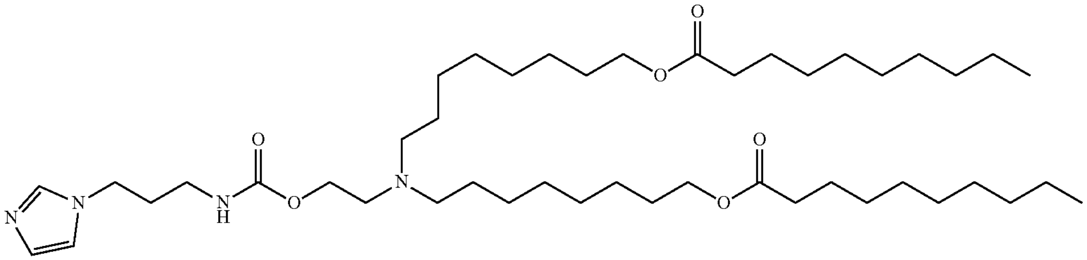 [SMILES: CCCCCCCCCC(=O)OCCCCCCCCN(CCCCCCCCOC(=O)CCCCCCCCC)CCOC(=O)NCCCn1ccnc1] | 777.2 |
| 552. | 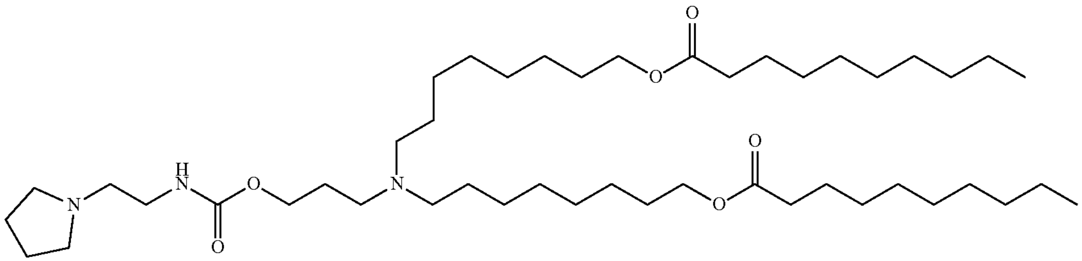 [SMILES: CCCCCCCCCC(=O)OCCCCCCCCN(CCCCCCCCOC(=O)CCCCCCCCC)CCCOC(=O)NCCN1CCCC1] | 780.2 |

TABLE 1-continued
| # | Structure | Mw |
|---|---|---|
| 553. | 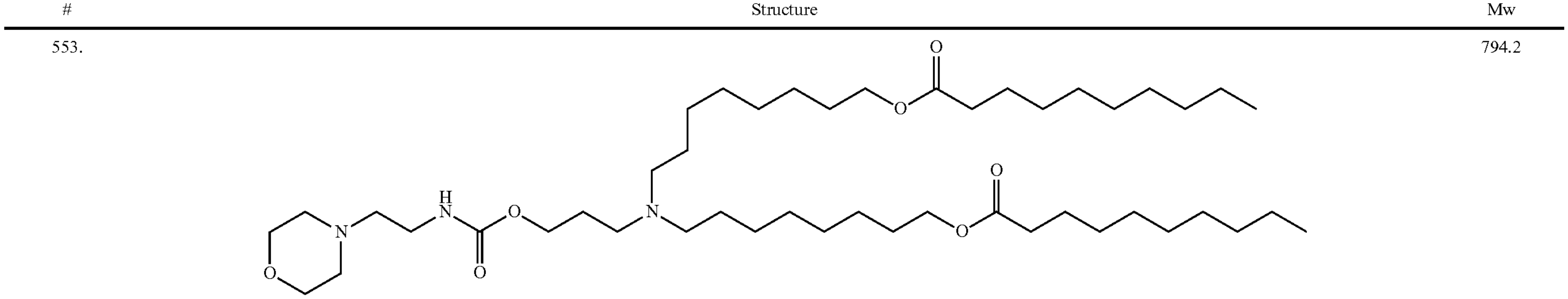 | 794.2 |
| 554. | 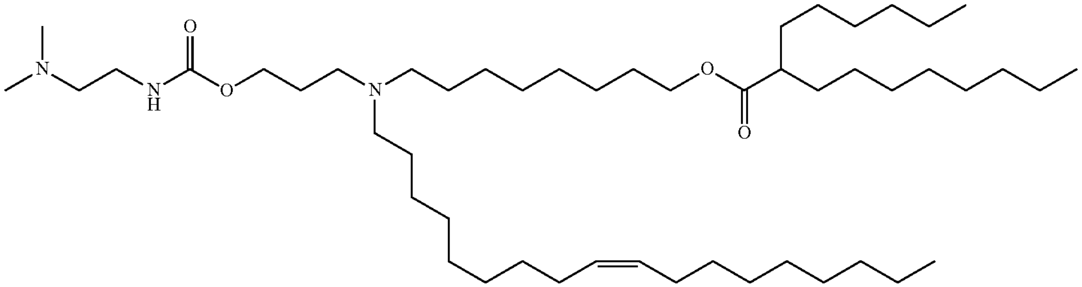 [SMILES: CCCCCCCC/C=C\CCCCCCCCN(CCCCCCCCOC(=O)C(CCCCCC)CCCCCCCC)CCCOC(=O)NCCN(C)C] | 806.3 |
| 555. | 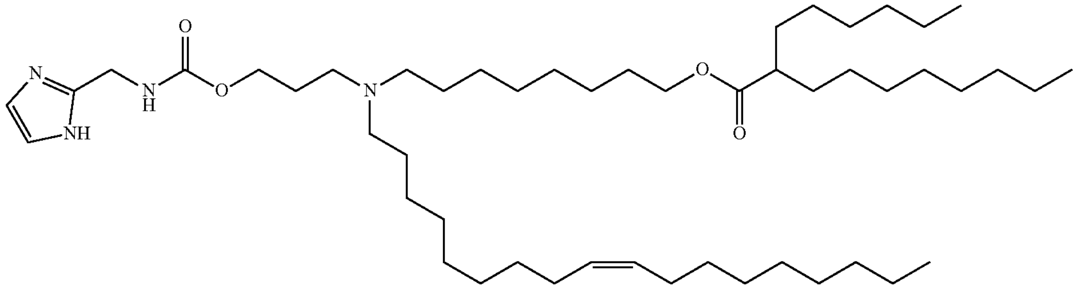 [SMILES: CCCCCCCC/C=C\CCCCCCCCN(CCCCCCCCOC(=O)C(CCCCCC)CCCCCCCC)CCCOC(=O)NCc1ncc[nH]1] | 815.3 |

TABLE 1-continued
| # | Structure | Mw |
|---|---|---|
| 556. | 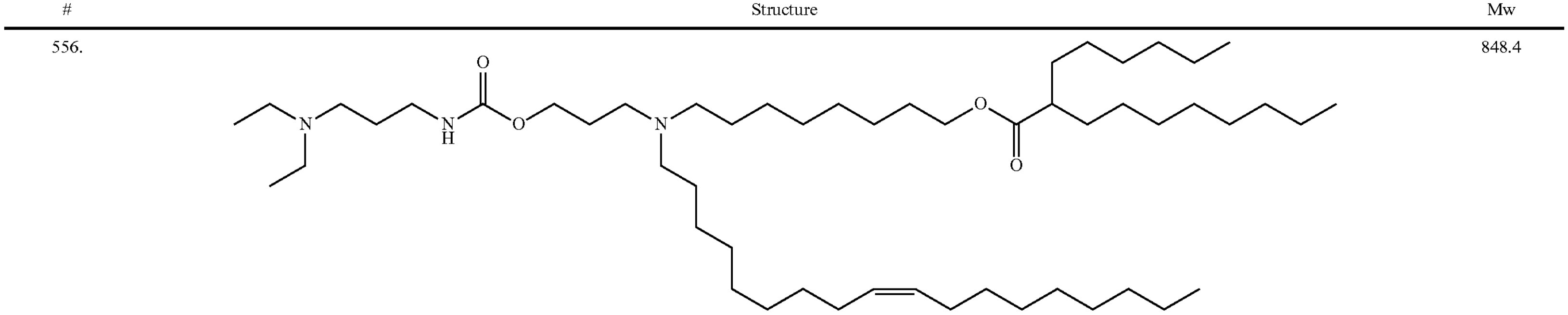 | 848.4 |
| 557. | 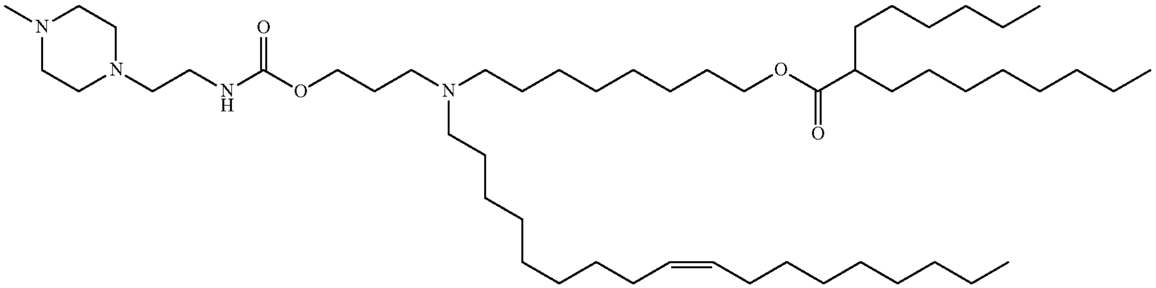 [SMILES: CCCCCCCC/C=C\CCCCCCCCN(CCCCCCCCOC(=O)C(CCCCCC)CCCCCCCC)CCCOC(=O)NCCN1CCN(C)CC1] | 861.4 |
| 558. | 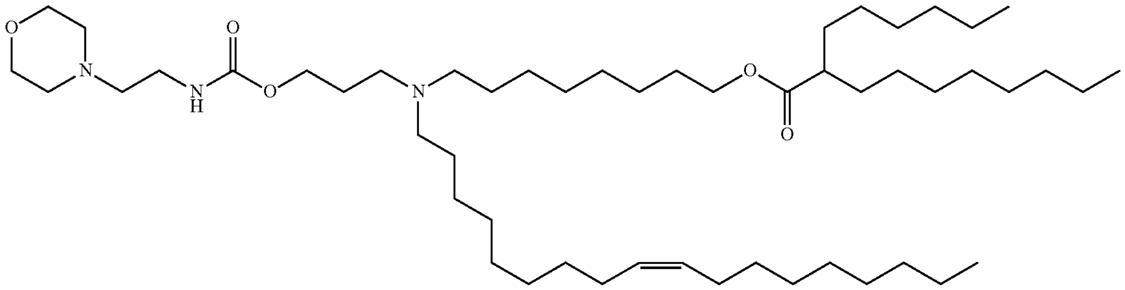 [SMILES: CCCCCCCC/C=C\CCCCCCCCN(CCCCCCCCOC(=O)C(CCCCCC)CCCCCCCC)CCCOC(=O)NCCN1CCOCC1] | 848.4 |

TABLE 1-continued
| # | Structure | Mw |
|---|---|---|
| 559. | 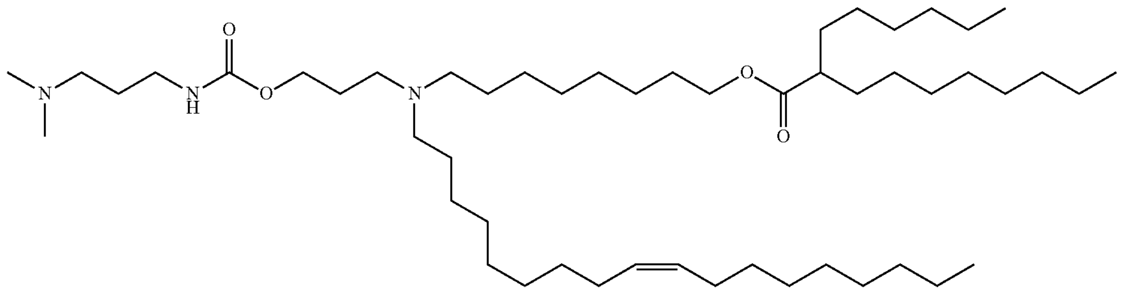 [SMILES: CCCCCCCC/C=C\CCCCCCCCN(CCCCCCCCOC(=O)C(CCCCCC)CCCCCCCC)CCCOC(=O)NCCCN(C)C] | 820.4 |
| 560. | 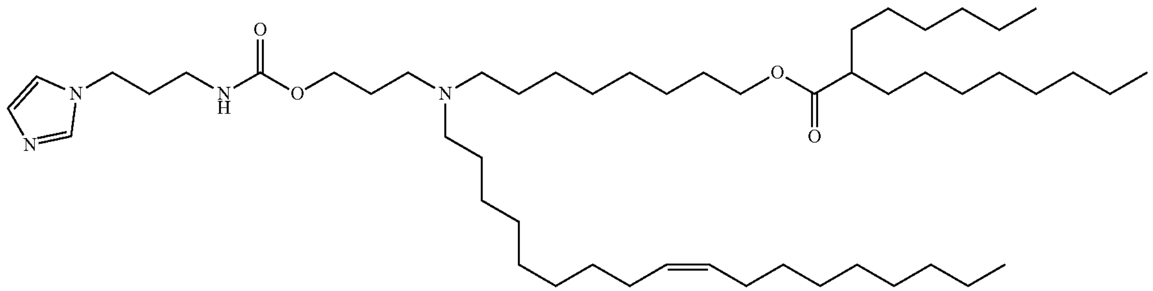 [SMILES: CCCCCCCC/C=C\CCCCCCCCN(CCCCCCCCOC(=O)C(CCCCCC)CCCCCCCC)CCCOC(=O)NCCCn1ccnc1] | 843.4 |
| 561. | 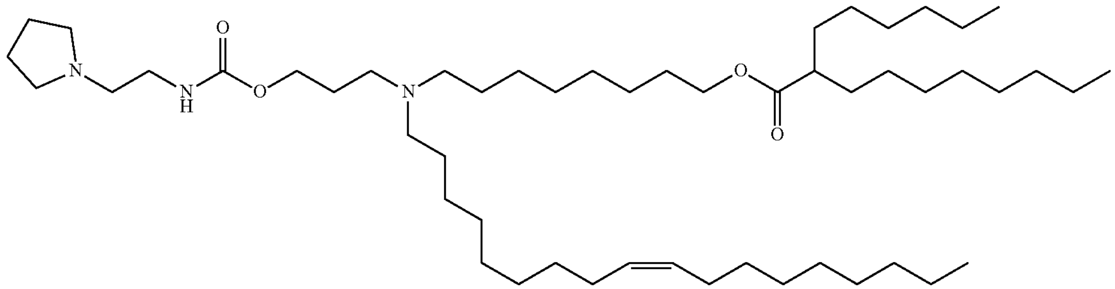 [SMILES: CCCCCCCC/C=C\CCCCCCCCN(CCCCCCCCOC(=O)C(CCCCCC)CCCCCCCC)CCCOC(=O)NCCN1CCCC1] | 832.4 |

TABLE 1-continued
| # | Structure | Mw |
| --- | --- | --- |
| 562. | 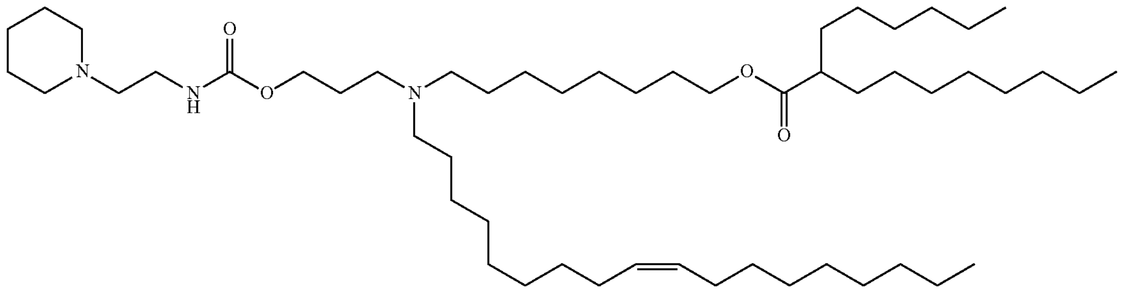 [SMILES: CCCCCCCC/C=C\CCCCCCCCN(CCCCCCCCOC(=O)C(CCCCCC)CCCCCCCC)CCCOC(=O)NCCN1CCCCC1] | 846.4 |
| 563. | 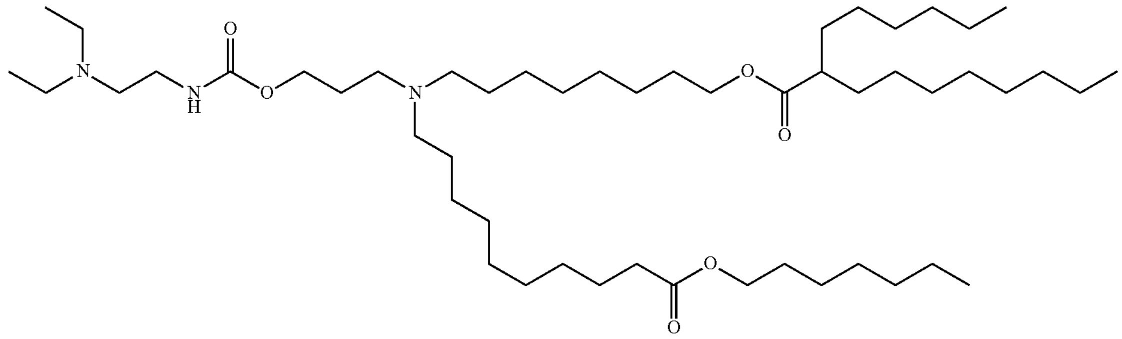 [SMILES: CCCCCCCCC(CCCCCC)C(=O)OCCCCCCCCN(CCCCCCCCCC(=O)OCCCCCCC)CCCOC(=O)NCCN(CC)CC] | 824.3 |
| 564. | 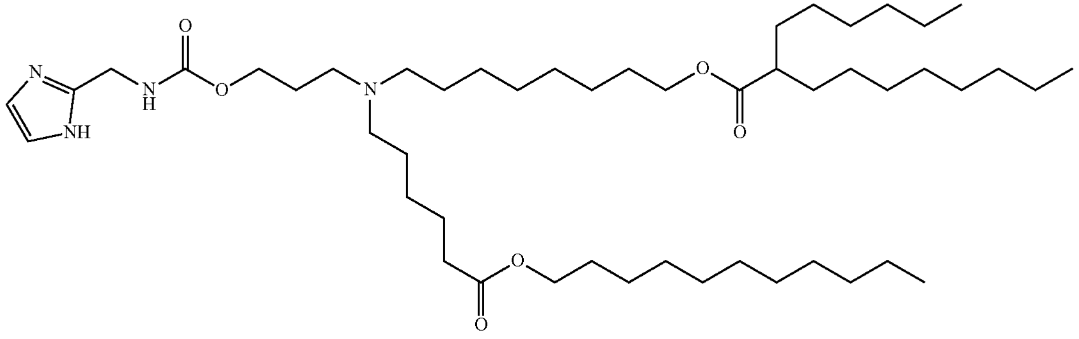 [SMILES: CCCCCCCCCCCOC(=O)CCCCCN(CCCCCCCCOC(=O)C(CCCCCC)CCCCCCCC)CCCOC(=O)NCc1ncc[nH]1] | 833.3 |

TABLE 1-continued
| # | Structure | Mw |
|---|---|---|
| 565. | 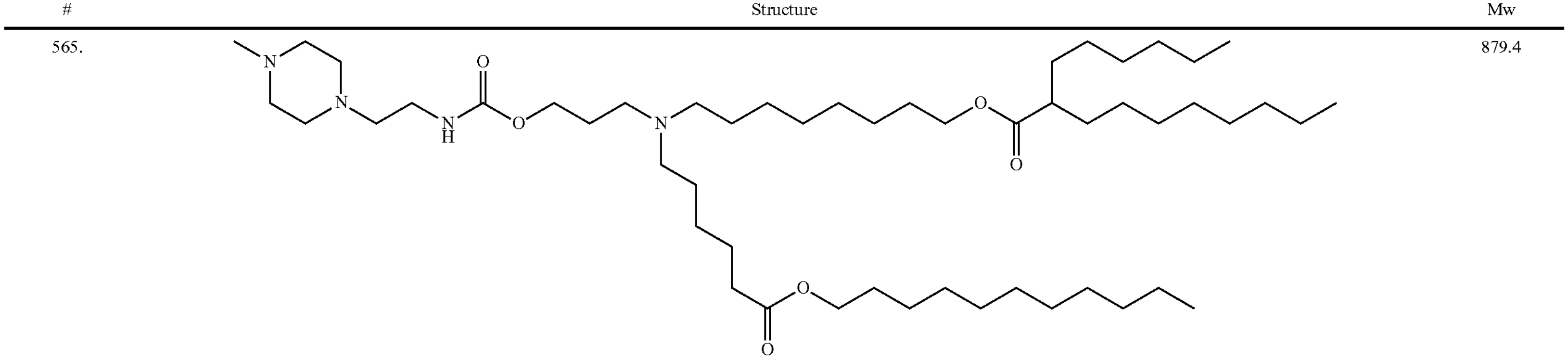 | 879.4 |
| 566. | 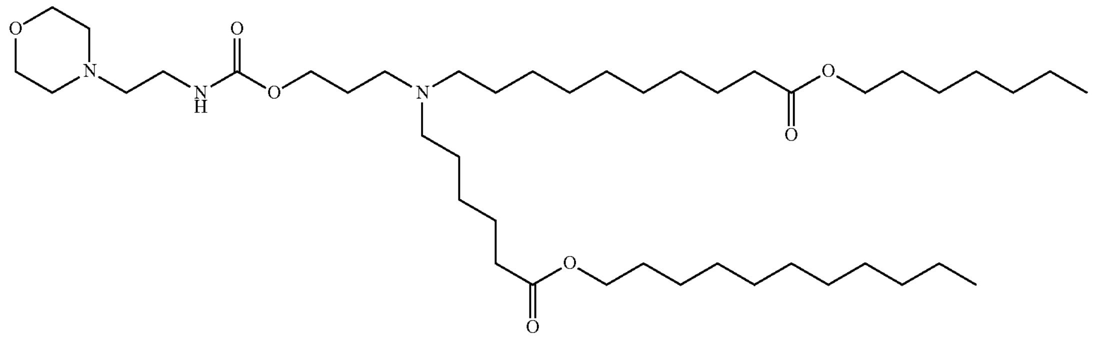 [SMILES: CCCCCCCCCCCOC(=O)CCCCCN(CCCCCCCCCC(=O)OCCCCCCC)CCCOC(=O)NCCN1CCOCC1] | 866.3 |
| 567. | 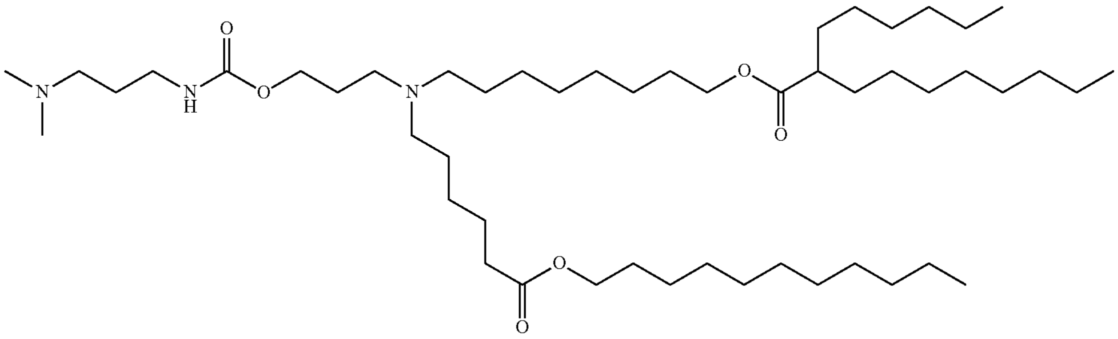 [SMILES: CCCCCCCCCCCOC(=O)CCCCCN(CCCCCCCCOC(=O)C(CCCCCC)CCCCCCCC)CCCOC(=O)NCCCN(C)C] | 838.3 |

TABLE 1-continued
| # | Structure | Mw |
|---|---|---|
| 568. | 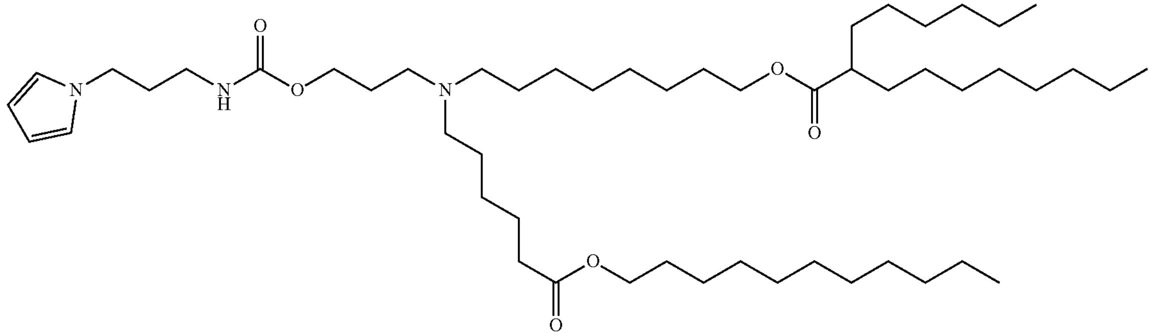 [SMILES: CCCCCCCCCCCOC(=O)CCCCCN(CCCCCCCCOC(=O)C(CCCCCC)CCCCCCCC)CCCOC(=O)NCCCn1cccc1] | 861.3 |
| 569. | 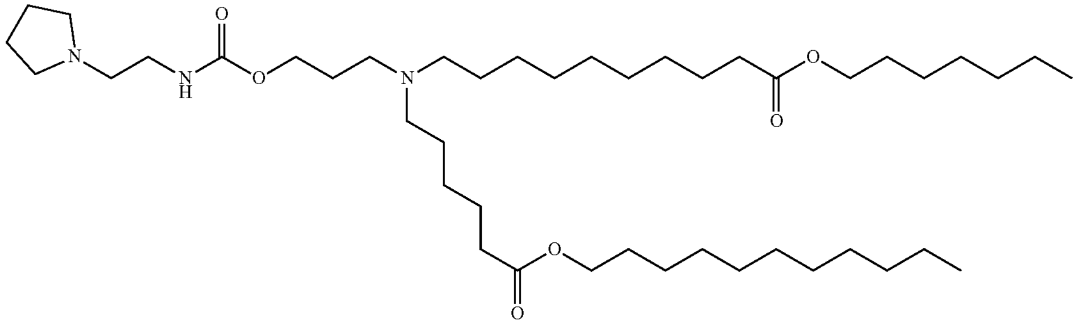 [SMILES: CCCCCCCCCCCOC(=O)CCCCCN(CCCCCCCCCC(=O)OCCCCCCC)CCCOC(=O)NCCN1CCCC1] | 850.4 |
| 570. | 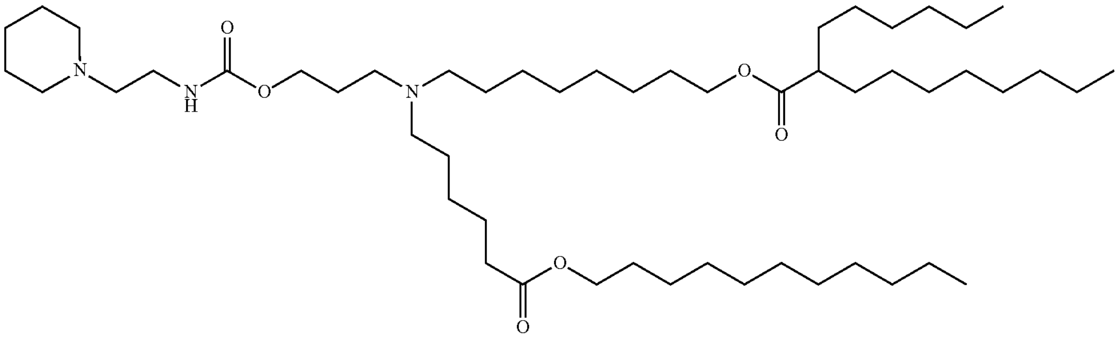 [SMILES: CCCCCCCCCCCOC(=O)CCCCCN(CCCCCCCCOC(=O)C(CCCCCC)CCCCCCCC)CCCOC(=O)NCCN1CCCCC1] | 864.4 |

TABLE 1-continued
| # | Structure | Mw |
| --- | --- | --- |
| 571. | 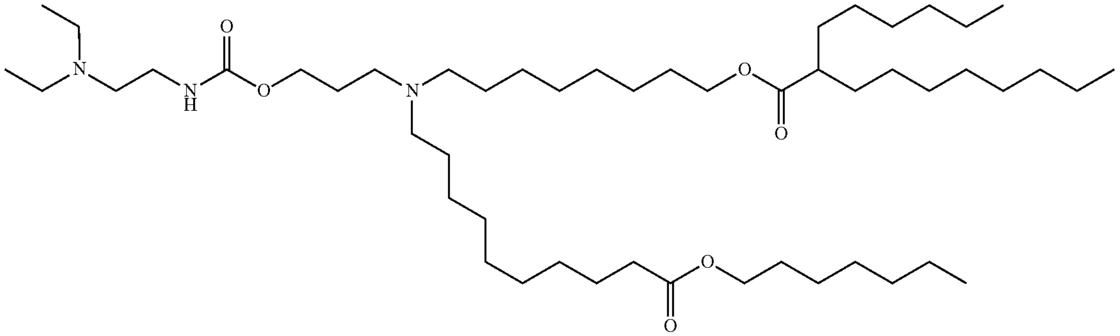 [SMILES: CCCCCCCCC(CCCCCC)C(=O)OCCCCCCCCN(CCCCCCCCCC(=O)OCCCCCCC)CCCOC(=O)NCCN(CC)CC] | 852.4 |
| 572. | 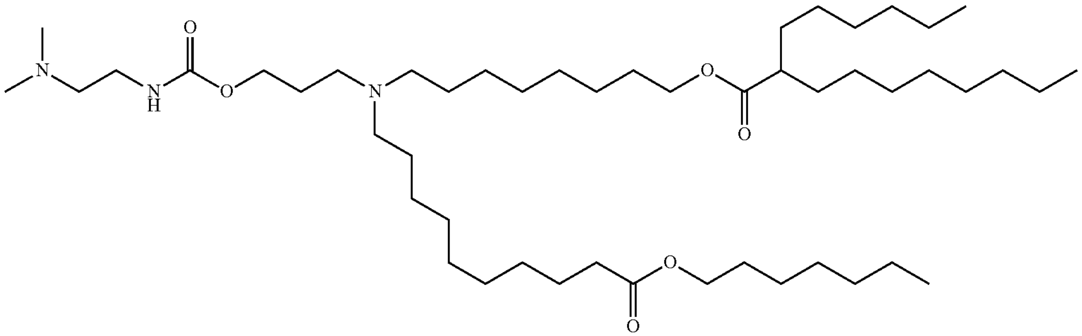 [SMILES: CCCCCCCCC(CCCCCC)C(=O)OCCCCCCCCN(CCCCCCCCCC(=O)OCCCCCCC)CCCOC(=O)NCCN(C)C] | 824.3 |
| 573. | 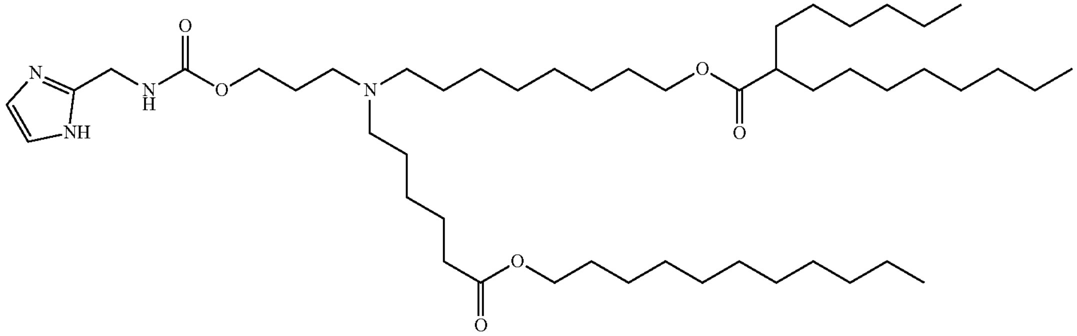 [SMILES: CCCCCCCCCCCOC(=O)CCCCCN(CCCCCCCCOC(=O)C(CCCCCC)CCCCCCCC)CCCOC(=O)NCc1ncc[nH]1] | 833.3 |

TABLE 1-continued
| # | Structure | Mw |
|---|---|---|
| 574. | 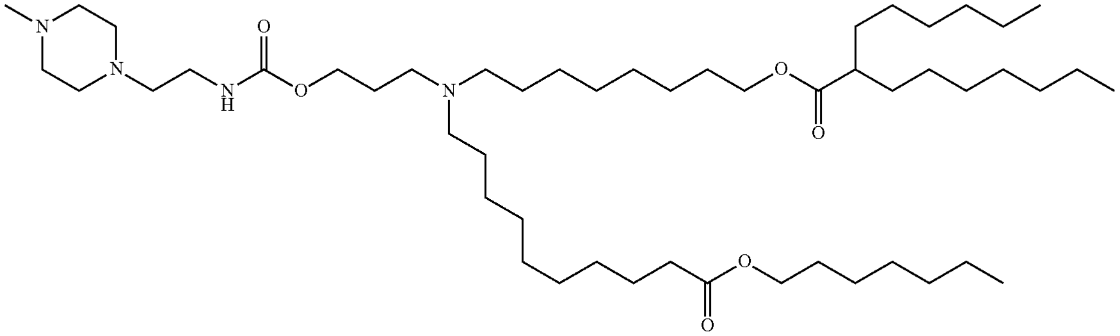 [SMILES: CCCCCCCOC(=O)CCCCCCCCCN(CCCCCCCCOC(=O)C(CCCCCC)CCCCCCC)CCCOC(=O)NCCN1CCN(C)CC1] | 879.4 |
| 575. | 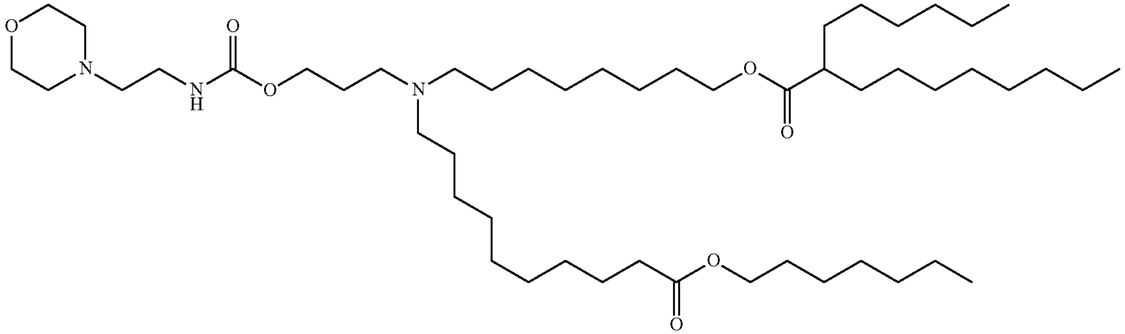 [SMILES: CCCCCCCCC(CCCCCC)C(=O)OCCCCCCCCN(CCCCCCCCCC(=O)OCCCCCCC)CCCOC(=O)NCCN1CCOCC1] | 866.3 |
| 576. | 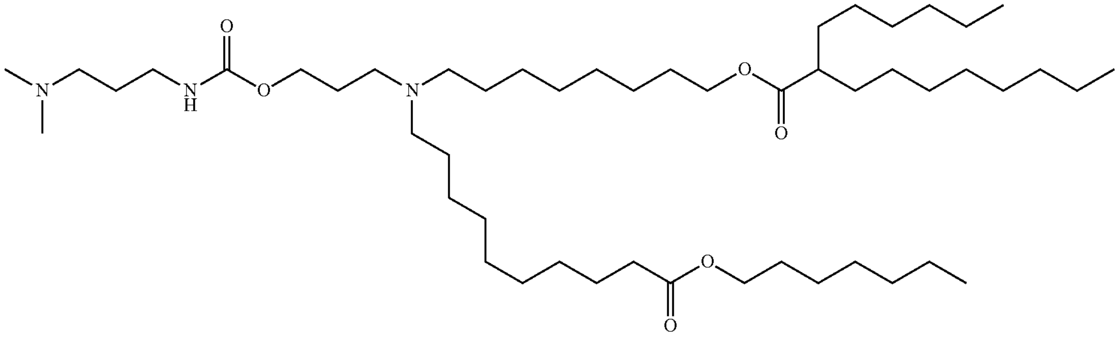 [SMILES: CCCCCCCCC(CCCCCC)C(=O)OCCCCCCCCN(CCCCCCCCCC(=O)OCCCCCCC)CCCOC(=O)NCCCN(C)C] | 838.3 |

TABLE 1-continued
| # | Structure | Mw |
|---|---|---|
| 577. | 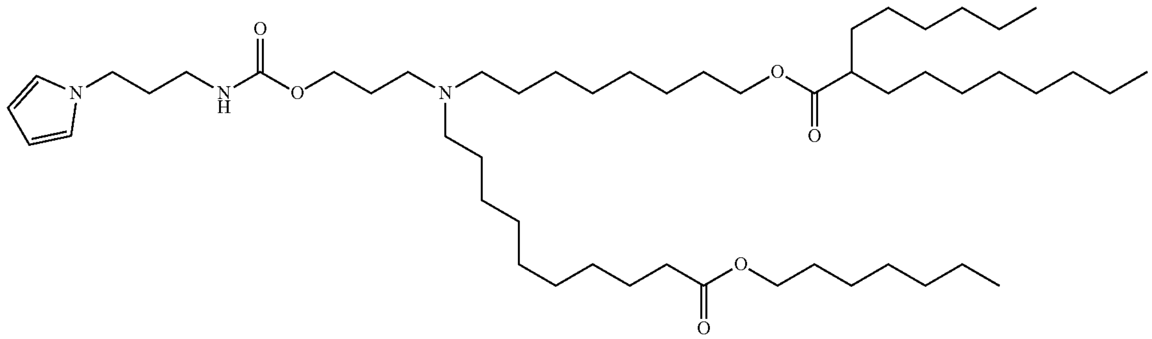 [SMILES: CCCCCCCCC(CCCCCC)C(=O)OCCCCCCCCN(CCCCCCCCCC(=O)OCCCCCCC)CCCOC(=O)NCCCn1cccc1] | 861.3 |
| 578. | 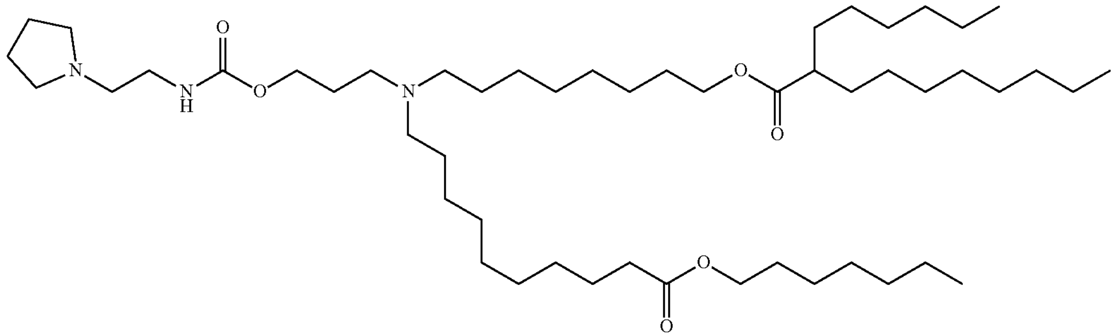 [SMILES: CCCCCCCCC(CCCCCC)C(=O)OCCCCCCCCN(CCCCCCCCCC(=O)OCCCCCCC)CCCOC(=O)NCCN1CCCC1] | 850.3 |
| 579. | 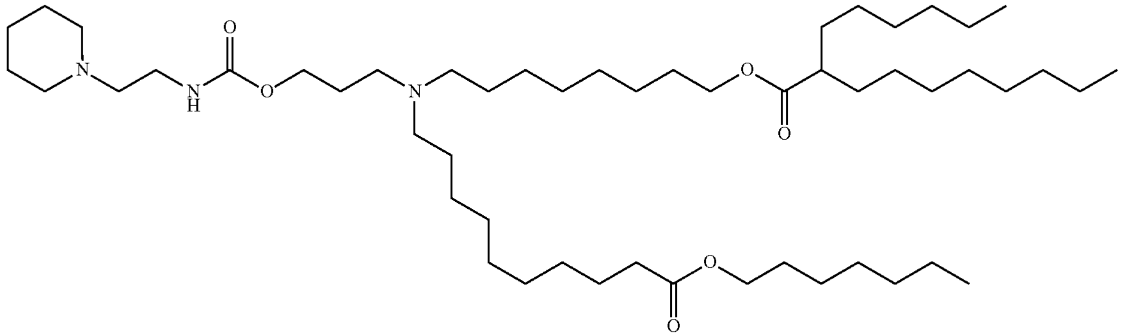 [SMILES: CCCCCCCCC(CCCCCC)C(=O)OCCCCCCCCN(CCCCCCCCCC(=O)OCCCCCCC)CCCOC(=O)NCCN1CCCCC1] | 864.4 |

TABLE 1-continued
| # | Structure | Mw |
|---|---|---|
| 580. | 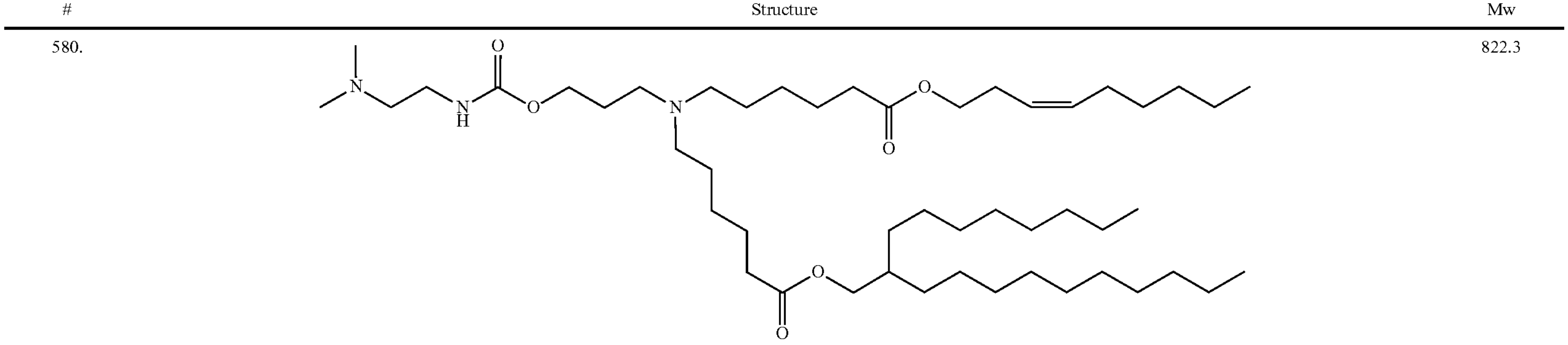 | 822.3 |
| 581. | 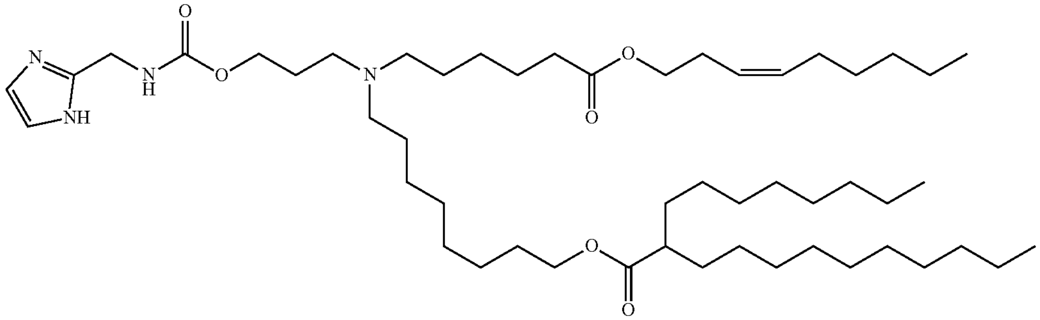 [SMILES: CCCCC/C=C\CCOC(=O)CCCCCN(CCCCCCCCOC(=O)C(CCCCCCCC)CCCCCCCCCC)CCCOC(=O)NCc1ncc[nH]1] | 831.3 |
| 582. | 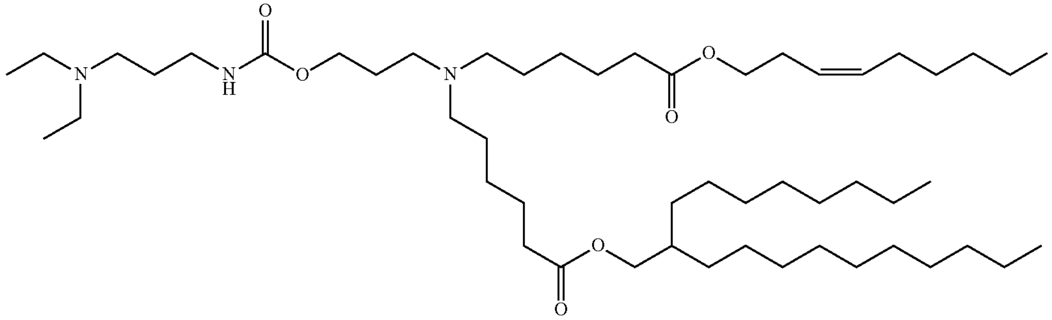 [SMILES: CCCCC/C=C\CCOC(=O)CCCCCN(CCCCCC(=O)OCC(CCCCCCCC)CCCCCCCCCC)CCCOC(=O)NCCCN(CC)CC] | 864.4 |

TABLE 1-continued
| # | Structure | Mw |
|---|---|---|
| 583. | 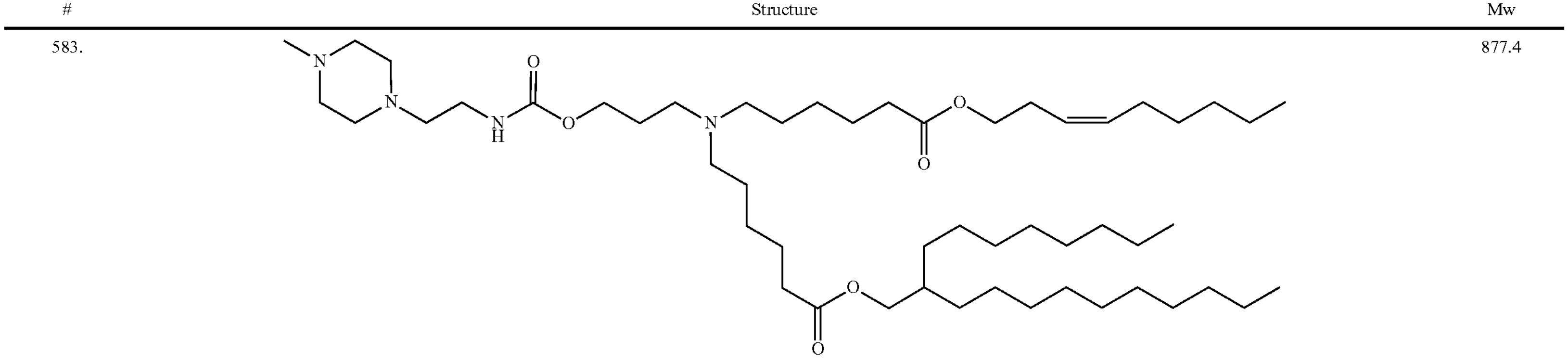 | 877.4 |
| 584. | 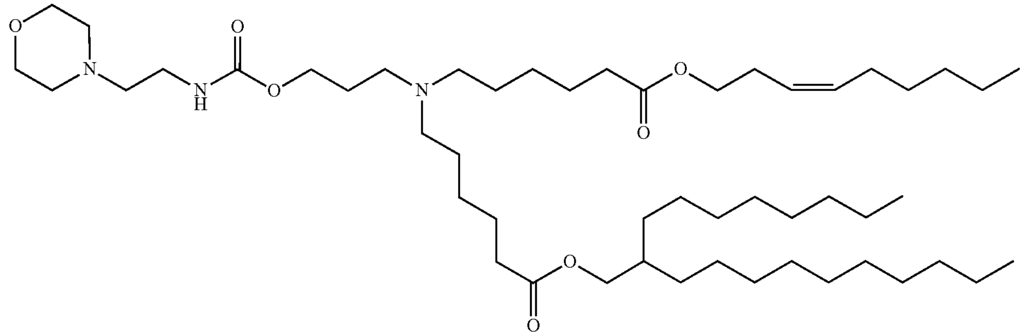 [SMILES: CCCCC/C=C\CCOC(=O)CCCCCN(CCCCCC(=O)OCC(CCCCCCCC)CCCCCCCCCC)CCCOC(=O)NCCN1CCOCC1] | 864.3 |
| 585. | 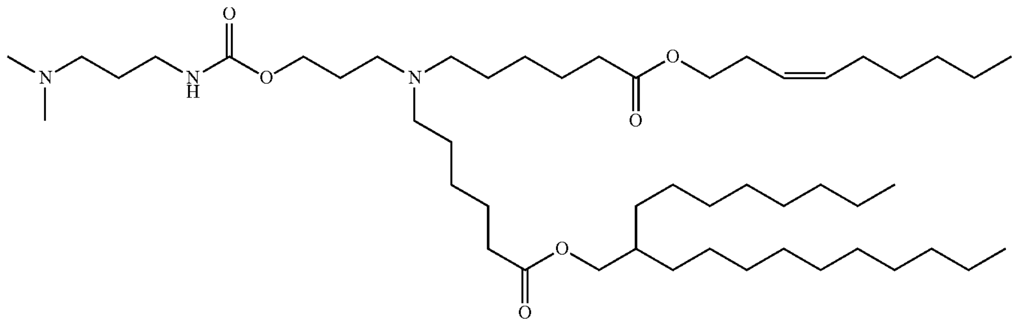 [SMILES: CCCCC/C=C\CCOC(=O)CCCCCN(CCCCCC(=O)OCC(CCCCCCCC)CCCCCCCCCC)CCCOC(=O)NCCCN(C)C] | 836.3 |

TABLE 1-continued
| # | Structure | Mw |
| --- | --- | --- |
| 586. | 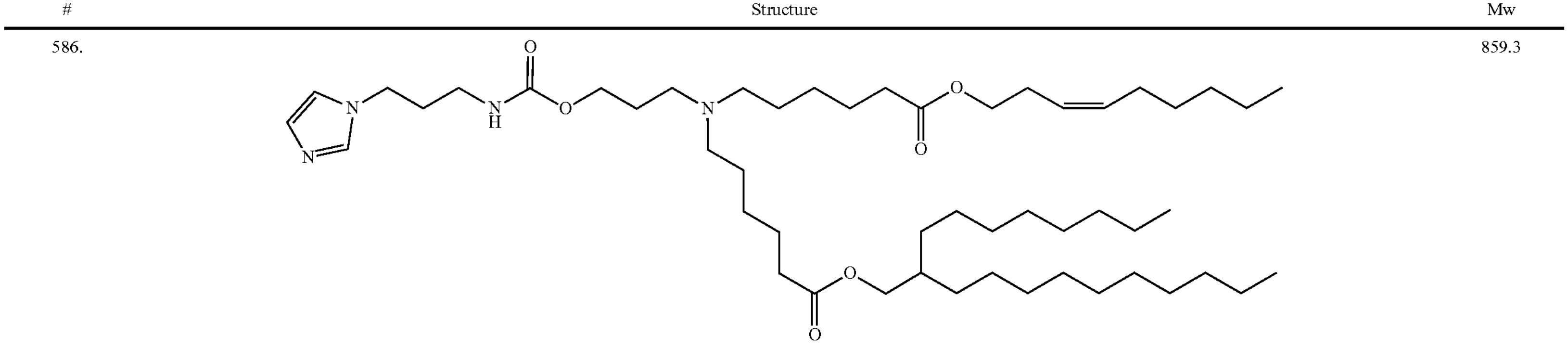 | 859.3 |
| 587. | 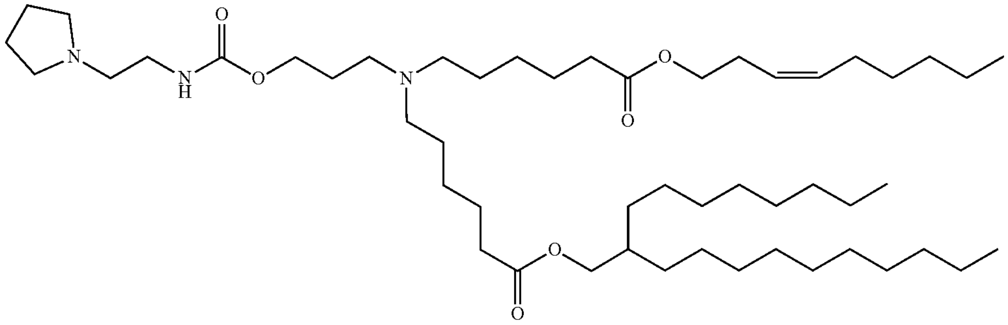 [SMILES: CCCCC/C=C\CCOC(=O)CCCCCN(CCCCCC(=O)OCC(CCCCCCCC)CCCCCCCCCC)CCCOC(=O)NCCN1CCCC1] | 848.3 |
| 588. | 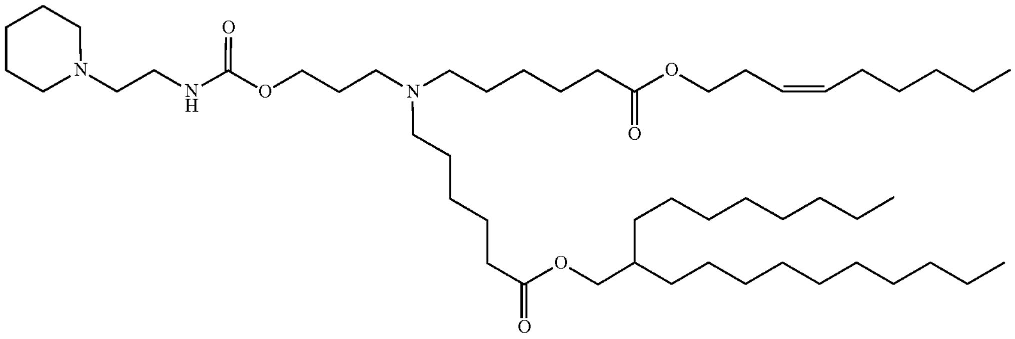 [SMILES: CCCCC/C=C\CCOC(=O)CCCCCN(CCCCCC(=O)OCC(CCCCCCCC)CCCCCCCCCC)CCCOC(=O)NCCN1CCCCC1] | 862.4 |

TABLE 1-continued
| # | Structure | Mw |
| --- | --- | --- |
| 589. | 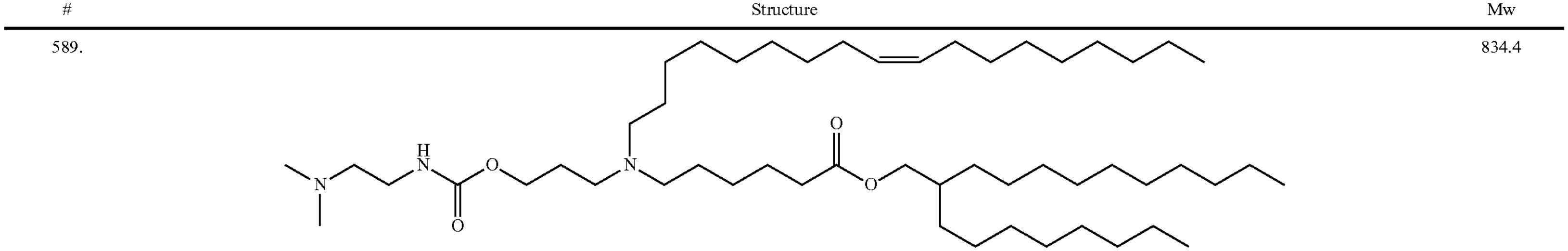 | 834.4 |
| 590. | 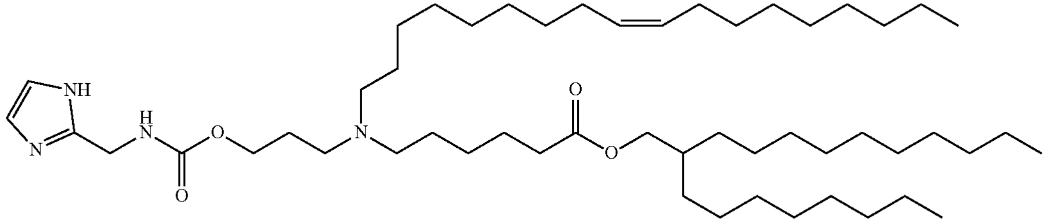 [SMILES: CCCCCCCC/C=C\CCCCCCCCN(CCCCCC(=O)OCC(CCCCCCCC)CCCCCCCCCC)CCCOC(=O)NCc1ncc[nH]1] | 843.4 |
| 591. | 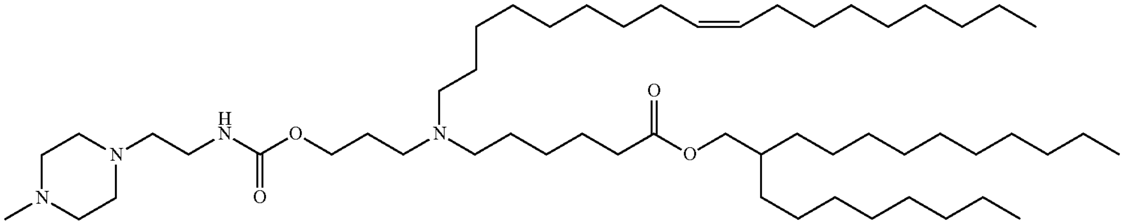 [SMILES: CCCCCCCC/C=C\CCCCCCCCN(CCCCCC(=O)OCC(CCCCCCCC)CCCCCCCCCC)CCCOC(=O)NCCN1CCN(C)CC1] | 889.5 |
| 592. | 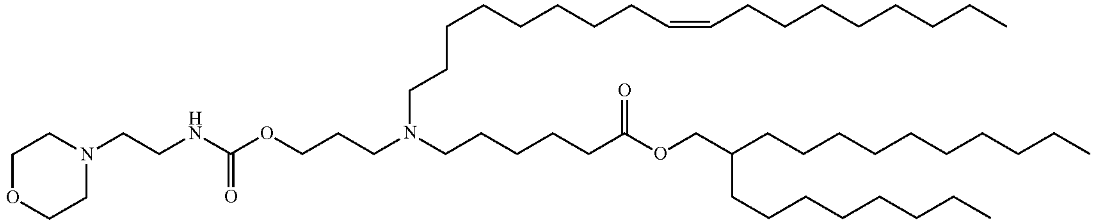 [SMILES: CCCCCCCC/C=C\CCCCCCCCN(CCCCCC(=O)OCC(CCCCCCCC)CCCCCCCCCC)CCCOC(=O)NCCN1CCOCC1] | 875.4 |

TABLE 1-continued
| # | Structure | Mw |
|---|---|---|
| 593. | 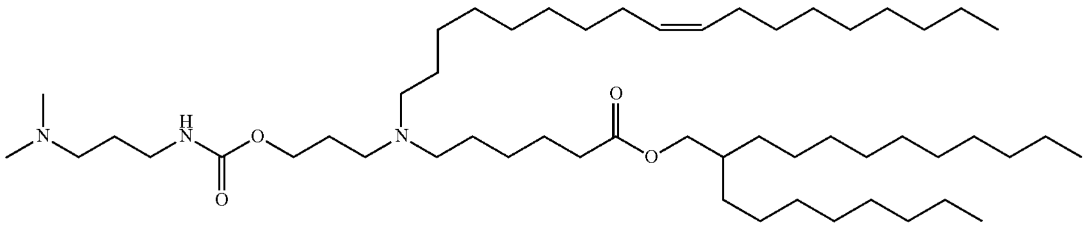 [SMILES: CCCCCCCC/C=C\CCCCCCCCN(CCCCCC(=O)OCC(CCCCCCCC)CCCCCCCCCC)CCCOC(=O)NCCCN(C)C] | 848.4 |
| 594. | 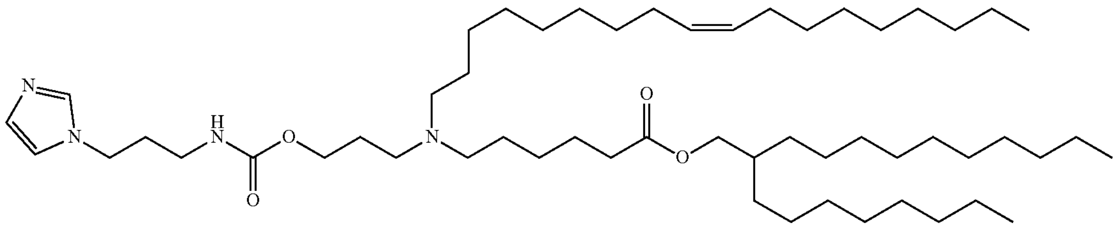 [SMILES: CCCCCCCC/C=C\CCCCCCCCN(CCCCCC(=O)OCC(CCCCCCCC)CCCCCCCCCC)CCCOC(=O)NCCCn1ccnc1] | 871.4 |
| 595. | 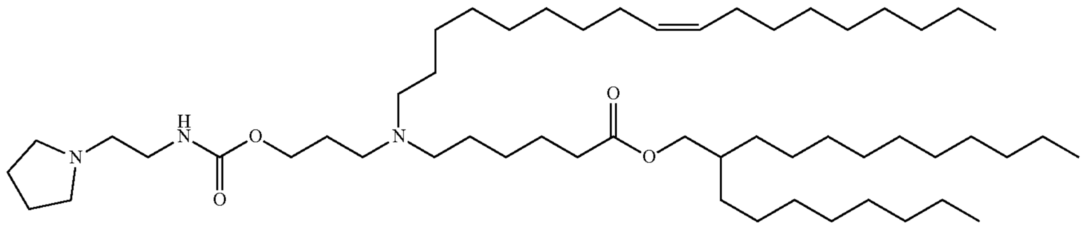 [SMILES: CCCCCCCC/C=C\CCCCCCCCN(CCCCCC(=O)OCC(CCCCCCCC)CCCCCCCCCC)CCCOC(=O)NCCN1CCCC1] | 860.4 |
| 596. | 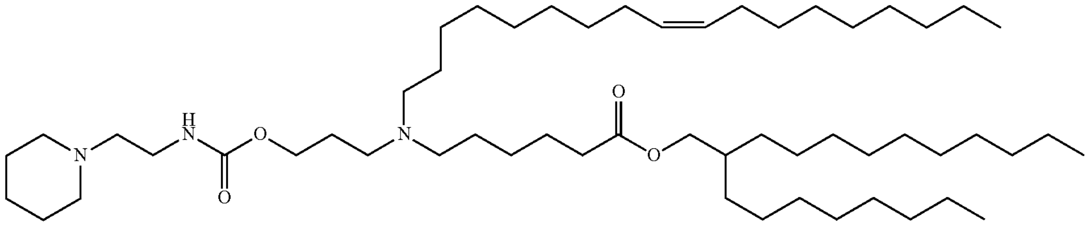 [SMILES: CCCCCCCC/C=C\CCCCCCCCN(CCCCCC(=O)OCC(CCCCCCCC)CCCCCCCCCC)CCCOC(=O)NCCN1CCCCC1] | 874.5 |

TABLE 1-continued
| # | Structure | Mw |
|---|---|---|
| 597. | 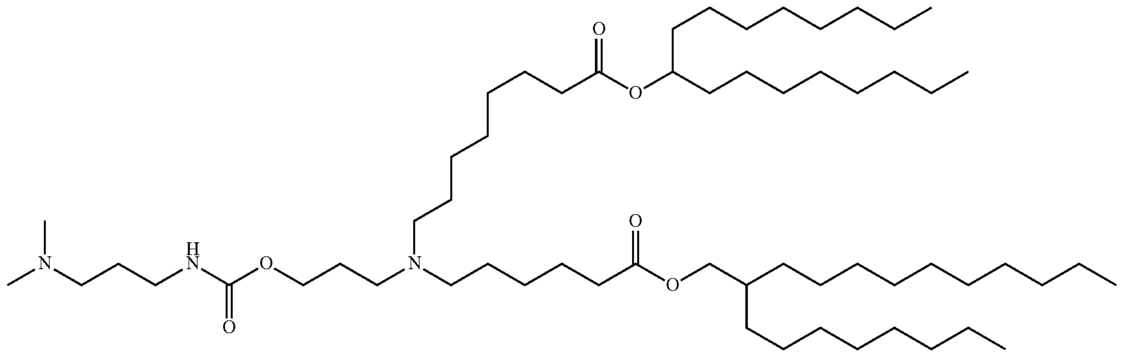 [SMILES: CCCCCCCCCCC(CCCCCCCC)COC(=O)CCCCCN(CCCCCCCC(=O)OC(CCCCCCCC)CCCCCCCC)CCCOC(=O)NCCCN(C)C] | 978.6 |
| 598. | 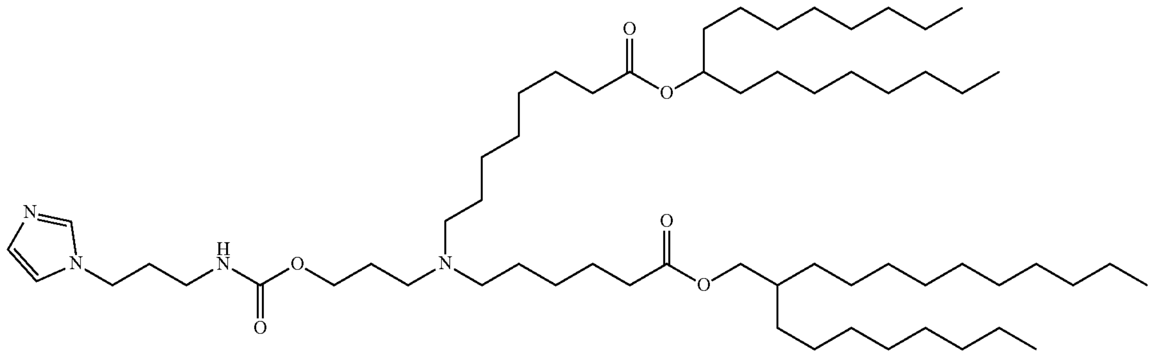 [SMILES: CCCCCCCCCCC(CCCCCCCC)COC(=O)CCCCCN(CCCCCCCC(=O)OC(CCCCCCCC)CCCCCCCC)CCCOC(=O)NCCCn1ccnc1] | 1001.6 |
| 599. | 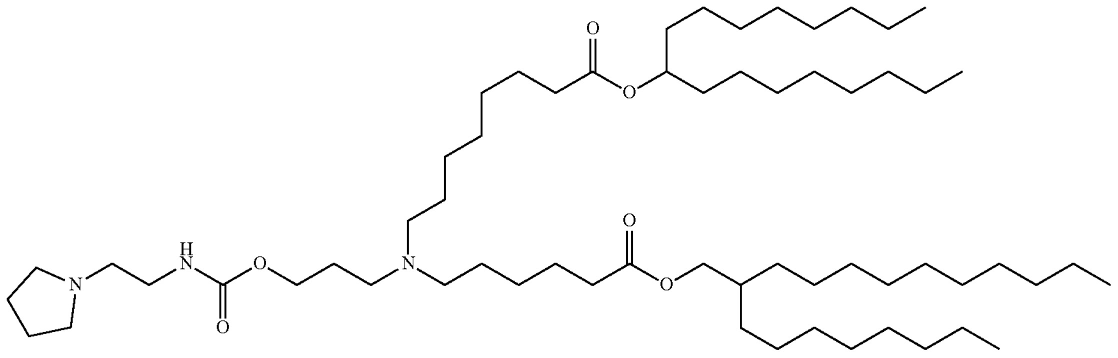 [SMILES: CCCCCCCCCCC(CCCCCCCC)COC(=O)CCCCCN(CCCCCCCC(=O)OC(CCCCCCCC)CCCCCCCC)CCCOC(=O)NCCN1CCCC1] | 990.6 |

TABLE 1-continued
| # | Structure | Mw |
| --- | --- | --- |
| 600. | 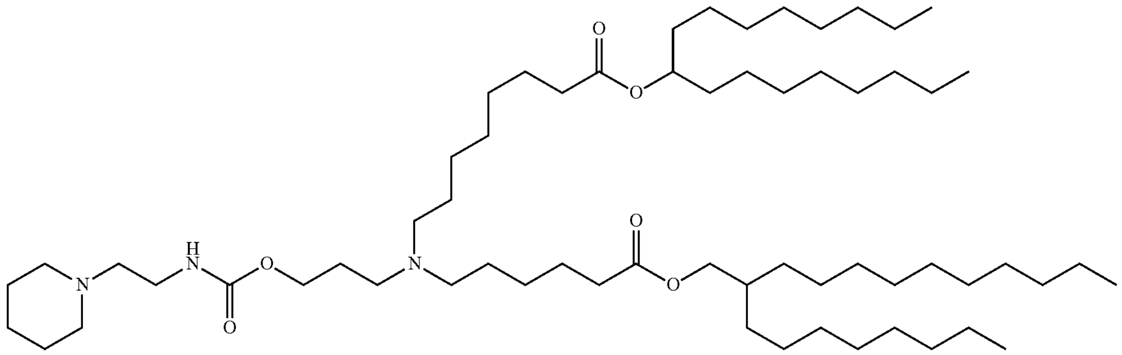 [SMILES: CCCCCCCCCCC(CCCCCCCC)COC(=O)CCCCCN(CCCCCCCC(=O)OC(CCCCCCCC)CCCCCCCC)CCCOC(=O)NCCN1CCCCC1] | 1004.6 |
| 601. | 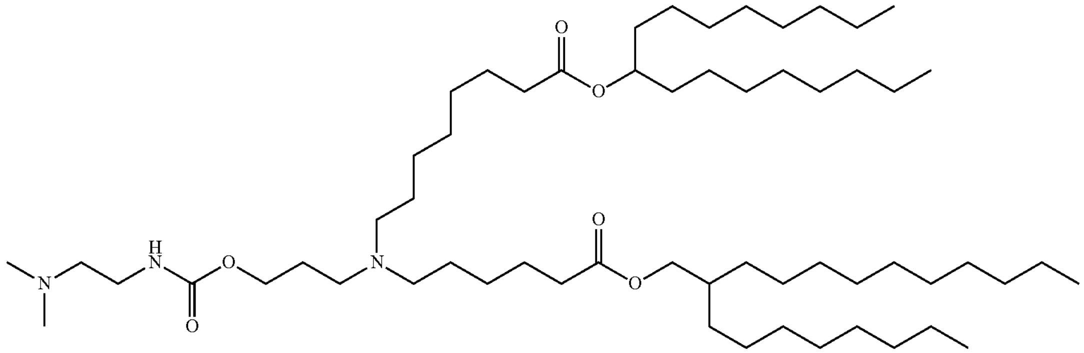 [SMILES: CCCCCCCCCCC(CCCCCCCC)COC(=O)CCCCCN(CCCCCCCC(=O)OC(CCCCCCCC)CCCCCCCC)CCCOC(=O)NCCN(C)C] | 964.6 |

TABLE 1-continued
| # | Structure | Mw |
|---|---|---|
| 602. | 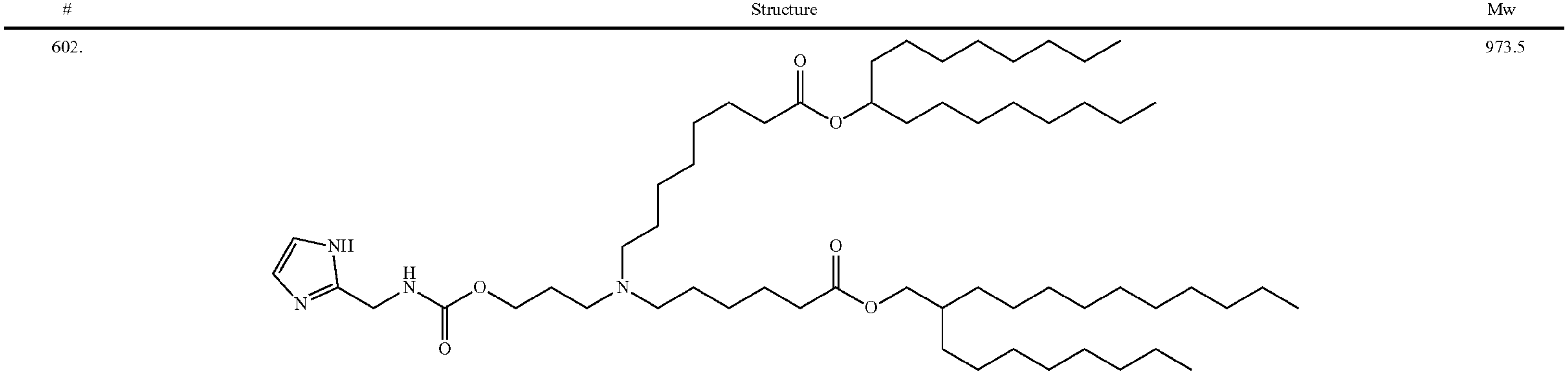 | 973.5 |
| 603. | 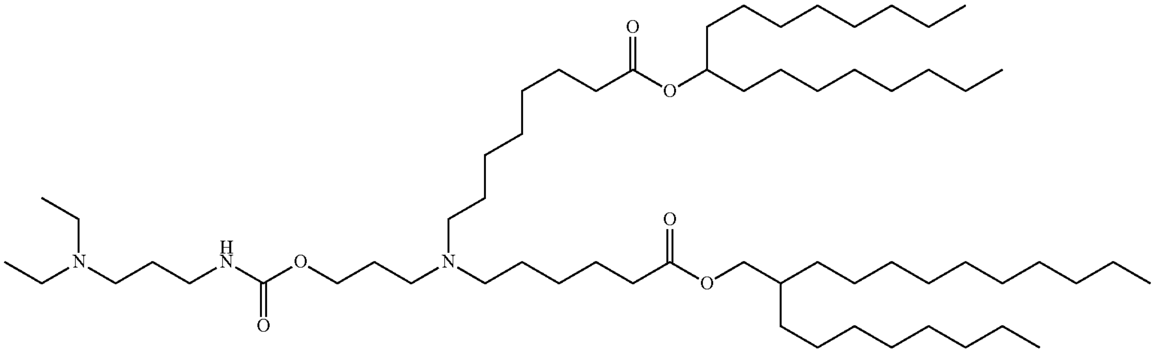 [SMILES: CCCCCCCCCCC(CCCCCCCC)COC(=O)CCCCCN(CCCCCCCC(=O)OC(CCCCCCCC)CCCCCCCC)CCCOC(=O)NCCCN(CC)CC] | 1006.7 |
| 604. | 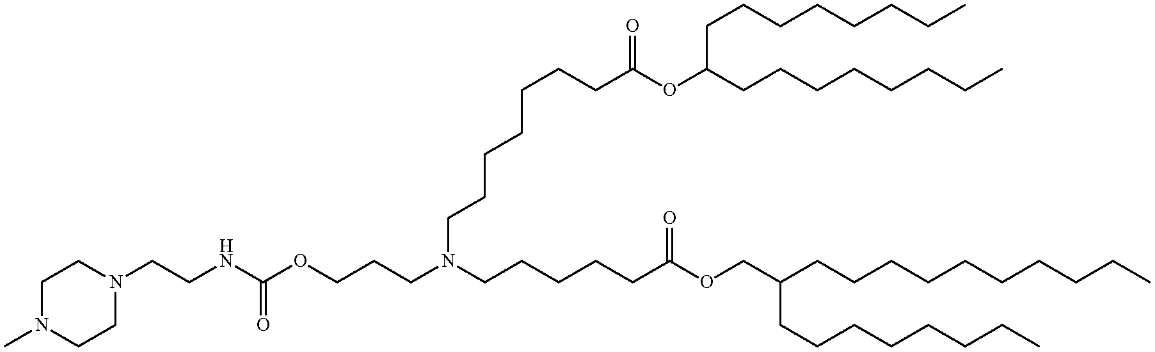 [SMILES: CCCCCCCCCCC(CCCCCCCC)COC(=O)CCCCCN(CCCCCCCC(=O)OC(CCCCCCCC)CCCCCCCC)CCCOC(=O)NCCN1CCN(C)CC1] | 1019.7 |

TABLE 1-continued
| # | Structure | Mw |
| --- | --- | --- |
| 605. | 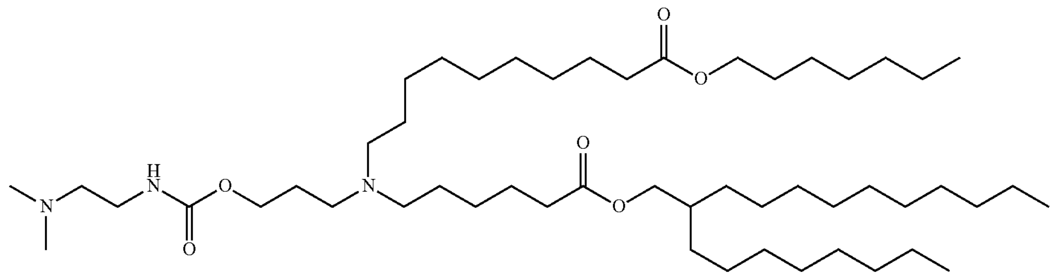 [SMILES: CCCCCCCCCCC(CCCCCCCC)COC(=O)CCCCCN(CCCCCCCCCC(=O)OCCCCCCC)CCCOC(=O)NCCN(C)C] | 852.4 |
| 606. | 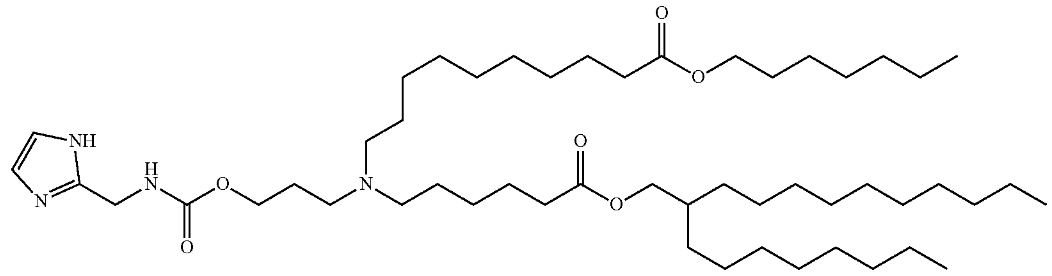 [SMILES: CCCCCCCCCCC(CCCCCCCC)COC(=O)CCCCCN(CCCCCCCCCC(=O)OCCCCCCC)CCCOC(=O)NCc1ncc[nH]1] | 861.3 |
| 607. | 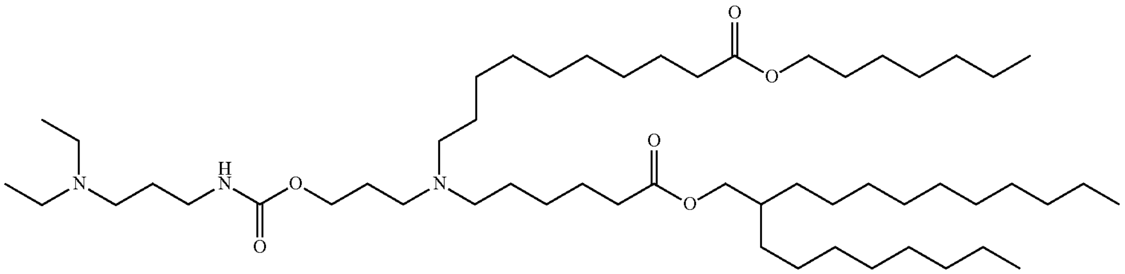 [SMILES: CCCCCCCCCCC(CCCCCCCC)COC(=O)CCCCCN(CCCCCCCCCC(=O)OCCCCCCC)CCCOC(=O)NCCCN(CC)CC] | 894.4 |

TABLE 1-continued
| # | Structure | Mw |
|---|---|---|
| 608. | 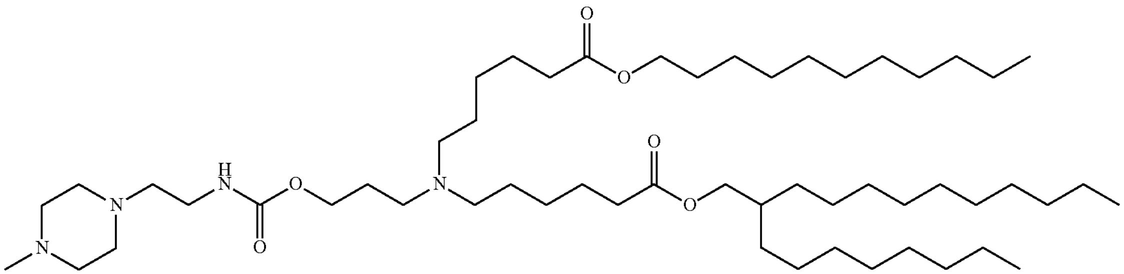 [SMILES: CCCCCCCCCCCOC(=O)CCCCCN(CCCCCC(=O)OCC(CCCCCCCC)CCCCCCCCCC)CCCOC(=O)NCCN1CCN(C)CC1] | 907.4 |
| 609. | 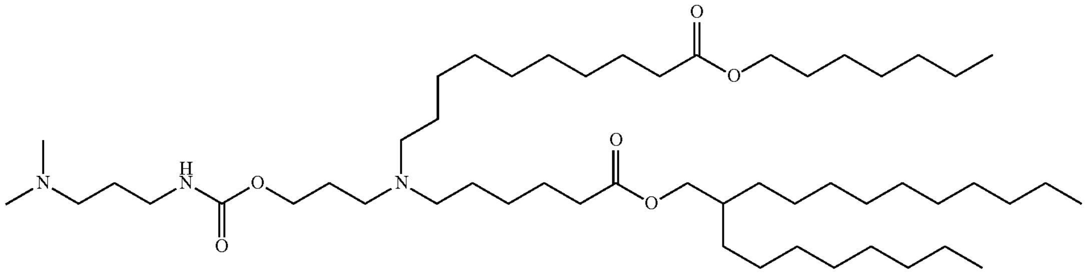 [SMILES: CCCCCCCCCCC(CCCCCCCC)COC(=O)CCCCCN(CCCCCCCCCC(=O)OCCCCCCC)CCCOC(=O)NCCCN(C)C] | 866.4 |
| 610. | 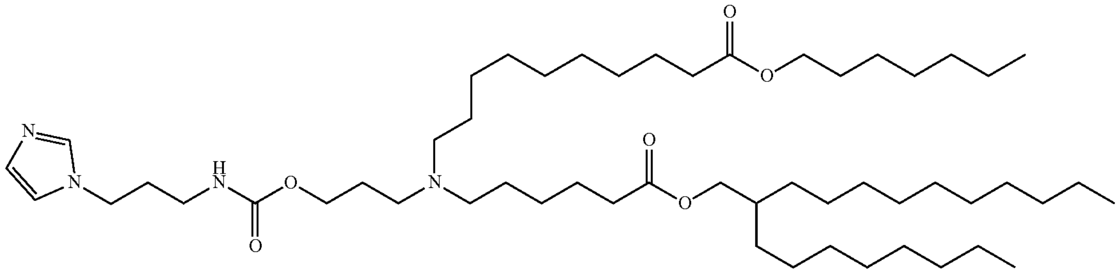 [SMILES: CCCCCCCCCCC(CCCCCCCC)COC(=O)CCCCCN(CCCCCCCCCC(=O)OCCCCCCC)CCCOC(=O)NCCCn1ccnc1] | 889.4 |

TABLE 1-continued
| # | Structure | Mw |
|---|---|---|
| 611. | 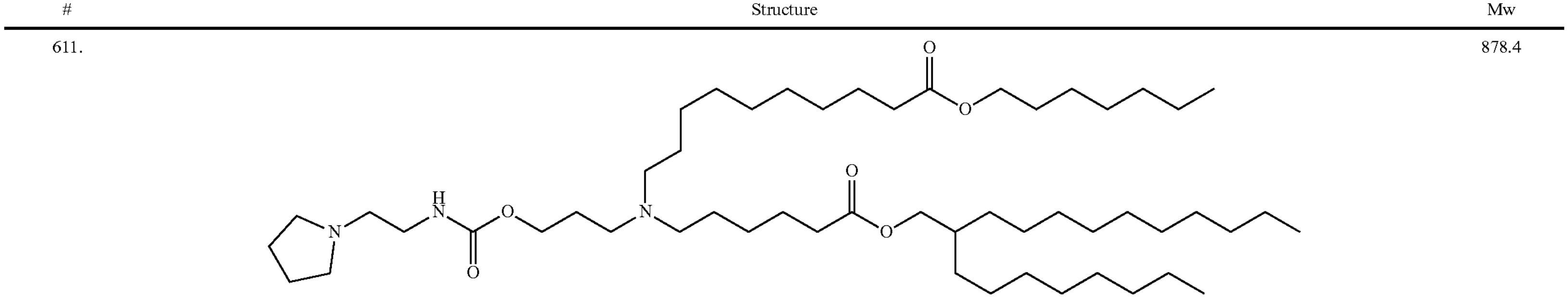 | 878.4 |
| 612. | 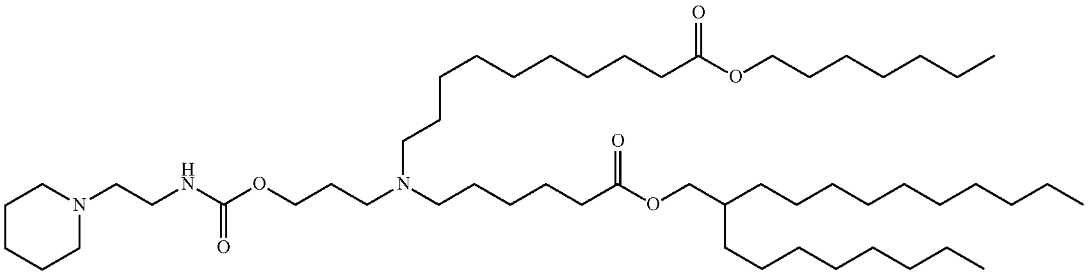 [SMILES: CCCCCCCCCCC(CCCCCCCC)COC(=O)CCCCCN(CCCCCCCCCC(=O)OCCCCCCC)CCCOC(=O)NCCN1CCCCC1] | 892.4 |
| 613. | 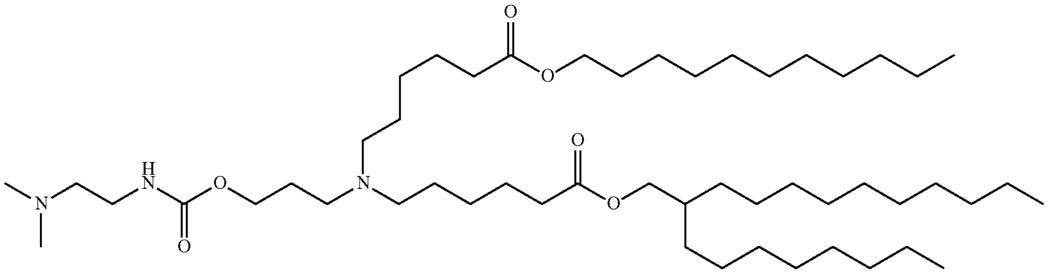 [SMILES: CCCCCCCCCCCOC(=O)CCCCCN(CCCCCC(=O)OCC(CCCCCCCC)CCCCCCCCCC)CCCOC(=O)NCCN(C)C] | 852.4 |

TABLE 1-continued
| # | Structure | Mw |
|---|---|---|
| 614. | 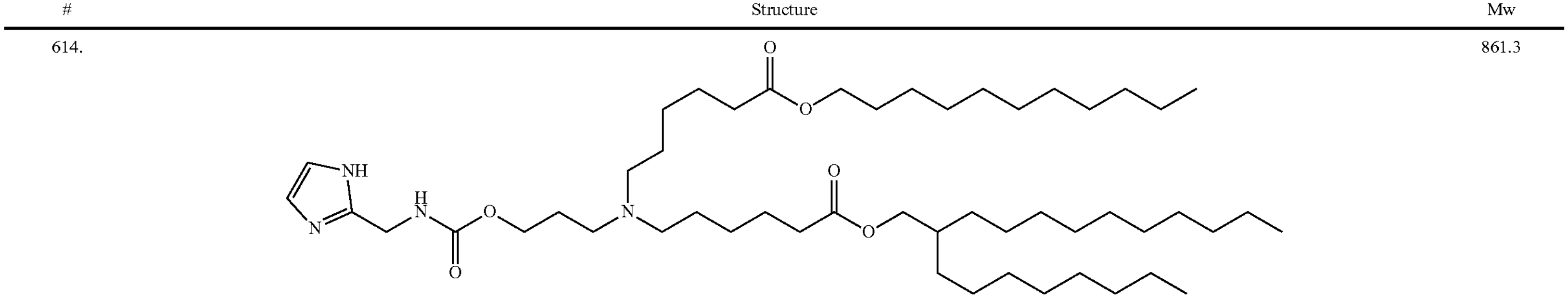 | 861.3 |
| 615. | 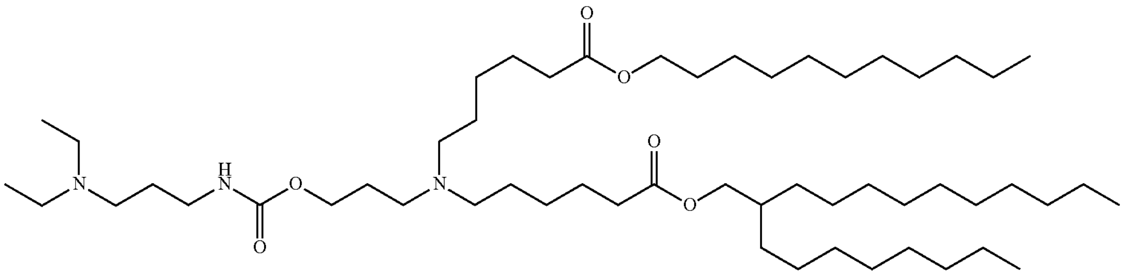 [SMILES: CCCCCCCCCCCOC(=O)CCCCCN(CCCCCC(=O)OCC(CCCCCCCC)CCCCCCCCCC)CCCOC(=O)NCCCN(CC)CC] | 894.4 |
| 616. | 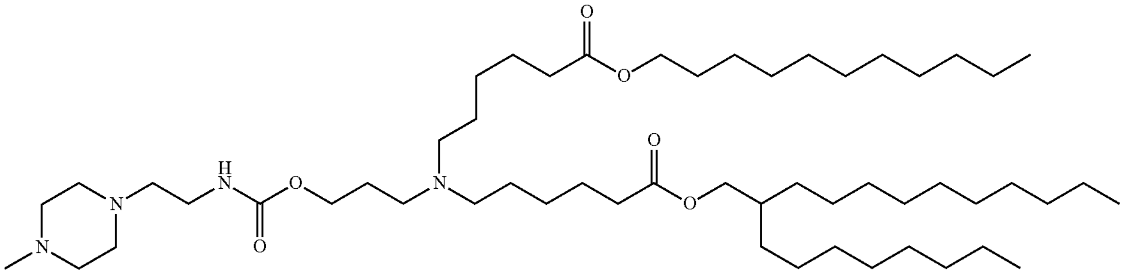 [SMILES: CCCCCCCCCCCOC(=O)CCCCCN(CCCCCC(=O)OCC(CCCCCCCC)CCCCCCCCCC)CCCOC(=O)NCCN1CCN(C)CC1] | 907.4 |

TABLE 1-continued
| # | Structure | Mw |
|---|---|---|
| 617. | 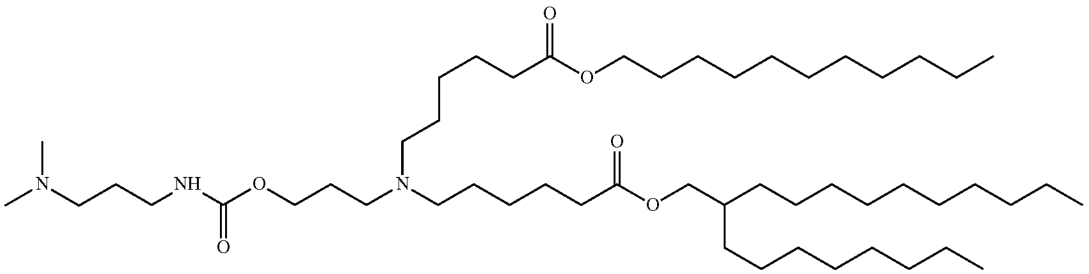 [SMILES: CCCCCCCCCCCOC(=O)CCCCCN(CCCCCC(=O)OCC(CCCCCCCC)CCCCCCCCCC)CCCOC(=O)NCCCN(C)C] | 866.4 |
| 618. | 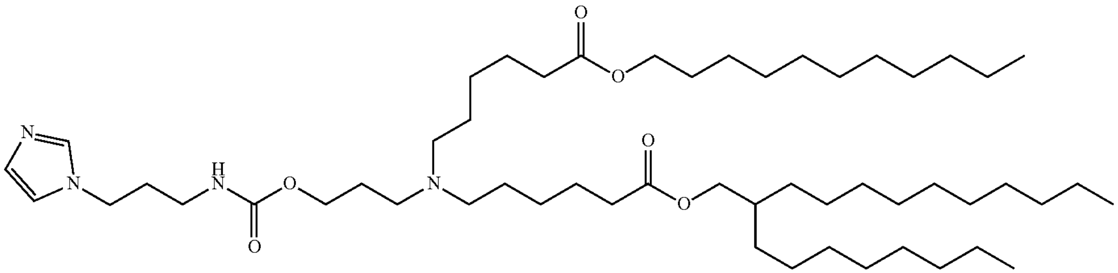 [SMILES: CCCCCCCCCCCOC(=O)CCCCCN(CCCCCC(=O)OCC(CCCCCCCC)CCCCCCCCCC)CCCOC(=O)NCCCn1ccnc1] | 889.4 |
| 619. | 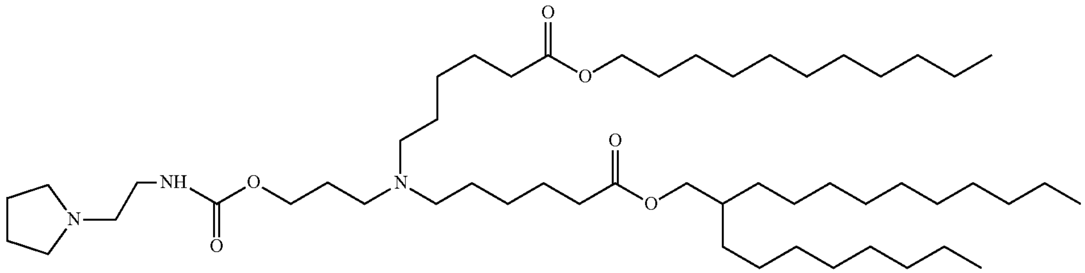 [SMILES: CCCCCCCCCCCOC(=O)CCCCCN(CCCCCC(=O)OCC(CCCCCCCC)CCCCCCCCCC)CCCOC(=O)NCCN1CCCC1] | 878.4 |

TABLE 1-continued
| # | Structure | Mw |
| --- | --- | --- |
| 620. | 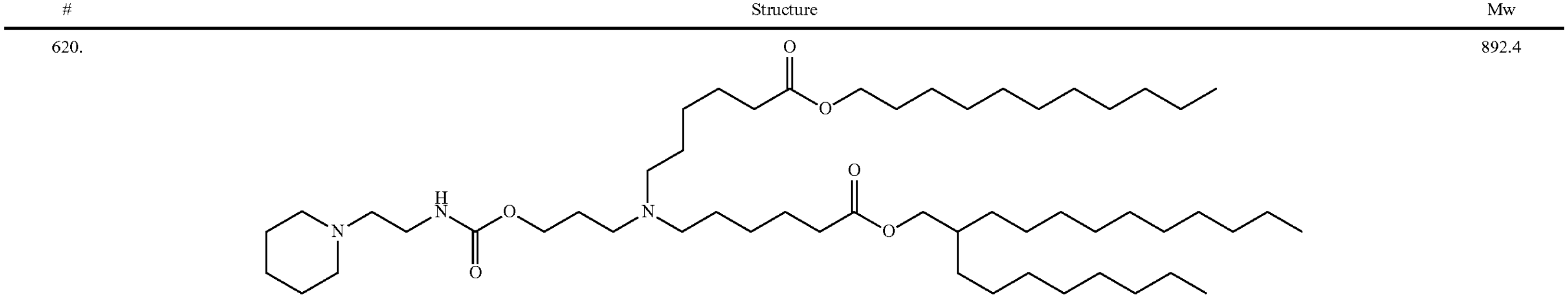 | 892.4 |
| 621. | 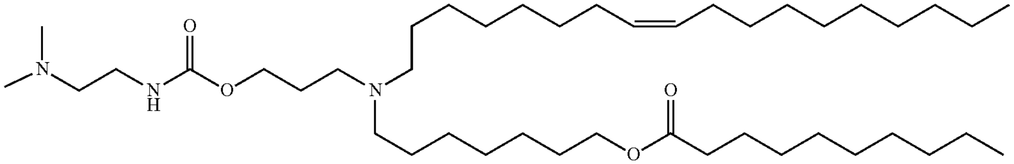 [SMILES: CCCCCCCCC/C=C\CCCCCCCN(CCCCCCCOC(=O)CCCCCCCCC)CCCOC(=O)NCCN(C)C] | 708.1 |
| 622. | 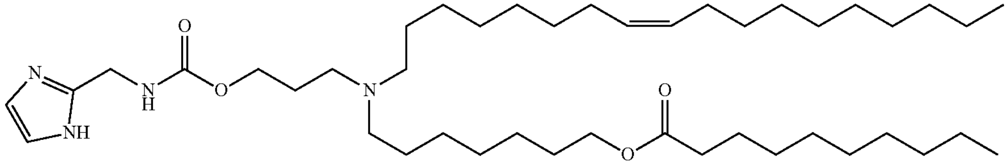 [SMILES: CCCCCCCCC/C=C\CCCCCCCN(CCCCCCCOC(=O)CCCCCCCCC)CCCOC(=O)NCc1ncc[nH]1] | 717.1 |
| 623. | 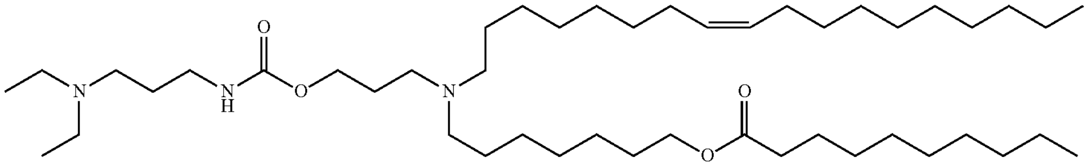 [SMILES: CCCCCCCCC/C=C\CCCCCCCN(CCCCCCCOC(=O)CCCCCCCCC)CCCOC(=O)NCCCN(CC)CC] | 750.2 |
| 624. | 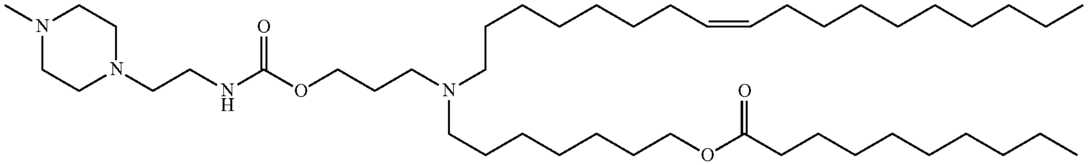 [SMILES: CCCCCCCCC/C=C\CCCCCCCN(CCCCCCCOC(=O)CCCCCCCCC)CCCOC(=O)NCCN1CCN(C)CC1] | 763.2 |

TABLE 1-continued
| # | Structure | Mw |
|---|---|---|
| 625. | 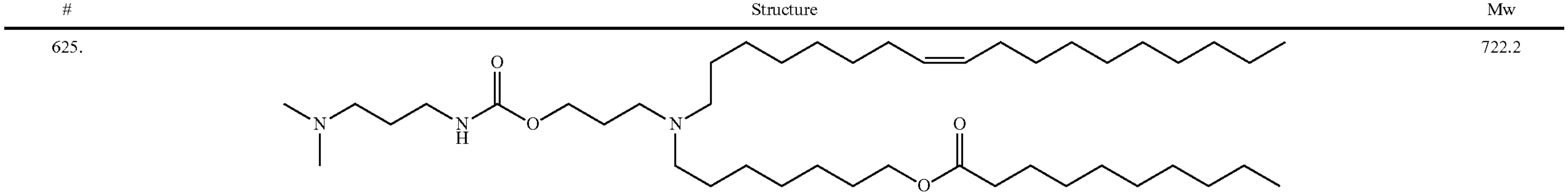 | 722.2 |
| 626. | 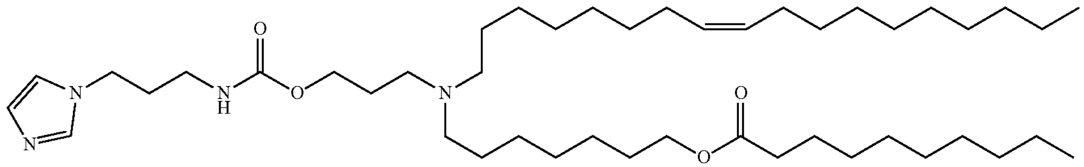 [SMILES: CCCCCCCCC/C=C\CCCCCCCN(CCCCCCCOC(=O)CCCCCCCCC)CCCOC(=O)NCCCn1ccnc1] | 745.2 |
| 627. | 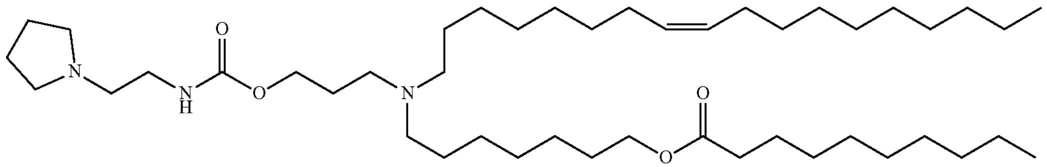 [SMILES: CCCCCCCCC/C=C\CCCCCCCN(CCCCCCCOC(=O)CCCCCCCCC)CCCOC(=O)NCCN1CCCC1] | 734.2 |
| 628. | 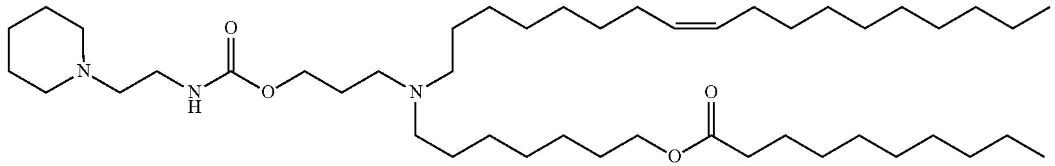 [SMILES: CCCCCCCCC/C=C\CCCCCCCN(CCCCCCCOC(=O)CCCCCCCCC)CCCOC(=O)NCCN1CCCCC1] | 748.2 |
| 629. | 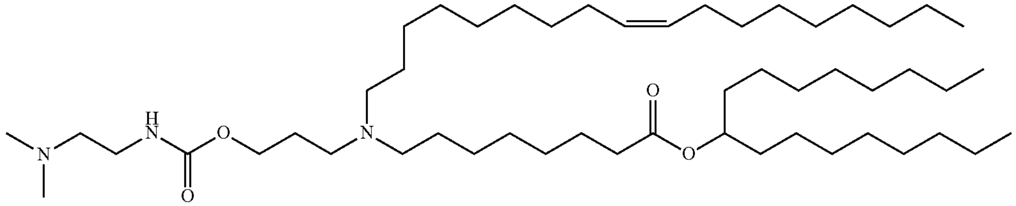 [SMILES: CCCCCCCC/C=C\CCCCCCCCN(CCCCCCCC(=O)OC(CCCCCCCC)CCCCCCCC)CCCOC(=O)NCCN(C)C] | 820.4 |

TABLE 1-continued
| # | Structure | Mw |
| --- | --- | --- |
| 630. | 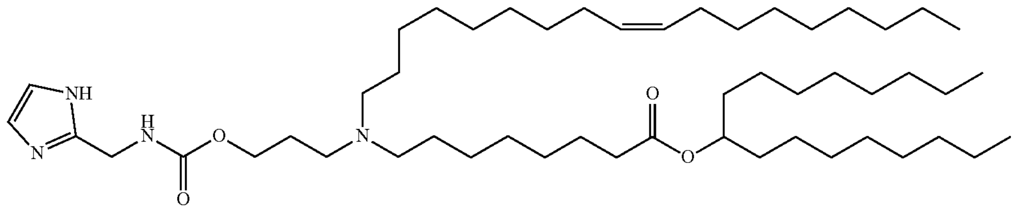 [SMILES: CCCCCCCC/C=C\CCCCCCCCN(CCCCCCCC(=O)OC(CCCCCCCC)CCCCCCCC)CCCOC(=O)NCc1ncc[nH]1] | 829.3 |
| 631. | 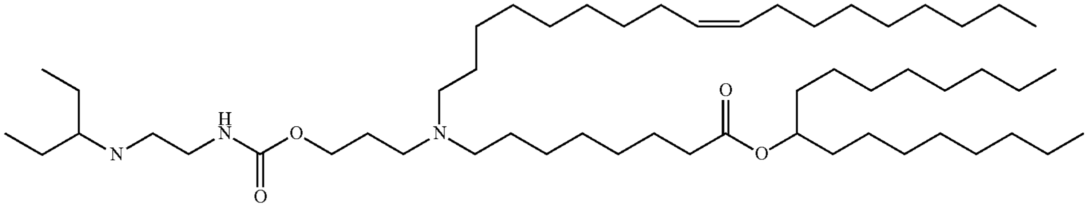 [SMILES: CCCCCCCC/C=C\CCCCCCCCN(CCCCCCCC(=O)OC(CCCCCCCC)CCCCCCCC)CCCOC(=O)NCCNC(CC)CC] | 862.4 |
| 632. | 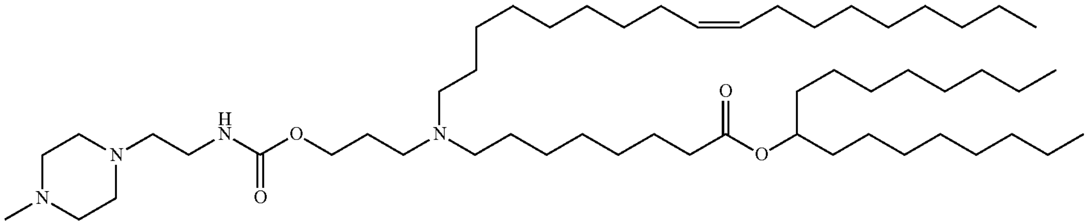 [SMILES: CCCCCCCC/C=C\CCCCCCCCN(CCCCCCCC(=O)OC(CCCCCCCC)CCCCCCCC)CCCOC(=O)NCCN1CCN(C)CC1] | 875.4 |
| 633. | 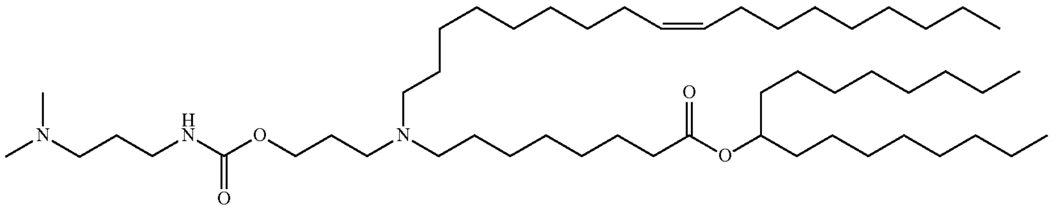 [SMILES: CCCCCCCC/C=C\CCCCCCCCN(CCCCCCCC(=O)OC(CCCCCCCC)CCCCCCCC)CCCOC(=O)NCCCN(C)C] | 834.4 |

TABLE 1-continued
| # | Structure | Mw |
| --- | --- | --- |
| 634. | 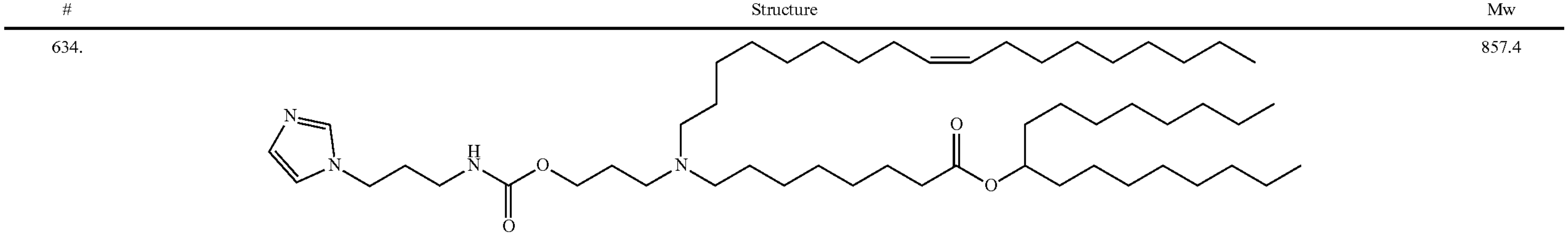 | 857.4 |
| 635. | 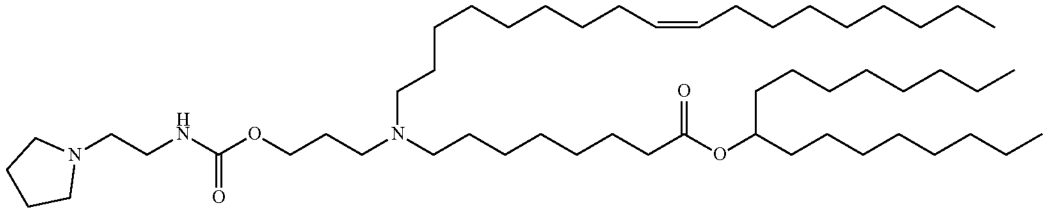 [SMILES: CCCCCCCC/C=C\CCCCCCCCN(CCCCCCCC(=O)OC(CCCCCCCC)CCCCCCCC)CCCOC(=O)NCCN1CCCC1] | 846.4 |
| 636. | 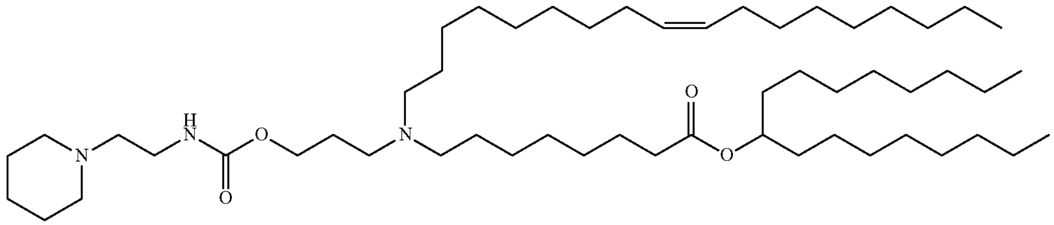 [SMILES: CCCCCCCC/C=C\CCCCCCCCN(CCCCCCCC(=O)OC(CCCCCCCC)CCCCCCCC)CCCOC(=O)NCCN1CCCCC1] | 860.4 |
| 637. | 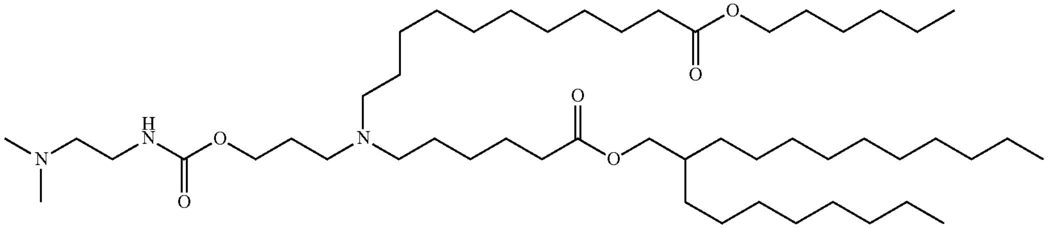 [SMILES: CCCCCCCCCCC(CCCCCCCC)COC(=O)CCCCCN(CCCCCCCCCCC(=O)OCCCCCC)CCCOC(=O)NCCN(C)C] | 852.4 |

TABLE 1-continued
| # | Structure | Mw |
| --- | --- | --- |
| 638. | 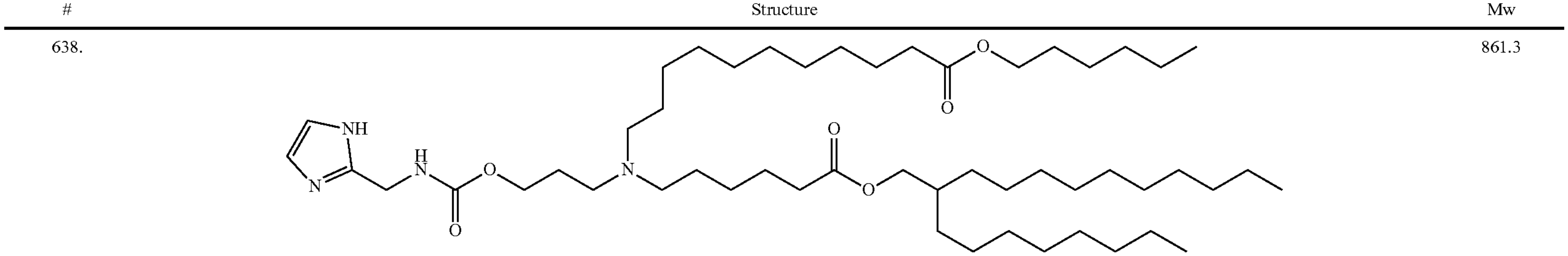 | 861.3 |
| 639. | 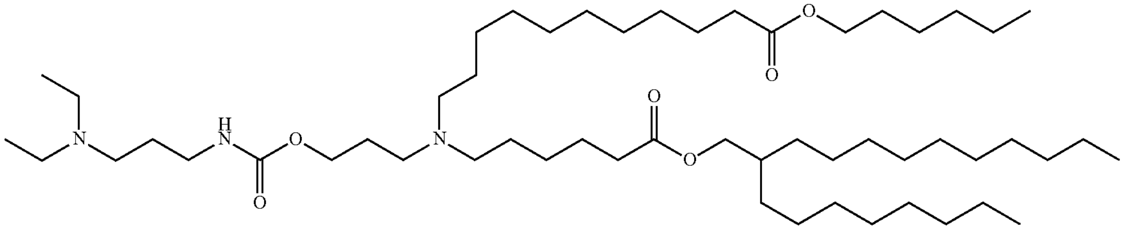 [SMILES: CCCCCCCCCCC(CCCCCCCC)COC(=O)CCCCCN(CCCCCCCCCCC(=O)OCCCCCC)CCCOC(=O)NCCCN(CC)CC] | 894.4 |
| 640. | 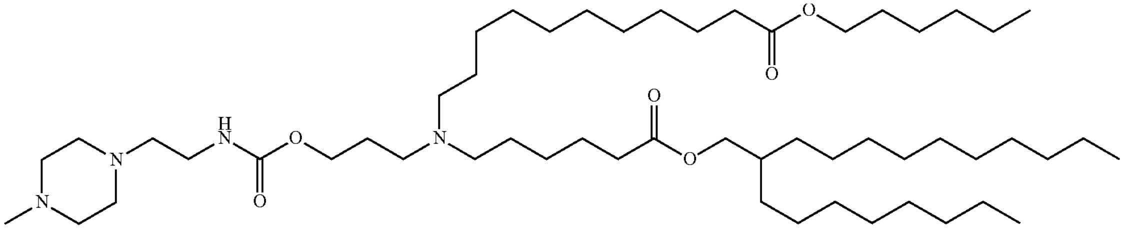 [SMILES: CCCCCCCCCCC(CCCCCCCC)COC(=O)CCCCCN(CCCCCCCCCCC(=O)OCCCCCC)CCCOC(=O)NCCN1CCN(C)CC1] | 893.4 |
| 641. | 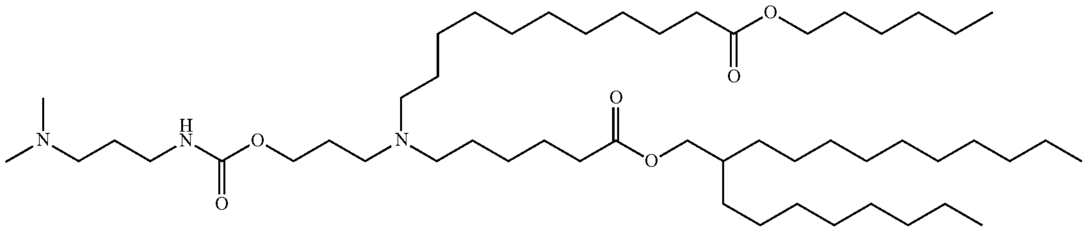 [SMILES: CCCCCCCCCCC(CCCCCCCC)COC(=O)CCCCCN(CCCCCCCCCCC(=O)OCCCCCC)CCCOC(=O)NCCCN(C)C] | 866.4 |

TABLE 1-continued
| # | Structure | Mw |
|---|---|---|
| 642. | 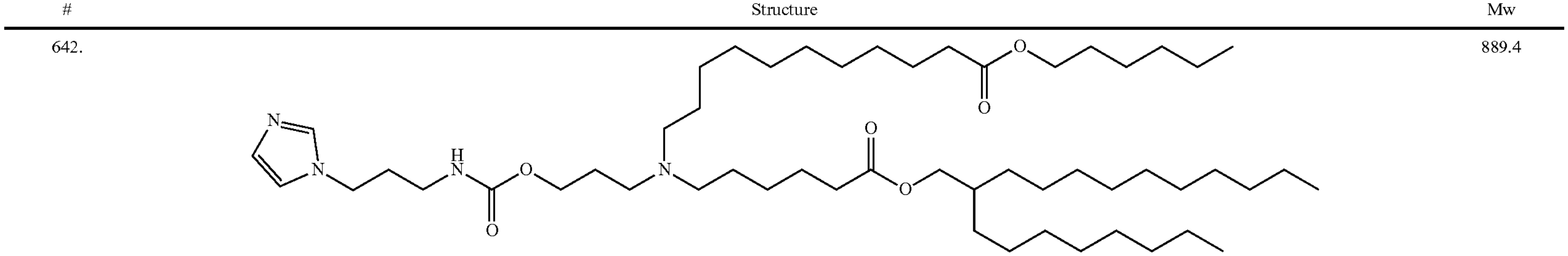 | 889.4 |
| 643. | 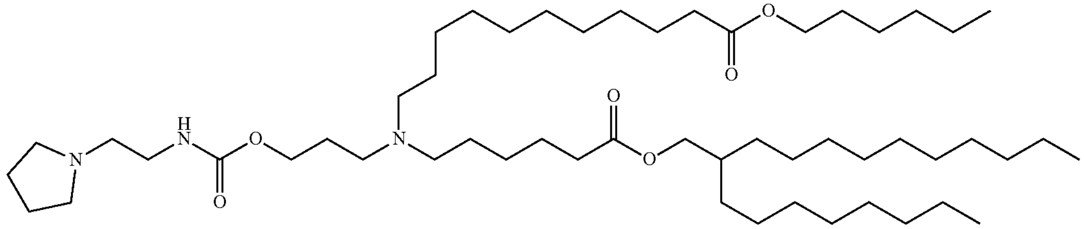 [SMILES: CCCCCCCCCCC(CCCCCCCC)COC(=O)CCCCCN(CCCCCCCCCCC(=O)OCCCCCC)CCCOC(=O)NCCN1CCCC1] | 878.4 |
| 644. | 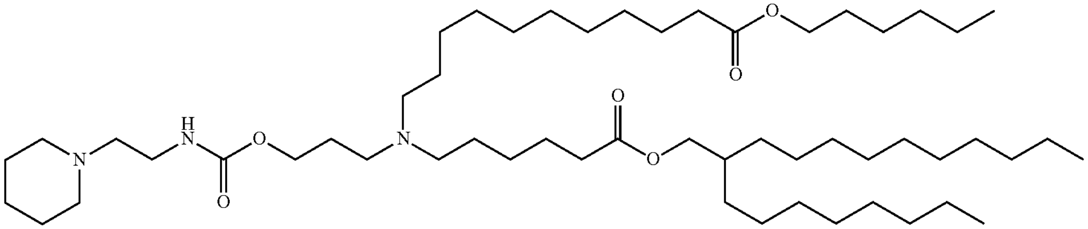 [SMILES: CCCCCCCCCCC(CCCCCCCC)COC(=O)CCCCCN(CCCCCCCCCCC(=O)OCCCCCC)CCCOC(=O)NCCN1CCCCC1] | 892.4 |
| 645. | 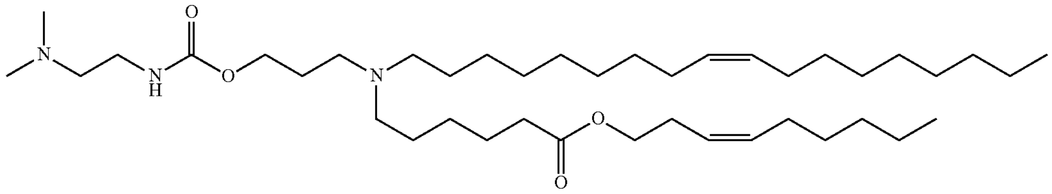 [SMILES: CCCCC/C=C\CCOC(=O)CCCCCN(CCCCCCCC/C=C\CCCCCCCC)CCCOC(=O)NCCN(C)C] | 678.1 |

TABLE 1-continued
| # | Structure | Mw |
| --- | --- | --- |
| 646. | 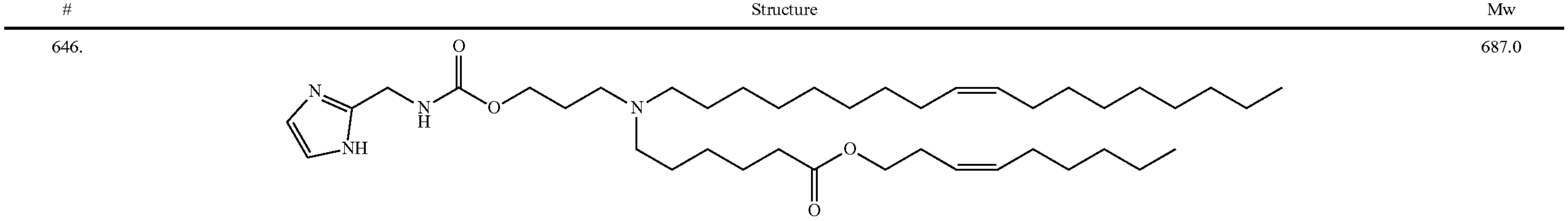 | 687.0 |
| 647. | 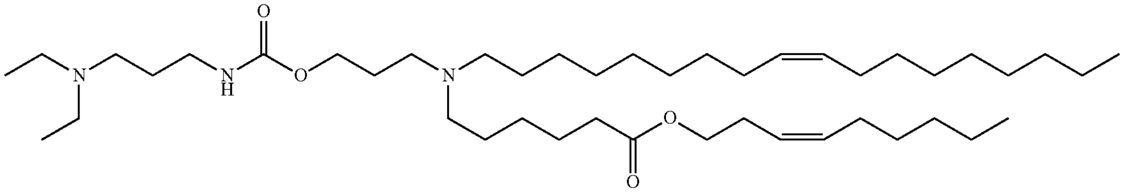 [SMILES: CCCCC/C=C\CCOC(=O)CCCCCN(CCCCCCCC/C=C\CCCCCCCC)CCCOC(=O)NCCCN(CC)CC] | 720.2 |
| 648. | 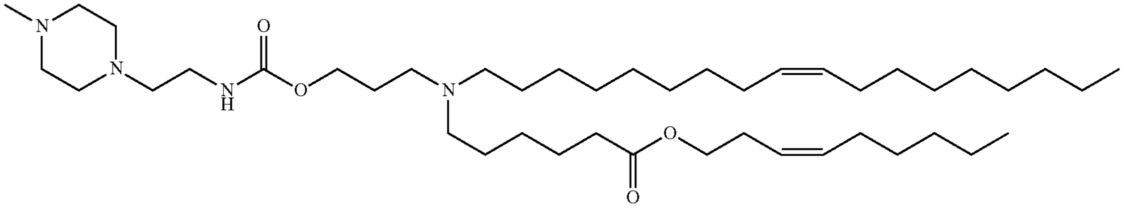 [SMILES: CCCCC/C=C\CCOC(=O)CCCCCN(CCCCCCCC/C=C\CCCCCCCC)CCCOC(=O)NCCN1CCN(C)CC1] | 733.2 |
| 649. | 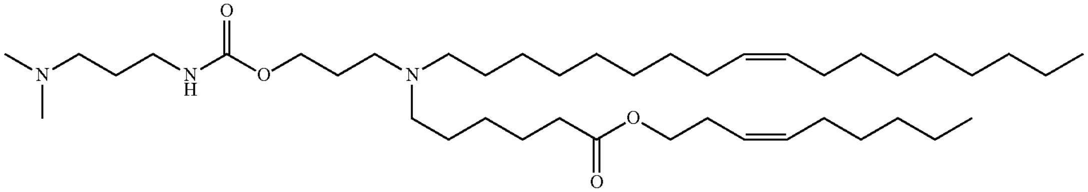 [SMILES: CCCCC/C=C\CCOC(=O)CCCCCN(CCCCCCCC/C=C\CCCCCCCC)CCCOC(=O)NCCCN(C)C] | 692.1 |
| 650. | 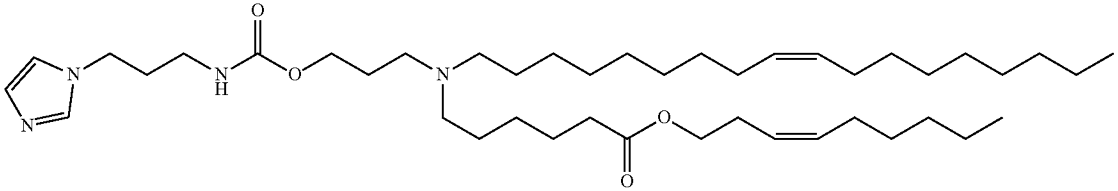 [SMILES: CCCCC/C=C\CCOC(=O)CCCCCN(CCCCCCCC/C=C\CCCCCCCC)CCCOC(=O)NCCCn1ccnc1] | 715.1 |

TABLE 1-continued
| # | Structure | Mw |
| --- | --- | --- |
| 651. | 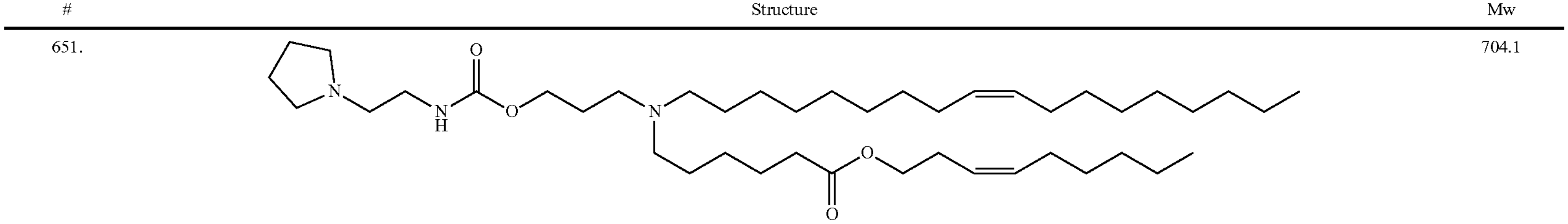 | 704.1 |
| 652. | 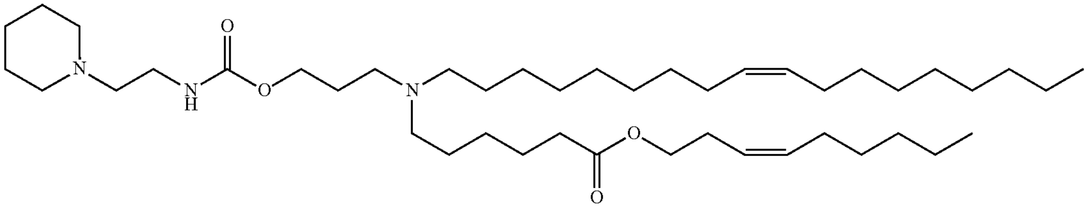 [SMILES: CCCCC/C=C\CCOC(=O)CCCCCN(CCCCCCCC/C=C\CCCCCCCC)CCCOC(=O)NCCN1CCCCC1] | 718.1 |
| 653. | 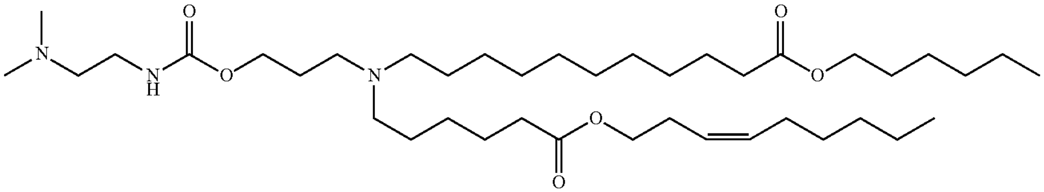 [SMILES: CCCCC/C=C\CCOC(=O)CCCCCN(CCCCCCCCCCC(=O)OCCCCCC)CCCOC(=O)NCCN(C)C] | 696.0 |
| 654. | 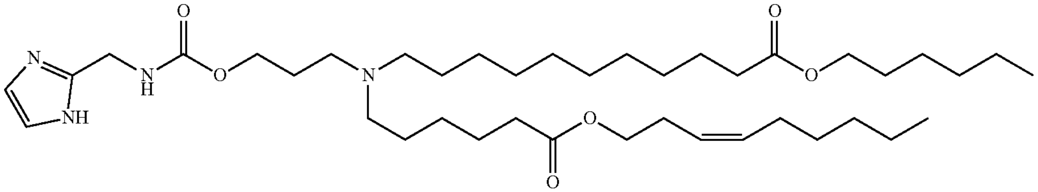 [SMILES: CCCCC/C=C\CCOC(=O)CCCCCN(CCCCCCCCCCC(=O)OCCCCCC)CCCOC(=O)NCc1ncc[nH]1] | 705.0 |
| 655. | 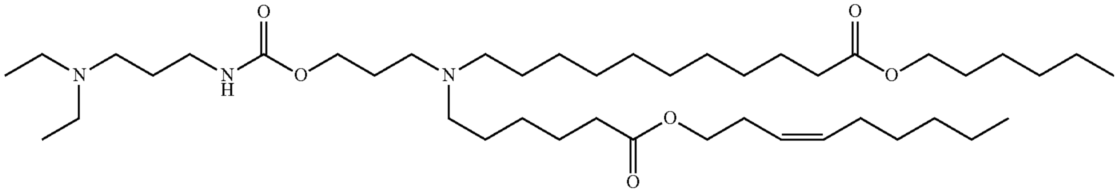 [SMILES: CCCCC/C=C\CCOC(=O)CCCCCN(CCCCCCCCCCC(=O)OCCCCCC)CCCOC(=O)NCCCN(CC)CC] | 738.1 |

TABLE 1-continued
| # | Structure | Mw |
| --- | --- | --- |
| 656. | 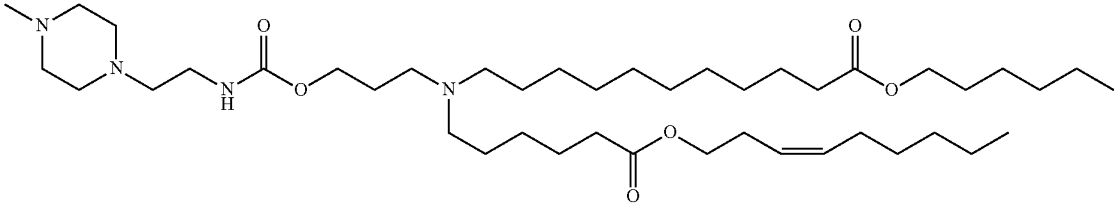 [SMILES: CCCCC/C=C\CCOC(=O)CCCCCN(CCCCCCCCCCC(=O)OCCCCCC)CCCOC(=O)NCCN1CCN(C)CC1] | 751.1 |
| 657. | 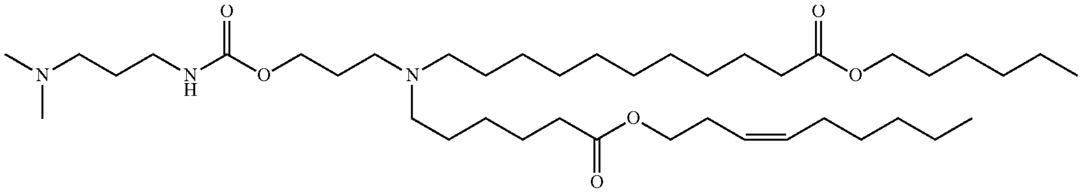 [SMILES: CCCCC/C=C\CCOC(=O)CCCCCN(CCCCCCCCCCC(=O)OCCCCCC)CCCOC(=O)NCCCN(C)C] | 710.1 |
| 658. | 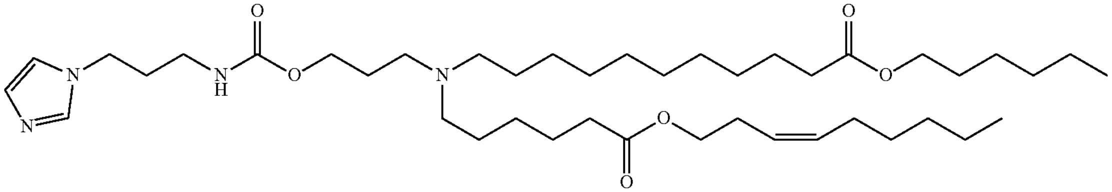 [SMILES: CCCCC/C=C\CCOC(=O)CCCCCN(CCCCCCCCCCC(=O)OCCCCCC)CCCOC(=O)NCCCn1ccnc1] | 733.1 |
| 659. | 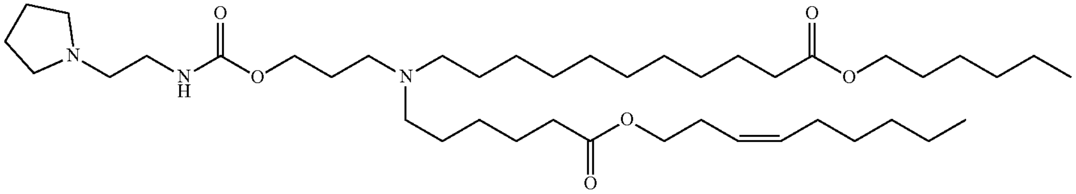 [SMILES: CCCCC/C=C\CCOC(=O)CCCCCN(CCCCCCCCCCC(=O)OCCCCCC)CCCOC(=O)NCCN1CCCC1] | 722.1 |
| 660. | 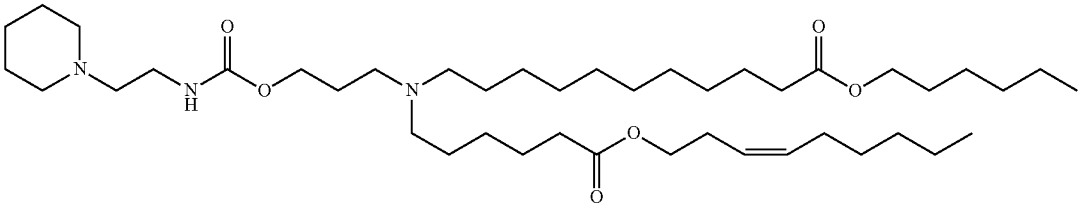 [SMILES: CCCCC/C=C\CCOC(=O)CCCCCN(CCCCCCCCCCC(=O)OCCCCCC)CCCOC(=O)NCCN1CCCCC1] | 736.1 |

TABLE 1-continued
| # | Structure | Mw |
|---|---|---|
| 661. | 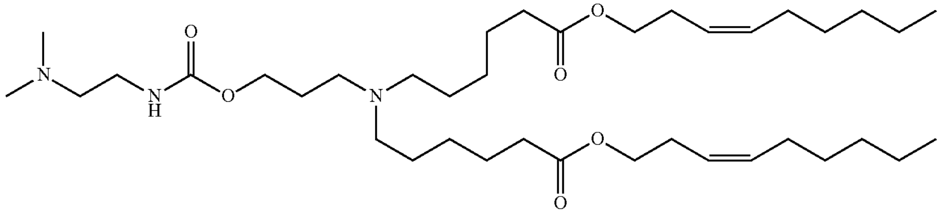 [SMILES: CCCCC/C=C\CCOC(=O)CCCCCN(CCCCCC(=O)OCC/C=C\CCCCC)CCCOC(=O)NCCN(C)C] | 666.0 |
| 662. | 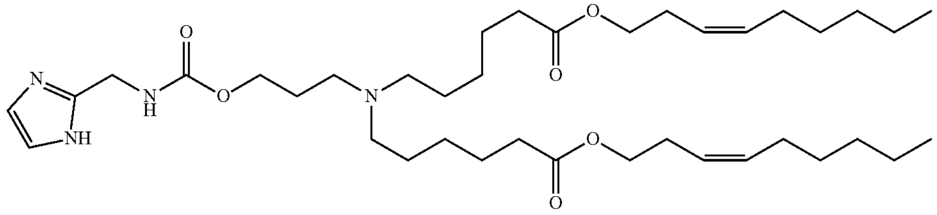 [SMILES: CCCCC/C=C\CCOC(=O)CCCCCN(CCCCCC(=O)OCC/C=C\CCCCC)CCCOC(=O)NCc1ncc[nH]1] | 674.9 |
| 663. | 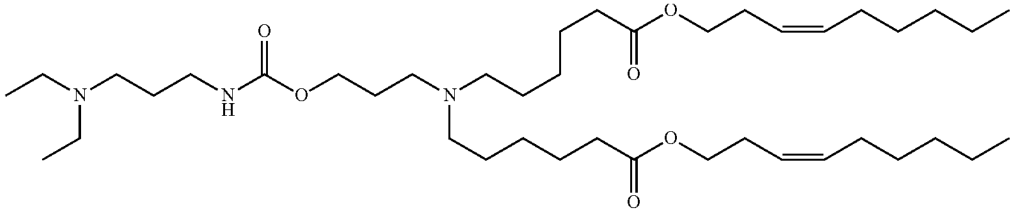 [SMILES: CCCCC/C=C\CCOC(=O)CCCCCN(CCCCCC(=O)OCC/C=C\CCCCC)CCCOC(=O)NCCCN(CC)CC] | 708.1 |
| 664. | 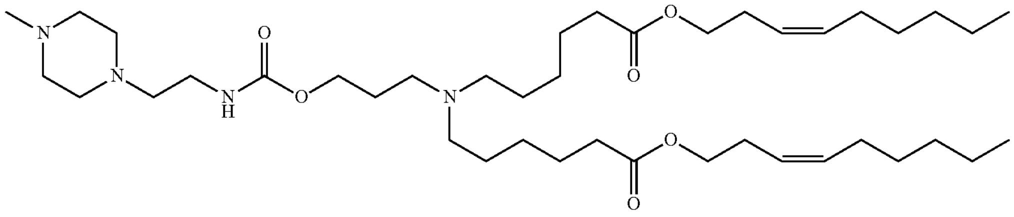 [SMILES: CCCCC/C=C\CCOC(=O)CCCCCN(CCCCCC(=O)OCC/C=C\CCCCC)CCCOC(=O)NCCN1CCN(C)CC1] | 721.1 |

TABLE 1-continued
| # | Structure | Mw |
|---|---|---|
| 665. | 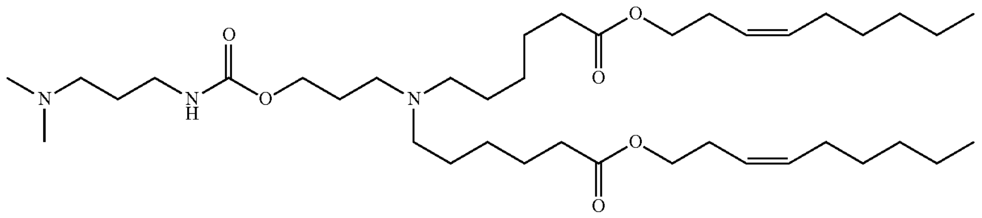 [SMILES: CCCCC/C=C\CCOC(=O)CCCCCN(CCCCCC(=O)OCC/C=C\CCCCC)CCCOC(=O)NCCCN(C)C] | 680.0 |
| 666. | 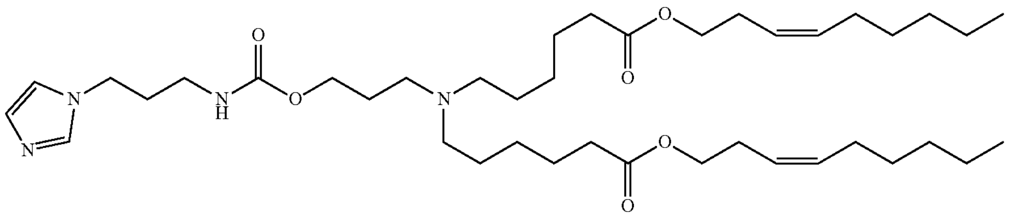 [SMILES: CCCCC/C=C\CCOC(=O)CCCCCN(CCCCCC(=O)OCC/C=C\CCCCC)CCCOC(=O)NCCCn1ccnc1] | 703.0 |
| 667. | 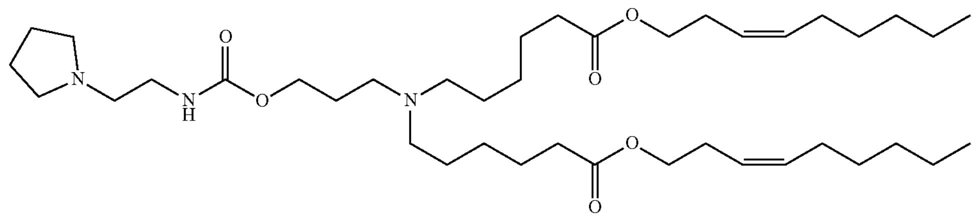 [SMILES: CCCCC/C=C\CCOC(=O)CCCCCN(CCCCCC(=O)OCC/C=C\CCCCC)CCCOC(=O)NCCN1CCCC1] | 692.0 |
| 668. | 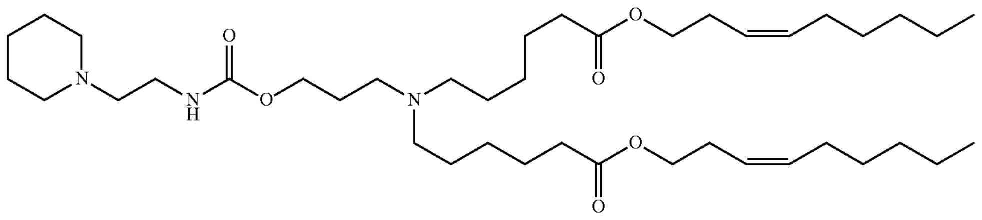 [SMILES: CCCCC/C=C\CCOC(=O)CCCCCN(CCCCCC(=O)OCC/C=C\CCCCC)CCCOC(=O)NCCN1CCCCC1] | 706.1 |

TABLE 1-continued
| # | Structure | Mw |
| --- | --- | --- |
| 669. | 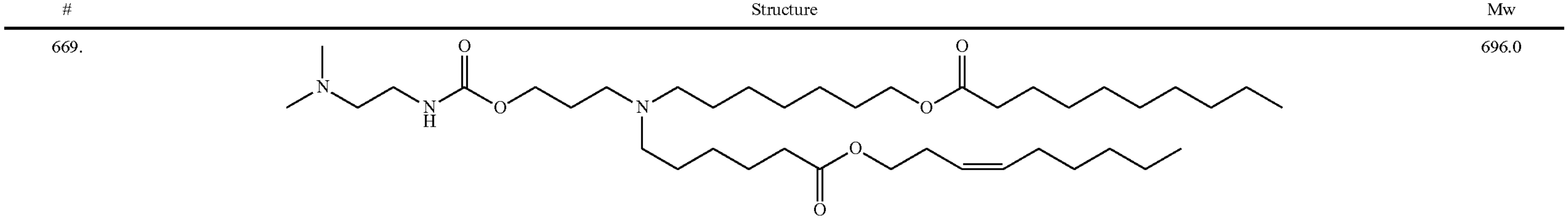 | 696.0 |
| 670. | 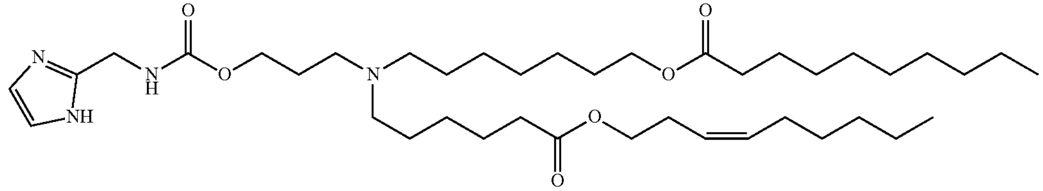 [SMILES: CCCCC/C=C\CCOC(=O)CCCCCN(CCCCCCCOC(=O)CCCCCCCCC)CCCOC(=O)NCc1ncc[nH]1] | 705.0 |
| 671. | 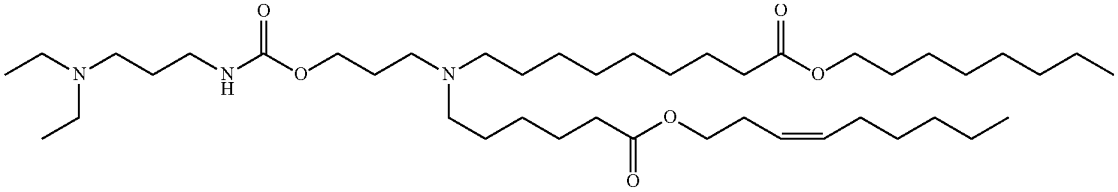 [SMILES: CCCCC/C=C\CCOC(=O)CCCCCN(CCCCCCCCC(=O)OCCCCCCCC)CCCOC(=O)NCCCN(CC)CC] | 738.1 |
| 672. | 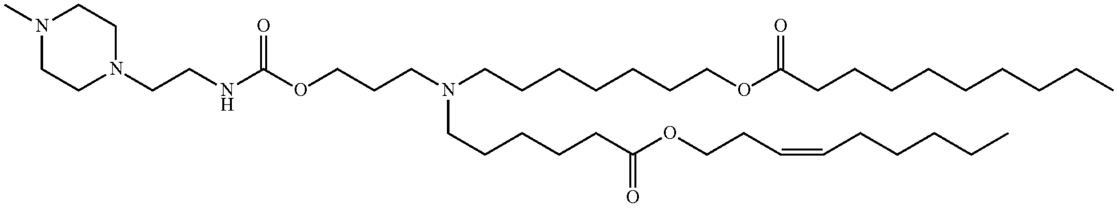 [SMILES: CCCCC/C=C\CCOC(=O)CCCCCN(CCCCCCCOC(=O)CCCCCCCCC)CCCOC(=O)NCCN1CCN(C)CC1] | 751.1 |
| 673. | 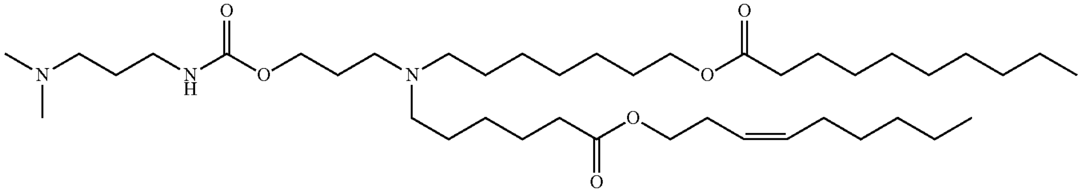 [SMILES: CCCCC/C=C\CCOC(=O)CCCCCN(CCCCCCCOC(=O)CCCCCCCCC)CCCOC(=O)NCCCN(C)C] | 710.1 |

TABLE 1-continued
| # | Structure | Mw |
| --- | --- | --- |
| 674. | 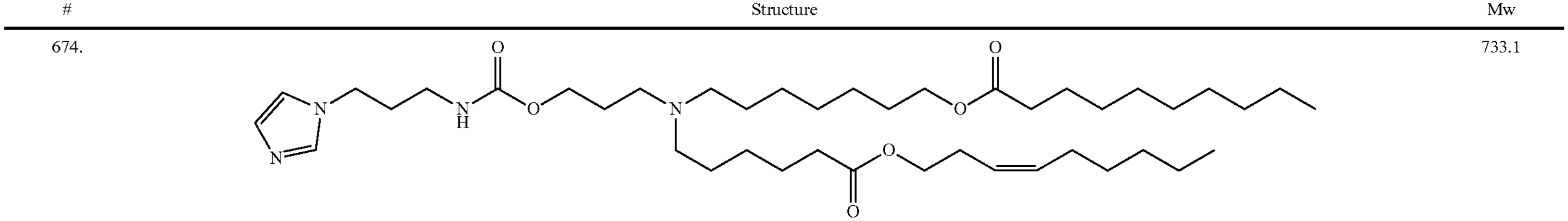 | 733.1 |
| 675. | 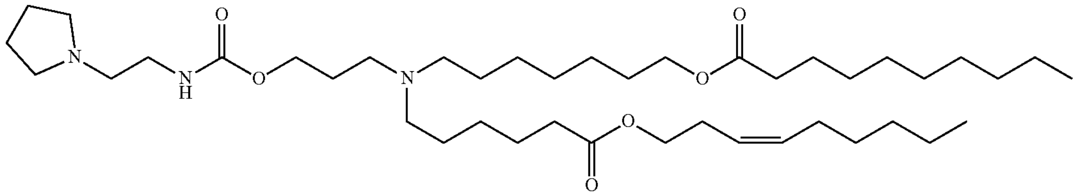 [SMILES: CCCCC/C=C\CCOC(=O)CCCCCN(CCCCCCCOC(=O)CCCCCCCCC)CCCOC(=O)NCCN1CCCC1] | 722.1 |
| 676. | 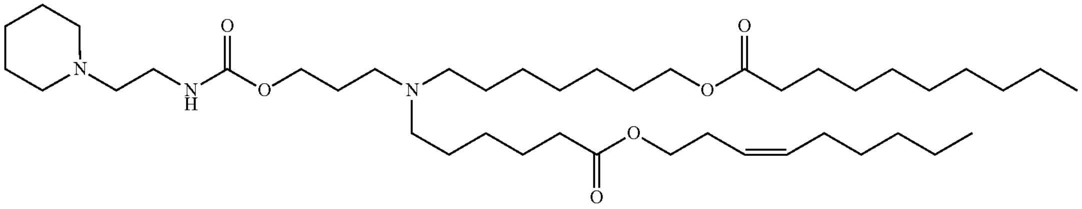 [SMILES: CCCCC/C=C\CCOC(=O)CCCCCN(CCCCCCCOC(=O)CCCCCCCCC)CCCOC(=O)NCCN1CCCCC1] | 736.1 |
| 677. | 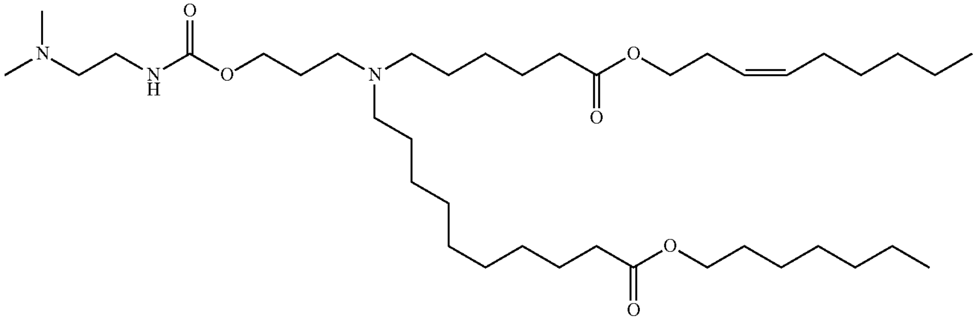 [SMILES: CCCCC/C=C\CCOC(=O)CCCCCN(CCCCCCCCCC(=O)OCCCCCCC)CCCOC(=O)NCCN(C)C] | 696.0 |

TABLE 1-continued
| # | Structure | Mw |
|---|---|---|
| 678. | 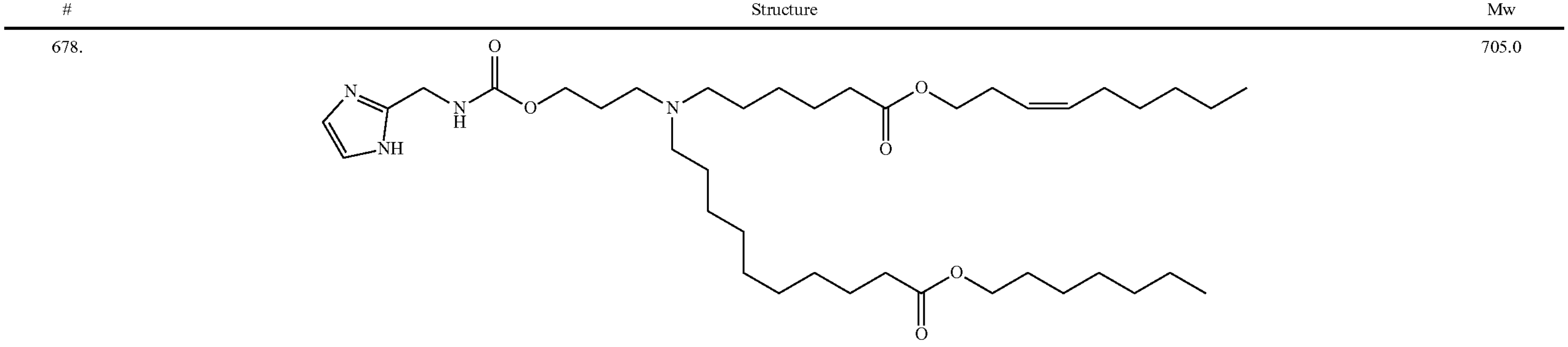 | 705.0 |
| 679. | 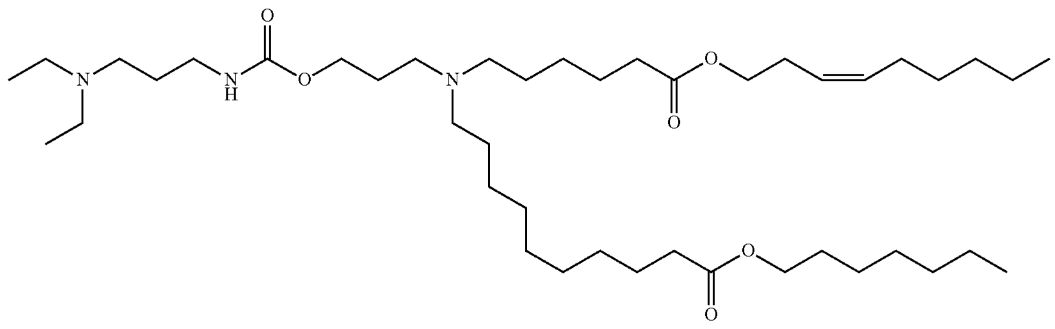 [SMILES: CCCCC/C=C\CCOC(=O)CCCCCN(CCCCCCCCCC(=O)OCCCCCCC)CCCOC(=O)NCCCN(CC)CC] | 738.1 |
| 680. | 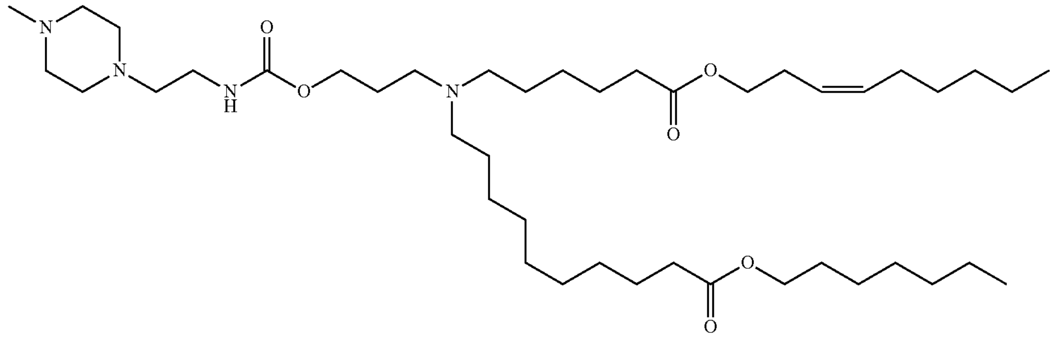 [SMILES: CCCCC/C=C\CCOC(=O)CCCCCN(CCCCCCCCCC(=O)OCCCCCCC)CCCOC(=O)NCCN1CCN(C)CC1] | 751.1 |

TABLE 1-continued
| # | Structure | Mw |
|---|---|---|
| 681. | 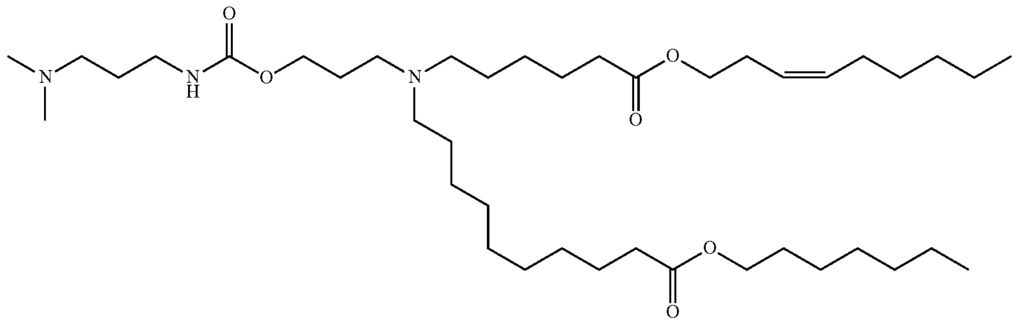 [SMILES: CCCCC/C=C\CCOC(=O)CCCCCN(CCCCCCCCCC(=O)OCCCCCCC)CCCOC(=O)NCCCN(C)C] | 710.1 |
| 682. | 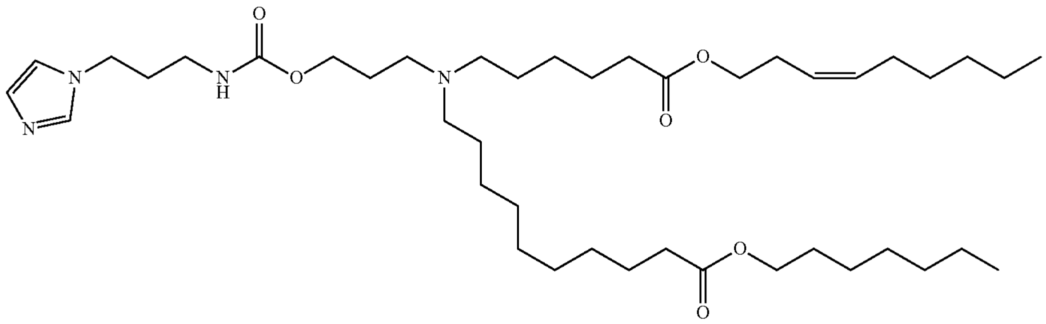 [SMILES: CCCCC/C=C\CCOC(=O)CCCCCN(CCCCCCCCCC(=O)OCCCCCCC)CCCOC(=O)NCCCn1ccnc1] | 733.1 |
| 683. | 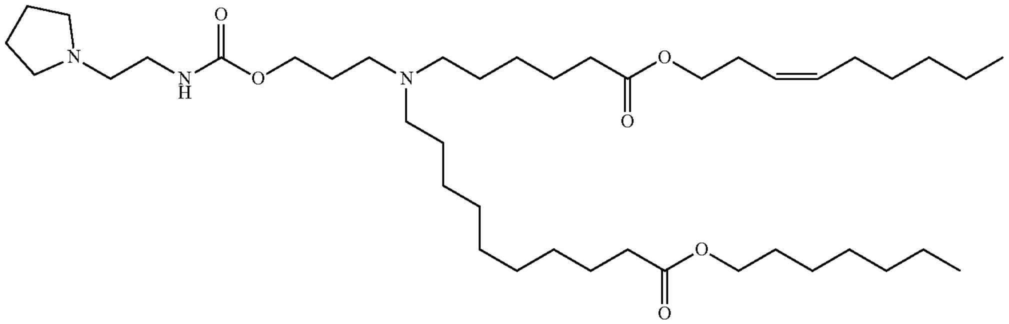 [SMILES: CCCCC/C=C\CCOC(=O)CCCCCN(CCCCCCCCCC(=O)OCCCCCCC)CCCOC(=O)NCCN1CCCC1] | 722.1 |

TABLE 1-continued
| # | Structure | Mw |
|---|---|---|
| 684. | 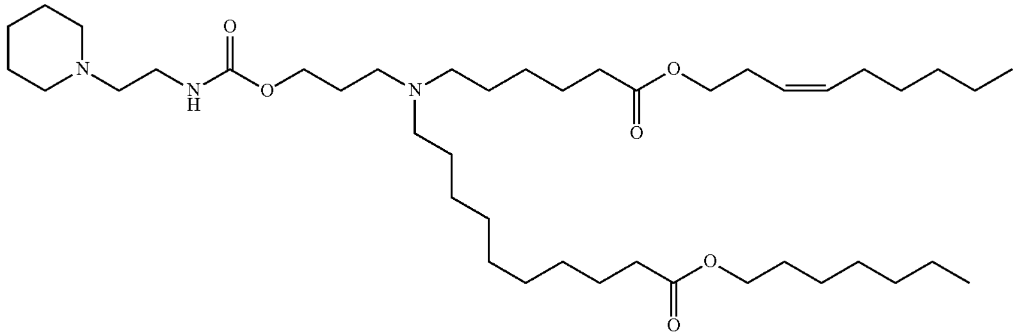 [SMILES: CCCCC/C=C\CCOC(=O)CCCCCN(CCCCCCCCCC(=O)OCCCCCCC)CCCOC(=O)NCCN1CCCCC1] | 736.1 |
| 685. | 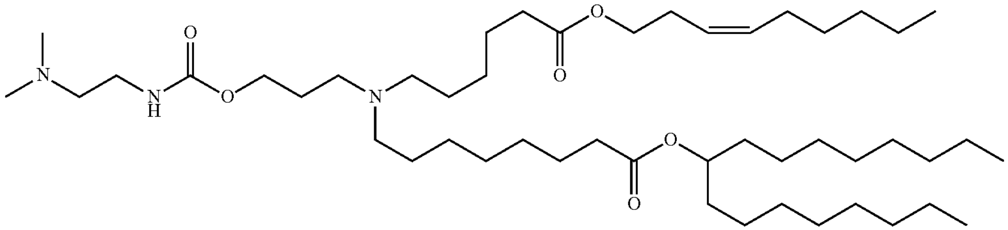 [SMILES: CCCCC/C=C\CCOC(=O)CCCCCN(CCCCCCCC(=O)OC(CCCCCCCC)CCCCCCCC)CCCOC(=O)NCCN(C)C] | 808.3 |
| 686. | 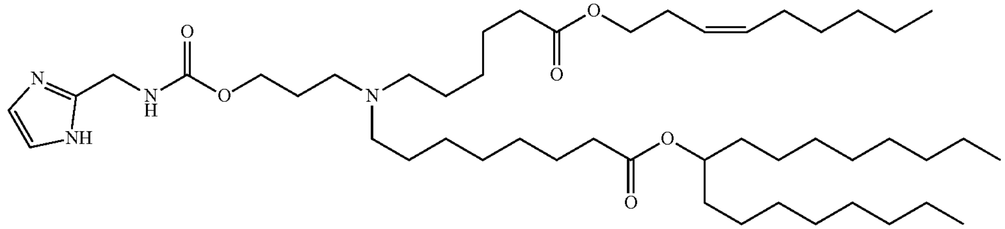 [SMILES: CCCCC/C=C\CCOC(=O)CCCCCN(CCCCCCCC(=O)OC(CCCCCCCC)CCCCCCCC)CCCOC(=O)NCc1ncc[nH]1] | 817.2 |
| 687. | 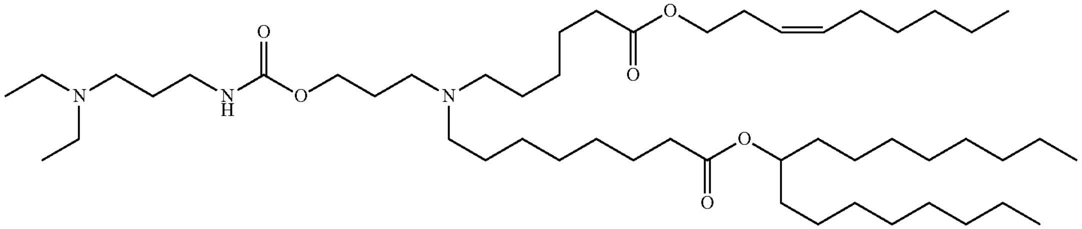 [SMILES: CCCCC/C=C\CCOC(=O)CCCCCN(CCCCCCCC(=O)OC(CCCCCCCC)CCCCCCCC)CCCOC(=O)NCCCN(CC)CC] | 850.3 |

TABLE 1-continued
| # | Structure | Mw |
|---|---|---|
| 688. | 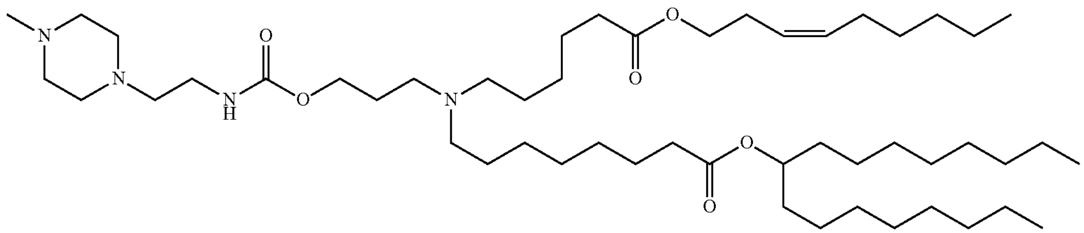 [SMILES: CCCCC/C=C\CCOC(=O)CCCCCN(CCCCCCCC(=O)OC(CCCCCCCC)CCCCCCCC)CCCOC(=O)NCCN1CCN(C)CC1] | 863.3 |
| 689. | 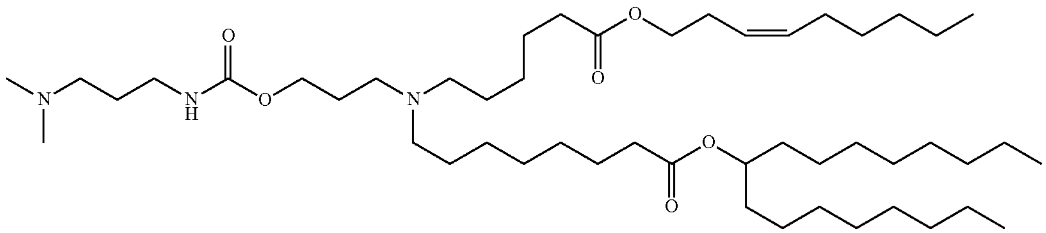 [SMILES: CCCCC/C=C\CCOC(=O)CCCCCN(CCCCCCCC(=O)OC(CCCCCCCC)CCCCCCCC)CCCOC(=O)NCCCN(C)C] | 822.3 |
| 690. | 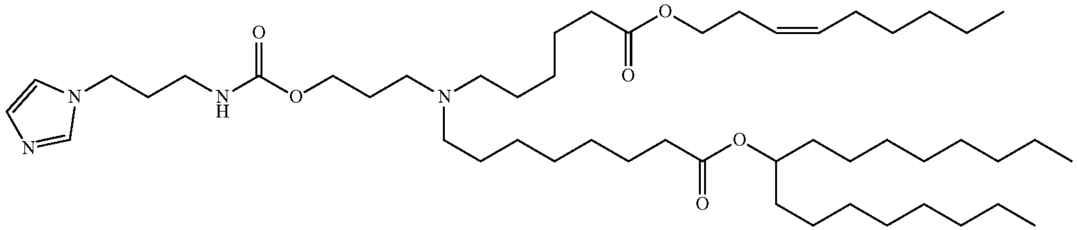 [SMILES: CCCCC/C=C\CCOC(=O)CCCCCN(CCCCCCCC(=O)OC(CCCCCCCC)CCCCCCCC)CCCOC(=O)NCCCn1ccnc1] | 845.3 |
| 691. | 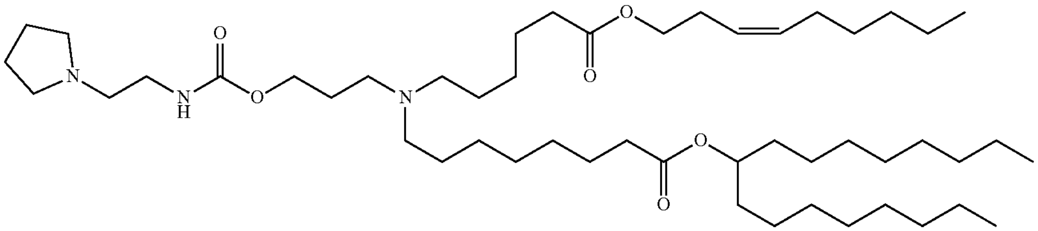 [SMILES: CCCCC/C=C\CCOC(=O)CCCCCN(CCCCCCCC(=O)OC(CCCCCCCC)CCCCCCCC)CCCOC(=O)NCCN1CCCC1] | 834.3 |

TABLE 1-continued
| # | Structure | Mw |
|---|---|---|
| 692. | 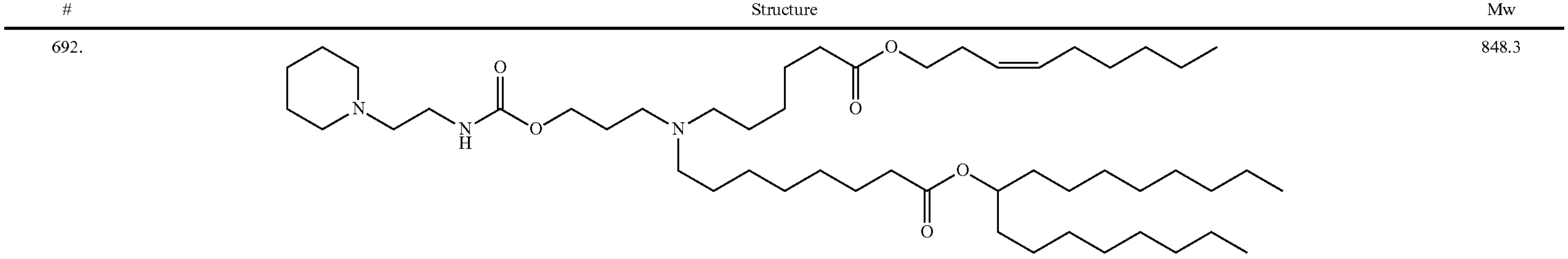 | 848.3 |
| 693. | 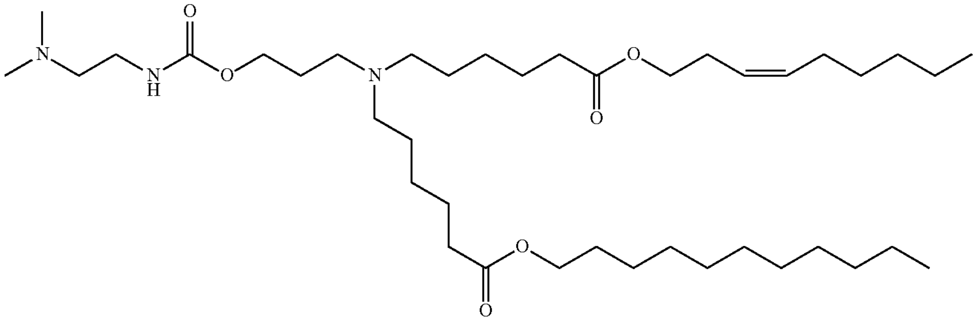 [SMILES: CCCCC/C=C\CCOC(=O)CCCCCN(CCCCCC(=O)OCCCCCCCCCCC)CCCOC(=O)NCCN(C)C] | 696.0 |
| 694. | 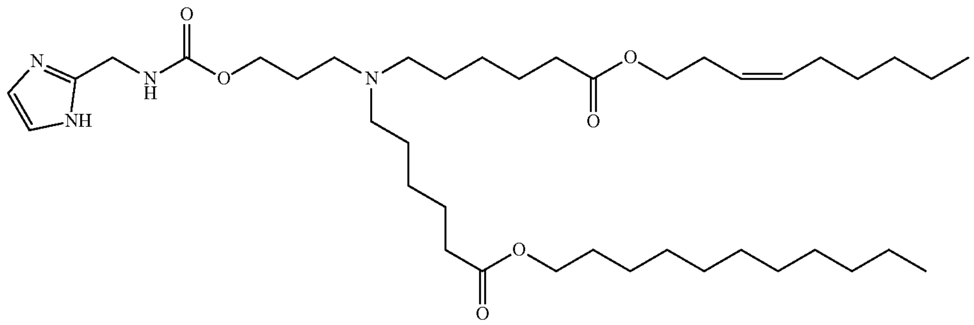 [SMILES: CCCCC/C=C\CCOC(=O)CCCCCN(CCCCCC(=O)OCCCCCCCCCCC)CCCOC(=O)NCc1ncc[nH]1] | 705.0 |

TABLE 1-continued
| # | Structure | Mw |
| --- | --- | --- |
| 695. | 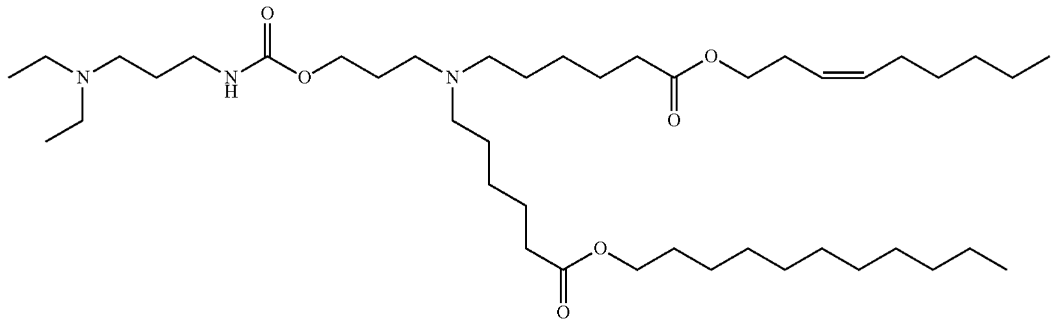 [SMILES: CCCCC/C=C\CCOC(=O)CCCCCN(CCCCCC(=O)OCCCCCCCCCCC)CCCOC(=O)NCCCN(CC)CC] | 738.1 |
| 696. | 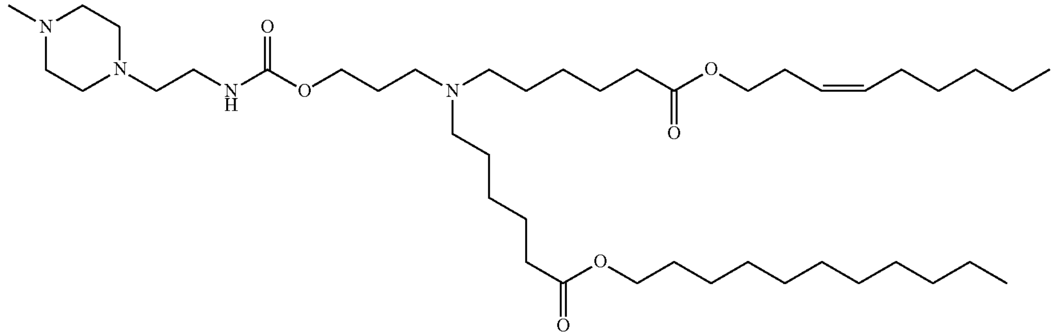 [SMILES: CCCCC/C=C\CCOC(=O)CCCCCN(CCCCCC(=O)OCCCCCCCCCCC)CCCOC(=O)NCCN1CCN(C)CC1] | 751.1 |
| 697. | 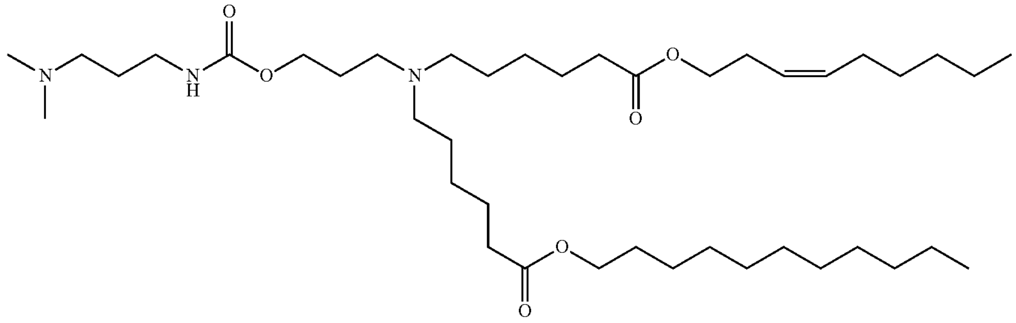 [SMILES: CCCCC/C=C\CCOC(=O)CCCCCN(CCCCCC(=O)OCCCCCCCCCCC)CCCOC(=O)NCCCN(C)C] | 710.1 |

TABLE 1-continued
| # | Structure | Mw |
|---|---|---|
| 698. | 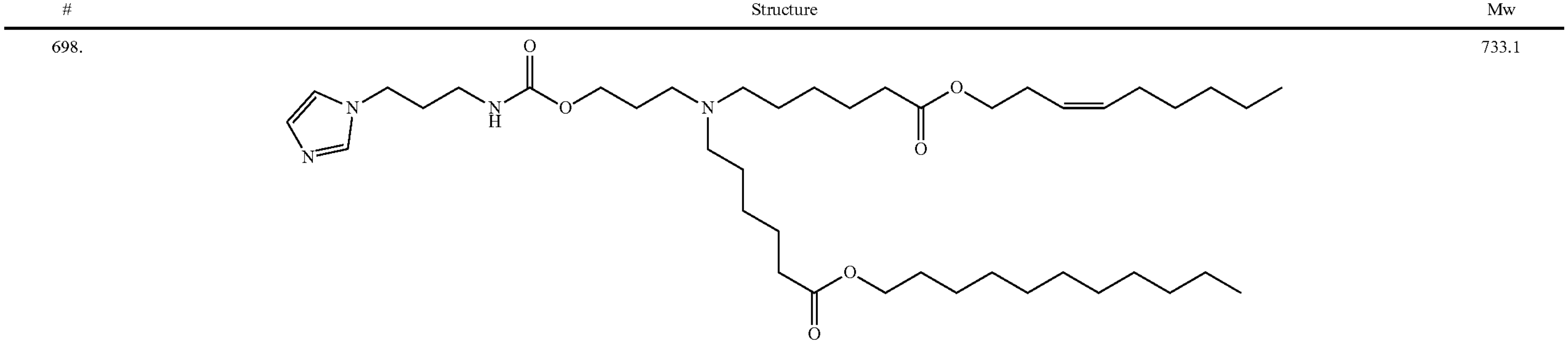 | 733.1 |
| 699. | 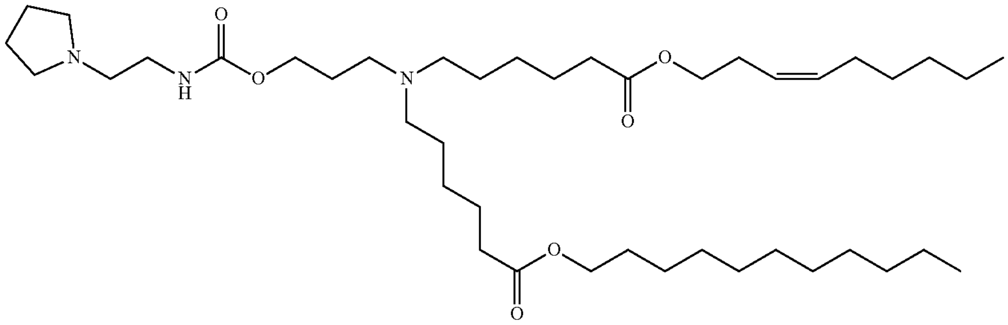 [SMILES: CCCCC/C=C\CCOC(=O)CCCCCN(CCCCCC(=O)OCCCCCCCCCCC)CCCOC(=O)NCCN1CCCC1] | 722.1 |
| 700. | 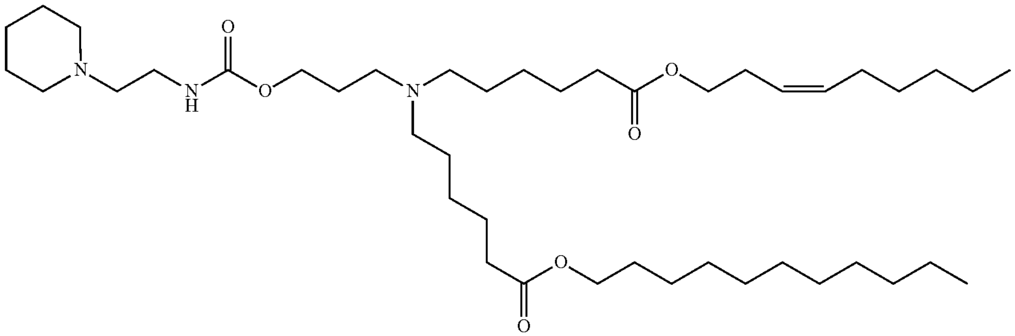 [SMILES: CCCCC/C=C\CCOC(=O)CCCCCN(CCCCCC(=O)OCCCCCCCCCCC)CCCOC(=O)NCCN1CCCCC1] | 736.1 |

TABLE 1-continued
| # | Structure | Mw |
| --- | --- | --- |
| 701. | 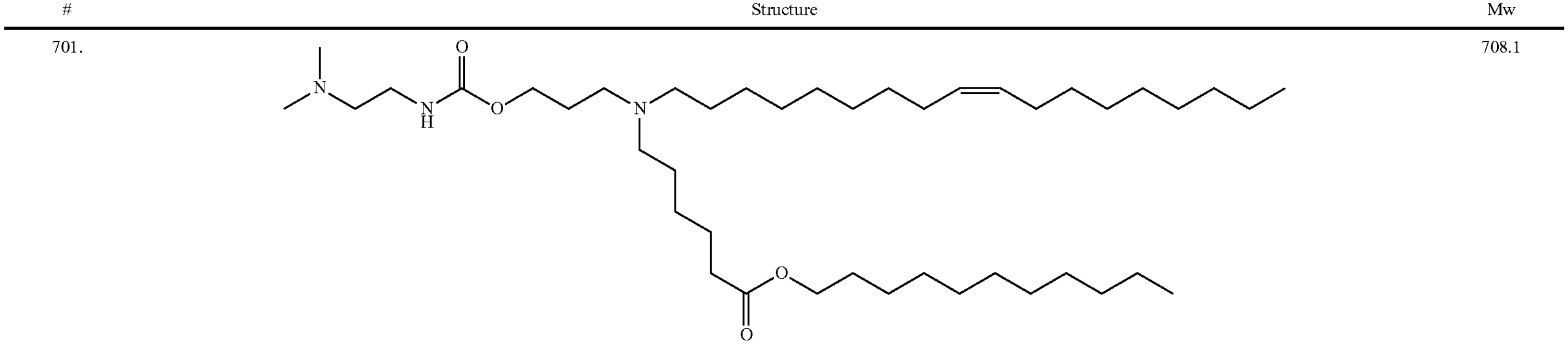 | 708.1 |
| 702. | 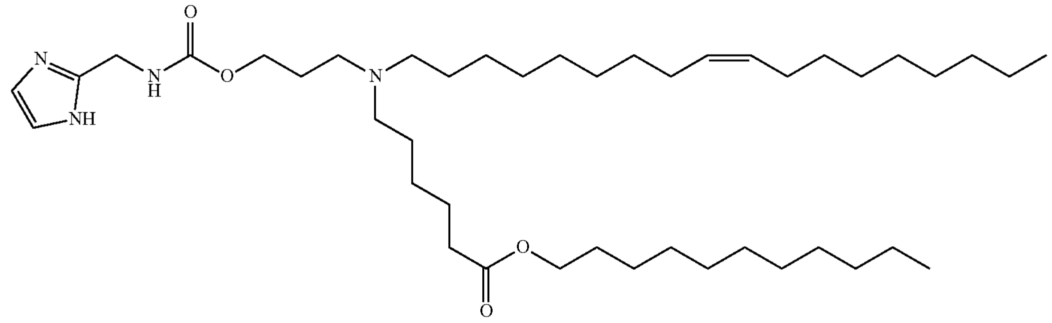 [SMILES: CCCCCCCC/C=C\CCCCCCCCN(CCCCCC(=O)OCCCCCCCCCCC)CCCOC(=O)NCc1ncc[nH]1] | 717.1 |
| 703. | 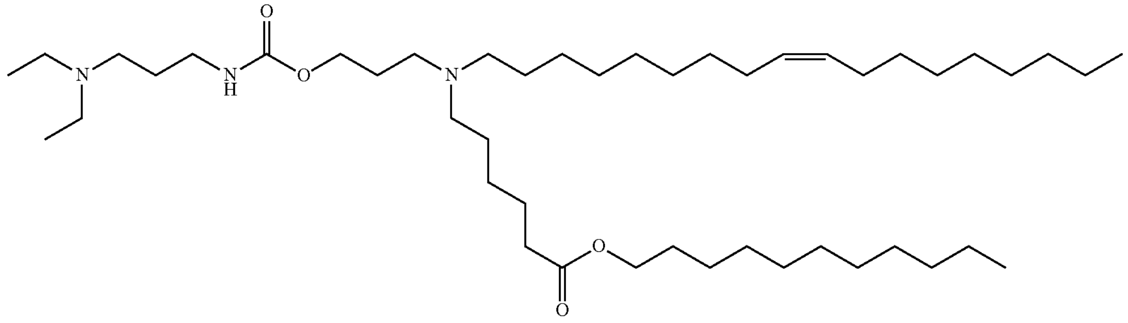 [SMILES: CCCCCCCC/C=C\CCCCCCCCN(CCCCCC(=O)OCCCCCCCCCCC)CCCOC(=O)NCCCN(CC)CC] | 750.2 |

TABLE 1-continued
| # | Structure | Mw |
|---|---|---|
| 704. | 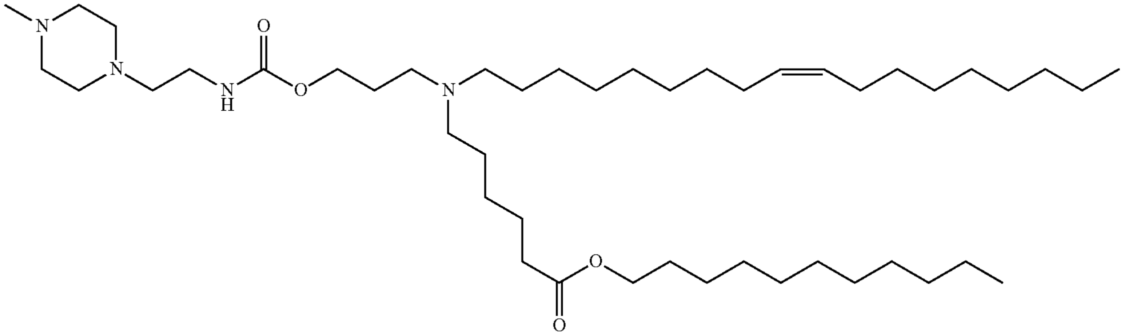 [SMILES: CCCCCCCC/C=C\CCCCCCCCN(CCCCCC(=O)OCCCCCCCCCCC)CCCOC(=O)NCCN1CCN(C)CC1] | 763.2 |
| 705. | 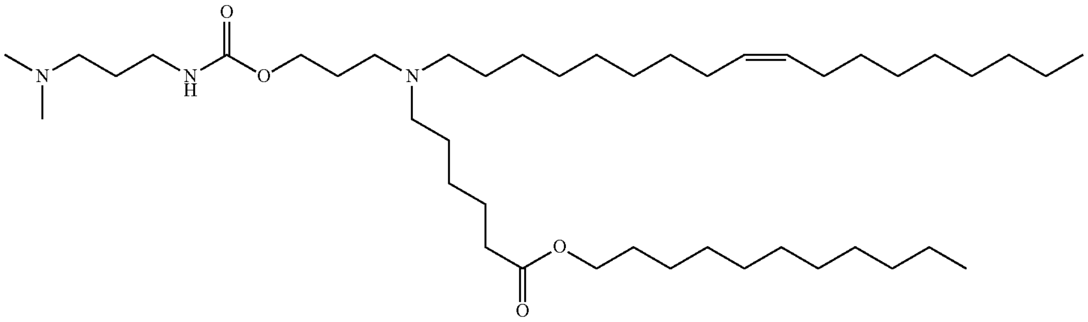 [SMILES: CCCCCCCC/C=C\CCCCCCCCN(CCCCCC(=O)OCCCCCCCCCCC)CCCOC(=O)NCCCN(C)C] | 722.2 |
| 706. | 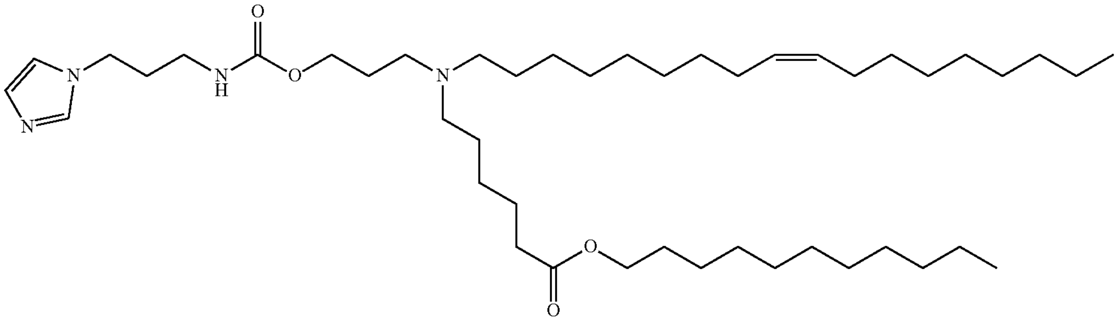 [SMILES: CCCCCCCC/C=C\CCCCCCCCN(CCCCCC(=O)OCCCCCCCCCCC)CCCOC(=O)NCCCn1ccnc1] | 745.2 |

TABLE 1-continued
| # | Structure | Mw |
|---|---|---|
| 707. | 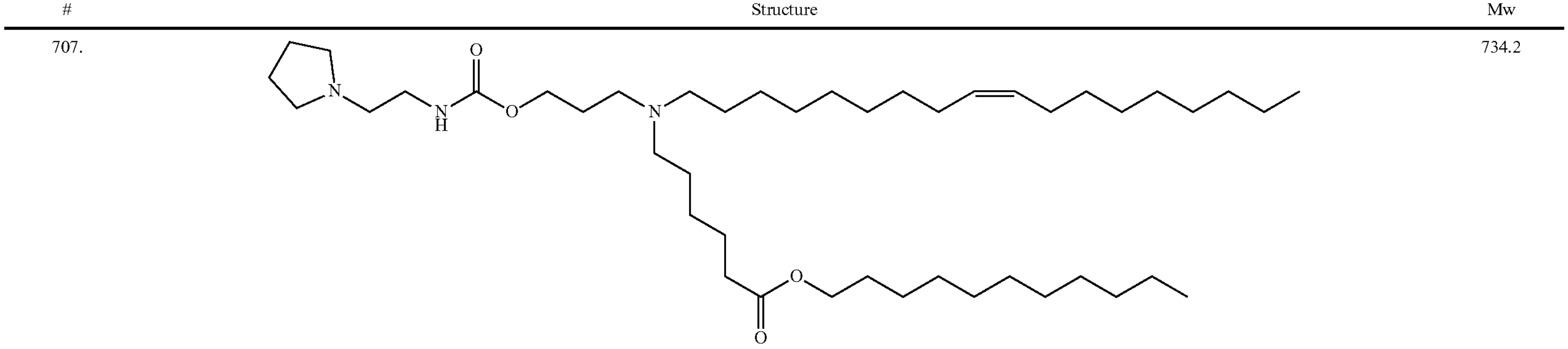 | 734.2 |
| 708. | 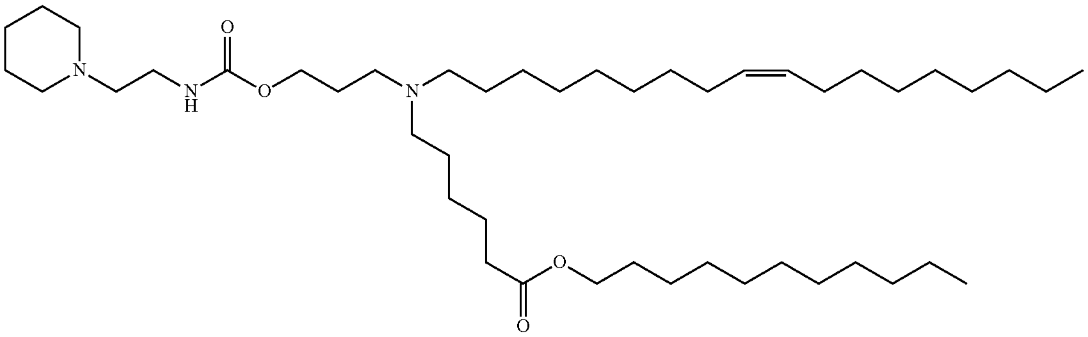 [SMILES: CCCCCCCC/C=C\CCCCCCCCN(CCCCCC(=O)OCCCCCCCCCCC)CCCOC(=O)NCCN1CCCCC1] | 748.2 |
| 709. | 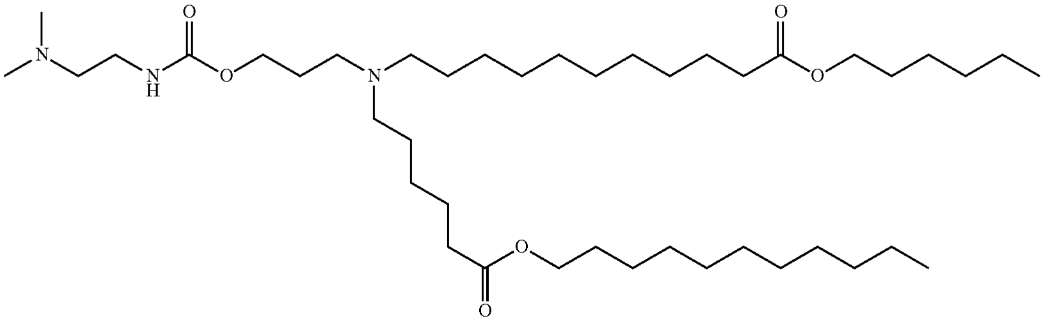 [SMILES: CCCCCCCCCCCOC(=O)CCCCCN(CCCCCCCCCCC(=O)OCCCCCC)CCCOC(=O)NCCN(C)C] | 726.1 |

TABLE 1-continued
| # | Structure | Mw |
|---|---|---|
| 710. | 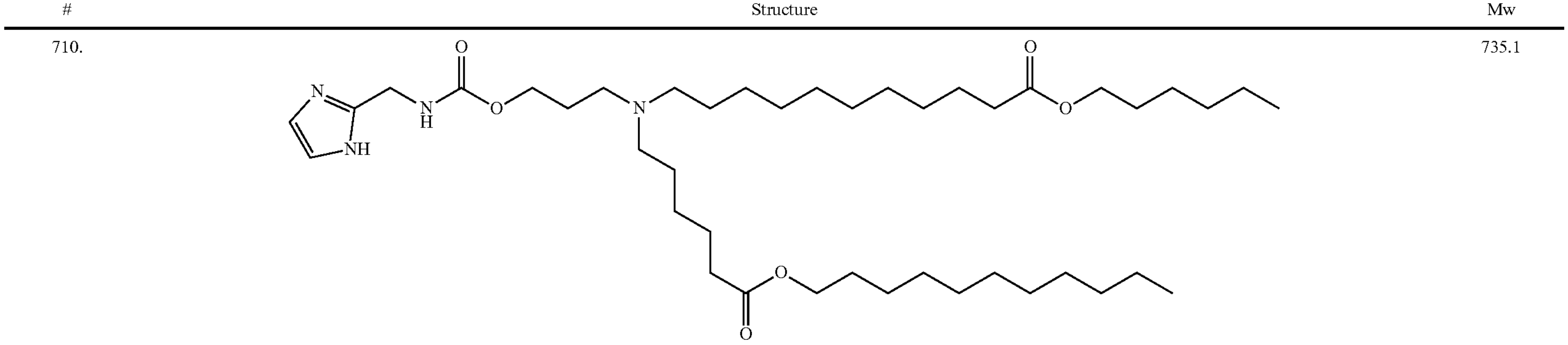 | 735.1 |
| 711. | 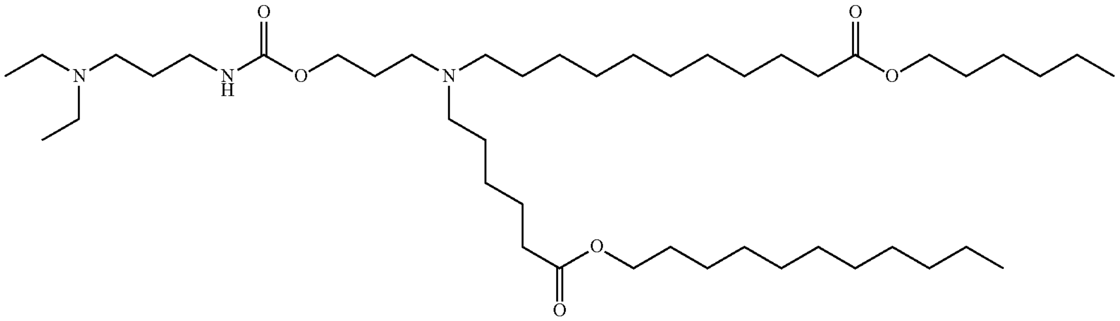 [SMILES: CCCCCCCCCCCOC(=O)CCCCCN(CCCCCCCCCCC(=O)OCCCCCC)CCCOC(=O)NCCCN(CC)CC] | 768.2 |
| 712. | 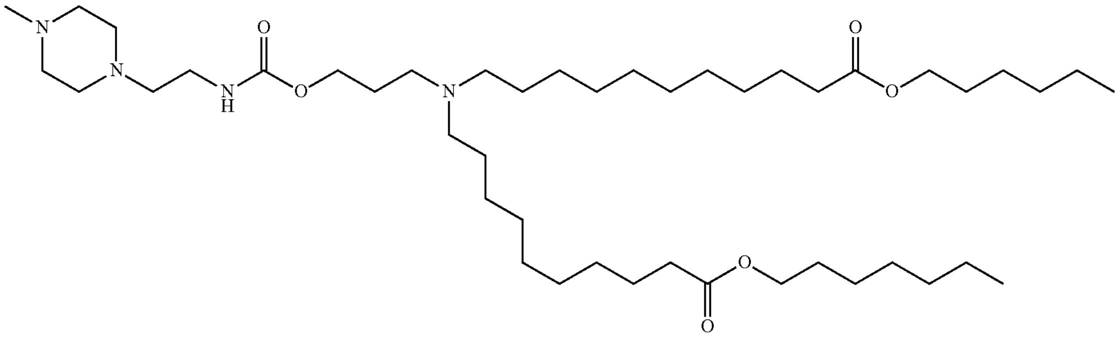 [SMILES: CCCCCCCOC(=O)CCCCCCCCCN(CCCCCCCCCCC(=O)OCCCCCC)CCCOC(=O)NCCN1CCN(C)CC1] | 781.2 |

TABLE 1-continued
| # | Structure | Mw |
|---|---|---|
| 713. | 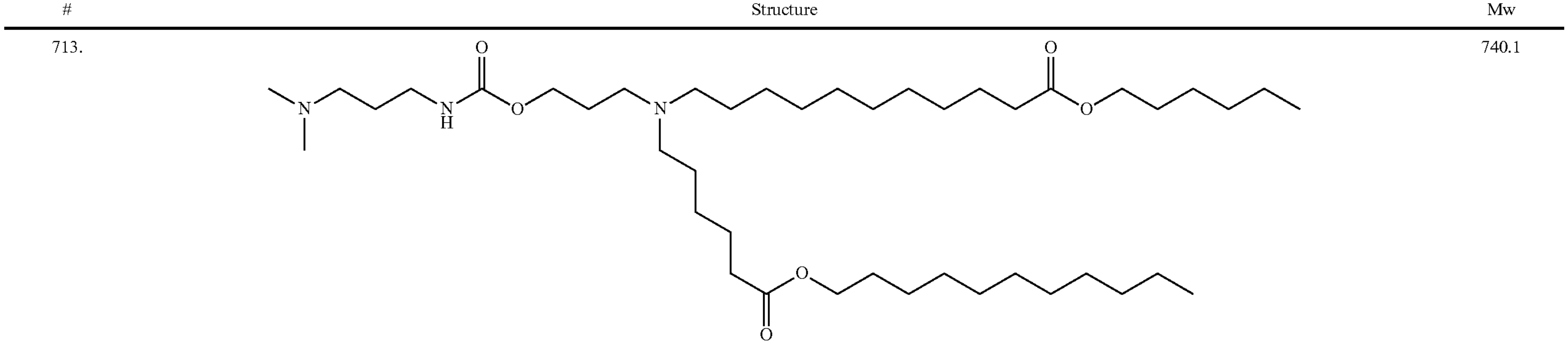 | 740.1 |
| 714. | 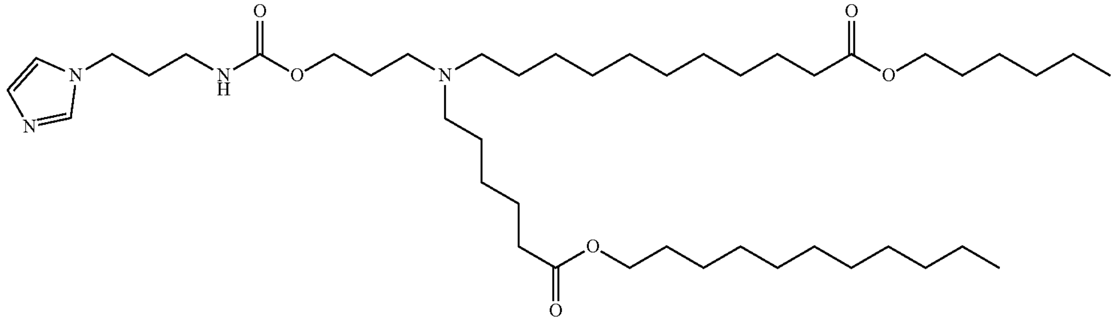 [SMILES: CCCCCCCCCCCOC(=O)CCCCCN(CCCCCCCCCCC(=O)OCCCCCC)CCCOC(=O)NCCCn1ccnc1] | 763.1 |
| 715. | 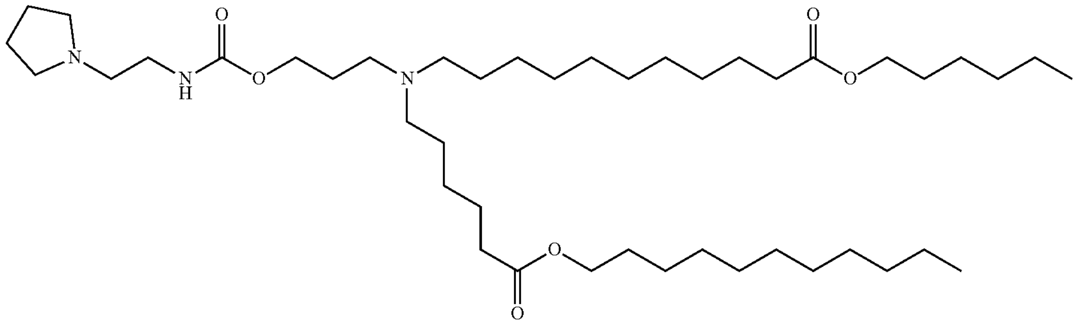 [SMILES: CCCCCCCCCCCOC(=O)CCCCCN(CCCCCCCCCCC(=O)OCCCCCC)CCCOC(=O)NCCN1CCCC1] | 752.2 |

TABLE 1-continued
| # | Structure | Mw |
| --- | --- | --- |
| 716. | 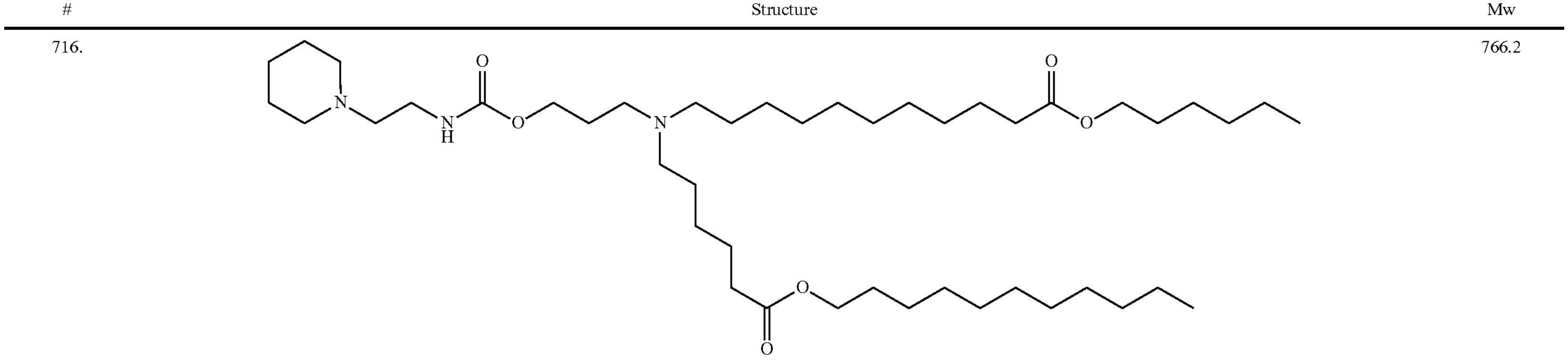 | 766.2 |
| 717. | 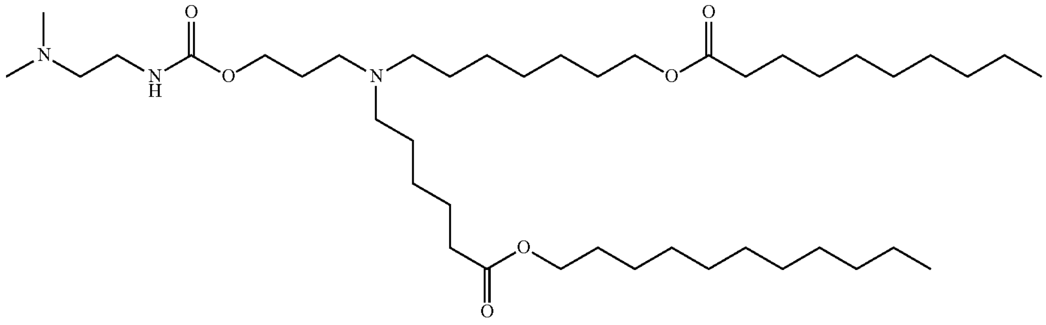 [SMILES: CCCCCCCCCCCOC(=O)CCCCCN(CCCCCCCOC(=O)CCCCCCCCC)CCCOC(=O)NCCN(C)C] | 726.1 |
| 718. | 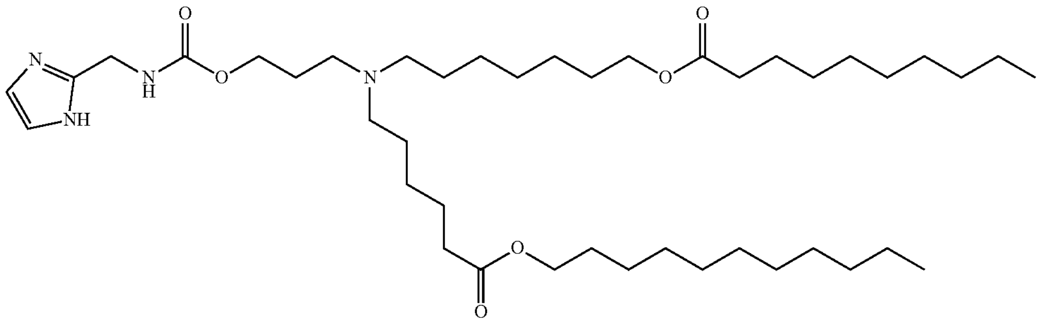 [SMILES: CCCCCCCCCCCOC(=O)CCCCCN(CCCCCCCOC(=O)CCCCCCCCC)CCCOC(=O)NCc1ncc[nH]1] | 735.1 |

TABLE 1-continued
| # | Structure | Mw |
|---|---|---|
| 719. | 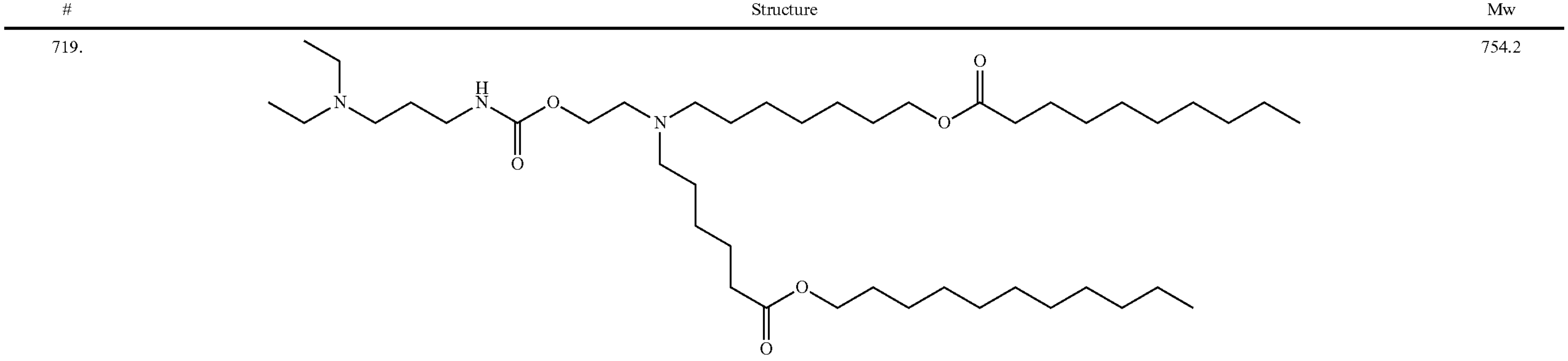 | 754.2 |
| 720. | 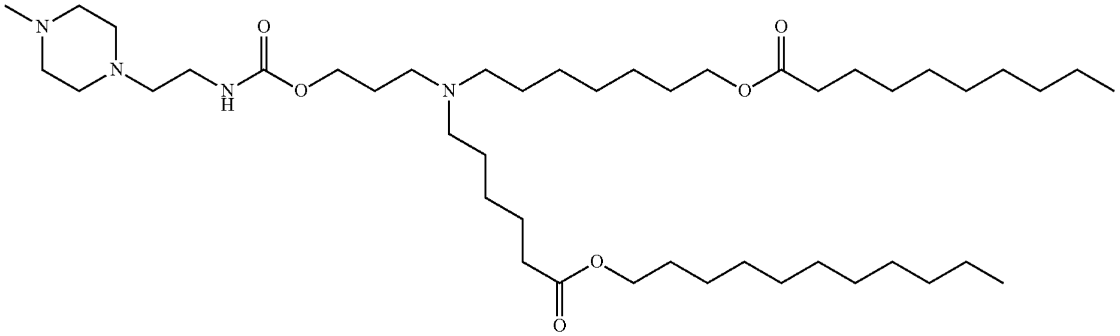 [SMILES: CCCCCCCCCCCOC(=O)CCCCCN(CCCCCCCOC(=O)CCCCCCCCC)CCCOC(=O)NCCN1CCN(C)CC1] | 781.2 |
| 721. | 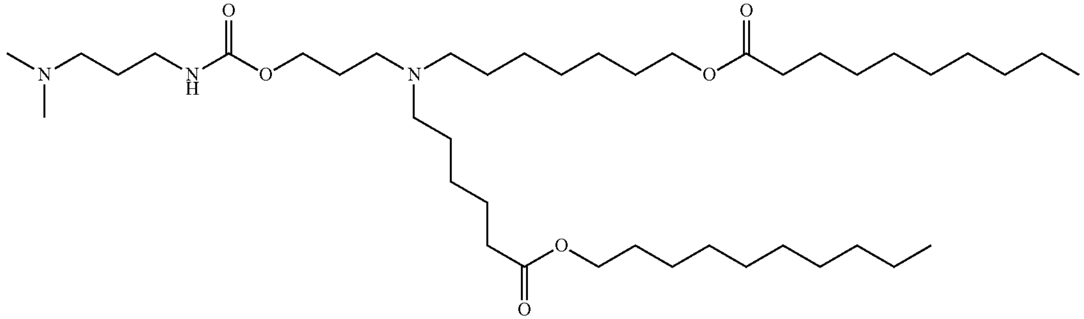 [SMILES: CCCCCCCCCCOC(=O)CCCCCN(CCCCCCCOC(=O)CCCCCCCCC)CCCOC(=O)NCCCN(C)C] | 726.1 |

TABLE 1-continued
| # | Structure | Mw |
|---|---|---|
| 722. | 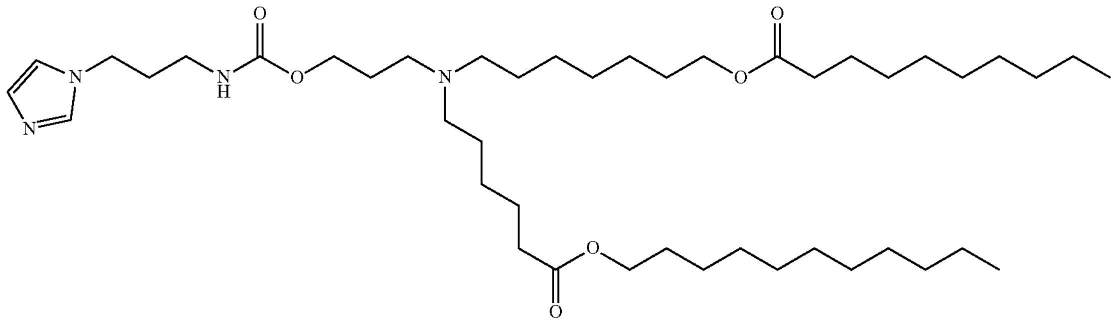 [SMILES: CCCCCCCCCCCOC(=O)CCCCCN(CCCCCCCOC(=O)CCCCCCCCC)CCCOC(=O)NCCCn1ccnc1] | 763.1 |
| 723. | 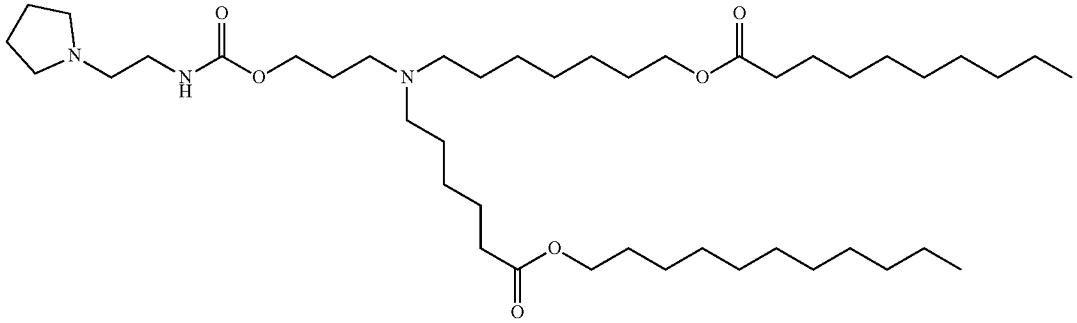 [SMILES: CCCCCCCCCCCOC(=O)CCCCCN(CCCCCCCOC(=O)CCCCCCCCC)CCCOC(=O)NCCN1CCCC1] | 752.2 |
| 724. | 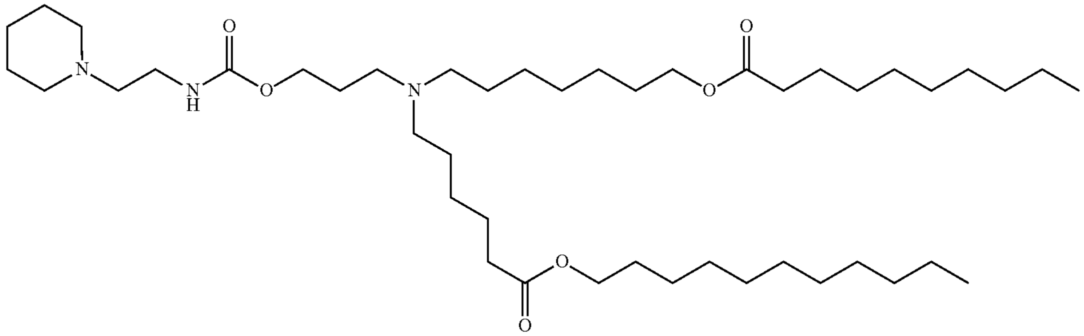 [SMILES: CCCCCCCCCCCOC(=O)CCCCCN(CCCCCCCOC(=O)CCCCCCCCC)CCCOC(=O)NCCN1CCCCC1] | 766.2 |

TABLE 1-continued
| # | Structure | Mw |
|---|---|---|
| 725. | 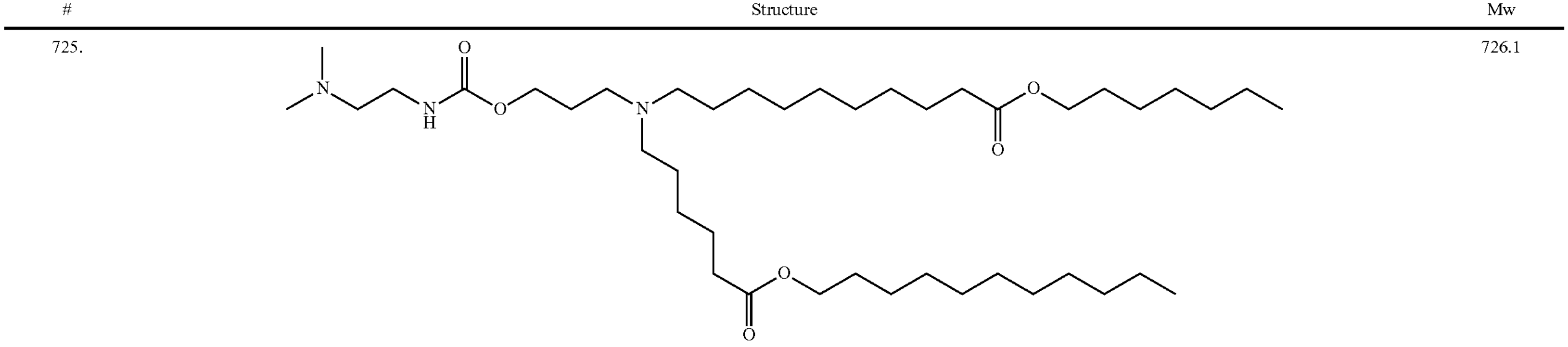 | 726.1 |
| 726. | 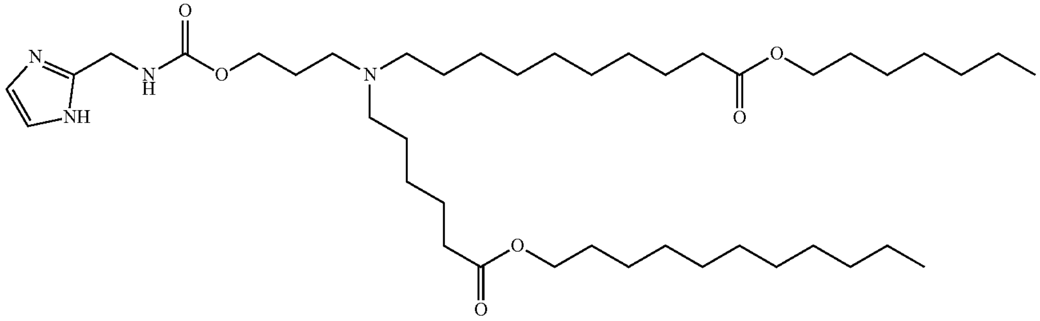 [SMILES: CCCCCCCCCCCOC(=O)CCCCCN(CCCCCCCCCC(=O)OCCCCCCC)CCCOC(=O)NCc1ncc[nH]1] | 735.1 |
| 727. | 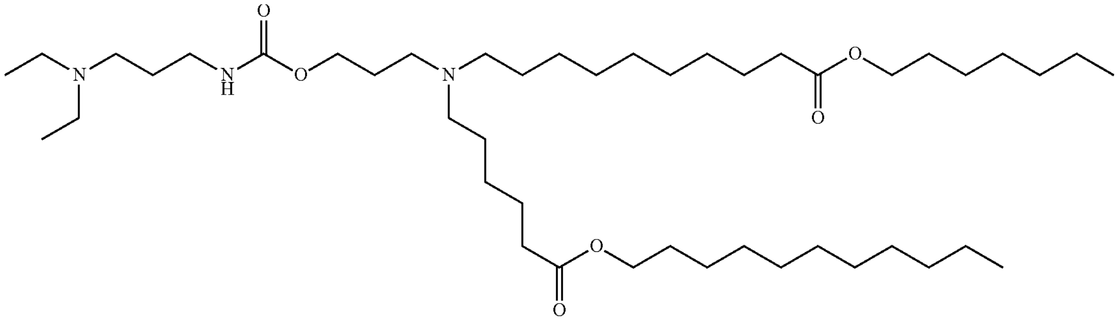 [SMILES: CCCCCCCCCCCOC(=O)CCCCCN(CCCCCCCCCC(=O)OCCCCCCC)CCCOC(=O)NCCCN(CC)CC] | 768.2 |

TABLE 1-continued
| # | Structure | Mw |
|---|---|---|
| 728. | 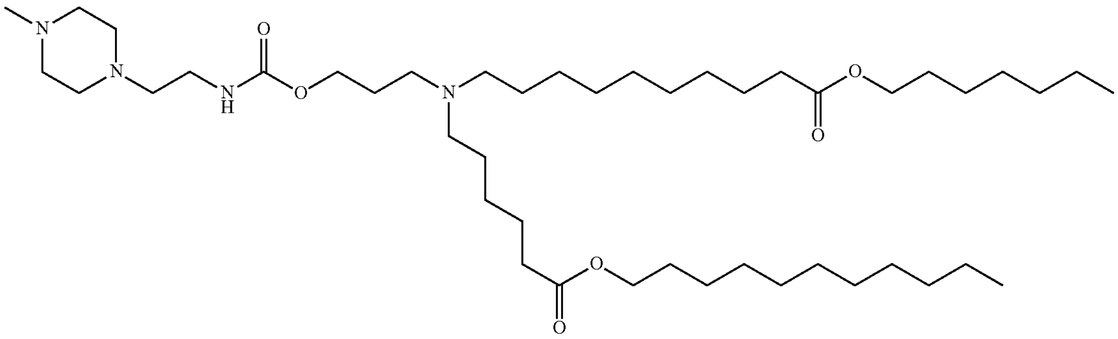 [SMILES: CCCCCCCCCCCOC(=O)CCCCCN(CCCCCCCCCC(=O)OCCCCCCC)CCCOC(=O)NCCN1CCN(C)CC1] | 781.2 |
| 729. | 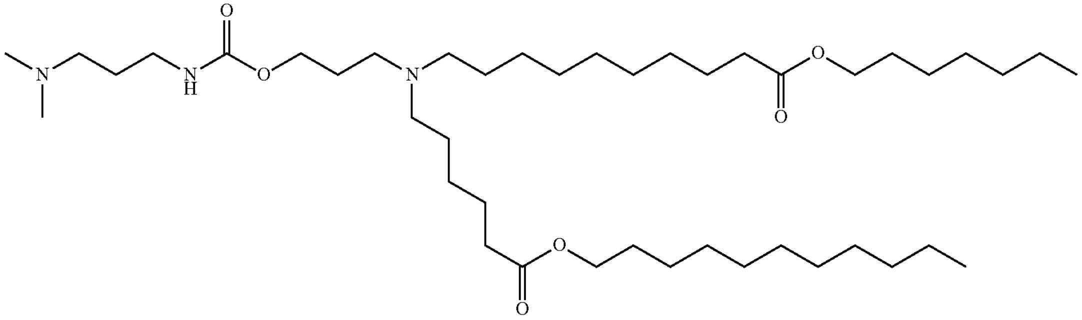 [SMILES: CCCCCCCCCCCOC(=O)CCCCCN(CCCCCCCCCC(=O)OCCCCCCC)CCCOC(=O)NCCCN(C)C] | 740.1 |
| 730. | 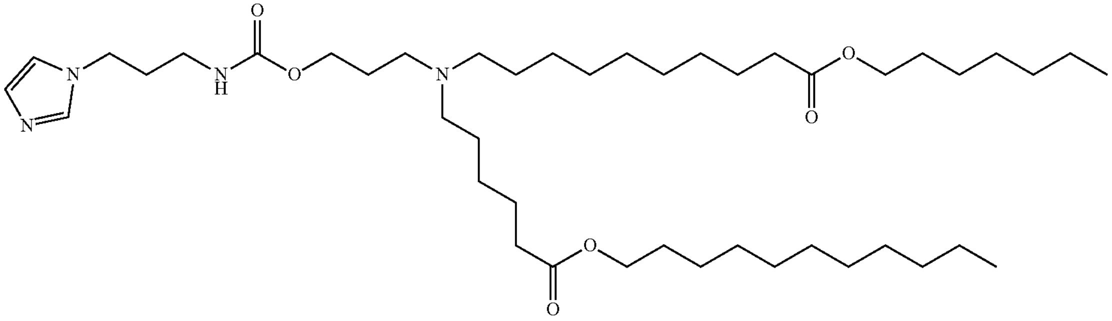 [SMILES: CCCCCCCCCCCOC(=O)CCCCCN(CCCCCCCCCC(=O)OCCCCCCC)CCCOC(=O)NCCCn1ccnc1] | 763.1 |

TABLE 1-continued
| # | Structure | Mw |
|---|---|---|
| 731. | 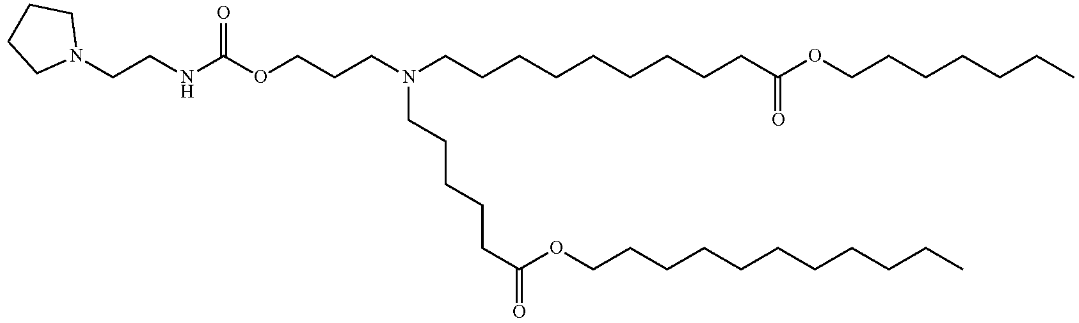 [SMILES: CCCCCCCCCCCOC(=O)CCCCCN(CCCCCCCCCC(=O)OCCCCCCC)CCCOC(=O)NCCN1CCCC1] | 752.2 |
| 732. | 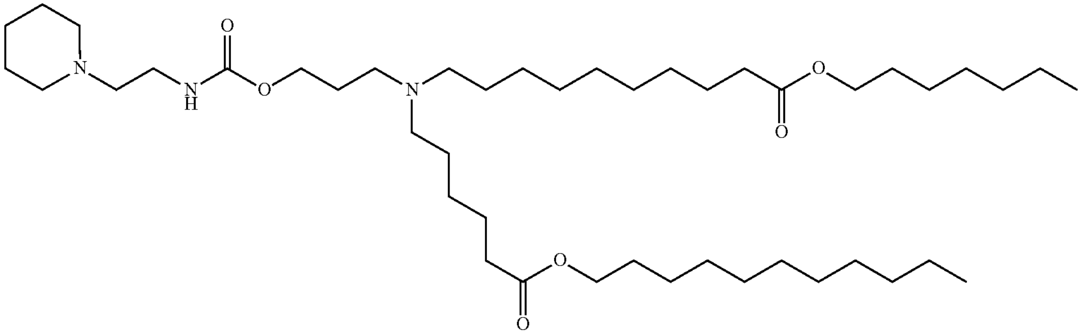 [SMILES: CCCCCCCCCCCOC(=O)CCCCCN(CCCCCCCCCC(=O)OCCCCCCC)CCCOC(=O)NCCN1CCCCC1] | 766.2 |
| 733. | 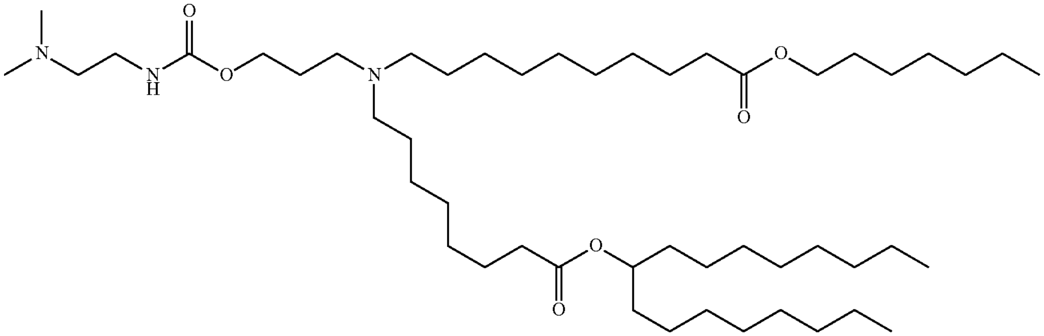 [SMILES: CCCCCCCCC(CCCCCCCC)OC(=O)CCCCCCCN(CCCCCCCCCC(=O)OCCCCCCC)CCCOC(=O)NCCN(C)C] | 838.3 |

TABLE 1-continued
| # | Structure | Mw |
| --- | --- | --- |
| 734. | 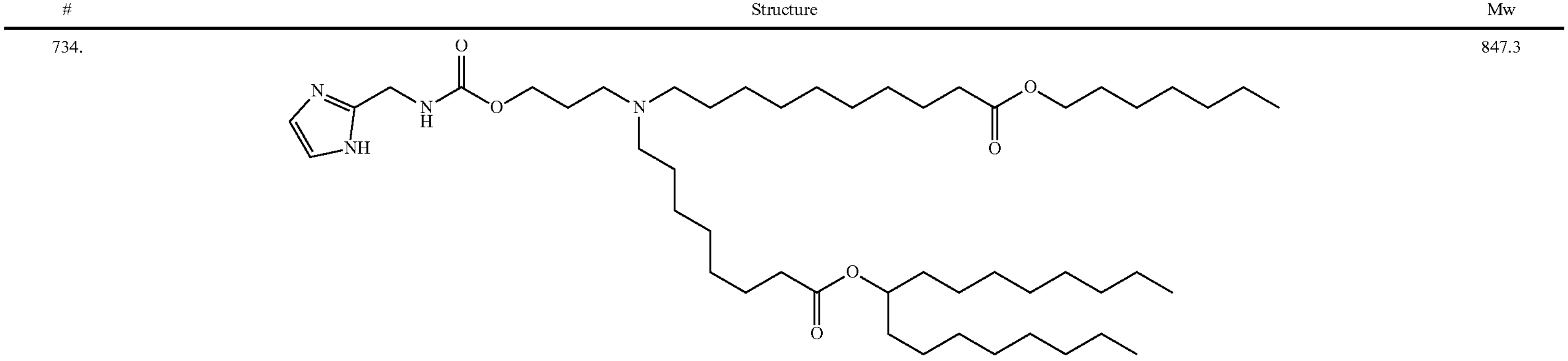 | 847.3 |
| 735. | 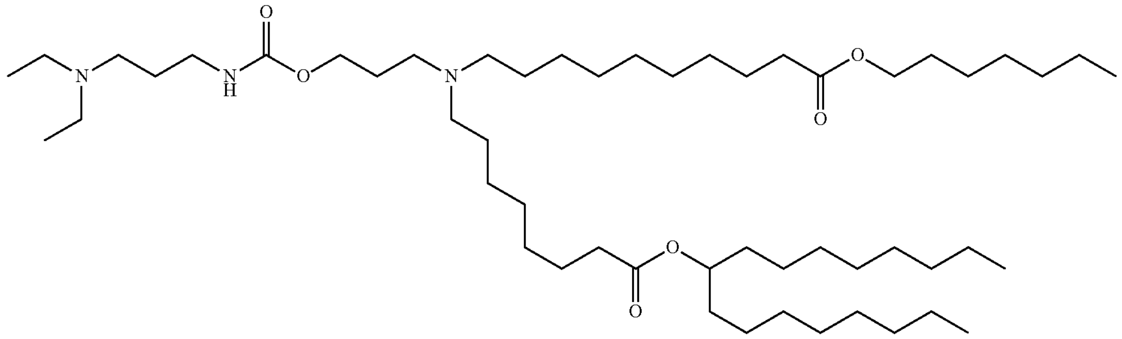 [SMILES: CCCCCCCCC(CCCCCCCC)OC(=O)CCCCCCCN(CCCCCCCCCC(=O)OCCCCCCC)CCCOC(=O)NCCCN(CC)CC] | 880.4 |
| 736. | 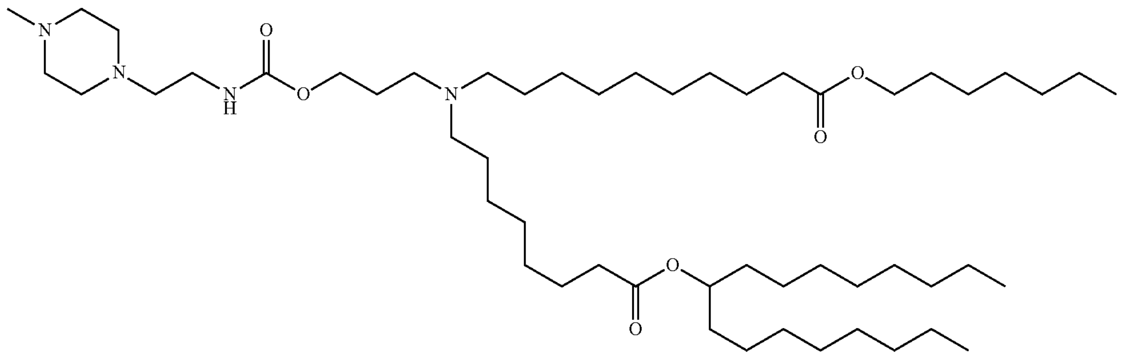 [SMILES: CCCCCCCCC(CCCCCCCC)OC(=O)CCCCCCCN(CCCCCCCCCC(=O)OCCCCCCC)CCCOC(=O)NCCN1CCN(C)CC1] | 893.4 |

TABLE 1-continued
| # | Structure | Mw |
|---|---|---|
| 737. | 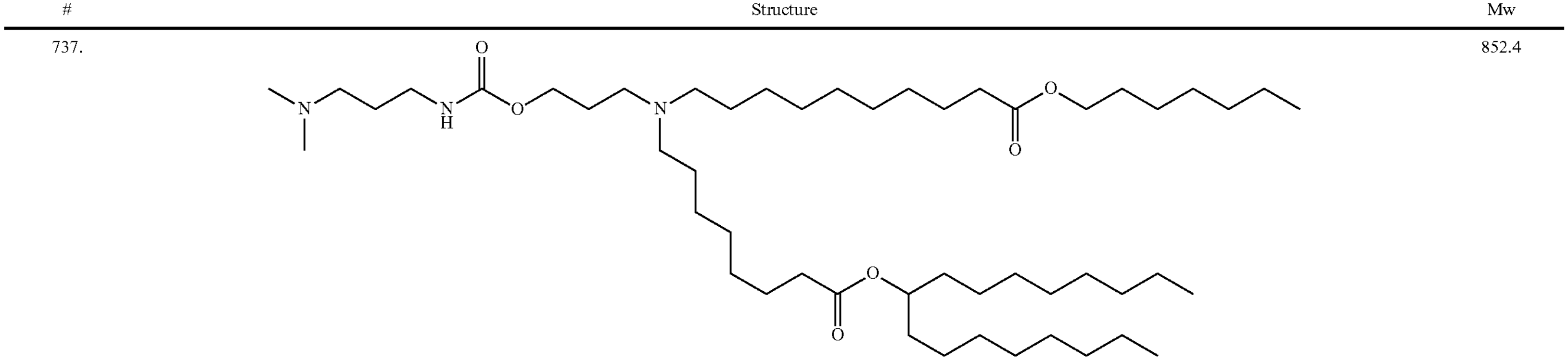 | 852.4 |
| 738. | 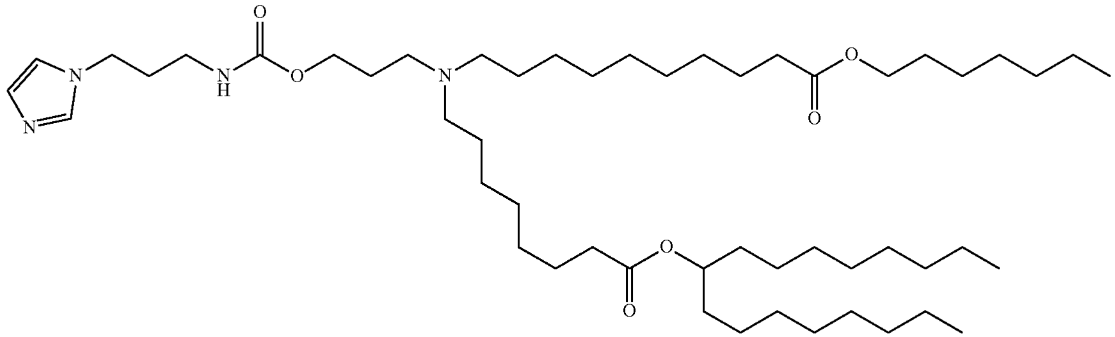 [SMILES: CCCCCCCCC(CCCCCCCC)OC(=O)CCCCCCCN(CCCCCCCCCC(=O)OCCCCCCC)CCCOC(=O)NCCCn1ccnc1] | 875.4 |
| 739. | 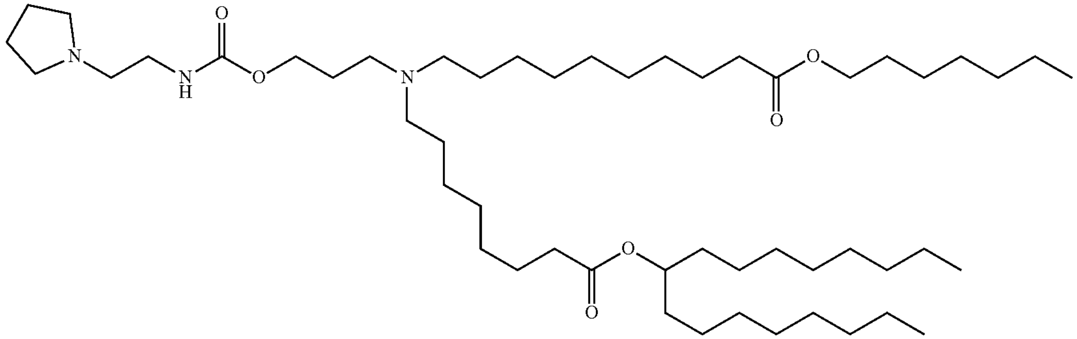 [SMILES: CCCCCCCCC(CCCCCCCC)OC(=O)CCCCCCCN(CCCCCCCCCC(=O)OCCCCCCC)CCCOC(=O)NCCN1CCCC1] | 864.4 |

TABLE 1-continued
| # | Structure | Mw |
| --- | --- | --- |
| 740. | 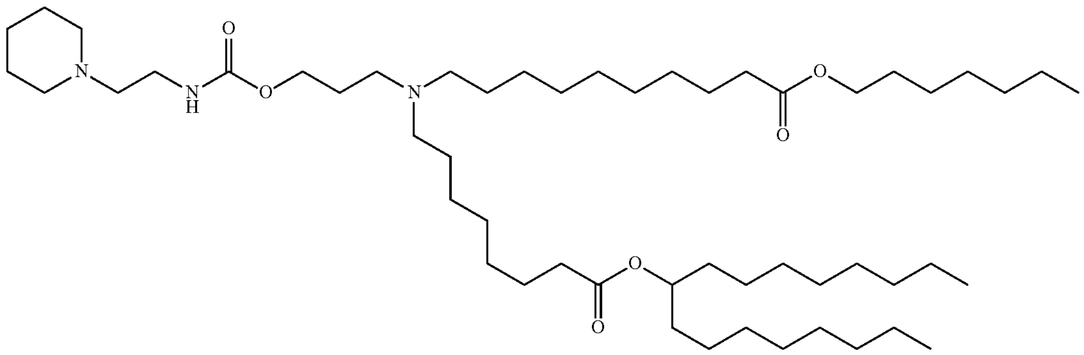 [SMILES: CCCCCCCCC(CCCCCCCC)OC(=O)CCCCCCCN(CCCCCCCCCC(=O)OCCCCCCC)CCCOC(=O)NCCN1CCCCC1] | 878.4 |
| 741. | 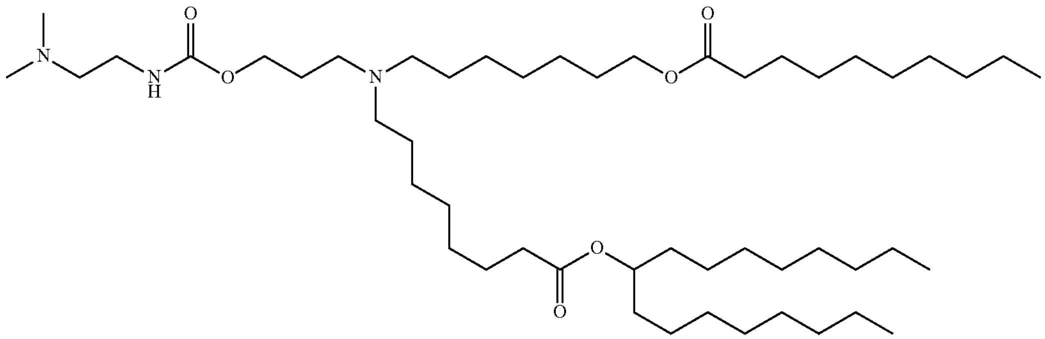 [SMILES: CCCCCCCCCC(=O)OCCCCCCCN(CCCCCCCC(=O)OC(CCCCCCCC)CCCCCCCC)CCCOC(=O)NCCN(C)C] | 838.3 |
| 742. | 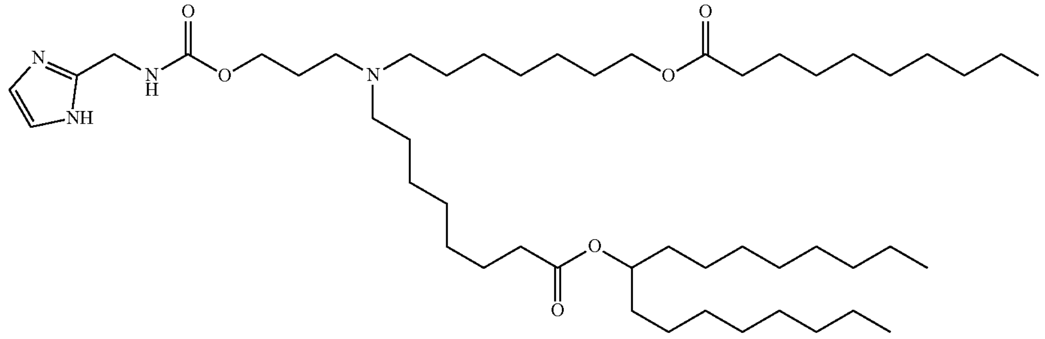 [SMILES: CCCCCCCCCC(=O)OCCCCCCCN(CCCCCCCC(=O)OC(CCCCCCCC)CCCCCCCC)CCCOC(=O)NCc1ncc[nH]1] | 847.3 |

TABLE 1-continued
| # | Structure | Mw |
| --- | --- | --- |
| 743. | 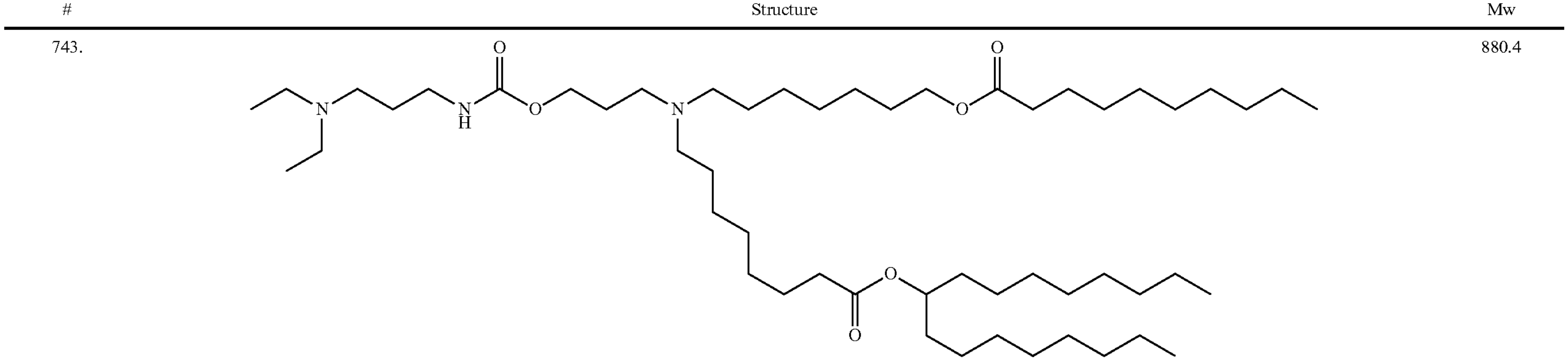 | 880.4 |
| 744. | 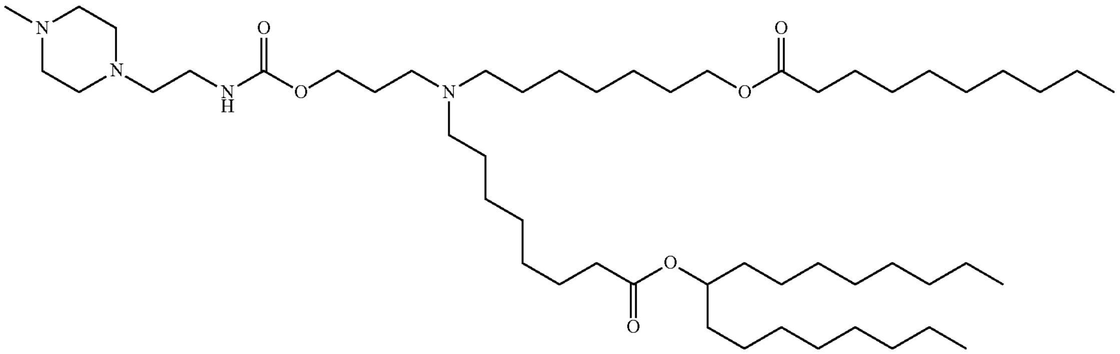 [SMILES: CCCCCCCCCC(=O)OCCCCCCCN(CCCCCCCC(=O)OC(CCCCCCCC)CCCCCCCC)CCCOC(=O)NCCN1CCN(C)CC1] | 893.4 |
| 745. | 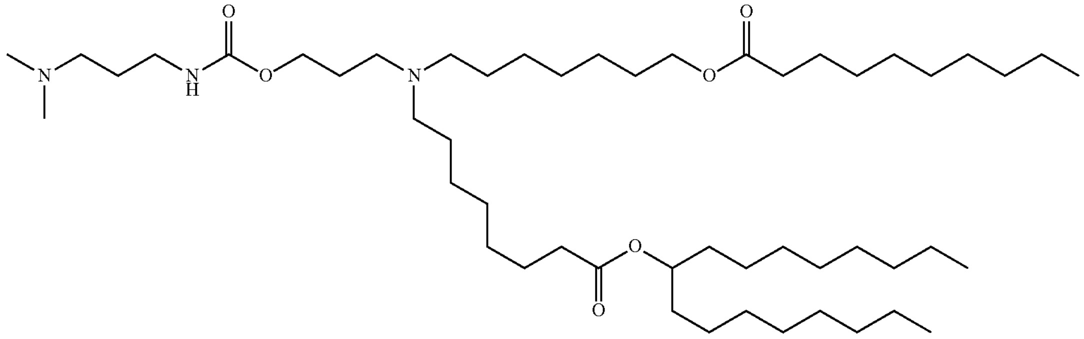 [SMILES: CCCCCCCCCC(=O)OCCCCCCCN(CCCCCCCC(=O)OC(CCCCCCCC)CCCCCCCC)CCCOC(=O)NCCCN(C)C] | 852.4 |

TABLE 1-continued
| # | Structure | Mw |
| --- | --- | --- |
| 746. | 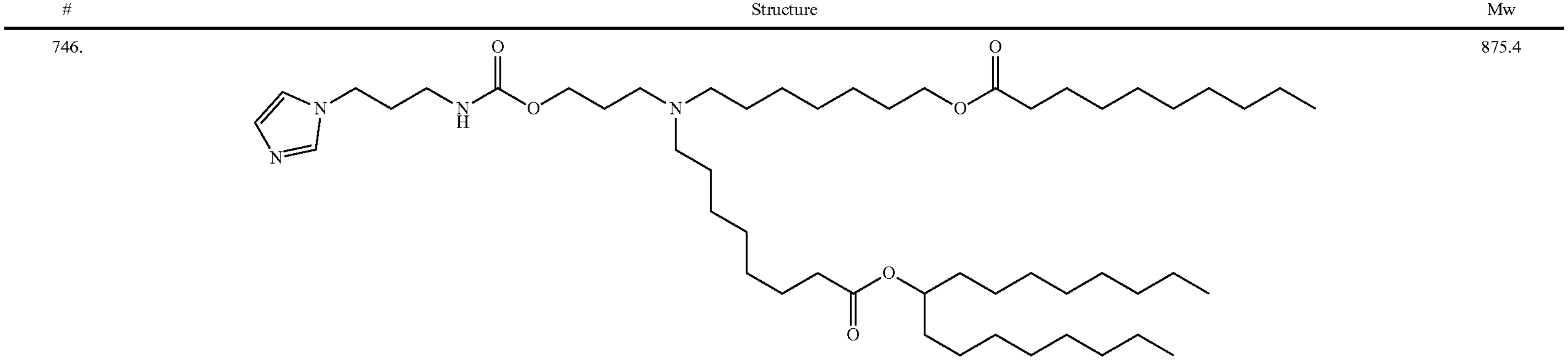 | 875.4 |
| 747. | 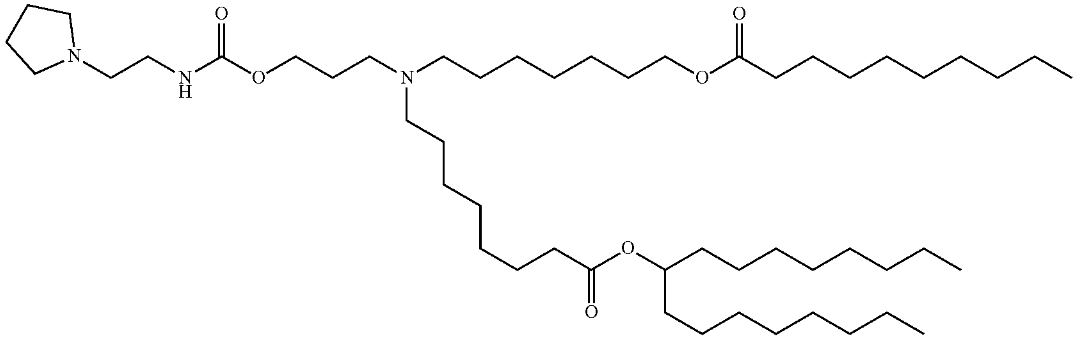 [SMILES: CCCCCCCCCC(=O)OCCCCCCCN(CCCCCCCC(=O)OC(CCCCCCCC)CCCCCCCC)CCCOC(=O)NCCN1CCCC1] | 864.4 |
| 748. | 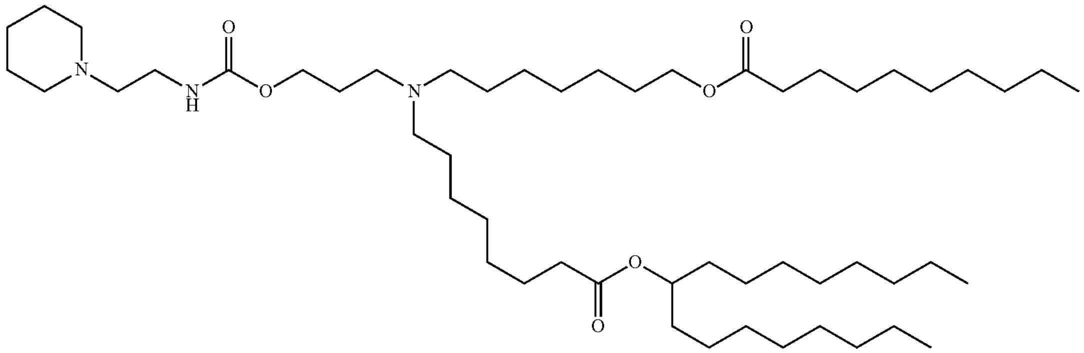 [SMILES: CCCCCCCCCC(=O)OCCCCCCCN(CCCCCCCC(=O)OC(CCCCCCCC)CCCCCCCC)CCCOC(=O)NCCN1CCCCC1] | 878.4 |

TABLE 1-continued
| # | Structure | Mw |
| --- | --- | --- |
| 749. | 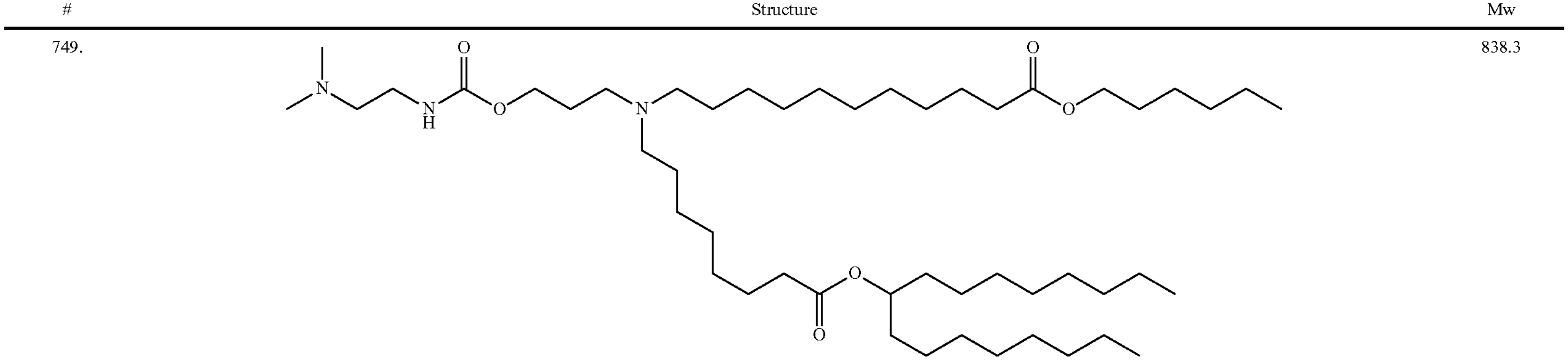 | 838.3 |
| 750. | 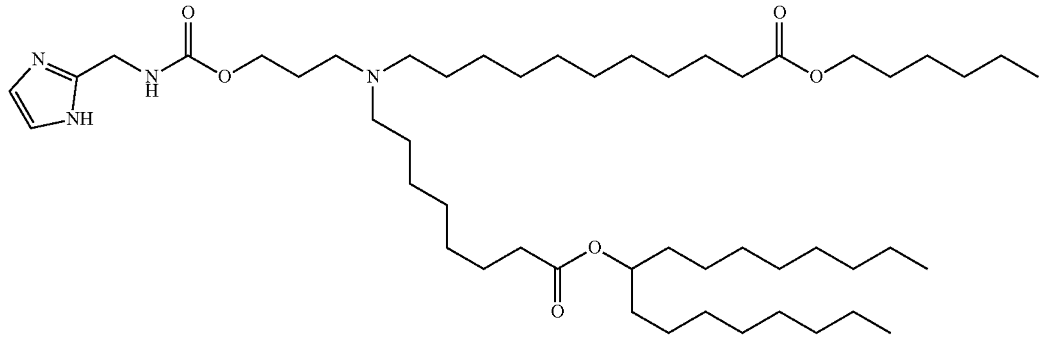 [SMILES: CCCCCCCCC(CCCCCCCC)OC(=O)CCCCCCCN(CCCCCCCCCCC(=O)OCCCCCC)CCCOC(=O)NCc1ncc[nH]1] | 847.3 |
| 751. | 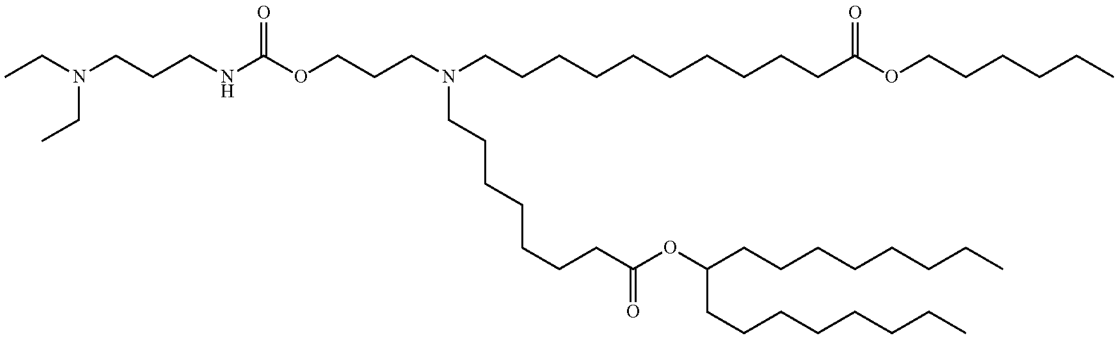 [SMILES: CCCCCCCCC(CCCCCCCC)OC(=O)CCCCCCCN(CCCCCCCCCCC(=O)OCCCCCC)CCCOC(=O)NCCCN(CC)CC] | 880.4 |

TABLE 1-continued
| # | Structure | Mw |
| --- | --- | --- |
| 752. | 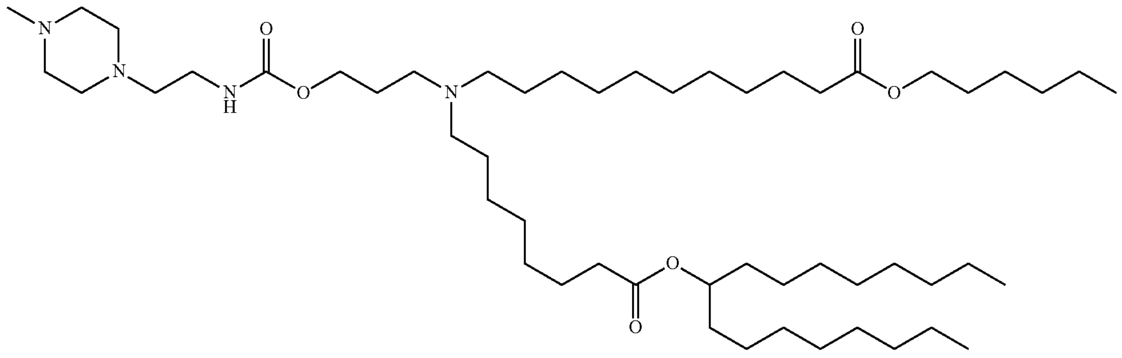 [SMILES: CCCCCCCCC(CCCCCCCC)OC(=O)CCCCCCCN(CCCCCCCCCCC(=O)OCCCCCC)CCCOC(=O)NCCN1CCN(C)CC1] | 893.4 |
| 753. | 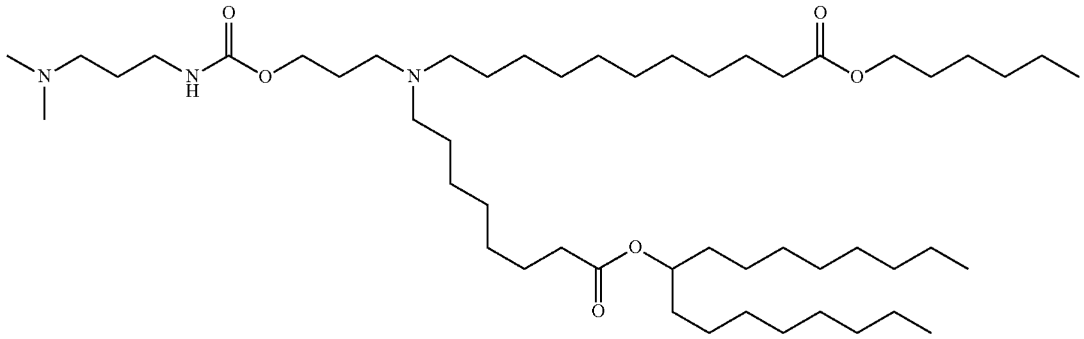 [SMILES: CCCCCCCCC(CCCCCCCC)OC(=O)CCCCCCCN(CCCCCCCCCCC(=O)OCCCCCC)CCCOC(=O)NCCCN(C)C] | 852.4 |
| 754. | 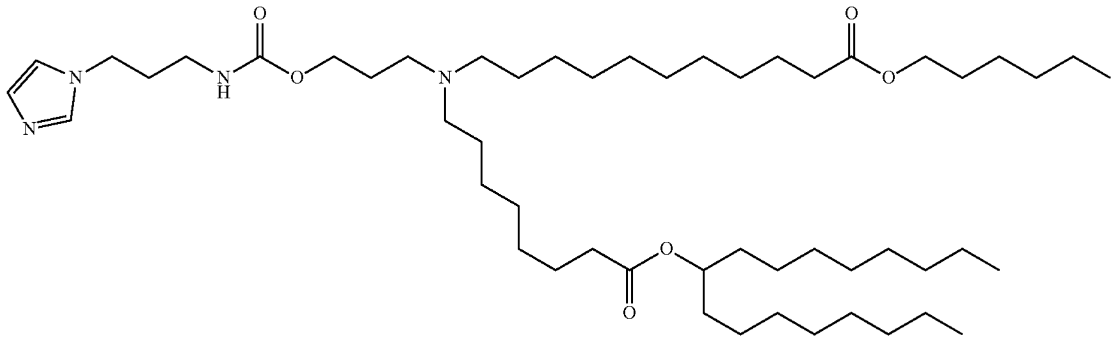 [SMILES: CCCCCCCCC(CCCCCCCC)OC(=O)CCCCCCCN(CCCCCCCCCCC(=O)OCCCCCC)CCCOC(=O)NCCCn1ccnc1] | 875.4 |

TABLE 1-continued
| # | Structure | Mw |
| --- | --- | --- |
| 755. | 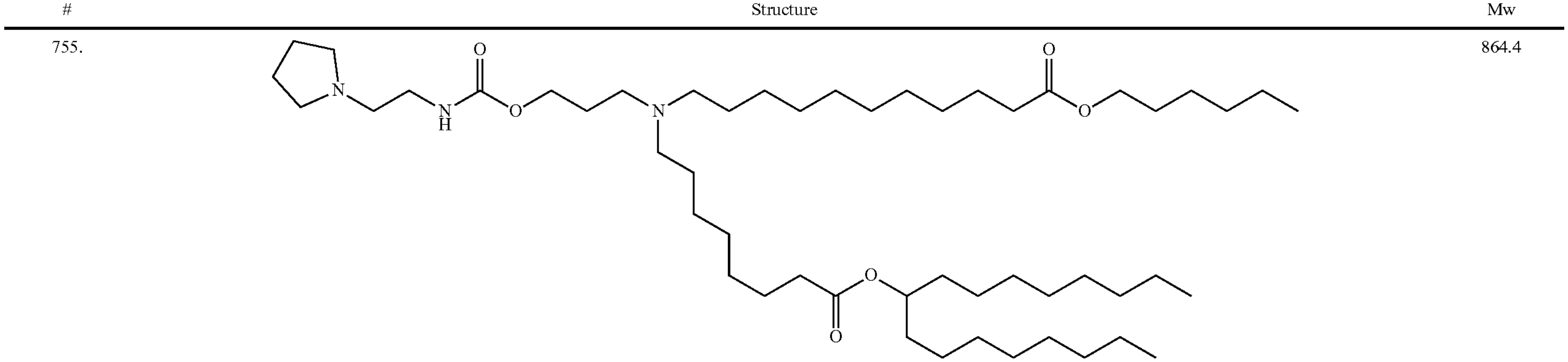 | 864.4 |
| 756. | 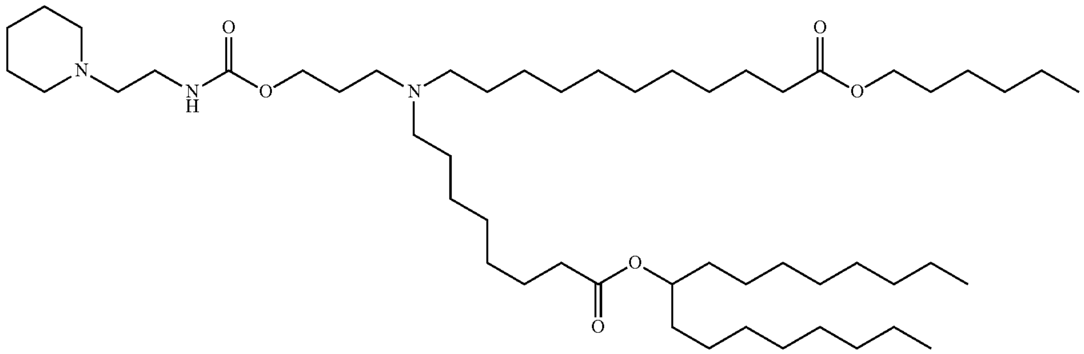 [SMILES: CCCCCCCCC(CCCCCCCC)OC(=O)CCCCCCCN(CCCCCCCCCCC(=O)OCCCCCC)CCCOC(=O)NCCN1CCCCC1] | 878.4 |
| 757. | 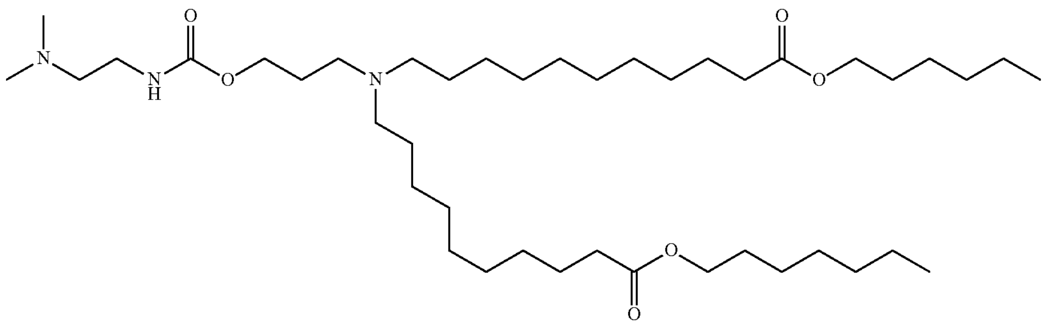 [SMILES: CCCCCCCOC(=O)CCCCCCCCCN(CCCCCCCCCCC(=O)OCCCCCC)CCCOC(=O)NCCN(C)C] | 726.1 |

TABLE 1-continued
| # | Structure | Mw |
| --- | --- | --- |
| 758. | 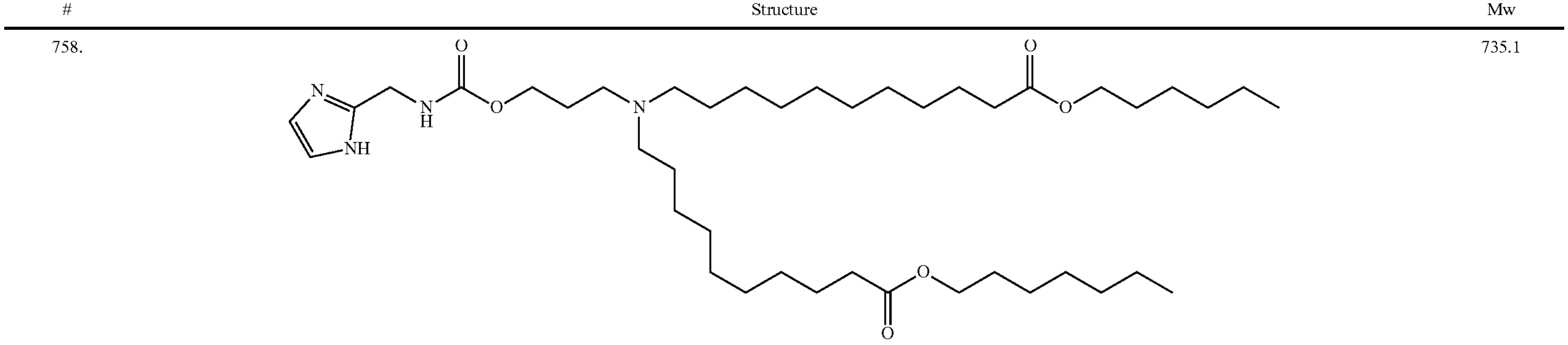 | 735.1 |
| 759. | 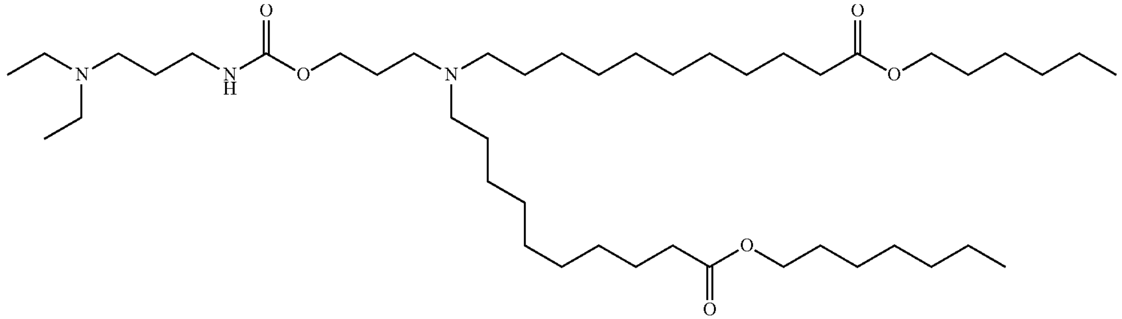 [SMILES: CCCCCCCOC(=O)CCCCCCCCCN(CCCCCCCCCCC(=O)OCCCCCC)CCCOC(=O)NCCCN(CC)CC] | 768.2 |
| 760. | 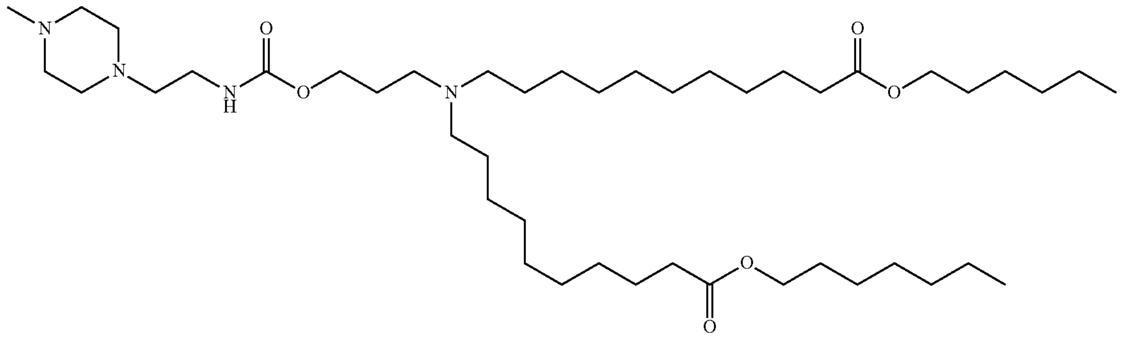 [SMILES: CCCCCCCOC(=O)CCCCCCCCCN(CCCCCCCCCCC(=O)OCCCCCC)CCCOC(=O)NCCN1CCN(C)CC1] | 781.2 |

TABLE 1-continued
| # | Structure | Mw |
| --- | --- | --- |
| 761. | 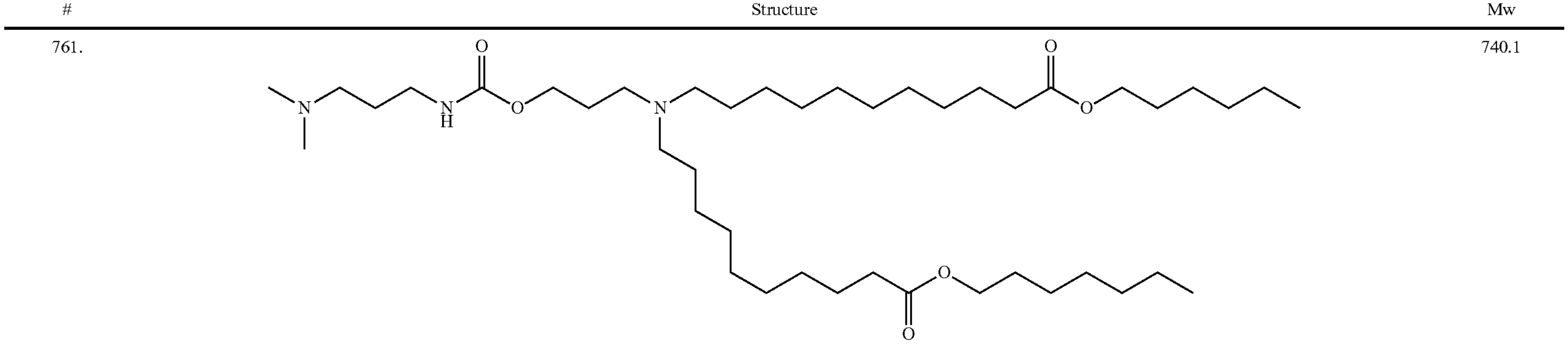 | 740.1 |
| 762. | 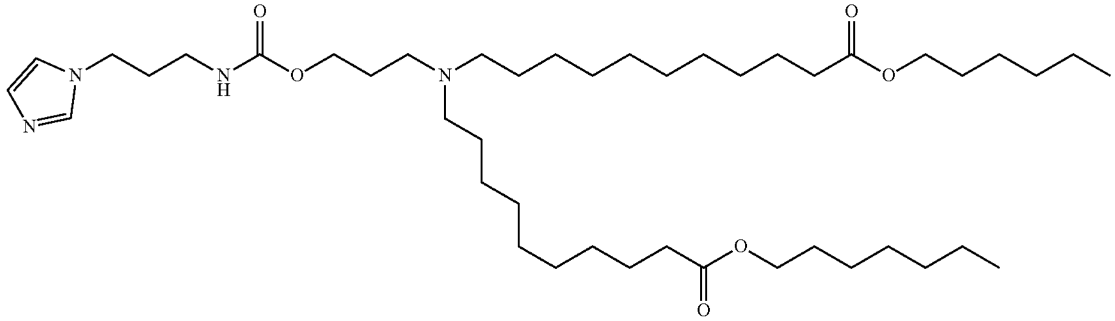 [SMILES: CCCCCCCOC(=O)CCCCCCCCCN(CCCCCCCCCCC(=O)OCCCCCC)CCCOC(=O)NCCCn1ccnc1] | 763.1 |
| 763. | 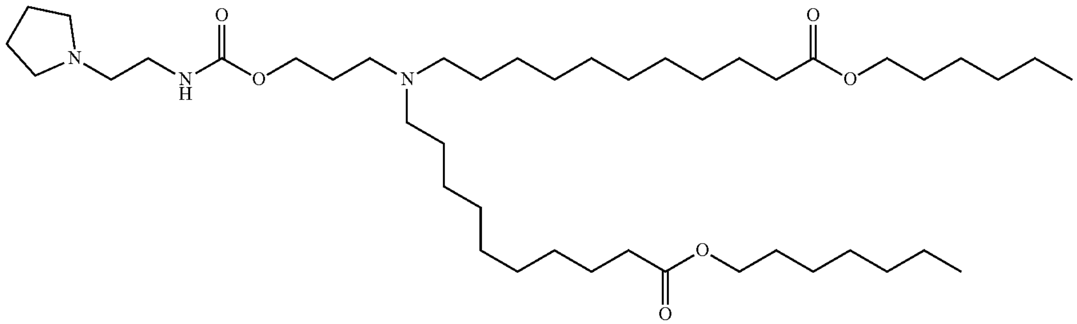 [SMILES: CCCCCCCOC(=O)CCCCCCCCCN(CCCCCCCCCCC(=O)OCCCCCC)CCCOC(=O)NCCN1CCCC1] | 752.2 |

TABLE 1-continued
| # | Structure | Mw |
| --- | --- | --- |
| 764. | 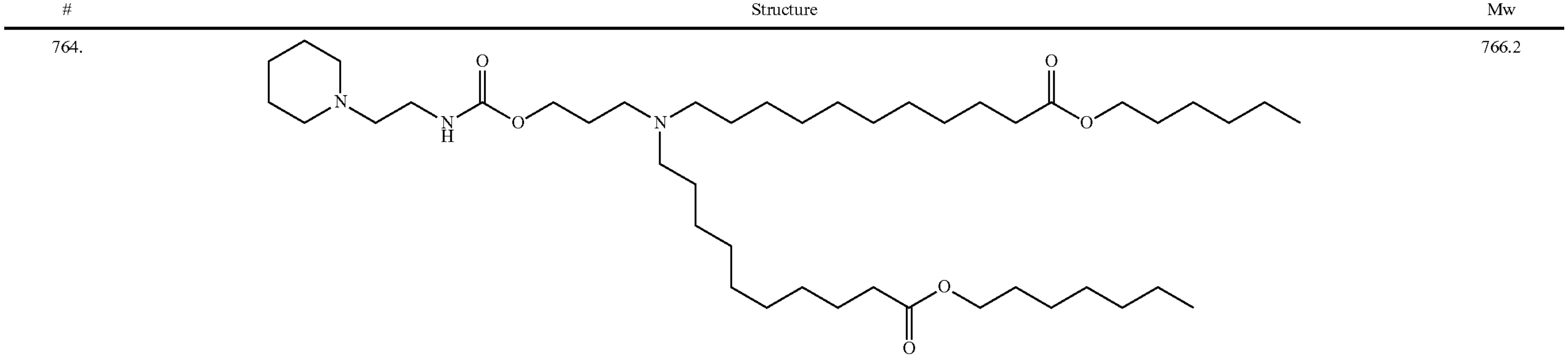 | 766.2 |
| 765. | 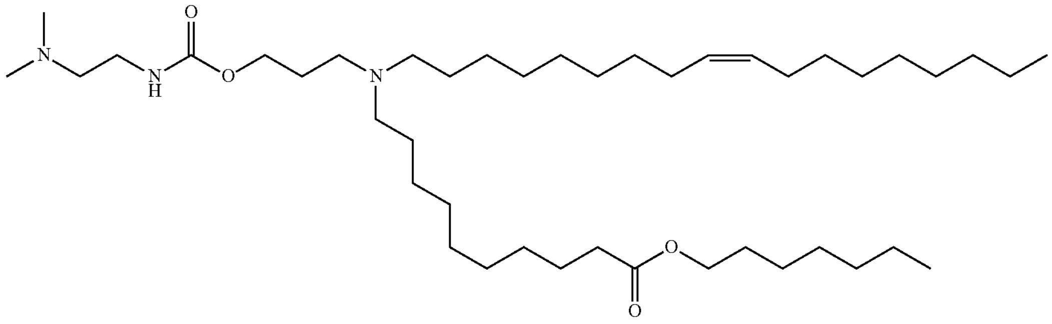 [SMILES: CCCCCCCC/C=C\CCCCCCCCN(CCCCCCCCCC(=O)OCCCCCCC)CCCOC(=O)NCCN(C)C] | 708.1 |
| 766. | 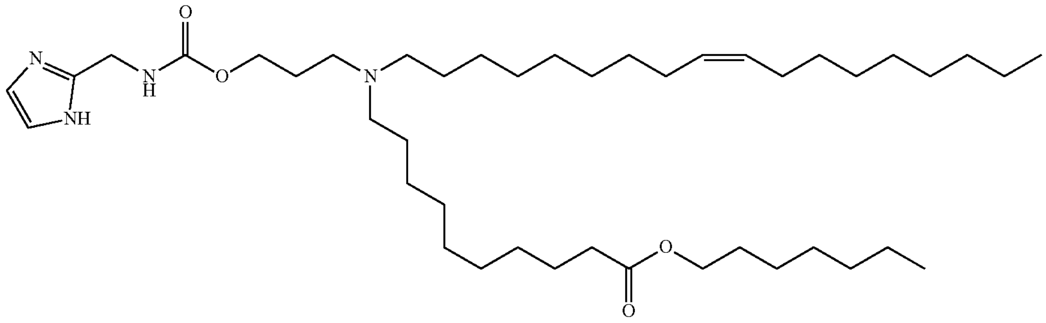 [SMILES: CCCCCCCC/C=C\CCCCCCCCN(CCCCCCCCCC(=O)OCCCCCCC)CCCOC(=O)NCc1ncc[nH]1] | 717.1 |

TABLE 1-continued
| # | Structure | Mw |
| --- | --- | --- |
| 767. | 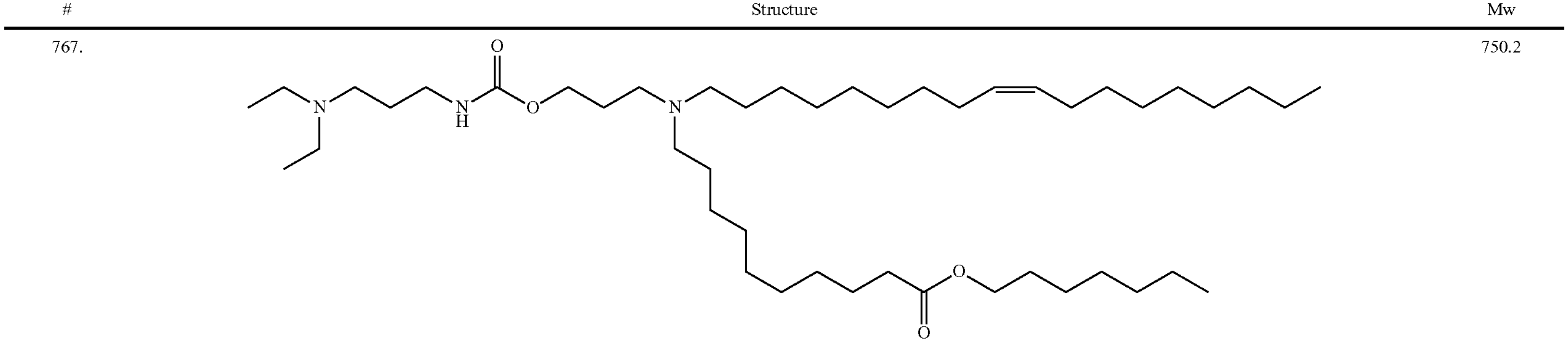 | 750.2 |
| 768. | 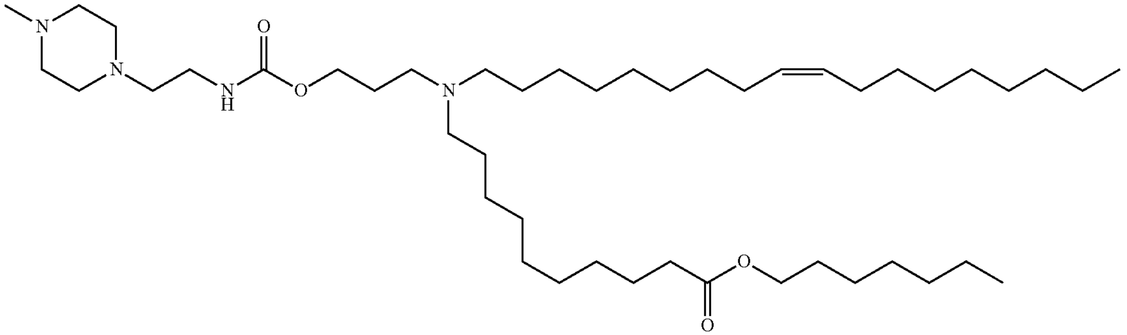 [SMILES: CCCCCCCC/C=C\CCCCCCCCN(CCCCCCCCCC(=O)OCCCCCCC)CCCOC(=O)NCCN1CCN(C)CC1] | 763.2 |
| 769. | 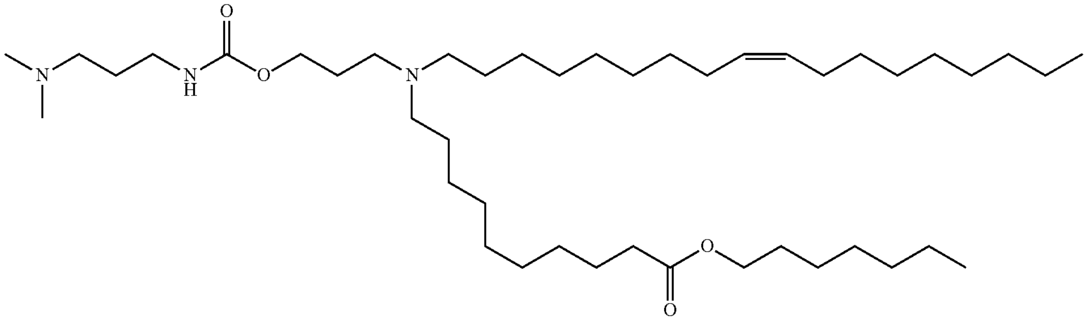 [SMILES: CCCCCCCC/C=C\CCCCCCCCN(CCCCCCCCCC(=O)OCCCCCCC)CCCOC(=O)NCCCN(C)C] | 722.2 |

TABLE 1-continued
| # | Structure | Mw |
| --- | --- | --- |
| 770. | 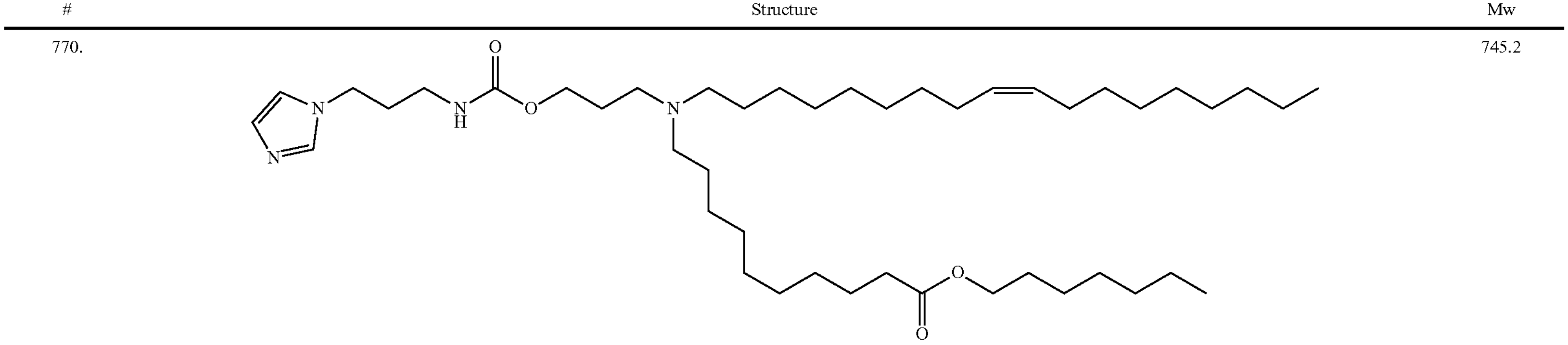 | 745.2 |
| 771. | 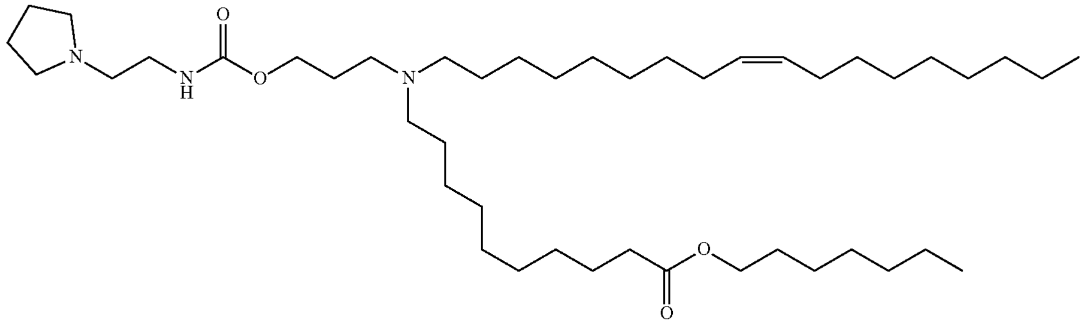 [SMILES: CCCCCCCC/C=C\CCCCCCCCN(CCCCCCCCCC(=O)OCCCCCCC)CCCOC(=O)NCCN1CCCC1] | 734.2 |
| 772. | 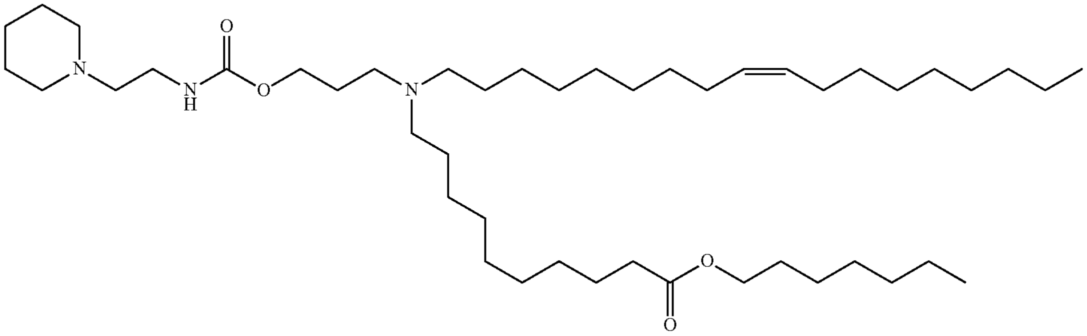 [SMILES: CCCCCCCC/C=C\CCCCCCCCN(CCCCCCCCCC(=O)OCCCCCCC)CCCOC(=O)NCCN1CCCCC1] | 748.2 |

TABLE 1-continued
| # | Structure | Mw |
|---|---|---|
| 773. | 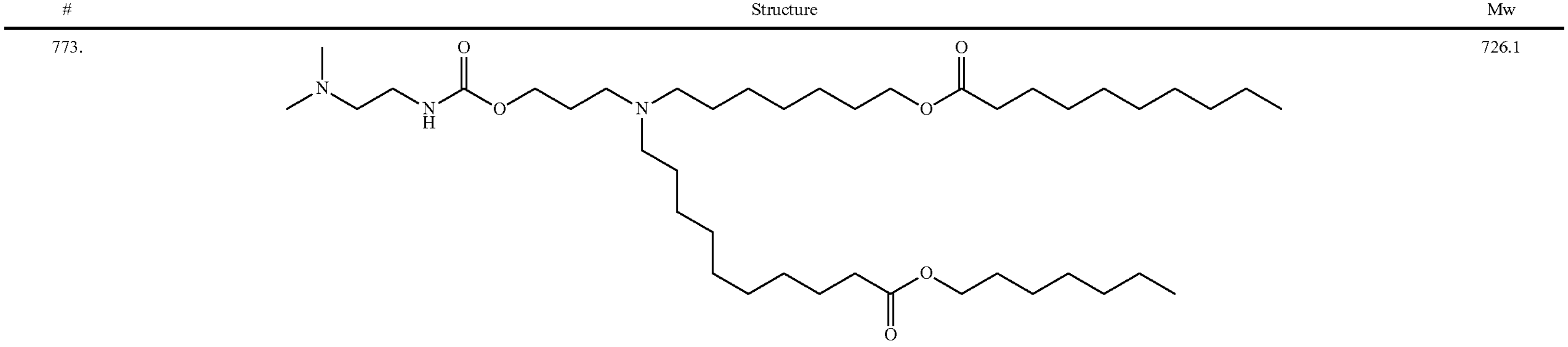 | 726.1 |
| 774. | 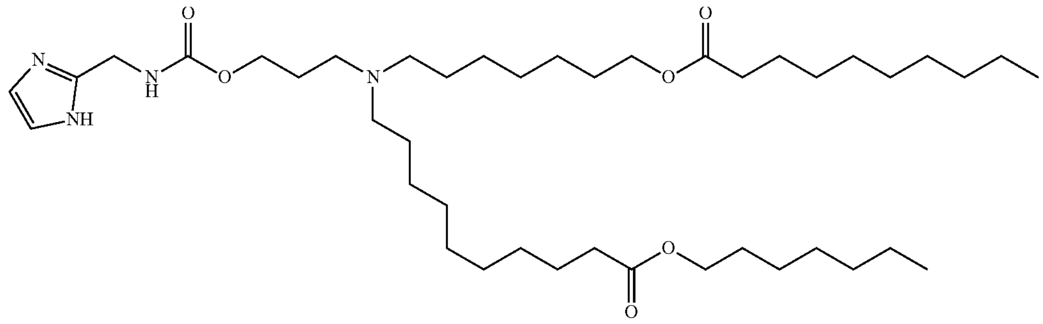 [SMILES: CCCCCCCCCC(=O)OCCCCCCCN(CCCCCCCCCC(=O)OCCCCCCC)CCCOC(=O)NCc1ncc[nH]1] | 735.1 |
| 775. | 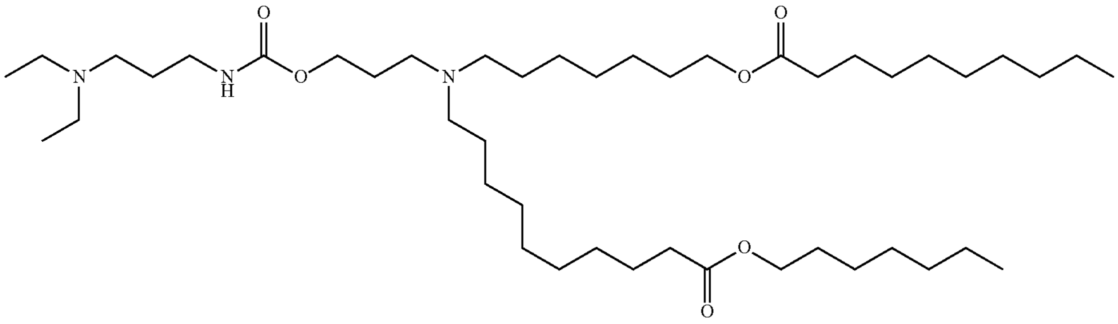 [SMILES: CCCCCCCCCC(=O)OCCCCCCCN(CCCCCCCCCC(=O)OCCCCCCC)CCCOC(=O)NCCCN(CC)CC] | 768.2 |

TABLE 1-continued
| # | Structure | Mw |
|---|---|---|
| 776. | 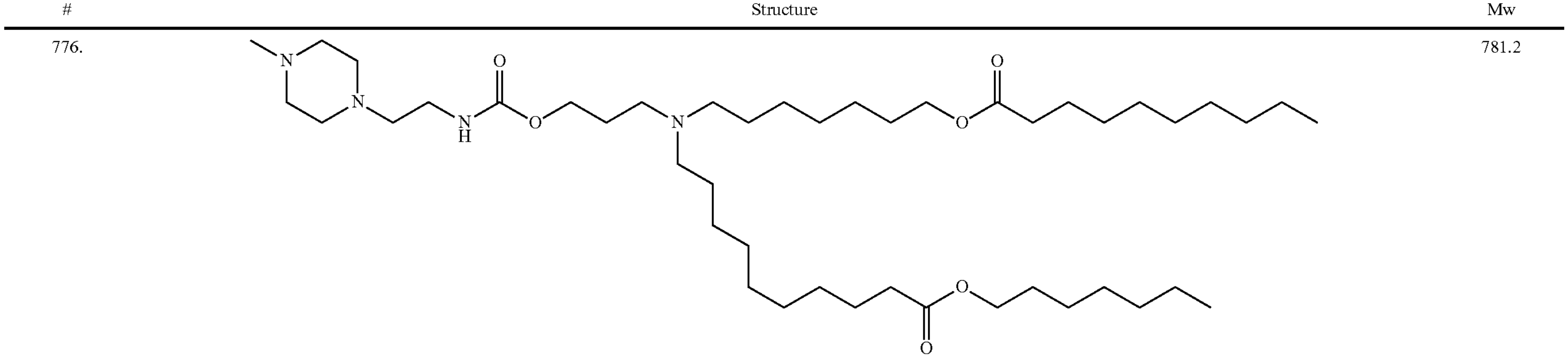 | 781.2 |
| 777. | 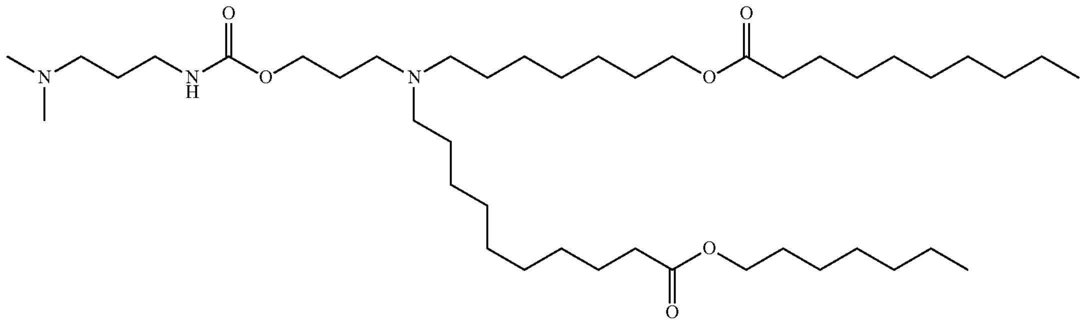 [SMILES: CCCCCCCCCC(=O)OCCCCCCCN(CCCCCCCCCC(=O)OCCCCCCC)CCCOC(=O)NCCCN(C)C] | 740.1 |
| 778. | 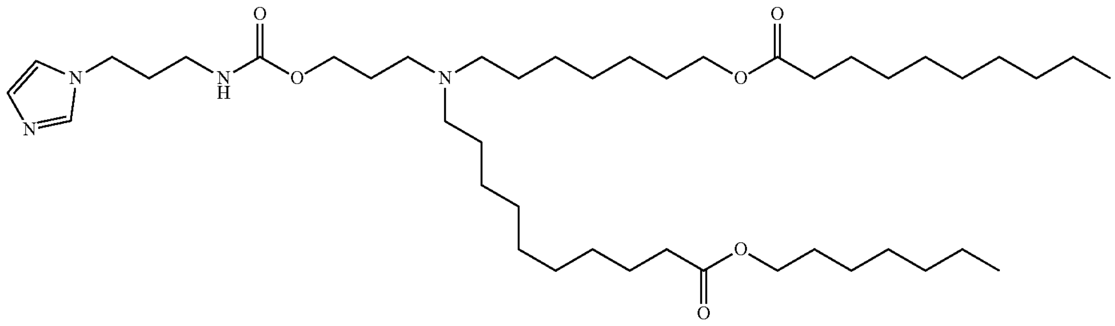 [SMILES: CCCCCCCCCC(=O)OCCCCCCCN(CCCCCCCCCC(=O)OCCCCCCC)CCCOC(=O)NCCCn1ccnc1] | 763.1 |

TABLE 1-continued
| # | Structure | Mw |
| --- | --- | --- |
| 779. | 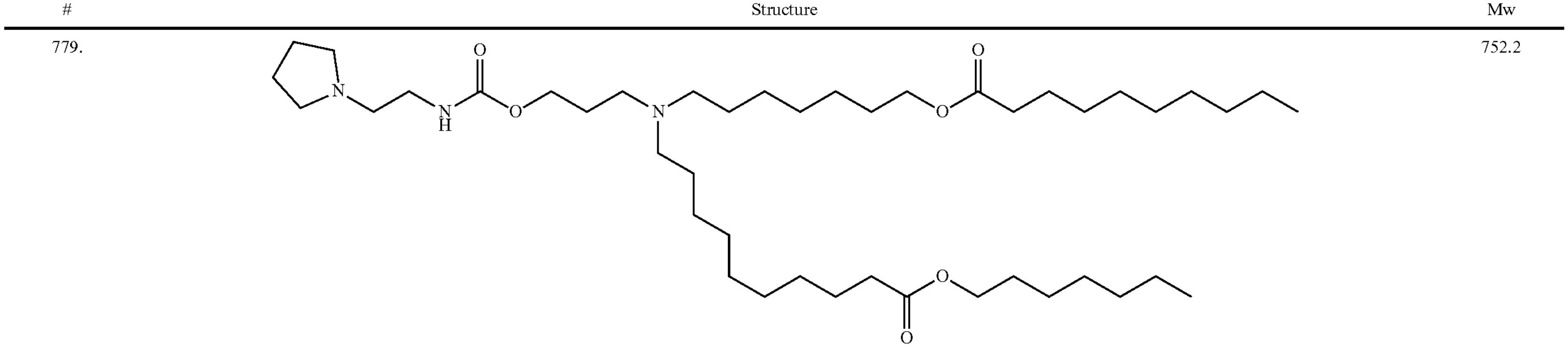 | 752.2 |
| 780. | 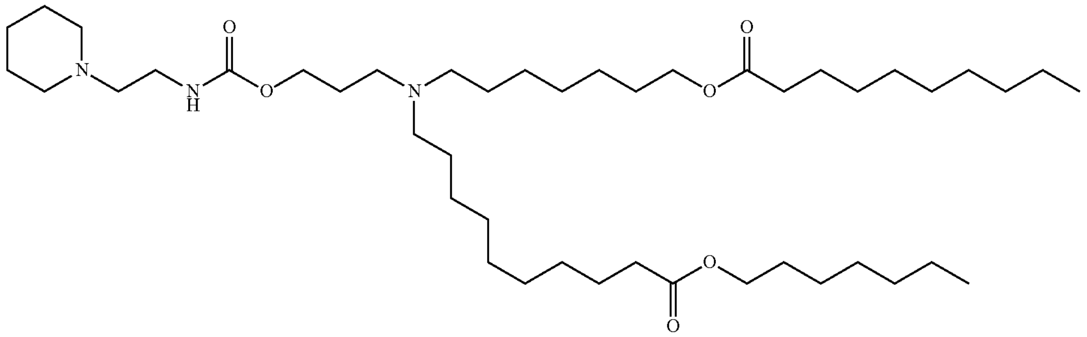 [SMILES: CCCCCCCCCC(=O)OCCCCCCCN(CCCCCCCCCC(=O)OCCCCCCC)CCCOC(=O)NCCN1CCCCC1] | 766.2 |
| 781. | 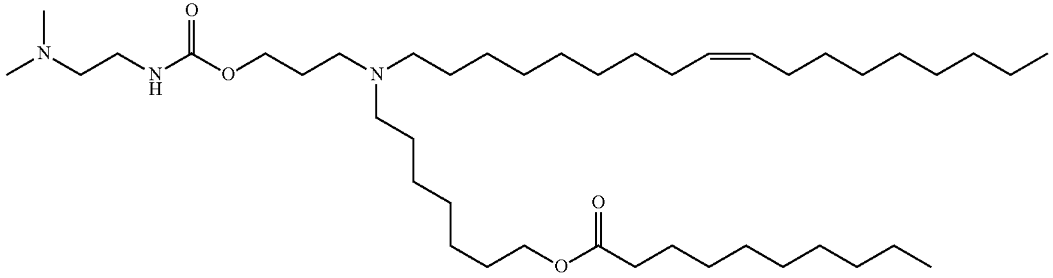 [SMILES: CCCCCCCC/C=C\CCCCCCCCN(CCCCCCCOC(=O)CCCCCCCCC)CCCOC(=O)NCCN(C)C] | 708.1 |

TABLE 1-continued
| # | Structure | Mw |
| --- | --- | --- |
| 782. | 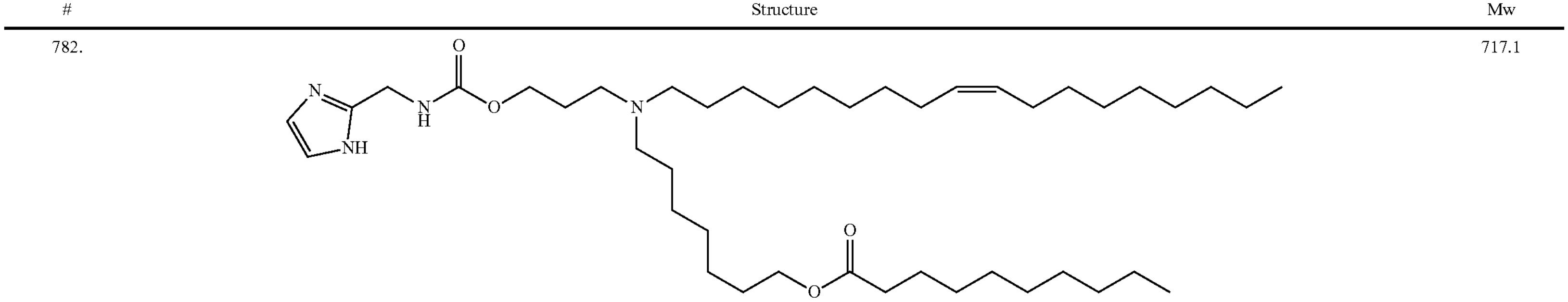 | 717.1 |
| 783. | 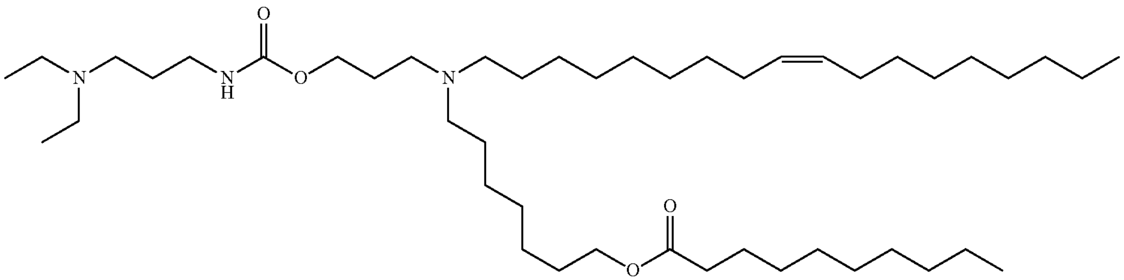 [SMILES: CCCCCCCC/C=C\CCCCCCCCN(CCCCCCCOC(=O)CCCCCCCCC)CCCOC(=O)NCCCN(CC)CC] | 750.2 |
| 784. | 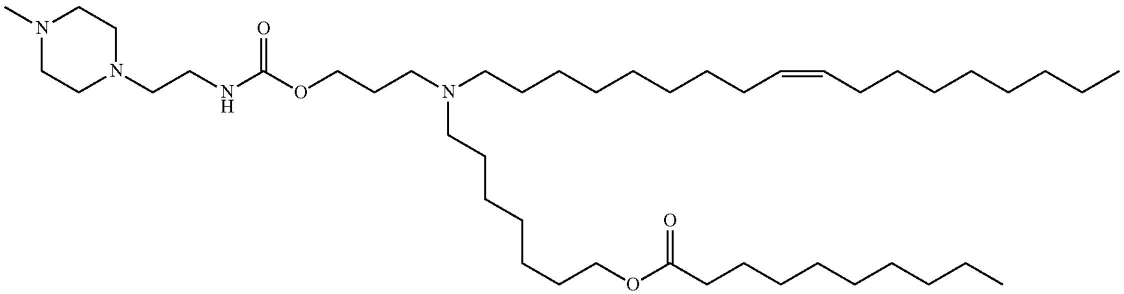 [SMILES: CCCCCCCC/C=C\CCCCCCCCN(CCCCCCCOC(=O)CCCCCCCCC)CCCOC(=O)NCCN1CCN(C)CC1] | 763.2 |

TABLE 1-continued
| # | Structure | Mw |
|---|---|---|
| 785. | 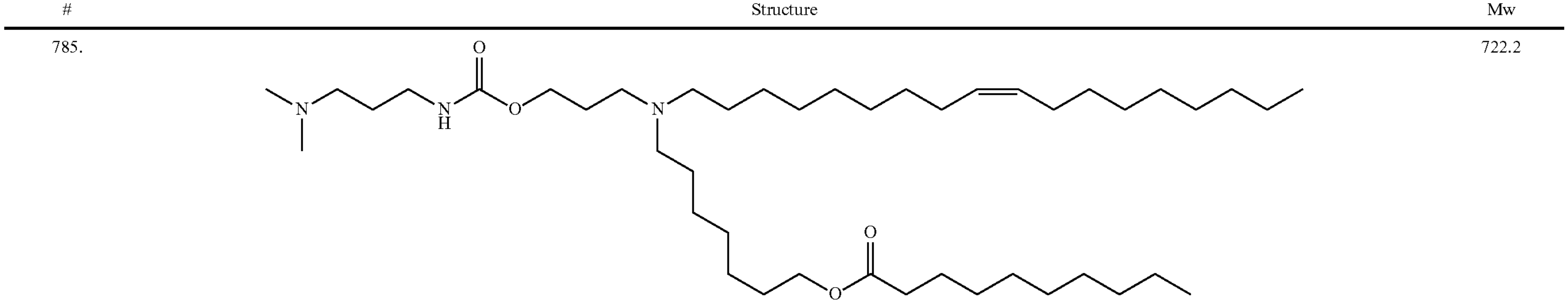 | 722.2 |
| 786. | 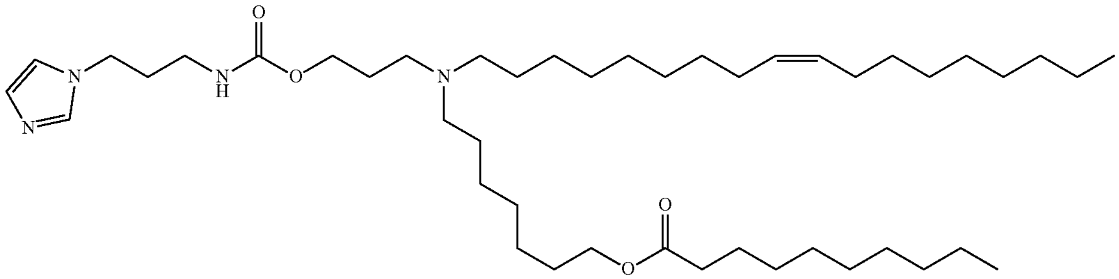 [SMILES: CCCCCCCC/C=C\CCCCCCCCN(CCCCCCCOC(=O)CCCCCCCCC)CCCOC(=O)NCCCn1ccnc1] | 745.2 |
| 787. | 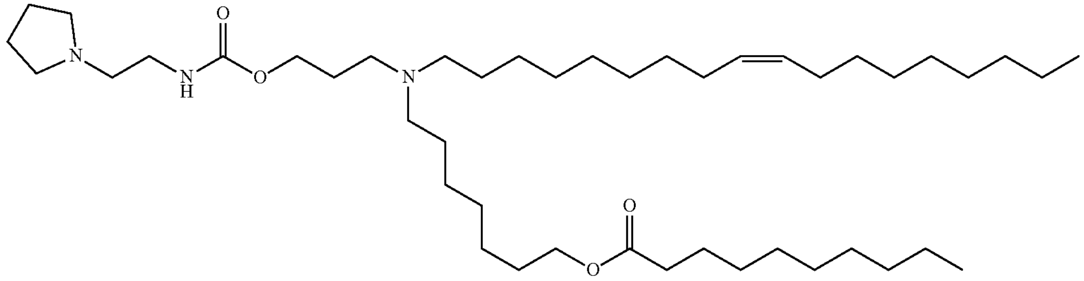 [SMILES: CCCCCCCC/C=C\CCCCCCCCN(CCCCCCCOC(=O)CCCCCCCCC)CCCOC(=O)NCCN1CCCC1] | 734.2 |

TABLE 1-continued
| # | Structure | Mw |
|---|---|---|
| 788. | 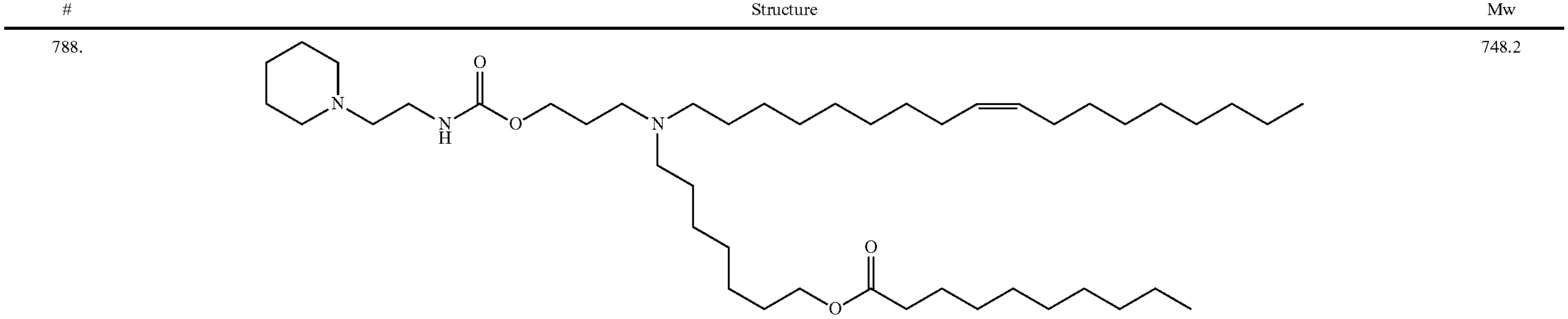 | 748.2 |
| 789. | 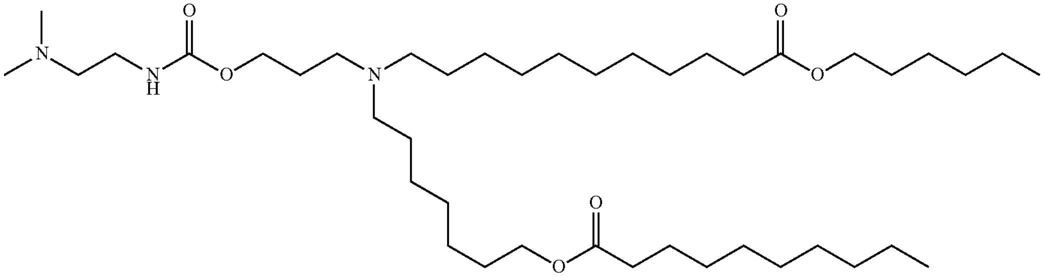 [SMILES: CCCCCCCCCC(=O)OCCCCCCCN(CCCCCCCCCCC(=O)OCCCCCC)CCCOC(=O)NCCN(C)C] | 726.1 |
| 790. | 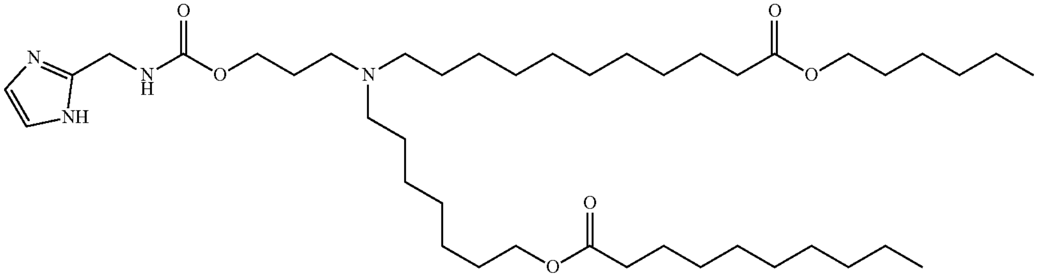 [SMILES: CCCCCCCCCC(=O)OCCCCCCCN(CCCCCCCCCCC(=O)OCCCCCC)CCCOC(=O)NCc1ncc[nH]1] | 735.1 |

TABLE 1-continued
| # | Structure | Mw |
| --- | --- | --- |
| 791. | 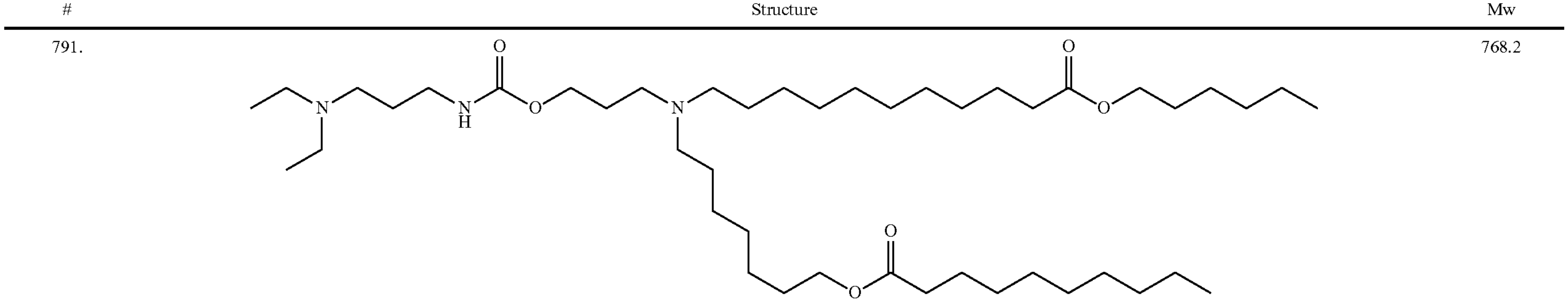 | 768.2 |
| 792. | 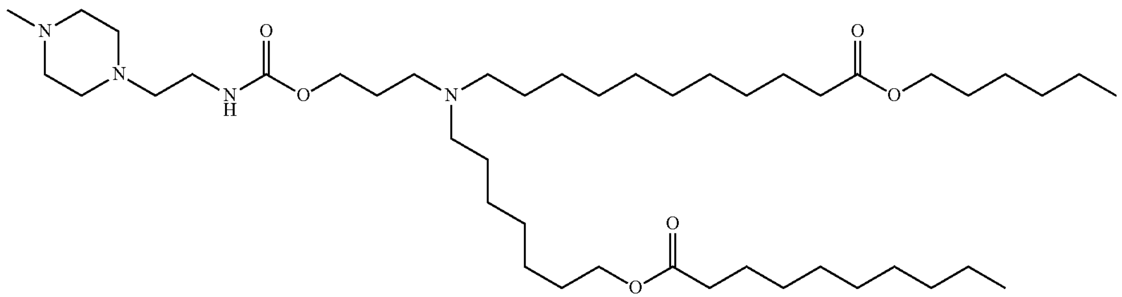 [SMILES: CCCCCCCCCC(=O)OCCCCCCCN(CCCCCCCCCCC(=O)OCCCCCC)CCCOC(=O)NCCN1CCN(C)CC1] | 781.2 |
| 793. | 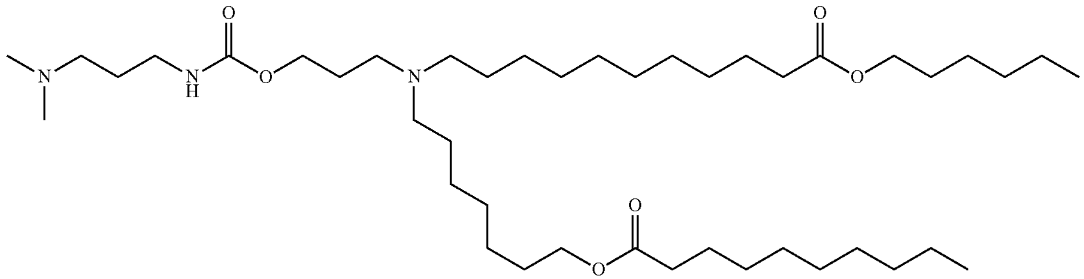 [SMILES: CCCCCCCCCC(=O)OCCCCCCCN(CCCCCCCCCCC(=O)OCCCCCC)CCCOC(=O)NCCCN(C)C] | 740.1 |

TABLE 1-continued
| # | Structure | Mw |
| --- | --- | --- |
| 794. | 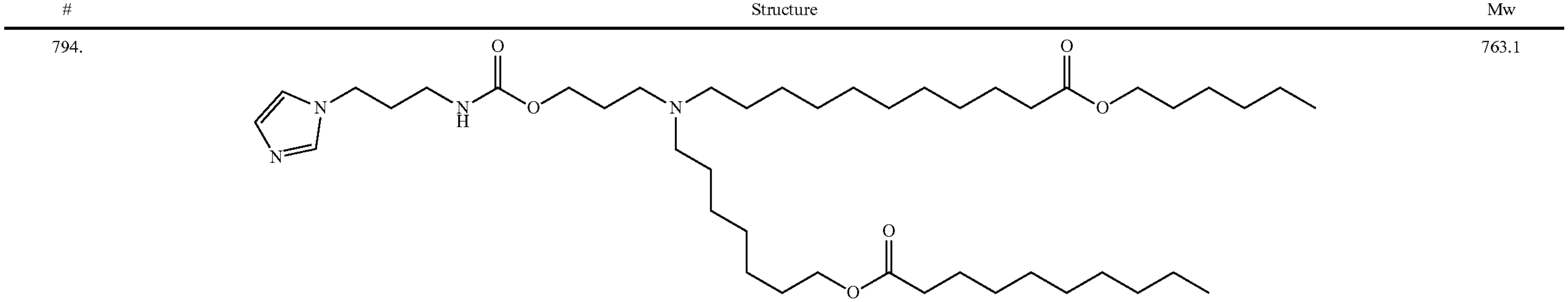 | 763.1 |
| 795. | 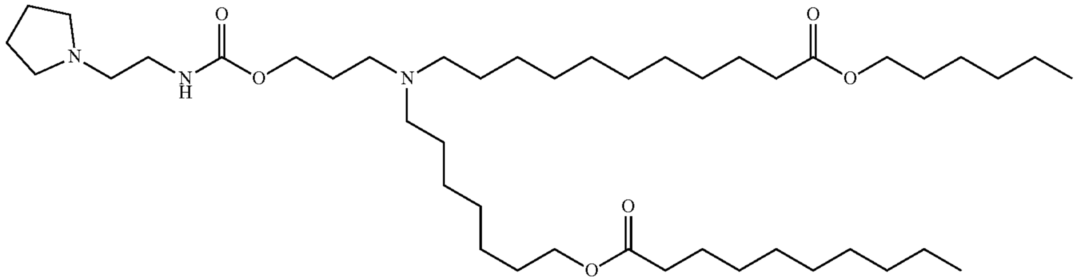 [SMILES: CCCCCCCCCC(=O)OCCCCCCCN(CCCCCCCCCCC(=O)OCCCCCC)CCCOC(=O)NCCN1CCCC1] | 752.2 |
| 796. | 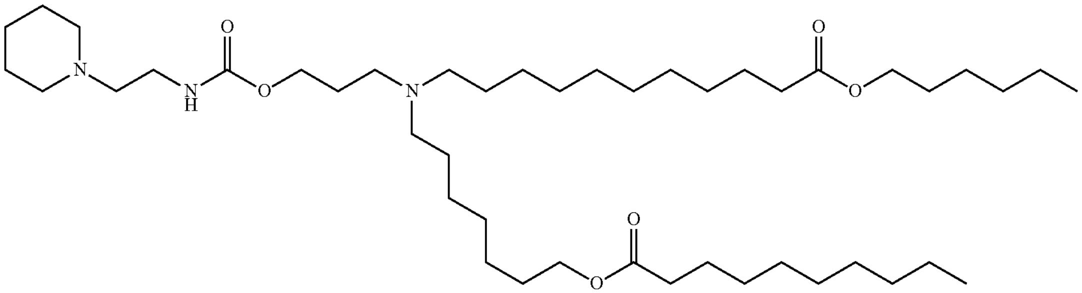 [SMILES: CCCCCCCCCC(=O)OCCCCCCCN(CCCCCCCCCCC(=O)OCCCCCC)CCCOC(=O)NCCN1CCCCC1] | 766.2 |

TABLE 1-continued
| # | Structure | Mw |
|---|---|---|
| 797. | 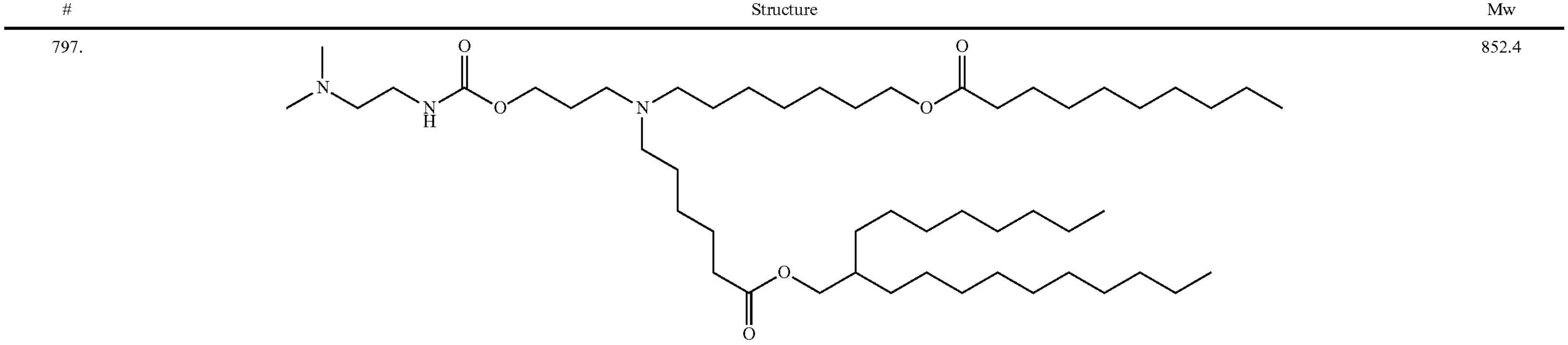 | 852.4 |
| 798. | 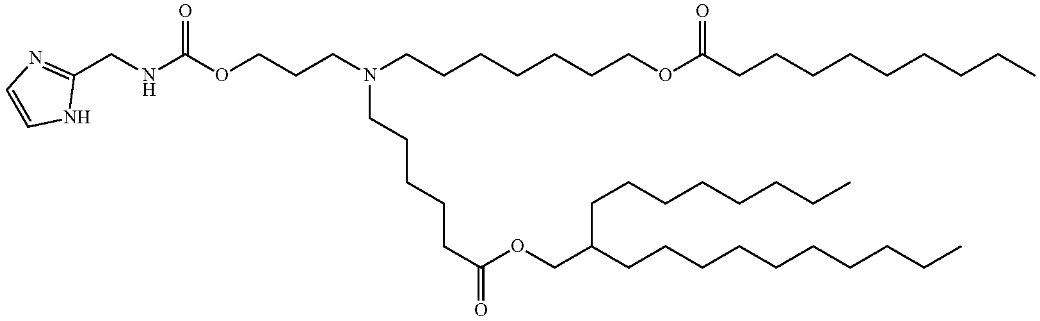 [SMILES: CCCCCCCCCCC(CCCCCCCC)COC(=O)CCCCCN(CCCCCCCOC(=O)CCCCCCCCC)CCCOC(=O)NCc1ncc[nH]1] | 861.3 |
| 799. | 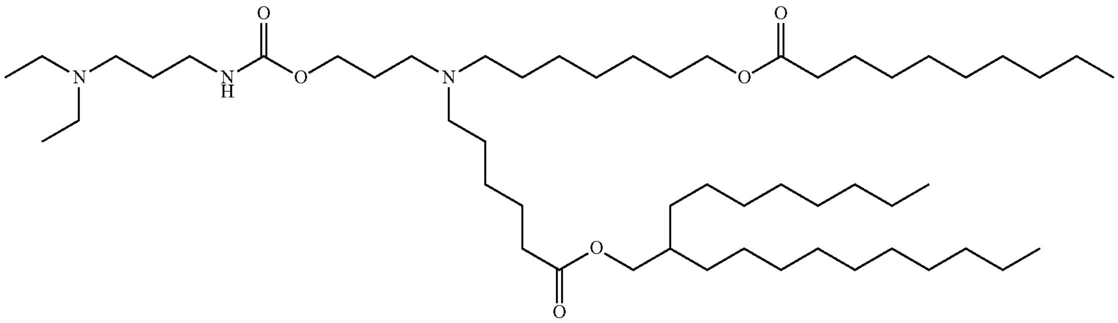 [SMILES: CCCCCCCCCCC(CCCCCCCC)COC(=O)CCCCCN(CCCCCCCOC(=O)CCCCCCCCC)CCCOC(=O)NCCCN(CC)CC] | 894.4 |

TABLE 1-continued
| # | Structure | Mw |
| --- | --- | --- |
| 800. | 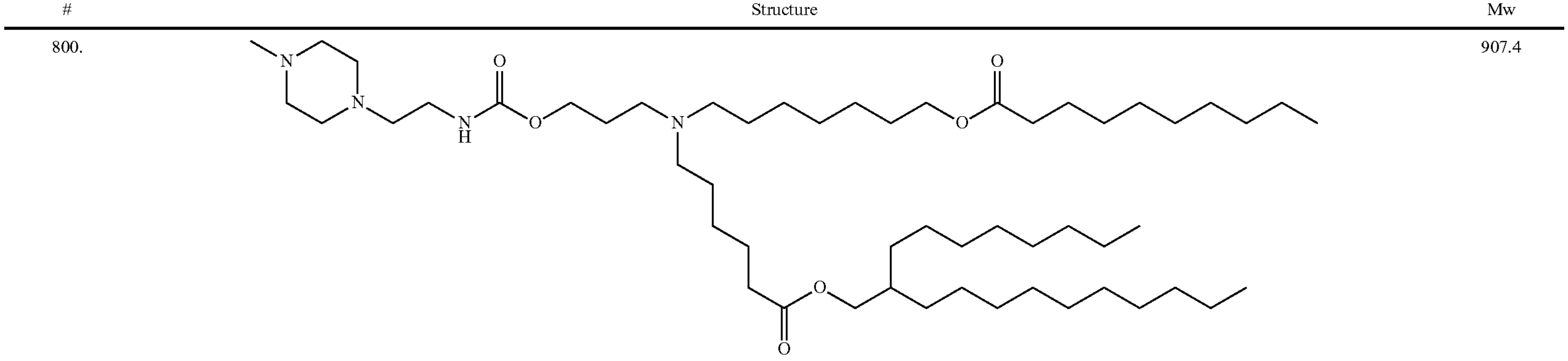 | 907.4 |
| 801. | 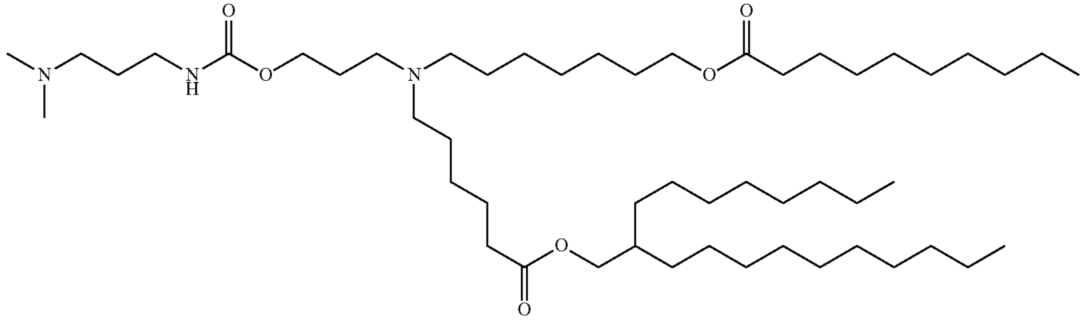 [SMILES: CCCCCCCCCCC(CCCCCCCC)COC(=O)CCCCCN(CCCCCCCOC(=O)CCCCCCCCC)CCCOC(=O)NCCCN(C)C] | 866.4 |
| 802. | 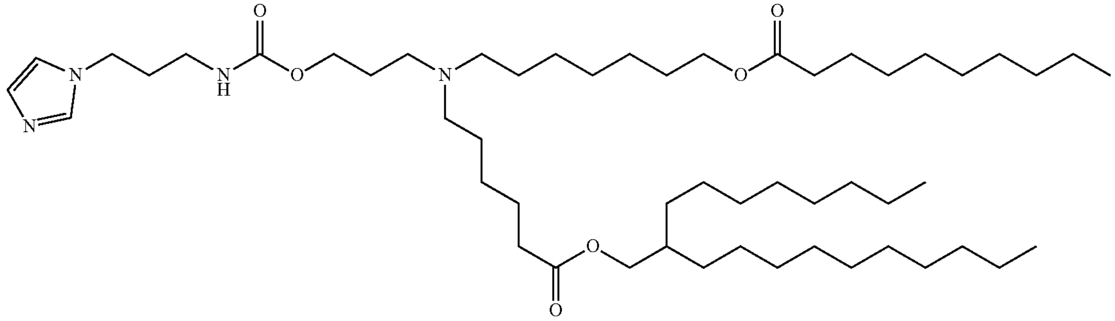 [SMILES: CCCCCCCCCCC(CCCCCCCC)COC(=O)CCCCCN(CCCCCCCOC(=O)CCCCCCCCC)CCCOC(=O)NCCCn1ccnc1] | 889.4 |

TABLE 1-continued
| # | Structure | Mw |
| --- | --- | --- |
| 803. | 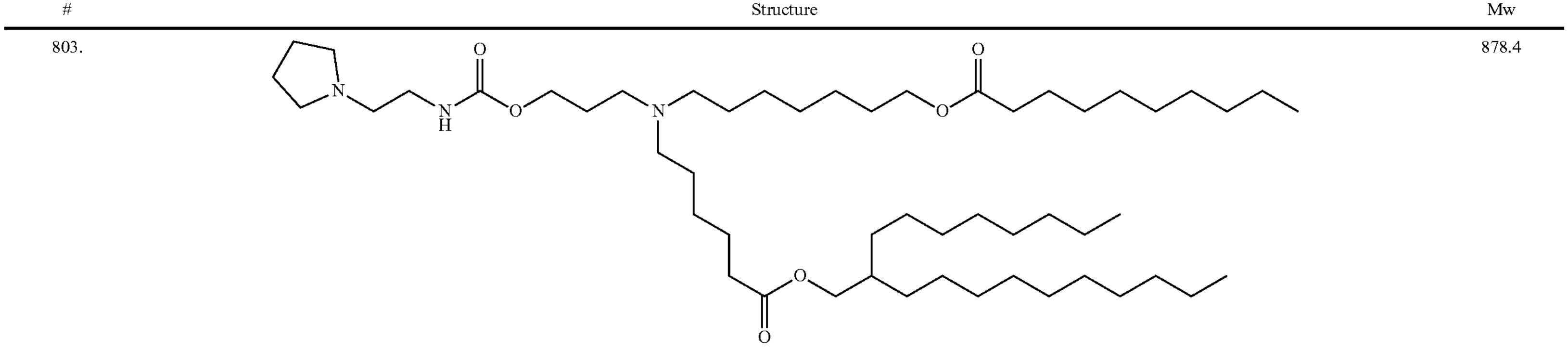 | 878.4 |
| 804. | 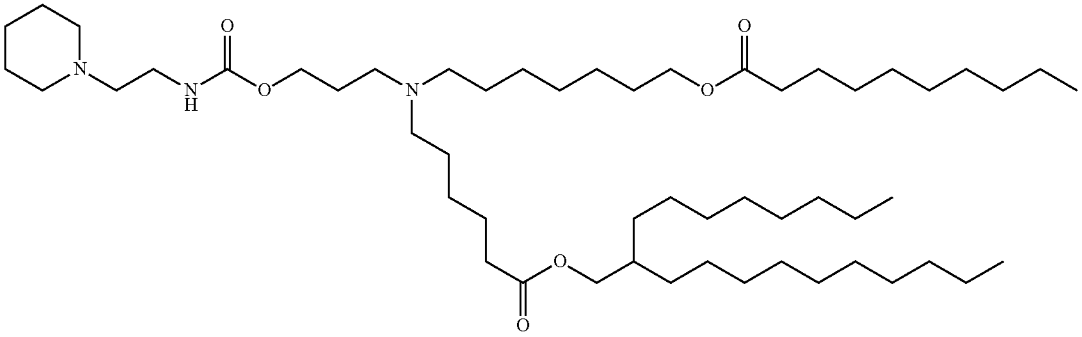 [SMILES: CCCCCCCCCCC(CCCCCCCC)COC(=O)CCCCCN(CCCCCCCOC(=O)CCCCCCCCC)CCCOC(=O)NCCN1CCCCC1] | 892.4 |
| 805. | 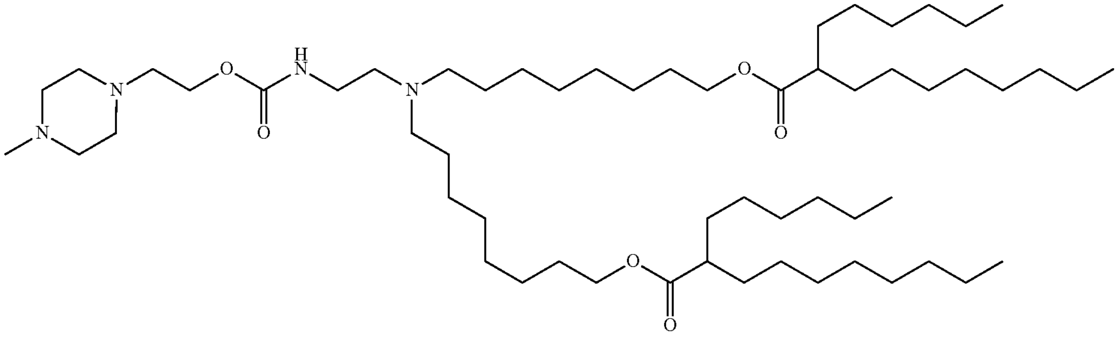 [SMILES: CCCCCCCCC(CCCCCC)C(=O)OCCCCCCCCN(CCCCCCCCOC(=O)C(CCCCCC)CCCCCCCC)CCNC(=O)OCCN1CCN(C)CC1] | 963.6 |

TABLE 1-continued
| # | Structure | Mw |
|---|---|---|
| 806. | 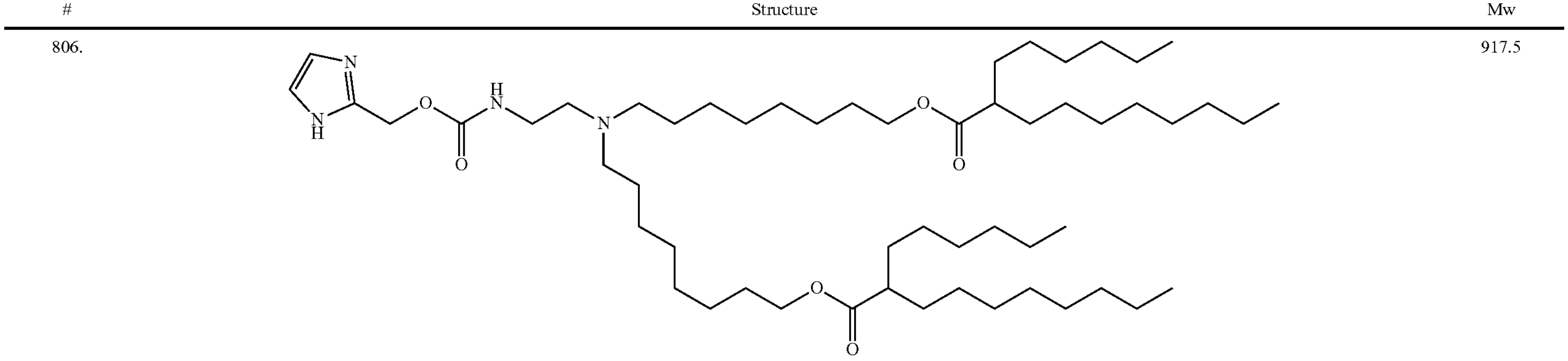 | 917.5 |
| 807. | 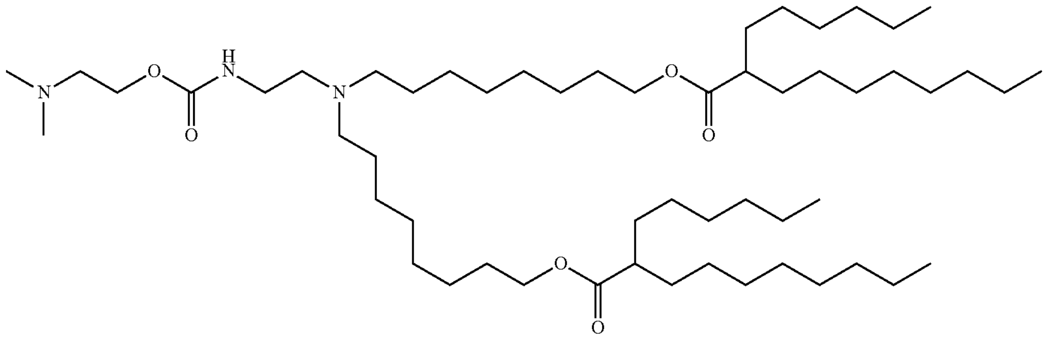 [SMILES: CCCCCCCCC(CCCCCC)C(=O)OCCCCCCCCN(CCCCCCCCOC(=O)C(CCCCCC)CCCCCCCC)CCNC(=O)OCCN(C)C] | 908.5 |
| 808. | 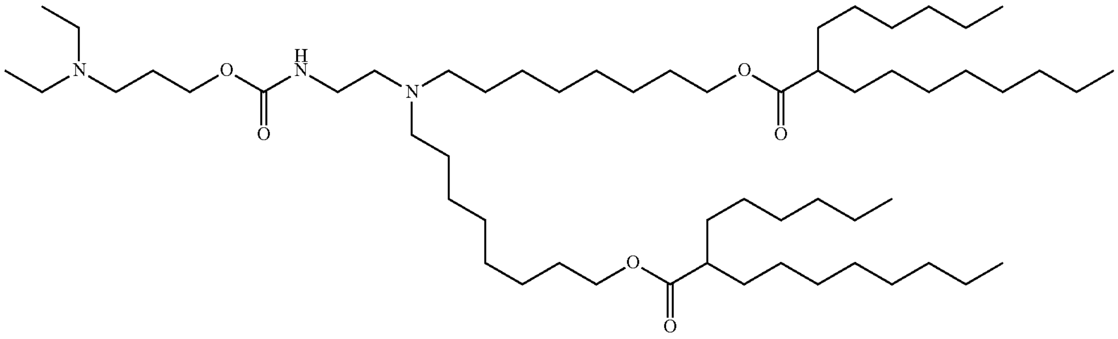 [SMILES: CCCCCCCCC(CCCCCC)C(=O)OCCCCCCCCN(CCCCCCCCOC(=O)C(CCCCCC)CCCCCCCC)CCNC(=O)OCCCN(CC)CC] | 950.6 |

TABLE 1-continued
| # | Structure | Mw |
|---|---|---|
| 809. | 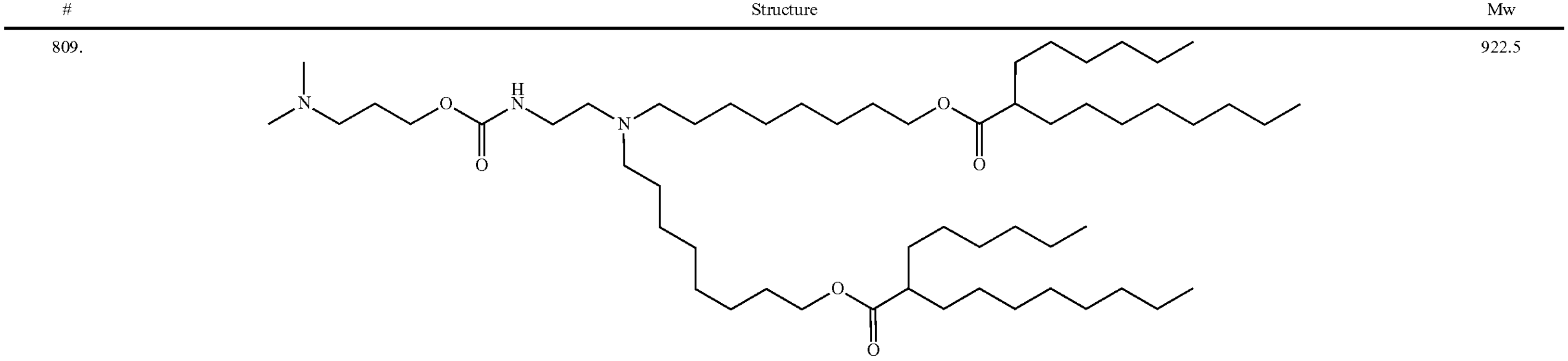 | 922.5 |
| 810. | 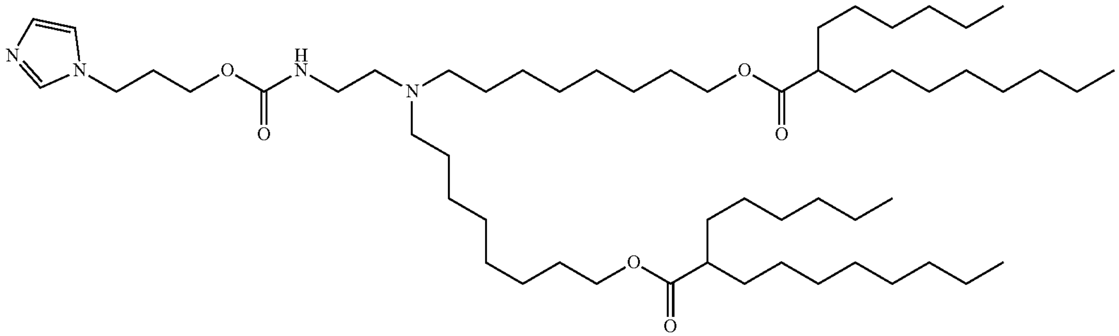 [SMILES: CCCCCCCCC(CCCCCC)C(=O)OCCCCCCCCN(CCCCCCCCOC(=O)C(CCCCCC)CCCCCCCC)CCNC(=O)OCCCn1ccnc1] | 945.5 |
| 811. | 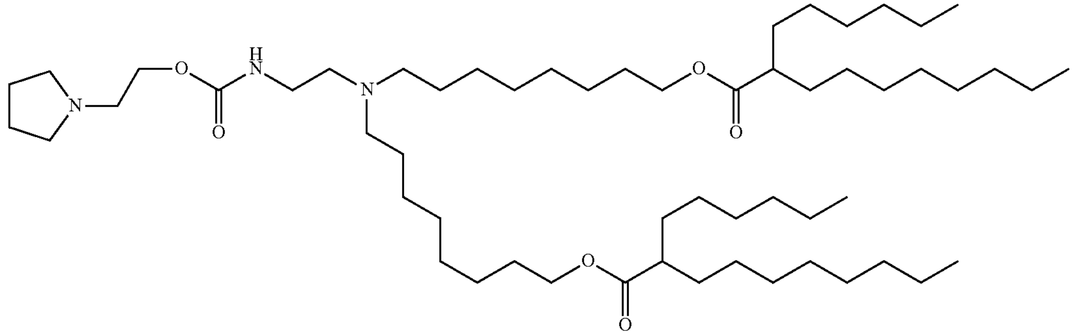 [SMILES: CCCCCCCCC(CCCCCC)C(=O)OCCCCCCCCN(CCCCCCCCOC(=O)C(CCCCCC)CCCCCCCC)CCNC(=O)OCCN1CCCC1] | 934.5 |

TABLE 1-continued
| # | Structure | Mw |
|---|---|---|
| 812. | 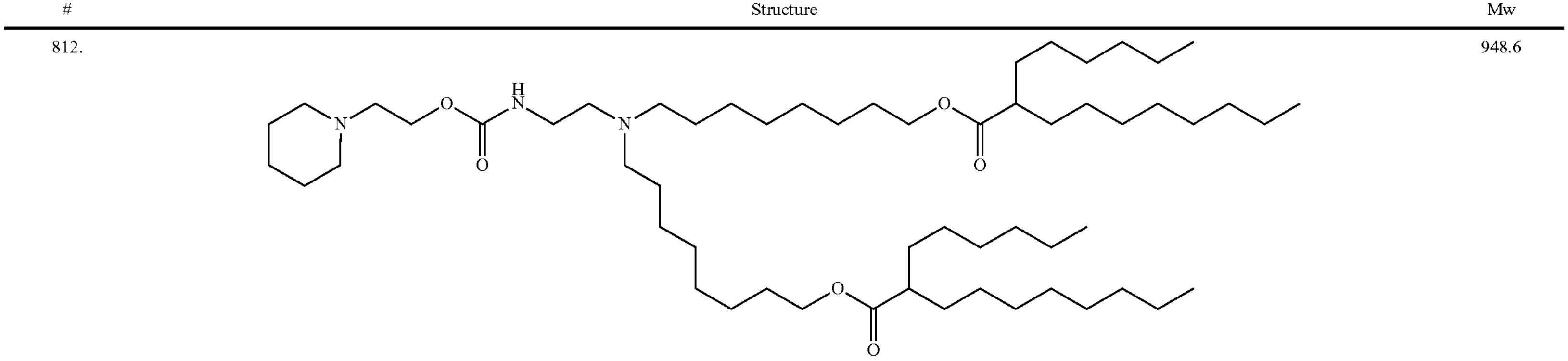 | 948.6 |
| 813. | 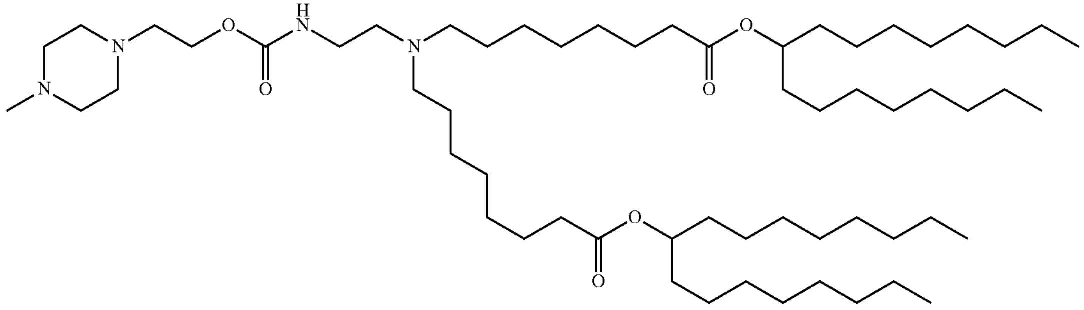 [SMILES: CCCCCCCCC(CCCCCCCC)OC(=O)CCCCCCCN(CCCCCCCC(=O)OC(CCCCCCCC)CCCCCCCC)CCNC(=O)OCCN1CCN(C)CC1] | 991.6 |
| 814. | 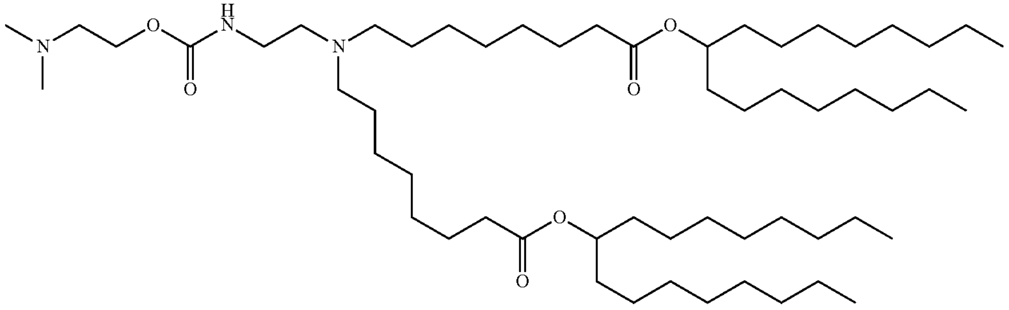 [SMILES: CCCCCCCCC(CCCCCCCC)OC(=O)CCCCCCCN(CCCCCCCC(=O)OC(CCCCCCCC)CCCCCCCC)CCNC(=O)OCCN(C)C] | 936.5 |

TABLE 1-continued
| # | Structure | Mw |
| --- | --- | --- |
| 815. | 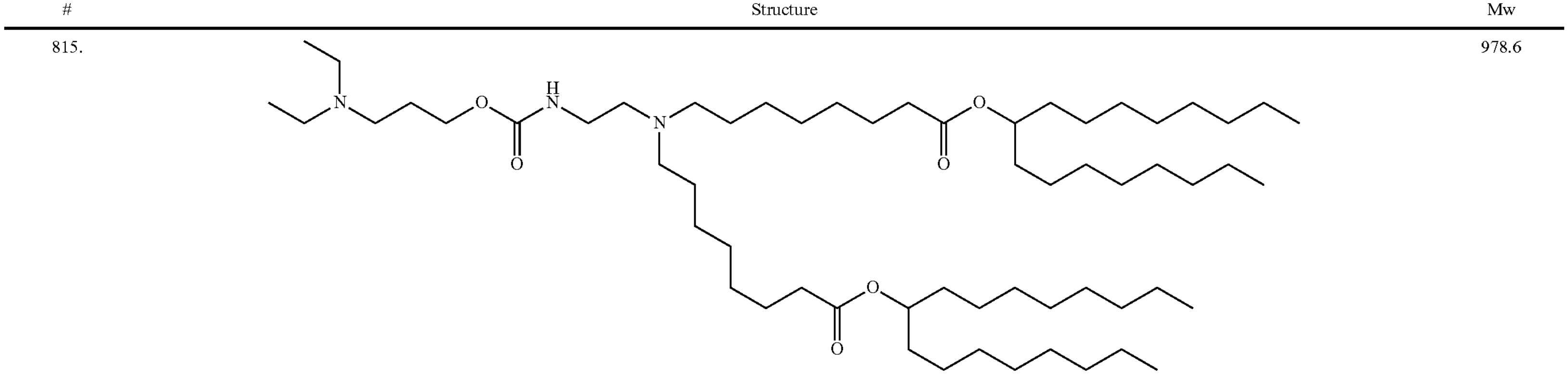 | 978.6 |
| 816. | 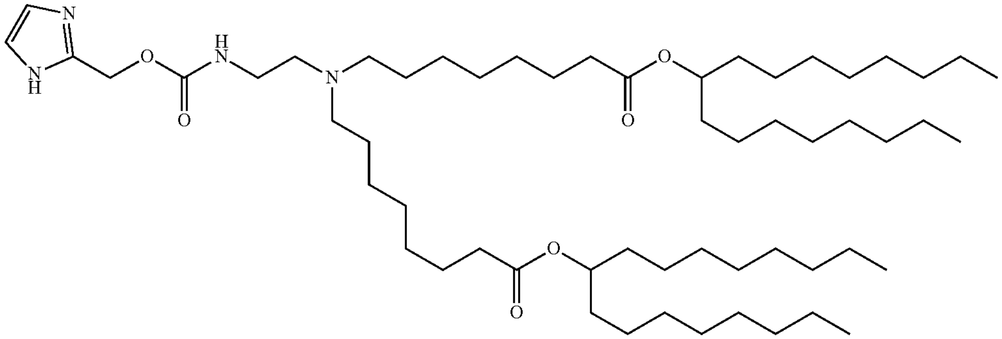 [SMILES: CCCCCCCCC(CCCCCCCC)OC(=O)CCCCCCCN(CCCCCCCC(=O)OC(CCCCCCCC)CCCCCCCC)CCNC(=O)OCc1ncc[nH]1] | 945.5 |
| 817. | 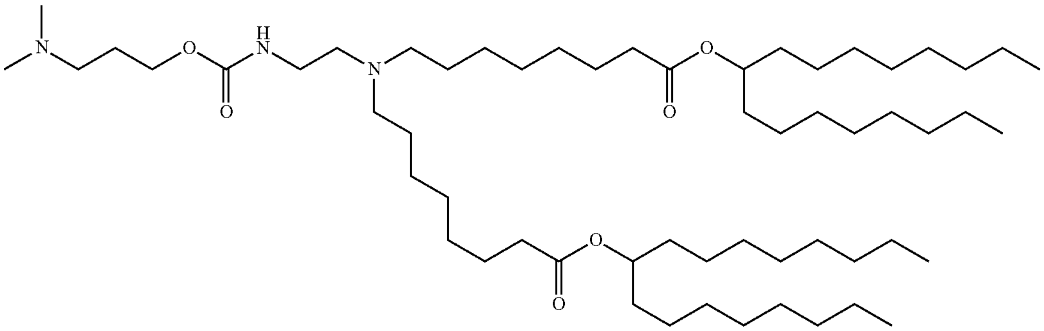 [SMILES: CCCCCCCCC(CCCCCCCC)OC(=O)CCCCCCCN(CCCCCCCC(=O)OC(CCCCCCCC)CCCCCCCC)CCNC(=O)OCCCN(C)C] | 950.6 |

TABLE 1-continued
| # | Structure | Mw |
|---|---|---|
| 818. | 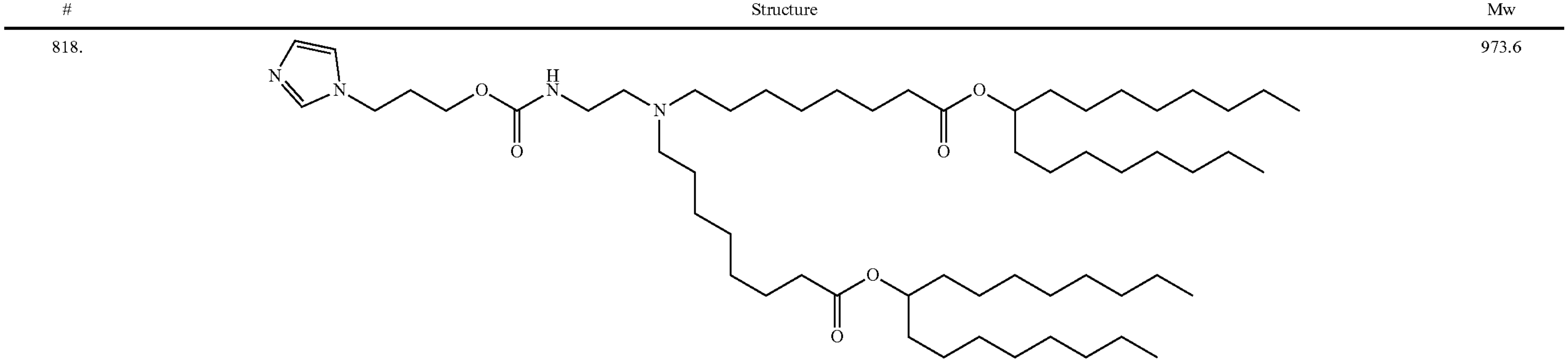 | 973.6 |
| 819. | 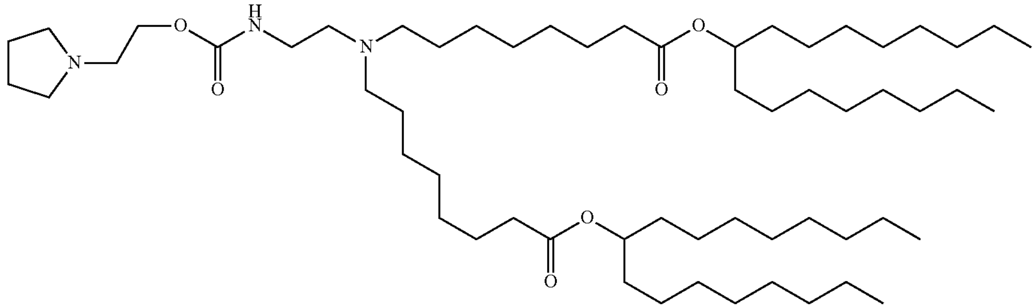 [SMILES: CCCCCCCCC(CCCCCCCC)OC(=O)CCCCCCCN(CCCCCCCC(=O)OC(CCCCCCCC)CCCCCCCC)CCNC(=O)OCCN1CCCC1] | 962.6 |
| 820. | 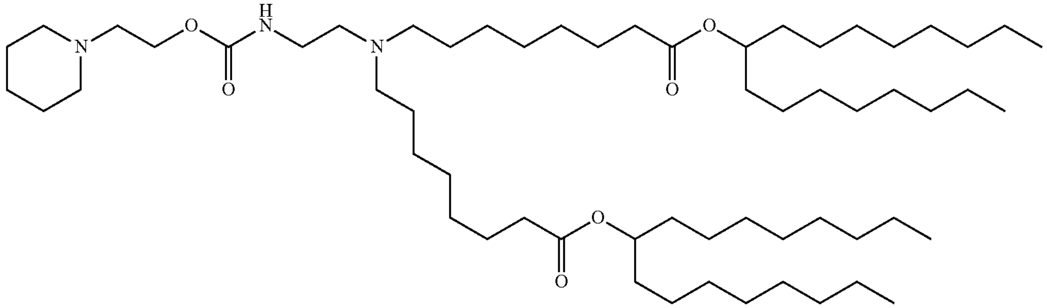 [SMILES: CCCCCCCCC(CCCCCCCC)OC(=O)CCCCCCCN(CCCCCCCC(=O)OC(CCCCCCCC)CCCCCCCC)CCNC(=O)OCCN1CCCCC1] | 976.6 |

TABLE 1-continued
| # | Structure | Mw |
| --- | --- | --- |
| 821. | 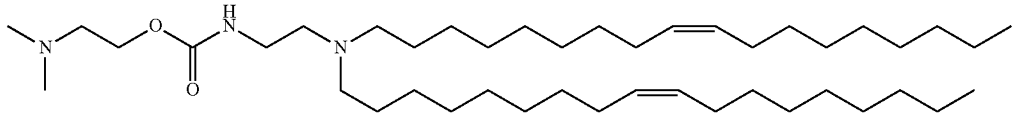 [SMILES: CCCCCCCC/C=C\CCCCCCCCN(CCCCCCCC/C=C\CCCCCCCC)CCNC(=O)OCCN(C)C] | 676.2 |
| 822. | 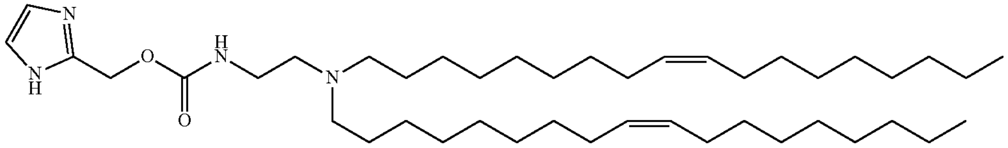 [SMILES: CCCCCCCC/C=C\CCCCCCCCN(CCCCCCCC/C=C\CCCCCCCC)CCNC(=O)OCc1ncc[nH]1] | 685.1 |
| 823. | 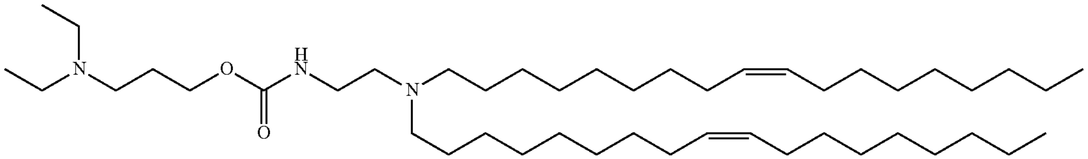 [SMILES: CCCCCCCC/C=C\CCCCCCCCN(CCCCCCCC/C=C\CCCCCCCC)CCNC(=O)OCCCN(CC)CC] | 718.3 |
| 824. | 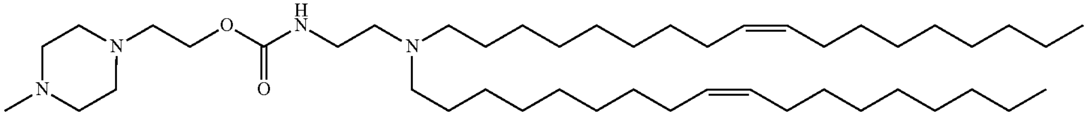 [SMILES: CCCCCCCC/C=C\CCCCCCCCN(CCCCCCCC/C=C\CCCCCCCC)CCNC(=O)OCCN1CCN(C)CC1] | 731.3 |
| 825. | 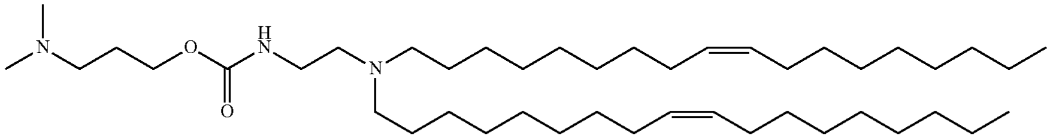 [SMILES: CCCCCCCC/C=C\CCCCCCCCN(CCCCCCCC/C=C\CCCCCCCC)CCNC(=O)OCCCN(C)C] | 690.2 |
| 826. | 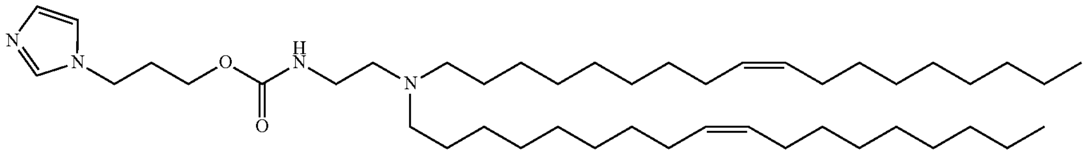 [SMILES: CCCCCCCC/C=C\CCCCCCCCN(CCCCCCCC/C=C\CCCCCCCC)CCNC(=O)OCCCn1ccnc1] | 713.2 |
| 827. | 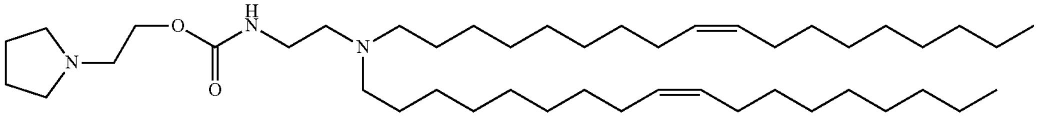 | 702.2 |

TABLE 1-continued
| # | Structure | Mw |
|---|---|---|
| 828. | 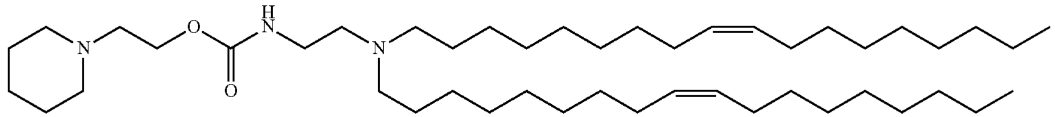 [SMILES: CCCCCCCC/C=C\CCCCCCCCN(CCCCCCCC/C=C\CCCCCCCC)CCNC(=O)OCCN1CCCCC1] | 716.2 |
| 829. | 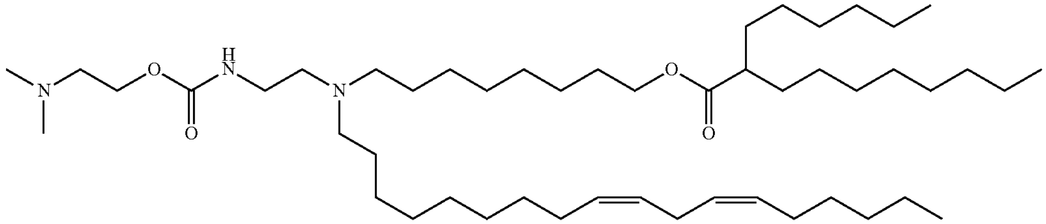 [SMILES: CCCCC/C=C\C/C=C\CCCCCCCCN(CCCCCCCCOC(=O)C(CCCCCC)CCCCCCCC)CCNC(=O)OCCN(C)C] | 790.3 |
| 830. | 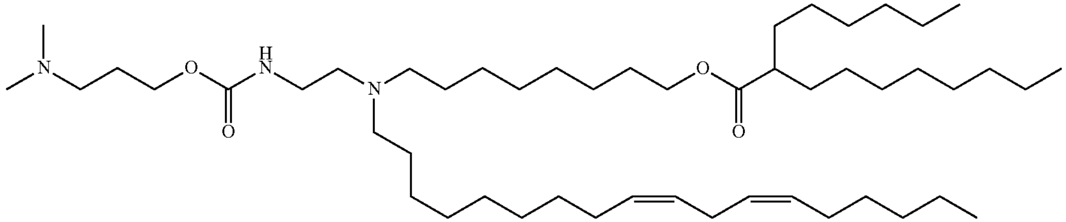 [SMILES: CCCCC/C=C\C/C=C\CCCCCCCCN(CCCCCCCCOC(=O)C(CCCCCC)CCCCCCCC)CCNC(=O)OCCCN(C)C] | 804.3 |
| 831. | 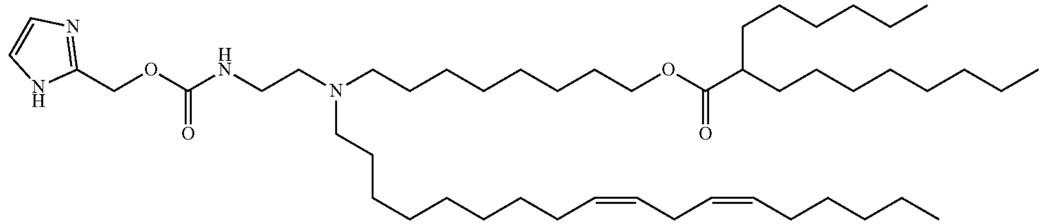 [SMILES: CCCCC/C=C\C/C=C\CCCCCCCCN(CCCCCCCCOC(=O)C(CCCCCC)CCCCCCCC)CCNC(=O)OCc1ncc[nH]1] | 799.3 |
| 832. | 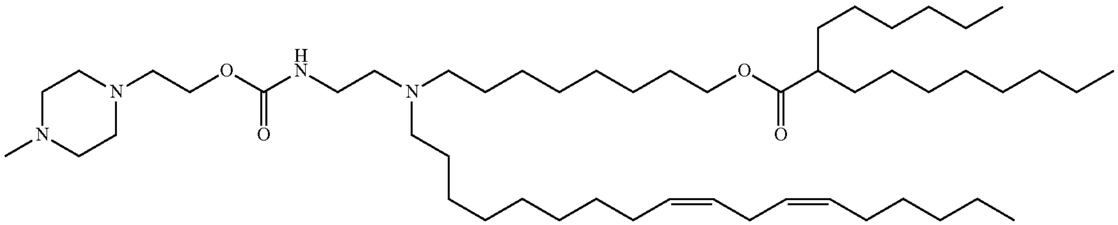 [SMILES: CCCCC/C=C\C/C=C\CCCCCCCCN(CCCCCCCCOC(=O)C(CCCCCC)CCCCCCCC)CCNC(=O)OCCN1CCN(C)CC1] | 845.4 |

TABLE 1-continued
| # | Structure | Mw |
|---|---|---|
| 833. | 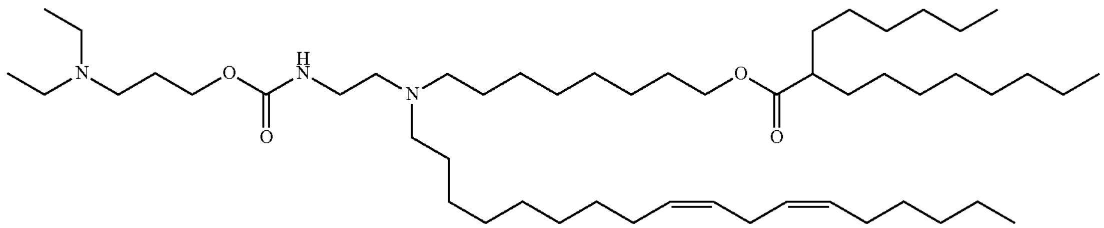 [SMILES: CCCCC/C=C\C/C=C\CCCCCCCCN(CCCCCCCCOC(=O)C(CCCCCC)CCCCCCCC)CCNC(=O)OCCCN(CC)CC] | 832.4 |
| 834. | 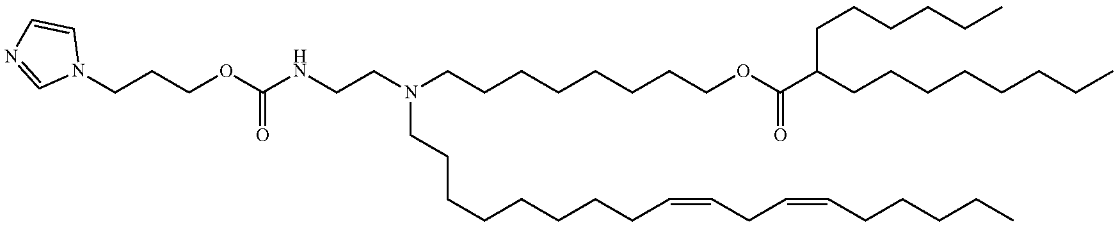 [SMILES: CCCCC/C=C\C/C=C\CCCCCCCCN(CCCCCCCCOC(=O)C(CCCCCC)CCCCCCCC)CCNC(=O)OCCCn1ccnc1] | 827.3 |
| 835. | 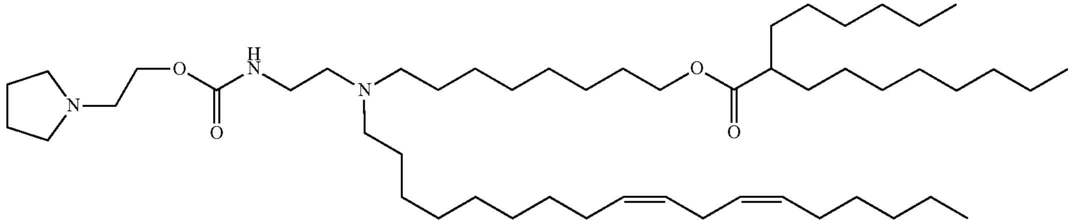 | 816.4 |
| 836. | 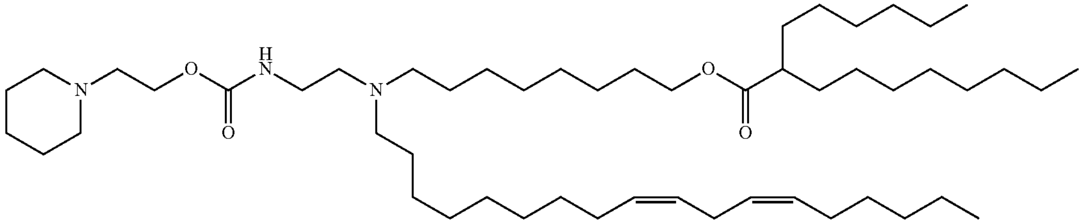 [SMILES: CCCCC/C=C\C/C=C\CCCCCCCCN(CCCCCCCCOC(=O)C(CCCCCC)CCCCCCCC)CCNC(=O)OCCN1CCCCC1] | 830.4 |

TABLE 1-continued
| # | Structure | Mw |
|---|---|---|
| 837. | 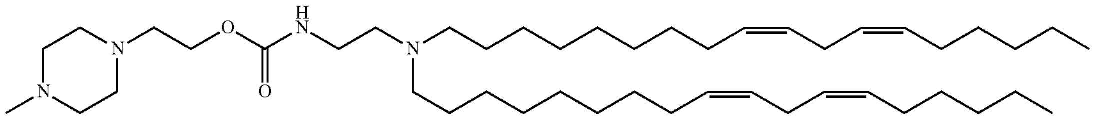 | 727.2 |
| 838. | 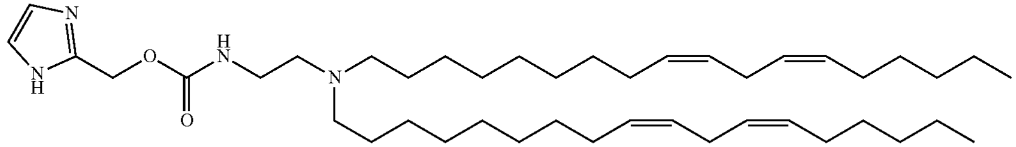 | 681.1 |
| 839. | 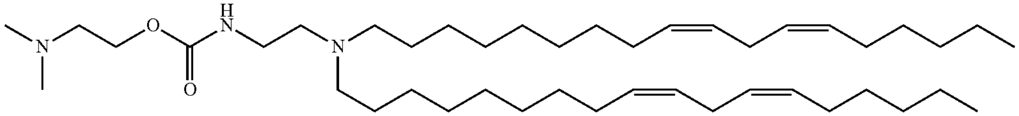 | 672.1 |
| 840. | 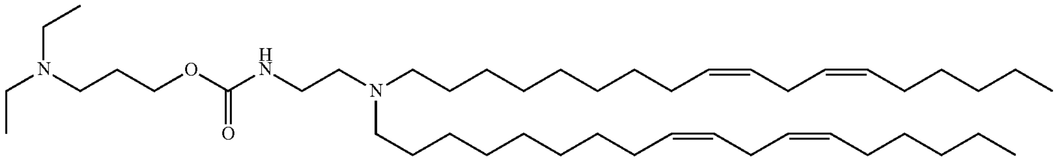 | 714.2 |
| 841. | 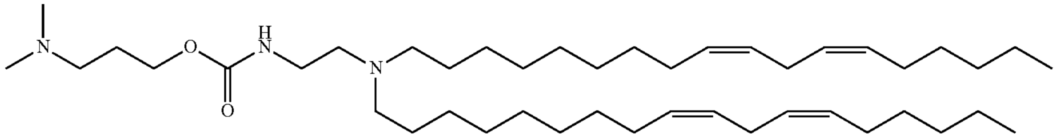 [SMILES: CCCCC/C=C\C/C=C\CCCCCCCCN(CCCCCCCC/C=C\C/C=C\CCCCC)CCNC(=O)OCCCN(C)C] | 686.2 |
| 842. | 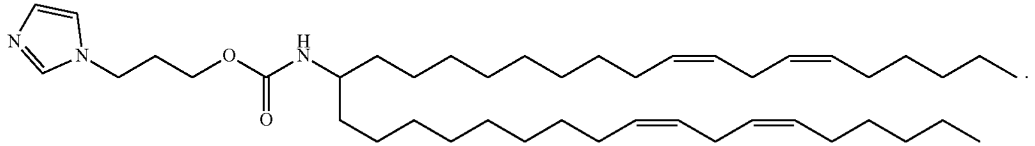 [SMILES: CCCCC/C=C\C/C=C\CCCCCCCCC(CCCCCCCC/C=C\C/C=C\CCCCC)NC(=O)OCCCn1ccnc1] | 709.2 |
| 843. | 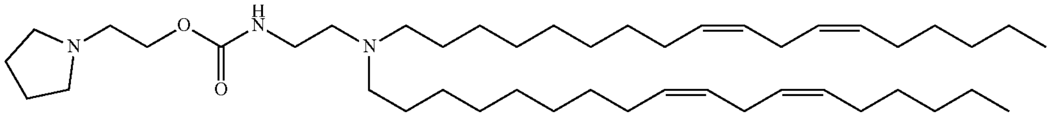 [SMILES: CCCCC/C=C\C/C=C\CCCCCCCCN(CCCCCCCC/C=C\C/C=C\CCCCC)CCNC(=O)OCCN1CCCC1] | 698.2 |

TABLE 1-continued
| # | Structure | Mw |
| --- | --- | --- |
| 844. | 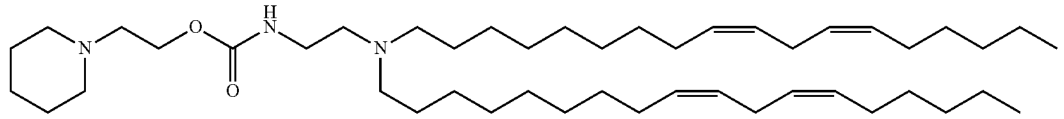 | 712.2 |
| 845. | 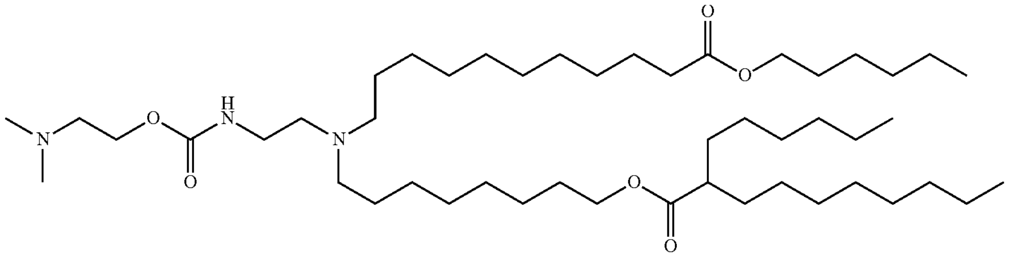 [SMILES: CCCCCCCCC(CCCCCC)C(=O)OCCCCCCCCN(CCCCCCCCCCC(=O)OCCCCCC)CCNC(=O)OCCN(C)C] | 810.3 |
| 846. | 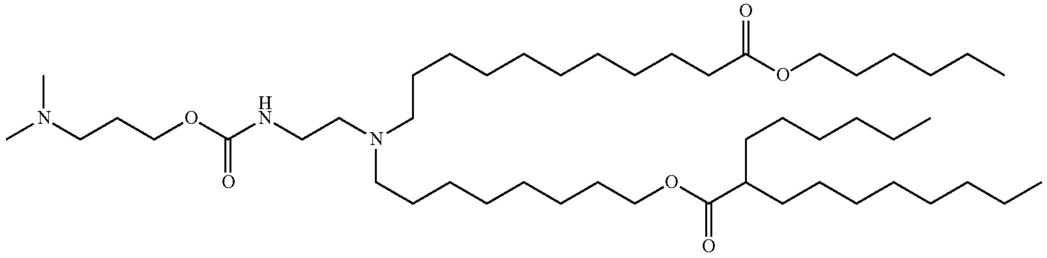 [SMILES: CCCCCCCCC(CCCCCC)C(=O)OCCCCCCCCN(CCCCCCCCCCC(=O)OCCCCCC)CCNC(=O)OCCCN(C)C] | 824.3 |
| 847. | 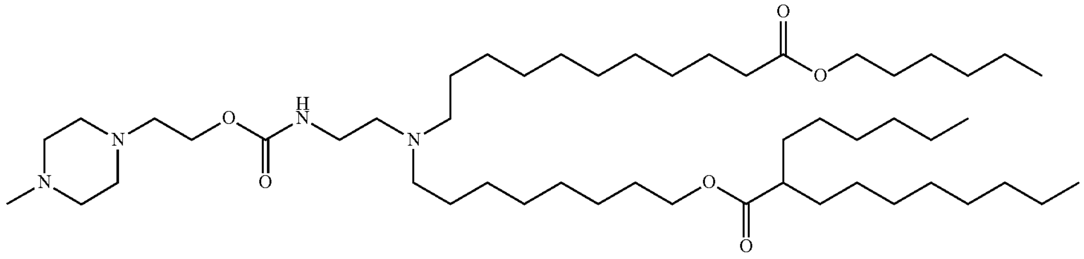 [SMILES: CCCCCCCCC(CCCCCC)C(=O)OCCCCCCCCN(CCCCCCCCCCC(=O)OCCCCCC)CCNC(=O)OCCN1CCN(C)CC1] | 865.4 |

TABLE 1-continued
| # | Structure | Mw |
|---|---|---|
| 848. | 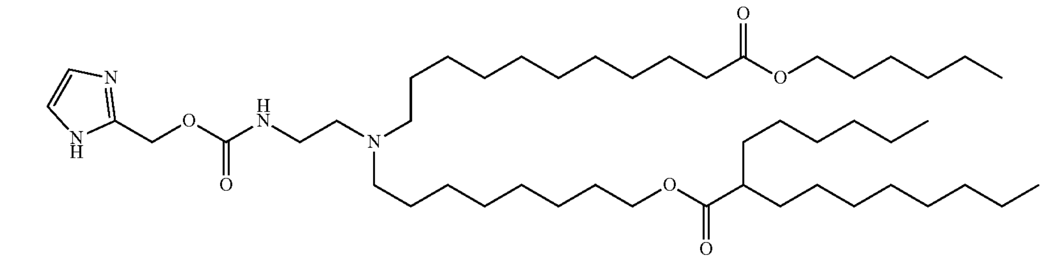 [SMILES: CCCCCCCCC(CCCCCC)C(=O)OCCCCCCCCN(CCCCCCCCCCC(=O)OCCCCCC)CCNC(=O)OCc1ncc[nH]1] | 819.3 |
| 849. | 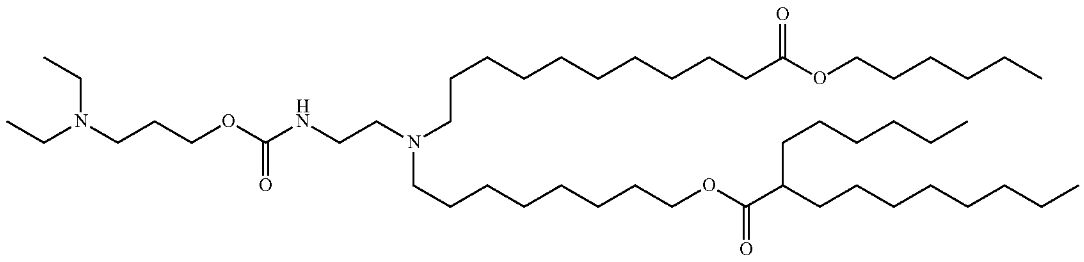 [SMILES: CCCCCCCCC(CCCCCC)C(=O)OCCCCCCCCN(CCCCCCCCCCC(=O)OCCCCCC)CCNC(=O)OCCCN(CC)CC] | 852.4 |
| 850. | 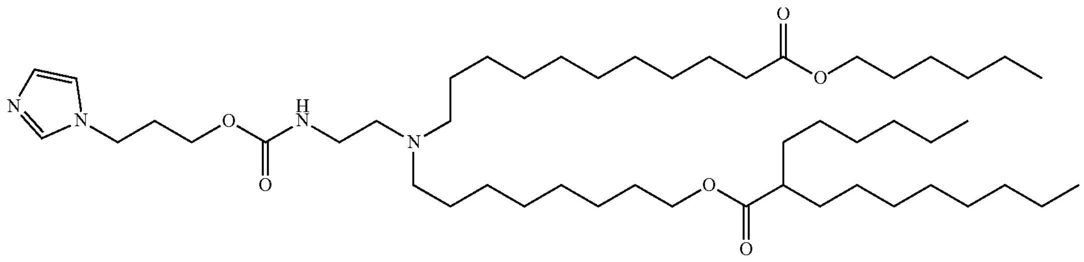 [SMILES: CCCCCCCCC(CCCCCC)C(=O)OCCCCCCCCN(CCCCCCCCCCC(=O)OCCCCCC)CCNC(=O)OCCCn1ccnc1] | 847.3 |
| 851. | 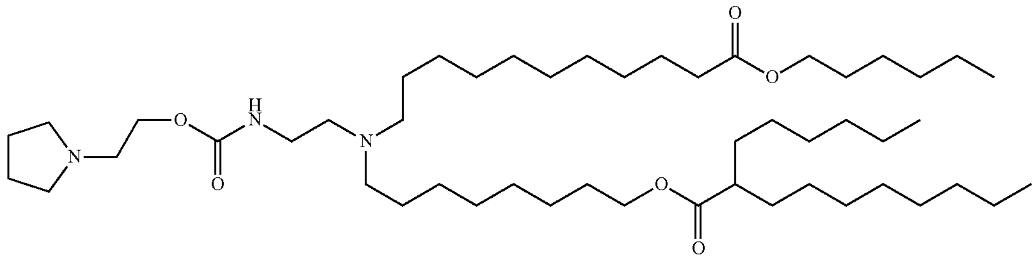 [SMILES: CCCCCCCCC(CCCCCC)C(=O)OCCCCCCCCN(CCCCCCCCCCC(=O)OCCCCCC)CCNC(=O)OCCN1CCCC1] | 836.3 |

TABLE 1-continued
| # | Structure | Mw |
| --- | --- | --- |
| 852. | 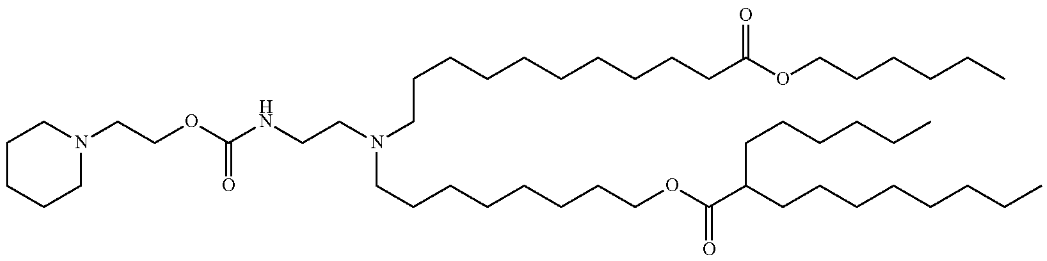 [SMILES: CCCCCCCCC(CCCCCC)C(=O)OCCCCCCCCN(CCCCCCCCCCC(=O)OCCCCCC)CCNC(=O)OCCN1CCCCC1] | 850.4 |
| 853. | 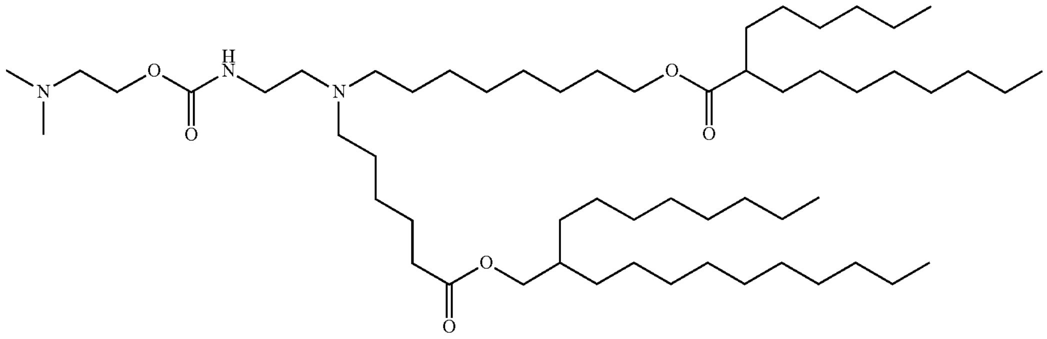 [SMILES: CCCCCCCCCCC(CCCCCCCC)COC(=O)CCCCCN(CCCCCCCCOC(=O)C(CCCCCC)CCCCCCCC)CCNC(=O)OCCN(C)C] | 936.5 |
| 854. | 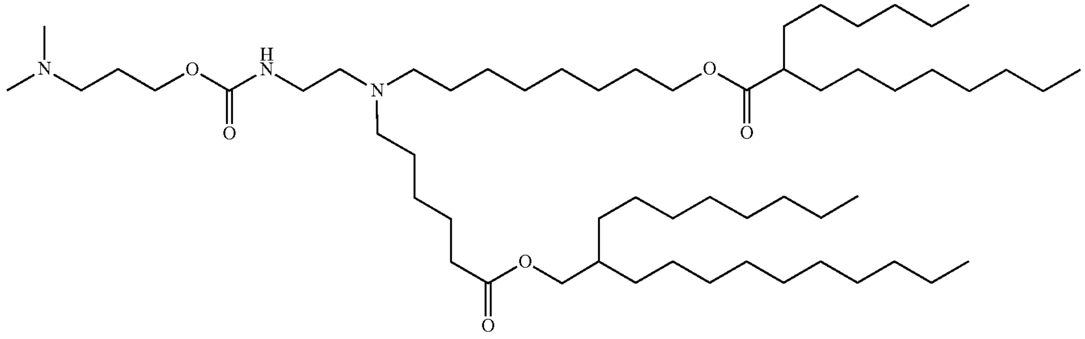 [SMILES: CCCCCCCCCCC(CCCCCCCC)COC(=O)CCCCCN(CCCCCCCCOC(=O)C(CCCCCC)CCCCCCCC)CCNC(=O)OCCCN(C)C] | 950.6 |

TABLE 1-continued
| # | Structure | Mw |
| --- | --- | --- |
| 855. | 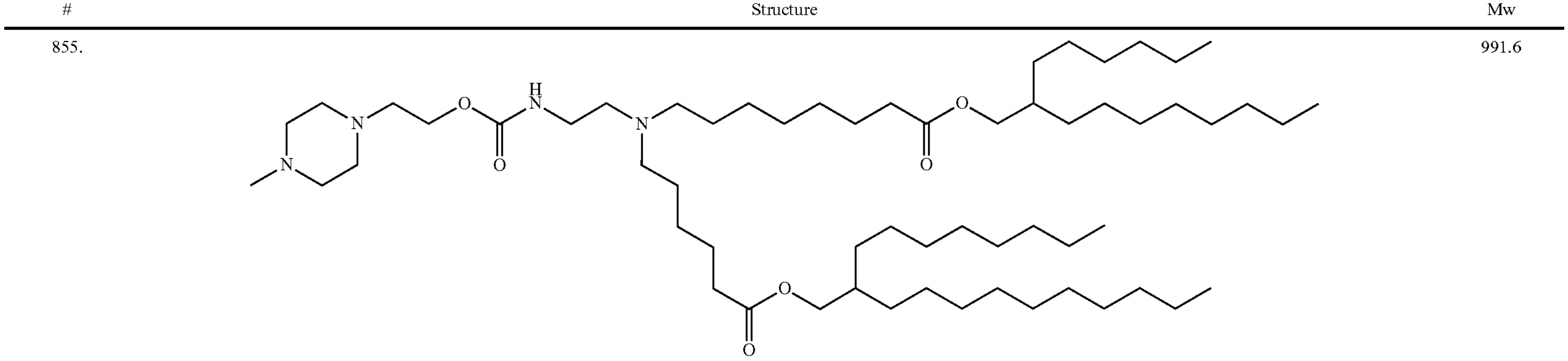 | 991.6 |
| 856. | 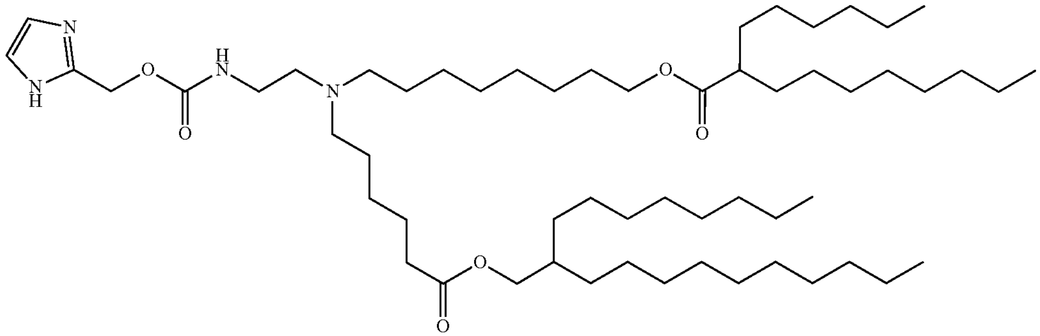 [SMILES: CCCCCCCCCCC(CCCCCCCC)COC(=O)CCCCCN(CCCCCCCCOC(=O)C(CCCCCC)CCCCCCCC)CCNC(=O)OCc1ncc[nH]1] | 945.5 |
| 857. | 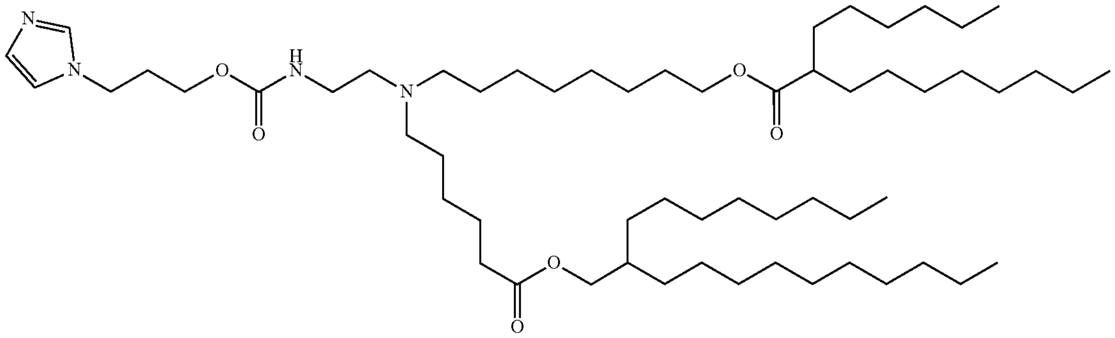 [SMILES: CCCCCCCCCCC(CCCCCCCC)COC(=O)CCCCCN(CCCCCCCCOC(=O)C(CCCCCC)CCCCCCCC)CCNC(=O)OCCCn1ccnc1] | 973.6 |

TABLE 1-continued
| # | Structure | Mw |
| --- | --- | --- |
| 858. | 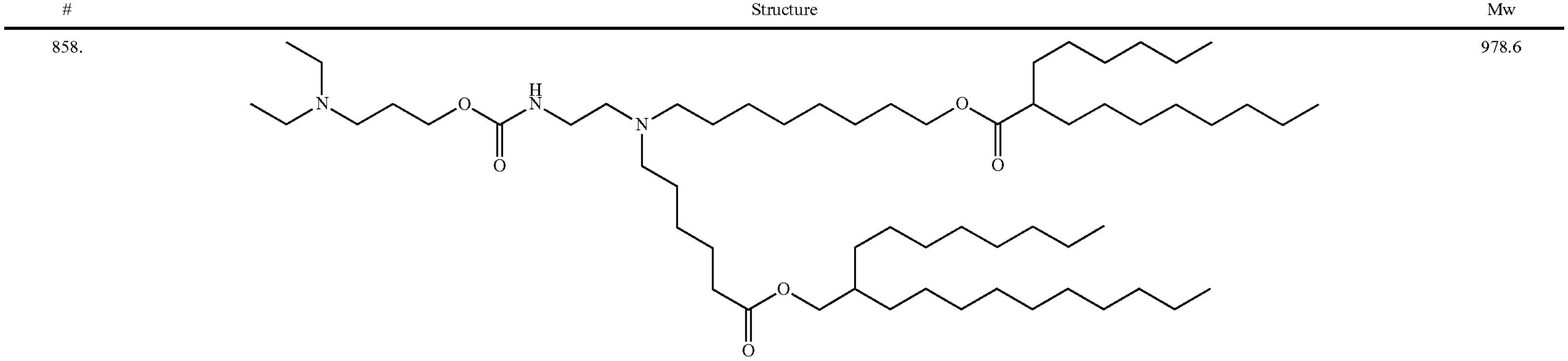 | 978.6 |
| 859. | 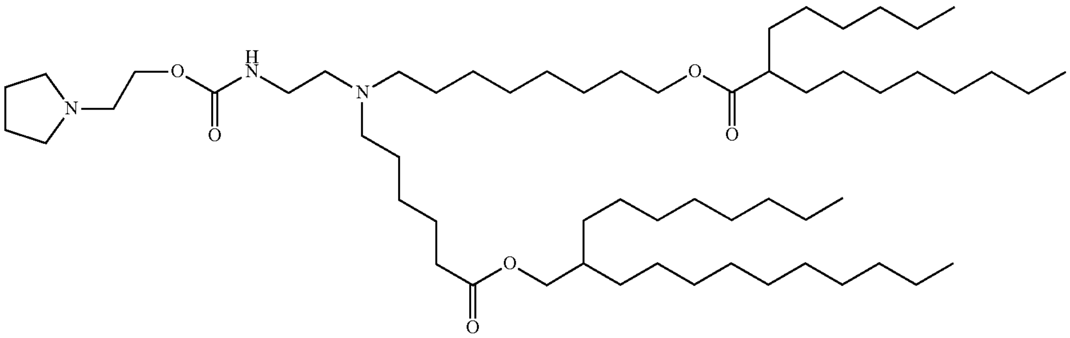 [SMILES: CCCCCCCCCCC(CCCCCCCC)COC(=O)CCCCCN(CCCCCCCCOC(=O)C(CCCCCC)CCCCCCCC)CCNC(=O)OCCN1CCCC1] | 962.6 |
| 860. | 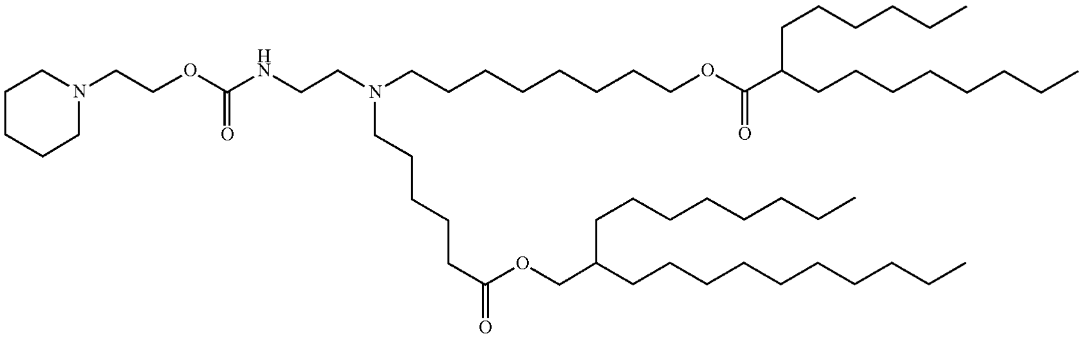 [SMILES: CCCCCCCCCCC(CCCCCCCC)COC(=O)CCCCCN(CCCCCCCCOC(=O)C(CCCCCC)CCCCCCCC)CCNC(=O)OCCN1CCCCC1] | 976.6 |

TABLE 1-continued
| # | Structure | Mw |
| --- | --- | --- |
| 861. | 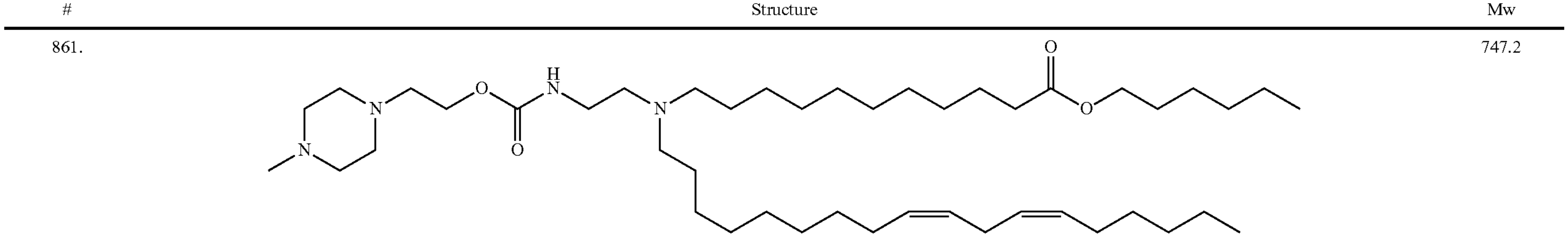 | 747.2 |
| 862. | 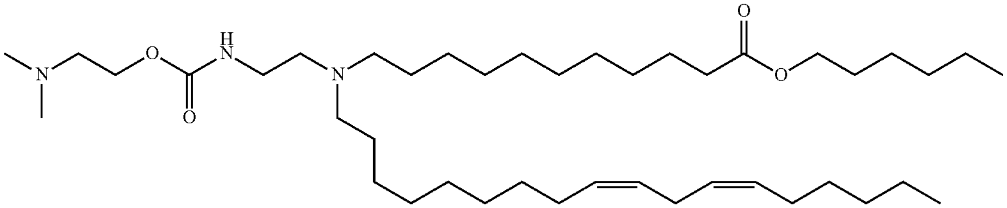 [SMILES: CCCCC/C=C\C/C=C\CCCCCCCCN(CCCCCCCCCCC(=O)OCCCCCC)CCNC(=O)OCCN(C)C] | 692.1 |
| 863. | 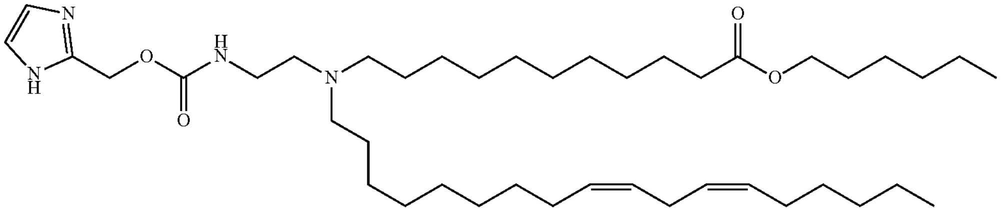 [SMILES: CCCCC/C=C\C/C=C\CCCCCCCCN(CCCCCCCCCCC(=O)OCCCCCC)CCNC(=O)OCc1ncc[nH]1] | 701.1 |
| 864. | 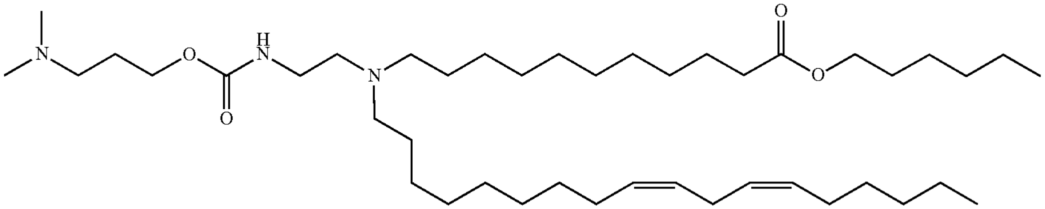 [SMILES: CCCCC/C=C\C/C=C\CCCCCCCCN(CCCCCCCCCCC(=O)OCCCCCC)CCNC(=O)OCCCN(C)C] | 706.2 |

TABLE 1-continued
| # | Structure | Mw |
|---|---|---|
| 865. | 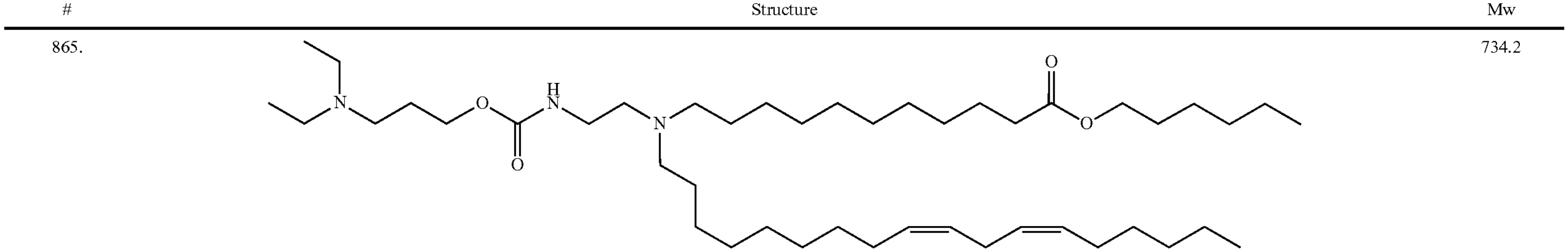 | 734.2 |
| 866. | 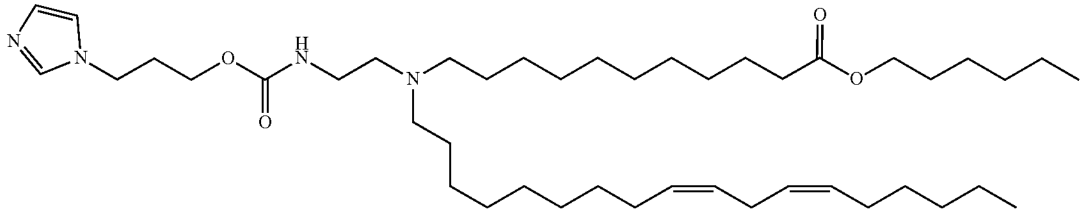 | 729.1 |
| 867. | 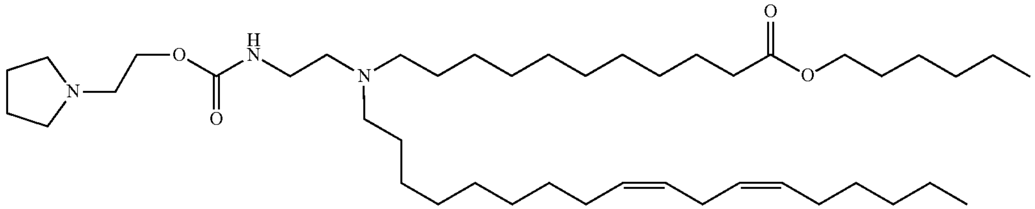 [SMILES: CCCCC/C=C\C/C=C\CCCCCCCCN(CCCCCCCCCCC(=O)OCCCCCC)CCNC(=O)OCCN1CCCC1] | 718.2 |
| 868. | 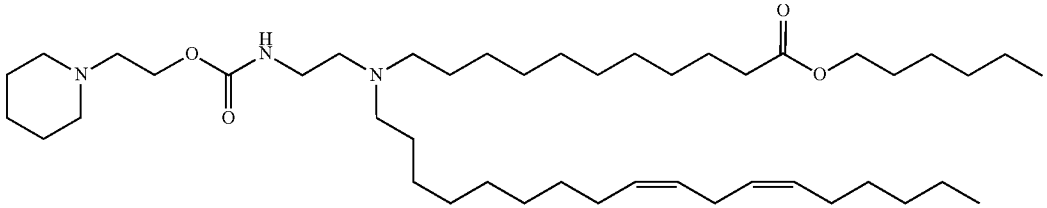 [SMILES: CCCCC/C=C\C/C=C\CCCCCCCCN(CCCCCCCCCCC(=O)OCCCCCC)CCNC(=O)OCCN1CCCCC1] | 732.2 |
| 869. | 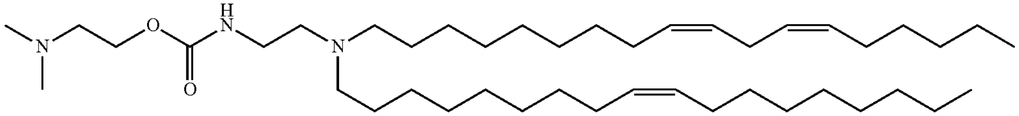 | 674.2 |

TABLE 1-continued
| # | Structure | Mw |
|---|---|---|
| 870. | 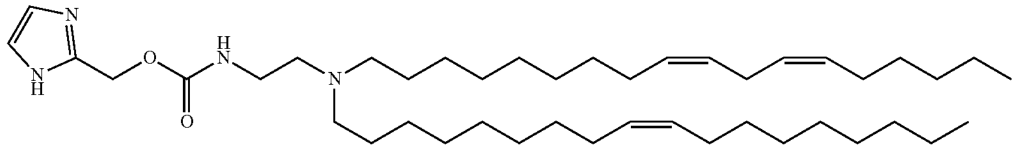 | 683.1 |
| 871. | 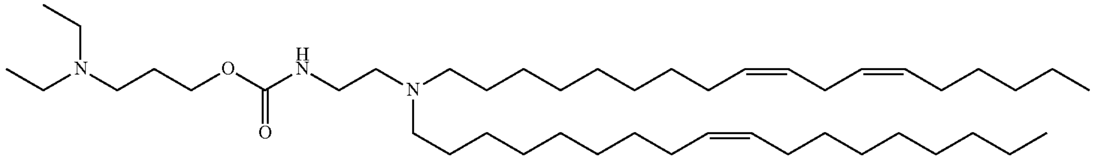 [SMILES: CCCCC/C=C\C/C=C\CCCCCCCCN(CCCCCCCC/C=C\CCCCCCCC)CCNC(=O)OCCCN(CC)CC] | 716.2 |
| 872. | 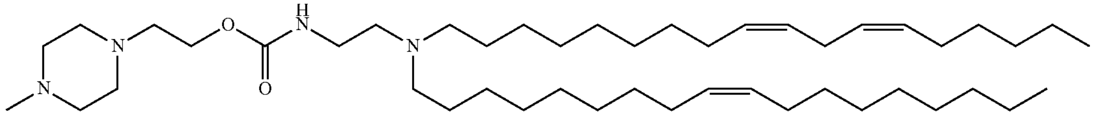 | 729.2 |
| 873. | 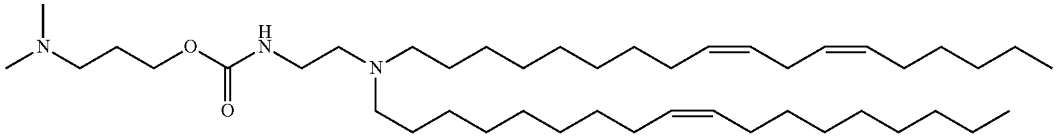 [SMILES: CCCCC/C=C\C/C=C\CCCCCCCCN(CCCCCCCC/C=C\CCCCCCCC)CCNC(=O)OCCCN(C)C] | 688.2 |
| 874. | 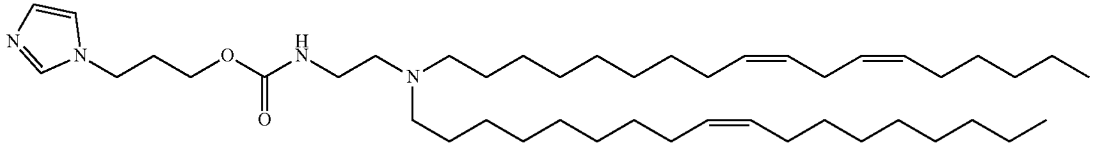 [SMILES: CCCCC/C=C\C/C=C\CCCCCCCCN(CCCCCCCC/C=C\CCCCCCCC)CCNC(=O)OCCCn1ccnc1] | 711.2 |
| 875. | 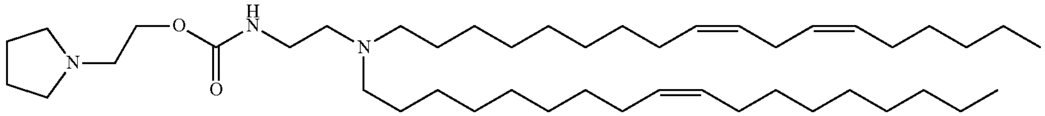 [SMILES: CCCCC/C=C\C/C=C\CCCCCCCCN(CCCCCCCC/C=C\CCCCCCCC)CCNC(=O)OCCN1CCCC1] | 700.2 |
| 876. | 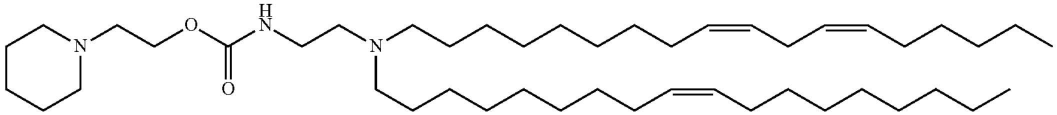 [SMILES: CCCCC/C=C\C/C=C\CCCCCCCCN(CCCCCCCC/C=C\CCCCCCCC)CCNC(=O)OCCN1CCCCC1] | 714.2 |

TABLE 1-continued
| # | Structure | Mw |
| --- | --- | --- |
| 877. | 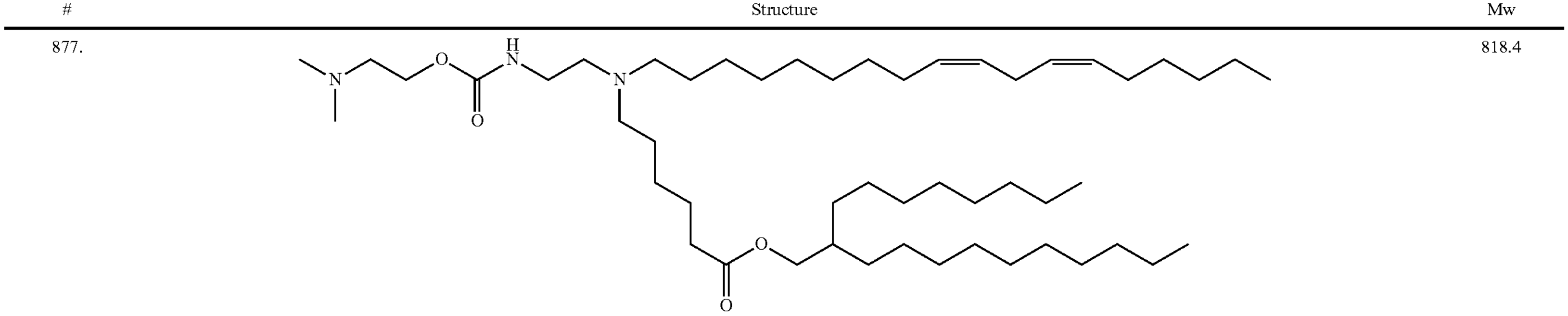 | 818.4 |
| 878. | 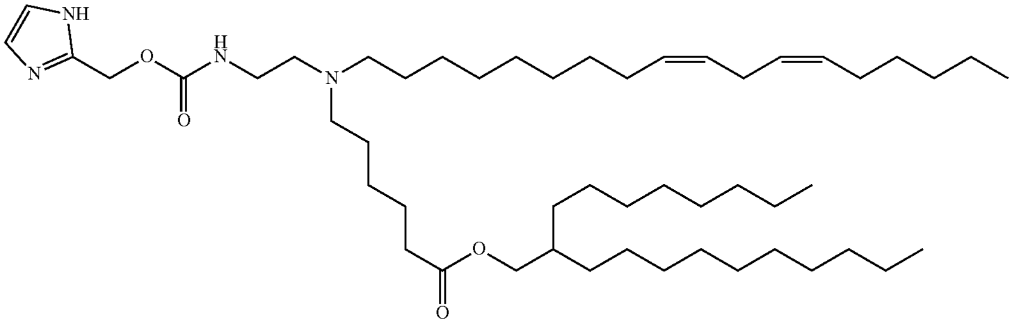 [SMILES: CCCCC/C=C\C/C=C\CCCCCCCCN(CCCCCC(=O)OCC(CCCCCCCC)CCCCCCCCCC)CCNC(=O)OCc1ncc[nH]1] | 827.3 |
| 879. | 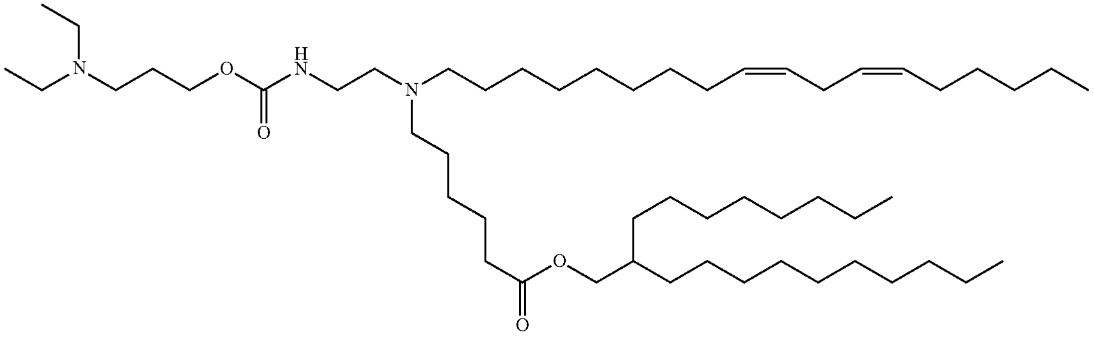 | 860.5 |

TABLE 1-continued
| # | Structure | Mw |
|---|---|---|
| 880. | 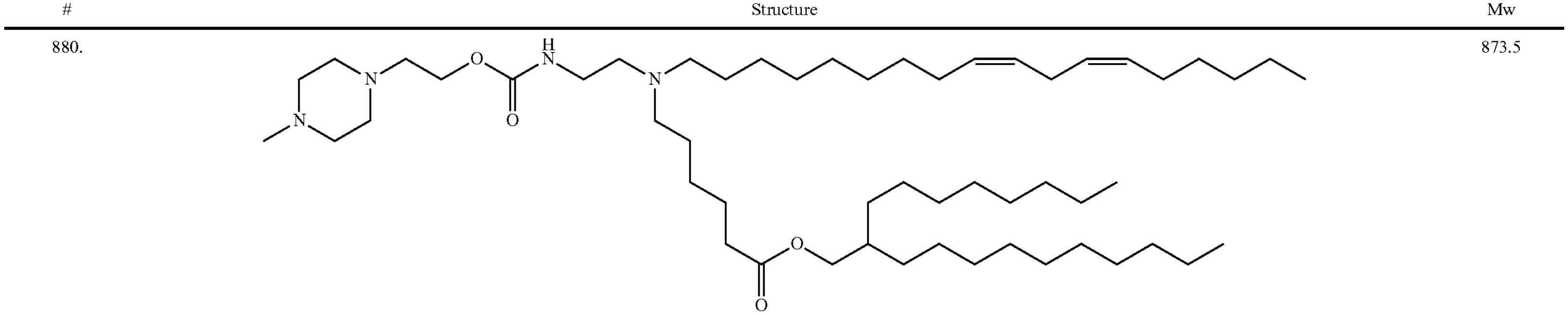 | 873.5 |
| 881. | 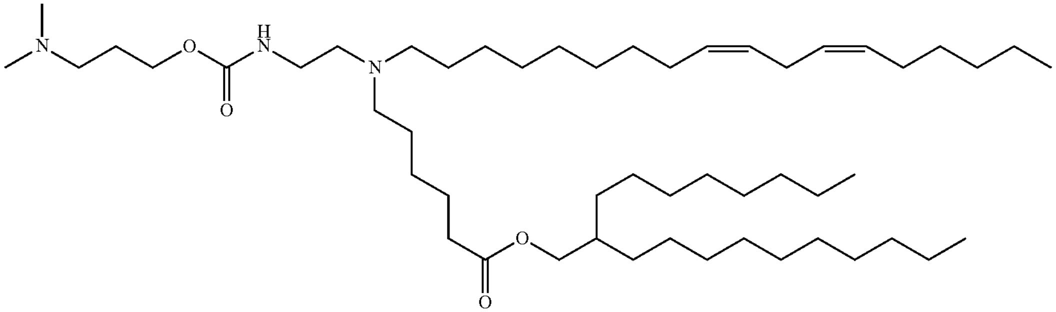 | 832.4 |
| 882. | 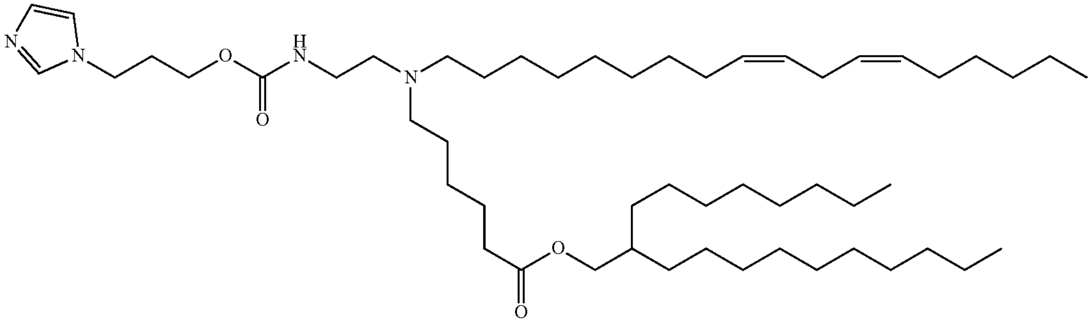 [SMILES: CCCCC/C=C\C/C=C\CCCCCCCCN(CCCCCC(=O)OCC(CCCCCCCC)CCCCCCCCCC)CCNC(=O)OCCCn1ccnc1] | 855.4 |

TABLE 1-continued
| # | Structure | Mw |
|---|---|---|
| 883. | 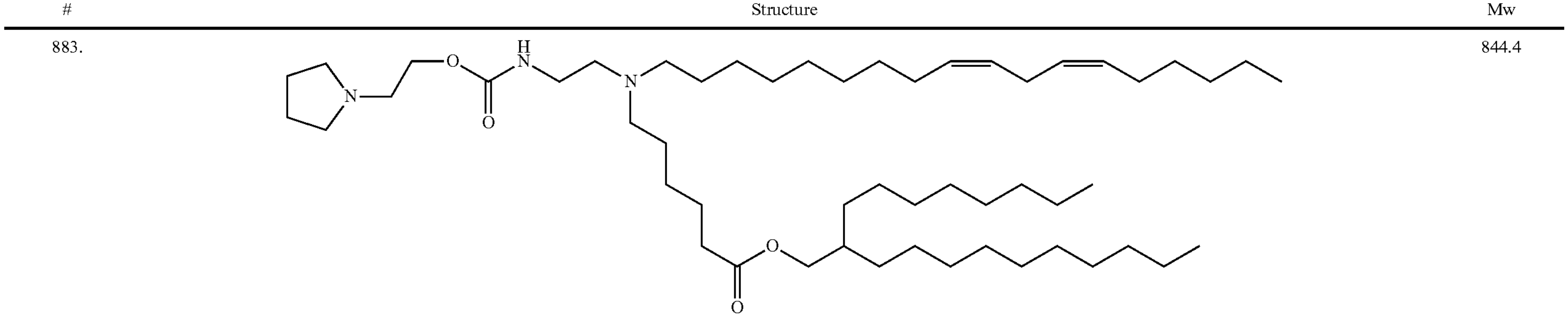 | 844.4 |
| 884. | 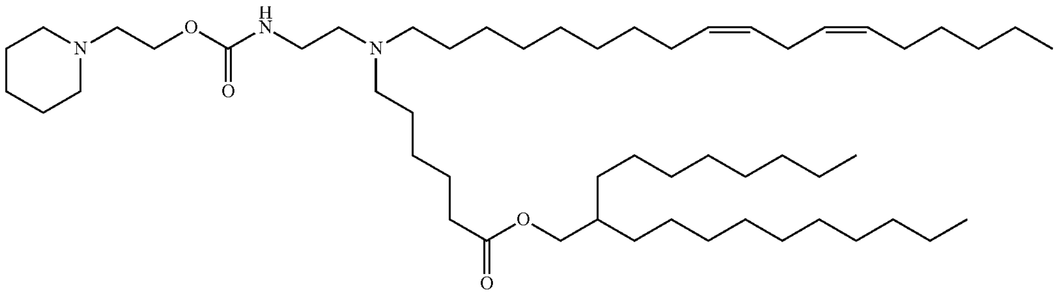 [SMILES: CCCCC/C=C\C/C=C\CCCCCCCCN(CCCCCC(=O)OCC(CCCCCCCC)CCCCCCCCCC)CCNC(=O)OCCN1CCCCC1] | 858.4 |
| 885. | 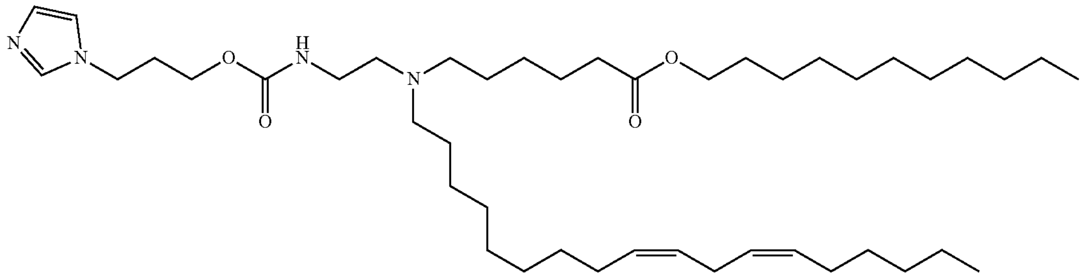 [SMILES: CCCCC/C=C\C/C=C\CCCCCCCCN(CCCCCC(=O)OCCCCCCCCCCC)CCNC(=O)OCCCn1ccnc1] | 729.1 |

TABLE 1-continued
| # | Structure | Mw |
| --- | --- | --- |
| 886. | 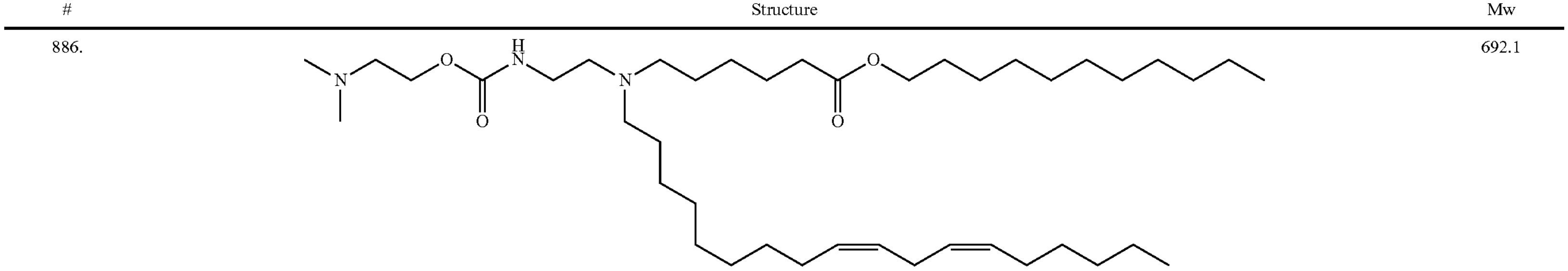 | 692.1 |
| 887. | 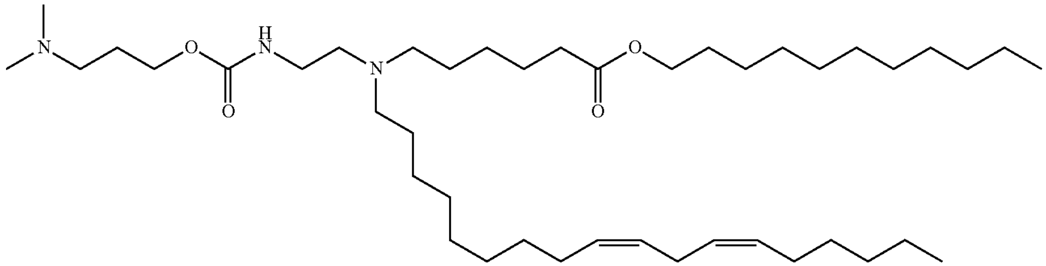 | 706.2 |
| 888. | 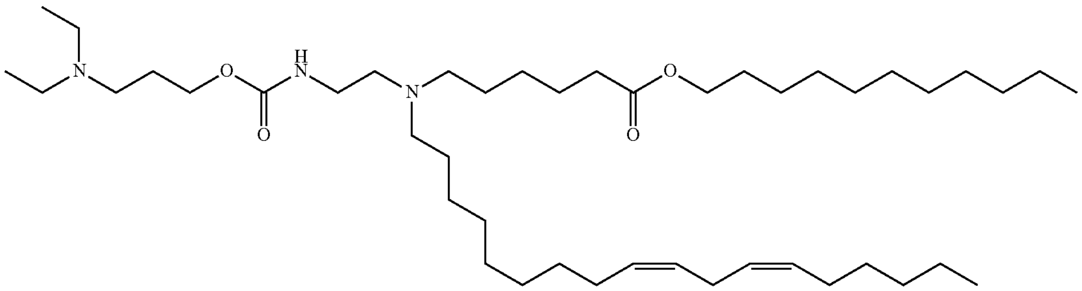 [SMILES: CCCCC/C=C\C/C=C\CCCCCCCCN(CCCCCC(=O)OCCCCCCCCCCC)CCNC(=O)OCCCN(CC)CC] | 734.2 |

TABLE 1-continued
| # | Structure | Mw |
| --- | --- | --- |
| 889. | 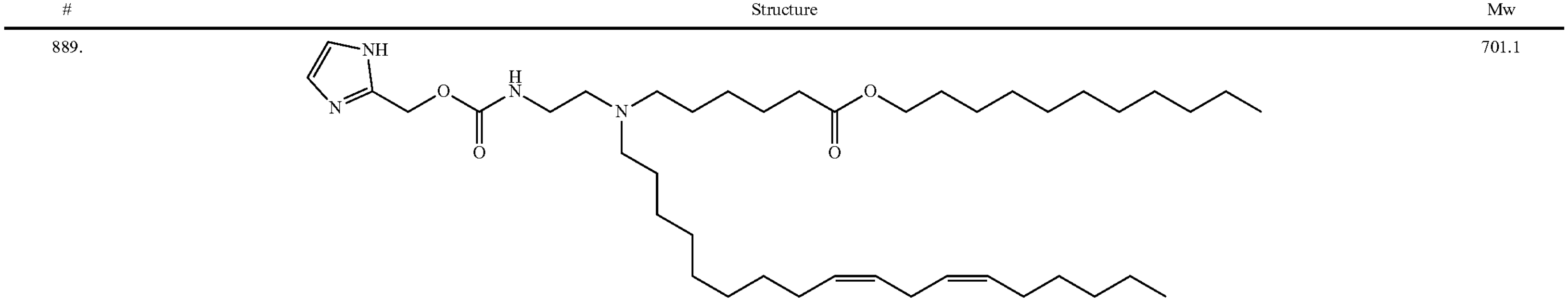 | 701.1 |
| 890. | 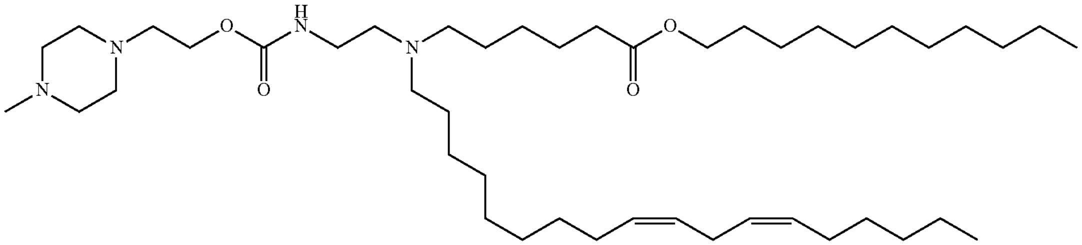 [SMILES: CCCCC/C=C\C/C=C\CCCCCCCCN(CCCCCC(=O)OCCCCCCCCCCC)CCNC(=O)OCCN1CCN(C)CC1] | 747.2 |
| 891. | 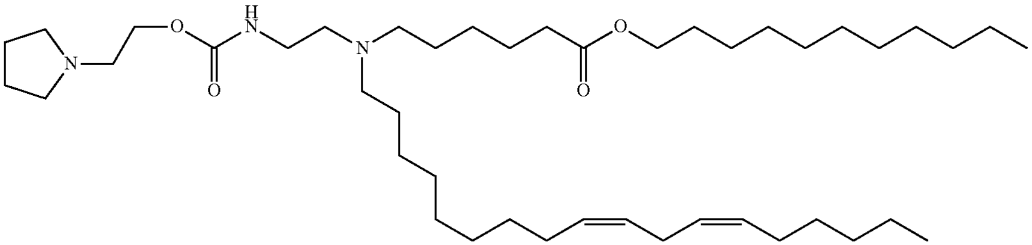 [SMILES: CCCCC/C=C\C/C=C\CCCCCCCCN(CCCCCC(=O)OCCCCCCCCCCC)CCNC(=O)OCCN1CCCC1] | 718.2 |
| 892. | 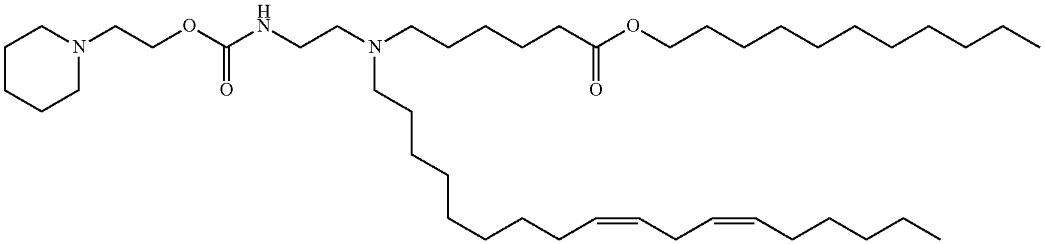 [SMILES: CCCCC/C=C\C/C=C\CCCCCCCCN(CCCCCC(=O)OCCCCCCCCCCC)CCNC(=O)OCCN1CCCCC1] | 732.2 |

TABLE 1-continued
| # | Structure | Mw |
|---|---|---|
| 893. | 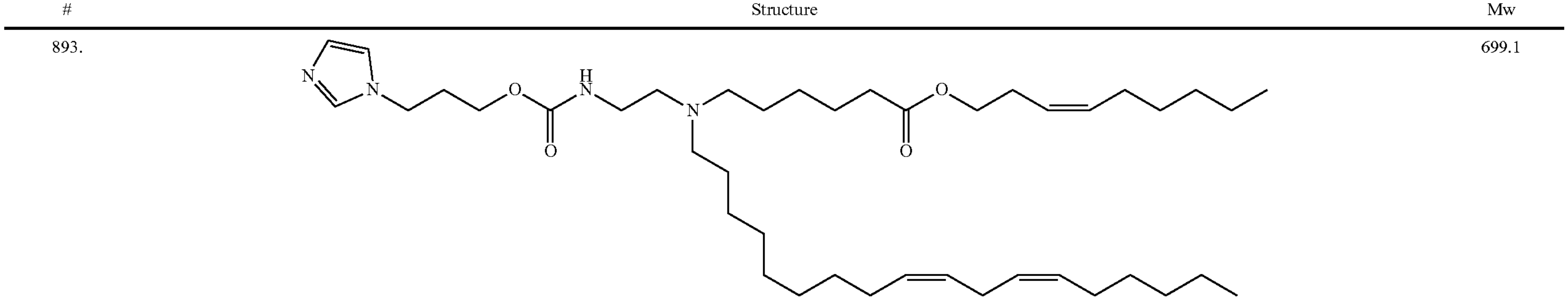 | 699.1 |
| 894. | 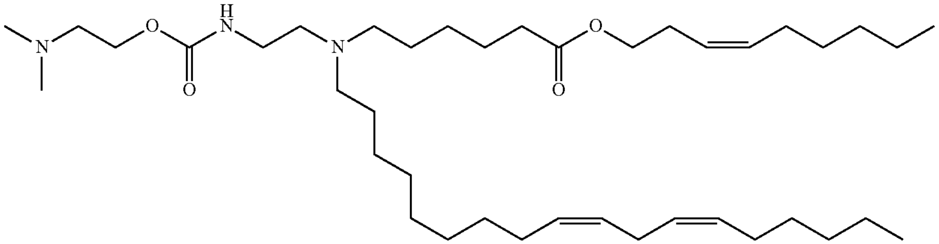 [SMILES: CCCCC/C=C\C/C=C\CCCCCCCCN(CCCCCC(=O)OCC/C=C\CCCCC)CCNC(=O)OCCN(C)C] | 662.1 |
| 895. | 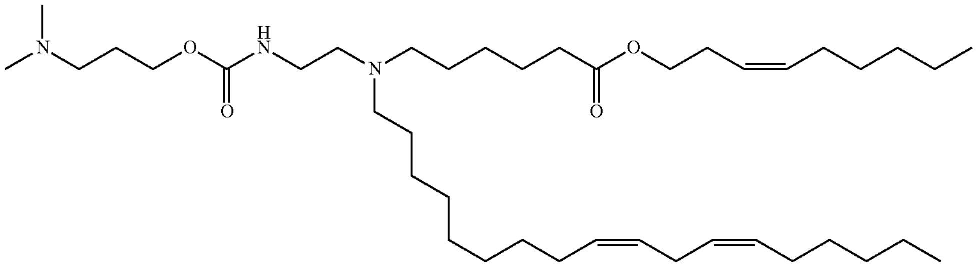 [SMILES: CCCCC/C=C\C/C=C\CCCCCCCCN(CCCCCC(=O)OCC/C=C\CCCCC)CCNC(=O)OCCCN(C)C] | 676.1 |
| 896. | +get,2392 | 704.1 |

TABLE 1-continued
| # | Structure | Mw |
|---|---|---|
| 897. | 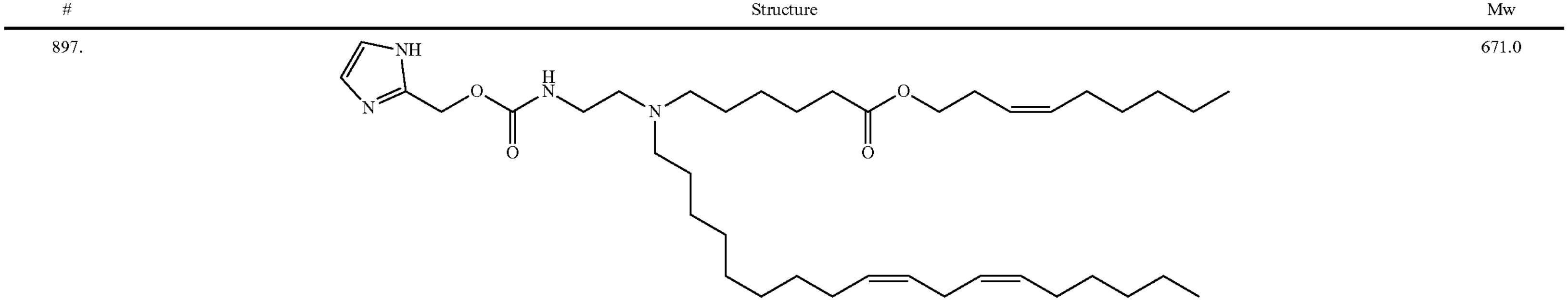 | 671.0 |
| 898. | 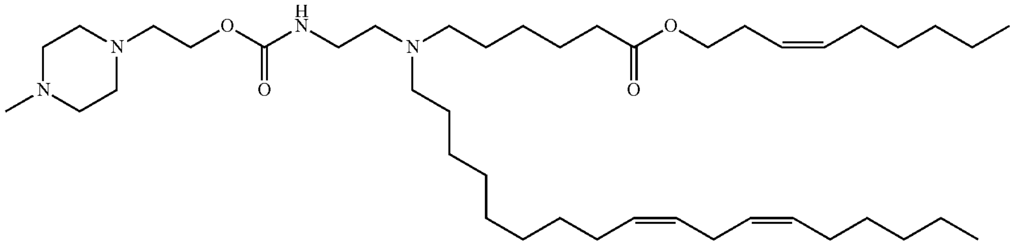 | 717.1 |
| 899. | 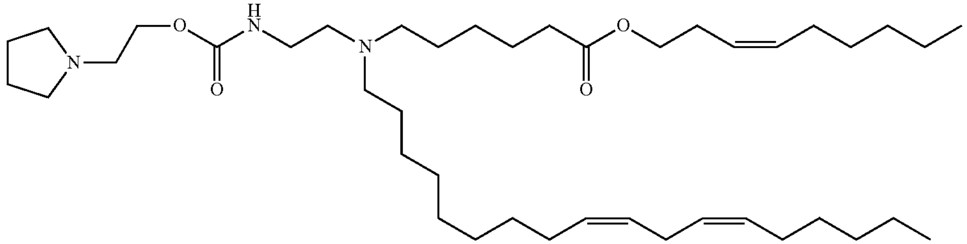 | 688.1 |
| 900. | 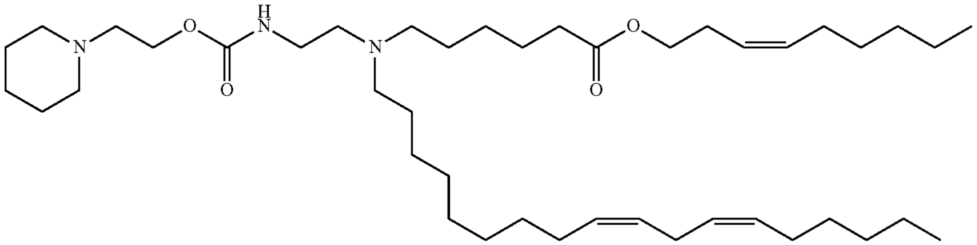 | 702.1 |

TABLE 1-continued
| # | Structure | Mw |
| --- | --- | --- |
| 901. | 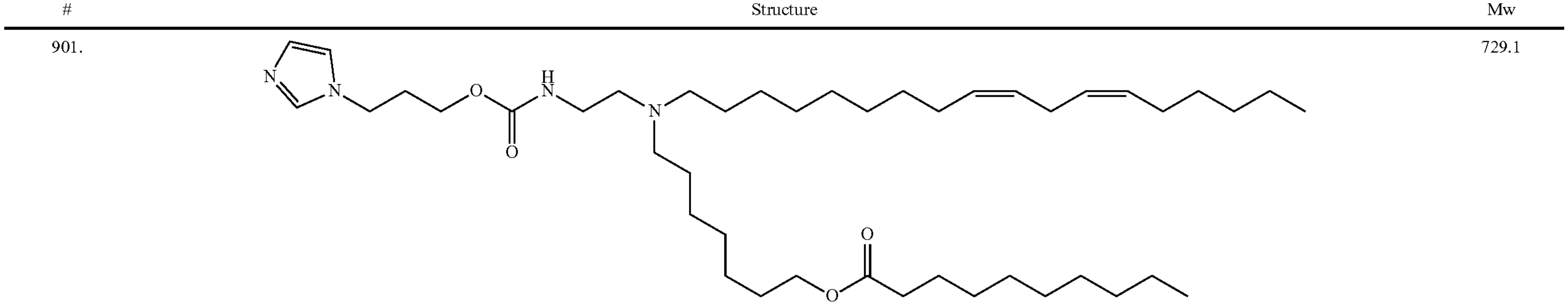 | 729.1 |
| 902. | 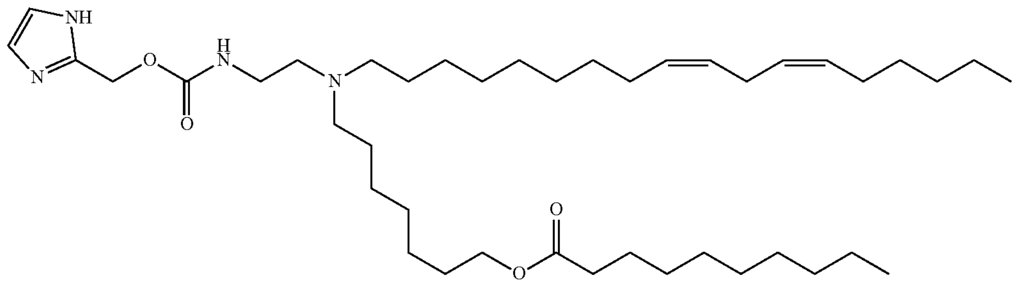 [SMILES: CCCCC/C=C\C/C=C\CCCCCCCCN(CCCCCCCOC(=O)CCCCCCCCC)CCNC(=O)OCc1ncc[nH]1] | 701.1 |
| 903. | 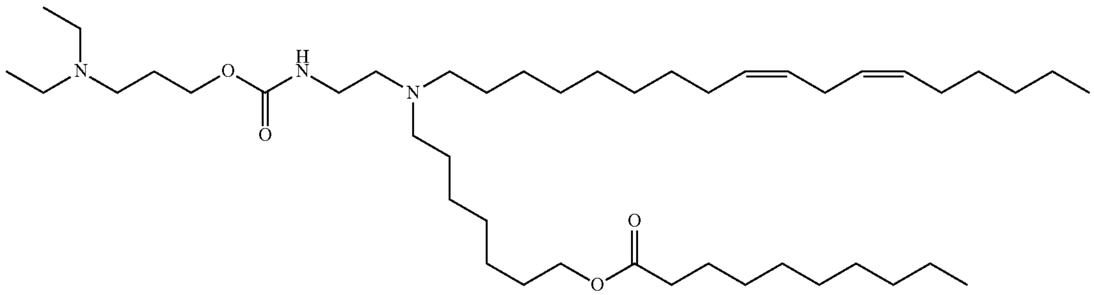 [SMILES: CCCCC/C=C\C/C=C\CCCCCCCCN(CCCCCCCOC(=O)CCCCCCCCC)CCNC(=O)OCCCN(CC)CC] | 734.2 |

TABLE 1-continued
| # | Structure | Mw |
| --- | --- | --- |
| 904. | 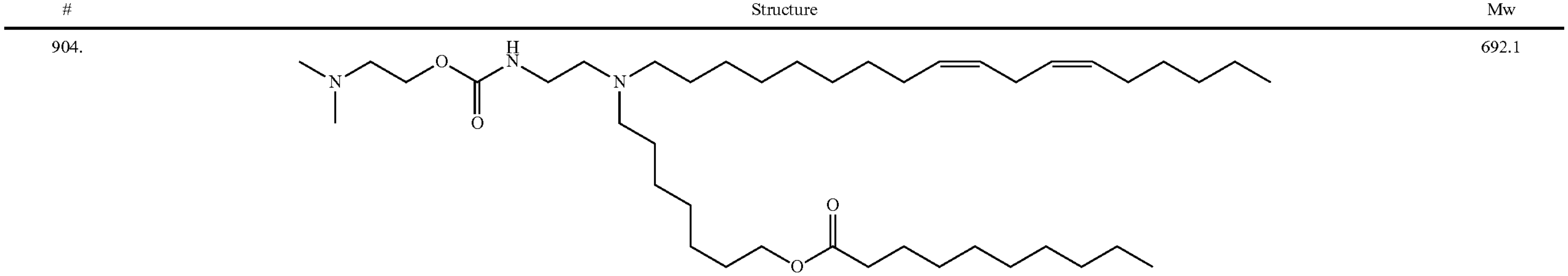 | 692.1 |
| 905. | 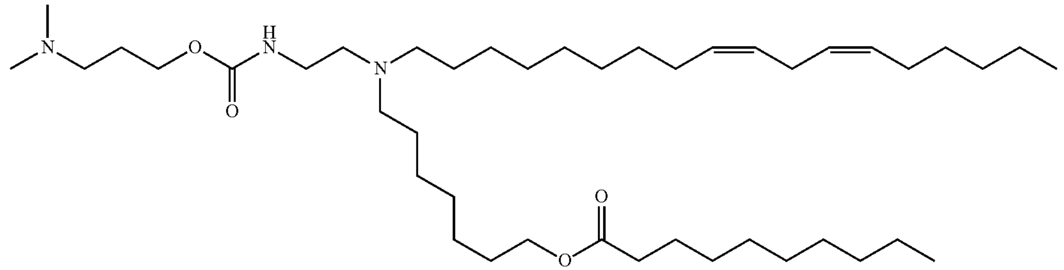 [SMILES: CCCCC/C=C\C/C=C\CCCCCCCCN(CCCCCCCOC(=O)CCCCCCCCC)CCNC(=O)OCCCN(C)C] | 706.2 |
| 906. | 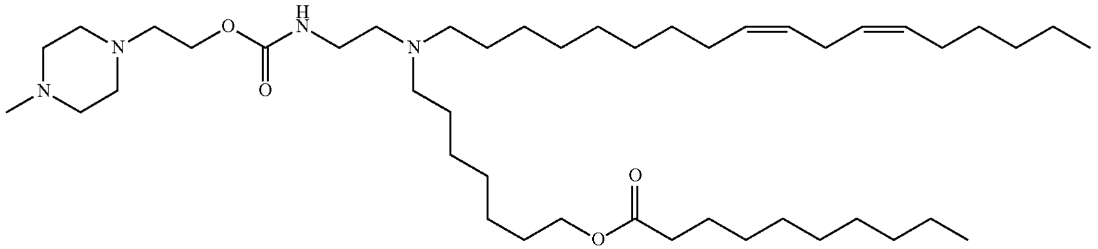 [SMILES: CCCCC/C=C\C/C=C\CCCCCCCCN(CCCCCCCOC(=O)CCCCCCCCC)CCNC(=O)OCCN1CCN(C)CC1] | 747.2 |
| 907. | 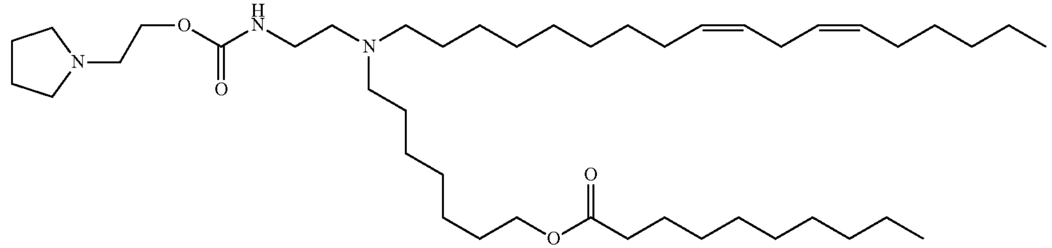 [SMILES: CCCCC/C=C\C/C=C\CCCCCCCCN(CCCCCCCOC(=O)CCCCCCCCC)CCNC(=O)OCCN1CCCC1] | 718.2 |

TABLE 1-continued
| # | Structure | Mw |
|---|---|---|
| 908. | 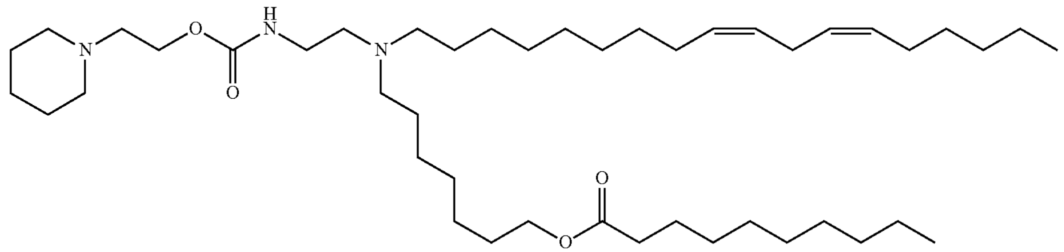 | 732.2 |
| 909. | 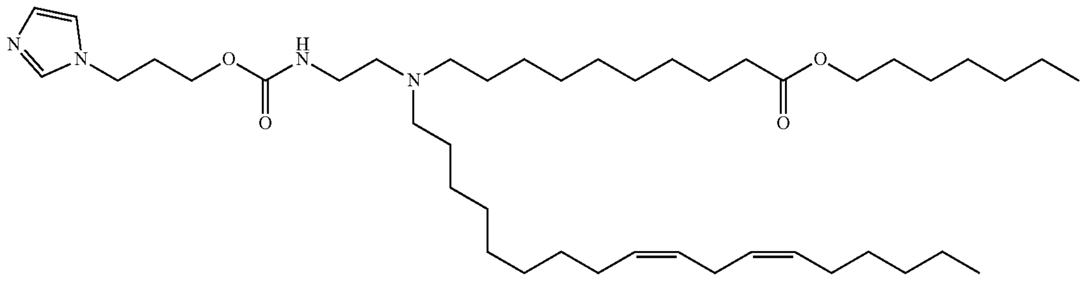 | 729.1 |
| 910. | 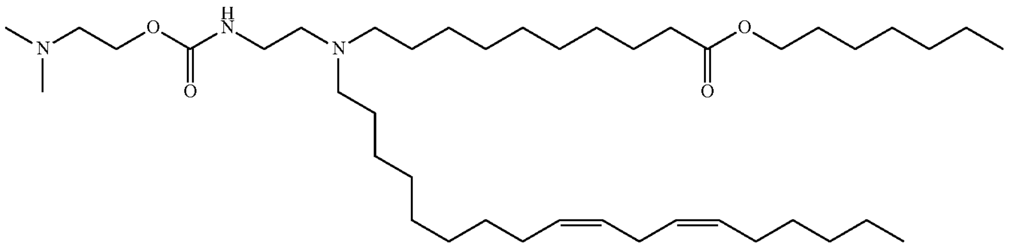 [SMILES: CCCCC/C=C\C/C=C\CCCCCCCCN(CCCCCCCCCC(=O)OCCCCCCC)CCNC(=O)OCCN(C)C] | 692.1 |

TABLE 1-continued
| # | Structure | Mw |
| --- | --- | --- |
| 911. | 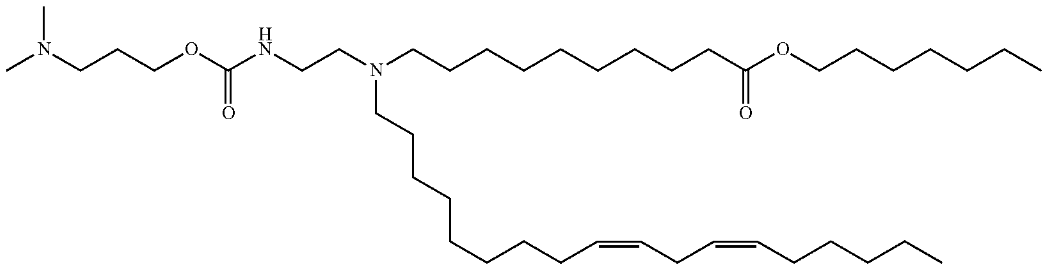 [SMILES: CCCCC/C=C\C/C=C\CCCCCCCCN(CCCCCCCCCC(=O)OCCCCCCC)CCNC(=O)OCCCN(C)C] | 706.2 |
| 912. | 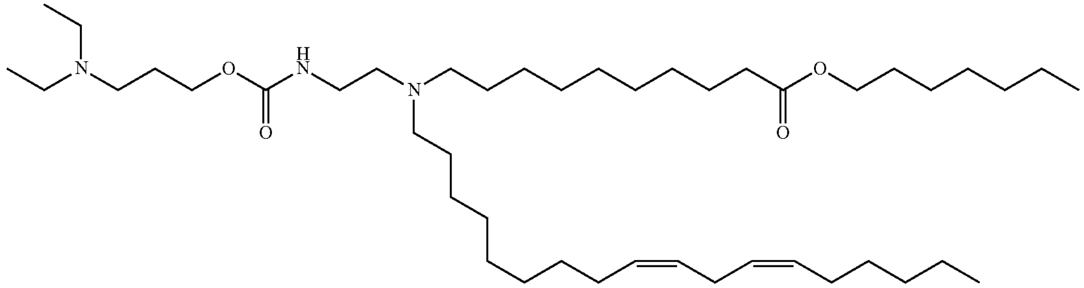 [SMILES: CCCCC/C=C\C/C=C\CCCCCCCCN(CCCCCCCCCC(=O)OCCCCCCC)CCNC(=O)OCCCN(CC)CC] | 734.2 |
| 913. | 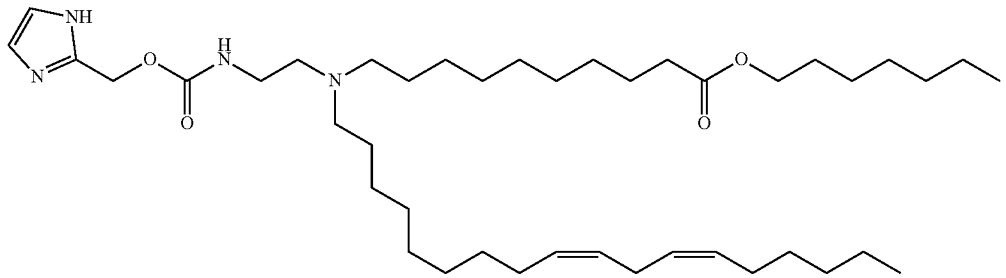 [SMILES: CCCCC/C=C\C/C=C\CCCCCCCCN(CCCCCCCCCC(=O)OCCCCCCC)CCNC(=O)OCc1ncc[nH]1] | 701.1 |

TABLE 1-continued
| # | Structure | Mw |
|---|---|---|
| 914. | 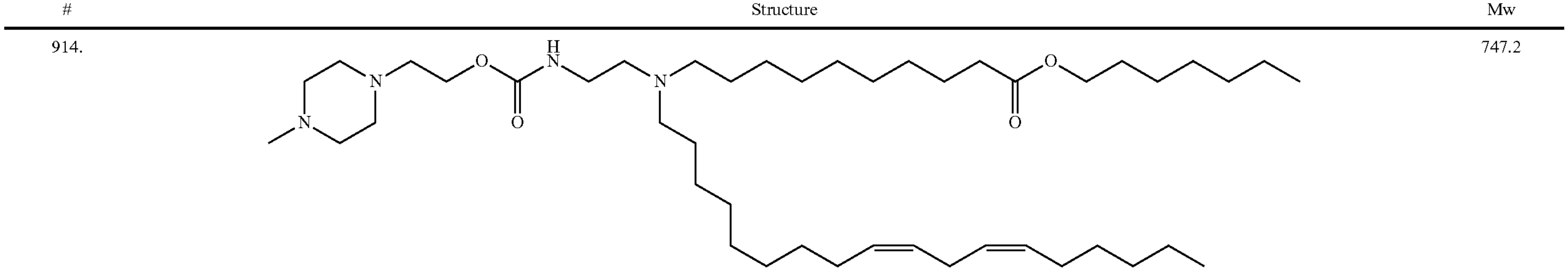 | 747.2 |
| 915. | 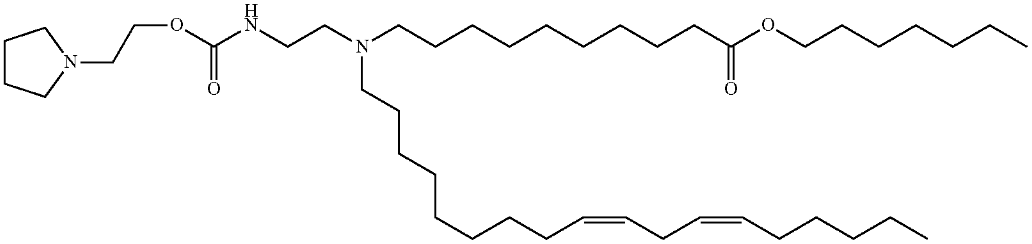 [SMILES: CCCCC/C=C\C/C=C\CCCCCCCCN(CCCCCCCCCC(=O)OCCCCCCC)CCNC(=O)OCCN1CCCC1] | 718.2 |
| 916. | 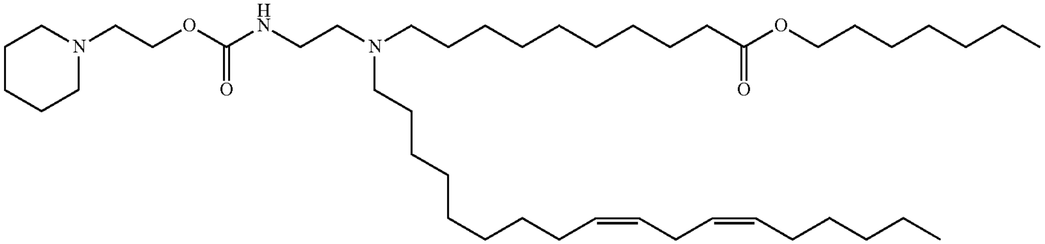 | 732.2 |
| 917. | 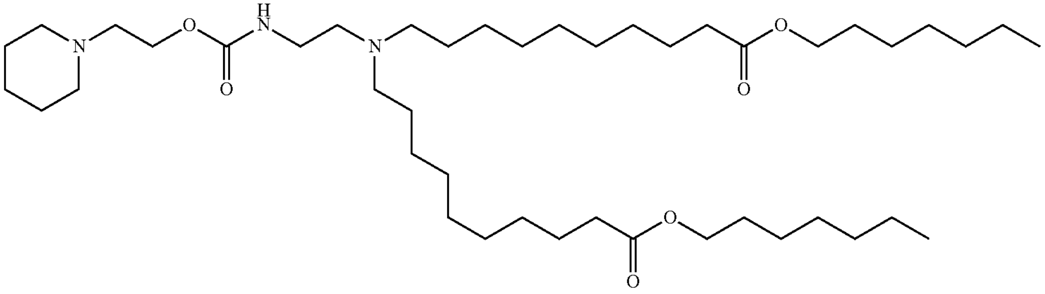 [SMILES: CCCCCCCOC(=O)CCCCCCCCCN(CCCCCCCCCC(=O)OCCCCCCC)CCNC(=O)OCCN1CCCCC1] | 752.2 |

TABLE 1-continued
| # | Structure | Mw |
| --- | --- | --- |
| 918. | 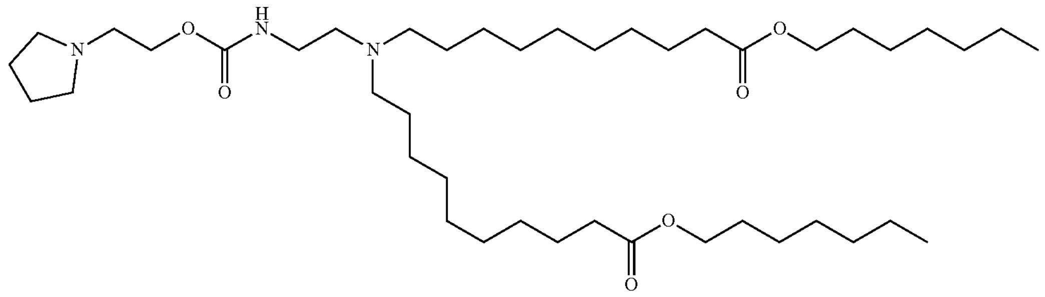 [SMILES: CCCCCCCOC(=O)CCCCCCCCCN(CCCCCCCCCC(=O)OCCCCCCC)CCNC(=O)OCCN1CCCC1] | 738.2 |
| 919. | 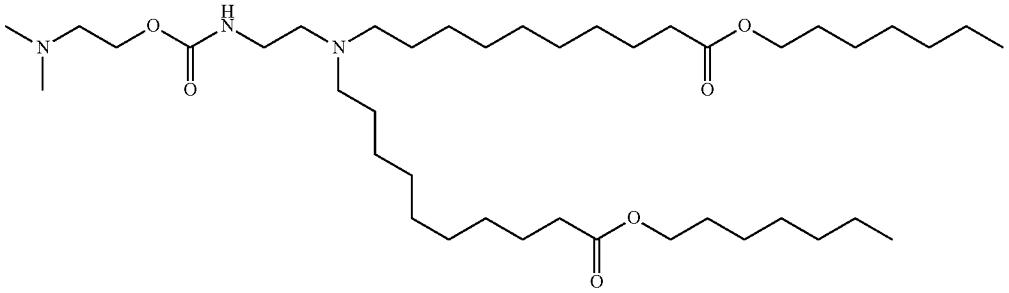 [SMILES: CCCCCCCOC(=O)CCCCCCCCCN(CCCCCCCCCC(=O)OCCCCCCC)CCNC(=O)OCCN(C)C] | 712.1 |
| 920. | 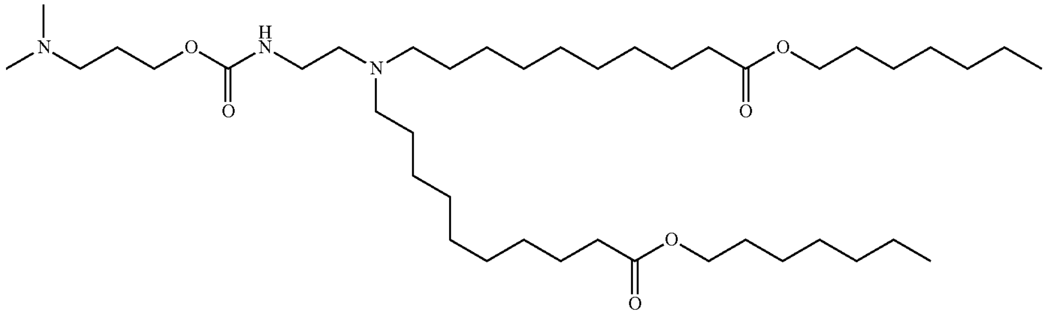 [SMILES: CCCCCCCOC(=O)CCCCCCCCCN(CCCCCCCCCC(=O)OCCCCCCC)CCNC(=O)OCCCN(C)C] | 726.1 |

TABLE 1-continued
| # | Structure | Mw |
| --- | --- | --- |
| 921. | 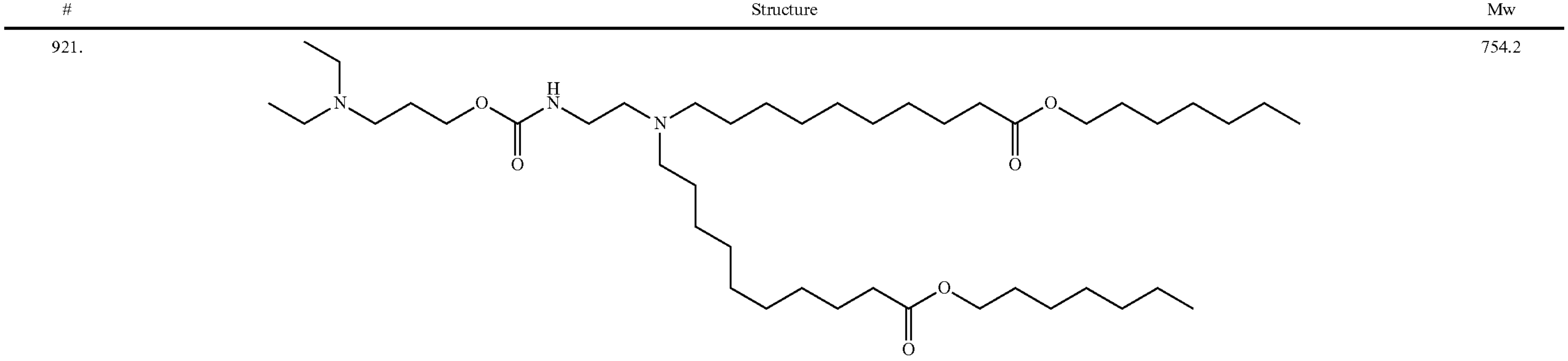 | 754.2 |
| 922. | 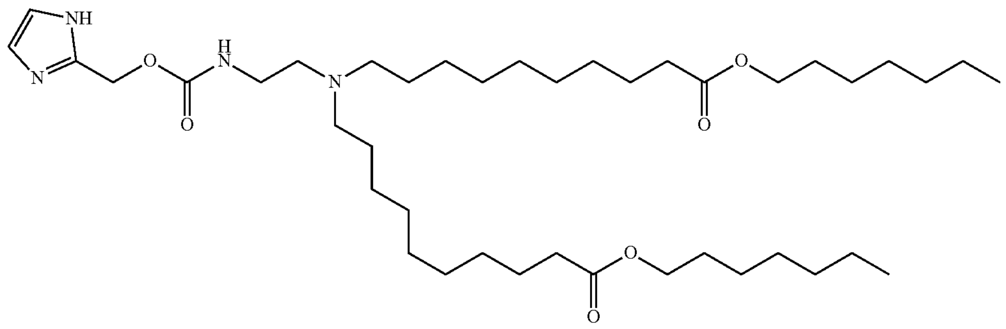 [SMILES: CCCCCCCOC(=O)CCCCCCCCCN(CCCCCCCCCC(=O)OCCCCCCC)CCNC(=O)OCc1ncc[nH]1] | 721.1 |
| 923. | 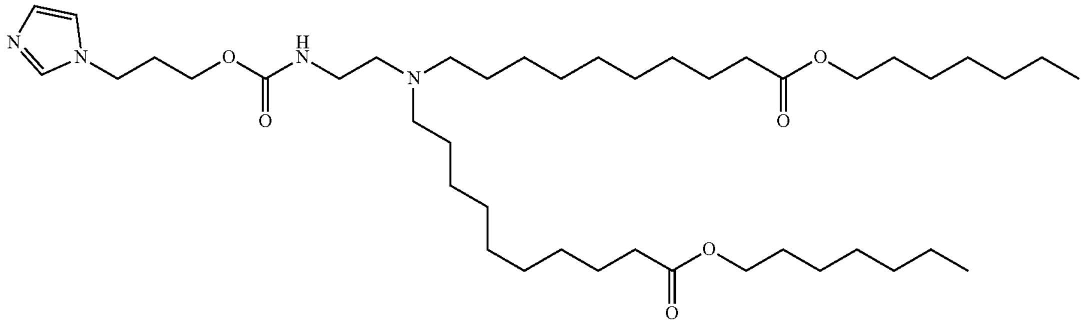 [SMILES: CCCCCCCOC(=O)CCCCCCCCCN(CCCCCCCCCC(=O)OCCCCCCC)CCNC(=O)OCCCn1ccnc1] | 749.1 |

TABLE 1-continued
| # | Structure | Mw |
| --- | --- | --- |
| 924. | 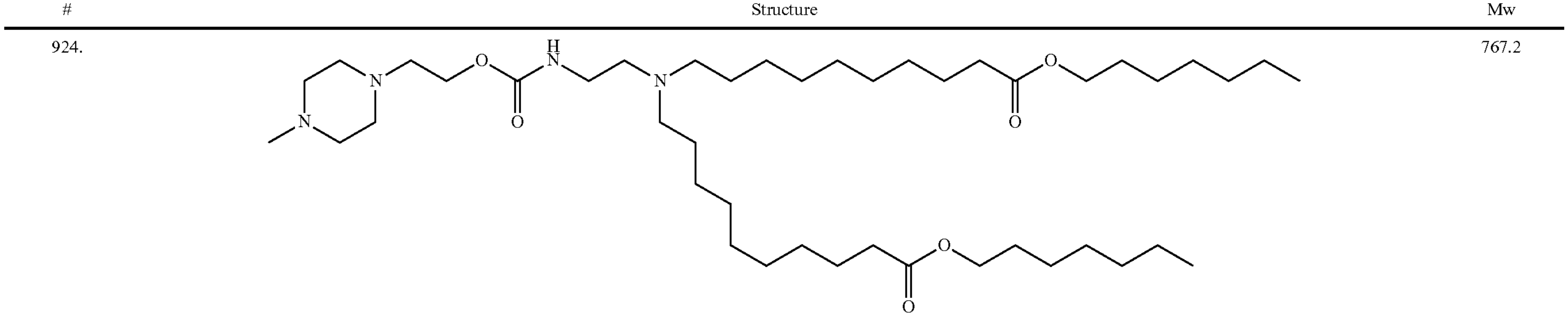 | 767.2 |
| 925. | 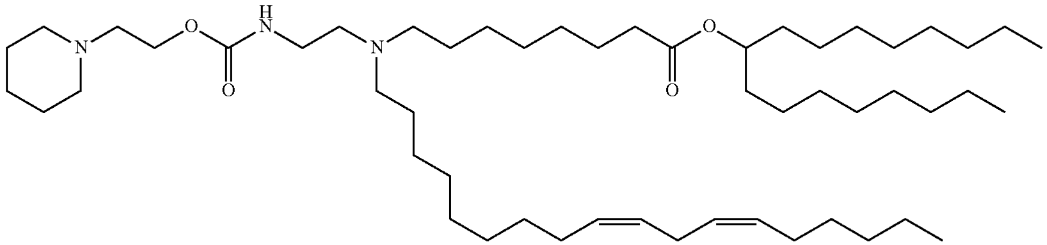 [SMILES: CCCCC/C=C\C/C=C\CCCCCCCCN(CCCCCCCC(=O)OC(CCCCCCCC)CCCCCCCC)CCNC(=O)OCCN1CCCCC1] | 844.4 |
| 926. | 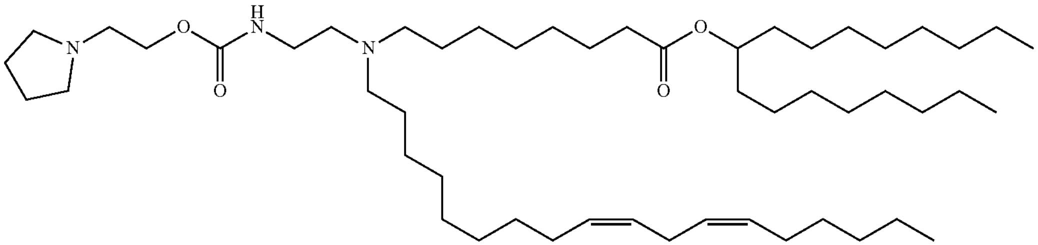 | 830.4 |
| 927. | 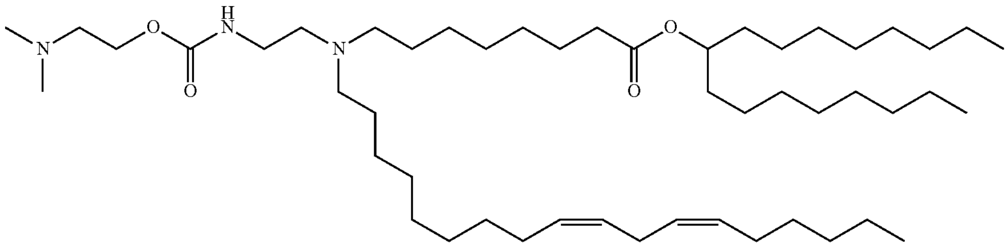 [SMILES: CCCCC/C=C\C/C=C\CCCCCCCCN(CCCCCCCC(=O)OC(CCCCCCCC)CCCCCCCC)CCNC(=O)OCCN(C)C] | 804.3 |

TABLE 1-continued
| # | Structure | Mw |
| --- | --- | --- |
| 928. | 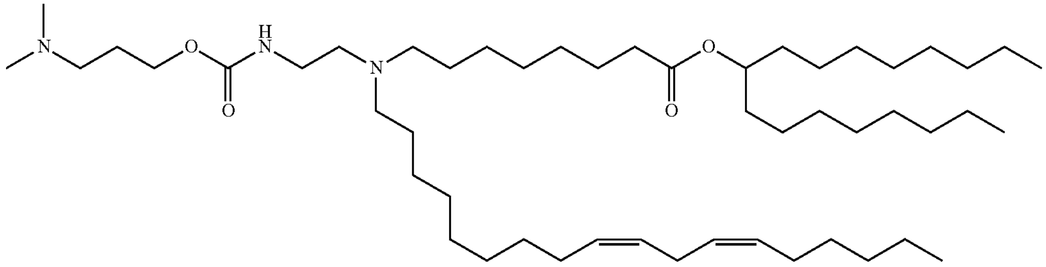 [SMILES: CCCCC/C=C\C/C=C\CCCCCCCCN(CCCCCCCC(=O)OC(CCCCCCCC)CCCCCCCC)CCNC(=O)OCCCN(C)C] | 818.4 |
| 929. | 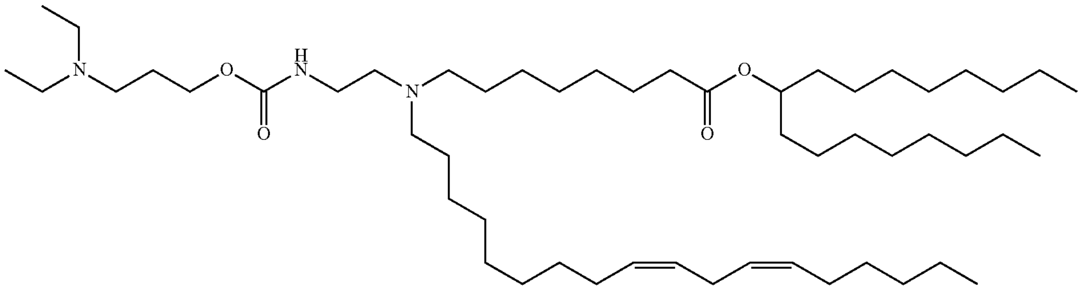 | 846.4 |
| 930. | 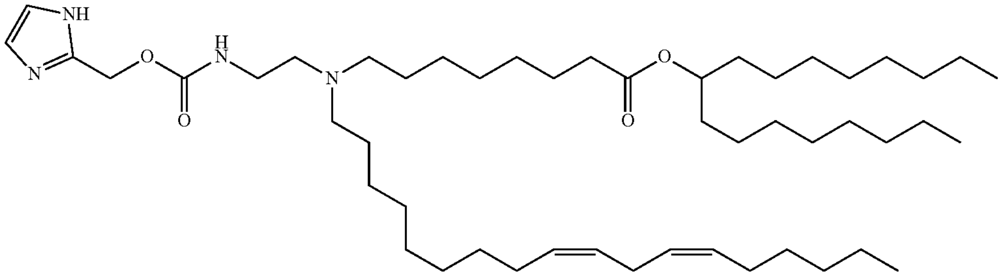 [SMILES: CCCCC/C=C\C/C=C\CCCCCCCCN(CCCCCCCC(=O)OC(CCCCCCCC)CCCCCCCC)CCNC(=O)OCc1ncc[nH]1] | 813.3 |

TABLE 1-continued
| # | Structure | Mw |
|---|---|---|
| 931. | 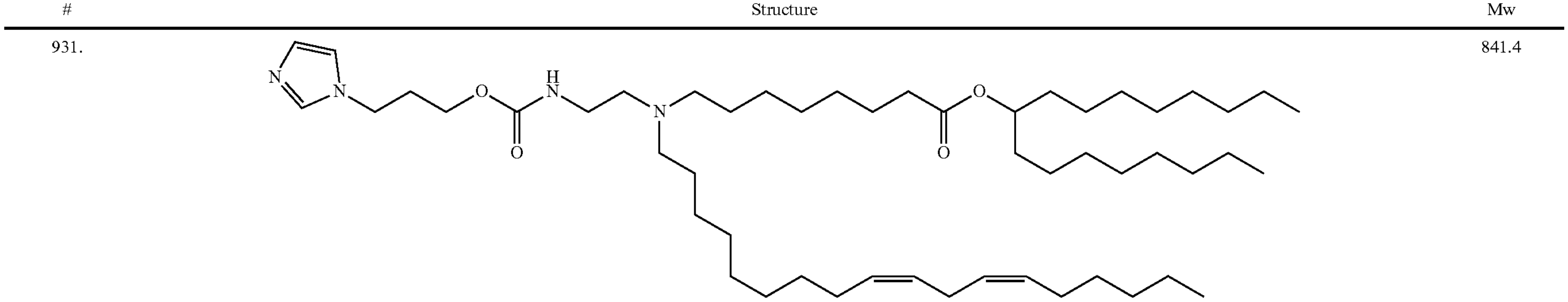 | 841.4 |
| 932. | 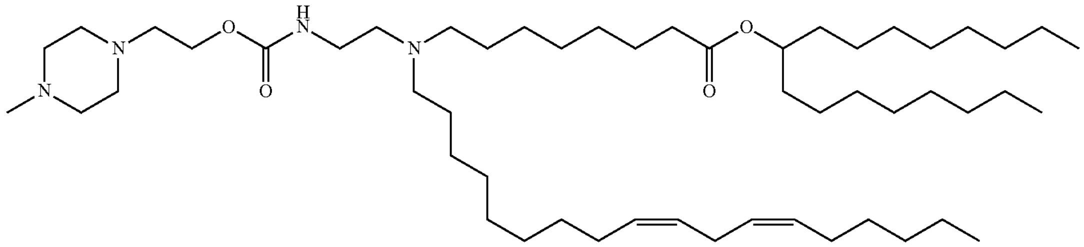 [SMILES: CCCCC/C=C\C/C=C\CCCCCCCCN(CCCCCCCC(=O)OC(CCCCCCCC)CCCCCCCC)CCNC(=O)OCCN1CCN(C)CC1] | 859.4 |
| 933. | 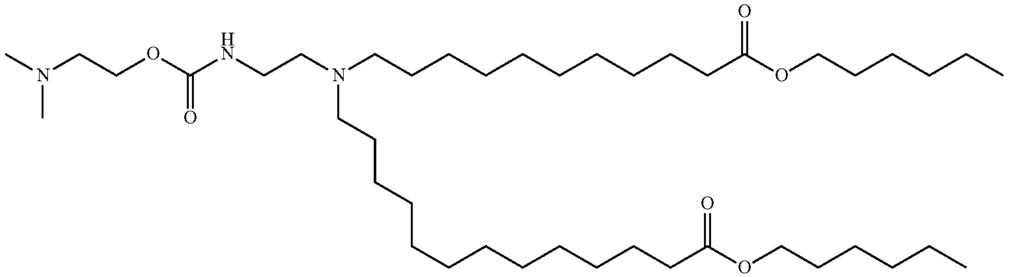 [SMILES: CCCCCCOC(=O)CCCCCCCCCCCCN(CCCCCCCCCCC(=O)OCCCCCC)CCNC(=O)OCCN(C)C] | 712.1 |
| 934. | 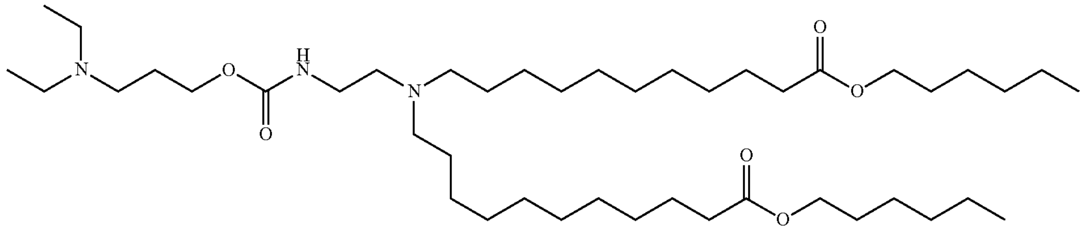 [SMILES: CCCCCCOC(=O)CCCCCCCCCCN(CCCCCCCCCCC(=O)OCCCCCC)CCNC(=O)OCCCN(CC)CC] | 754.2 |

TABLE 1-continued
| # | Structure | Mw |
| --- | --- | --- |
| 935. | 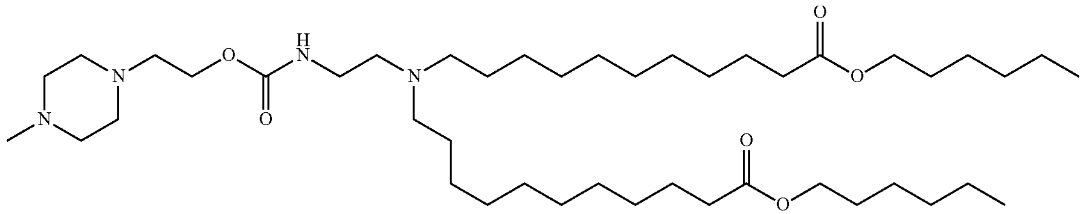 [SMILES: CCCCCCOC(=O)CCCCCCCCCCN(CCCCCCCCCCC(=O)OCCCCCC)CCNC(=O)OCCN1CCN(C)CC1] | 767.2 |
| 936. | 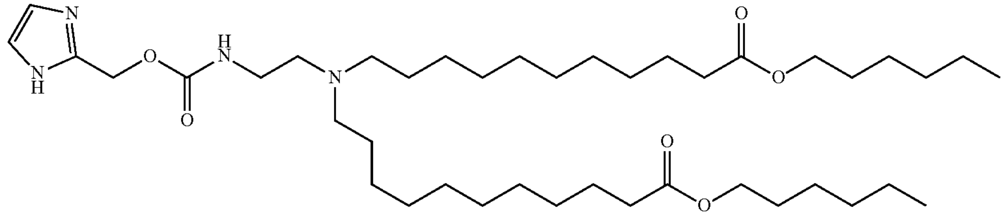 [SMILES: CCCCCCOC(=O)CCCCCCCCCCN(CCCCCCCCCCC(=O)OCCCCCC)CCNC(=O)OCc1ncc[nH]1] | 721.1 |
| 937. | 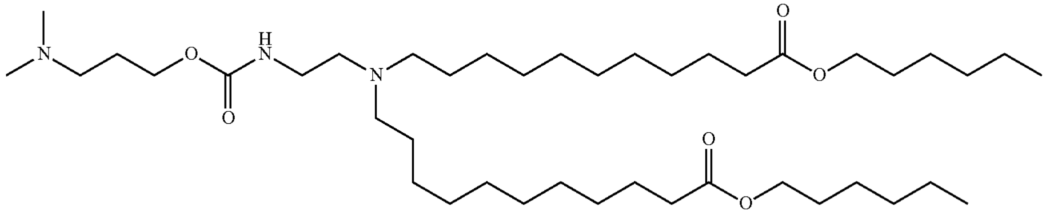 [SMILES: CCCCCCOC(=O)CCCCCCCCCCN(CCCCCCCCCCC(=O)OCCCCCC)CCNC(=O)OCCCN(C)C] | 726.1 |
| 938. | 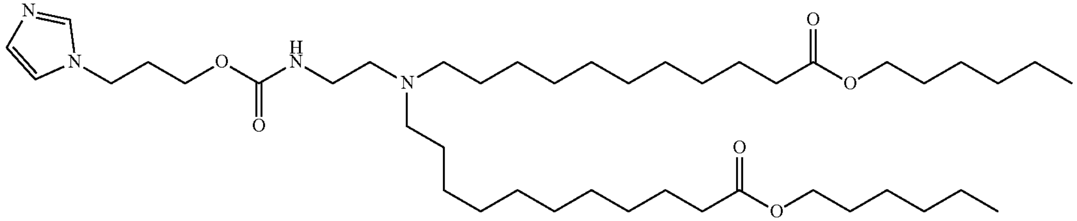 [SMILES: CCCCCCOC(=O)CCCCCCCCCCN(CCCCCCCCCCC(=O)OCCCCCC)CCNC(=O)OCCCn1ccnc1] | 749.1 |

TABLE 1-continued
| # | Structure | Mw |
| --- | --- | --- |
| 939. | 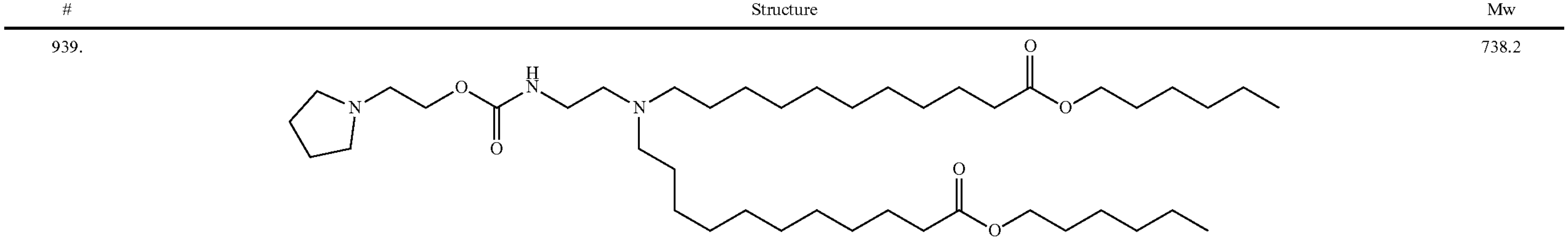 | 738.2 |
| 940. | 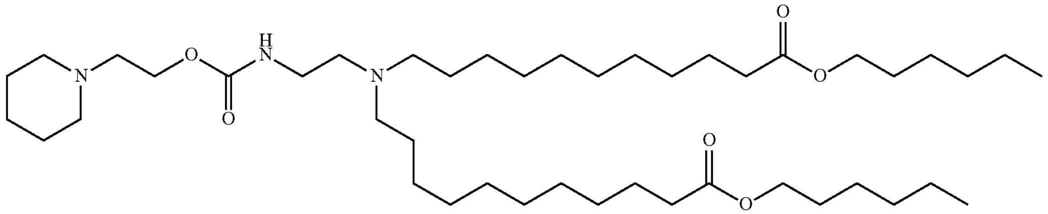 [SMILES: CCCCCCOC(=O)CCCCCCCCCCN(CCCCCCCCCCC(=O)OCCCCCC)CCNC(=O)OCCN1CCCCC1] | 752.2 |
| 941. | 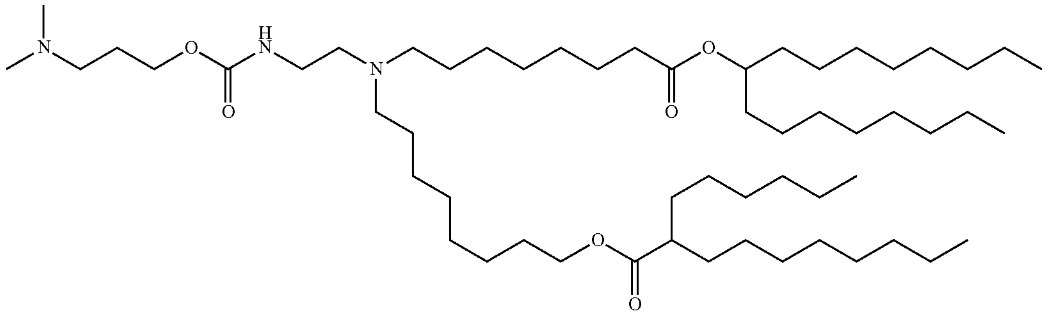 [SMILES: CCCCCCCCC(CCCCCCCC)OC(=O)CCCCCCCN(CCCCCCCCOC(=O)C(CCCCCC)CCCCCCCC)CCNC(=O)OCCCN(C)C] | 936.5 |

TABLE 1-continued
| # | Structure | Mw |
|---|---|---|
| 942. | 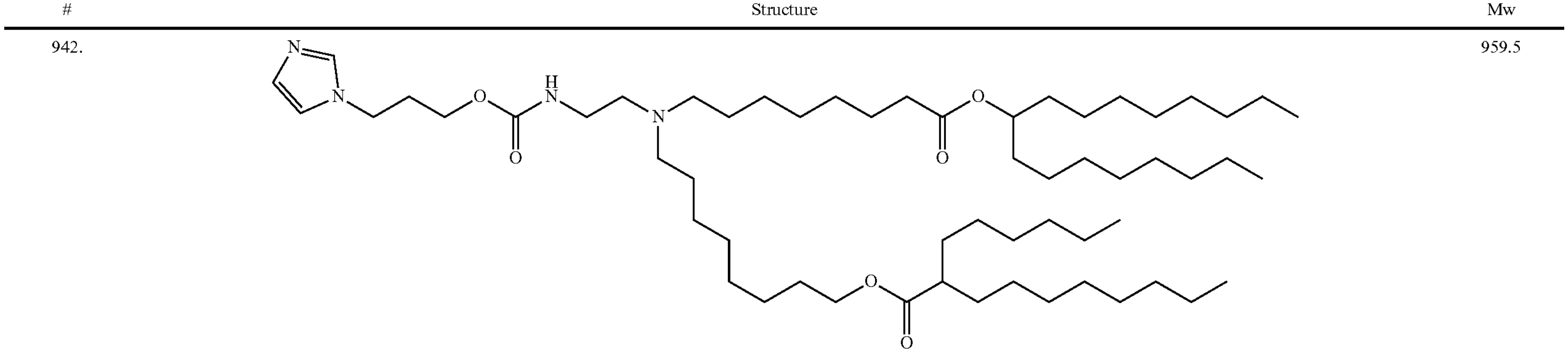 | 959.5 |
| 943. | 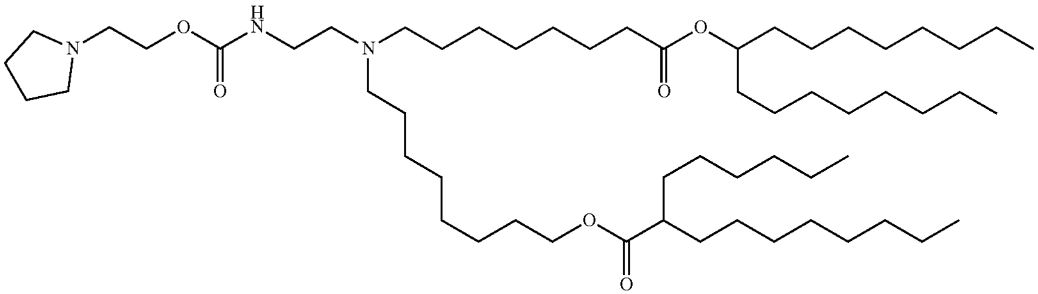 [SMILES: CCCCCCCCC(CCCCCCCC)OC(=O)CCCCCCCN(CCCCCCCCOC(=O)C(CCCCCC)CCCCCCCC)CCNC(=O)OCCN1CCCC1] | 948.6 |
| 944. | 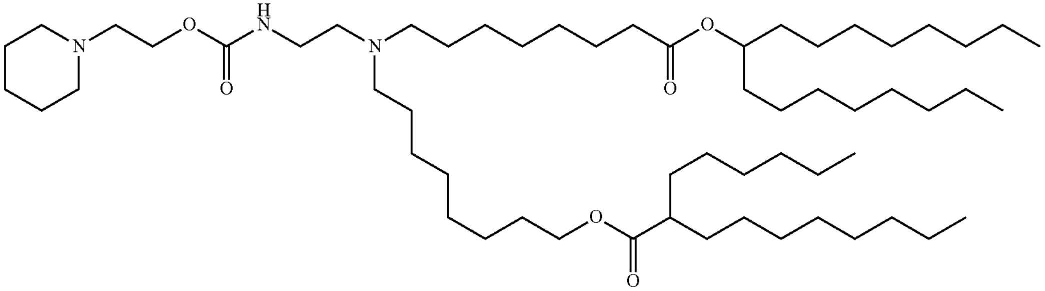 [SMILES: CCCCCCCCC(CCCCCCCC)OC(=O)CCCCCCCN(CCCCCCCCOC(=O)C(CCCCCC)CCCCCCCC)CCNC(=O)OCCN1CCCCC1] | 962.6 |

TABLE 1-continued
| # | Structure | Mw |
|---|---|---|
| 945. | 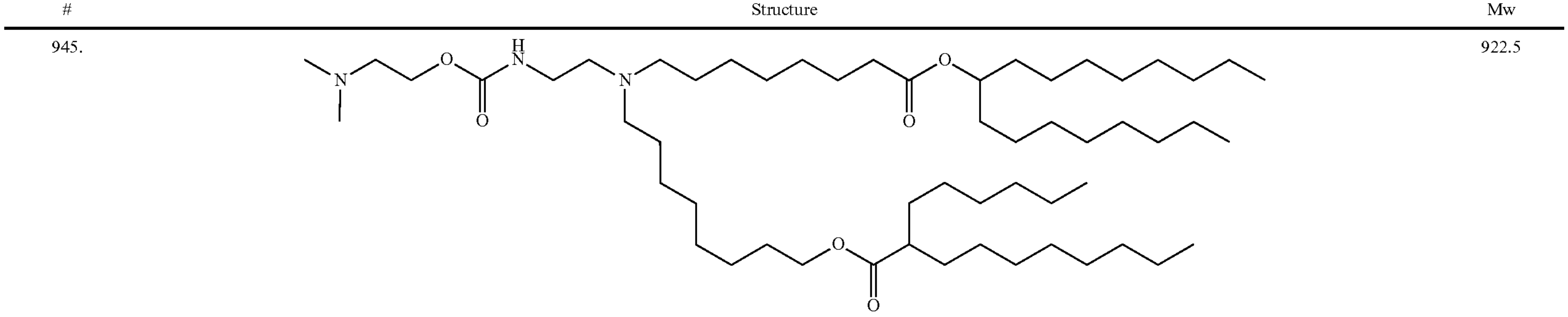 | 922.5 |
| 946. | 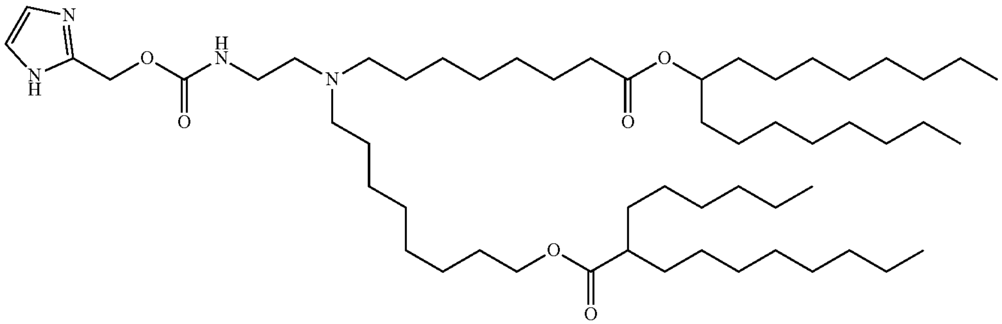 [SMILES: CCCCCCCCC(CCCCCCCC)OC(=O)CCCCCCCN(CCCCCCCCOC(=O)C(CCCCCC)CCCCCCCC)CCNC(=O)OCc1ncc[nH]1] | 931.5 |
| 947. | 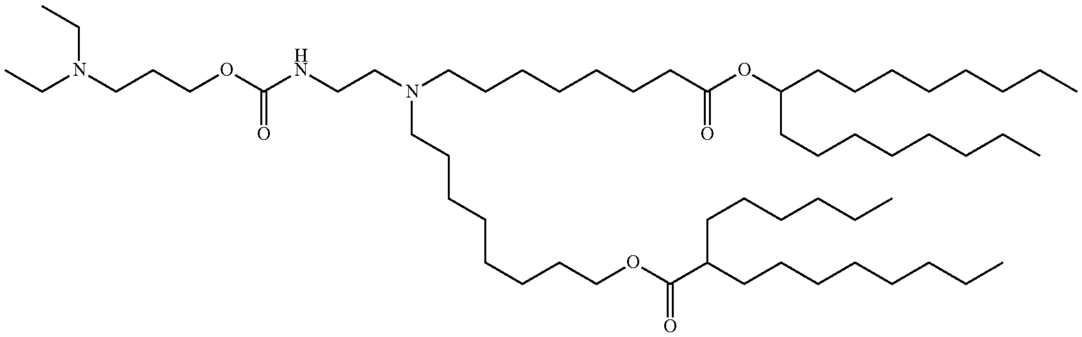 [SMILES: CCCCCCCCC(CCCCCCCC)OC(=O)CCCCCCCN(CCCCCCCCOC(=O)C(CCCCCC)CCCCCCCC)CCNC(=O)OCCCN(CC)CC] | 964.6 |

TABLE 1-continued
| # | Structure | Mw |
| --- | --- | --- |
| 948. | 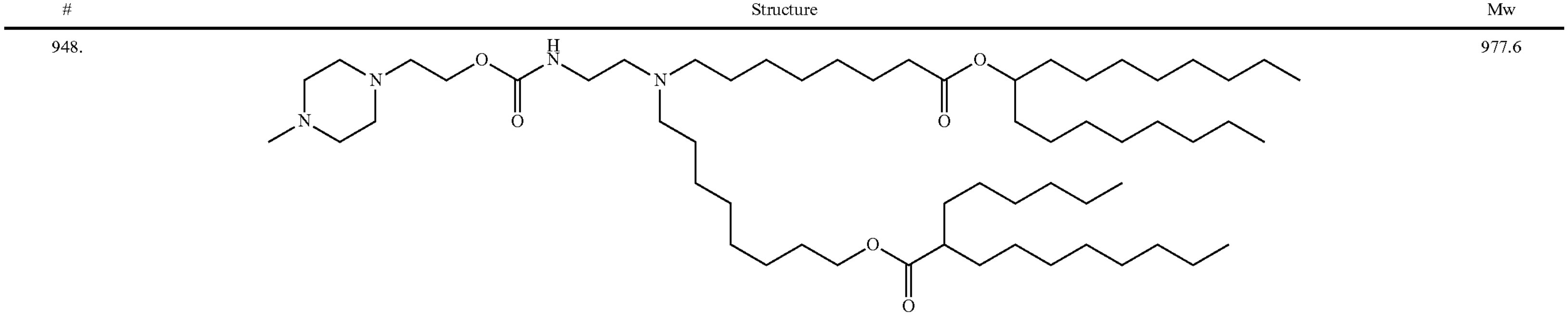 | 977.6 |
| 949. | 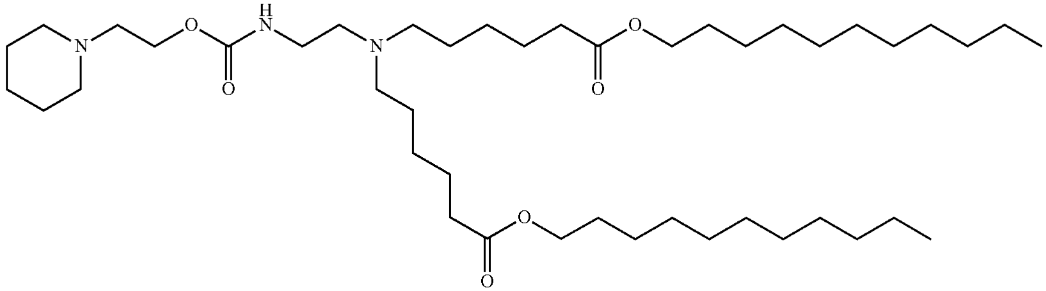 [SMILES: CCCCCCCCCCCOC(=O)CCCCCN(CCCCCC(=O)OCCCCCCCCCCC)CCNC(=O)OCCN1CCCCC1] | 752.2 |
| 950. | 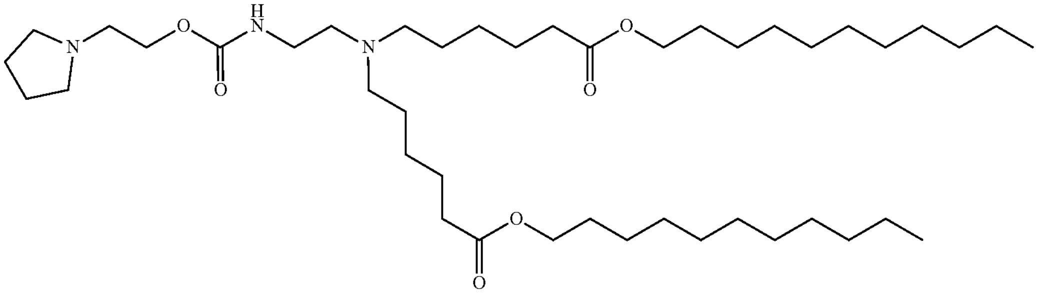 [SMILES: CCCCCCCCCCCOC(=O)CCCCCN(CCCCCC(=O)OCCCCCCCCCCC)CCNC(=O)OCCN1CCCC1] | 738.2 |

TABLE 1-continued
| # | Structure | Mw |
| --- | --- | --- |
| 951. | 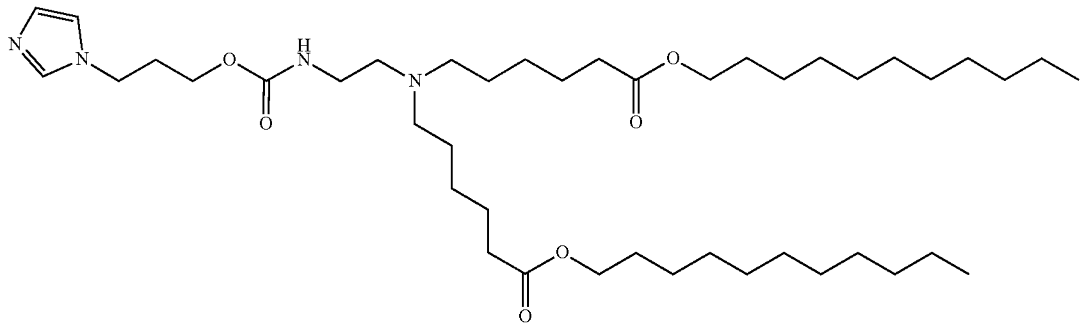 [SMILES: CCCCCCCCCCCOC(=O)CCCCCN(CCCCCC(=O)OCCCCCCCCCCC)CCNC(=O)OCCCn1ccnc1] | 749.1 |
| 952. | 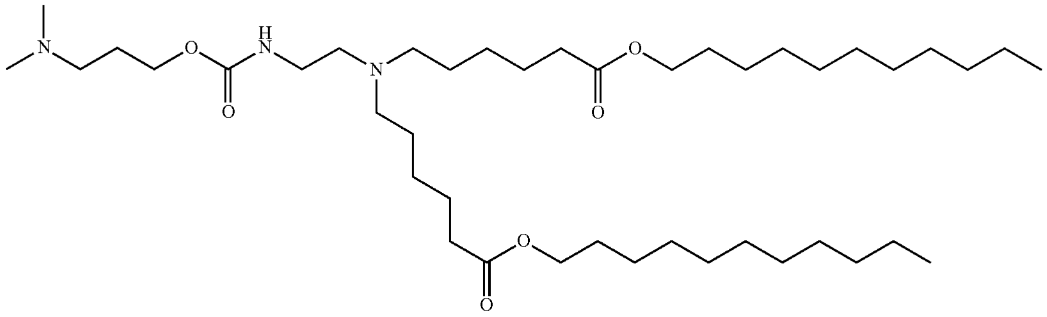 [SMILES: CCCCCCCCCCCOC(=O)CCCCCN(CCCCCC(=O)OCCCCCCCCCCC)CCNC(=O)OCCCN(C)C] | 726.1 |
| 953. | 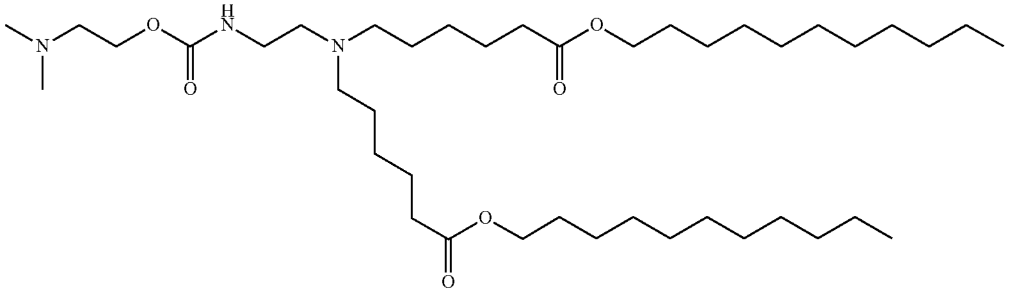 [SMILES: CCCCCCCCCCCOC(=O)CCCCCN(CCCCCC(=O)OCCCCCCCCCCC)CCNC(=O)OCCN(C)C] | 712.1 |

TABLE 1-continued
| # | Structure | Mw |
| --- | --- | --- |
| 954. | 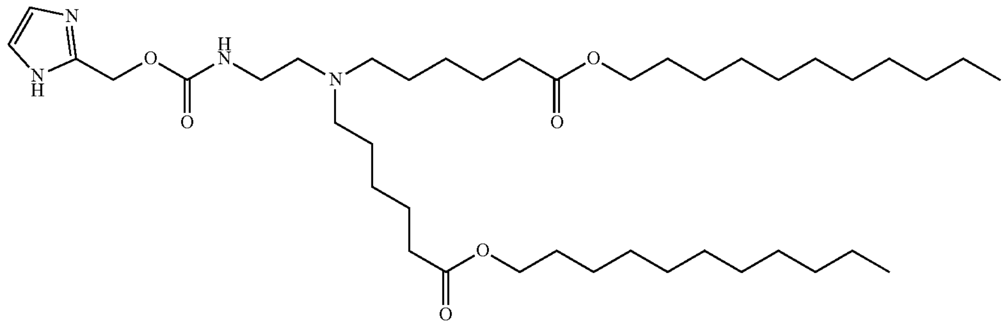 [SMILES: CCCCCCCCCCCOC(=O)CCCCCN(CCCCCC(=O)OCCCCCCCCCCC)CCNC(=O)OCc1ncc[nH]1] | 721.1 |
| 955. | 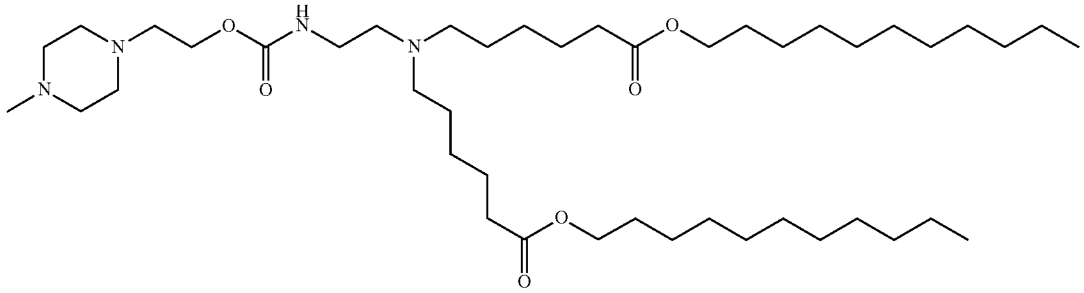 [SMILES: CCCCCCCCCCCOC(=O)CCCCCN(CCCCCC(=O)OCCCCCCCCCCC)CCNC(=O)OCCN1CCN(C)CC1] | 767.2 |
| 956. | 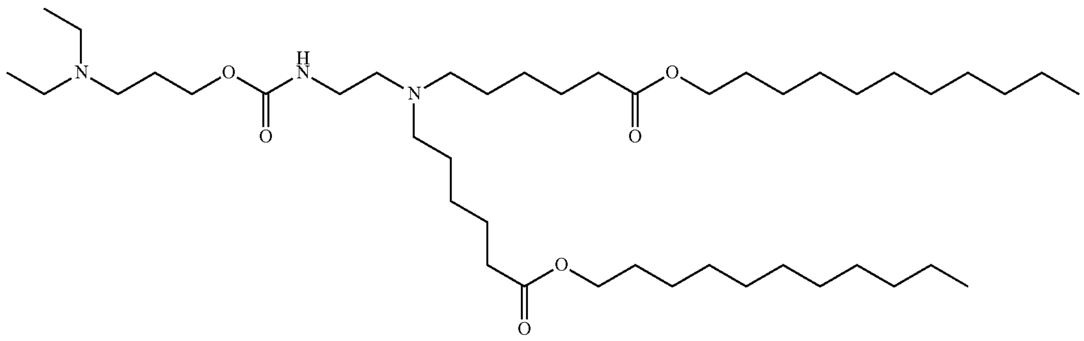 [SMILES: CCCCCCCCCCCOC(=O)CCCCCN(CCCCCC(=O)OCCCCCCCCCCC)CCNC(=O)OCCCN(CC)CC] | 754.2 |

TABLE 1-continued
| # | Structure | Mw |
| --- | --- | --- |
| 957. | 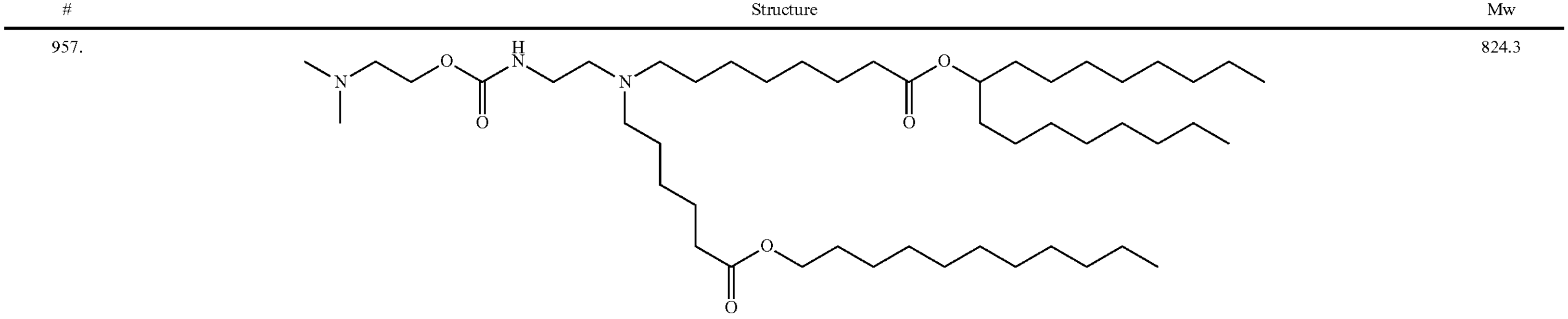 | 824.3 |
| 958. | 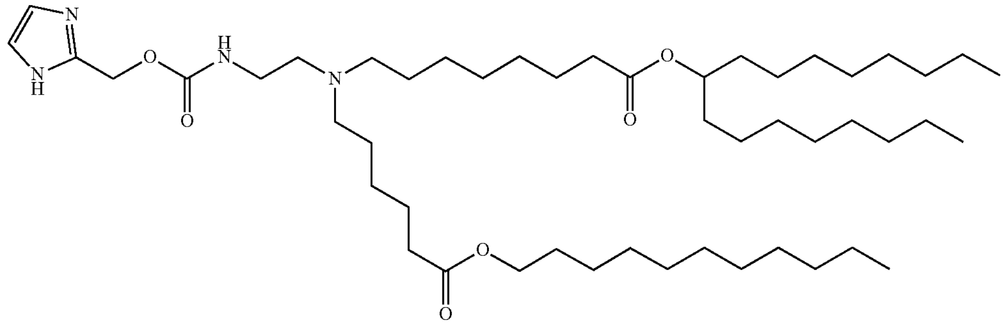 [SMILES: CCCCCCCCCCCOC(=O)CCCCCN(CCCCCCCC(=O)OC(CCCCCCCC)CCCCCCCC)CCNC(=O)OCc1ncc[nH]1] | 833.3 |
| 959. | 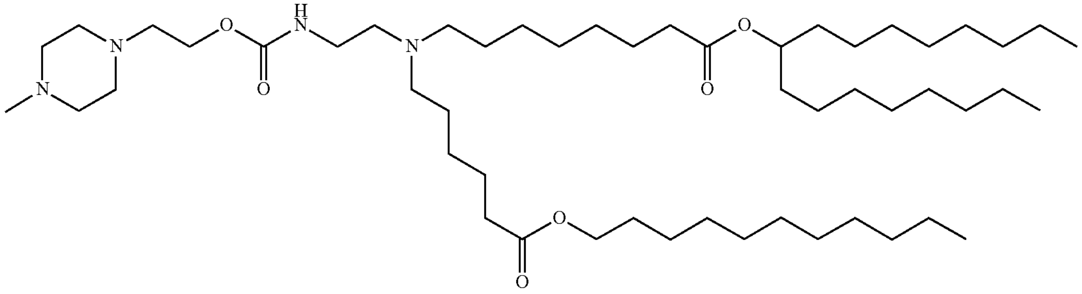 [SMILES: CCCCCCCCCCCOC(=O)CCCCCN(CCCCCCCC(=O)OC(CCCCCCCC)CCCCCCCC)CCNC(=O)OCCN1CCN(C)CC1] | 879.4 |

TABLE 1-continued
| # | Structure | Mw |
|---|---|---|
| 960. | 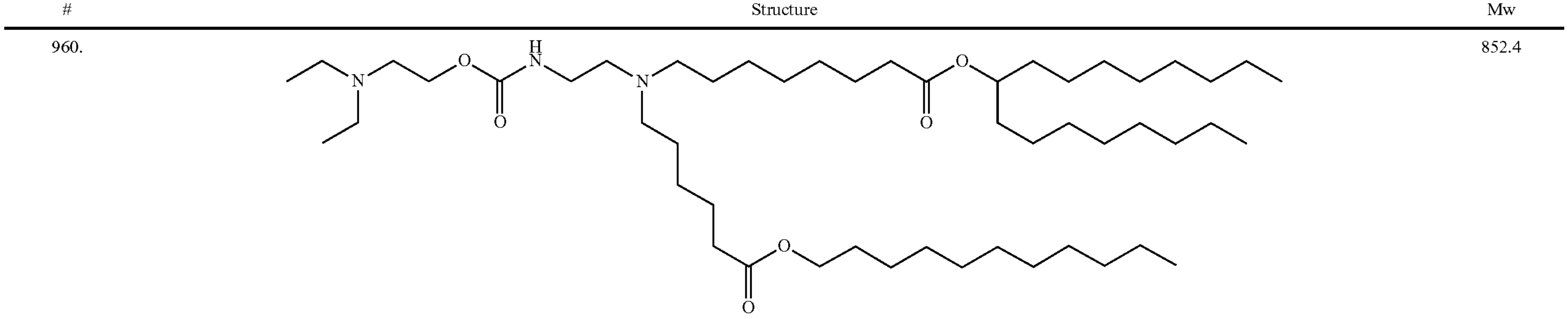 | 852.4 |
| 961. | 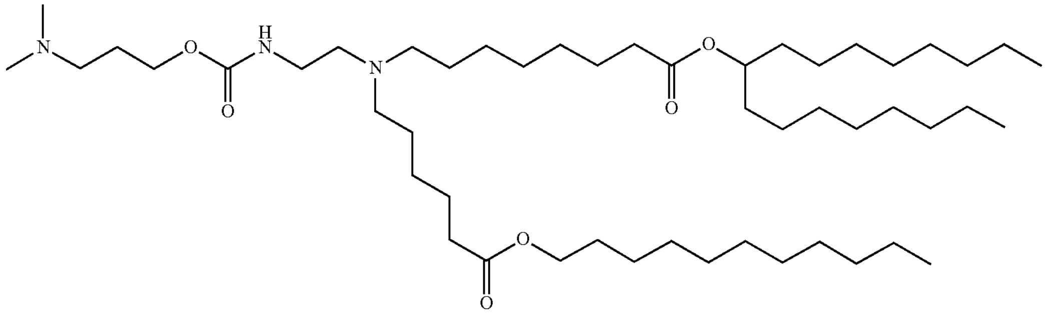 [SMILES: CCCCCCCCCCCOC(=O)CCCCCN(CCCCCCCC(=O)OC(CCCCCCCC)CCCCCCCC)CCNC(=O)OCCCN(C)C] | 838.4 |
| 962. | 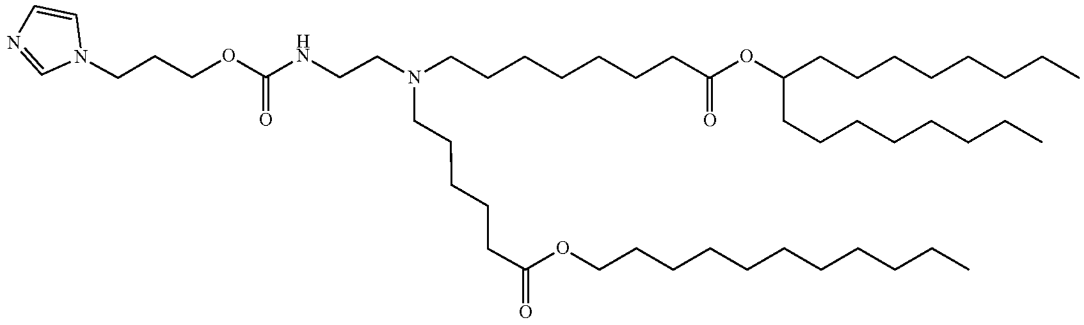 [SMILES: CCCCCCCCCCCOC(=O)CCCCCN(CCCCCCCC(=O)OC(CCCCCCCC)CCCCCCCC)CCNC(=O)OCCCn1ccnc1] | 861.4 |

TABLE 1-continued
| # | Structure | Mw |
| --- | --- | --- |
| 963. | 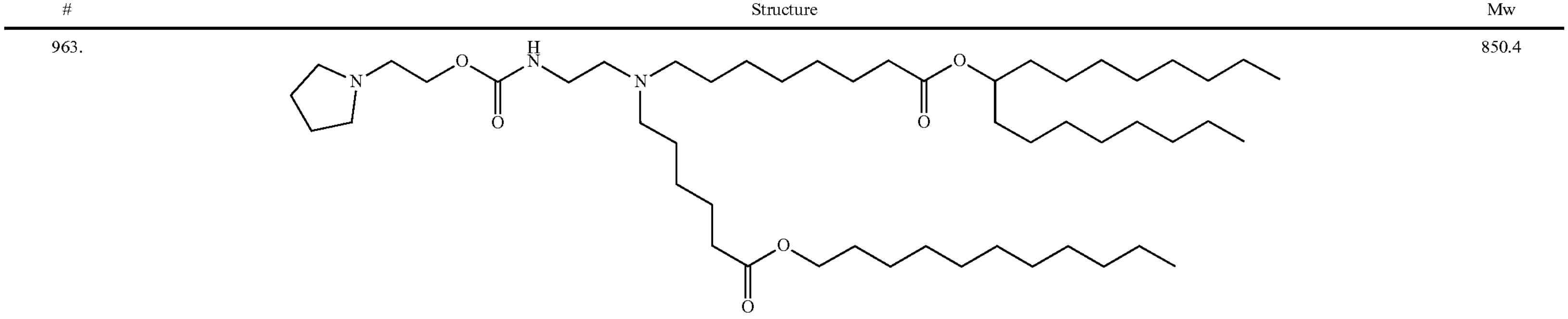 | 850.4 |
| 964. | 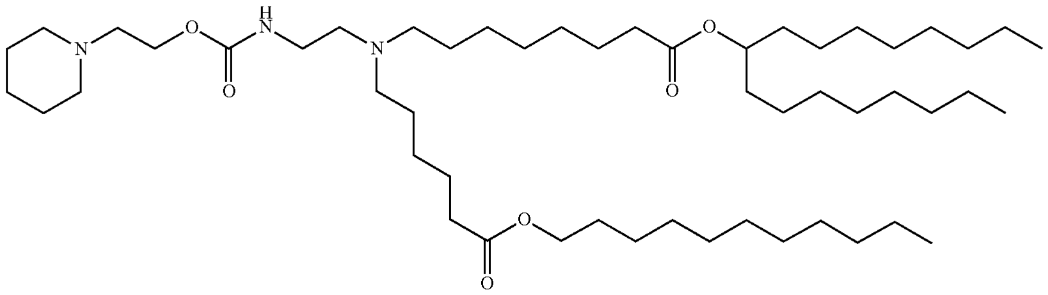 [SMILES: CCCCCCCCCCCOC(=O)CCCCCN(CCCCCCCC(=O)OC(CCCCCCCC)CCCCCCCC)CCNC(=O)OCCN1CCCCC1] | 864.4 |
| 965. | 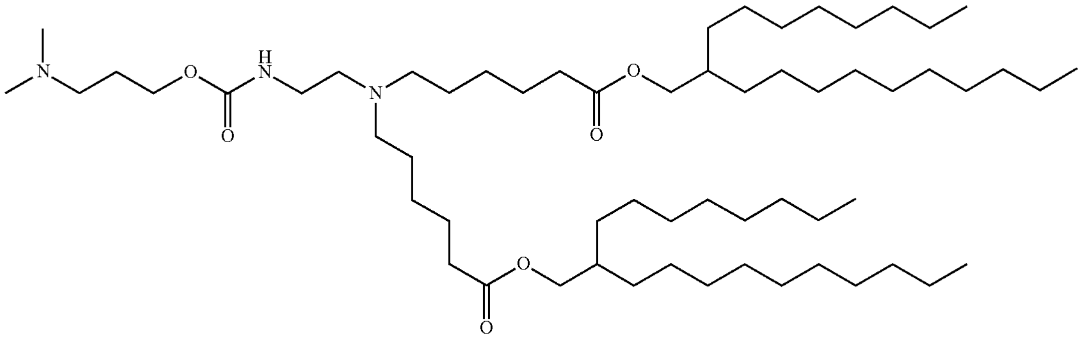 [SMILES: CCCCCCCCCCC(CCCCCCCC)COC(=O)CCCCCN(CCCCCC(=O)OCC(CCCCCCCC)CCCCCCCCCC)CCNC(=O)OCCCN(C)C] | 978.6 |

TABLE 1-continued
| # | Structure | Mw |
|---|---|---|
| 966. | 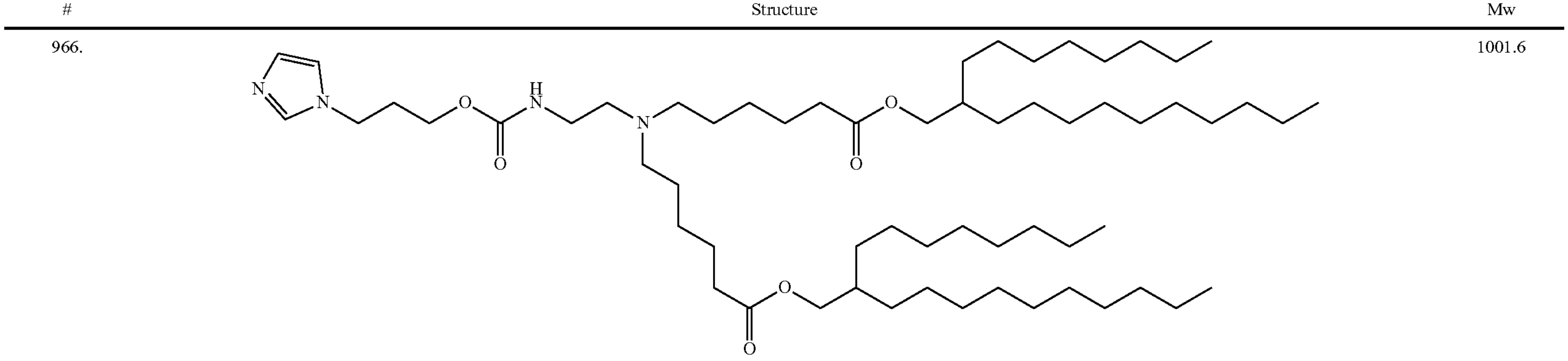 | 1001.6 |
| 967. | 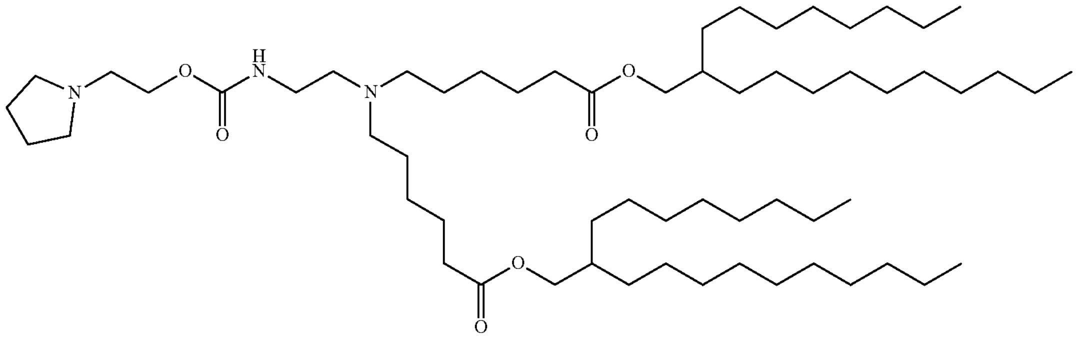 [SMILES: CCCCCCCCCCC(CCCCCCCC)COC(=O)CCCCCN(CCCCCC(=O)OCC(CCCCCCCC)CCCCCCCCCC)CCNC(=O)OCCN1CCCC1] | 990.6 |
| 968. | 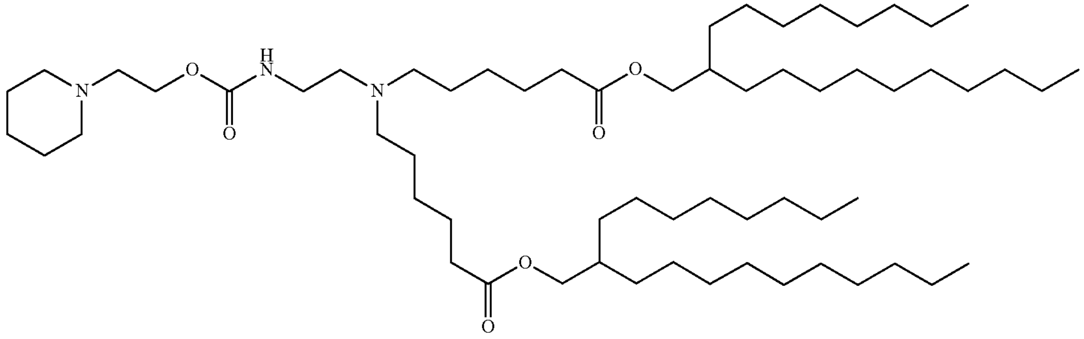 [SMILES: CCCCCCCCCCC(CCCCCCCC)COC(=O)CCCCCN(CCCCCC(=O)OCC(CCCCCCCC)CCCCCCCCCC)CCNC(=O)OCCN1CCCCC1] | 1004.7 |

TABLE 1-continued
| # | Structure | Mw |
|---|---|---|
| 969. | 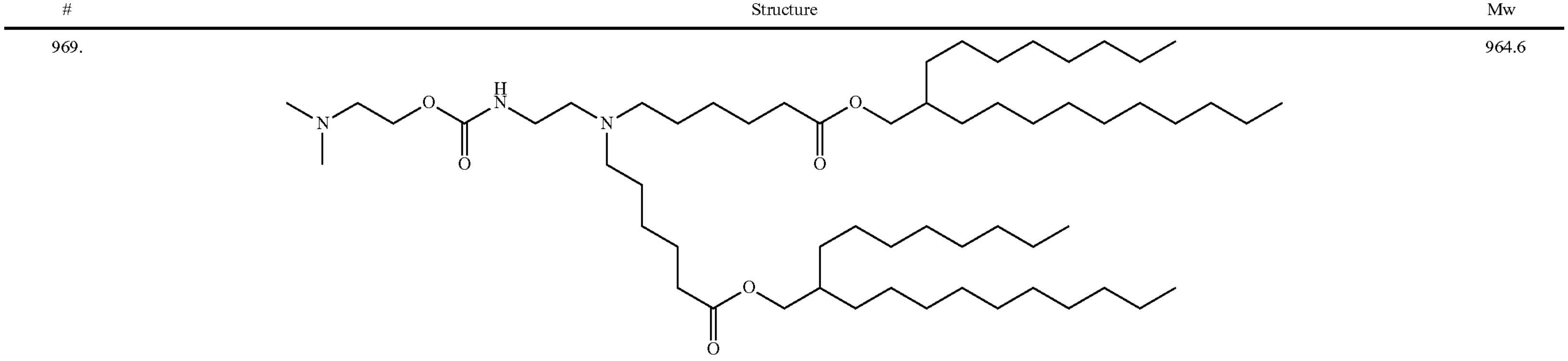 | 964.6 |
| 970. | 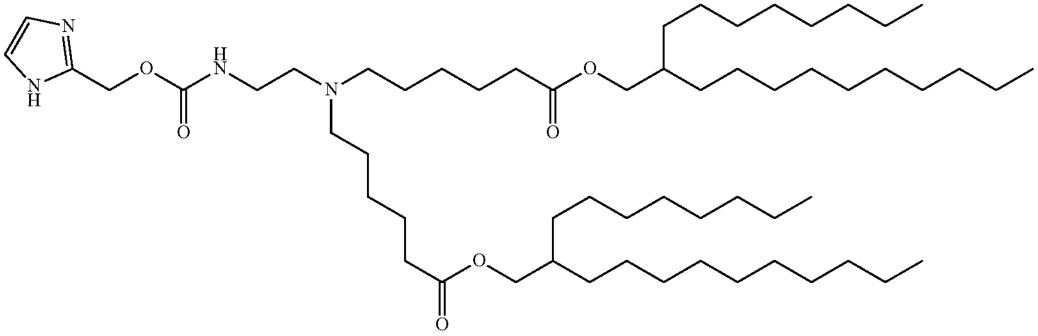 [SMILES: CCCCCCCCCCC(CCCCCCCC)COC(=O)CCCCCN(CCCCCC(=O)OCC(CCCCCCCC)CCCCCCCCCC)CCNC(=O)OCc1ncc[nH]1] | 973.6 |
| 971. | 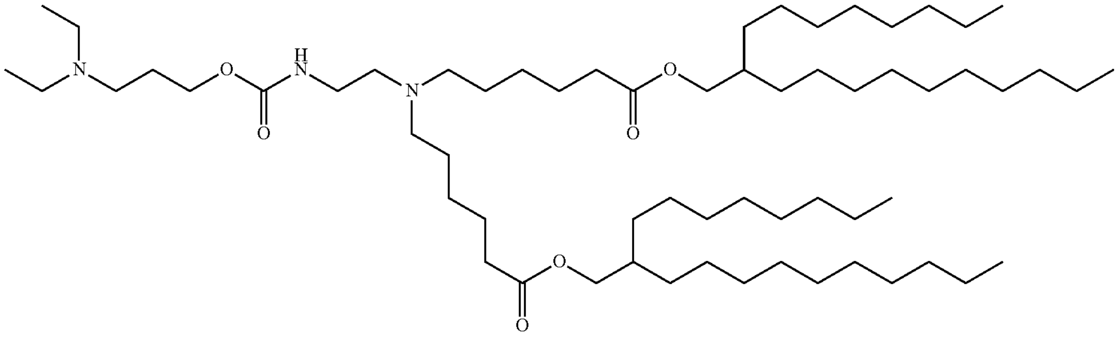 [SMILES: CCCCCCCCCCC(CCCCCCCC)COC(=O)CCCCCN(CCCCCC(=O)OCC(CCCCCCCC)CCCCCCCCCC)CCNC(=O)OCCCN(CC)CC] | 1006.7 |

TABLE 1-continued
| # | Structure | Mw |
|---|---|---|
| 972. | 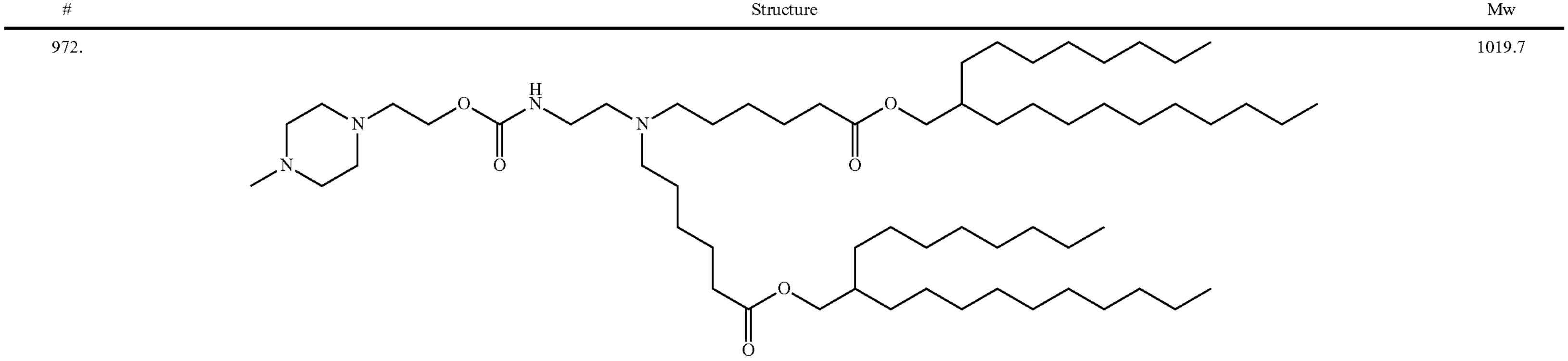 | 1019.7 |
| 973. | 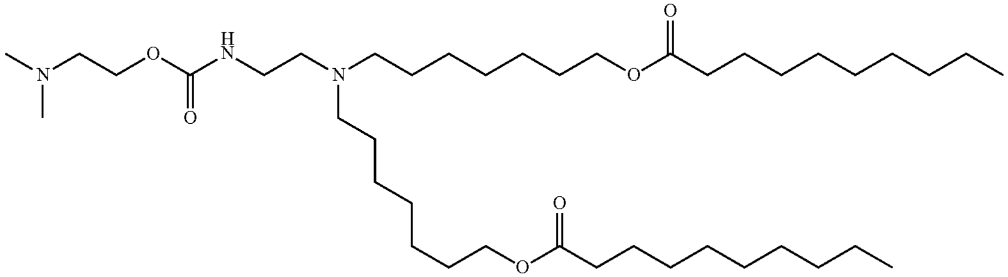 [SMILES: CCCCCCCCCC(=O)OCCCCCCCN(CCCCCCCOC(=O)CCCCCCCCC)CCNC(=O)OCCN(C)C] | 712.1 |
| 974. | 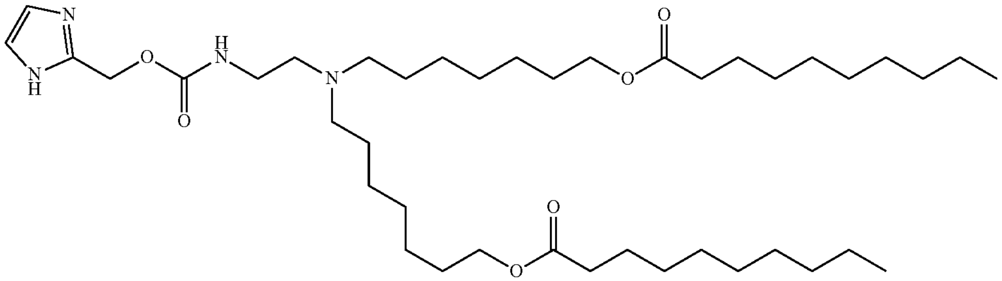 [SMILES: CCCCCCCCCC(=O)OCCCCCCCN(CCCCCCCOC(=O)CCCCCCCCC)CCNC(=O)OCc1ncc[nH]1] | 721.1 |

TABLE 1-continued
| # | Structure | Mw |
| --- | --- | --- |
| 975. | 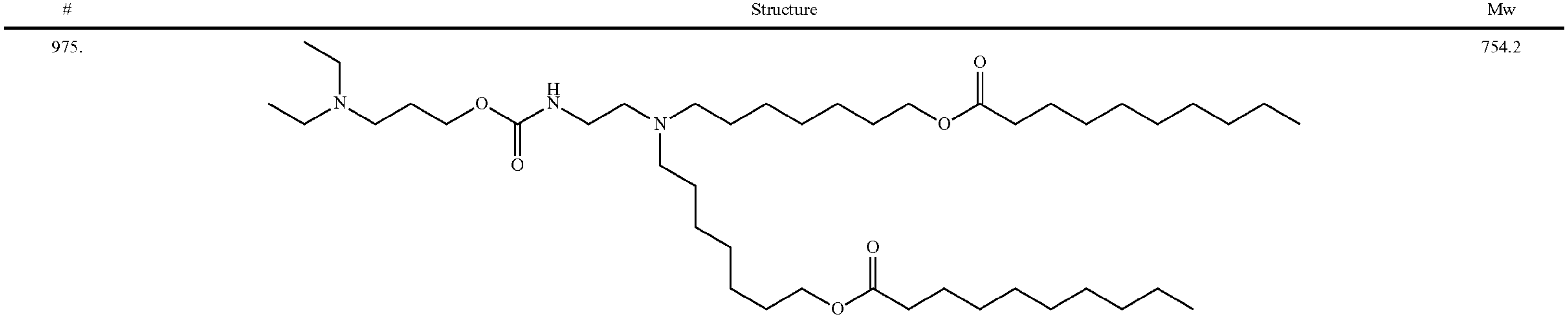 | 754.2 |
| 976. | 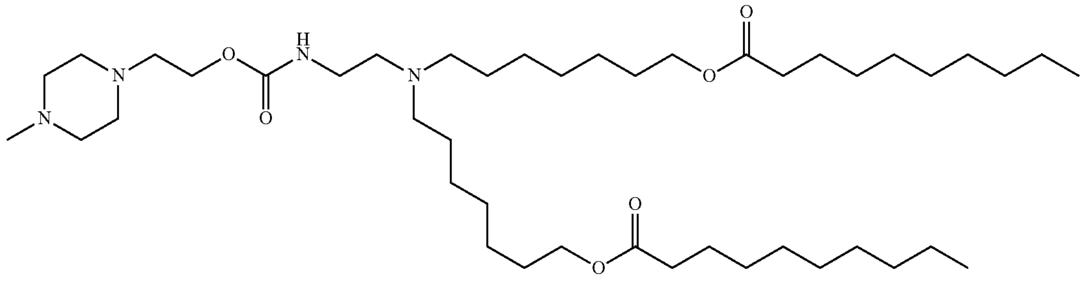 [SMILES: CCCCCCCCCC(=O)OCCCCCCCN(CCCCCCCOC(=O)CCCCCCCCC)CCNC(=O)OCCN1CCN(C)CC1] | 767.2 |
| 977. | 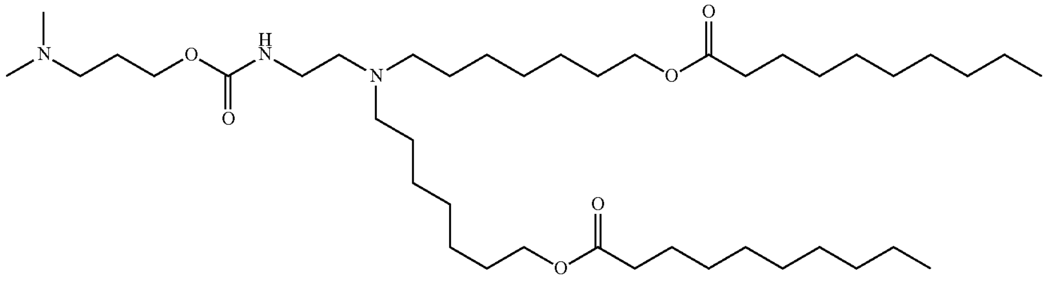 [SMILES: CCCCCCCCCC(=O)OCCCCCCCN(CCCCCCCOC(=O)CCCCCCCCC)CCNC(=O)OCCCN(C)C] | 726.1 |

TABLE 1-continued
| # | Structure | Mw |
|---|---|---|
| 978. | 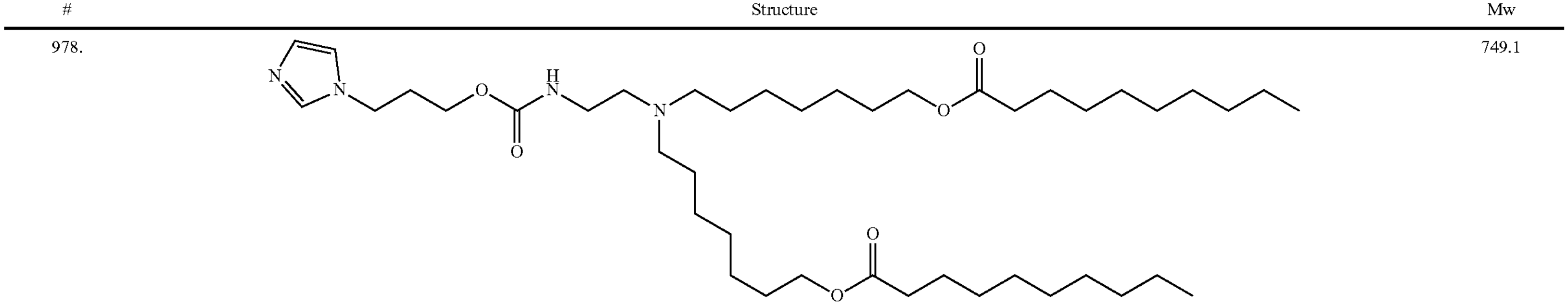 | 749.1 |
| 979. | 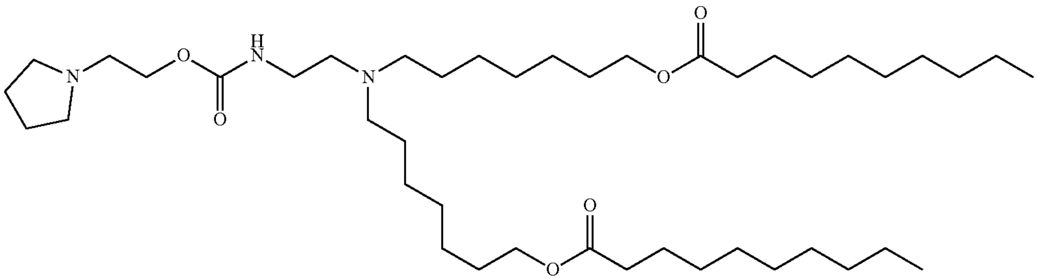 [SMILES: CCCCCCCCCC(=O)OCCCCCCCN(CCCCCCCOC(=O)CCCCCCCCC)CCNC(=O)OCCN1CCCC1] | 738.2 |
| 980. | 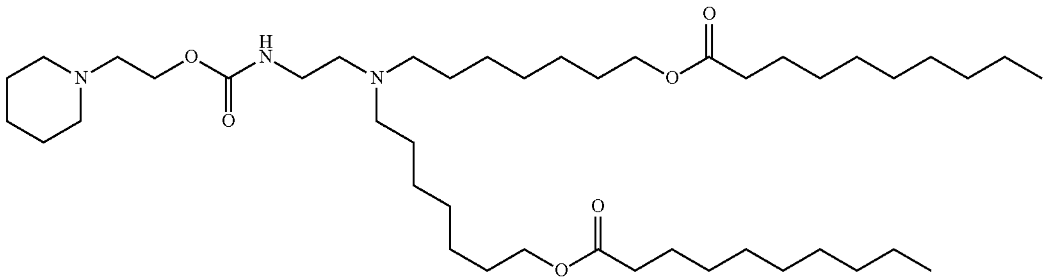 [SMILES: CCCCCCCCCC(=O)OCCCCCCCN(CCCCCCCOC(=O)CCCCCCCCC)CCNC(=O)OCCN1CCCCC1] | 752.2 |

TABLE 1-continued
| # | Structure | Mw |
|---|---|---|
| 981. | 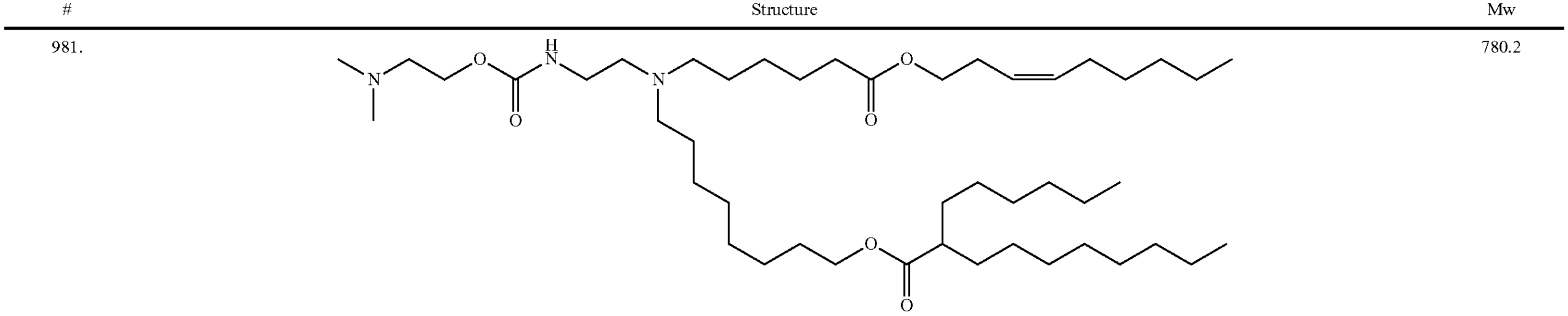 | 780.2 |
| 982. | 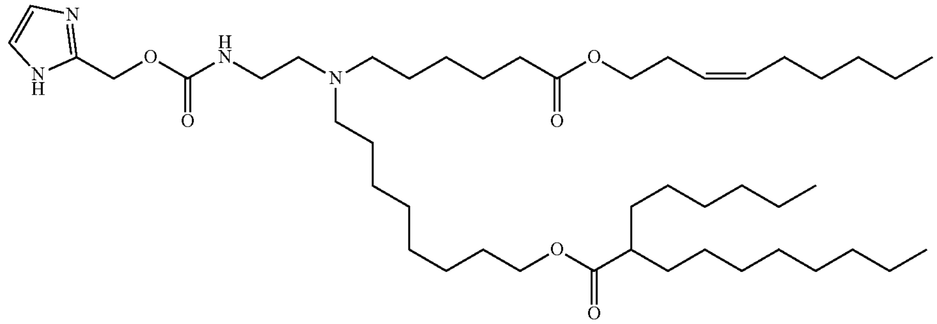 | 789.2 |
| 983. | 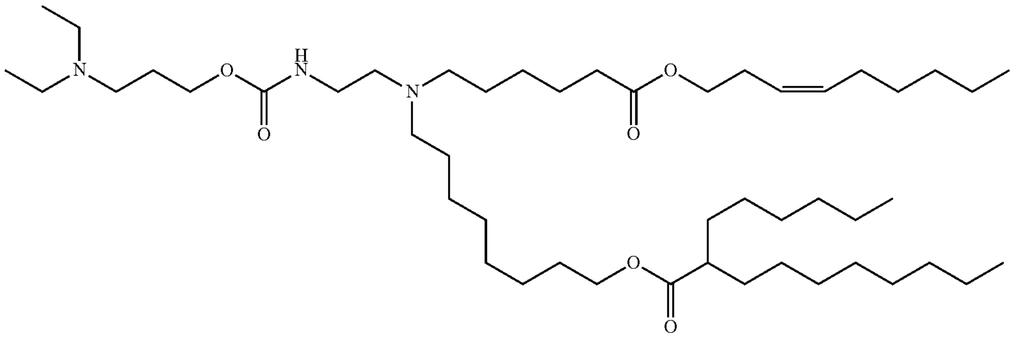 [SMILES: CCCCC/C=C\CCOC(=O)CCCCCN(CCCCCCCCOC(=O)C(CCCCCC)CCCCCCCC)CCNC(=O)OCCCN(CC)CC] | 822.3 |

TABLE 1-continued
| # | Structure | Mw |
| --- | --- | --- |
| 984. | 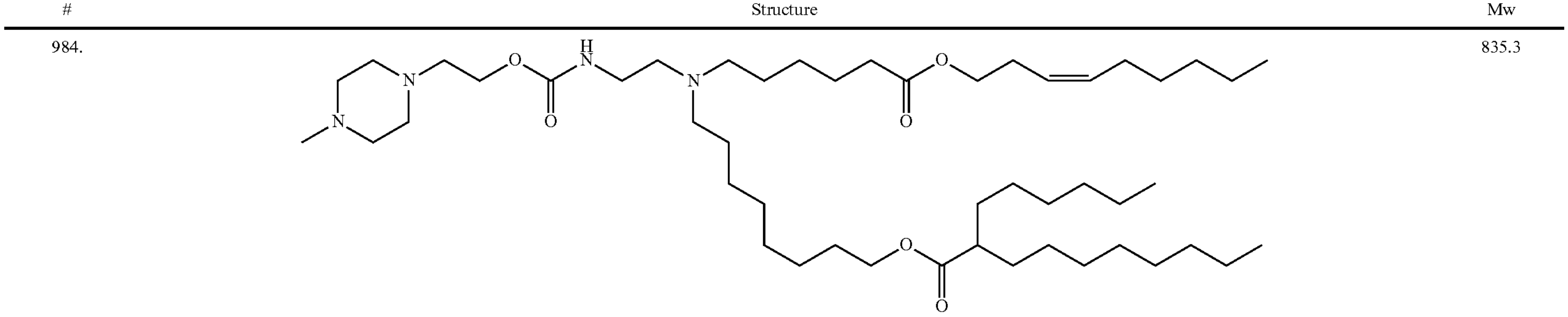 | 835.3 |
| 985. | 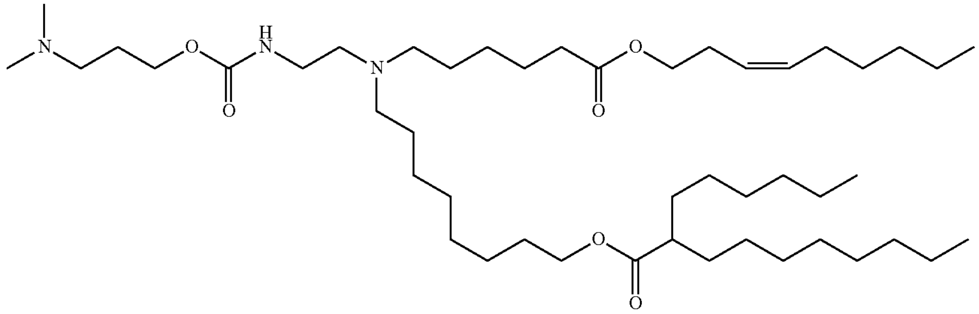 [SMILES: CCCCC/C=C\CCOC(=O)CCCCCN(CCCCCCCCOC(=O)C(CCCCCC)CCCCCCCC)CCNC(=O)OCCCN(C)C] | 794.3 |
| 986. | 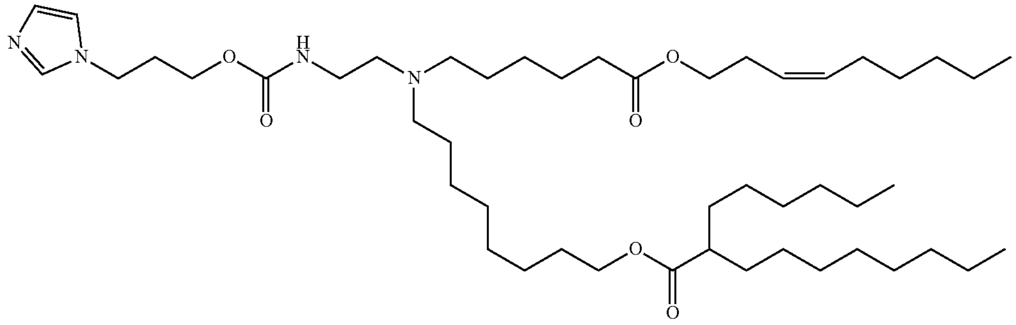 [SMILES: CCCCC/C=C\CCOC(=O)CCCCCN(CCCCCCCCOC(=O)C(CCCCCC)CCCCCCCC)CCNC(=O)OCCCn1ccnc1] | 817.3 |

TABLE 1-continued
| # | Structure | Mw |
| --- | --- | --- |
| 987. | 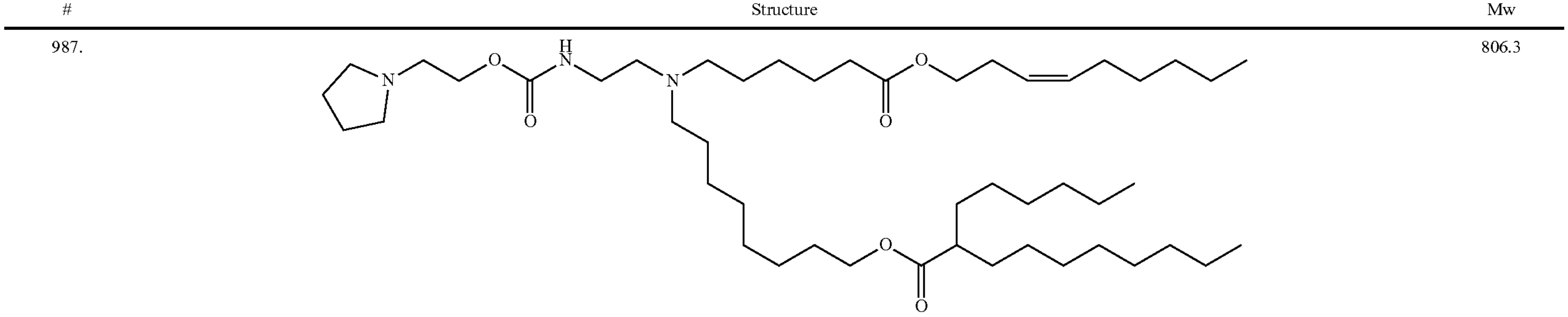 | 806.3 |
| 988. | 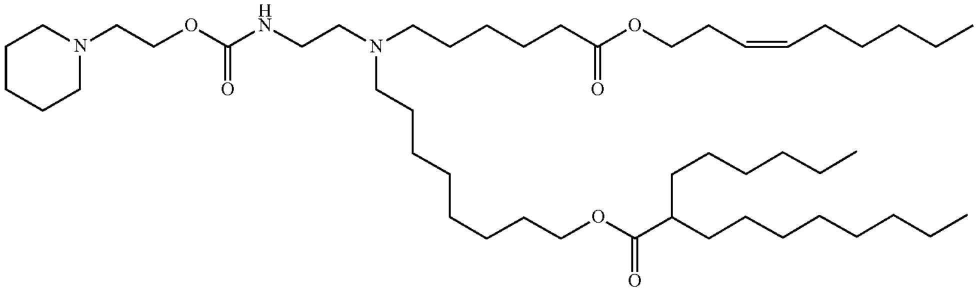 [SMILES: CCCCC/C=C\CCOC(=O)CCCCCN(CCCCCCCCOC(=O)C(CCCCCC)CCCCCCCC)CCNC(=O)OCCN1CCCCC1] | 820.3 |
| 989. | 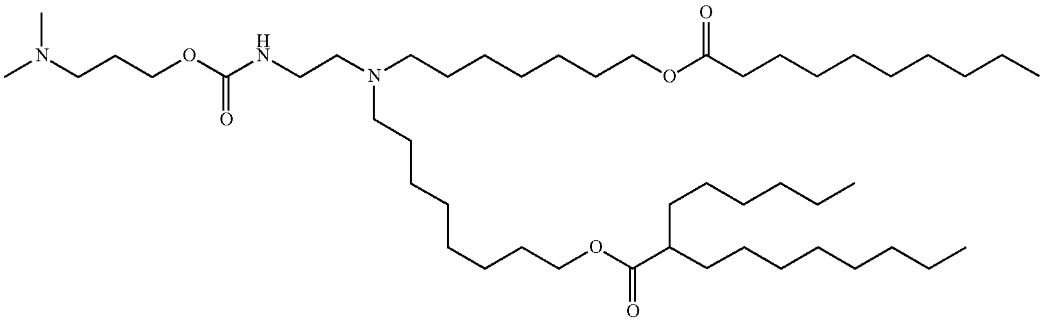 [SMILES: CCCCCCCCCC(=O)OCCCCCCCN(CCCCCCCCOC(=O)C(CCCCCC)CCCCCCCC)CCNC(=O)OCCCN(C)C] | 824.3 |

TABLE 1-continued
| # | Structure | Mw |
|---|---|---|
| 990. | 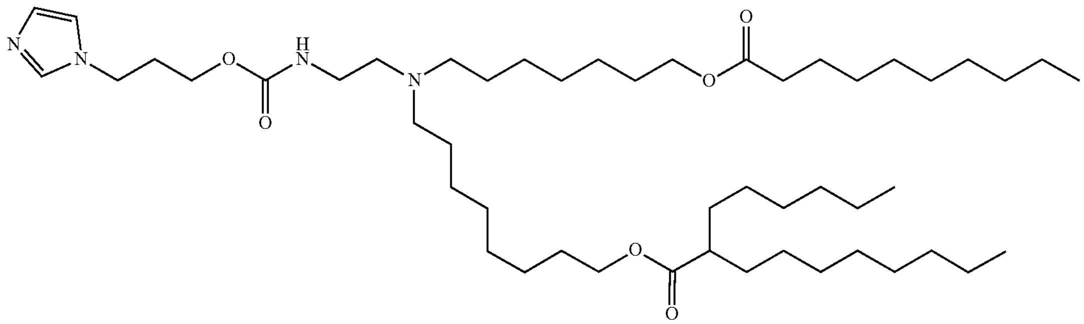 [SMILES: CCCCCCCCCC(=O)OCCCCCCCN(CCCCCCCCOC(=O)C(CCCCCC)CCCCCCCC)CCNC(=O)OCCCn1ccnc1] | 847.3 |
| 991. | 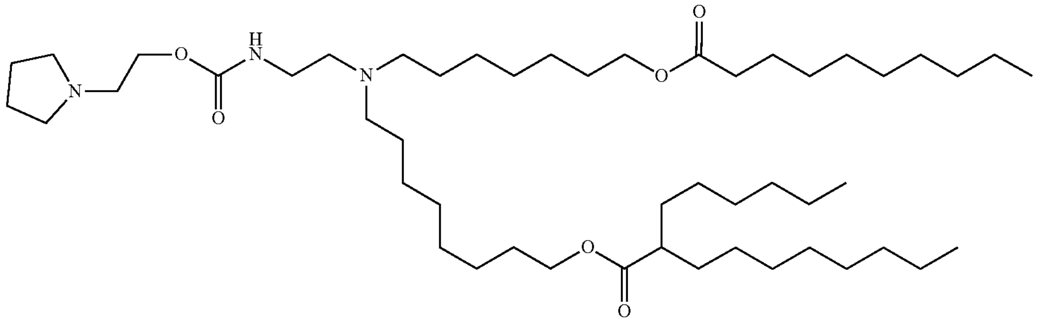 [SMILES: CCCCCCCCCC(=O)OCCCCCCCN(CCCCCCCCOC(=O)C(CCCCCC)CCCCCCCC)CCNC(=O)OCCN1CCCC1] | 836.3 |
| 992. | 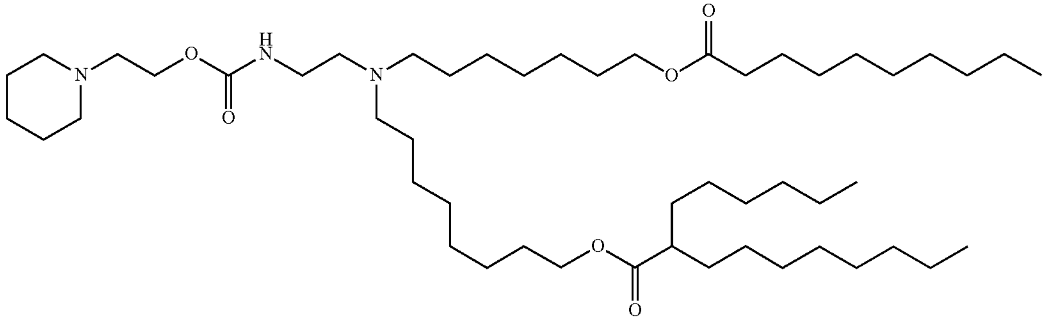 [SMILES: CCCCCCCCCC(=O)OCCCCCCCN(CCCCCCCCOC(=O)C(CCCCCC)CCCCCCCC)CCNC(=O)OCCN1CCCCC1] | 850.4 |

TABLE 1-continued
| # | Structure | Mw |
| --- | --- | --- |
| 993. | 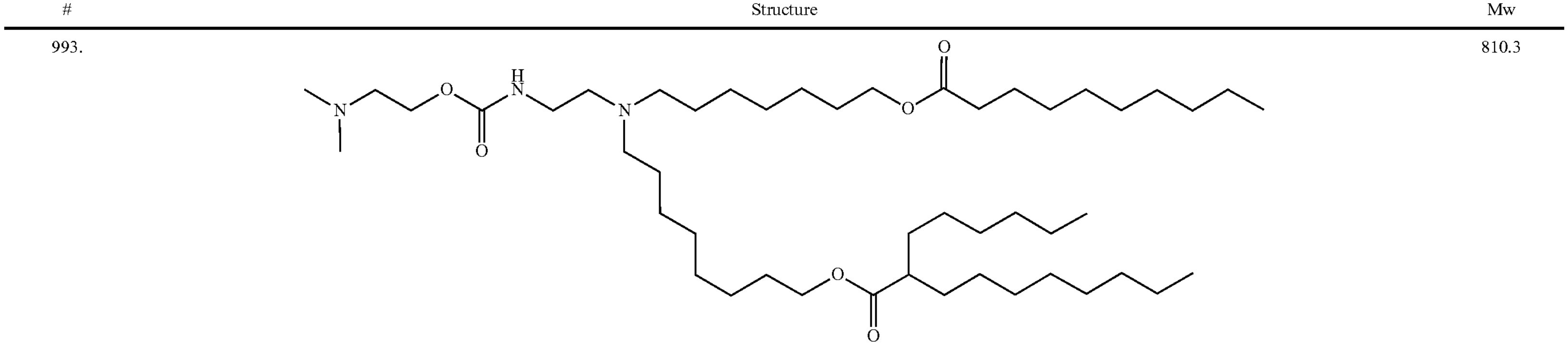 | 810.3 |
| 994. | 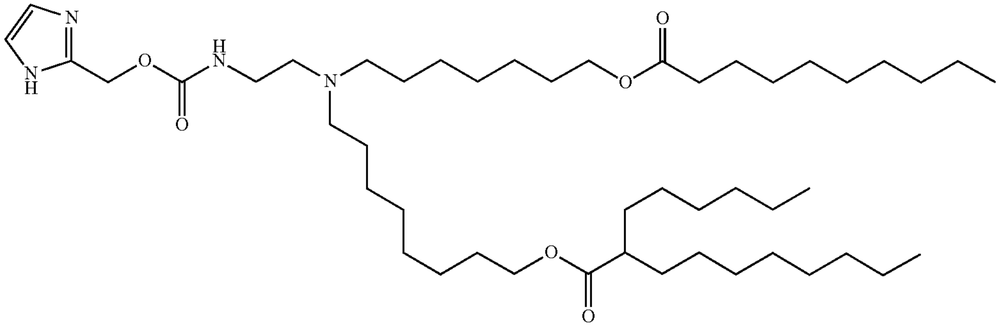 [SMILES: CCCCCCCCCC(=O)OCCCCCCCN(CCCCCCCCOC(=O)C(CCCCCC)CCCCCCCC)CCNC(=O)OCc1ncc[nH]1] | 819.3 |
| 995. | 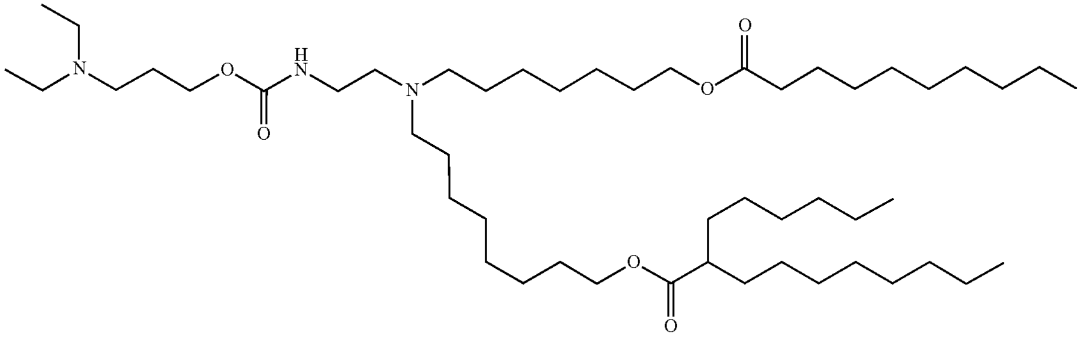 [SMILES: CCCCCCCCCC(=O)OCCCCCCCN(CCCCCCCCOC(=O)C(CCCCCC)CCCCCCCC)CCNC(=O)OCCCN(CC)CC] | 852.4 |

TABLE 1-continued
| # | Structure | Mw |
| --- | --- | --- |
| 996. | 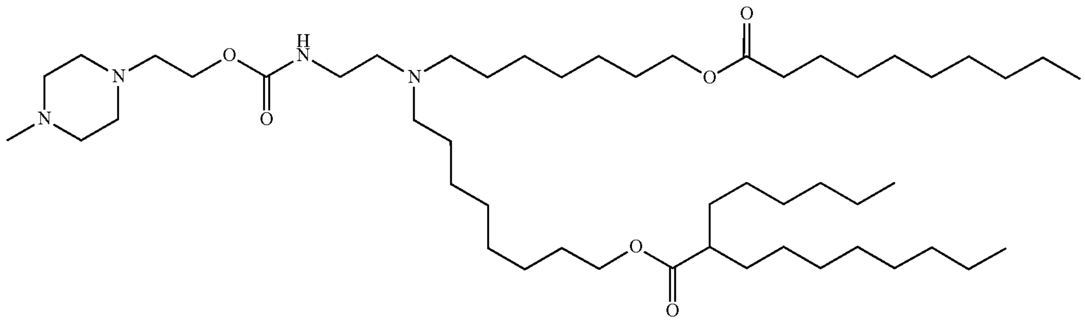 [SMILES: CCCCCCCCCC(=O)OCCCCCCCN(CCCCCCCCOC(=O)C(CCCCCC)CCCCCCCC)CCNC(=O)OCCN1CCN(C)CC1] | 865.4 |
| 997. | 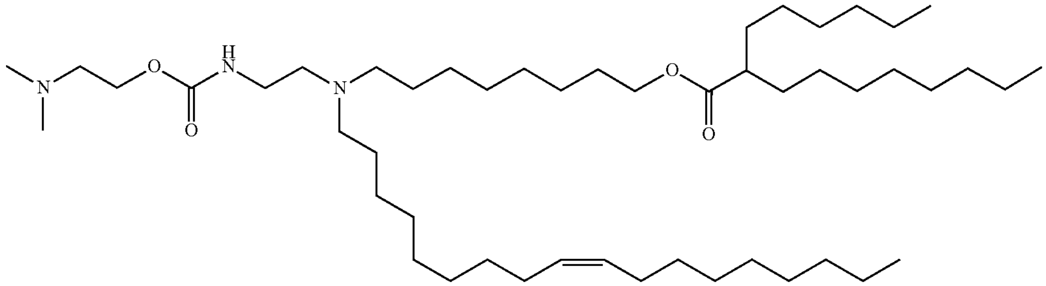 [SMILES: CCCCCCCC/C=C\CCCCCCCCN(CCCCCCCCOC(=O)C(CCCCCC)CCCCCCCC)CCNC(=O)OCCN(C)C] | 792.3 |
| 998. | 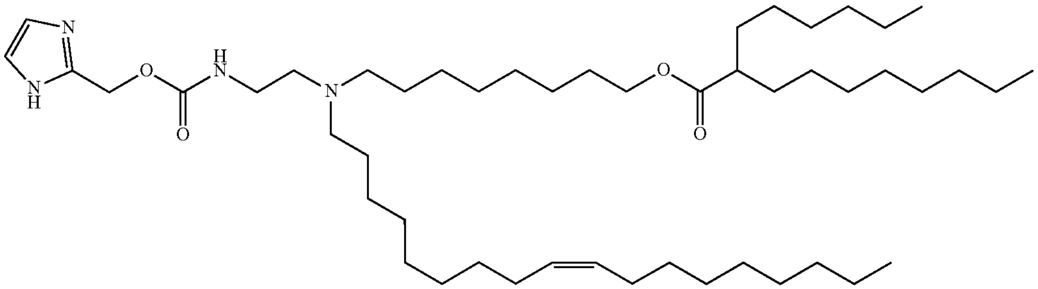 [SMILES: CCCCCCCC/C=C\CCCCCCCCN(CCCCCCCCOC(=O)C(CCCCCC)CCCCCCCC)CCNC(=O)OCc1ncc[nH]1] | 801.3 |

TABLE 1-continued
| # | Structure | Mw |
|---|---|---|
| 999. | 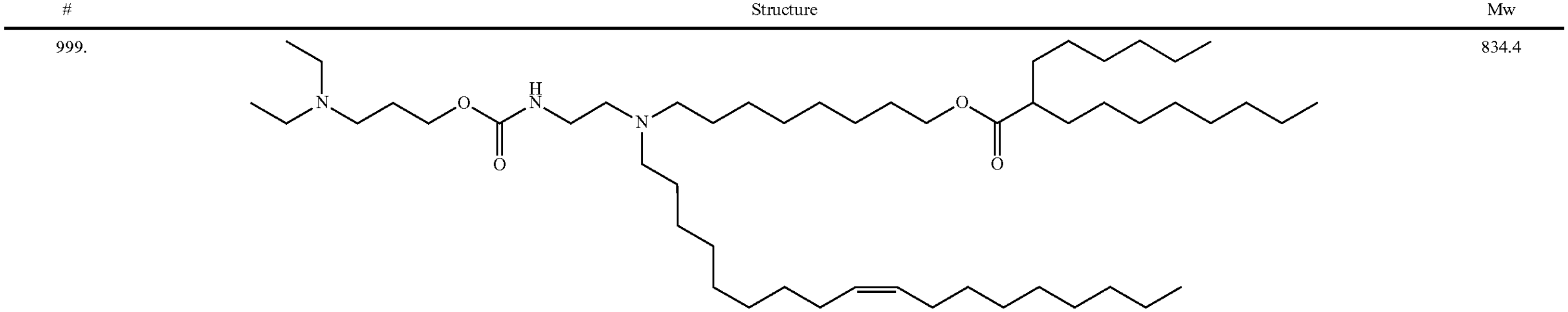 | 834.4 |
| 1000. | 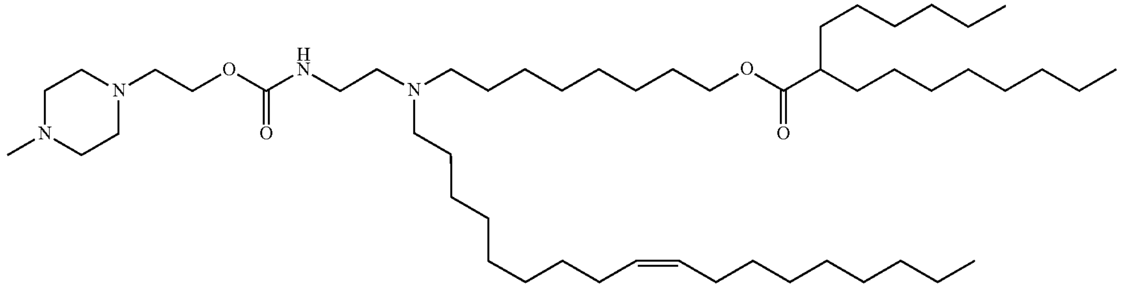 [SMILES: CCCCCCCC/C=C\CCCCCCCCN(CCCCCCCCOC(=O)C(CCCCCC)CCCCCCCC)CCNC(=O)OCCN1CCN(C)CC1] | 847.4 |
| 1001. | +get,2499 | 806.4 |
| 1002. | 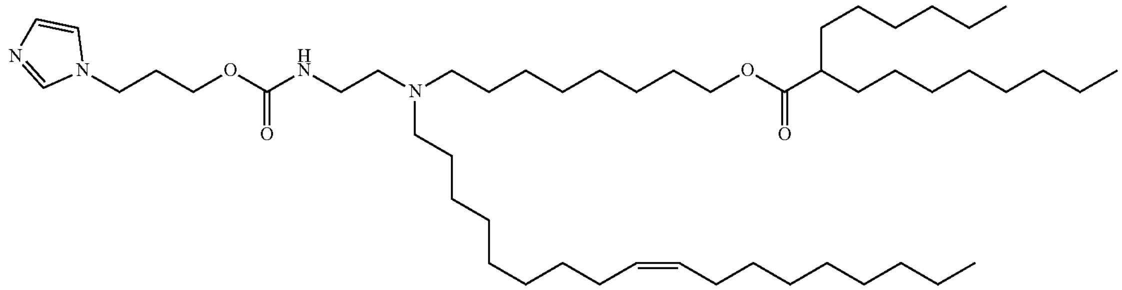 [SMILES: CCCCCCCC/C=C\CCCCCCCCN(CCCCCCCCOC(=O)C(CCCCCC)CCCCCCCC)CCNC(=O)OCCCn1ccnc1] | 829.4 |

TABLE 1-continued
| # | Structure | Mw |
| --- | --- | --- |
| 1003. | 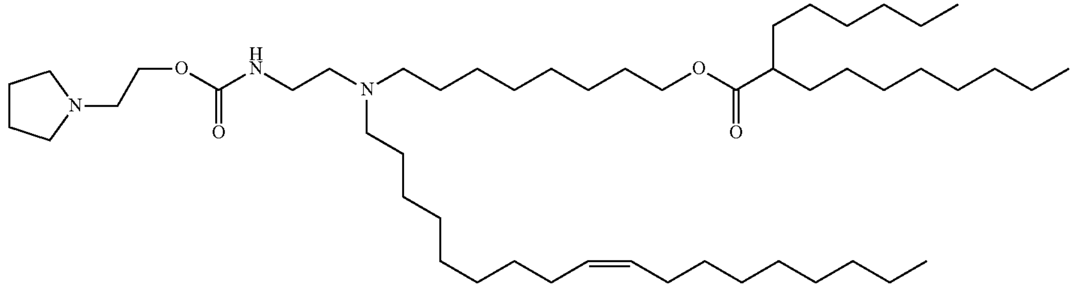 [SMILES: CCCCCCCC/C=C\CCCCCCCCN(CCCCCCCCOC(=O)C(CCCCCC)CCCCCCCC)CCNC(=O)OCCN1CCCC1] | 818.4 |
| 1004. | 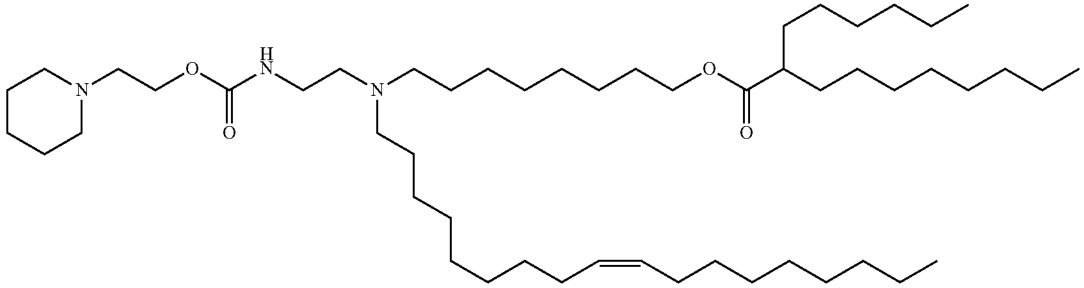 | 832.4 |
| 1005. | 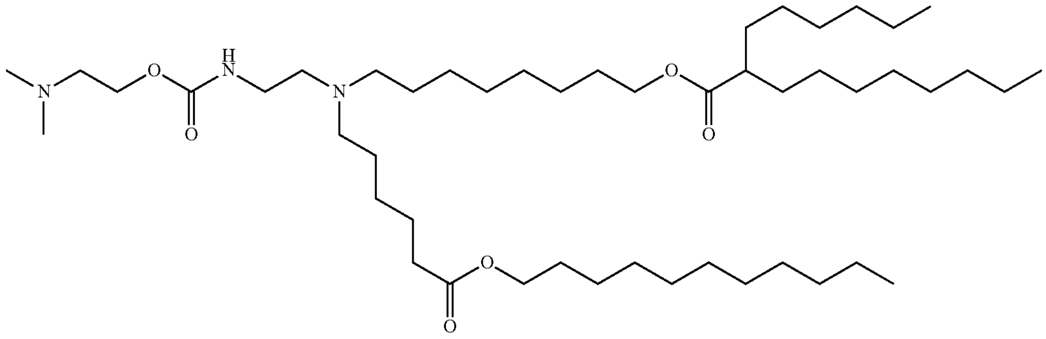 [SMILES: CCCCCCCCCCCOC(=O)CCCCCN(CCCCCCCCOC(=O)C(CCCCCC)CCCCCCCC)CCNC(=O)OCCN(C)C] | 810.3 |

TABLE 1-continued
| # | Structure | Mw |
| --- | --- | --- |
| 1006. | 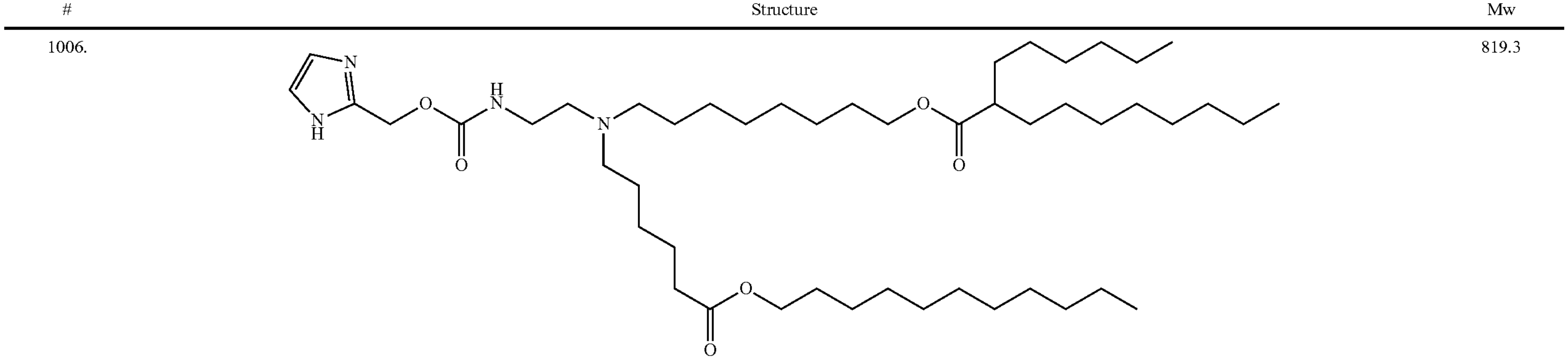 | 819.3 |
| 1007. | 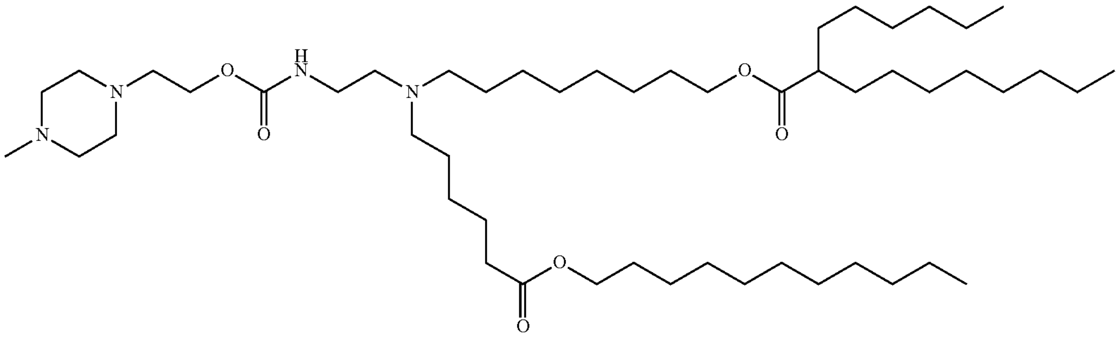 [SMILES: CCCCCCCCCCCOC(=O)CCCCCN(CCCCCCCCOC(=O)C(CCCCCC)CCCCCCCC)CCNC(=O)OCCN1CCN(C)CC1] | 865.4 |
| 1008. | 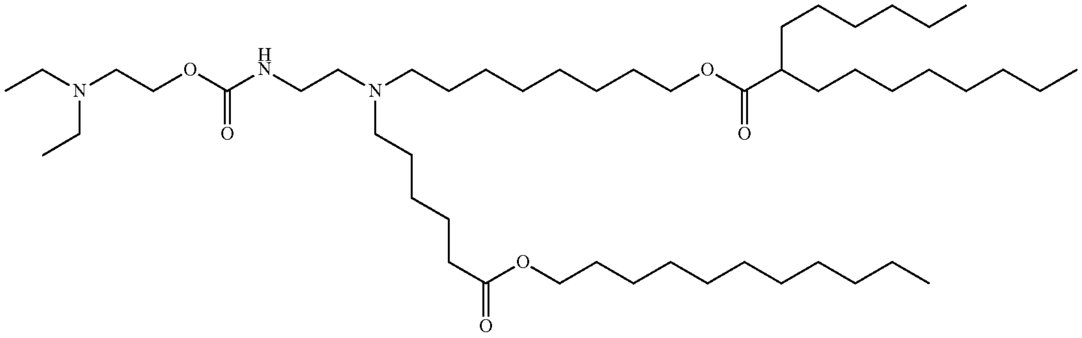 [SMILES: CCCCCCCCCCCOC(=O)CCCCCN(CCCCCCCCOC(=O)C(CCCCCC)CCCCCCCC)CCNC(=O)OCCN(CC)CC] | 838.4 |

TABLE 1-continued
| # | Structure | Mw |
| --- | --- | --- |
| 1009. | 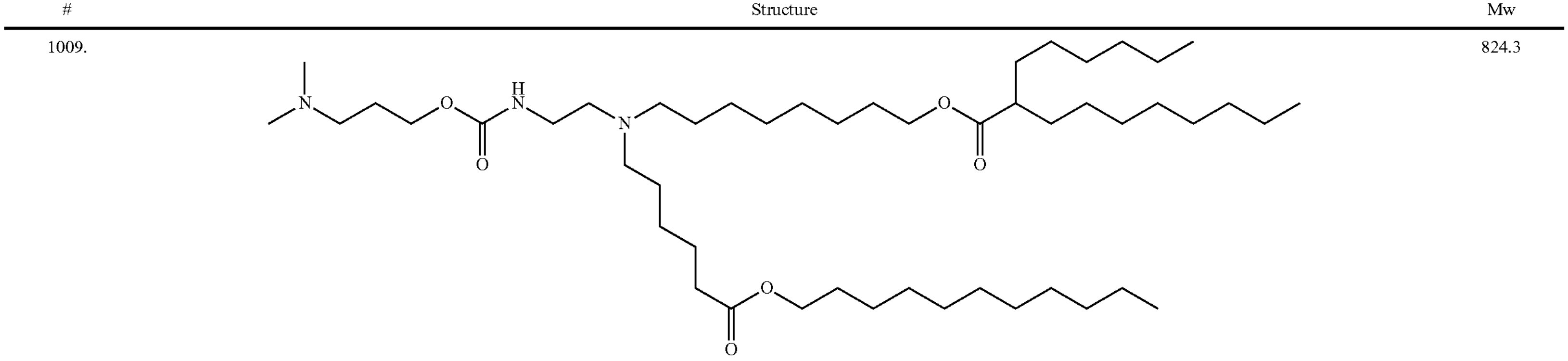 | 824.3 |
| 1010. | 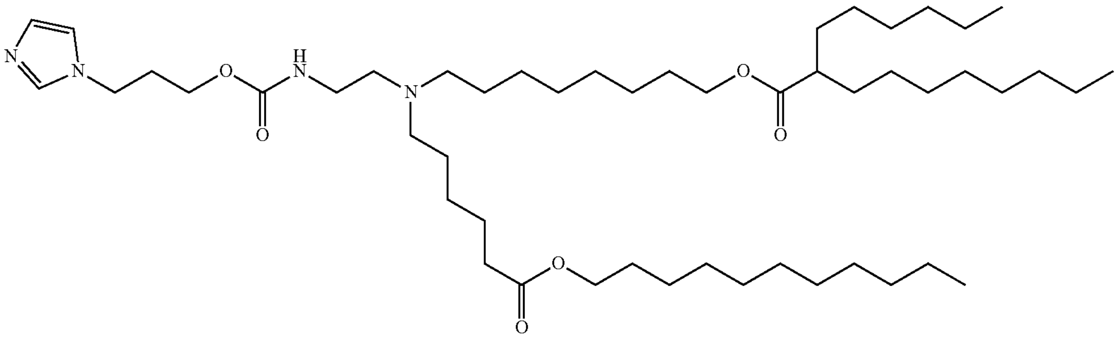 [SMILES: CCCCCCCCCCCOC(=O)CCCCCN(CCCCCCCCOC(=O)C(CCCCCC)CCCCCCCC)CCNC(=O)OCCCn1ccnc1] | 847.3 |
| 1011. | 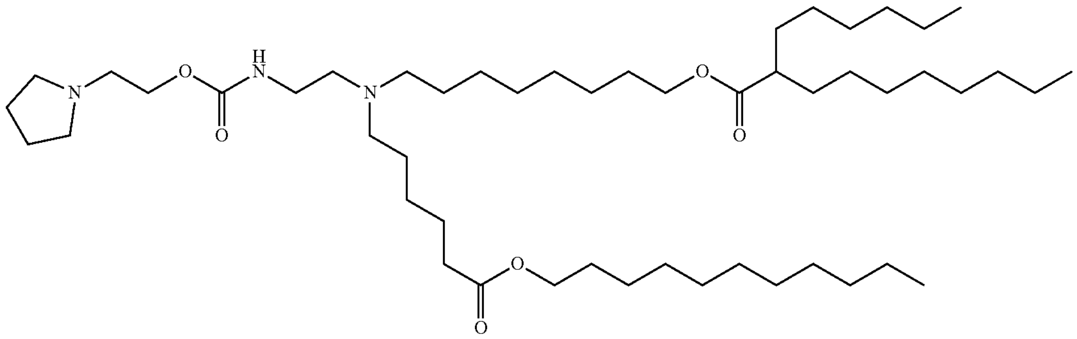 [SMILES: CCCCCCCCCCCOC(=O)CCCCCN(CCCCCCCCOC(=O)C(CCCCCC)CCCCCCCC)CCNC(=O)OCCN1CCCC1] | 836.3 |

TABLE 1-continued
| # | Structure | Mw |
| --- | --- | --- |
| 1012. | 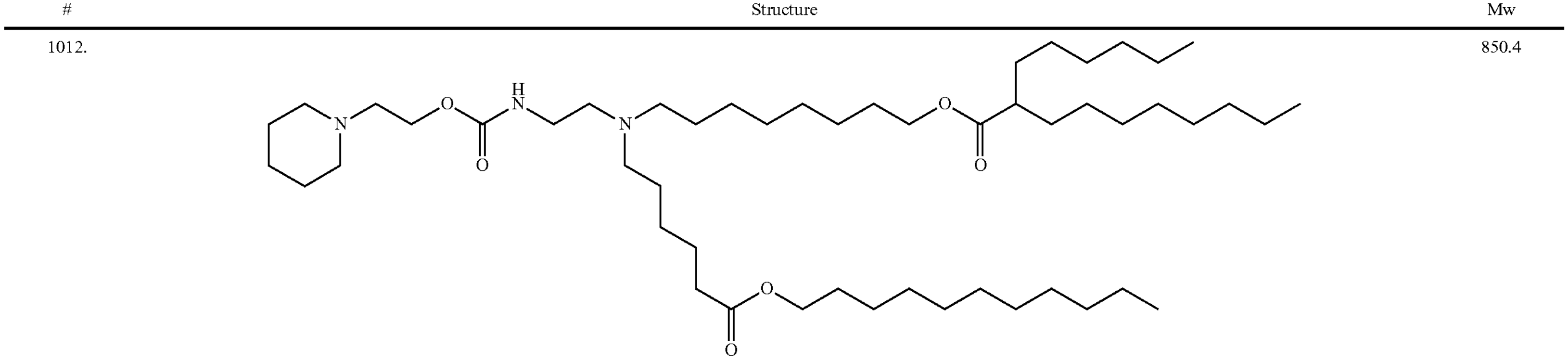 | 850.4 |
| 1013. | 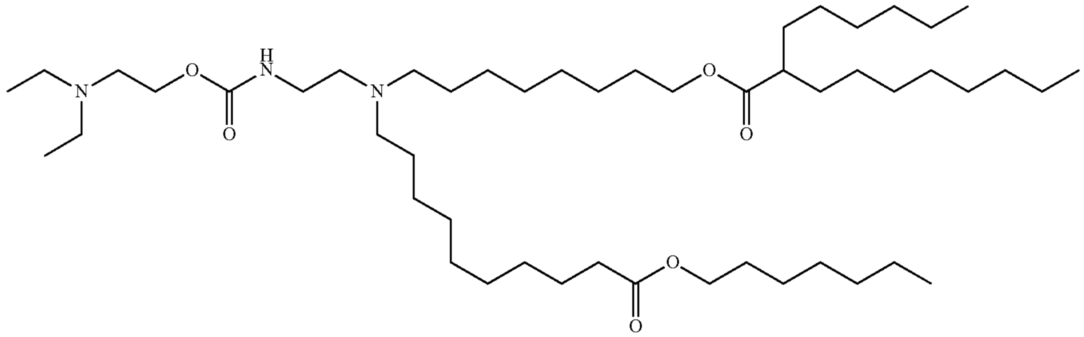 [SMILES: CCCCCCCCC(CCCCCC)C(=O)OCCCCCCCCN(CCCCCCCCCC(=O)OCCCCCCC)CCNC(=O)OCCN(CC)CC] | 838.4 |
| 1014. | 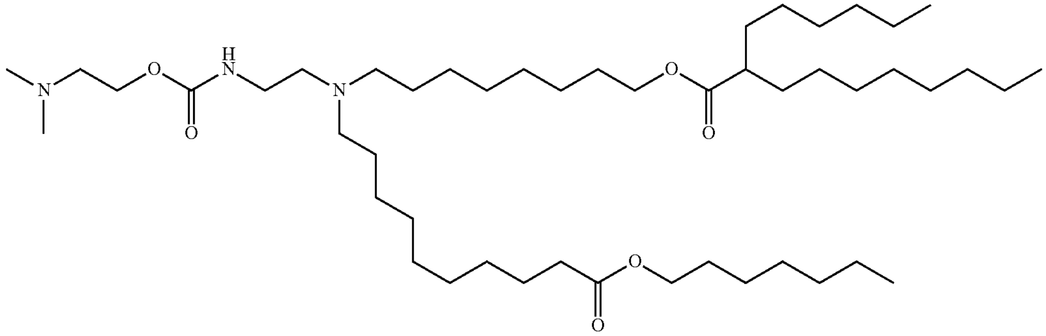 [SMILES: CCCCCCCCC(CCCCCC)C(=O)OCCCCCCCCN(CCCCCCCCCC(=O)OCCCCCCC)CCNC(=O)OCCN(C)C] | 810.3 |

TABLE 1-continued
| # | Structure | Mw |
| --- | --- | --- |
| 1015. | 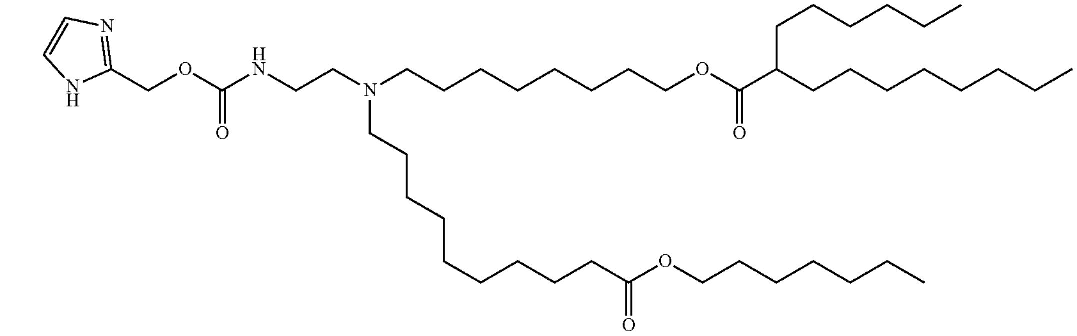 [SMILES: CCCCCCCCC(CCCCCC)C(=O)OCCCCCCCCN(CCCCCCCCCC(=O)OCCCCCCC)CCNC(=O)OCc1ncc[nH]1] | 819.3 |
| 1016. | 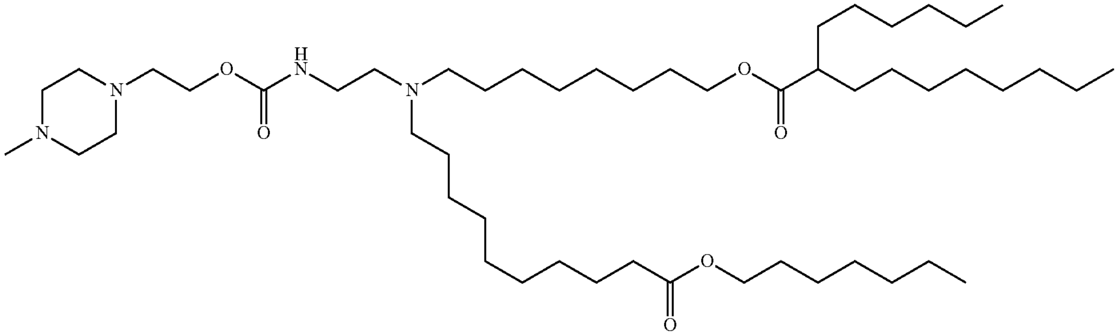 [SMILES: CCCCCCCCC(CCCCCC)C(=O)OCCCCCCCCN(CCCCCCCCCC(=O)OCCCCCCC)CCNC(=O)OCCN1CCN(C)CC1] | 865.4 |
| 1017. | 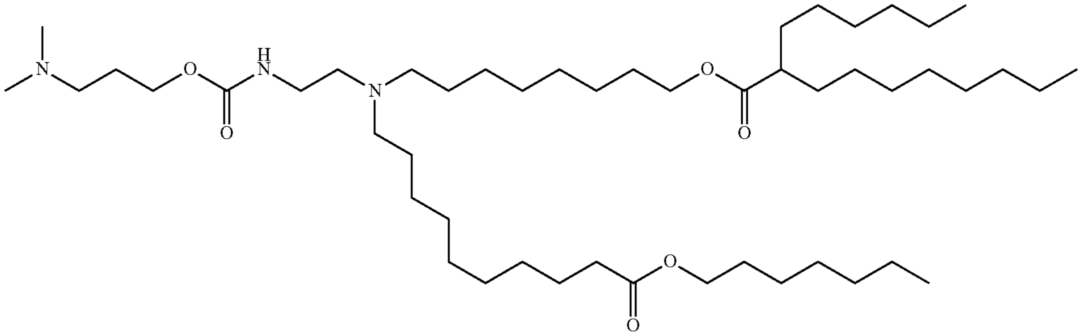 [SMILES: CCCCCCCCC(CCCCCC)C(=O)OCCCCCCCCN(CCCCCCCCCC(=O)OCCCCCCC)CCNC(=O)OCCCN(C)C] | 824.3 |

TABLE 1-continued
| # | Structure | Mw |
| --- | --- | --- |
| 1018. | 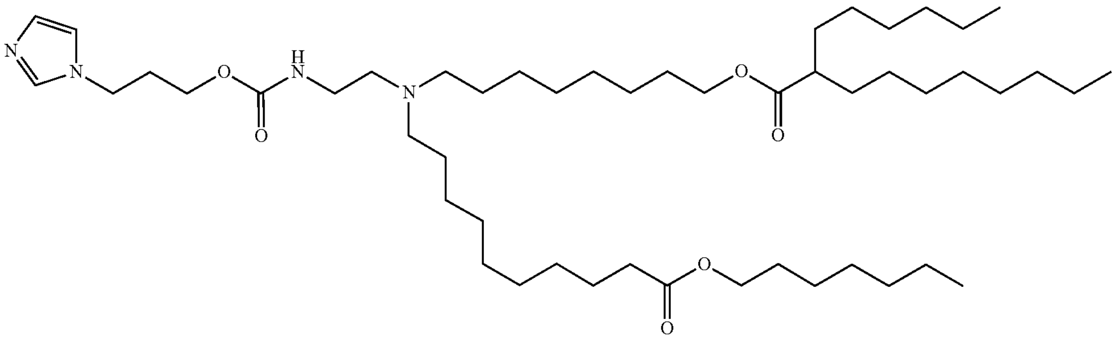 [SMILES: CCCCCCCCC(CCCCCC)C(=O)OCCCCCCCCN(CCCCCCCCCC(=O)OCCCCCCC)CCNC(=O)OCCCn1ccnc1] | 847.3 |
| 1019. | 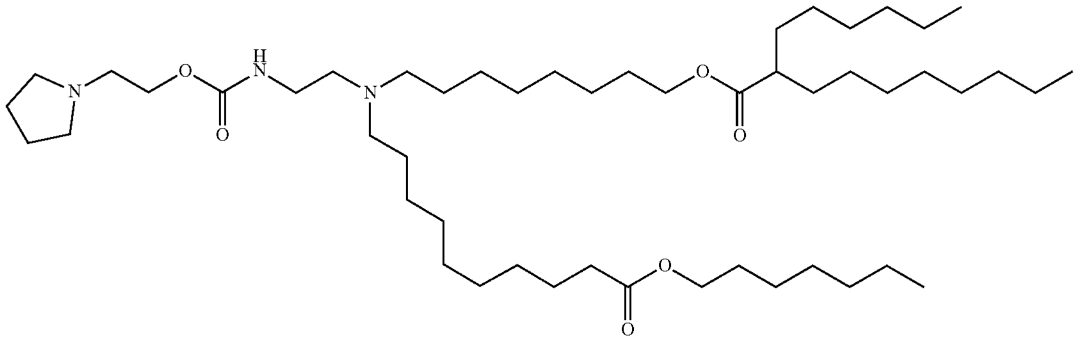 [SMILES: CCCCCCCCC(CCCCCC)C(=O)OCCCCCCCCN(CCCCCCCCCC(=O)OCCCCCCC)CCNC(=O)OCCN1CCCC1] | 836.3 |
| 1020. | 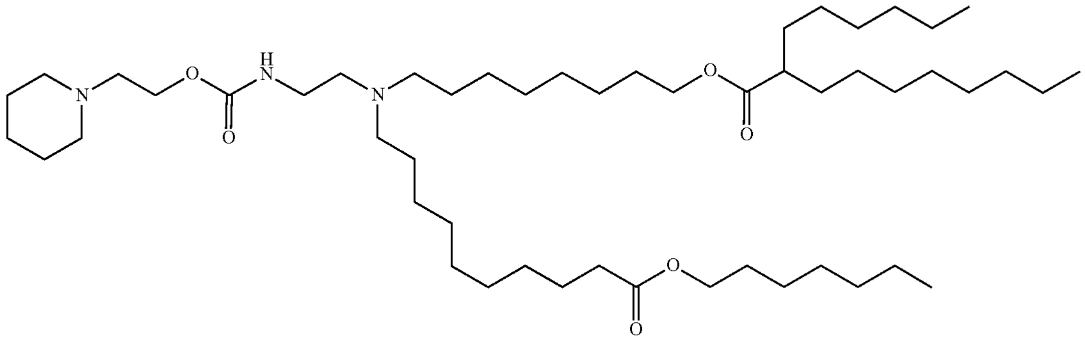 [SMILES: CCCCCCCCC(CCCCCC)C(=O)OCCCCCCCCN(CCCCCCCCCC(=O)OCCCCCCC)CCNC(=O)OCCN1CCCCC1] | 850.4 |

TABLE 1-continued
| # | Structure | Mw |
| --- | --- | --- |
| 1021. | 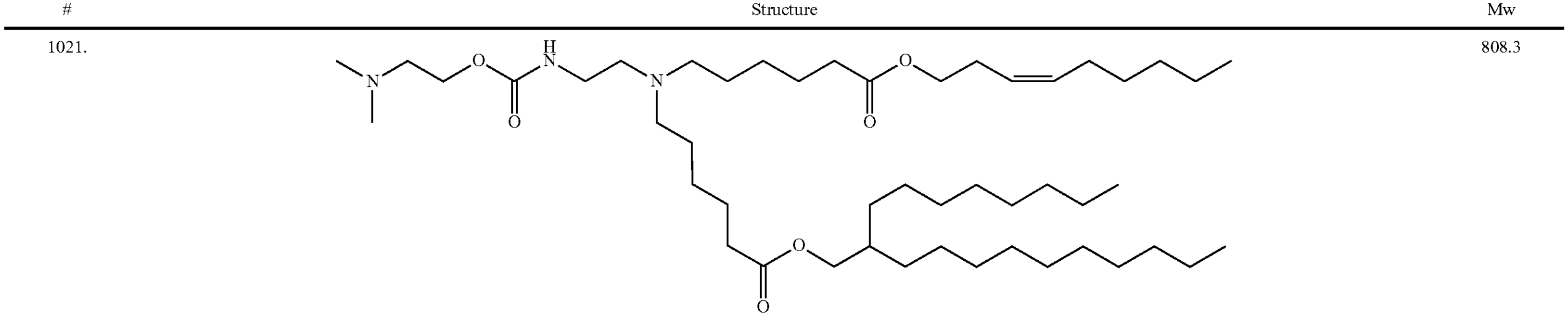 | 808.3 |
| 1022. | 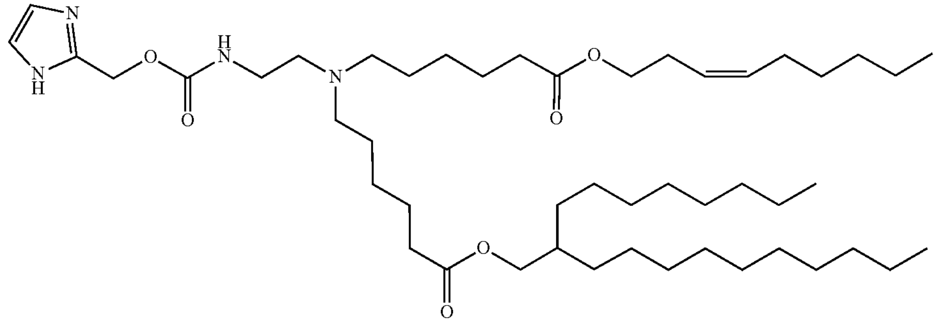 [SMILES: CCCCC/C=C\CCOC(=O)CCCCCN(CCCCCC(=O)OCC(CCCCCCCC)CCCCCCCCCC)CCNC(=O)OCc1ncc[nH]1] | 817.3 |
| 1023. | 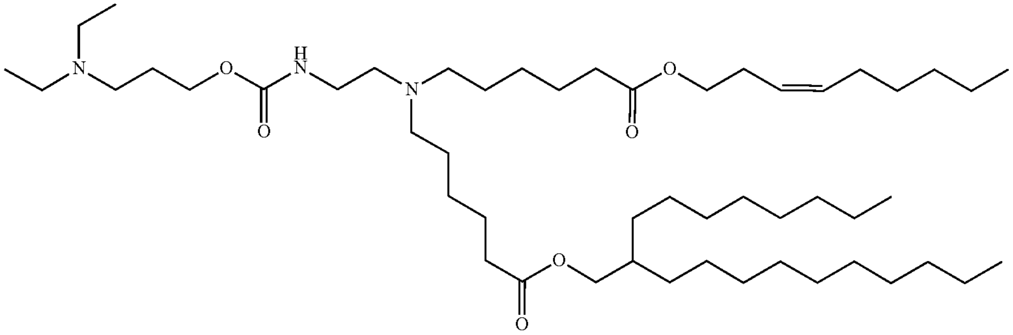 [SMILES: CCCCC/C=C\CCOC(=O)CCCCCN(CCCCCC(=O)OCC(CCCCCCCC)CCCCCCCCCC)CCNC(=O)OCCCN(CC)CC] | 850.4 |

TABLE 1-continued
| # | Structure | Mw |
|---|---|---|
| 1024. | 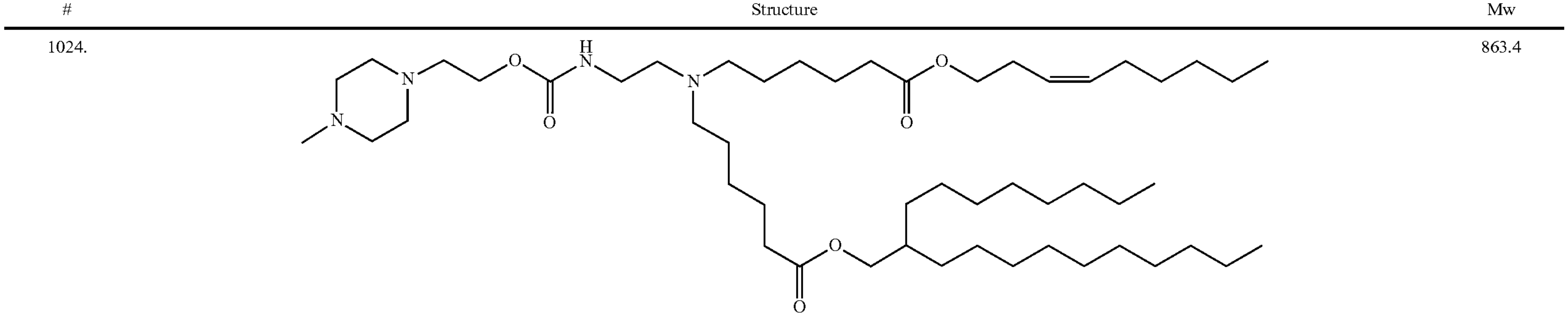 | 863.4 |
| 1025. | 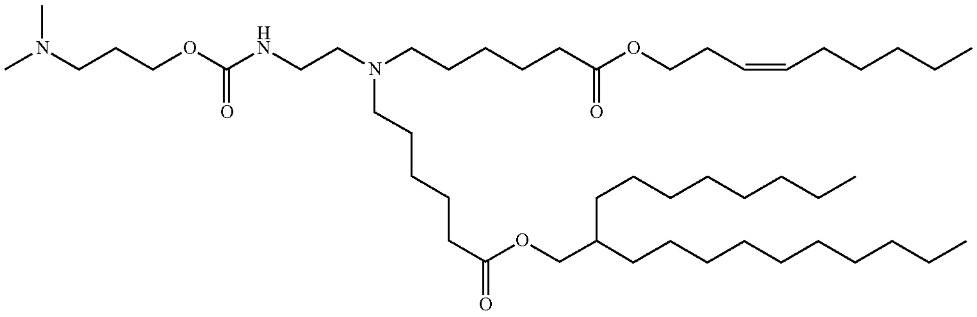 [SMILES: CCCCC/C=C\CCOC(=O)CCCCCN(CCCCCC(=O)OCC(CCCCCCCC)CCCCCCCCCC)CCNC(=O)OCCCN(C)C] | 822.3 |
| 1026. | 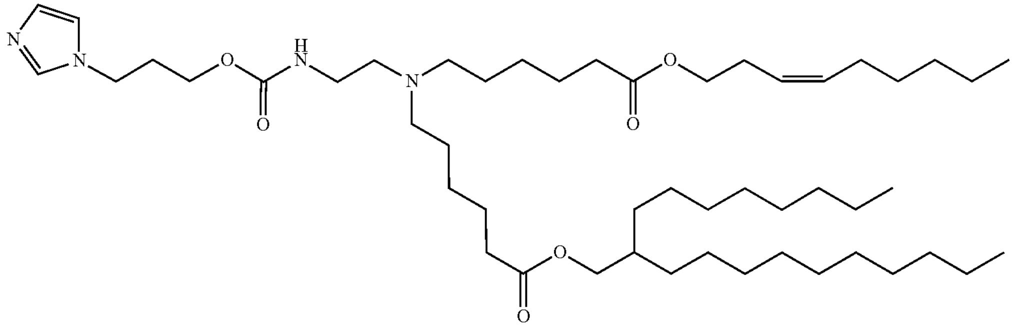 [SMILES: CCCCC/C=C\CCOC(=O)CCCCCN(CCCCCC(=O)OCC(CCCCCCCC)CCCCCCCCCC)CCNC(=O)OCCCn1ccnc1] | 845.3 |

TABLE 1-continued
| # | Structure | Mw |
|---|---|---|
| 1027. | 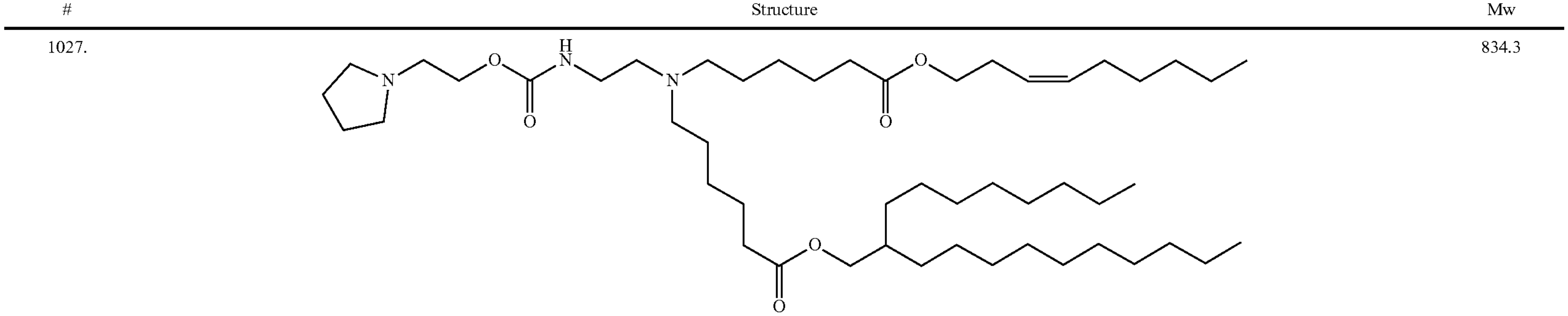 | 834.3 |
| 1028. | 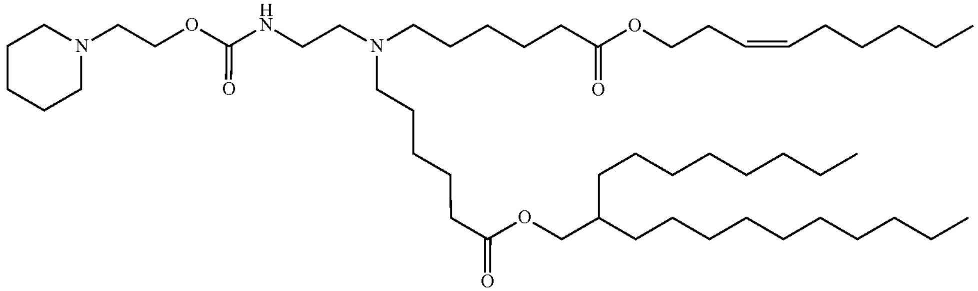 [SMILES: CCCCC/C=C\CCOC(=O)CCCCCN(CCCCCC(=O)OCC(CCCCCCCC)CCCCCCCCCC)CCNC(=O)OCCN1CCCCC1] | 848.4 |
| 1029. | 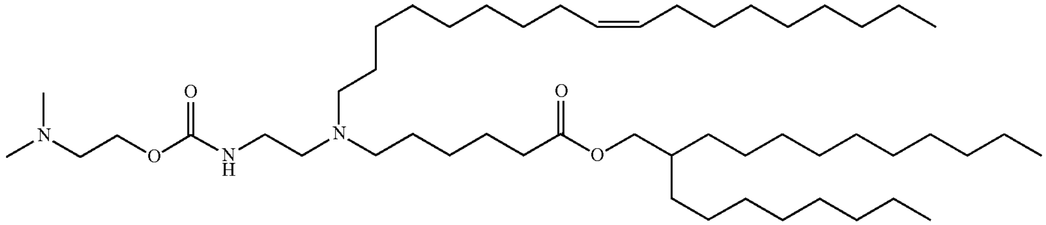 [SMILES: CCCCCCCC/C=C\CCCCCCCCN(CCCCCC(=O)OCC(CCCCCCCC)CCCCCCCCCC)CCNC(=O)OCCN(C)C] | 820.4 |
| 1030. | 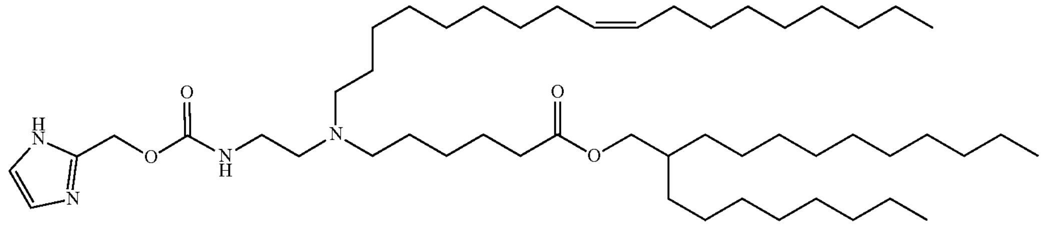 [SMILES: CCCCCCCC/C=C\CCCCCCCCN(CCCCCC(=O)OCC(CCCCCCCC)CCCCCCCCCC)CCNC(=O)OCc1ncc[nH]1] | 829.4 |

TABLE 1-continued
| # | Structure | Mw |
|---|---|---|
| 1031. | 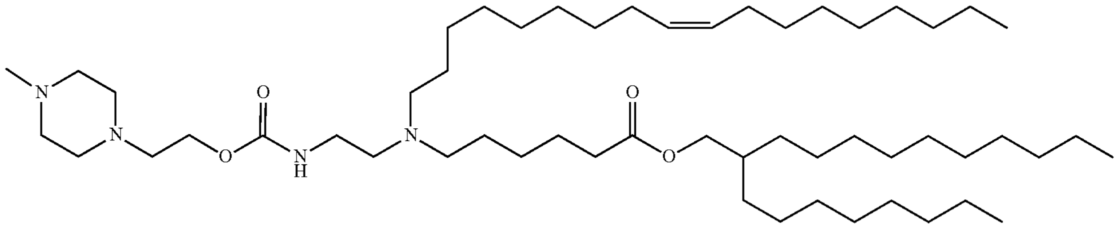 [SMILES: CCCCCCCC/C=C\CCCCCCCCN(CCCCCC(=O)OCC(CCCCCCCC)CCCCCCCCCC)CCNC(=O)OCCN1CCN(C)CC1] | 875.5 |
| 1032. | 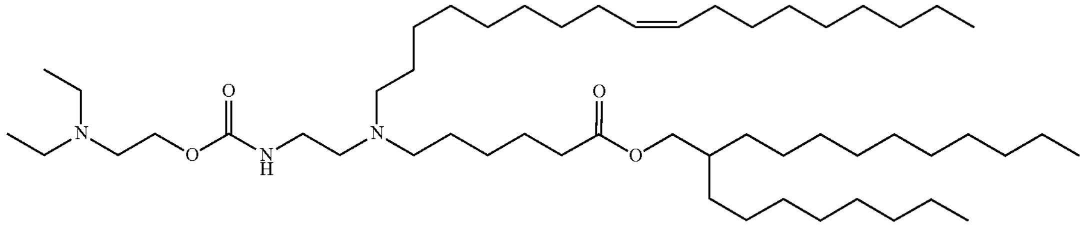 [SMILES: CCCCCCCC/C=C\CCCCCCCCN(CCCCCC(=O)OCC(CCCCCCCC)CCCCCCCCCC)CCNC(=O)OCCN(CC)CC] | 848.4 |
| 1033. | 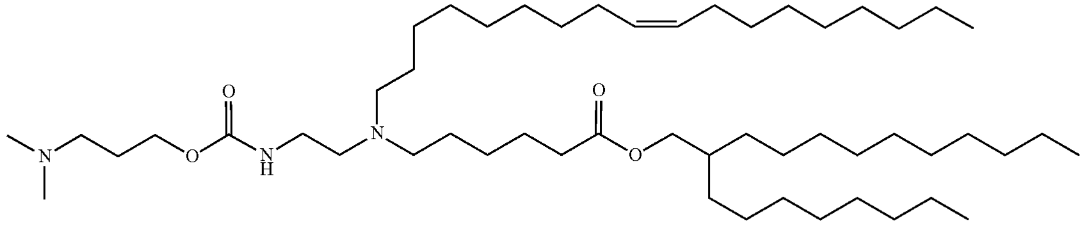 [SMILES: CCCCCCCC/C=C\CCCCCCCCN(CCCCCC(=O)OCC(CCCCCCCC)CCCCCCCCCC)CCNC(=O)OCCCN(C)C] | 834.4 |
| 1034. | 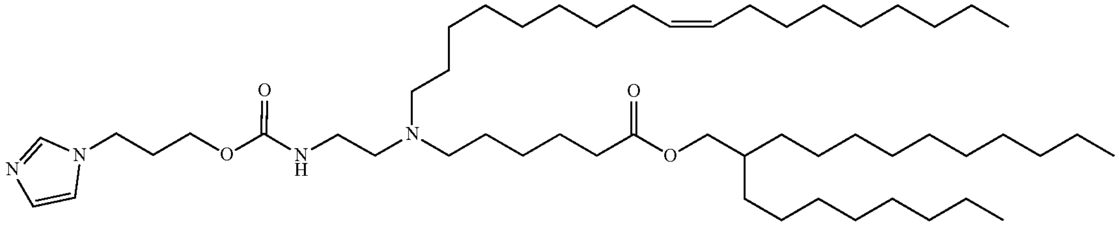 [SMILES: CCCCCCCC/C=C\CCCCCCCCN(CCCCCC(=O)OCC(CCCCCCCC)CCCCCCCCCC)CCNC(=O)OCCCn1ccnc1] | 857.4 |

TABLE 1-continued
| # | Structure | Mw |
|---|---|---|
| 1035. | 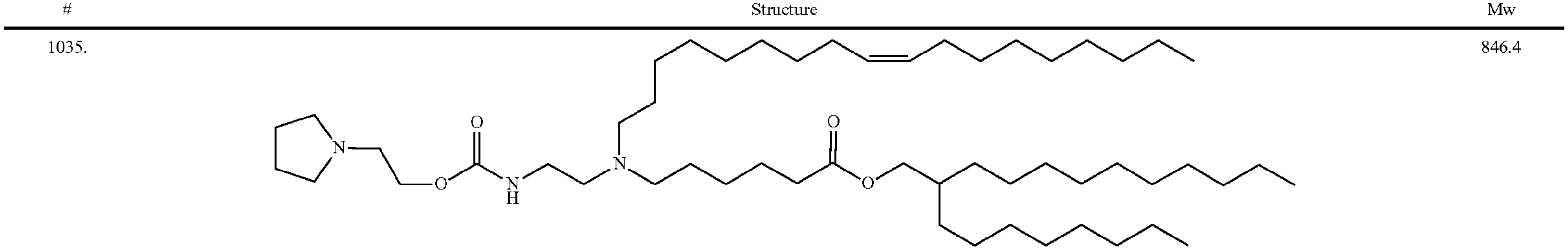 | 846.4 |
| 1036. | 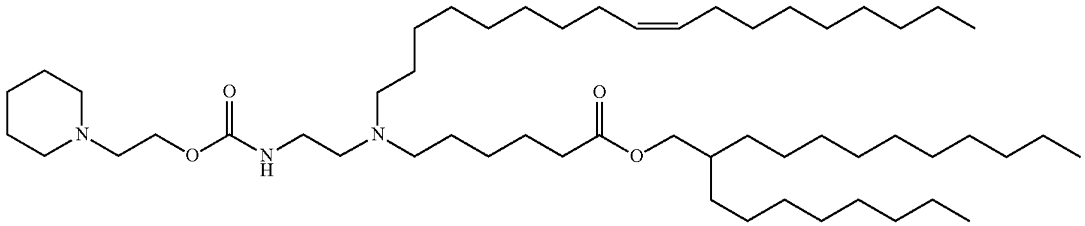 [SMILES: CCCCCCCC/C=C\CCCCCCCCN(CCCCCC(=O)OCC(CCCCCCCC)CCCCCCCCCC)CCNC(=O)OCCN1CCCCC1] | 860.5 |
| 1037. | 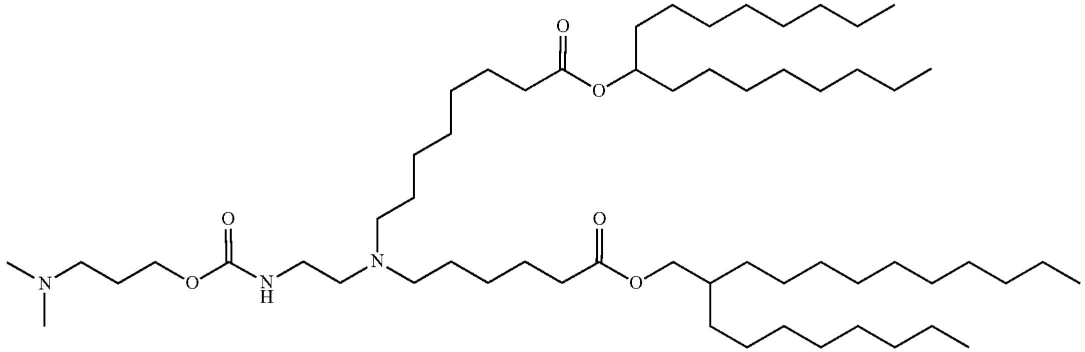 [SMILES: CCCCCCCCCCC(CCCCCCCC)COC(=O)CCCCCN(CCCCCCCC(=O)OC(CCCCCCCC)CCCCCCCC)CCNC(=O)OCCCN(C)C] | 964.6 |

TABLE 1-continued
| # | Structure | Mw |
| --- | --- | --- |
| 1038. | 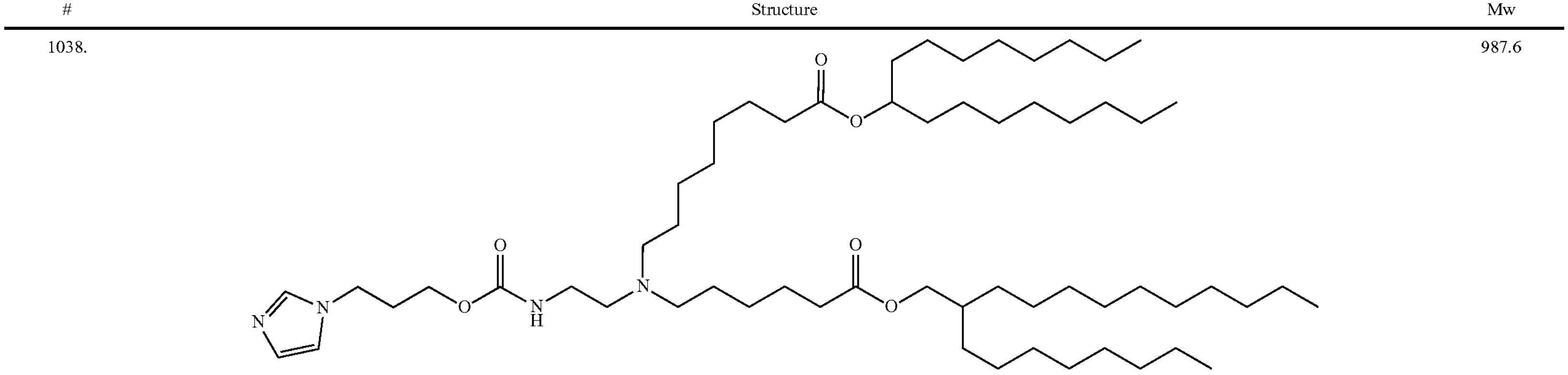 | 987.6 |
| 1039. | 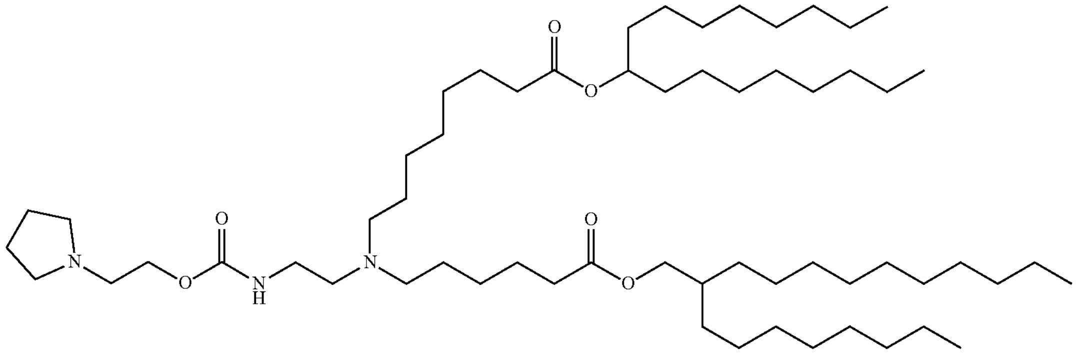 [SMILES: CCCCCCCCCCC(CCCCCCCC)COC(=O)CCCCCN(CCCCCCCC(=O)OC(CCCCCCCC)CCCCCCCC)CCNC(=O)OCCN1CCCC1] | 976.6 |
| 1040. | 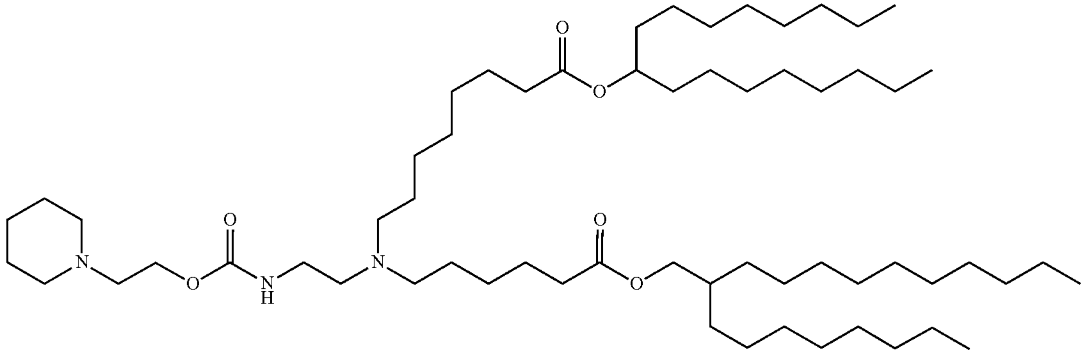 [SMILES: CCCCCCCCCCC(CCCCCCCC)COC(=O)CCCCCN(CCCCCCCC(=O)OC(CCCCCCCC)CCCCCCCC)CCNC(=O)OCCN1CCCCC1] | 990.6 |

TABLE 1-continued
| # | Structure | Mw |
| --- | --- | --- |
| 1041. | 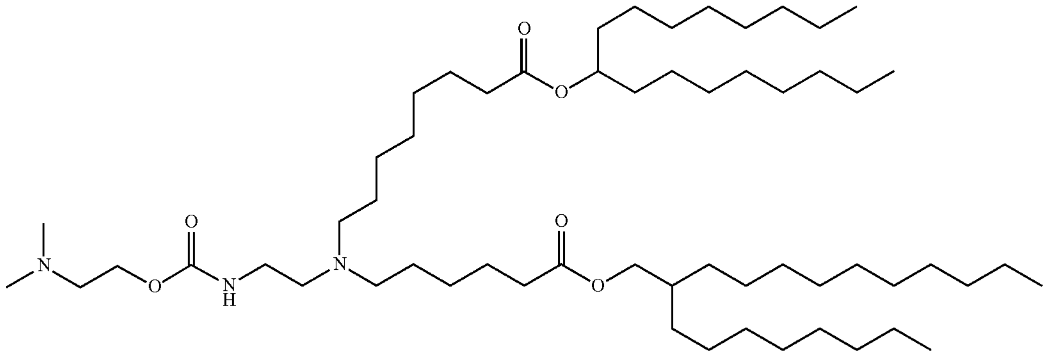 [SMILES: CCCCCCCCCCC(CCCCCCCC)COC(=O)CCCCCN(CCCCCCCC(=O)OC(CCCCCCCC)CCCCCCCC)CCNC(=O)OCCN(C)C] | 950.6 |
| 1042. | 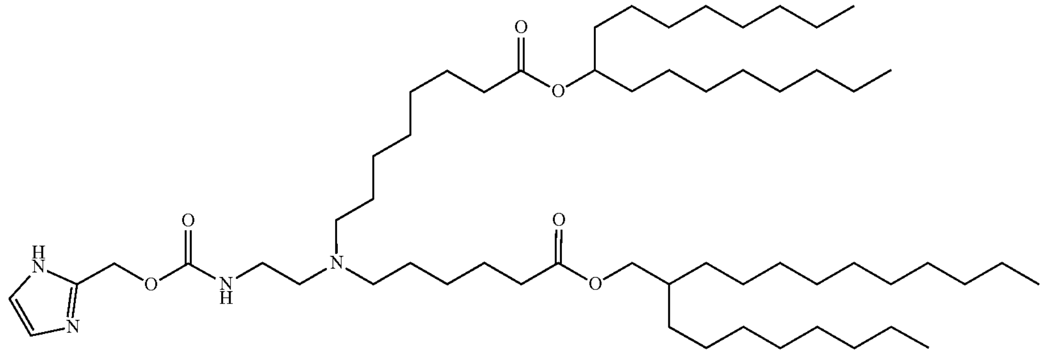 [SMILES: CCCCCCCCCCC(CCCCCCCC)COC(=O)CCCCCN(CCCCCCCC(=O)OC(CCCCCCCC)CCCCCCCC)CCNC(=O)OCc1ncc[nH]1] | 959.5 |

TABLE 1-continued
| # | Structure | Mw |
| --- | --- | --- |
| 1043. | 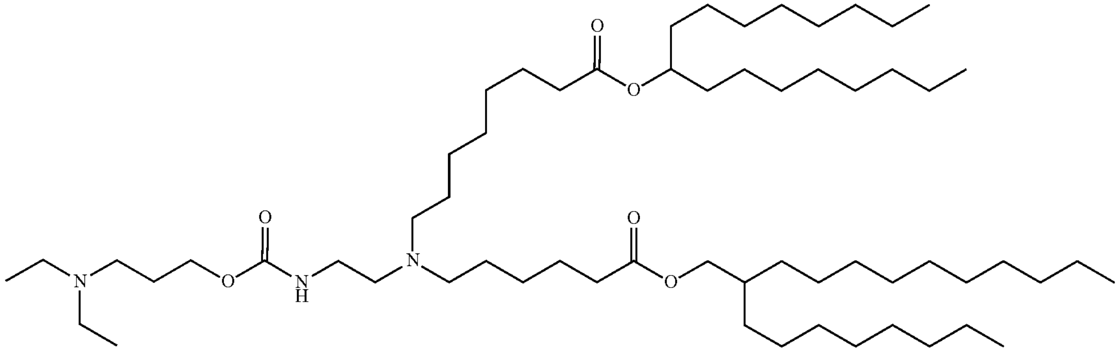 [SMILES: CCCCCCCCCCC(CCCCCCCC)COC(=O)CCCCCN(CCCCCCCC(=O)OC(CCCCCCCC)CCCCCCCC)CCNC(=O)OCCCN(CC)CC] | 992.7 |
| 1044. | 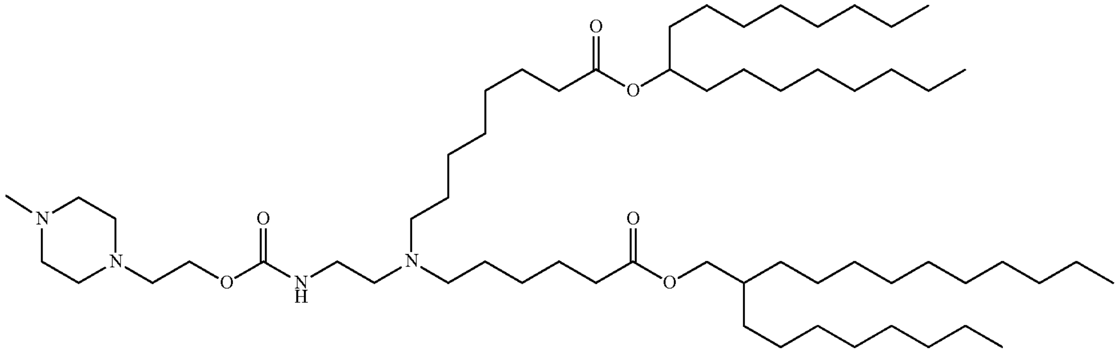 [SMILES: CCCCCCCCCCC(CCCCCCCC)COC(=O)CCCCCN(CCCCCCCC(=O)OC(CCCCCCCC)CCCCCCCC)CCNC(=O)OCCN1CCN(C)CC1] | 1005.7 |
| 1045. | 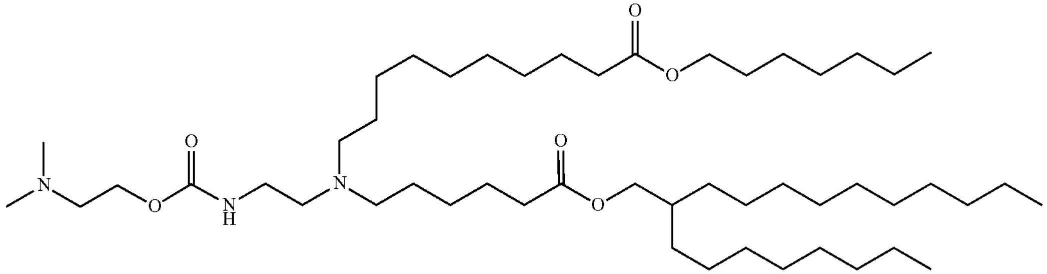 [SMILES: CCCCCCCCCCC(CCCCCCCC)COC(=O)CCCCCN(CCCCCCCCCC(=O)OCCCCCCC)CCNC(=O)OCCN(C)C] | 838.4 |

TABLE 1-continued
| # | Structure | Mw |
| --- | --- | --- |
| 1046. | 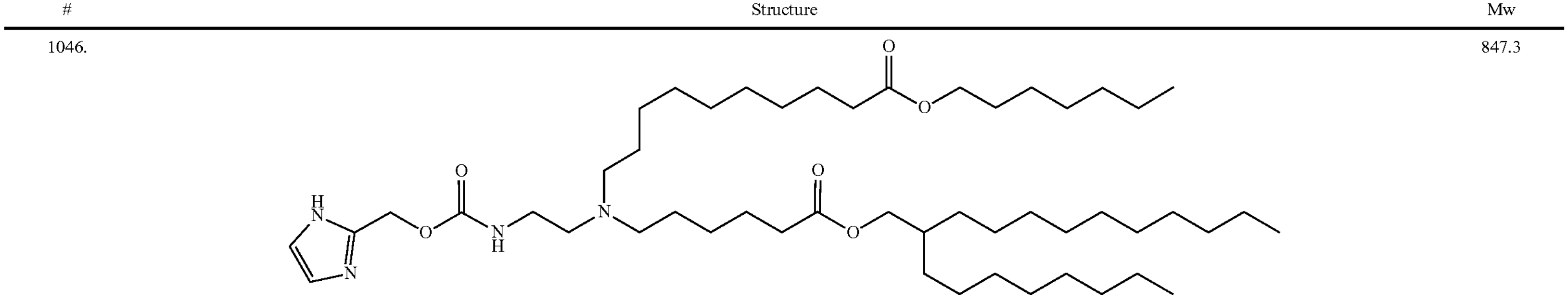 | 847.3 |
| 1047. | 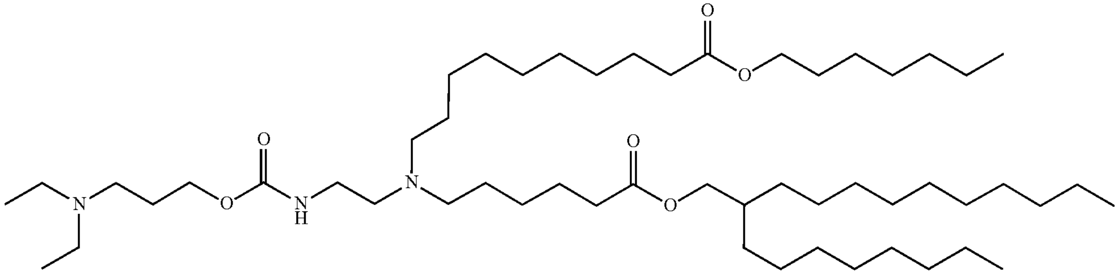 [SMILES: CCCCCCCCCCC(CCCCCCCC)COC(=O)CCCCCN(CCCCCCCCCC(=O)OCCCCCCC)CCNC(=O)OCCCN(CC)CC] | 880.4 |
| 1048. | 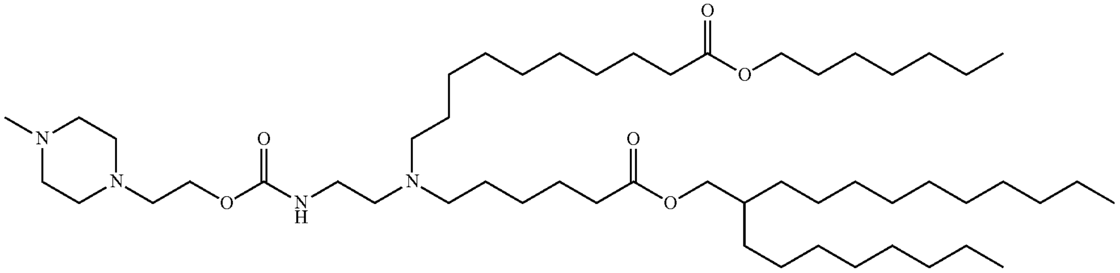 [SMILES: CCCCCCCCCCC(CCCCCCCC)COC(=O)CCCCCN(CCCCCCCCCC(=O)OCCCCCCC)CCNC(=O)OCCN1CCN(C)CC1] | 893.4 |

TABLE 1-continued
| # | Structure | Mw |
| --- | --- | --- |
| 1049. | 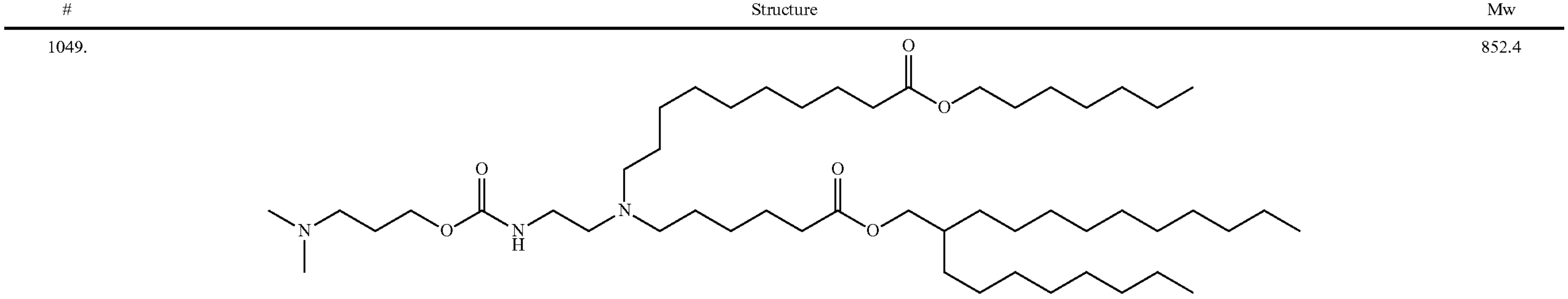 | 852.4 |
| 1050. | 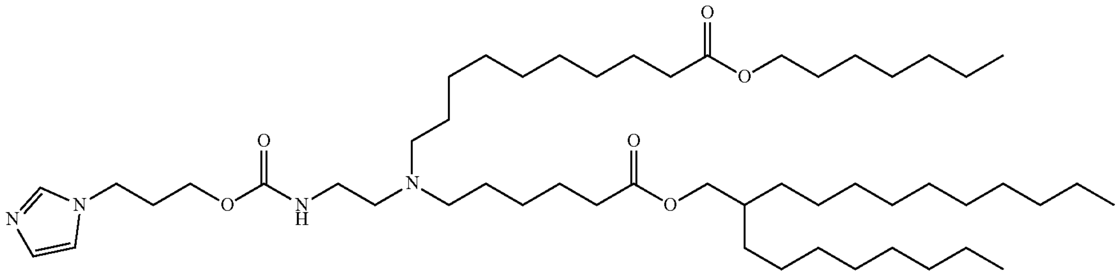 [SMILES: CCCCCCCCCCC(CCCCCCCC)COC(=O)CCCCCN(CCCCCCCCCC(=O)OCCCCCCC)CCNC(=O)OCCCn1ccnc1] | 875.4 |
| 1051. | 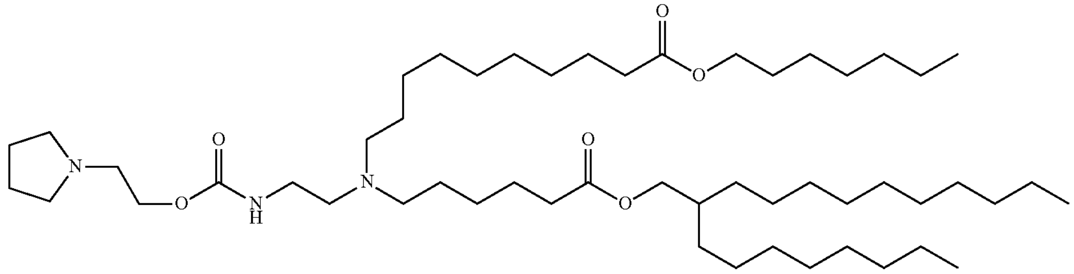 [SMILES: CCCCCCCCCCC(CCCCCCCC)COC(=O)CCCCCN(CCCCCCCCCC(=O)OCCCCCCC)CCNC(=O)OCCN1CCCC1] | 864.4 |

TABLE 1-continued
| # | Structure | Mw |
|---|---|---|
| 1052. | 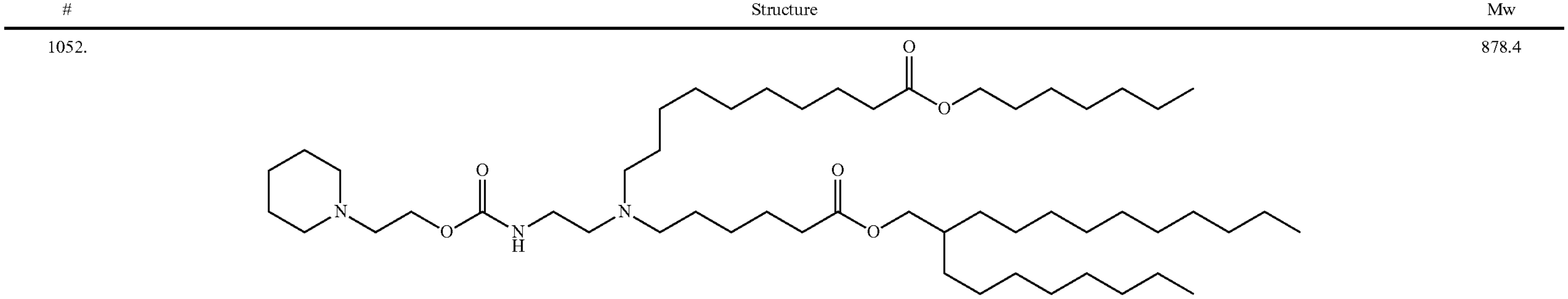 | 878.4 |
| 1053. | 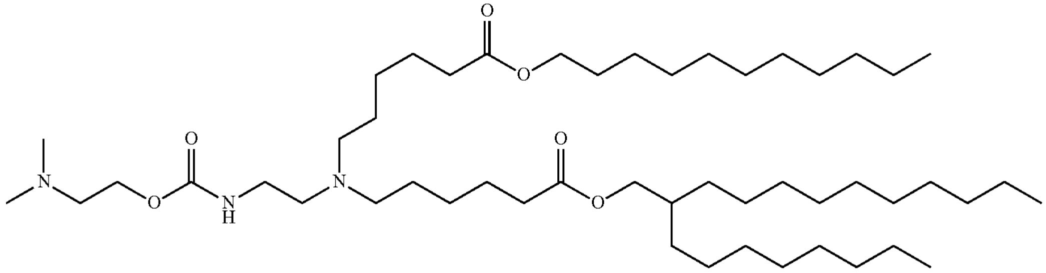 [SMILES: CCCCCCCCCCCOC(=O)CCCCCN(CCCCCC(=O)OCC(CCCCCCCC)CCCCCCCCCC)CCNC(=O)OCCN(C)C] | 838.4 |
| 1054. | 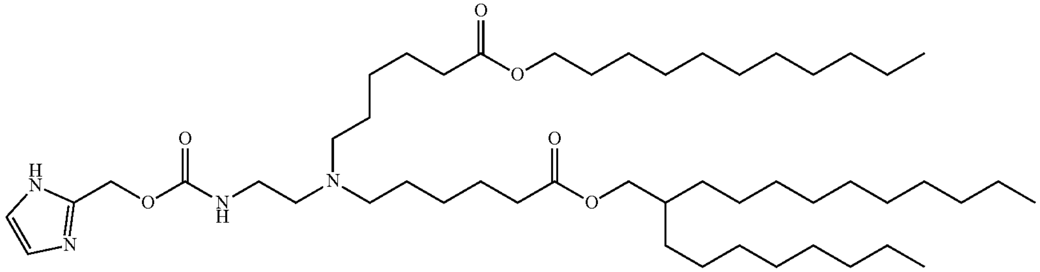 [SMILES: CCCCCCCCCCCOC(=O)CCCCCN(CCCCCC(=O)OCC(CCCCCCCC)CCCCCCCCCC)CCNC(=O)OCc1ncc[nH]1] | 847.3 |

TABLE 1-continued
| # | Structure | Mw |
|---|---|---|
| 1055. | 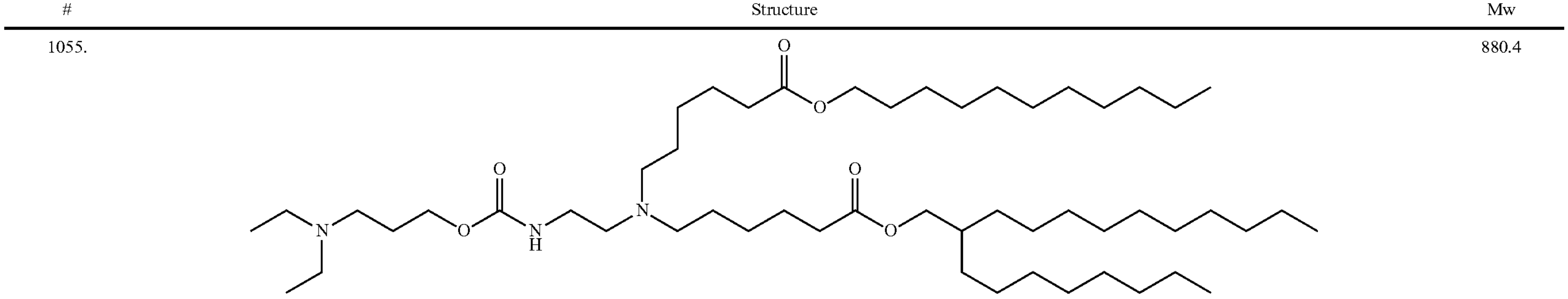 | 880.4 |
| 1056. | 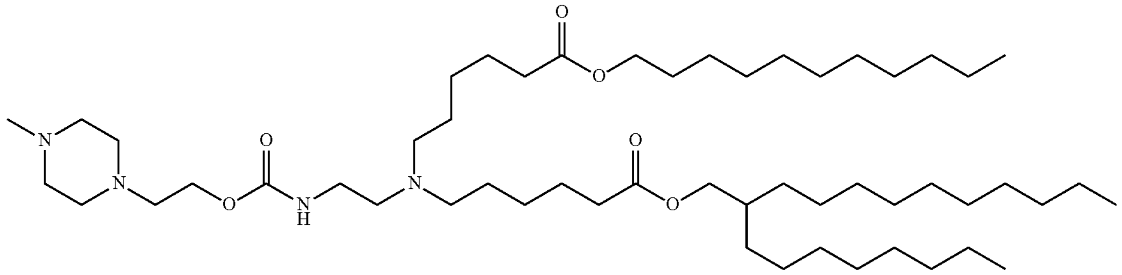 [SMILES: CCCCCCCCCCCOC(=O)CCCCCN(CCCCCC(=O)OCC(CCCCCCCC)CCCCCCCCCC)CCNC(=O)OCCN1CCN(C)CC1] | 893.4 |
| 1057. | 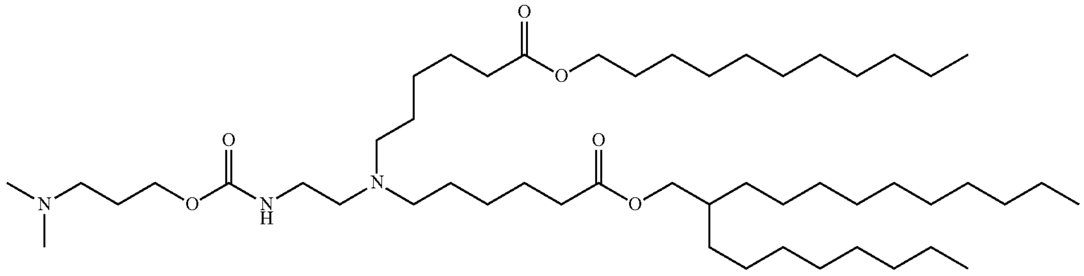 [SMILES: CCCCCCCCCCCOC(=O)CCCCCN(CCCCCC(=O)OCC(CCCCCCCC)CCCCCCCCCC)CCNC(=O)OCCCN(C)C] | 852.4 |

TABLE 1-continued
| # | Structure | Mw |
|---|---|---|
| 1058. | 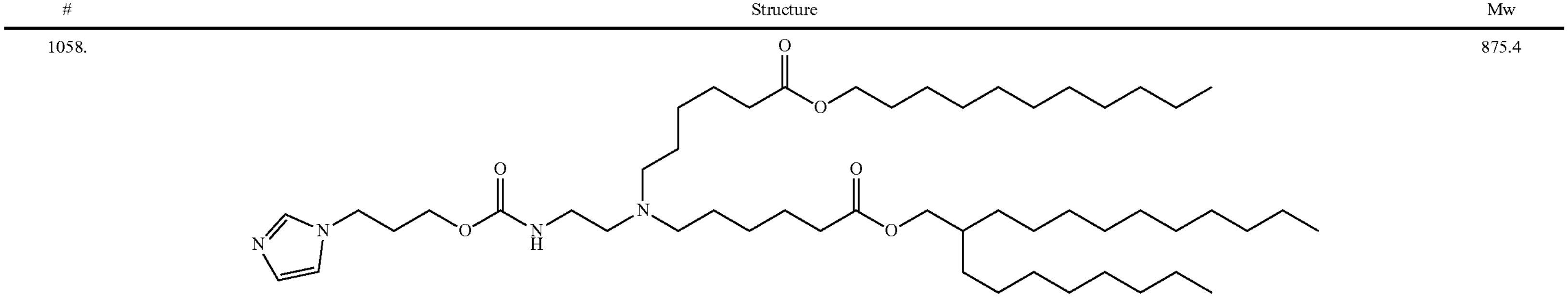 | 875.4 |
| 1059. | 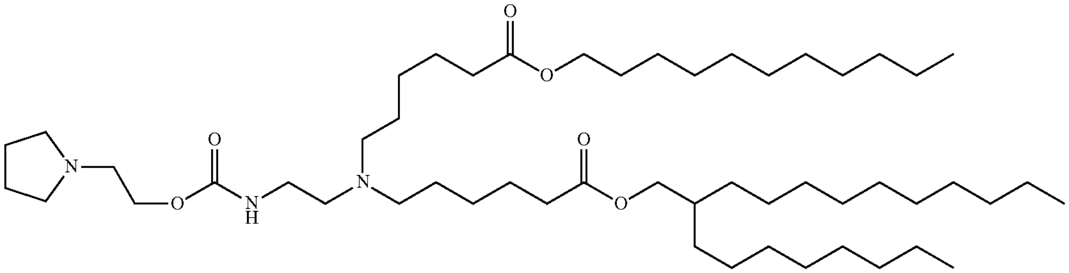 [SMILES: CCCCCCCCCCCOC(=O)CCCCCN(CCCCCC(=O)OCC(CCCCCCCC)CCCCCCCCCC)CCNC(=O)OCCN1CCCC1] | 864.4 |
| 1060. | 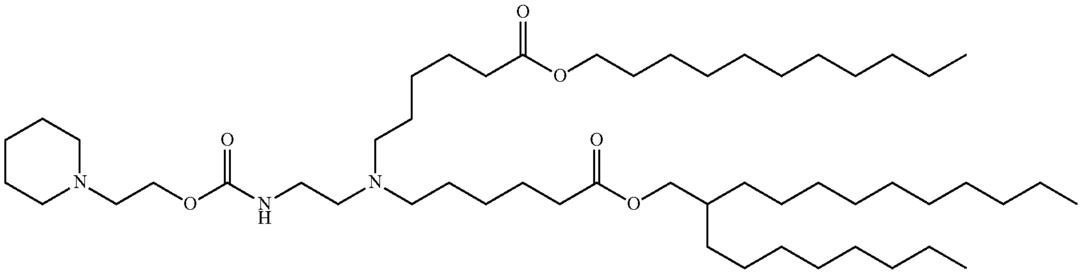 [SMILES: CCCCCCCCCCCOC(=O)CCCCCN(CCCCCC(=O)OCC(CCCCCCCC)CCCCCCCCCC)CCNC(=O)OCCN1CCCCC1] | 878.4 |
| 1061. | 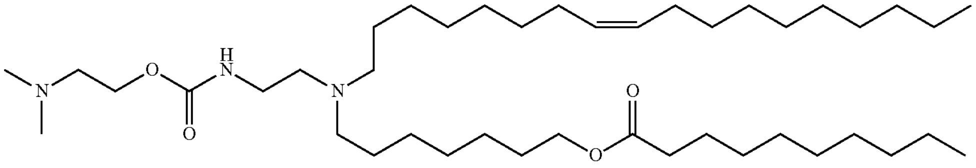 [SMILES: CCCCCCCCC/C=C\CCCCCCCN(CCCCCCCOC(=O)CCCCCCCCC)CCNC(=O)OCCN(C)C] | 694.1 |

TABLE 1-continued
| # | Structure | Mw |
|---|---|---|
| 1062. | 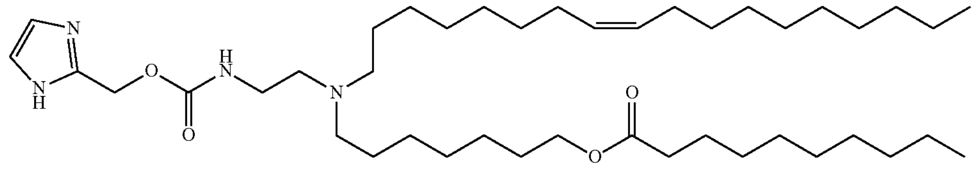 [SMILES: CCCCCCCCC/C=C\CCCCCCCN(CCCCCCCOC(=O)CCCCCCCCC)CCNC(=O)OCc1ncc[nH]1] | 703.1 |
| 1063. | 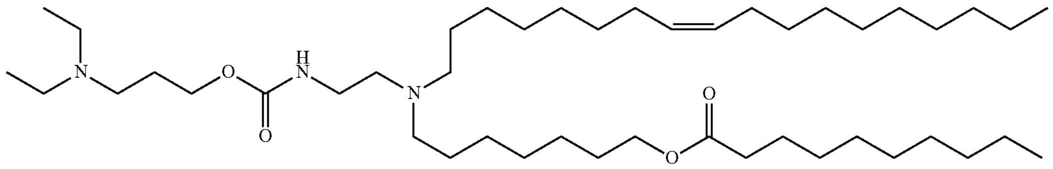 [SMILES: CCCCCCCCC/C=C\CCCCCCCN(CCCCCCCOC(=O)CCCCCCCCC)CCNC(=O)OCCCN(CC)CC] | 736.2 |
| 1064. | 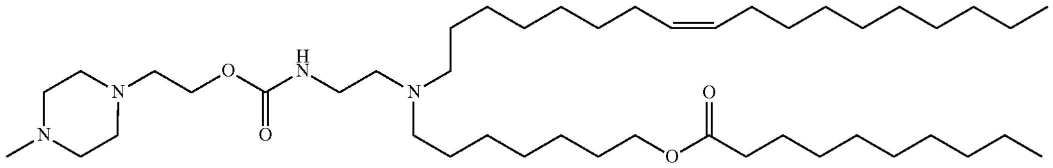 [SMILES: CCCCCCCCC/C=C\CCCCCCCN(CCCCCCCOC(=O)CCCCCCCCC)CCNC(=O)OCCN1CCN(C)CC1] | 749.2 |
| 1065. | 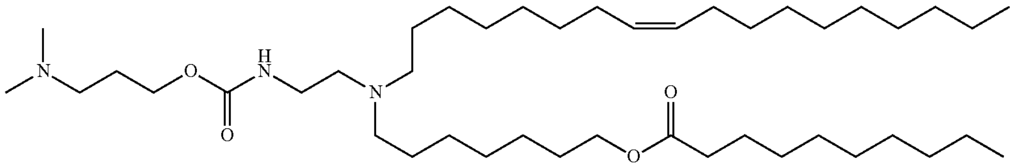 [SMILES: CCCCCCCCC/C=C\CCCCCCCN(CCCCCCCOC(=O)CCCCCCCCC)CCNC(=O)OCCCN(C)C] | 708.2 |
| 1066. | 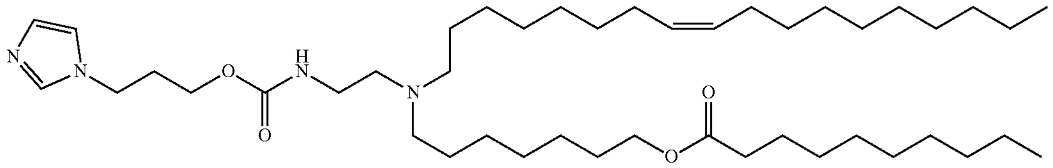 [SMILES: CCCCCCCCC/C=C\CCCCCCCN(CCCCCCCOC(=O)CCCCCCCCC)CCNC(=O)OCCCn1ccnc1] | 731.2 |
| 1067. | 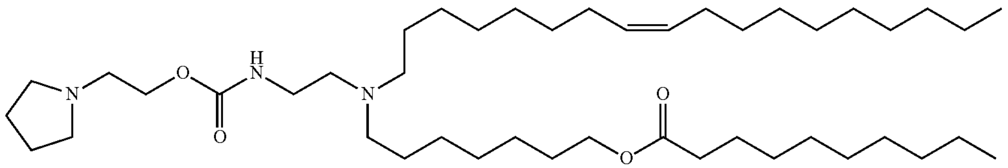 [SMILES: CCCCCCCCC/C=C\CCCCCCCN(CCCCCCCOC(=O)CCCCCCCCC)CCNC(=O)OCCN1CCCC1] | 720.2 |

TABLE 1-continued
| # | Structure | Mw |
| --- | --- | --- |
| 1068. | 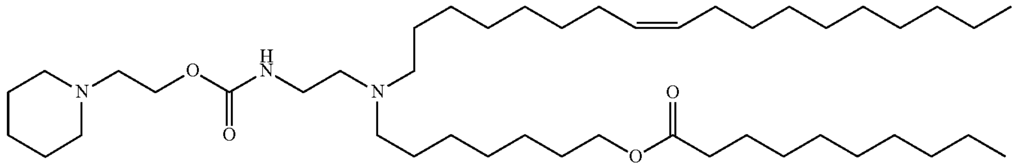 [SMILES: CCCCCCCCC/C=C\CCCCCCCN(CCCCCCCOC(=O)CCCCCCCCC)CCNC(=O)OCCN1CCCCC1] | 734.2 |
| 1069. | 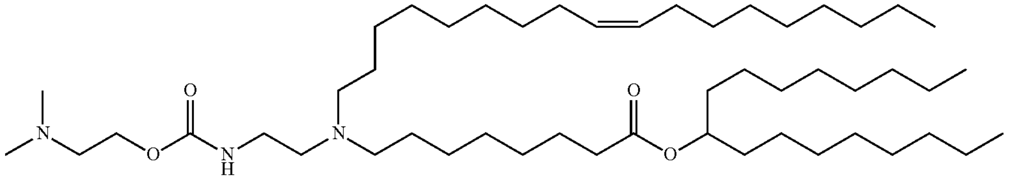 [SMILES: CCCCCCCC/C=C\CCCCCCCCN(CCCCCCCC(=O)OC(CCCCCCCC)CCCCCCCC)CCNC(=O)OCCN(C)C] | 806.4 |
| 1070. | 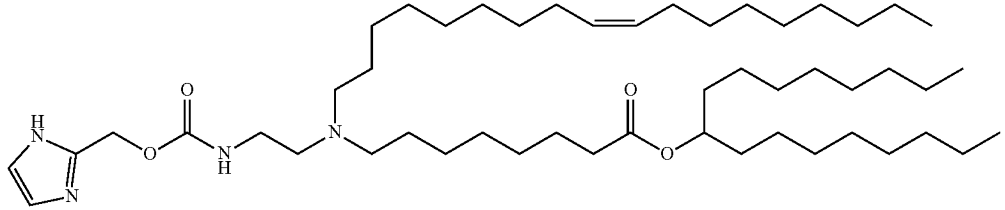 [SMILES: CCCCCCCC/C=C\CCCCCCCCN(CCCCCCCC(=O)OC(CCCCCCCC)CCCCCCCC)CCNC(=O)OCc1ncc[nH]1] | 815.3 |
| 1071. | 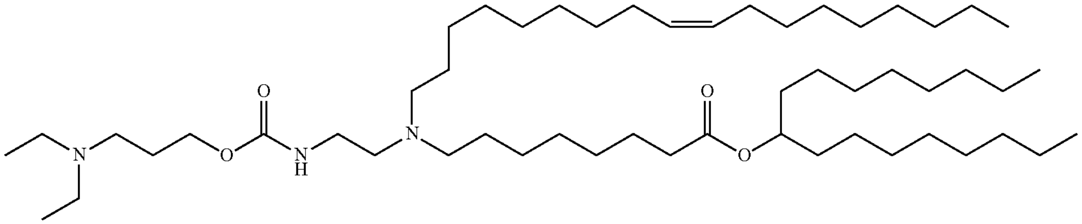 [SMILES: CCCCCCCC/C=C\CCCCCCCCN(CCCCCCCC(=O)OC(CCCCCCCC)CCCCCCCC)CCNC(=O)OCCCN(CC)CC] | 848.4 |
| 1072. | 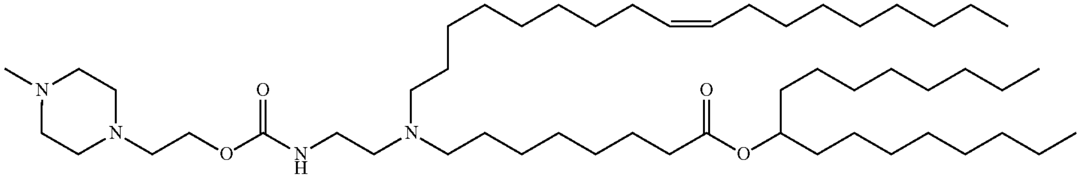 [SMILES: CCCCCCCC/C=C\CCCCCCCCN(CCCCCCCC(=O)OC(CCCCCCCC)CCCCCCCC)CCNC(=O)OCCN1CCN(C)CC1] | 861.4 |

TABLE 1-continued
| # | Structure | Mw |
|---|---|---|
| 1073. | 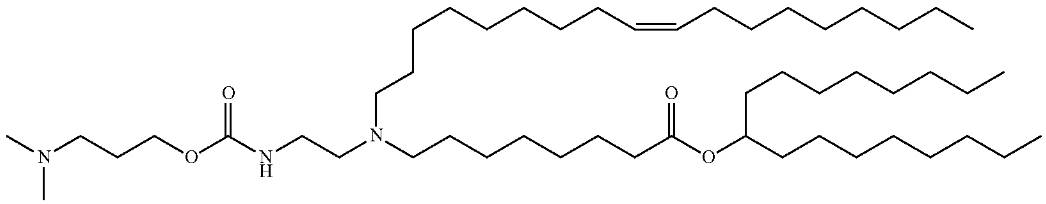 [SMILES: CCCCCCCC/C=C\CCCCCCCCN(CCCCCCCC(=O)OC(CCCCCCCC)CCCCCCCC)CCNC(=O)OCCCN(C)C] | 820.4 |
| 1074. | 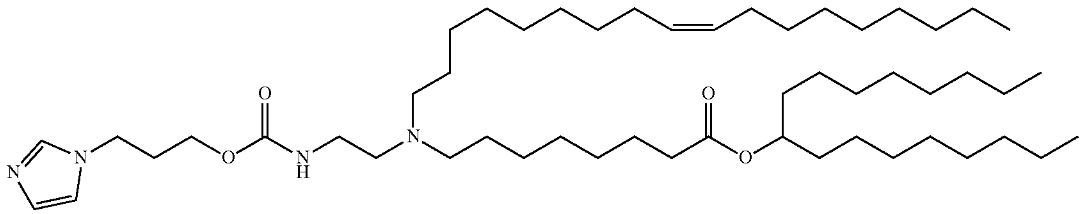 [SMILES: CCCCCCCC/C=C\CCCCCCCCN(CCCCCCCC(=O)OC(CCCCCCCC)CCCCCCCC)CCNC(=O)OCCCn1ccnc1] | 843.4 |
| 1075. | 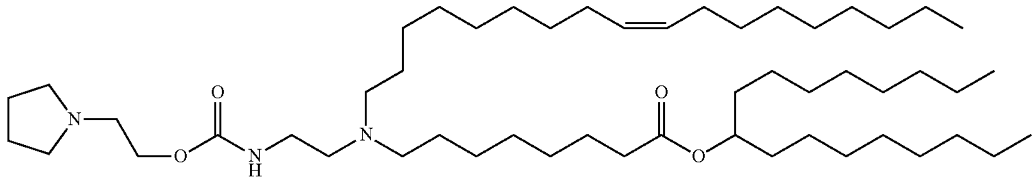 [SMILES: CCCCCCCC/C=C\CCCCCCCCN(CCCCCCCC(=O)OC(CCCCCCCC)CCCCCCCC)CCNC(=O)OCCN1CCCC1] | 832.4 |
| 1076. | 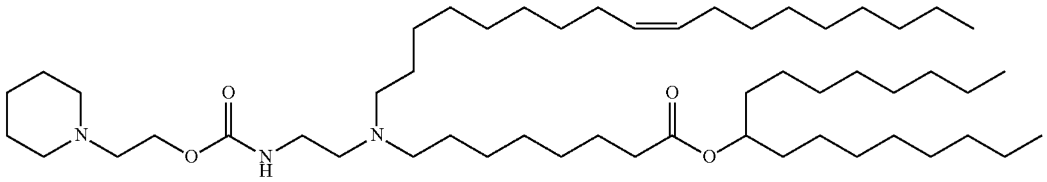 [SMILES: CCCCCCCC/C=C\CCCCCCCCN(CCCCCCCC(=O)OC(CCCCCCCC)CCCCCCCC)CCNC(=O)OCCN1CCCCC1] | 846.4 |
| 1077. | 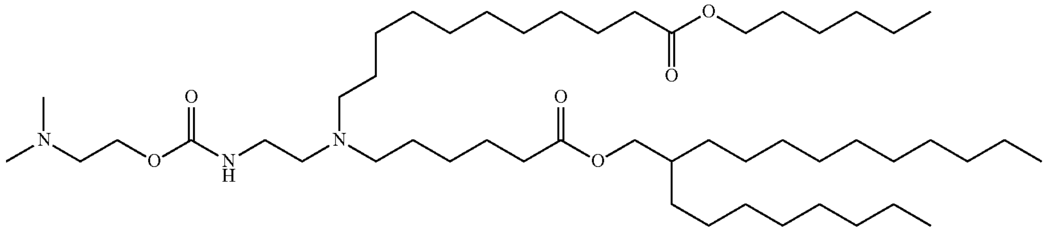 [SMILES: CCCCCCCCCCC(CCCCCCCC)COC(=O)CCCCCN(CCCCCCCCCCC(=O)OCCCCCC)CCNC(=O)OCCN(C)C] | 838.4 |

TABLE 1-continued
| # | Structure | Mw |
| --- | --- | --- |
| 1078. | 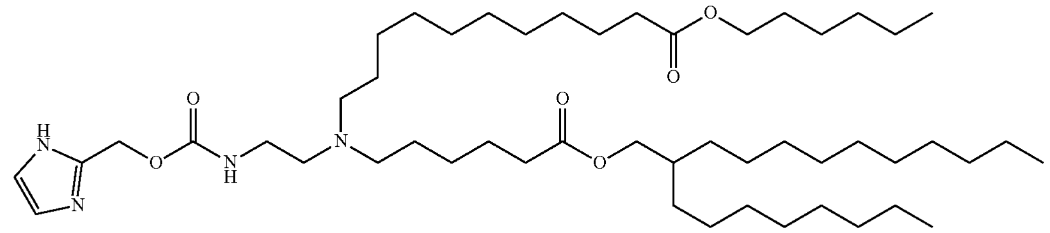 [SMILES: CCCCCCCCCCC(CCCCCCCC)COC(=O)CCCCCN(CCCCCCCCCCC(=O)OCCCCCC)CCNC(=O)OCc1ncc[nH]1] | 847.3 |
| 1079. | 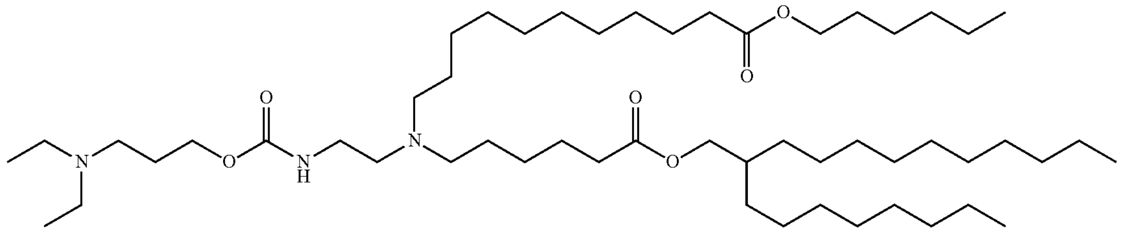 [SMILES: CCCCCCCCCCC(CCCCCCCC)COC(=O)CCCCCN(CCCCCCCCCCC(=O)OCCCCCC)CCNC(=O)OCCCN(CC)CC] | 880.4 |
| 1080. | 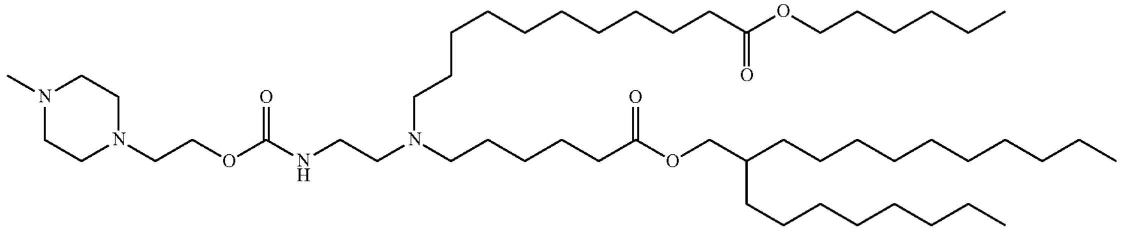 [SMILES: CCCCCCCCCCC(CCCCCCCC)COC(=O)CCCCCN(CCCCCCCCCCC(=O)OCCCCCC)CCNC(=O)OCCN1CCN(C)CC1] | 893.4 |
| 1081. | 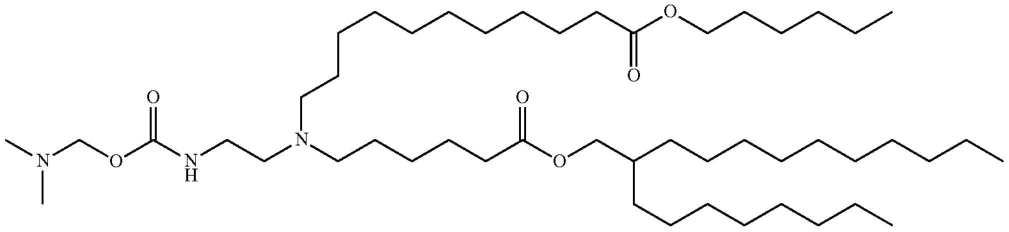 [SMILES: CCCCCCCCCCC(CCCCCCCC)COC(=O)CCCCCN(CCCCCCCCCCC(=O)OCCCCCC)CCNC(=O)OCN(C)C] | 852.4 |

TABLE 1-continued
| # | Structure | Mw |
|---|---|---|
| 1082. | 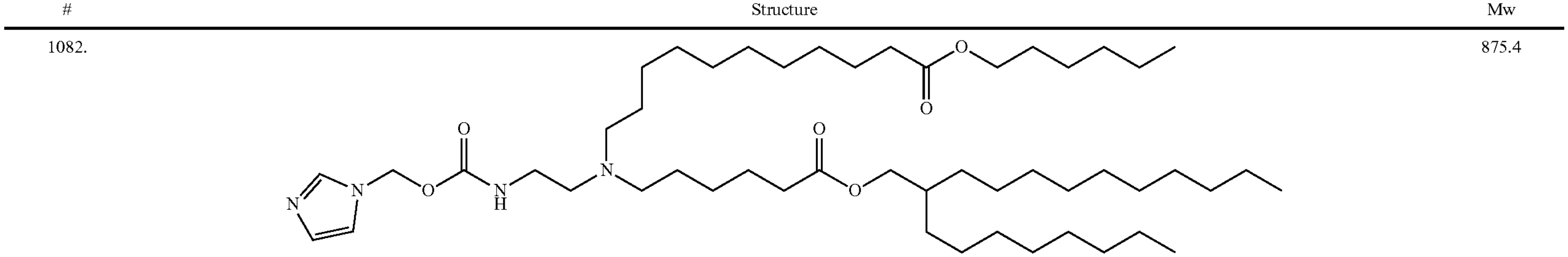 | 875.4 |
| 1083. | 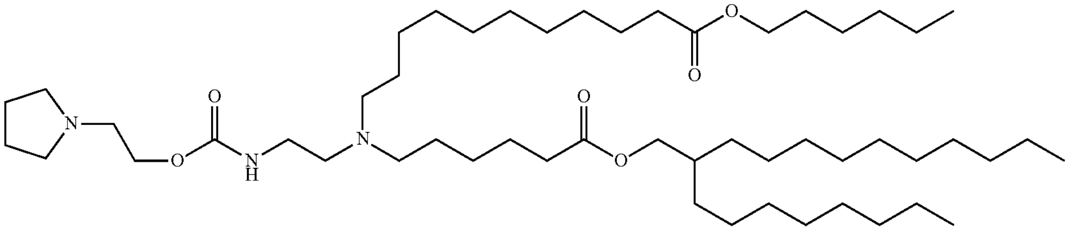 [SMILES: CCCCCCCCCCC(CCCCCCCC)COC(=O)CCCCCN(CCCCCCCCCCC(=O)OCCCCCC)CCNC(=O)OCCN1CCCC1] | 864.4 |
| 1084. | 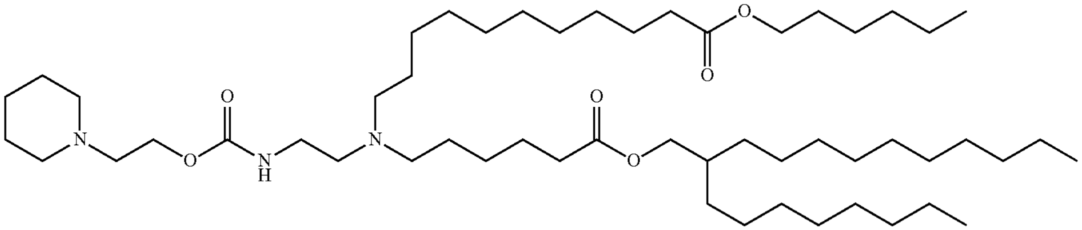 [SMILES: CCCCCCCCCCC(CCCCCCCC)COC(=O)CCCCCN(CCCCCCCCCCC(=O)OCCCCCC)CCNC(=O)OCCN1CCCCC1] | 878.4 |
| 1085. | 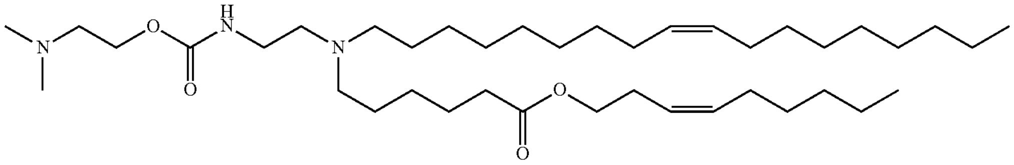 | 664.1 |

TABLE 1-continued
| # | Structure | Mw |
| --- | --- | --- |
| 1086. | 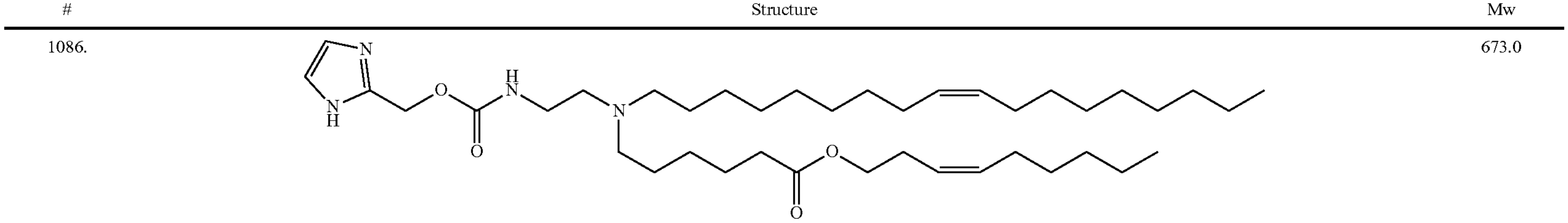 | 673.0 |
| 1087. | 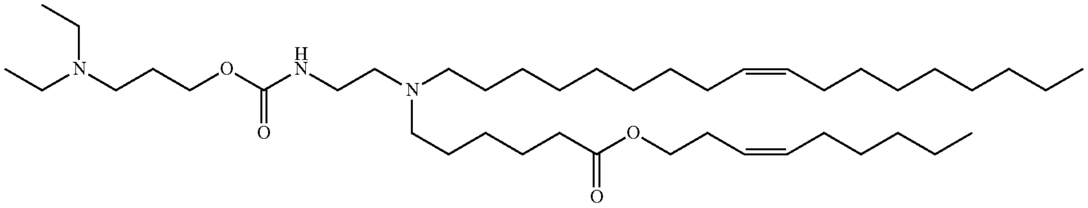 [SMILES: CCCCC/C=C\CCOC(=O)CCCCCN(CCCCCCCC/C=C\CCCCCCCC)CCNC(=O)OCCCN(CC)CC] | 706.2 |
| 1088. | 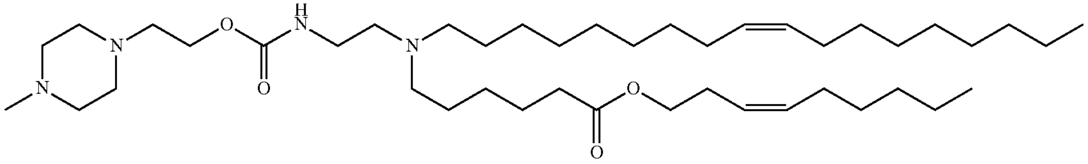 [SMILES: CCCCC/C=C\CCOC(=O)CCCCCN(CCCCCCCC/C=C\CCCCCCCC)CCNC(=O)OCCN1CCN(C)CC1] | 719.2 |
| 1089. | 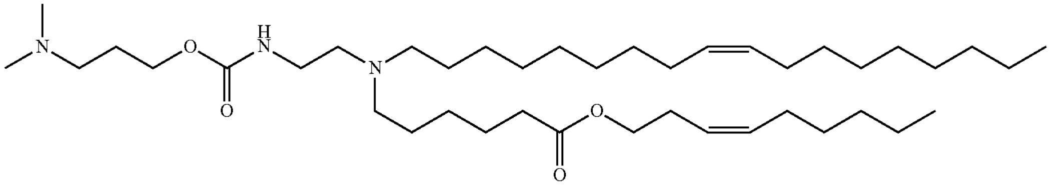 [SMILES: CCCCC/C=C\CCOC(=O)CCCCCN(CCCCCCCC/C=C\CCCCCCCC)CCNC(=O)OCCCN(C)C] | 678.1 |
| 1090. | 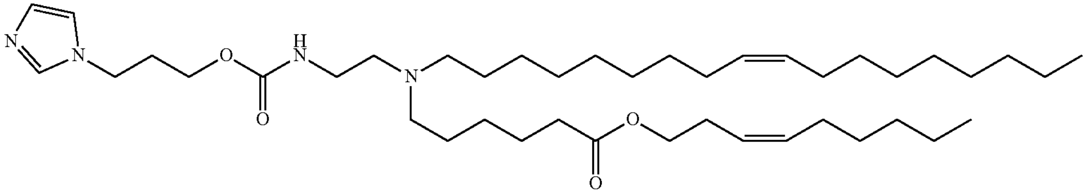 [SMILES: CCCCC/C=C\CCOC(=O)CCCCCN(CCCCCCCC/C=C\CCCCCCCC)CCNC(=O)OCCCn1ccnc1] | 701.1 |

TABLE 1-continued
| # | Structure | Mw |
| --- | --- | --- |
| 1091. | 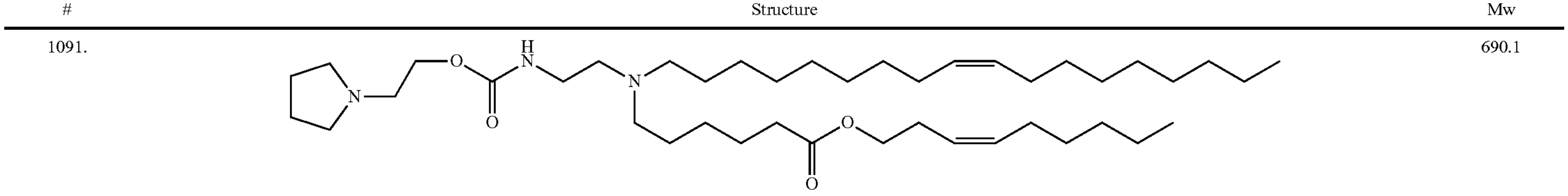 | 690.1 |
| 1092. | 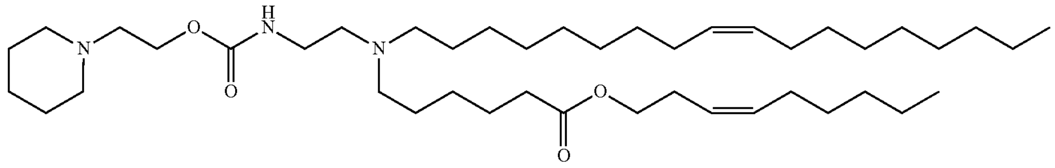 [SMILES: CCCCC/C=C\CCOC(=O)CCCCCN(CCCCCCCC/C=C\CCCCCCCC)CCNC(=O)OCCN1CCCCC1] | 704.1 |
| 1093. | 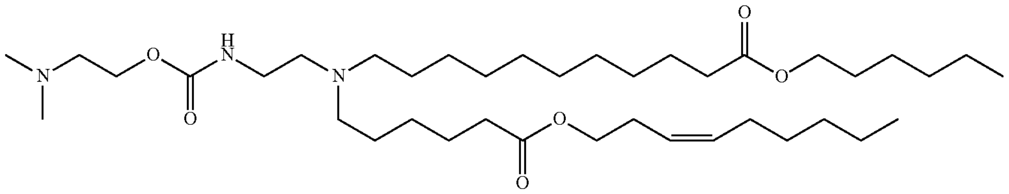 [SMILES: CCCCC/C=C\CCOC(=O)CCCCCN(CCCCCCCCCCC(=O)OCCCCCC)CCNC(=O)OCCN(C)C] | 682.0 |
| 1094. | 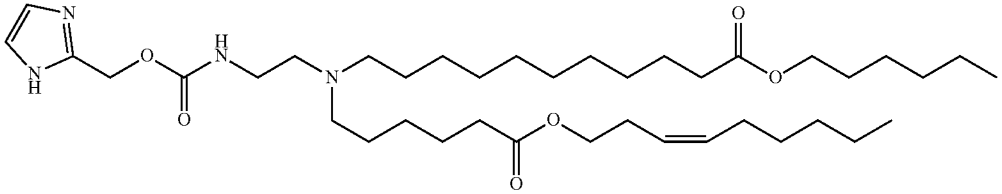 | 691.0 |
| 1095. | 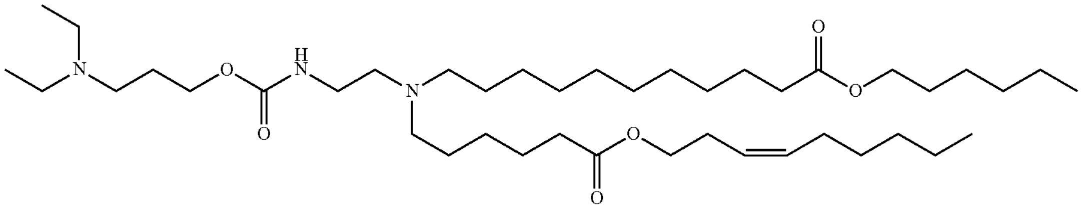 [SMILES: CCCCC/C=C\CCOC(=O)CCCCCN(CCCCCCCCCCC(=O)OCCCCCC)CCNC(=O)OCCCN(CC)CC] | 724.1 |

TABLE 1-continued
| # | Structure | Mw |
| --- | --- | --- |
| 1096. | 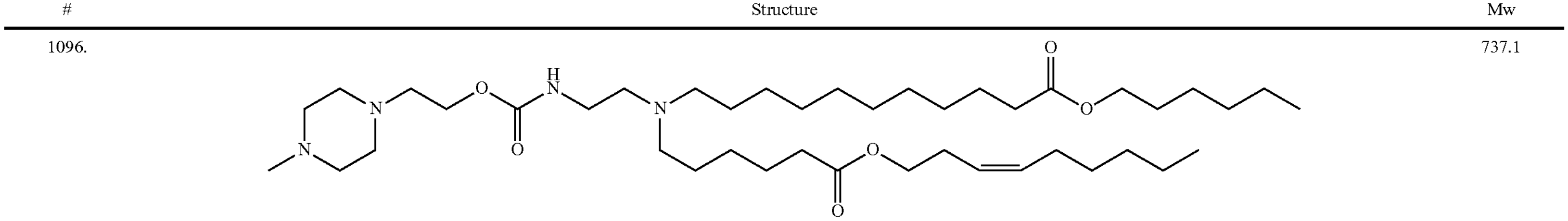 | 737.1 |
| 1097. | 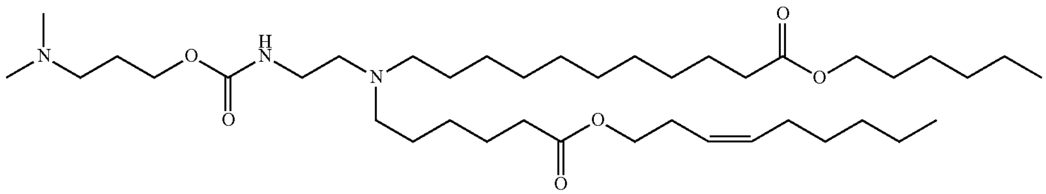 | 696.1 |
| 1098. | 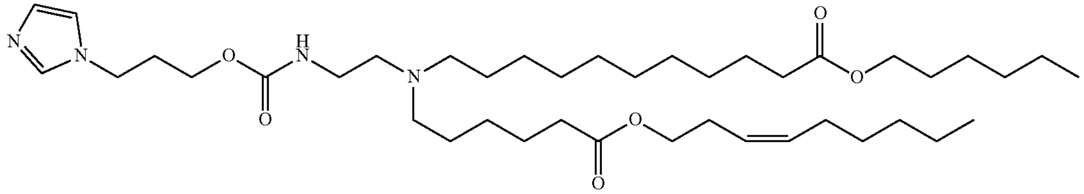 | 719.1 |
| 1099. | 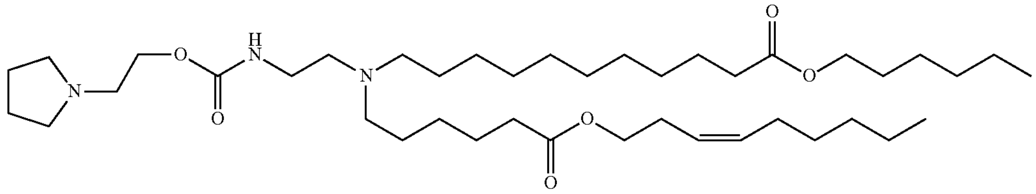 [SMILES: CCCCC/C=C\CCOC(=O)CCCCCN(CCCCCCCCCCC(=O)OCCCCCC)CCNC(=O)OCCN1CCCC1] | 708.1 |
| 1100. | 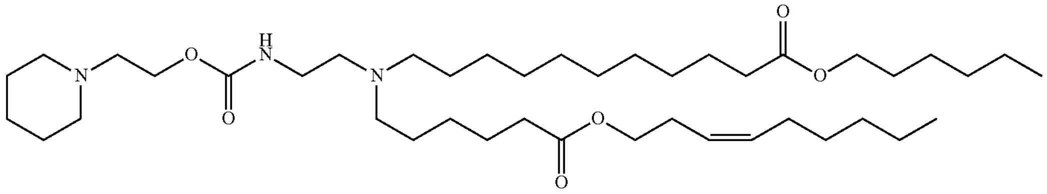 [SMILES: CCCCC/C=C\CCOC(=O)CCCCCN(CCCCCCCCCCC(=O)OCCCCCC)CCNC(=O)OCCN1CCCCC1] | 722.1 |

TABLE 1-continued
| # | Structure | Mw |
|---|---|---|
| 1101. | 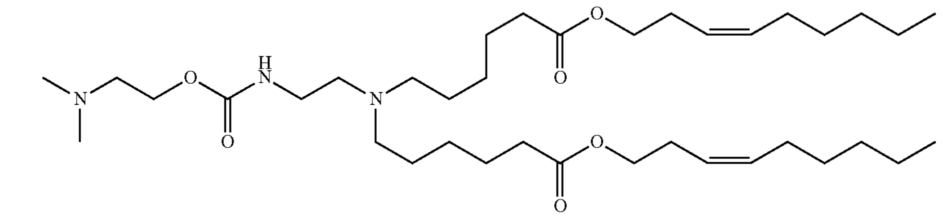 [SMILES: CCCCC/C=C\CCOC(=O)CCCCCN(CCCCCC(=O)OCC/C=C\CCCCC)CCNC(=O)OCCN(C)C] | 652.0 |
| 1102. | 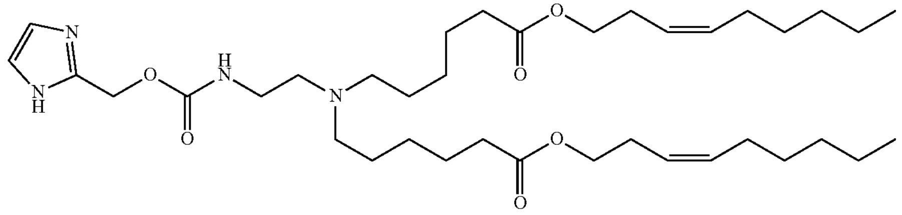 [SMILES: CCCCC/C=C\CCOC(=O)CCCCCN(CCCCCC(=O)OCC/C=C\CCCCC)CCNC(=O)OCc1ncc[nH]1] | 660.9 |
| 1103. | 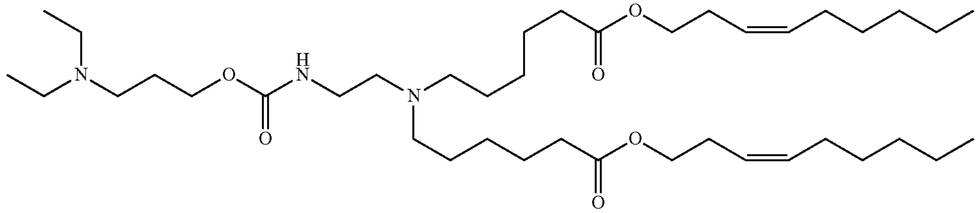 [SMILES: CCCCC/C=C\CCOC(=O)CCCCCN(CCCCCC(=O)OCC/C=C\CCCCC)CCNC(=O)OCCCN(CC)CC] | 694.1 |
| 1104. | 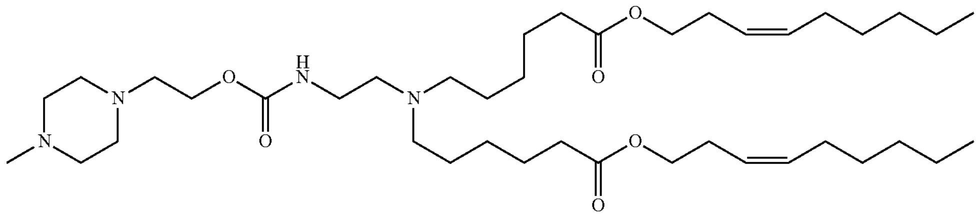 [SMILES: CCCCC/C=C\CCOC(=O)CCCCCN(CCCCCC(=O)OCC/C=C\CCCCC)CCNC(=O)OCCN1CCN(C)CC1] | 707.1 |

TABLE 1-continued
| # | Structure | Mw |
|---|---|---|
| 1105. | 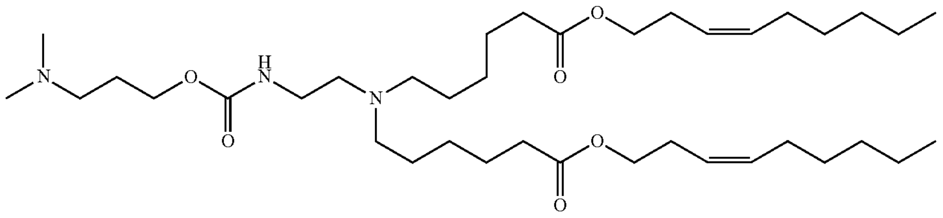 [SMILES: CCCCC/C=C\CCOC(=O)CCCCCN(CCCCCC(=O)OCC/C=C\CCCCC)CCNC(=O)OCCCN(C)C] | 666.0 |
| 1106. | 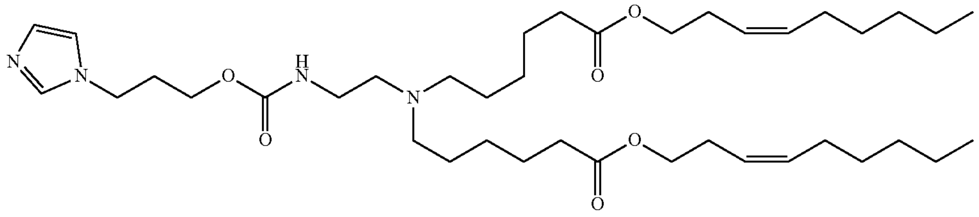 [SMILES: CCCCC/C=C\CCOC(=O)CCCCCN(CCCCCC(=O)OCC/C=C\CCCCC)CCNC(=O)OCCCn1ccnc1] | 689.0 |
| 1107. | 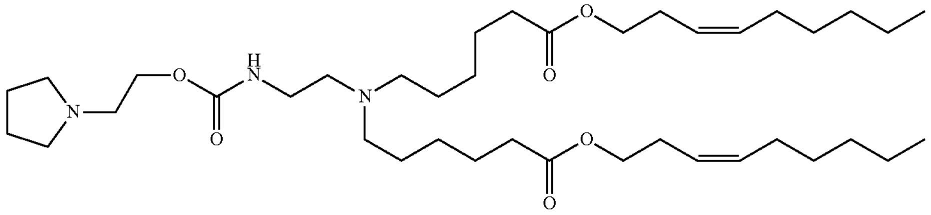 [SMILES: CCCCC/C=C\CCOC(=O)CCCCCN(CCCCCC(=O)OCC/C=C\CCCCC)CCNC(=O)OCCN1CCCC1] | 678.0 |
| 1108. | 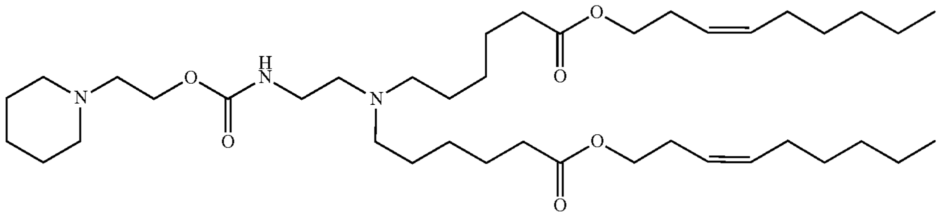 [SMILES: CCCCC/C=C\CCOC(=O)CCCCCN(CCCCCC(=O)OCC/C=C\CCCCC)CCNC(=O)OCCN1CCCCC1] | 692.0 |

TABLE 1-continued
| # | Structure | Mw |
| --- | --- | --- |
| 1109. | 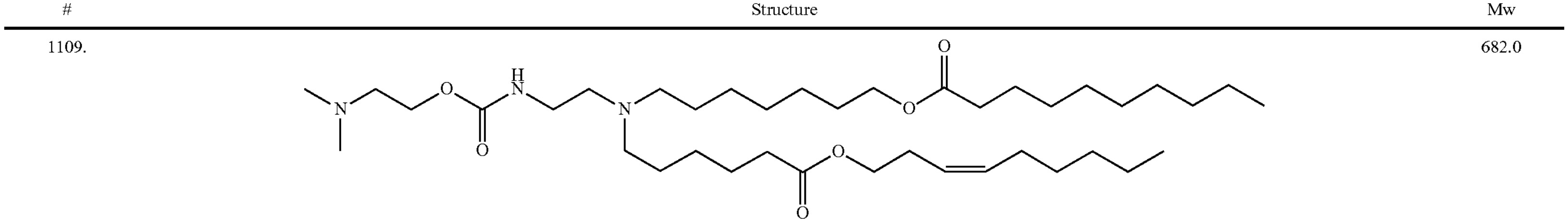 | 682.0 |
| 1110. | 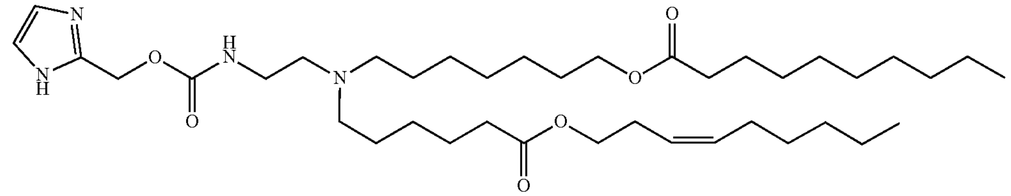 [SMILES: CCCCC/C=C\CCOC(=O)CCCCCN(CCCCCCCOC(=O)CCCCCCCCC)CCNC(=O)OCc1ncc[nH]1] | 691.0 |
| 1111. | 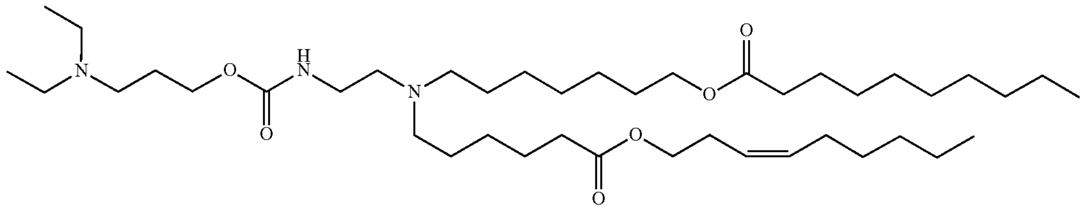 [SMILES: CCCCC/C=C\CCOC(=O)CCCCCN(CCCCCCCOC(=O)CCCCCCCCC)CCNC(=O)OCCCN(CC)CC] | 724.1 |
| 1112. | 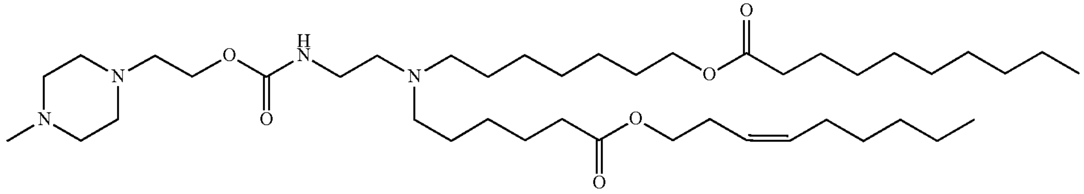 [SMILES: CCCCC/C=C\CCOC(=O)CCCCCN(CCCCCCCOC(=O)CCCCCCCCC)CCNC(=O)OCCN1CCN(C)CC1] | 737.1 |
| 1113. | 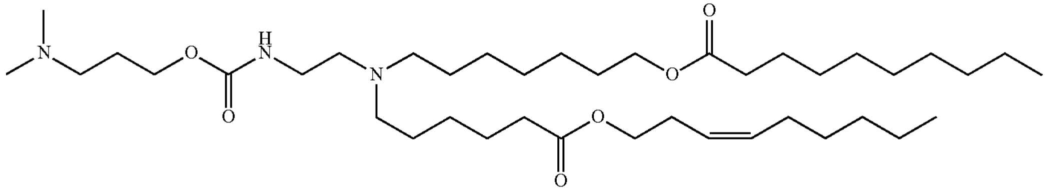 [SMILES: CCCCC/C=C\CCOC(=O)CCCCCN(CCCCCCCOC(=O)CCCCCCCCC)CCNC(=O)OCCCN(C)C] | 696.1 |

TABLE 1-continued
| # | Structure | Mw |
| --- | --- | --- |
| 1114. | 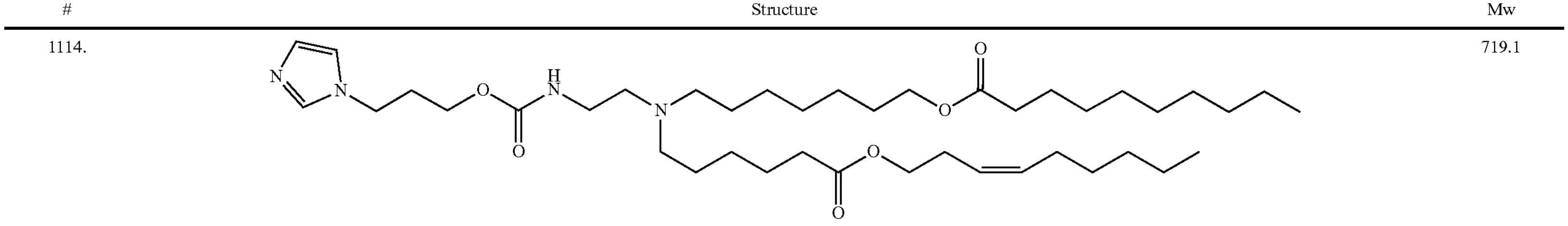 | 719.1 |
| 1115. | 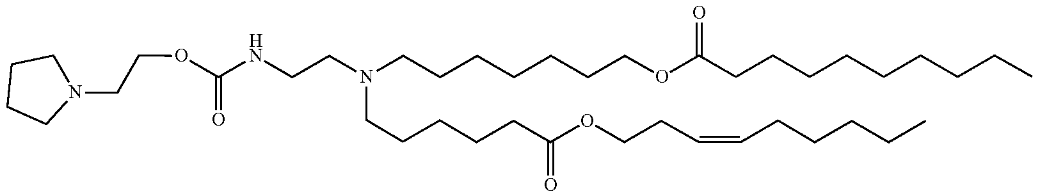 [SMILES: CCCCC/C=C\CCOC(=O)CCCCCN(CCCCCCCOC(=O)CCCCCCCCC)CCNC(=O)OCCN1CCCC1] | 708.1 |
| 1116. | 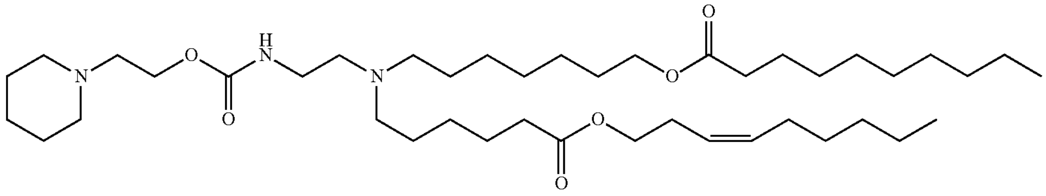 [SMILES: CCCCC/C=C\CCOC(=O)CCCCCN(CCCCCCCOC(=O)CCCCCCCCC)CCNC(=O)OCCN1CCCCC1] | 722.1 |
| 1117. | 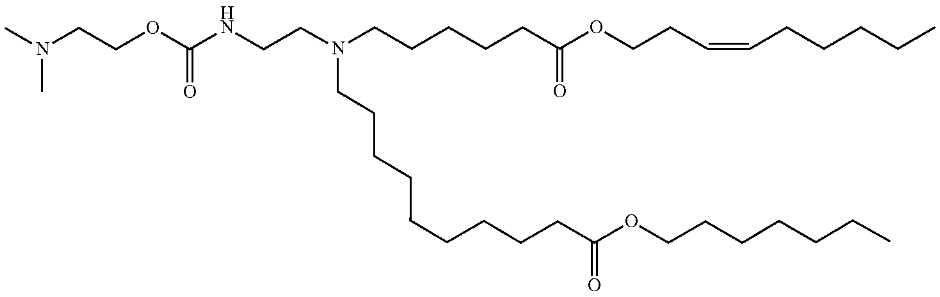 [SMILES: CCCCC/C=C\CCOC(=O)CCCCCN(CCCCCCCCCC(=O)OCCCCCCC)CCNC(=O)OCCN(C)C] | 682.0 |

TABLE 1-continued
| # | Structure | Mw |
|---|---|---|
| 1118. | 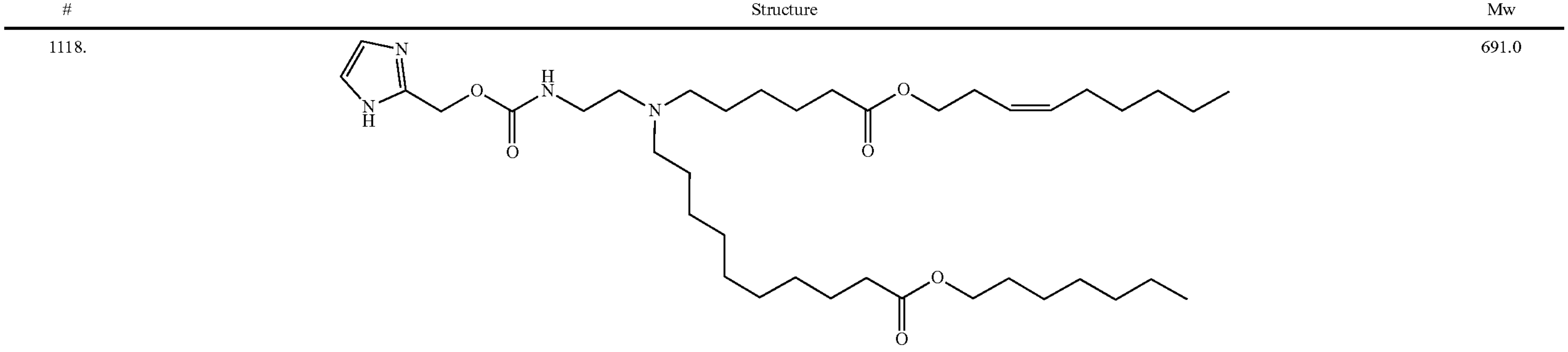 | 691.0 |
| 1119. | 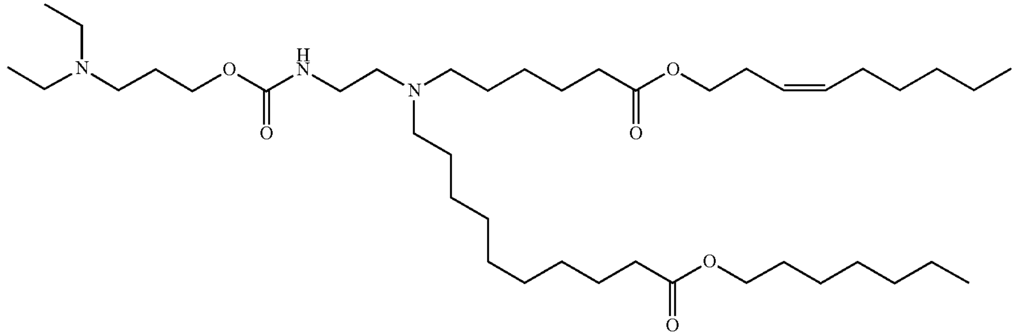 [SMILES: CCCCC/C=C\CCOC(=O)CCCCCN(CCCCCCCCCC(=O)OCCCCCCC)CCNC(=O)OCCCN(CC)CC] | 724.1 |
| 1120. | 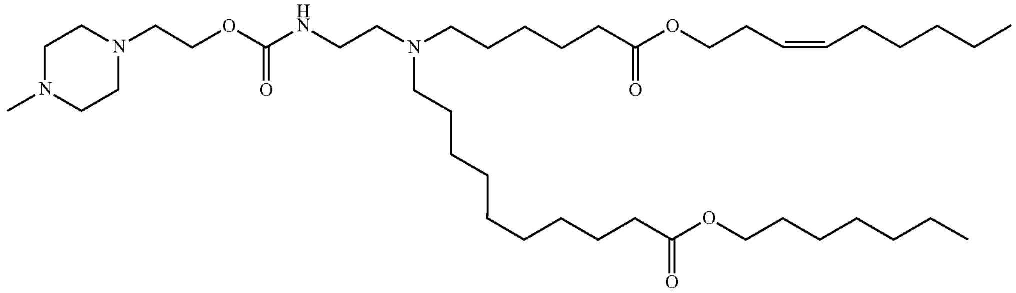 [SMILES: CCCCC/C=C\CCOC(=O)CCCCCN(CCCCCCCCCC(=O)OCCCCCCC)CCNC(=O)OCCN1CCN(C)CC1] | 737.1 |

TABLE 1-continued
| # | Structure | Mw |
| --- | --- | --- |
| 1121. | 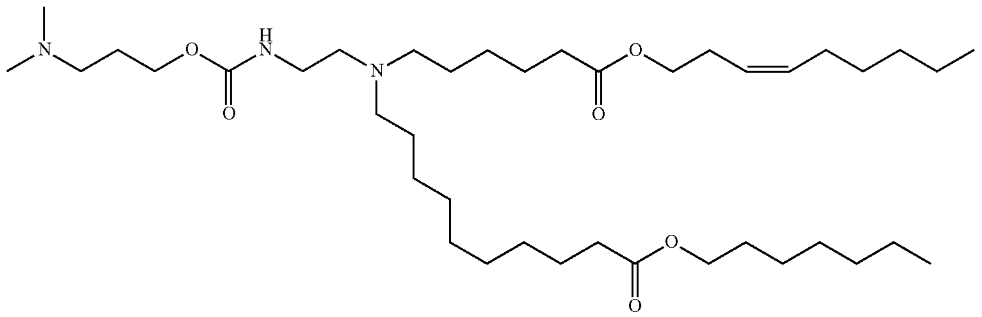 [SMILES: CCCCC/C=C\CCOC(=O)CCCCCN(CCCCCCCCCC(=O)OCCCCCCC)CCNC(=O)OCCCN(C)C] | 696.1 |
| 1122. | 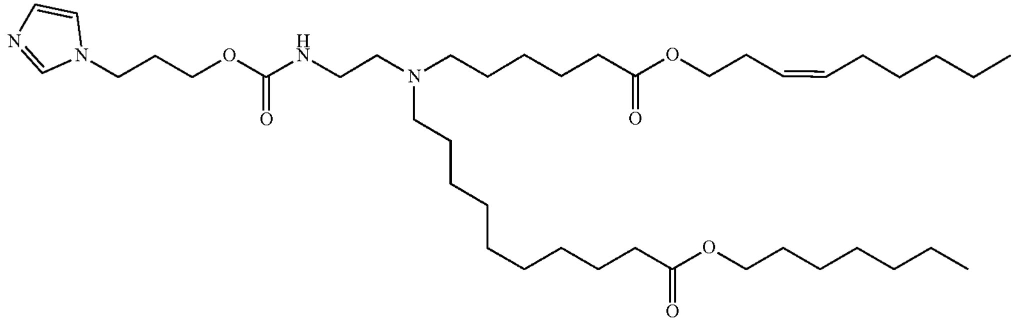 [SMILES: CCCCC/C=C\CCOC(=O)CCCCCN(CCCCCCCCCC(=O)OCCCCCCC)CCNC(=O)OCCCn1ccnc1] | 719.1 |
| 1123. | 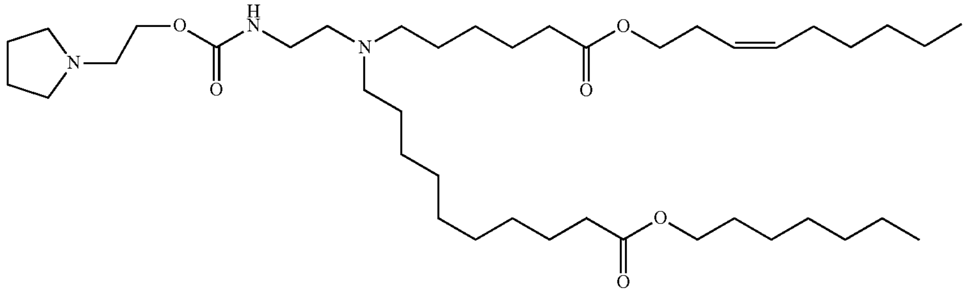 [SMILES: CCCCC/C=C\CCOC(=O)CCCCCN(CCCCCCCCCC(=O)OCCCCCCC)CCNC(=O)OCCN1CCCC1] | 708.1 |

TABLE 1-continued
| # | Structure | Mw |
| --- | --- | --- |
| 1124. | 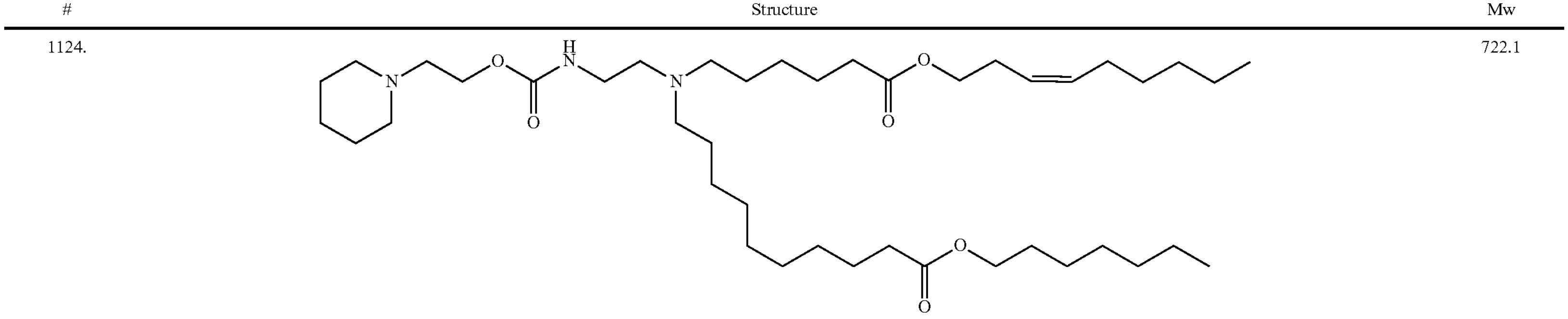 | 722.1 |
| 1125. | 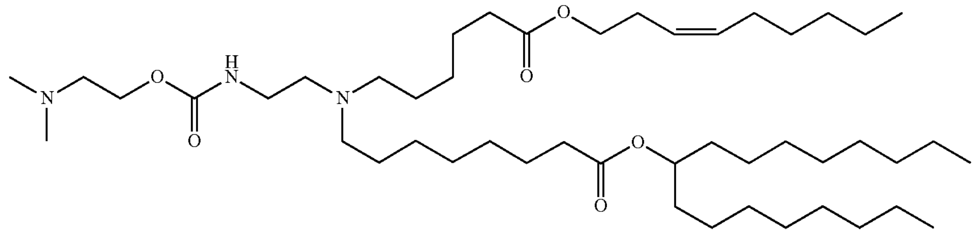 [SMILES: CCCCC/C=C\CCOC(=O)CCCCCN(CCCCCCCC(=O)OC(CCCCCCCC)CCCCCCCC)CCNC(=O)OCCN(C)C] | 794.3 |
| 1126. | 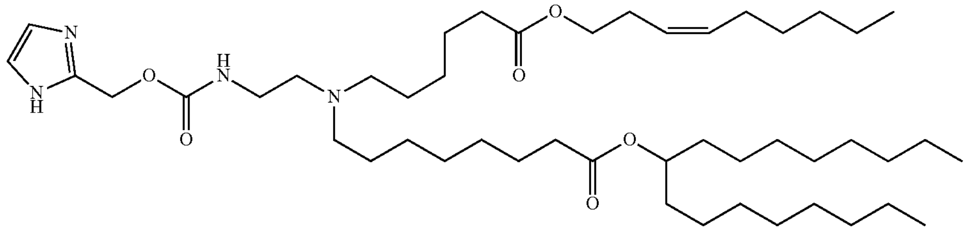 [SMILES: CCCCC/C=C\CCOC(=O)CCCCCN(CCCCCCCC(=O)OC(CCCCCCCC)CCCCCCCC)CCNC(=O)OCc1ncc[nH]1] | 803.2 |
| 1127. | 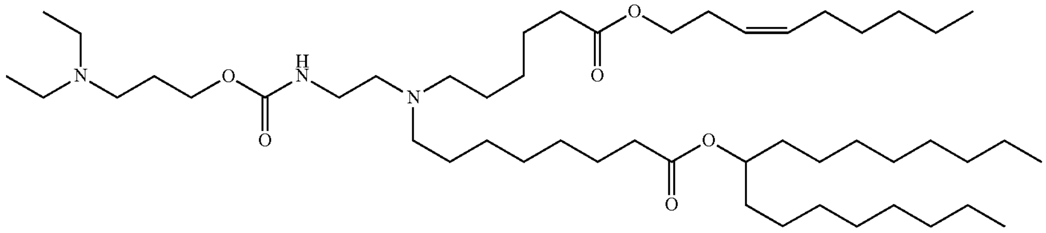 [SMILES: CCCCC/C=C\CCOC(=O)CCCCCN(CCCCCCCC(=O)OC(CCCCCCCC)CCCCCCCC)CCNC(=O)OCCCN(CC)CC] | 836.3 |

TABLE 1-continued
| # | Structure | Mw |
|---|---|---|
| 1128. | 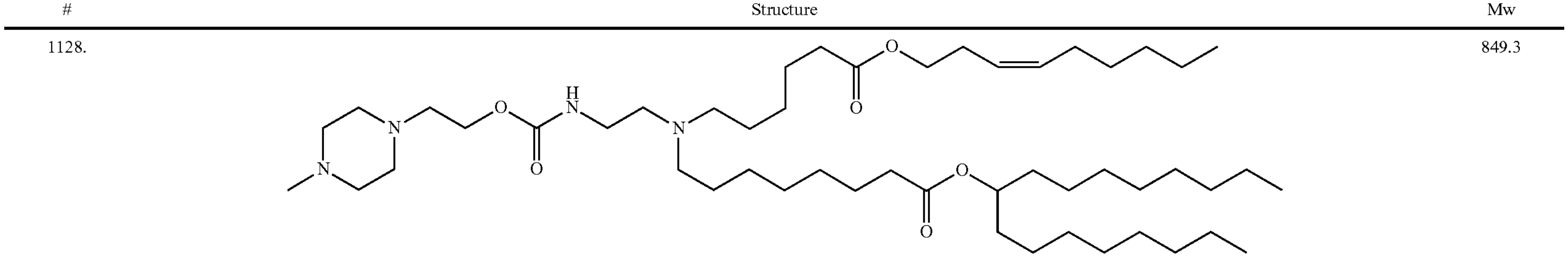 | 849.3 |
| 1129. | 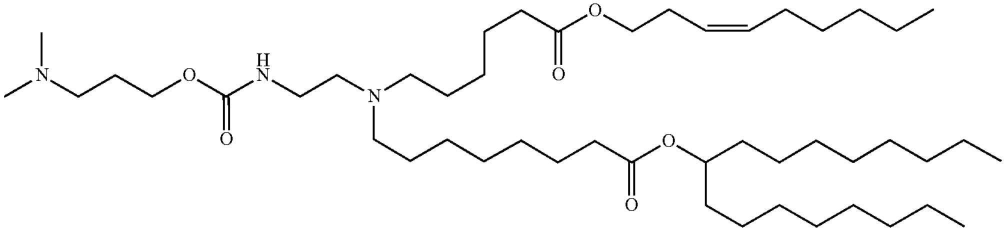 [SMILES: CCCCC/C=C\CCOC(=O)CCCCCN(CCCCCCCC(=O)OC(CCCCCCCC)CCCCCCCC)CCNC(=O)OCCCN(C)C] | 808.3 |
| 1130. | 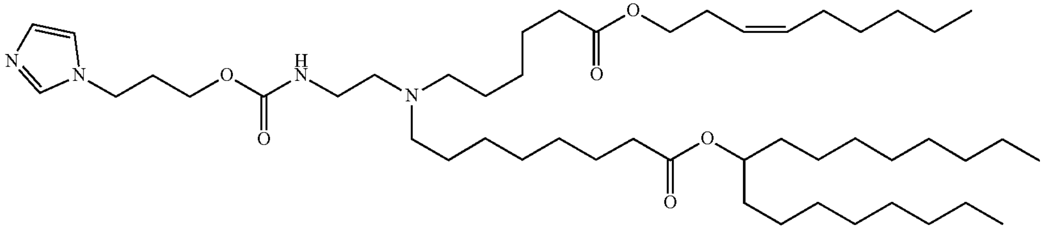 [SMILES: CCCCC/C=C\CCOC(=O)CCCCCN(CCCCCCCC(=O)OC(CCCCCCCC)CCCCCCCC)CCNC(=O)OCCCn1ccnc1] | 831.3 |
| 1131. | 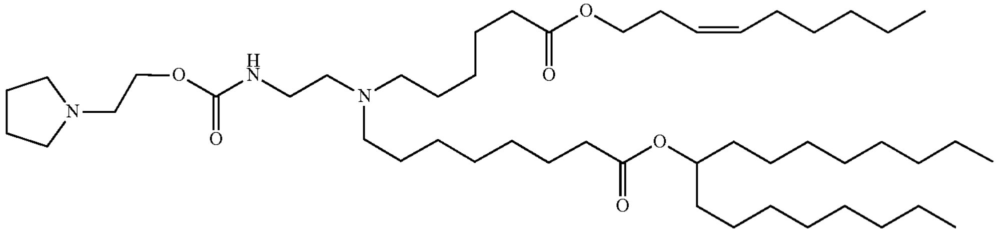 [SMILES: CCCCC/C=C\CCOC(=O)CCCCCN(CCCCCCCC(=O)OC(CCCCCCCC)CCCCCCCC)CCNC(=O)OCCN1CCCC1] | 820.3 |

TABLE 1-continued
| # | Structure | Mw |
| --- | --- | --- |
| 1132. | 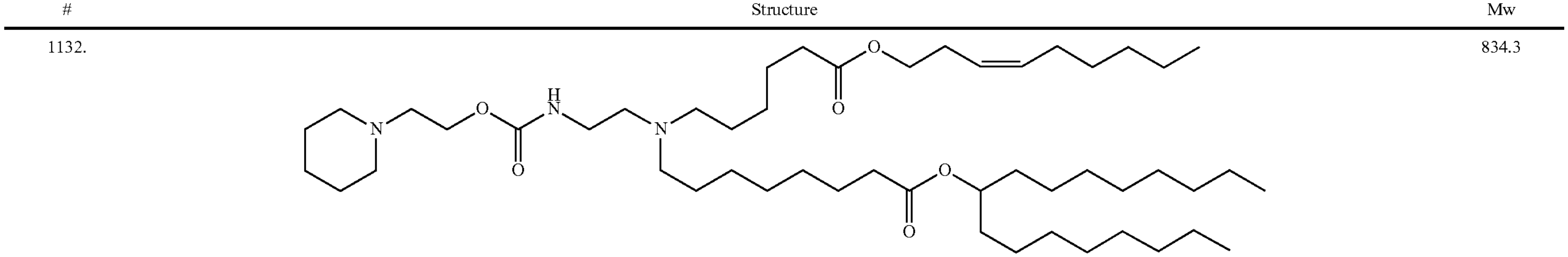 | 834.3 |
| 1133. | 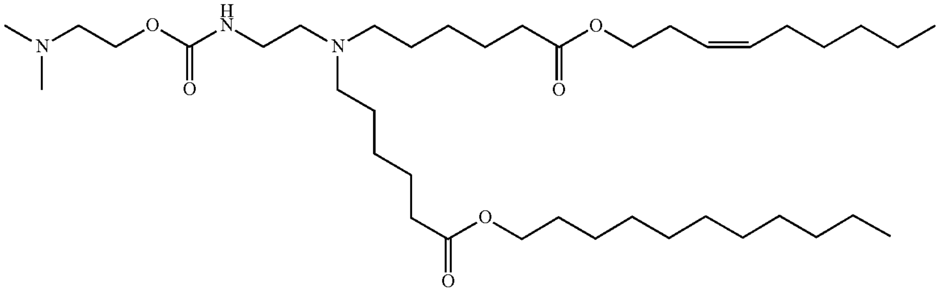 [SMILES: CCCCC/C=C\CCOC(=O)CCCCCN(CCCCCC(=O)OCCCCCCCCCCC)CCNC(=O)OCCN(C)C] | 682.0 |
| 1134. | 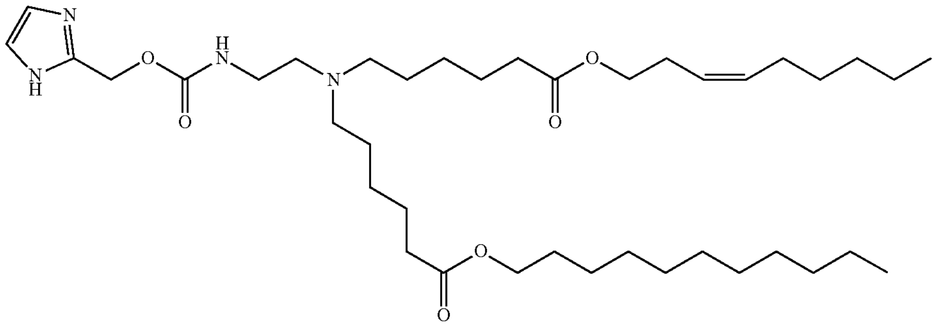 [SMILES: CCCCC/C=C\CCOC(=O)CCCCCN(CCCCCC(=O)OCCCCCCCCCCC)CCNC(=O)OCc1ncc[nH]1] | 691.0 |

TABLE 1-continued
| # | Structure | Mw |
|---|---|---|
| 1135. | 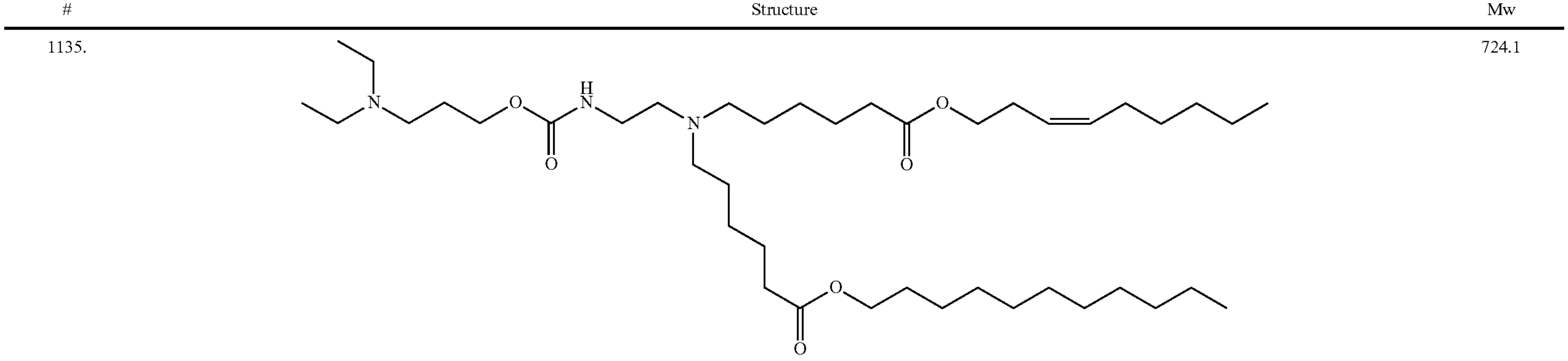 | 724.1 |
| 1136. | 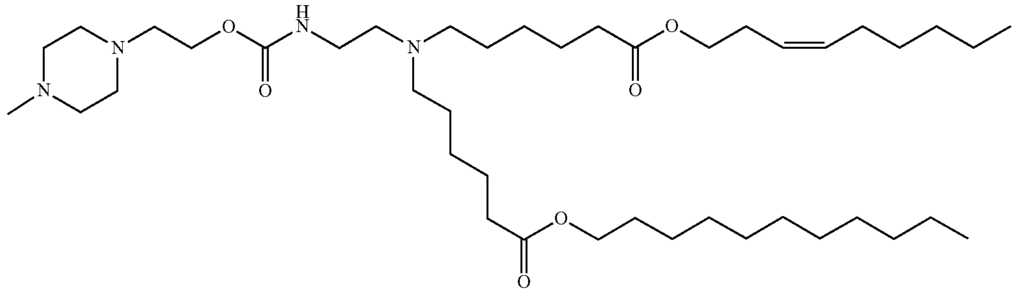 [SMILES: CCCCC/C=C\CCOC(=O)CCCCCN(CCCCCC(=O)OCCCCCCCCCCC)CCNC(=O)OCCN1CCN(C)CC1] | 737.1 |
| 1137. | 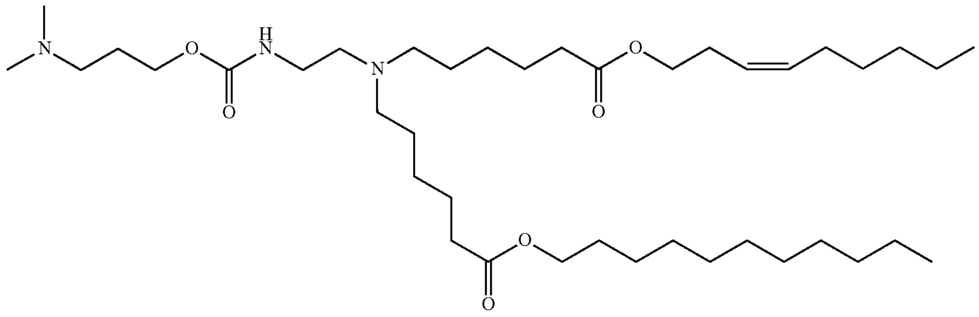 [SMILES: CCCCC/C=C\CCOC(=O)CCCCCN(CCCCCC(=O)OCCCCCCCCCCC)CCNC(=O)OCCCN(C)C] | 696.1 |

TABLE 1-continued
| # | Structure | Mw |
| --- | --- | --- |
| 1138. | 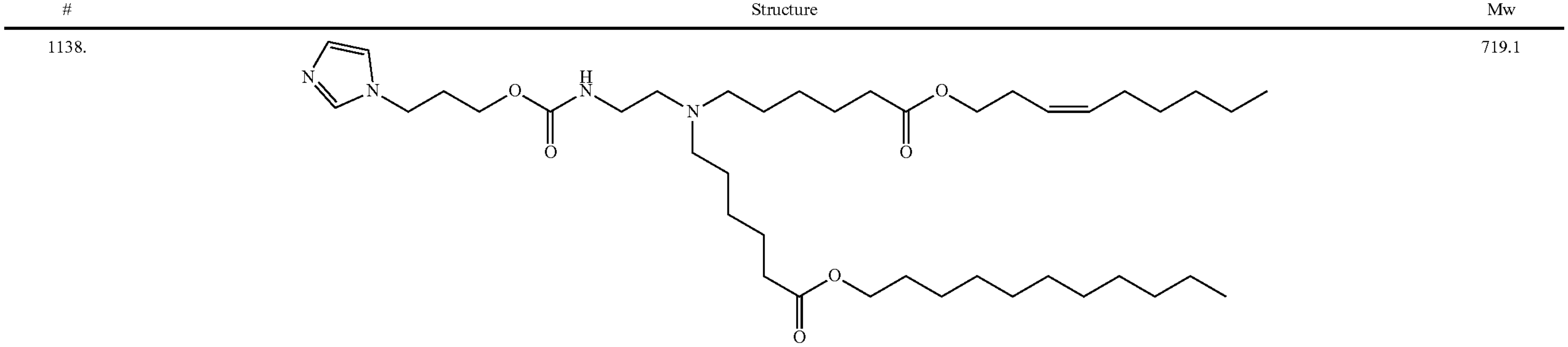 | 719.1 |
| 1139. | 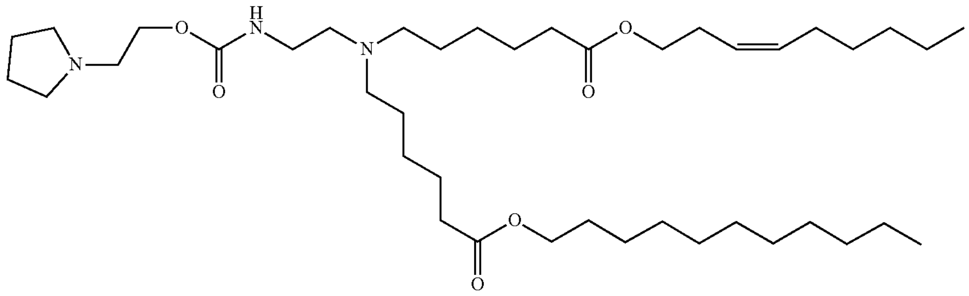 [SMILES: CCCCC/C=C\CCOC(=O)CCCCCN(CCCCCC(=O)OCCCCCCCCCCC)CCNC(=O)OCCN1CCCC1] | 708.1 |
| 1140. | 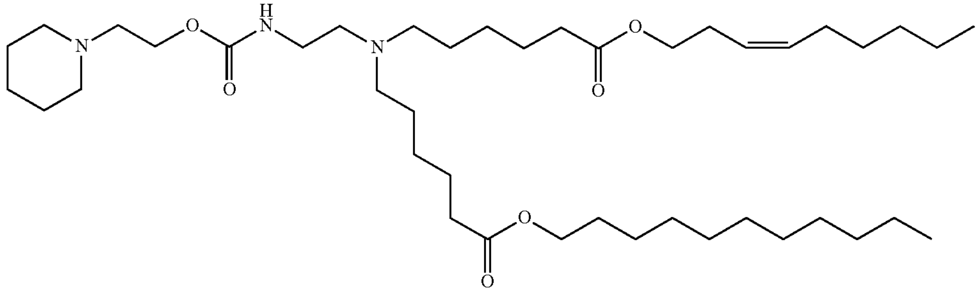 [SMILES: CCCCC/C=C\CCOC(=O)CCCCCN(CCCCCC(=O)OCCCCCCCCCCC)CCNC(=O)OCCN1CCCCC1] | 722.1 |

TABLE 1-continued
| # | Structure | Mw |
|---|---|---|
| 1141. | 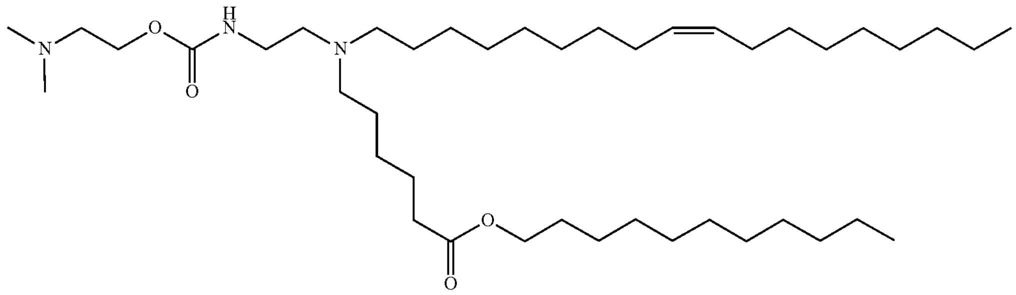 [SMILES: CCCCCCCC/C=C\CCCCCCCCN(CCCCCC(=O)OCCCCCCCCCCC)CCNC(=O)OCCN(C)C] | 694.1 |
| 1142. | 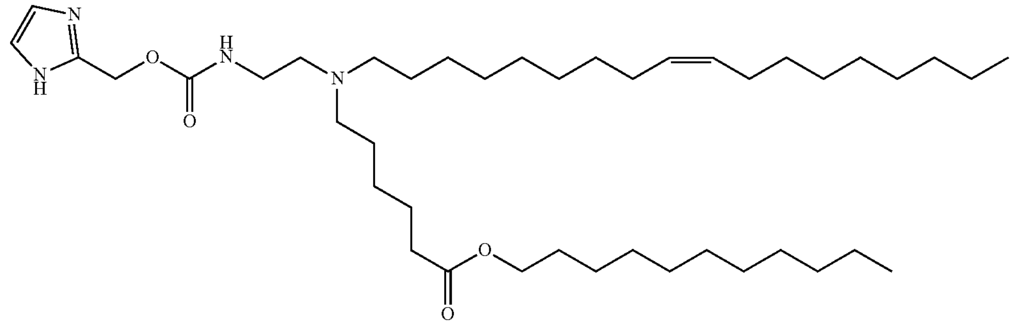 [SMILES: CCCCCCCC/C=C\CCCCCCCCN(CCCCCC(=O)OCCCCCCCCCCC)CCNC(=O)OCc1ncc[nH]1] | 703.1 |
| 1143. | 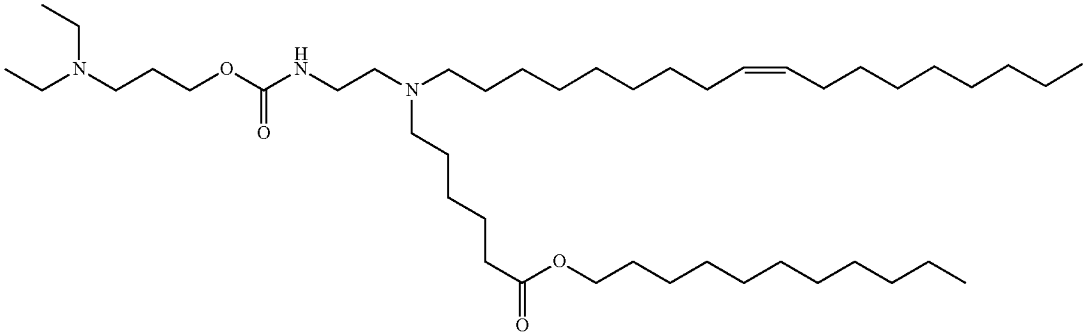 [SMILES: CCCCCCCC/C=C\CCCCCCCCN(CCCCCC(=O)OCCCCCCCCCCC)CCNC(=O)OCCCN(CC)CC] | 736.2 |

TABLE 1-continued
| # | Structure | Mw |
|---|---|---|
| 1144. | 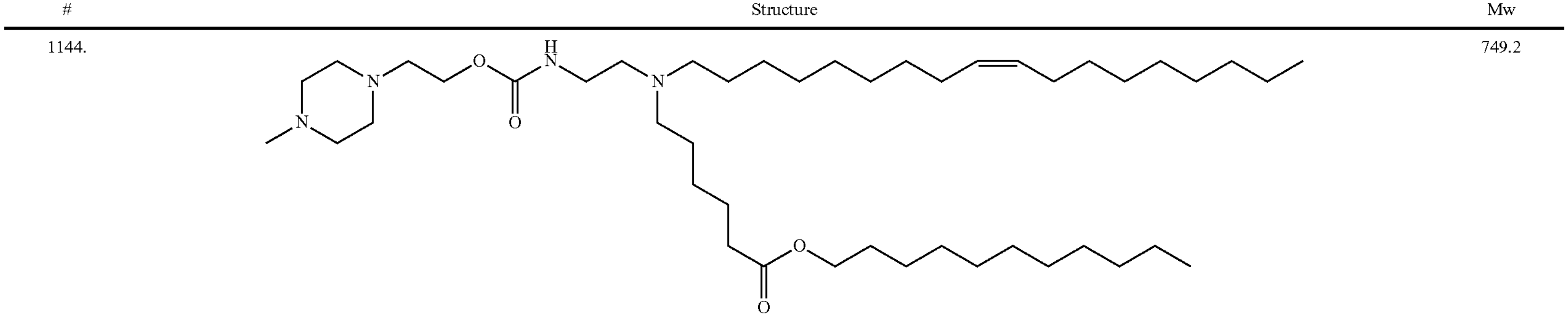 | 749.2 |
| 1145. | 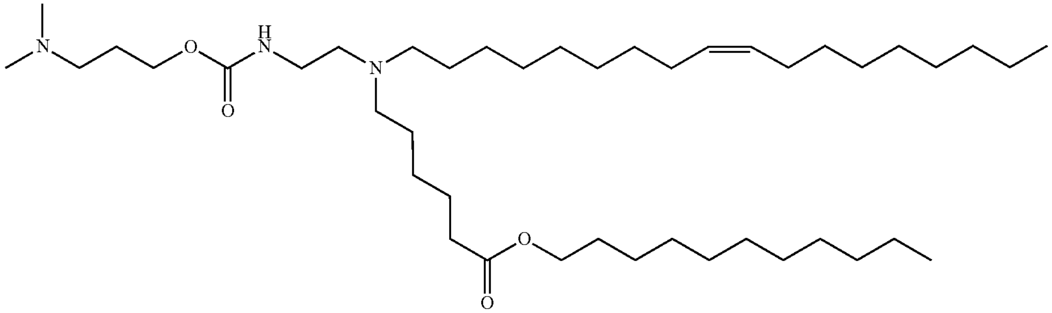 [SMILES: CCCCCCCC/C=C\CCCCCCCCN(CCCCCC(=O)OCCCCCCCCCCC)CCNC(=O)OCCCN(C)C] | 708.2 |
| 1146. | 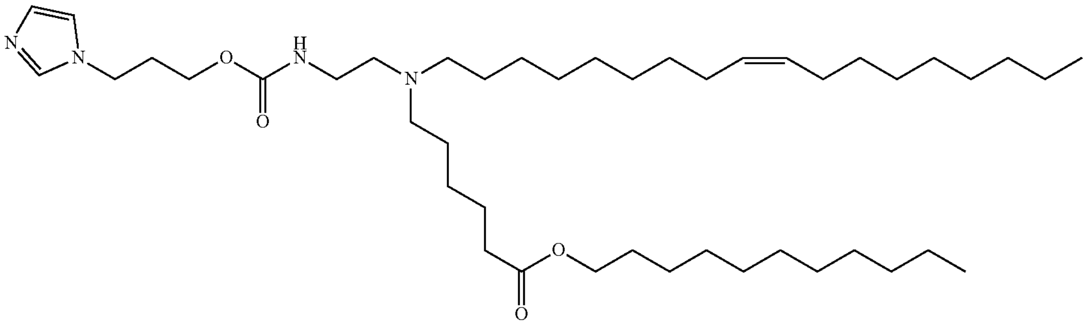 [SMILES: CCCCCCCC/C=C\CCCCCCCCN(CCCCCC(=O)OCCCCCCCCCCC)CCNC(=O)OCCCn1ccnc1] | 731.2 |

TABLE 1-continued
| # | Structure | Mw |
| --- | --- | --- |
| 1147. | 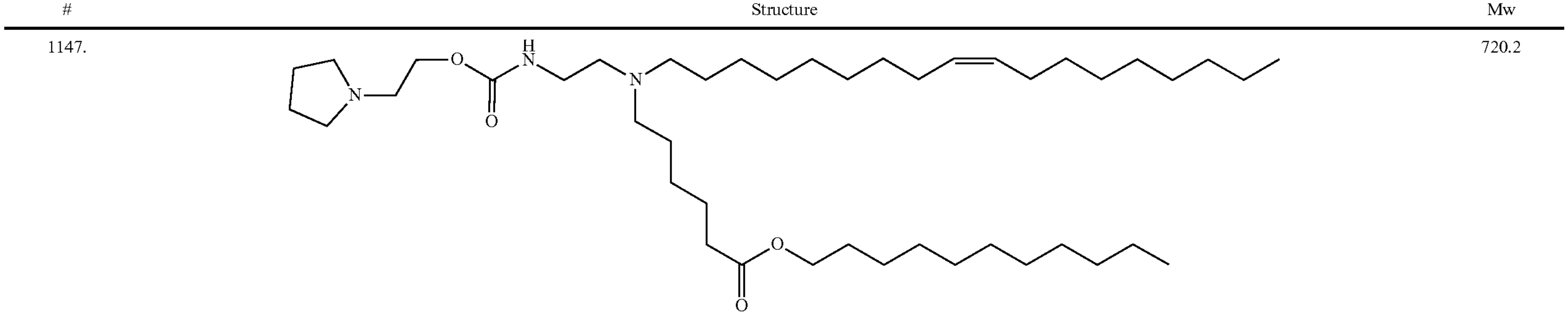 | 720.2 |
| 1148. | 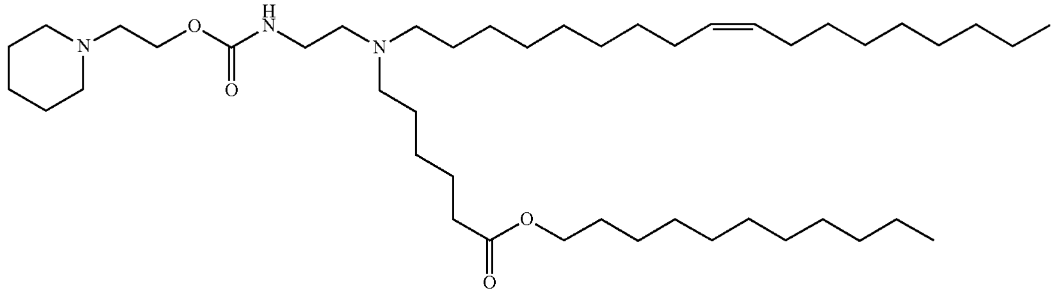 [SMILES: CCCCCCCC/C=C\CCCCCCCCN(CCCCCC(=O)OCCCCCCCCCCC)CCNC(=O)OCCN1CCCCC1] | 734.2 |
| 1149. | 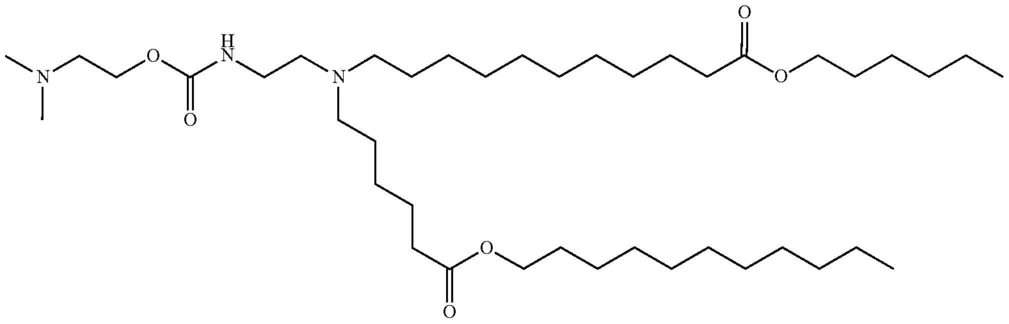 [SMILES: CCCCCCCCCCCOC(=O)CCCCCN(CCCCCCCCCCC(=O)OCCCCCC)CCNC(=O)OCCN(C)C] | 712.1 |

TABLE 1-continued
| # | Structure | Mw |
|---|---|---|
| 1150. | 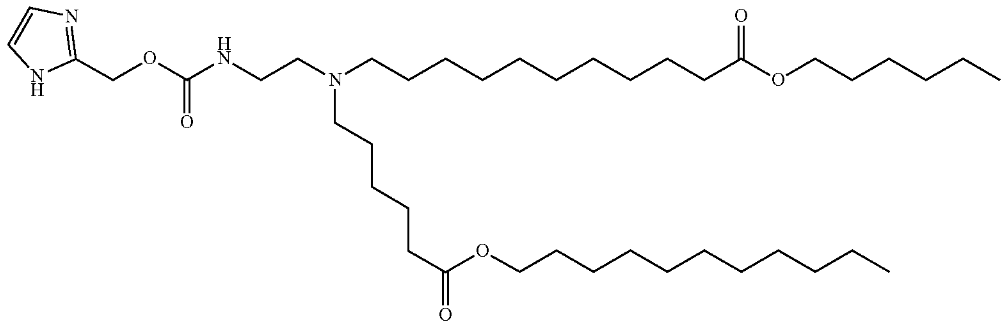 [SMILES: CCCCCCCCCCCOC(=O)CCCCCN(CCCCCCCCCCC(=O)OCCCCCC)CCNC(=O)OCc1ncc[nH]1] | 721.1 |
| 1151. | 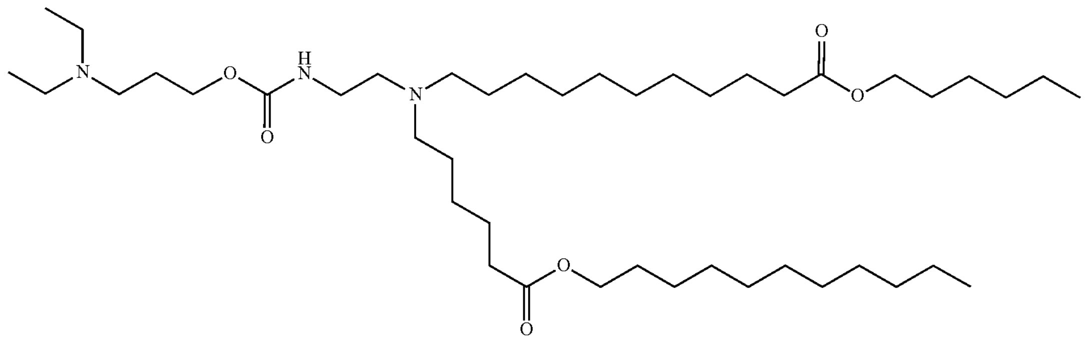 [SMILES: CCCCCCCCCCCOC(=O)CCCCCN(CCCCCCCCCCC(=O)OCCCCCC)CCNC(=O)OCCCN(CC)CC] | 754.2 |
| 1152. | 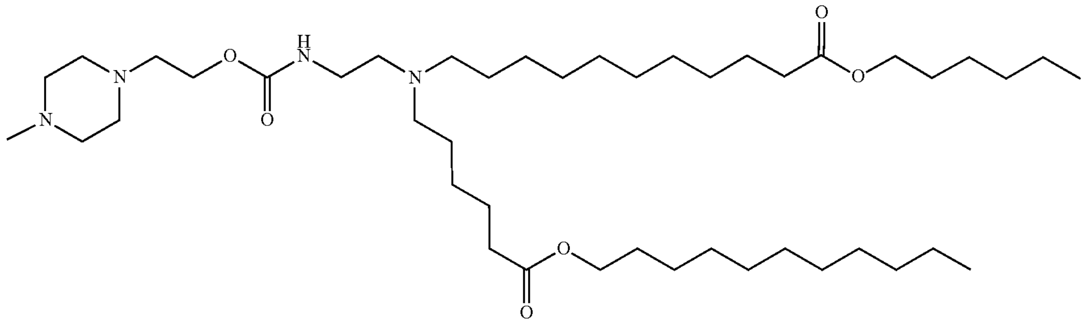 [SMILES: CCCCCCCCCCCOC(=O)CCCCCN(CCCCCCCCCCC(=O)OCCCCCC)CCNC(=O)OCCN1CCN(C)CC1] | 767.2 |

TABLE 1-continued
| # | Structure | Mw |
| --- | --- | --- |
| 1153. | 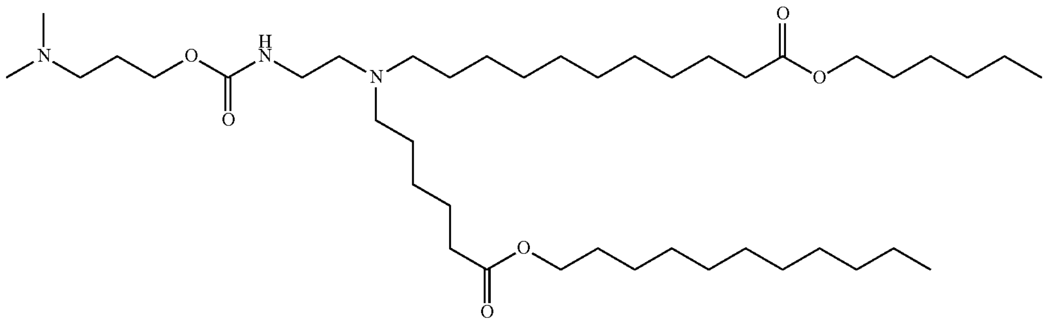 [SMILES: CCCCCCCCCCCOC(=O)CCCCCN(CCCCCCCCCCC(=O)OCCCCCC)CCNC(=O)OCCCN(C)C] | 726.1 |
| 1154. | 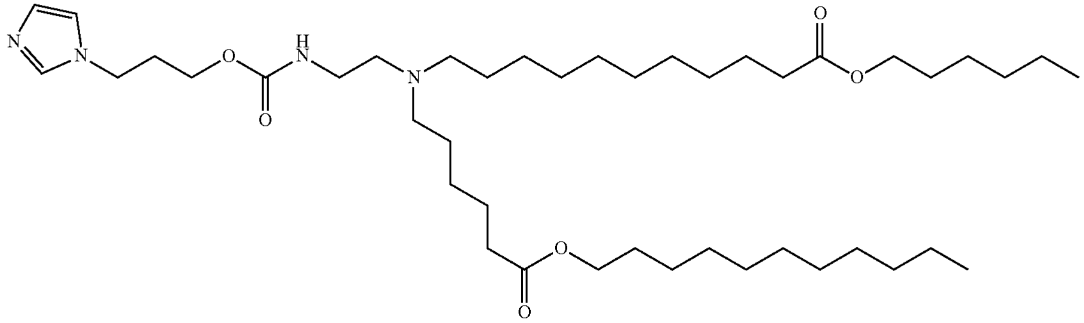 [SMILES: CCCCCCCCCCCOC(=O)CCCCCN(CCCCCCCCCCC(=O)OCCCCCC)CCNC(=O)OCCCn1ccnc1] | 749.1 |
| 1155. | 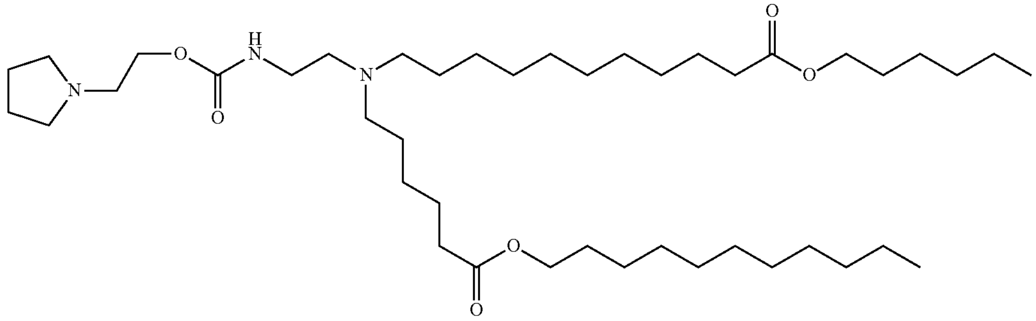 [SMILES: CCCCCCCCCCCOC(=O)CCCCCN(CCCCCCCCCCC(=O)OCCCCCC)CCNC(=O)OCCN1CCCC1] | 738.2 |

TABLE 1-continued
| # | Structure | Mw |
|---|---|---|
| 1156. | 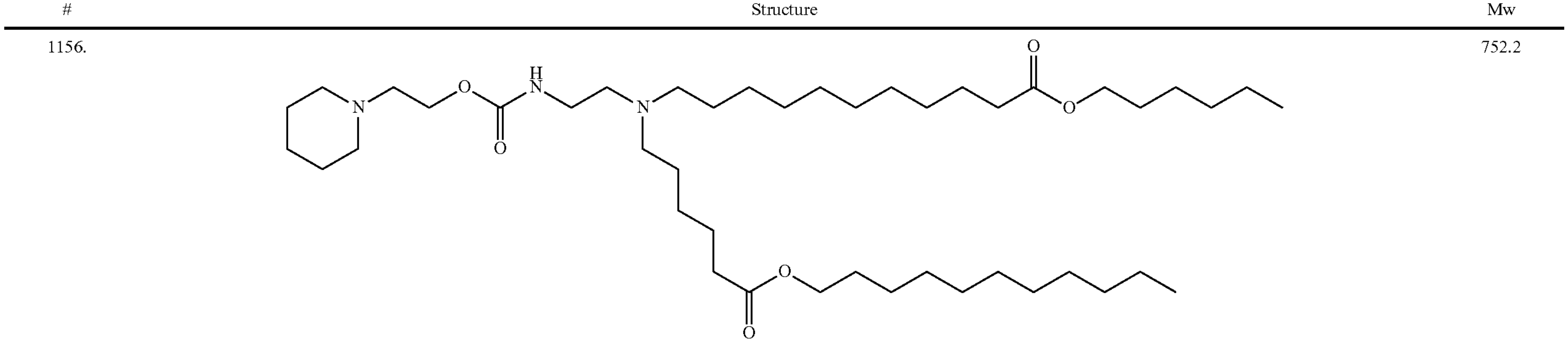 | 752.2 |
| 1157. | 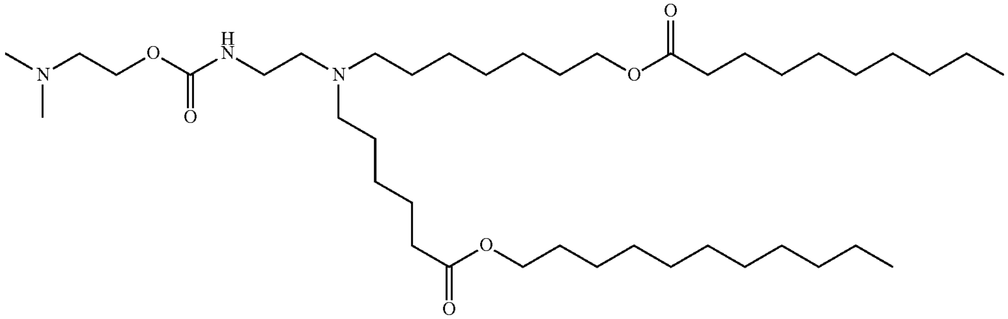 [SMILES: CCCCCCCCCCCOC(=O)CCCCCN(CCCCCCCOC(=O)CCCCCCCCC)CCNC(=O)OCCN(C)C] | 712.1 |
| 1158. | 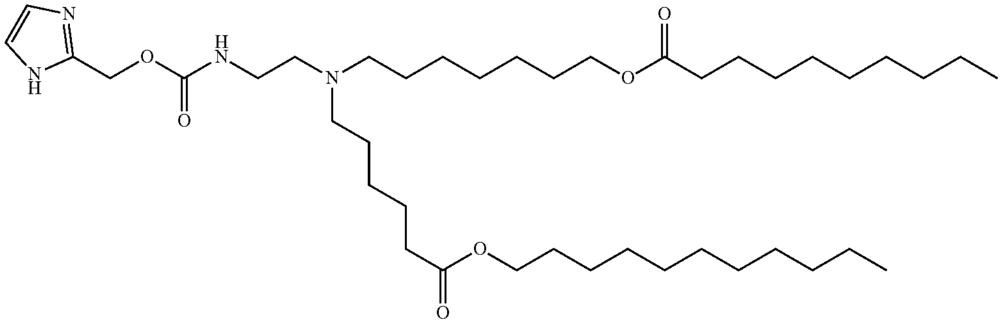 [SMILES: CCCCCCCCCCCOC(=O)CCCCCN(CCCCCCCOC(=O)CCCCCCCCC)CCNC(=O)OCc1ncc[nH]1] | 721.1 |

TABLE 1-continued
| # | Structure | Mw |
| --- | --- | --- |
| 1159. | 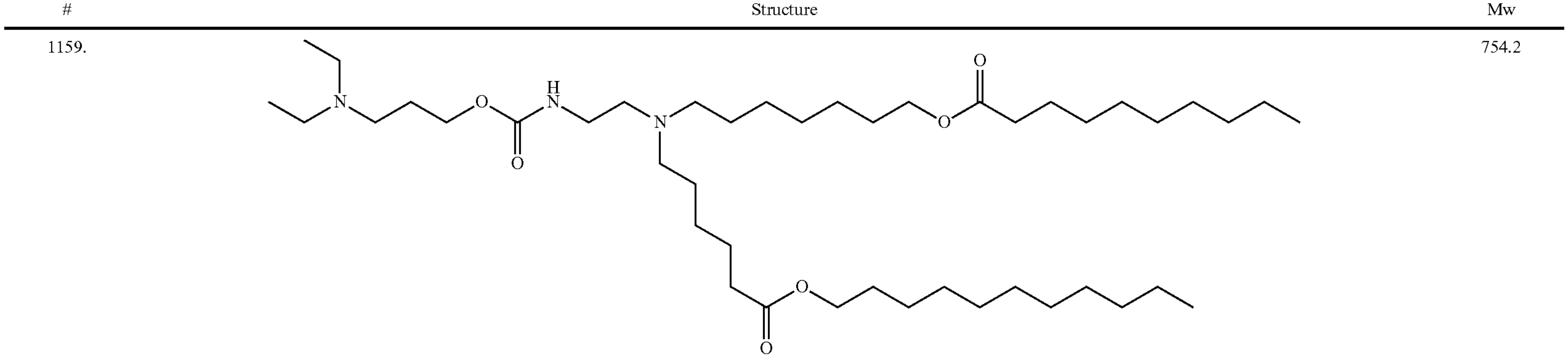 | 754.2 |
| 1160. | 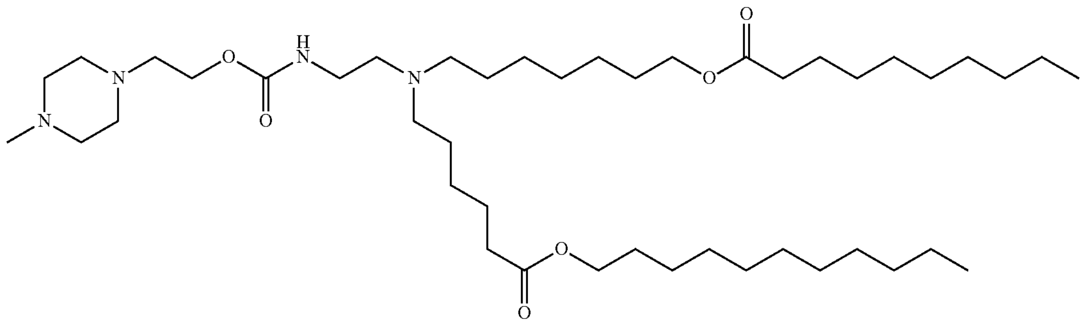 [SMILES: CCCCCCCCCCCOC(=O)CCCCCN(CCCCCCCOC(=O)CCCCCCCCC)CCNC(=O)OCCN1CCN(C)CC1] | 767.2 |
| 1161. | 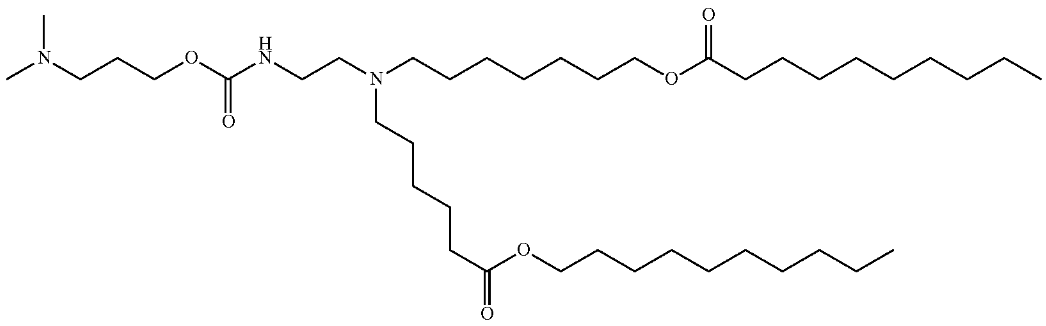 [SMILES: CCCCCCCCCCOC(=O)CCCCCN(CCCCCCCOC(=O)CCCCCCCCC)CCNC(=O)OCCCN(C)C] | 712.1 |

TABLE 1-continued
| # | Structure | Mw |
| --- | --- | --- |
| 1162. | 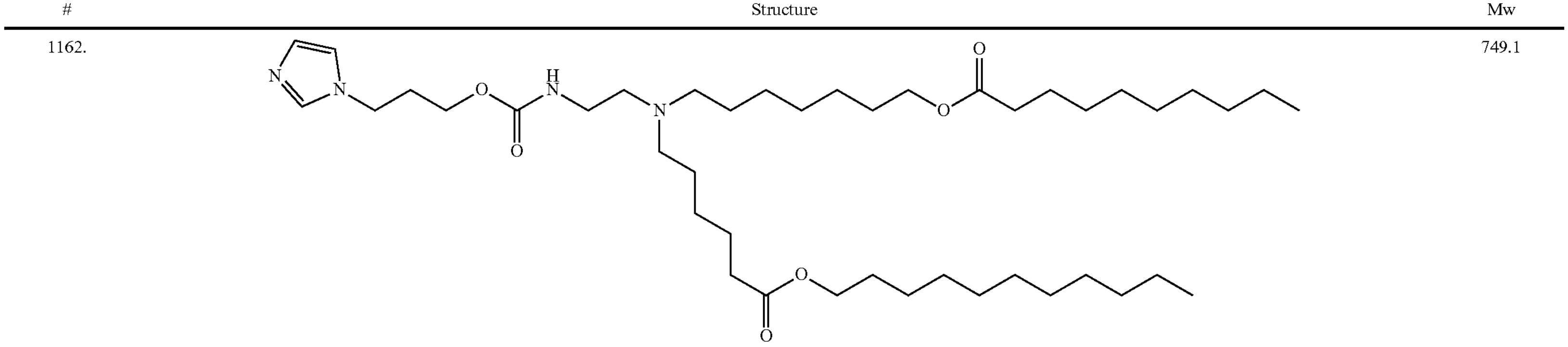 | 749.1 |
| 1163. | 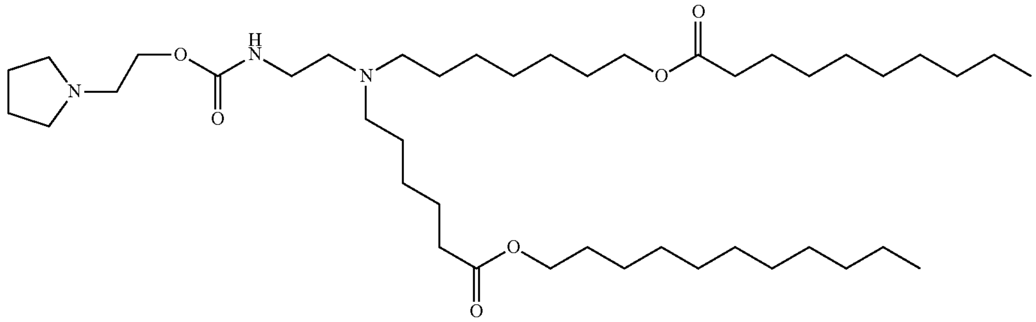 [SMILES: CCCCCCCCCCCOC(=O)CCCCCN(CCCCCCCOC(=O)CCCCCCCCC)CCNC(=O)OCCN1CCCC1] | 738.2 |
| 1164. | 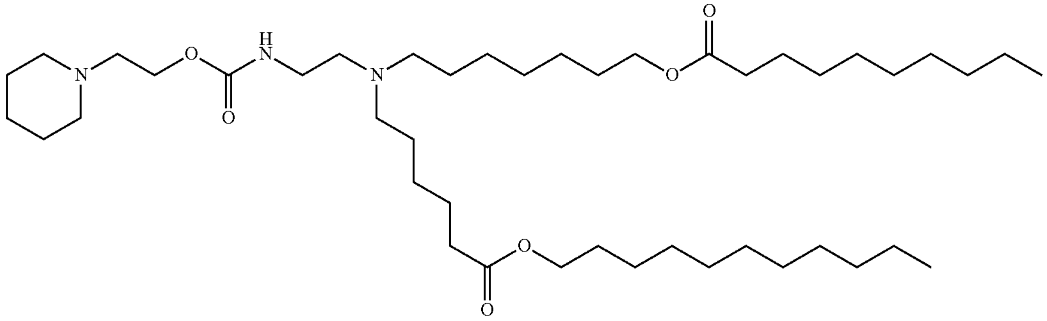 [SMILES: CCCCCCCCCCCOC(=O)CCCCCN(CCCCCCCOC(=O)CCCCCCCCC)CCNC(=O)OCCN1CCCCC1] | 752.2 |

TABLE 1-continued
| # | Structure | Mw |
| --- | --- | --- |
| 1165. | 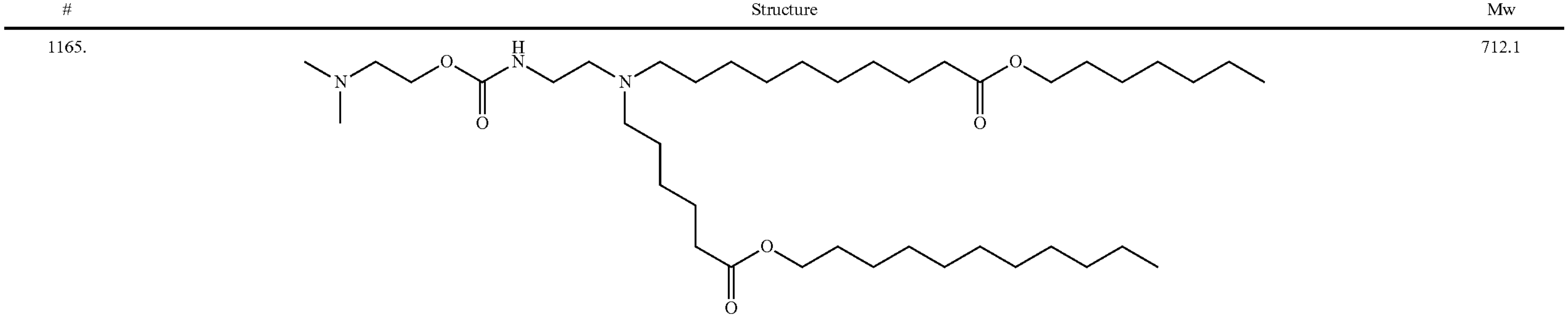 | 712.1 |
| 1166. | 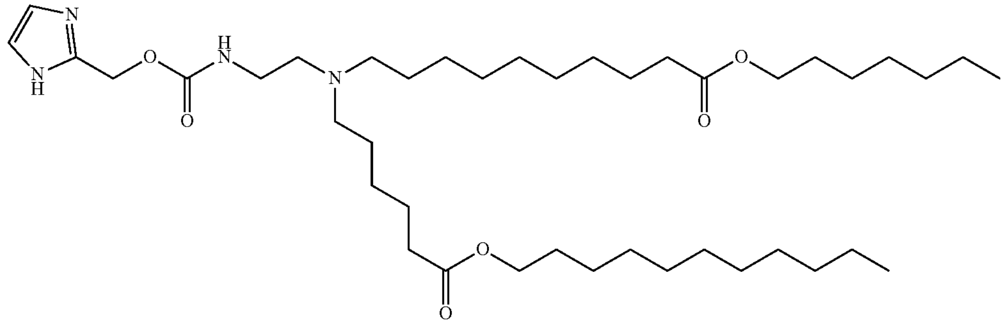 [SMILES: CCCCCCCCCCCOC(=O)CCCCCN(CCCCCCCCCC(=O)OCCCCCCC)CCNC(=O)OCc1ncc[nH]1] | 721.1 |
| 1167. | 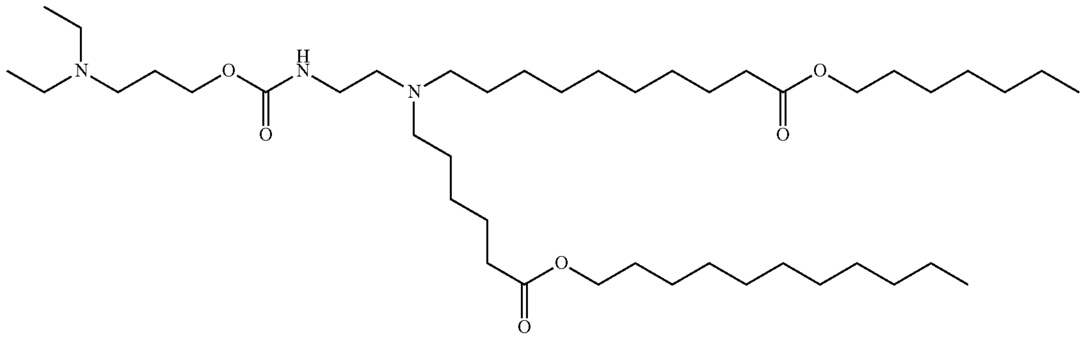 [SMILES: CCCCCCCCCCCOC(=O)CCCCCN(CCCCCCCCCC(=O)OCCCCCCC)CCNC(=O)OCCCN(CC)CC] | 754.2 |

TABLE 1-continued
| # | Structure | Mw |
|---|---|---|
| 1168. | 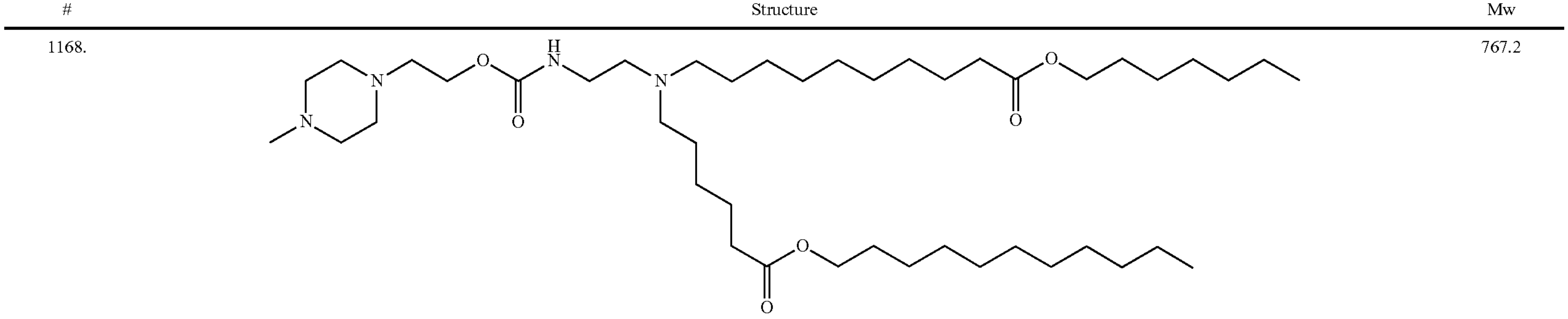 | 767.2 |
| 1169. | 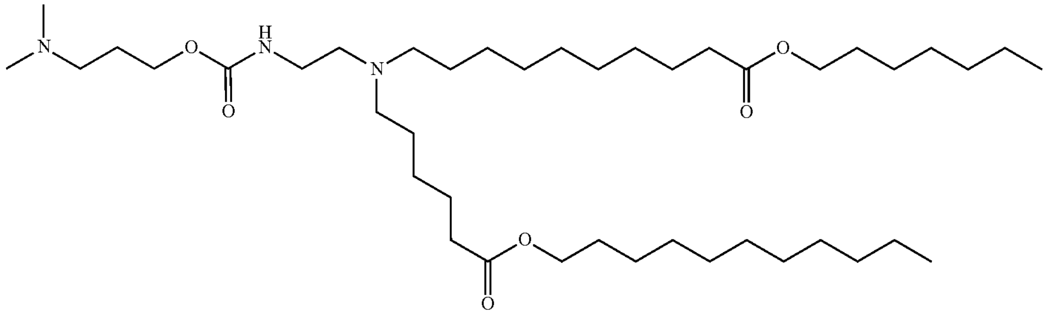 [SMILES: CCCCCCCCCCCOC(=O)CCCCCN(CCCCCCCCCC(=O)OCCCCCCC)CCNC(=O)OCCCN(C)C] | 726.1 |
| 1170. | 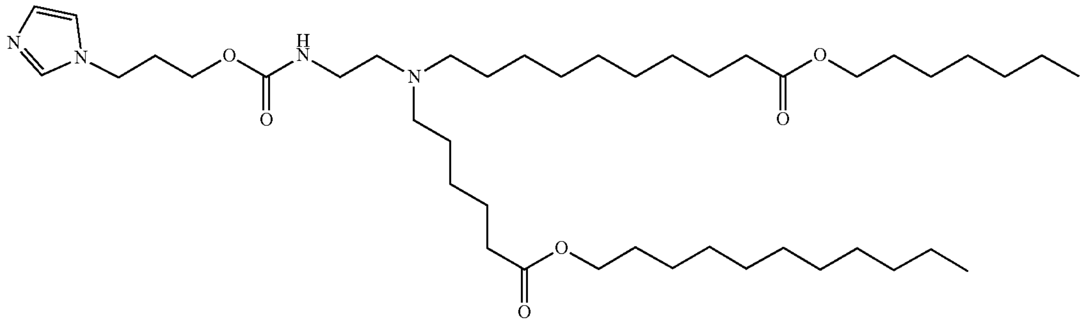 [SMILES: CCCCCCCCCCCOC(=O)CCCCCN(CCCCCCCCCC(=O)OCCCCCCC)CCNC(=O)OCCCn1ccnc1] | 749.1 |

TABLE 1-continued
| # | Structure | Mw |
| --- | --- | --- |
| 1171. | 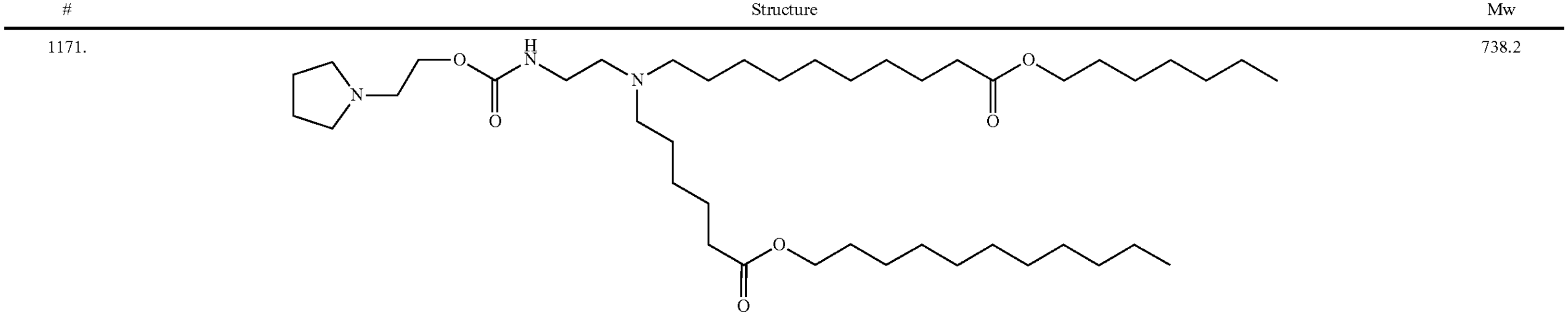 | 738.2 |
| 1172. | 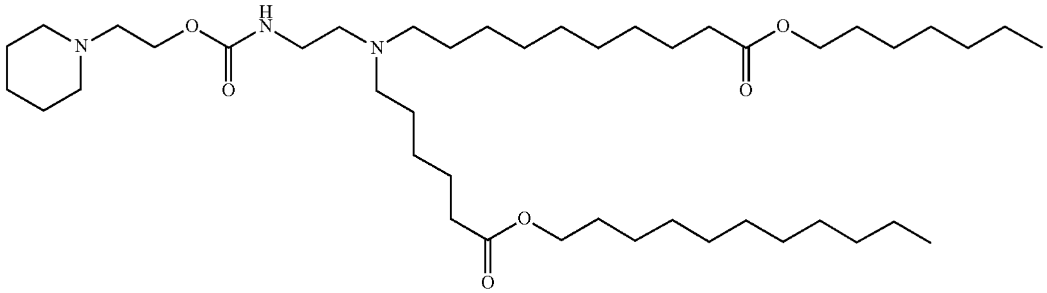 [SMILES: CCCCCCCCCCCOC(=O)CCCCCN(CCCCCCCCCC(=O)OCCCCCCC)CCNC(=O)OCCN1CCCCC1] | 752.2 |
| 1173. | 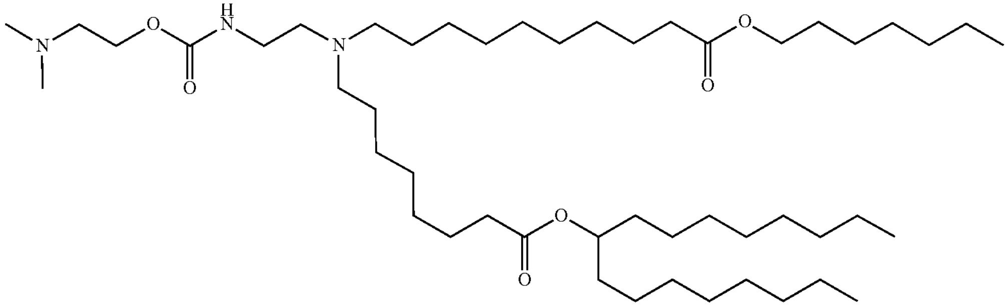 [SMILES: CCCCCCCCC(CCCCCCCC)OC(=O)CCCCCCCN(CCCCCCCCCC(=O)OCCCCCCC)CCNC(=O)OCCN(C)C] | 824.3 |

TABLE 1-continued
| # | Structure | Mw |
|---|---|---|
| 1174. | 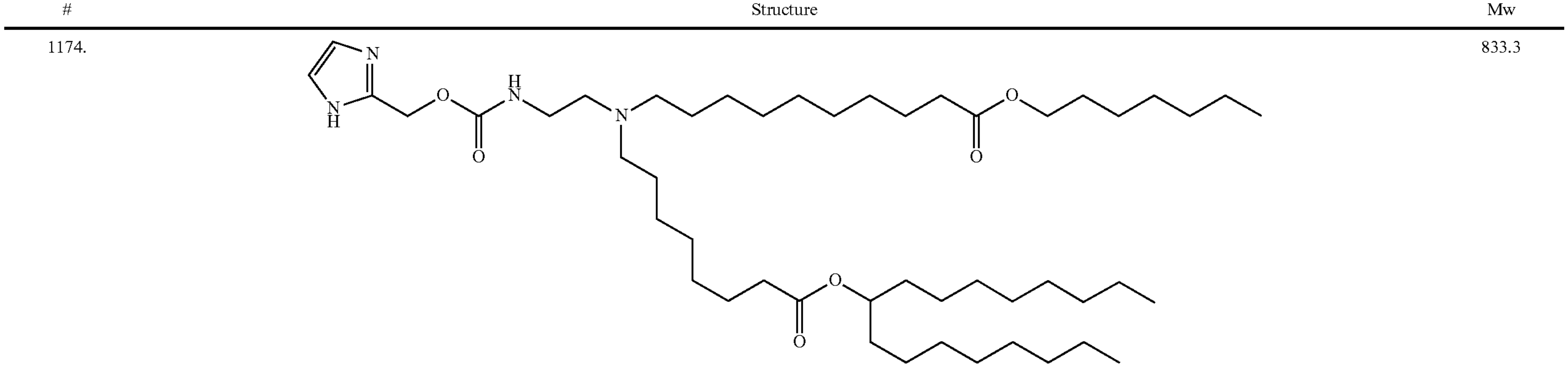 | 833.3 |
| 1175. | 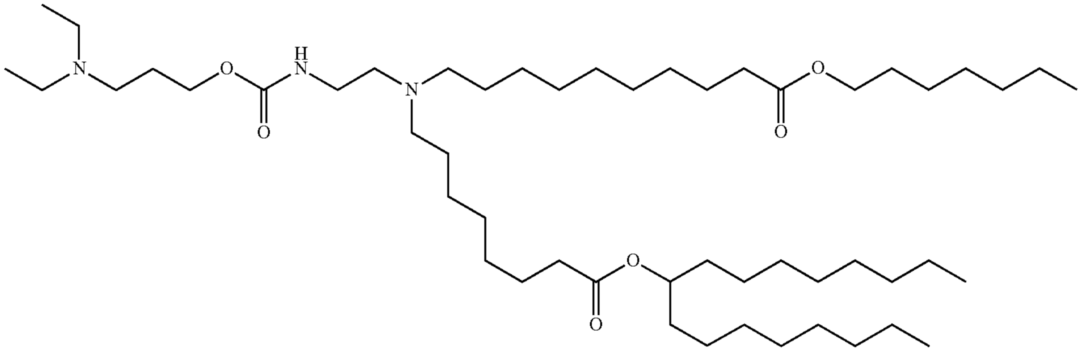 [SMILES: CCCCCCCCC(CCCCCCCC)OC(=O)CCCCCCCN(CCCCCCCCCC(=O)OCCCCCCC)CCNC(=O)OCCCN(CC)CC] | 866.4 |
| 1176. | 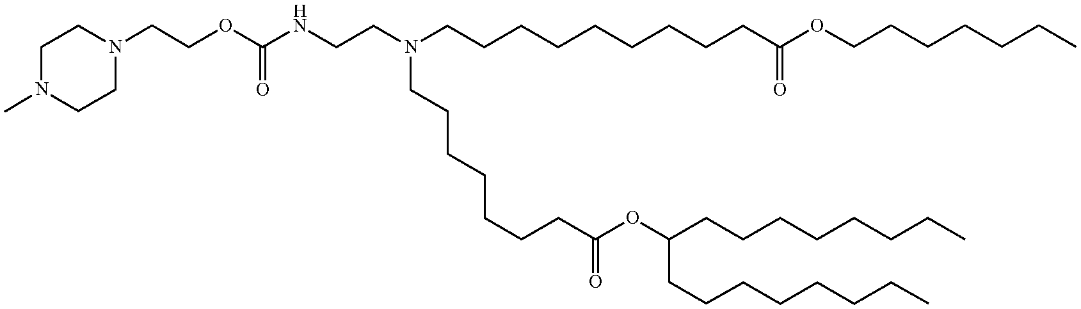 [SMILES: CCCCCCCCC(CCCCCCCC)OC(=O)CCCCCCCN(CCCCCCCCCC(=O)OCCCCCCC)CCNC(=O)OCCN1CCN(C)CC1] | 879.4 |

TABLE 1-continued
| # | Structure | Mw |
|---|---|---|
| 1177. | 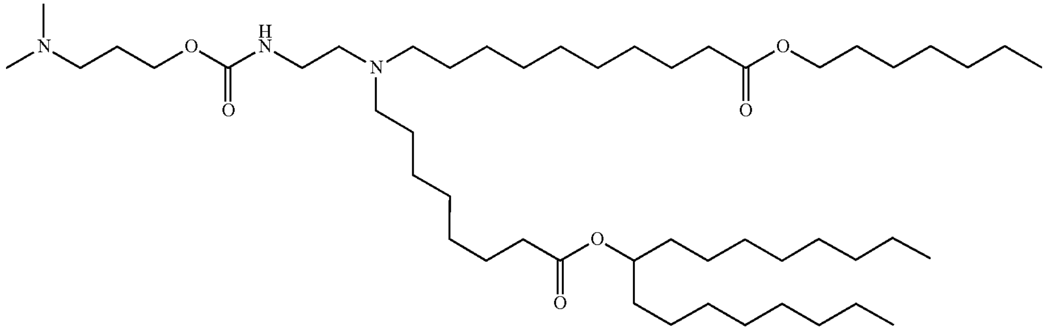 [SMILES: CCCCCCCCC(CCCCCCCC)OC(=O)CCCCCCCN(CCCCCCCCCC(=O)OCCCCCCC)CCNC(=O)OCCCN(C)C] | 838.4 |
| 1178. | 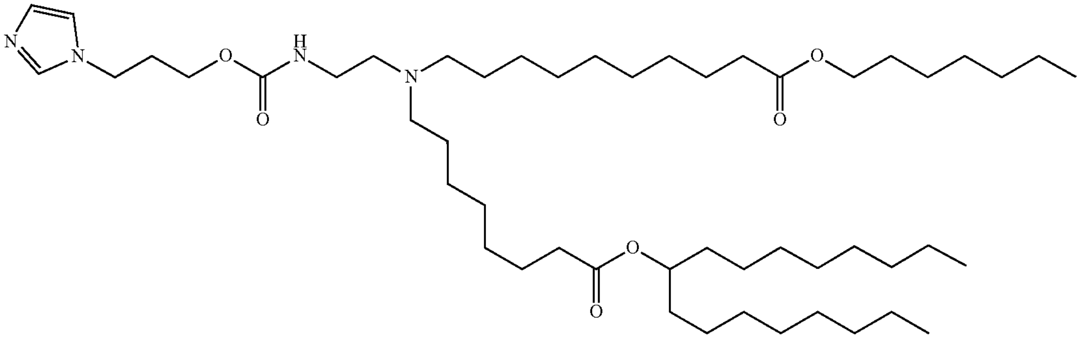 [SMILES: CCCCCCCCC(CCCCCCCC)OC(=O)CCCCCCCN(CCCCCCCCCC(=O)OCCCCCCC)CCNC(=O)OCCCn1ccnc1] | 861.4 |
| 1179. | 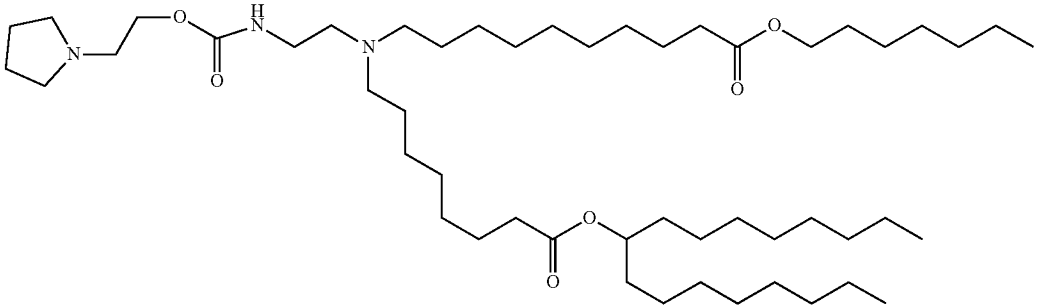 [SMILES: CCCCCCCCC(CCCCCCCC)OC(=O)CCCCCCCN(CCCCCCCCCC(=O)OCCCCCCC)CCNC(=O)OCCN1CCCC1] | 850.4 |

TABLE 1-continued
| # | Structure | Mw |
|---|---|---|
| 1180. | 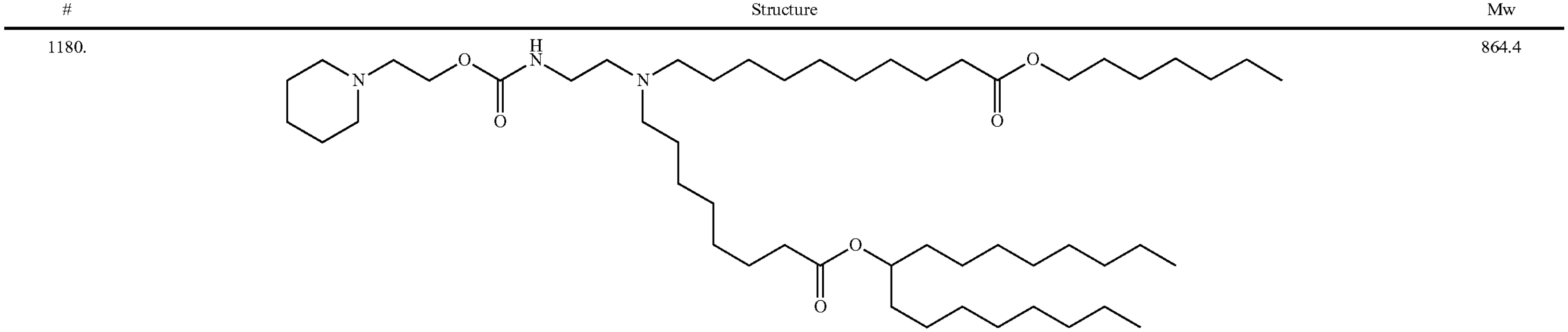 | 864.4 |
| 1181. | 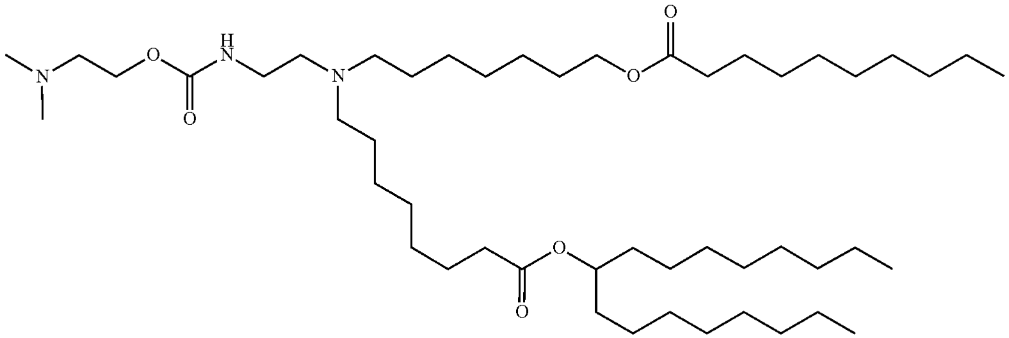 [SMILES: CCCCCCCCCC(=O)OCCCCCCCN(CCCCCCCC(=O)OC(CCCCCCCC)CCCCCCCC)CCNC(=O)OCCN(C)C] | 824.3 |
| 1182. | 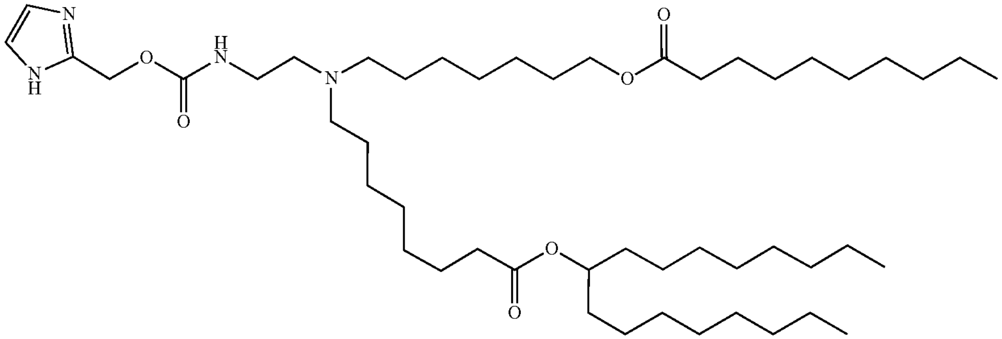 [SMILES: CCCCCCCCCC(=O)OCCCCCCCN(CCCCCCCC(=O)OC(CCCCCCCC)CCCCCCCC)CCNC(=O)OCc1ncc[nH]1] | 833.3 |

TABLE 1-continued
| # | Structure | Mw |
| --- | --- | --- |
| 1183. | 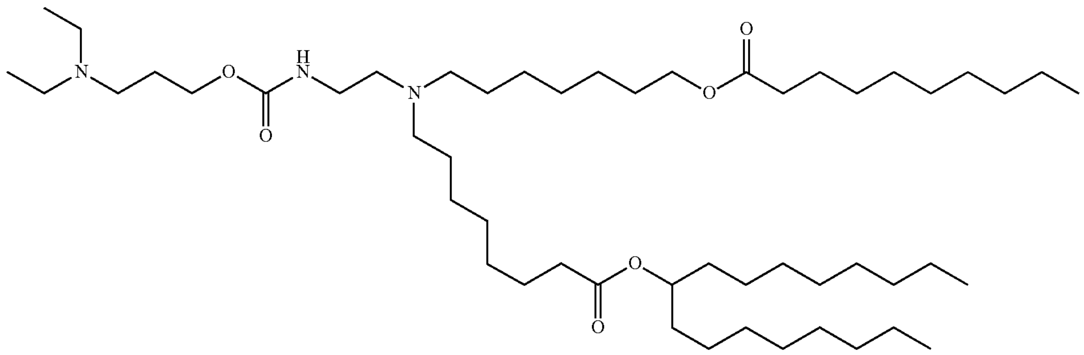 [SMILES: CCCCCCCCCC(=O)OCCCCCCCN(CCCCCCCC(=O)OC(CCCCCCCC)CCCCCCCC)CCNC(=O)OCCCN(CC)CC] | 866.4 |
| 1184. | 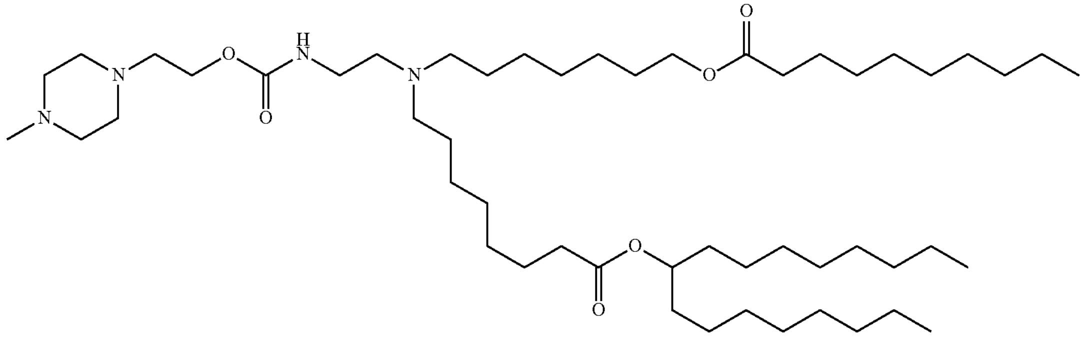 | 879.4 |
| 1185. | 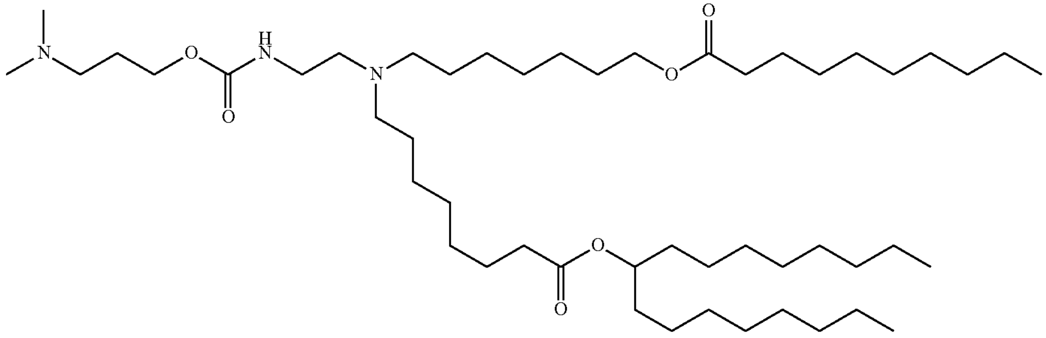 [SMILES: CCCCCCCCCC(=O)OCCCCCCCN(CCCCCCCC(=O)OC(CCCCCCCC)CCCCCCCC)CCNC(=O)OCCCN(C)C] | 838.4 |

TABLE 1-continued
| # | Structure | Mw |
|---|---|---|
| 1186. | 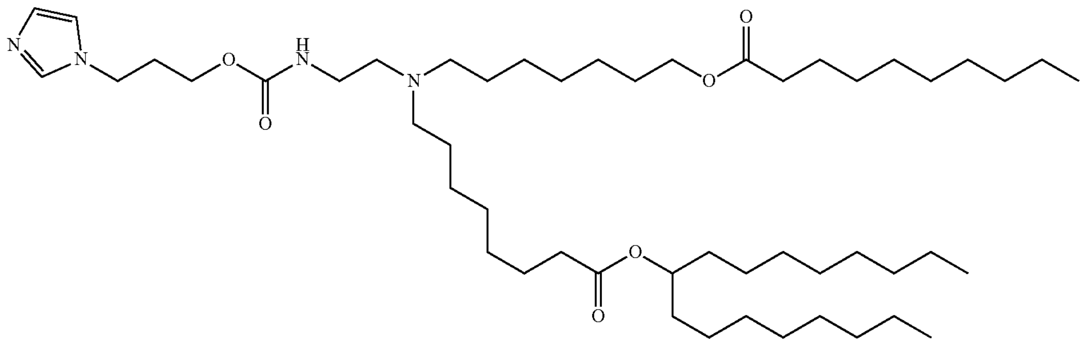 [SMILES: CCCCCCCCCC(=O)OCCCCCCCN(CCCCCCCC(=O)OC(CCCCCCCC)CCCCCCCC)CCNC(=O)OCCCn1ccnc1] | 861.4 |
| 1187. | 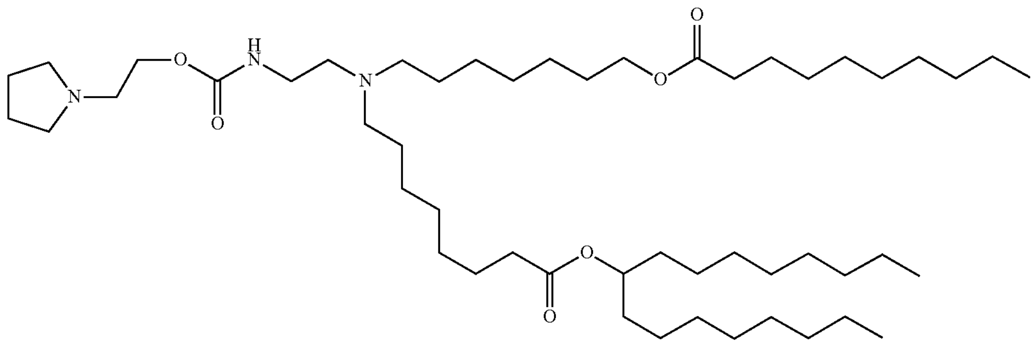 [SMILES: CCCCCCCCCC(=O)OCCCCCCCN(CCCCCCCC(=O)OC(CCCCCCCC)CCCCCCCC)CCNC(=O)OCCN1CCCC1] | 850.4 |
| 1188. | +get,2692 | 864.4 |
| 1189. | 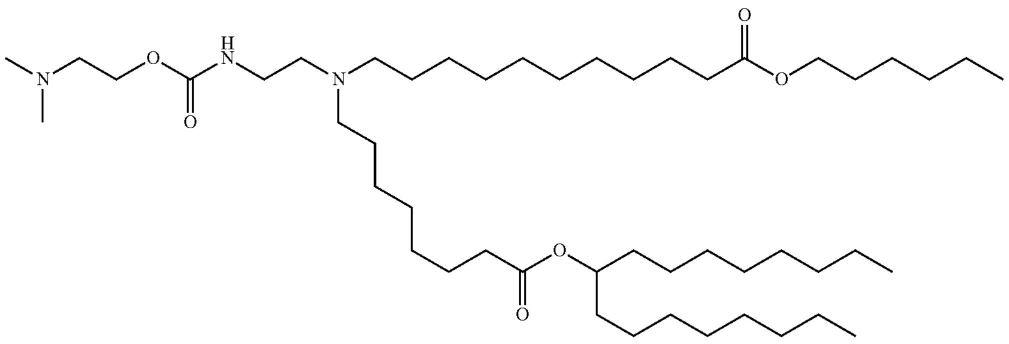 [SMILES: CCCCCCCCC(CCCCCCCC)OC(=O)CCCCCCCN(CCCCCCCCCCC(=O)OCCCCCC)CCNC(=O)OCCN(C)C] | 824.3 |

TABLE 1-continued
| # | Structure | Mw |
| --- | --- | --- |
| 1190. | 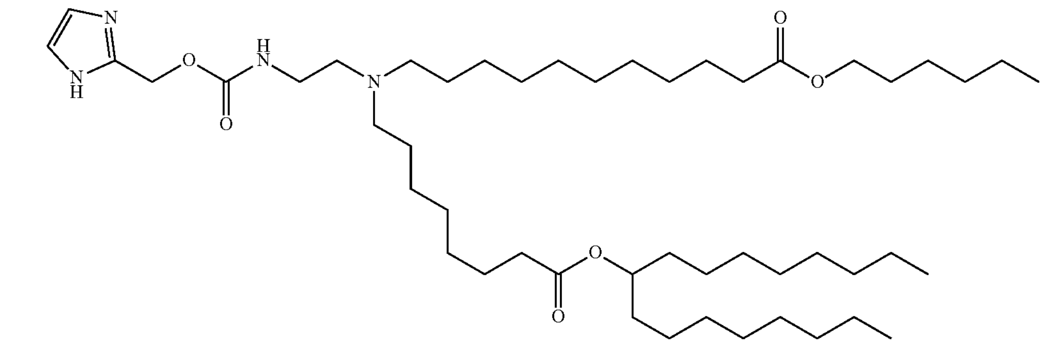 [SMILES: CCCCCCCCC(CCCCCCCC)OC(=O)CCCCCCCN(CCCCCCCCCCC(=O)OCCCCCC)CCNC(=O)OCc1ncc[nH]1] | 833.3 |
| 1191. | 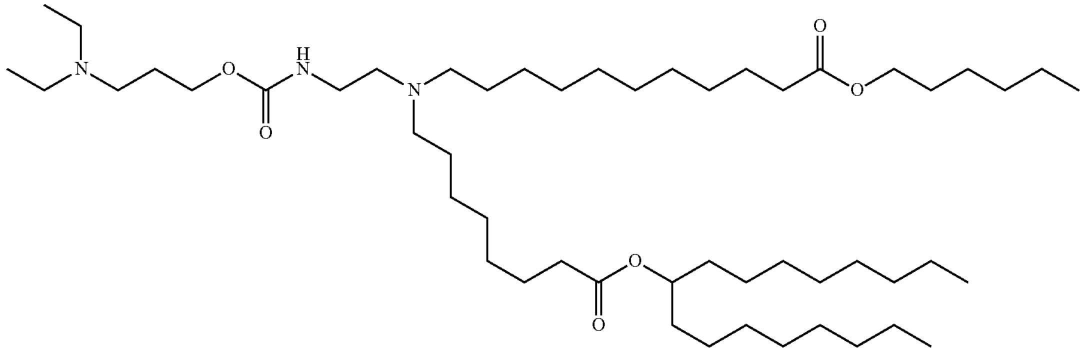 [SMILES: CCCCCCCCC(CCCCCCCC)OC(=O)CCCCCCCN(CCCCCCCCCCC(=O)OCCCCCC)CCNC(=O)OCCCN(CC)CC] | 866.4 |
| 1192. | 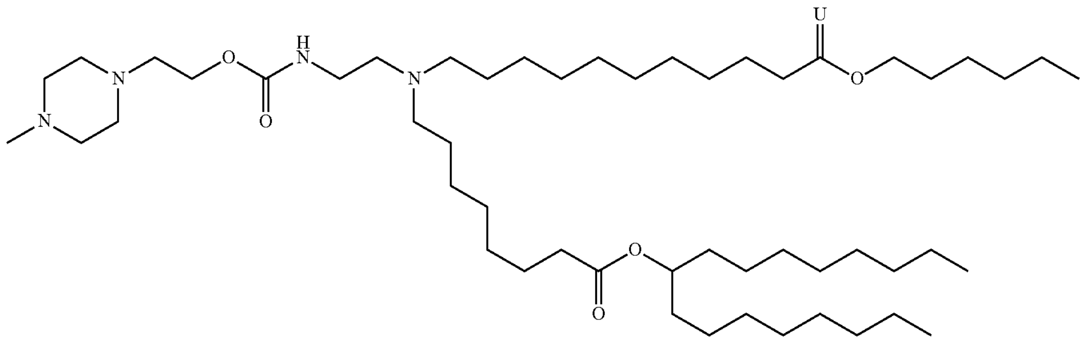 | 879.4 |

TABLE 1-continued
| # | Structure | Mw |
|---|---|---|
| 1193. | 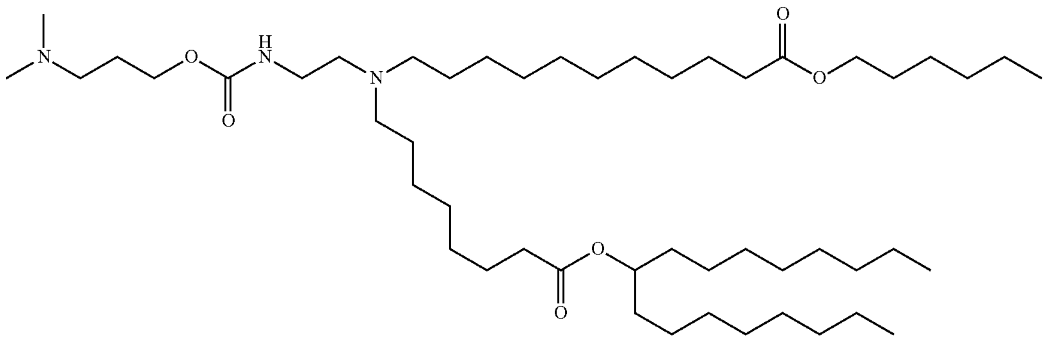 [SMILES: CCCCCCCCC(CCCCCCCC)OC(=O)CCCCCCCN(CCCCCCCCCCC(=O)OCCCCCC)CCNC(=O)OCCCN(C)C] | 838.4 |
| 1194. | 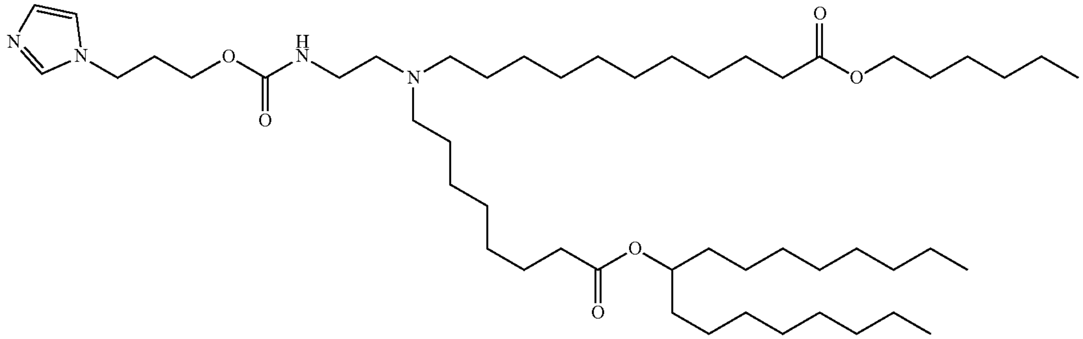 [SMILES: CCCCCCCCC(CCCCCCCC)OC(=O)CCCCCCCN(CCCCCCCCCCC(=O)OCCCCCC)CCNC(=O)OCCCn1ccnc1] | 861.4 |
| 1195. | 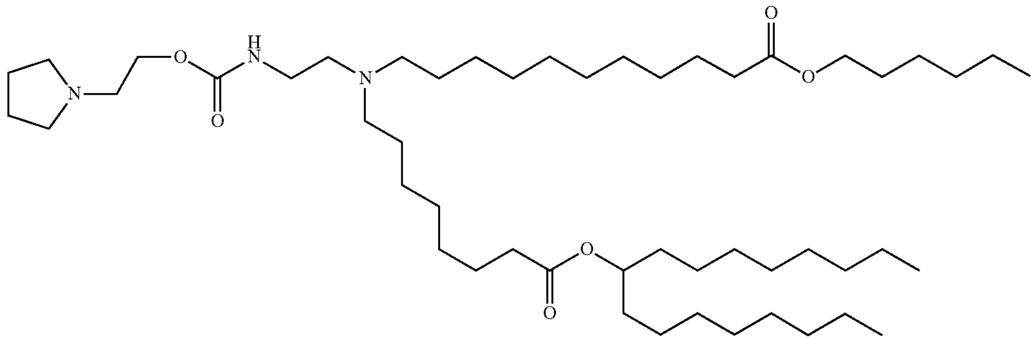 [SMILES: CCCCCCCCC(CCCCCCCC)OC(=O)CCCCCCCN(CCCCCCCCCCC(=O)OCCCCCC)CCNC(=O)OCCN1CCCC1] | 850.4 |

TABLE 1-continued
| # | Structure | Mw |
| --- | --- | --- |
| 1196. | 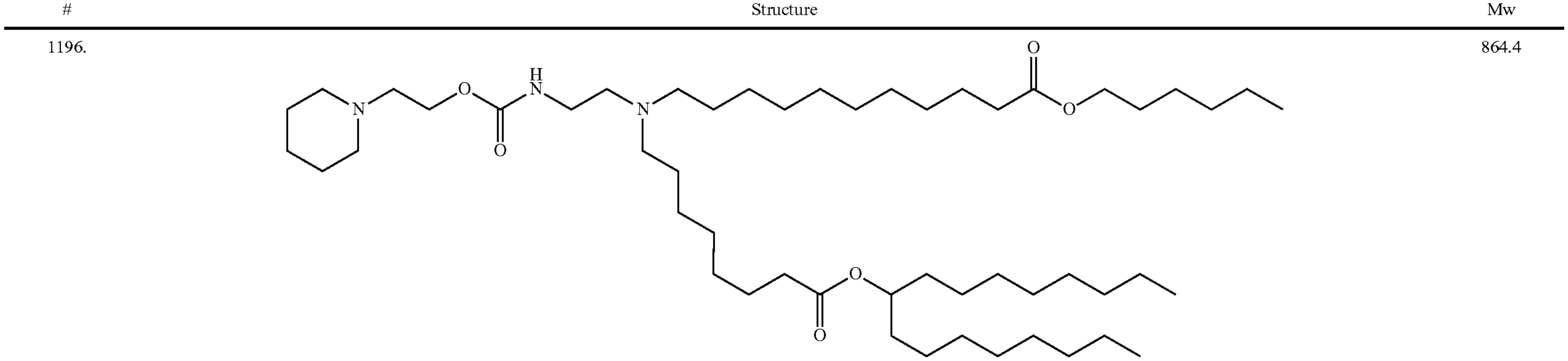 | 864.4 |
| 1197. | 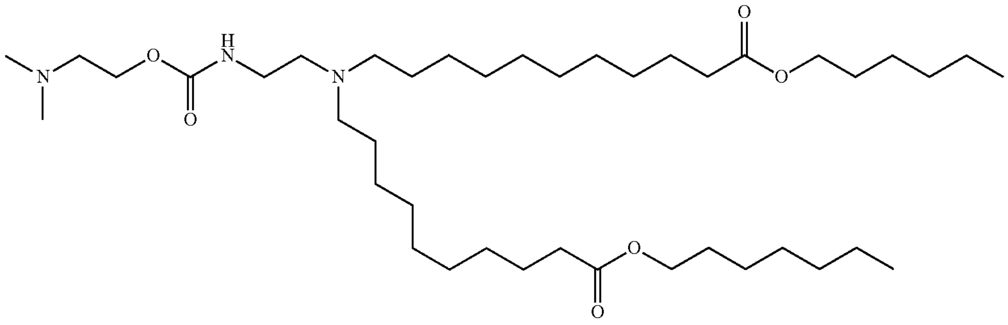 [SMILES: CCCCCCCOC(=O)CCCCCCCCCN(CCCCCCCCCCC(=O)OCCCCCC)CCNC(=O)OCCN(C)C] | 712.1 |
| 1198. | 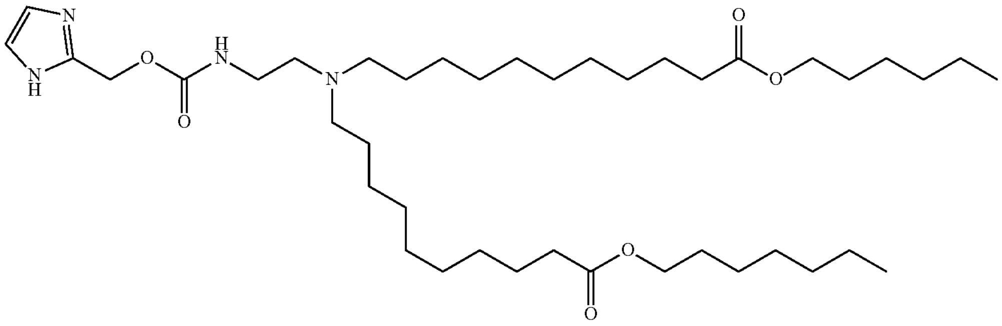 [SMILES: CCCCCCCOC(=O)CCCCCCCCCN(CCCCCCCCCCC(=O)OCCCCCC)CCNC(=O)OCc1ncc[nH]1] | 721.1 |

TABLE 1-continued
| # | Structure | Mw |
|---|---|---|
| 1199. | 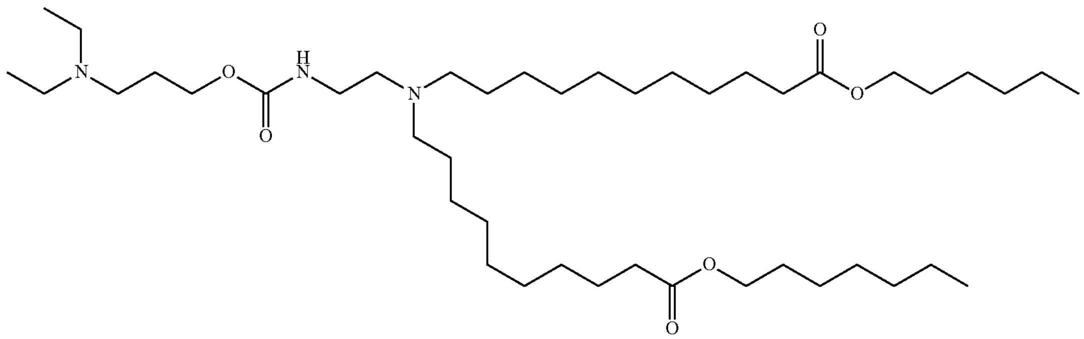 [SMILES: CCCCCCCOC(=O)CCCCCCCCCN(CCCCCCCCCCC(=O)OCCCCCC)CCNC(=O)OCCCN(CC)CC] | 754.2 |
| 1200. | 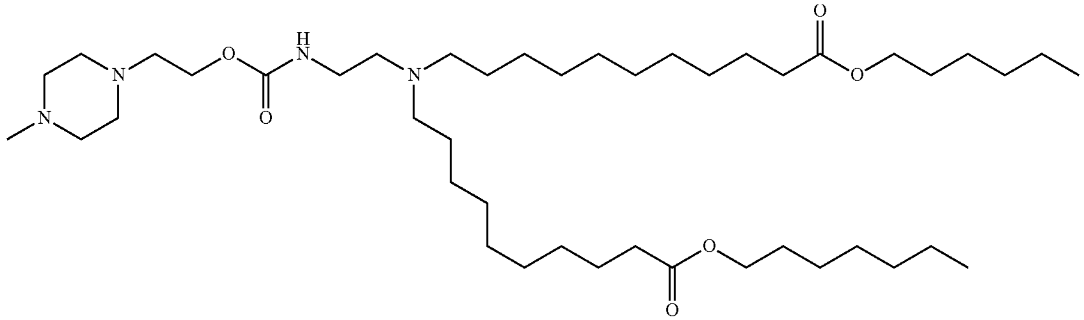 [SMILES: CCCCCCCOC(=O)CCCCCCCCCN(CCCCCCCCCCC(=O)OCCCCCC)CCNC(=O)OCCN1CCN(C)CC1] | 767.2 |
| 1201. | 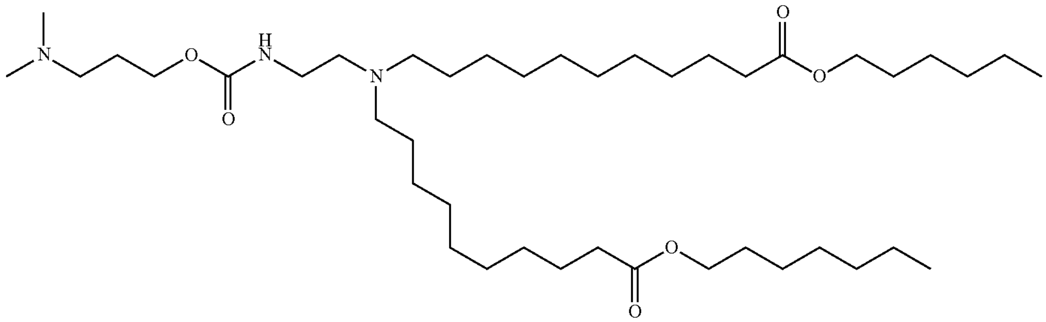 [SMILES: CCCCCCCOC(=O)CCCCCCCCCN(CCCCCCCCCCC(=O)OCCCCCC)CCNC(=O)OCCCN(C)C] | 726.1 |

TABLE 1-continued
| # | Structure | Mw |
|---|---|---|
| 1202. | 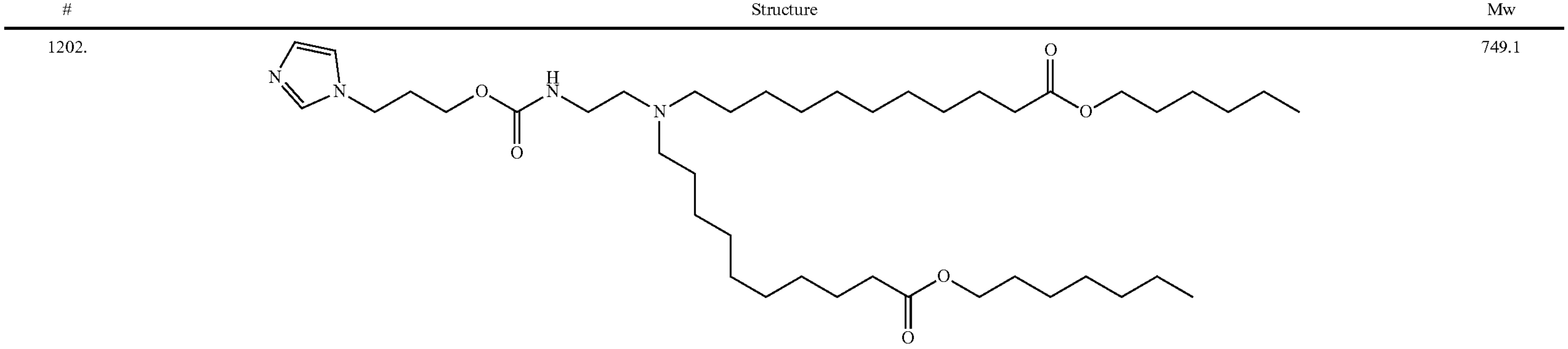 | 749.1 |
| 1203. | 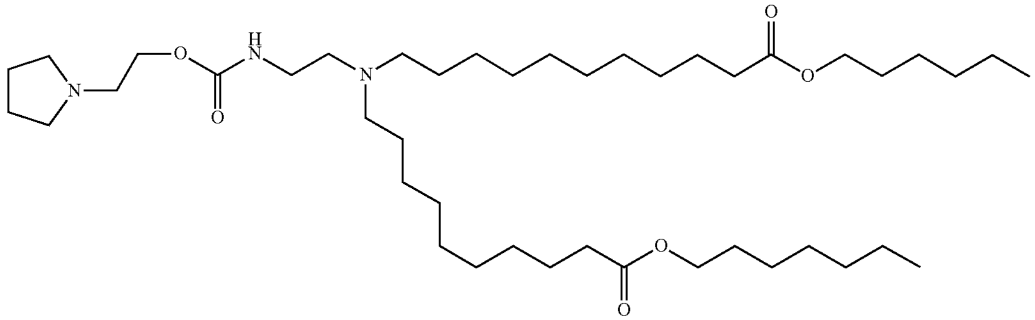 [SMILES: CCCCCCCOC(=O)CCCCCCCCCN(CCCCCCCCCCC(=O)OCCCCCC)CCNC(=O)OCCN1CCCC1] | 738.2 |
| 1204. | 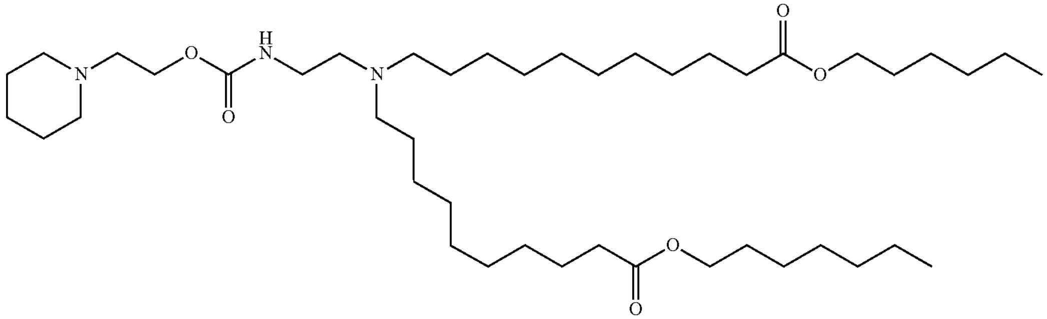 [SMILES: CCCCCCCOC(=O)CCCCCCCCCN(CCCCCCCCCCC(=O)OCCCCCC)CCNC(=O)OCCN1CCCCC1] | 752.2 |

TABLE 1-continued
| # | Structure | Mw |
|---|---|---|
| 1205. | 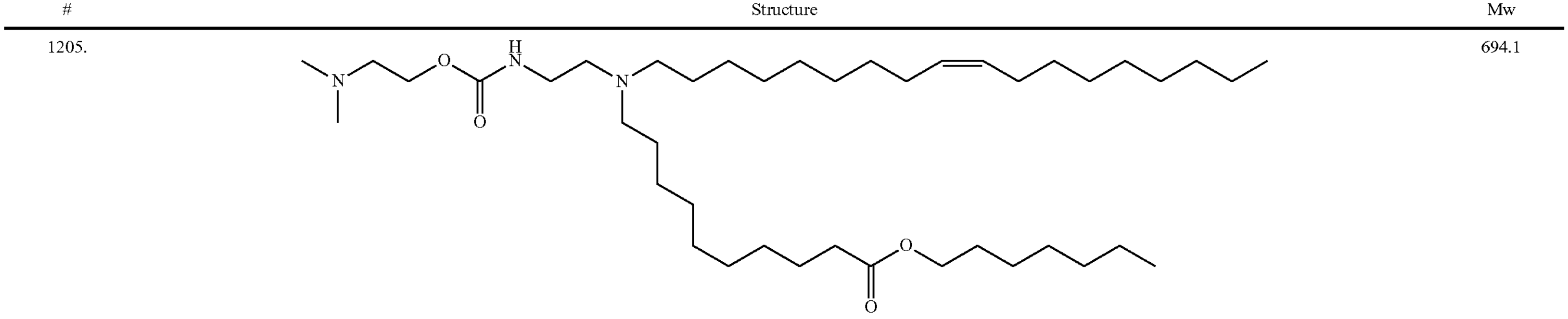 | 694.1 |
| 1206. | 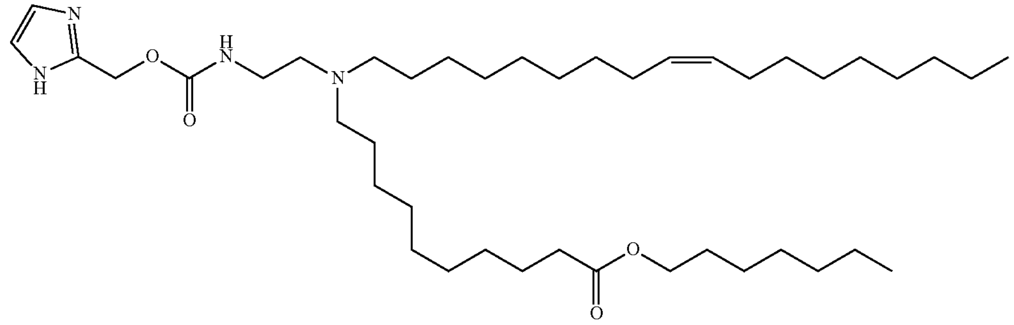 [SMILES: CCCCCCCC/C=C\CCCCCCCCN(CCCCCCCCCC(=O)OCCCCCCC)CCNC(=O)OCc1ncc[nH]1] | 703.1 |
| 1207. | 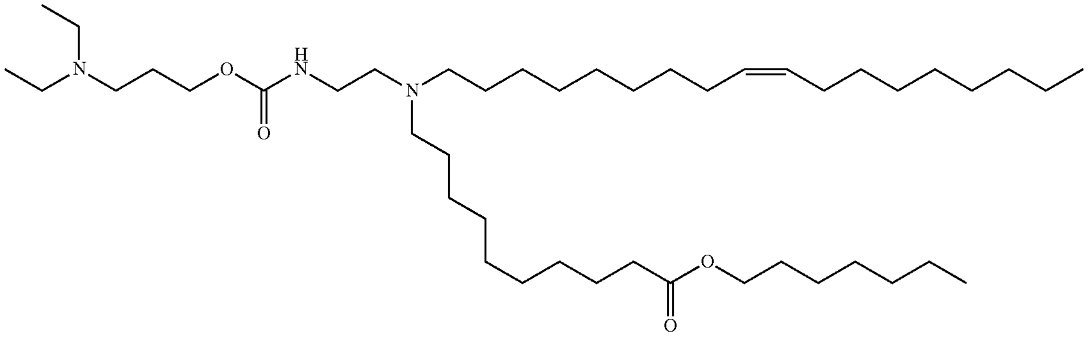 | 736.2 |

TABLE 1-continued
| # | Structure | Mw |
|---|---|---|
| 1208. | 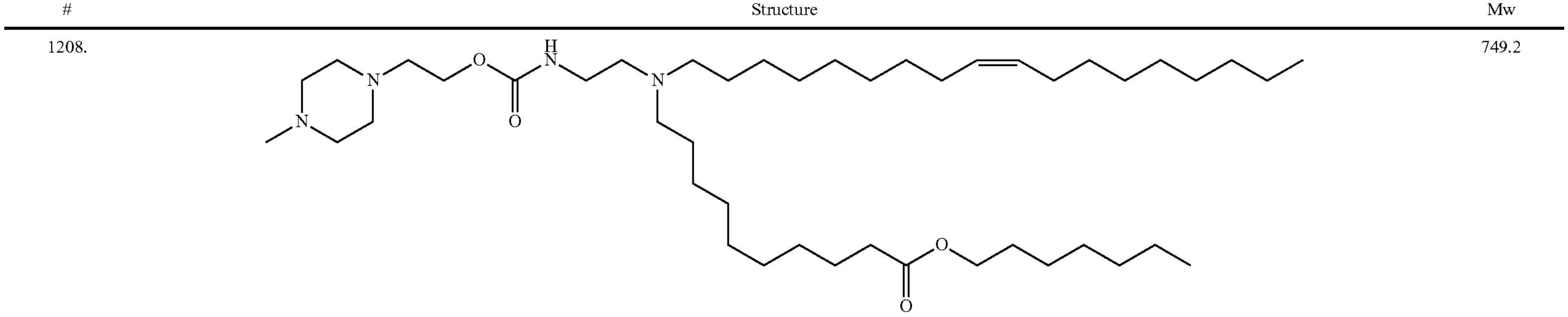 | 749.2 |
| 1209. | 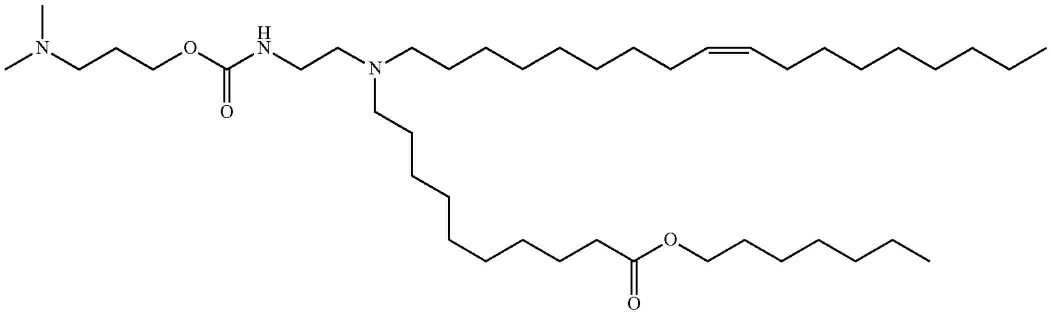 [SMILES: CCCCCCCC/C=C\CCCCCCCCN(CCCCCCCCCC(=O)OCCCCCCC)CCNC(=O)OCCCN(C)C] | 708.2 |
| 1210. | 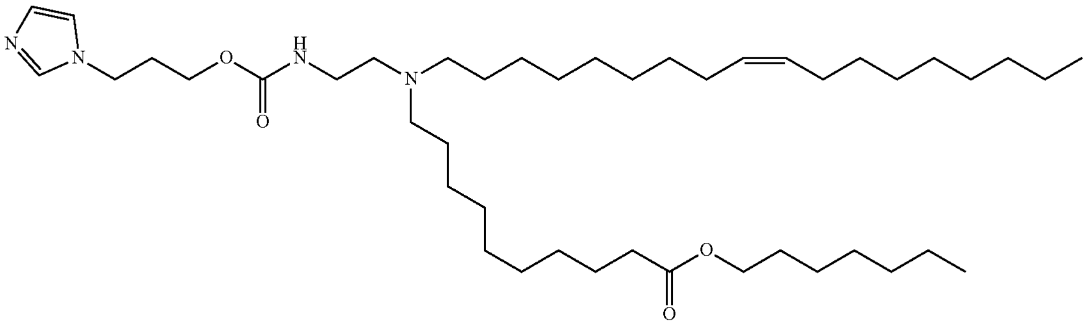 [SMILES: CCCCCCCC/C=C\CCCCCCCCN(CCCCCCCCCC(=O)OCCCCCCC)CCNC(=O)OCCCn1ccnc1] | 731.2 |

TABLE 1-continued
| # | Structure | Mw |
|---|---|---|
| 1211. | 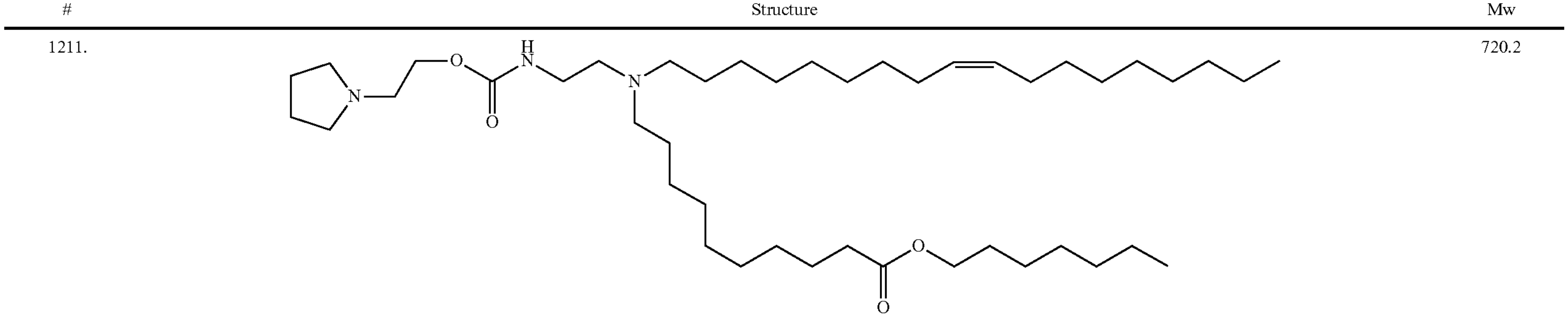 | 720.2 |
| 1212. | 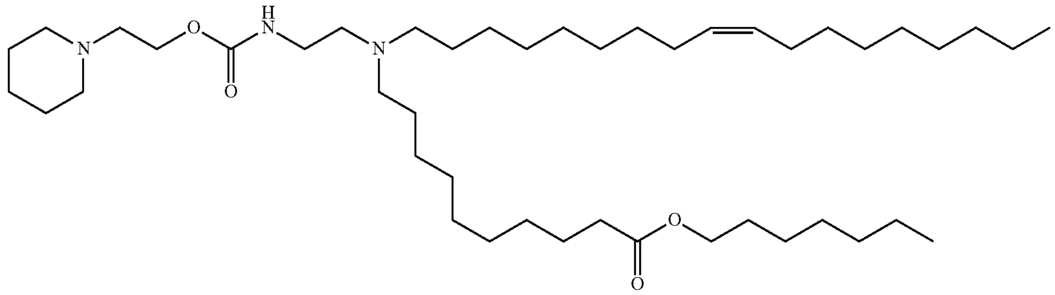 [SMILES: CCCCCCCC/C=C\CCCCCCCCN(CCCCCCCCCC(=O)OCCCCCCC)CCNC(=O)OCCN1CCCCC1] | 734.2 |
| 1213. | 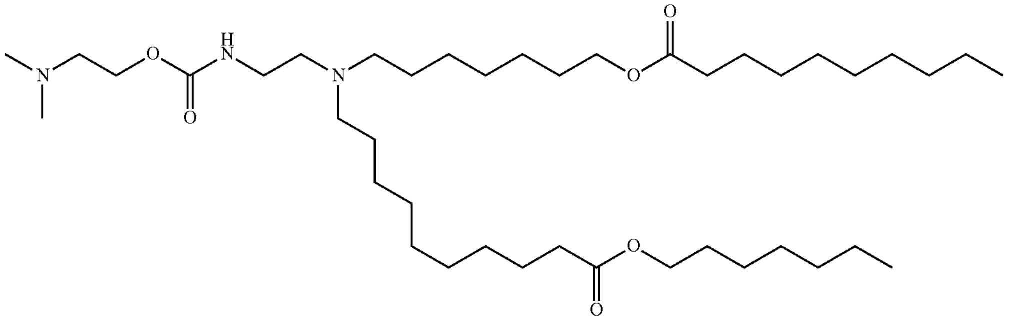 [SMILES: CCCCCCCCCC(=O)OCCCCCCCN(CCCCCCCCCC(=O)OCCCCCCC)CCNC(=O)OCCN(C)C] | 712.1 |

TABLE 1-continued
| # | Structure | Mw |
|---|---|---|
| 1214. | 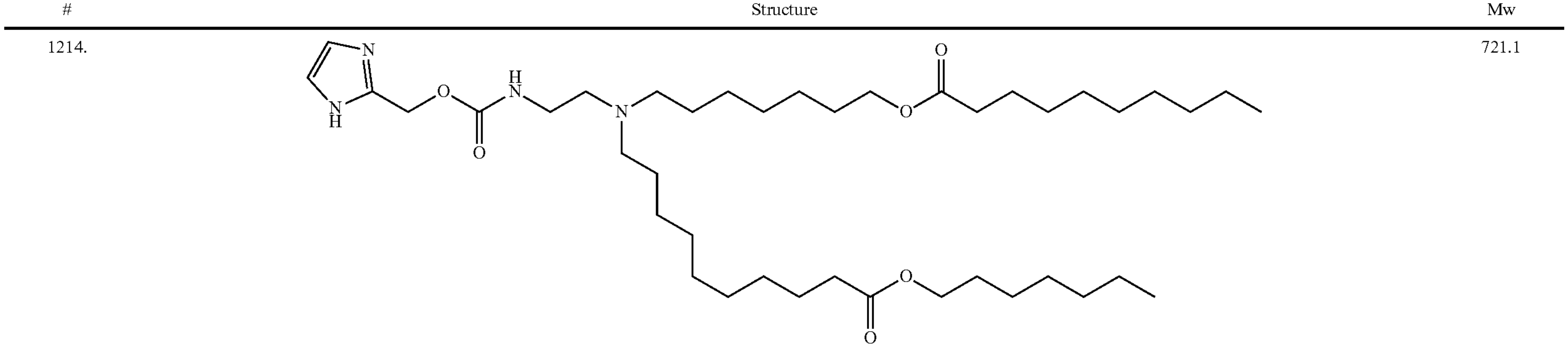 | 721.1 |
| 1215. | 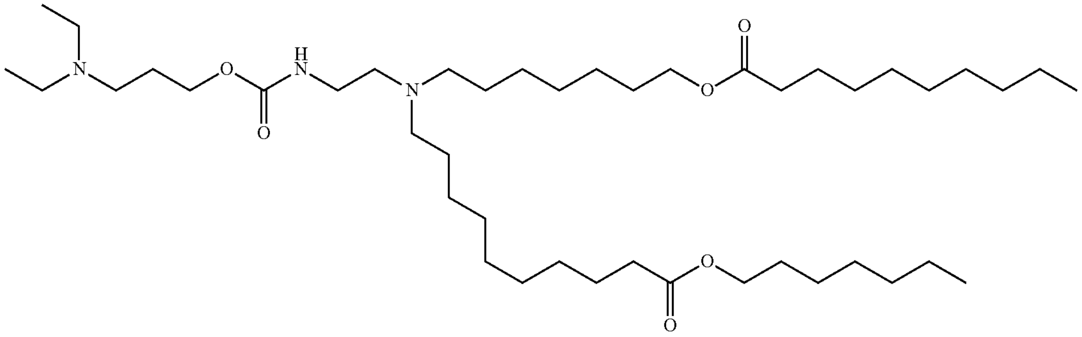 [SMILES: CCCCCCCCCC(=O)OCCCCCCCN(CCCCCCCCCC(=O)OCCCCCCC)CCNC(=O)OCCCN(CC)CC] | 754.2 |
| 1216. | 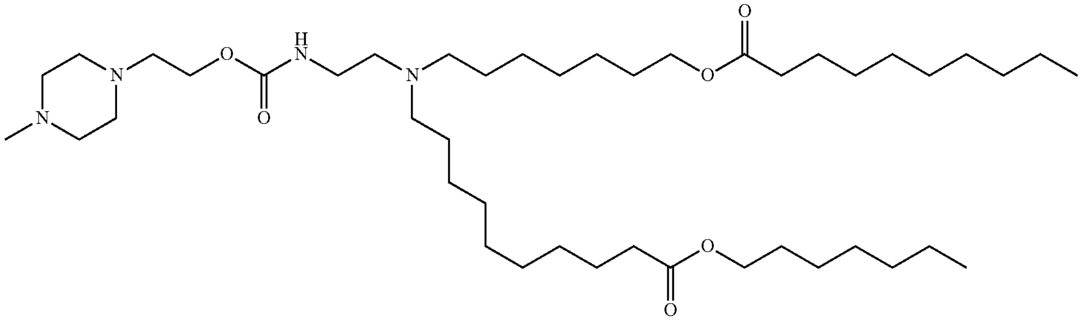 [SMILES: CCCCCCCCCC(=O)OCCCCCCCN(CCCCCCCCCC(=O)OCCCCCCC)CCNC(=O)OCCN1CCN(C)CC1] | 767.2 |

TABLE 1-continued
| # | Structure | Mw |
| --- | --- | --- |
| 1217. | 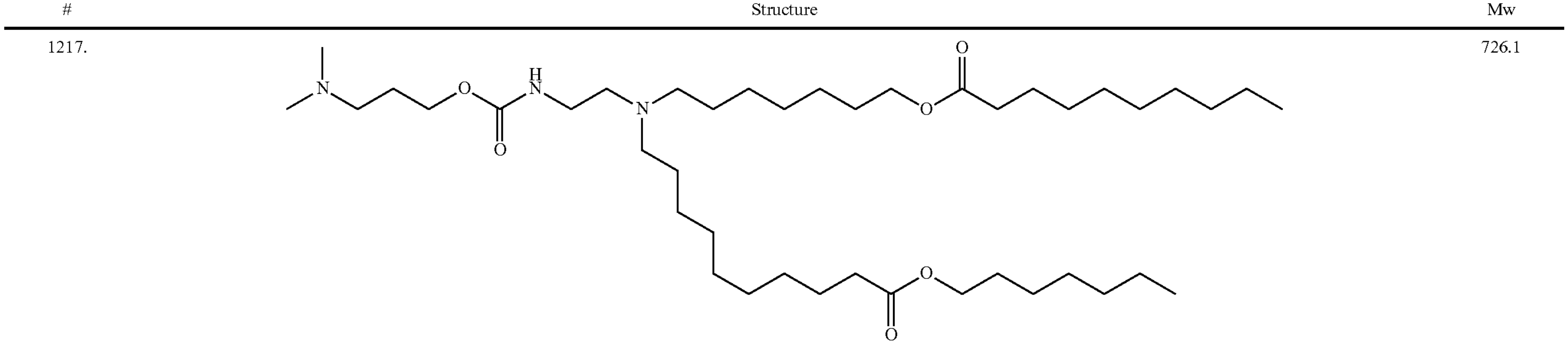 | 726.1 |
| 1218. | 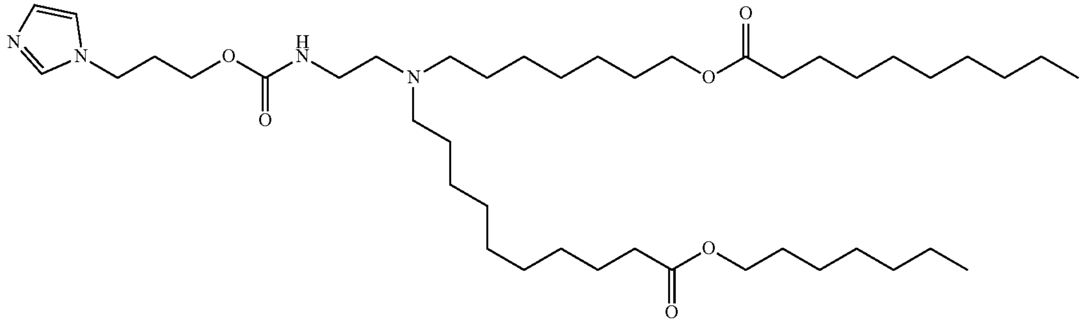 [SMILES: CCCCCCCCCC(=O)OCCCCCCCN(CCCCCCCCCC(=O)OCCCCCCC)CCNC(=O)OCCCn1ccnc1] | 749.1 |
| 1219. | 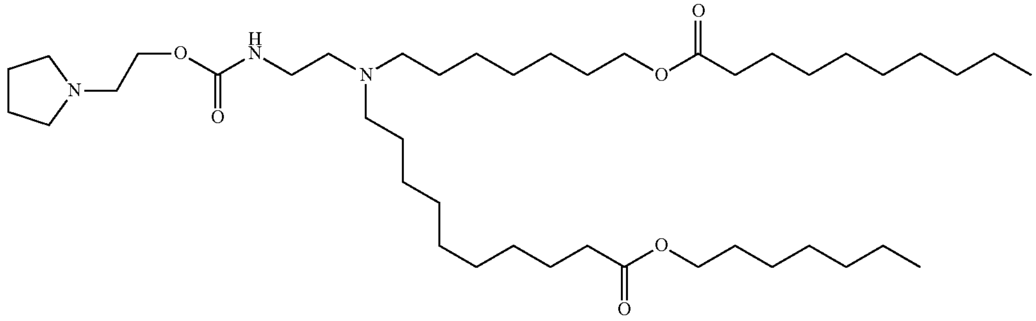 [SMILES: CCCCCCCCCC(=O)OCCCCCCCN(CCCCCCCCCC(=O)OCCCCCCC)CCNC(=O)OCCN1CCCC1] | 738.2 |

TABLE 1-continued
| # | Structure | Mw |
| --- | --- | --- |
| 1220. | 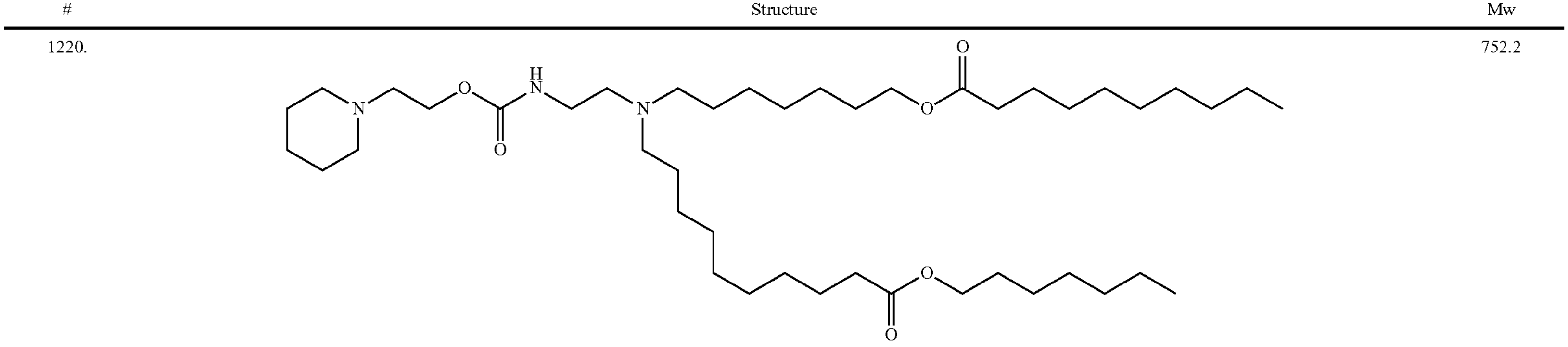 | 752.2 |
| 1221. | 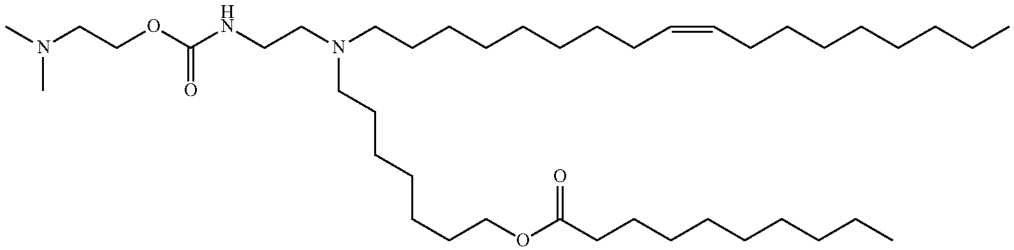 [SMILES: CCCCCCCC/C=C\CCCCCCCCN(CCCCCCCOC(=O)CCCCCCCCC)CCNC(=O)OCCN(C)C] | 694.1 |
| 1222. | 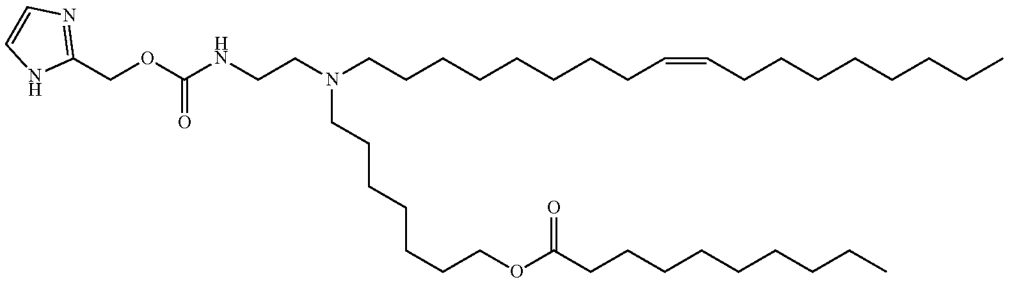 [SMILES: CCCCCCCC/C=C\CCCCCCCCN(CCCCCCCOC(=O)CCCCCCCCC)CCNC(=O)OCc1ncc[nH]1] | 703.1 |

TABLE 1-continued
| # | Structure | Mw |
| --- | --- | --- |
| 1223. | 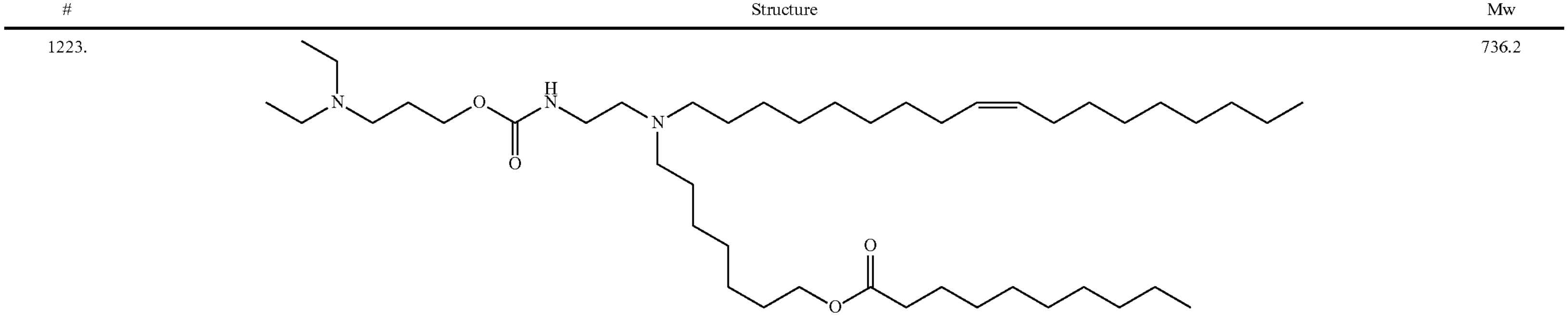 | 736.2 |
| 1224. | 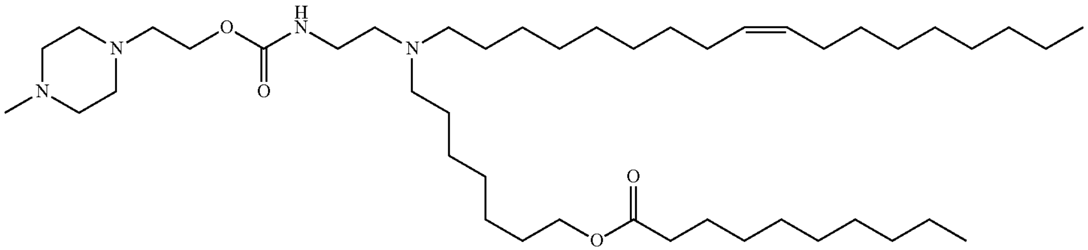 [SMILES: CCCCCCCC/C=C\CCCCCCCCN(CCCCCCCOC(=O)CCCCCCCCC)CCNC(=O)OCCN1CCN(C)CC1] | 749.2 |
| 1225. | 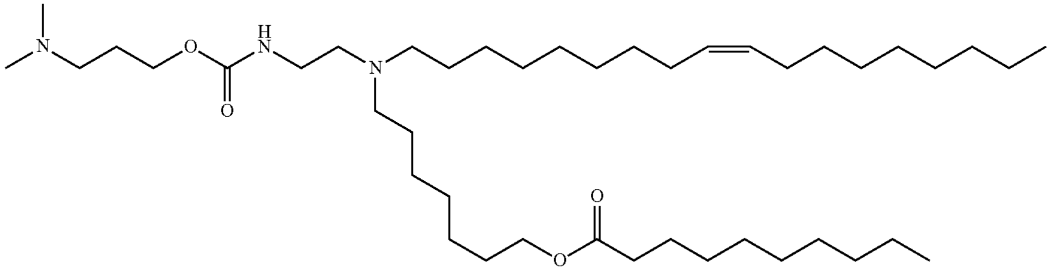 [SMILES: CCCCCCCC/C=C\CCCCCCCCN(CCCCCCCOC(=O)CCCCCCCCC)CCNC(=O)OCCCN(C)C] | 708.2 |

TABLE 1-continued
| # | Structure | Mw |
|---|---|---|
| 1226. | 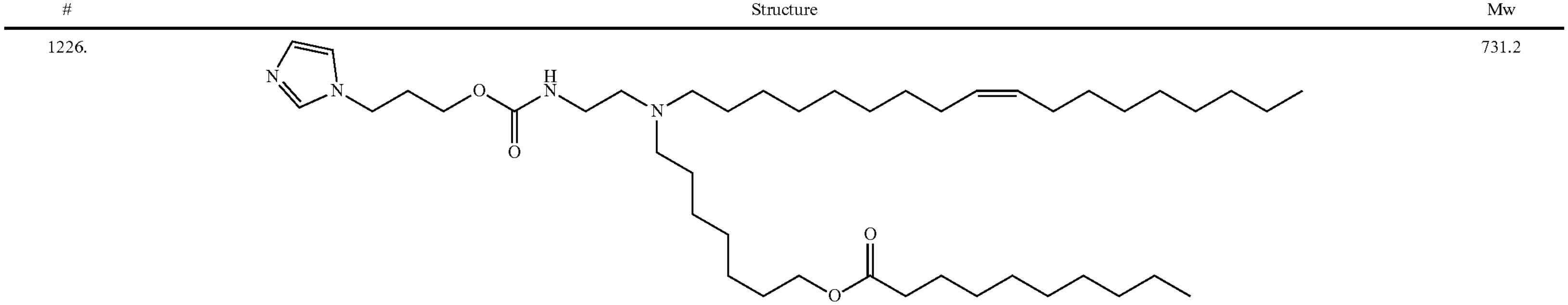 | 731.2 |
| 1227. | 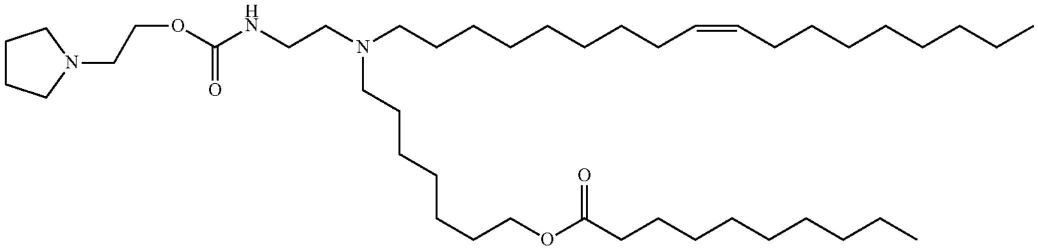 [SMILES: CCCCCCCC/C=C\CCCCCCCCN(CCCCCCCOC(=O)CCCCCCCCC)CCNC(=O)OCCN1CCCC1] | 720.2 |
| 1228. | 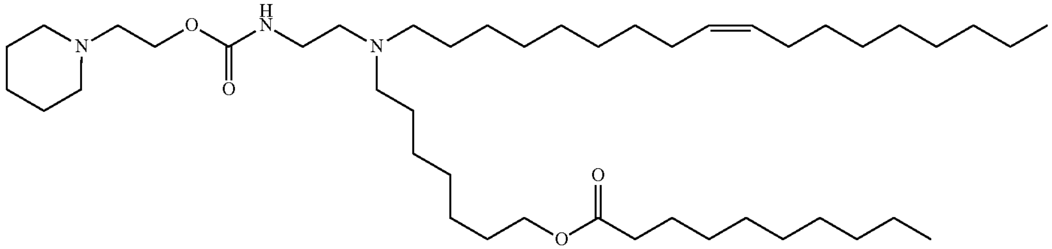 [SMILES: CCCCCCCC/C=C\CCCCCCCCN(CCCCCCCOC(=O)CCCCCCCCC)CCNC(=O)OCCN1CCCCC1] | 734.2 |

TABLE 1-continued
| # | Structure | Mw |
|---|---|---|
| 1229. | 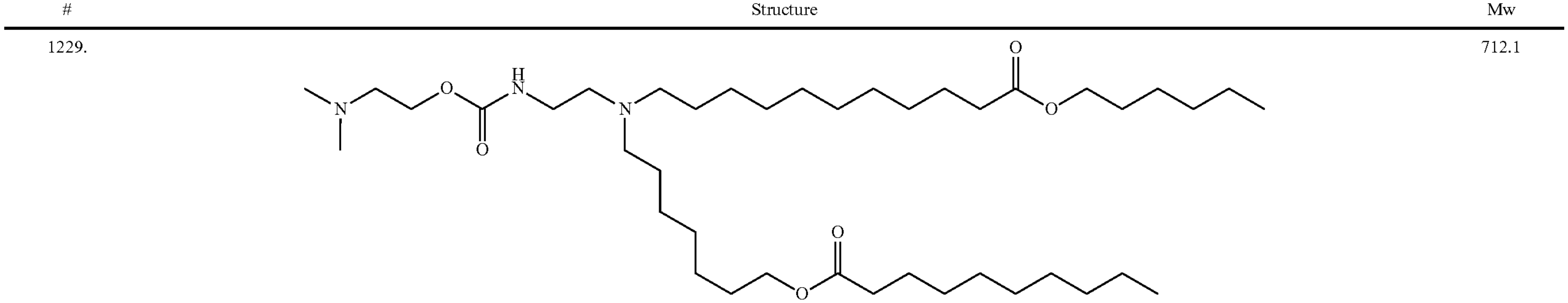 | 712.1 |
| 1230. | 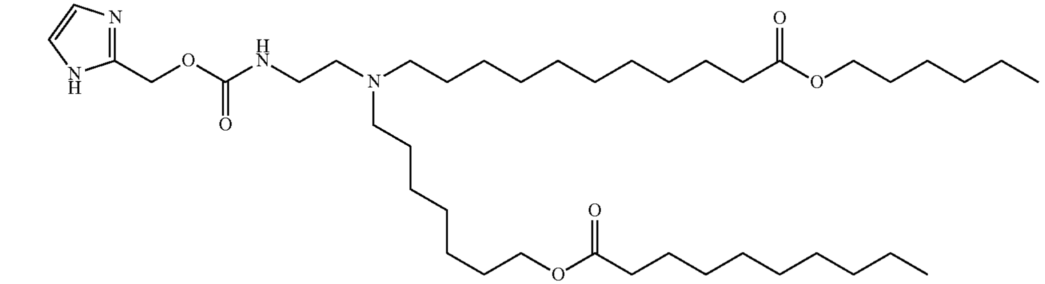 [SMILES: CCCCCCCCCC(=O)OCCCCCCCN(CCCCCCCCCCC(=O)OCCCCCC)CCNC(=O)OCc1ncc[nH]1] | 721.1 |
| 1231. | 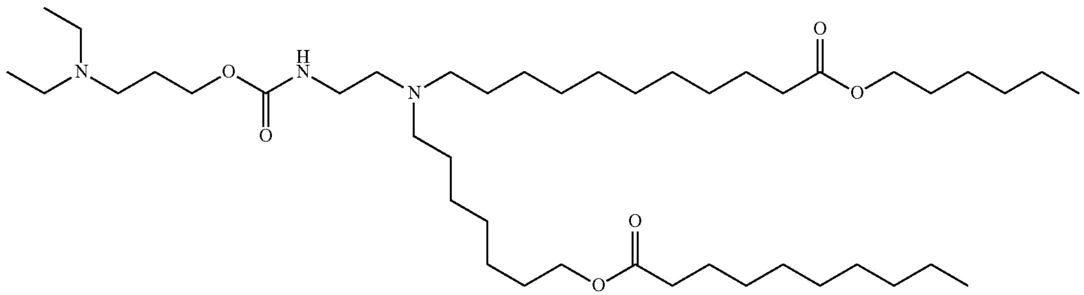 [SMILES: CCCCCCCCCC(=O)OCCCCCCCN(CCCCCCCCCCC(=O)OCCCCCC)CCNC(=O)OCCCN(CC)CC] | 754.2 |

TABLE 1-continued
| # | Structure | Mw |
| --- | --- | --- |
| 1232. | 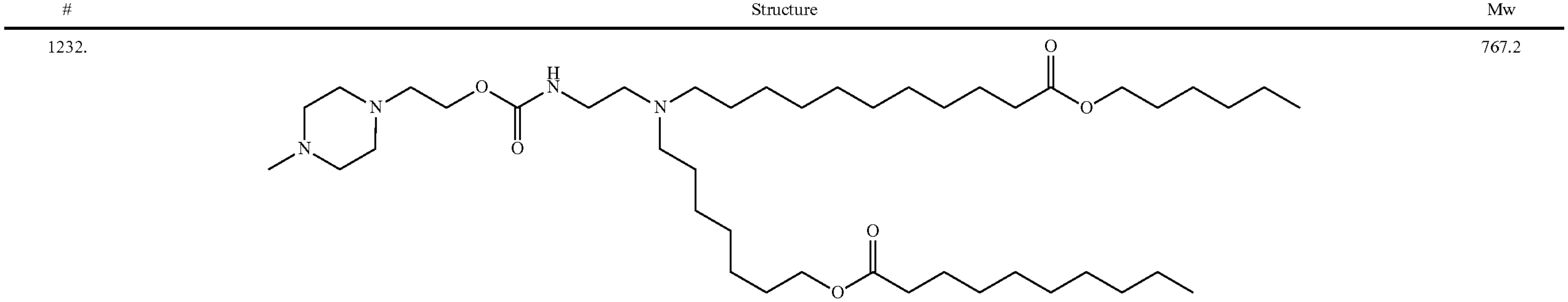 | 767.2 |
| 1233. | 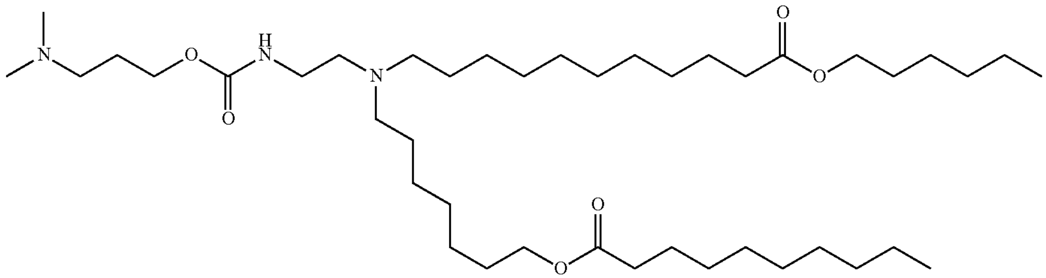 [SMILES: CCCCCCCCCC(=O)OCCCCCCCN(CCCCCCCCCCC(=O)OCCCCCC)CCNC(=O)OCCCN(C)C] | 726.1 |
| 1234. | 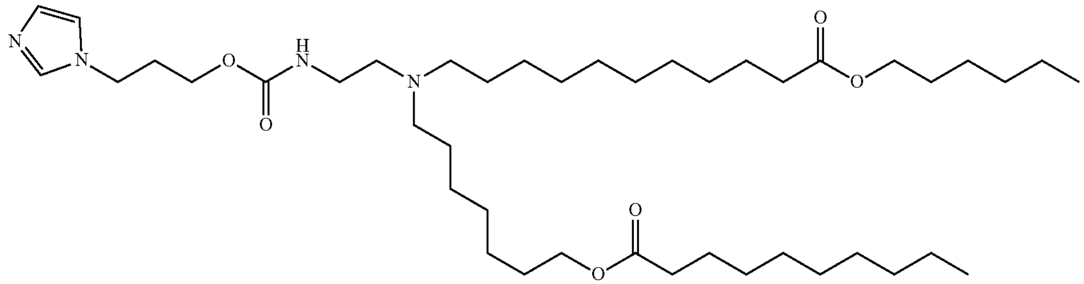 [SMILES: CCCCCCCCCC(=O)OCCCCCCCN(CCCCCCCCCCC(=O)OCCCCCC)CCNC(=O)OCCCn1ccnc1] | 749.1 |

TABLE 1-continued
| # | Structure | Mw |
| --- | --- | --- |
| 1235. | 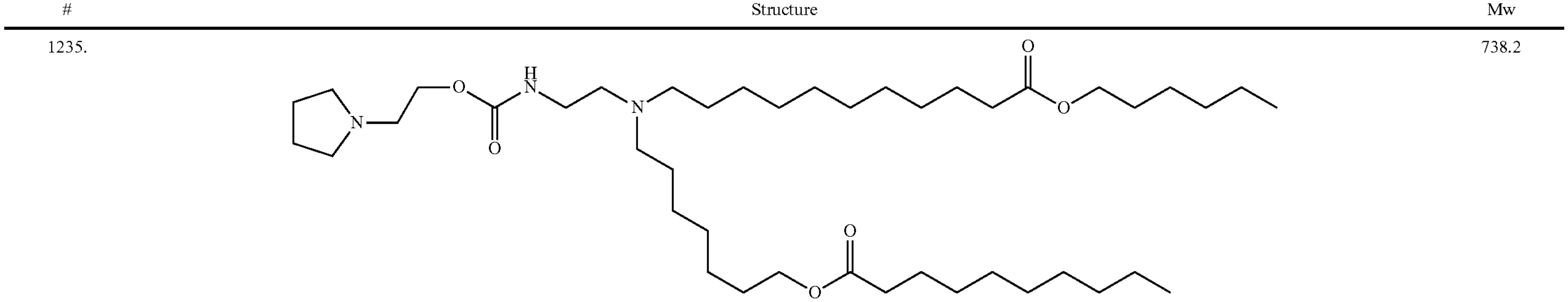 | 738.2 |
| 1236. | 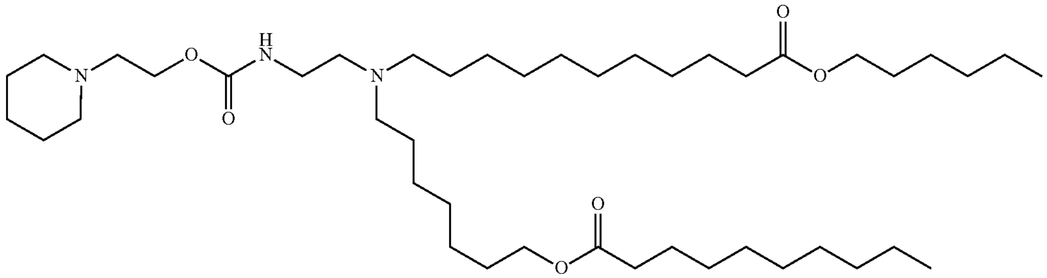 [SMILES: CCCCCCCCCC(=O)OCCCCCCCN(CCCCCCCCCCC(=O)OCCCCCC)CCNC(=O)OCCN1CCCCC1] | 752.2 |
| 1237. | 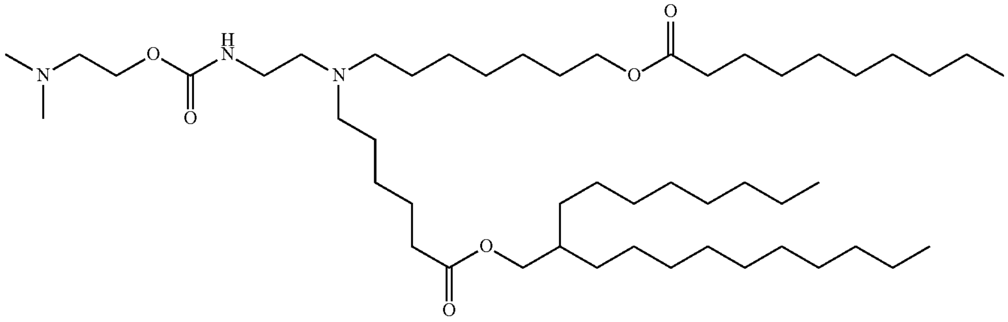 [SMILES: CCCCCCCCCCC(CCCCCCCC)COC(=O)CCCCCN(CCCCCCCOC(=O)CCCCCCCCC)CCNC(=O)OCCN(C)C] | 838.4 |

TABLE 1-continued
| # | Structure | Mw |
| --- | --- | --- |
| 1238. | 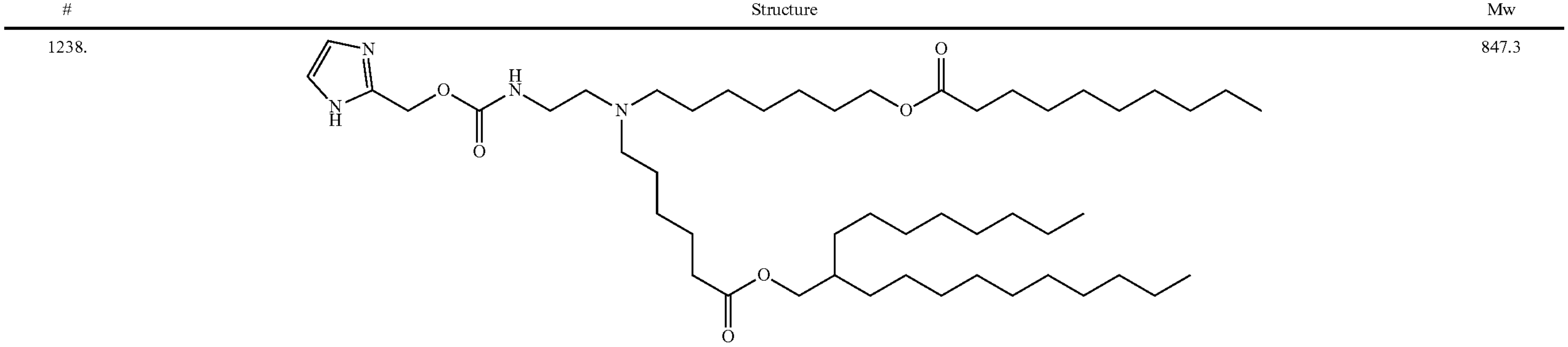 | 847.3 |
| 1239. | 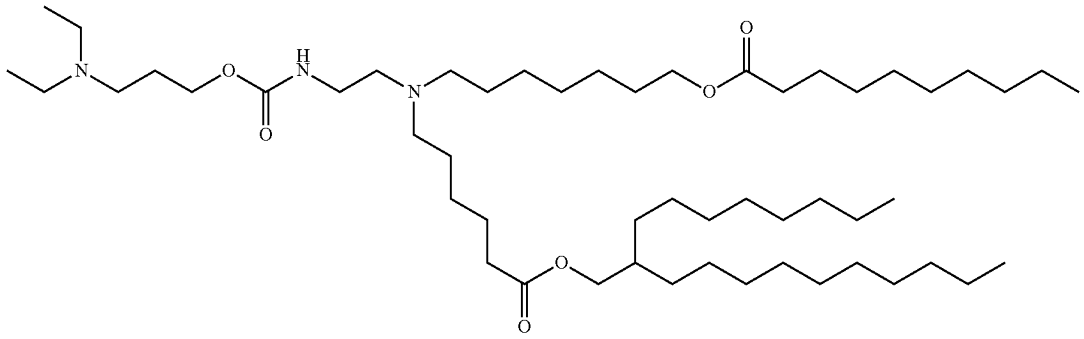 [SMILES: CCCCCCCCCCC(CCCCCCCC)COC(=O)CCCCCN(CCCCCCCOC(=O)CCCCCCCCC)CCNC(=O)OCCCN(CC)CC] | 880.4 |
| 1240. | 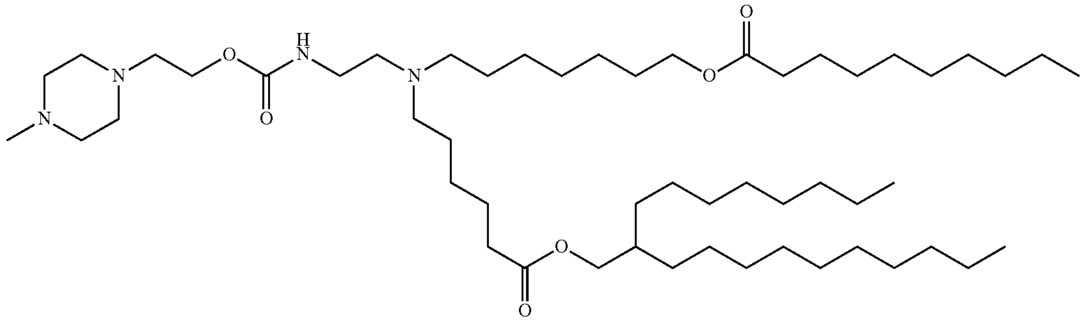 [SMILES: CCCCCCCCCCC(CCCCCCCC)COC(=O)CCCCCN(CCCCCCCOC(=O)CCCCCCCCC)CCNC(=O)OCCN1CCN(C)CC1] | 893.4 |

TABLE 1-continued
| # | Structure | Mw |
| --- | --- | --- |
| 1241. | 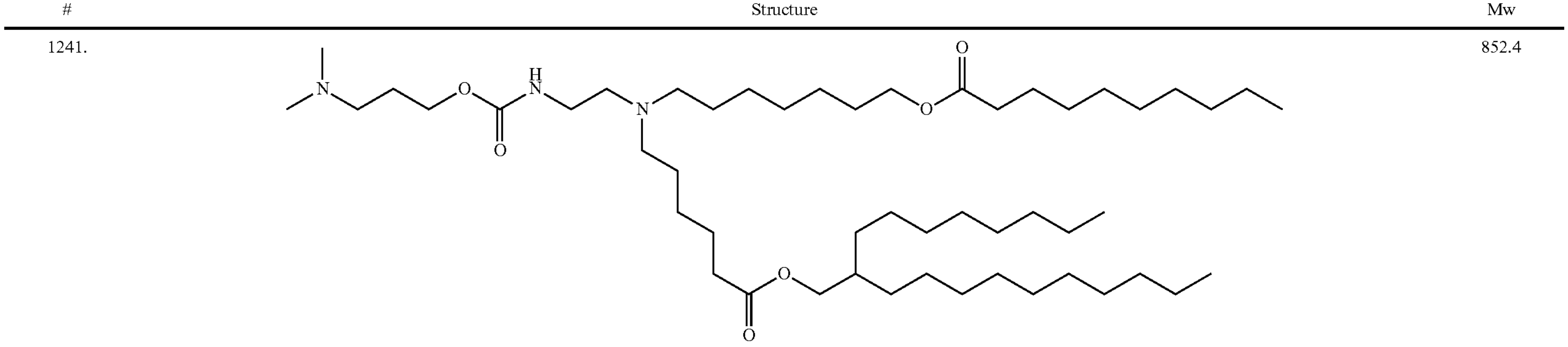 | 852.4 |
| 1242. | 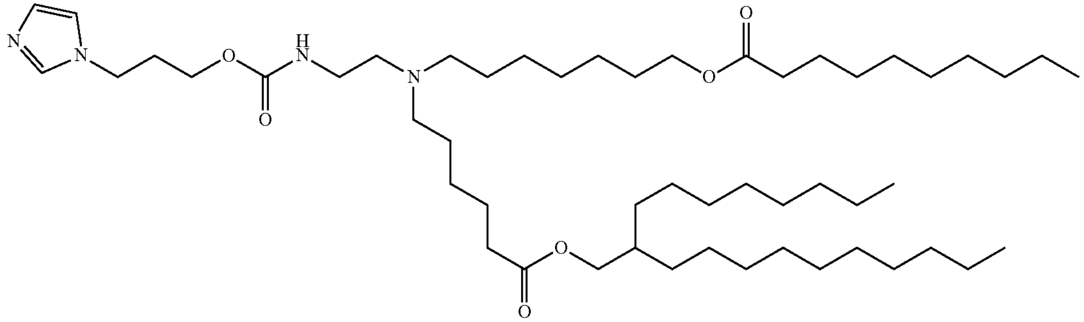 [SMILES: CCCCCCCCCCC(CCCCCCCC)COC(=O)CCCCCN(CCCCCCCOC(=O)CCCCCCCCC)CCNC(=O)OCCCn1ccnc1] | 875.4 |
| 1243. | 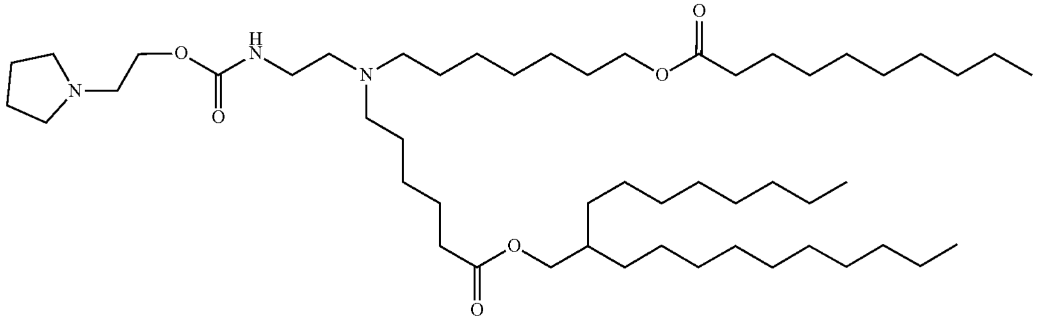 [SMILES: CCCCCCCCCCC(CCCCCCCC)COC(=O)CCCCCN(CCCCCCCOC(=O)CCCCCCCCC)CCNC(=O)OCCN1CCCC1] | 864.4 |

TABLE 1-continued
| # | Structure | Mw |
| --- | --- | --- |
| 1244. | 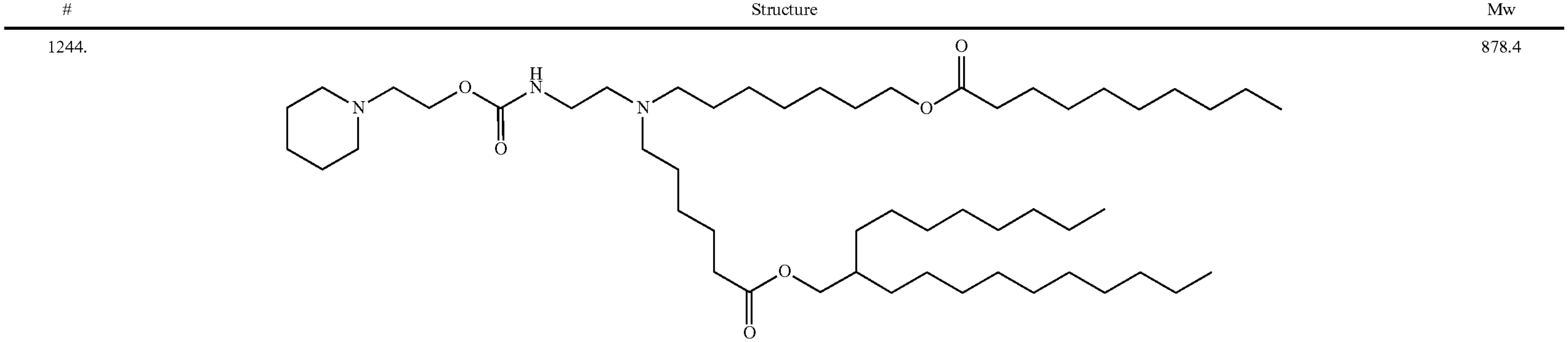 | 878.4 |
| 1245. | 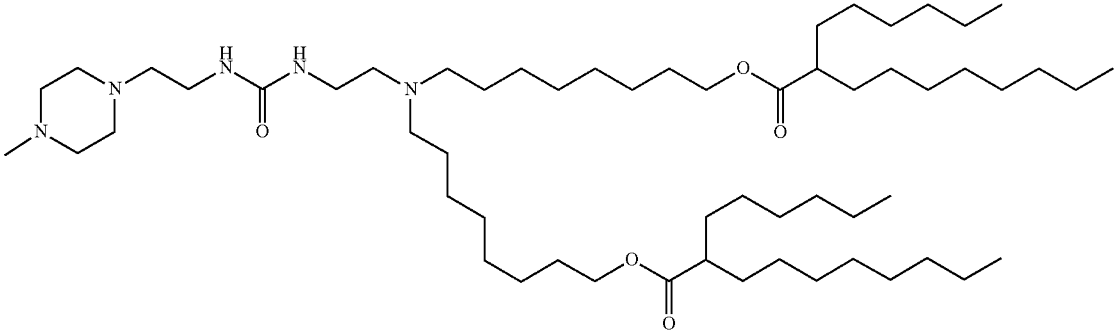 [SMILES: CCCCCCCCC(CCCCCC)C(=O)OCCCCCCCCN(CCCCCCCCOC(=O)C(CCCCCC)CCCCCCCC)CCNC(=O)NCCN1CCN(C)CC1] | 962.6 |
| 1246. | 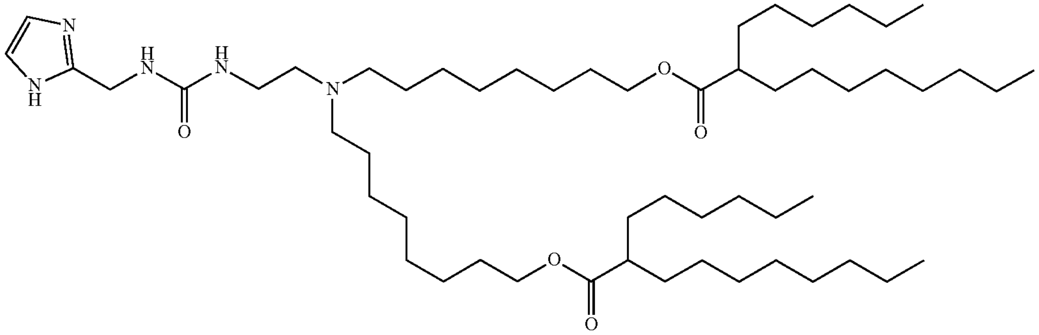 [SMILES: CCCCCCCCC(CCCCCC)C(=O)OCCCCCCCCN(CCCCCCCCOC(=O)C(CCCCCC)CCCCCCCC)CCNC(=O)NCc1ncc[nH]1] | 916.5 |

TABLE 1-continued
| # | Structure | Mw |
|---|---|---|
| 1247. | 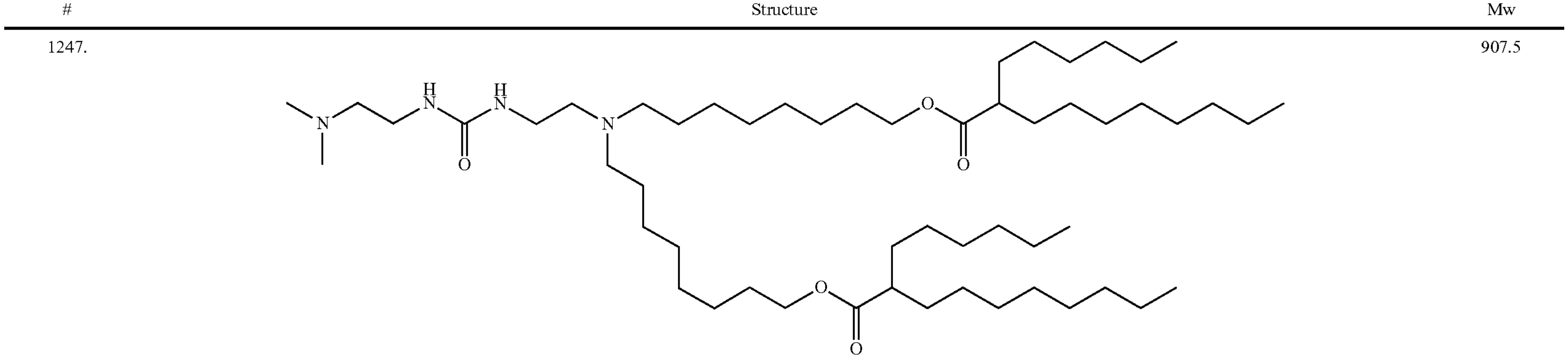 | 907.5 |
| 1248. | 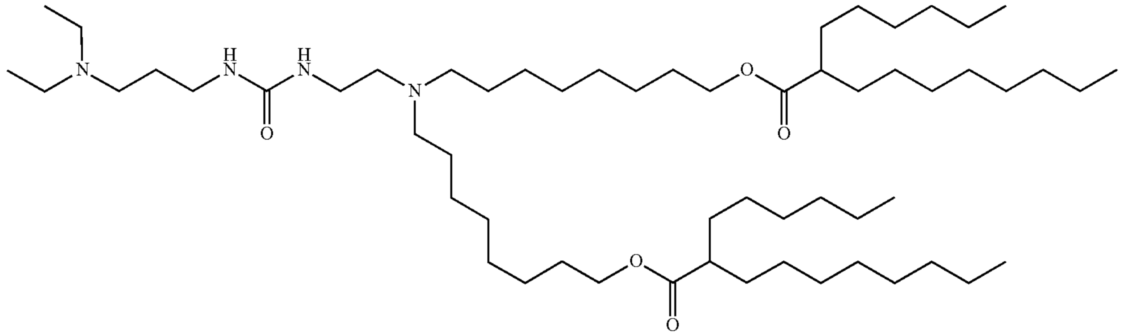 [SMILES: CCCCCCCCC(CCCCCC)C(=O)OCCCCCCCCN(CCCCCCCCOC(=O)C(CCCCCC)CCCCCCCC)CCNC(=O)NCCCN(CC)CC] | 949.6 |
| 1249. | 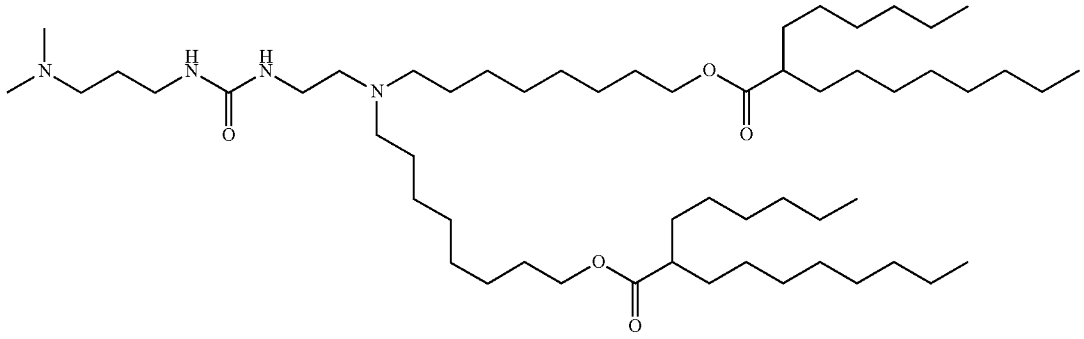 [SMILES: CCCCCCCCC(CCCCCC)C(=O)OCCCCCCCCN(CCCCCCCCOC(=O)C(CCCCCC)CCCCCCCC)CCNC(=O)NCCCN(C)C] | 921.5 |

TABLE 1-continued
| # | Structure | Mw |
|---|---|---|
| 1250. | 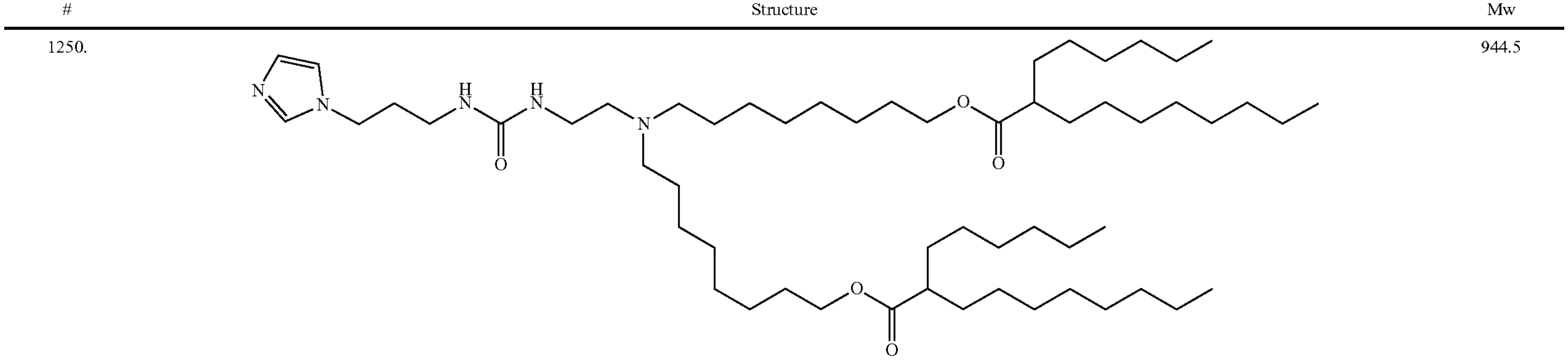 | 944.5 |
| 1251. | 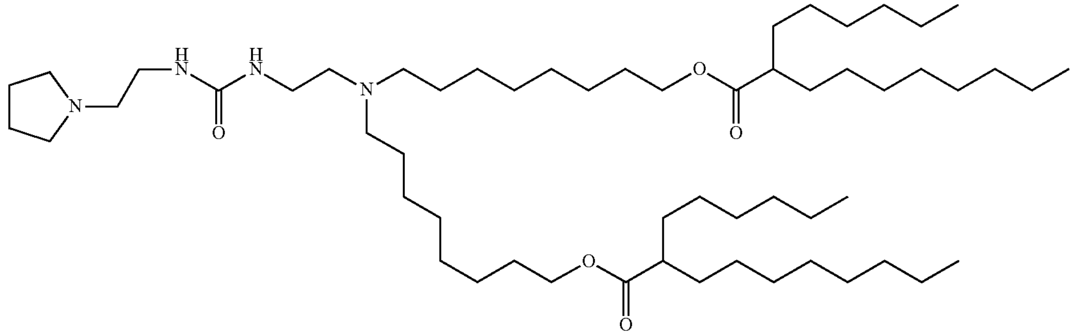 [SMILES: CCCCCCCCC(CCCCCC)C(=O)OCCCCCCCCN(CCCCCCCCOC(=O)C(CCCCCC)CCCCCCCC)CCNC(=O)NCCN1CCCC1] | 933.5 |
| 1252. | 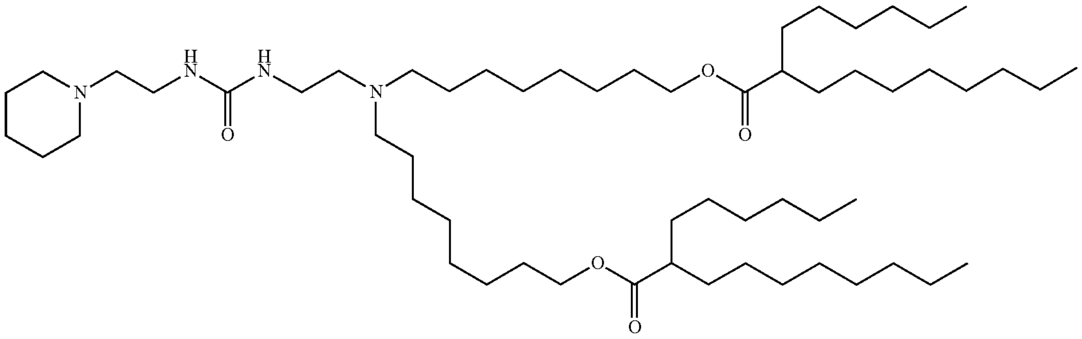 [SMILES: CCCCCCCCC(CCCCCC)C(=O)OCCCCCCCCN(CCCCCCCCOC(=O)C(CCCCCC)CCCCCCCC)CCNC(=O)NCCN1CCCCC1] | 947.6 |

TABLE 1-continued
| # | Structure | Mw |
| --- | --- | --- |
| 1253. | 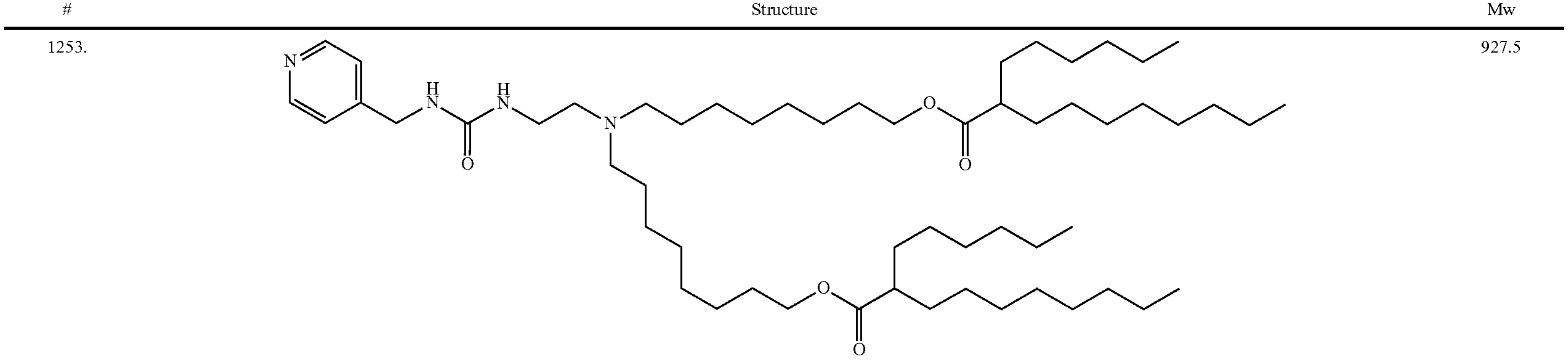 | 927.5 |
| 1254. | 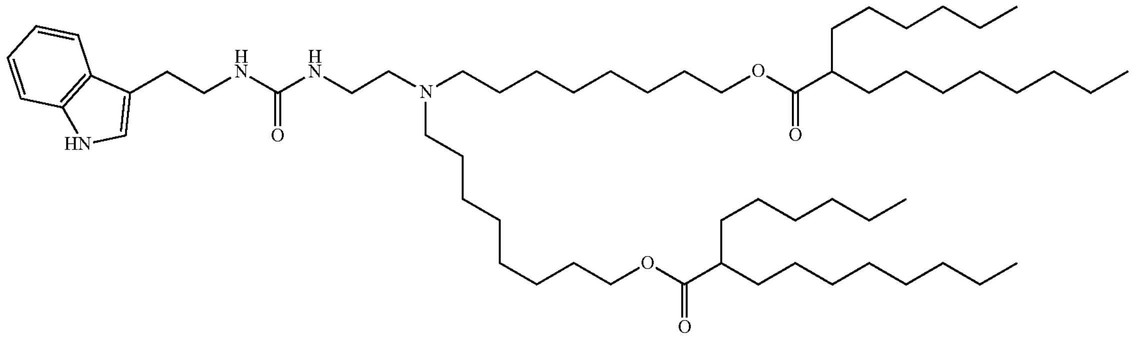 [SMILES: CCCCCCCCC(CCCCCC)C(=O)OCCCCCCCCN(CCCCCCCCOC(=O)C(CCCCCC)CCCCCCCC)CCNC(=O)NCCc1c[nH]c2ccccc12] | 979.6 |
| 1255. | 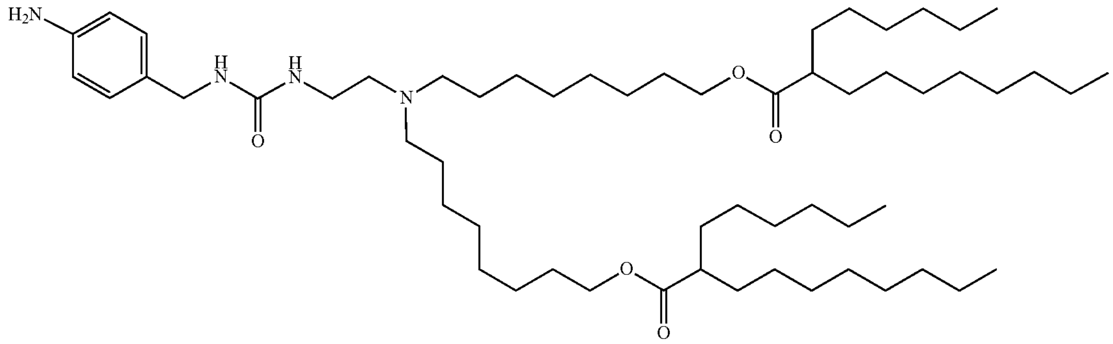 [SMILES: CCCCCCCCC(CCCCCC)C(=O)OCCCCCCCCN(CCCCCCCCOC(=O)C(CCCCCC)CCCCCCCC)CCNC(=O)NCc1ccc(N)cc1] | 941.5 |

TABLE 1-continued
| # | Structure | Mw |
| --- | --- | --- |
| 1256. | 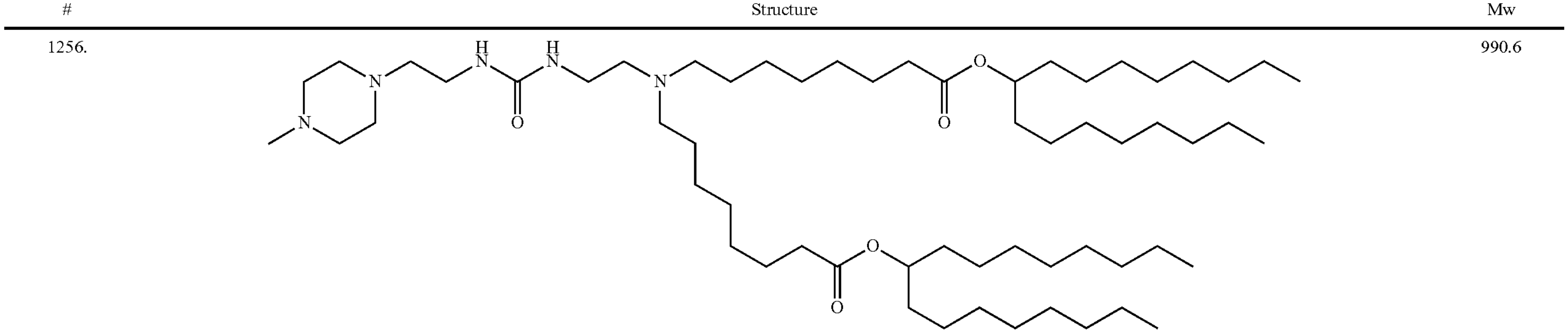 | 990.6 |
| 1257. | 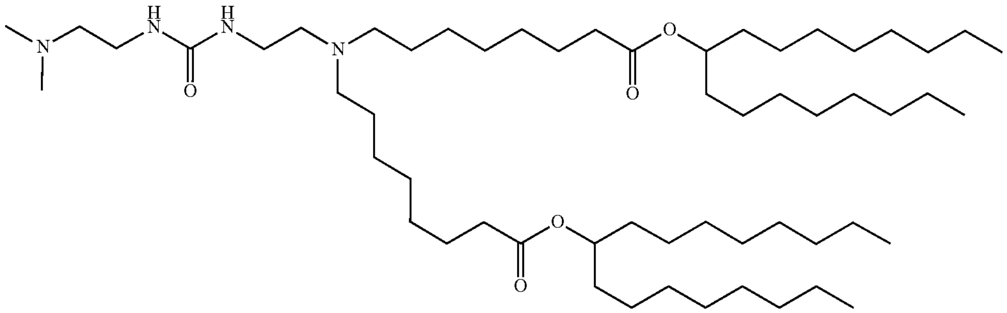 [SMILES: CCCCCCCCC(CCCCCCCC)OC(=O)CCCCCCCN(CCCCCCCC(=O)OC(CCCCCCCC)CCCCCCCC)CCNC(=O)NCCN(C)C] | 935.6 |
| 1258. | 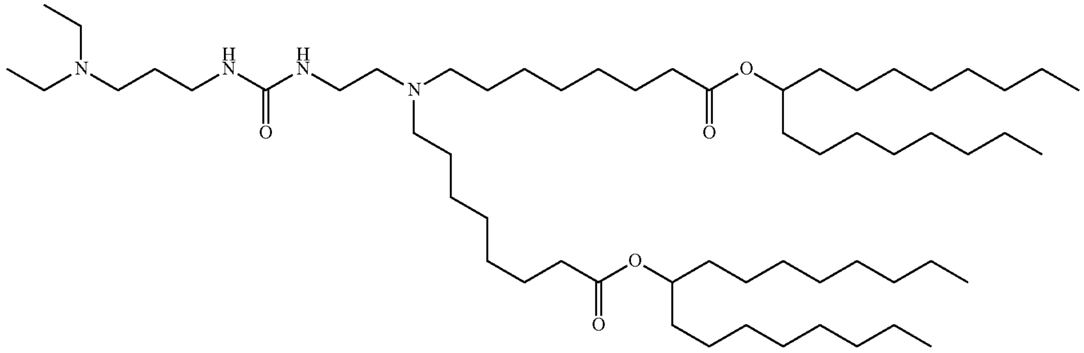 [SMILES: CCCCCCCCC(CCCCCCCC)OC(=O)CCCCCCCN(CCCCCCCC(=O)OC(CCCCCCCC)CCCCCCCC)CCNC(=O)NCCCN(CC)CC] | 977.6 |

TABLE 1-continued
| # | Structure | Mw |
| --- | --- | --- |
| 1259. | 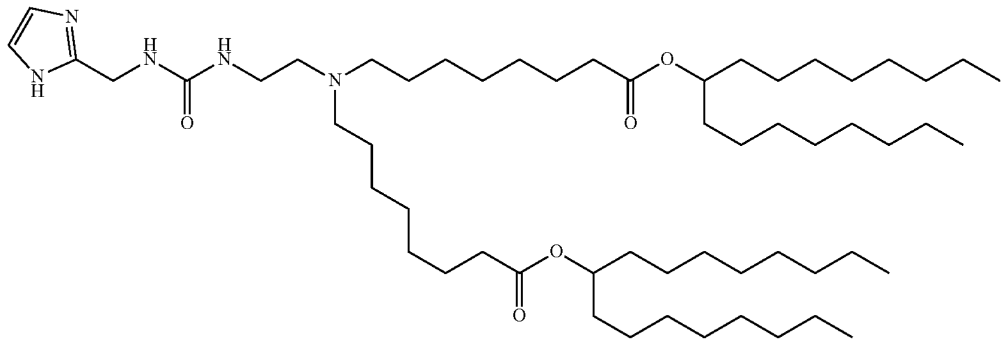 [SMILES: CCCCCCCCC(CCCCCCCC)OC(=O)CCCCCCCN(CCCCCCCC(=O)OC(CCCCCCCC)CCCCCCCC)CCNC(=O)NCc1ncc[nH]1] | 944.5 |
| 1260. | 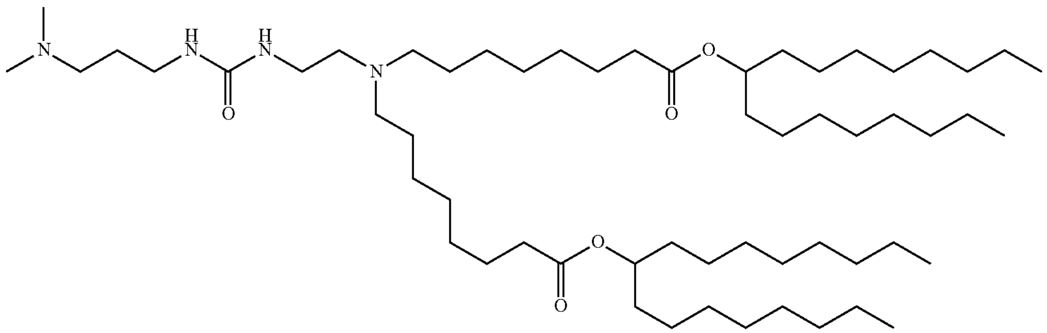 [SMILES: CCCCCCCCC(CCCCCCCC)OC(=O)CCCCCCCN(CCCCCCCC(=O)OC(CCCCCCCC)CCCCCCCC)CCNC(=O)NCCCN(C)C] | 949.6 |
| 1261. | 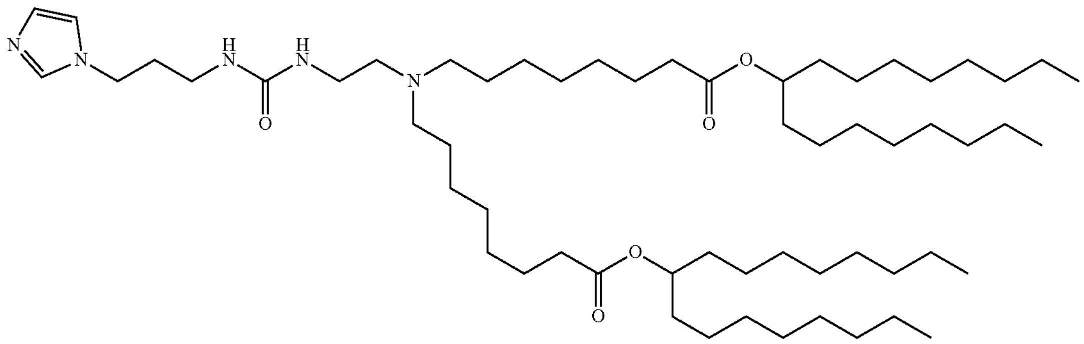 [SMILES: CCCCCCCCC(CCCCCCCC)OC(=O)CCCCCCCN(CCCCCCCC(=O)OC(CCCCCCCC)CCCCCCCC)CCNC(=O)NCCCn1ccnc1] | 972.6 |

TABLE 1-continued
| # | Structure | Mw |
|---|---|---|
| 1262. | 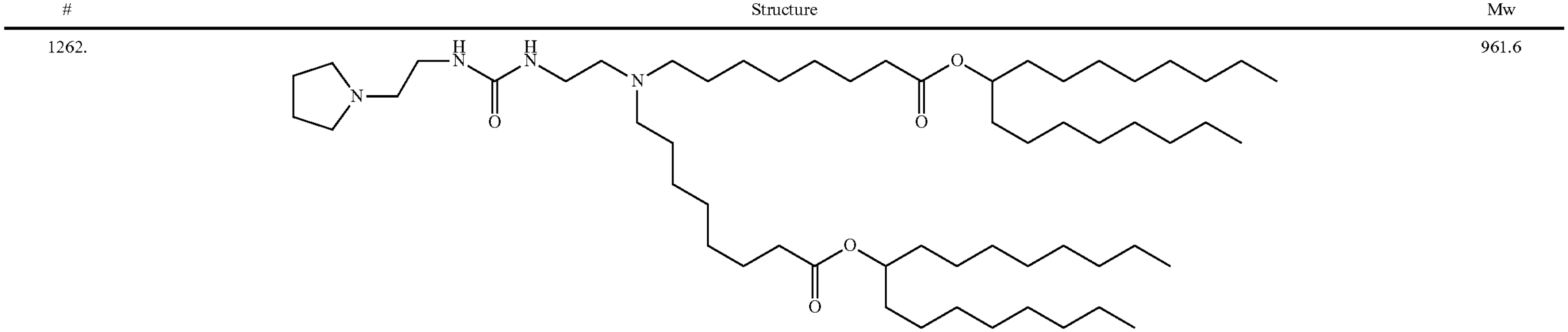 | 961.6 |
| 1263. | 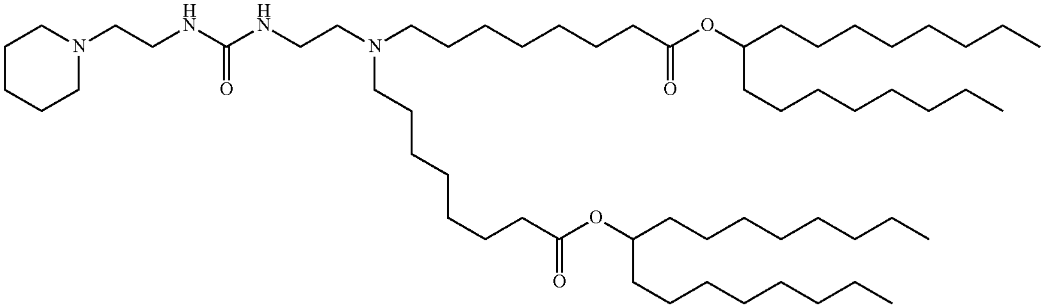 [SMILES: CCCCCCCCC(CCCCCCCC)OC(=O)CCCCCCCN(CCCCCCCC(=O)OC(CCCCCCCC)CCCCCCCC)CCNC(=O)NCCN1CCCCC1] | 975.6 |
| 1264. | 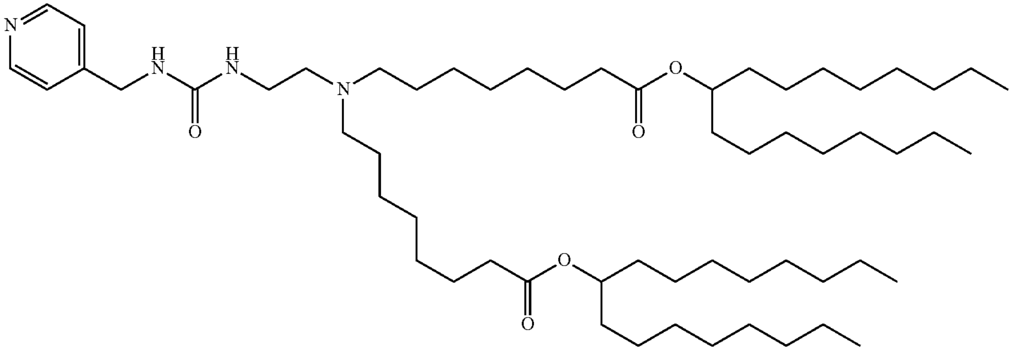 [SMILES: CCCCCCCCC(CCCCCCCC)OC(=O)CCCCCCCN(CCCCCCCC(=O)OC(CCCCCCCC)CCCCCCCC)CCNC(=O)NCc1ccncc1] | 955.6 |

TABLE 1-continued
| # | Structure | Mw |
| --- | --- | --- |
| 1265. | 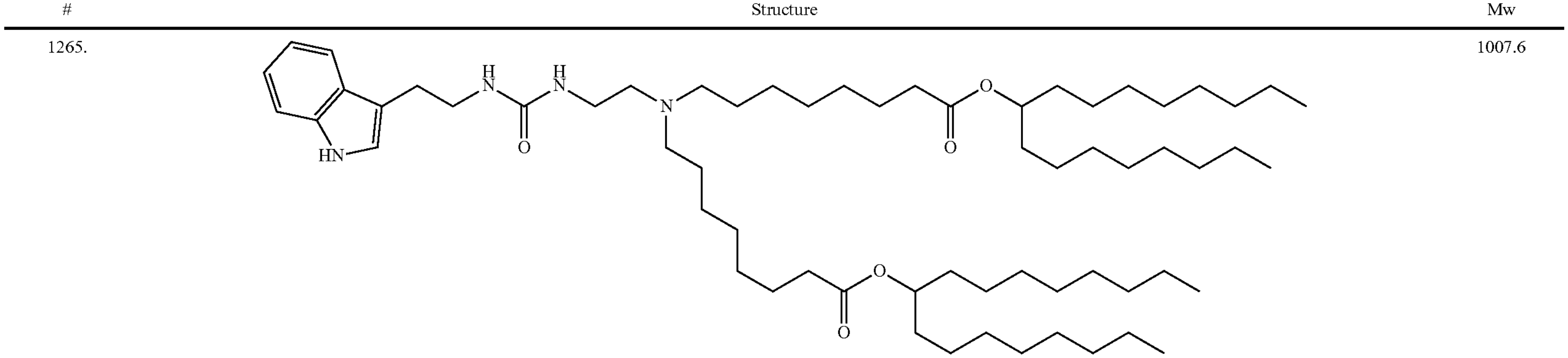 | 1007.6 |
| 1266. | 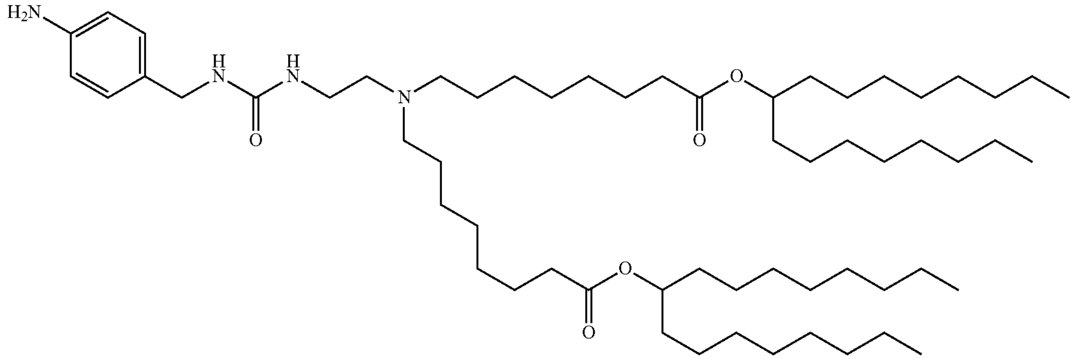 [SMILES: CCCCCCCCC(CCCCCCCC)OC(=O)CCCCCCCN(CCCCCCCC(=O)OC(CCCCCCCC)CCCCCCCC)CCNC(=O)NCc1ccc(N)cc1] | 969.6 |
| 1267. | 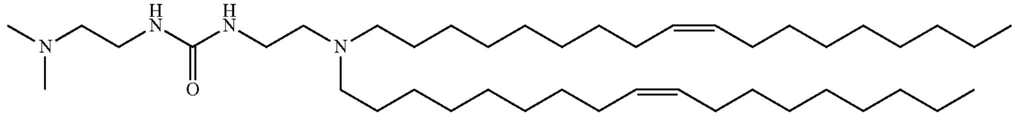 [SMILES: CCCCCCCC/C=C\CCCCCCCCN(CCCCCCCC/C=C\CCCCCCCC)CCNC(=O)NCCN(C)C] | 675.2 |
| 1268. | 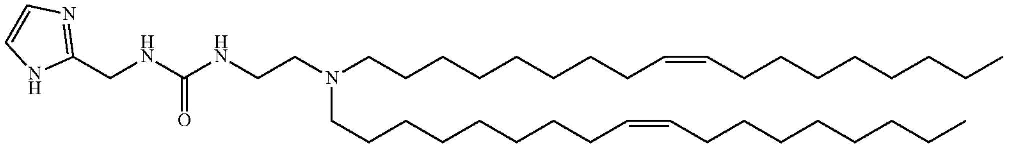 [SMILES: CCCCCCCC/C=C\CCCCCCCCN(CCCCCCCC/C=C\CCCCCCCC)CCNC(=O)NCc1ncc[nH]1] | 684.2 |

TABLE 1-continued
| # | Structure | Mw |
|---|---|---|
| 1269. | 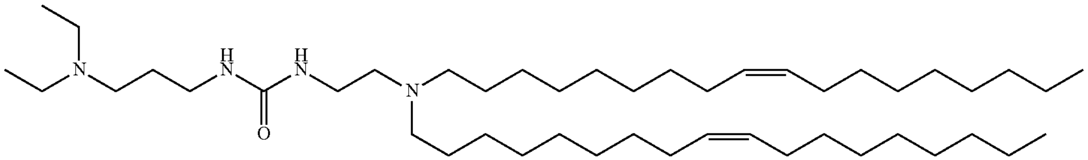 | 717.3 |
| 1270. | 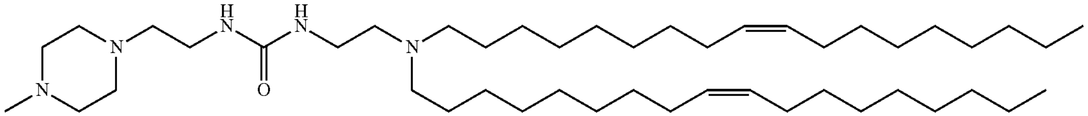 | 730.3 |
| 1271. | 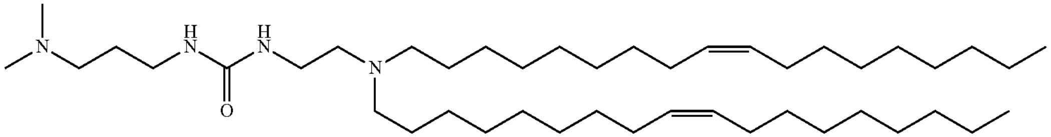 [SMILES: CCCCCCCC/C=C\CCCCCCCCN(CCCCCCCC/C=C\CCCCCCCC)CCNC(=O)NCCCN(C)C] | 689.2 |
| 1272. | 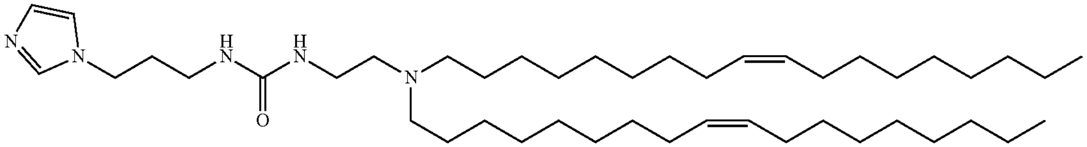 [SMILES: CCCCCCCC/C=C\CCCCCCCCN(CCCCCCCC/C=C\CCCCCCCC)CCNC(=O)NCCCn1ccnc1] | 712.2 |
| 1273. | 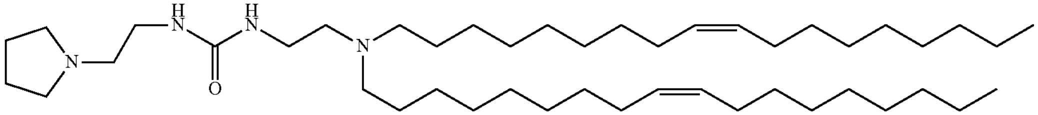 [SMILES: CCCCCCCC/C=C\CCCCCCCCN(CCCCCCCC/C=C\CCCCCCCC)CCNC(=O)NCCN1CCCC1] | 701.2 |
| 1274. | 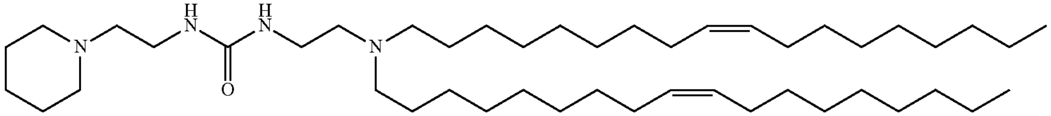 | 715.3 |
| 1275. | 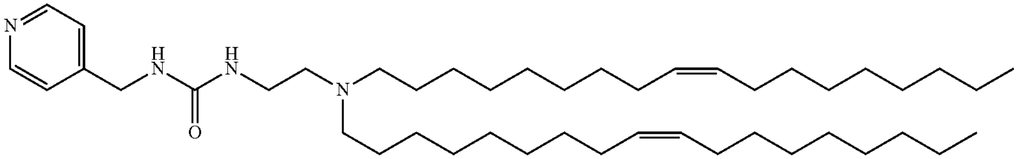 [SMILES: CCCCCCCC/C=C\CCCCCCCCN(CCCCCCCC/C=C\CCCCCCCC)CCNC(=O)NCc1ccncc1] | 695.2 |

TABLE 1-continued
| # | Structure | Mw |
| --- | --- | --- |
| 1276. | 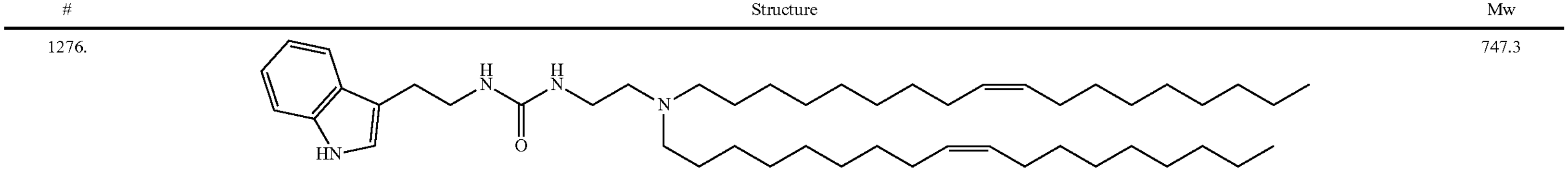 | 747.3 |
| 1277. | 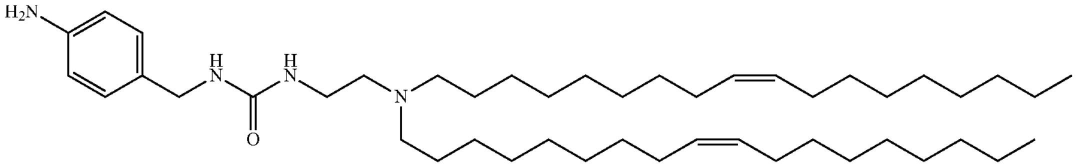 [SMILES: CCCCCCCC/C=C\CCCCCCCCN(CCCCCCCC/C=C\CCCCCCCC)CCNC(=O)NCc1ccc(N)cc1] | 709.2 |
| 1278. | 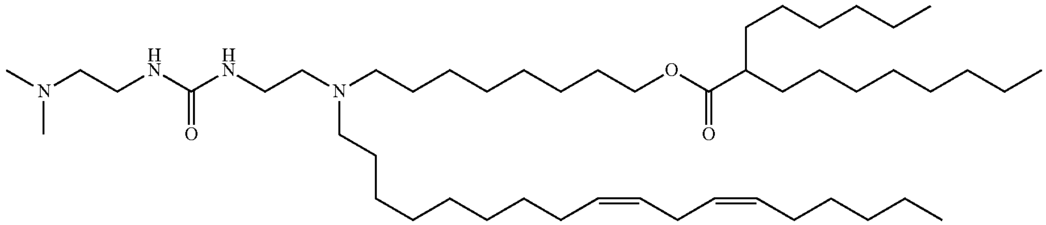 | 789.3 |
| 1279. | 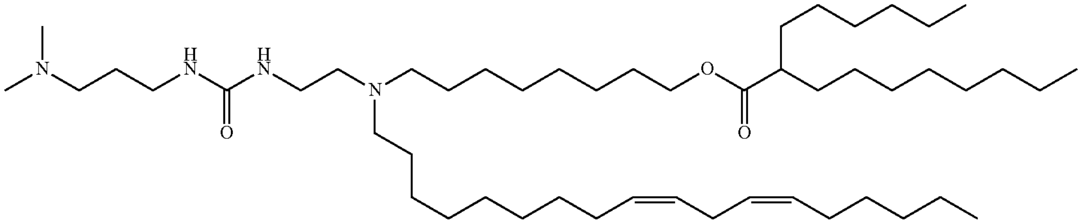 [SMILES: CCCCC/C=C\C/C=C\CCCCCCCCN(CCCCCCCCOC(=O)C(CCCCCC)CCCCCCCC)CCNC(=O)NCCCN(C)C] | 803.4 |
| 1280. | 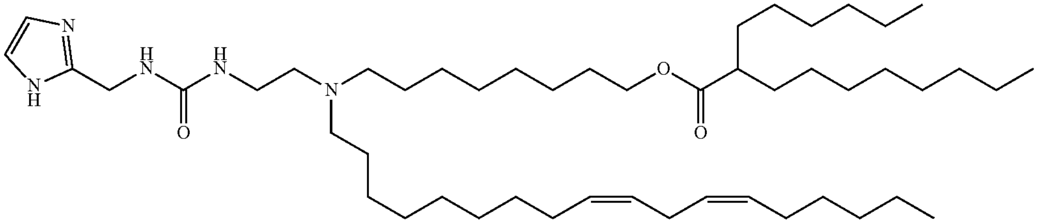 | 798.3 |

TABLE 1-continued
| # | Structure | Mw |
| --- | --- | --- |
| 1281. | 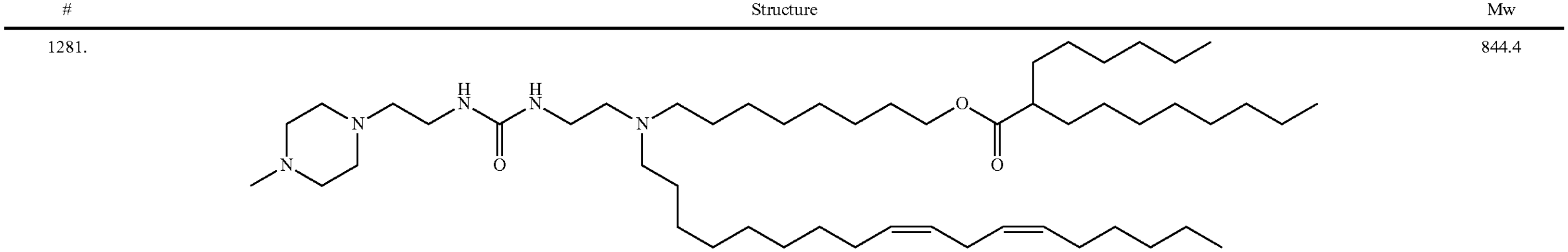 | 844.4 |
| 1282. | 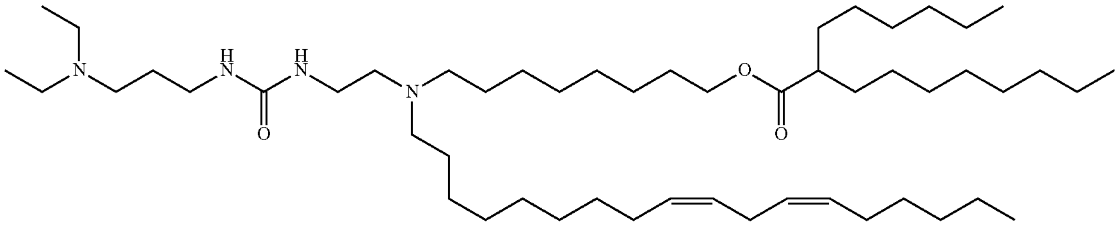 [SMILES: CCCCC/C=C\C/C=C\CCCCCCCCN(CCCCCCCCOC(=O)C(CCCCCC)CCCCCCCC)CCNC(=O)NCCCN(CC)CC] | 831.4 |
| 1283. | 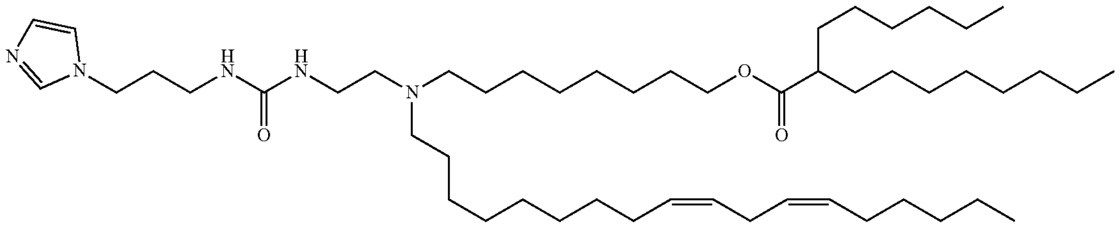 | 826.4 |
| 1284. | 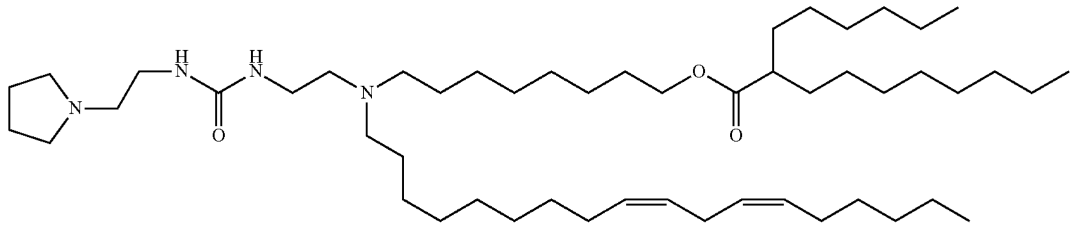 [SMILES: CCCCC/C=C\C/C=C\CCCCCCCCN(CCCCCCCCOC(=O)C(CCCCCC)CCCCCCCC)CCNC(=O)NCCN1CCCC1] | 815.4 |

TABLE 1-continued
| # | Structure | Mw |
|---|---|---|
| 1285. | 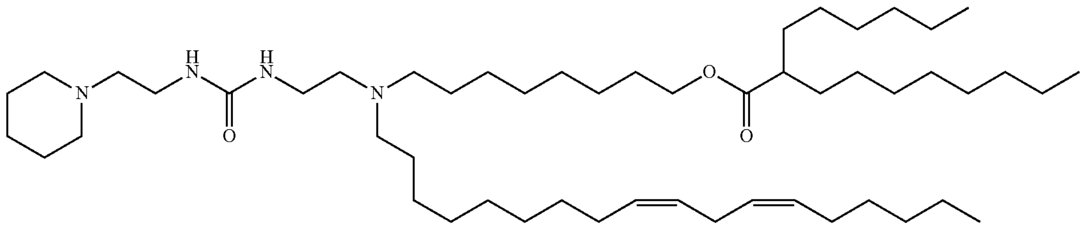 [SMILES: CCCCC/C=C\C/C=C\CCCCCCCCN(CCCCCCCCOC(=O)C(CCCCCC)CCCCCCCC)CCNC(=O)NCCN1CCCCC1] | 829.4 |
| 1286. | 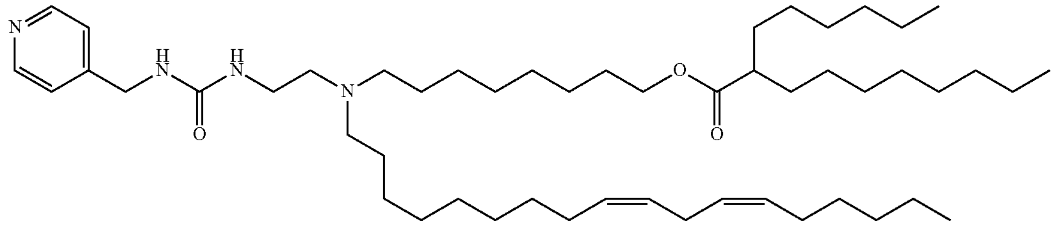 [SMILES: CCCCC/C=C\C/C=C\CCCCCCCCN(CCCCCCCCOC(=O)C(CCCCCC)CCCCCCCC)CCNC(=O)NCc1ccncc1] | 809.3 |
| 1287. | 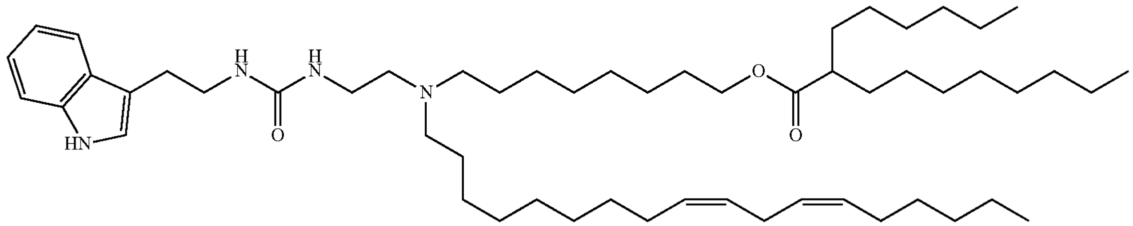 [SMILES: CCCCC/C=C\C/C=C\CCCCCCCCN(CCCCCCCCOC(=O)C(CCCCCC)CCCCCCCC)CCNC(=O)NCCc1c[nH]c2ccccc12] | 861.4 |
| 1288. | 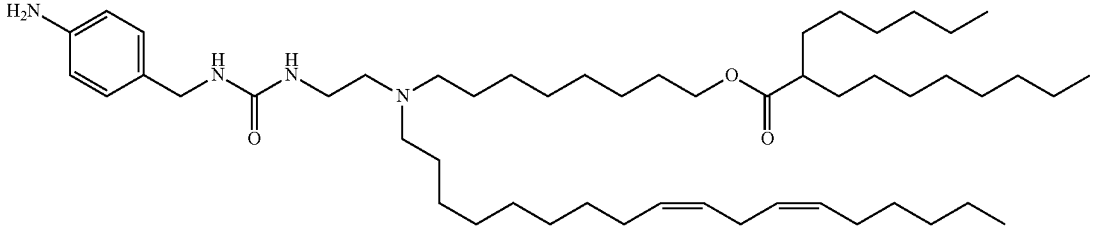 [SMILES: CCCCC/C=C\C/C=C\CCCCCCCCN(CCCCCCCCOC(=O)C(CCCCCC)CCCCCCCC)CCNC(=O)NCc1ccc(N)cc1] | 823.3 |
| 1289. | 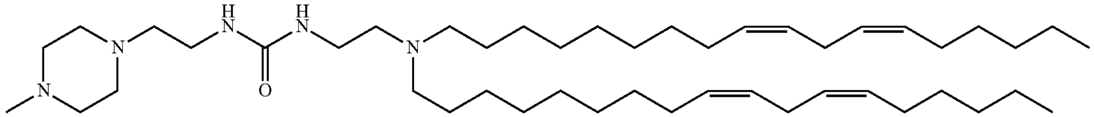 | 726.2 |

TABLE 1-continued
| # | Structure | Mw |
| --- | --- | --- |
| 1290. | 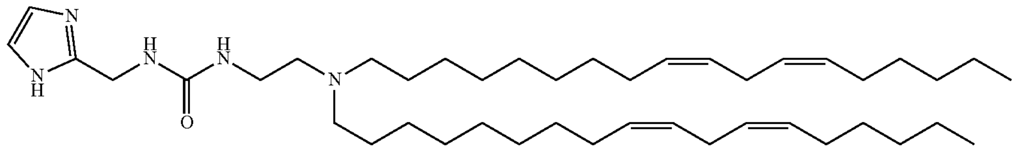 | 680.1 |
| 1291. | 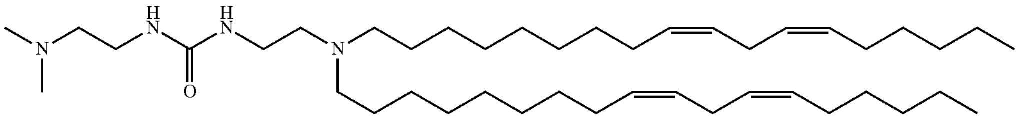 | 672.1 |
| 1292. | 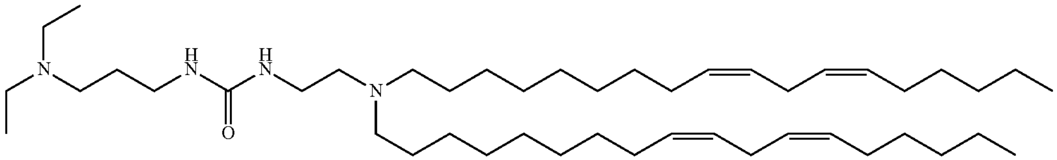 [SMILES: CCCCC/C=C\C/C=C\CCCCCCCCN(CCCCCCCC/C=C\C/C=C\CCCCC)CCNC(=O)NCCCN(CC)CC] | 713.2 |
| 1293. | 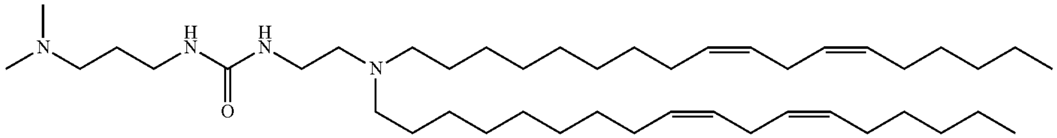 | 685.2 |
| 1294. | 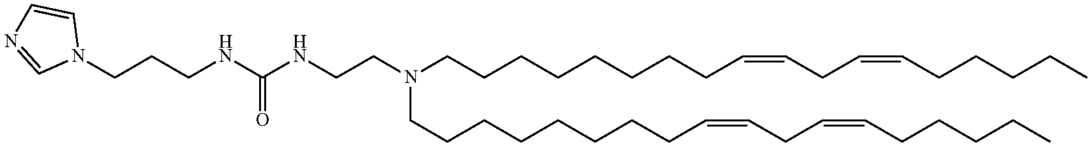 [SMILES: CCCCC/C=C\C/C=C\CCCCCCCCN(CCCCCCCC/C=C\C/C=C\CCCCC)CCNC(=O)NCCCn1ccnc1] | 708.2 |
| 1295. | 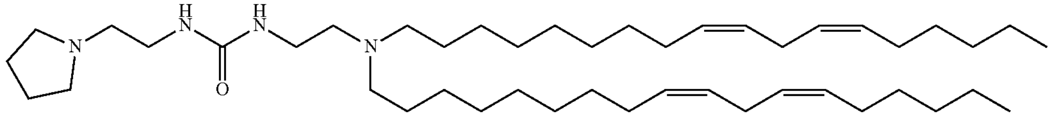 | 697.2 |
| 1296. | 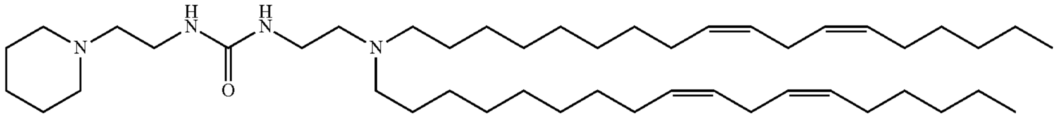 | 711.2 |

TABLE 1-continued
| # | Structure | Mw |
| --- | --- | --- |
| 1297. | 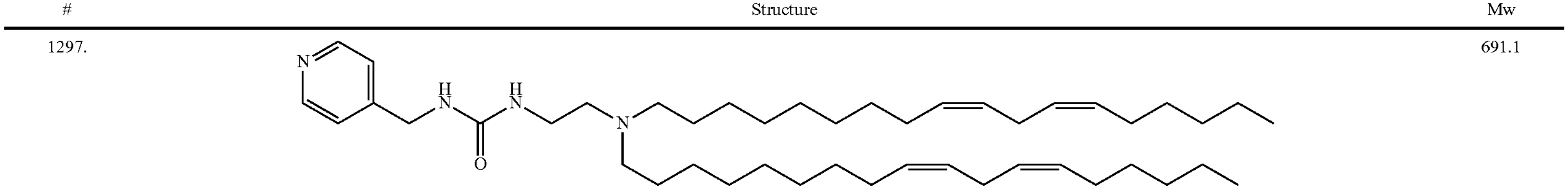 | 691.1 |
| 1298. | 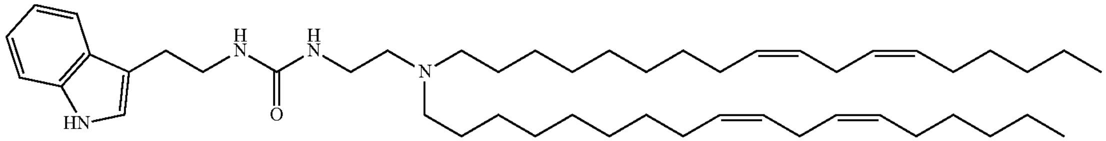 | 743.2 |
| 1299. | 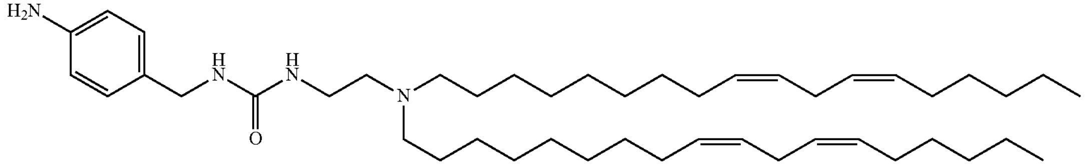 [SMILES: CCCCC/C=C\C/C=C\CCCCCCCCN(CCCCCCCC/C=C\C/C=C\CCCCC)CCNC(=O)NCc1ccc(N)cc1] | 705.2 |
| 1300. | 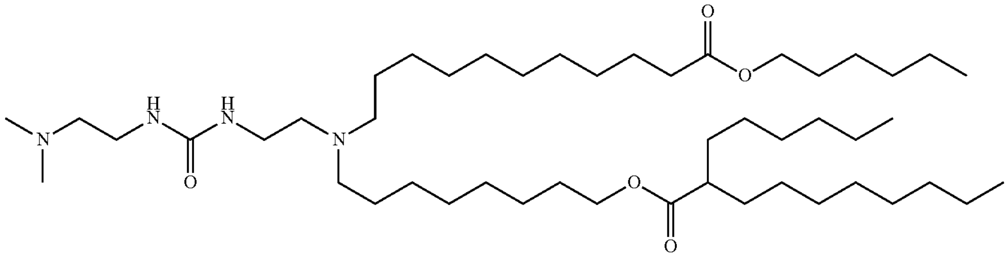 [SMILES: CCCCCCCCC(CCCCCC)C(=O)OCCCCCCCCN(CCCCCCCCCCC(=O)OCCCCCC)CCNC(=O)NCCN(C)C] | 809.3 |
| 1301. | 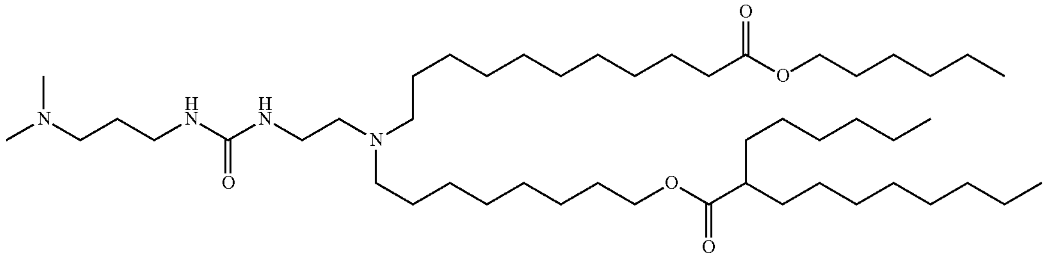 [SMILES: CCCCCCCCC(CCCCCC)C(=O)OCCCCCCCCN(CCCCCCCCCCC(=O)OCCCCCC)CCNC(=O)NCCCN(C)C] | 823.3 |

TABLE 1-continued
| # | Structure | Mw |
| --- | --- | --- |
| 1302. | 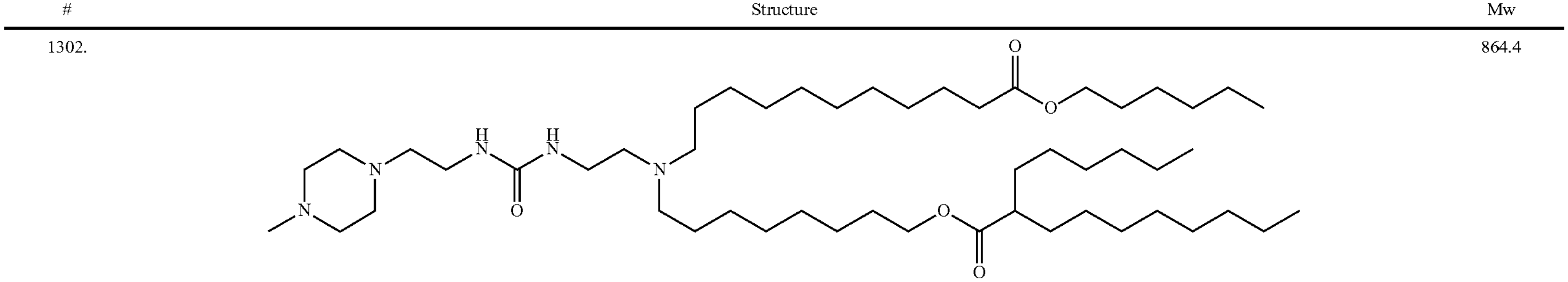 | 864.4 |
| 1303. | 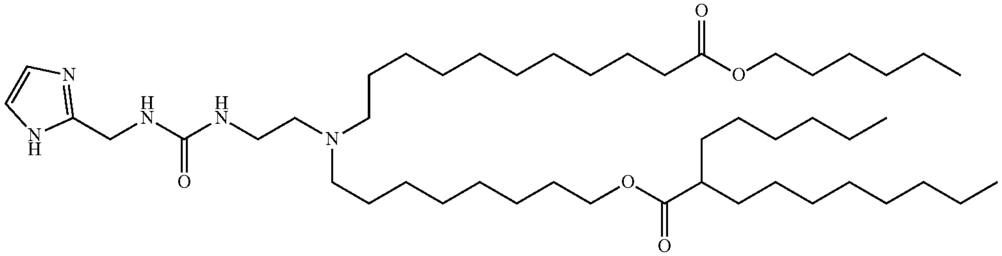 [SMILES: CCCCCCCCC(CCCCCC)C(=O)OCCCCCCCCN(CCCCCCCCCCC(=O)OCCCCCC)CCNC(=O)NCc1ncc[nH]1] | 818.3 |
| 1304. | 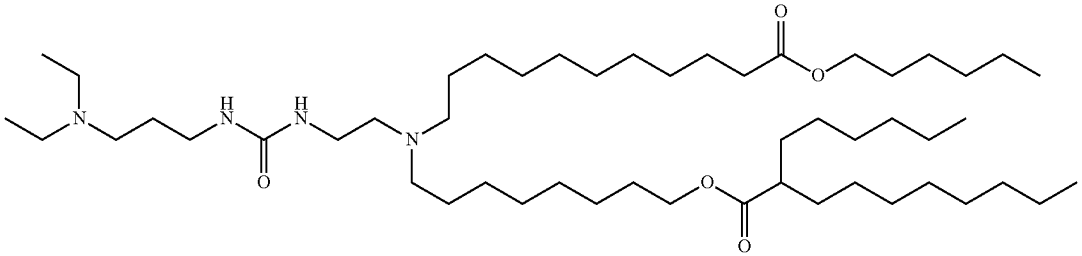 [SMILES: CCCCCCCCC(CCCCCC)C(=O)OCCCCCCCCN(CCCCCCCCCCC(=O)OCCCCCC)CCNC(=O)NCCCN(CC)CC] | 851.4 |
| 1305. | 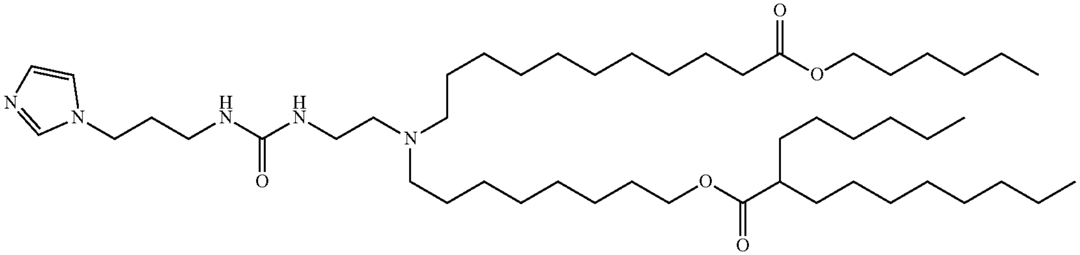 [SMILES: CCCCCCCCC(CCCCCC)C(=O)OCCCCCCCCN(CCCCCCCCCCC(=O)OCCCCCC)CCNC(=O)NCCCn1ccnc1] | 846.3 |

TABLE 1-continued
| # | Structure | Mw |
|---|---|---|
| 1306. | 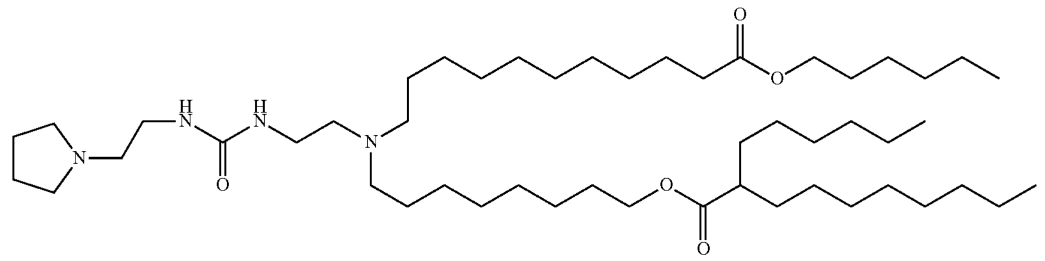 [SMILES: CCCCCCCCC(CCCCCC)C(=O)OCCCCCCCCN(CCCCCCCCCCC(=O)OCCCCCC)CCNC(=O)NCCN1CCCC1] | 835.4 |
| 1307. | 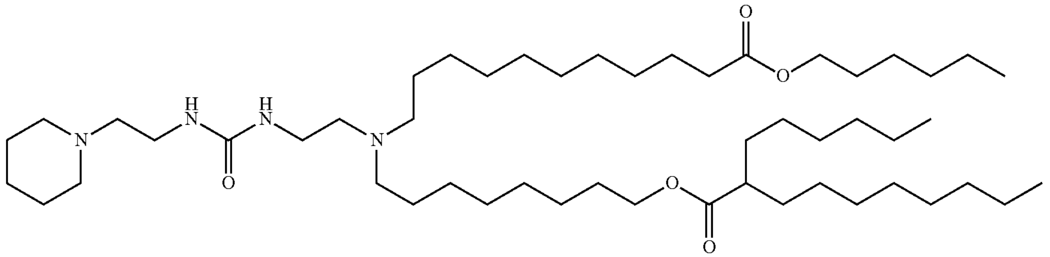 [SMILES: CCCCCCCCC(CCCCCC)C(=O)OCCCCCCCCN(CCCCCCCCCCC(=O)OCCCCCC)CCNC(=O)NCCN1CCCCC1] | 849.4 |
| 1308. | 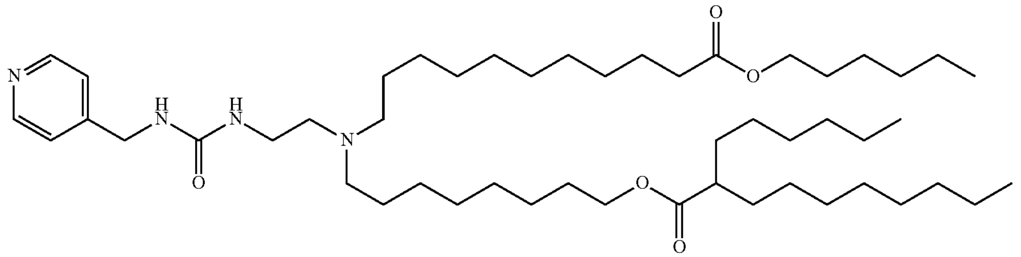 [SMILES: CCCCCCCCC(CCCCCC)C(=O)OCCCCCCCCN(CCCCCCCCCCC(=O)OCCCCCC)CCNC(=O)NCc1ccncc1] | 829.3 |

TABLE 1-continued
| # | Structure | Mw |
| --- | --- | --- |
| 1309. | 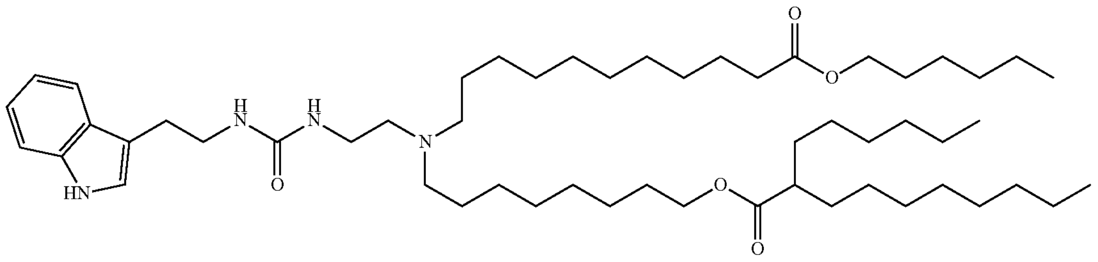 [SMILES: CCCCCCCCC(CCCCCC)C(=O)OCCCCCCCCN(CCCCCCCCCCC(=O)OCCCCCC)CCNC(=O)NCCc1c[nH]c2ccccc12] | 881.4 |
| 1310. | 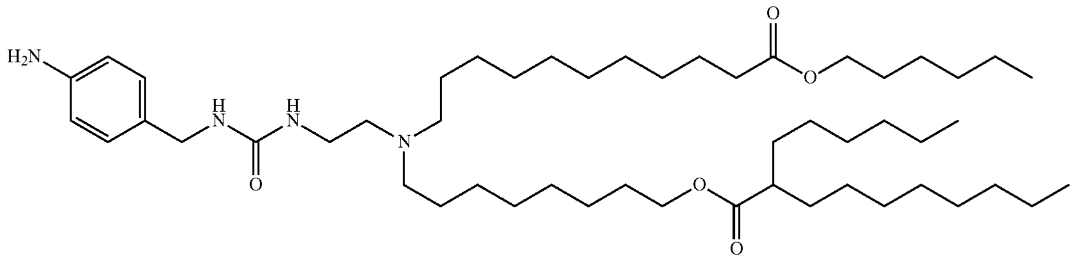 [SMILES: CCCCCCCCC(CCCCCC)C(=O)OCCCCCCCCN(CCCCCCCCCCC(=O)OCCCCCC)CCNC(=O)NCc1ccc(N)cc1] | 843.3 |
| 1311. | 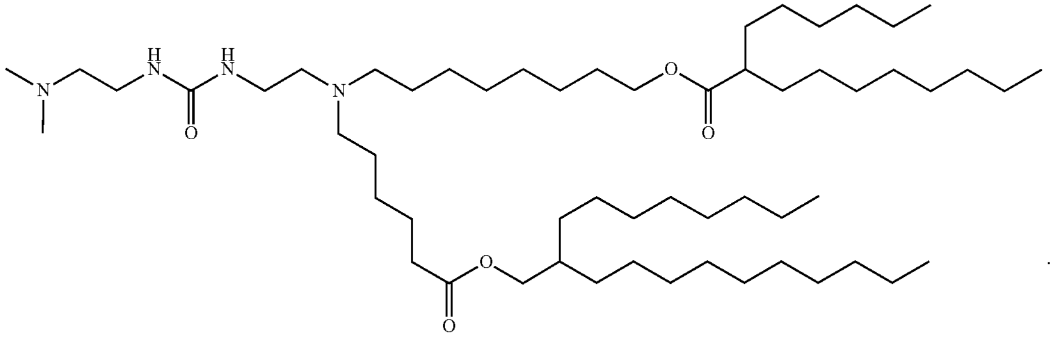 [SMILES: CCCCCCCCCCC(CCCCCCCC)COC(=O)CCCCCN(CCCCCCCCOC(=O)C(CCCCCC)CCCCCCCC)CCNC(=O)NCCN(C)C] | 935.6 |

TABLE 1-continued
| # | Structure | Mw |
|---|---|---|
| 1312. | 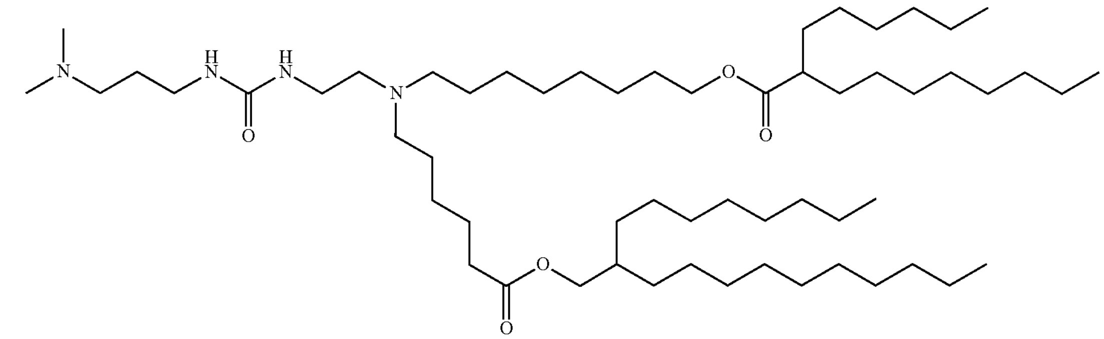 [SMILES: CCCCCCCCCCC(CCCCCCCC)COC(=O)CCCCCN(CCCCCCCCOC(=O)C(CCCCCC)CCCCCCCC)CCNC(=O)NCCCN(C)C] | 949.6 |
| 1313. | 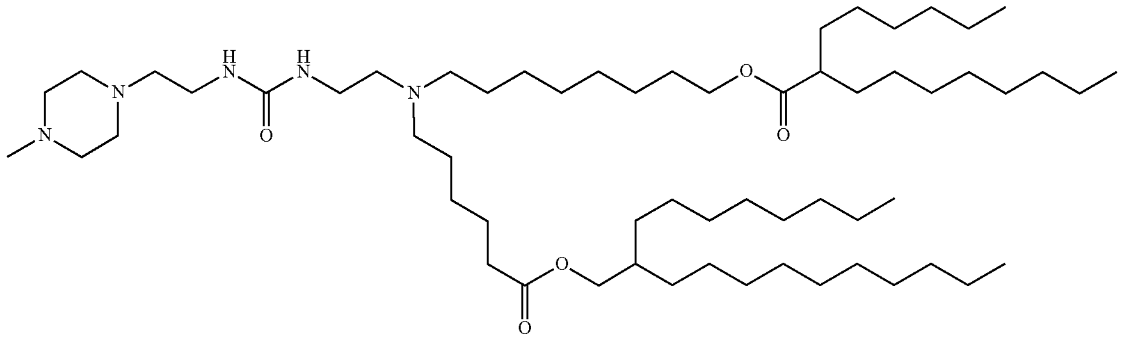 [SMILES: CCCCCCCCCCC(CCCCCCCC)COC(=O)CCCCCN(CCCCCCCCOC(=O)C(CCCCCC)CCCCCCCC)CCNC(=O)NCCN1CCN(C)CC1] | 990.6 |
| 1314. | 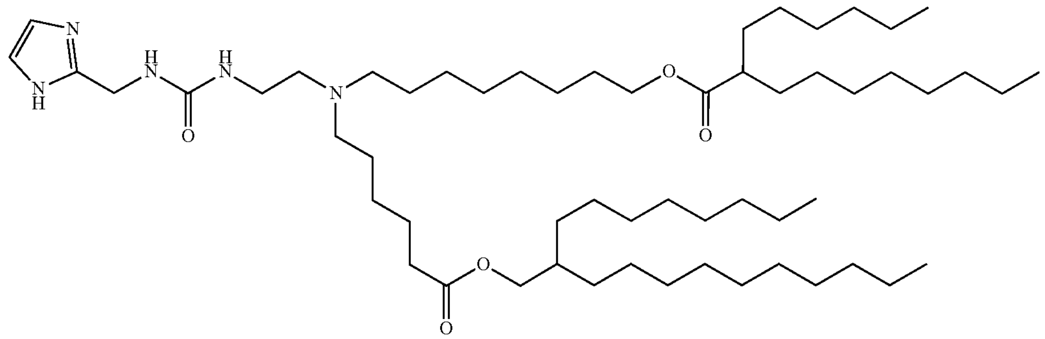 [SMILES: CCCCCCCCCCC(CCCCCCCC)COC(=O)CCCCCN(CCCCCCCCOC(=O)C(CCCCCC)CCCCCCCC)CCNC(=O)NCc1ncc[nH]1] | 944.5 |

TABLE 1-continued
| # | Structure | Mw |
|---|---|---|
| 1315. | 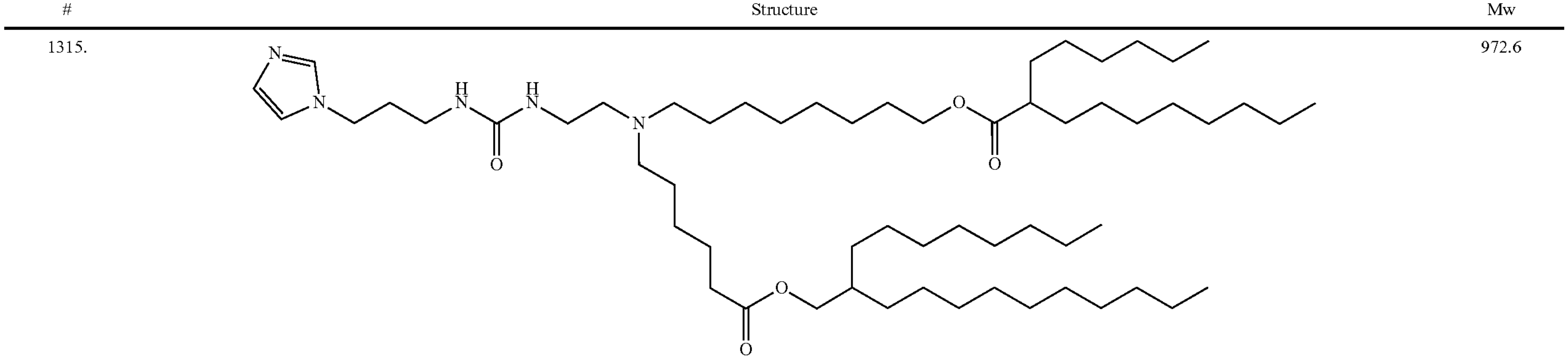 | 972.6 |
| 1316. | 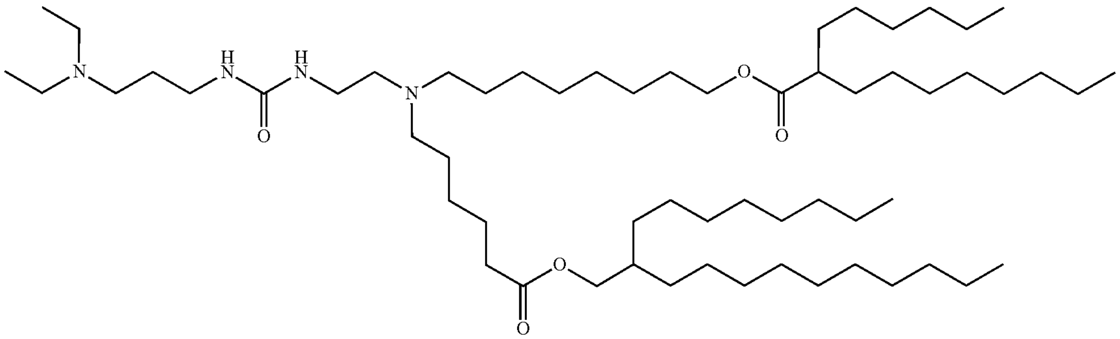 [SMILES: CCCCCCCCCCC(CCCCCCCC)COC(=O)CCCCCN(CCCCCCCCOC(=O)C(CCCCCC)CCCCCCCC)CCNC(=O)NCCCN(CC)CC] | 977.6 |
| 1317. | 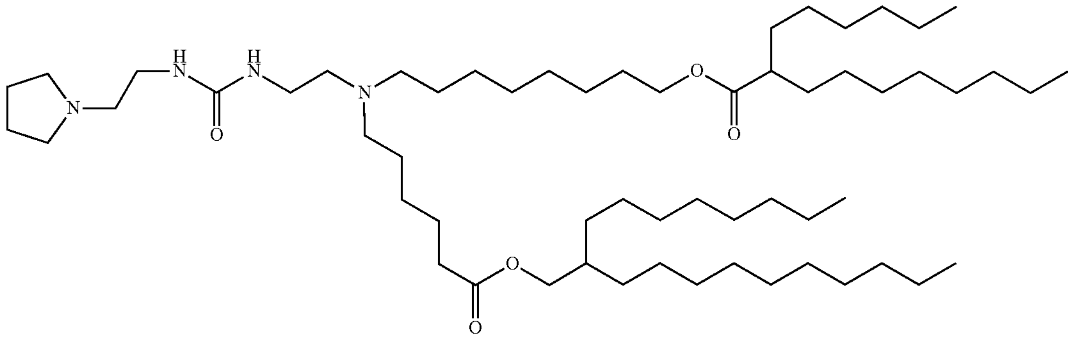 [SMILES: CCCCCCCCCCC(CCCCCCCC)COC(=O)CCCCCN(CCCCCCCCOC(=O)C(CCCCCC)CCCCCCCC)CCNC(=O)NCCN1CCCC1] | 961.6 |

TABLE 1-continued
| # | Structure | Mw |
| --- | --- | --- |
| 1318. | 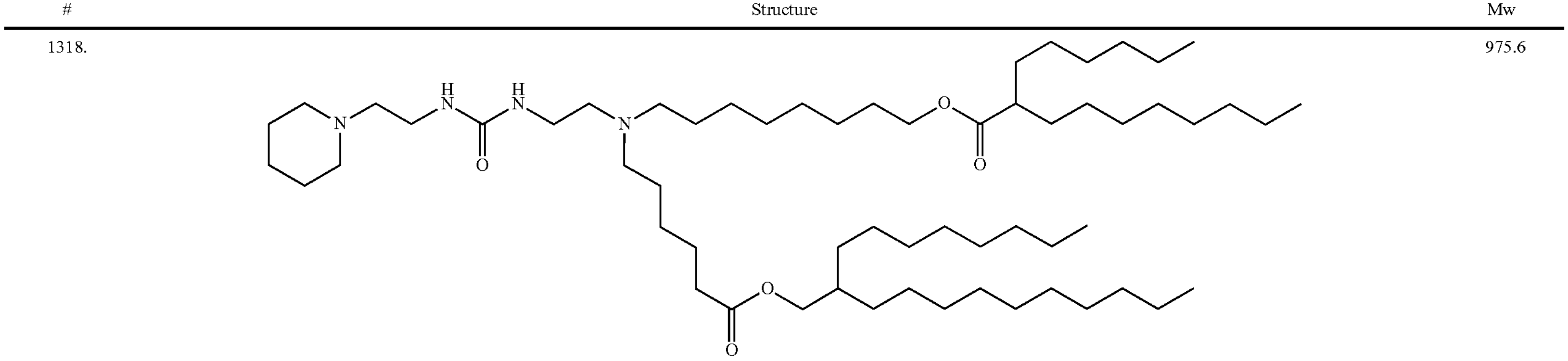 | 975.6 |
| 1319. | 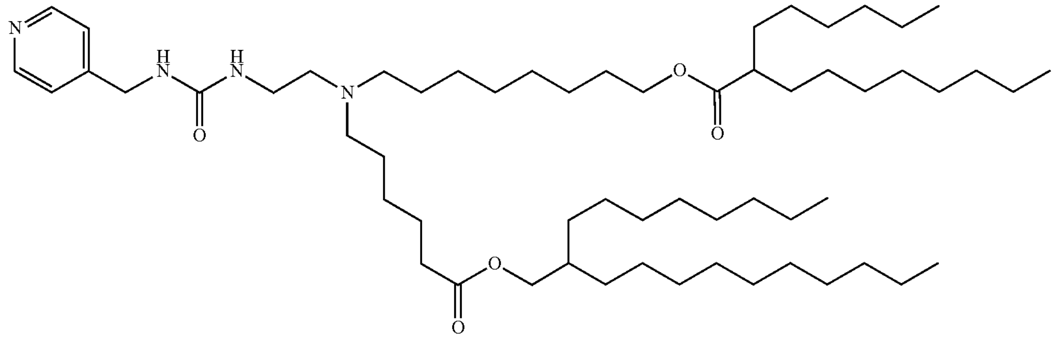 [SMILES: CCCCCCCCCCC(CCCCCCCC)COC(=O)CCCCCN(CCCCCCCCOC(=O)C(CCCCCC)CCCCCCCC)CCNC(=O)NCc1ccncc1] | 955.6 |
| 1320. | 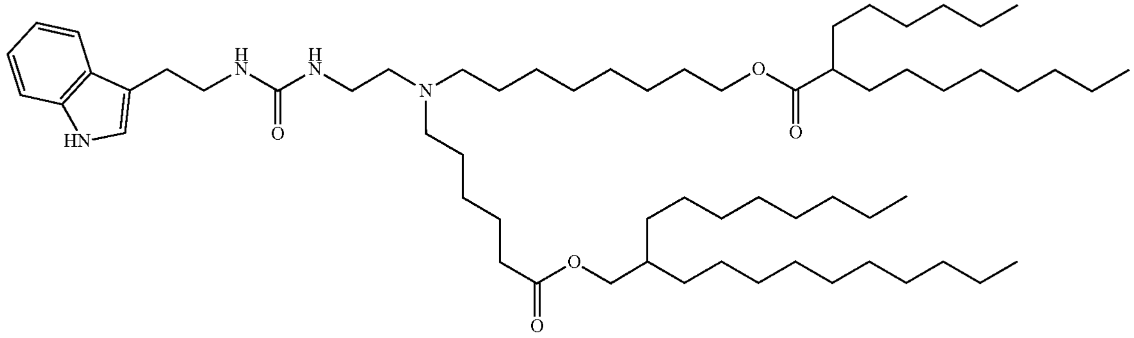 [SMILES: CCCCCCCCCCC(CCCCCCCC)COC(=O)CCCCCN(CCCCCCCCOC(=O)C(CCCCCC)CCCCCCCC)CCNC(=O)NCCc1c[nH]c2ccccc12] | 1007.6 |

TABLE 1-continued
| # | Structure | Mw |
| --- | --- | --- |
| 1321. | 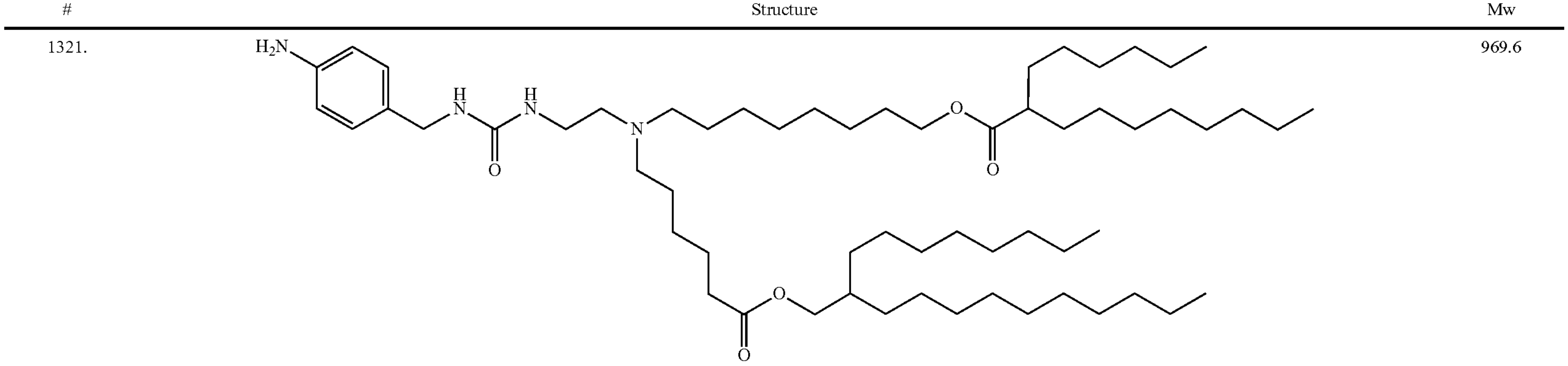 | 969.6 |
| 1322. | 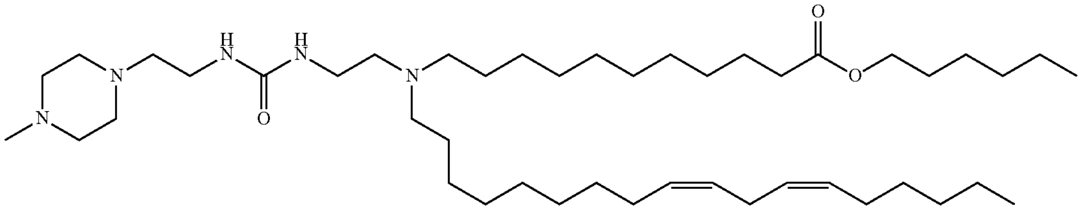 [SMILES: CCCCC/C=C\C/C=C\CCCCCCCCN(CCCCCCCCCCC(=O)OCCCCCC)CCNC(=O)NCCN1CCN(C)CC1] | 746.2 |
| 1323. | 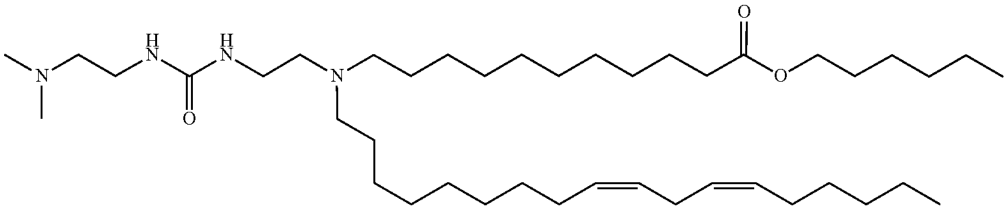 [SMILES: CCCCC/C=C\C/C=C\CCCCCCCCN(CCCCCCCCCCC(=O)OCCCCCC)CCNC(=O)NCCN(C)C] | 691.1 |
| 1324. | 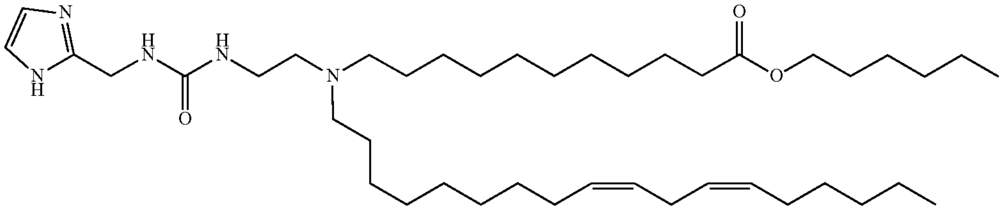 [SMILES: CCCCC/C=C\C/C=C\CCCCCCCCN(CCCCCCCCCCC(=O)OCCCCCC)CCNC(=O)NCc1ncc[nH]1] | 700.1 |

TABLE 1-continued
| # | Structure | Mw |
|---|---|---|
| 1325. | 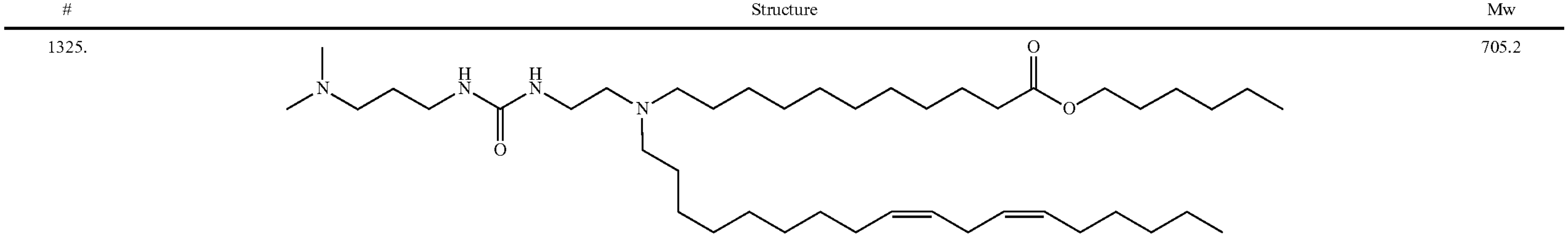 | 705.2 |
| 1326. | 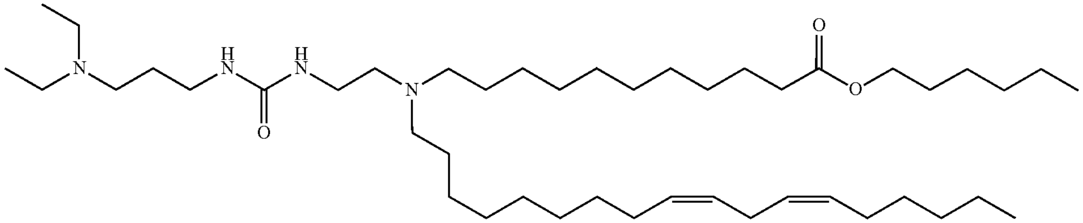 [SMILES: CCCCC/C=C\C/C=C\CCCCCCCCN(CCCCCCCCCCC(=O)OCCCCCC)CCNC(=O)NCCCN(CC)CC] | 733.2 |
| 1327. | 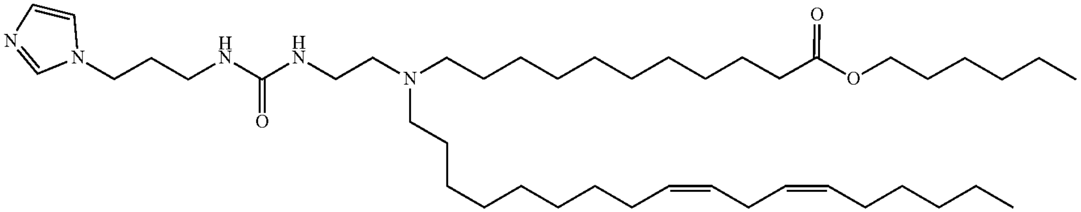 [SMILES: CCCCC/C=C\C/C=C\CCCCCCCCN(CCCCCCCCCCC(=O)OCCCCCC)CCNC(=O)NCCCn1ccnc1] | 728.2 |
| 1328. | 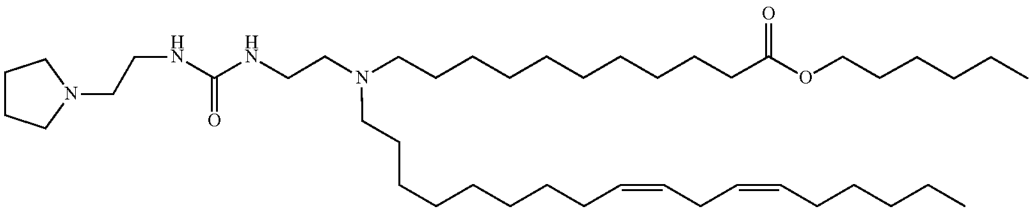 | 717.2 |

TABLE 1-continued
| # | Structure | Mw |
| --- | --- | --- |
| 1329. | 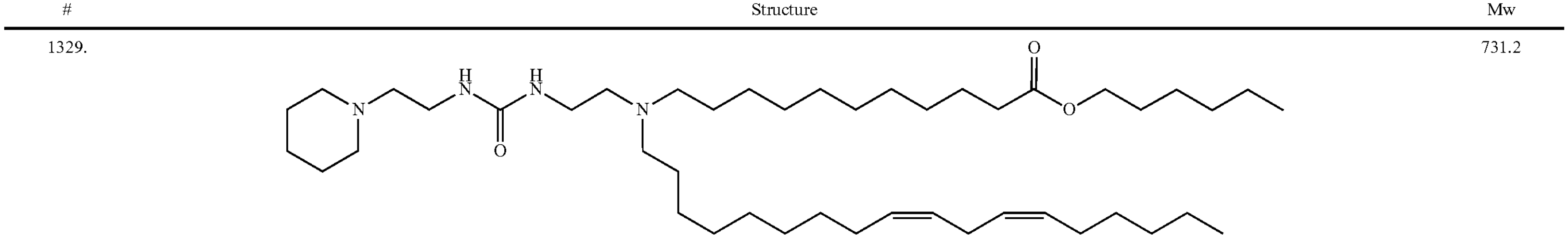 | 731.2 |
| 1330. | 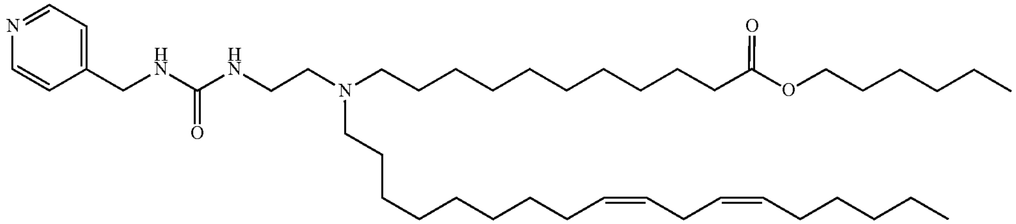 [SMILES: CCCCC/C=C\C/C=C\CCCCCCCCN(CCCCCCCCCCC(=O)OCCCCCC)CCNC(=O)NCc1ccncc1] | 711.1 |
| 1331. | 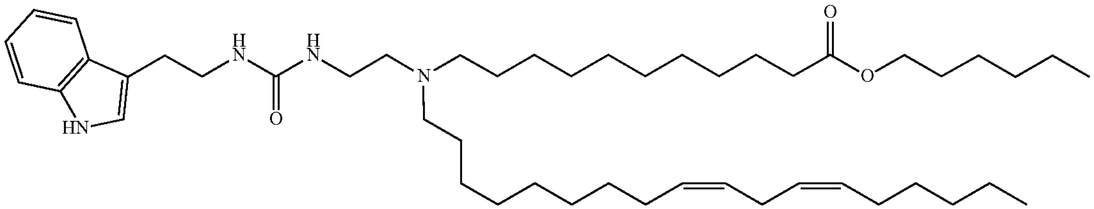 [SMILES: CCCCC/C=C\C/C=C\CCCCCCCCN(CCCCCCCCCCC(=O)OCCCCCC)CCNC(=O)NCCc1c[nH]c2ccccc12] | 763.2 |
| 1332. | 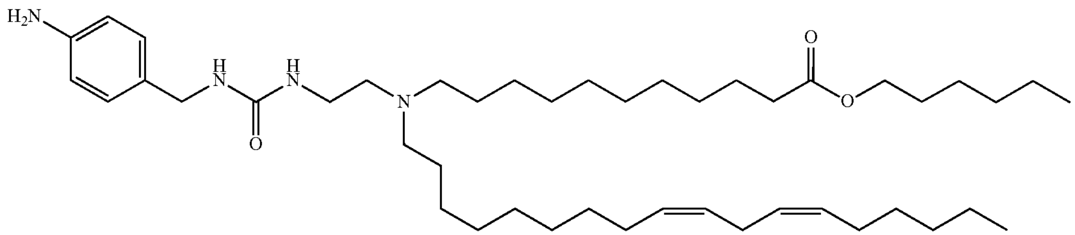 [SMILES: CCCCC/C=C\C/C=C\CCCCCCCCN(CCCCCCCCCCC(=O)OCCCCCC)CCNC(=O)NCc1ccc(N)cc1] | 725.2 |
| 1333. | 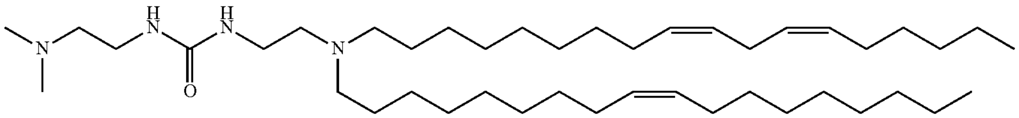 [SMILES: CCCCC/C=C\C/C=C\CCCCCCCCN(CCCCCCCC/C=C\CCCCCCCC)CCNC(=O)NCCN(C)C] | 673.2 |

TABLE 1-continued
| # | Structure | Mw |
| --- | --- | --- |
| 1334. | 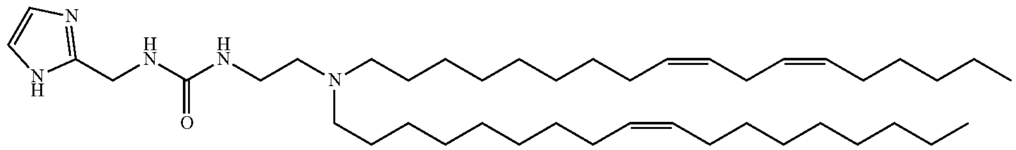 [SMILES: CCCCC/C=C\C/C=C\CCCCCCCCN(CCCCCCCC/C=C\CCCCCCCC)CCNC(=O)NCc1ncc[nH]1] | 682.1 |
| 1335. | 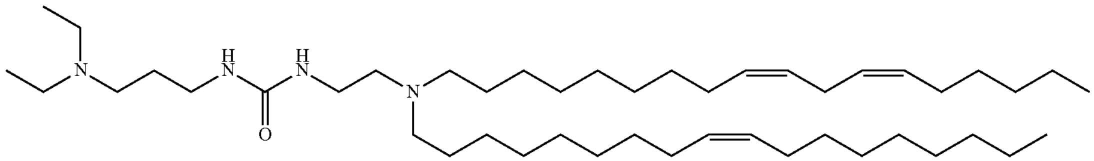 [SMILES: CCCCC/C=C\C/C=C\CCCCCCCCN(CCCCCCCC/C=C\CCCCCCCC)CCNC(=O)NCCCN(CC)CC] | 715.3 |
| 1336. | 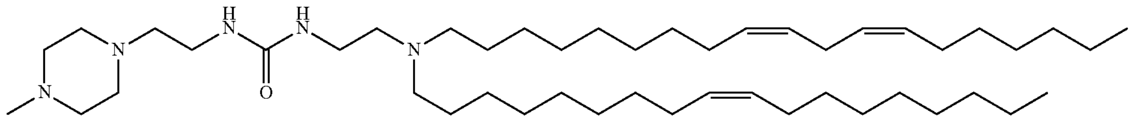 [SMILES: CCCCCC/C=C\C/C=C\CCCCCCCCN(CCCCCCCC/C=C\CCCCCCCC)CCNC(=O)NCCN1CCN(C)CC1] | 728.3 |
| 1337. | 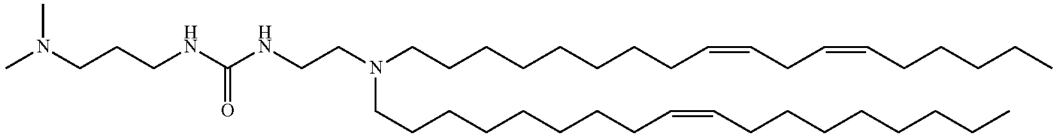 [SMILES: CCCCC/C=C\C/C=C\CCCCCCCCN(CCCCCCCC/C=C\CCCCCCCC)CCNC(=O)NCCCN(C)C] | 687.2 |
| 1338. | 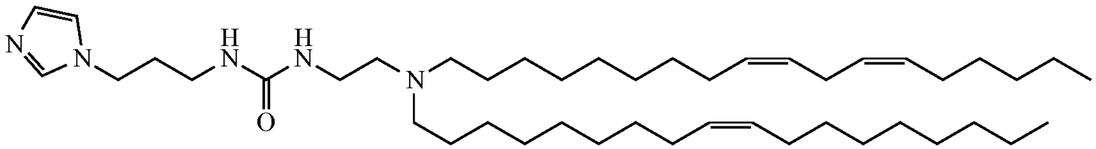 [SMILES: CCCCC/C=C\C/C=C\CCCCCCCCN(CCCCCCCC/C=C\CCCCCCCC)CCNC(=O)NCCCn1ccnc1] | 710.2 |
| 1339. | 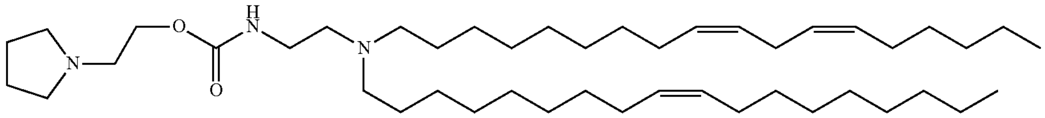 [SMILES: CCCCC/C=C\C/C=C\CCCCCCCCN(CCCCCCCC/C=C\CCCCCCCC)CCNC(=O)OCCN1CCCC1] | 699.2 |
| 1340. | 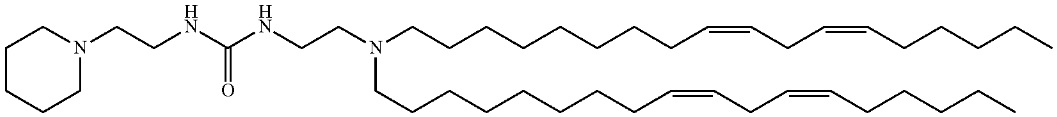 | 713.2 |

TABLE 1-continued
| # | Structure | Mw |
| --- | --- | --- |
| 1341. | 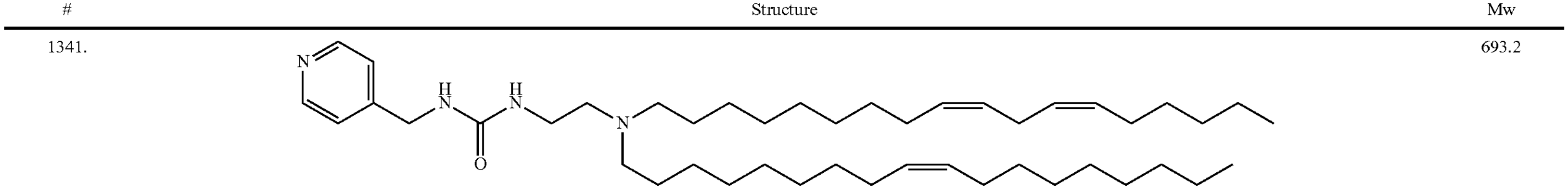 | 693.2 |
| 1342. | 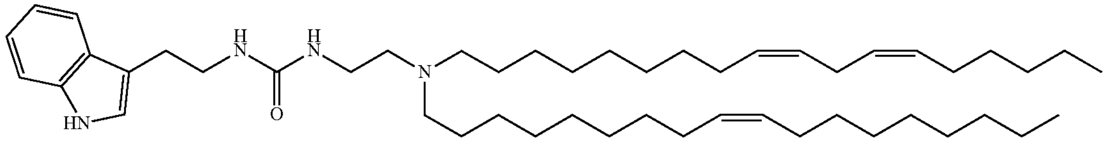 [SMILES: CCCCC/C=C\C/C=C\CCCCCCCCN(CCCCCCCC/C=C\CCCCCCCC)CCNC(=O)NCCc1c[nH]c2ccccc12] | 745.2 |
| 1343. | 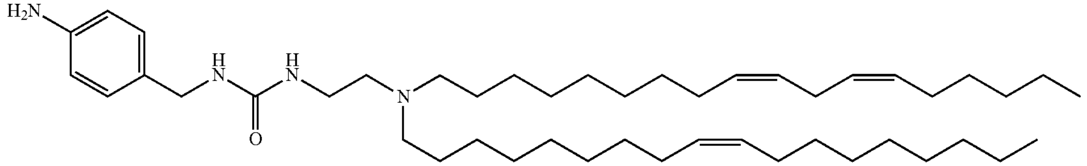 [SMILES: CCCCC/C=C\C/C=C\CCCCCCCCN(CCCCCCCC/C=C\CCCCCCCC)CCNC(=O)NCc1ccc(N)cc1] | 707.2 |
| 1344. | 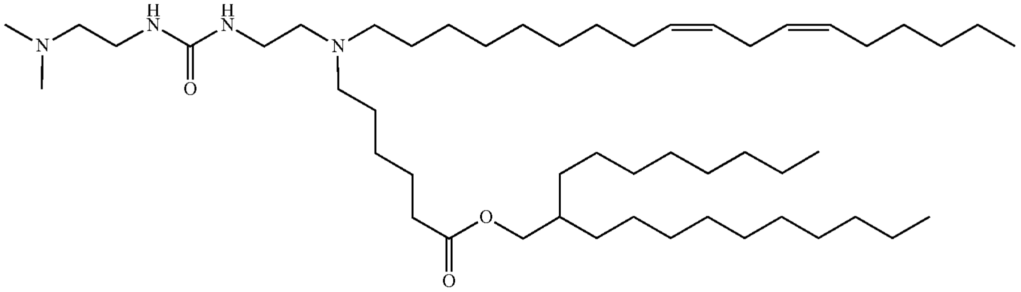 | 817.4 |

TABLE 1-continued
| # | Structure | Mw |
|---|---|---|
| 1345. | 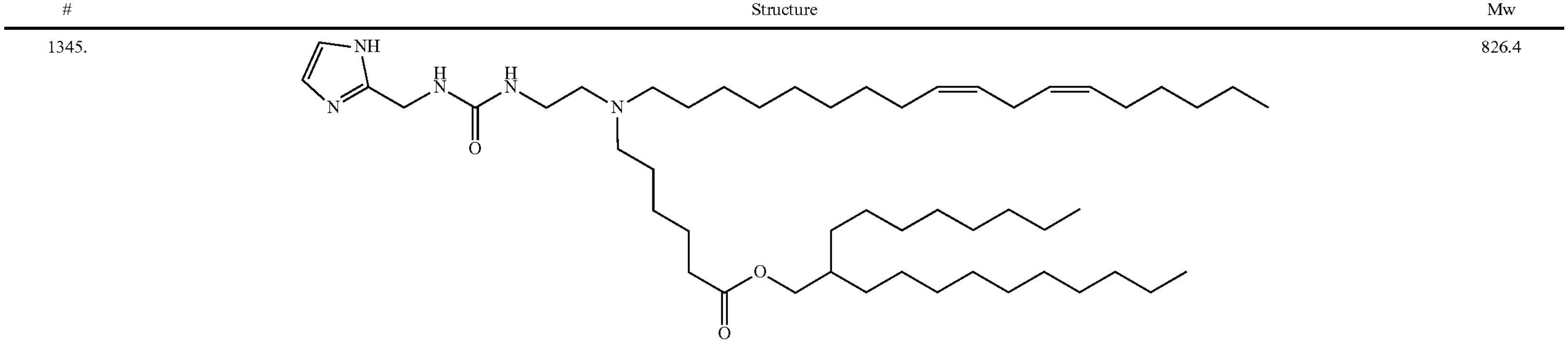 | 826.4 |
| 1346. | 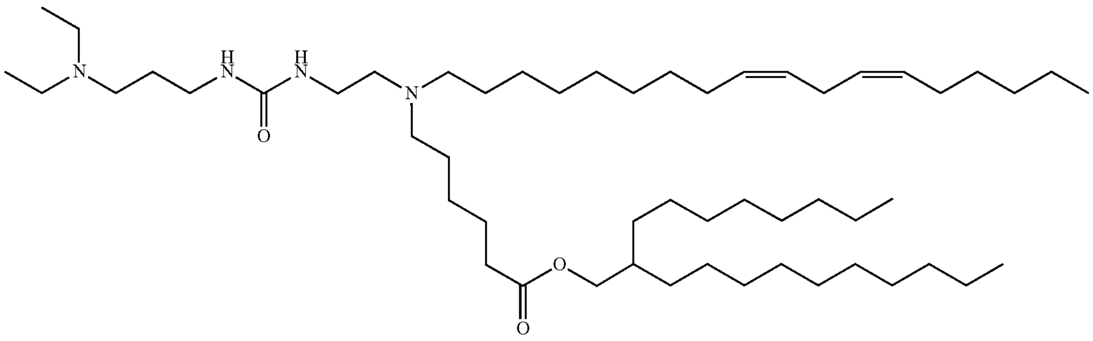 [SMILES: CCCCC/C=C\C/C=C\CCCCCCCCN(CCCCCC(=O)OCC(CCCCCCCC)CCCCCCCCCC)CCNC(=O)NCCCN(CC)CC] | 859.5 |
| 1347. | 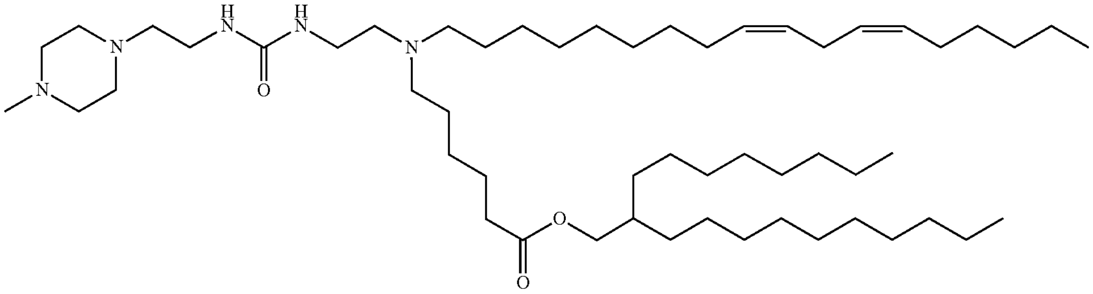 [SMILES: CCCCC/C=C\C/C=C\CCCCCCCCN(CCCCCC(=O)OCC(CCCCCCCC)CCCCCCCCCC)CCNC(=O)NCCN1CCN(C)CC1] | 872.5 |

TABLE 1-continued
| # | Structure | Mw |
| --- | --- | --- |
| 1348. | 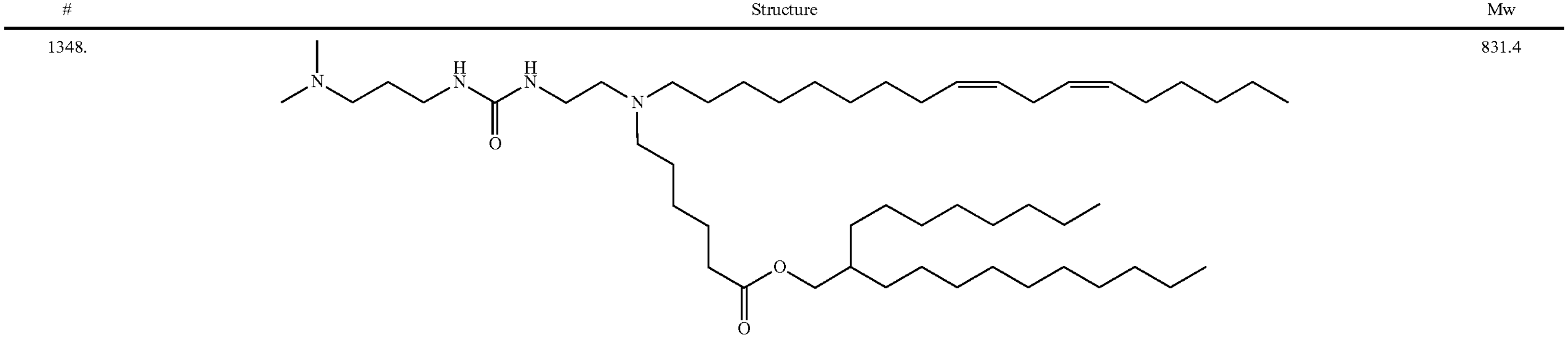 | 831.4 |
| 1349. | 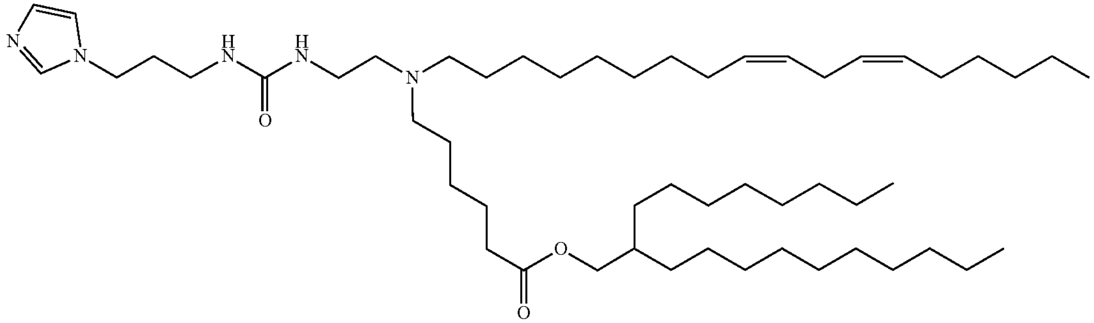 [SMILES: CCCCC/C=C\C/C=C\CCCCCCCCN(CCCCCC(=O)OCC(CCCCCCCC)CCCCCCCCCC)CCNC(=O)NCCCn1ccnc1] | 854.4 |
| 1350. | 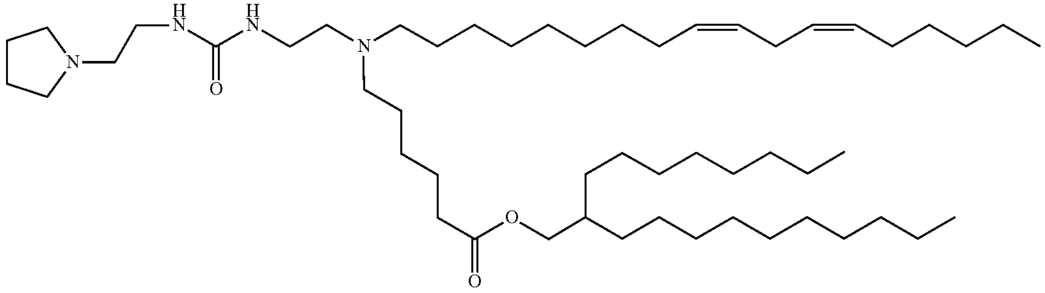 | 843.4 |

TABLE 1-continued
| # | Structure | Mw |
| --- | --- | --- |
| 1351. | 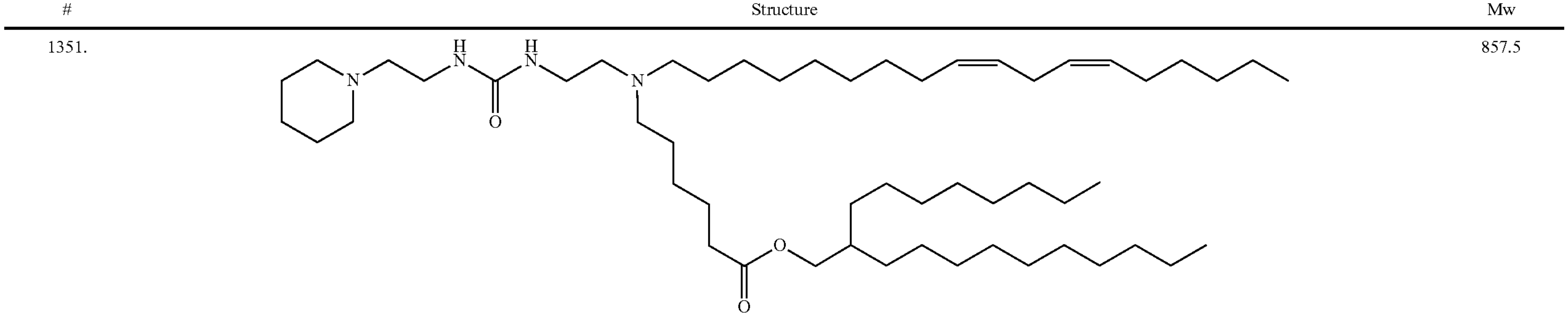 | 857.5 |
| 1352. | 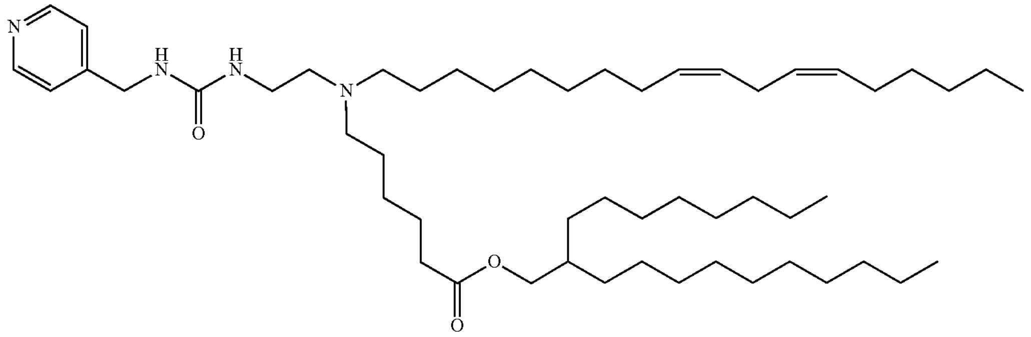 [SMILES: CCCCC/C=C\C/C=C\CCCCCCCCN(CCCCCC(=O)OCC(CCCCCCCC)CCCCCCCCCC)CCNC(=O)NCc1ccncc1] | 837.4 |
| 1353. | 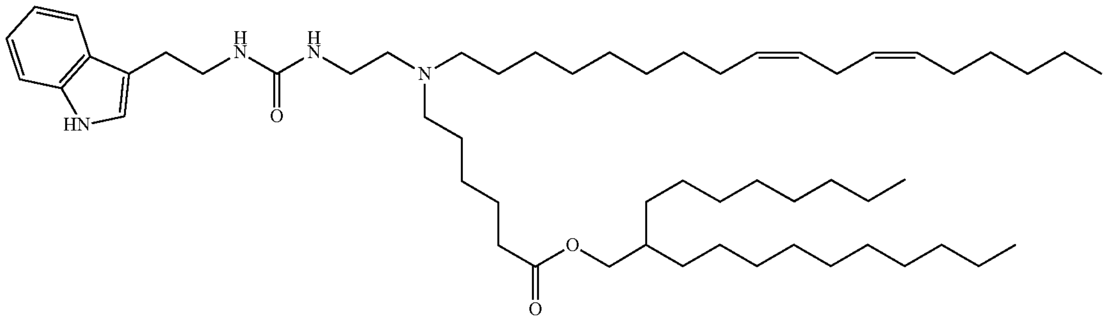 [SMILES: CCCCC/C=C\C/C=C\CCCCCCCCN(CCCCCC(=O)OCC(CCCCCCCC)CCCCCCCCCC)CCNC(=O)NCCc1c[nH]c2ccccc12] | 889.5 |

TABLE 1-continued
| # | Structure | Mw |
| --- | --- | --- |
| 1354. | 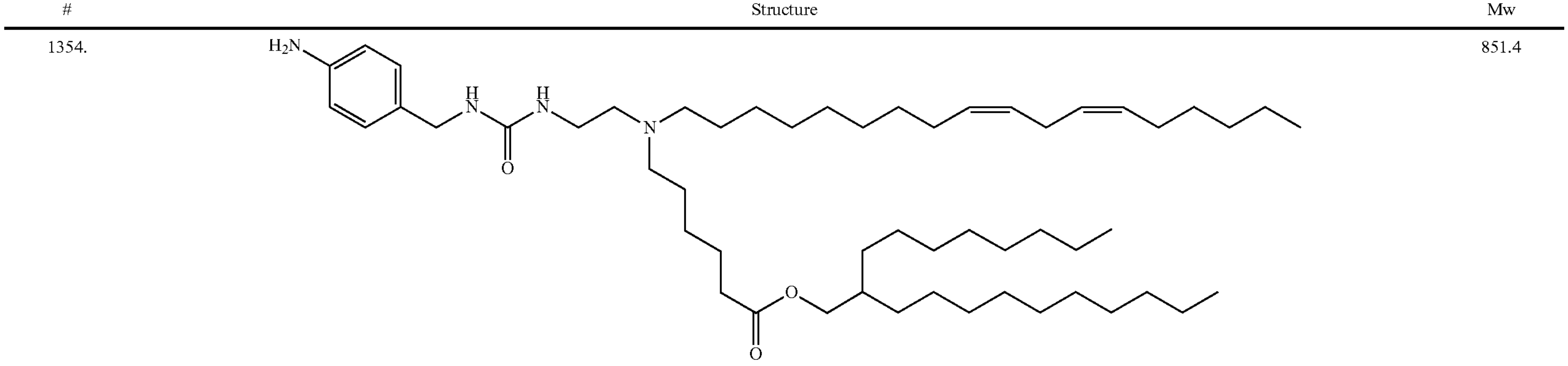 | 851.4 |
| 1355. | 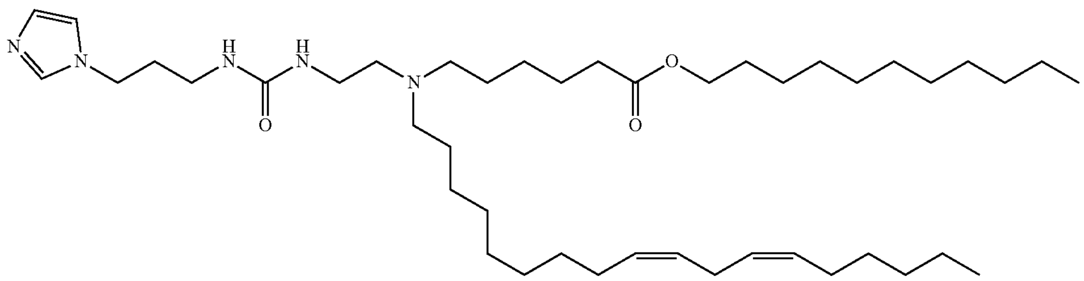 | 728.2 |
| 1356. | 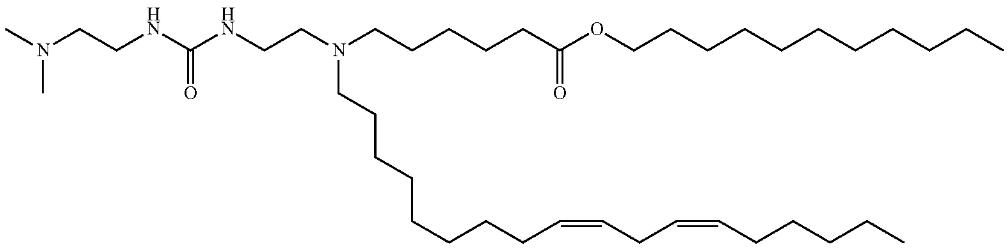 | 691.1 |

TABLE 1-continued
| # | Structure | Mw |
| --- | --- | --- |
| 1357. | 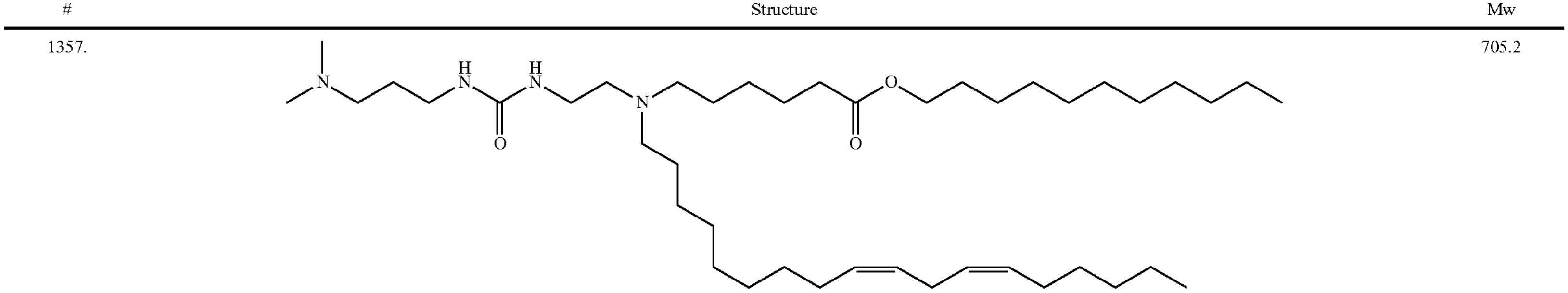 | 705.2 |
| 1358. | 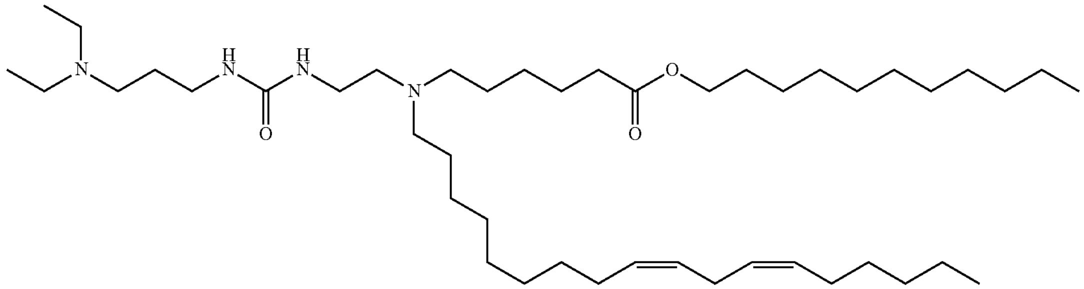 [SMILES: CCCCC/C=C\C/C=C\CCCCCCCCN(CCCCCC(=O)OCCCCCCCCCCC)CCNC(=O)NCCCN(CC)CC] | 733.2 |
| 1359. | 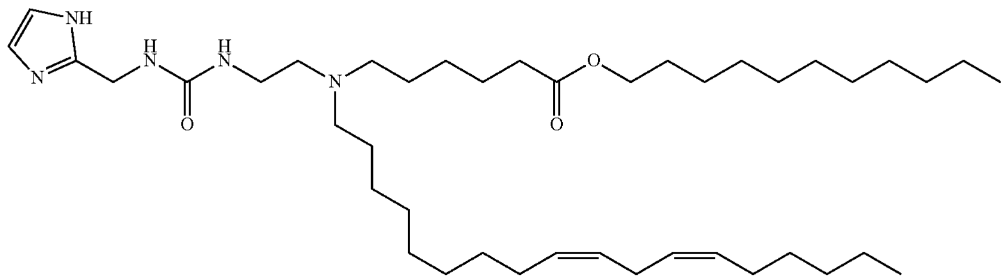 [SMILES: CCCCC/C=C\C/C=C\CCCCCCCCN(CCCCCC(=O)OCCCCCCCCCCC)CCNC(=O)NCc1ncc[nH]1] | 700.1 |

TABLE 1-continued
| # | Structure | Mw |
|---|---|---|
| 1360. | 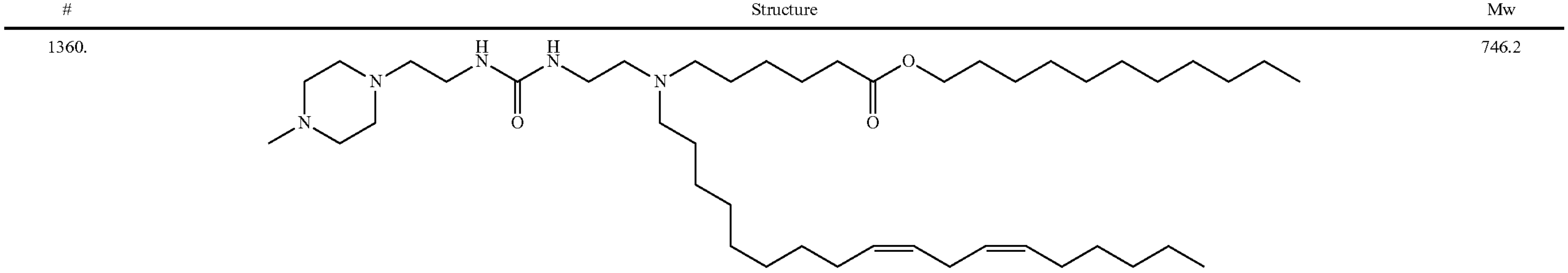 | 746.2 |
| 1361. | 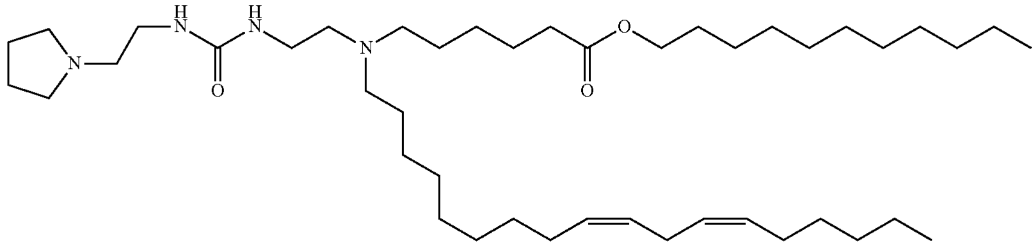 [SMILES: CCCCC/C=C\C/C=C\CCCCCCCCN(CCCCCC(=O)OCCCCCCCCCCC)CCNC(=O)NCCN1CCCC1] | 717.2 |
| 1362. | 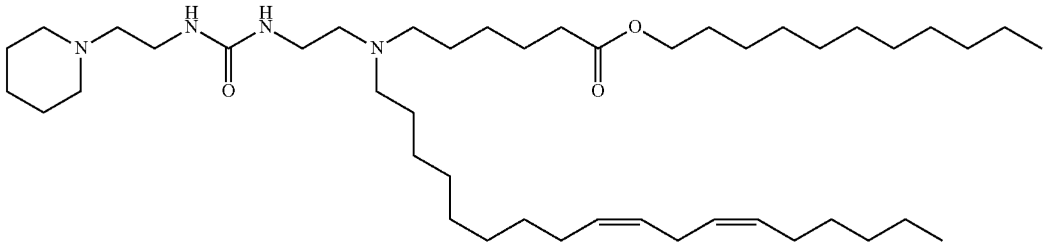 [SMILES: CCCCC/C=C\C/C=C\CCCCCCCCN(CCCCCC(=O)OCCCCCCCCCCC)CCNC(=O)NCCN1CCCCC1] | 731.2 |
| 1363. | 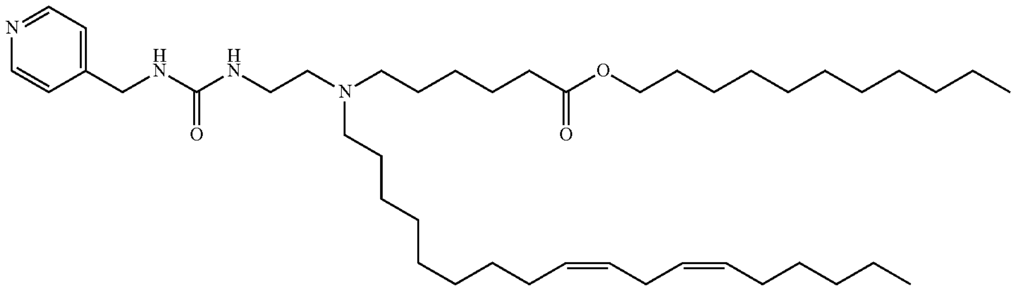 [SMILES: CCCCC/C=C\C/C=C\CCCCCCCCN(CCCCCC(=O)OCCCCCCCCCCC)CCNC(=O)NCc1ccncc1] | 711.1 |

TABLE 1-continued
| # | Structure | Mw |
| --- | --- | --- |
| 1364. | 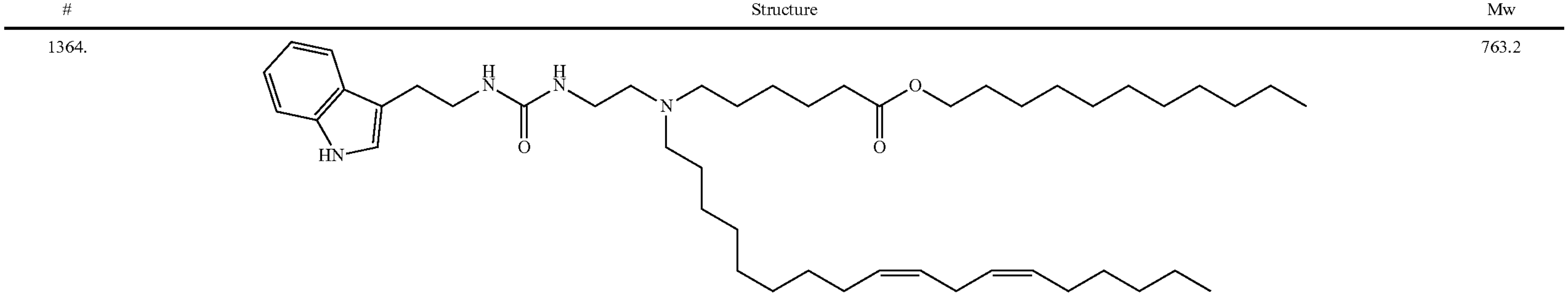 | 763.2 |
| 1365. | 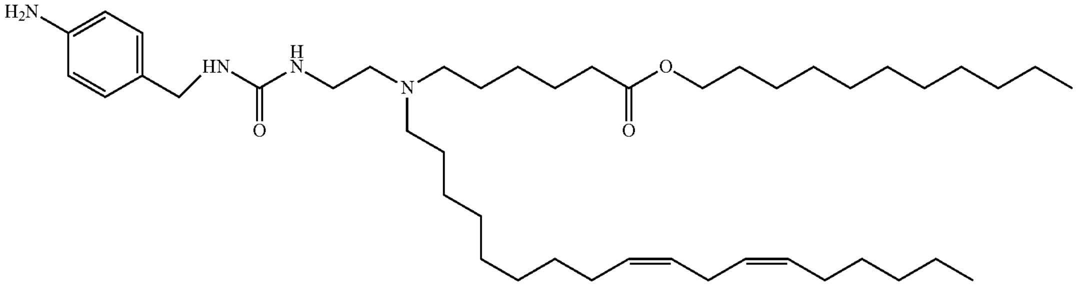 [SMILES: CCCCC/C=C\C/C=C\CCCCCCCCN(CCCCCC(=O)OCCCCCCCCCCC)CCNC(=O)NCc1ccc(N)cc1] | 725.2 |
| 1366. | 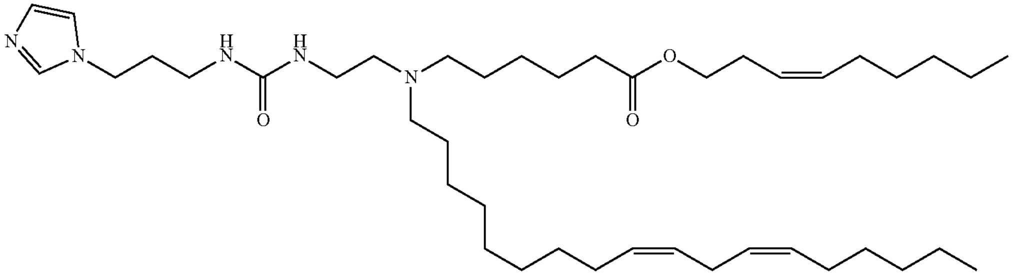 [SMILES: CCCCC/C=C\C/C=C\CCCCCCCCN(CCCCCC(=O)OCC/C=C\CCCCC)CCNC(=O)NCCCn1ccnc1] | 698.1 |

TABLE 1-continued
| # | Structure | Mw |
| --- | --- | --- |
| 1367. | 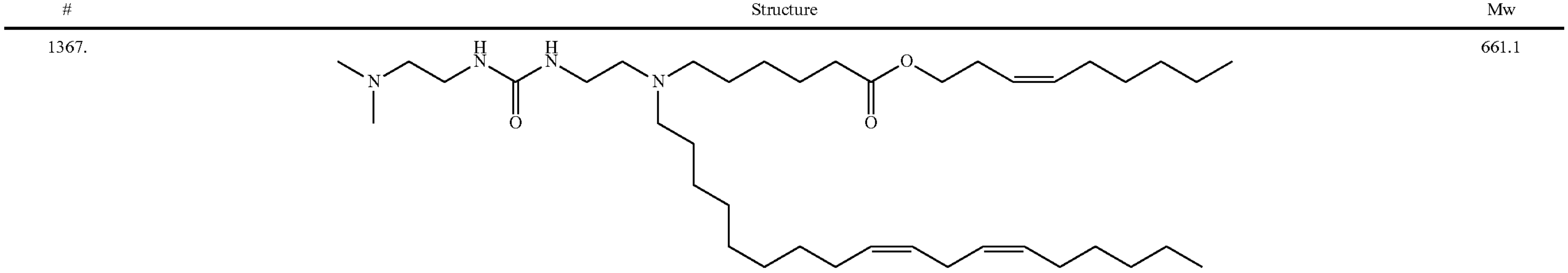 | 661.1 |
| 1368. | 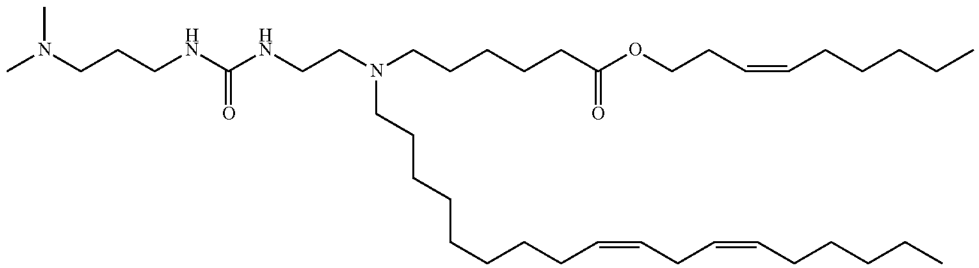 [SMILES: CCCCC/C=C\C/C=C\CCCCCCCCN(CCCCCC(=O)OCC/C=C\CCCCC)CCNC(=O)NCCCN(C)C] | 675.1 |
| 1369. | 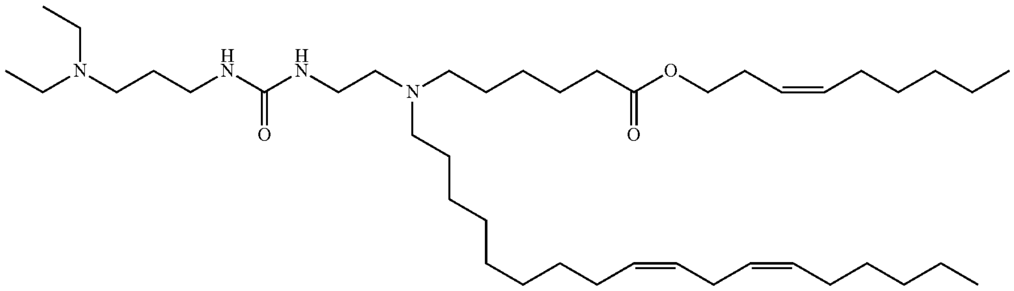 [SMILES: CCCCC/C=C\C/C=C\CCCCCCCCN(CCCCCC(=O)OCC/C=C\CCCCC)CCNC(=O)NCCCN(CC)CC] | 703.2 |

TABLE 1-continued
| # | Structure | Mw |
| --- | --- | --- |
| 1370. | 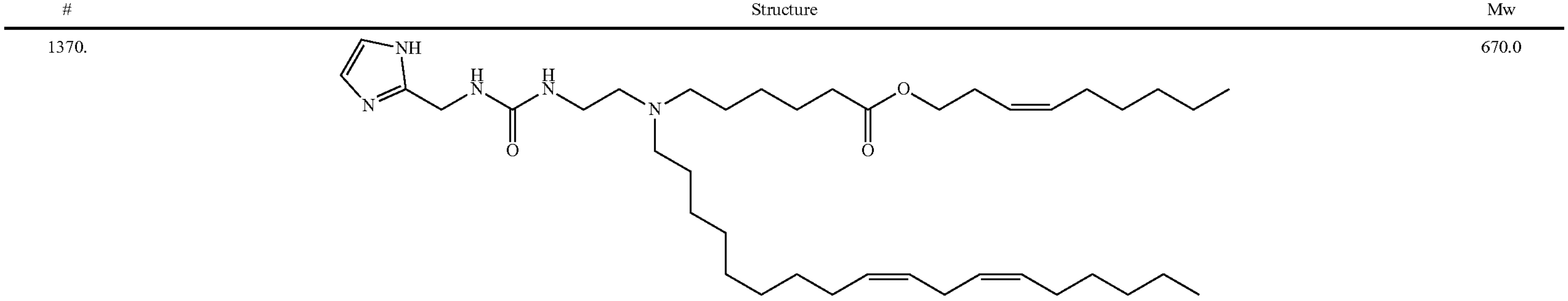 | 670.0 |
| 1371. | 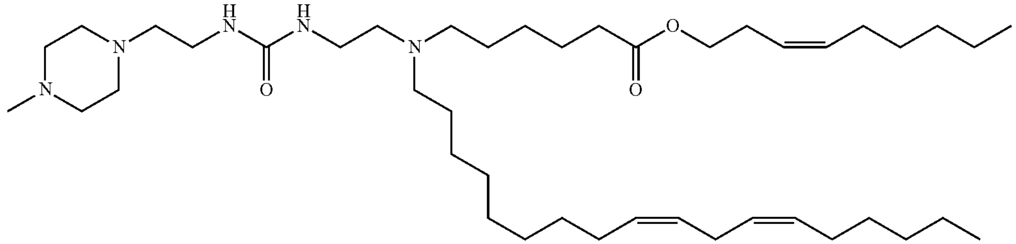 | 716.2 |
| 1372. | 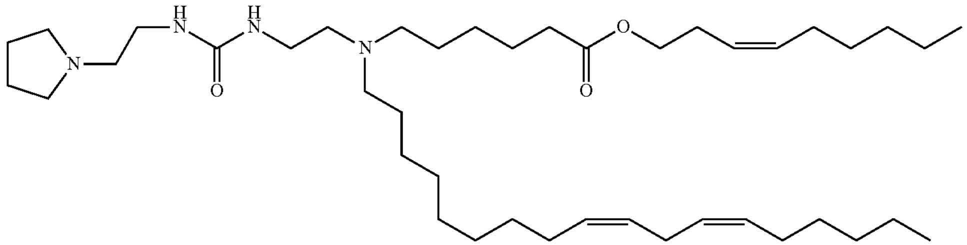 [SMILES: CCCCC/C=C\C/C=C\CCCCCCCCN(CCCCCC(=O)OCC/C=C\CCCCC)CCNC(=O)NCCN1CCCC1] | 687.1 |
| 1373. | 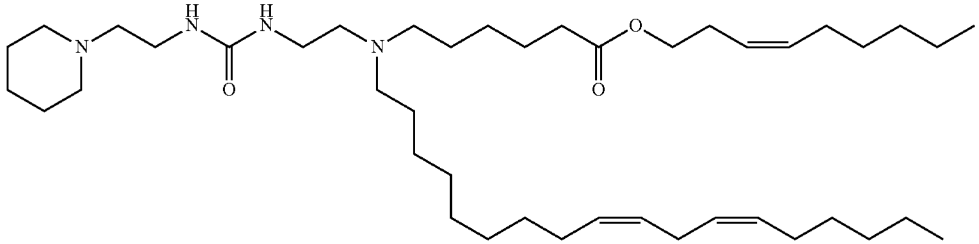 [SMILES: CCCCC/C=C\C/C=C\CCCCCCCCN(CCCCCC(=O)OCC/C=C\CCCCC)CCNC(=O)NCCN1CCCCC1] | 701.1 |

TABLE 1-continued
| # | Structure | Mw |
| --- | --- | --- |
| 1374. | 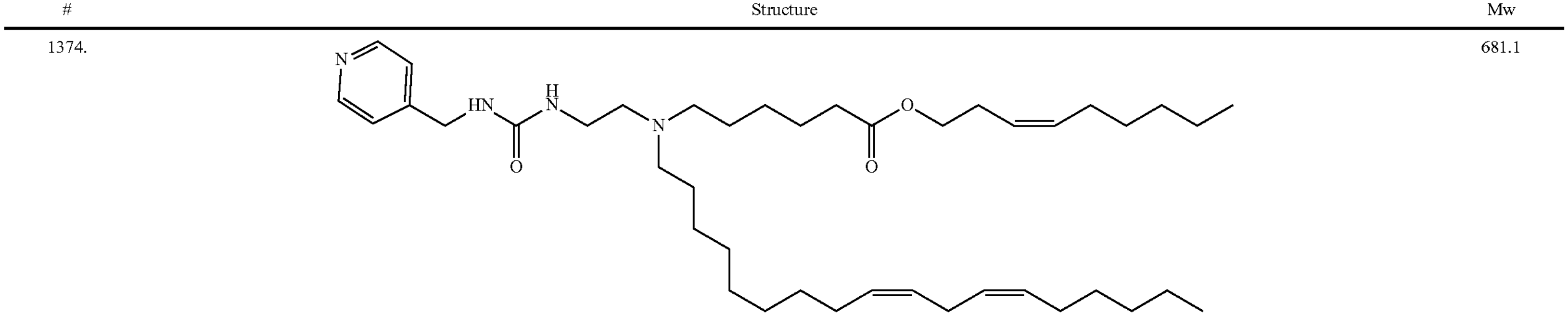 | 681.1 |
| 1375. | 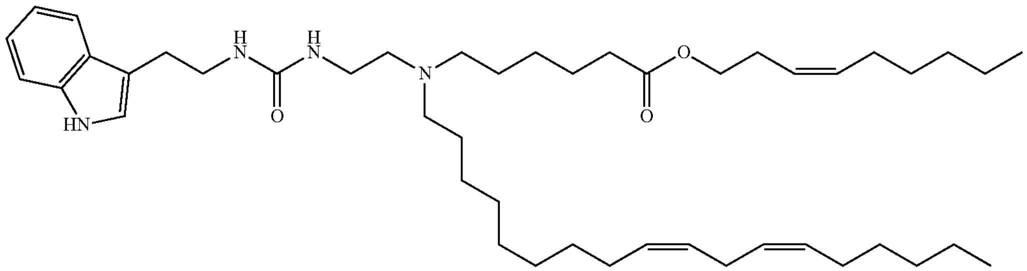 [SMILES: CCCCC/C=C\C/C=C\CCCCCCCCN(CCCCCC(=O)OCC/C=C\CCCCC)CCNC(=O)NCCc1c[nH]c2ccccc12] | 733.1 |
| 1376. | 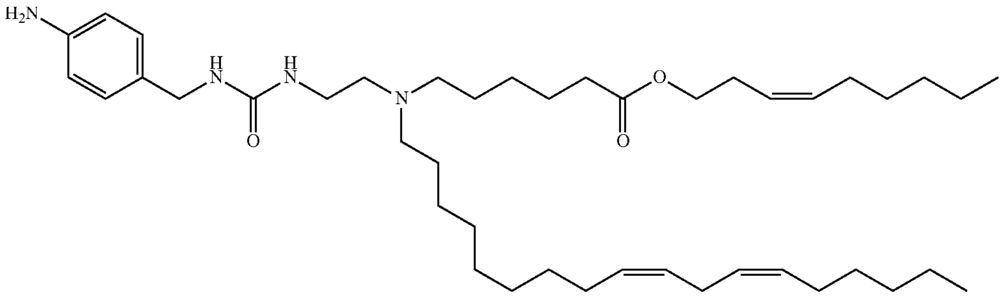 [SMILES: CCCCC/C=C\C/C=C\CCCCCCCCN(CCCCCC(=O)OCC/C=C\CCCCC)CCNC(=O)NCc1ccc(N)cc1] | 695.1 |

TABLE 1-continued
| # | Structure | Mw |
| --- | --- | --- |
| 1377. | 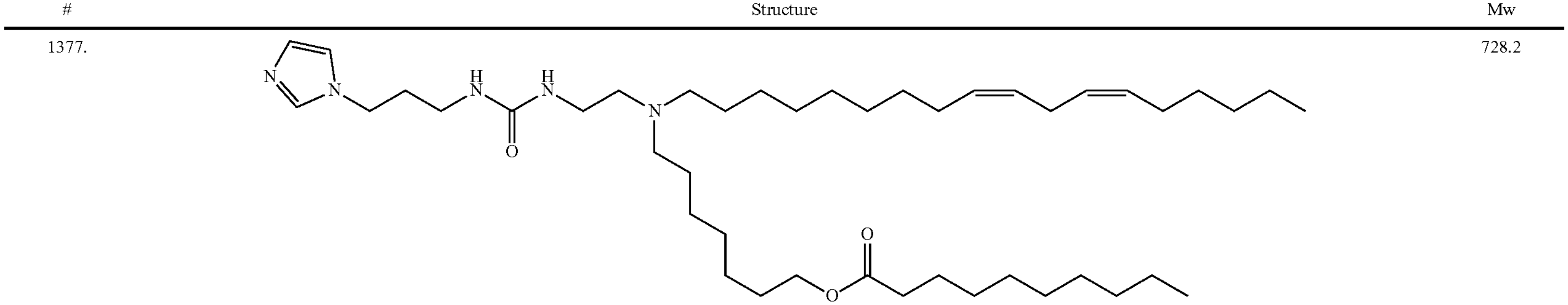 | 728.2 |
| 1378. | 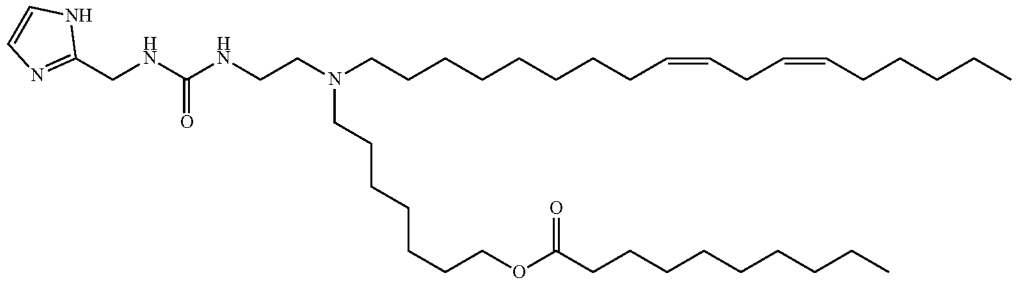 [SMILES: CCCCC/C=C\C/C=C\CCCCCCCCN(CCCCCCCOC(=O)CCCCCCCCC)CCNC(=O)NCc1ncc[nH]1] | 700.1 |
| 1379. | 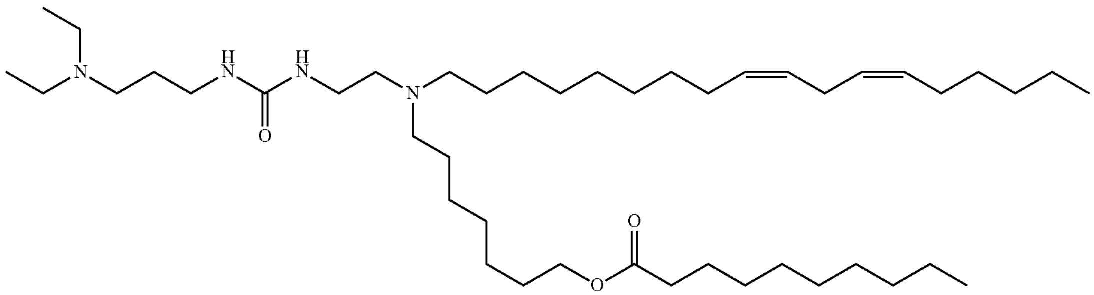 [SMILES: CCCCC/C=C\C/C=C\CCCCCCCCN(CCCCCCCOC(=O)CCCCCCCCC)CCNC(=O)NCCCN(CC)CC] | 733.2 |

TABLE 1-continued
| # | Structure | Mw |
| --- | --- | --- |
| 1380. | 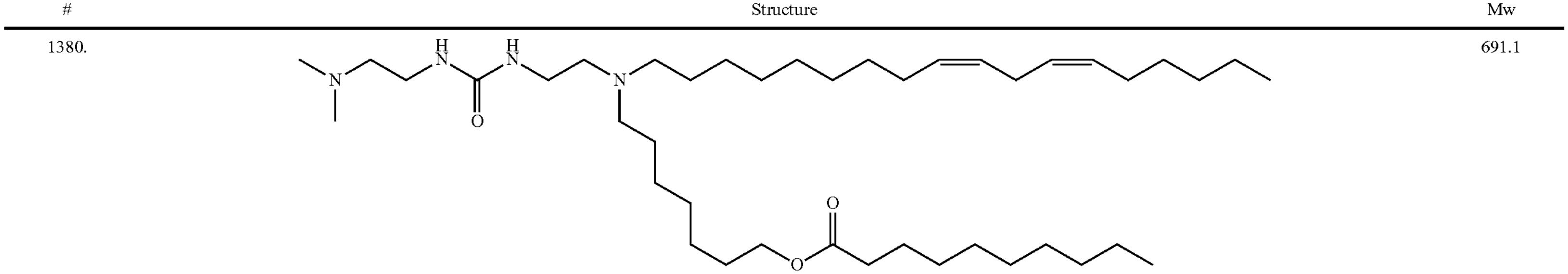 | 691.1 |
| 1381. | 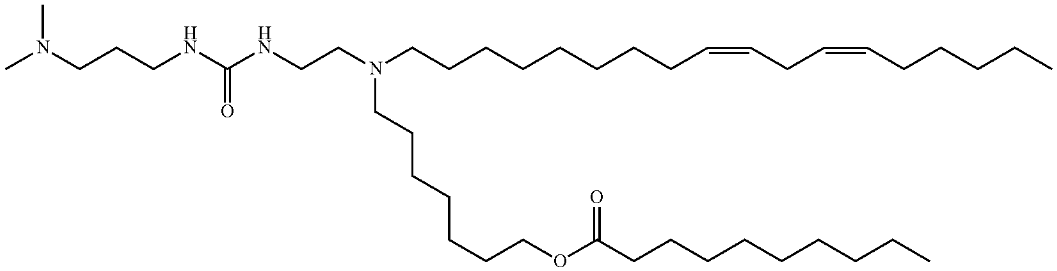 [SMILES: CCCCC/C=C\C/C=C\CCCCCCCCN(CCCCCCCOC(=O)CCCCCCCCC)CCNC(=O)NCCCN(C)C] | 705.2 |
| 1382. | 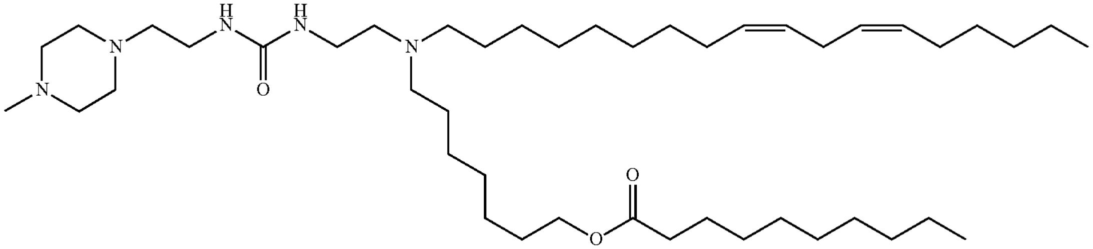 | 746.2 |
| 1383. | 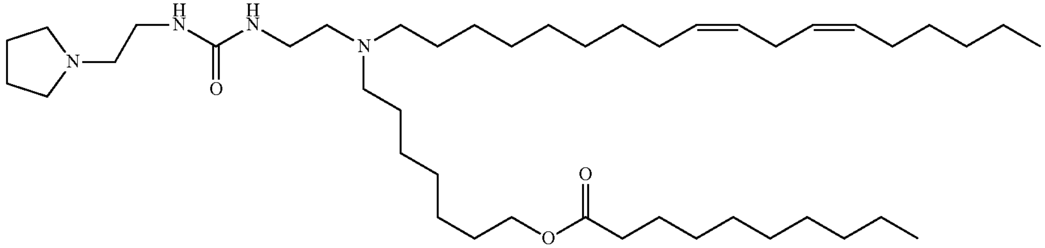 [SMILES: CCCCC/C=C\C/C=C\CCCCCCCCN(CCCCCCCOC(=O)CCCCCCCCC)CCNC(=O)NCCN1CCCC1] | 717.2 |

TABLE 1-continued
| # | Structure | Mw |
|---|---|---|
| 1384. | 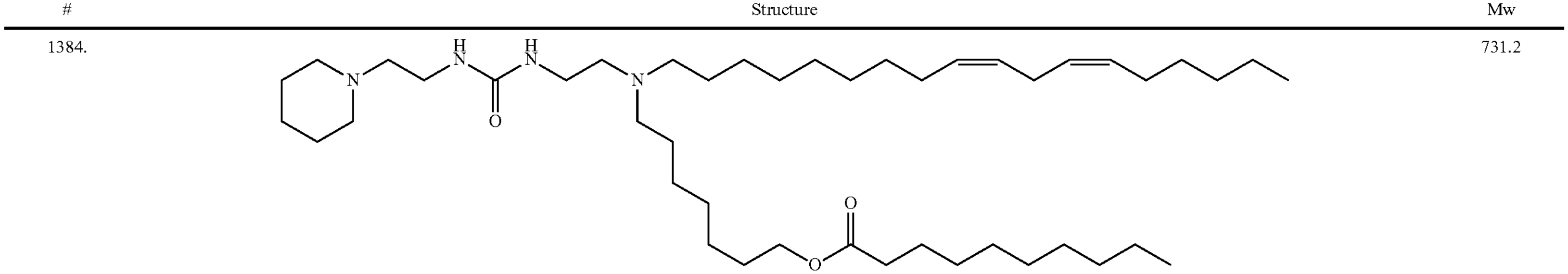 | 731.2 |
| 1385. | 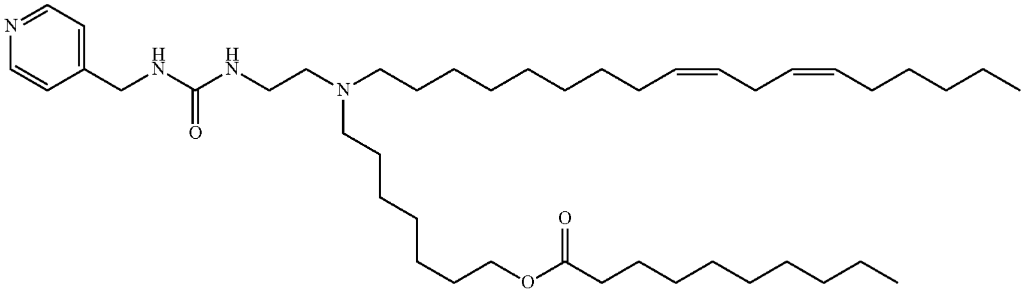 [SMILES: CCCCC/C=C\C/C=C\CCCCCCCCN(CCCCCCCOC(=O)CCCCCCCCC)CCNC(=O)NCc1ccncc1] | 711.1 |
| 1386. | 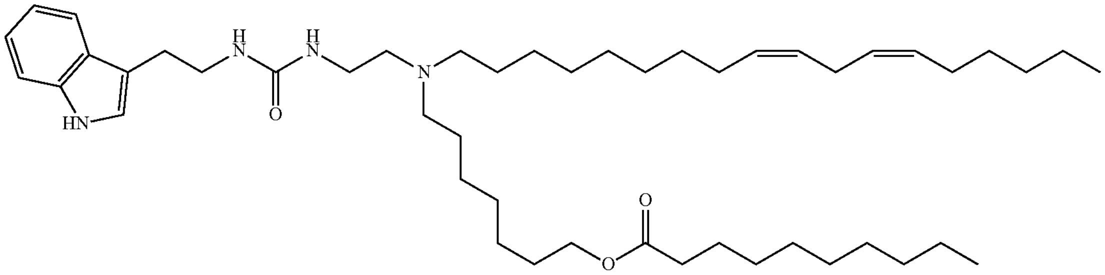 [SMILES: CCCCC/C=C\C/C=C\CCCCCCCCN(CCCCCCCOC(=O)CCCCCCCCC)CCNC(=O)NCCc1c[nH]c2ccccc12] | 763.2 |

TABLE 1-continued
| # | Structure | Mw |
|---|---|---|
| 1387. | 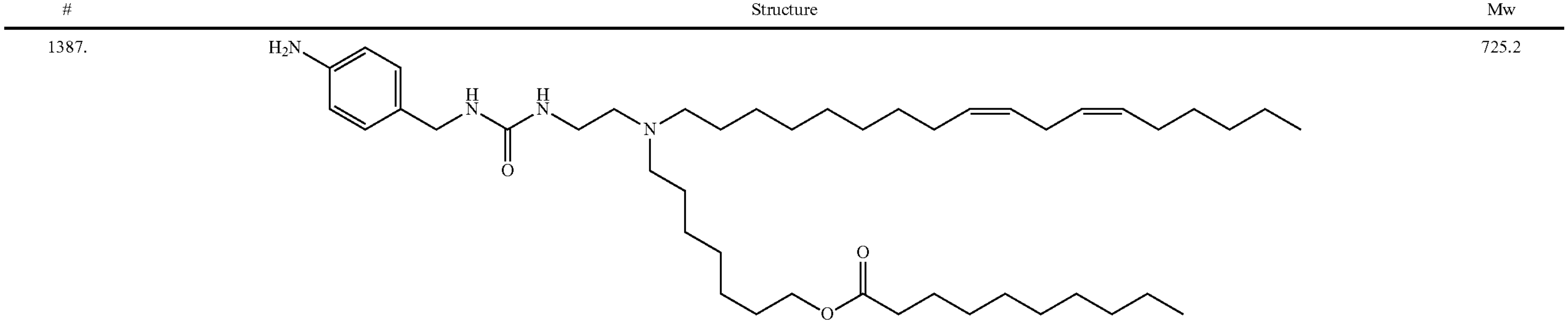 | 725.2 |
| 1388. | 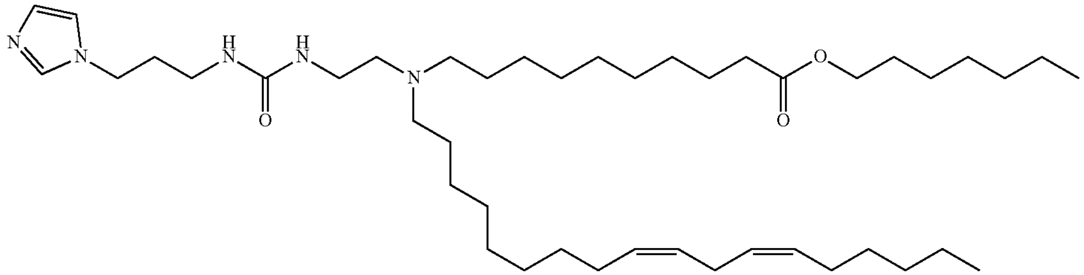 [SMILES: CCCCC/C=C\C/C=C\CCCCCCCCN(CCCCCCCCCC(=O)OCCCCCCC)CCNC(=O)NCCCn1ccnc1] | 728.2 |
| 1389. | 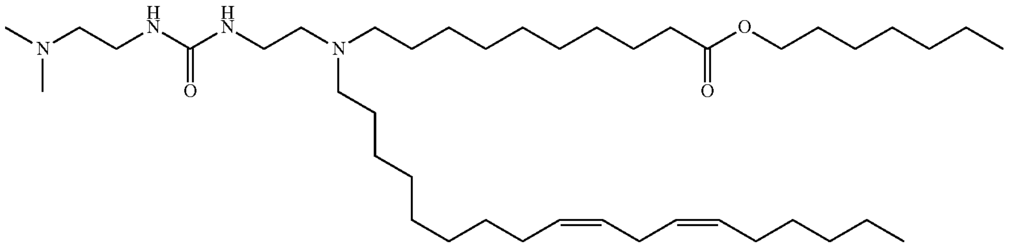 [SMILES: CCCCC/C=C\C/C=C\CCCCCCCCN(CCCCCCCCCC(=O)OCCCCCCC)CCNC(=O)NCCN(C)C] | 691.1 |

TABLE 1-continued
| # | Structure | Mw |
|---|---|---|
| 1390. | 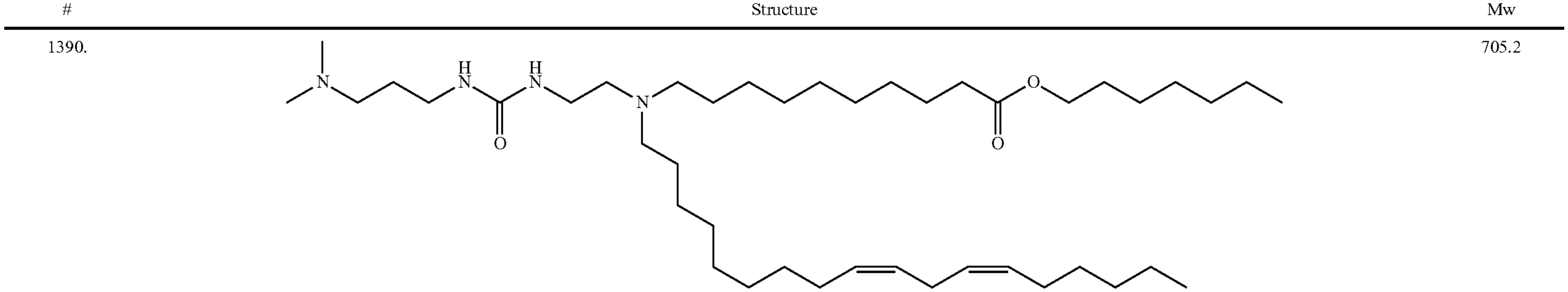 | 705.2 |
| 1391. | 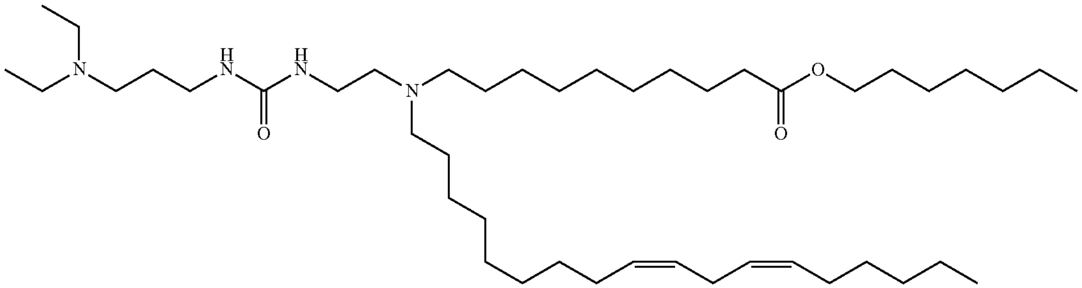 [SMILES: CCCCC/C=C\C/C=C\CCCCCCCCN(CCCCCCCCCC(=O)OCCCCCCC)CCNC(=O)NCCCN(CC)CC] | 733.2 |
| 1392. | 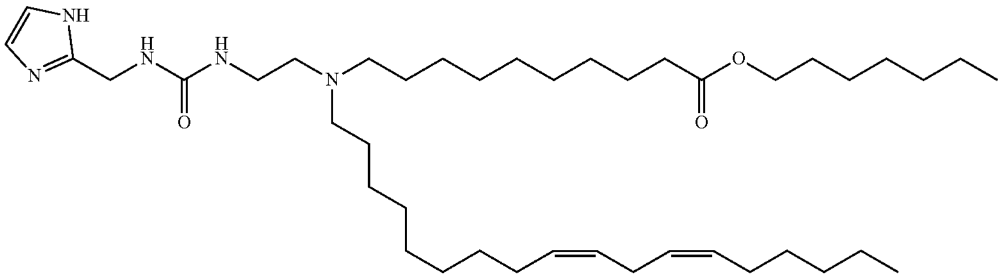 [SMILES: CCCCC/C=C\C/C=C\CCCCCCCCN(CCCCCCCCCC(=O)OCCCCCCC)CCNC(=O)NCc1ncc[nH]1] | 700.1 |

TABLE 1-continued
| # | Structure | Mw |
|---|---|---|
| 1393. | 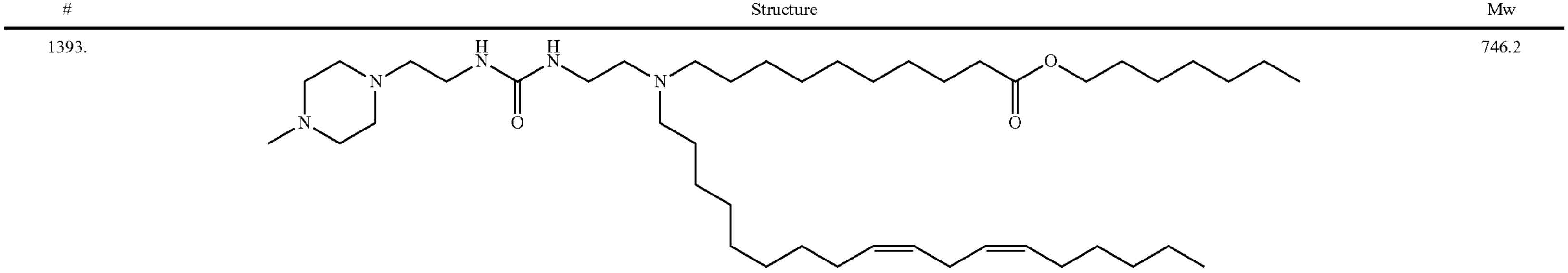 | 746.2 |
| 1394. | 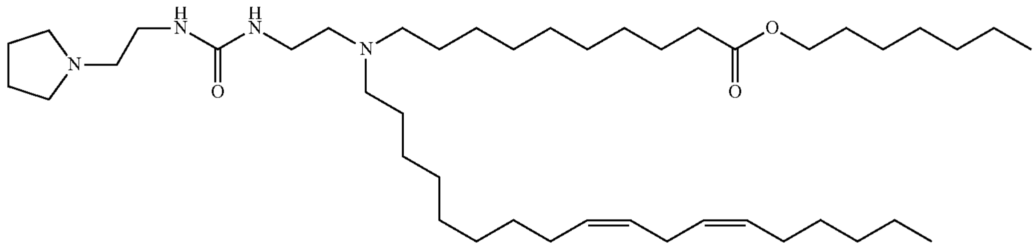 [SMILES: CCCCC/C=C\C/C=C\CCCCCCCCN(CCCCCCCCCC(=O)OCCCCCCC)CCNC(=O)NCCN1CCCC1] | 717.2 |
| 1395. | 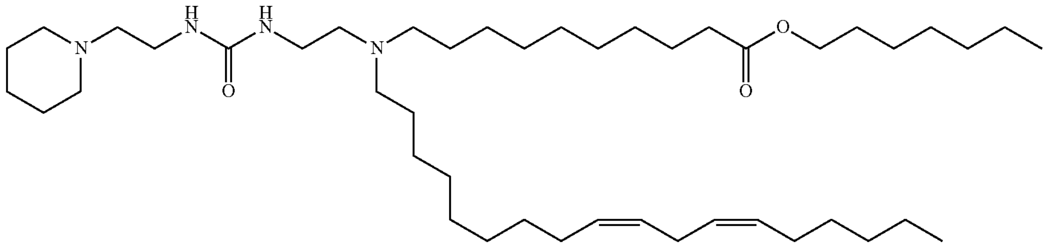 [SMILES: CCCCC/C=C\C/C=C\CCCCCCCCN(CCCCCCCCCC(=O)OCCCCCCC)CCNC(=O)NCCN1CCCCC1] | 731.2 |
| 1396. | 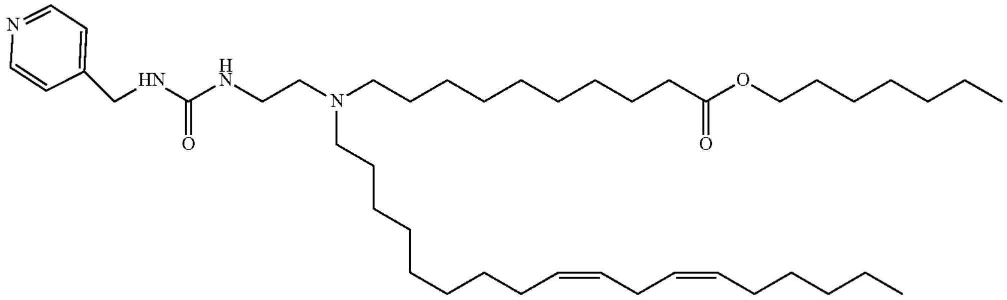 [SMILES: CCCCC/C=C\C/C=C\CCCCCCCCN(CCCCCCCCCC(=O)OCCCCCCC)CCNC(=O)NCc1ccncc1] | 711.1 |

TABLE 1-continued
| # | Structure | Mw |
|---|---|---|
| 1397. | 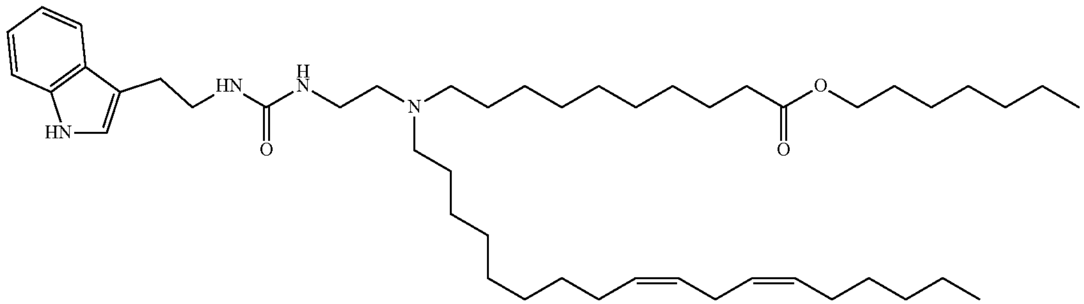 [SMILES: CCCCC/C=C\C/C=C\CCCCCCCCN(CCCCCCCCCC(=O)OCCCCCCC)CCNC(=O)NCCc1c[nH]c2ccccc12] | 763.2 |
| 1398. | 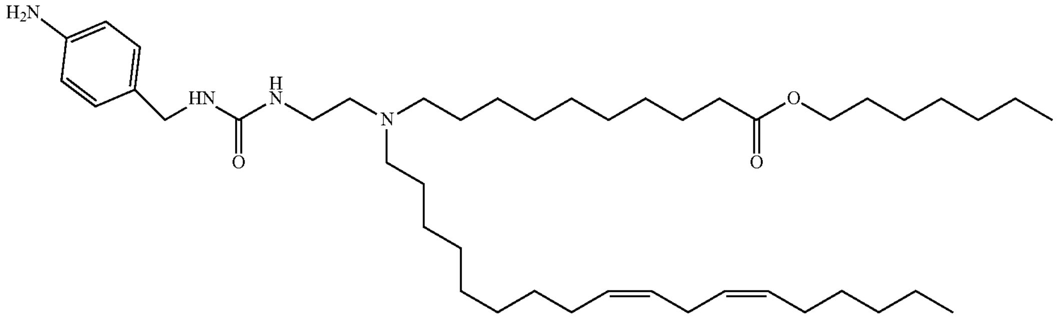 [SMILES: CCCCC/C=C\C/C=C\CCCCCCCCN(CCCCCCCCCC(=O)OCCCCCCC)CCNC(=O)NCc1ccc(N)cc1] | 725.2 |
| 1399. | 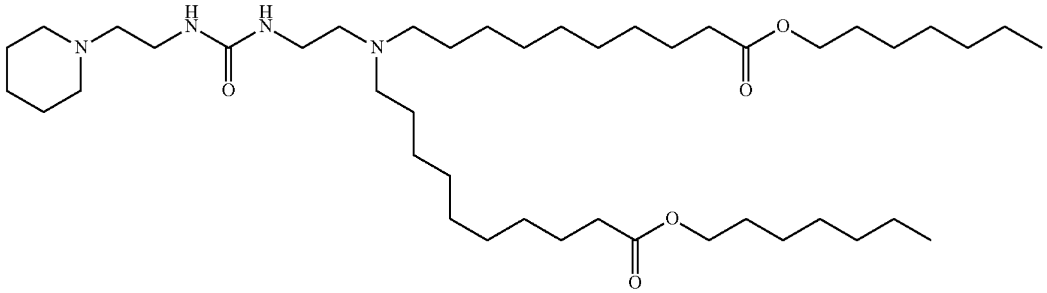 [SMILES: CCCCCCCOC(=O)CCCCCCCCCN(CCCCCCCCCC(=O)OCCCCCCC)CCNC(=O)NCCN1CCCCC1] | 751.2 |

TABLE 1-continued
| # | Structure | Mw |
| --- | --- | --- |
| 1400. | 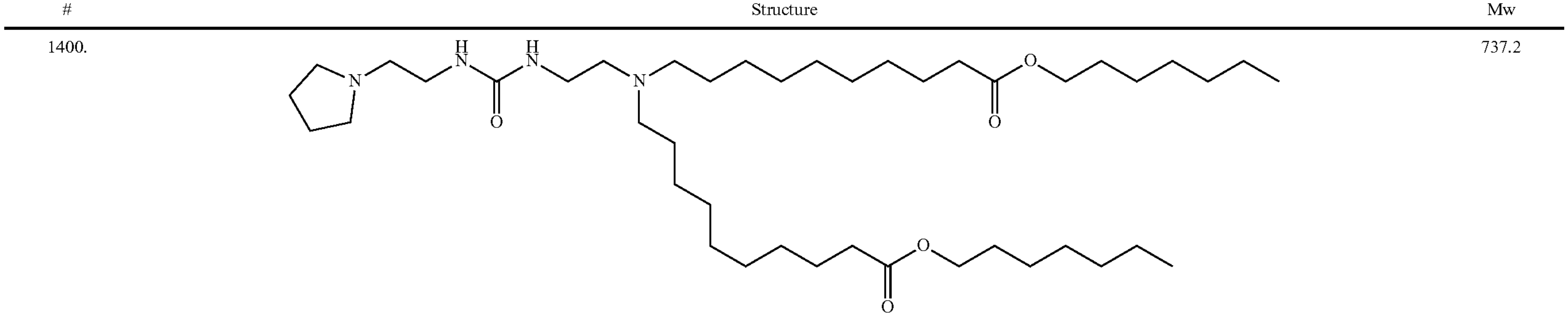 | 737.2 |
| 1401. | 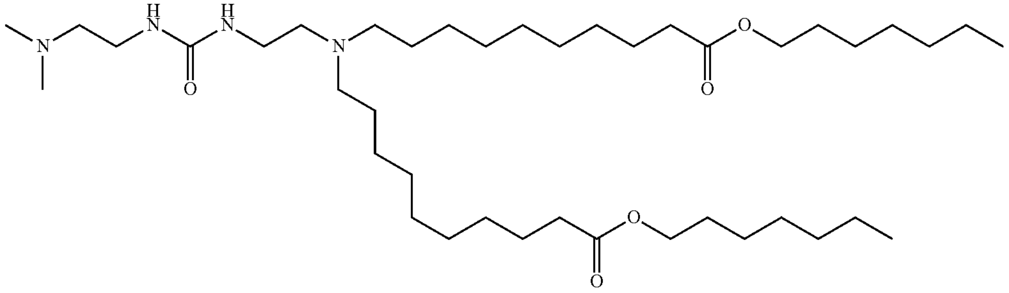 [SMILES: CCCCCCCOC(=O)CCCCCCCCCN(CCCCCCCCCC(=O)OCCCCCCC)CCNC(=O)NCCN(C)C] | 711.1 |
| 1402. | 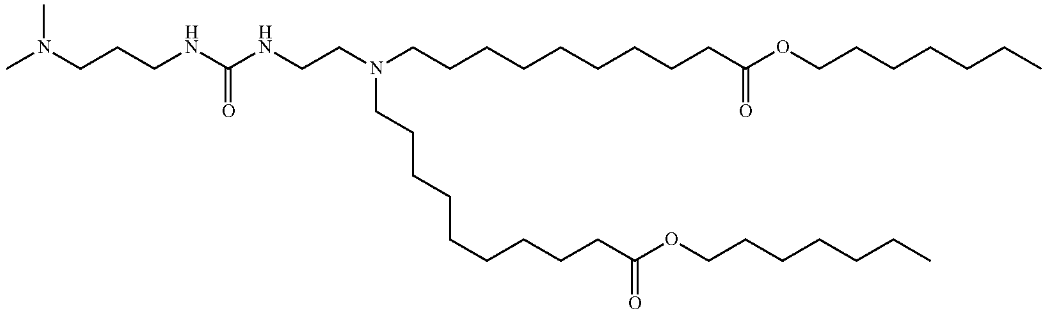 | 725.2 |

TABLE 1-continued
| # | Structure | Mw |
| --- | --- | --- |
| 1403. | 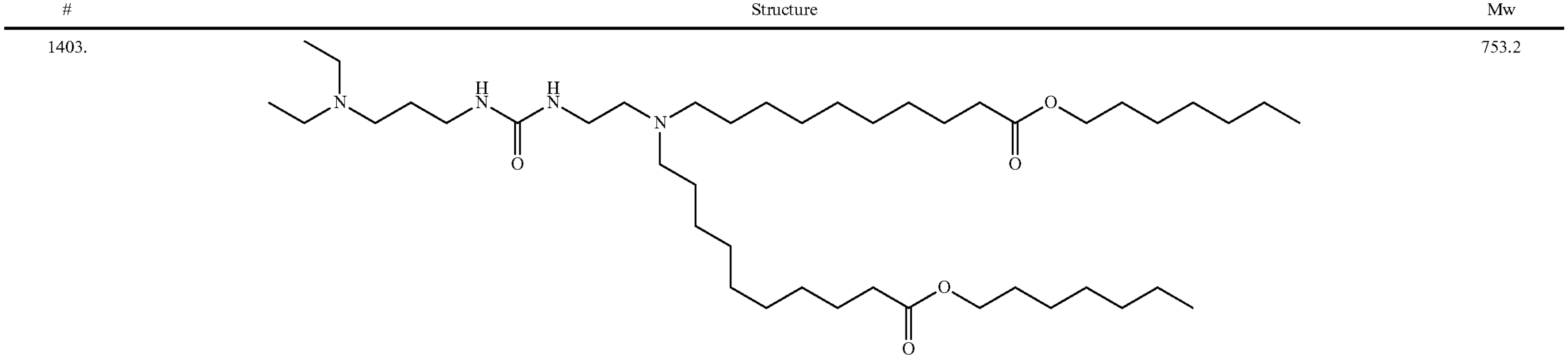 | 753.2 |
| 1404. | 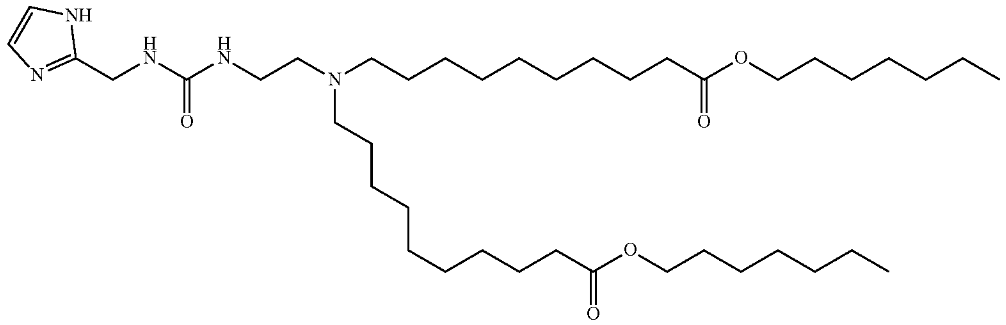 [SMILES: CCCCCCCOC(=O)CCCCCCCCCN(CCCCCCCCCC(=O)OCCCCCCC)CCNC(=O)NCc1ncc[nH]1] | 720.1 |
| 1405. | 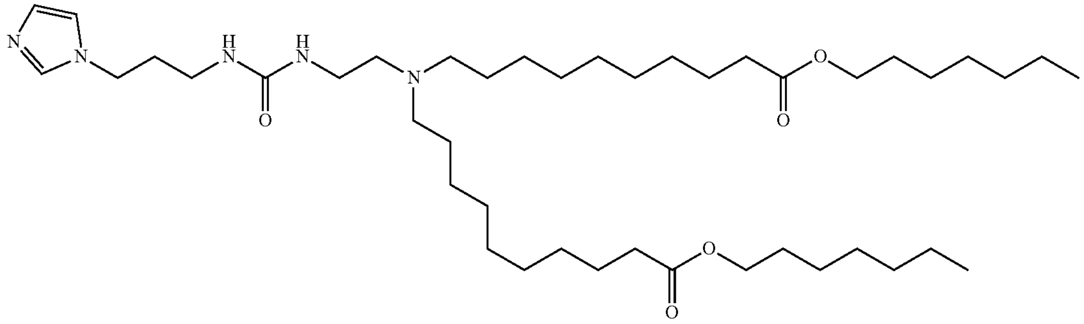 [SMILES: CCCCCCCOC(=O)CCCCCCCCCN(CCCCCCCCCC(=O)OCCCCCCC)CCNC(=O)NCCCn1ccnc1] | 748.2 |

TABLE 1-continued
| # | Structure | Mw |
|---|---|---|
| 1406. | 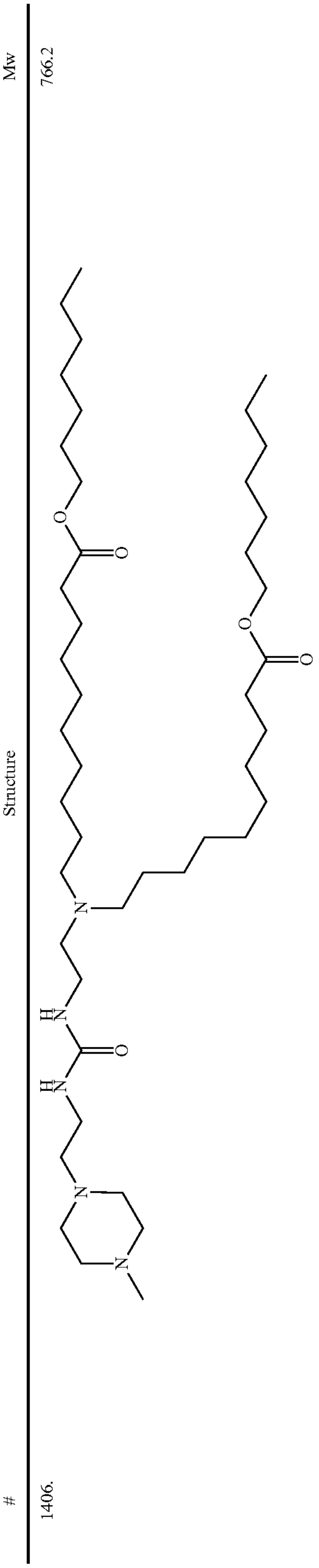 | 766.2 |
| 1407. | 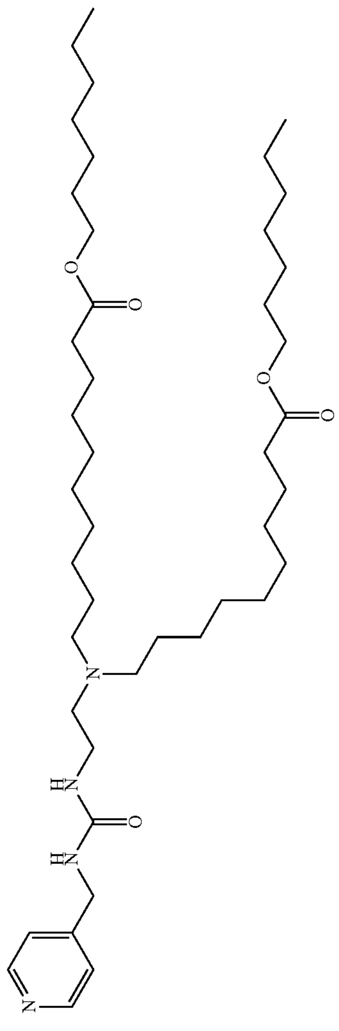 | 731.1 |
| 1408. | 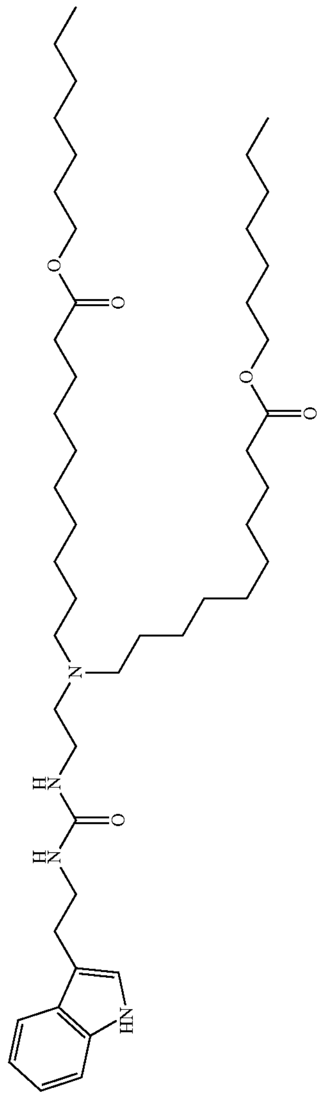 | 783.2 |

TABLE 1-continued
| # | Structure | Mw |
| --- | --- | --- |
| 1409. | 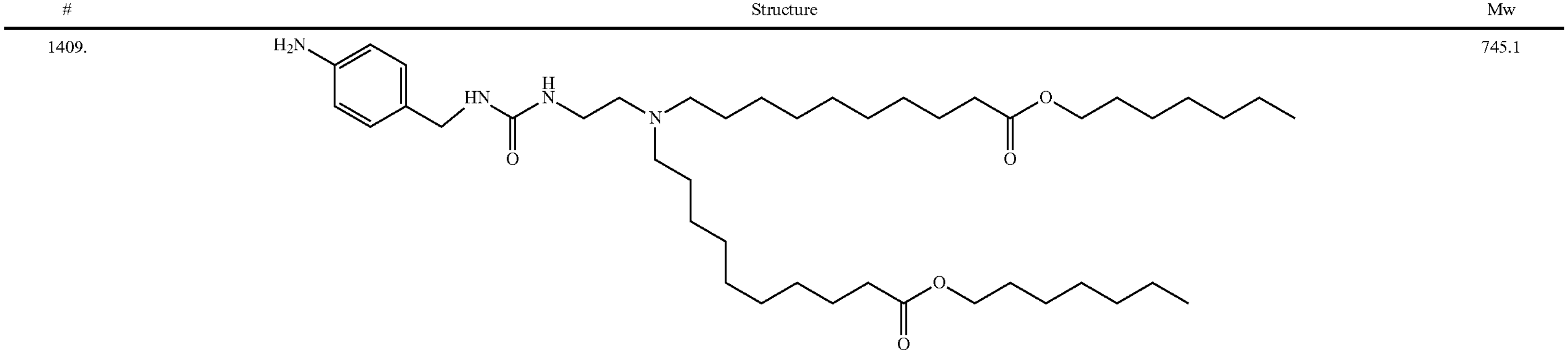 | 745.1 |
| 1410. | 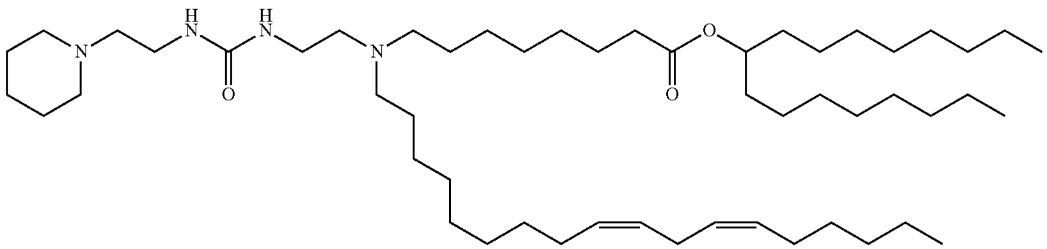 | 843.4 |
| 1411. | 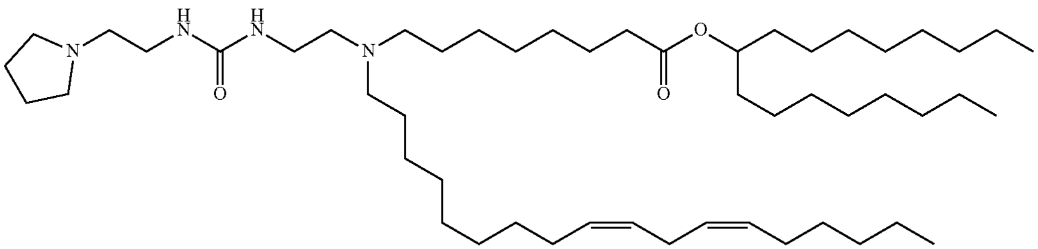 | 829.4 |

TABLE 1-continued
| # | Structure | Mw |
|---|---|---|
| 1412. | 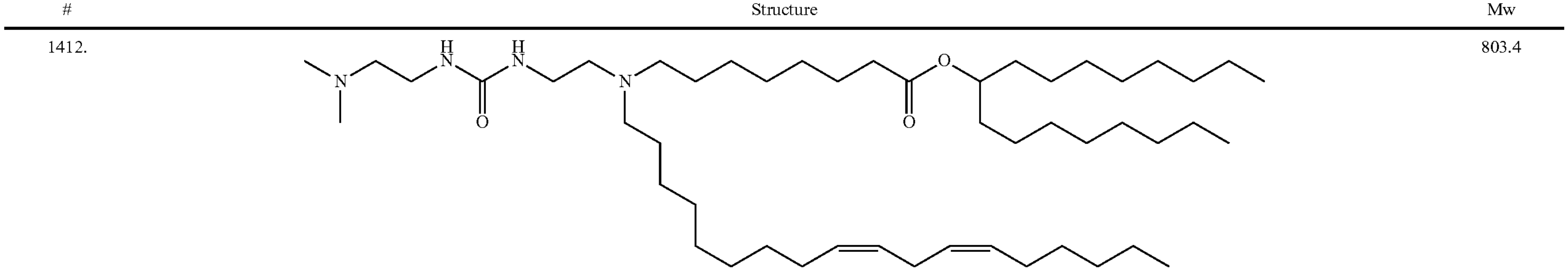 | 803.4 |
| 1413. | 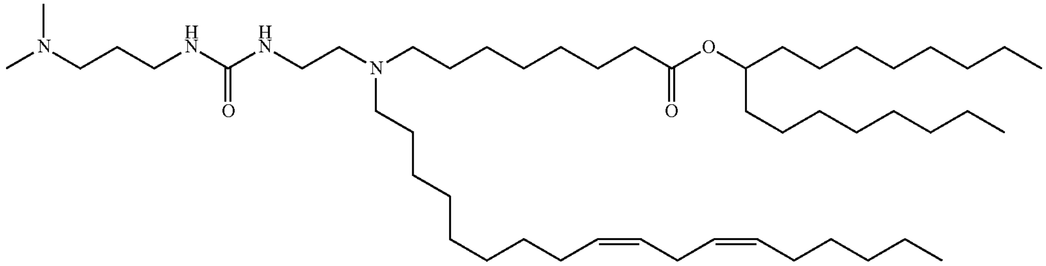 [SMILES: CCCCC/C=C\C/C=C\CCCCCCCCN(CCCCCCCC(=O)OC(CCCCCCCC)CCCCCCCC)CCNC(=O)NCCCN(C)C] | 817.4 |
| 1414. | 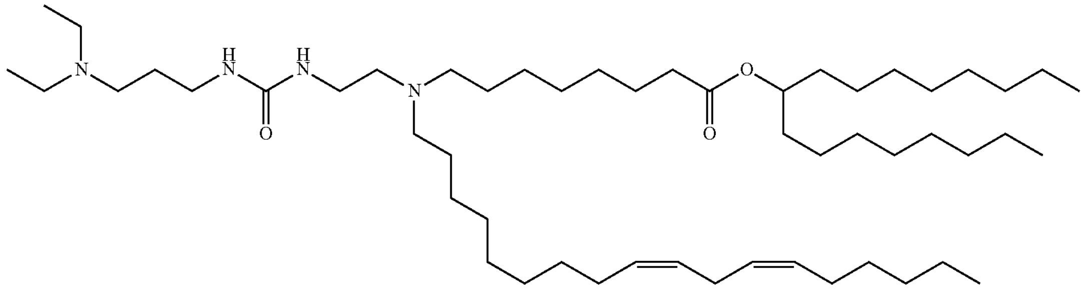 [SMILES: CCCCC/C=C\C/C=C\CCCCCCCCN(CCCCCCCC(=O)OC(CCCCCCCC)CCCCCCCC)CCNC(=O)NCCCN(CC)CC] | 845.4 |

TABLE 1-continued
| # | Structure | Mw |
| --- | --- | --- |
| 1415. | 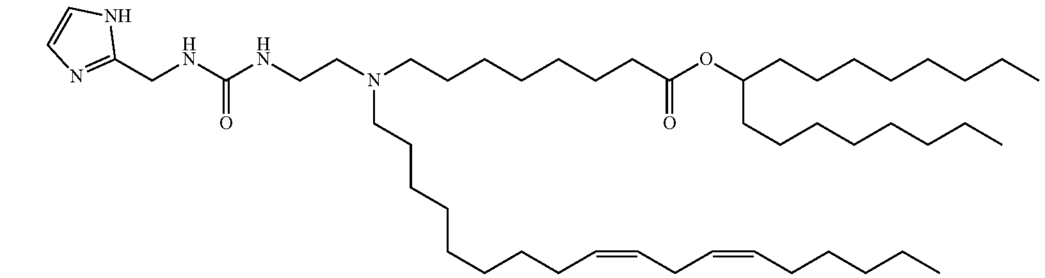 [SMILES: CCCCC/C=C\C/C=C\CCCCCCCCN(CCCCCCCC(=O)OC(CCCCCCCC)CCCCCCCC)CCNC(=O)NCc1ncc[nH]1] | 812.3 |
| 1416. | 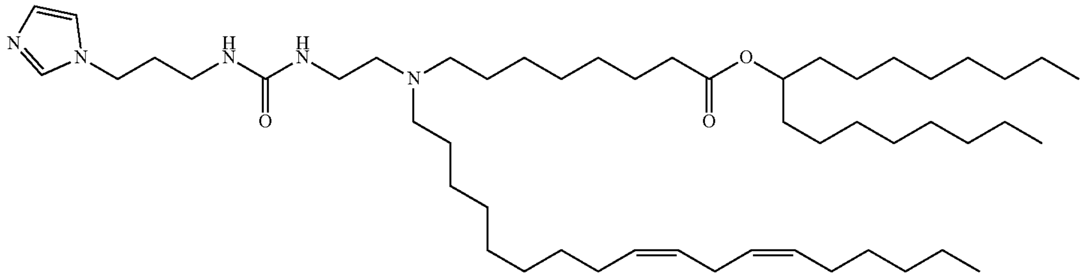 [SMILES: CCCCC/C=C\C/C=C\CCCCCCCCN(CCCCCCCC(=O)OC(CCCCCCCC)CCCCCCCC)CCNC(=O)NCCCn1ccnc1] | 840.4 |
| 1417. | 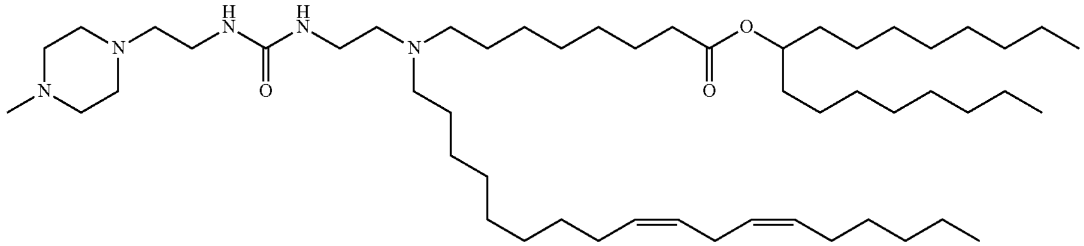 | 858.4 |

TABLE 1-continued
| # | Structure | Mw |
|---|---|---|
| 1418. | 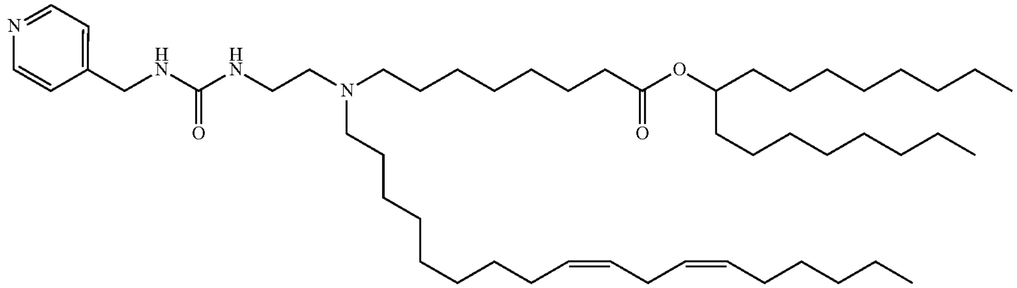 [SMILES: CCCCC/C=C\C/C=C\CCCCCCCCN(CCCCCCCC(=O)OC(CCCCCCCC)CCCCCCCC)CCNC(=O)NCc1ccncc1] | 823.3 |
| 1419. | 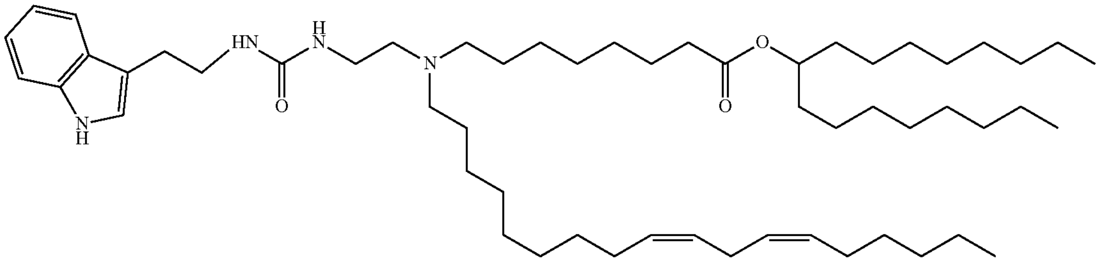 [SMILES: CCCCC/C=C\C/C=C\CCCCCCCCN(CCCCCCCC(=O)OC(CCCCCCCC)CCCCCCCC)CCNC(=O)NCCc1c[nH]c2ccccc12] | 875.4 |
| 1420. | 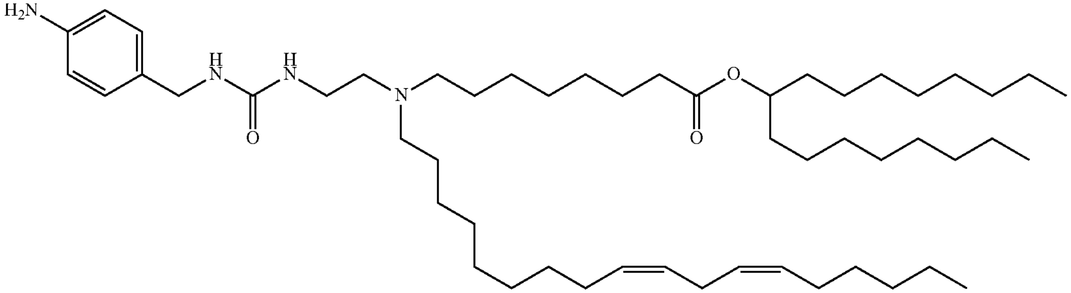 [SMILES: CCCCC/C=C\C/C=C\CCCCCCCCN(CCCCCCCC(=O)OC(CCCCCCCC)CCCCCCCC)CCNC(=O)NCc1ccc(N)cc1] | 837.4 |

TABLE 1-continued
| # | Structure | Mw |
|---|---|---|
| 1421. | 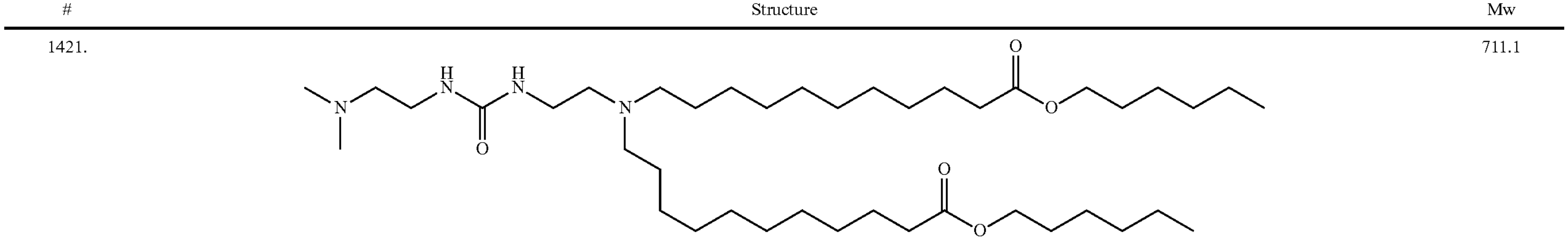 | 711.1 |
| 1422. | 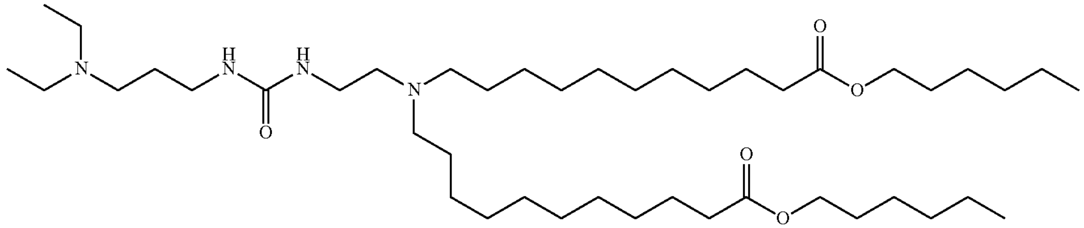 [SMILES: CCCCCCOC(=O)CCCCCCCCCCN(CCCCCCCCCCC(=O)OCCCCCC)CCNC(=O)NCCCN(CC)CC] | 753.2 |
| 1423. | 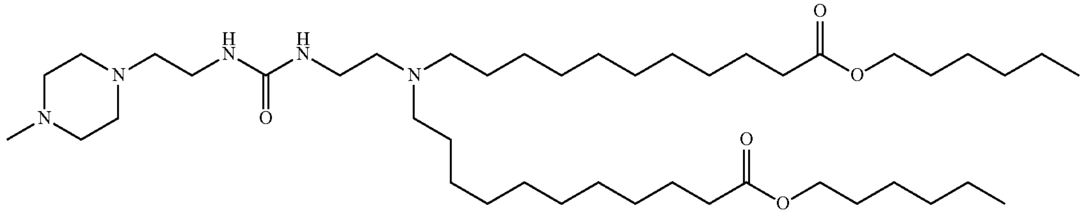 | 766.2 |
| 1424. | 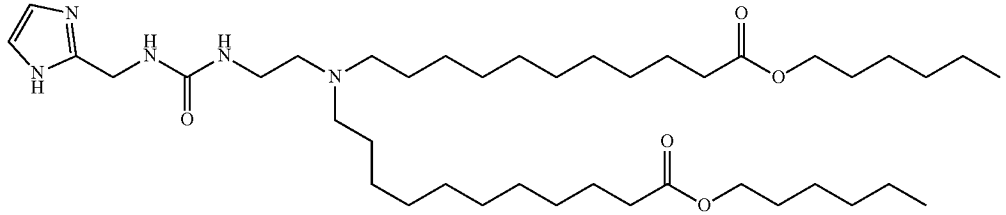 [SMILES: CCCCCCOC(=O)CCCCCCCCCCN(CCCCCCCCCCC(=O)OCCCCCC)CCNC(=O)NCc1ncc[nH]1] | 720.1 |

TABLE 1-continued
| # | Structure | Mw |
| --- | --- | --- |
| 1425. | 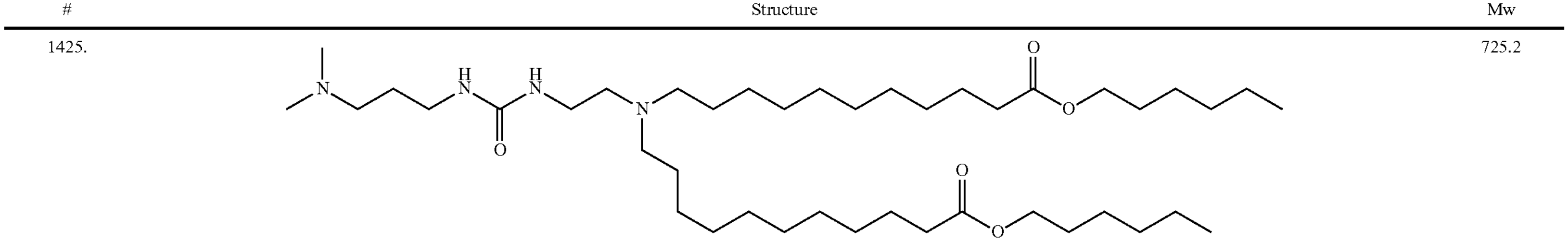 | 725.2 |
| 1426. | 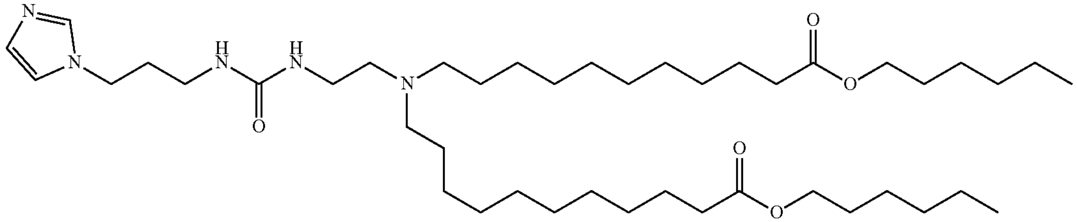 [SMILES: CCCCCCOC(=O)CCCCCCCCCCN(CCCCCCCCCCC(=O)OCCCCCC)CCNC(=O)NCCCn1ccnc1] | 748.2 |
| 1427. | 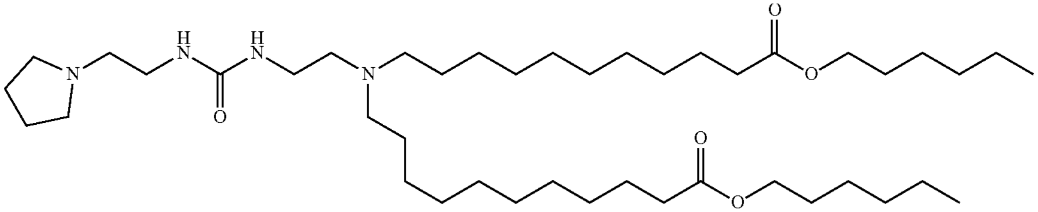 [SMILES: CCCCCCOC(=O)CCCCCCCCCCN(CCCCCCCCCCC(=O)OCCCCCC)CCNC(=O)NCCN1CCCC1] | 737.2 |
| 1428. | 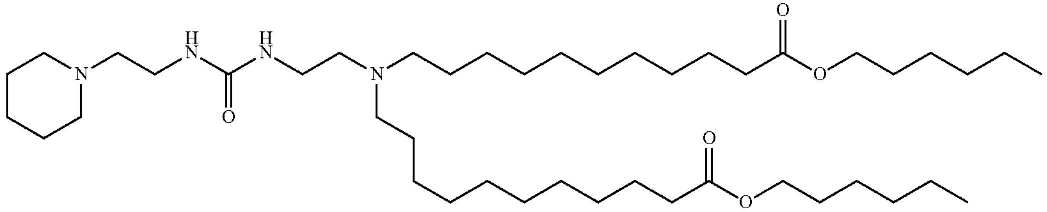 [SMILES: CCCCCCOC(=O)CCCCCCCCCCN(CCCCCCCCCCC(=O)OCCCCCC)CCNC(=O)NCCN1CCCCC1] | 751.2 |

TABLE 1-continued
| # | Structure | Mw |
|---|---|---|
| 1429. | 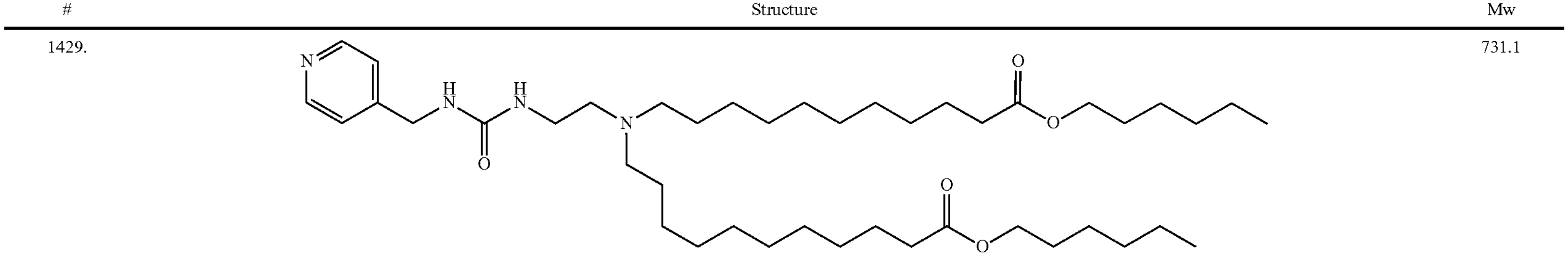 | 731.1 |
| 1430. | 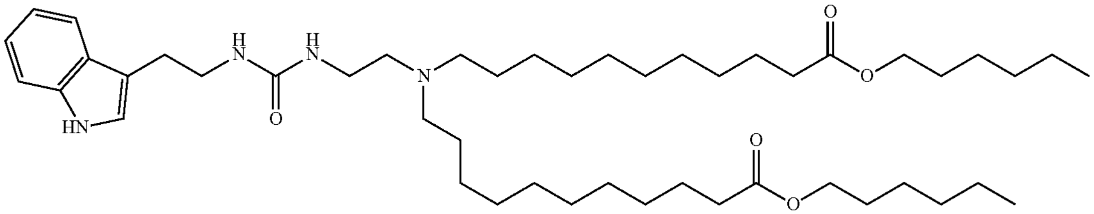 [SMILES: CCCCCCOC(=O)CCCCCCCCCCN(CCCCCCCCCCC(=O)OCCCCCC)CCNC(=O)NCCc1c[nH]c2ccccc12] | 783.2 |
| 1431. | 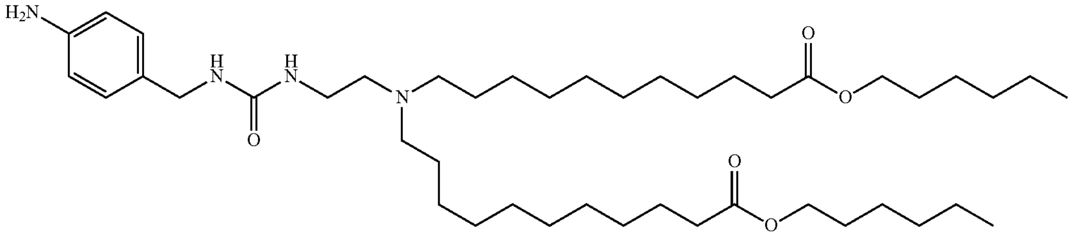 [SMILES: CCCCCCOC(=O)CCCCCCCCCCN(CCCCCCCCCCC(=O)OCCCCCC)CCNC(=O)NCc1ccc(N)cc1] | 745.1 |
| 1432. | 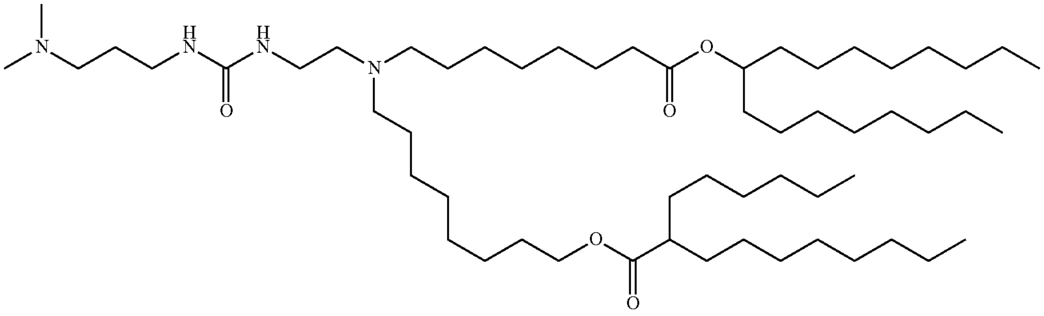 [SMILES: CCCCCCCCC(CCCCCCCC)OC(=O)CCCCCCCN(CCCCCCCCOC(=O)C(CCCCCC)CCCCCCCC)CCNC(=O)NCCCN(C)C] | 935.6 |

TABLE 1-continued
| # | Structure | Mw |
|---|---|---|
| 1433. | 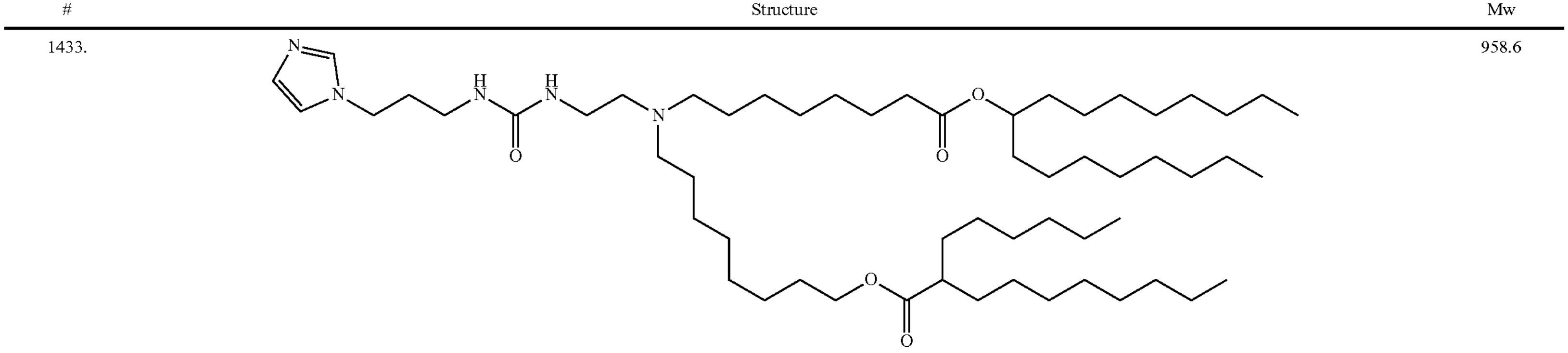 | 958.6 |
| 1434. | 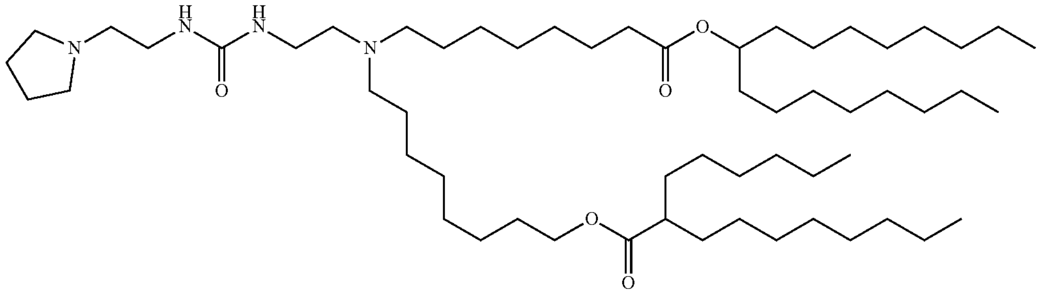 | 947.6 |
| 1435. | 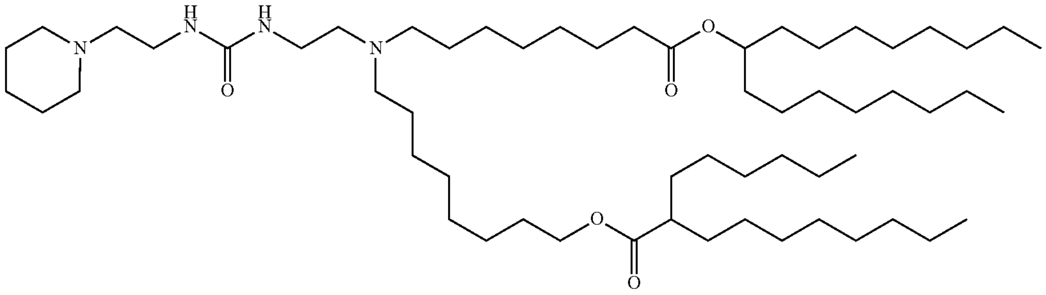 [SMILES: CCCCCCCCC(CCCCCCCC)OC(=O)CCCCCCCN(CCCCCCCCOC(=O)C(CCCCCC)CCCCCCCC)CCNC(=O)NCCN1CCCCC1] | 961.6 |

TABLE 1-continued
| # | Structure | Mw |
| --- | --- | --- |
| 1436. | 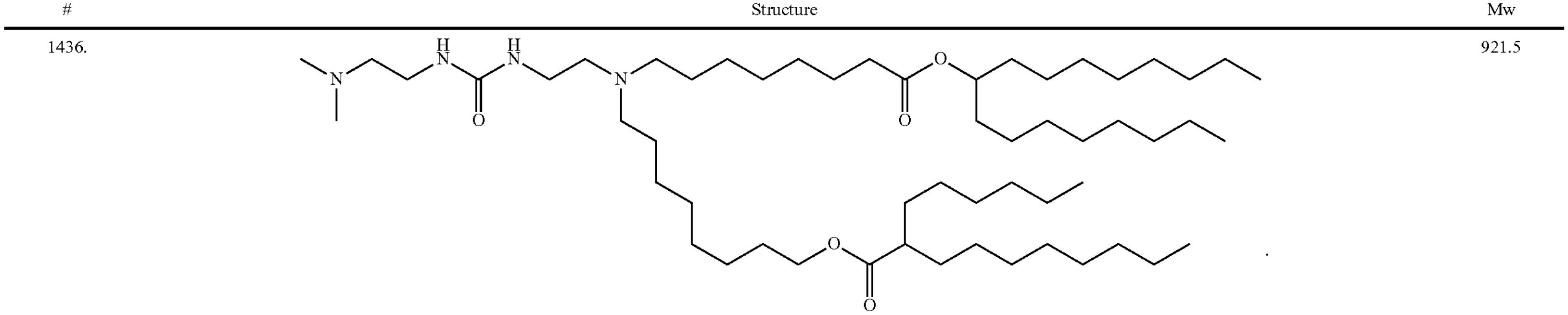 | 921.5 |
| 1437. | 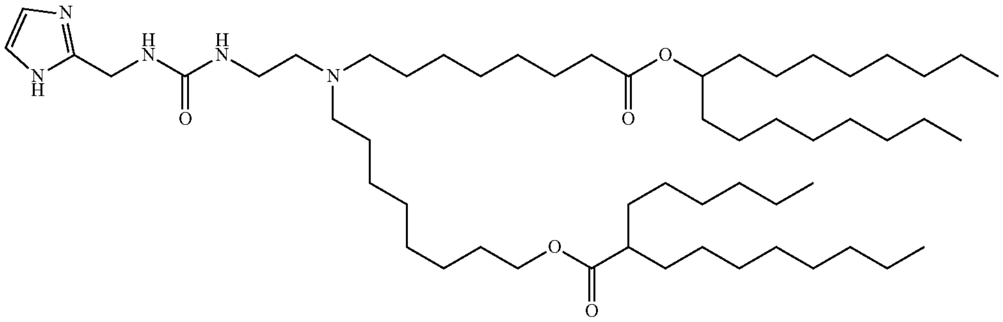 [SMILES: CCCCCCCCC(CCCCCCCC)OC(=O)CCCCCCCN(CCCCCCCCOC(=O)C(CCCCCC)CCCCCCCC)CCNC(=O)NCc1ncc[nH]1] | 930.5 |
| 1438. | 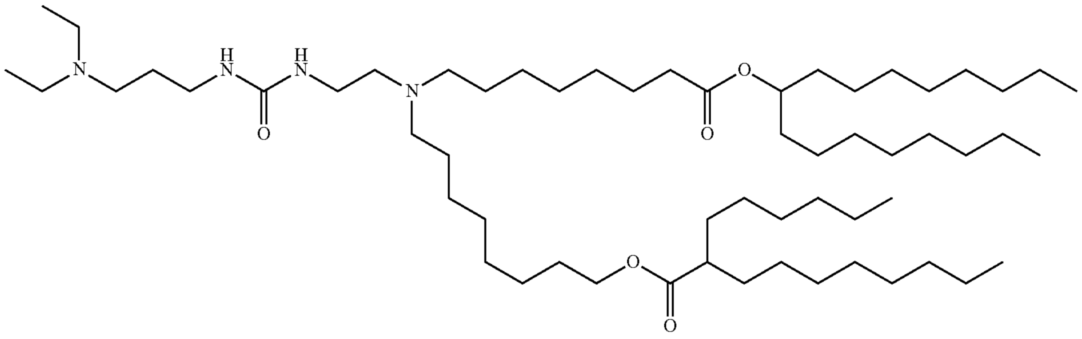 [SMILES: CCCCCCCCC(CCCCCCCC)OC(=O)CCCCCCCN(CCCCCCCCOC(=O)C(CCCCCC)CCCCCCCC)CCNC(=O)NCCCN(CC)CC] | 963.6 |

TABLE 1-continued
| # | Structure | Mw |
|---|---|---|
| 1439. | 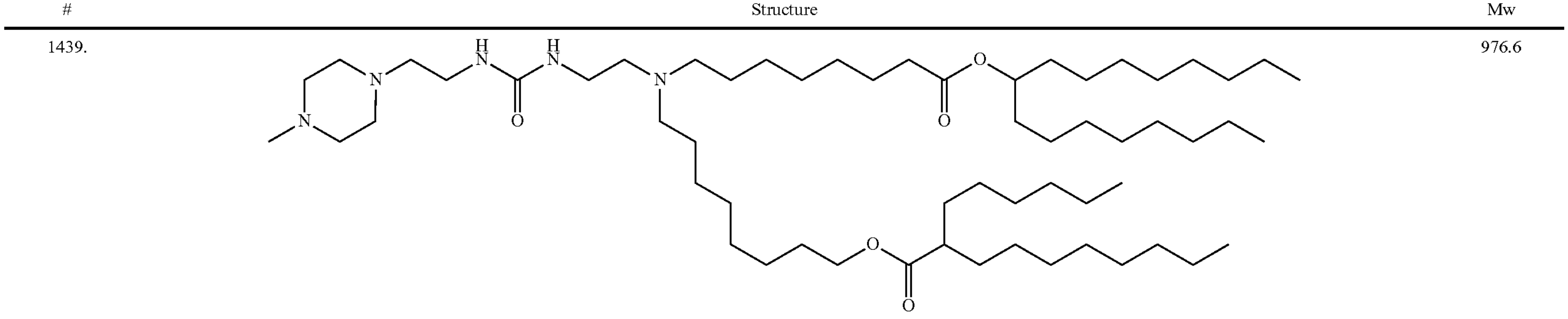 | 976.6 |
| 1440. | 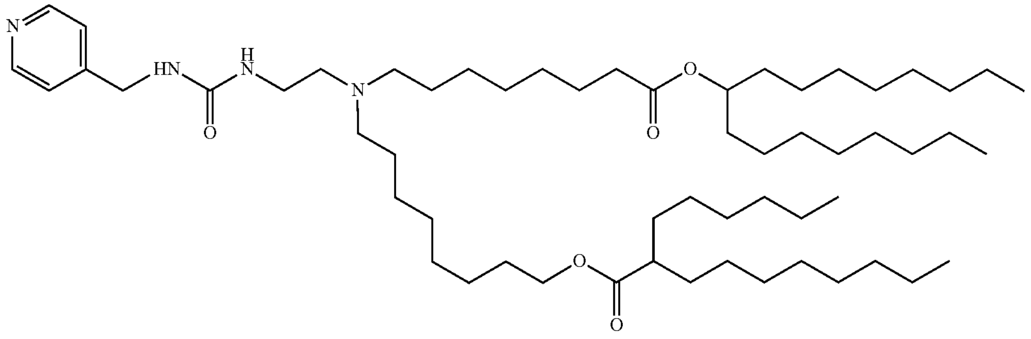 [SMILES: CCCCCCCCC(CCCCCCCC)OC(=O)CCCCCCCN(CCCCCCCCOC(=O)C(CCCCCC)CCCCCCCC)CCNC(=O)NCc1ccncc1] | 941.5 |
| 1441. | 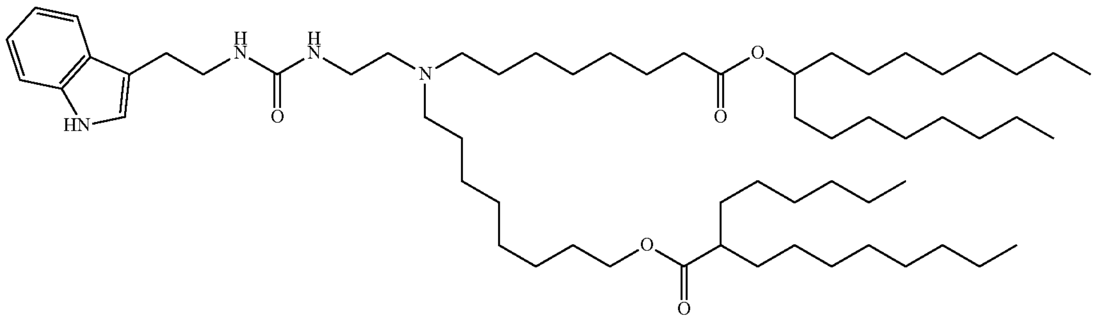 [SMILES: CCCCCCCCC(CCCCCCCC)OC(=O)CCCCCCCN(CCCCCCCCOC(=O)C(CCCCCC)CCCCCCCC)CCNC(=O)NCCc1c[nH]c2ccccc12] | 993.6 |

TABLE 1-continued
| # | Structure | Mw |
| --- | --- | --- |
| 1442. | 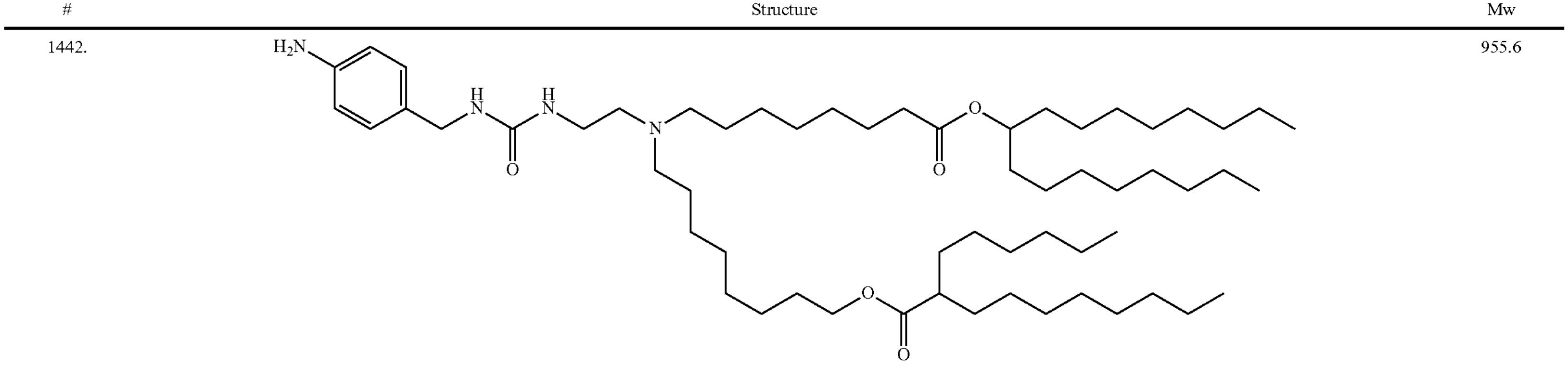 | 955.6 |
| 1443. | 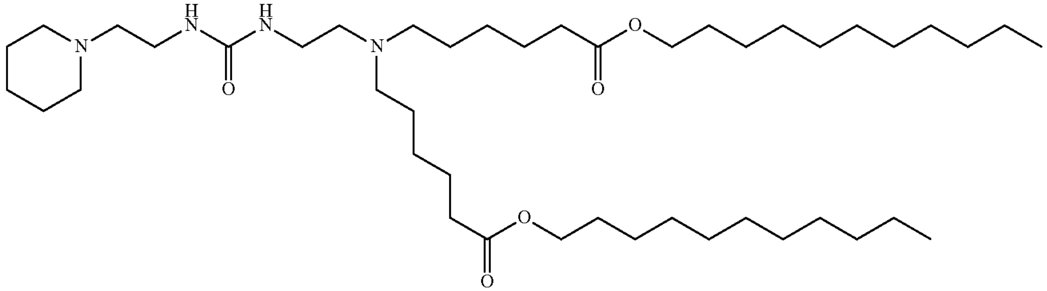 [SMILES: CCCCCCCCCCCOC(=O)CCCCCN(CCCCCC(=O)OCCCCCCCCCCC)CCNC(=O)NCCN1CCCCC1] | 751.2 |
| 1444. | 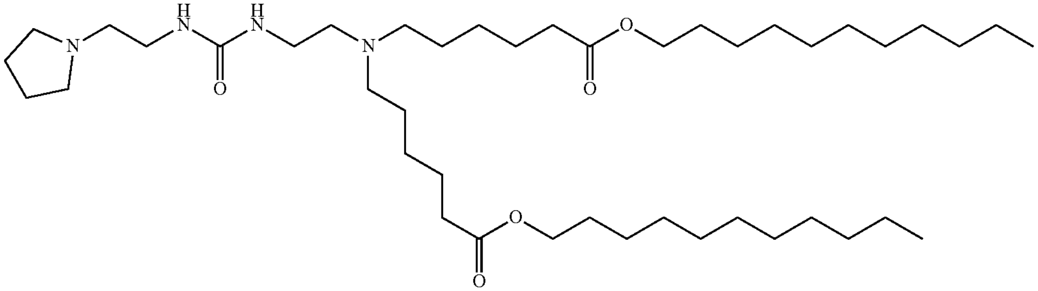 [SMILES: CCCCCCCCCCCOC(=O)CCCCCN(CCCCCC(=O)OCCCCCCCCCCC)CCNC(=O)NCCN1CCCC1] | 737.2 |

TABLE 1-continued
| # | Structure | Mw |
| --- | --- | --- |
| 1445. | 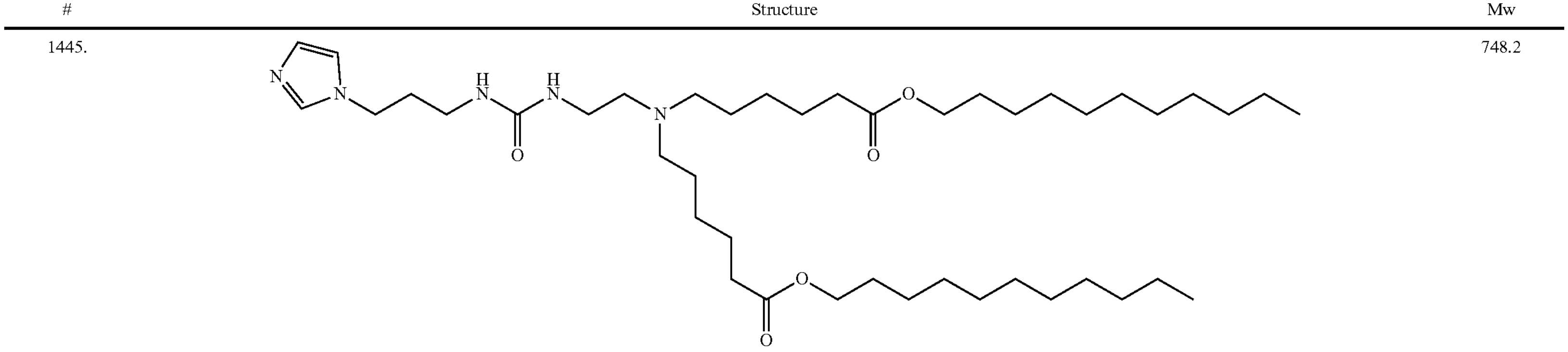 | 748.2 |
| 1446. | 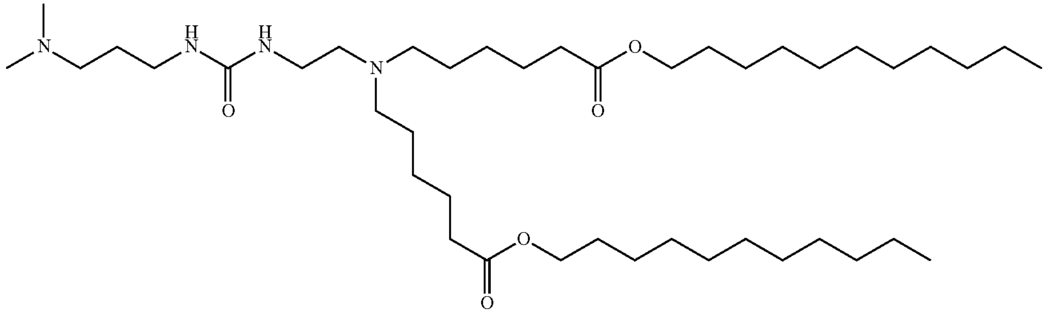 [SMILES: CCCCCCCCCCCOC(=O)CCCCCN(CCCCCC(=O)OCCCCCCCCCCC)CCNC(=O)NCCCN(C)C] | 725.2 |
| 1447. | 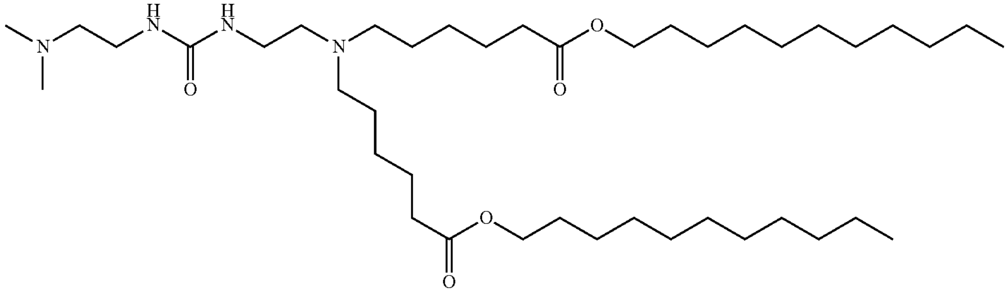 [SMILES: CCCCCCCCCCCOC(=O)CCCCCN(CCCCCC(=O)OCCCCCCCCCCC)CCNC(=O)NCCN(C)C] | 711.1 |

TABLE 1-continued
| # | Structure | Mw |
| --- | --- | --- |
| 1448. | 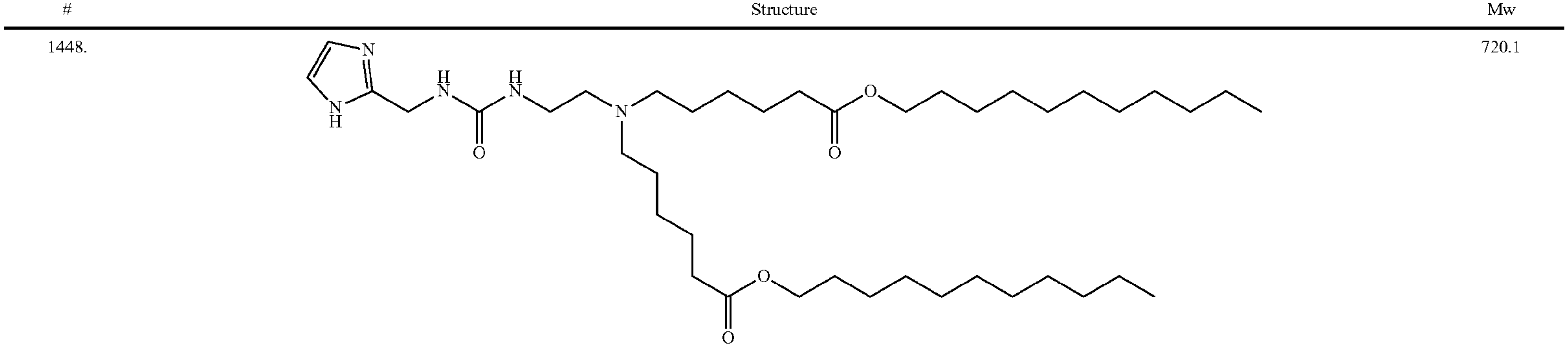 | 720.1 |
| 1449. | 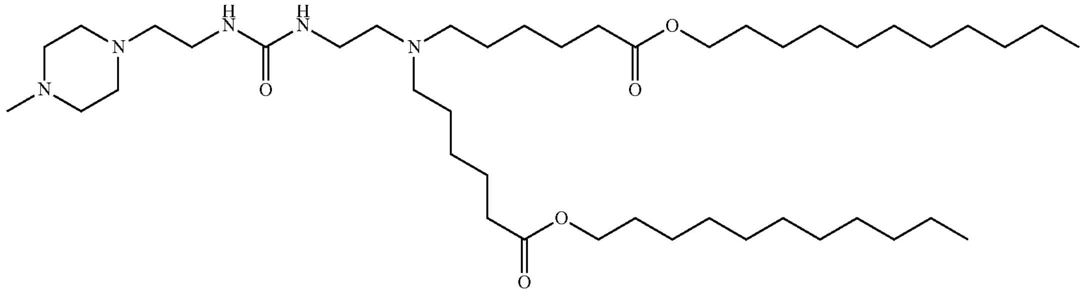 [SMILES: CCCCCCCCCCCOC(=O)CCCCCN(CCCCCC(=O)OCCCCCCCCCCC)CCNC(=O)NCCN1CCN(C)CC1] | 766.2 |
| 1450. | 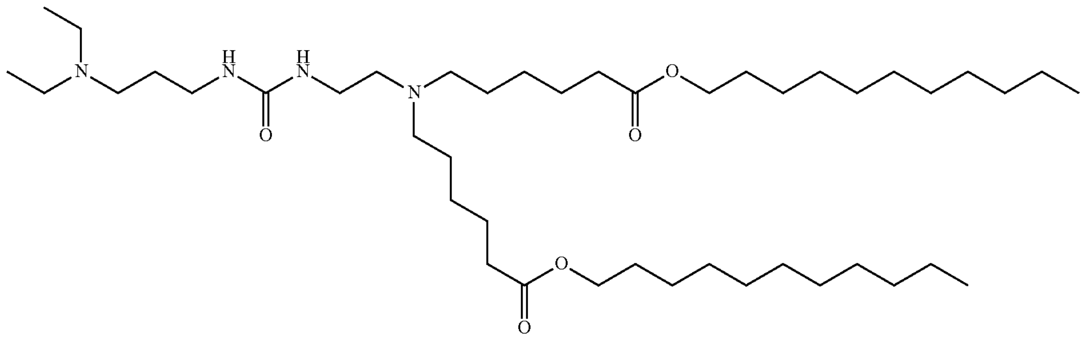 [SMILES: CCCCCCCCCCCOC(=O)CCCCCN(CCCCCC(=O)OCCCCCCCCCCC)CCNC(=O)NCCCN(CC)CC] | 753.2 |

TABLE 1-continued
| # | Structure | Mw |
| --- | --- | --- |
| 1451. | 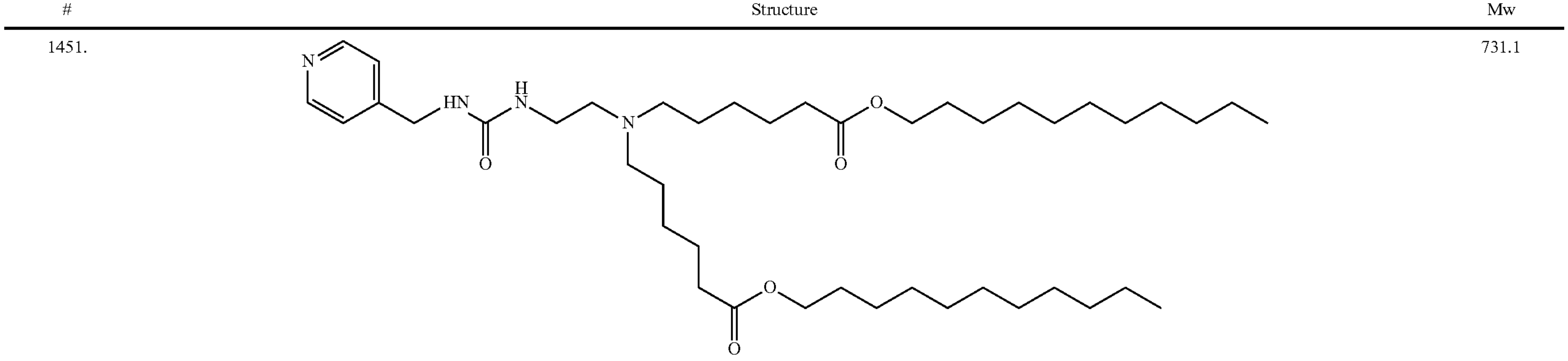 | 731.1 |
| 1452. | 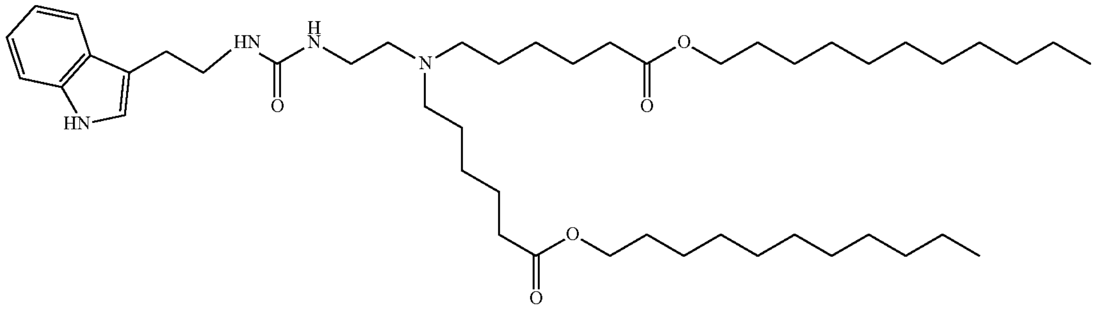 [SMILES: CCCCCCCCCCCOC(=O)CCCCCN(CCCCCC(=O)OCCCCCCCCCCC)CCNC(=O)NCCc1c[nH]c2ccccc12] | 783.2 |
| 1453. | 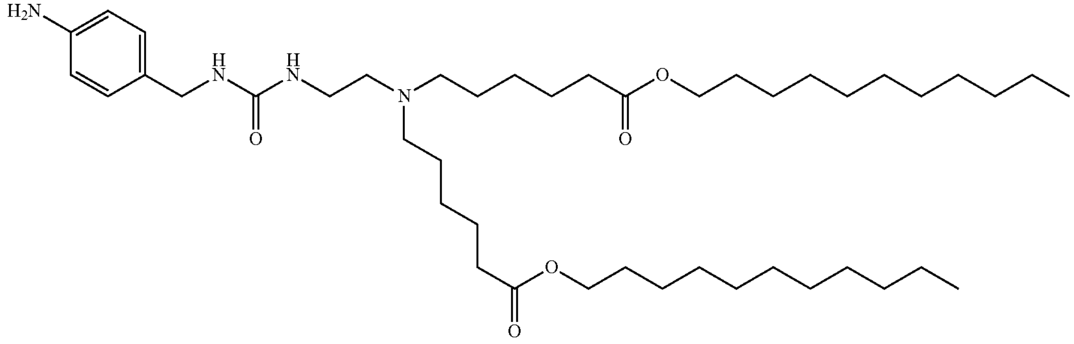 [SMILES: CCCCCCCCCCCOC(=O)CCCCCN(CCCCCC(=O)OCCCCCCCCCCC)CCNC(=O)NCc1ccc(N)cc1] | 745.1 |

TABLE 1-continued
| # | Structure | Mw |
| --- | --- | --- |
| 1454. | 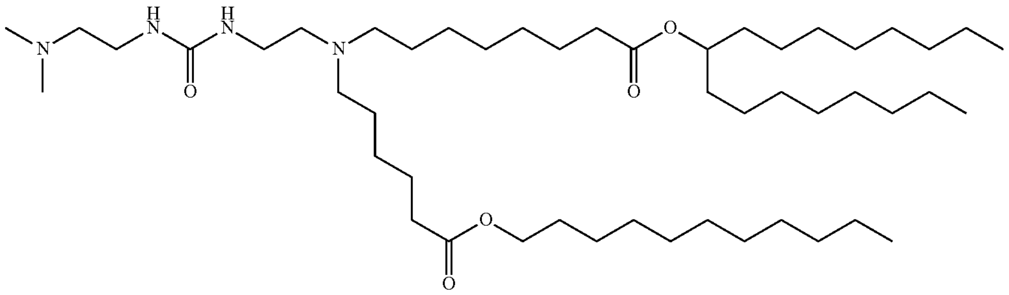 [SMILES: CCCCCCCCCCCOC(=O)CCCCCN(CCCCCCCC(=O)OC(CCCCCCCC)CCCCCCCC)CCNC(=O)NCCN(C)C] | 823.3 |
| 1455. | 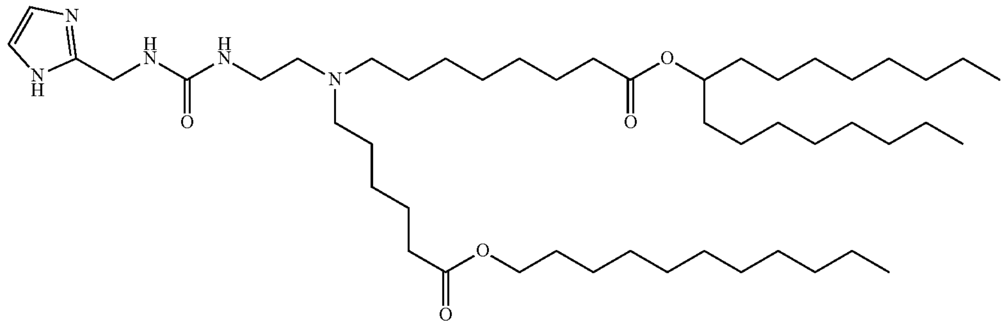 | 832.3 |
| 1456. | 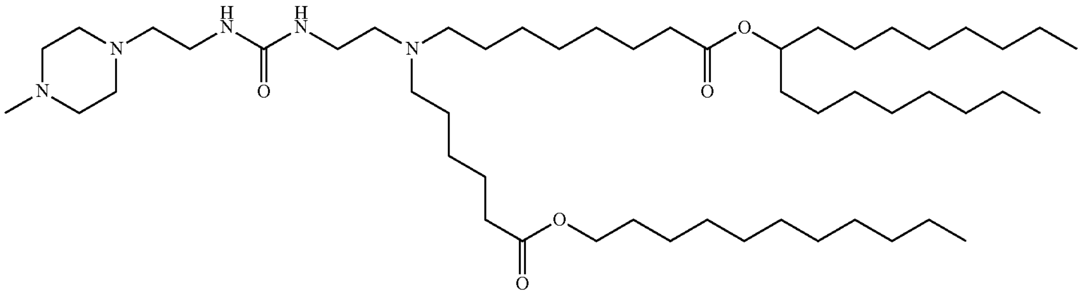 [SMILES: CCCCCCCCCCCOC(=O)CCCCCN(CCCCCCCC(=O)OC(CCCCCCCC)CCCCCCCC)CCNC(=O)NCCN1CCN(C)CC1] | 878.4 |

TABLE 1-continued
| # | Structure | Mw |
|---|---|---|
| 1457. | 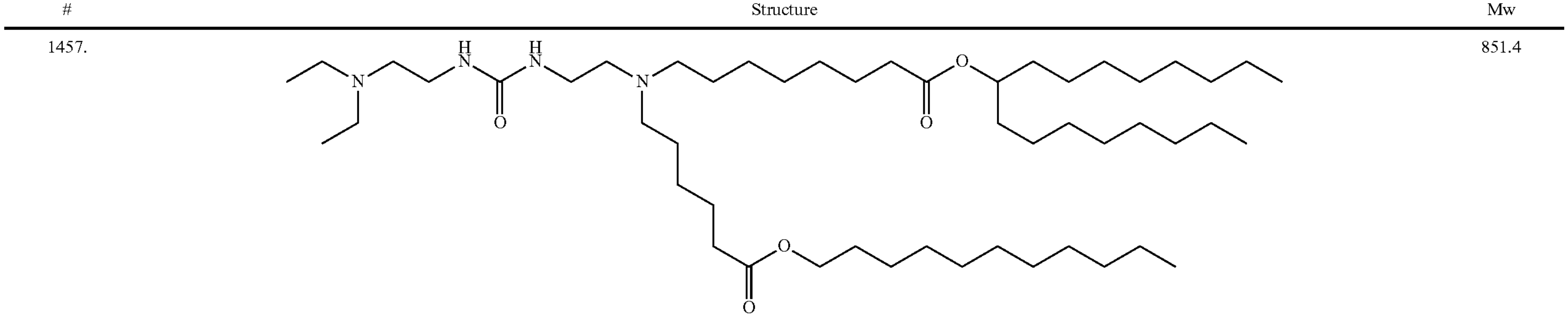 | 851.4 |
| 1458. | 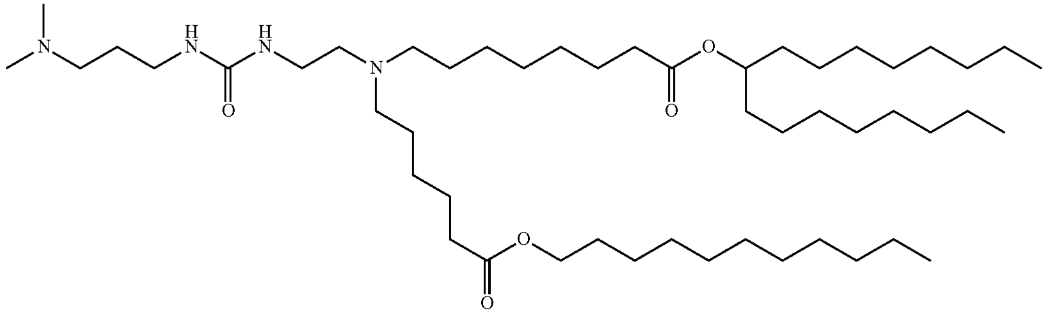 [SMILES: CCCCCCCCCCCOC(=O)CCCCCN(CCCCCCCC(=O)OC(CCCCCCCC)CCCCCCCC)CCNC(=O)NCCCN(C)C] | 837.4 |
| 1459. | 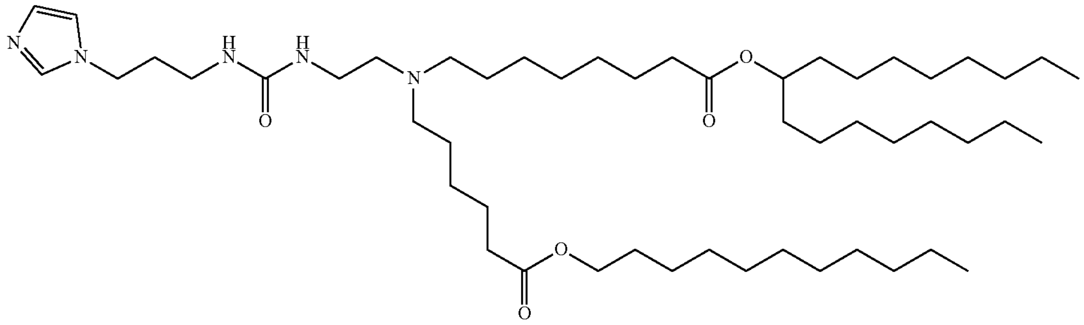 [SMILES: CCCCCCCCCCCOC(=O)CCCCCN(CCCCCCCC(=O)OC(CCCCCCCC)CCCCCCCC)CCNC(=O)NCCCn1ccnc1] | 860.4 |

TABLE 1-continued
| # | Structure | Mw |
| --- | --- | --- |
| 1460. | 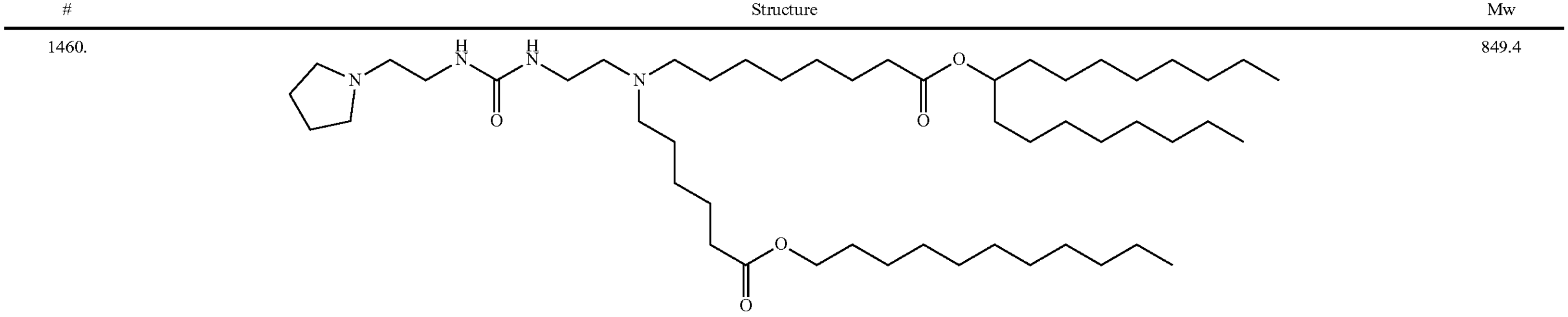 | 849.4 |
| 1461. | 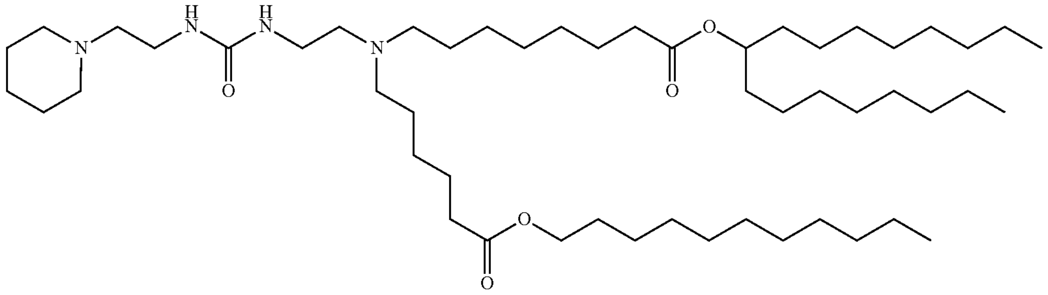 [SMILES: CCCCCCCCCCCOC(=O)CCCCCN(CCCCCCCC(=O)OC(CCCCCCCC)CCCCCCCC)CCNC(=O)NCCN1CCCCC1] | 863.4 |
| 1462. | 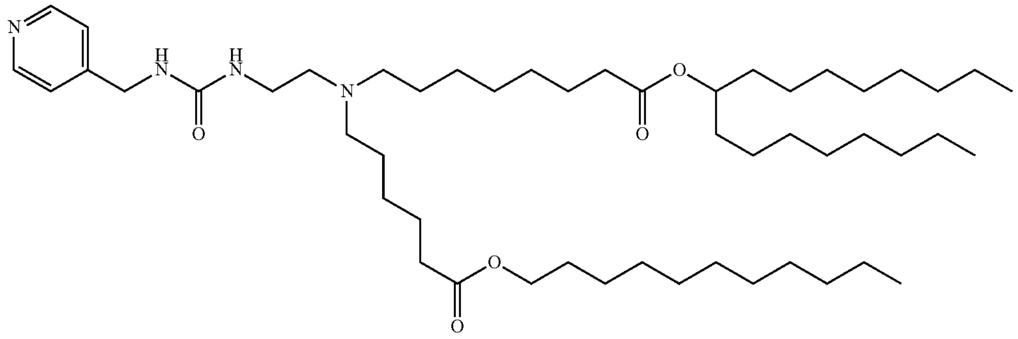 [SMILES: CCCCCCCCCCCOC(=O)CCCCCN(CCCCCCCC(=O)OC(CCCCCCCC)CCCCCCCC)CCNC(=O)NCc1ccncc1] | 843.3 |

TABLE 1-continued
| # | Structure | Mw |
| --- | --- | --- |
| 1463. | 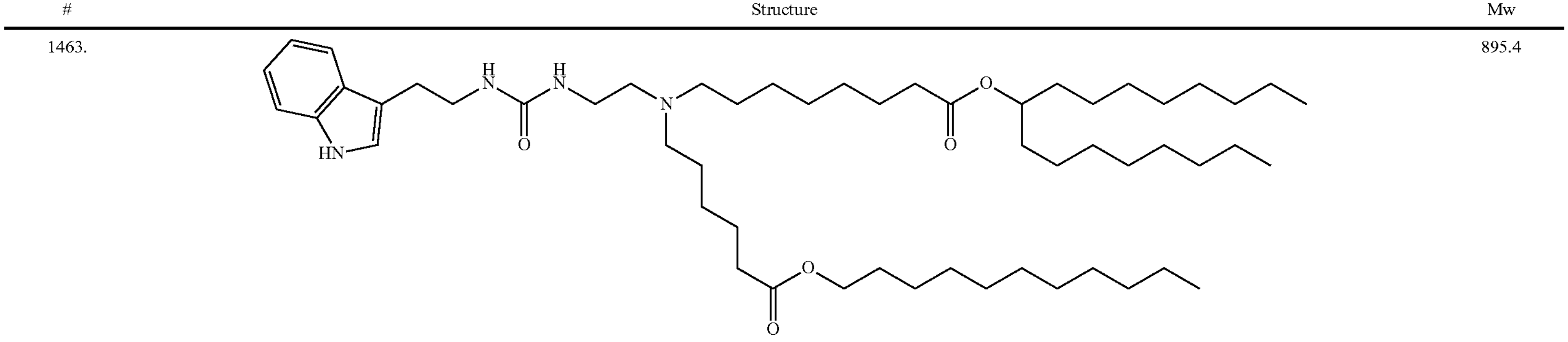 | 895.4 |
| 1464. | 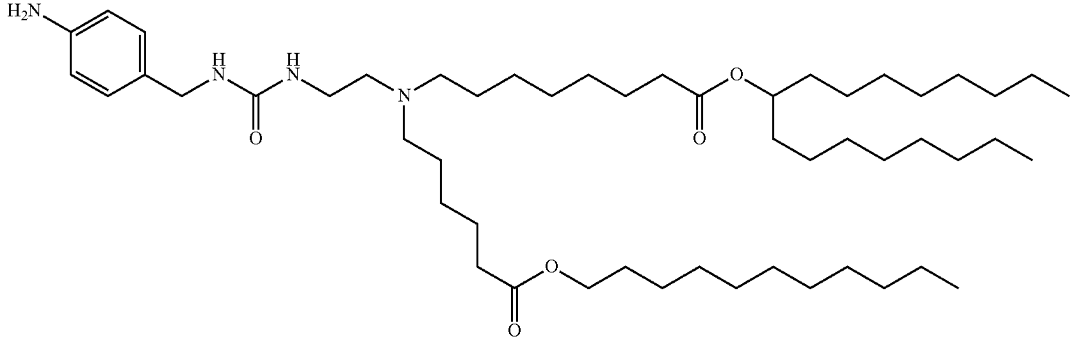 [SMILES: CCCCCCCCCCCOC(=O)CCCCCN(CCCCCCCC(=O)OC(CCCCCCCC)CCCCCCCC)CCNC(=O)NCc1ccc(N)cc1] | 857.4 |
| 1465. | 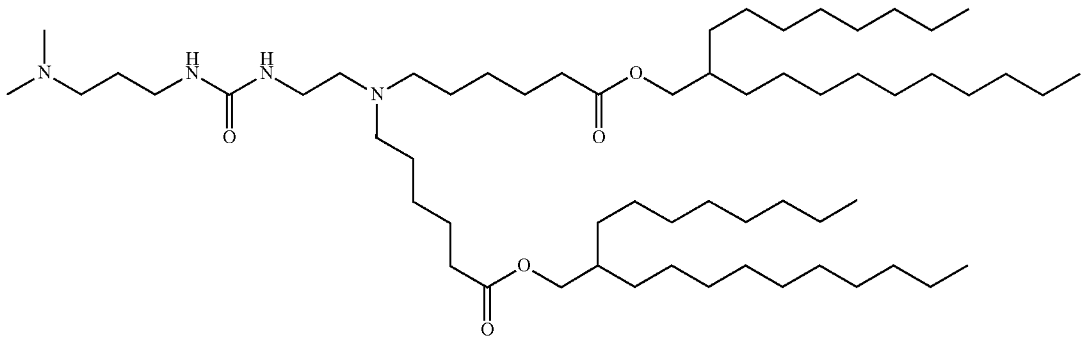 [SMILES: CCCCCCCCCCC(CCCCCCCC)COC(=O)CCCCCN(CCCCCC(=O)OCC(CCCCCCCC)CCCCCCCCCC)CCNC(=O)NCCCN(C)C] | 977.6 |

TABLE 1-continued
| # | Structure | Mw |
|---|---|---|
| 1466. | 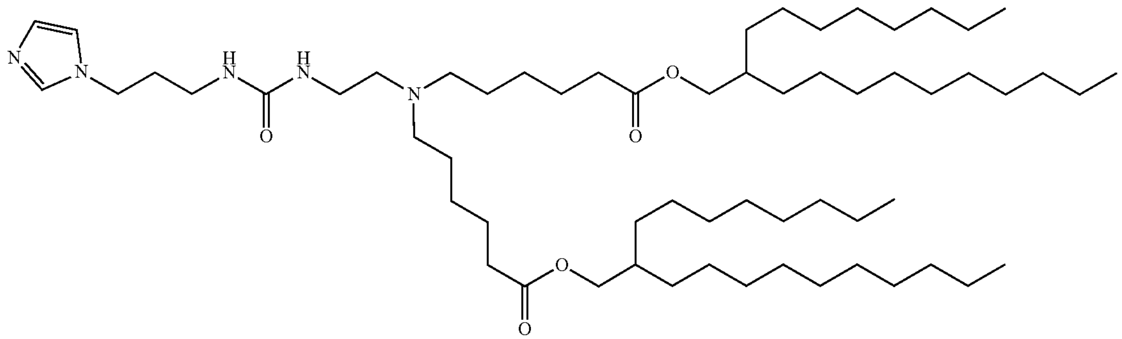 [SMILES: CCCCCCCCCCC(CCCCCCCC)COC(=O)CCCCCN(CCCCCC(=O)OCC(CCCCCCCC)CCCCCCCCCC)CCNC(=O)NCCCn1ccnc1] | 1000.6 |
| 1467. | 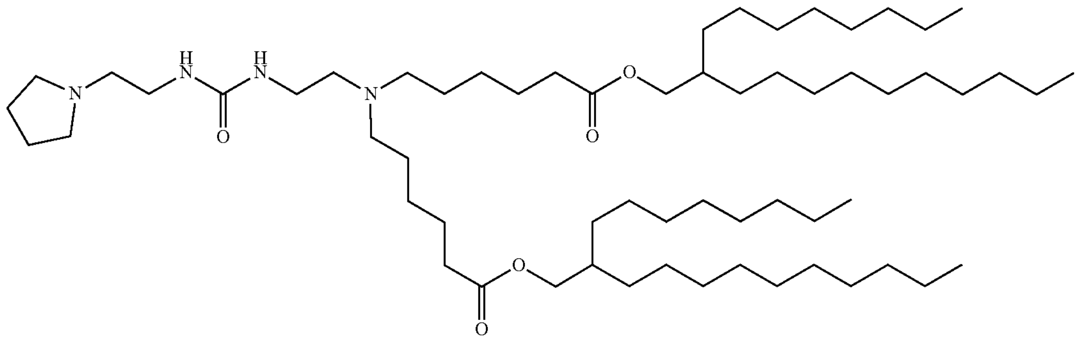 [SMILES: CCCCCCCCCCC(CCCCCCCC)COC(=O)CCCCCN(CCCCCC(=O)OCC(CCCCCCCC)CCCCCCCCCC)CCNC(=O)NCCN1CCCC1] | 989.7 |
| 1468. | 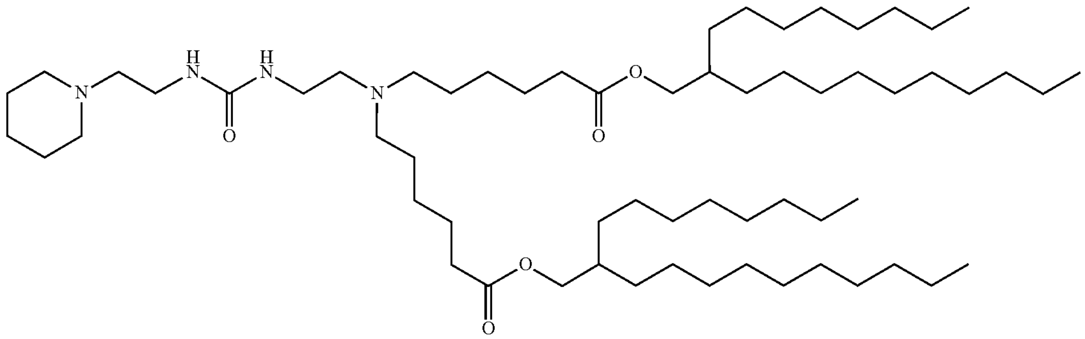 [SMILES: CCCCCCCCCCC(CCCCCCCC)COC(=O)CCCCCN(CCCCCC(=O)OCC(CCCCCCCC)CCCCCCCCCC)CCNC(=O)NCCN1CCCCC1] | 1003.7 |

TABLE 1-continued
| # | Structure | Mw |
| --- | --- | --- |
| 1469. | 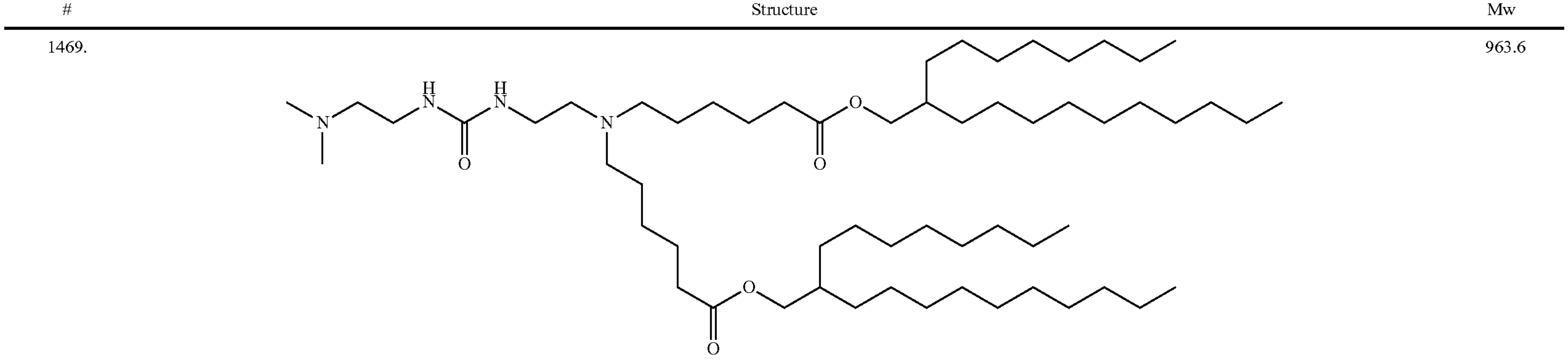 | 963.6 |
| 1470. | 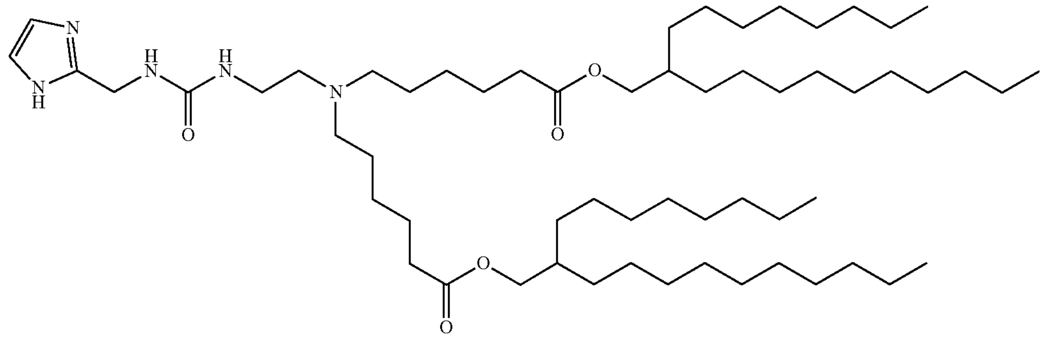 [SMILES: CCCCCCCCCCC(CCCCCCCC)COC(=O)CCCCCN(CCCCCC(=O)OCC(CCCCCCCC)CCCCCCCCCC)CCNC(=O)NCc1ncc[nH]1] | 972.6 |
| 1471. | 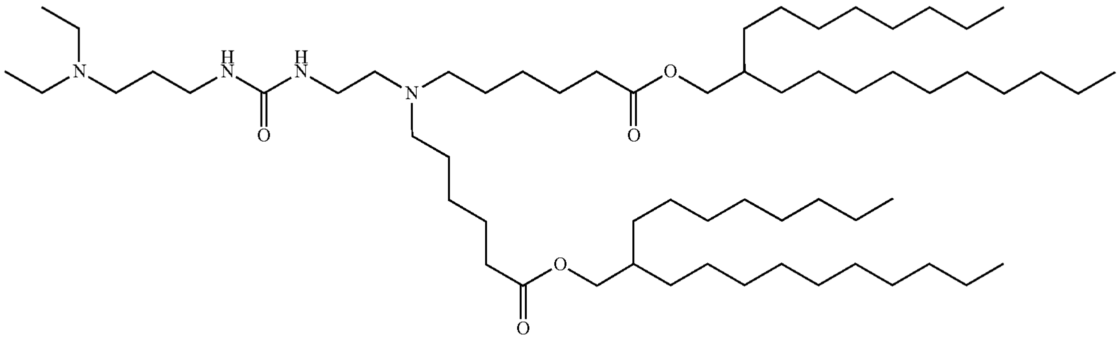 [SMILES: CCCCCCCCCCC(CCCCCCCC)COC(=O)CCCCCN(CCCCCC(=O)OCC(CCCCCCCC)CCCCCCCCCC)CCNC(=O)NCCCN(CC)CC] | 1005.7 |

TABLE 1-continued
| # | Structure | Mw |
|---|---|---|
| 1472. | 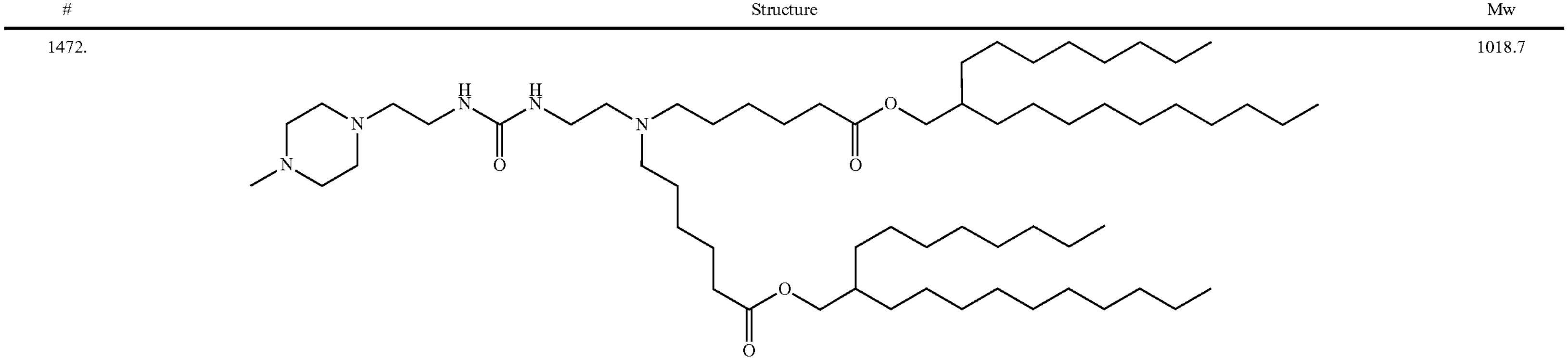 | 1018.7 |
| 1473. | 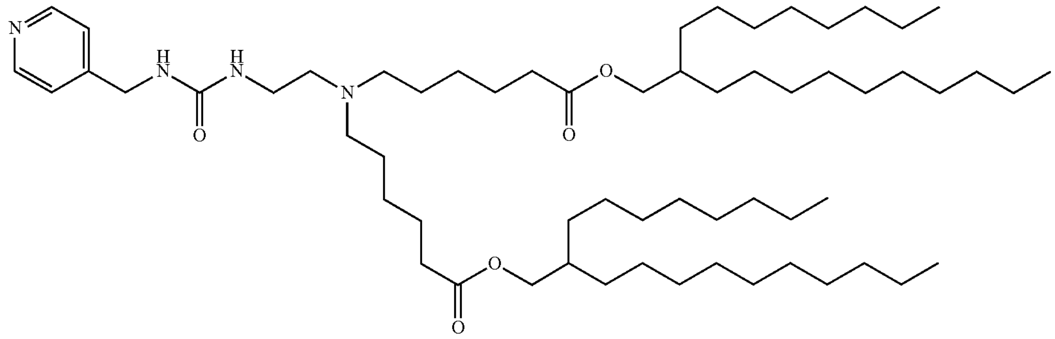 [SMILES: CCCCCCCCCCC(CCCCCCCC)COC(=O)CCCCCN(CCCCCC(=O)OCC(CCCCCCCC)CCCCCCCCCC)CCNC(=O)NCc1ccncc1] | 983.6 |
| 1474. | 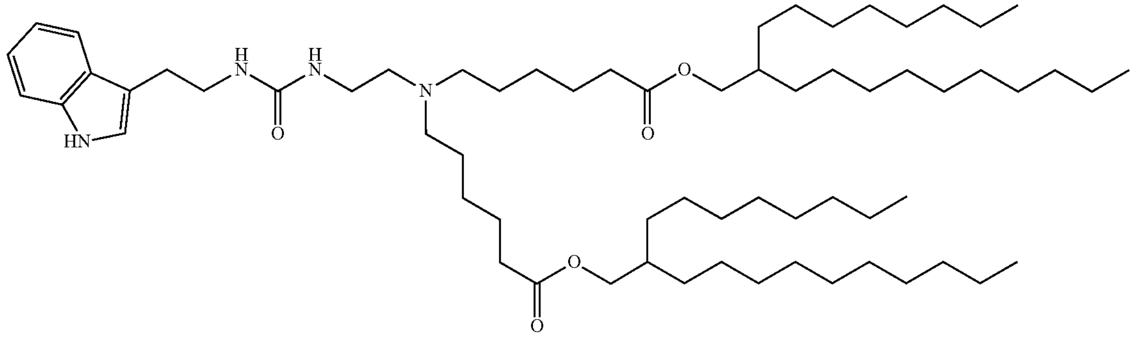 [SMILES: CCCCCCCCCCC(CCCCCCCC)COC(=O)CCCCCN(CCCCCC(=O)OCC(CCCCCCCC)CCCCCCCCCC)CCNC(=O)NCCc1c[nH]c2ccccc12] | 1035.7 |

TABLE 1-continued
| # | Structure | Mw |
| --- | --- | --- |
| 1475. | 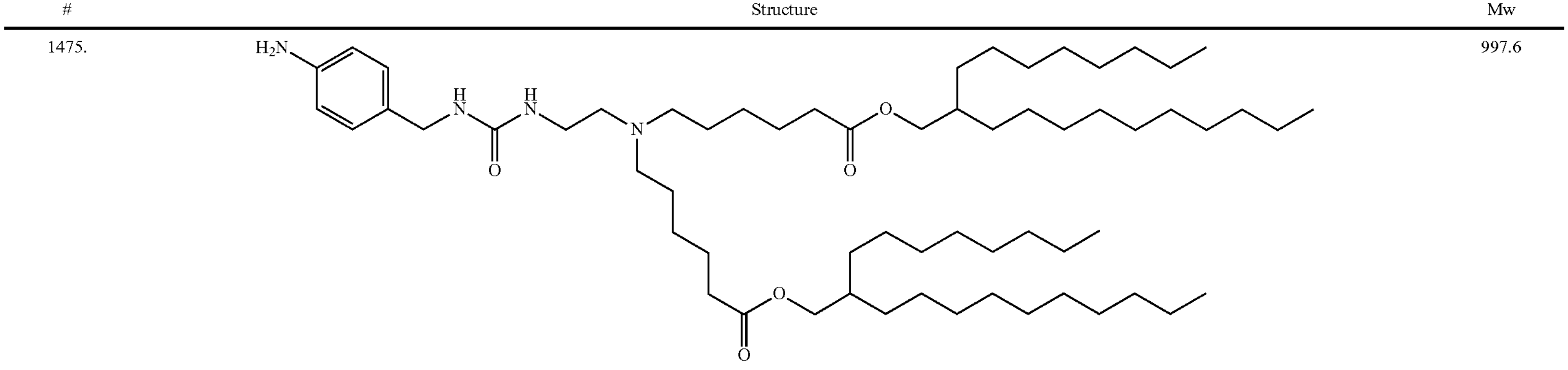 | 997.6 |
| 1476. | 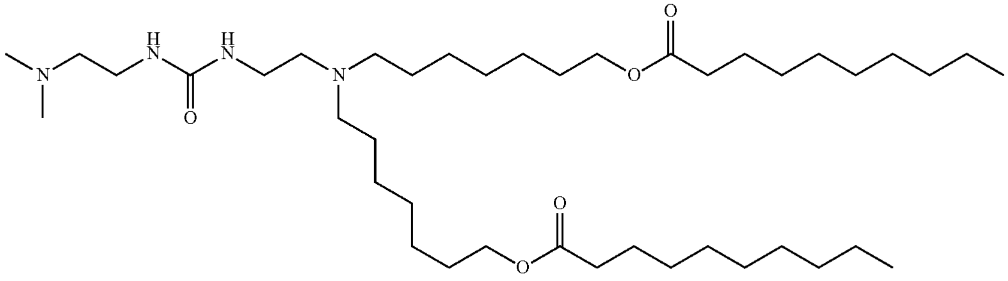 [SMILES: CCCCCCCCCC(=O)OCCCCCCCN(CCCCCCCOC(=O)CCCCCCCCC)CCNC(=O)NCCN(C)C] | 711.1 |
| 1477. | 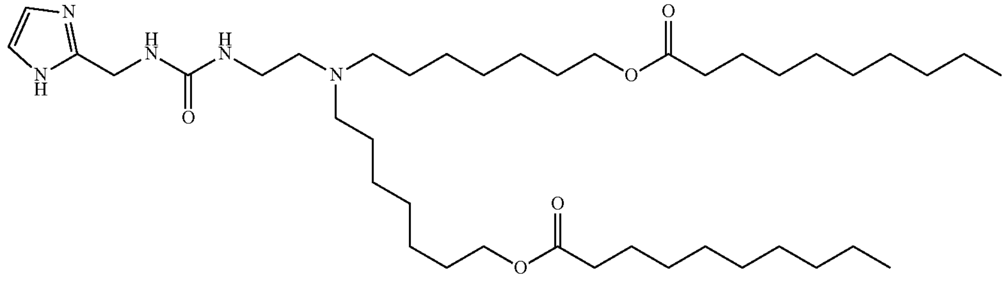 [SMILES: CCCCCCCCCC(=O)OCCCCCCCN(CCCCCCCOC(=O)CCCCCCCCC)CCNC(=O)NCc1ncc[nH]1] | 720.1 |

TABLE 1-continued
| # | Structure | Mw |
|---|---|---|
| 1478. | 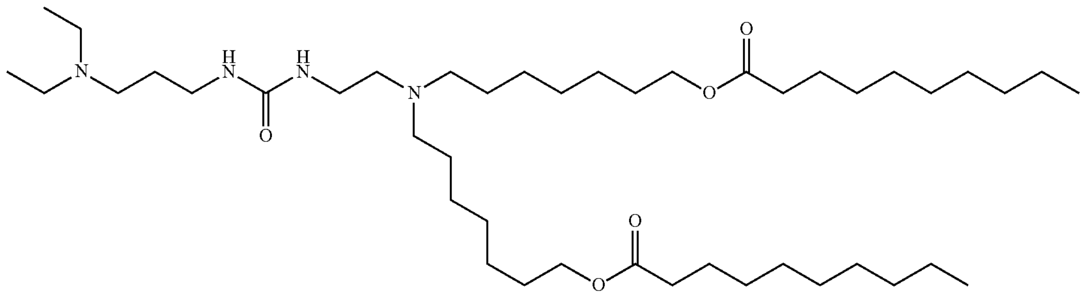 [SMILES: CCCCCCCCCC(=O)OCCCCCCCN(CCCCCCCOC(=O)CCCCCCCCC)CCNC(=O)NCCCN(CC)CC] | 753.2 |
| 1479. | 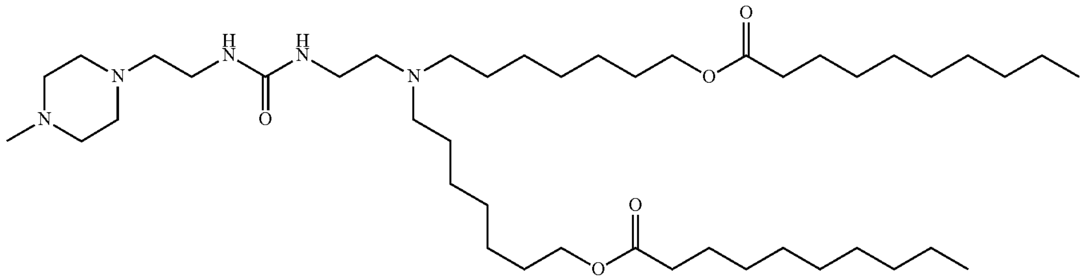 [SMILES: CCCCCCCCCC(=O)OCCCCCCCN(CCCCCCCOC(=O)CCCCCCCCC)CCNC(=O)NCCN1CCN(C)CC1] | 766.2 |
| 1480. | 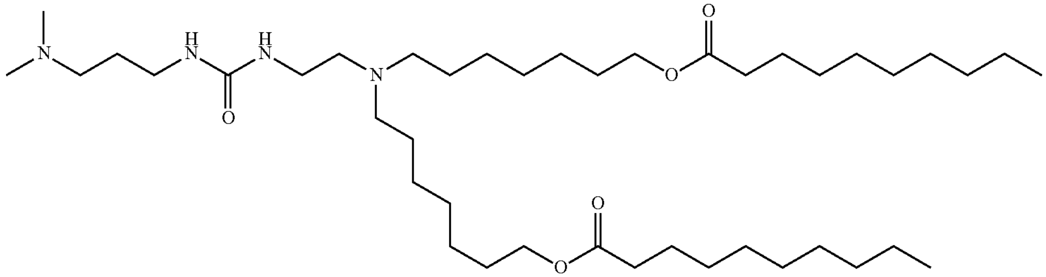 [SMILES: CCCCCCCCCC(=O)OCCCCCCCN(CCCCCCCOC(=O)CCCCCCCCC)CCNC(=O)NCCCN(C)C] | 725.2 |

TABLE 1-continued
| # | Structure | Mw |
|---|---|---|
| 1481. | 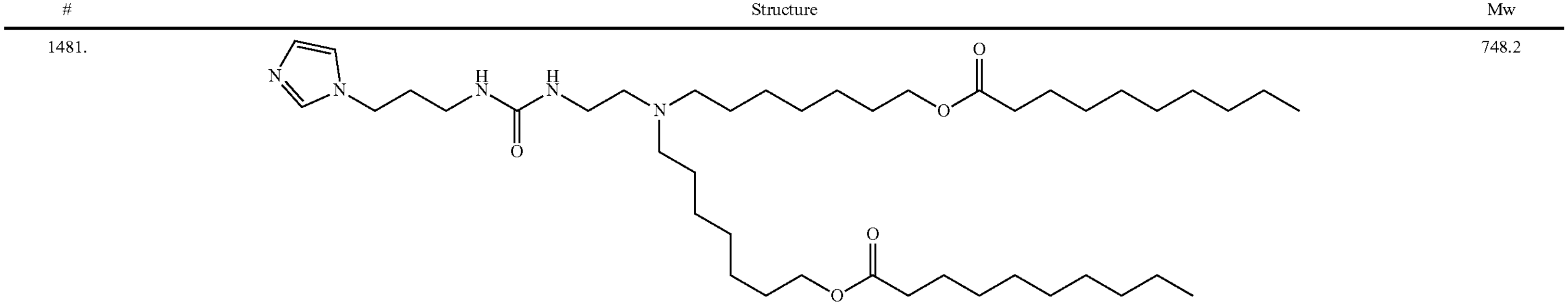 | 748.2 |
| 1482. | 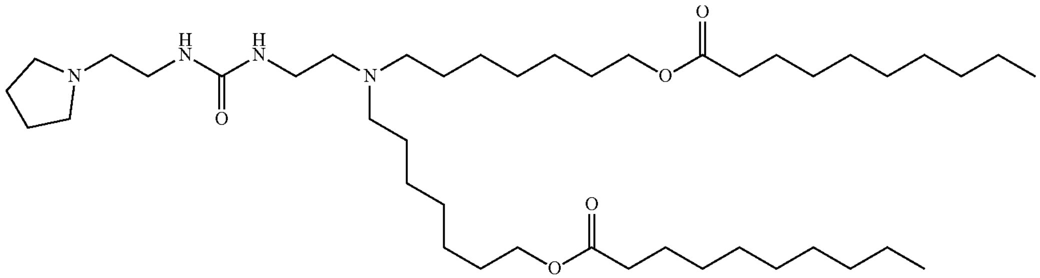 [SMILES: CCCCCCCCCC(=O)OCCCCCCCN(CCCCCCCOC(=O)CCCCCCCCC)CCNC(=O)NCCN1CCCC1] | 737.2 |
| 1483. | 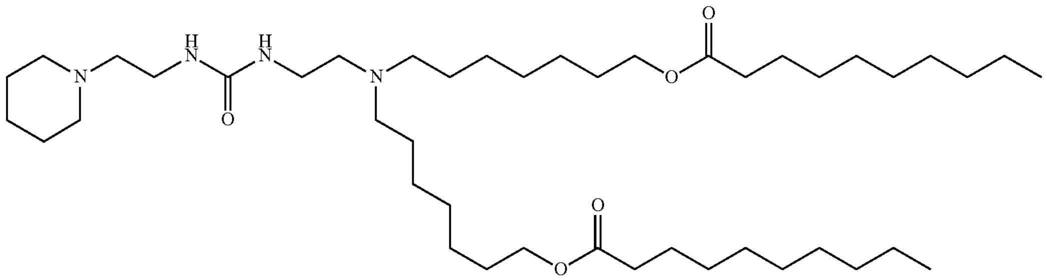 [SMILES: CCCCCCCCCC(=O)OCCCCCCCN(CCCCCCCOC(=O)CCCCCCCCC)CCNC(=O)NCCN1CCCCC1] | 751.2 |

TABLE 1-continued
| # | Structure | Mw |
|---|---|---|
| 1484. | 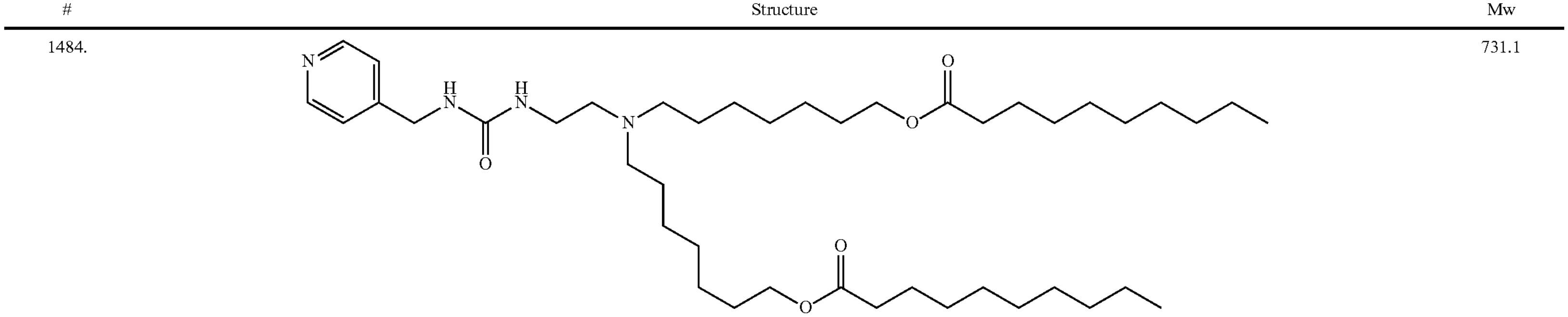 | 731.1 |
| 1485. | 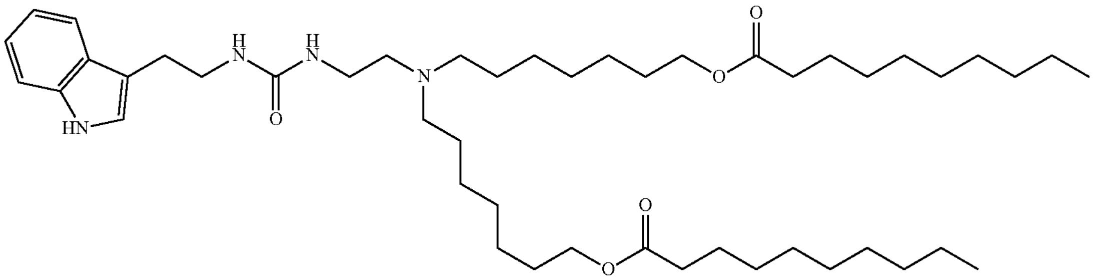 [SMILES: CCCCCCCCCC(=O)OCCCCCCCN(CCCCCCCOC(=O)CCCCCCCCC)CCNC(=O)NCCc1c[nH]c2ccccc12] | 783.2 |
| 1486. | 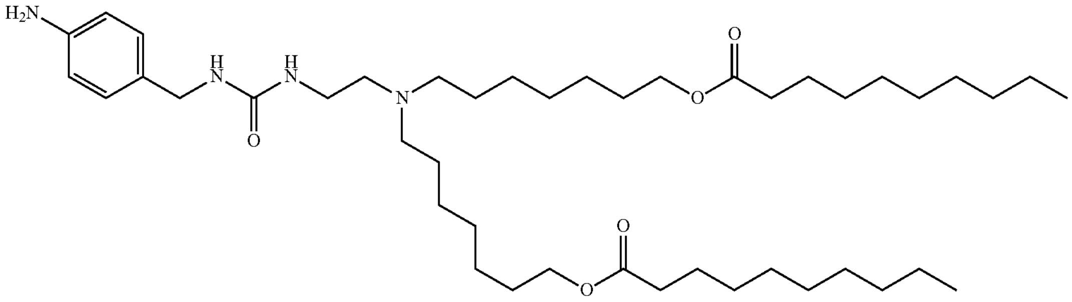 [SMILES: CCCCCCCCCC(=O)OCCCCCCCN(CCCCCCCOC(=O)CCCCCCCCC)CCNC(=O)NCc1ccc(N)cc1] | 745.1 |

TABLE 1-continued
| # | Structure | Mw |
|---|---|---|
| 1487. | 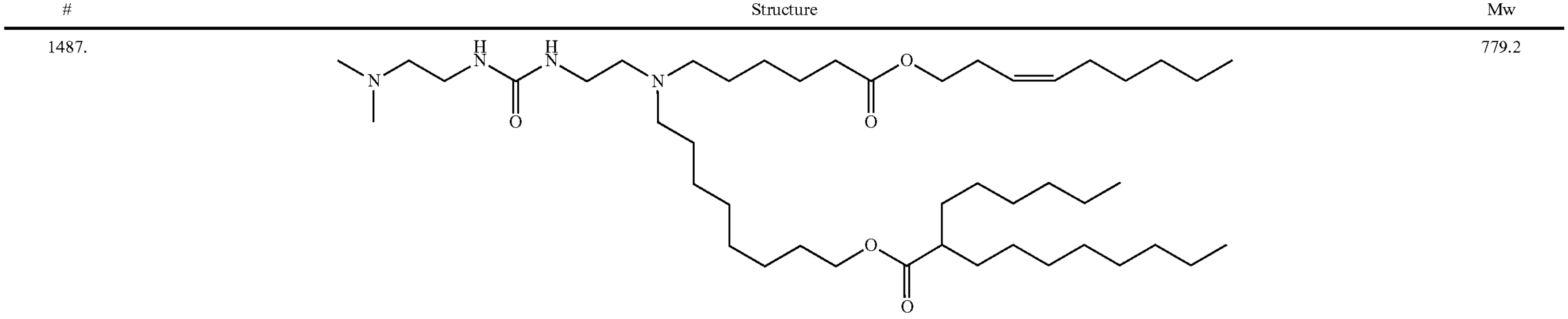 | 779.2 |
| 1488. | 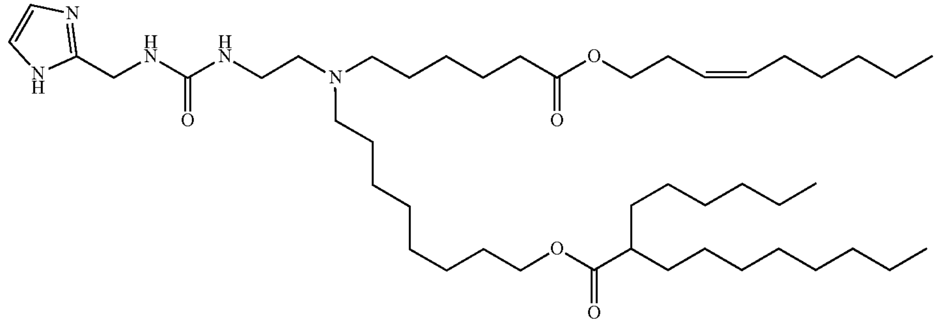 [SMILES: CCCCC/C=C\CCOC(=O)CCCCCN(CCCCCCCCOC(=O)C(CCCCCC)CCCCCCCC)CCNC(=O)NCc1ncc[nH]1] | 788.2 |
| 1489. | 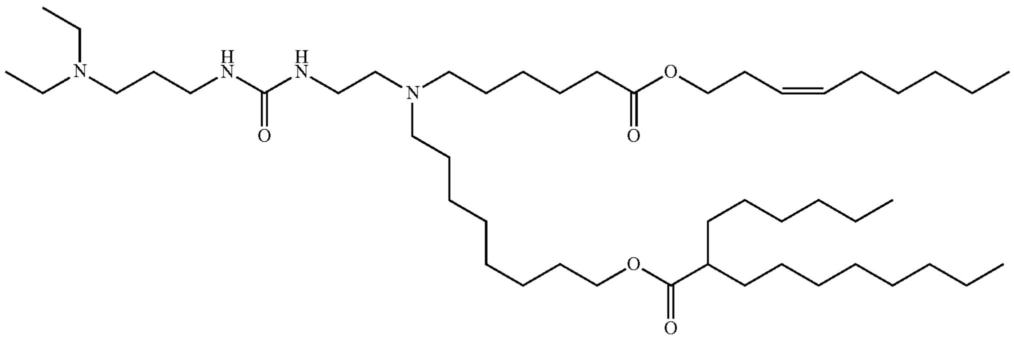 [SMILES: CCCCC/C=C\CCOC(=O)CCCCCN(CCCCCCCCOC(=O)C(CCCCCC)CCCCCCCC)CCNC(=O)NCCCN(CC)CC] | 821.3 |

TABLE 1-continued
| # | Structure | Mw |
|---|---|---|
| 1490. | 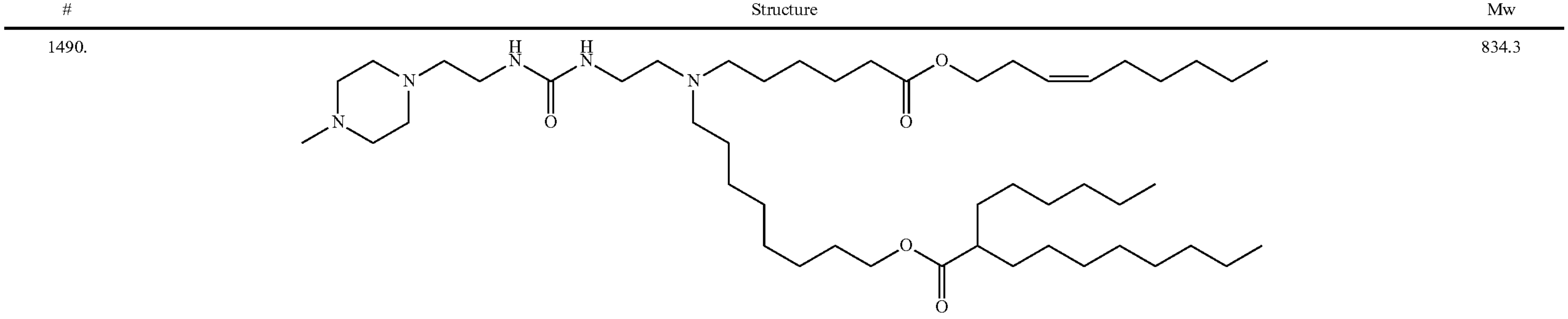 | 834.3 |
| 1491. | 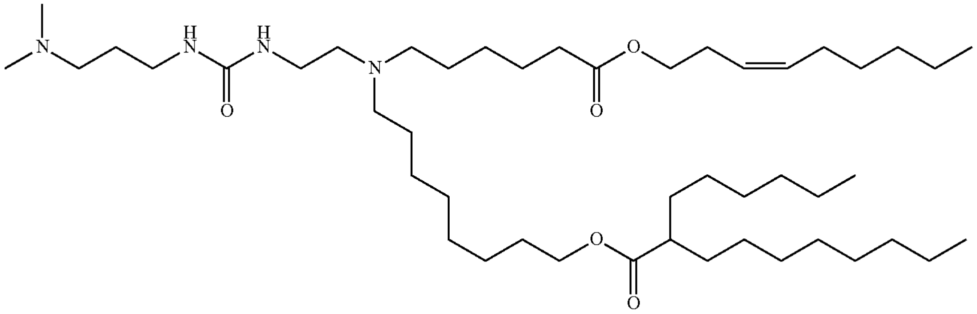 [SMILES: CCCCC/C=C\CCOC(=O)CCCCCN(CCCCCCCCOC(=O)C(CCCCCC)CCCCCCCC)CCNC(=O)NCCCN(C)C] | 793.3 |
| 1492. | 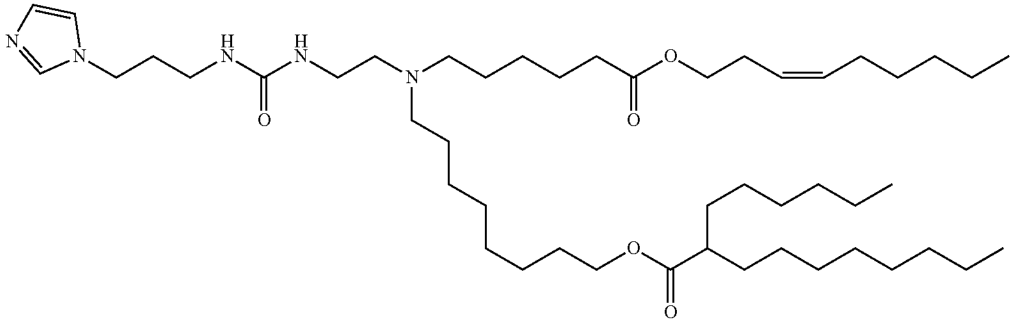 [SMILES: CCCCC/C=C\CCOC(=O)CCCCCN(CCCCCCCCOC(=O)C(CCCCCC)CCCCCCCC)CCNC(=O)NCCCn1ccnc1] | 816.3 |

TABLE 1-continued
| # | Structure | Mw |
|---|---|---|
| 1493. | 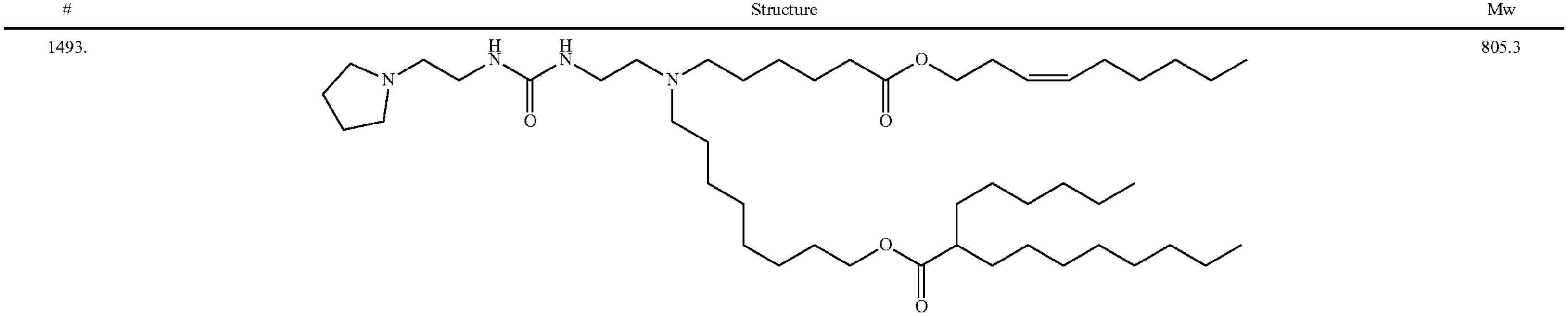 | 805.3 |
| 1494. | 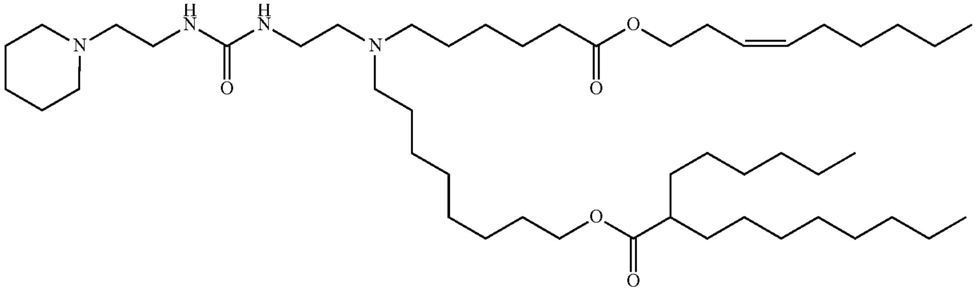 [SMILES: CCCCC/C=C\CCOC(=O)CCCCCN(CCCCCCCCOC(=O)C(CCCCCC)CCCCCCCC)CCNC(=O)NCCN1CCCCC1] | 819.3 |
| 1495. | 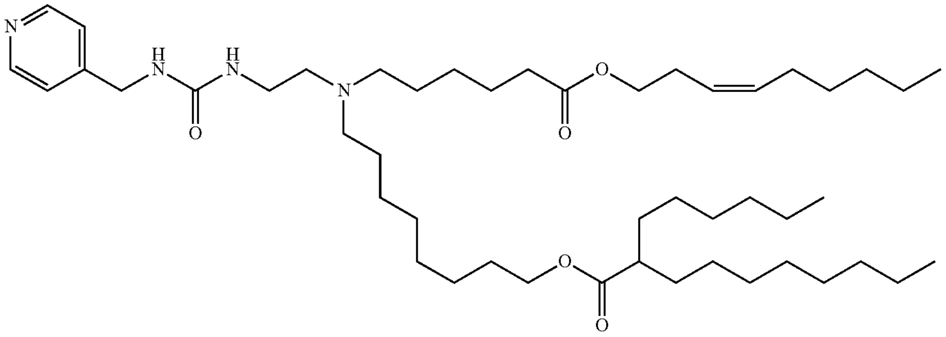 [SMILES: CCCCC/C=C\CCOC(=O)CCCCCN(CCCCCCCCOC(=O)C(CCCCCC)CCCCCCCC)CCNC(=O)NCc1ccncc1] | 799.2 |

TABLE 1-continued
| # | Structure | Mw |
| --- | --- | --- |
| 1496. | 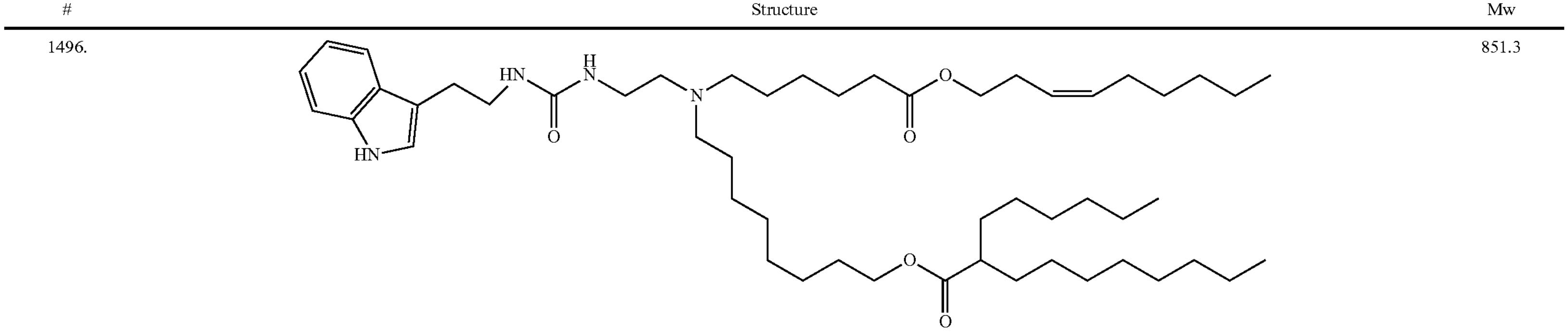 | 851.3 |
| 1497. | 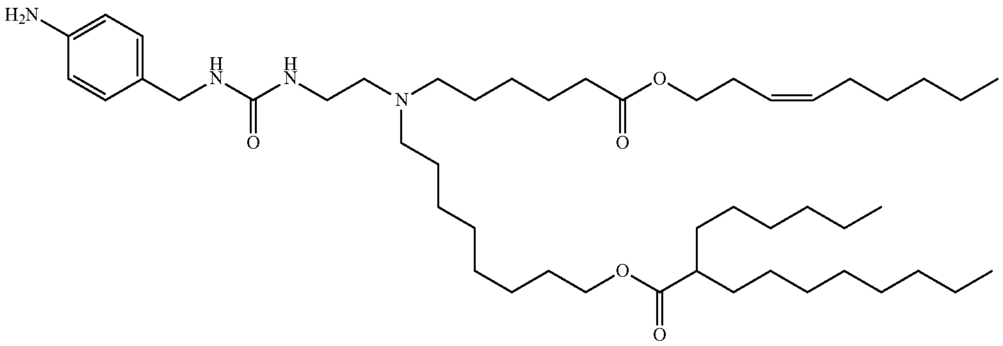 [SMILES: CCCCC/C=C\CCOC(=O)CCCCCN(CCCCCCCCOC(=O)C(CCCCCC)CCCCCCCC)CCNC(=O)NCc1ccc(N)cc1] | 813.3 |
| 1498. | 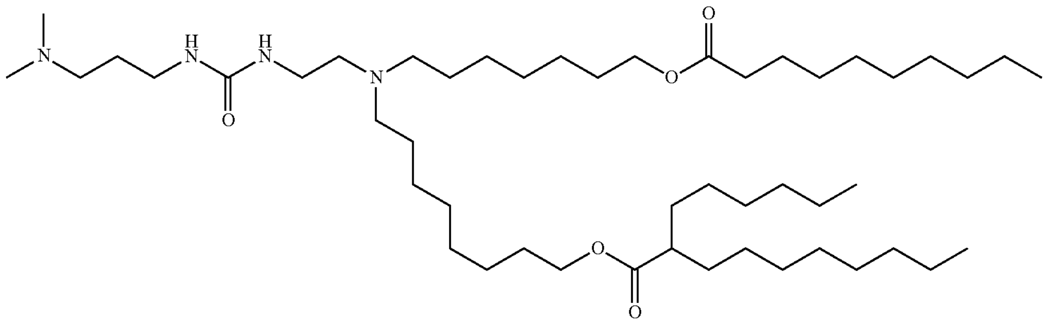 | 823.3 |

TABLE 1-continued
| # | Structure | Mw |
|---|---|---|
| 1499. | 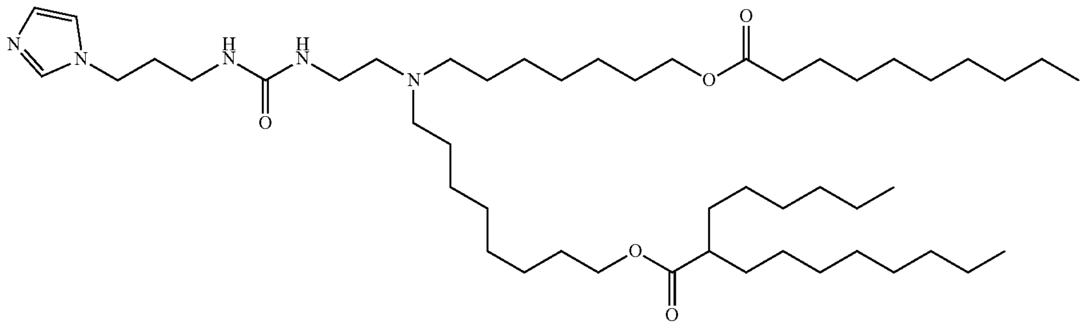 [SMILES: CCCCCCCCCC(=O)OCCCCCCCN(CCCCCCCCOC(=O)C(CCCCCC)CCCCCCCC)CCNC(=O)NCCCn1ccnc1] | 846.3 |
| 1500. | 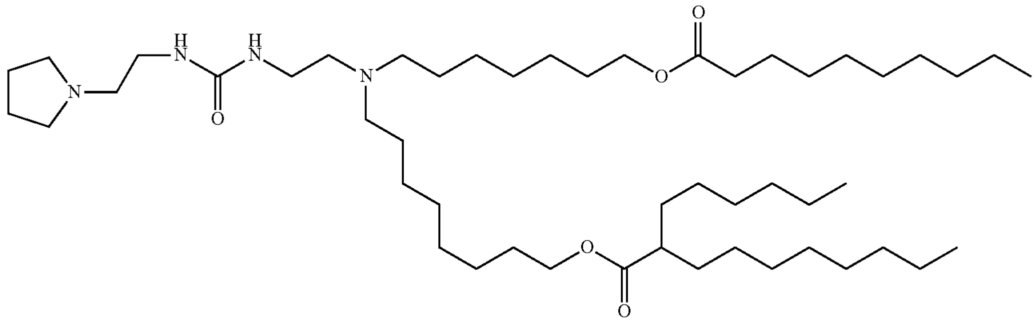 [SMILES: CCCCCCCCCC(=O)OCCCCCCCN(CCCCCCCCOC(=O)C(CCCCCC)CCCCCCCC)CCNC(=O)NCCN1CCCC1] | 835.4 |
| 1501. | 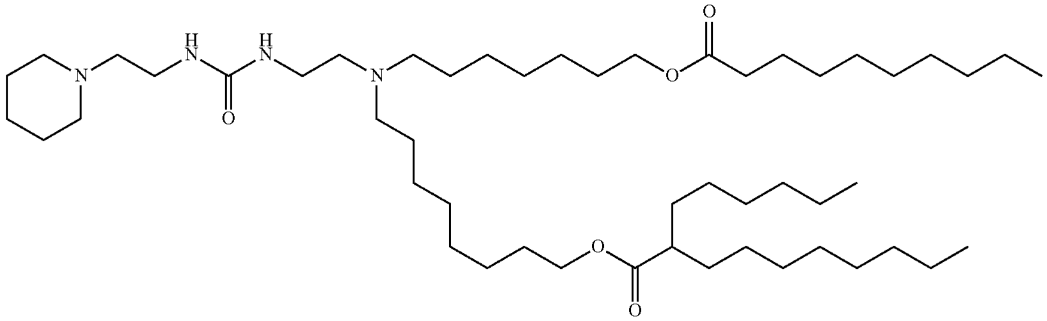 [SMILES: CCCCCCCCCC(=O)OCCCCCCCN(CCCCCCCCOC(=O)C(CCCCCC)CCCCCCCC)CCNC(=O)NCCN1CCCCC1] | 849.4 |

TABLE 1-continued
| # | Structure | Mw |
|---|---|---|
| 1502. | 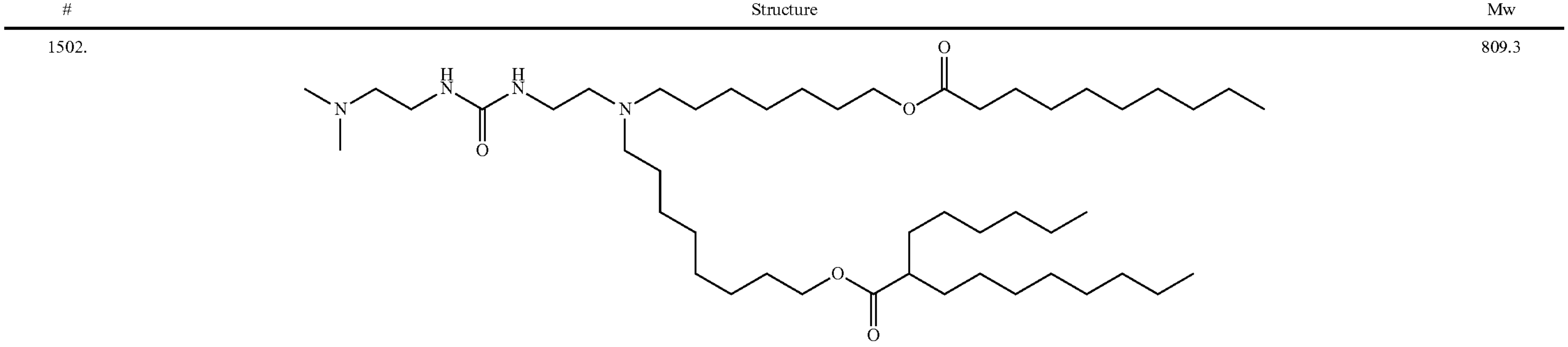 | 809.3 |
| 1503. | 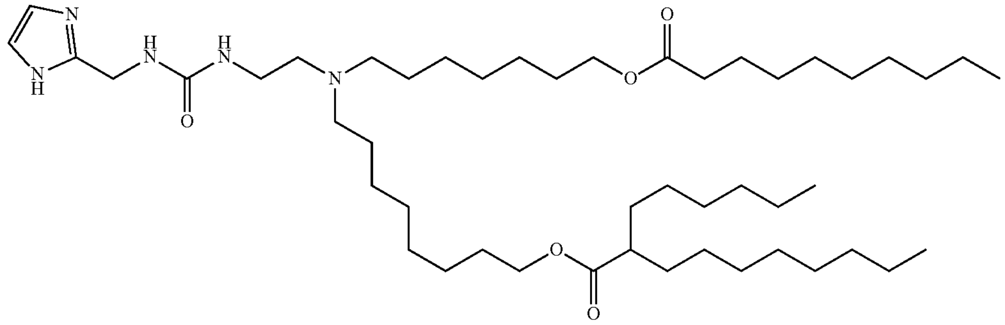 [SMILES: CCCCCCCCCC(=O)OCCCCCCCN(CCCCCCCCOC(=O)C(CCCCCC)CCCCCCCC)CCNC(=O)NCc1ncc[nH]1] | 818.3 |
| 1504. | 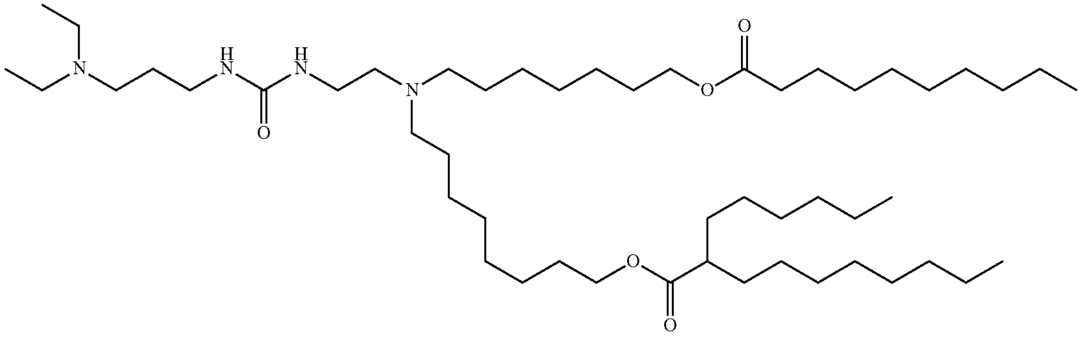 [SMILES: CCCCCCCCCC(=O)OCCCCCCCN(CCCCCCCCOC(=O)C(CCCCCC)CCCCCCCC)CCNC(=O)NCCCN(CC)CC] | 851.4 |

TABLE 1-continued
| # | Structure | Mw |
| --- | --- | --- |
| 1505. | 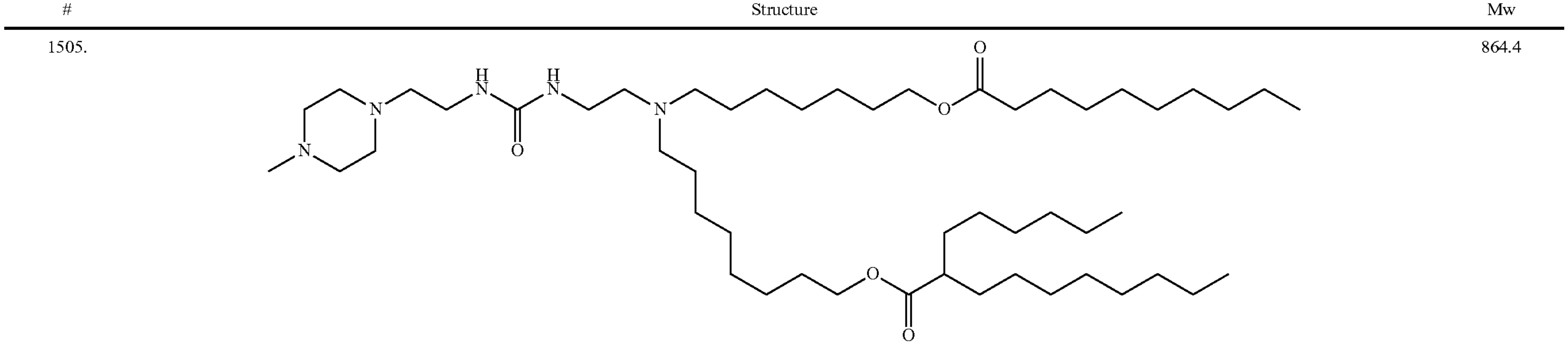 | 864.4 |
| 1506. | 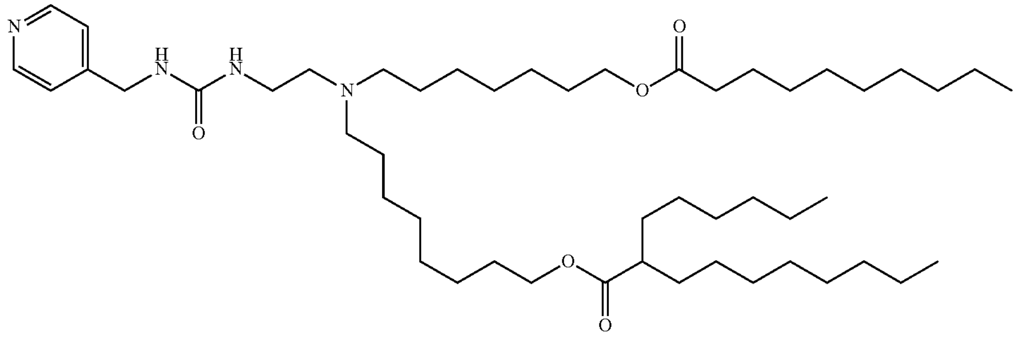 [SMILES: CCCCCCCCCC(=O)OCCCCCCCN(CCCCCCCCOC(=O)C(CCCCCC)CCCCCCCC)CCNC(=O)NCc1ccncc1] | 829.3 |
| 1507. | 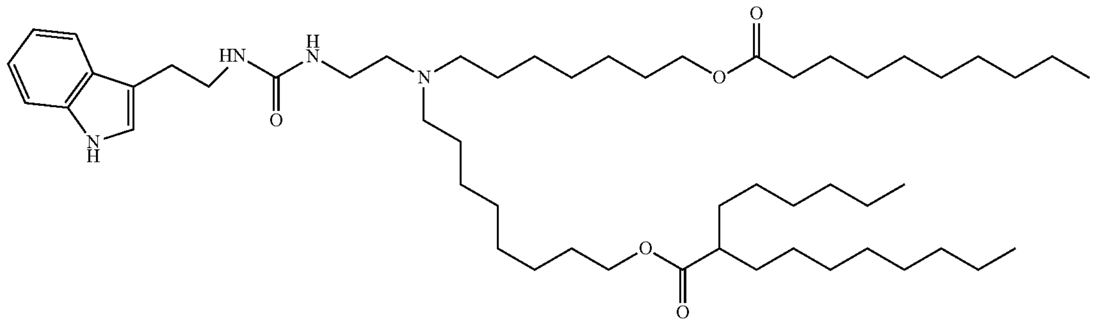 [SMILES: CCCCCCCCCC(=O)OCCCCCCCN(CCCCCCCCOC(=O)C(CCCCCC)CCCCCCCC)CCNC(=O)NCCc1c[nH]c2ccccc12] | 881.4 |

TABLE 1-continued
| # | Structure | Mw |
|---|---|---|
| 1508. | 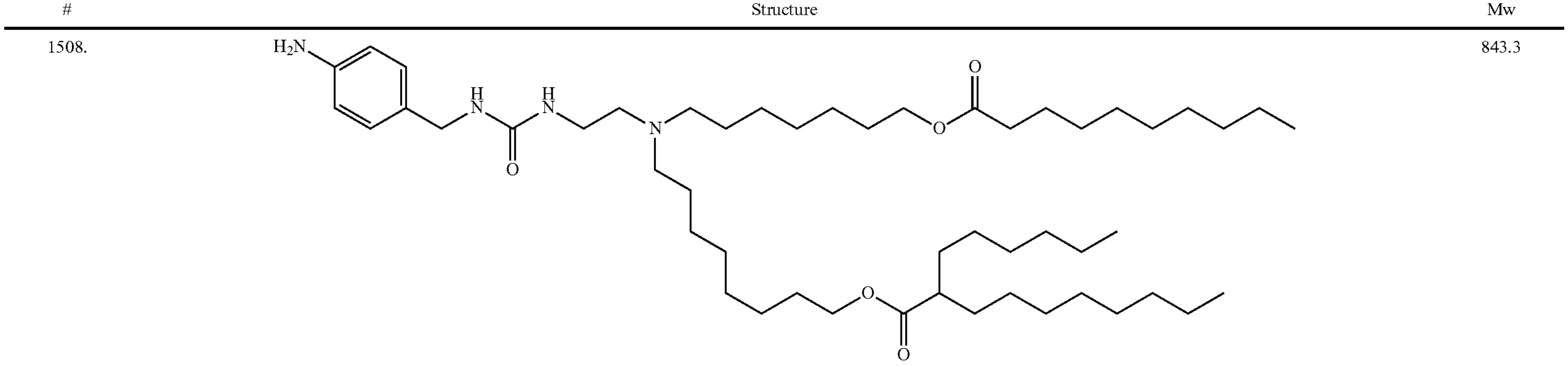 | 843.3 |
| 1509. | 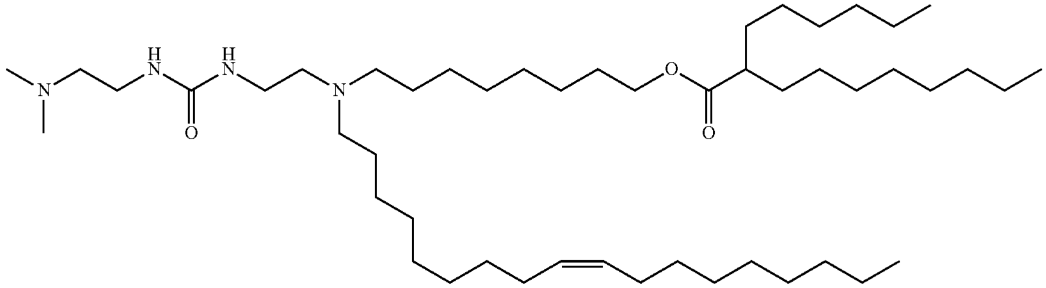 [SMILES: CCCCCCCC/C=C\CCCCCCCCN(CCCCCCCCOC(=O)C(CCCCCC)CCCCCCCC)CCNC(=O)NCCN(C)C] | 791.3 |
| 1510. | 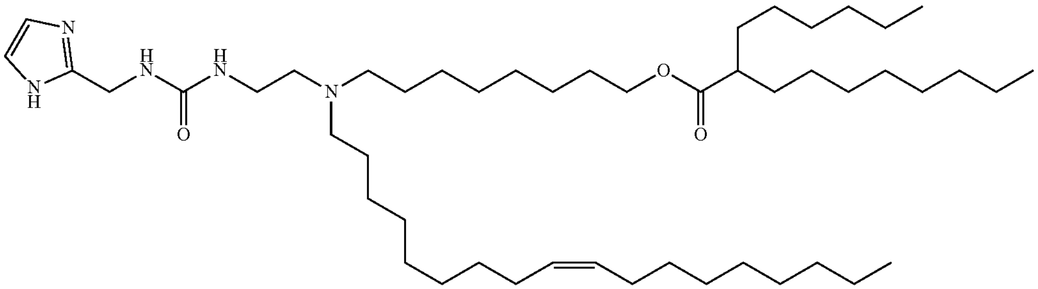 [SMILES: CCCCCCCC/C=C\CCCCCCCCN(CCCCCCCCOC(=O)C(CCCCCC)CCCCCCCC)CCNC(=O)NCc1ncc[nH]1] | 800.3 |

TABLE 1-continued
| # | Structure | Mw |
| --- | --- | --- |
| 1511. | 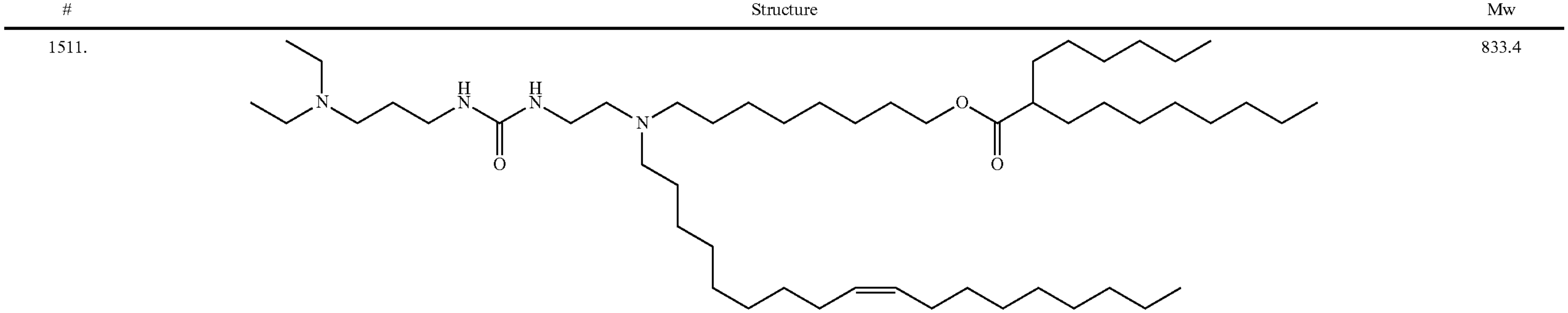 | 833.4 |
| 1512. | 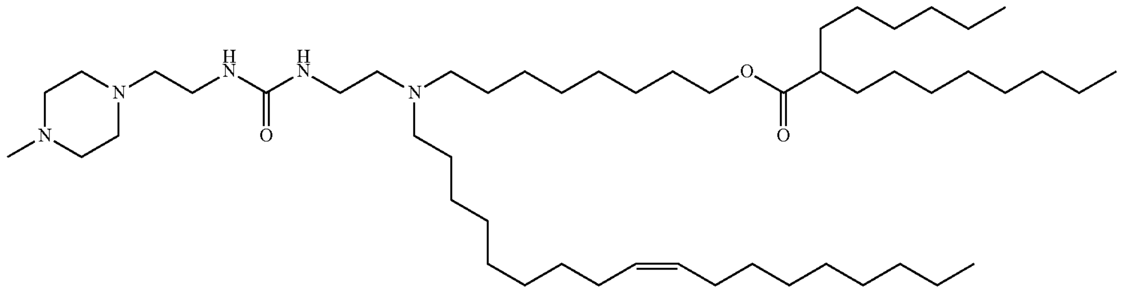 [SMILES: CCCCCCCC/C=C\CCCCCCCCN(CCCCCCCCOC(=O)C(CCCCCC)CCCCCCCC)CCNC(=O)NCCN1CCN(C)CC1] | 846.4 |
| 1513. | 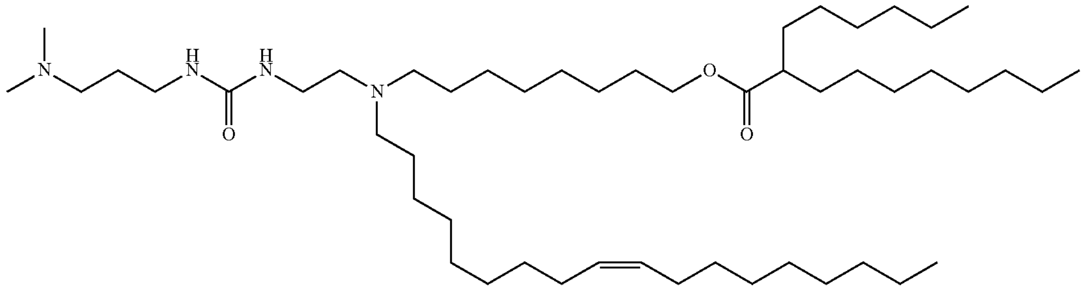 [SMILES: CCCCCCCC/C=C\CCCCCCCCN(CCCCCCCCOC(=O)C(CCCCCC)CCCCCCCC)CCNC(=O)NCCCN(C)C] | 805.4 |

TABLE 1-continued
| # | Structure | Mw |
| --- | --- | --- |
| 1514. | 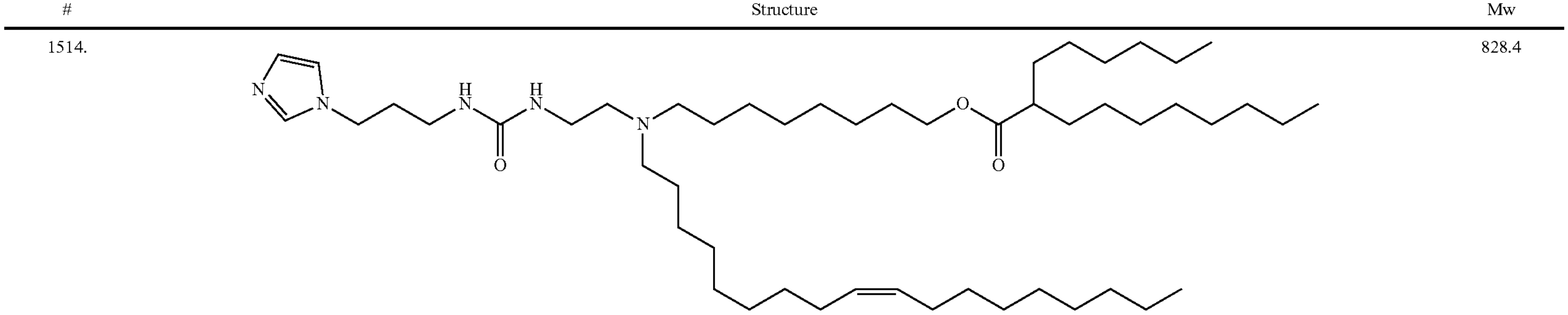 | 828.4 |
| 1515. | 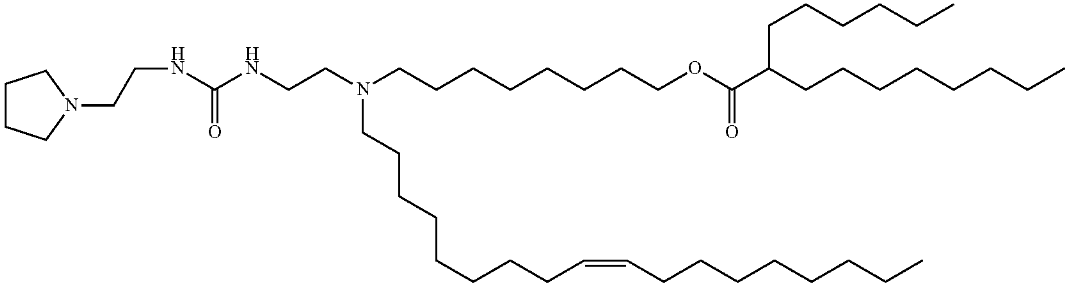 [SMILES: CCCCCCCC/C=C\CCCCCCCCN(CCCCCCCCOC(=O)C(CCCCCC)CCCCCCCC)CCNC(=O)NCCN1CCCC1] | 817.4 |
| 1516. | 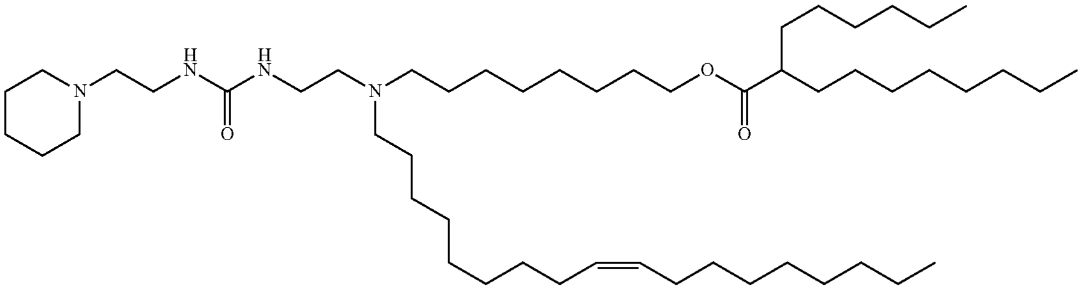 [SMILES: CCCCCCCC/C=C\CCCCCCCCN(CCCCCCCCOC(=O)C(CCCCCC)CCCCCCCC)CCNC(=O)NCCN1CCCCC1] | 831.4 |

TABLE 1-continued
| # | Structure | Mw |
|---|---|---|
| 1517. | 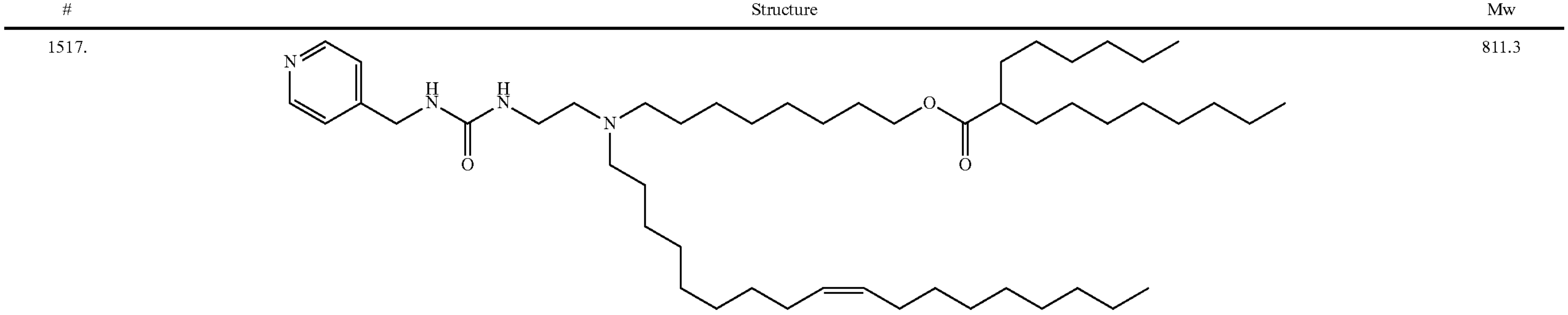 | 811.3 |
| 1518. | 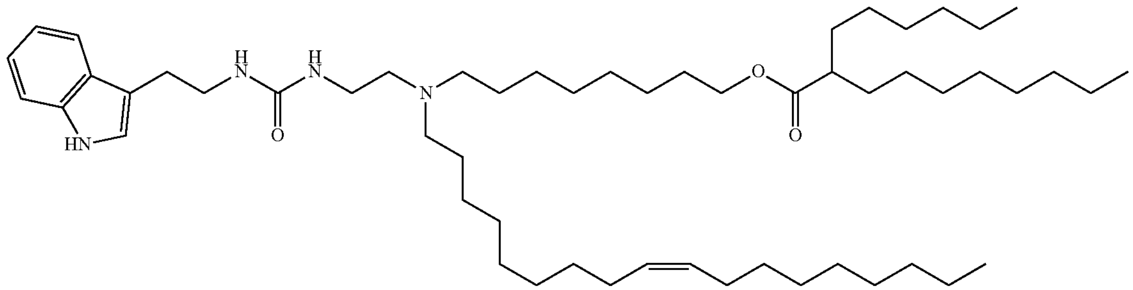 [SMILES: CCCCCCCC/C=C\CCCCCCCCN(CCCCCCCCOC(=O)C(CCCCCC)CCCCCCCC)CCNC(=O)NCCc1c[nH]c2ccccc12] | 863.4 |
| 1519. | 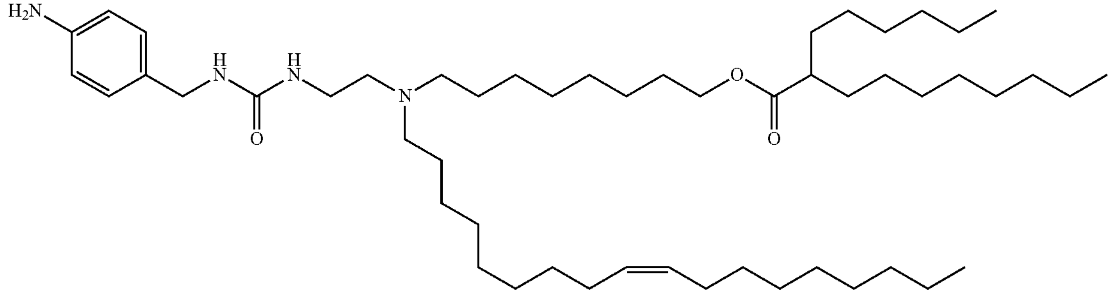 [SMILES: CCCCCCCC/C=C\CCCCCCCCN(CCCCCCCCOC(=O)C(CCCCCC)CCCCCCCC)CCNC(=O)NCc1ccc(N)cc1] | 825.4 |

TABLE 1-continued
| # | Structure | Mw |
|---|---|---|
| 1520. | 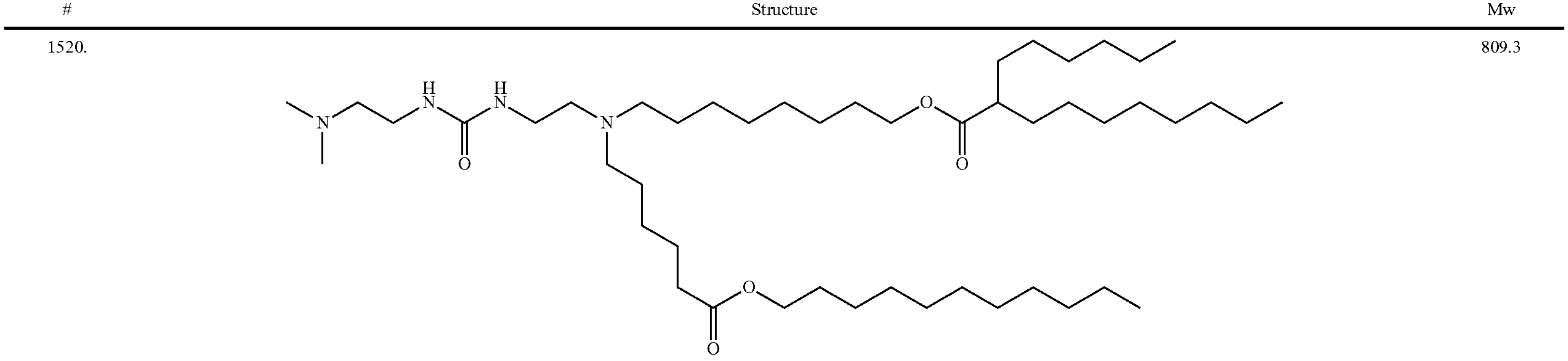 | 809.3 |
| 1521. | 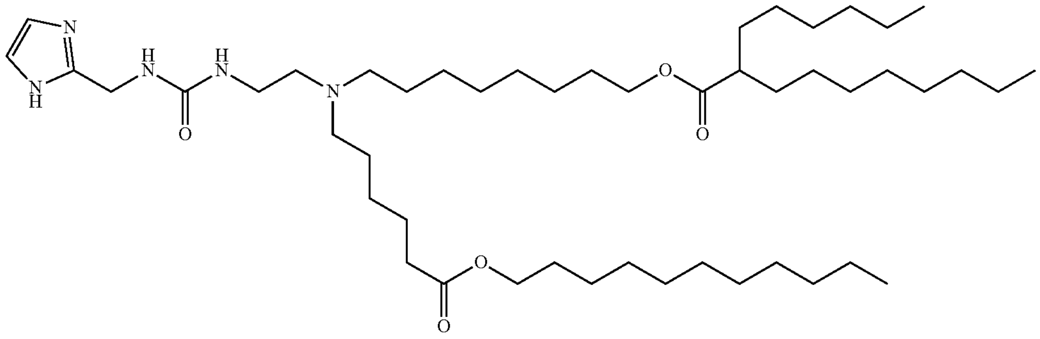 [SMILES: CCCCCCCCCCCOC(=O)CCCCCN(CCCCCCCCOC(=O)C(CCCCCC)CCCCCCCC)CCNC(=O)NCc1ncc[nH]1] | 818.3 |
| 1522. | 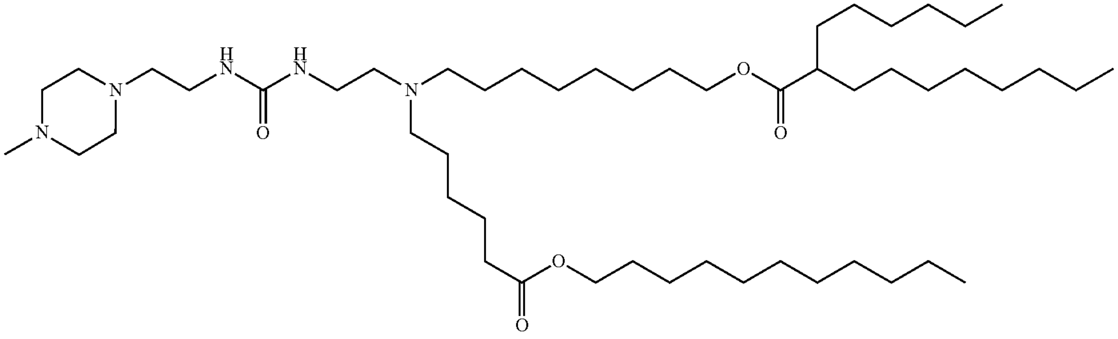 [SMILES: CCCCCCCCCCCOC(=O)CCCCCN(CCCCCCCCOC(=O)C(CCCCCC)CCCCCCCC)CCNC(=O)NCCN1CCN(C)CC1] | 864.4 |

TABLE 1-continued
| # | Structure | Mw |
| --- | --- | --- |
| 1523. | 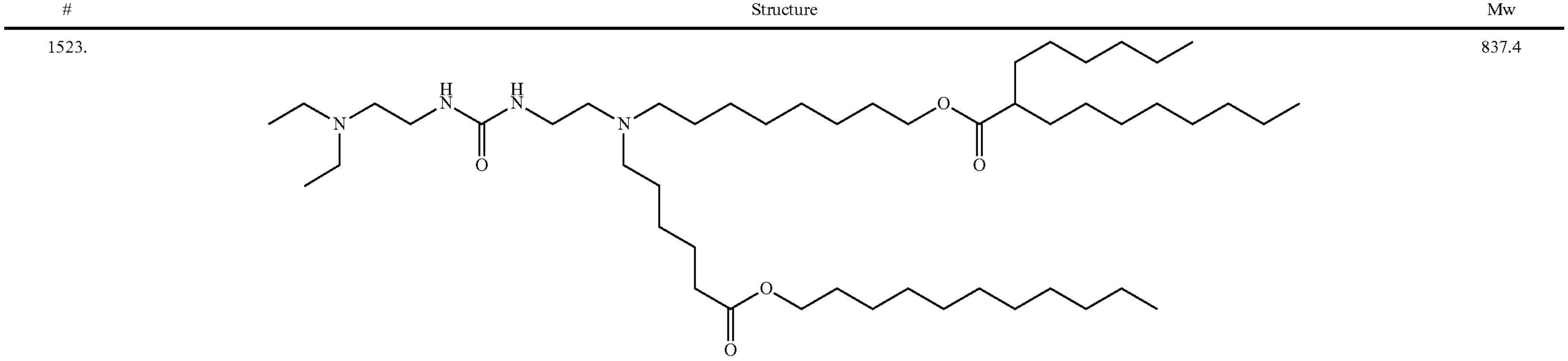 | 837.4 |
| 1524. | 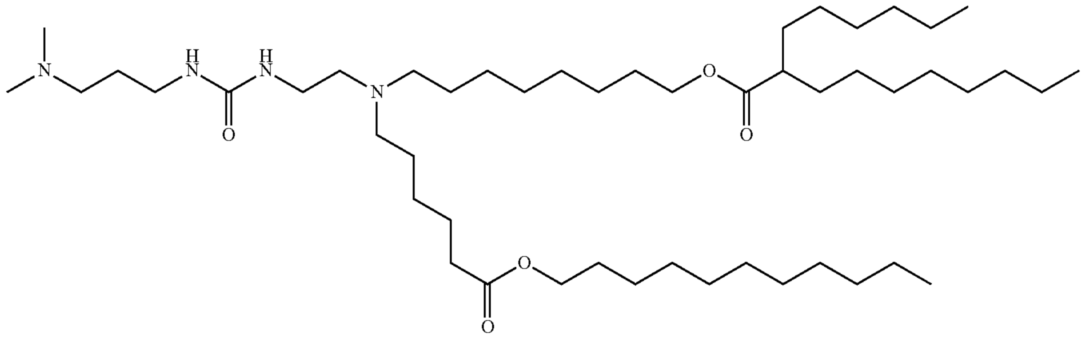 [SMILES: CCCCCCCCCCCOC(=O)CCCCCN(CCCCCCCCOC(=O)C(CCCCCC)CCCCCCCC)CCNC(=O)NCCCN(C)C] | 823.3 |
| 1525. | 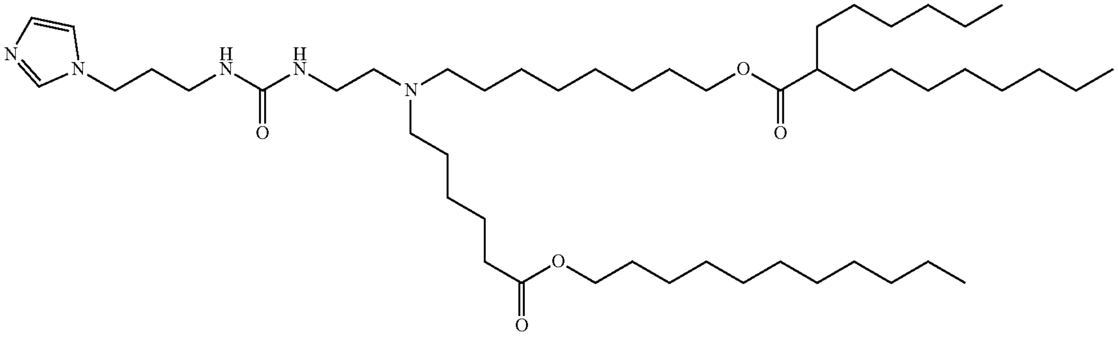 [SMILES: CCCCCCCCCCCOC(=O)CCCCCN(CCCCCCCCOC(=O)C(CCCCCC)CCCCCCCC)CCNC(=O)NCCCn1ccnc1] | 846.3 |

TABLE 1-continued
| # | Structure | Mw |
|---|---|---|
| 1526. | 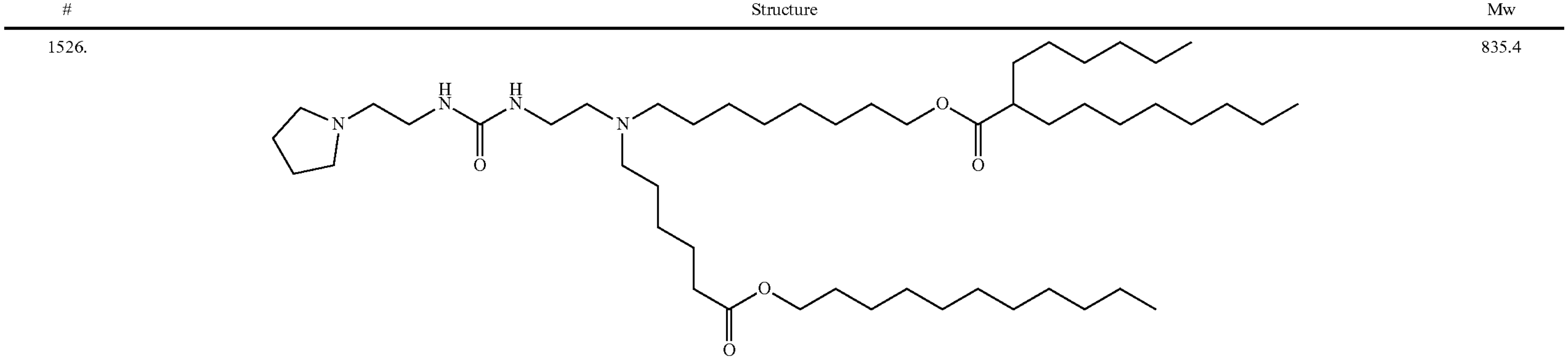 | 835.4 |
| 1527. | 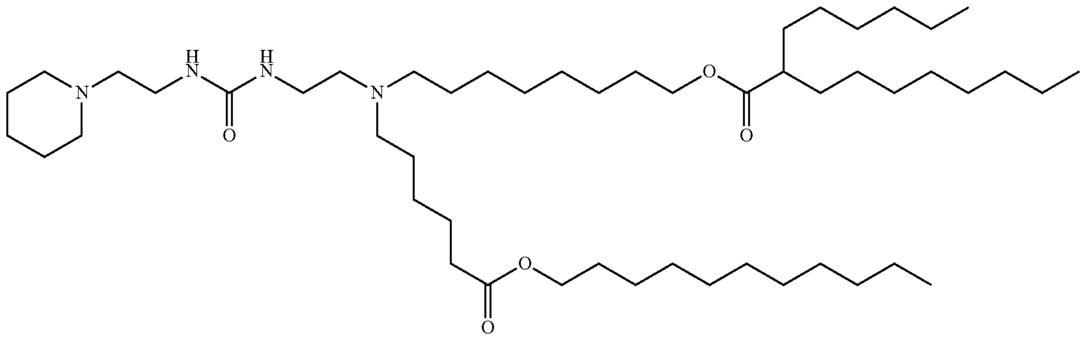 [SMILES: CCCCCCCCCCCOC(=O)CCCCCN(CCCCCCCCOC(=O)C(CCCCCC)CCCCCCCC)CCNC(=O)NCCN1CCCCC1] | 849.4 |
| 1528. | 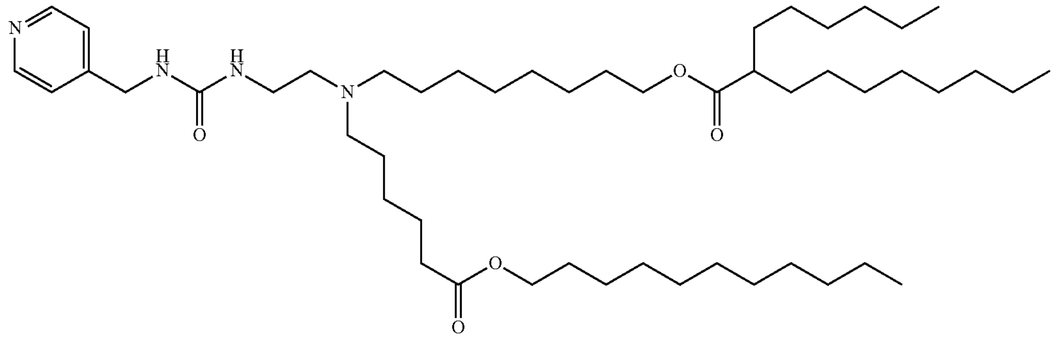 [SMILES: CCCCCCCCCCCOC(=O)CCCCCN(CCCCCCCCOC(=O)C(CCCCCC)CCCCCCCC)CCNC(=O)NCc1ccncc1] | 829.3 |

TABLE 1-continued
| # | Structure | Mw |
|---|---|---|
| 1529. | 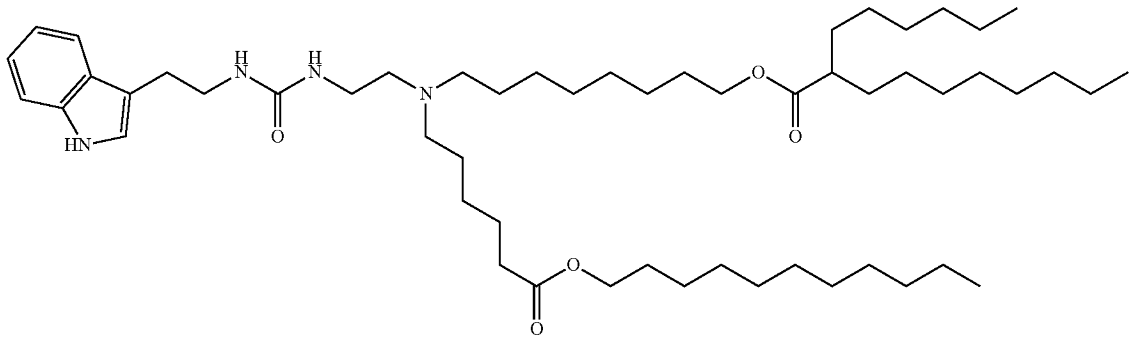 [SMILES: CCCCCCCCCCCOC(=O)CCCCCN(CCCCCCCCOC(=O)C(CCCCCC)CCCCCCCC)CCNC(=O)NCCc1c[nH]c2ccccc12] | 881.4 |
| 1530. | 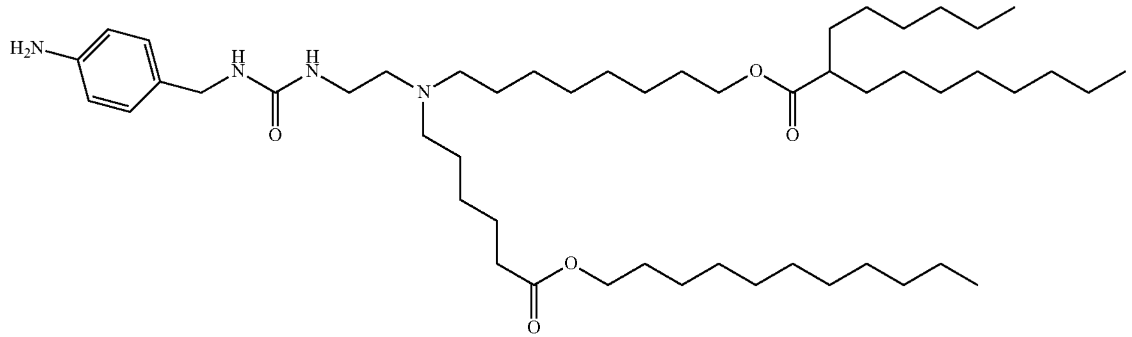 [SMILES: CCCCCCCCCCCOC(=O)CCCCCN(CCCCCCCCOC(=O)C(CCCCCC)CCCCCCCC)CCNC(=O)NCc1ccc(N)cc1] | 843.3 |
| 1531. | 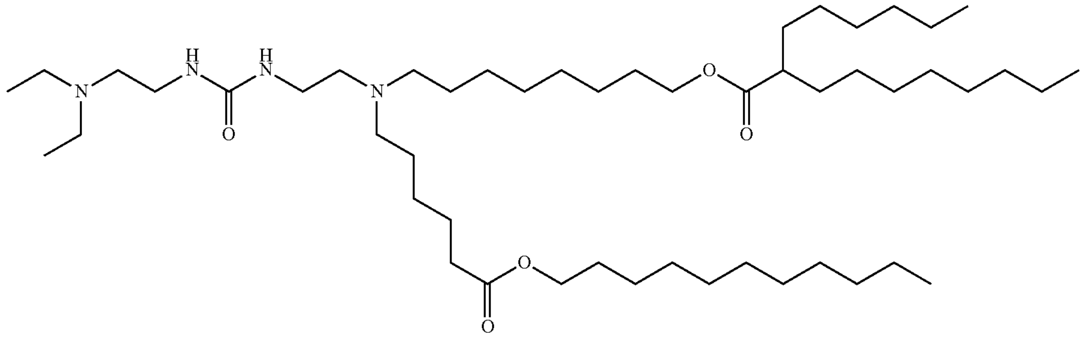 [SMILES: CCCCCCCCCCCOC(=O)CCCCCN(CCCCCCCCOC(=O)C(CCCCCC)CCCCCCCC)CCNC(=O)NCCN(CC)CC] | 837.4 |

TABLE 1-continued
| # | Structure | Mw |
| --- | --- | --- |
| 1532. | 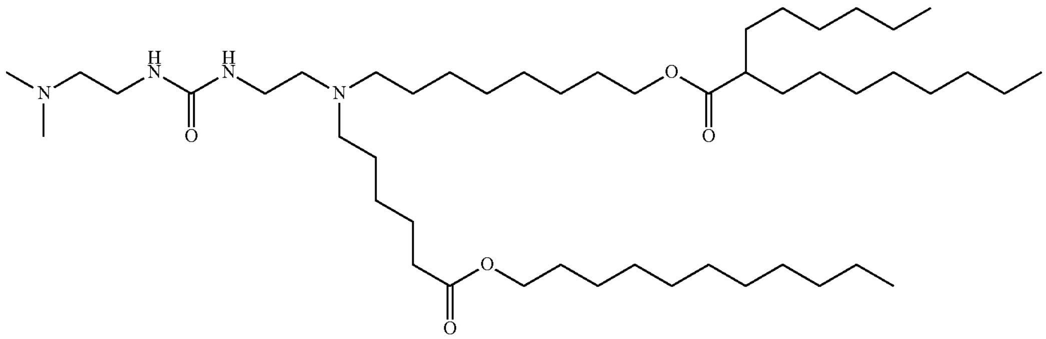 [SMILES: CCCCCCCCCCCOC(=O)CCCCCN(CCCCCCCCOC(=O)C(CCCCCC)CCCCCCCC)CCNC(=O)NCCN(C)C] | 809.3 |
| 1533. | 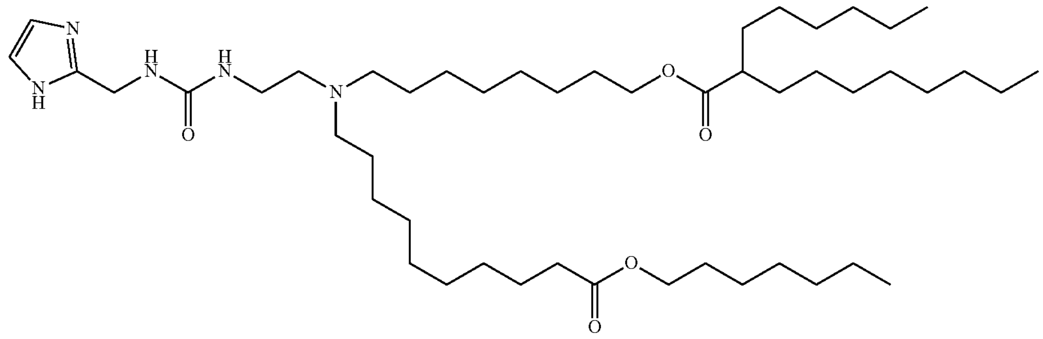 [SMILES: CCCCCCCCC(CCCCCC)C(=O)OCCCCCCCCN(CCCCCCCCCC(=O)OCCCCCCC)CCNC(=O)NCc1ncc[nH]1] | 818.3 |
| 1534. | 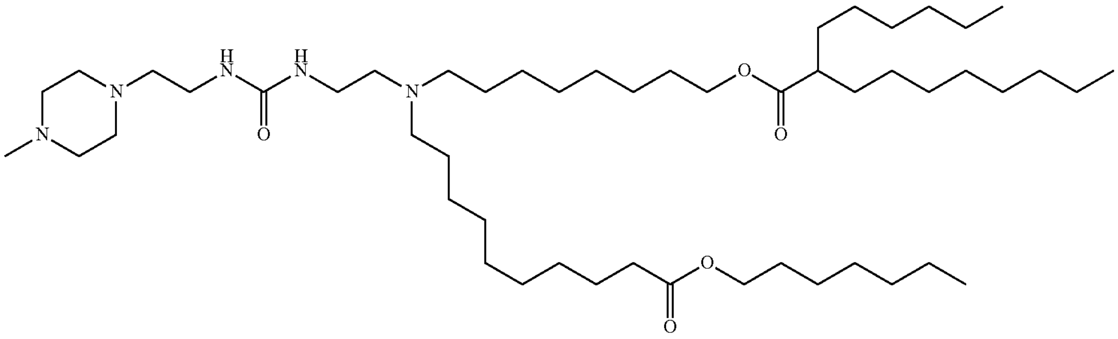 [SMILES: CCCCCCCCC(CCCCCC)C(=O)OCCCCCCCCN(CCCCCCCCCC(=O)OCCCCCCC)CCNC(=O)NCCN1CCN(C)CC1] | 864.4 |

TABLE 1-continued
| # | Structure | Mw |
|---|---|---|
| 1535. | 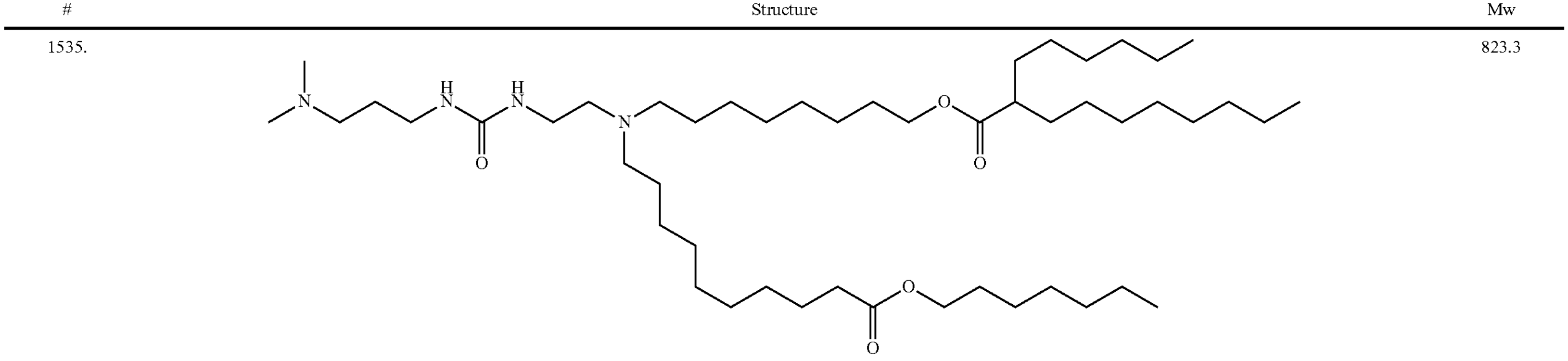 | 823.3 |
| 1536. | 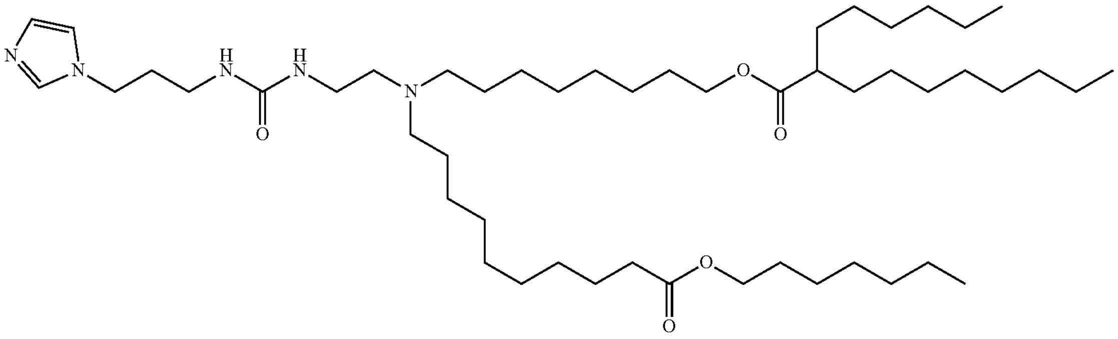 [SMILES: CCCCCCCCC(CCCCCC)C(=O)OCCCCCCCCN(CCCCCCCCCC(=O)OCCCCCCC)CCNC(=O)NCCCn1ccnc1] | 846.3 |
| 1537. | 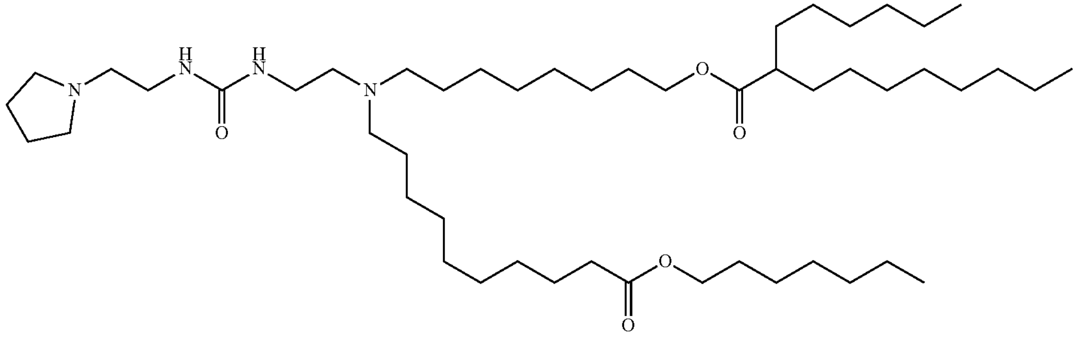 [SMILES: CCCCCCCCC(CCCCCC)C(=O)OCCCCCCCCN(CCCCCCCCCC(=O)OCCCCCCC)CCNC(=O)NCCN1CCCC1] | 835.4 |

TABLE 1-continued
| # | Structure | Mw |
|---|---|---|
| 1538. | 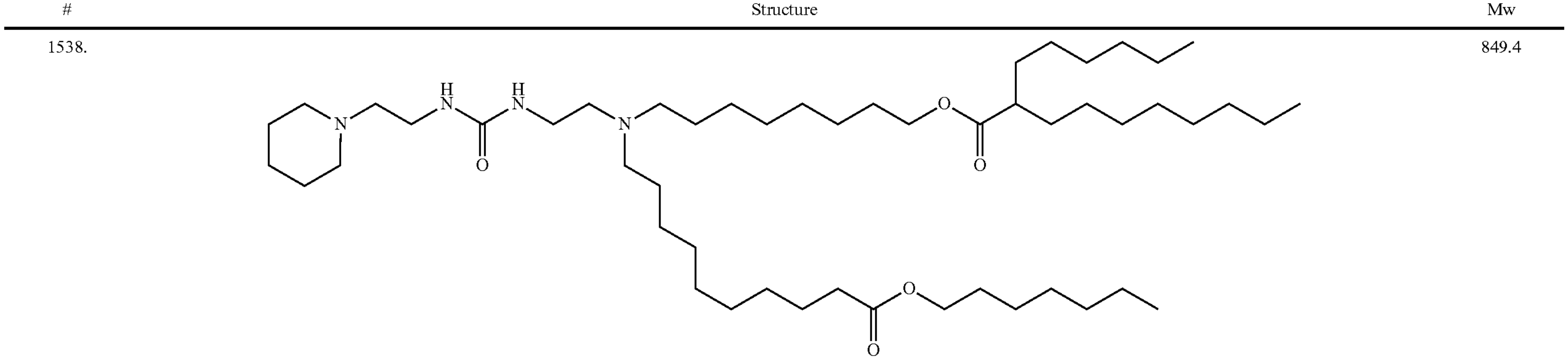 | 849.4 |
| 1539. | 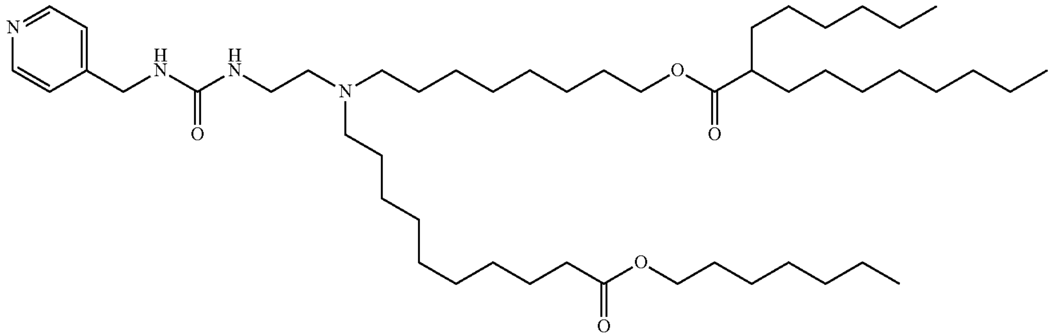 [SMILES: CCCCCCCCC(CCCCCC)C(=O)OCCCCCCCCN(CCCCCCCCCC(=O)OCCCCCCC)CCNC(=O)NCc1ccncc1] | 829.3 |
| 1540. | 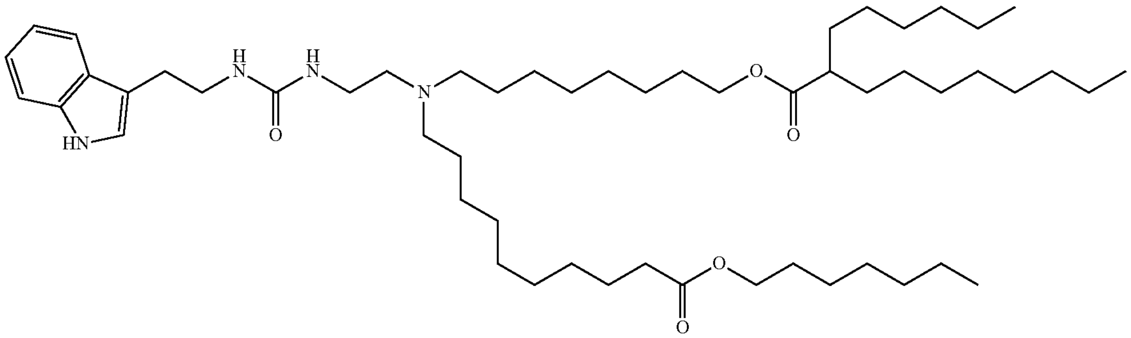 [SMILES: CCCCCCCCC(CCCCCC)C(=O)OCCCCCCCCN(CCCCCCCCCC(=O)OCCCCCCC)CCNC(=O)NCCc1c[nH]c2ccccc12] | 881.4 |

TABLE 1-continued
| # | Structure | Mw |
| --- | --- | --- |
| 1541. | 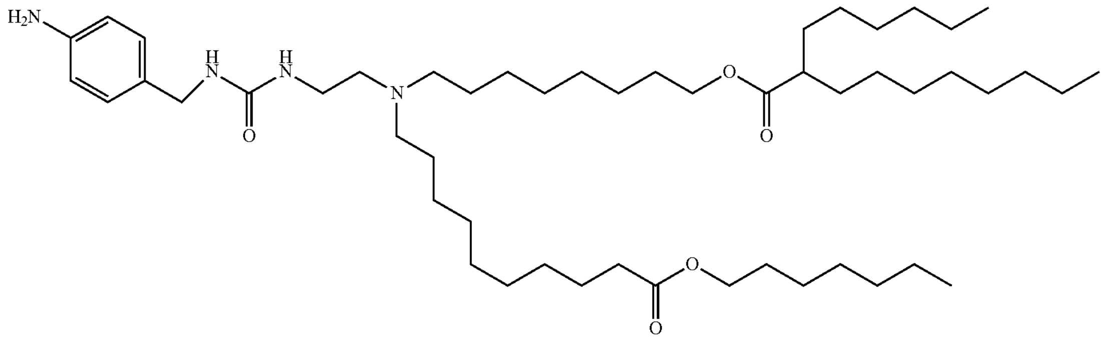 [SMILES: CCCCCCCCC(CCCCCC)C(=O)OCCCCCCCCN(CCCCCCCCCC(=O)OCCCCCCC)CCNC(=O)NCc1ccc(N)cc1] | 843.3 |
| 1542. | 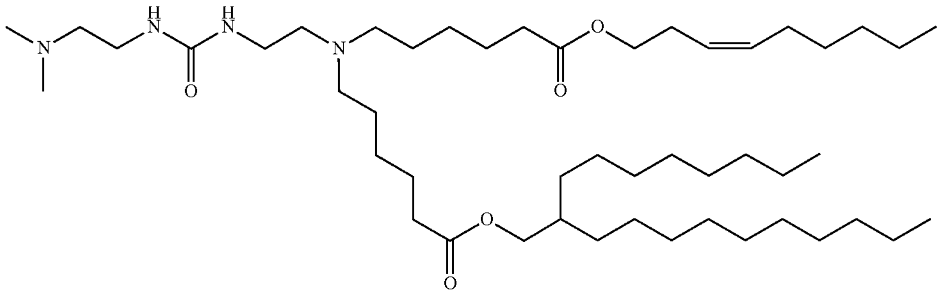 [SMILES: CCCCC/C=C\CCOC(=O)CCCCCN(CCCCCC(=O)OCC(CCCCCCCC)CCCCCCCCCC)CCNC(=O)NCCN(C)C] | 807.3 |
| 1543. | 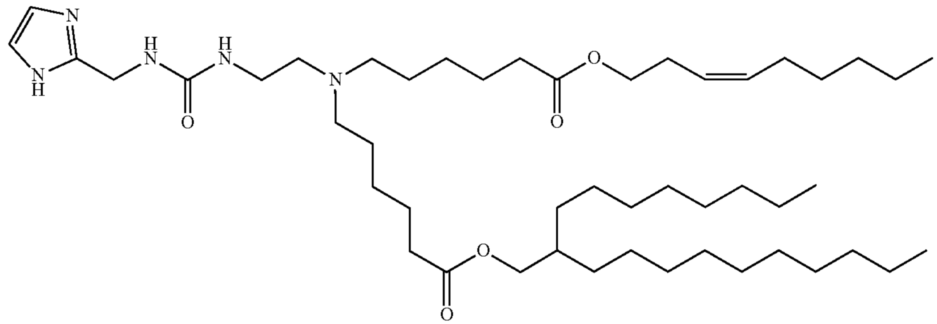 [SMILES: CCCCC/C=C\CCOC(=O)CCCCCN(CCCCCC(=O)OCC(CCCCCCCC)CCCCCCCCCC)CCNC(=O)NCc1ncc[nH]1] | 816.3 |

TABLE 1-continued
| # | Structure | Mw |
| --- | --- | --- |
| 1544. | 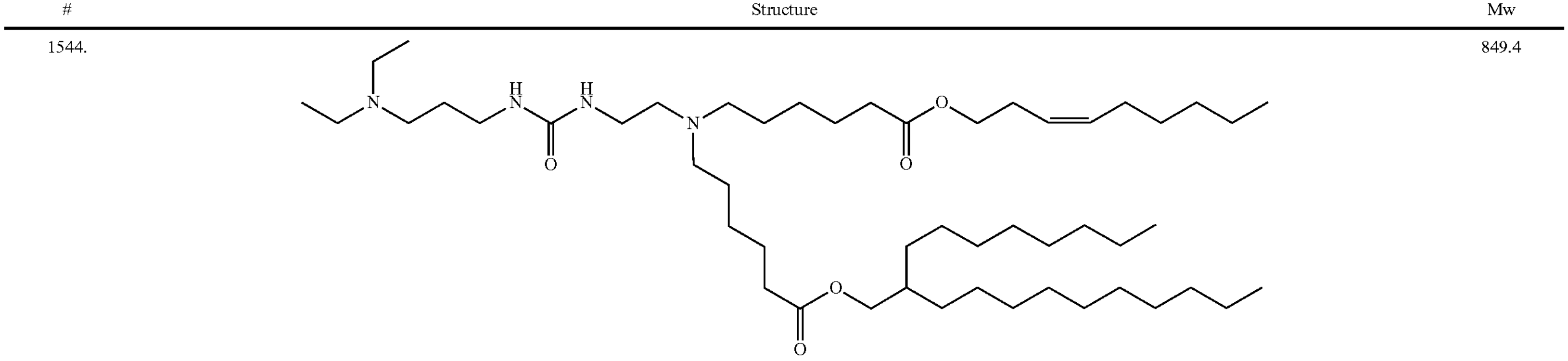 | 849.4 |
| 1545. | 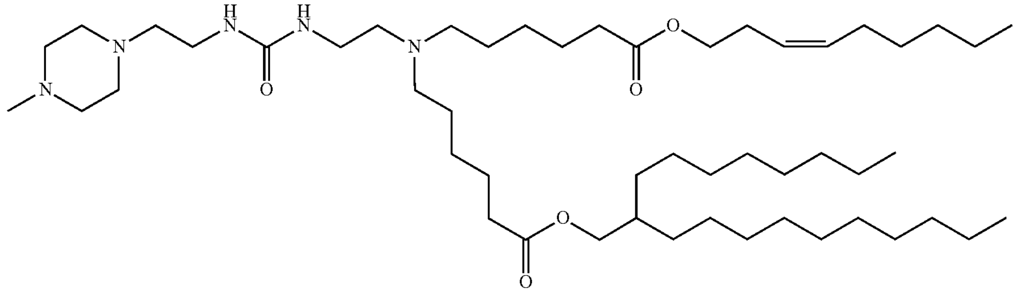 [SMILES: CCCCC/C=C\CCOC(=O)CCCCCN(CCCCCC(=O)OCC(CCCCCCCC)CCCCCCCCCC)CCNC(=O)NCCN1CCN(C)CC1] | 862.4 |
| 1546. | 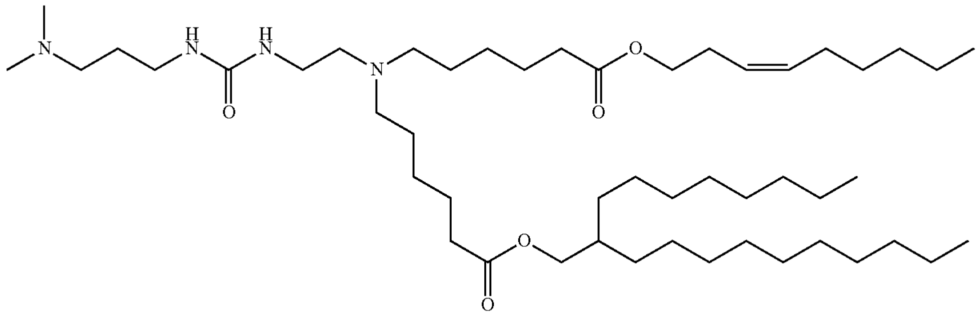 | 821.3 |

TABLE 1-continued
| # | Structure | Mw |
|---|---|---|
| 1547. | 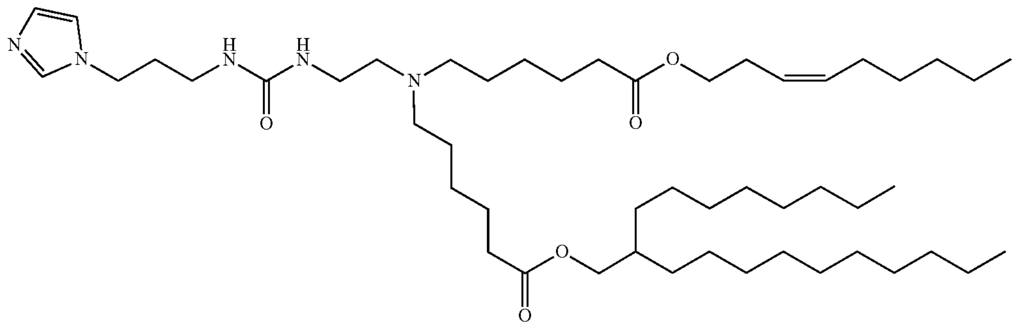 [SMILES: CCCCC/C=C\CCOC(=O)CCCCCN(CCCCCC(=O)OCC(CCCCCCCC)CCCCCCCCCC)CCNC(=O)NCCCn1ccnc1] | 844.3 |
| 1548. | 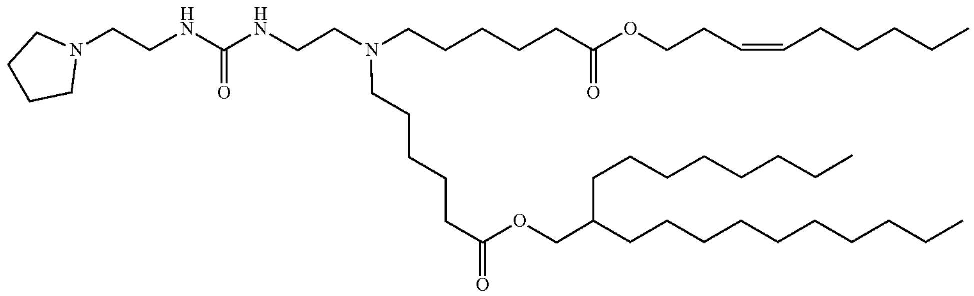 [SMILES: CCCCC/C=C\CCOC(=O)CCCCCN(CCCCCC(=O)OCC(CCCCCCCC)CCCCCCCCCC)CCNC(=O)NCCN1CCCC1] | 833.3 |
| 1549. | 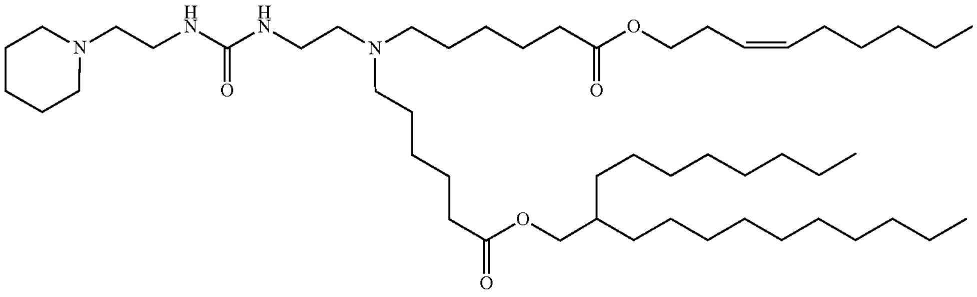 [SMILES: CCCCC/C=C\CCOC(=O)CCCCCN(CCCCCC(=O)OCC(CCCCCCCC)CCCCCCCCCC)CCNC(=O)NCCN1CCCCC1] | 847.4 |

TABLE 1-continued
| # | Structure | Mw |
| --- | --- | --- |
| 1550. | 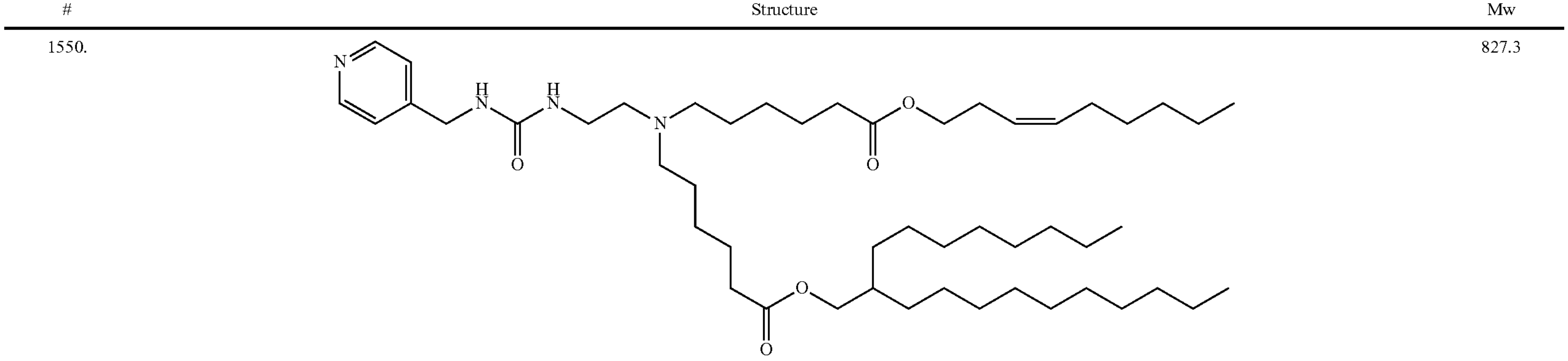 | 827.3 |
| 1551. | 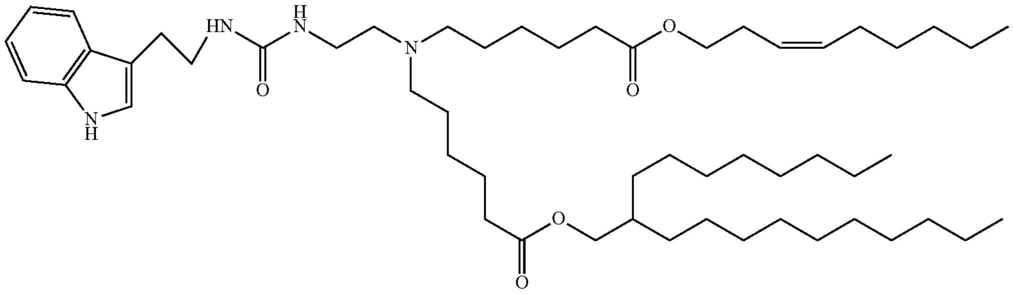 [SMILES: CCCCC/C=C\CCOC(=O)CCCCCN(CCCCCC(=O)OCC(CCCCCCCC)CCCCCCCCCC)CCNC(=O)NCCc1c[nH]c2ccccc12] | 879.4 |
| 1552. | 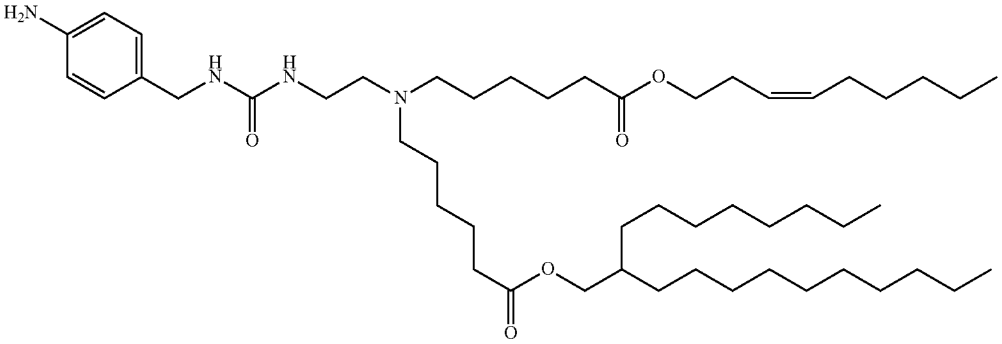 [SMILES: CCCCC/C=C\CCOC(=O)CCCCCN(CCCCCC(=O)OCC(CCCCCCCC)CCCCCCCCCC)CCNC(=O)NCc1ccc(N)cc1] | 841.3 |

TABLE 1-continued
| # | Structure | Mw |
|---|---|---|
| 1553. | 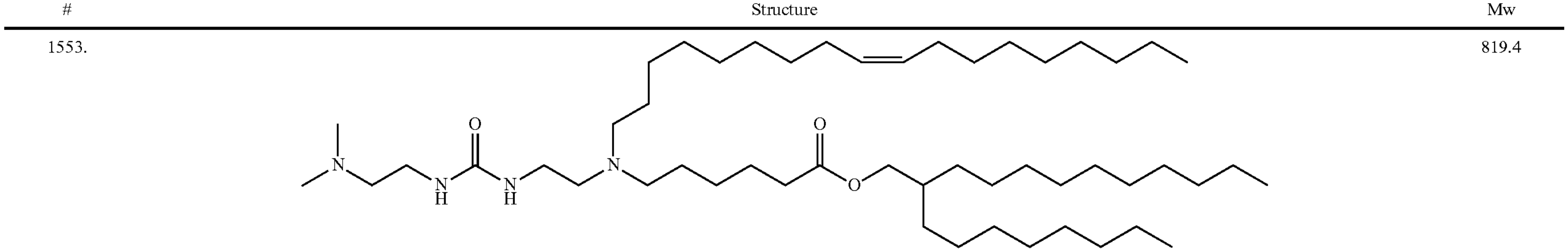 | 819.4 |
| 1554. | 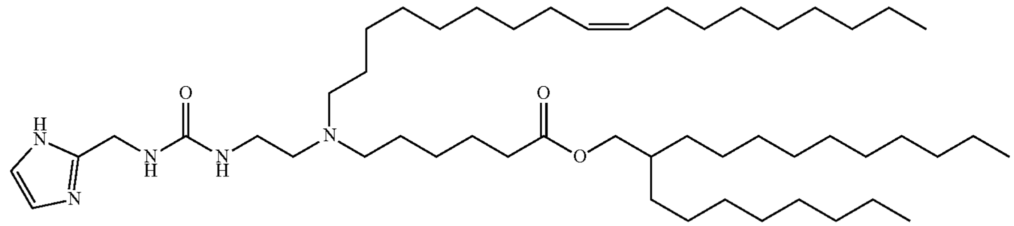 [SMILES: CCCCCCCC/C=C\CCCCCCCCN(CCCCCC(=O)OCC(CCCCCCCC)CCCCCCCCCC)CCNC(=O)NCc1ncc[nH]1] | 828.4 |
| 1555. | 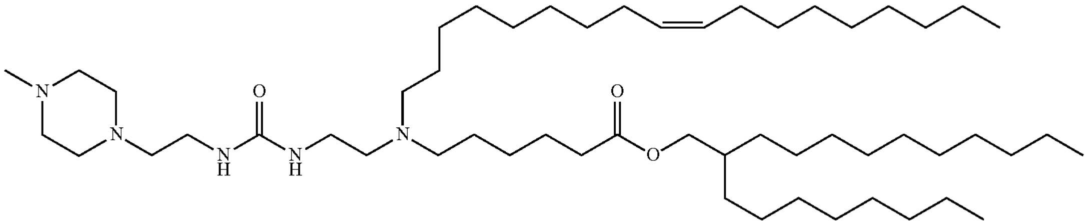 [SMILES: CCCCCCCC/C=C\CCCCCCCCN(CCCCCC(=O)OCC(CCCCCCCC)CCCCCCCCCC)CCNC(=O)NCCN1CCN(C)CC1] | 874.5 |
| 1556. | 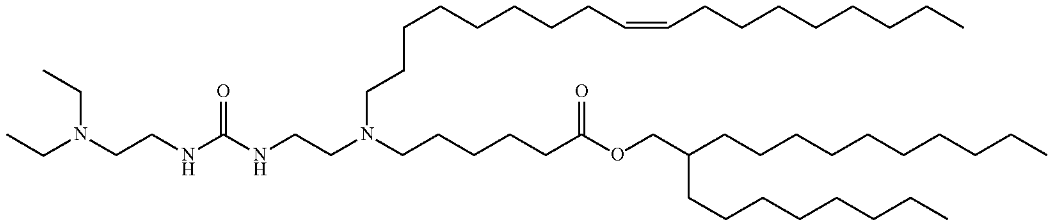 [SMILES: CCCCCCCC/C=C\CCCCCCCCN(CCCCCC(=O)OCC(CCCCCCCC)CCCCCCCCCC)CCNC(=O)NCCN(CC)CC] | 847.5 |

TABLE 1-continued
| # | Structure | Mw |
| --- | --- | --- |
| 1557. | 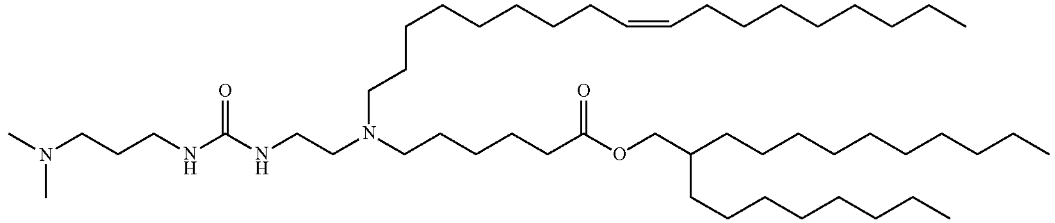 [SMILES: CCCCCCCC/C=C\CCCCCCCCN(CCCCCC(=O)OCC(CCCCCCCC)CCCCCCCCCC)CCNC(=O)NCCCN(C)C] | 833.4 |
| 1558. | 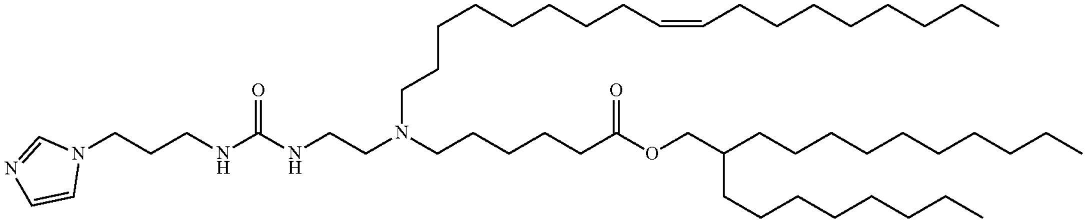 [SMILES: CCCCCCCC/C=C\CCCCCCCCN(CCCCCC(=O)OCC(CCCCCCCC)CCCCCCCCCC)CCNC(=O)NCCCn1ccnc1] | 856.4 |
| 1559. | 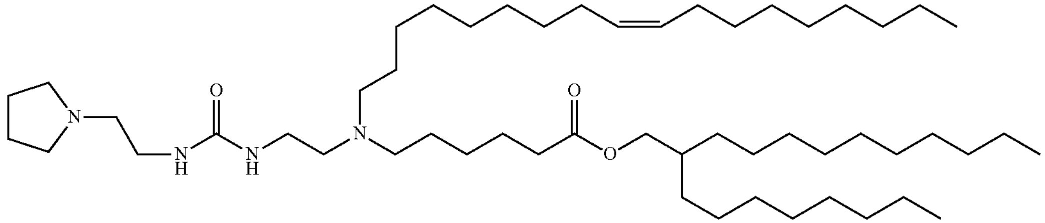 [SMILES: CCCCCCCC/C=C\CCCCCCCCN(CCCCCC(=O)OCC(CCCCCCCC)CCCCCCCCCC)CCNC(=O)NCCN1CCCC1] | 845.4 |
| 1560. | 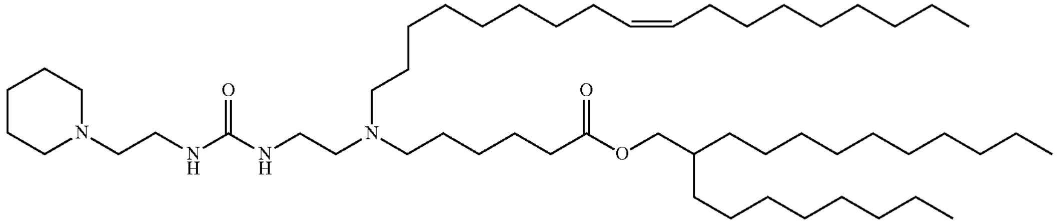 [SMILES: CCCCCCCC/C=C\CCCCCCCCN(CCCCCC(=O)OCC(CCCCCCCC)CCCCCCCCCC)CCNC(=O)NCCN1CCCCC1] | 859.5 |

TABLE 1-continued
| # | Structure | Mw |
| --- | --- | --- |
| 1561. | 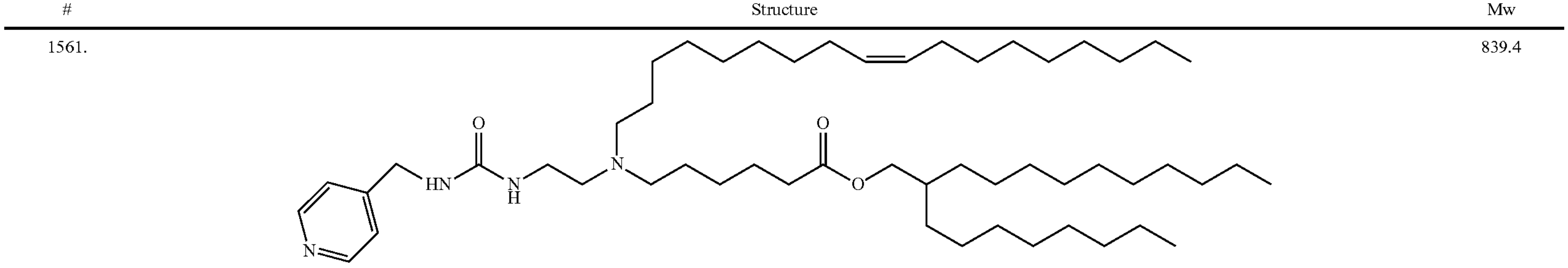 | 839.4 |
| 1562. | 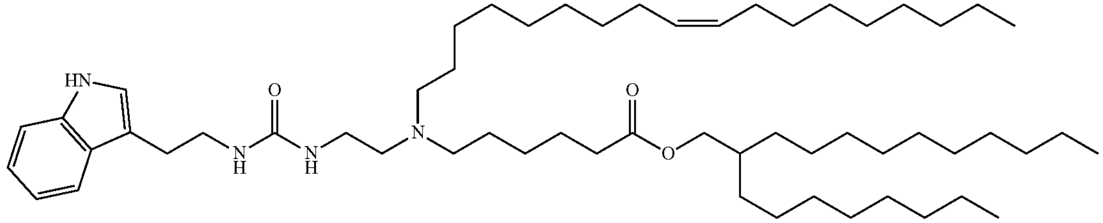 [SMILES: CCCCCCCC/C=C\CCCCCCCCN(CCCCCC(=O)OCC(CCCCCCCC)CCCCCCCCCC)CCNC(=O)NCCc1c[nH]c2ccccc12] | 891.5 |
| 1563. | 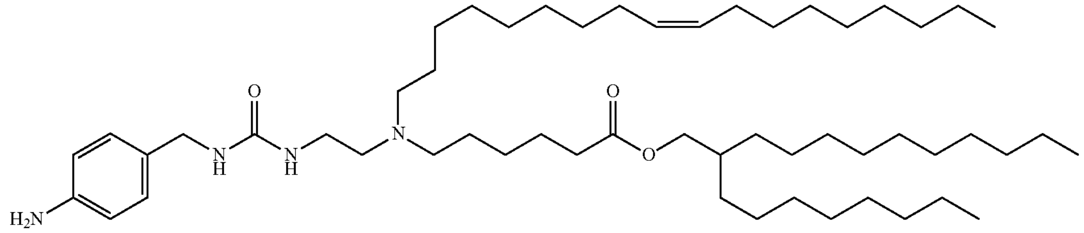 [SMILES: CCCCCCCC/C=C\CCCCCCCCN(CCCCCC(=O)OCC(CCCCCCCC)CCCCCCCCCC)CCNC(=O)NCc1ccc(N)cc1] | 853.4 |

TABLE 1-continued
| # | Structure | Mw |
| --- | --- | --- |
| 1564. | 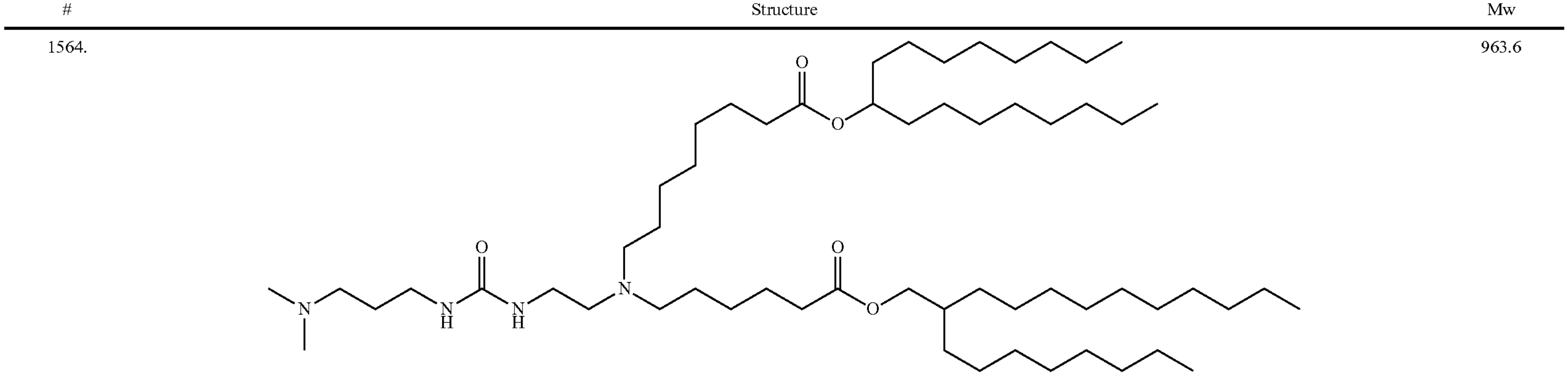 | 963.6 |
| 1565. | 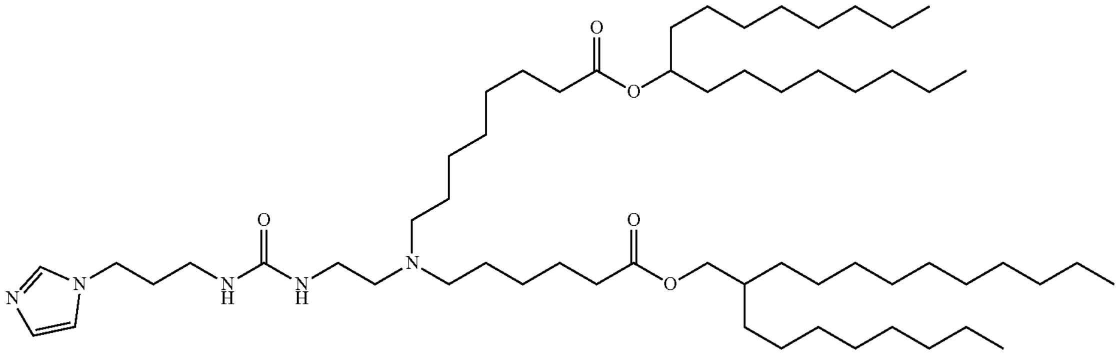 [SMILES: CCCCCCCCCCC(CCCCCCCC)COC(=O)CCCCCN(CCCCCCCC(=O)OC(CCCCCCCC)CCCCCCCC)CCNC(=O)NCCCn1ccnc1] | 986.6 |
| 1566. | 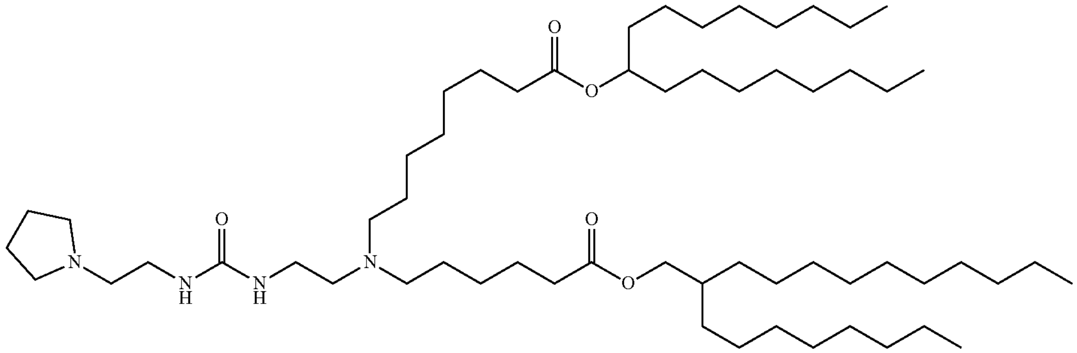 [SMILES: CCCCCCCCCCC(CCCCCCCC)COC(=O)CCCCCN(CCCCCCCC(=O)OC(CCCCCCCC)CCCCCCCC)CCNC(=O)NCCN1CCCC1] | 975.6 |

TABLE 1-continued
| # | Structure | Mw |
|---|---|---|
| 1567. | 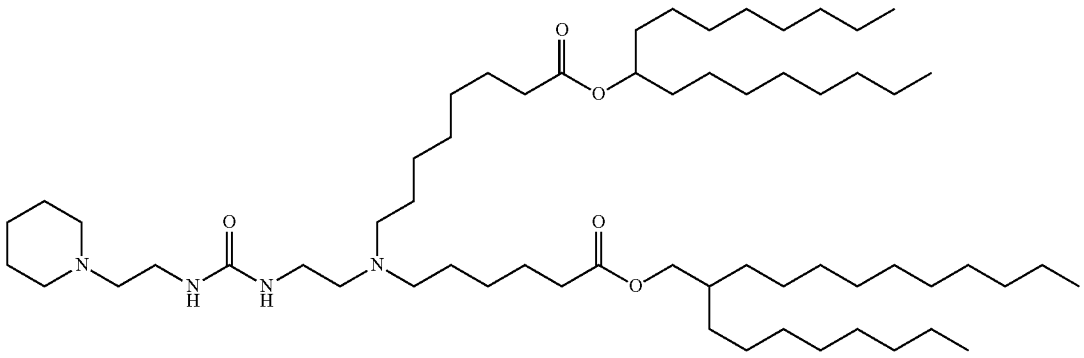 [SMILES: CCCCCCCCCCC(CCCCCCCC)COC(=O)CCCCCN(CCCCCCCC(=O)OC(CCCCCCCC)CCCCCCCC)CCNC(=O)NCCN1CCCCC1] | 989.7 |
| 1568. | 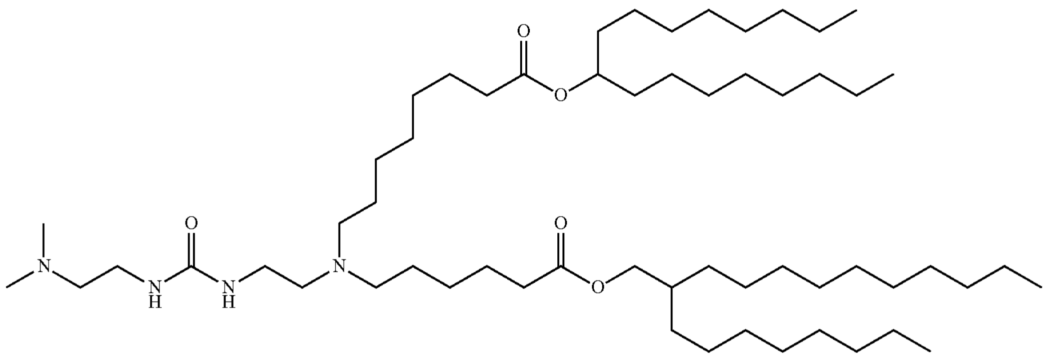 [SMILES: CCCCCCCCCCC(CCCCCCCC)COC(=O)CCCCCN(CCCCCCCC(=O)OC(CCCCCCCC)CCCCCCCC)CCNC(=O)NCCN(C)C] | 949.6 |

TABLE 1-continued
| # | Structure | Mw |
| --- | --- | --- |
| 1569. | 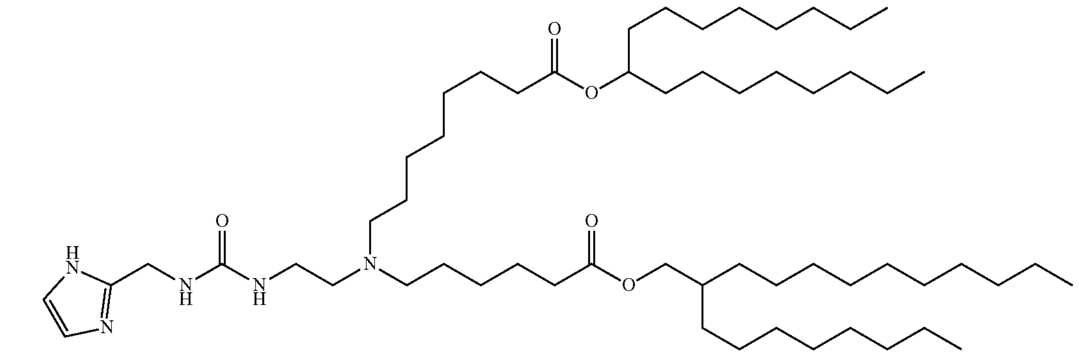 [SMILES: CCCCCCCCCCC(CCCCCCCC)COC(=O)CCCCCN(CCCCCCCC(=O)OC(CCCCCCCC)CCCCCCCC)CCNC(=O)NCc1ncc[nH]1] | 958.6 |
| 1570. | 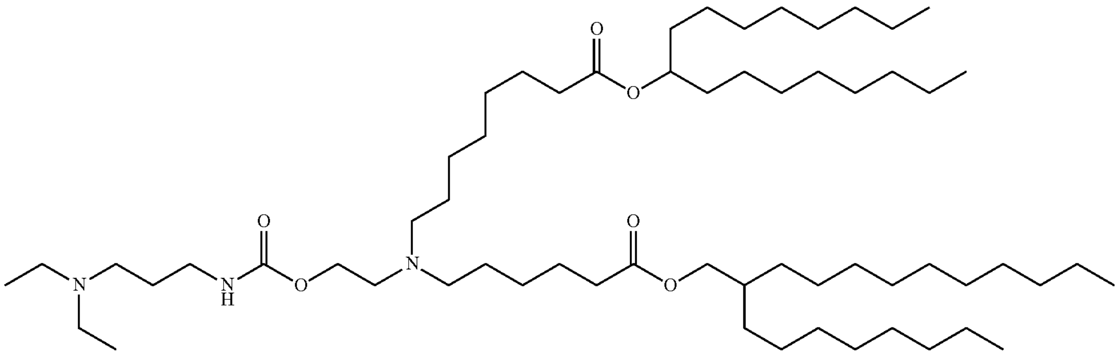 [SMILES: CCCCCCCCCCC(CCCCCCCC)COC(=O)CCCCCN(CCCCCCCC(=O)OC(CCCCCCCC)CCCCCCCC)CCOC(=O)NCCCN(CC)CC] | 991.7 |
| 1571. | 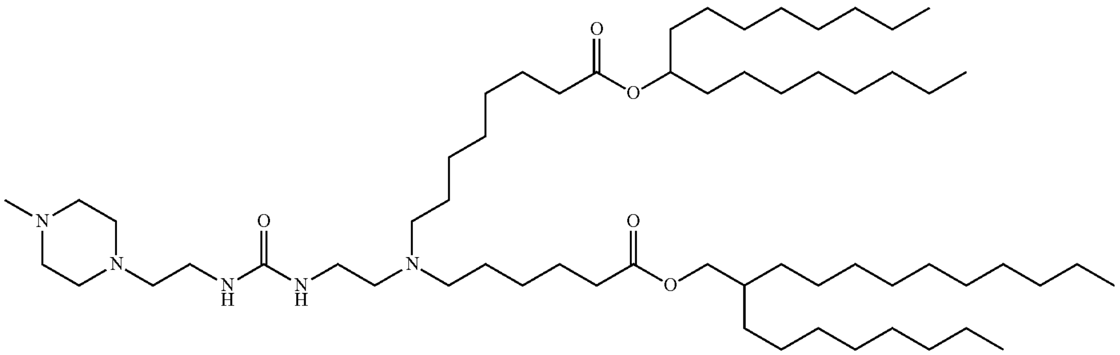 [SMILES: CCCCCCCCCCC(CCCCCCCC)COC(=O)CCCCCN(CCCCCCCC(=O)OC(CCCCCCCC)CCCCCCCC)CCNC(=O)NCCN1CCN(C)CC1] | 1004.7 |

TABLE 1-continued
| # | Structure | Mw |
| --- | --- | --- |
| 1572. | 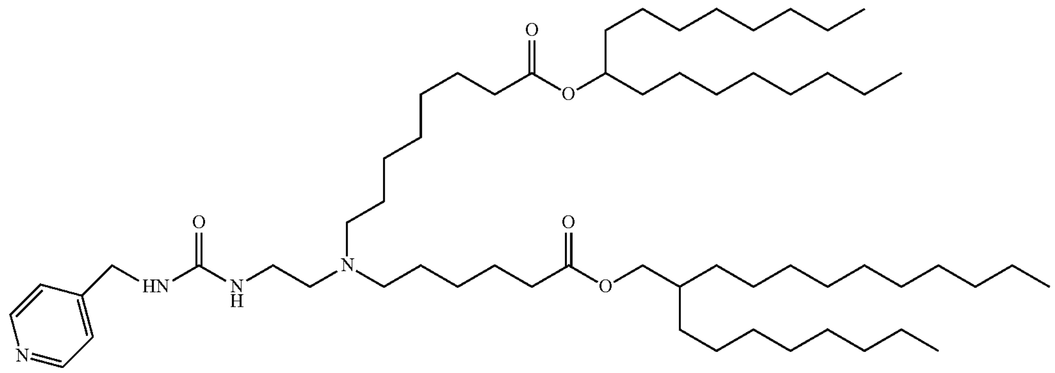 [SMILES: CCCCCCCCCCC(CCCCCCCC)COC(=O)CCCCCN(CCCCCCCC(=O)OC(CCCCCCCC)CCCCCCCC)CCNC(=O)NCc1ccncc1] | 969.6 |
| 1573. | 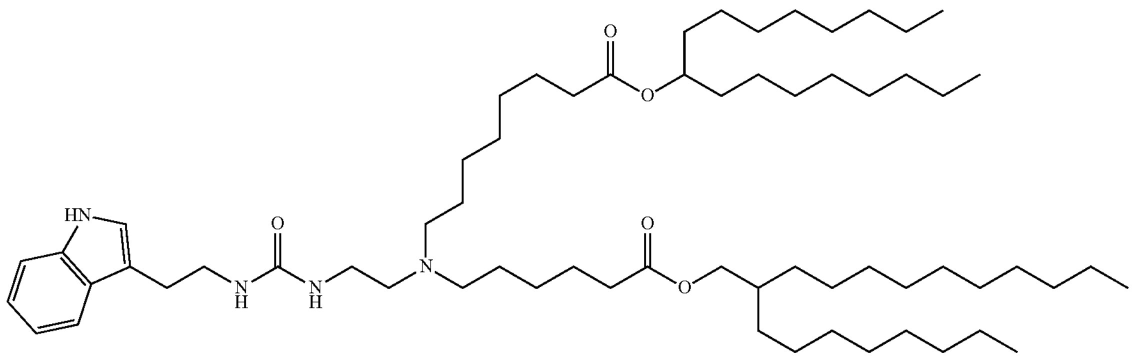 [SMILES: CCCCCCCCCCC(CCCCCCCC)COC(=O)CCCCCN(CCCCCCCC(=O)OC(CCCCCCCC)CCCCCCCC)CCNC(=O)NCCc1c[nH]c2ccccc12] | 1021.7 |

TABLE 1-continued
| # | Structure | Mw |
|---|---|---|
| 1574. | 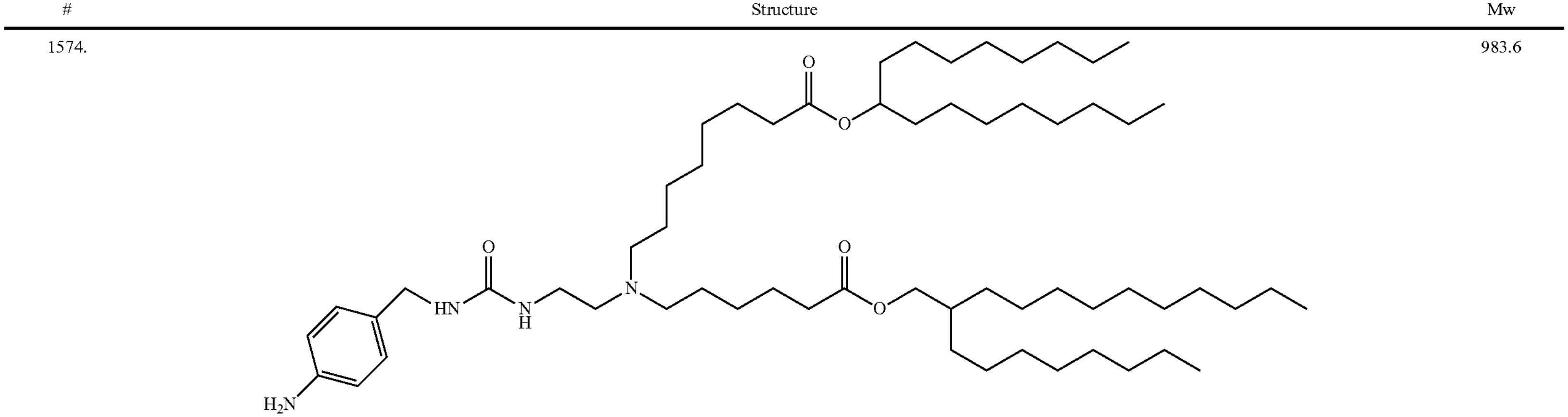 | 983.6 |
| 1575. | 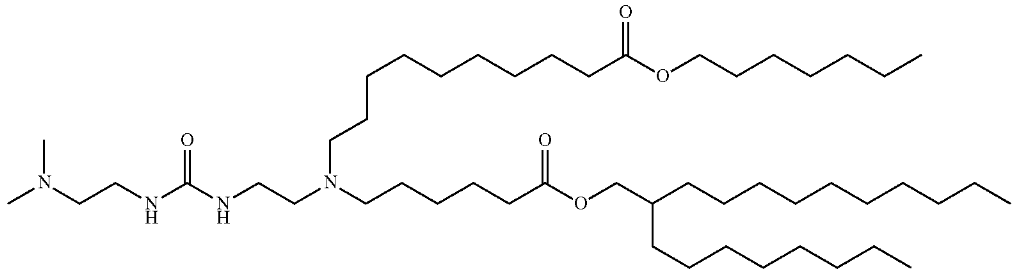 [SMILES: CCCCCCCCCCC(CCCCCCCC)COC(=O)CCCCCN(CCCCCCCCCC(=O)OCCCCCCC)CCNC(=O)NCCN(C)C] | 837.4 |
| 1576. | 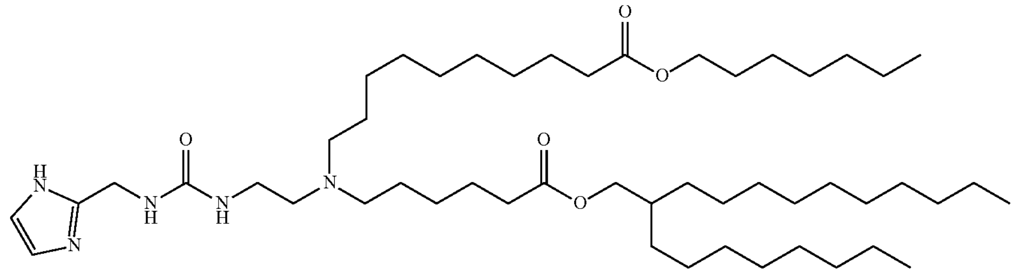 [SMILES: CCCCCCCCCCC(CCCCCCCC)COC(=O)CCCCCN(CCCCCCCCCC(=O)OCCCCCCC)CCNC(=O)NCc1ncc[nH]1] | 846.3 |

TABLE 1-continued
| # | Structure | Mw |
| --- | --- | --- |
| 1577. | 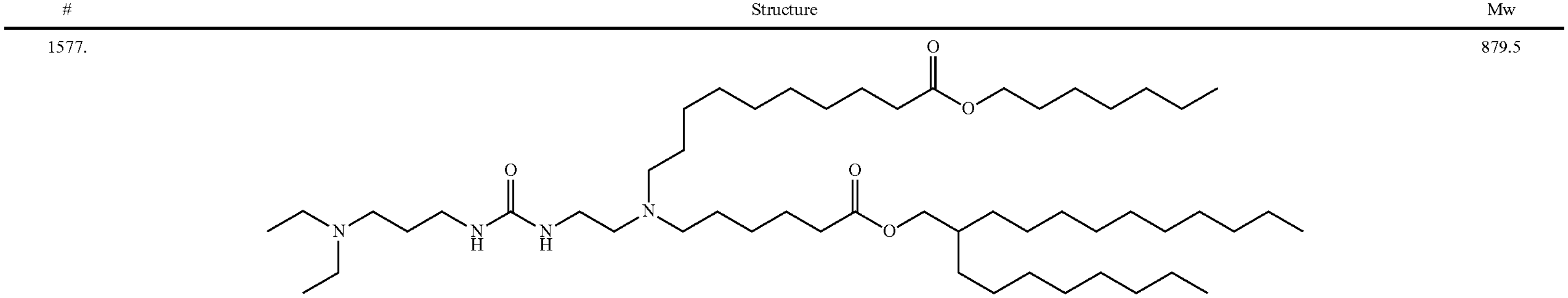 | 879.5 |
| 1578. | 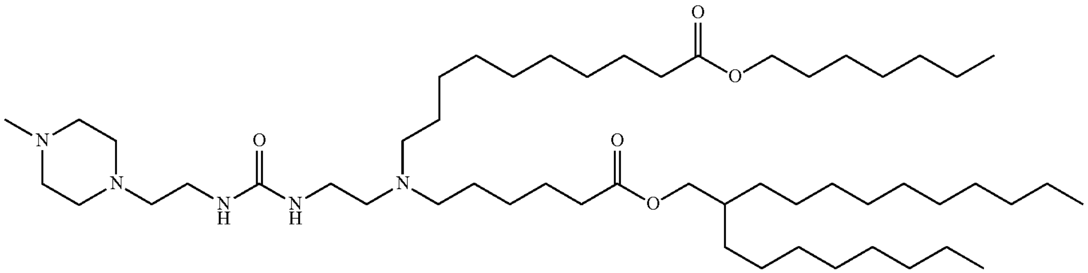 [SMILES: CCCCCCCCCCC(CCCCCCCC)COC(=O)CCCCCN(CCCCCCCCCC(=O)OCCCCCCC)CCNC(=O)NCCN1CCN(C)CC1] | 892.5 |
| 1579. | 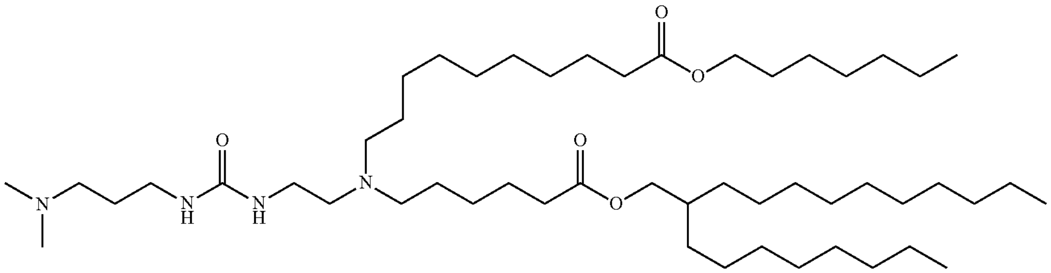 [SMILES: CCCCCCCCCCC(CCCCCCCC)COC(=O)CCCCCN(CCCCCCCCCC(=O)OCCCCCCC)CCNC(=O)NCCCN(C)C] | 851.4 |

TABLE 1-continued
| # | Structure | Mw |
|---|---|---|
| 1580. | 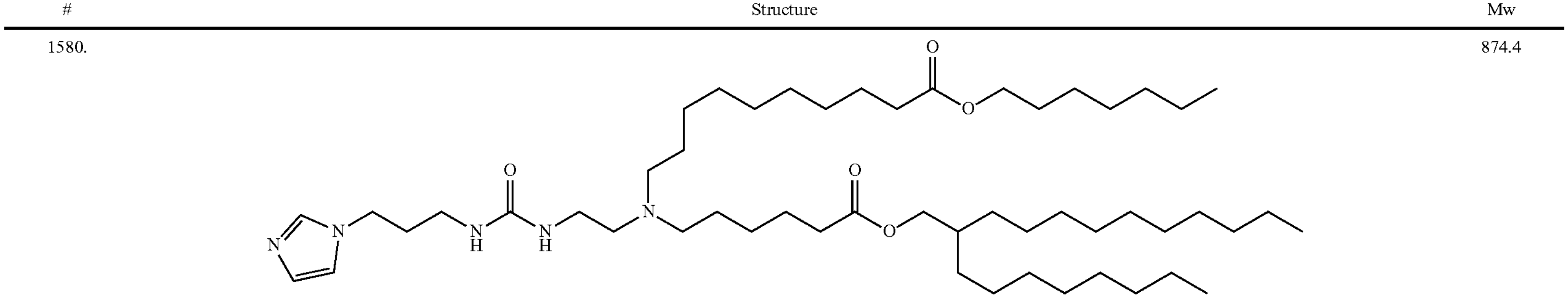 | 874.4 |
| 1581. | 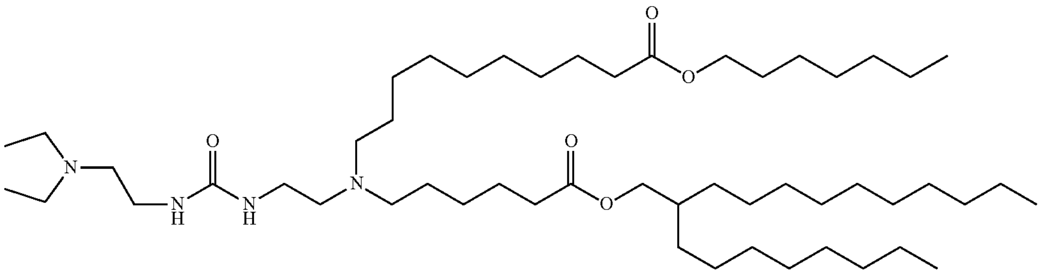 [SMILES: CCCCCCCCCCC(CCCCCCCC)COC(=O)CCCCCN(CCCCCCCCCC(=O)OCCCCCCC)CCNC(=O)NCCN(CC)CC] | 863.4 |
| 1582. | 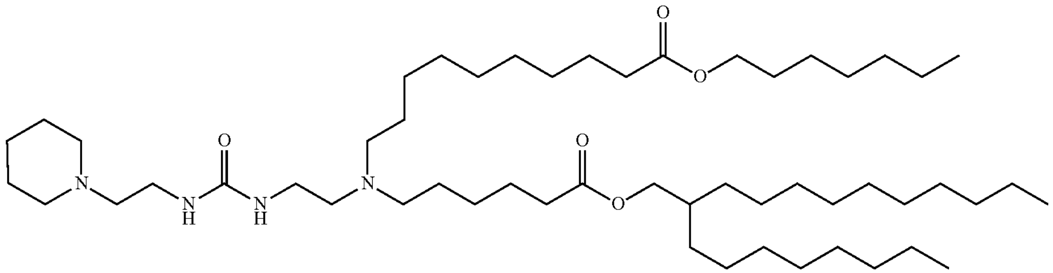 [SMILES: CCCCCCCCCCC(CCCCCCCC)COC(=O)CCCCCN(CCCCCCCCCC(=O)OCCCCCCC)CCNC(=O)NCCN1CCCCC1] | 877.4 |

TABLE 1-continued
| # | Structure | Mw |
| --- | --- | --- |
| 1583. | 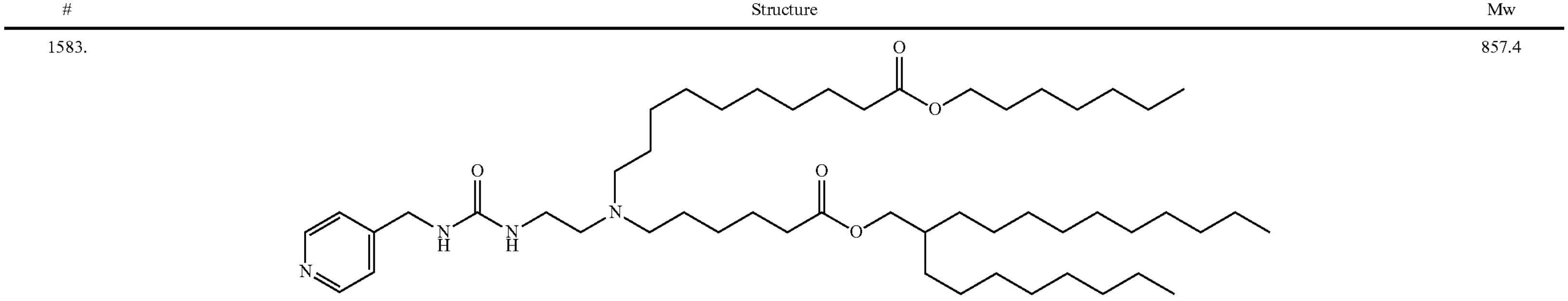 | 857.4 |
| 1584. | 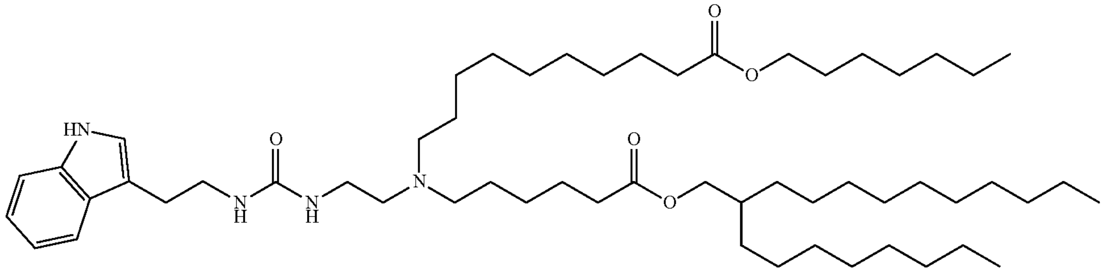 [SMILES: CCCCCCCCCCC(CCCCCCCC)COC(=O)CCCCCN(CCCCCCCCCC(=O)OCCCCCCC)CCNC(=O)NCCc1c[nH]c2ccccc12] | 909.4 |
| 1585. | 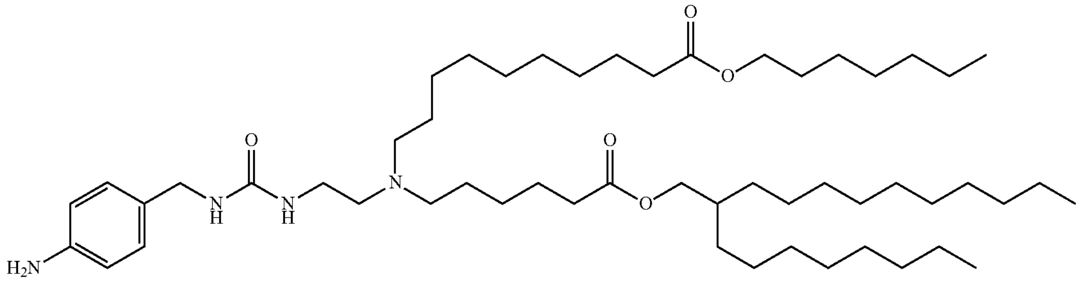 [SMILES: CCCCCCCCCCC(CCCCCCCC)COC(=O)CCCCCN(CCCCCCCCCC(=O)OCCCCCCC)CCNC(=O)NCc1ccc(N)cc1] | 871.4 |

TABLE 1-continued
| # | Structure | Mw |
|---|---|---|
| 1586. | 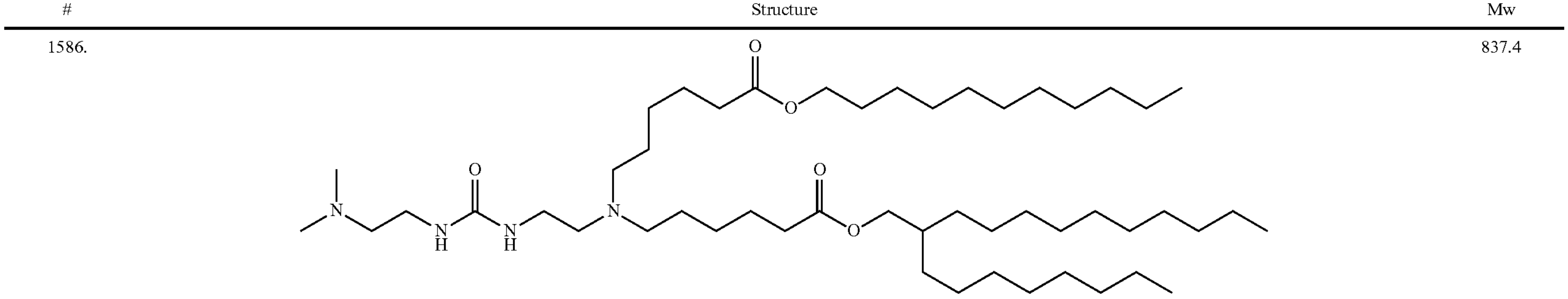 | 837.4 |
| 1587. | 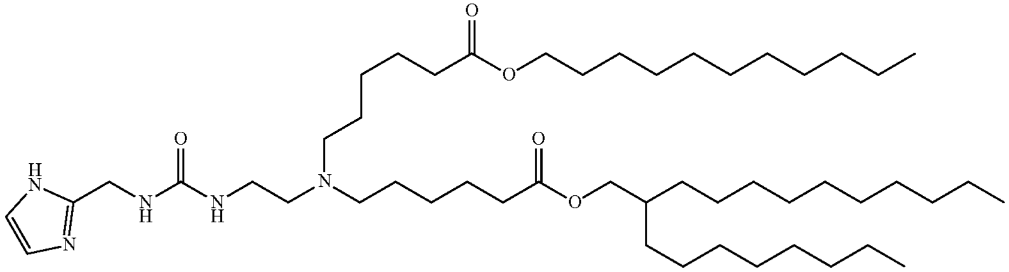 [SMILES: CCCCCCCCCCCOC(=O)CCCCCN(CCCCCC(=O)OCC(CCCCCCCC)CCCCCCCCCC)CCNC(=O)NCc1ncc[nH]1] | 846.3 |
| 1588. | 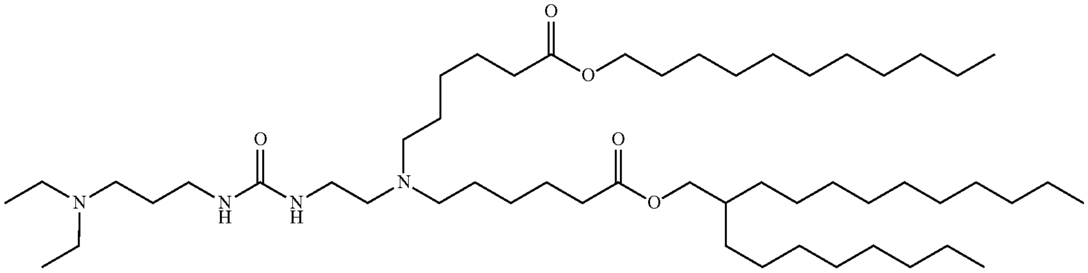 [SMILES: CCCCCCCCCCCOC(=O)CCCCCN(CCCCCC(=O)OCC(CCCCCCCC)CCCCCCCCCC)CCNC(=O)NCCCN(CC)CC] | 879.5 |

TABLE 1-continued
| # | Structure | Mw |
| --- | --- | --- |
| 1589. | 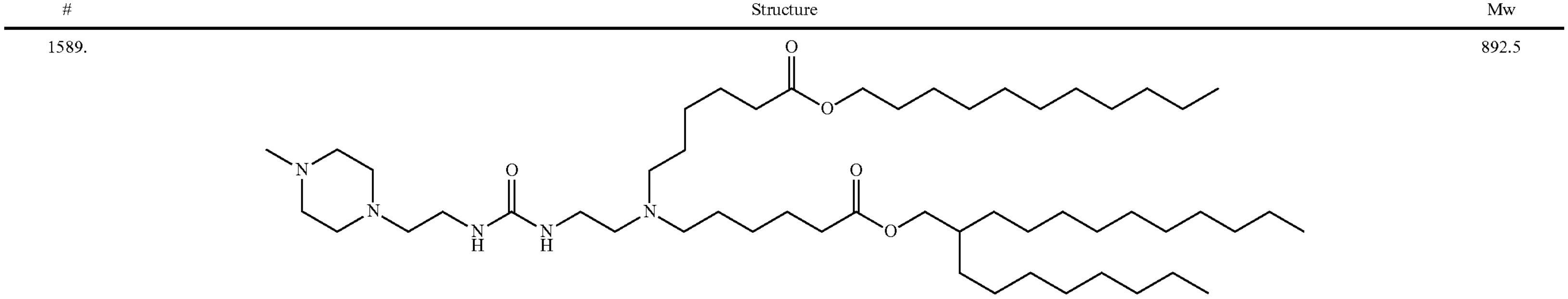 | 892.5 |
| 1590. | 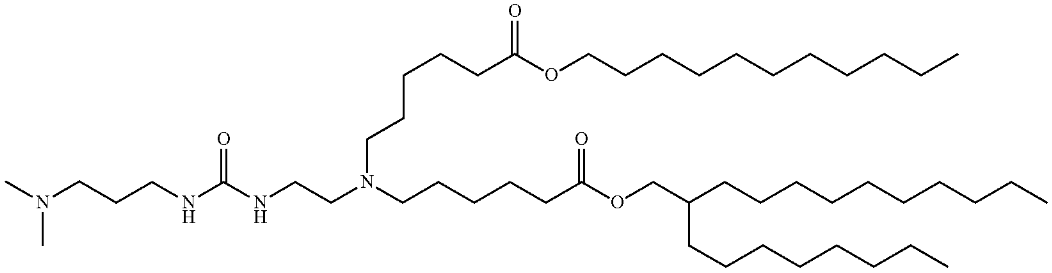 [SMILES: CCCCCCCCCCCOC(=O)CCCCCN(CCCCCC(=O)OCC(CCCCCCCC)CCCCCCCCCC)CCNC(=O)NCCCN(C)C] | 851.4 |
| 1591. | 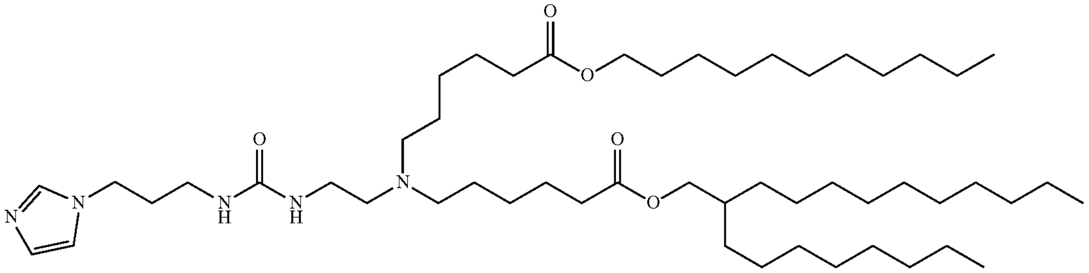 [SMILES: CCCCCCCCCCCOC(=O)CCCCCN(CCCCCC(=O)OCC(CCCCCCCC)CCCCCCCCCC)CCNC(=O)NCCCn1ccnc1] | 874.4 |

TABLE 1-continued
| # | Structure | Mw |
| --- | --- | --- |
| 1592. | 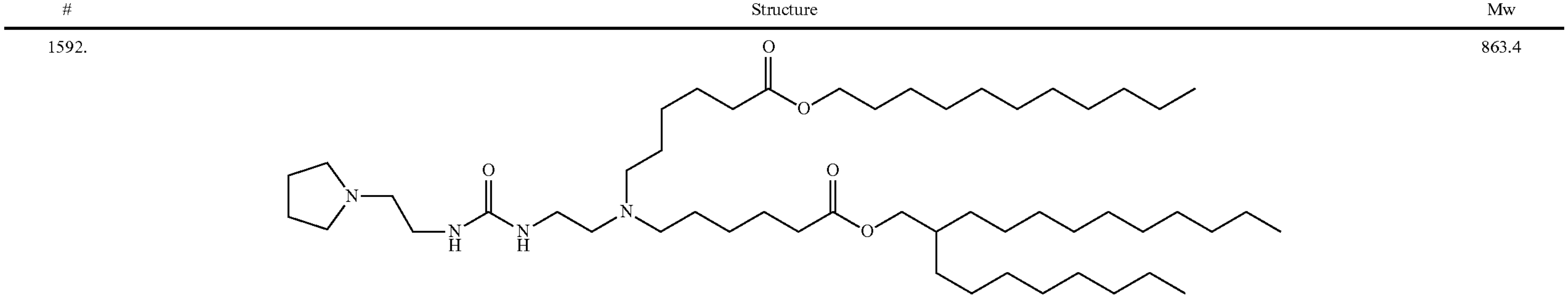 | 863.4 |
| 1593. | 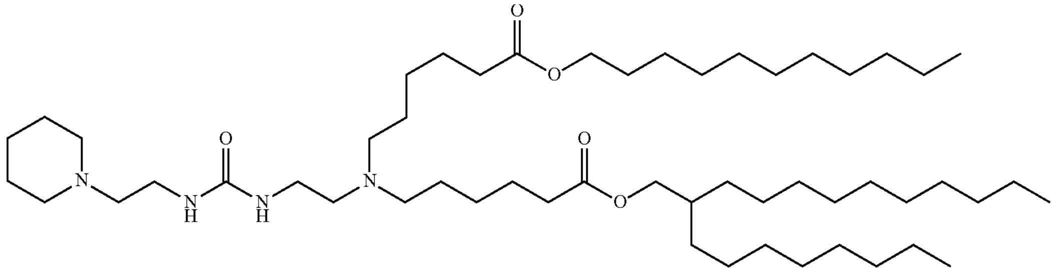 [SMILES: CCCCCCCCCCCOC(=O)CCCCCN(CCCCCC(=O)OCC(CCCCCCCC)CCCCCCCCCC)CCNC(=O)NCCN1CCCCC1] | 877.4 |
| 1594. | 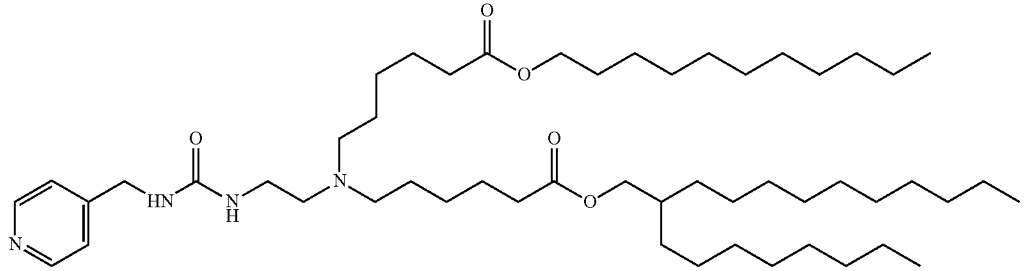 [SMILES: CCCCCCCCCCCOC(=O)CCCCCN(CCCCCC(=O)OCC(CCCCCCCC)CCCCCCCCCC)CCNC(=O)NCc1ccncc1] | 857.4 |

TABLE 1-continued
| # | Structure | Mw |
| --- | --- | --- |
| 1595. | 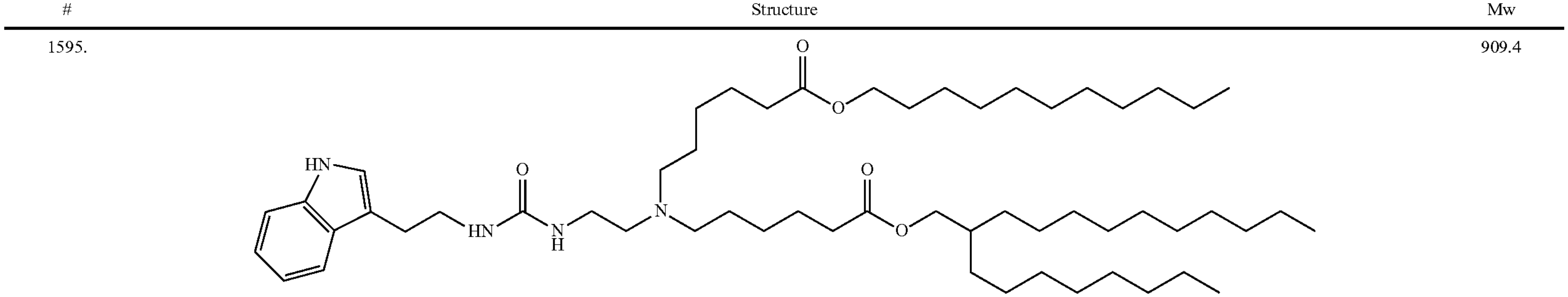 | 909.4 |
| 1596. | 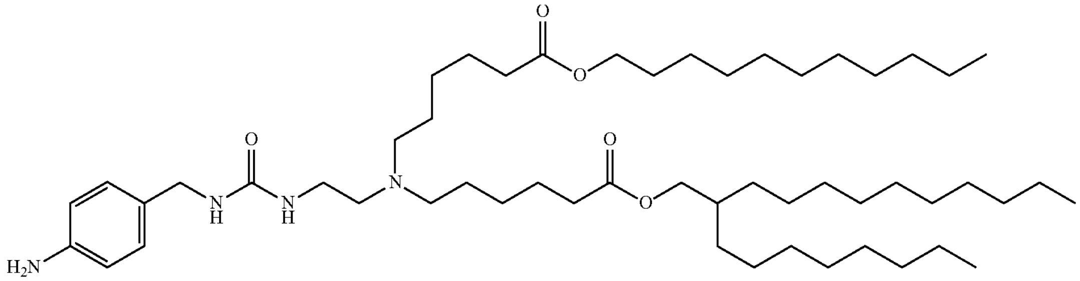 [SMILES: CCCCCCCCCCCOC(=O)CCCCCN(CCCCCC(=O)OCC(CCCCCCCC)CCCCCCCCCC)CCNC(=O)NCc1ccc(N)cc1] | 871.4 |
| 1597. | 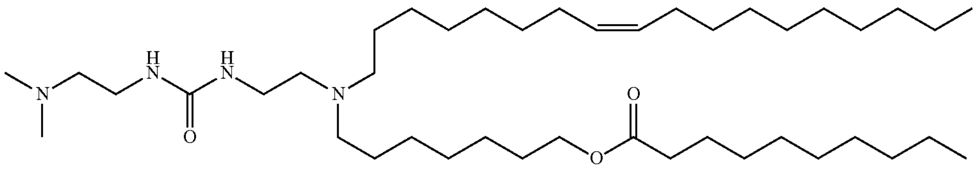 [SMILES: CCCCCCCCC/C=C\CCCCCCCN(CCCCCCCOC(=O)CCCCCCCCC)CCNC(=O)NCCN(C)C] | 693.2 |
| 1598. | 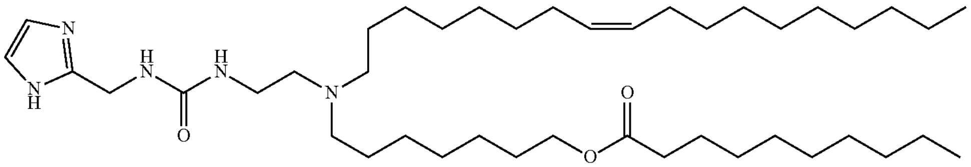 [SMILES: CCCCCCCCC/C=C\CCCCCCCN(CCCCCCCOC(=O)CCCCCCCCC)CCNC(=O)NCc1ncc[nH]1] | 702.1 |

TABLE 1-continued
| # | Structure | Mw |
|---|---|---|
| 1599. | 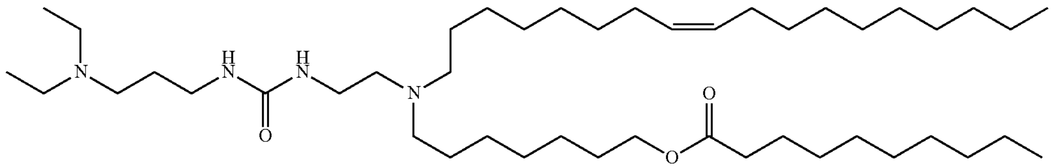 [SMILES: CCCCCCCCC/C=C\CCCCCCCN(CCCCCCCOC(=O)CCCCCCCCC)CCNC(=O)NCCCN(CC)CC] | 735.2 |
| 1600. | 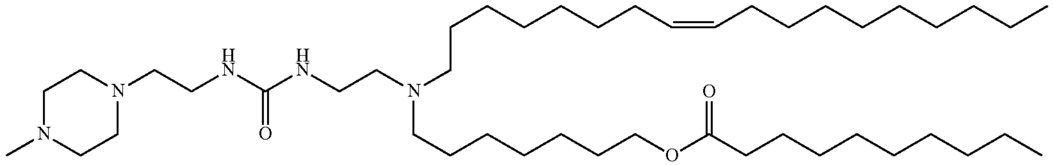 [SMILES: CCCCCCCCC/C=C\CCCCCCCN(CCCCCCCOC(=O)CCCCCCCCC)CCNC(=O)NCCN1CCN(C)CC1] | 748.2 |
| 1601. | 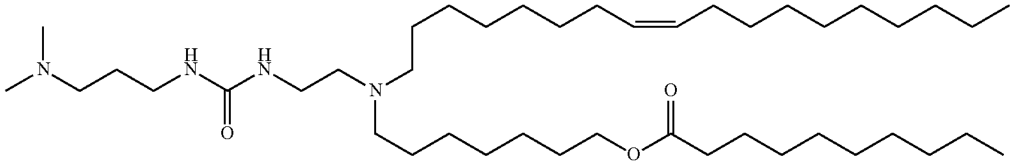 [SMILES: CCCCCCCCC/C=C\CCCCCCCN(CCCCCCCOC(=O)CCCCCCCCC)CCNC(=O)NCCCN(C)C] | 707.2 |
| 1602. | 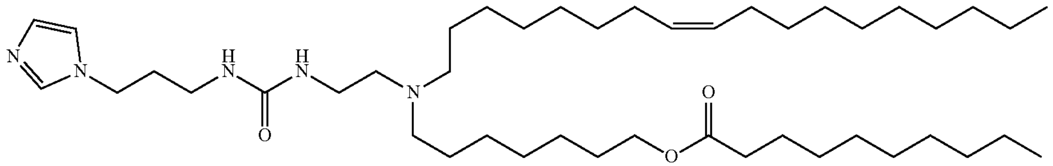 [SMILES: CCCCCCCCC/C=C\CCCCCCCN(CCCCCCCOC(=O)CCCCCCCCC)CCNC(=O)NCCCn1ccnc1] | 730.2 |
| 1603. | 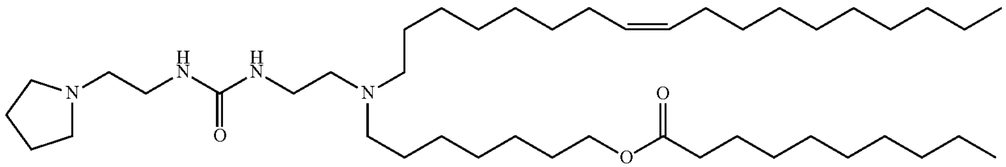 [SMILES: CCCCCCCCC/C=C\CCCCCCCN(CCCCCCCOC(=O)CCCCCCCCC)CCNC(=O)NCCN1CCCC1] | 719.2 |
| 1604. | 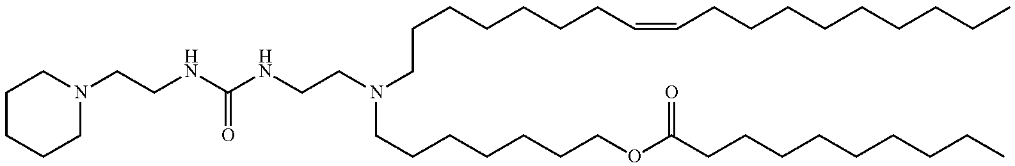 [SMILES: CCCCCCCCC/C=C\CCCCCCCN(CCCCCCCOC(=O)CCCCCCCCC)CCNC(=O)NCCN1CCCCC1] | 733.2 |

TABLE 1-continued
| # | Structure | Mw |
| --- | --- | --- |
| 1605. | 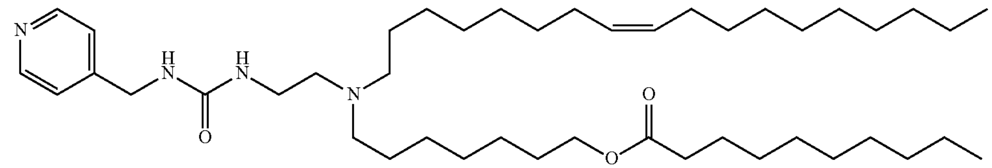 [SMILES: CCCCCCCCC/C=C\CCCCCCCN(CCCCCCCOC(=O)CCCCCCCCC)CCNC(=O)NCc1ccncc1] | 713.1 |
| 1606. | 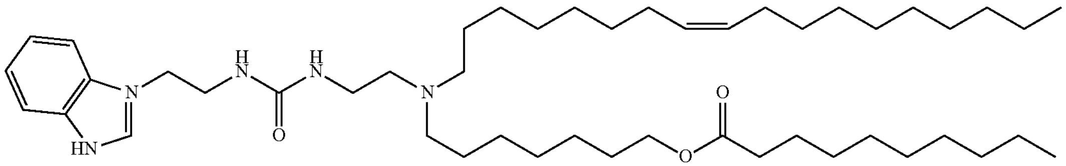 | 765.2 |
| 1607. | 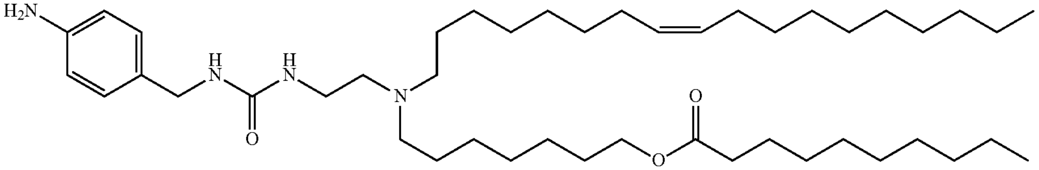 [SMILES: CCCCCCCCC/C=C\CCCCCCCN(CCCCCCCOC(=O)CCCCCCCCC)CCNC(=O)NCc1ccc(N)cc1] | 727.2 |
| 1608. | 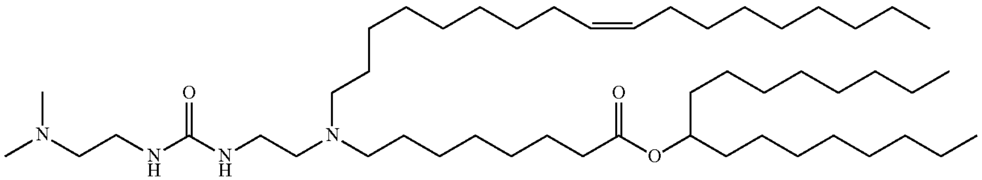 [SMILES: CCCCCCCC/C=C\CCCCCCCCN(CCCCCCCC(=O)OC(CCCCCCCC)CCCCCCCC)CCNC(=O)NCCN(C)C] | 805.4 |
| 1609. | 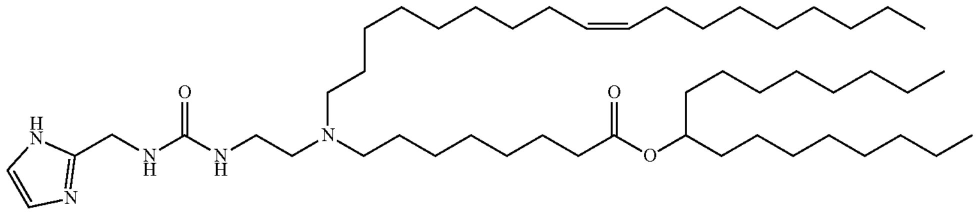 [SMILES: CCCCCCCC/C=C\CCCCCCCCN(CCCCCCCC(=O)OC(CCCCCCCC)CCCCCCCC)CCNC(=O)NCc1ncc[nH]1] | 814.3 |

TABLE 1-continued
| # | Structure | Mw |
|---|---|---|
| 1610. | 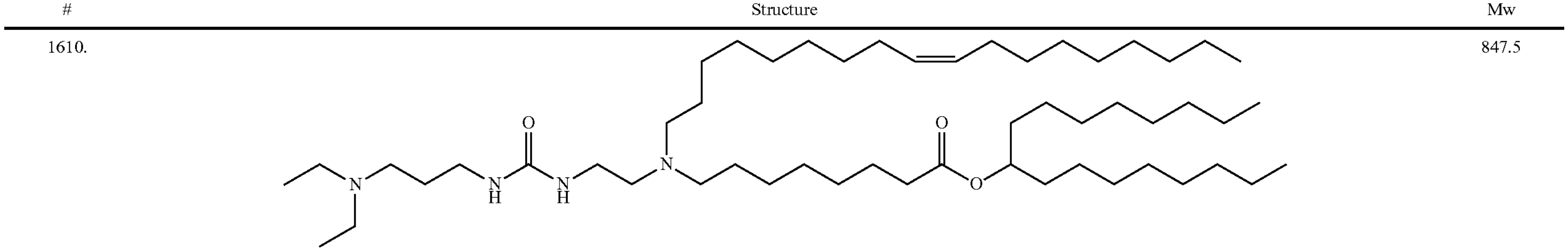 | 847.5 |
| 1611. | 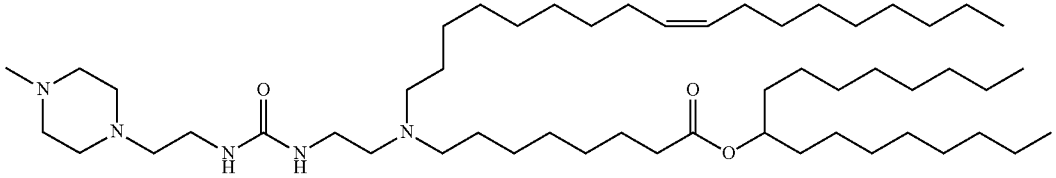 [SMILES: CCCCCCCC/C=C\CCCCCCCCN(CCCCCCCC(=O)OC(CCCCCCCC)CCCCCCCC)CCNC(=O)NCCN1CCN(C)CC1] | 860.5 |
| 1612. | 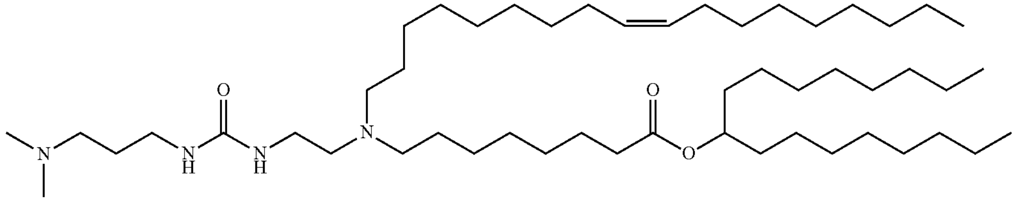 [SMILES: CCCCCCCC/C=C\CCCCCCCCN(CCCCCCCC(=O)OC(CCCCCCCC)CCCCCCCC)CCNC(=O)NCCCN(C)C] | 819.4 |
| 1613. | 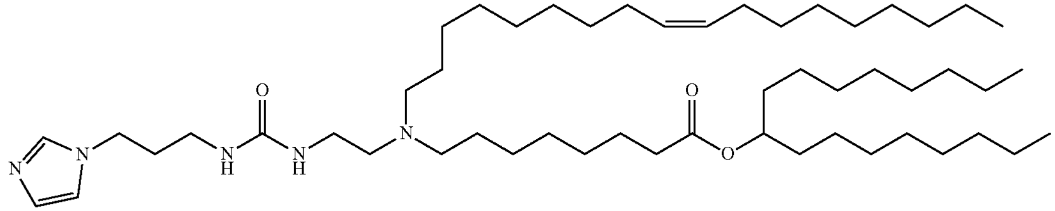 | 842.4 |
| 1614. | 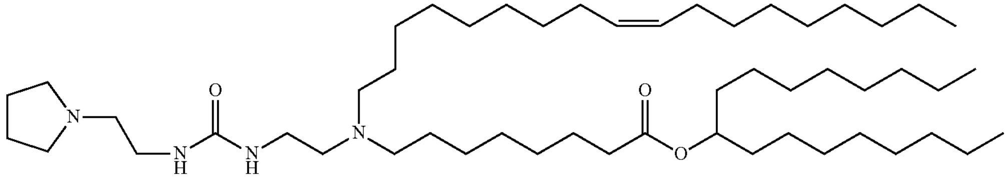 [SMILES: CCCCCCCC/C=C\CCCCCCCCN(CCCCCCCC(=O)OC(CCCCCCCC)CCCCCCCC)CCNC(=O)NCCN1CCCC1] | 831.4 |

TABLE 1-continued
| # | Structure | Mw |
|---|---|---|
| 1615. | 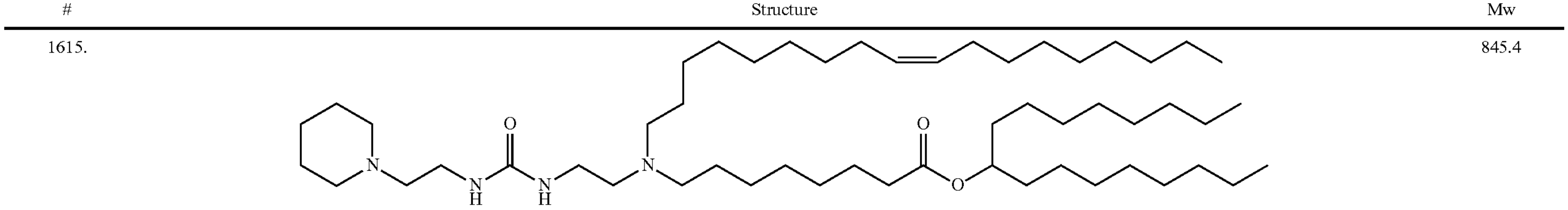 | 845.4 |
| 1616. | 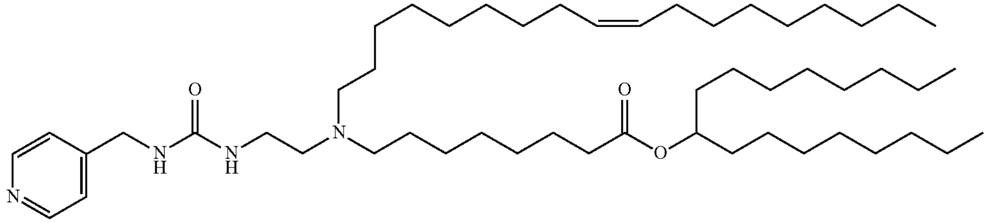 [SMILES: CCCCCCCC/C=C\CCCCCCCCN(CCCCCCCC(=O)OC(CCCCCCCC)CCCCCCCC)CCNC(=O)NCc1ccncc1] | 825.4 |
| 1617. | 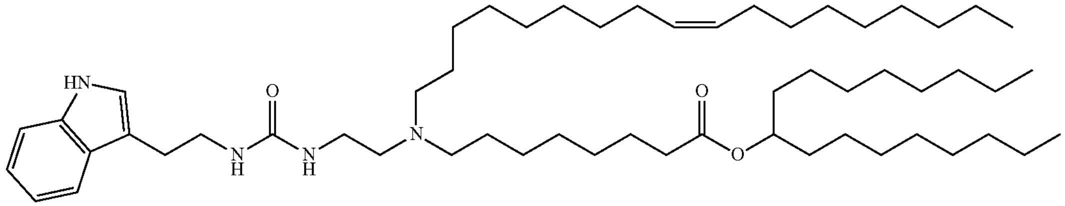 [SMILES: CCCCCCCC/C=C\CCCCCCCCN(CCCCCCCC(=O)OC(CCCCCCCC)CCCCCCCC)CCNC(=O)NCCc1c[nH]c2ccccc12] | 877.4 |
| 1618. | 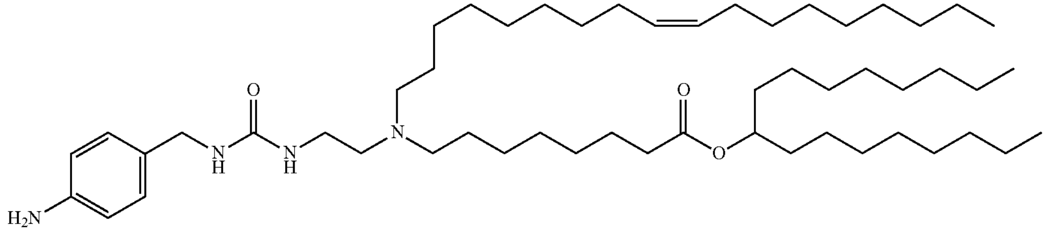 [SMILES: CCCCCCCC/C=C\CCCCCCCCN(CCCCCCCC(=O)OC(CCCCCCCC)CCCCCCCC)CCNC(=O)NCc1ccc(N)cc1] | 839.4 |

TABLE 1-continued
| # | Structure | Mw |
| --- | --- | --- |
| 1619. | 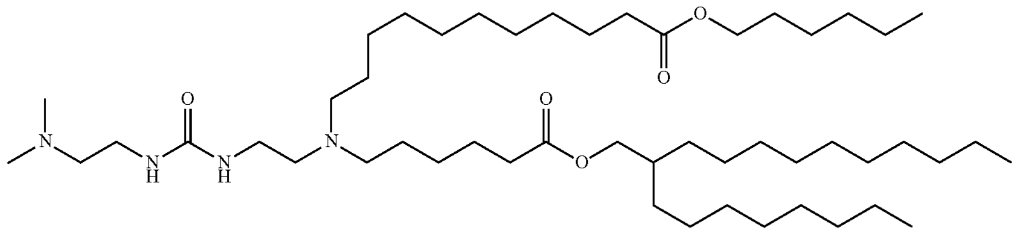 [SMILES: CCCCCCCCCCC(CCCCCCCC)COC(=O)CCCCCN(CCCCCCCCCCC(=O)OCCCCCC)CCNC(=O)NCCN(C)C] | 837.4 |
| 1620. | 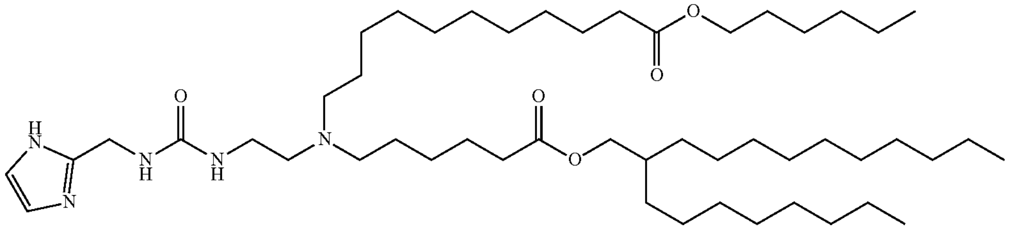 [SMILES: CCCCCCCCCCC(CCCCCCCC)COC(=O)CCCCCN(CCCCCCCCCCC(=O)OCCCCCC)CCNC(=O)NCc1ncc[nH]1] | 846.3 |
| 1621. | 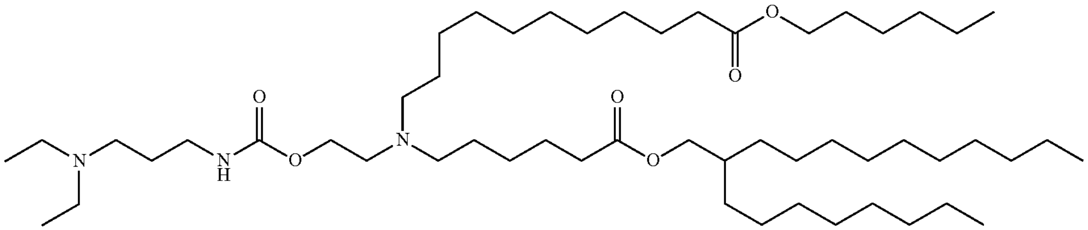 [SMILES: CCCCCCCCCCC(CCCCCCCC)COC(=O)CCCCCN(CCCCCCCCCCC(=O)OCCCCCC)CCOC(=O)NCCCN(CC)CC] | 879.5 |
| 1622. | 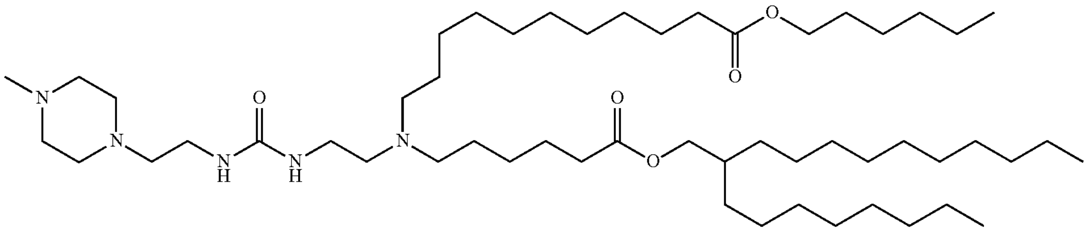 [SMILES: CCCCCCCCCCC(CCCCCCCC)COC(=O)CCCCCN(CCCCCCCCCCC(=O)OCCCCCC)CCNC(=O)NCCN1CCN(C)CC1] | 892.5 |

TABLE 1-continued
| # | Structure | Mw |
| --- | --- | --- |
| 1623. | 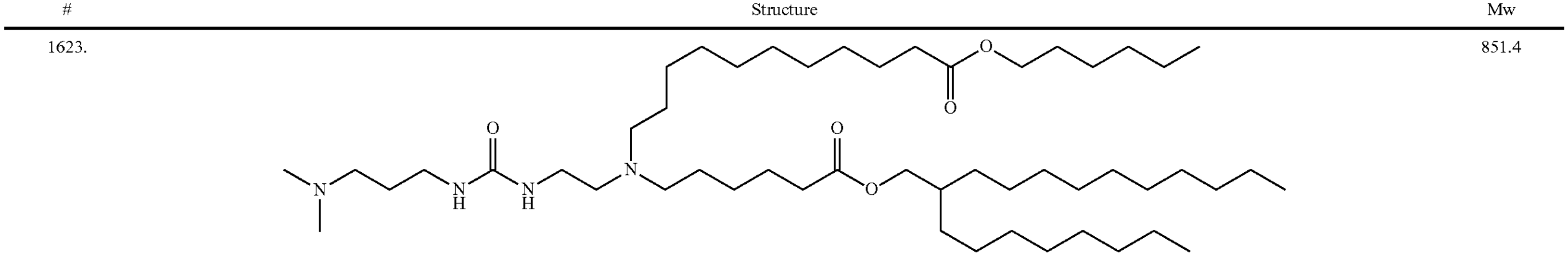 | 851.4 |
| 1624. | 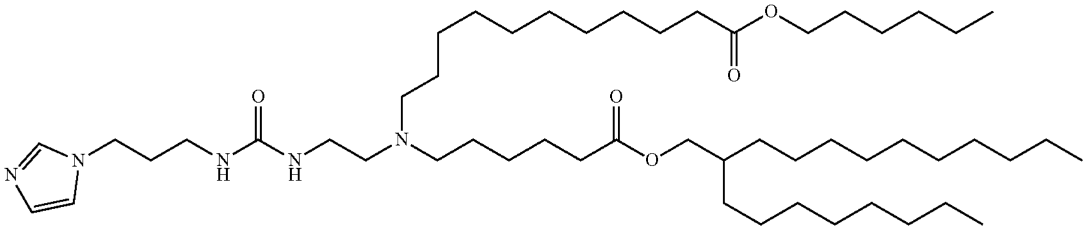 [SMILES: CCCCCCCCCCC(CCCCCCCC)COC(=O)CCCCCN(CCCCCCCCCCC(=O)OCCCCCC)CCNC(=O)NCCCn1ccnc1] | 874.4 |
| 1625. | 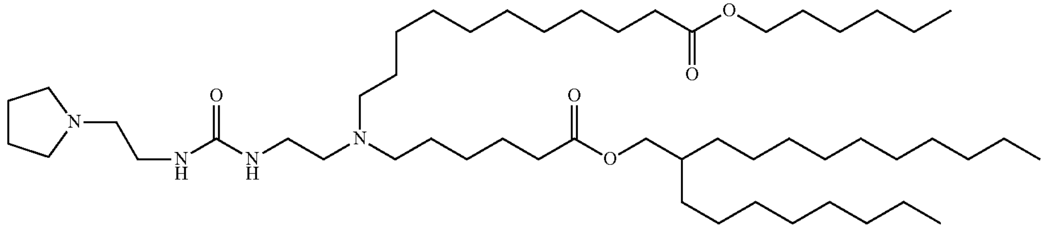 [SMILES: CCCCCCCCCCC(CCCCCCCC)COC(=O)CCCCCN(CCCCCCCCCCC(=O)OCCCCCC)CCNC(=O)NCCN1CCCC1] | 863.4 |
| 1626. | 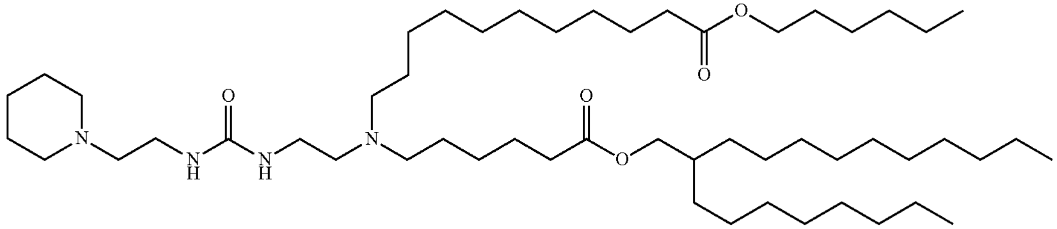 [SMILES: CCCCCCCCCCC(CCCCCCCC)COC(=O)CCCCCN(CCCCCCCCCCC(=O)OCCCCCC)CCNC(=O)NCCN1CCCCC1] | 877.4 |

TABLE 1-continued
| # | Structure | Mw |
|---|---|---|
| 1627. | 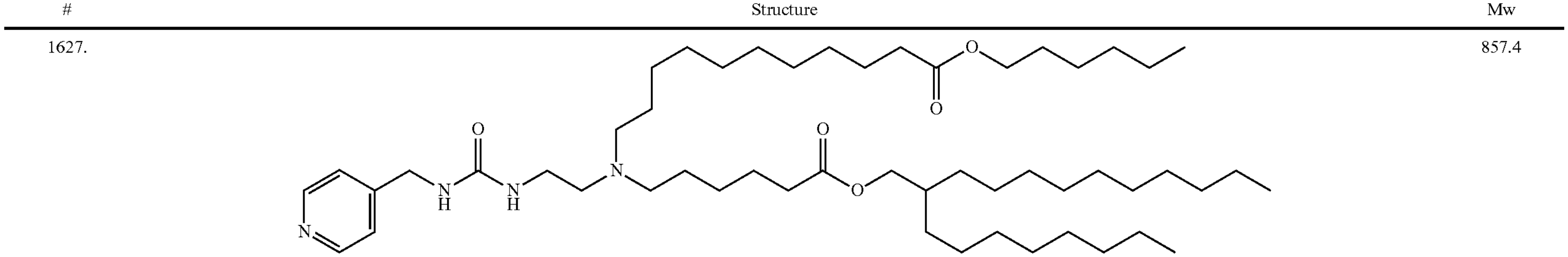 | 857.4 |
| 1628. | 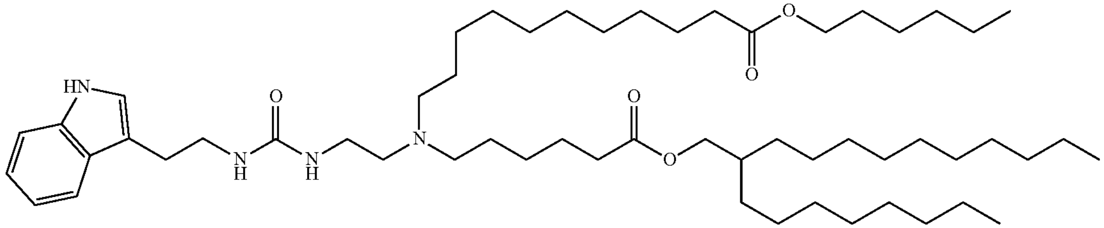 [SMILES: CCCCCCCCCCC(CCCCCCCC)COC(=O)CCCCCN(CCCCCCCCCCC(=O)OCCCCCC)CCNC(=O)NCCc1c[nH]c2ccccc12] | 909.4 |
| 1629. | 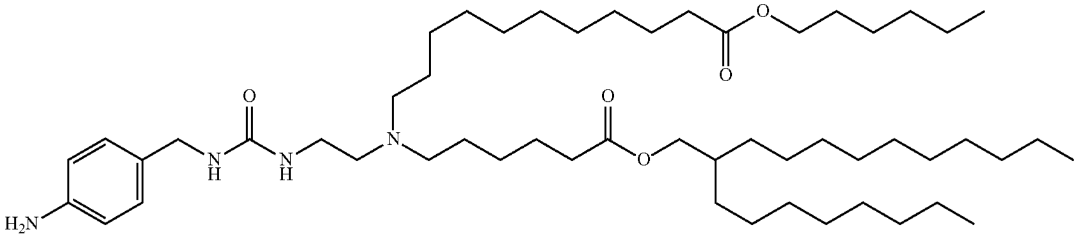 [SMILES: CCCCCCCCCCC(CCCCCCCC)COC(=O)CCCCCN(CCCCCCCCCCC(=O)OCCCCCC)CCNC(=O)NCc1ccc(N)cc1] | 871.4 |
| 1630. | 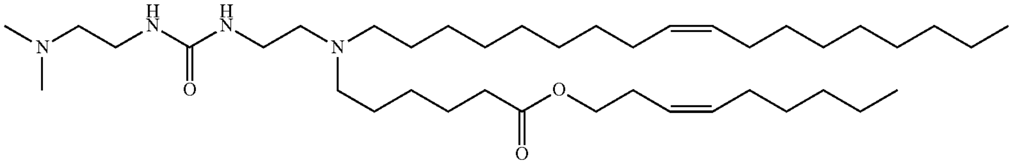 [SMILES: CCCCC/C=C\CCOC(=O)CCCCCN(CCCCCCCC/C=C\CCCCCCCC)CCNC(=O)NCCN(C)C] | 663.1 |

TABLE 1-continued
| # | Structure | Mw |
|---|---|---|
| 1631. | 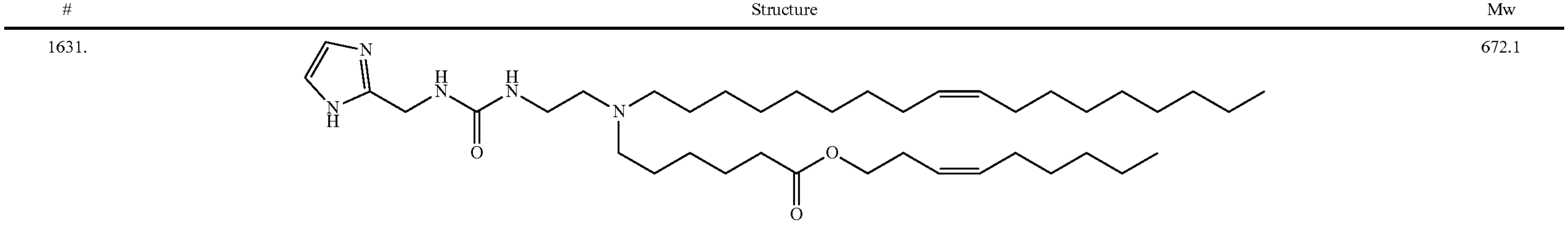 | 672.1 |
| 1632. | 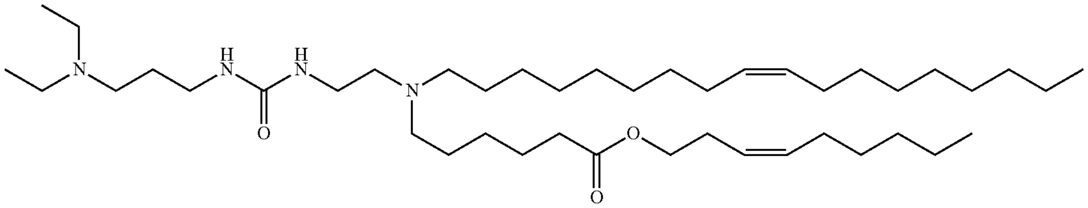 [SMILES: CCCCC/C=C\CCOC(=O)CCCCCN(CCCCCCCC/C=C\CCCCCCCC)CCNC(=O)NCCCN(CC)CC] | 705.2 |
| 1633. | 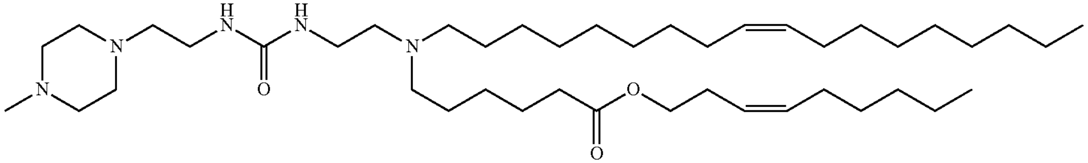 [SMILES: CCCCC/C=C\CCOC(=O)CCCCCN(CCCCCCCC/C=C\CCCCCCCC)CCNC(=O)NCCN1CCN(C)CC1] | 718.2 |
| 1634. | 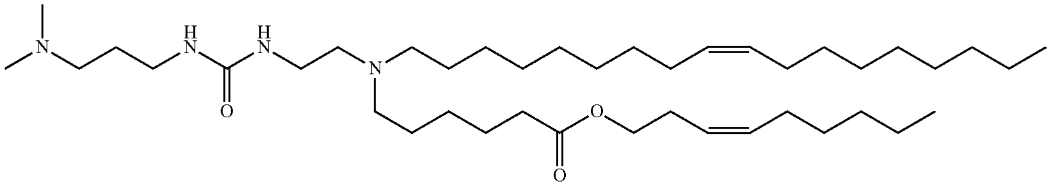 | 677.1 |
| 1635. | 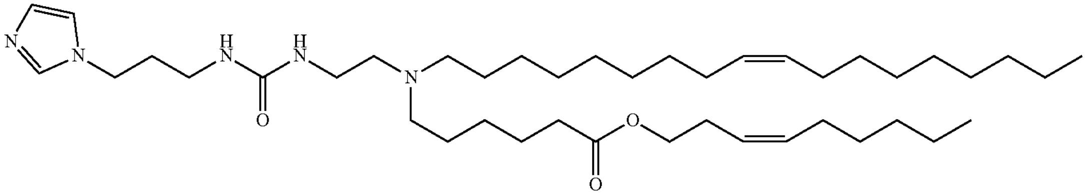 [SMILES: CCCCC/C=C\CCOC(=O)CCCCCN(CCCCCCCC/C=C\CCCCCCCC)CCNC(=O)NCCCn1ccnc1] | 700.1 |

TABLE 1-continued
| # | Structure | Mw |
|---|---|---|
| 1636. | 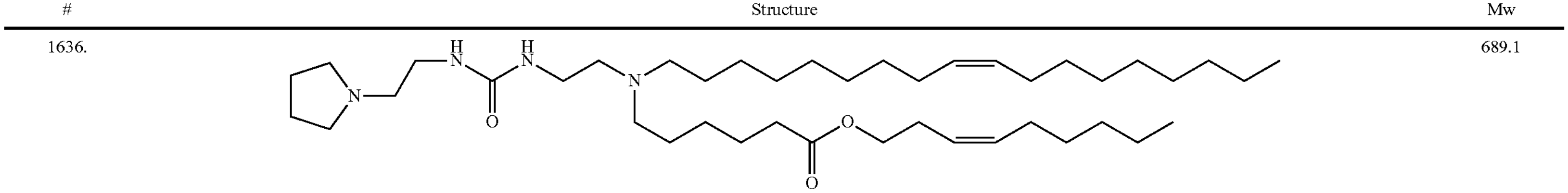 | 689.1 |
| 1637. | 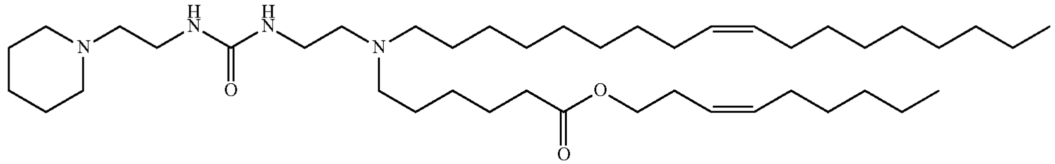 [SMILES: CCCCC/C=C\CCOC(=O)CCCCCN(CCCCCCCC/C=C\CCCCCCCC)CCNC(=O)NCCN1CCCCC1] | 703.2 |
| 1638. | 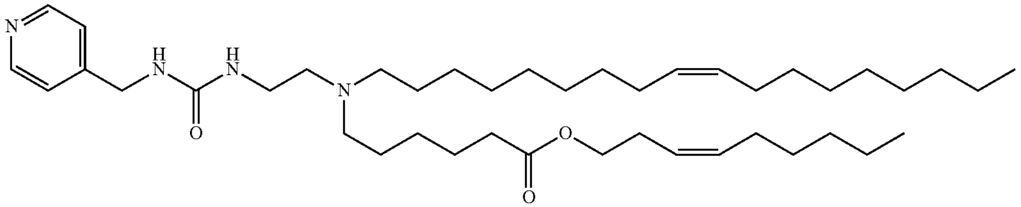 [SMILES: CCCCC/C=C\CCOC(=O)CCCCCN(CCCCCCCC/C=C\CCCCCCCC)CCNC(=O)NCc1ccncc1] | 683.1 |
| 1639. | 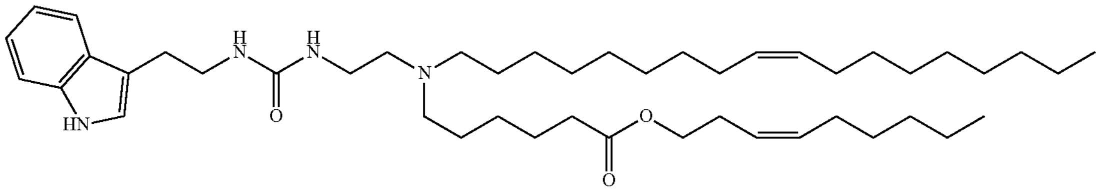 [SMILES: CCCCC/C=C\CCOC(=O)CCCCCN(CCCCCCCC/C=C\CCCCCCCC)CCNC(=O)NCCc1c[nH]c2ccccc12] | 735.2 |
| 1640. | 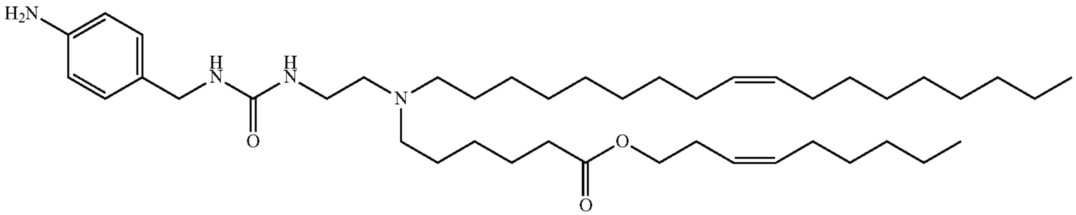 [SMILES: CCCCC/C=C\CCOC(=O)CCCCCN(CCCCCCCC/C=C\CCCCCCCC)CCNC(=O)NCc1ccc(N)cc1] | 697.1 |

TABLE 1-continued
| # | Structure | Mw |
|---|---|---|
| 1641. | 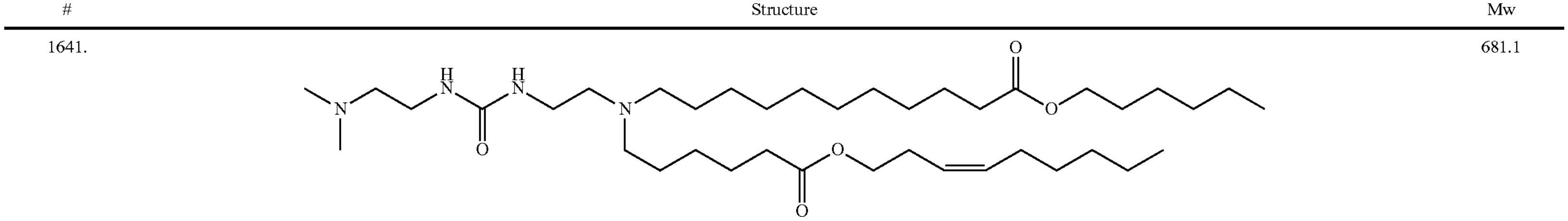 | 681.1 |
| 1642. | 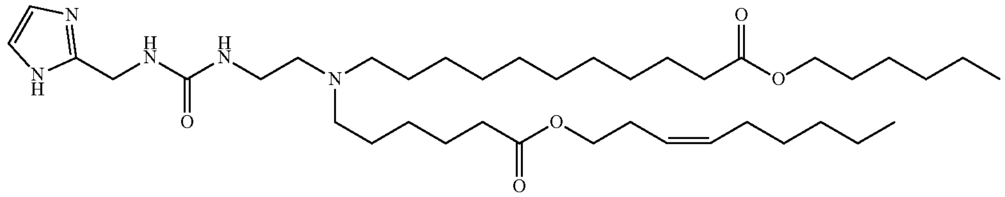 [SMILES: CCCCC/C=C\CCOC(=O)CCCCCN(CCCCCCCCCCC(=O)OCCCCCC)CCNC(=O)NCc1ncc[nH]1] | 690.0 |
| 1643. | 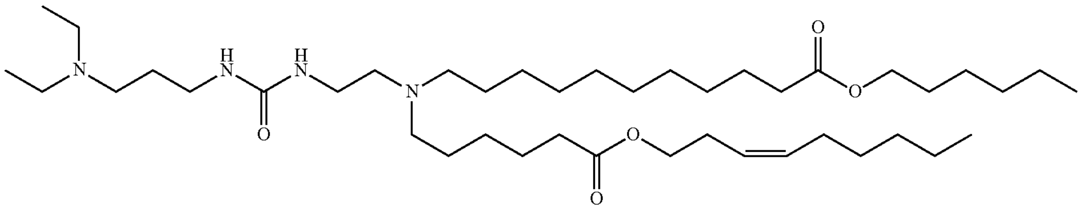 [SMILES: CCCCC/C=C\CCOC(=O)CCCCCN(CCCCCCCCCCC(=O)OCCCCCC)CCNC(=O)NCCCN(CC)CC] | 723.1 |
| 1644. | 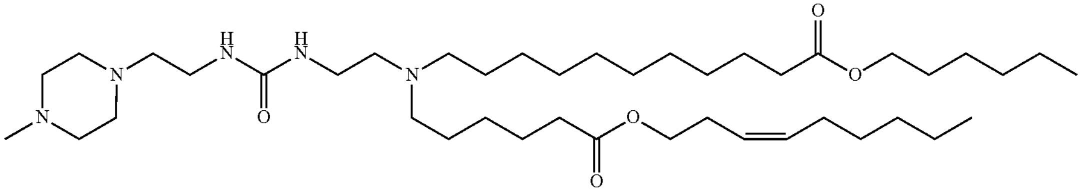 [SMILES: CCCCC/C=C\CCOC(=O)CCCCCN(CCCCCCCCCCC(=O)OCCCCCC)CCNC(=O)NCCN1CCN(C)CC1] | 736.1 |
| 1645. | 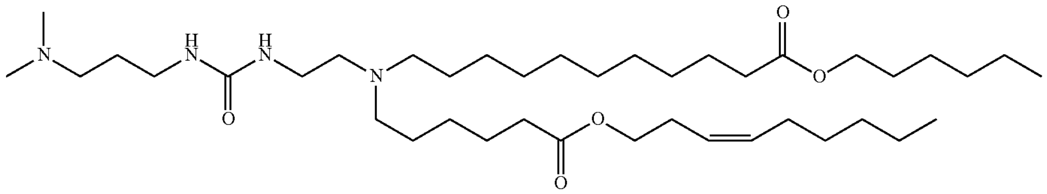 [SMILES: CCCCC/C=C\CCOC(=O)CCCCCN(CCCCCCCCCCC(=O)OCCCCCC)CCNC(=O)NCCCN(C)C] | 695.1 |

TABLE 1-continued
| # | Structure | Mw |
| --- | --- | --- |
| 1646. | 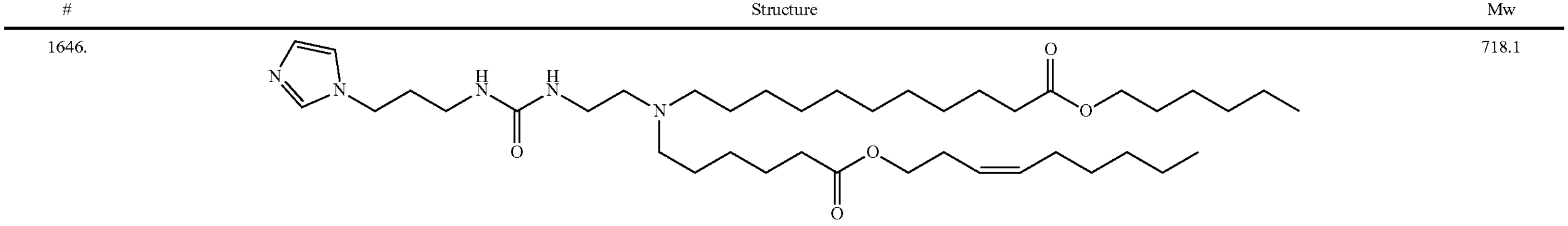 | 718.1 |
| 1647. | 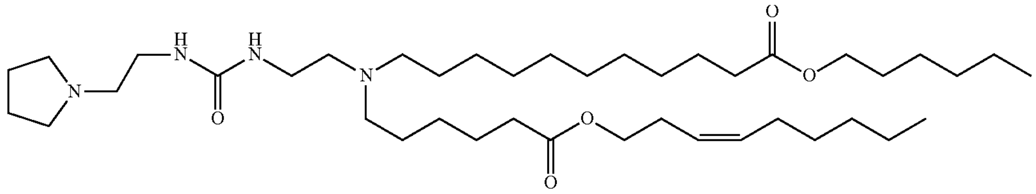 [SMILES: CCCCC/C=C\CCOC(=O)CCCCCN(CCCCCCCCCCC(=O)OCCCCCC)CCNC(=O)NCCN1CCCC1] | 707.1 |
| 1648. | 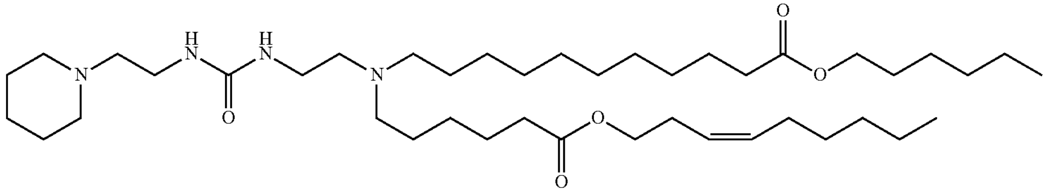 [SMILES: CCCCC/C=C\CCOC(=O)CCCCCN(CCCCCCCCCCC(=O)OCCCCCC)CCNC(=O)NCCN1CCCCC1] | 721.1 |
| 1649. | 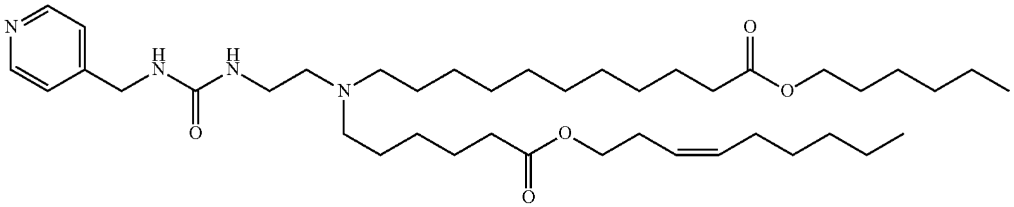 [SMILES: CCCCC/C=C\CCOC(=O)CCCCCN(CCCCCCCCCCC(=O)OCCCCCC)CCNC(=O)NCc1ccncc1] | 701.1 |
| 1650. | 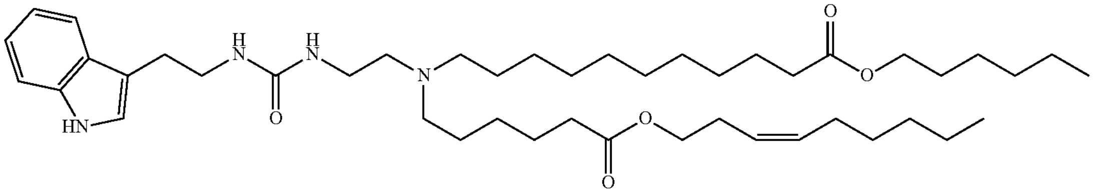 [SMILES: CCCCC/C=C\CCOC(=O)CCCCCN(CCCCCCCCCCC(=O)OCCCCCC)CCNC(=O)NCCc1c[nH]c2ccccc12] | 753.1 |

TABLE 1-continued
| # | Structure | Mw |
| --- | --- | --- |
| 1651. | 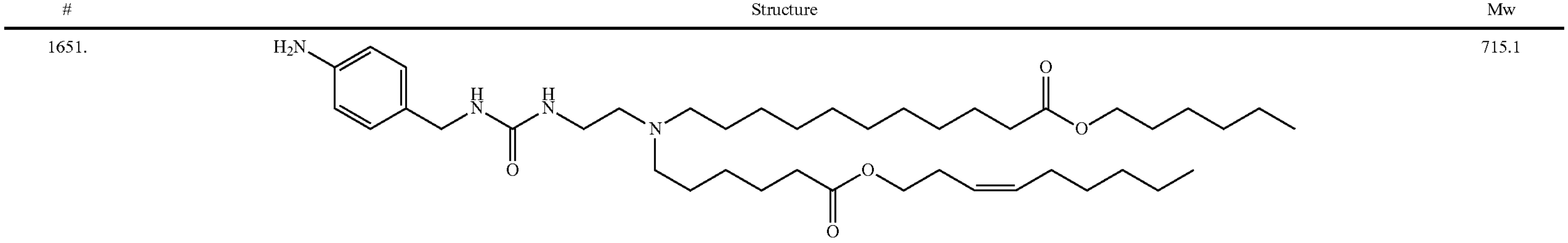 | 715.1 |
| 1652. | 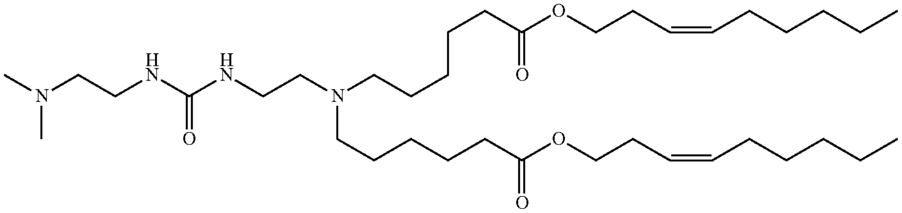 [SMILES: CCCCC/C=C\CCOC(=O)CCCCCN(CCCCCC(=O)OCC/C=C\CCCCC)CCNC(=O)NCCN(C)C] | 651.0 |
| 1653. | 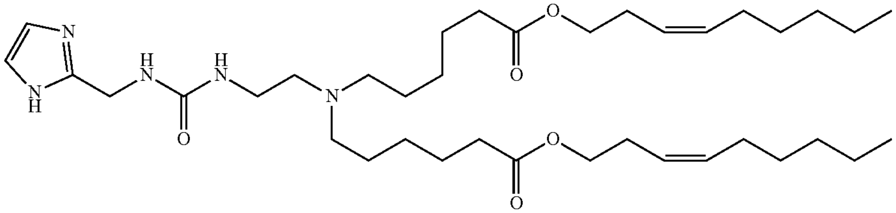 | 660.0 |
| 1654. | 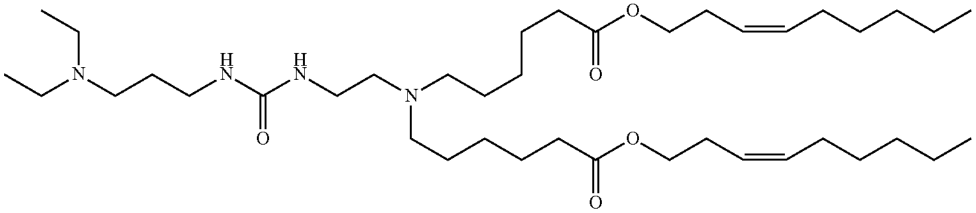 [SMILES: CCCCC/C=C\CCOC(=O)CCCCCN(CCCCCC(=O)OCC/C=C\CCCCC)CCNC(=O)NCCCN(CC)CC] | 693.1 |

TABLE 1-continued
| # | Structure | Mw |
| --- | --- | --- |
| 1655. | 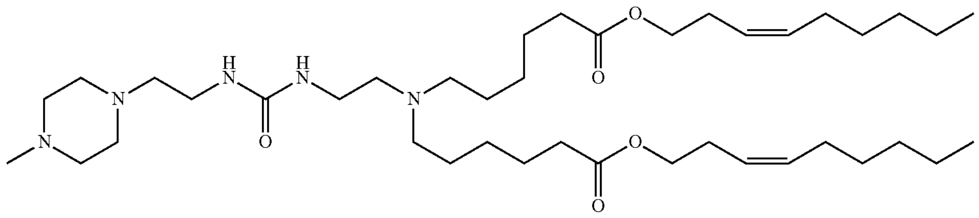 [SMILES: CCCCC/C=C\CCOC(=O)CCCCCN(CCCCCC(=O)OCC/C=C\CCCCC)CCNC(=O)NCCN1CCN(C)CC1] | 706.1 |
| 1656. | 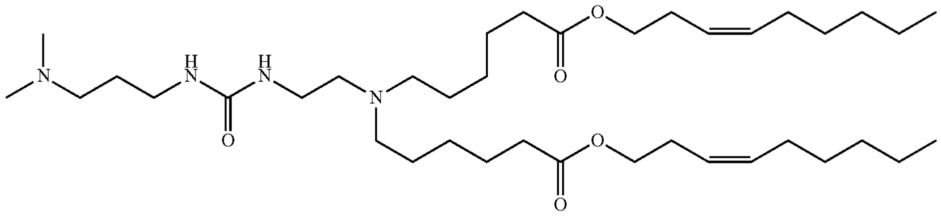 [SMILES: CCCCC/C=C\CCOC(=O)CCCCCN(CCCCCC(=O)OCC/C=C\CCCCC)CCNC(=O)NCCCN(C)C] | 665.0 |
| 1657. | 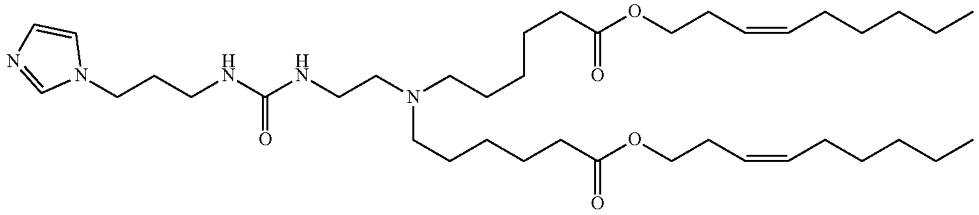 | 688.0 |
| 1658. | 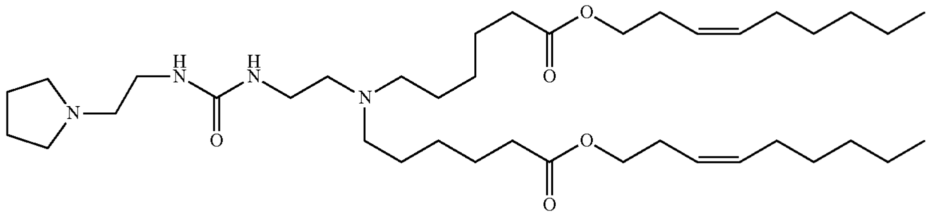 | 677.0 |

TABLE 1-continued
| # | Structure | Mw |
| --- | --- | --- |
| 1659. | 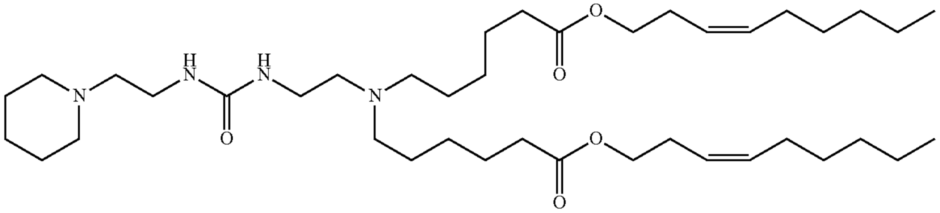 [SMILES: CCCCC/C=C\CCOC(=O)CCCCCN(CCCCCC(=O)OCC/C=C\CCCCC)CCNC(=O)NCCN1CCCCC1] | 691.1 |
| 1660. | 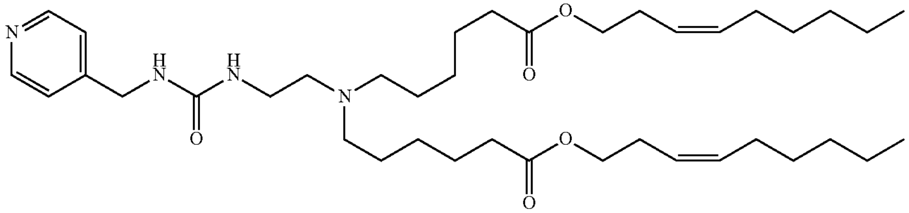 [SMILES: CCCCC/C=C\CCOC(=O)CCCCCN(CCCCCC(=O)OCC/C=C\CCCCC)CCNC(=O)NCc1ccncc1] | 671.0 |
| 1661. | 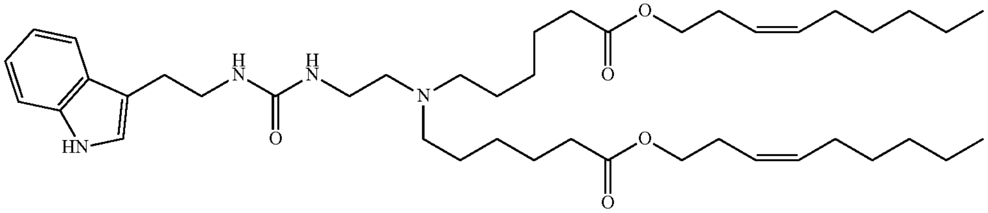 [SMILES: CCCCC/C=C\CCOC(=O)CCCCCN(CCCCCC(=O)OCC/C=C\CCCCC)CCNC(=O)NCCc1c[nH]c2ccccc12] | 723.1 |
| 1662. | 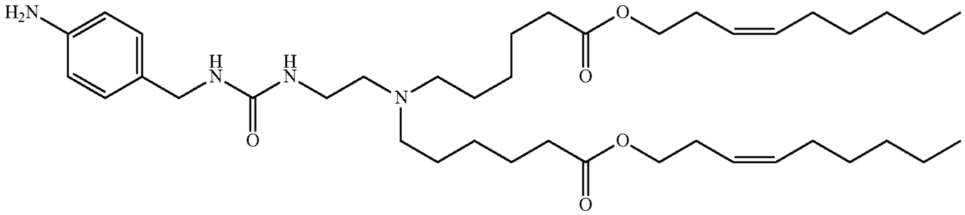 [SMILES: CCCCC/C=C\CCOC(=O)CCCCCN(CCCCCC(=O)OCC/C=C\CCCCC)CCNC(=O)NCc1ccc(N)cc1] | 685.0 |

TABLE 1-continued
| # | Structure | Mw |
|---|---|---|
| 1663. | 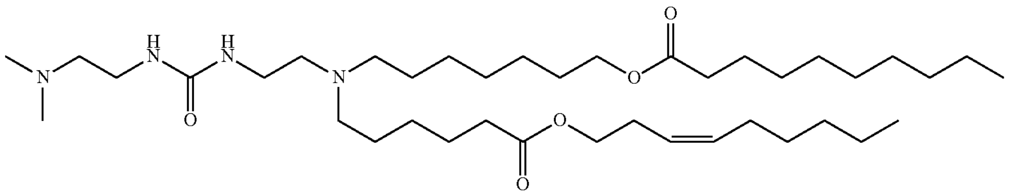 [SMILES: CCCCC/C=C\CCOC(=O)CCCCCN(CCCCCCCOC(=O)CCCCCCCCC)CCNC(=O)NCCN(C)C] | 681.1 |
| 1664. | 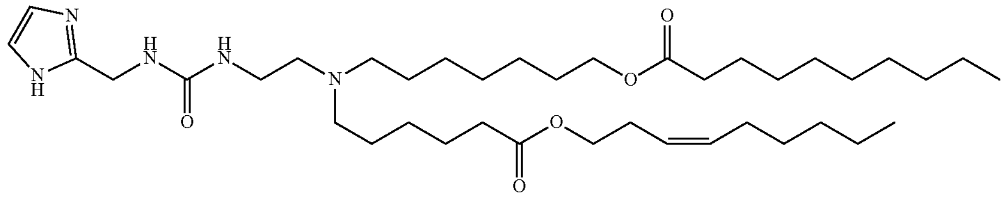 [SMILES: CCCCC/C=C\CCOC(=O)CCCCCN(CCCCCCCOC(=O)CCCCCCCCC)CCNC(=O)NCc1ncc[nH]1] | 690.0 |
| 1665. | 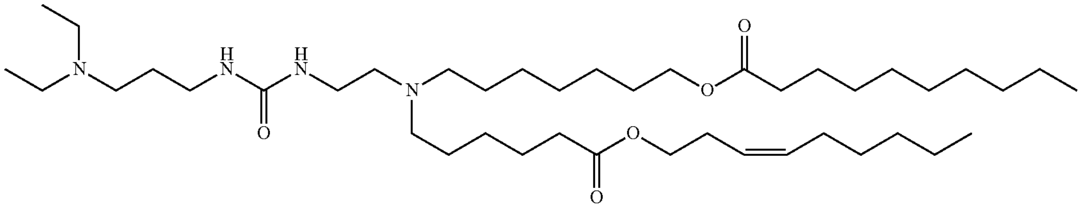 [SMILES: CCCCC/C=C\CCOC(=O)CCCCCN(CCCCCCCOC(=O)CCCCCCCCC)CCNC(=O)NCCCN(CC)CC] | 723.1 |
| 1666. | 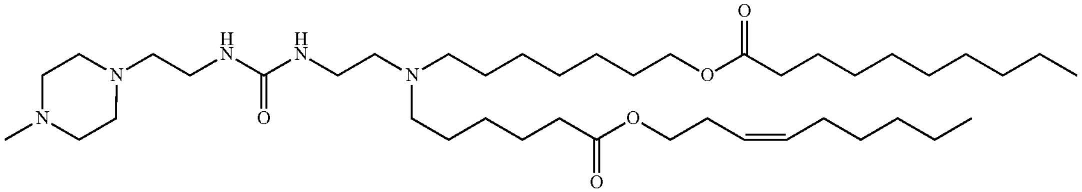 [SMILES: CCCCC/C=C\CCOC(=O)CCCCCN(CCCCCCCOC(=O)CCCCCCCCC)CCNC(=O)NCCN1CCN(C)CC1] | 736.1 |
| 1667. | 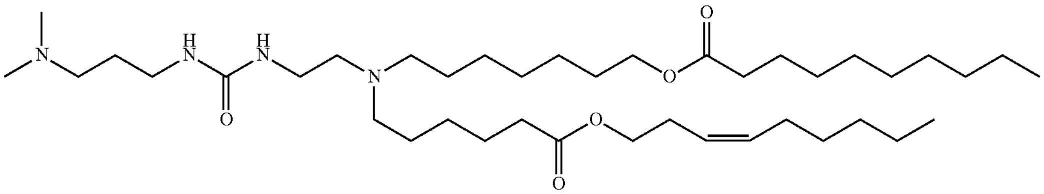 [SMILES: CCCCC/C=C\CCOC(=O)CCCCCN(CCCCCCCOC(=O)CCCCCCCCC)CCNC(=O)NCCCN(C)C] | 695.1 |

TABLE 1-continued
| # | Structure | Mw |
| --- | --- | --- |
| 1668. | 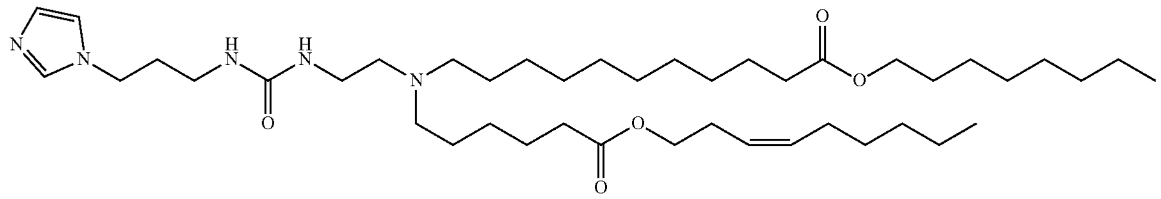 [SMILES: CCCCC/C=C\CCOC(=O)CCCCCN(CCCCCCCCCCC(=O)OCCCCCCCC)CCNC(=O)NCCCn1ccnc1] | 718.1 |
| 1669. | 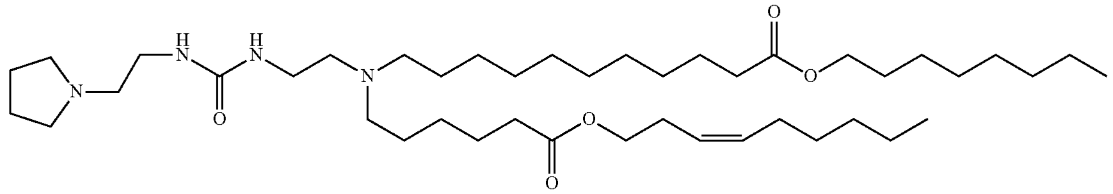 [SMILES: CCCCC/C=C\CCOC(=O)CCCCCN(CCCCCCCCCCC(=O)OCCCCCCCC)CCNC(=O)NCCN1CCCC1] | 707.1 |
| 1670. | 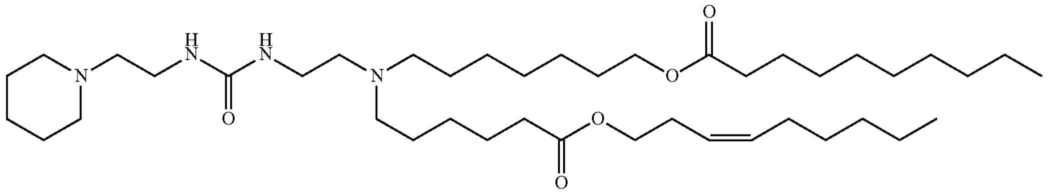 | 721.1 |
| 1671. | 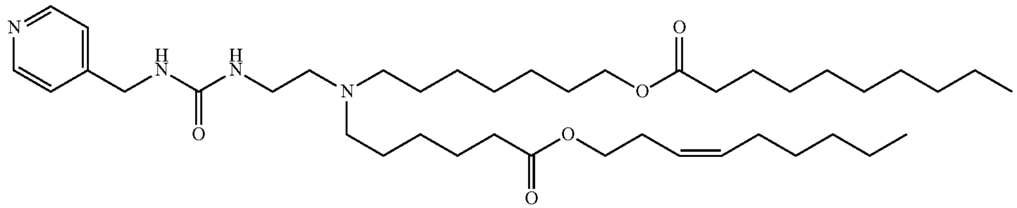 [SMILES: CCCCC/C=C\CCOC(=O)CCCCCN(CCCCCCCOC(=O)CCCCCCCCC)CCNC(=O)NCc1ccncc1] | 701.1 |
| 1672. | 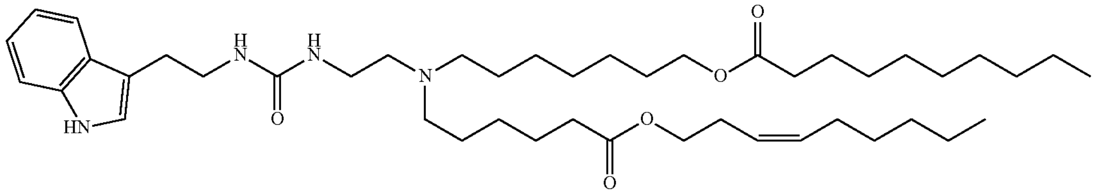 [SMILES: CCCCC/C=C\CCOC(=O)CCCCCN(CCCCCCCOC(=O)CCCCCCCCC)CCNC(=O)NCCc1c[nH]c2ccccc12] | 753.1 |

TABLE 1-continued
| # | Structure | Mw |
|---|---|---|
| 1673. | 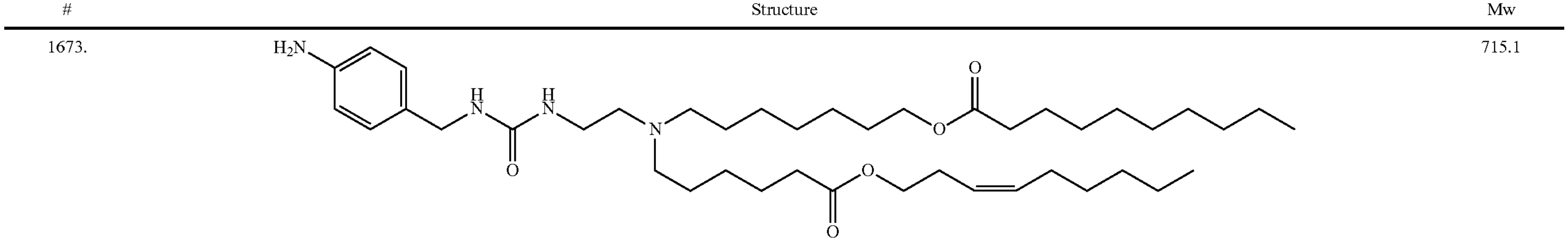 | 715.1 |
| 1674. | 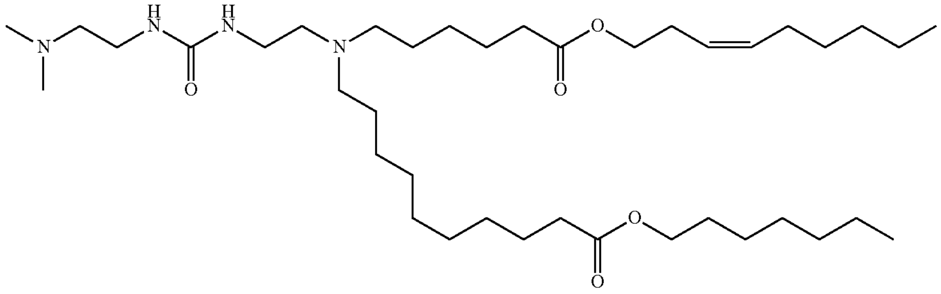 [SMILES: CCCCC/C=C\CCOC(=O)CCCCCN(CCCCCCCCCC(=O)OCCCCCCC)CCNC(=O)NCCN(C)C] | 681.1 |
| 1675. | 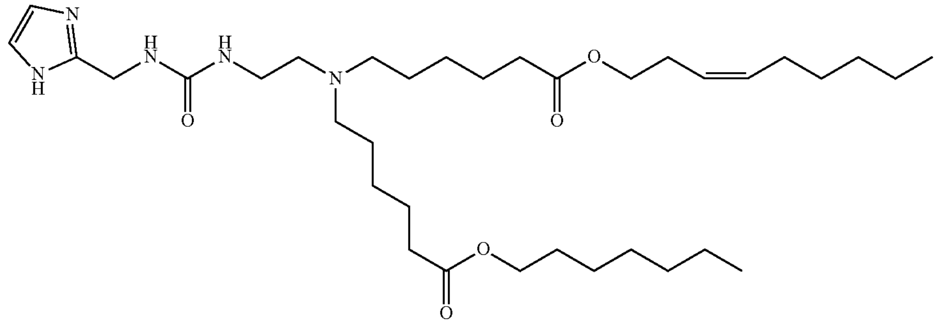 [SMILES: CCCCC/C=C\CCOC(=O)CCCCCN(CCCCCC(=O)OCCCCCCC)CCNC(=O)NCc1ncc[nH]1] | 690.0 |

TABLE 1-continued
| # | Structure | Mw |
| --- | --- | --- |
| 1676. | 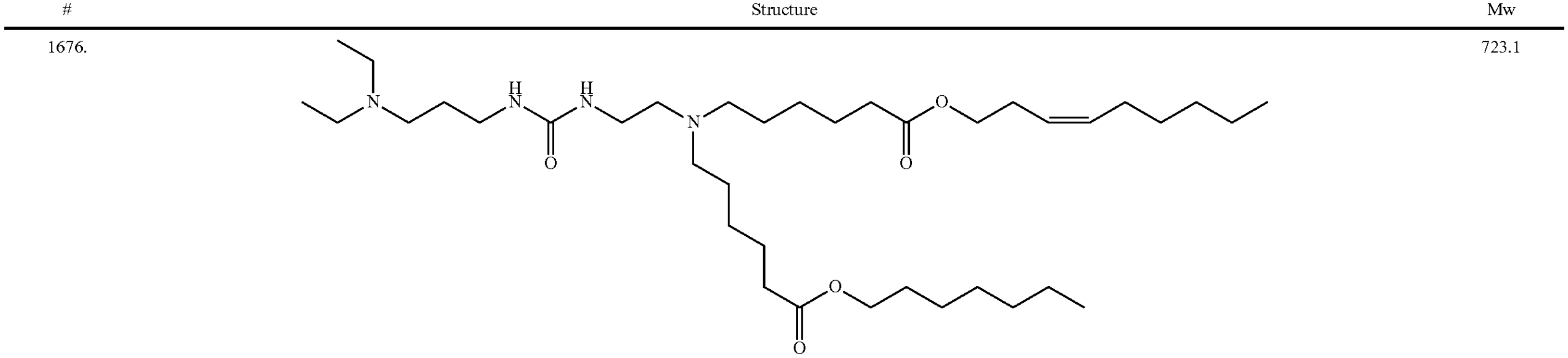 | 723.1 |
| 1677. | 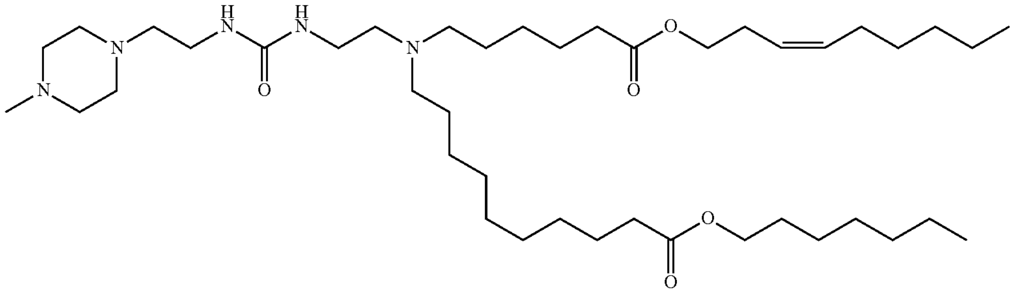 [SMILES: CCCCC/C=C\CCOC(=O)CCCCCN(CCCCCCCCCC(=O)OCCCCCCC)CCNC(=O)NCCN1CCN(C)CC1] | 736.1 |
| 1678. | 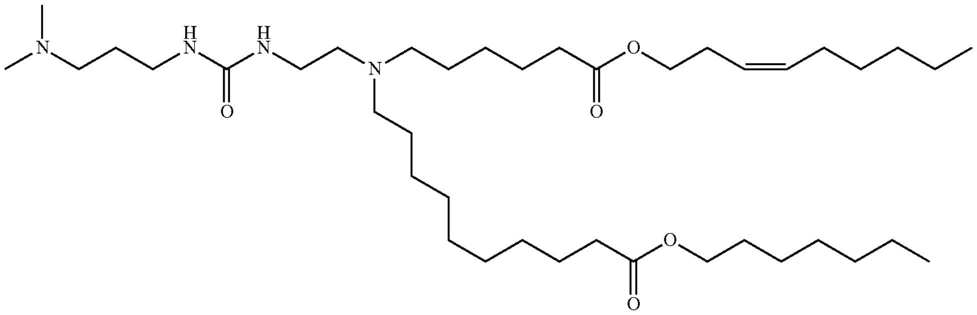 [SMILES: CCCCC/C=C\CCOC(=O)CCCCCN(CCCCCCCCCC(=O)OCCCCCCC)CCNC(=O)NCCCN(C)C] | 695.1 |

TABLE 1-continued
| # | Structure | Mw |
|---|---|---|
| 1679. | 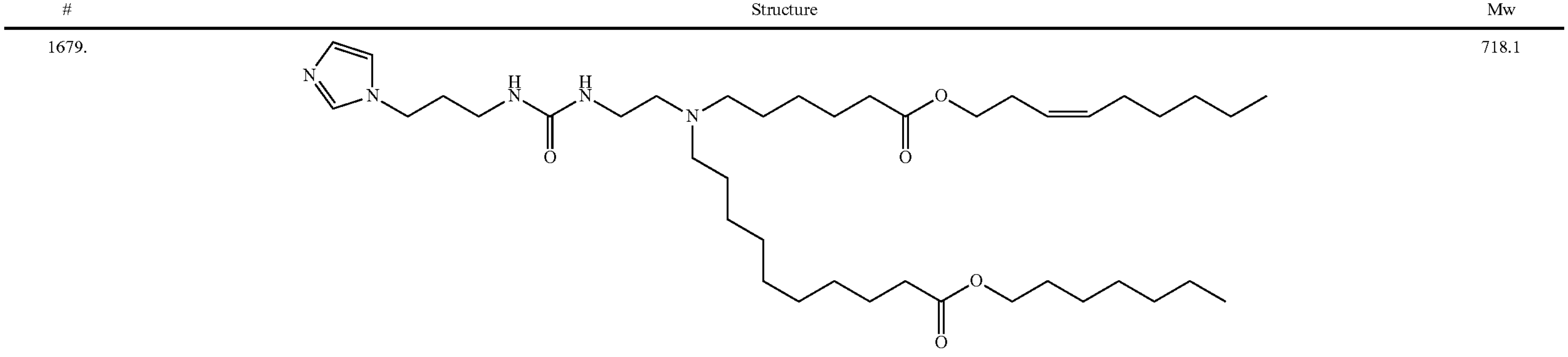 | 718.1 |
| 1680. | 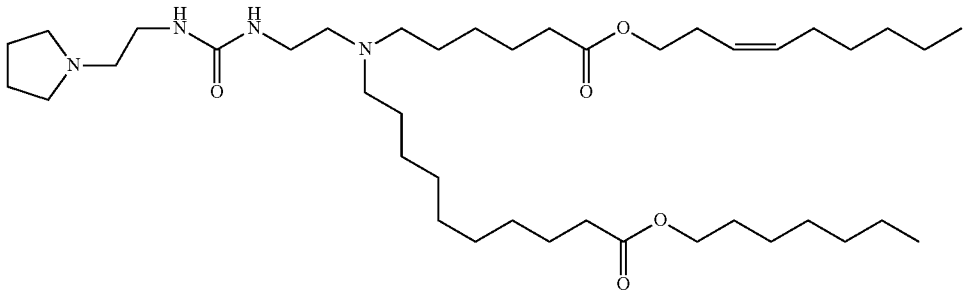 [SMILES: CCCCC/C=C\CCOC(=O)CCCCCN(CCCCCCCCCC(=O)OCCCCCCC)CCNC(=O)NCCN1CCCC1] | 707.1 |
| 1681. | 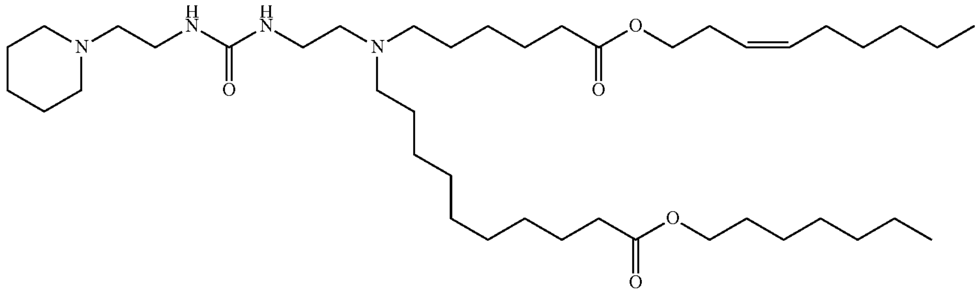 [SMILES: CCCCC/C=C\CCOC(=O)CCCCCN(CCCCCCCCCC(=O)OCCCCCCC)CCNC(=O)NCCN1CCCCC1] | 721.1 |

TABLE 1-continued
| # | Structure | Mw |
| --- | --- | --- |
| 1682. | 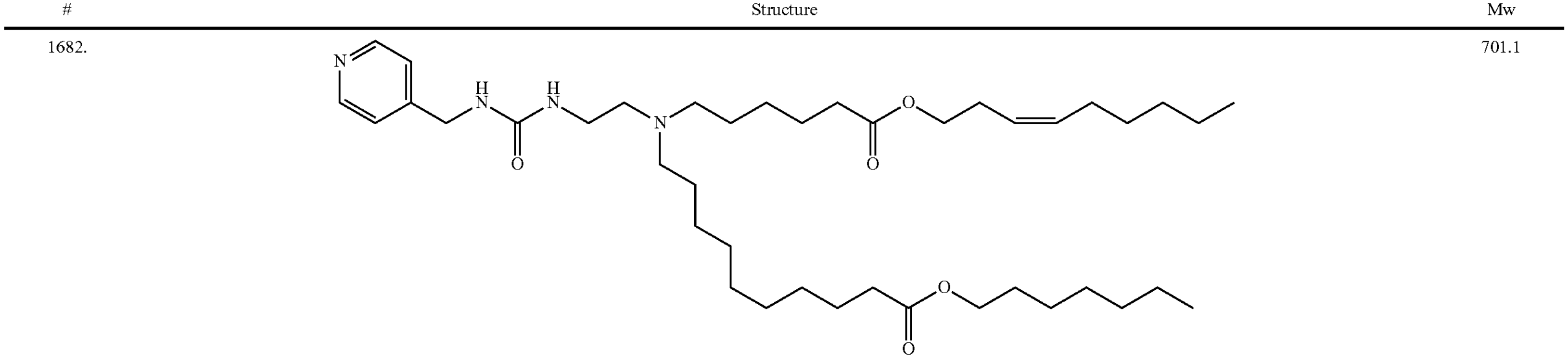 | 701.1 |
| 1683. | 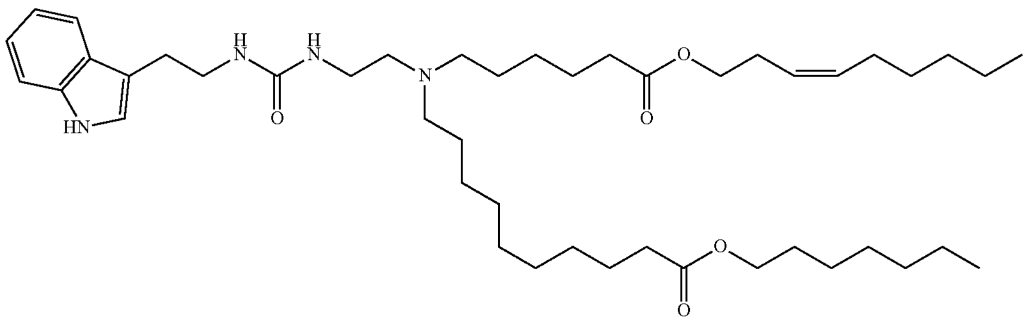 [SMILES: CCCCC/C=C\CCOC(=O)CCCCCN(CCCCCCCCCC(=O)OCCCCCCC)CCNC(=O)NCCc1c[nH]c2ccccc12] | 753.1 |
| 1684. | 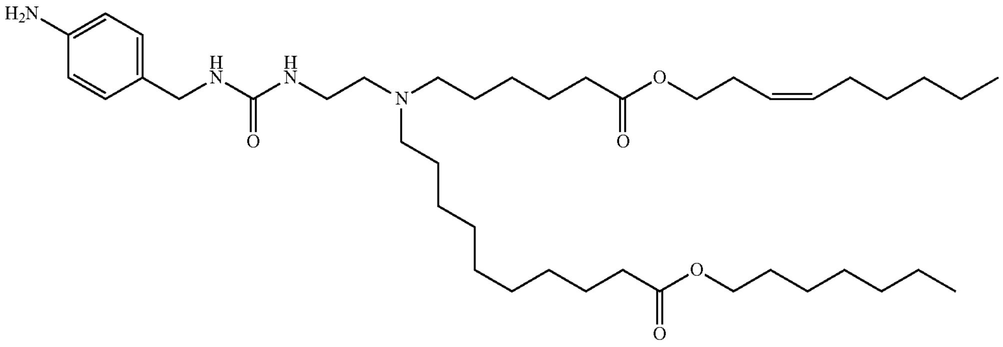 [SMILES: CCCCC/C=C\CCOC(=O)CCCCCN(CCCCCCCCCC(=O)OCCCCCCC)CCNC(=O)NCc1ccc(N)cc1] | 715.1 |

TABLE 1-continued
| # | Structure | Mw |
| --- | --- | --- |
| 1685. | 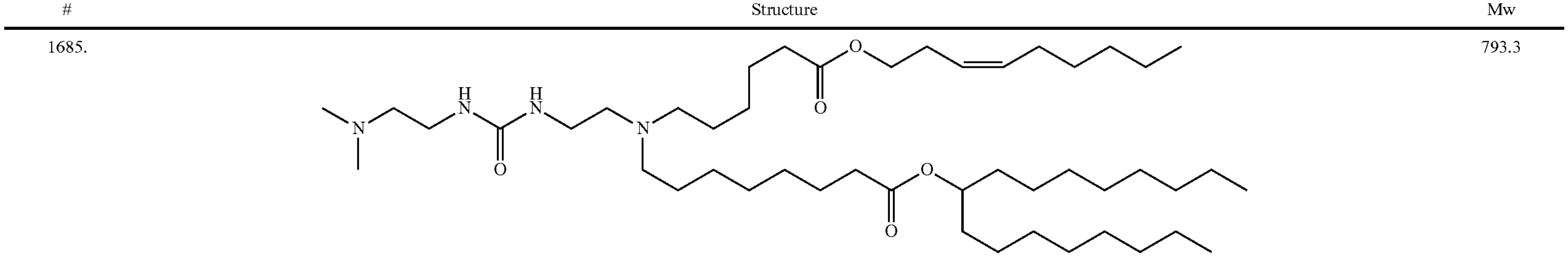 | 793.3 |
| 1686. | 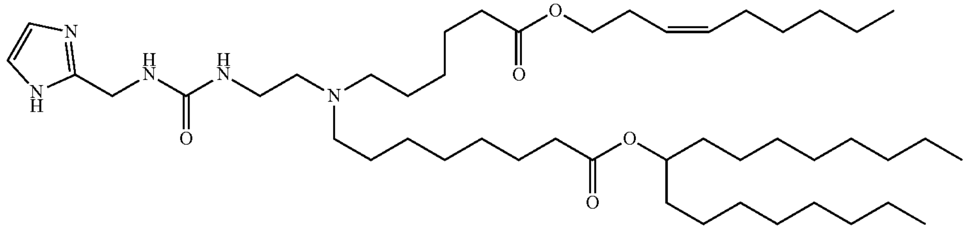 [SMILES: CCCCC/C=C\CCOC(=O)CCCCCN(CCCCCCCC(=O)OC(CCCCCCCC)CCCCCCCC)CCNC(=O)NCc1ncc[nH]1] | 802.2 |
| 1687. | 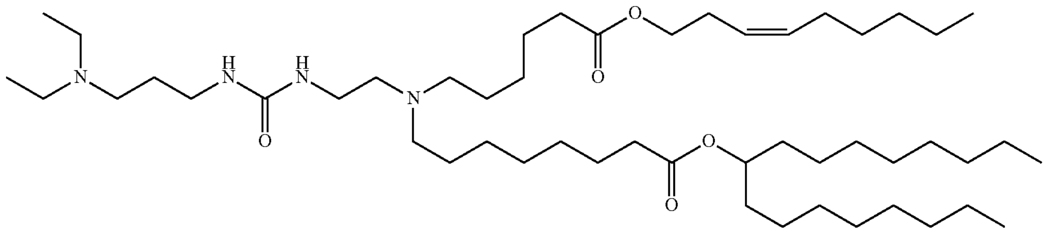 [SMILES: CCCCC/C=C\CCOC(=O)CCCCCN(CCCCCCCC(=O)OC(CCCCCCCC)CCCCCCCC)CCNC(=O)NCCCN(CC)CC] | 835.4 |
| 1688. | 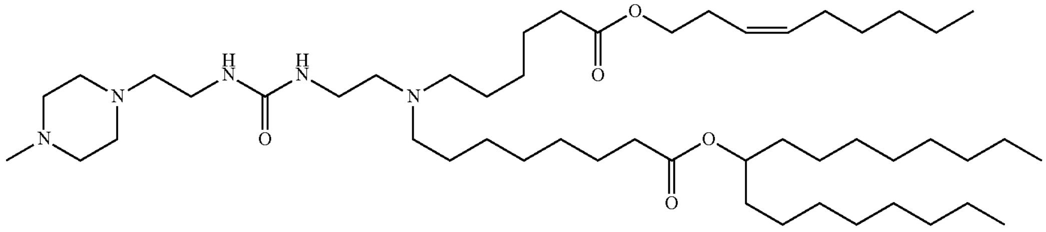 [SMILES: CCCCC/C=C\CCOC(=O)CCCCCN(CCCCCCCC(=O)OC(CCCCCCCC)CCCCCCCC)CCNC(=O)NCCN1CCN(C)CC1] | 848.4 |

TABLE 1-continued
| # | Structure | Mw |
|---|---|---|
| 1689. | 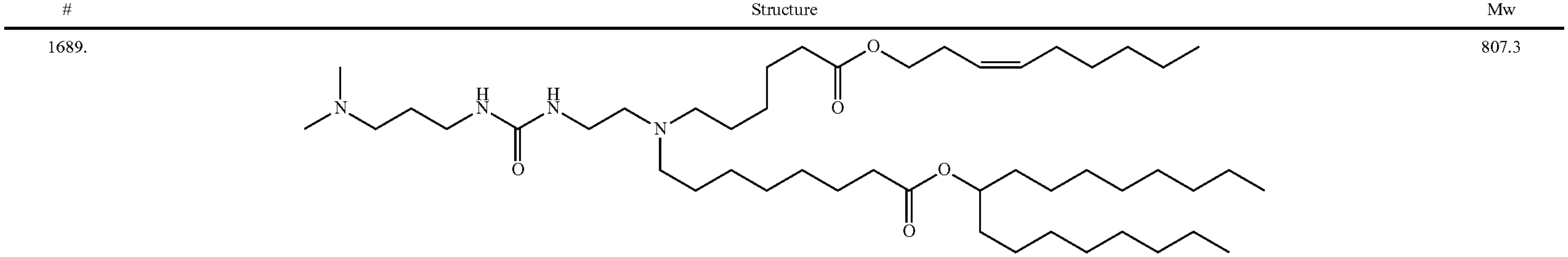 | 807.3 |
| 1690. | 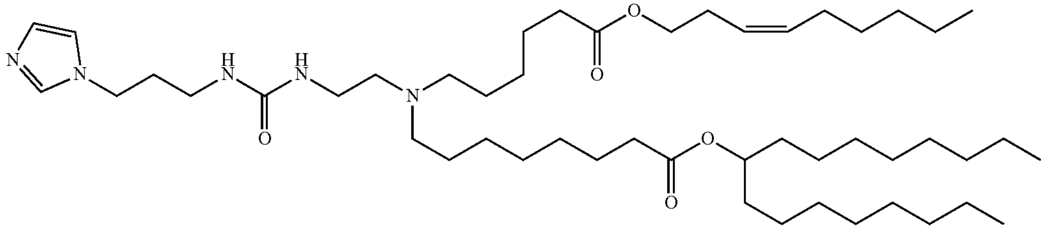 [SMILES: CCCCC/C=C\CCOC(=O)CCCCCN(CCCCCCCC(=O)OC(CCCCCCCC)CCCCCCCC)CCNC(=O)NCCCn1ccnc1] | 830.3 |
| 1691. | 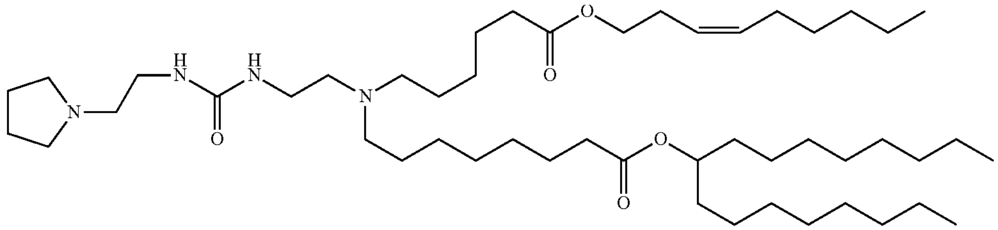 [SMILES: CCCCC/C=C\CCOC(=O)CCCCCN(CCCCCCCC(=O)OC(CCCCCCCC)CCCCCCCC)CCNC(=O)NCCN1CCCC1] | 819.3 |
| 1692. | 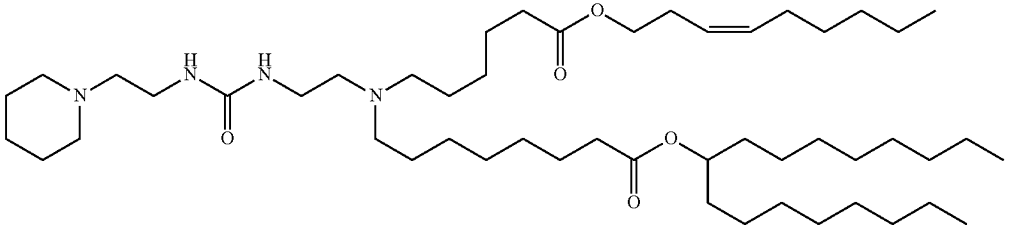 [SMILES: CCCCC/C=C\CCOC(=O)CCCCCN(CCCCCCCC(=O)OC(CCCCCCCC)CCCCCCCC)CCNC(=O)NCCN1CCCCC1] | 833.3 |

TABLE 1-continued
| # | Structure | Mw |
|---|---|---|
| 1693. | 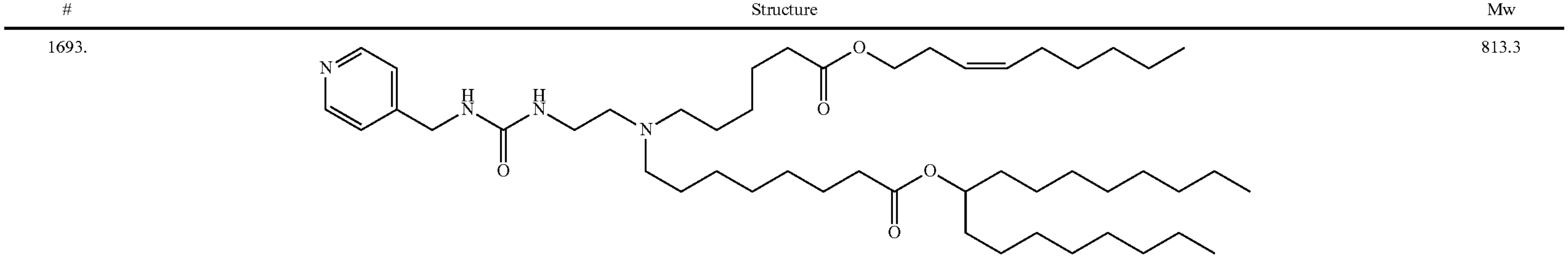 | 813.3 |
| 1694. | 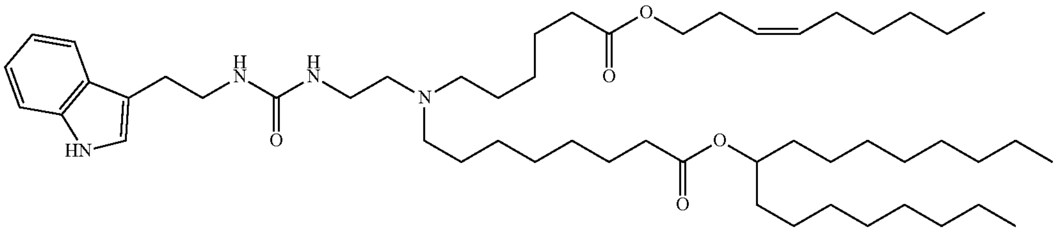 [SMILES: CCCCC/C=C\CCOC(=O)CCCCCN(CCCCCCCC(=O)OC(CCCCCCCC)CCCCCCCC)CCNC(=O)NCCc1c[nH]c2ccccc12] | 865.3 |
| 1695. | 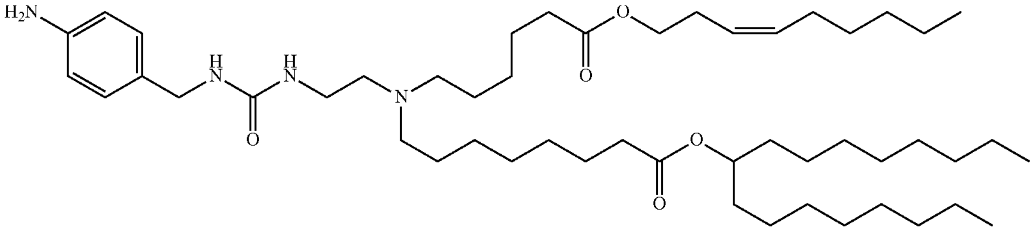 [SMILES: CCCCC/C=C\CCOC(=O)CCCCCN(CCCCCCCC(=O)OC(CCCCCCCC)CCCCCCCC)CCNC(=O)NCc1ccc(N)cc1] | 827.3 |
| 1696. | 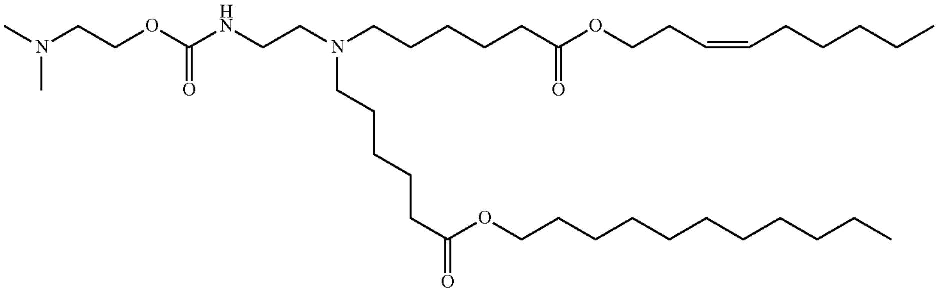 [SMILES: CCCCC/C=C\CCOC(=O)CCCCCN(CCCCCC(=O)OCCCCCCCCCCC)CCNC(=O)OCCN(C)C] | 681.1 |

TABLE 1-continued
| # | Structure | Mw |
|---|---|---|
| 1697. | 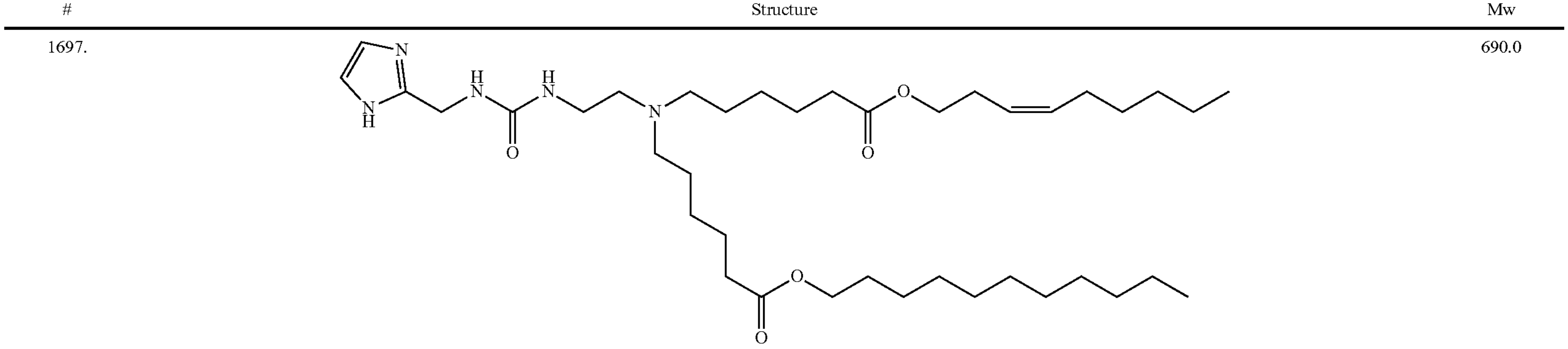 | 690.0 |
| 1698. | 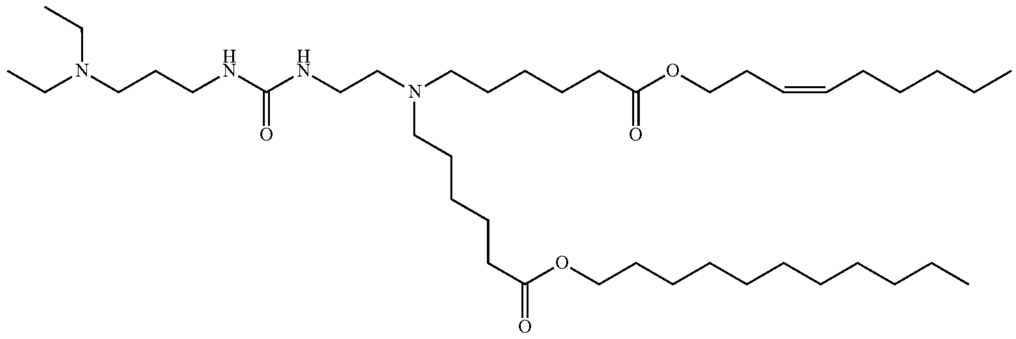 [SMILES: CCCCC/C=C\CCOC(=O)CCCCCN(CCCCCC(=O)OCCCCCCCCCCC)CCNC(=O)NCCCN(CC)CC] | 723.1 |
| 1699. | 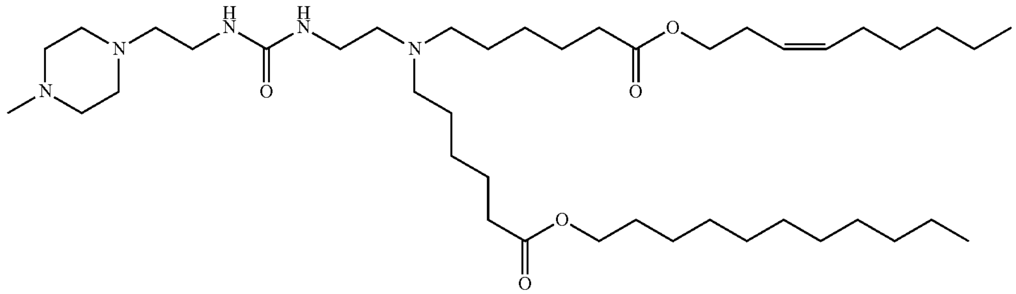 [SMILES: CCCCC/C=C\CCOC(=O)CCCCCN(CCCCCC(=O)OCCCCCCCCCCC)CCNC(=O)NCCN1CCN(C)CC1] | 736.1 |

TABLE 1-continued
| # | Structure | Mw |
|---|---|---|
| 1700. | 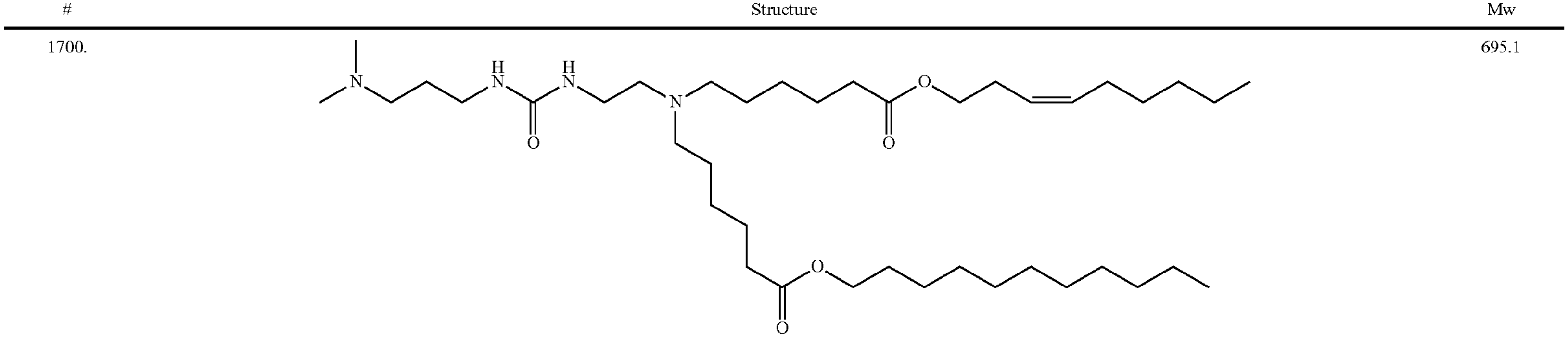 | 695.1 |
| 1701. | 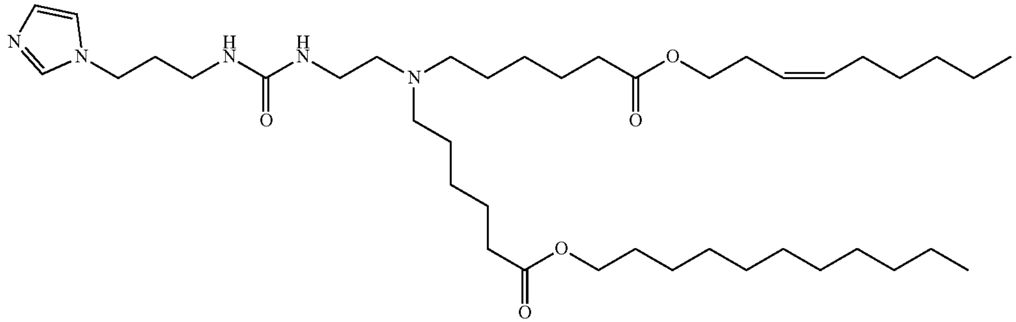 [SMILES: CCCCC/C=C\CCOC(=O)CCCCCN(CCCCCC(=O)OCCCCCCCCCCC)CCNC(=O)NCCCn1ccnc1] | 718.1 |
| 1702. | 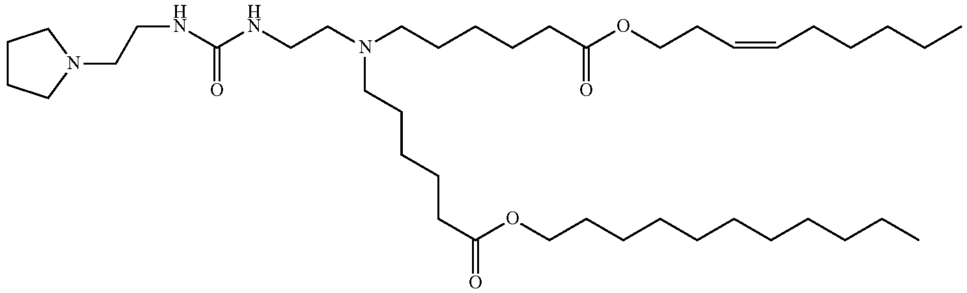 [SMILES: CCCCC/C=C\CCOC(=O)CCCCCN(CCCCCC(=O)OCCCCCCCCCCC)CCNC(=O)NCCN1CCCC1] | 707.1 |

TABLE 1-continued
| # | Structure | Mw |
| --- | --- | --- |
| 1703. | 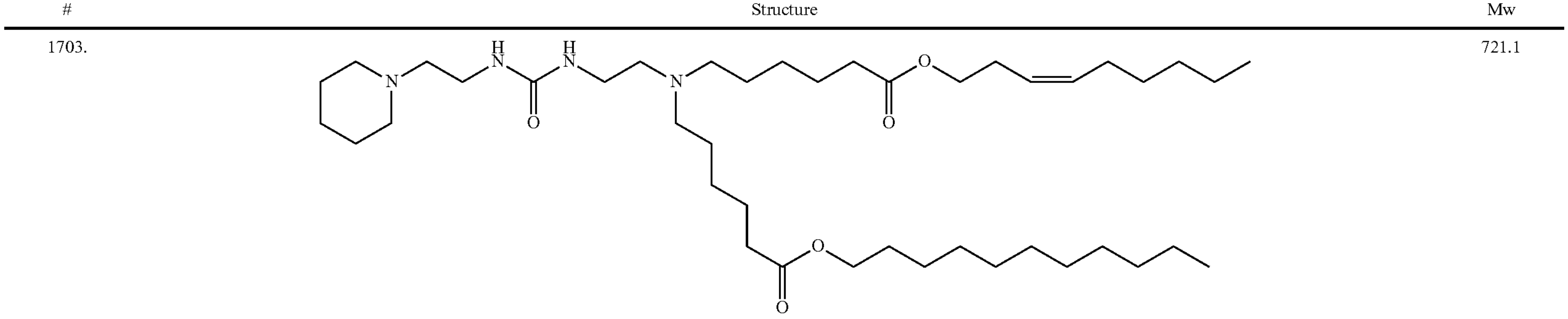 | 721.1 |
| 1704. | 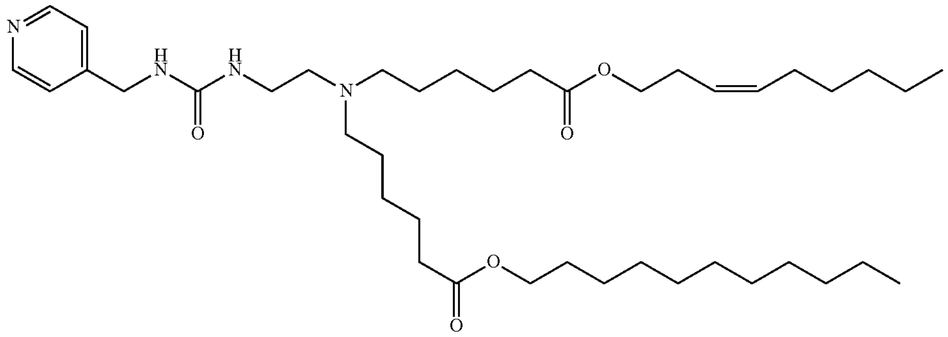 [SMILES: CCCCC/C=C\CCOC(=O)CCCCCN(CCCCCC(=O)OCCCCCCCCCCC)CCNC(=O)NCc1ccncc1] | 701.1 |
| 1705. | 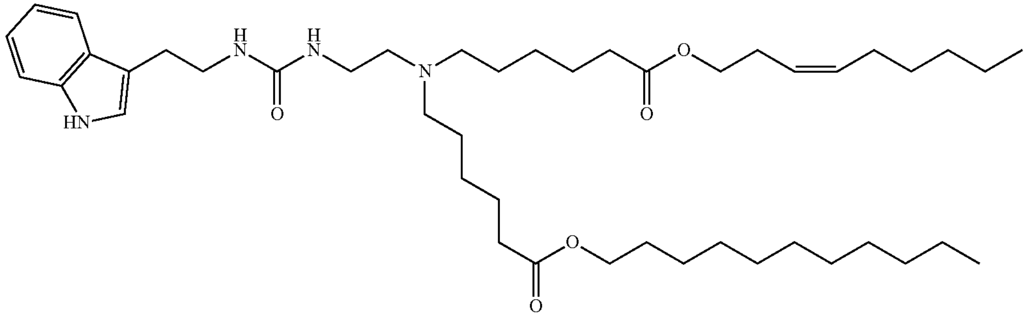 [SMILES: CCCCC/C=C\CCOC(=O)CCCCCN(CCCCCC(=O)OCCCCCCCCCCC)CCNC(=O)NCCc1c[nH]c2ccccc12] | 753.1 |

TABLE 1-continued
| # | Structure | Mw |
| --- | --- | --- |
| 1706. | 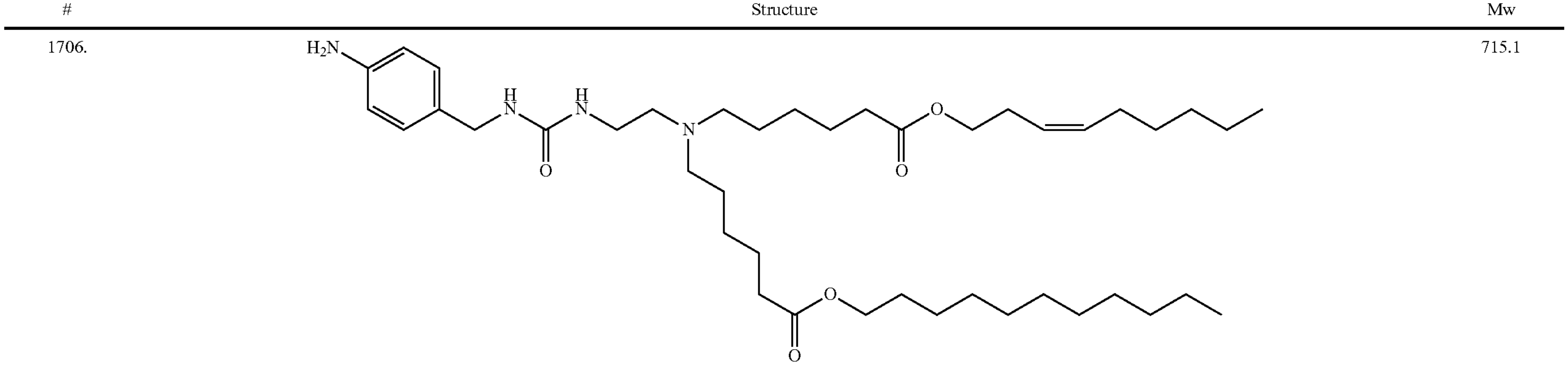 | 715.1 |
| 1707. | 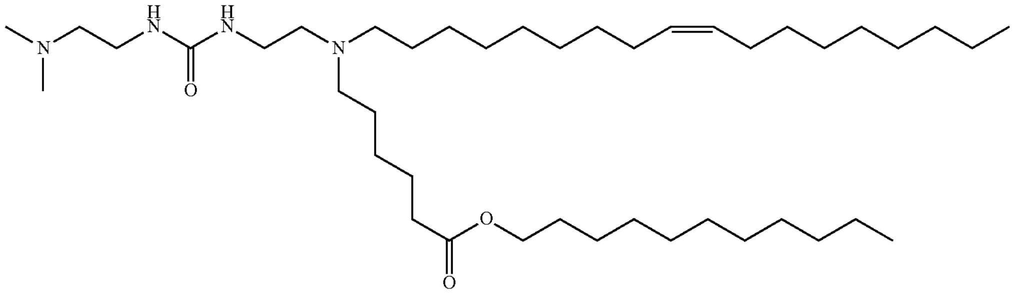 [SMILES: CCCCCCCC/C=C\CCCCCCCCN(CCCCCC(=O)OCCCCCCCCCCC)CCNC(=O)NCCN(C)C] | 693.2 |
| 1708. | 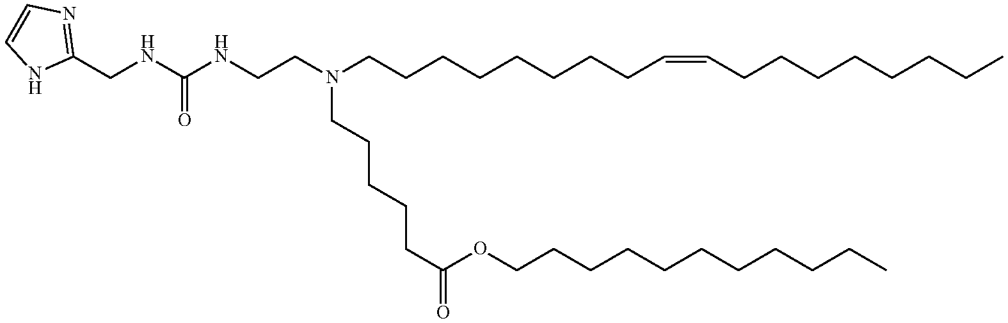 [SMILES: CCCCCCCC/C=C\CCCCCCCCN(CCCCCC(=O)OCCCCCCCCCCC)CCNC(=O)NCc1ncc[nH]1] | 702.1 |

TABLE 1-continued
| # | Structure | Mw |
|---|---|---|
| 1709. | 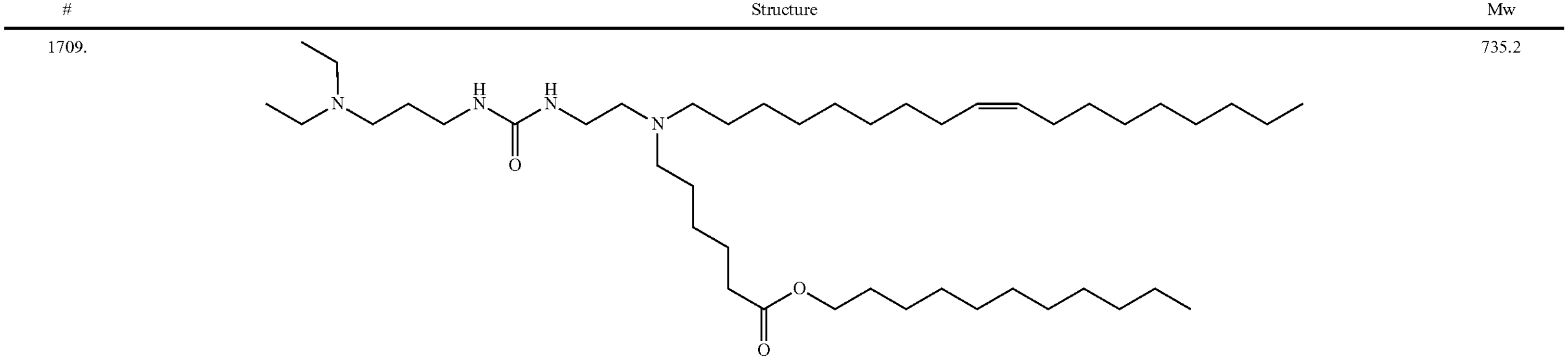 | 735.2 |
| 1710. | 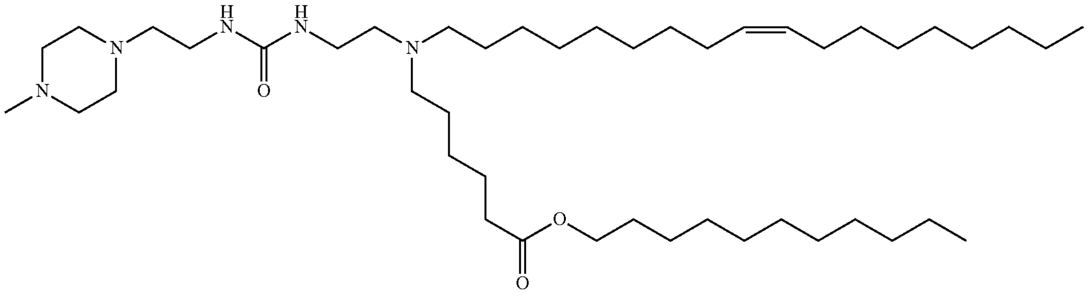 [SMILES: CCCCCCCC/C=C\CCCCCCCCN(CCCCCC(=O)OCCCCCCCCCCC)CCNC(=O)NCCN1CCN(C)CC1] | 748.2 |
| 1711. | 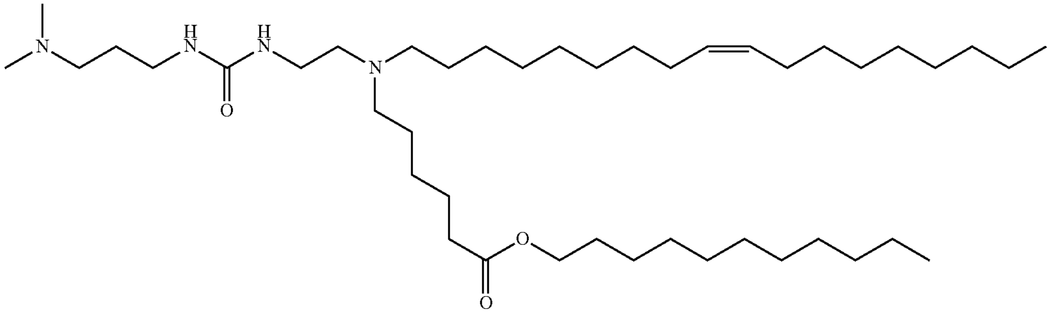 [SMILES: CCCCCCCC/C=C\CCCCCCCCN(CCCCCC(=O)OCCCCCCCCCCC)CCNC(=O)NCCCN(C)C] | 707.2 |

TABLE 1-continued
| # | Structure | Mw |
| --- | --- | --- |
| 1712. | 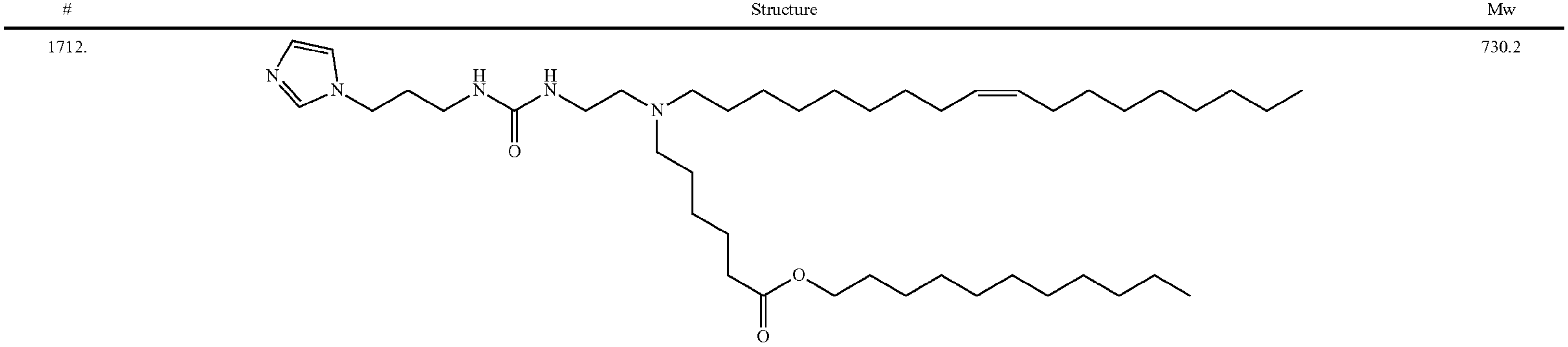 | 730.2 |
| 1713. | 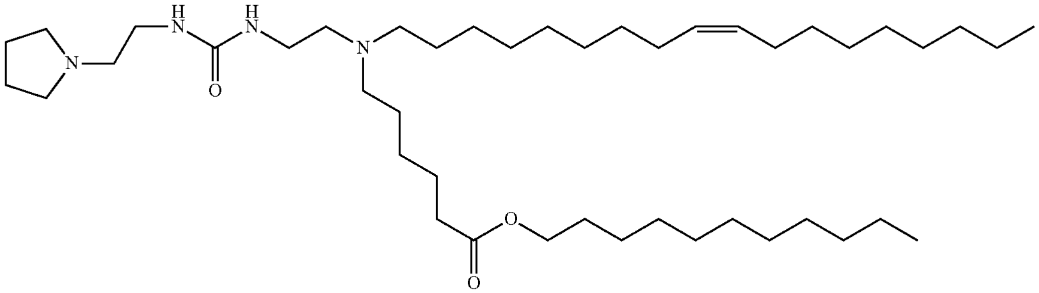 [SMILES: CCCCCCCC/C=C\CCCCCCCCN(CCCCCC(=O)OCCCCCCCCCCC)CCNC(=O)NCCN1CCCC1] | 719.2 |
| 1714. | 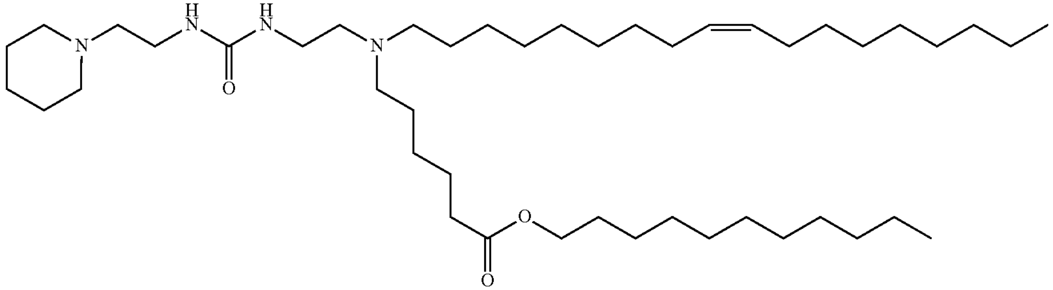 [SMILES: CCCCCCCC/C=C\CCCCCCCCN(CCCCCC(=O)OCCCCCCCCCCC)CCNC(=O)NCCN1CCCCC1] | 733.2 |

TABLE 1-continued
| # | Structure | Mw |
| --- | --- | --- |
| 1715. | 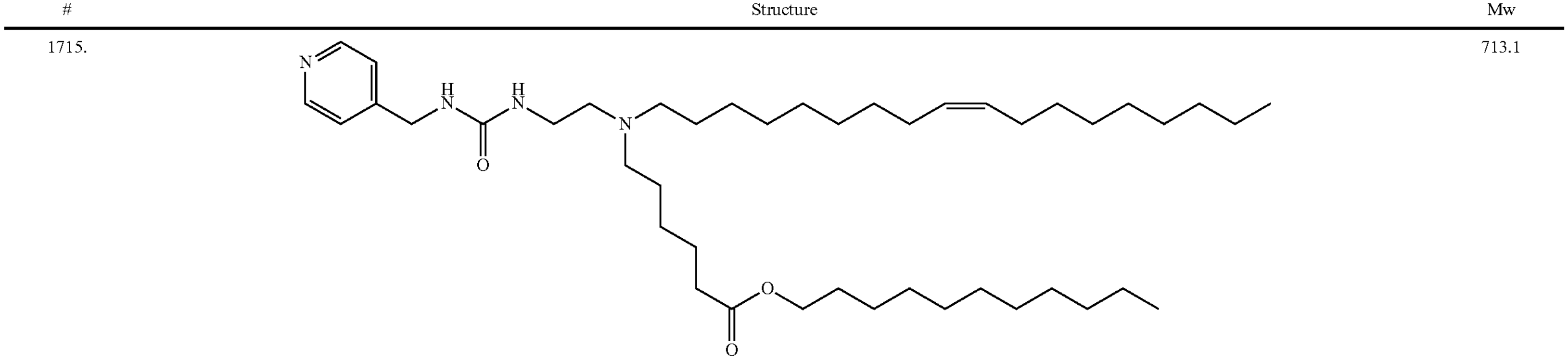 | 713.1 |
| 1716. | 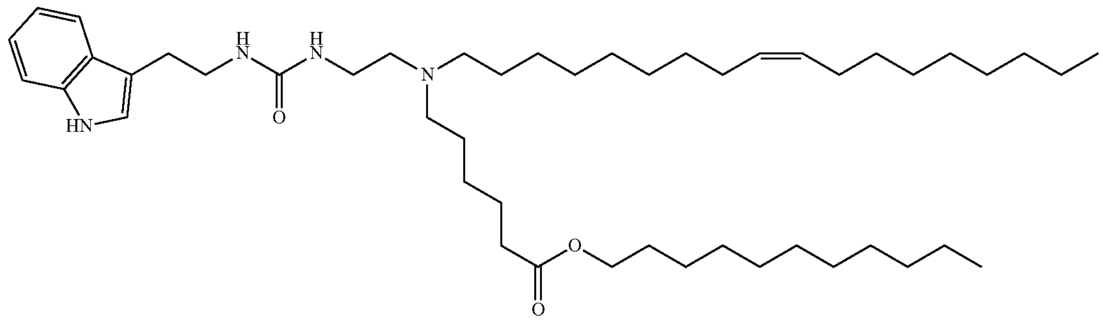 [SMILES: CCCCCCCC/C=C\CCCCCCCCN(CCCCCC(=O)OCCCCCCCCCCC)CCNC(=O)NCCc1c[nH]c2ccccc12] | 765.2 |
| 1717. | 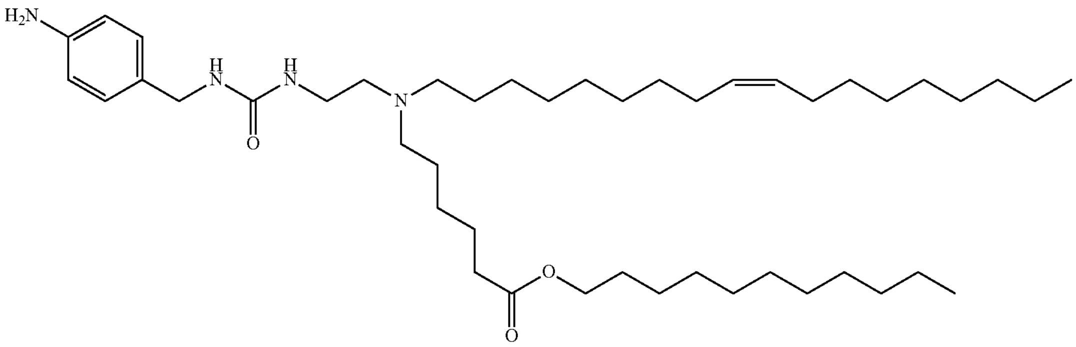 [SMILES: CCCCCCCC/C=C\CCCCCCCCN(CCCCCC(=O)OCCCCCCCCCCC)CCNC(=O)NCc1ccc(N)cc1] | 727.2 |

TABLE 1-continued
| # | Structure | Mw |
| --- | --- | --- |
| 1718. | 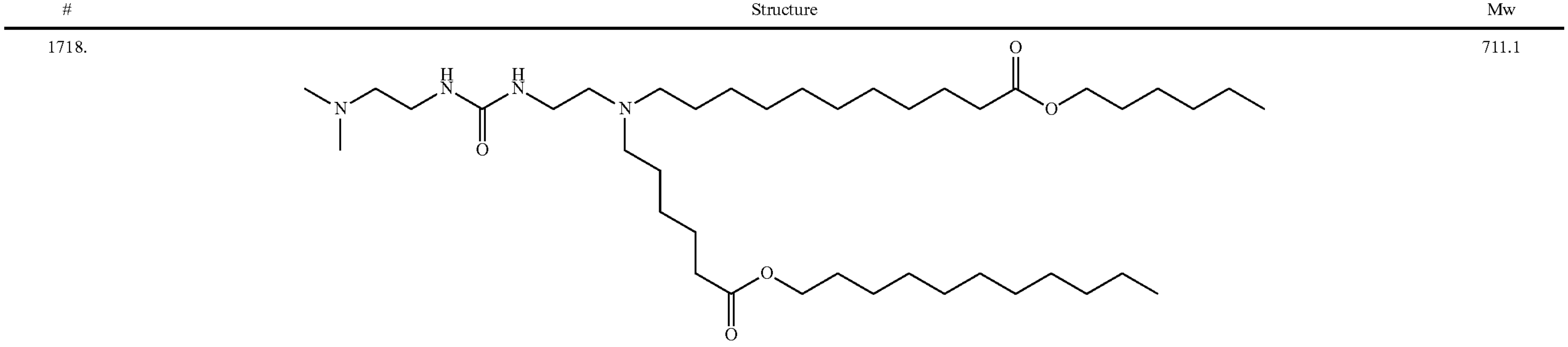 | 711.1 |
| 1719. | 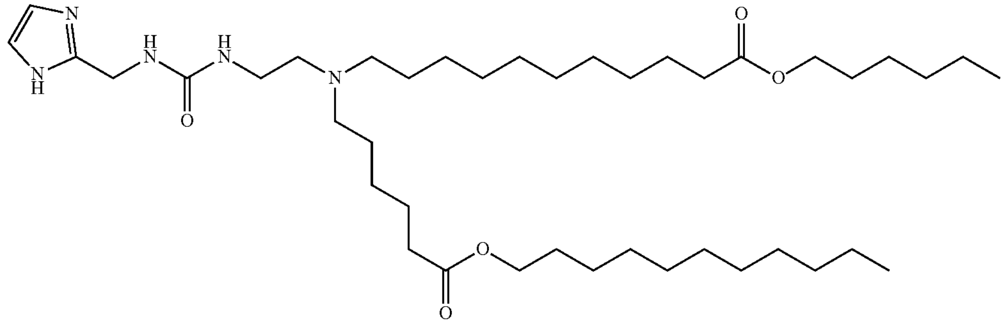 [SMILES: CCCCCCCCCCCOC(=O)CCCCCN(CCCCCCCCCCC(=O)OCCCCCC)CCNC(=O)NCc1ncc[nH]1] | 720.1 |
| 1720. | 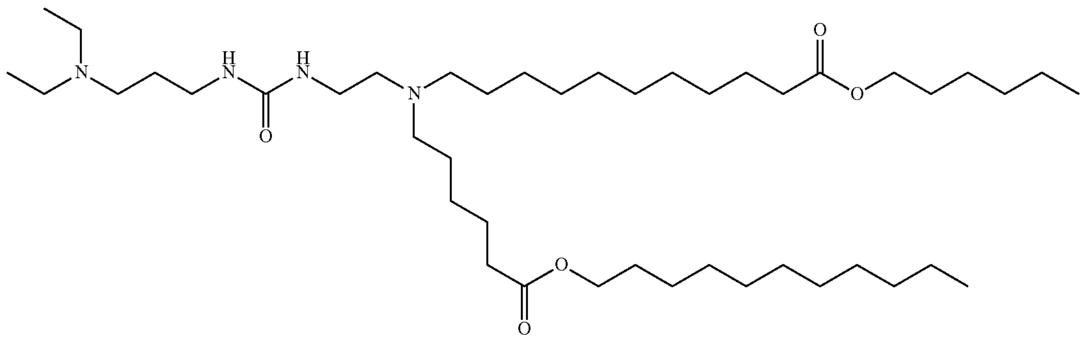 [SMILES: CCCCCCCCCCCOC(=O)CCCCCN(CCCCCCCCCCC(=O)OCCCCCC)CCNC(=O)NCCCN(CC)CC] | 753.2 |

TABLE 1-continued
| # | Structure | Mw |
| --- | --- | --- |
| 1721. | 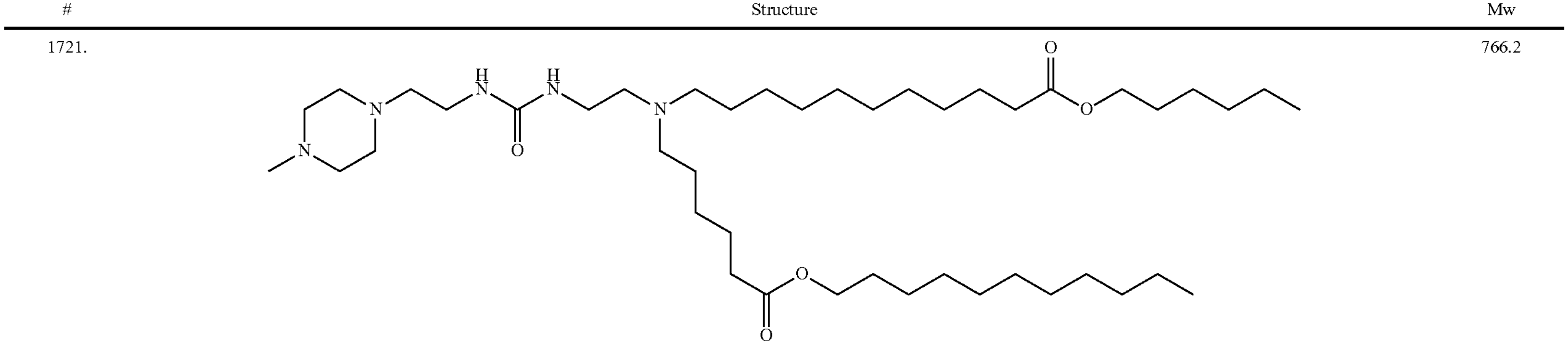 | 766.2 |
| 1722. | 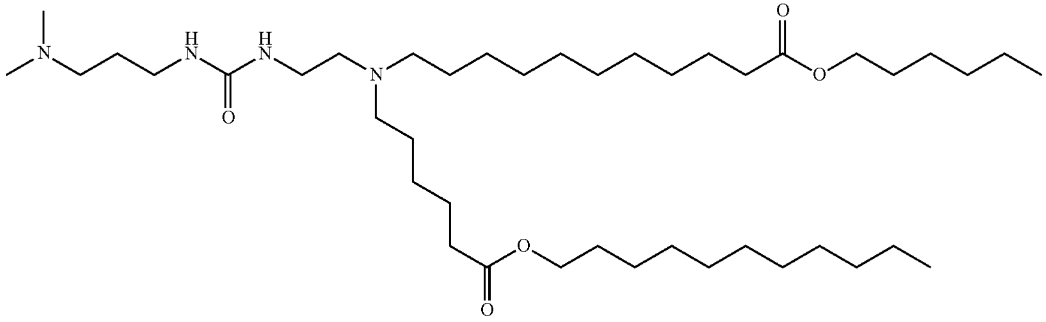 [SMILES: CCCCCCCCCCCOC(=O)CCCCCN(CCCCCCCCCCC(=O)OCCCCCC)CCNC(=O)NCCCN(C)C] | 725.2 |
| 1723. | 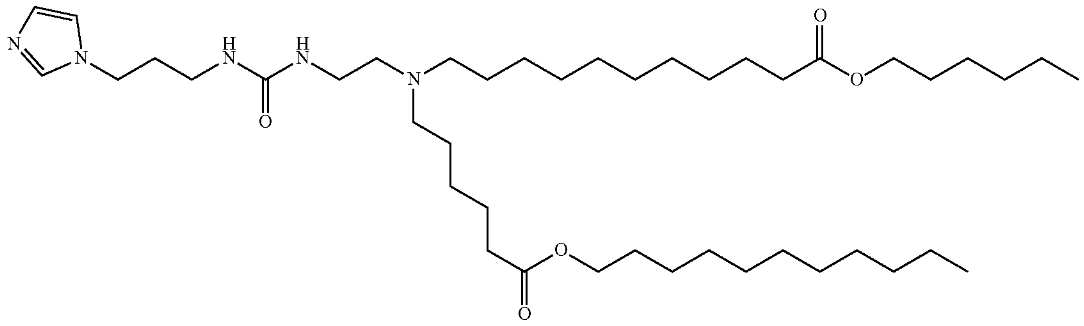 [SMILES: CCCCCCCCCCCOC(=O)CCCCCN(CCCCCCCCCCC(=O)OCCCCCC)CCNC(=O)NCCCn1ccnc1] | 748.2 |

TABLE 1-continued
| # | Structure | Mw |
|---|---|---|
| 1724. | 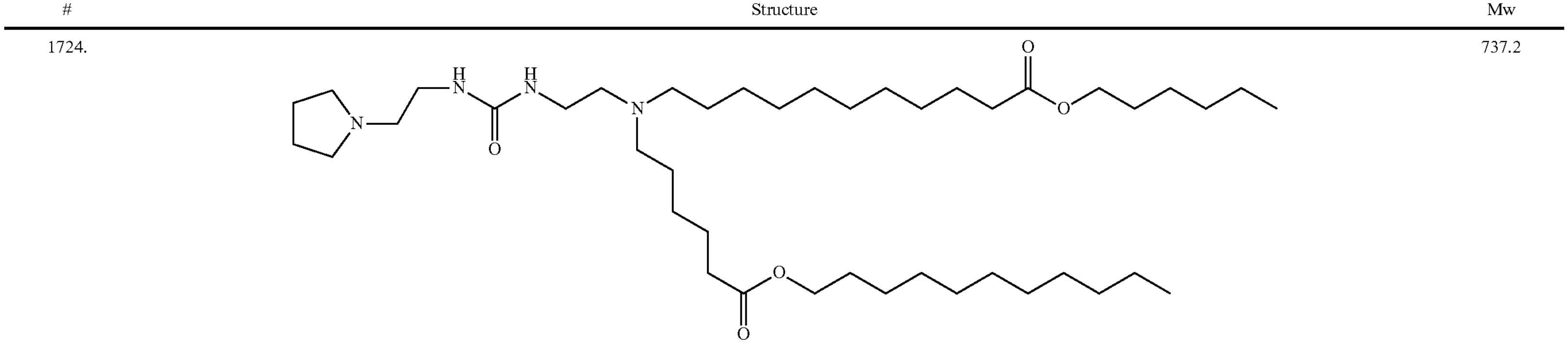 | 737.2 |
| 1725. | 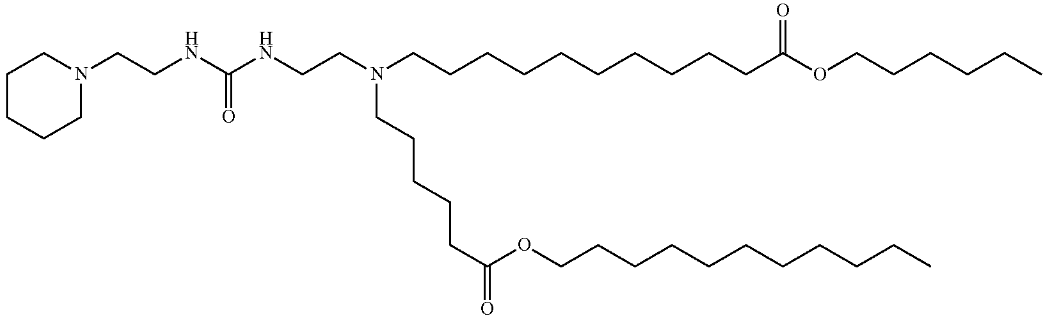 [SMILES: CCCCCCCCCCCOC(=O)CCCCCN(CCCCCCCCCCC(=O)OCCCCCC)CCNC(=O)NCCN1CCCCC1] | 751.2 |
| 1726. | 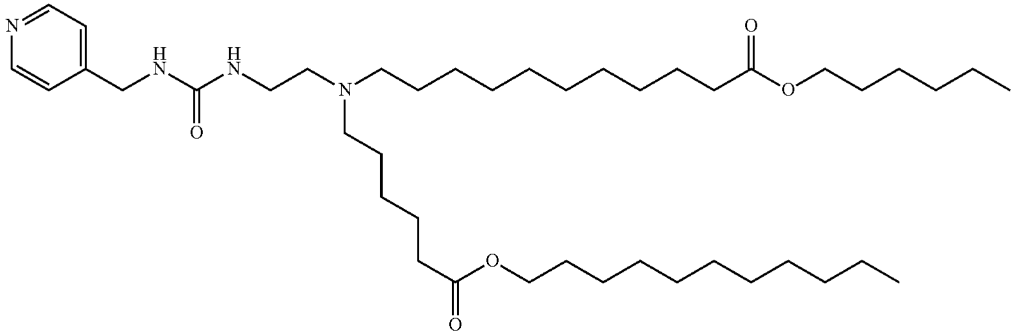 [SMILES: CCCCCCCCCCCOC(=O)CCCCCN(CCCCCCCCCCC(=O)OCCCCCC)CCNC(=O)NCc1ccncc1] | 731.1 |

TABLE 1-continued
| # | Structure | Mw |
|---|---|---|
| 1727. | 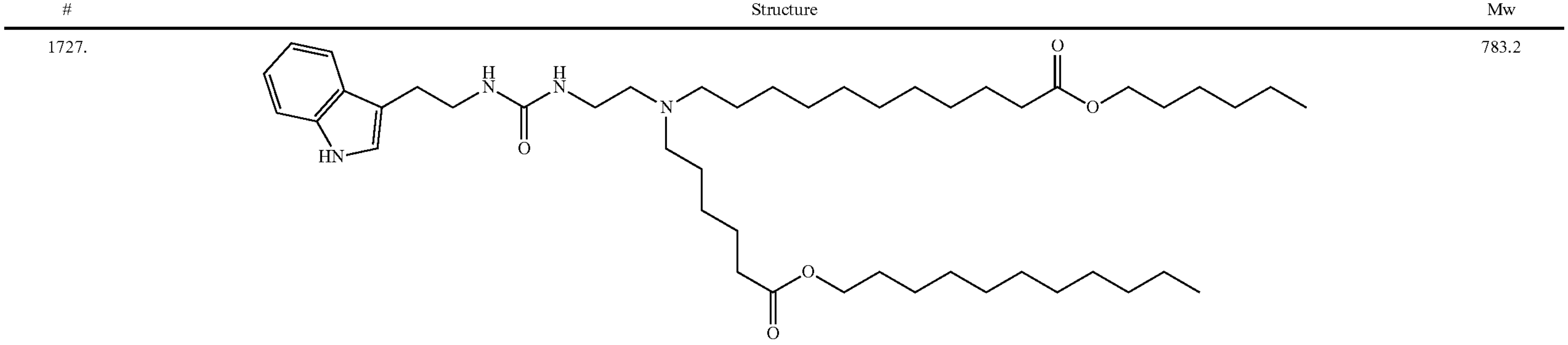 | 783.2 |
| 1728. | 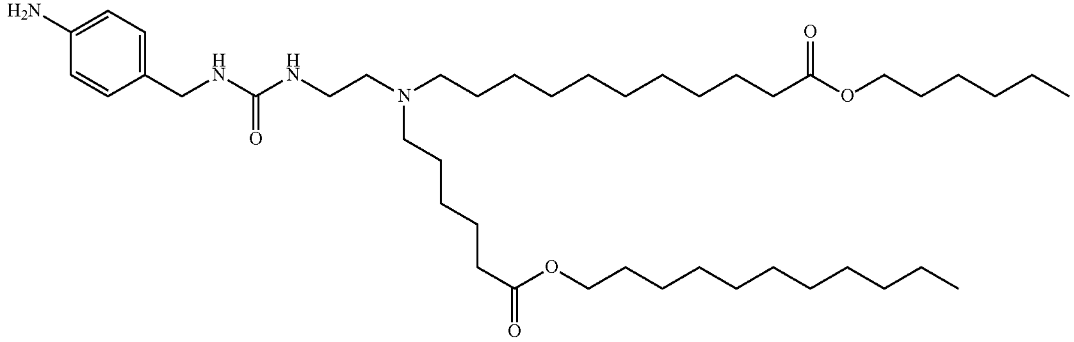 [SMILES: CCCCCCCCCCCOC(=O)CCCCCN(CCCCCCCCCCC(=O)OCCCCCC)CCNC(=O)NCc1ccc(N)cc1] | 745.1 |
| 1729. | 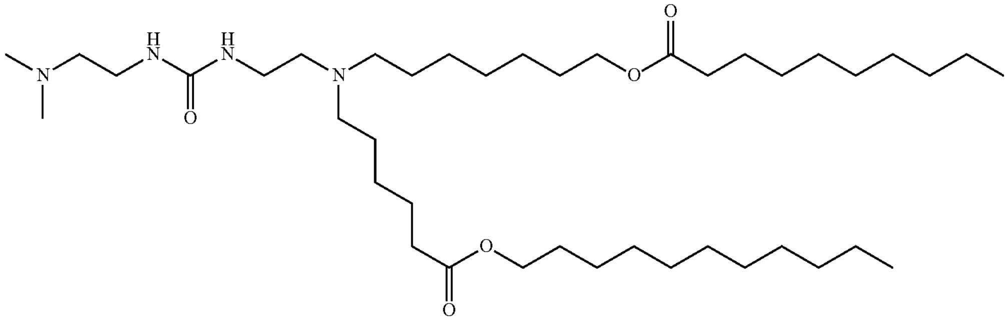 [SMILES: CCCCCCCCCCCOC(=O)CCCCCN(CCCCCCCOC(=O)CCCCCCCCC)CCNC(=O)NCCN(C)C] | 711.1 |

TABLE 1-continued
| # | Structure | Mw |
|---|---|---|
| 1730. | 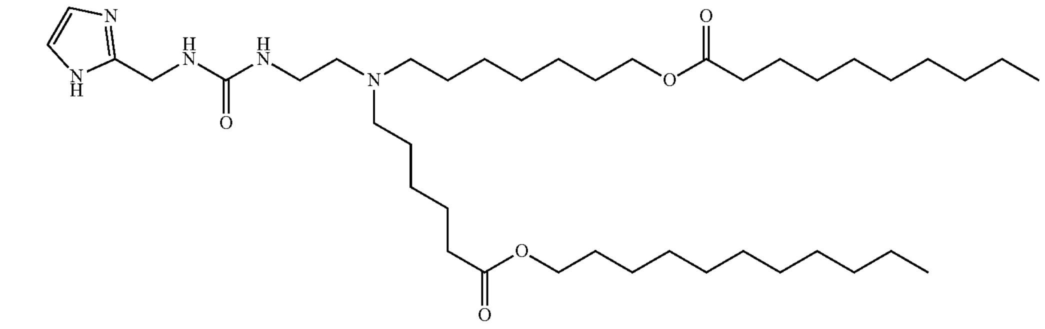 [SMILES: CCCCCCCCCCCOC(=O)CCCCCN(CCCCCCCOC(=O)CCCCCCCCC)CCNC(=O)NCc1ncc[nH]1] | 720.1 |
| 1731. | 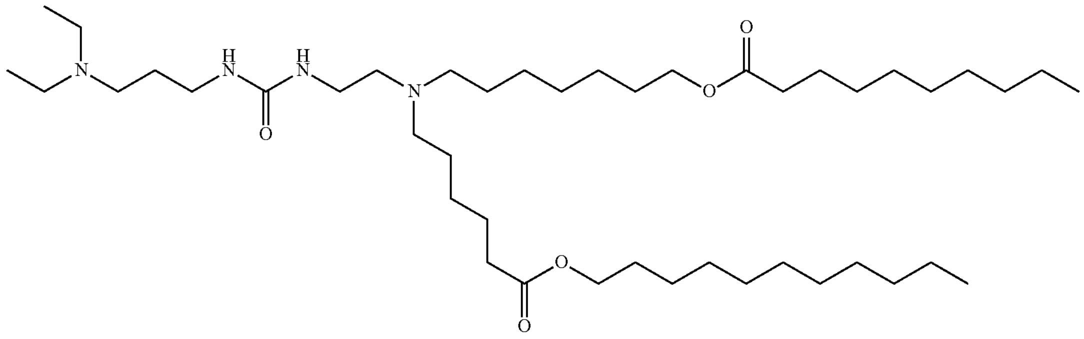 [SMILES: CCCCCCCCCCCOC(=O)CCCCCN(CCCCCCCOC(=O)CCCCCCCCC)CCNC(=O)NCCCN(CC)CC] | 753.2 |
| 1732. | 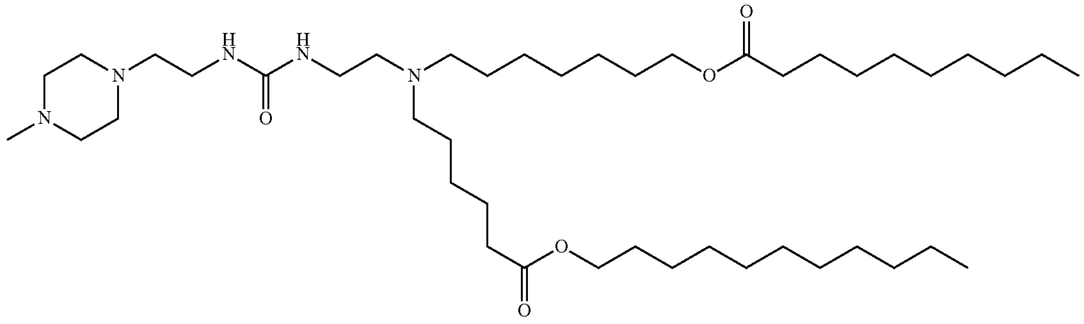 [SMILES: CCCCCCCCCCCOC(=O)CCCCCN(CCCCCCCOC(=O)CCCCCCCCC)CCNC(=O)NCCN1CCN(C)CC1] | 766.2 |

TABLE 1-continued
| # | Structure | Mw |
|---|---|---|
| 1733. | 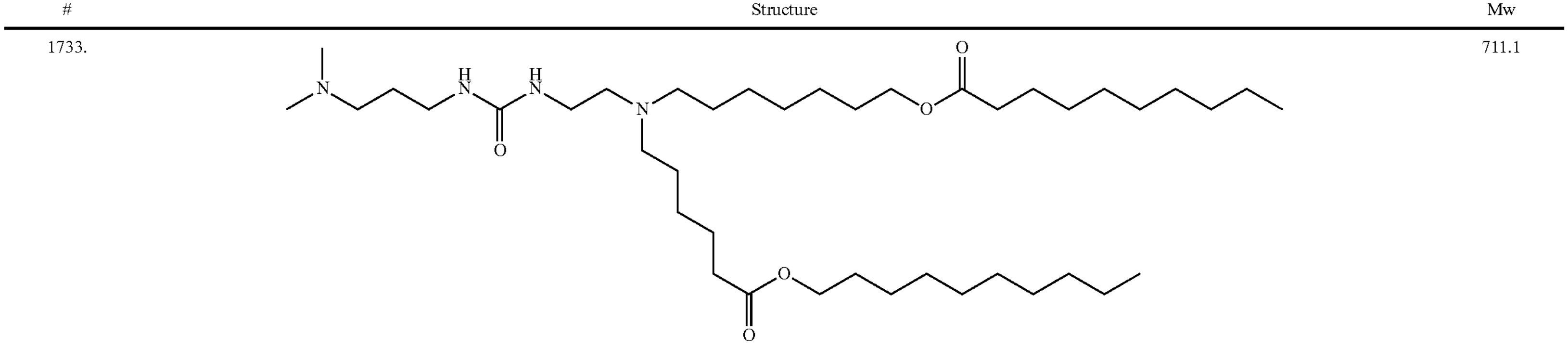 | 711.1 |
| 1734. | 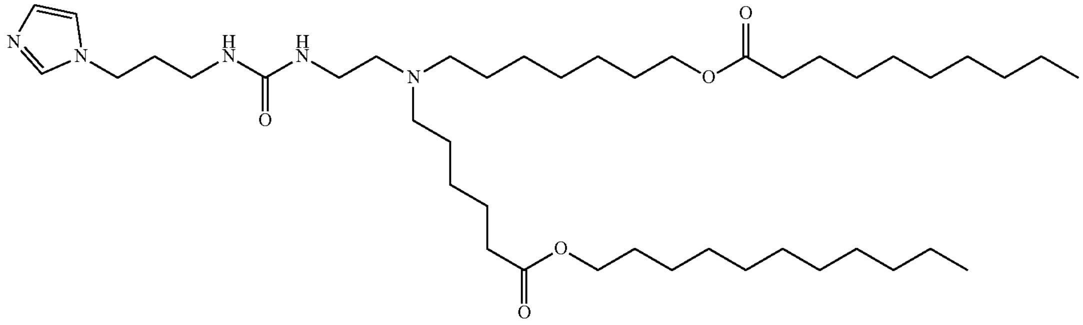 [SMILES: CCCCCCCCCCCOC(=O)CCCCCN(CCCCCCCOC(=O)CCCCCCCCC)CCNC(=O)NCCCn1ccnc1] | 748.2 |
| 1735. | 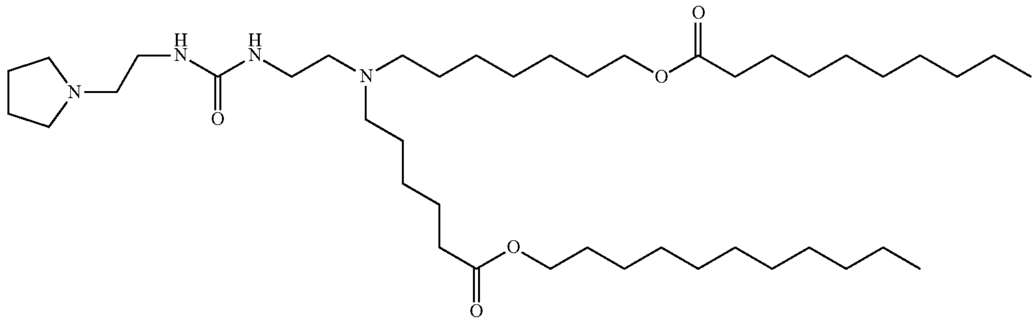 [SMILES: CCCCCCCCCCCOC(=O)CCCCCN(CCCCCCCOC(=O)CCCCCCCCC)CCNC(=O)NCCN1CCCC1] | 737.2 |

TABLE 1-continued
| # | Structure | Mw |
| --- | --- | --- |
| 1736. | 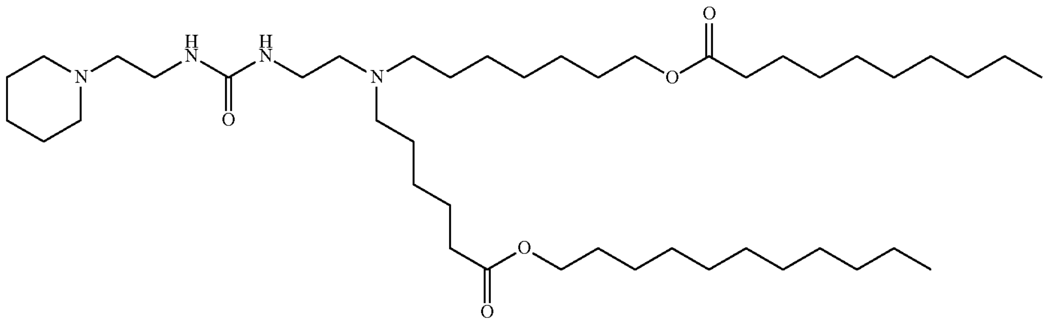 [SMILES: CCCCCCCCCCCOC(=O)CCCCCN(CCCCCCCOC(=O)CCCCCCCCC)CCNC(=O)NCCN1CCCCC1] | 751.2 |
| 1737. | 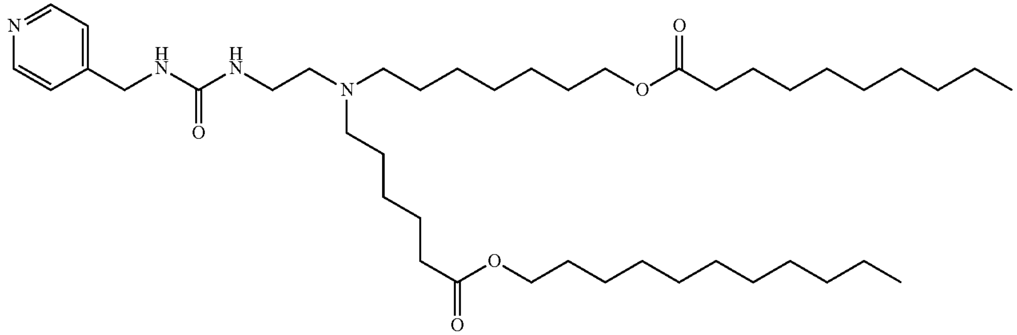 [SMILES: CCCCCCCCCCCOC(=O)CCCCCN(CCCCCCCOC(=O)CCCCCCCCC)CCNC(=O)NCc1ccncc1] | 731.1 |
| 1738. | 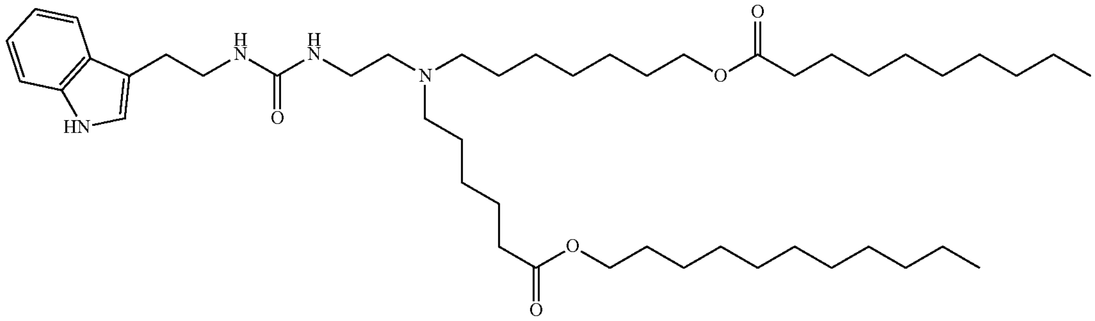 [SMILES: CCCCCCCCCCCOC(=O)CCCCCN(CCCCCCCOC(=O)CCCCCCCCC)CCNC(=O)NCCc1c[nH]c2ccccc12] | 783.2 |

TABLE 1-continued
| # | Structure | Mw |
|---|---|---|
| 1739. | 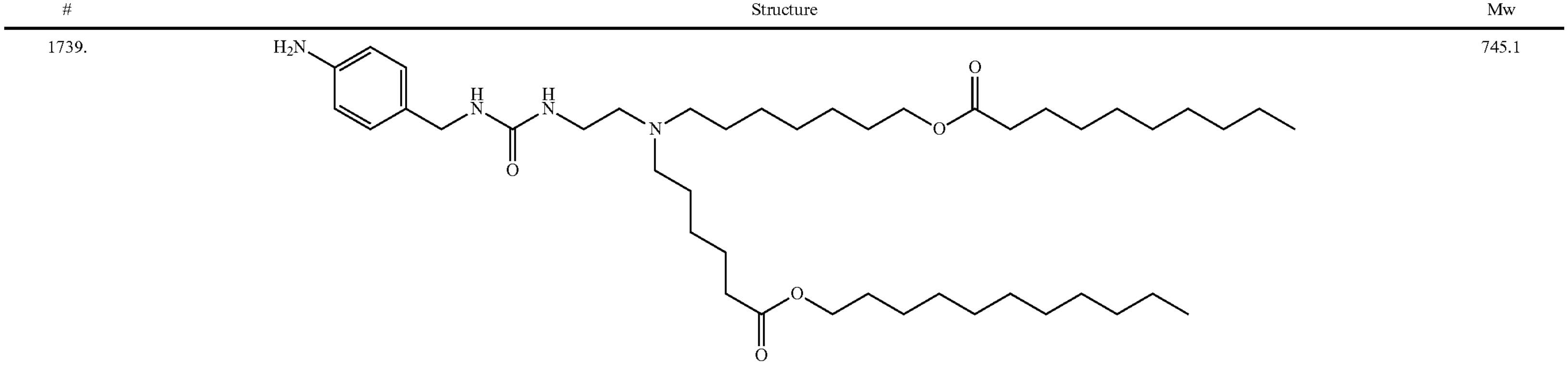 | 745.1 |
| 1740. | 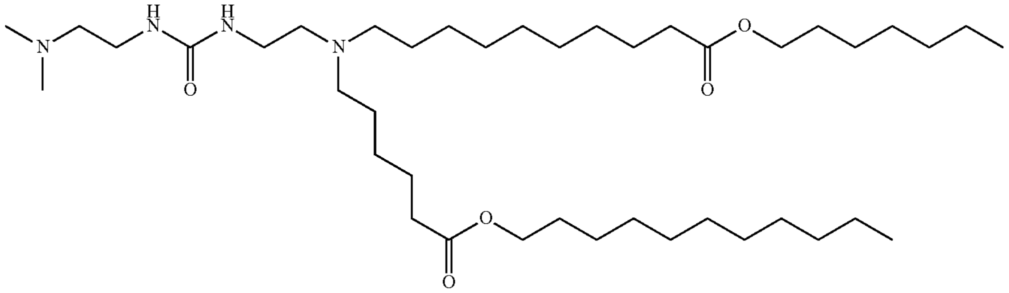 [SMILES: CCCCCCCCCCCOC(=O)CCCCCN(CCCCCCCCCC(=O)OCCCCCCC)CCNC(=O)NCCN(C)C] | 711.1 |
| 1741. | 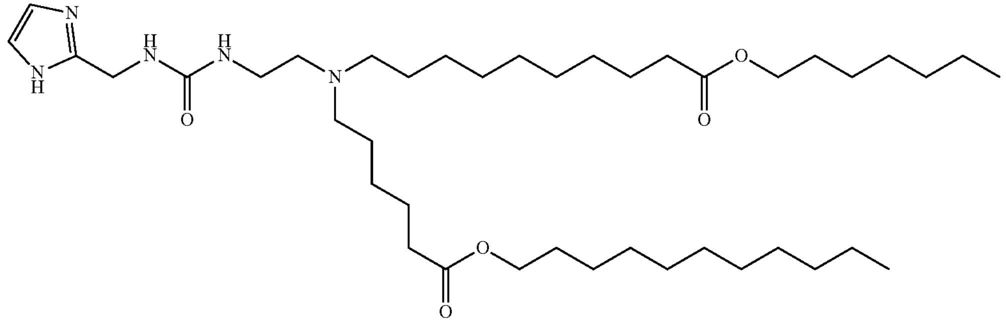 [SMILES: CCCCCCCCCCCOC(=O)CCCCCN(CCCCCCCCCC(=O)OCCCCCCC)CCNC(=O)NCc1ncc[nH]1] | 720.1 |

TABLE 1-continued
| # | Structure | Mw |
| --- | --- | --- |
| 1742. | 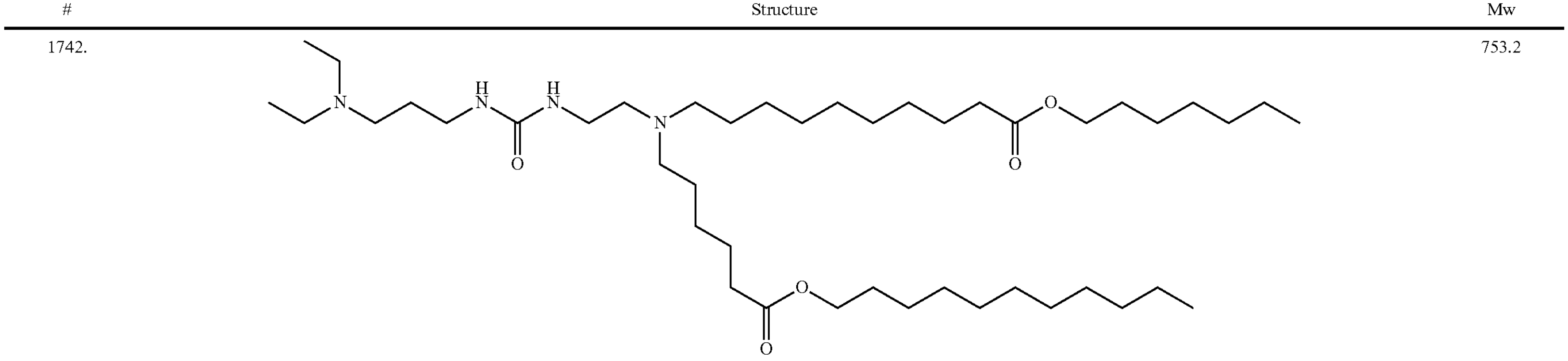 | 753.2 |
| 1743. | 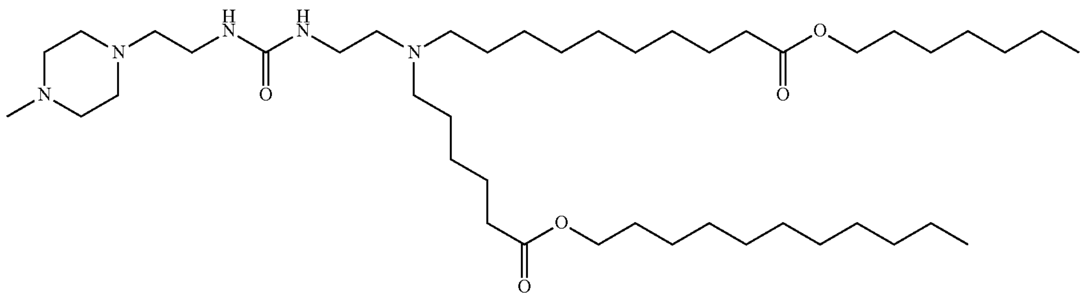 [SMILES: CCCCCCCCCCCOC(=O)CCCCCN(CCCCCCCCCC(=O)OCCCCCCC)CCNC(=O)NCCN1CCN(C)CC1] | 766.2 |
| 1744. | 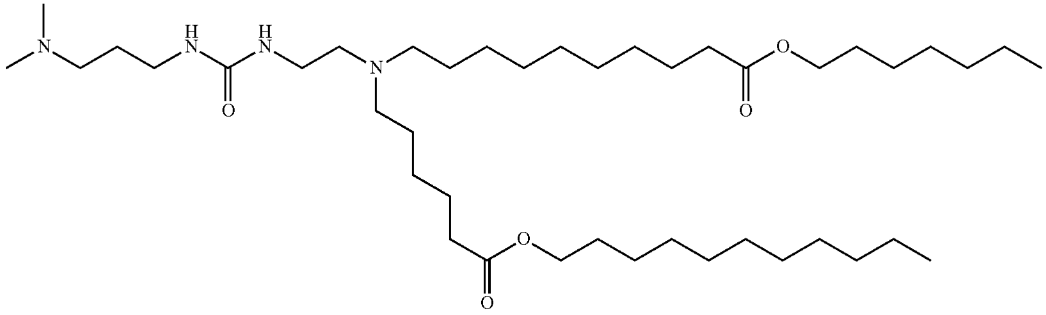 [SMILES: CCCCCCCCCCCOC(=O)CCCCCN(CCCCCCCCCC(=O)OCCCCCCC)CCNC(=O)NCCCN(C)C] | 725.2 |

TABLE 1-continued
| # | Structure | Mw |
| --- | --- | --- |
| 1745. | 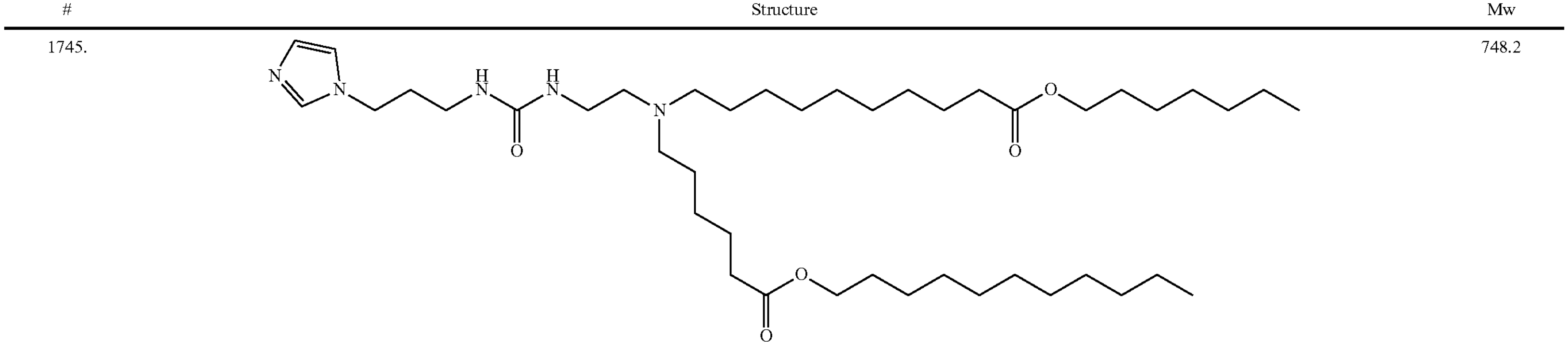 | 748.2 |
| 1746. | 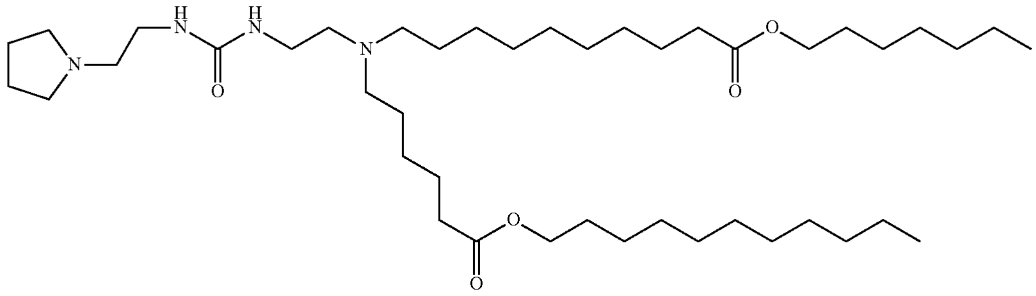 [SMILES: CCCCCCCCCCCOC(=O)CCCCCN(CCCCCCCCCC(=O)OCCCCCCC)CCNC(=O)NCCN1CCCC1] | 737.2 |
| 1747. | 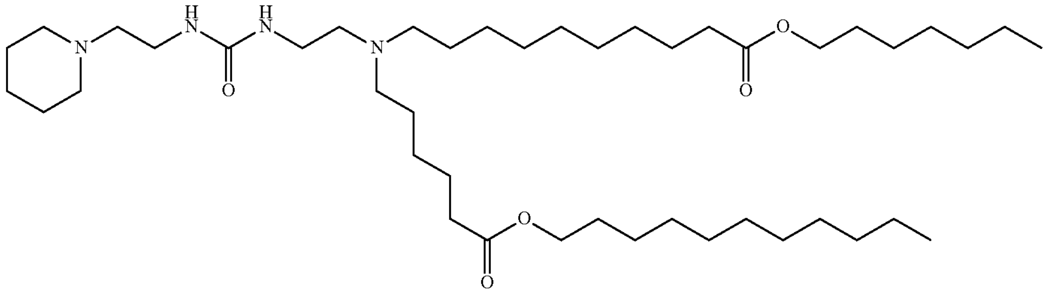 [SMILES: CCCCCCCCCCCOC(=O)CCCCCN(CCCCCCCCCC(=O)OCCCCCCC)CCNC(=O)NCCN1CCCCC1] | 751.2 |

TABLE 1-continued
| # | Structure | Mw |
| --- | --- | --- |
| 1748. | 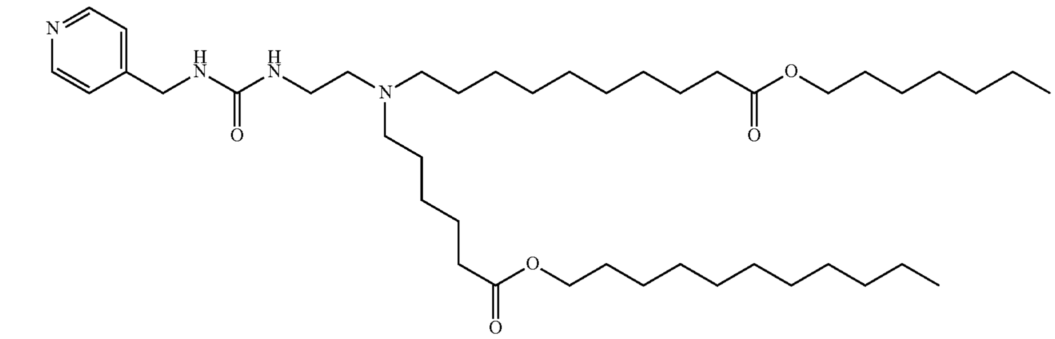 [SMILES: CCCCCCCCCCCOC(=O)CCCCCN(CCCCCCCCCC(=O)OCCCCCCC)CCNC(=O)NCc1ccncc1] | 731.1 |
| 1749. | 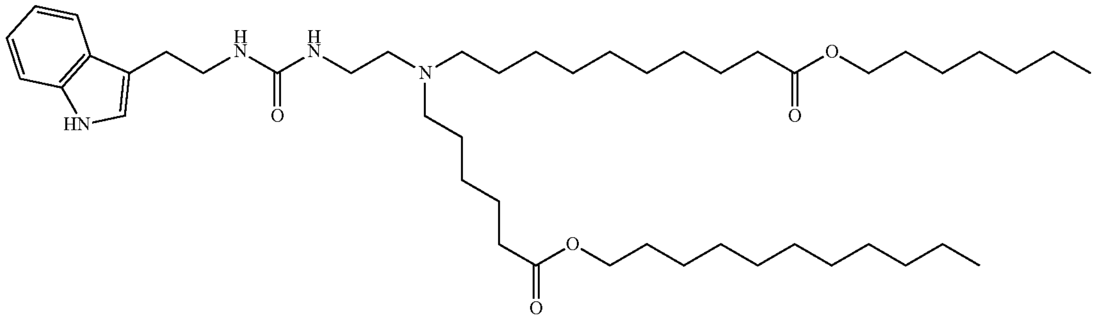 [SMILES: CCCCCCCCCCCOC(=O)CCCCCN(CCCCCCCCCC(=O)OCCCCCCC)CCNC(=O)NCCc1c[nH]c2ccccc12] | 783.2 |
| 1750. | 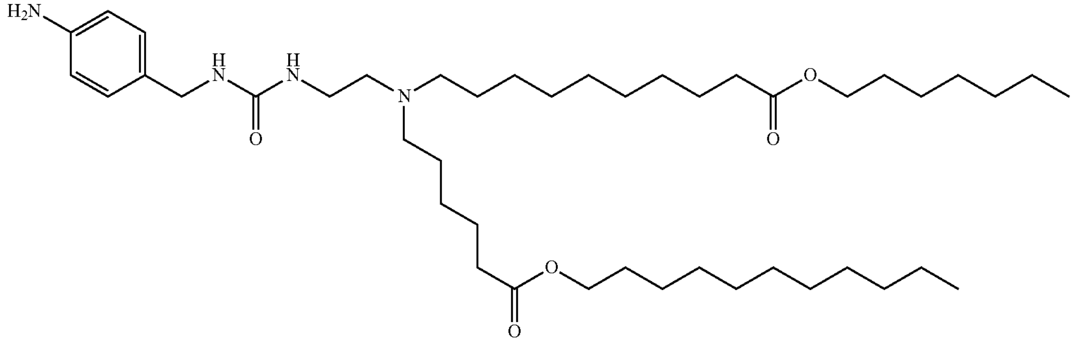 [SMILES: CCCCCCCCCCCOC(=O)CCCCCN(CCCCCCCCCC(=O)OCCCCCCC)CCNC(=O)NCc1ccc(N)cc1] | 745.1 |

TABLE 1-continued
| # | Structure | Mw |
|---|---|---|
| 1751. | 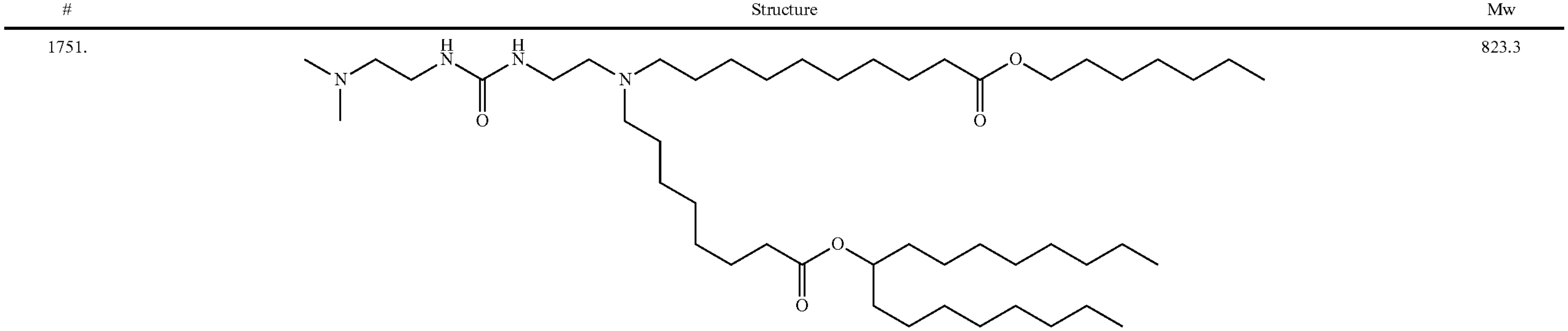 | 823.3 |
| 1752. | 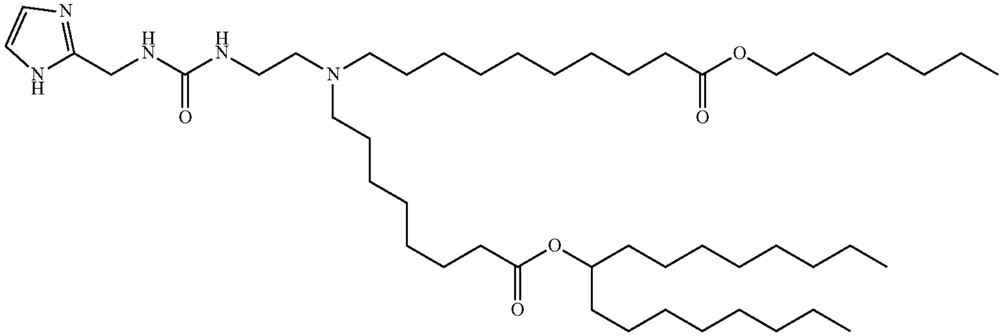 [SMILES: CCCCCCCCC(CCCCCCCC)OC(=O)CCCCCCCN(CCCCCCCCCC(=O)OCCCCCCC)CCNC(=O)NCc1ncc[nH]1] | 832.3 |
| 1753. | 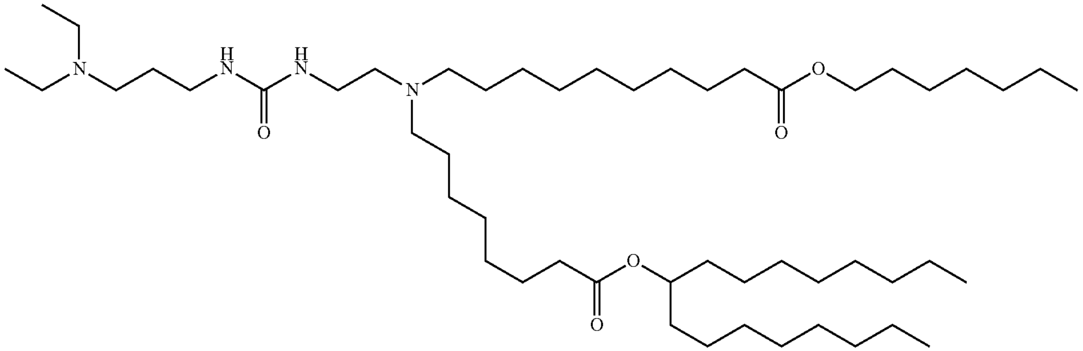 [SMILES: CCCCCCCCC(CCCCCCCC)OC(=O)CCCCCCCN(CCCCCCCCCC(=O)OCCCCCCC)CCNC(=O)NCCCN(CC)CC] | 865.4 |

TABLE 1-continued
| # | Structure | Mw |
|---|---|---|
| 1754. | 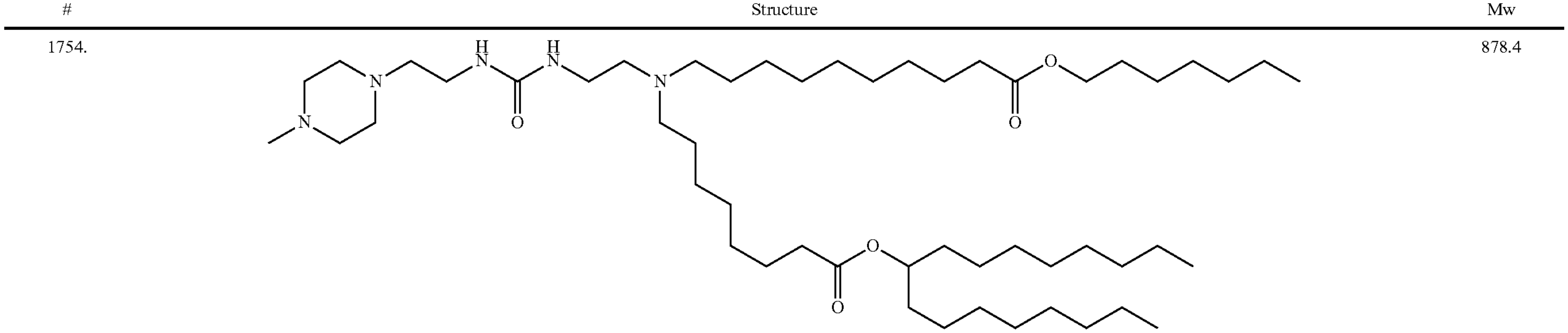 | 878.4 |
| 1755. | 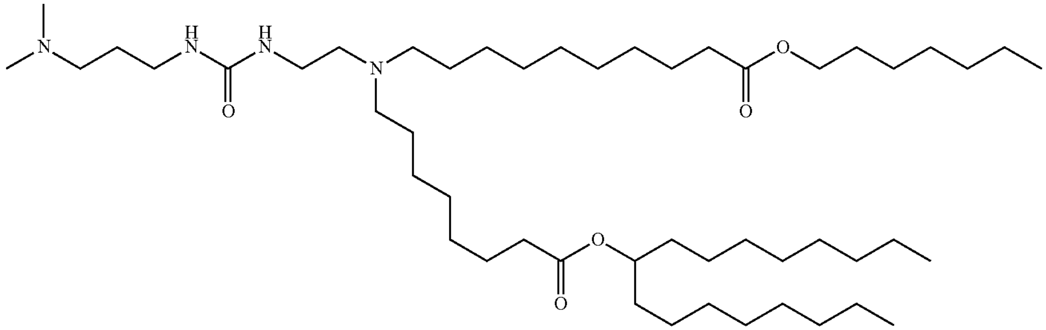 [SMILES: CCCCCCCCC(CCCCCCCC)OC(=O)CCCCCCCN(CCCCCCCCCC(=O)OCCCCCCC)CCNC(=O)NCCCN(C)C] | 837.4 |
| 1756. | 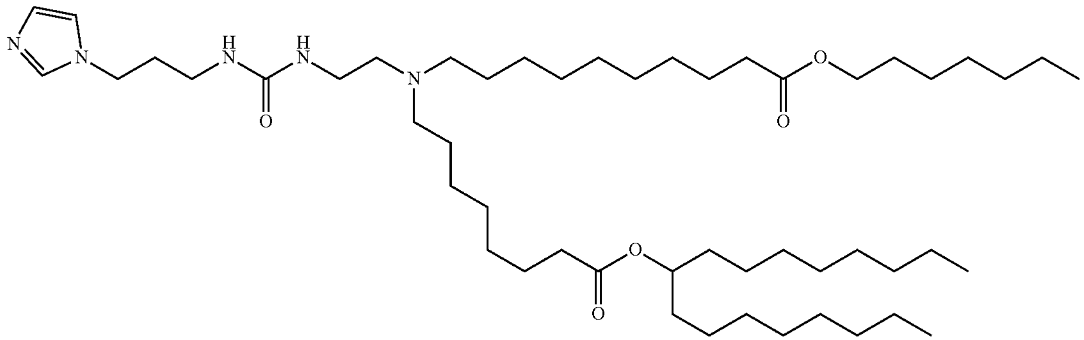 [SMILES: CCCCCCCCC(CCCCCCCC)OC(=O)CCCCCCCN(CCCCCCCCCC(=O)OCCCCCCC)CCNC(=O)NCCCn1ccnc1] | 860.4 |

TABLE 1-continued
| # | Structure | Mw |
|---|---|---|
| 1757. | 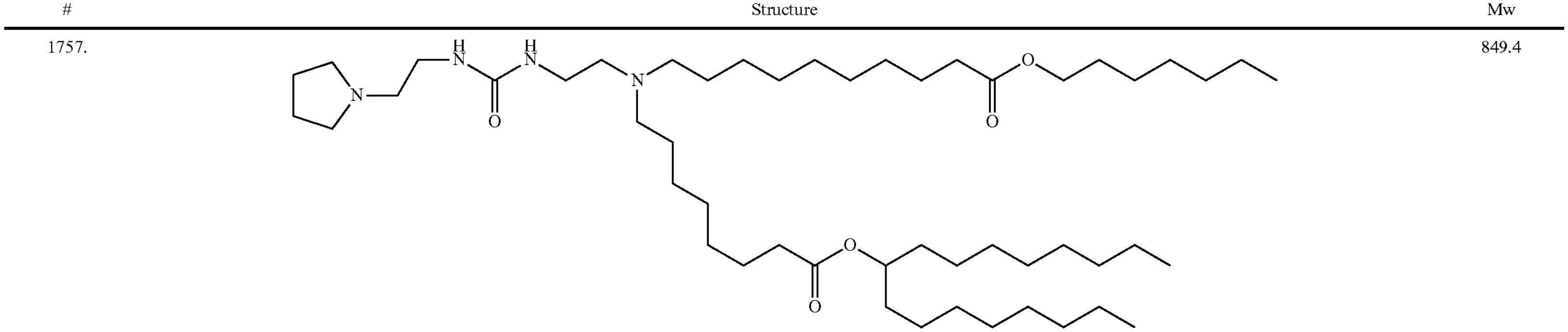 | 849.4 |
| 1758. | 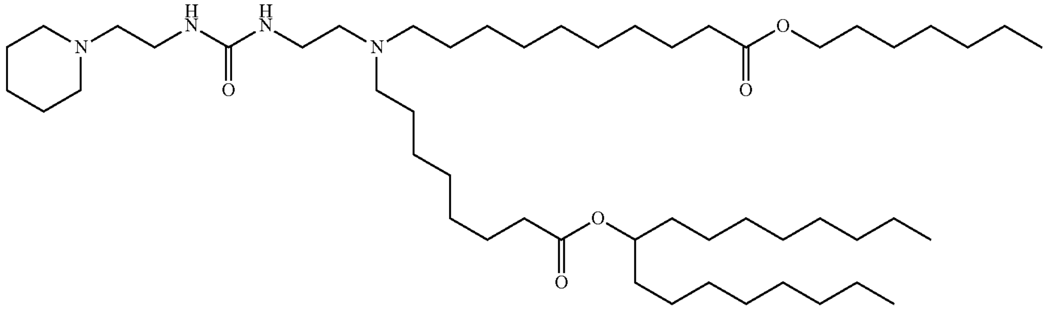 [SMILES: CCCCCCCCC(CCCCCCCC)OC(=O)CCCCCCCN(CCCCCCCCCC(=O)OCCCCCCC)CCNC(=O)NCCN1CCCCC1] | 863.4 |
| 1759. | 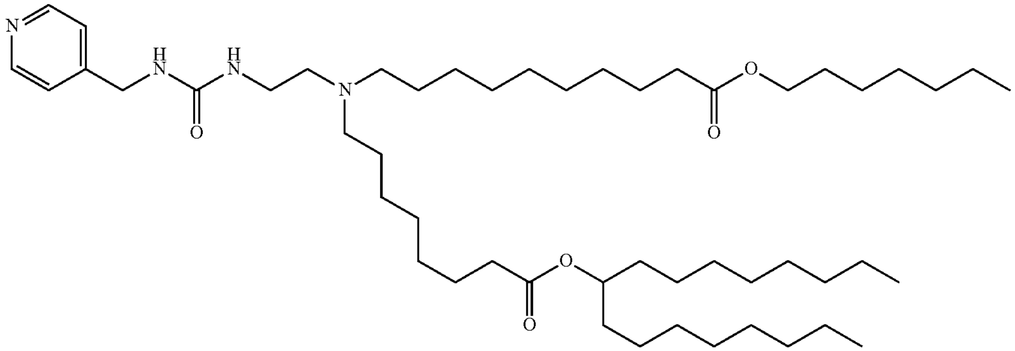 [SMILES: CCCCCCCCC(CCCCCCCC)OC(=O)CCCCCCCN(CCCCCCCCCC(=O)OCCCCCCC)CCNC(=O)NCc1ccncc1] | 843.3 |

TABLE 1-continued
| # | Structure | Mw |
| --- | --- | --- |
| 1760. | 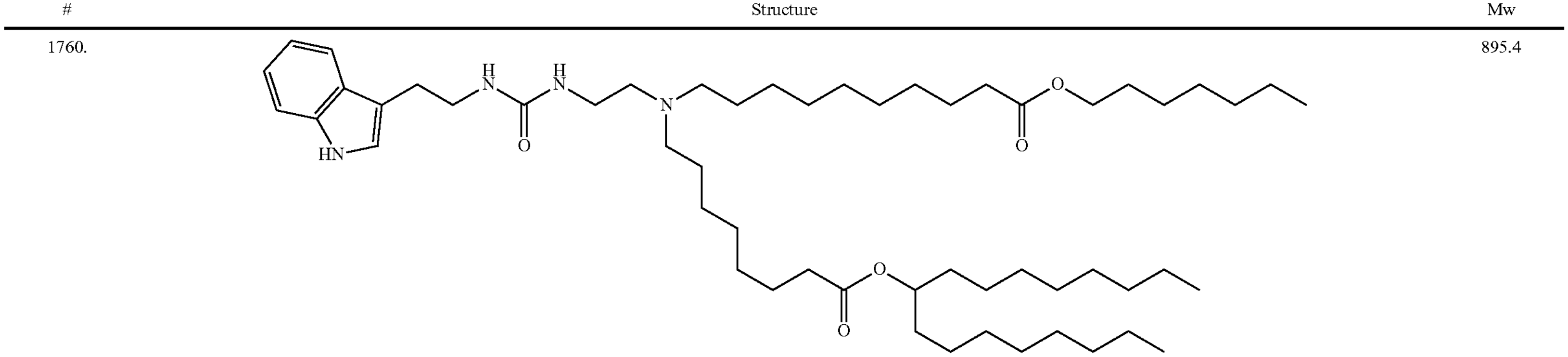 | 895.4 |
| 1761. | 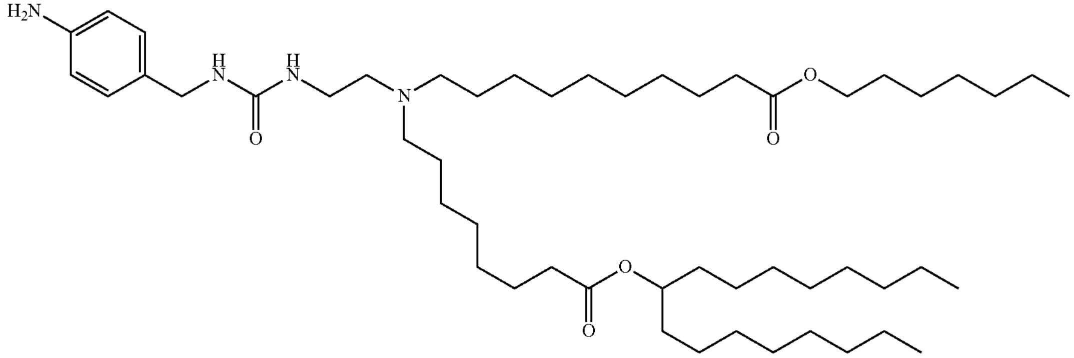 [SMILES: CCCCCCCCC(CCCCCCCC)OC(=O)CCCCCCCN(CCCCCCCCCC(=O)OCCCCCCC)CCNC(=O)NCc1ccc(N)cc1] | 857.4 |
| 1762. | 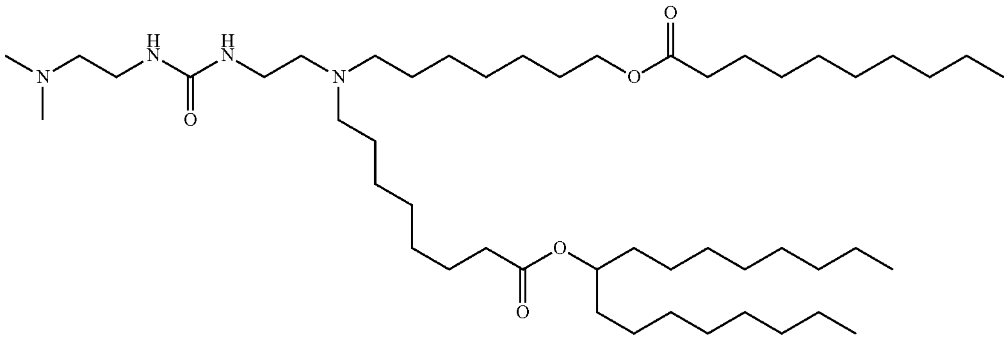 [SMILES: CCCCCCCCCC(=O)OCCCCCCCN(CCCCCCCC(=O)OC(CCCCCCCC)CCCCCCCC)CCNC(=O)NCCN(C)C] | 823.3 |

TABLE 1-continued
| # | Structure | Mw |
| --- | --- | --- |
| 1763. | 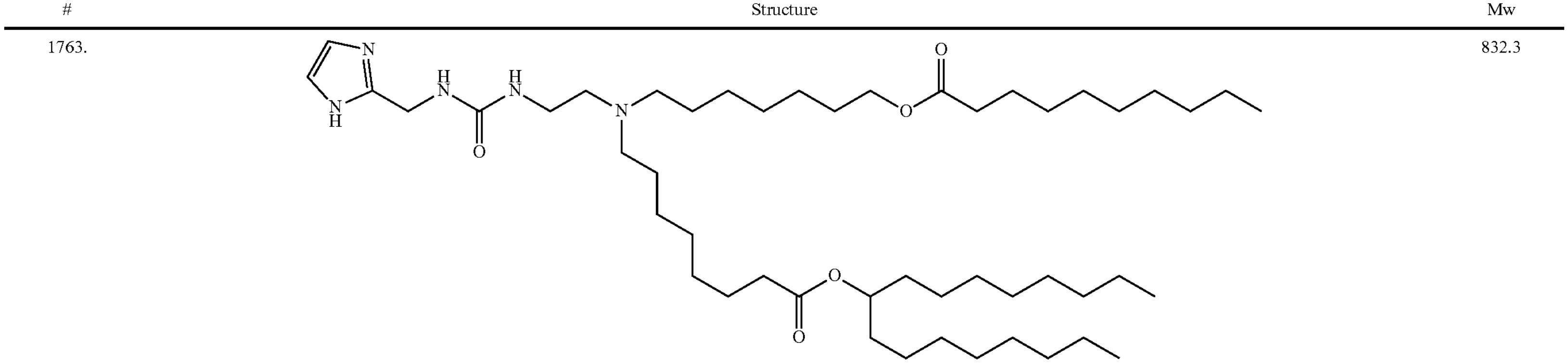 | 832.3 |
| 1764. | 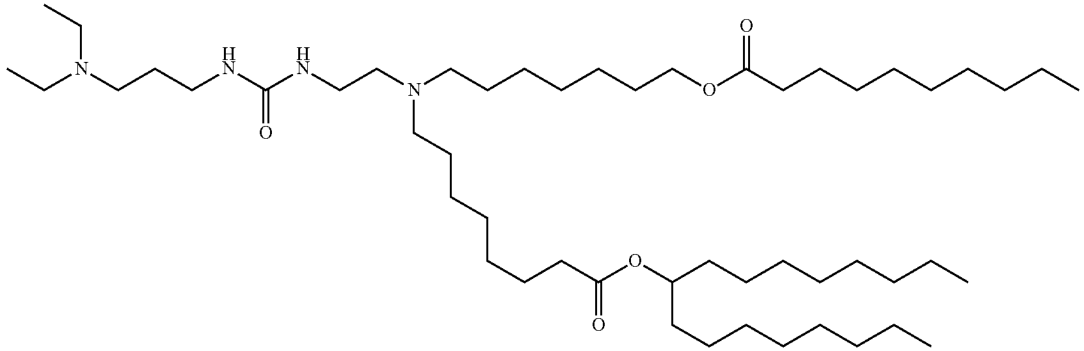 [SMILES: CCCCCCCCCC(=O)OCCCCCCCN(CCCCCCCC(=O)OC(CCCCCCCC)CCCCCCCC)CCNC(=O)NCCCN(CC)CC] | 865.4 |
| 1765. | 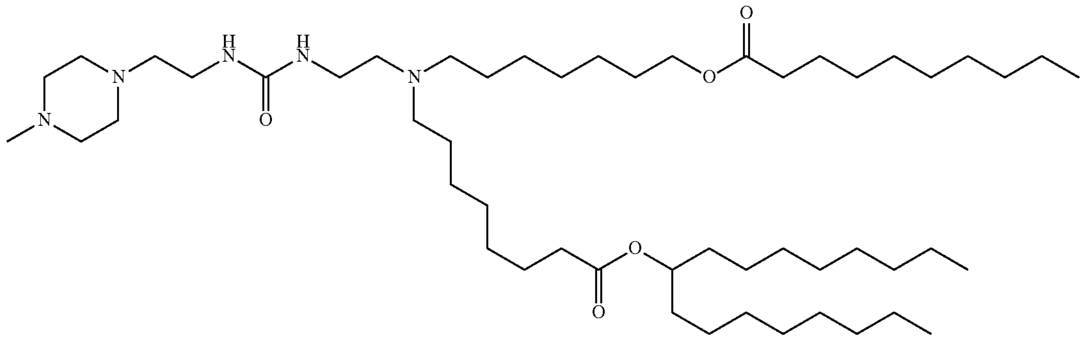 [SMILES: CCCCCCCCCC(=O)OCCCCCCCN(CCCCCCCC(=O)OC(CCCCCCCC)CCCCCCCC)CCNC(=O)NCCN1CCN(C)CC1] | 878.4 |

TABLE 1-continued
| # | Structure | Mw |
|---|---|---|
| 1766. | 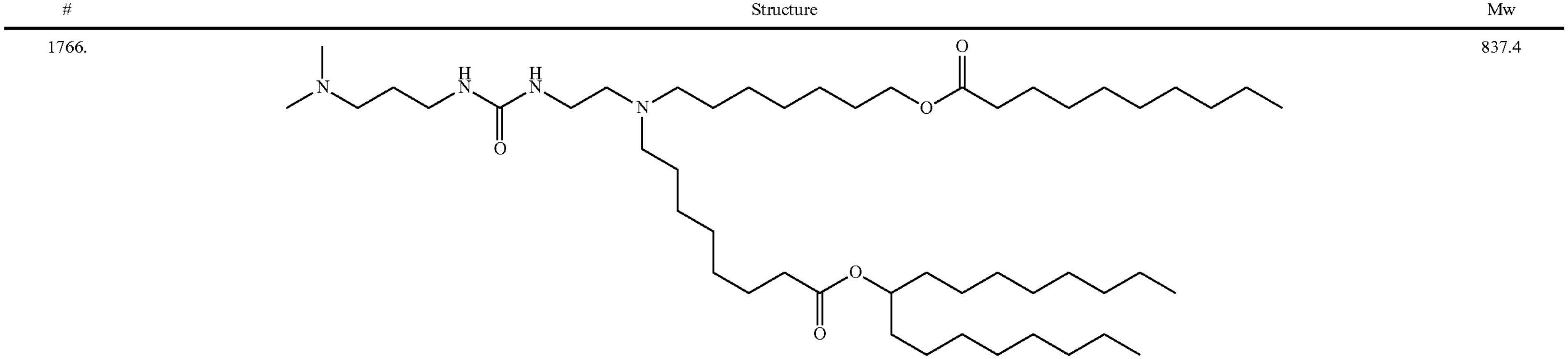 | 837.4 |
| 1767. | 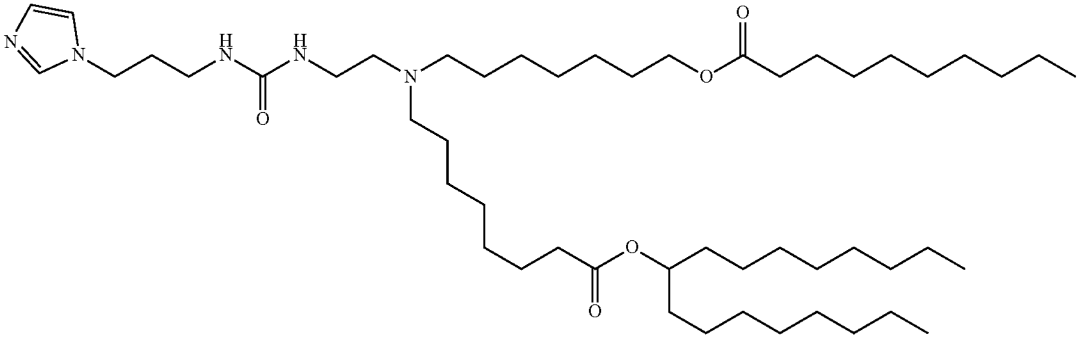 [SMILES: CCCCCCCCCC(=O)OCCCCCCCN(CCCCCCCC(=O)OC(CCCCCCCC)CCCCCCCC)CCNC(=O)NCCCn1ccnc1] | 860.4 |
| 1768. | 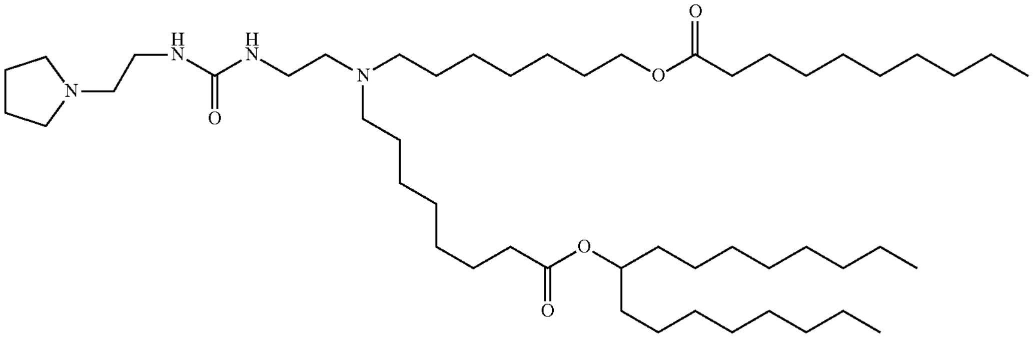 [SMILES: CCCCCCCCCC(=O)OCCCCCCCN(CCCCCCCC(=O)OC(CCCCCCCC)CCCCCCCC)CCNC(=O)NCCN1CCCC1] | 849.4 |

TABLE 1-continued
| # | Structure | Mw |
| --- | --- | --- |
| 1769. | 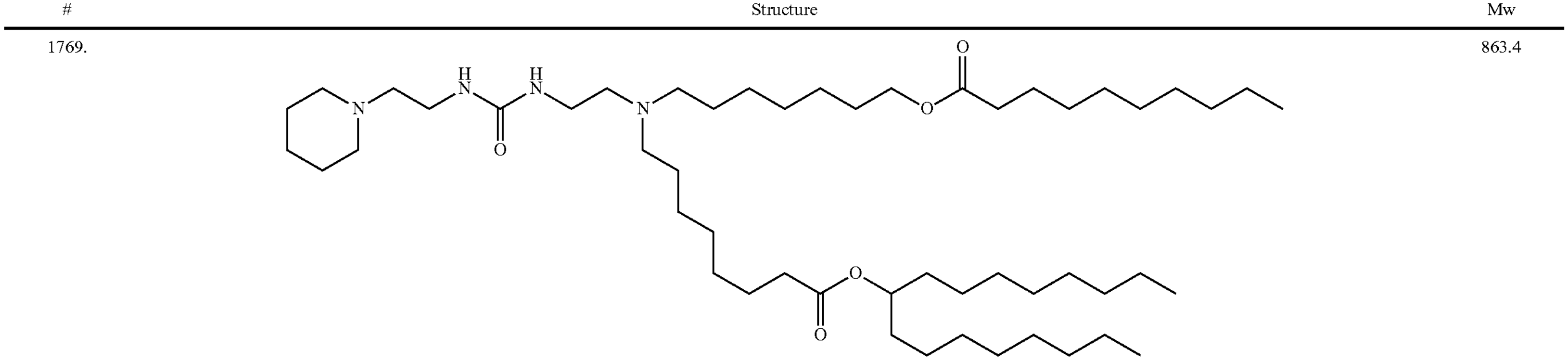 | 863.4 |
| 1770. | 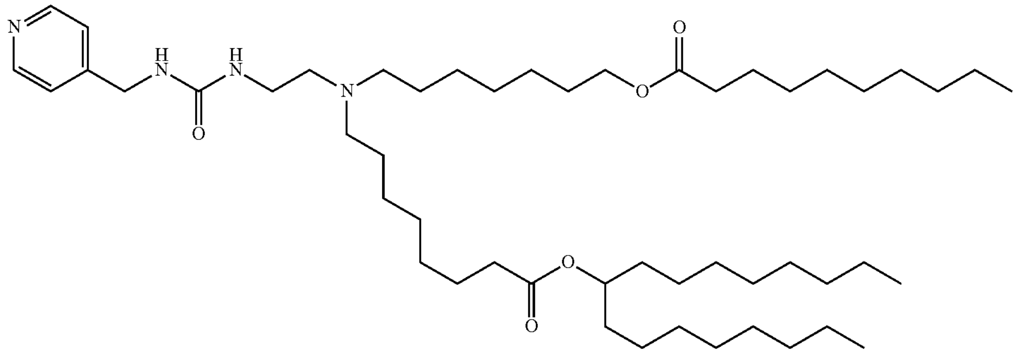 [SMILES: CCCCCCCCCC(=O)OCCCCCCCN(CCCCCCCC(=O)OC(CCCCCCCC)CCCCCCCC)CCNC(=O)NCc1ccncc1] | 843.3 |
| 1771. | 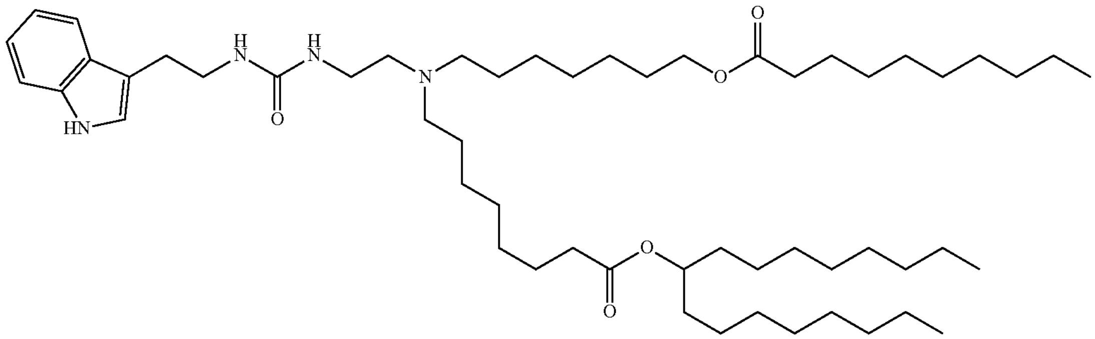 [SMILES: CCCCCCCCCC(=O)OCCCCCCCN(CCCCCCCC(=O)OC(CCCCCCCC)CCCCCCCC)CCNC(=O)NCCc1c[nH]c2ccccc12] | 895.4 |

TABLE 1-continued
| # | Structure | Mw |
|---|---|---|
| 1772. | 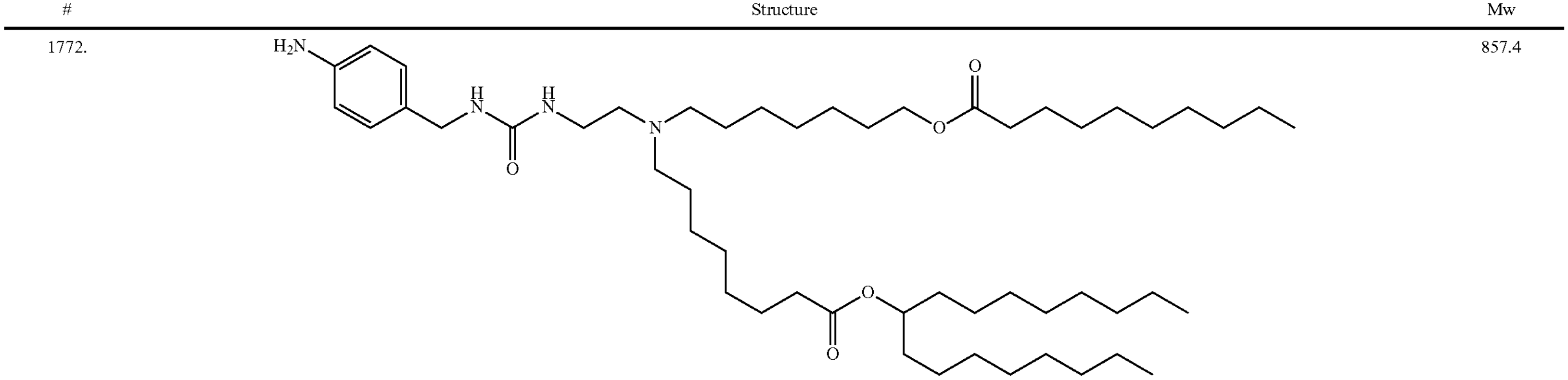 | 857.4 |
| 1773. | 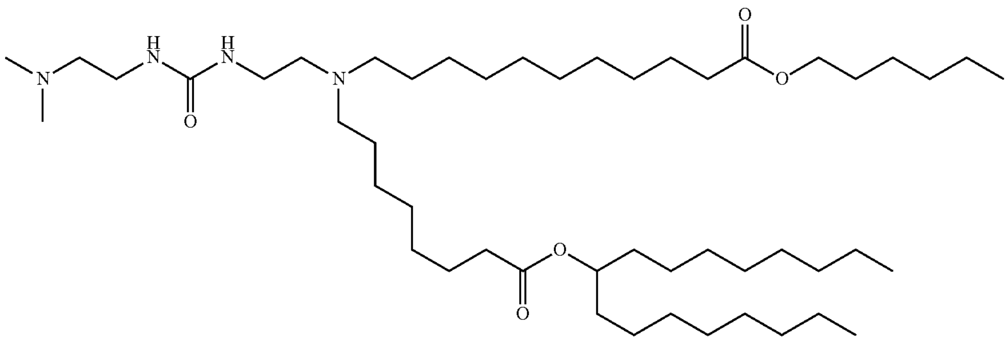 [SMILES: CCCCCCCCC(CCCCCCCC)OC(=O)CCCCCCCN(CCCCCCCCCCC(=O)OCCCCCC)CCNC(=O)NCCN(C)C] | 823.3 |
| 1774. | 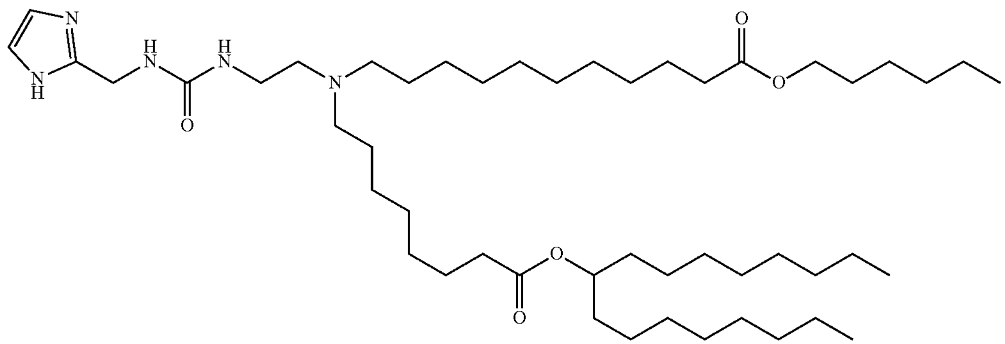 [SMILES: CCCCCCCCC(CCCCCCCC)OC(=O)CCCCCCCN(CCCCCCCCCCC(=O)OCCCCCC)CCNC(=O)NCc1ncc[nH]1] | 832.3 |

TABLE 1-continued
| # | Structure | Mw |
|---|---|---|
| 1775. | 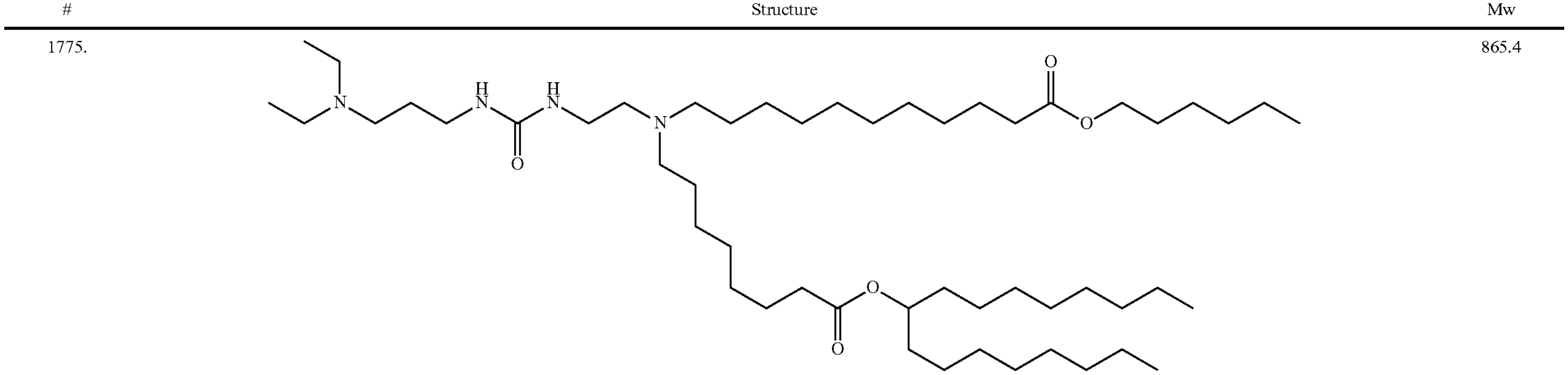 | 865.4 |
| 1776. | 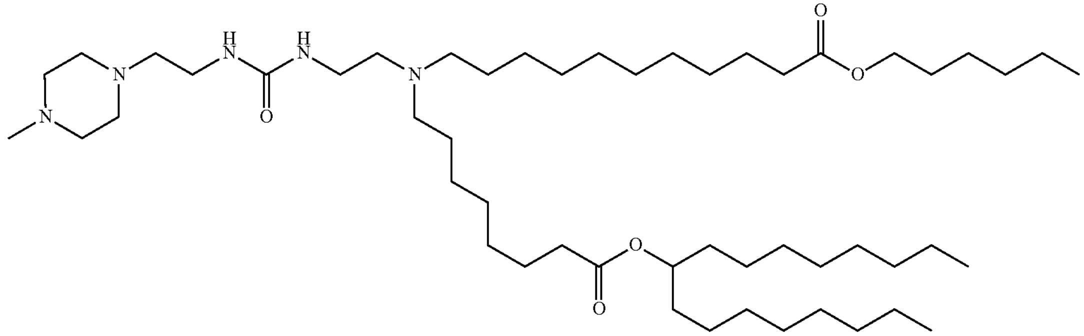 [SMILES: CCCCCCCCC(CCCCCCCC)OC(=O)CCCCCCCN(CCCCCCCCCCC(=O)OCCCCCC)CCNC(=O)NCCN1CCN(C)CC1] | 878.4 |
| 1777. | 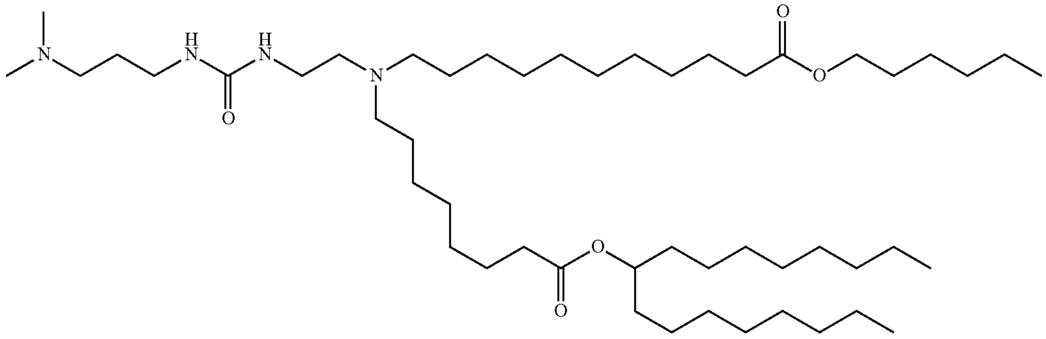 | 837.4 |

TABLE 1-continued
| # | Structure | Mw |
| --- | --- | --- |
| 1778. | 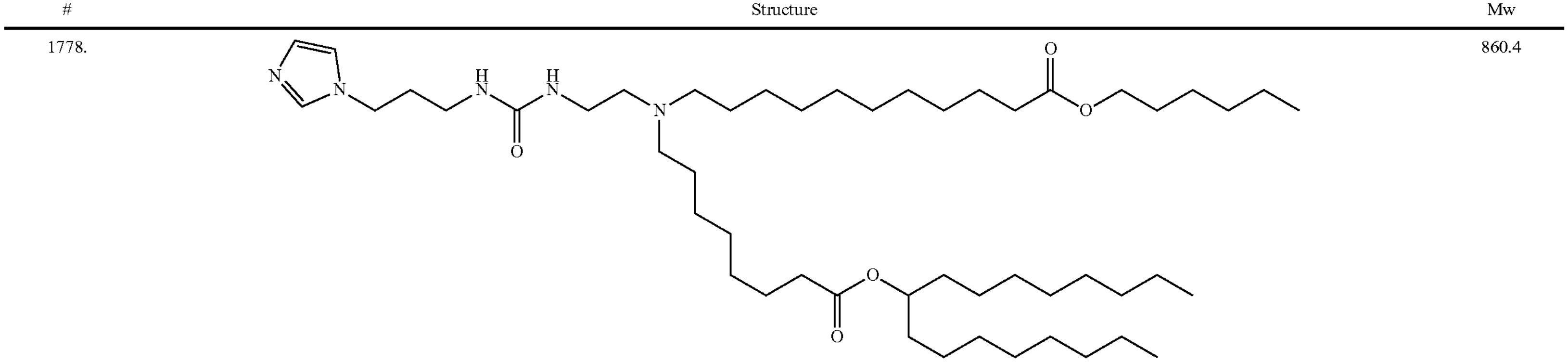 | 860.4 |
| 1779. | 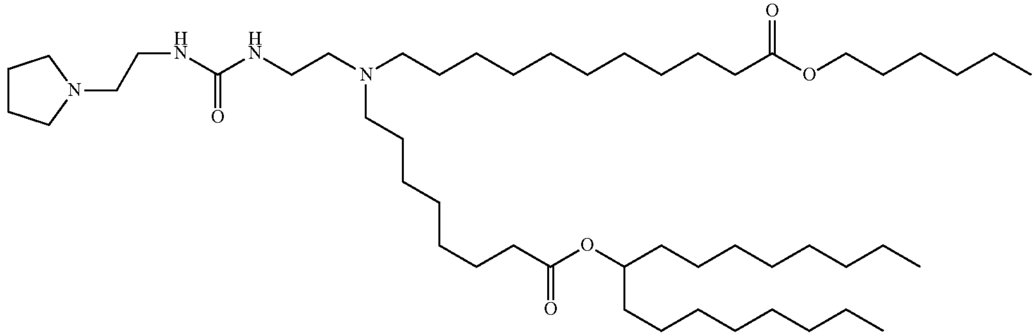 [SMILES: CCCCCCCCC(CCCCCCCC)OC(=O)CCCCCCCN(CCCCCCCCCCC(=O)OCCCCCC)CCNC(=O)NCCN1CCCC1] | 849.4 |
| 1780. | 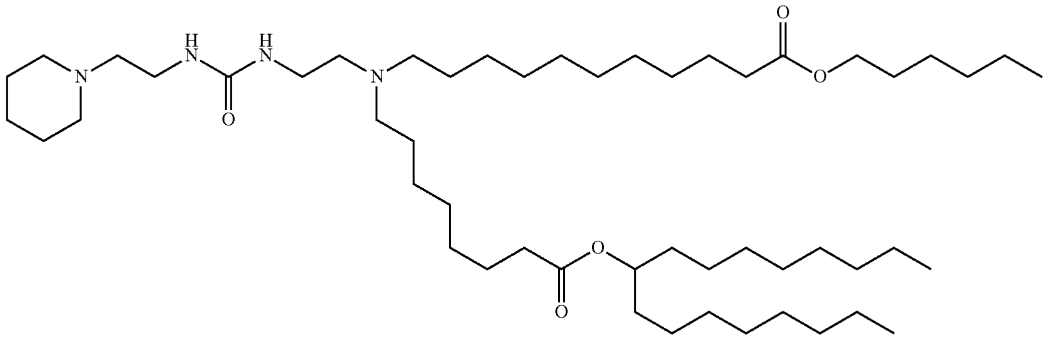 [SMILES: CCCCCCCCC(CCCCCCCC)OC(=O)CCCCCCCN(CCCCCCCCCCC(=O)OCCCCCC)CCNC(=O)NCCN1CCCCC1] | 863.4 |

TABLE 1-continued
| # | Structure | Mw |
|---|---|---|
| 1781. | 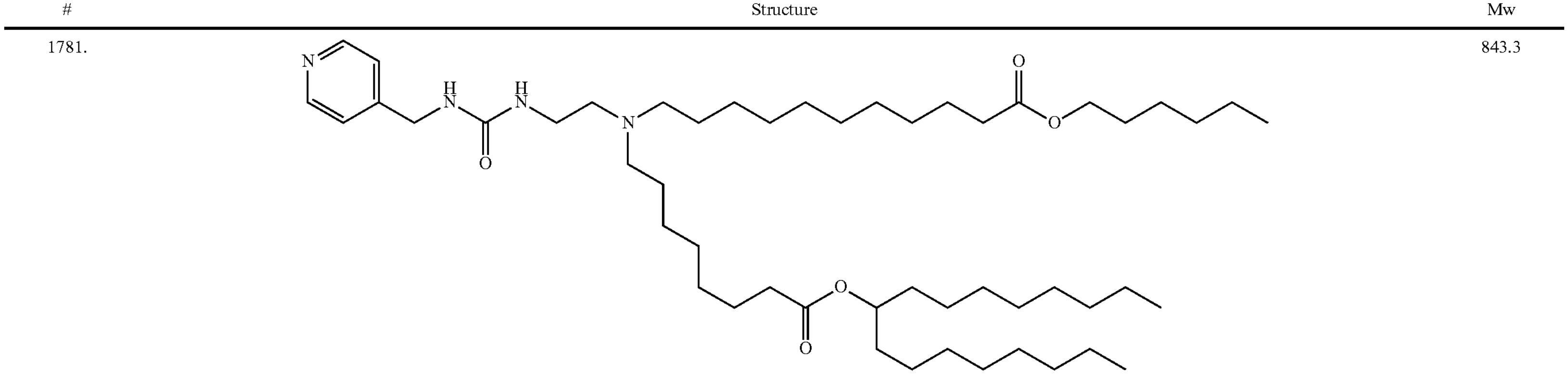 | 843.3 |
| 1782. | 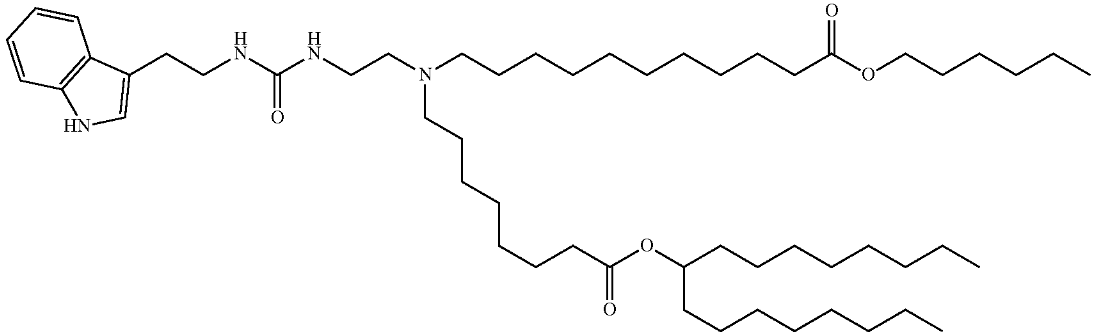 [SMILES: CCCCCCCCC(CCCCCCCC)OC(=O)CCCCCCCN(CCCCCCCCCCC(=O)OCCCCCC)CCNC(=O)NCCc1c[nH]c2ccccc12] | 895.4 |
| 1783. | 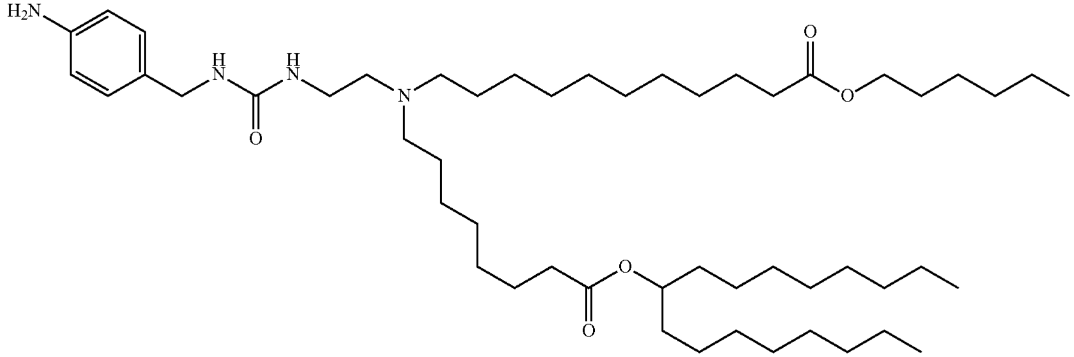 [SMILES: CCCCCCCCC(CCCCCCCC)OC(=O)CCCCCCCN(CCCCCCCCCCC(=O)OCCCCCC)CCNC(=O)NCc1ccc(N)cc1] | 857.4 |

TABLE 1-continued
| # | Structure | Mw |
|---|---|---|
| 1784. | 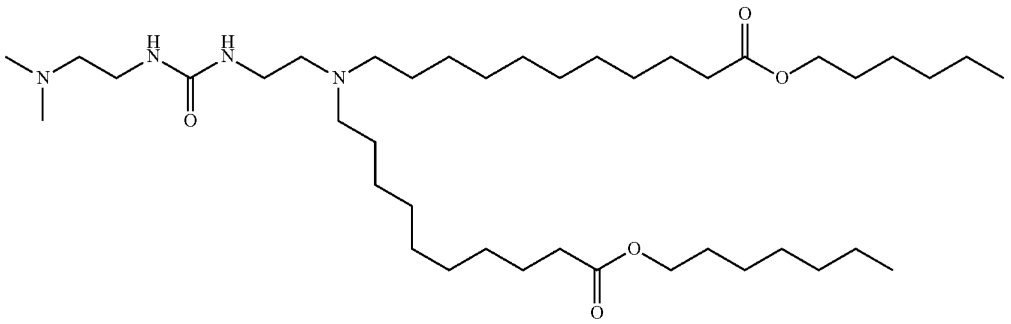 [SMILES: CCCCCCCOC(=O)CCCCCCCCCN(CCCCCCCCCCC(=O)OCCCCCC)CCNC(=O)NCCN(C)C] | 711.1 |
| 1785. | 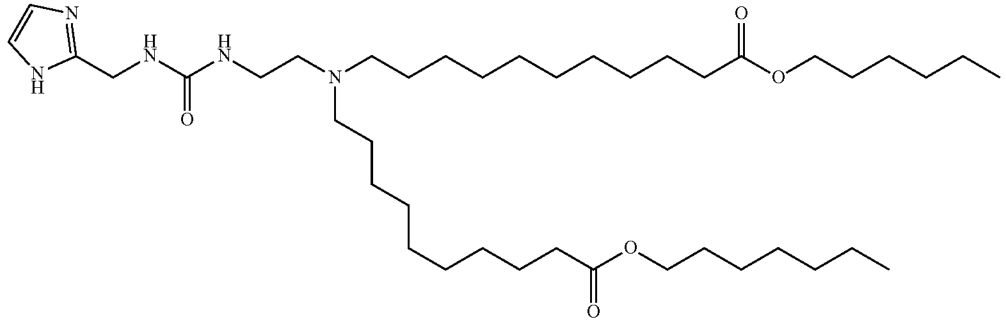 [SMILES: CCCCCCCOC(=O)CCCCCCCCCN(CCCCCCCCCCC(=O)OCCCCCC)CCNC(=O)NCc1ncc[nH]1] | 720.1 |
| 1786. | 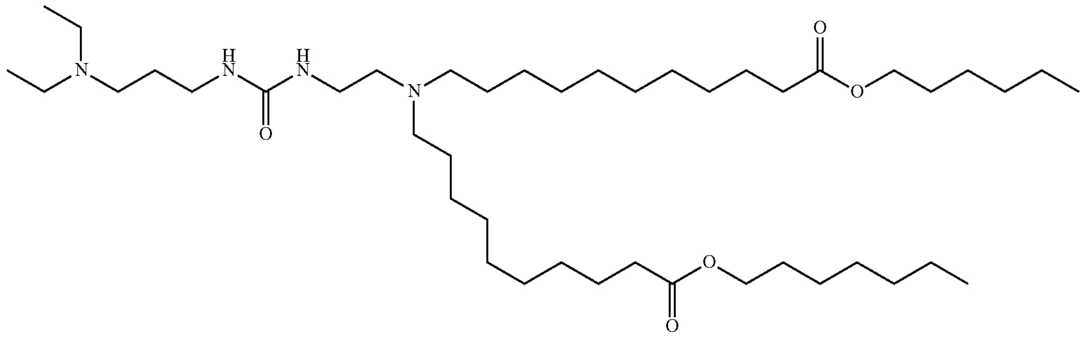 [SMILES: CCCCCCCOC(=O)CCCCCCCCCN(CCCCCCCCCCC(=O)OCCCCCC)CCNC(=O)NCCCN(CC)CC] | 753.2 |

TABLE 1-continued
| # | Structure | Mw |
| --- | --- | --- |
| 1787. | 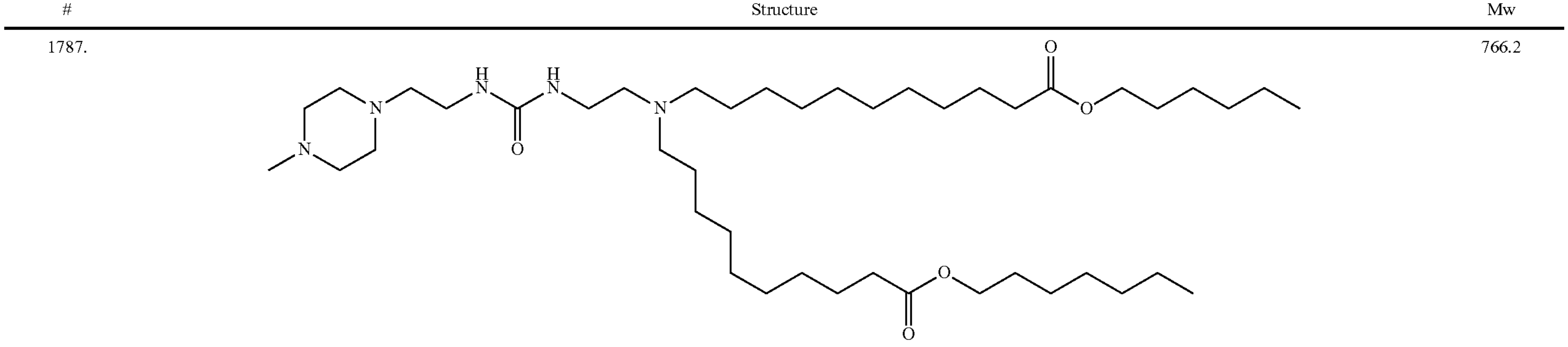 | 766.2 |
| 1788. | 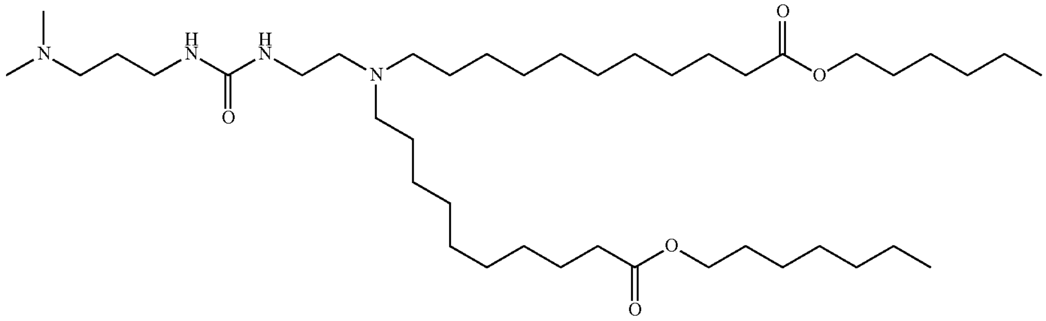 [SMILES: CCCCCCCOC(=O)CCCCCCCCCN(CCCCCCCCCCC(=O)OCCCCCC)CCNC(=O)NCCCN(C)C] | 725.2 |
| 1789. | 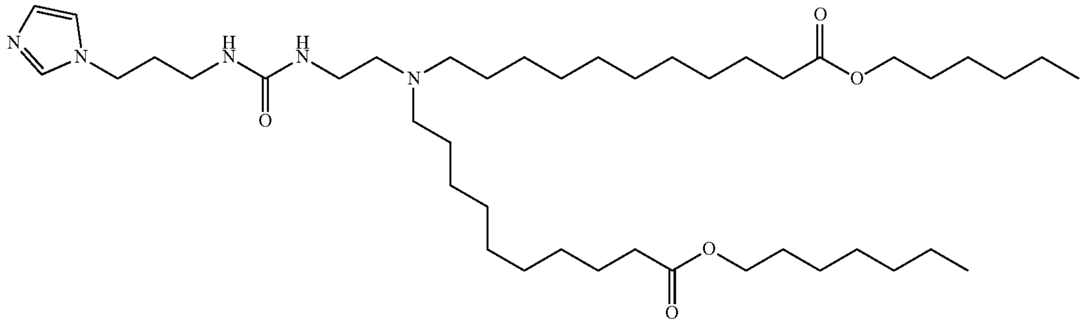 [SMILES: CCCCCCCOC(=O)CCCCCCCCCN(CCCCCCCCCCC(=O)OCCCCCC)CCNC(=O)NCCCn1ccnc1] | 748.2 |

TABLE 1-continued
| # | Structure | Mw |
|---|---|---|
| 1790. | 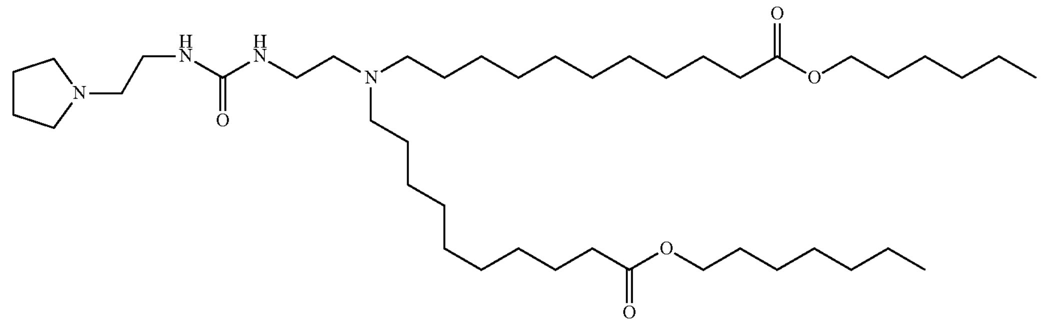 [SMILES: CCCCCCCOC(=O)CCCCCCCCCN(CCCCCCCCCCC(=O)OCCCCCC)CCNC(=O)NCCN1CCCC1] | 737.2 |
| 1791. | 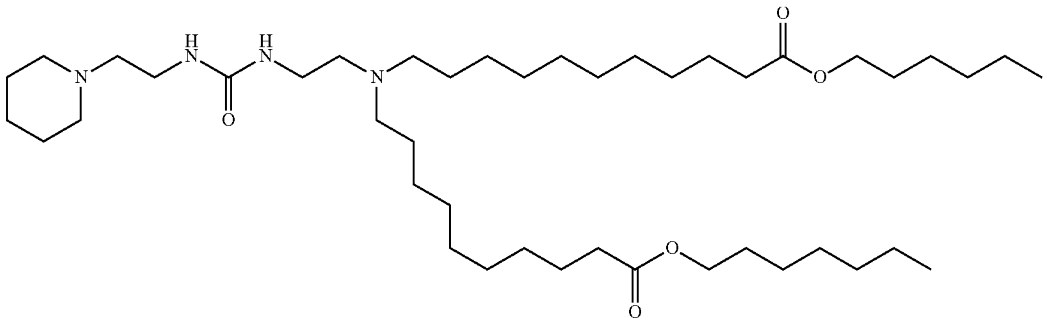 [SMILES: CCCCCCCOC(=O)CCCCCCCCCN(CCCCCCCCCCC(=O)OCCCCCC)CCNC(=O)NCCN1CCCCC1] | 751.2 |
| 1792. | 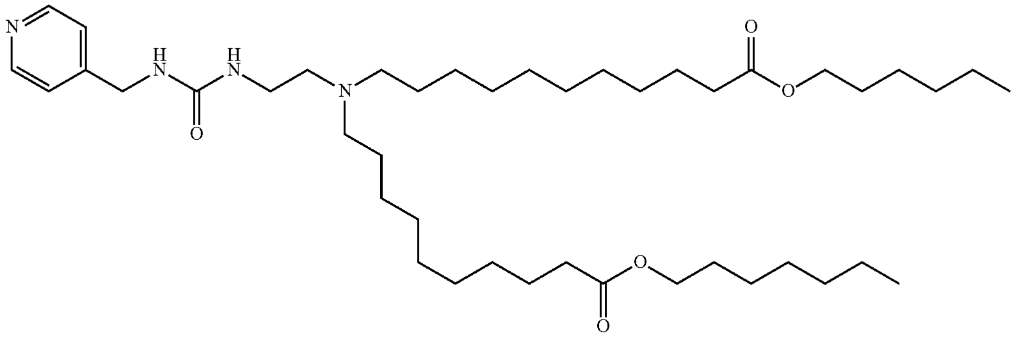 [SMILES: CCCCCCCOC(=O)CCCCCCCCCN(CCCCCCCCCCC(=O)OCCCCCC)CCNC(=O)NCc1ccncc1] | 731.1 |

TABLE 1-continued
| # | Structure | Mw |
|---|---|---|
| 1793. | 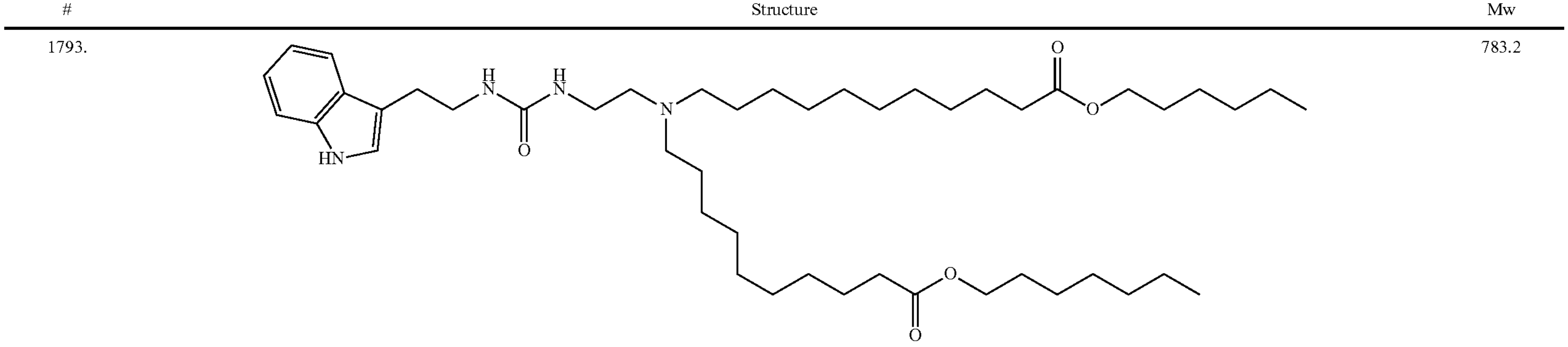 | 783.2 |
| 1794. | 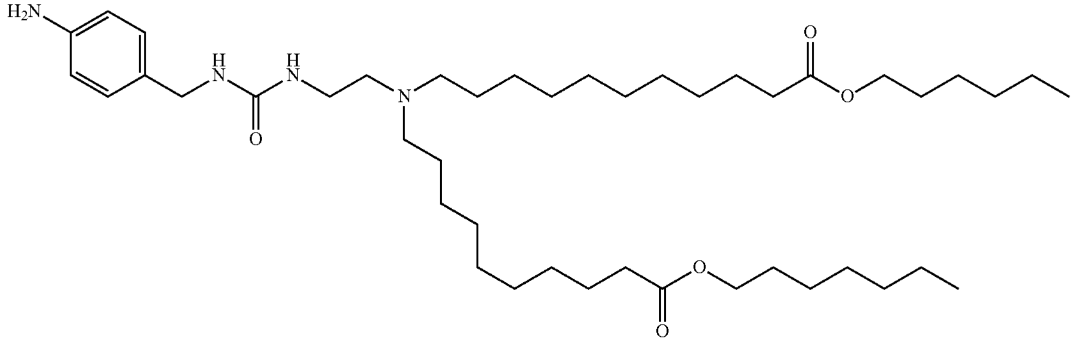 [SMILES: CCCCCCCOC(=O)CCCCCCCCCN(CCCCCCCCCCC(=O)OCCCCCC)CCNC(=O)NCc1ccc(N)cc1] | 745.1 |
| 1795. | 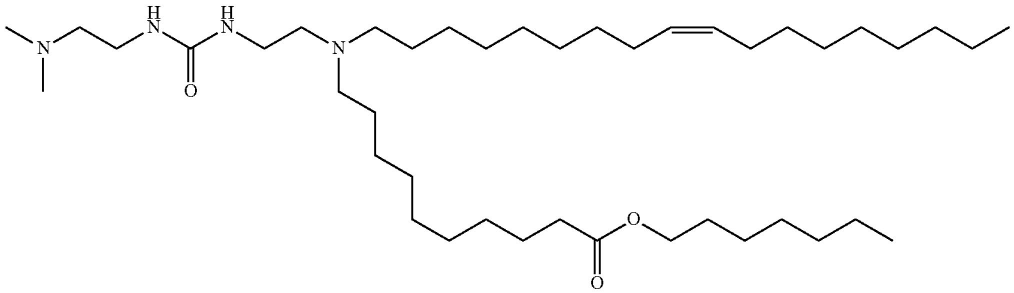 [SMILES: CCCCCCCC/C=C\CCCCCCCCN(CCCCCCCCCC(=O)OCCCCCCC)CCNC(=O)NCCN(C)C] | 693.2 |

TABLE 1-continued
| # | Structure | Mw |
| --- | --- | --- |
| 1796. | 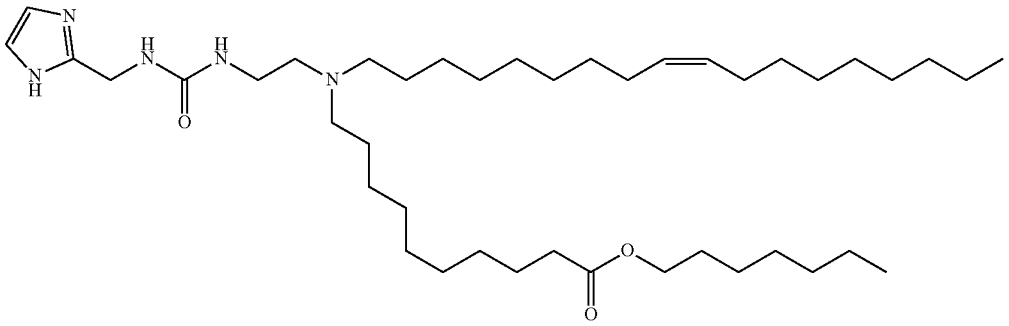 [SMILES: CCCCCCCC/C=C\CCCCCCCCN(CCCCCCCCCC(=O)OCCCCCCC)CCNC(=O)NCc1ncc[nH]1] | 702.1 |
| 1797. | 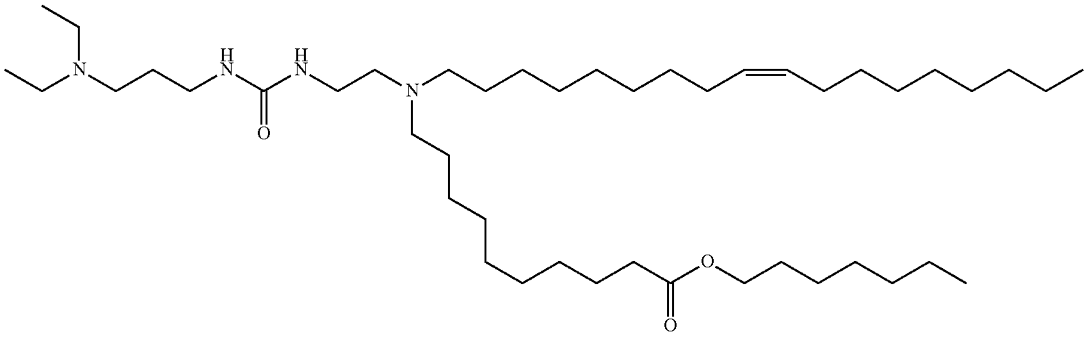 [SMILES: CCCCCCCC/C=C\CCCCCCCCN(CCCCCCCCCC(=O)OCCCCCCC)CCNC(=O)NCCCN(CC)CC] | 735.2 |
| 1798. | 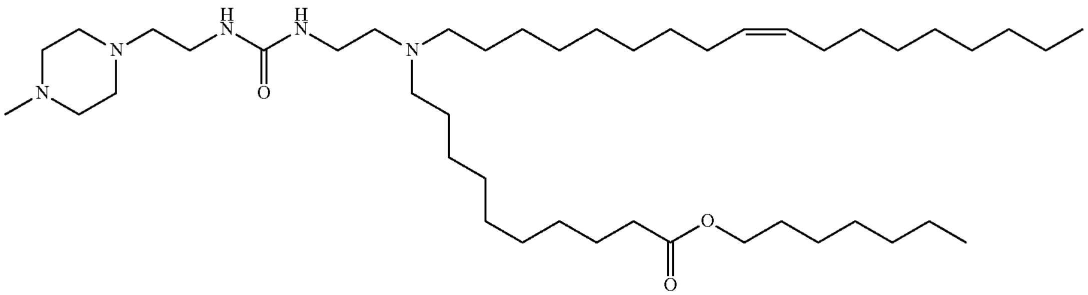 [SMILES: CCCCCCCC/C=C\CCCCCCCCN(CCCCCCCCCC(=O)OCCCCCCC)CCNC(=O)NCCN1CCN(C)CC1] | 748.2 |

TABLE 1-continued
| # | Structure | Mw |
| --- | --- | --- |
| 1799. | 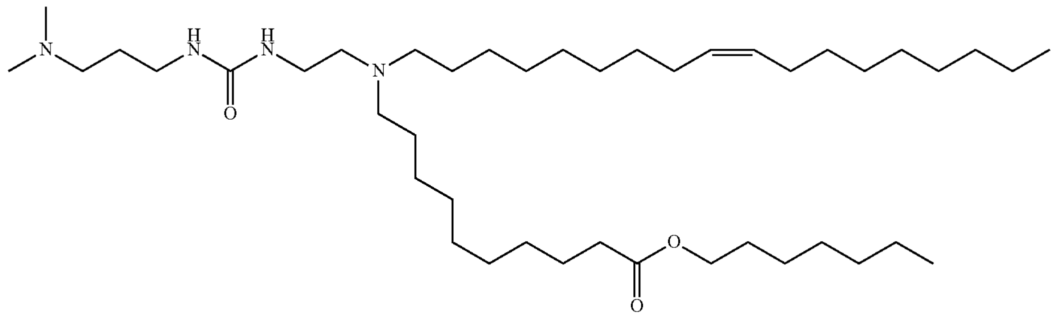 | 707.2 |
| 1800. | 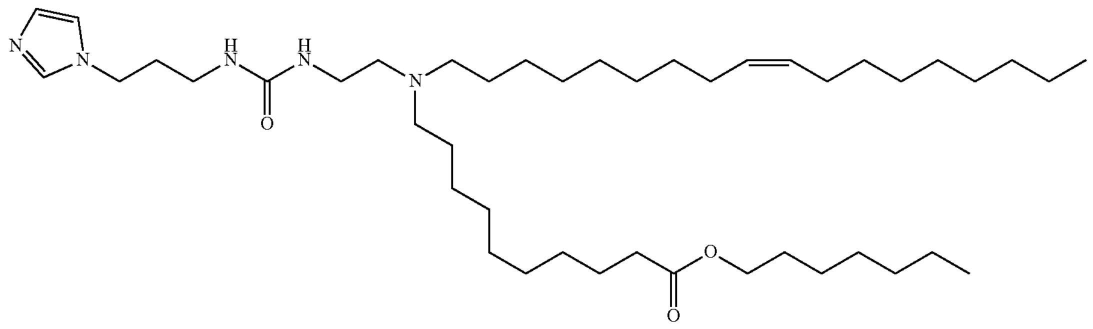 [SMILES: CCCCCCCC/C=C\CCCCCCCCN(CCCCCCCCCC(=O)OCCCCCCC)CCNC(=O)NCCCn1ccnc1] | 730.2 |
| 1801. | 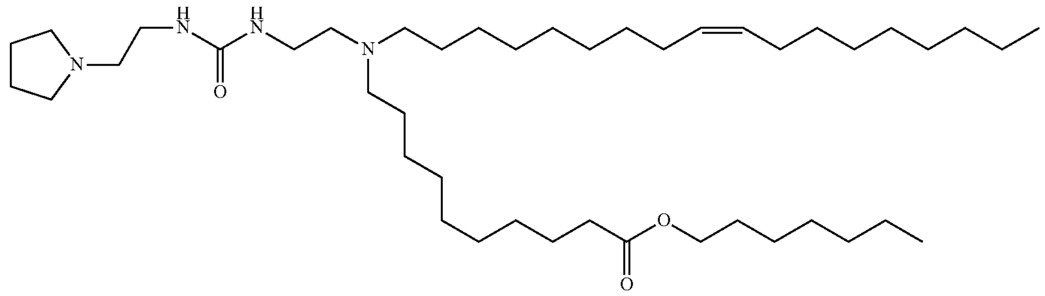 [SMILES: CCCCCCCC/C=C\CCCCCCCCN(CCCCCCCCCC(=O)OCCCCCCC)CCNC(=O)NCCN1CCCC1] | 719.2 |

TABLE 1-continued
| # | Structure | Mw |
|---|---|---|
| 1802. | 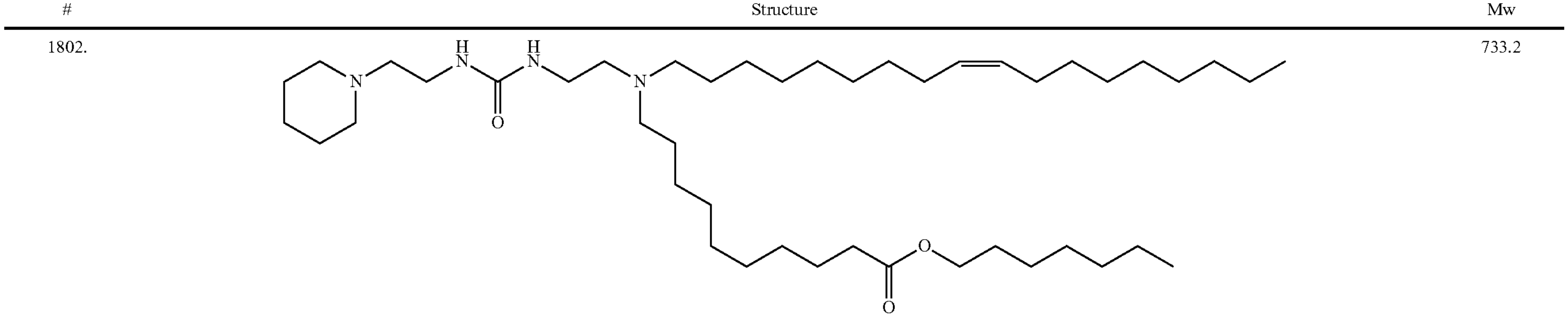 | 733.2 |
| 1803. | 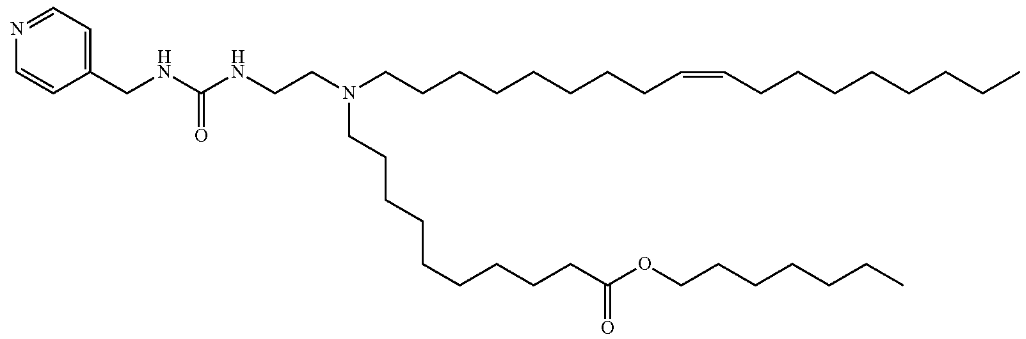 [SMILES: CCCCCCCC/C=C\CCCCCCCCN(CCCCCCCCCC(=O)OCCCCCCC)CCNC(=O)NCc1ccncc1] | 713.1 |
| 1804. | 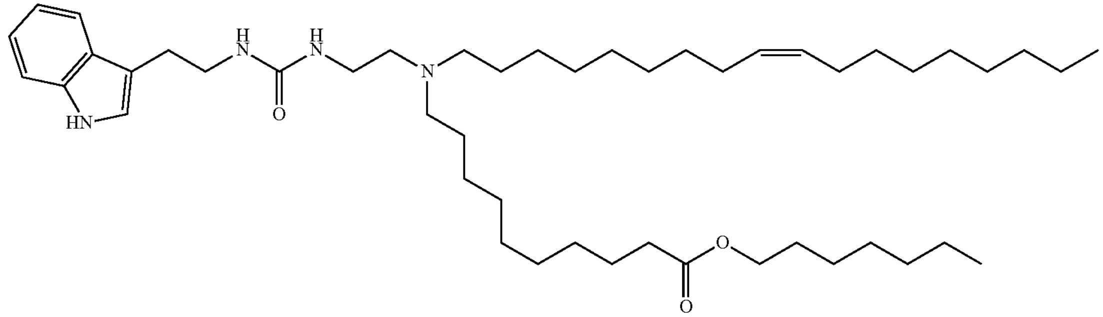 [SMILES: CCCCCCCC/C=C\CCCCCCCCN(CCCCCCCCCC(=O)OCCCCCCC)CCNC(=O)NCCc1c[nH]c2ccccc12] | 765.2 |

TABLE 1-continued
| # | Structure | Mw |
|---|---|---|
| 1805. | 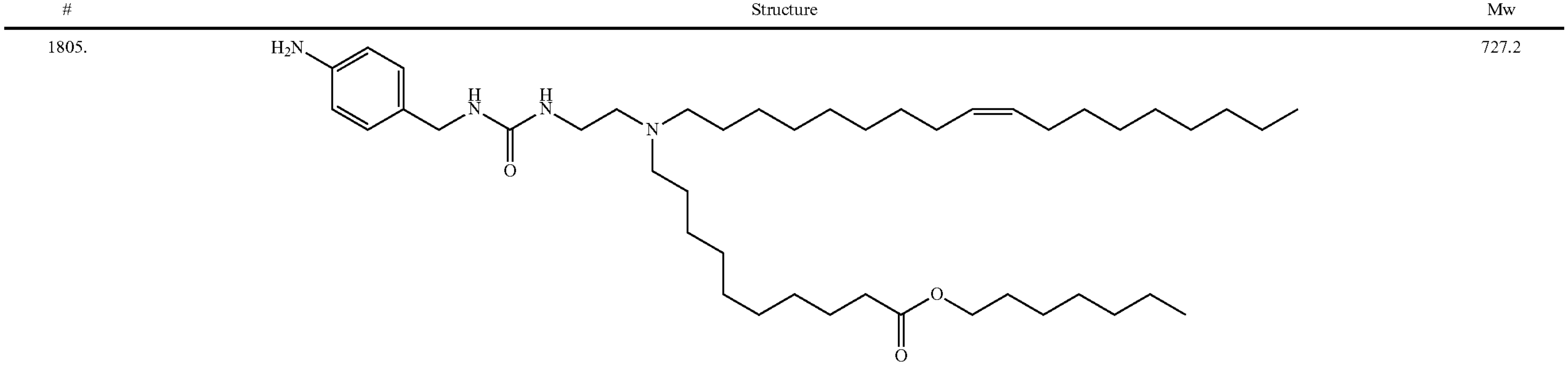 | 727.2 |
| 1806. | 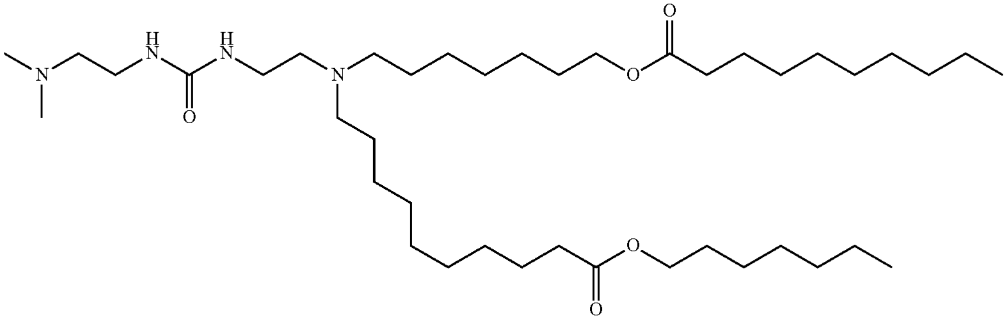 [SMILES: CCCCCCCCCC(=O)OCCCCCCCN(CCCCCCCCCC(=O)OCCCCCCC)CCNC(=O)NCCN(C)C] | 711.1 |
| 1807. | 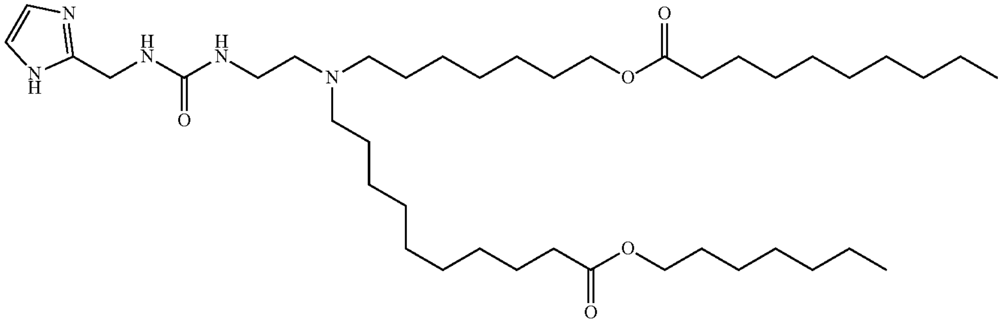 [SMILES: CCCCCCCCCC(=O)OCCCCCCCN(CCCCCCCCCC(=O)OCCCCCCC)CCNC(=O)NCc1ncc[nH]1] | 720.1 |

TABLE 1-continued
| # | Structure | Mw |
| --- | --- | --- |
| 1808. | 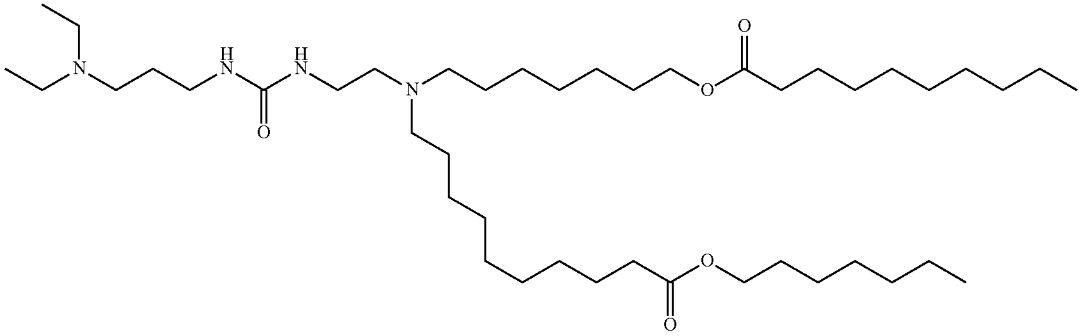 [SMILES: CCCCCCCCCC(=O)OCCCCCCCN(CCCCCCCCCC(=O)OCCCCCCC)CCNC(=O)NCCCN(CC)CC] | 753.2 |
| 1809. | 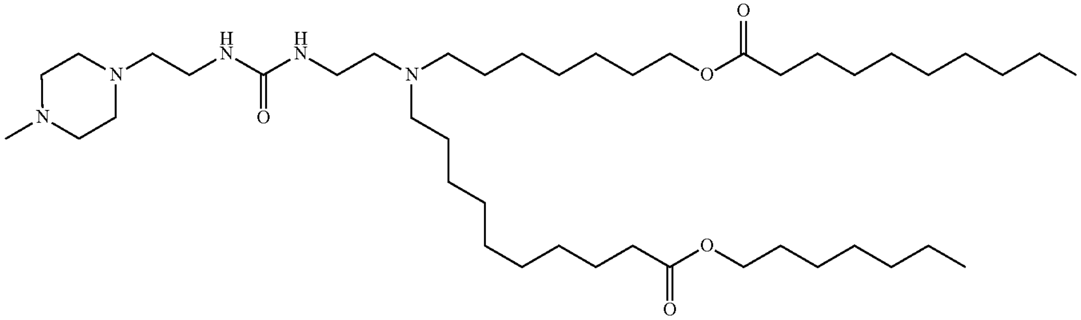 [SMILES: CCCCCCCCCC(=O)OCCCCCCCN(CCCCCCCCCC(=O)OCCCCCCC)CCNC(=O)NCCN1CCN(C)CC1] | 766.2 |
| 1810. | 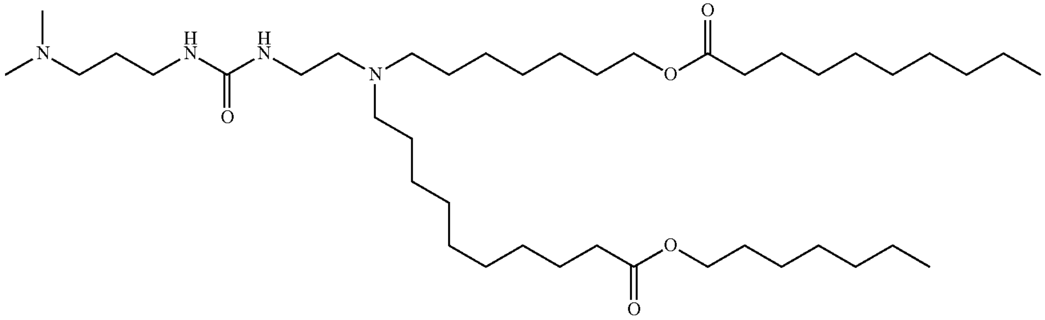 [SMILES: CCCCCCCCCC(=O)OCCCCCCCN(CCCCCCCCCC(=O)OCCCCCCC)CCNC(=O)NCCCN(C)C] | 725.2 |

TABLE 1-continued
| # | Structure | Mw |
| --- | --- | --- |
| 1811. | 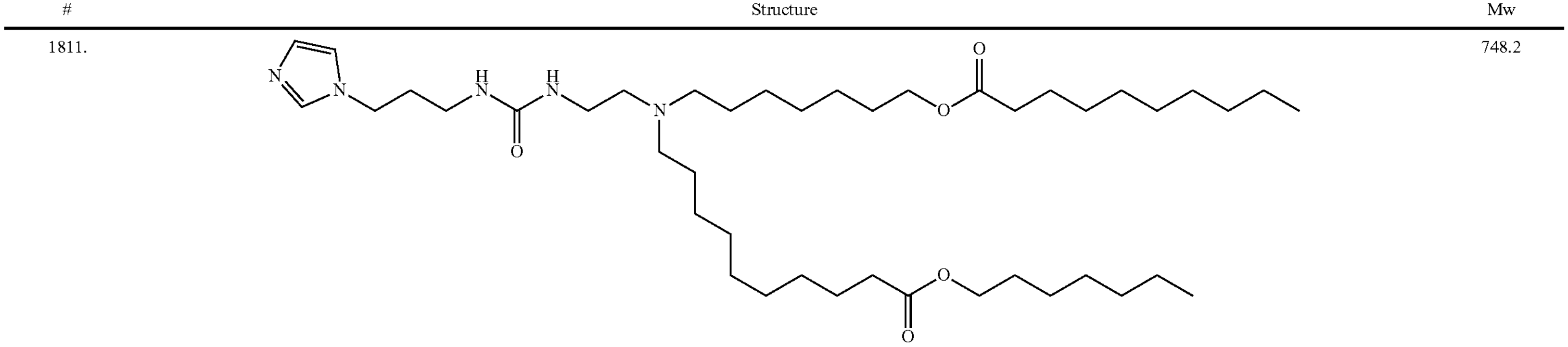 | 748.2 |
| 1812. | 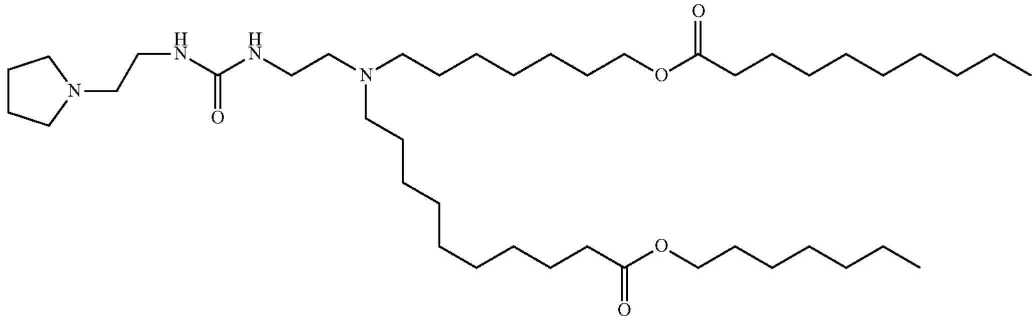 [SMILES: CCCCCCCCCC(=O)OCCCCCCCN(CCCCCCCCCC(=O)OCCCCCCC)CCNC(=O)NCCN1CCCC1] | 737.2 |
| 1813. | 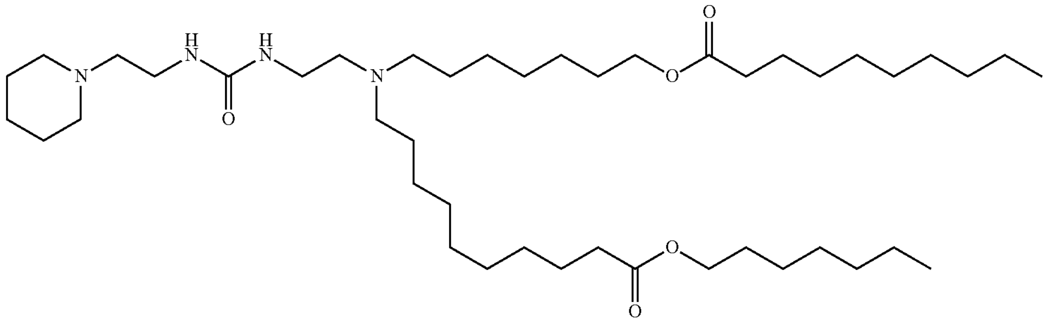 [SMILES: CCCCCCCCCC(=O)OCCCCCCCN(CCCCCCCCCC(=O)OCCCCCCC)CCNC(=O)NCCN1CCCCC1] | 751.2 |

TABLE 1-continued
| # | Structure | Mw |
| --- | --- | --- |
| 1814. | 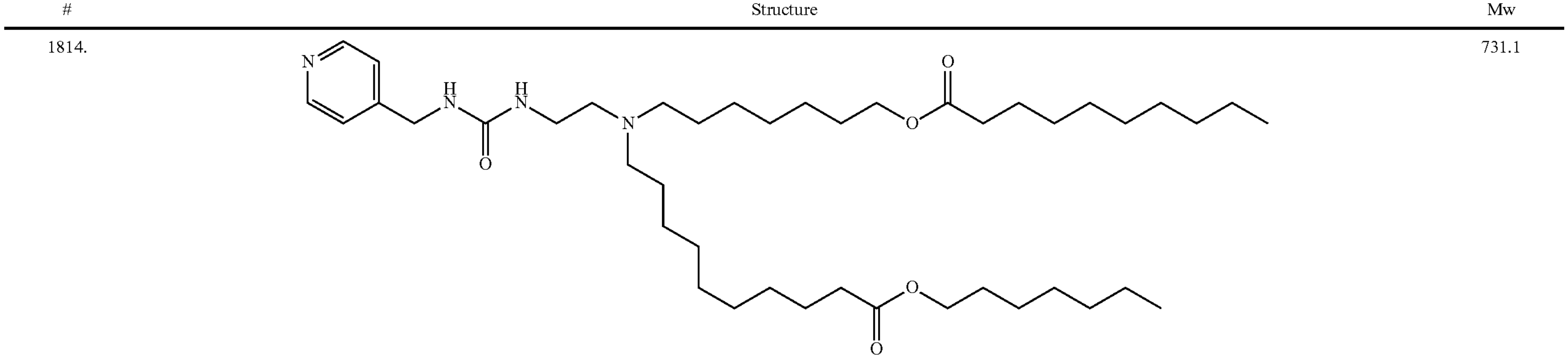 | 731.1 |
| 1815. | 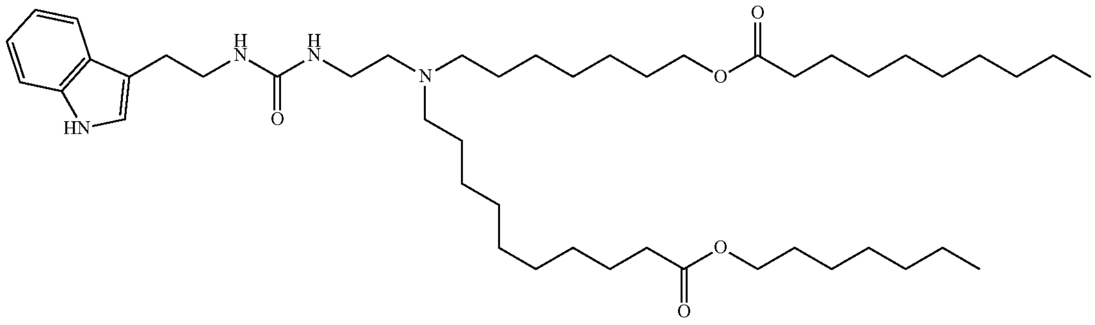 [SMILES: CCCCCCCCCC(=O)OCCCCCCCN(CCCCCCCCCC(=O)OCCCCCCC)CCNC(=O)NCCc1c[nH]c2ccccc12] | 783.2 |
| 1816. | 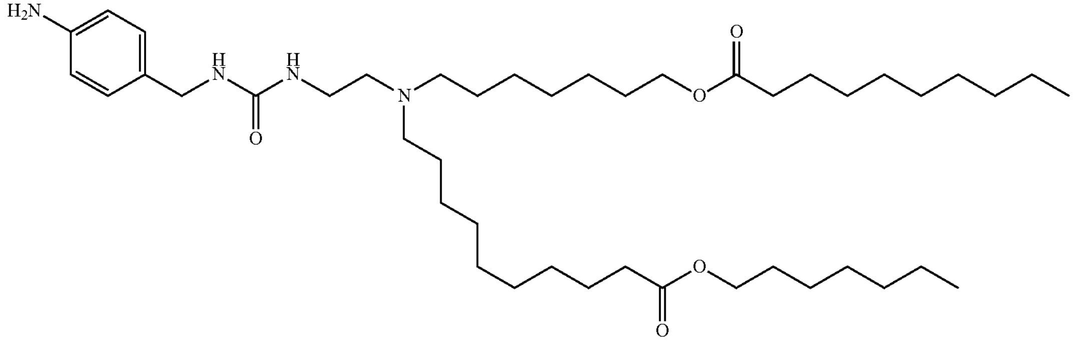 [SMILES: CCCCCCCCCC(=O)OCCCCCCCN(CCCCCCCCCC(=O)OCCCCCCC)CCNC(=O)NCc1ccc(N)cc1] | 745.1 |

TABLE 1-continued
| # | Structure | Mw |
| --- | --- | --- |
| 1817. | 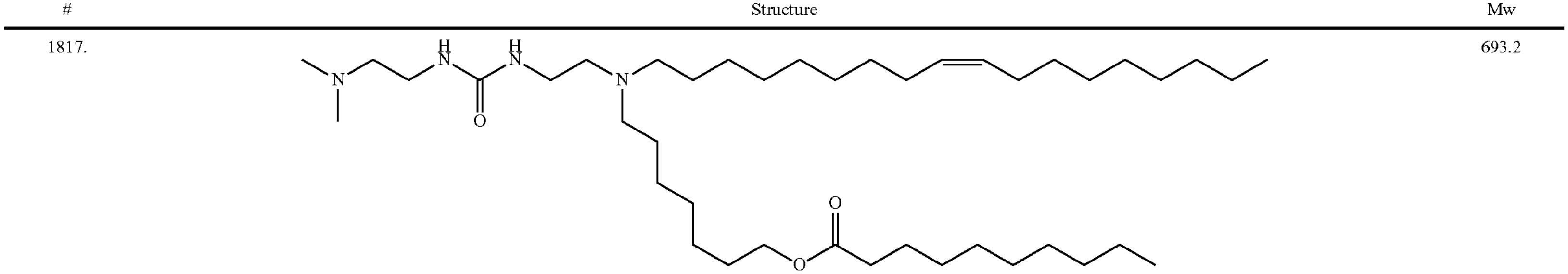 | 693.2 |
| 1818. | 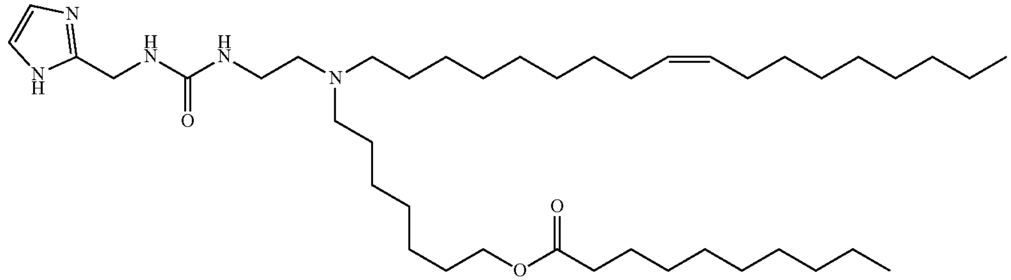 [SMILES: CCCCCCCC/C=C\CCCCCCCCN(CCCCCCCOC(=O)CCCCCCCCC)CCNC(=O)NCc1ncc[nH]1] | 702.1 |
| 1819. | 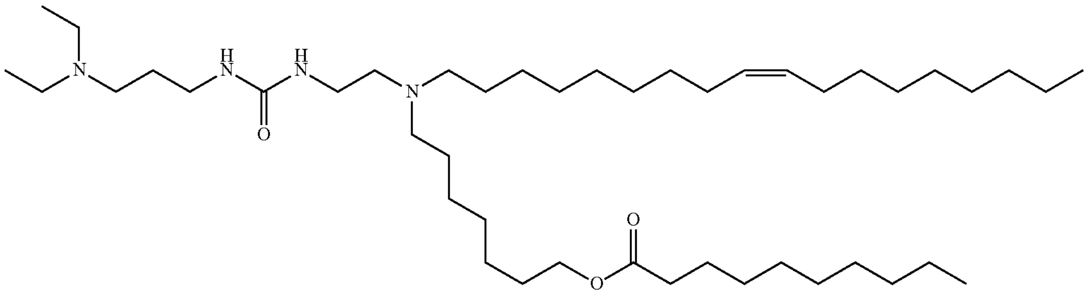 | 735.2 |

TABLE 1-continued
| # | Structure | Mw |
|---|---|---|
| 1820. | 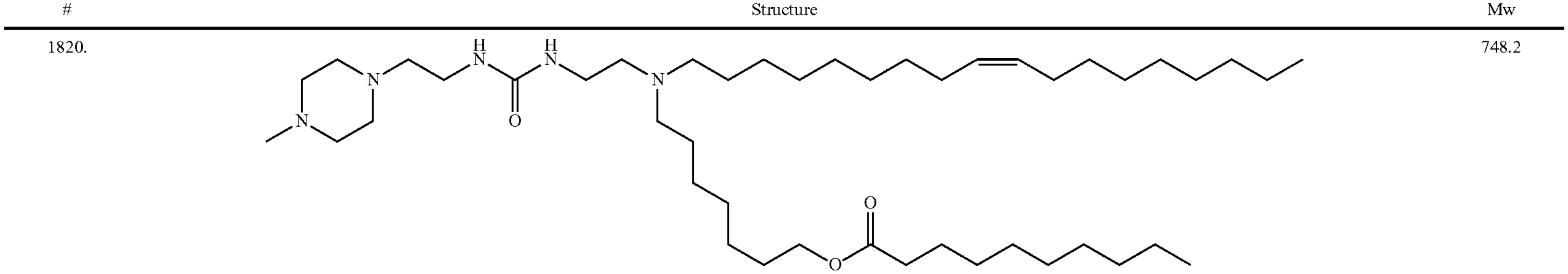 | 748.2 |
| 1821. | 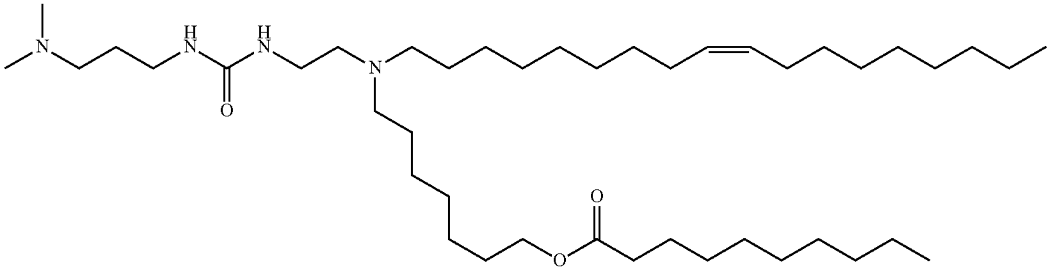 [SMILES: CCCCCCCC/C=C\CCCCCCCCN(CCCCCCCOC(=O)CCCCCCCCC)CCNC(=O)NCCCN(C)C] | 707.2 |
| 1822. | 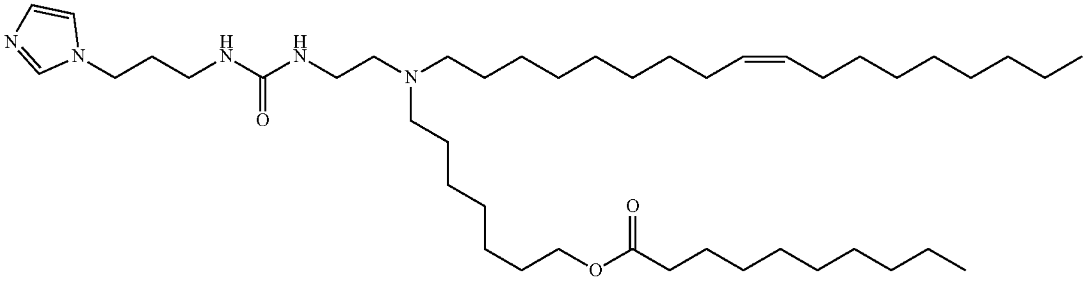 [SMILES: CCCCCCCC/C=C\CCCCCCCCN(CCCCCCCOC(=O)CCCCCCCCC)CCNC(=O)NCCCn1ccnc1] | 730.2 |

TABLE 1-continued
| # | Structure | Mw |
|---|---|---|
| 1823. | 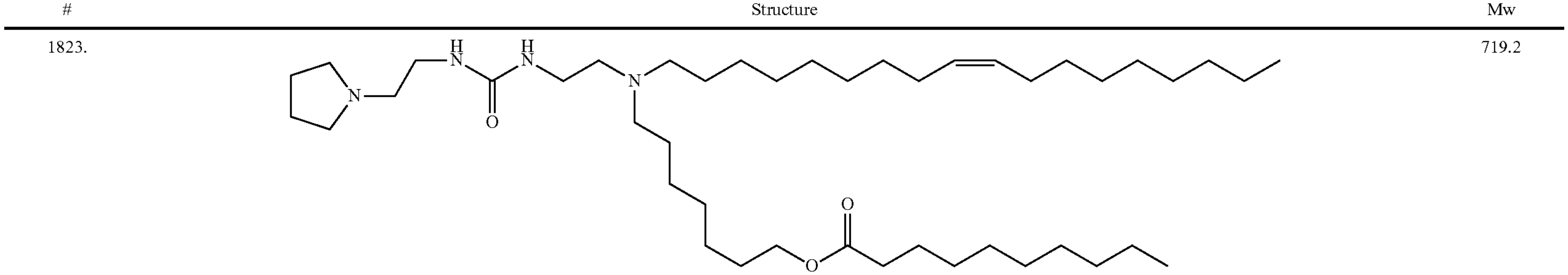 | 719.2 |
| 1824. | 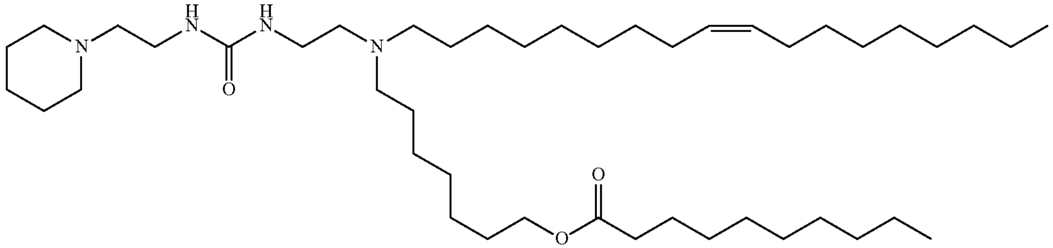 [SMILES: CCCCCCCC/C=C\CCCCCCCCN(CCCCCCCOC(=O)CCCCCCCCC)CCNC(=O)NCCN1CCCCC1] | 733.2 |
| 1825. | 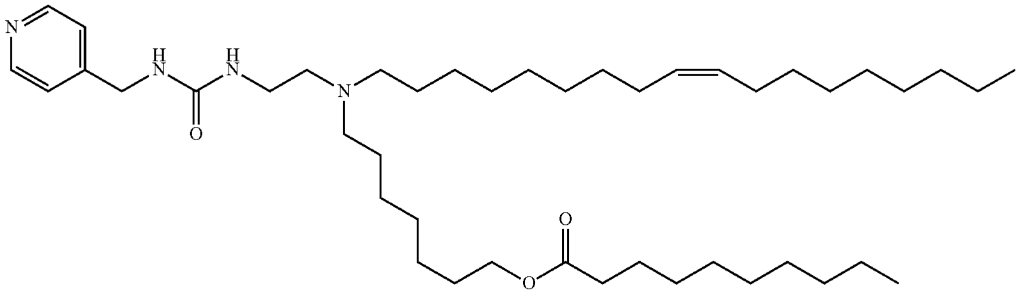 [SMILES: CCCCCCCC/C=C\CCCCCCCCN(CCCCCCCOC(=O)CCCCCCCCC)CCNC(=O)NCc1ccncc1] | 713.1 |

TABLE 1-continued
| # | Structure | Mw |
|---|---|---|
| 1826. | 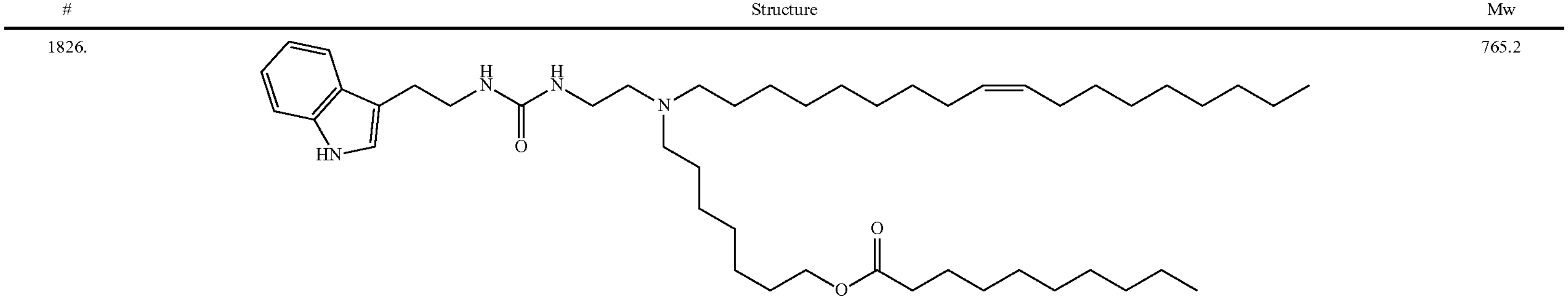 | 765.2 |
| 1827. | 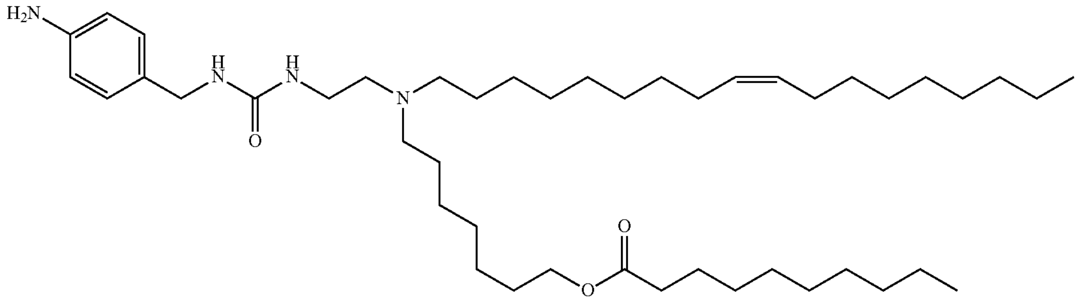 [SMILES: CCCCCCCC/C=C\CCCCCCCCN(CCCCCCCOC(=O)CCCCCCCCC)CCNC(=O)NCc1ccc(N)cc1] | 727.2 |
| 1828. | 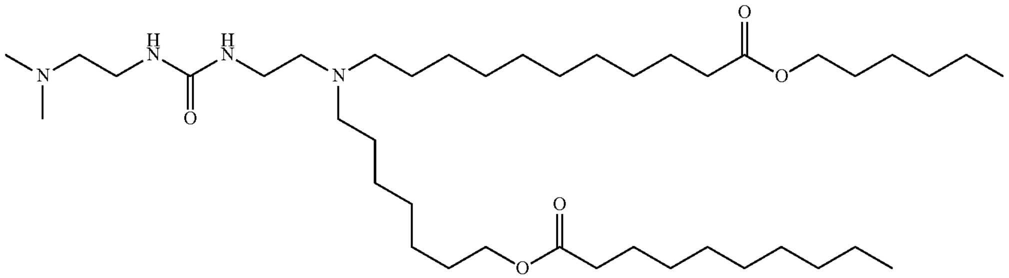 | 711.1 |

TABLE 1-continued
| # | Structure | Mw |
| --- | --- | --- |
| 1829. | 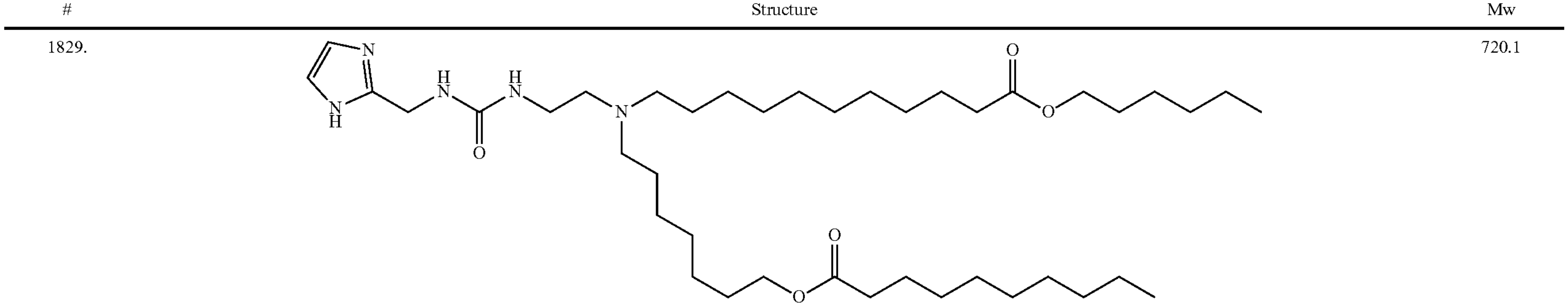 | 720.1 |
| 1830. | 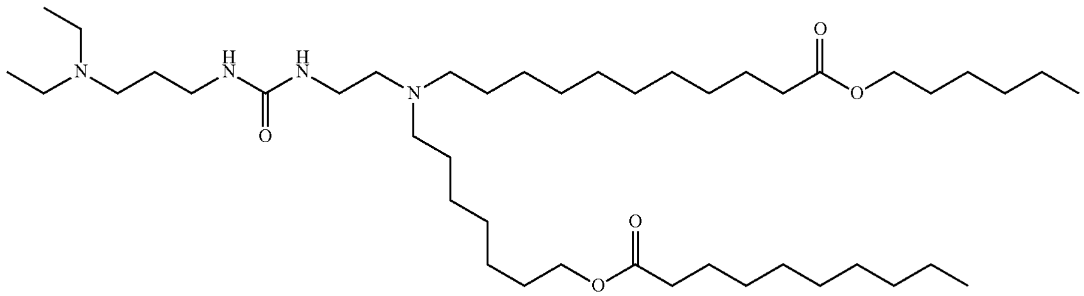 | 753.2 |
| 1831. | 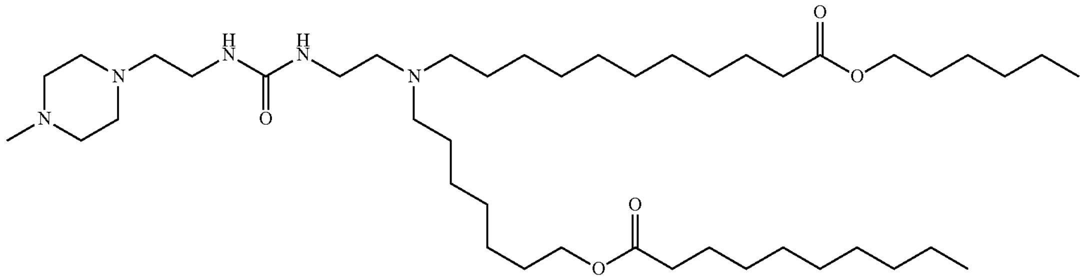 [SMILES: CCCCCCCCCC(=O)OCCCCCCCN(CCCCCCCCCCC(=O)OCCCCCC)CCNC(=O)NCCN1CCN(C)CC1] | 766.2 |

TABLE 1-continued
| # | Structure | Mw |
| --- | --- | --- |
| 1832. | 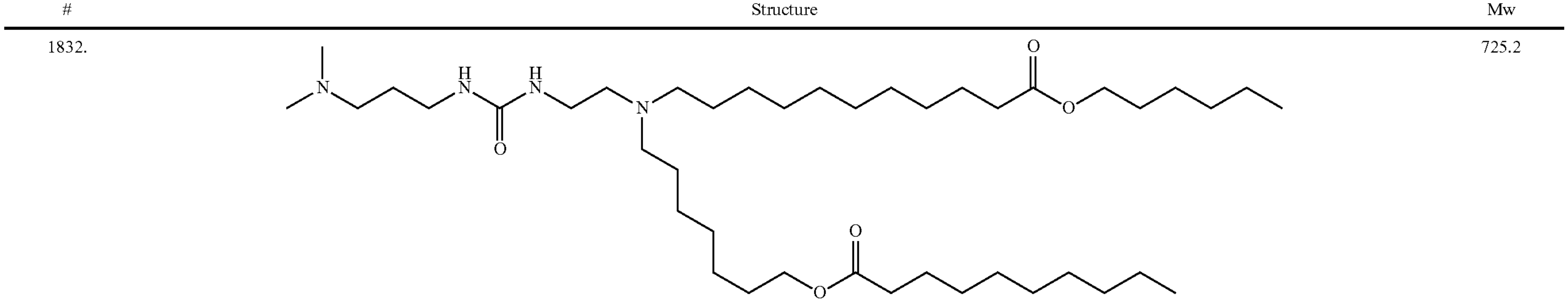 | 725.2 |
| 1833. | 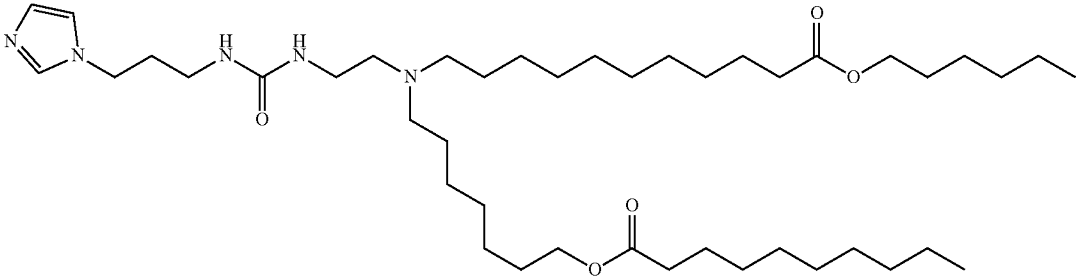 [SMILES: CCCCCCCCCC(=O)OCCCCCCCN(CCCCCCCCCCC(=O)OCCCCCC)CCNC(=O)NCCCn1ccnc1] | 748.2 |
| 1834. | 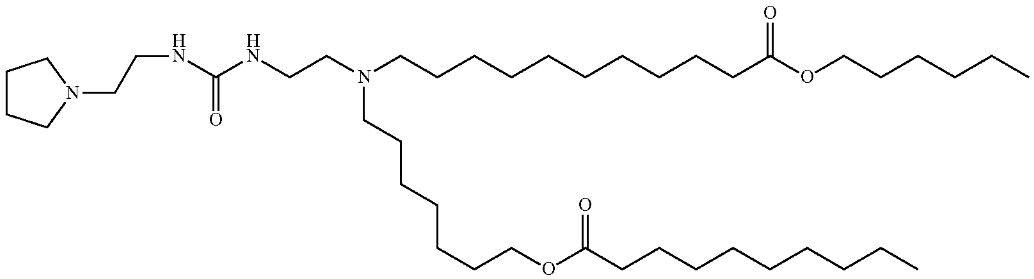 [SMILES: CCCCCCCCCC(=O)OCCCCCCCN(CCCCCCCCCCC(=O)OCCCCCC)CCNC(=O)NCCN1CCCC1] | 737.2 |

TABLE 1-continued
| # | Structure | Mw |
| --- | --- | --- |
| 1835. | 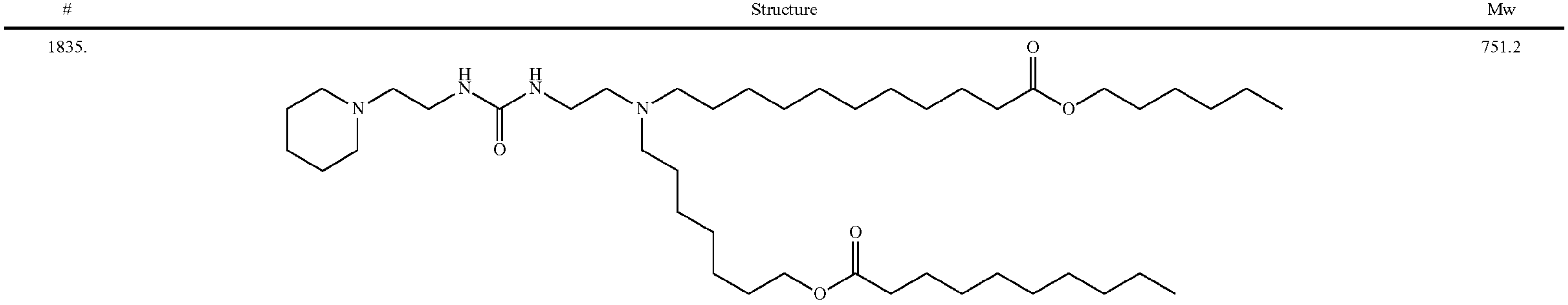 | 751.2 |
| 1836. | 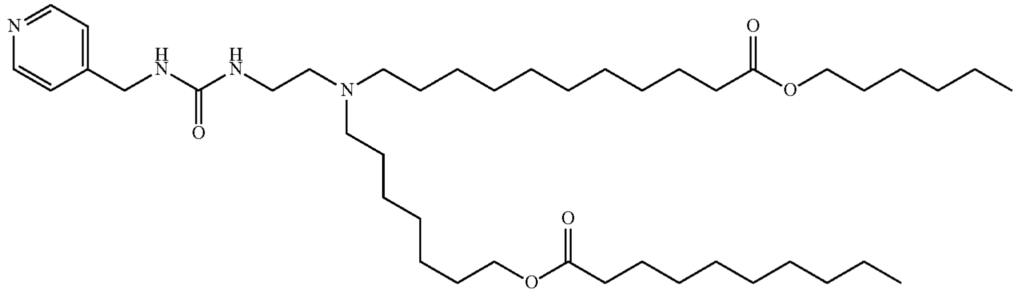 [SMILES: CCCCCCCCCC(=O)OCCCCCCCN(CCCCCCCCCCC(=O)OCCCCCC)CCNC(=O)NCc1ccncc1] | 731.1 |
| 1837. | 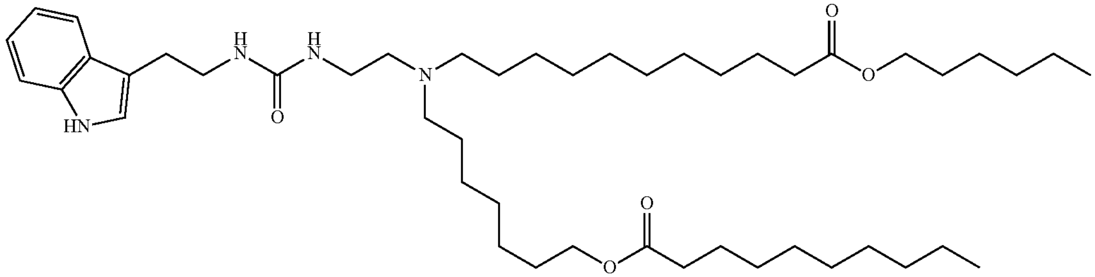 [SMILES: CCCCCCCCCC(=O)OCCCCCCCN(CCCCCCCCCCC(=O)OCCCCCC)CCNC(=O)NCCc1c[nH]c2ccccc12] | 783.2 |

TABLE 1-continued
| # | Structure | Mw |
| --- | --- | --- |
| 1838. | 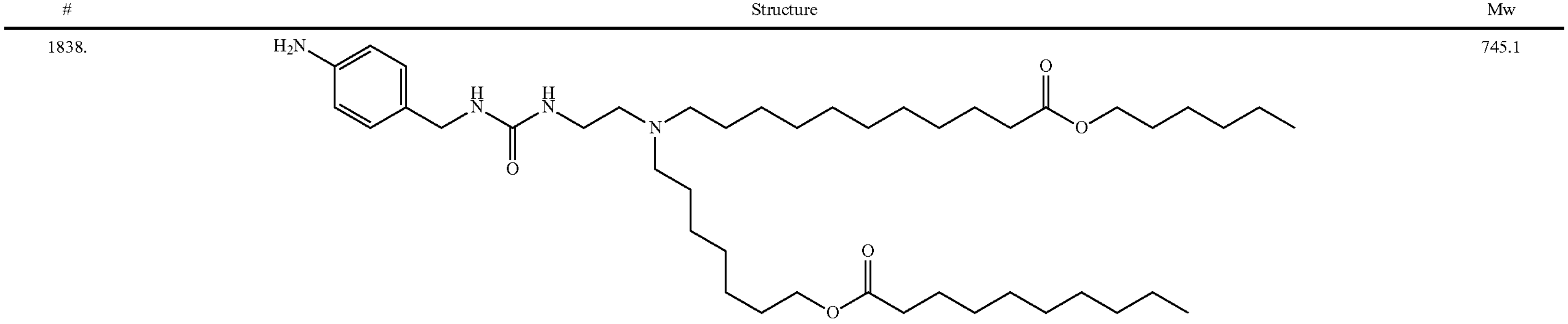 | 745.1 |
| 1839. | 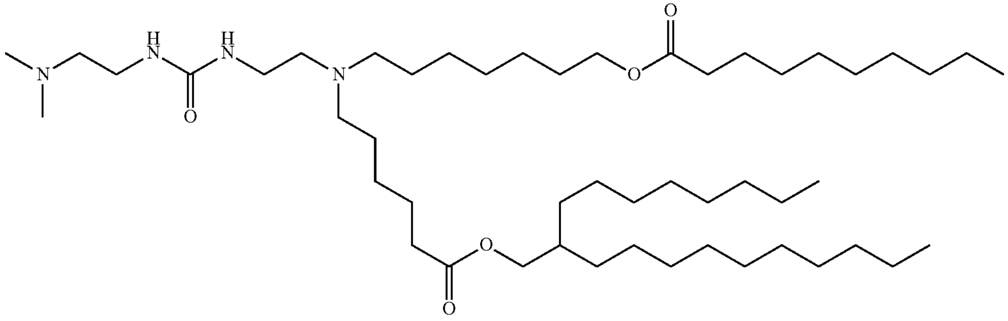 [SMILES: CCCCCCCCCCC(CCCCCCCC)COC(=O)CCCCCN(CCCCCCCOC(=O)CCCCCCCCC)CCNC(=O)NCCN(C)C] | 837.4 |
| 1840. | 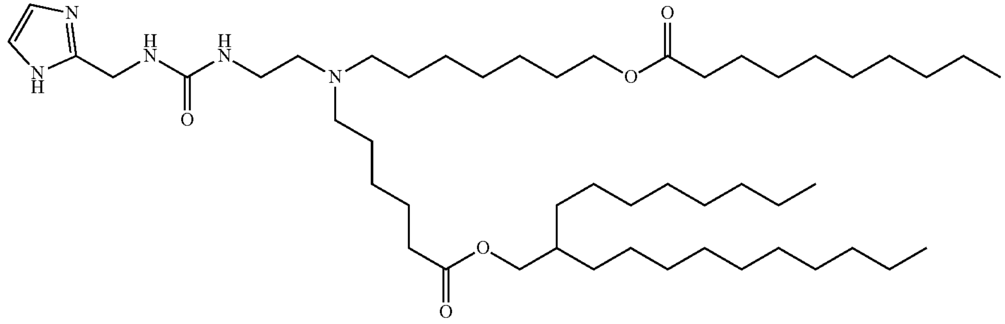 [SMILES: CCCCCCCCCCC(CCCCCCCC)COC(=O)CCCCCN(CCCCCCCOC(=O)CCCCCCCCC)CCNC(=O)NCc1ncc[nH]1] | 846.3 |

TABLE 1-continued
| # | Structure | Mw |
|---|---|---|
| 1841. | 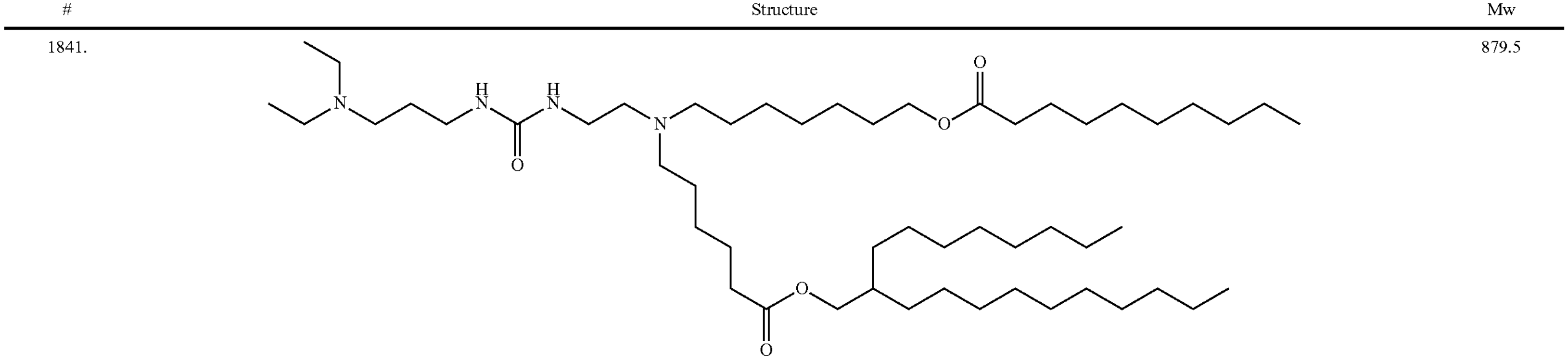 | 879.5 |
| 1842. | 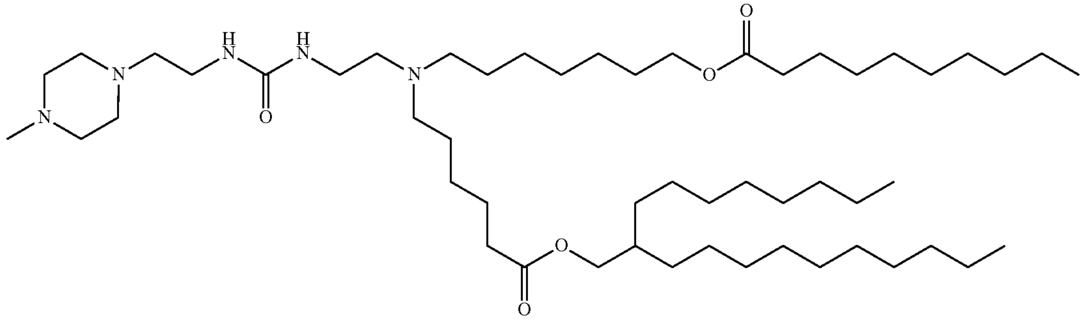 [SMILES: CCCCCCCCCCC(CCCCCCCC)COC(=O)CCCCCN(CCCCCCCOC(=O)CCCCCCCCC)CCNC(=O)NCCN1CCN(C)CC1] | 892.5 |
| 1843. | 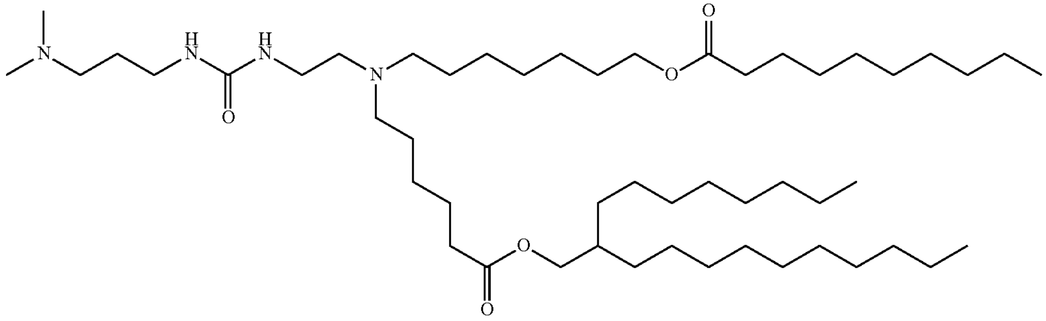 [SMILES: CCCCCCCCCCC(CCCCCCCC)COC(=O)CCCCCN(CCCCCCCOC(=O)CCCCCCCCC)CCNC(=O)NCCCN(C)C] | 851.4 |

TABLE 1-continued
| # | Structure | Mw |
|---|---|---|
| 1844. | 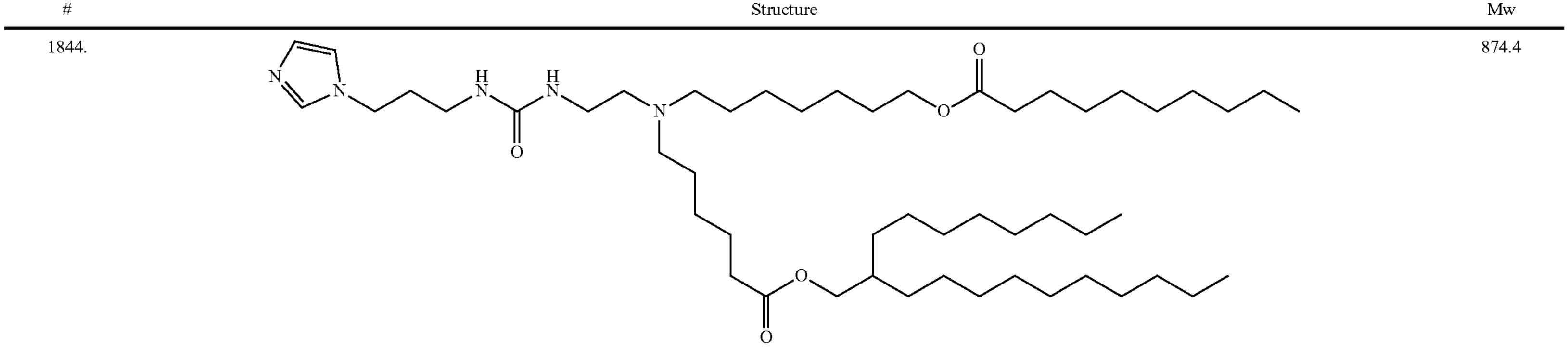 | 874.4 |
| 1845. | 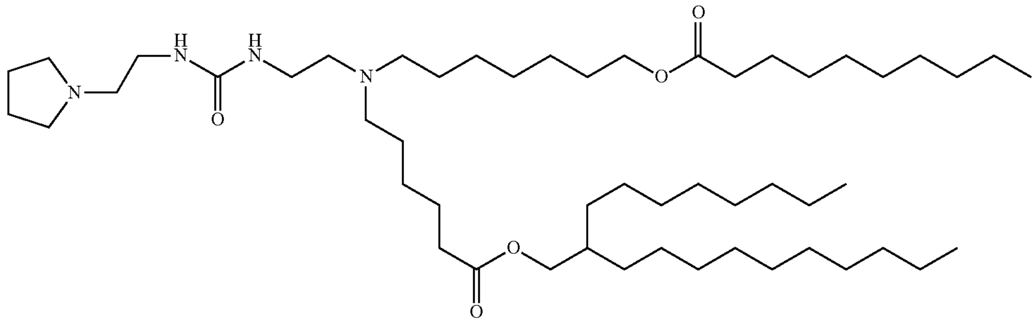 [SMILES: CCCCCCCCCCC(CCCCCCCC)COC(=O)CCCCCN(CCCCCCCOC(=O)CCCCCCCCC)CCNC(=O)NCCN1CCCC1] | 863.4 |
| 1846. | 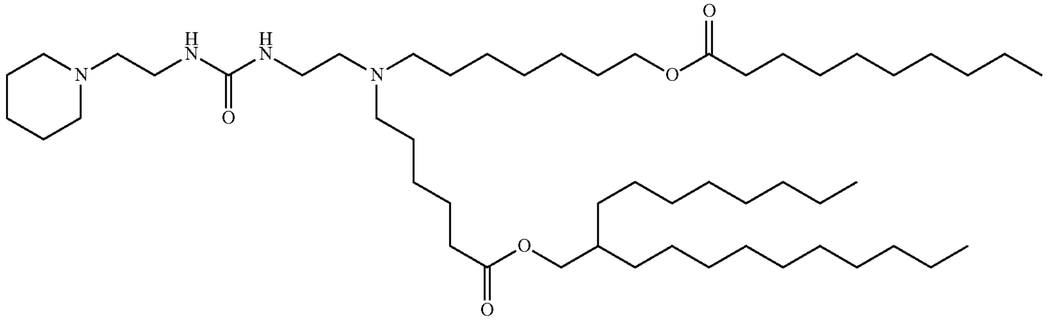 [SMILES: CCCCCCCCCCC(CCCCCCCC)COC(=O)CCCCCN(CCCCCCCOC(=O)CCCCCCCCC)CCNC(=O)NCCN1CCCCC1] | 877.4 |

TABLE 1-continued
| # | Structure | Mw |
| --- | --- | --- |
| 1847. | 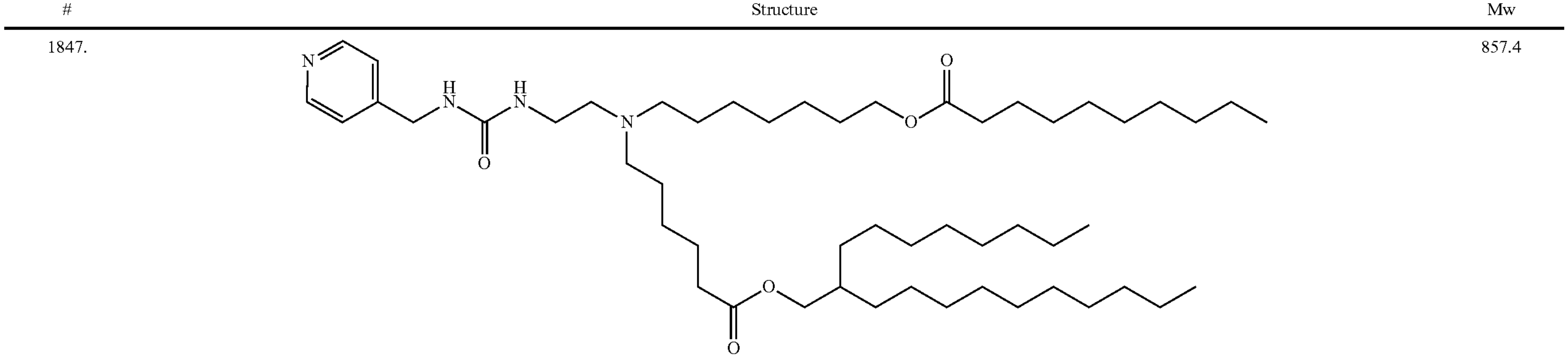 | 857.4 |
| 1848. | 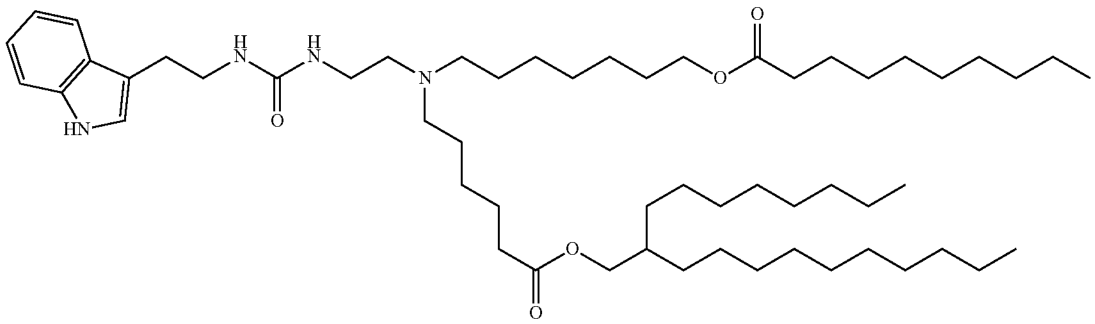 [SMILES: CCCCCCCCCCC(CCCCCCCC)COC(=O)CCCCCN(CCCCCCCOC(=O)CCCCCCCCC)CCNC(=O)NCCc1c[nH]c2ccccc12] | 909.4 |
| 1849. | 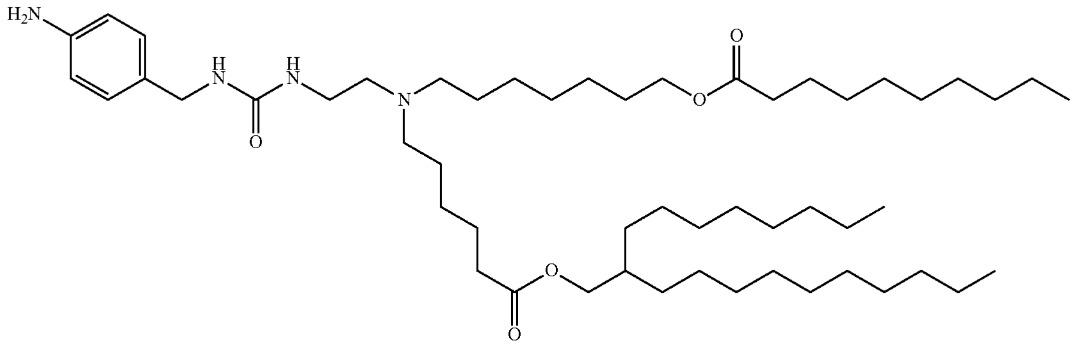 [SMILES: CCCCCCCCCCC(CCCCCCCC)COC(=O)CCCCCN(CCCCCCCOC(=O)CCCCCCCCC)CCNC(=O)NCc1ccc(N)cc1] | 871.4 |

TABLE P1
| Lipid no | Structure | MW |
|---|---|---|
| P6 | 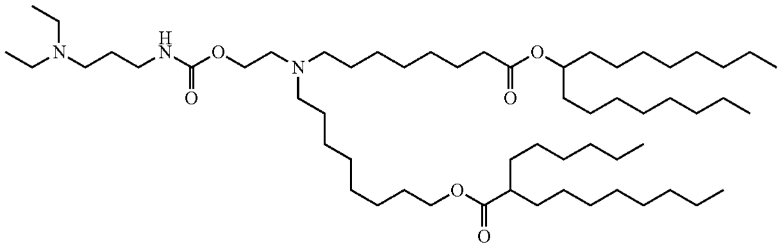 [SMILES: CCCCCCCCC(CCCCCCCC)OC(=O)CCCCCCCN(CCCCCCCCOC(=O)C(CCCCCC)CCCCCCCC)CCOC(=O)NCCCN(CC)CC] | 964.6 |
| P7 | 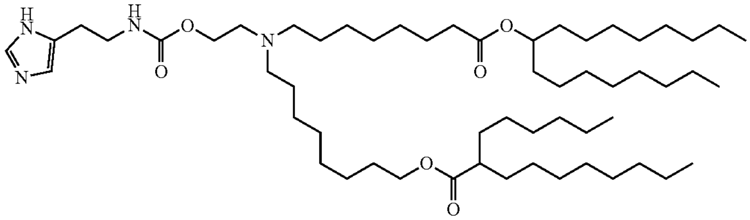 [SMILES: CCCCCCCCC(CCCCCCCC)OC(=O)CCCCCCCN(CCCCCCCCOC(=O)C(CCCCCC)CCCCCCCC)CCOC(=O)NCCc1cnc[nH]1] | 945.5 |
| P8 | 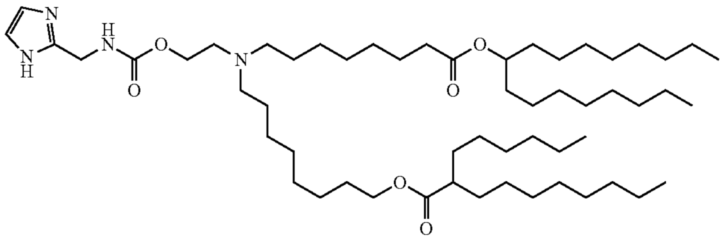 [SMILES: CCCCCCCCC(CCCCCCCC)OC(=O)CCCCCCCN(CCCCCCCCOC(=O)C(CCCCCC)CCCCCCCC)CCOC(=O)NCc1ncc[nH]1] | 931.4 |
| P9 | 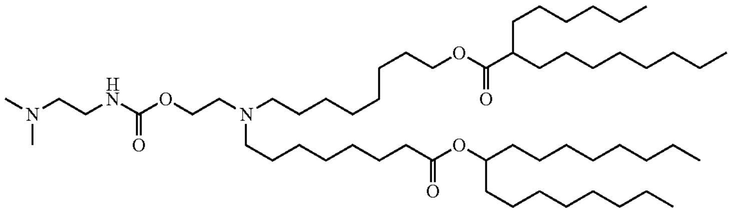 [SMILES: CCCCCCCCC(CCCCCCCC)OC(=O)CCCCCCCN(CCCCCCCCOC(=O)C(CCCCCC)CCCCCCCC)CCOC(=O)NCCN(C)C] | 922.5 |
| P10 | 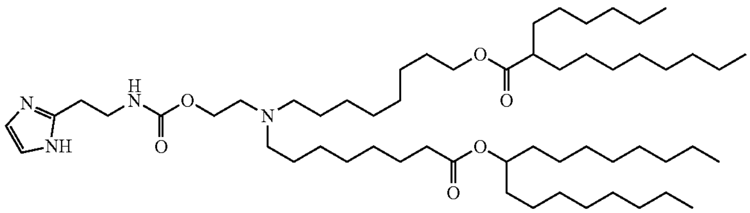 [SMILES: CCCCCCCCC(CCCCCCCC)OC(=O)CCCCCCCN(CCCCCCCCOC(=O)C(CCCCCC)CCCCCCCC)CCOC(=O)NCCc1ncc[nH]1] | 945.5 |
| P11 | 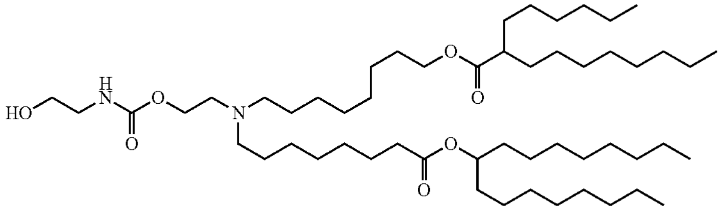 [SMILES: CCCCCCCCC(CCCCCCCC)OC(=O)CCCCCCCN(CCCCCCCCOC(=O)C(CCCCCC)CCCCCCCC)CCOC(=O)NCCO] | 895.4 |

TABLE P1-continued
| Lipid no | Structure | MW |
|---|---|---|
| P15 | 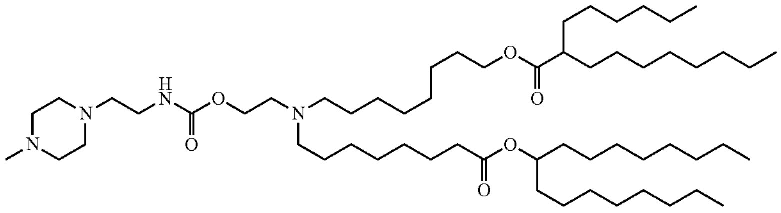 [SMILES: CCCCCCCCC(CCCCCCCC)OC(=O)CCCCCCCN(CCCCCCCCOC(=O)C(CCCCCC)CCCCCCCC)CCOC(=O)NCCN1CCN(C)CC1] | 977.6 |
| P16 | 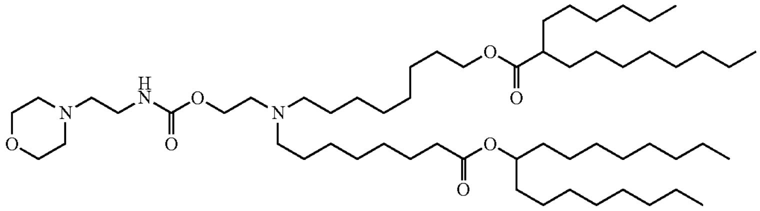 [SMILES: CCCCCCCCC(CCCCCCCC)OC(=O)CCCCCCCN(CCCCCCCCOC(=O)C(CCCCCC)CCCCCCCC)CCOC(=O)NCCN1CCOCC1] | 964.6 |
| P17 | 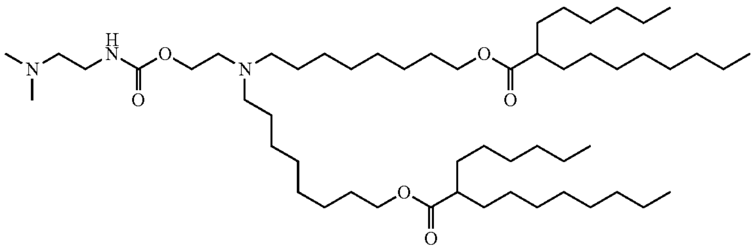 [SMILES: CCCCCCCCC(CCCCCC)C(=O)OCCCCCCCCN(CCCCCCCCOC(=O)C(CCCCCC)CCCCCCCC)CCOC(=O)NCCN(C)C] | 908.49 |
| P18 | 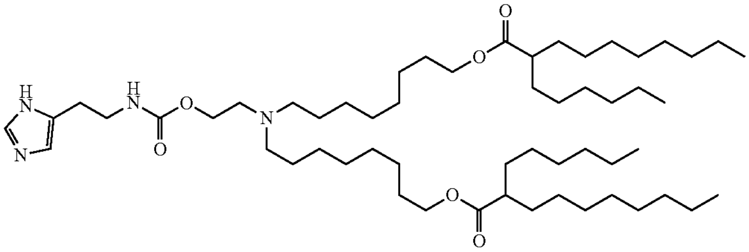 [SMILES: CCCCCCCCC(CCCCCC)C(=O)OCCCCCCCCN(CCCCCCCCOC(=O)C(CCCCCC)CCCCCCCC)CCOC(=O)NCCc1cnc[nH]1] | 931.5 |
| P19 | 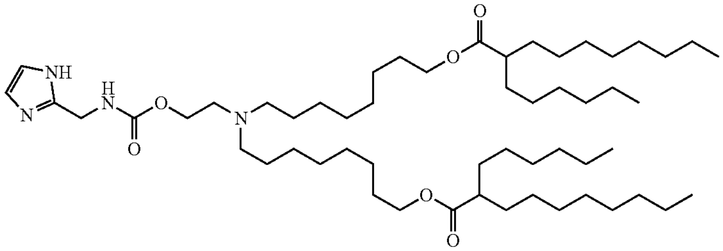 [SMILES: CCCCCCCCC(CCCCCC)C(=O)OCCCCCCCCN(CCCCCCCCOC(=O)C(CCCCCC)CCCCCCCC)CCOC(=O)NCc1ncc[nH]1] | 917.5 |
| P20 | 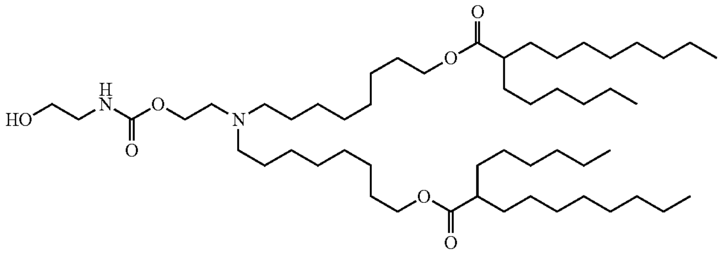 [SMILES: CCCCCCCCC(CCCCCC)C(=O)OCCCCCCCCN(CCCCCCCCOC(=O)C(CCCCCC)CCCCCCCC)CCOC(=O)NCCO] | 881.4 |

TABLE P1-continued
| Lipid no | Structure | MW |
| --- | --- | --- |
| P21 | 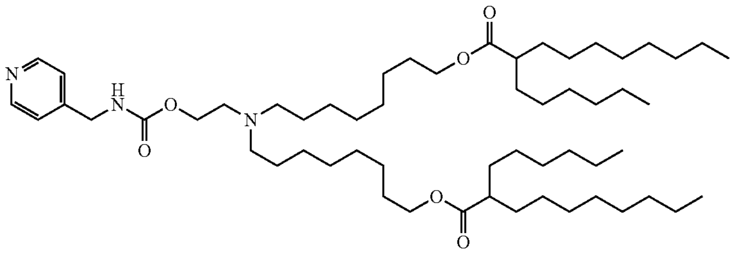 [SMILES: CCCCCCCCC(CCCCCC)C(=O)OCCCCCCCCN(CCCCCCCCOC(=O)C(CCCCCC)CCCCCCCC)CCOC(=O)NCc1ccncc1] | 928.5 |
| P22 | 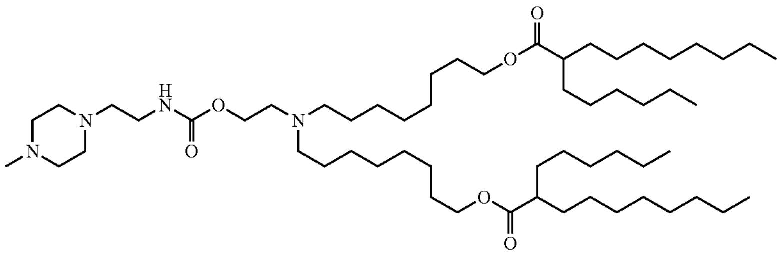 [SMILES: CCCCCCCCC(CCCCCC)C(=O)OCCCCCCCCN(CCCCCCCCOC(=O)C(CCCCCC)CCCCCCCC)CCOC(=O)NCCN1CCN(C)CC1] | 963.6 |
| P23 | 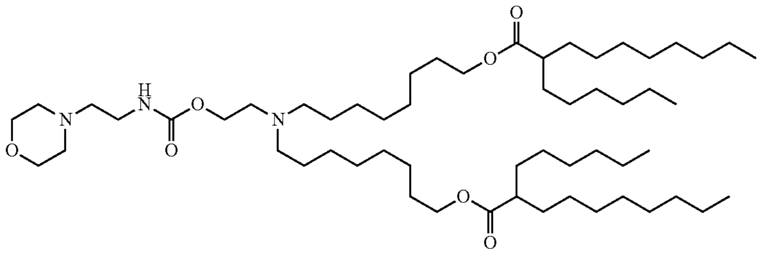 [SMILES: CCCCCCCCC(CCCCCC)C(=O)OCCCCCCCCN(CCCCCCCCOC(=O)C(CCCCCC)CCCCCCCC)CCOC(=O)NCCN1CCOCC1] | 950.5 |
| P24 | 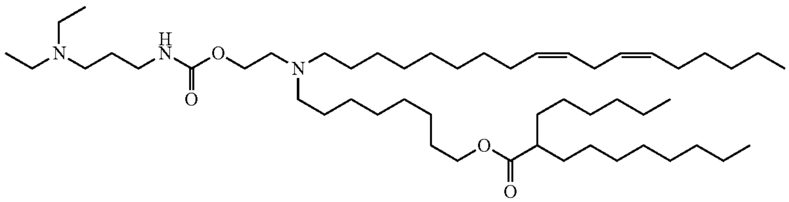 [SMILES: CCCCC/C=C\C/C=C\CCCCCCCCN(CCCCCCCCOC(=O)C(CCCCCC)CCCCCCCC)CCOC(=O)NCCCN(CC)CC] | 832.4 |
| P25 | 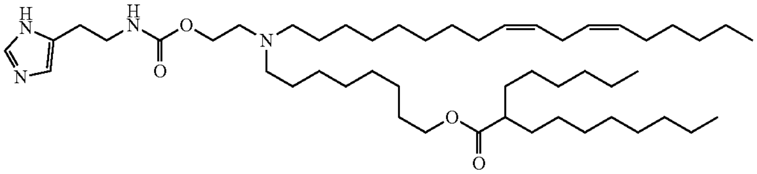 [SMILES: CCCCC/C=C\C/C=C\CCCCCCCCN(CCCCCCCCOC(=O)C(CCCCCC)CCCCCCCC)CCOC(=O)NCCc1cnc[nH]1] | 813.3 |
| P26 | 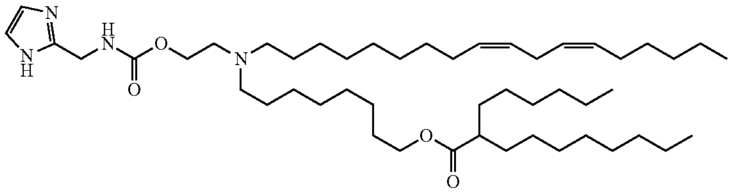 [SMILES: CCCCC/C=C\C/C=C\CCCCCCCCN(CCCCCCCCOC(=O)C(CCCCCC)CCCCCCCC)CCOC(=O)NCc1ncc[nH]1] | 799.3 |
| P27 | 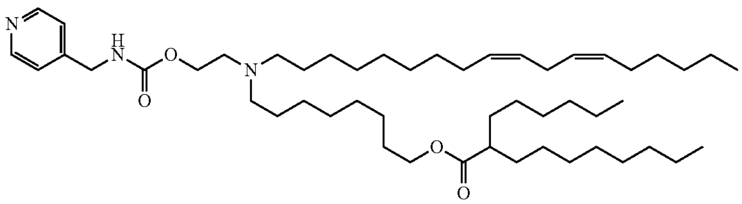 [SMILES: CCCCC/C=C\C/C=C\CCCCCCCCN(CCCCCCCCOC(=O)C(CCCCCC)CCCCCCCC)CCOC(=O)NCc1ccncc1] | 810.3 |

TABLE P1-continued
| Lipid no | Structure | MW |
|---|---|---|
| P28 | 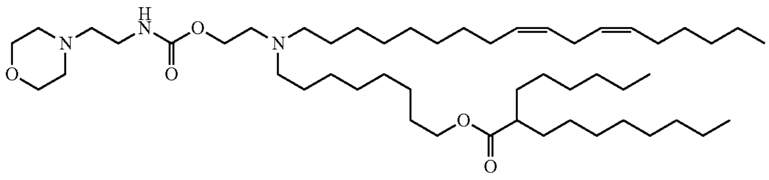 [SMILES: CCCCC/C=C\C/C=C\CCCCCCCCN(CCCCCCCCOC(=O)C(CCCCCC)CCCCCCCC)CCOC(=O)NCCN1CCOCC1] | 832.4 |
| P29 | 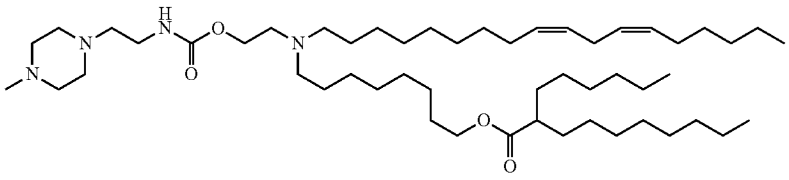 [SMILES: CCCCC/C=C\C/C=C\CCCCCCCCN(CCCCCCCCOC(=O)C(CCCCCC)CCCCCCCC)CCOC(=O)NCCN1CCN(C)CC1] | 845.4 |
| P30 | 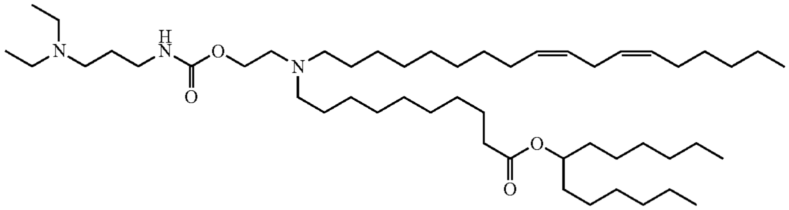 [SMILES: CCCCC/C=C\C/C=C\CCCCCCCCN(CCCCCCCCCC(=O)OC(CCCCCC)CCCCCC)CCOC(=O)NCCCN(CC)CC] | 818.4 |
| P31 | 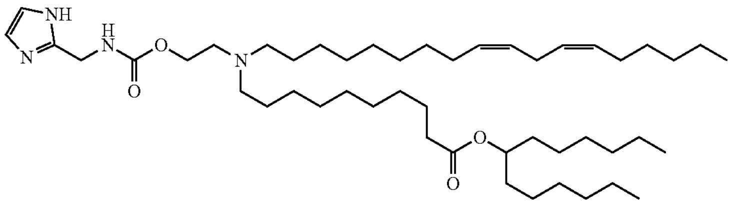 [SMILES: CCCCC/C=C\C/C=C\CCCCCCCCN(CCCCCCCCCC(=O)OC(CCCCCC)CCCCCC)CCOC(=O)NCc1ncc[nH]1] | 785.3 |
| P32 | 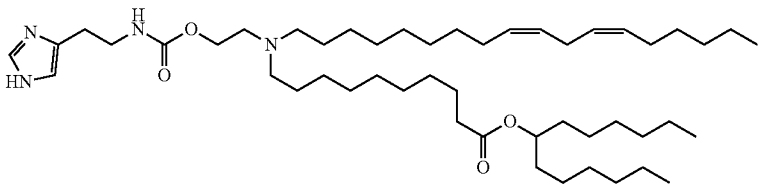 [SMILES: CCCCC/C=C\C/C=C\CCCCCCCCN(CCCCCCCCCC(=O)OC(CCCCCC)CCCCCC)CCOC(=O)NCCc1c[nH]cn1] | 799.3 |
| P33 | 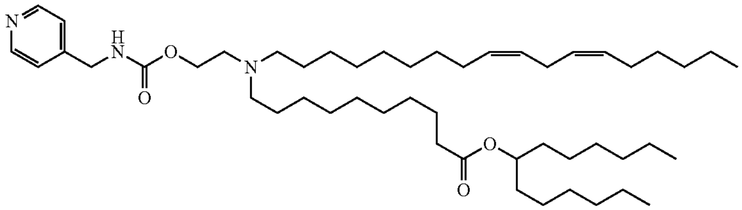 [SMILES: CCCCC/C=C\C/C=C\CCCCCCCCN(CCCCCCCCCC(=O)OC(CCCCCC)CCCCCC)CCOC(=O)NCc1ccncc1] | 796.3 |
| P34 | 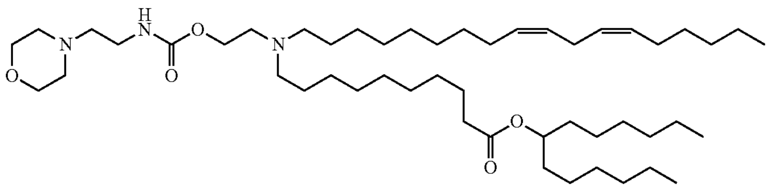 [SMILES: CCCCC/C=C\C/C=C\CCCCCCCCN(CCCCCCCCCC(=O)OC(CCCCCC)CCCCCC)CCOC(=O)NCCN1CCOCC1] | 818.3 |
| P35 | 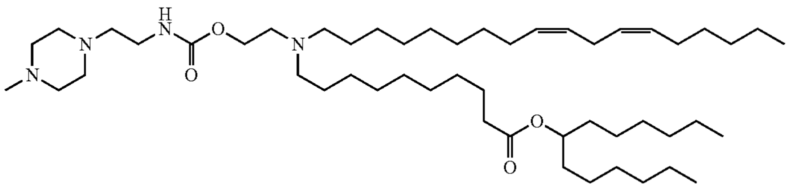 [SMILES: CCCCC/C=C\C/C=C\CCCCCCCCN(CCCCCCCCCC(=O)OC(CCCCCC)CCCCCC)CCOC(=O)NCCN1CCN(C)CC1] | 831.4 |

TABLE P1-continued
| Lipid no | Structure | MW |
|---|---|---|
| P36 | 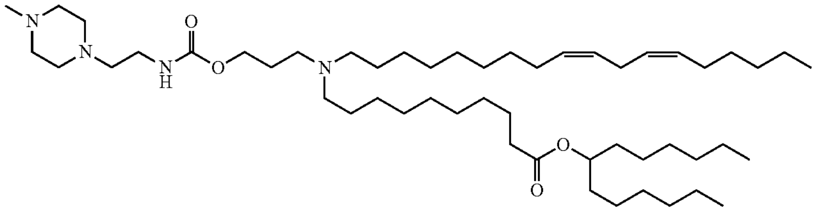 [SMILES: CCCCC/C=C\C/C=C\CCCCCCCCN(CCCCCCCCCC(=O)OC(CCCCCC)CCCCCC)CCCOC(=O)NCCN1CCN(C)CC1] | 845.4 |
| P37 | 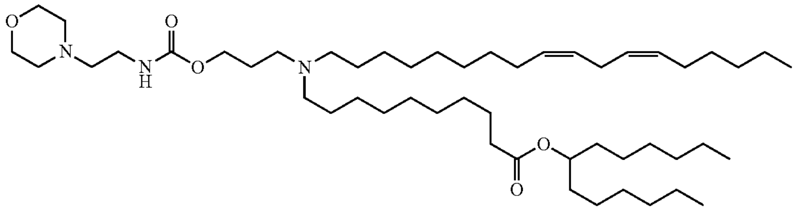 [SMILES: CCCCC/C=C\C/C=C\CCCCCCCCN(CCCCCCCCCC(=O)OC(CCCCCC)CCCCCC)CCCOC(=O)NCCN1CCOCC1] | 832.4 |
| P38 | 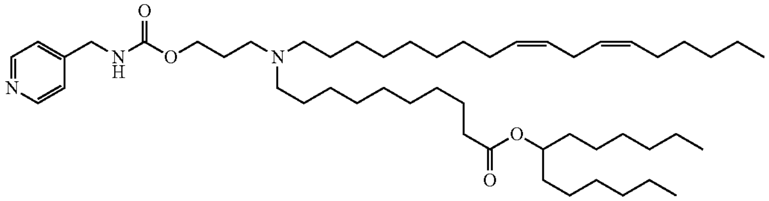 [SMILES: CCCCC/C=C\C/C=C\CCCCCCCCN(CCCCCCCCCC(=O)OC(CCCCCC)CCCCCC)CCCOC(=O)NCc1ccncc1] | 810.3 |
| P39 | 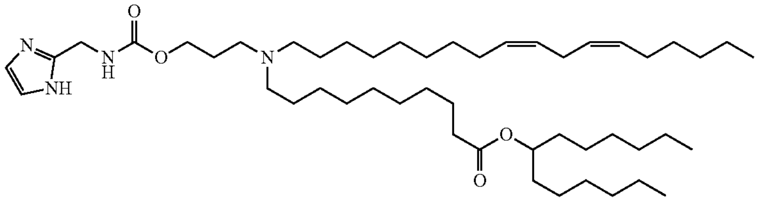 [SMILES: CCCCC/C=C\C/C=C\CCCCCCCCN(CCCCCCCCCC(=O)OC(CCCCCC)CCCCCC)CCCOC(=O)NCc1ncc[nH]1] | 799.3 |
| P40 | 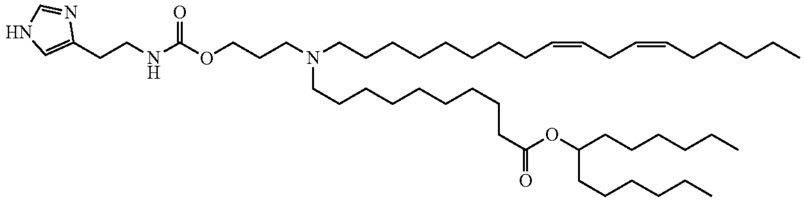 [SMILES: CCCCC/C=C\C/C=C\CCCCCCCCN(CCCCCCCCCC(=O)OC(CCCCCC)CCCCCC)CCCOC(=O)NCCc1c[nH]cn1] | 813.3 |
| P41 | 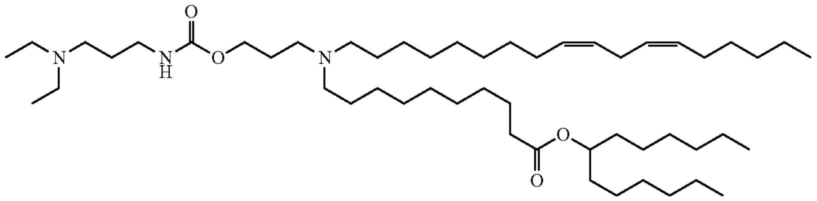 [SMILES: CCCCC/C=C\C/C=C\CCCCCCCCN(CCCCCCCCCC(=O)OC(CCCCCC)CCCCCC)CCCOC(=O)NCCCN(CC)CC] | 832.4 |
| P42 | 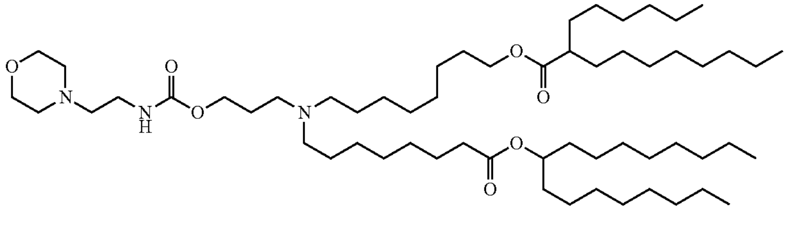 [SMILES: CCCCCCCCC(CCCCCCCC)OC(=O)CCCCCCCN(CCCCCCCCOC(=O)C(CCCCCC)CCCCCCCC)CCCOC(=O)NCCN1CCOCC1] | 991.6 |

TABLE P1-continued
| Lipid no | Structure | MW |
|---|---|---|
| P43 | 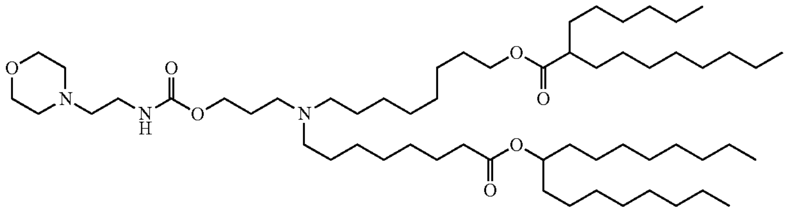 [SMILES: CCCCCCCCC(CCCCCCCC)OC(=O)CCCCCCCN(CCCCCCCCOC(=O)C(CCCCCC)CCCCCCCC)CCCOC(=O)NCCN1CCOCC1] | 978.6 |
| P44 | 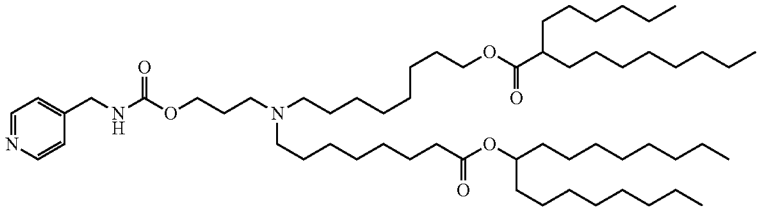 [SMILES: CCCCCCCCC(CCCCCCCC)OC(=O)CCCCCCCN(CCCCCCCCOC(=O)C(CCCCCC)CCCCCCCC)CCCOC(=O)NCc1ccncc1] | 956.5 |
| P45 | 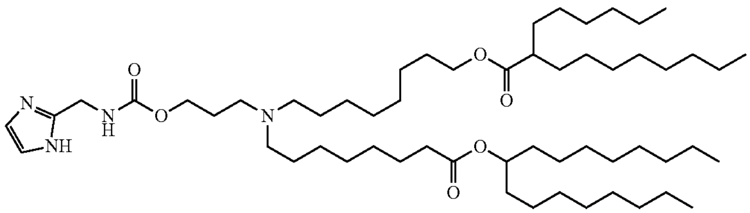 [SMILES: CCCCCCCCC(CCCCCCCC)OC(=O)CCCCCCCN(CCCCCCCCOC(=O)C(CCCCCC)CCCCCCCC)CCCOC(=O)NCc1ncc[nH]1] | 945.5 |
| P46 | 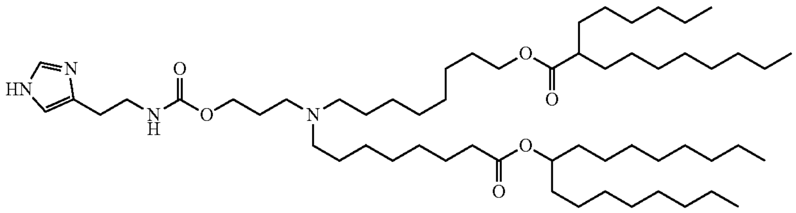 [SMILES: CCCCCCCCC(CCCCCCCC)OC(=O)CCCCCCCN(CCCCCCCCOC(=O)C(CCCCCC)CCCCCCCC)CCCOC(=O)NCCc1c[nH]cn1] | 959.5 |
| P47 | 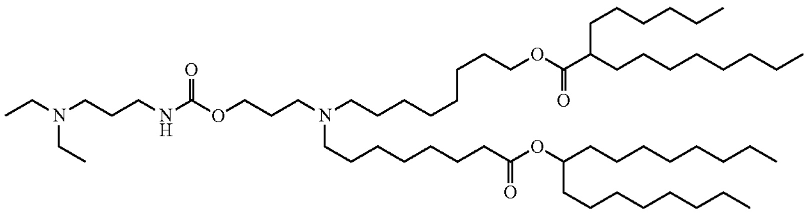 [SMILES: CCCCCCCCC(CCCCCCCC)OC(=O)CCCCCCCN(CCCCCCCCOC(=O)C(CCCCCC)CCCCCCCC)CCCOC(=O)NCCCN(CC)CC] | 978.6 |
| P48 | 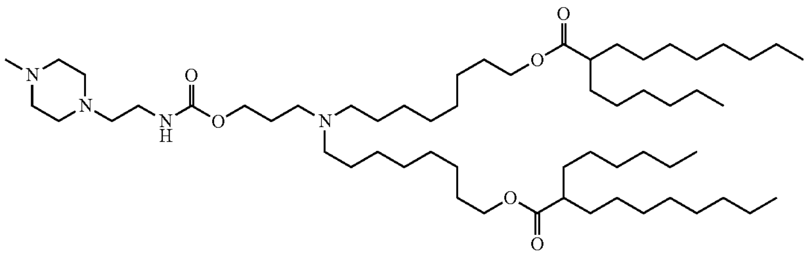 [SMILES: CCCCCCCCC(CCCCCC)C(=O)OCCCCCCCCN(CCCCCCCCOC(=O)C(CCCCCC)CCCCCCCC)CCCOC(=O)NCCN1CCN(C)CC1] | 977.6 |

TABLE P1-continued
| Lipid no | Structure | MW |
| --- | --- | --- |
| P49 | 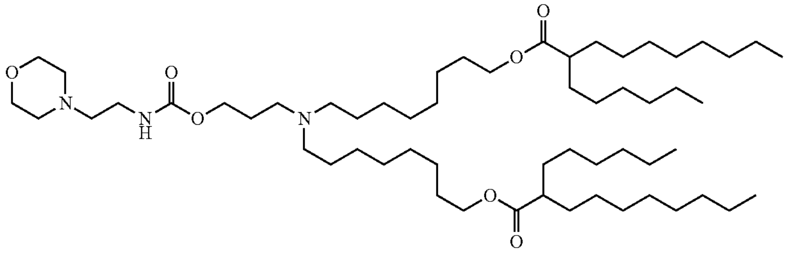 [SMILES: CCCCCCCCC(CCCCCC)C(=O)OCCCCCCCCN(CCCCCCCCOC(=O)C(CCCCCC)CCCCCCCC)CCCOC(=O)NCCN1CCOCC1] | 964.6 |
| P50 | 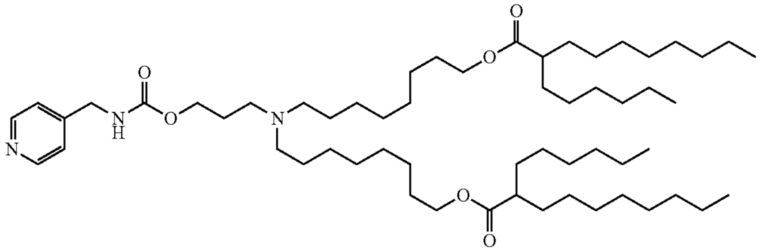 [SMILES: CCCCCCCCC(CCCCCC)C(=O)OCCCCCCCCN(CCCCCCCCOC(=O)C(CCCCCC)CCCCCCCC)CCCOC(=O)NCc1ccncc1] | 942.5 |
| P51 | 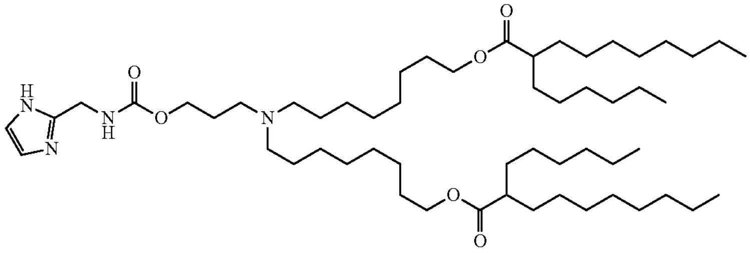 [SMILES: CCCCCCCCC(CCCCCC)C(=O)OCCCCCCCCN(CCCCCCCCOC(=O)C(CCCCCC)CCCCCCCC)CCCOC(=O)NCc1ncc[nH]1] | 931.5 |
| P52 | 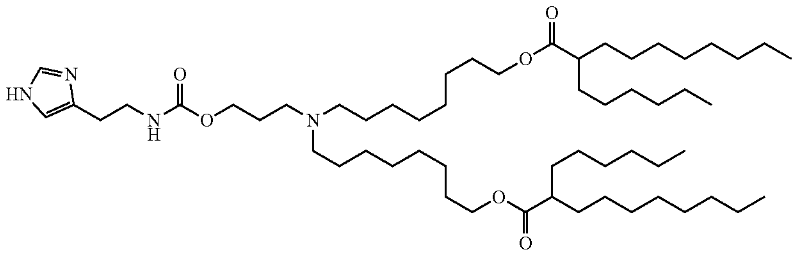 [SMILES: CCCCCCCCC(CCCCCC)C(=O)OCCCCCCCCN(CCCCCCCCOC(=O)C(CCCCCC)CCCCCCCC)CCCOC(=O)NCCc1c[nH]cn1] | 945.5 |
| P53 | 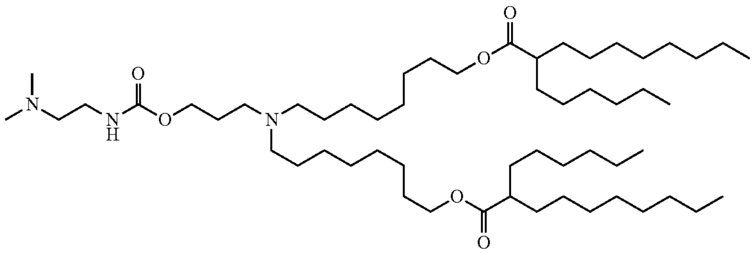 [SMILES: CCCCCCCCC(CCCCCC)C(=O)OCCCCCCCCN(CCCCCCCCOC(=O)C(CCCCCC)CCCCCCCC)CCCOC(=O)NCCN(C)C] | 922.5 |
| P54 | 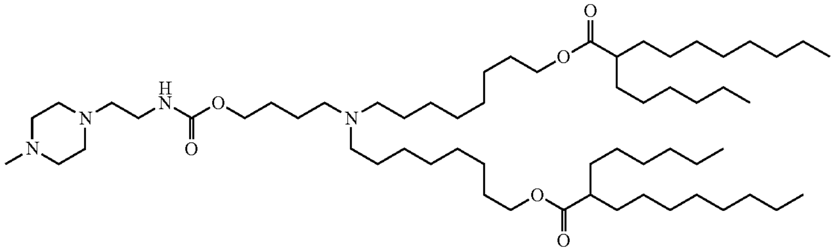 [SMILES: CCCCCCCCC(CCCCCC)C(=O)OCCCCCCCCN(CCCCCCCCOC(=O)C(CCCCCC)CCCCCCCC)CCCCOC(=O)NCCN1CCN(C)CC1] | 991.6 |

TABLE P1-continued
| Lipid no | Structure | MW |
|---|---|---|
| P55 | 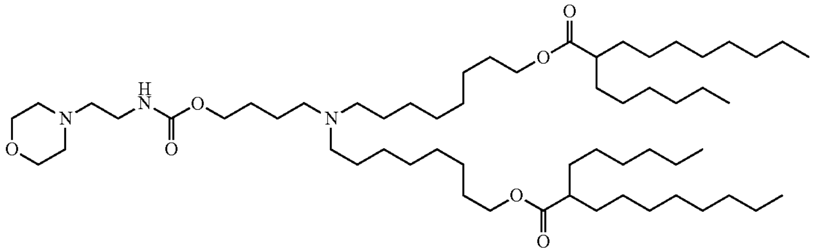 [SMILES: CCCCCCCCC(CCCCCC)C(=O)OCCCCCCCCN(CCCCCCCCOC(=O)C(CCCCCC)CCCCCCCC)CCCCOC(=O)NCCN1CCOCC1] | 978.6 |
| P56 | 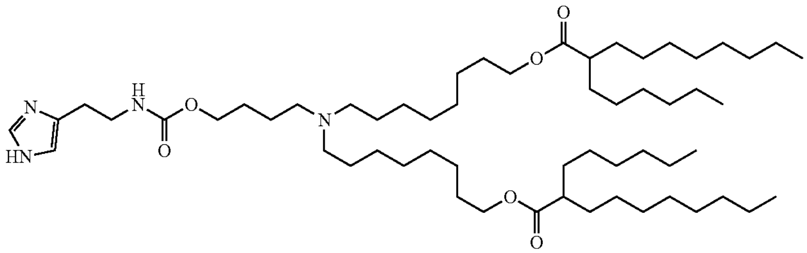 [SMILES: CCCCCCCCC(CCCCCC)C(=O)OCCCCCCCCN(CCCCCCCCOC(=O)C(CCCCCC)CCCCCCCC)CCCCOC(=O)NCCc1c[nH]cn1] | 959.5 |
| P57 | 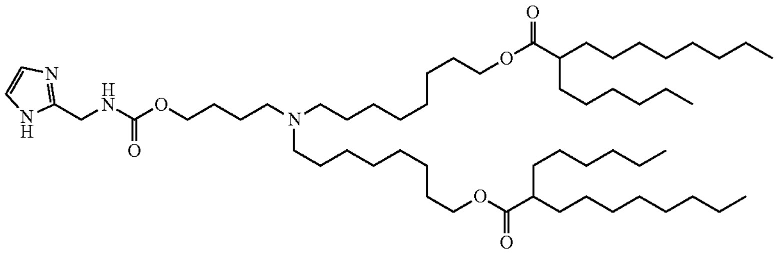 [SMILES: CCCCCCCCC(CCCCCC)C(=O)OCCCCCCCCN(CCCCCCCCOC(=O)C(CCCCCC)CCCCCCCC)CCCCOC(=O)NCc1ncc[nH]1] | 945.5 |
| P58 | 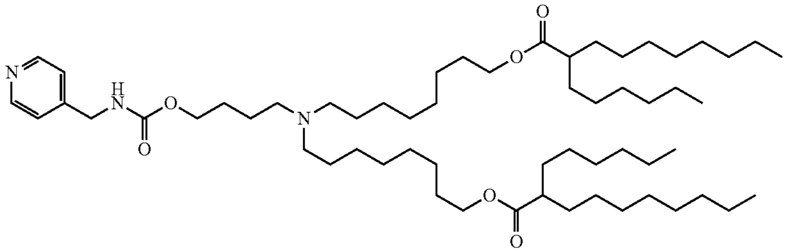 [SMILES: CCCCCCCCC(CCCCCC)C(=O)OCCCCCCCCN(CCCCCCCCOC(=O)C(CCCCCC)CCCCCCCC)CCCCOC(=O)NCc1ccncc1] | 956.5 |
| P59 | 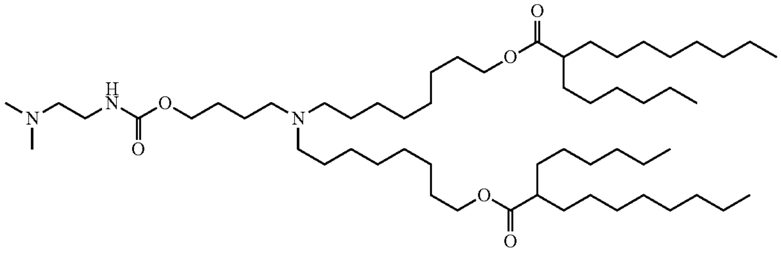 [SMILES: CCCCCCCCC(CCCCCC)C(=O)OCCCCCCCCN(CCCCCCCCOC(=O)C(CCCCCC)CCCCCCCC)CCCCOC(=O)NCCN(C)C] | 936.5 |
| P60 | 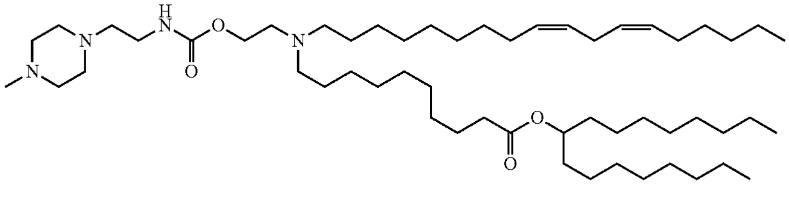 [SMILES: CCCCC/C=C\C/C=C\CCCCCCCCN(CCCCCCCCCC(=O)OC(CCCCCCCC)CCCCCCCC)CCOC(=O)NCCN1CCN(C)CC1] | 887.5 |

TABLE P1-continued
| Lipid no | Structure | MW |
| --- | --- | --- |
| P61 | 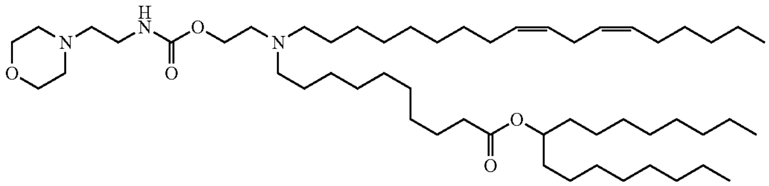 [SMILES: CCCCC/C=C\C/C=C\CCCCCCCCN(CCCCCCCCCC(=O)OC(CCCCCCCC)CCCCCCCC)CCOC(=O)NCCN1CCOCC1] | 874.4 |
| P62 | 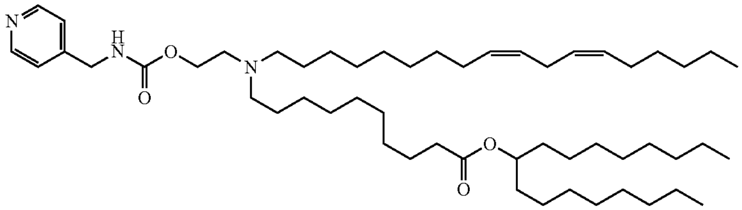 [SMILES: CCCCC/C=C\C/C=C\CCCCCCCCN(CCCCCCCCCC(=O)OC(CCCCCCCC)CCCCCCCC)CCOC(=O)NCc1ccncc1] | 852.4 |
| P63 | 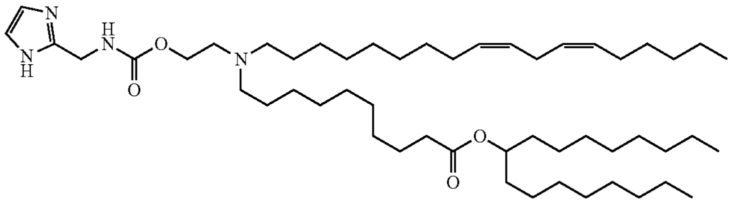 [SMILES: CCCCC/C=C\C/C=C\CCCCCCCCN(CCCCCCCCCC(=O)OC(CCCCCCCC)CCCCCCCC)CCOC(=O)NCc1ncc[nH]1] | 841.4 |
| P64 | 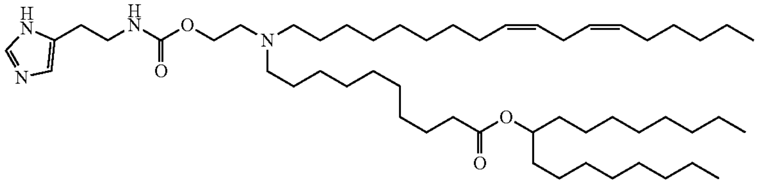 [SMILES: CCCCC/C=C\C/C=C\CCCCCCCCN(CCCCCCCCCC(=O)OC(CCCCCCCC)CCCCCCCC)CCOC(=O)NCCc1cnc[nH]1] | 855.4 |
| P65 | 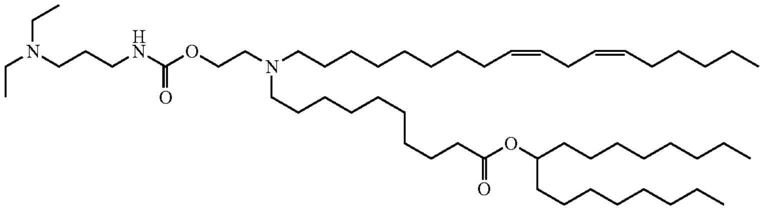 [SMILES: CCCCC/C=C\C/C=C\CCCCCCCCN(CCCCCCCCCC(=O)OC(CCCCCCCC)CCCCCCCC)CCOC(=O)NCCCN(CC)CC] | 874.5 |
| P66 | 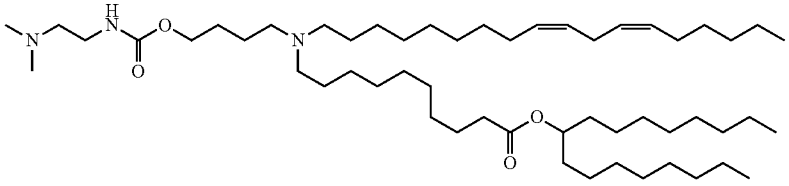 [SMILES: CCCCC/C=C\C/C=C\CCCCCCCCN(CCCCCCCCCC(=O)OC(CCCCCCCC)CCCCCCCC)CCCCOC(=O)NCCN(C)C] | 832.4 |
| P67 | 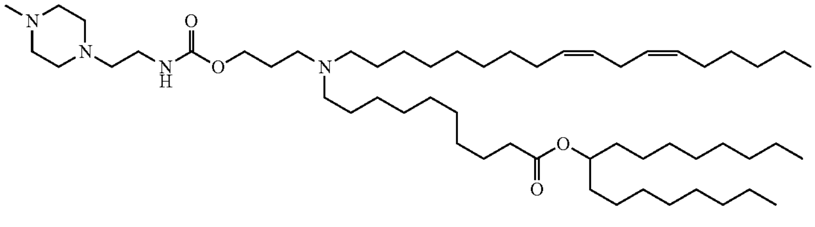 [SMILES: CCCCC/C=C\C/C=C\CCCCCCCCN(CCCCCCCCCC(=O)OC(CCCCCCCC)CCCCCCCC)CCCOC(=O)NCCN1CCN(C)CC1] | 901.5 |

TABLE P1-continued
| Lipid no | Structure | MW |
| --- | --- | --- |
| P68 | 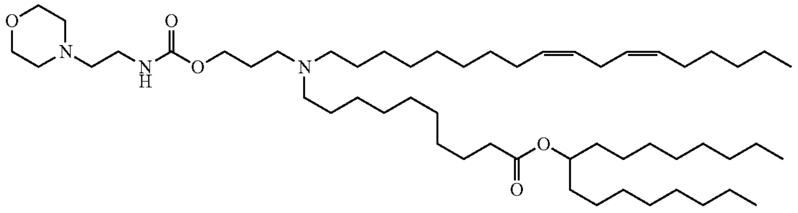 [SMILES: CCCCC/C=C\C/C=C\CCCCCCCCN(CCCCCCCCCC(=O)OC(CCCCCCCC)CCCCCCCC)CCCOC(=O)NCCN1CCOCC1] | 888.5 |
| P69 | 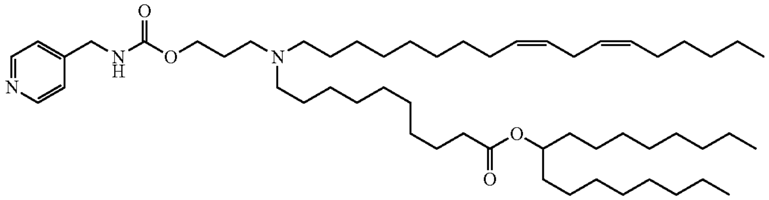 [SMILES: CCCCC/C=C\C/C=C\CCCCCCCCN(CCCCCCCCCC(=O)OC(CCCCCCCC)CCCCCCCC)CCCOC(=O)NCc1ccncc1] | 866.4 |
| P70 | 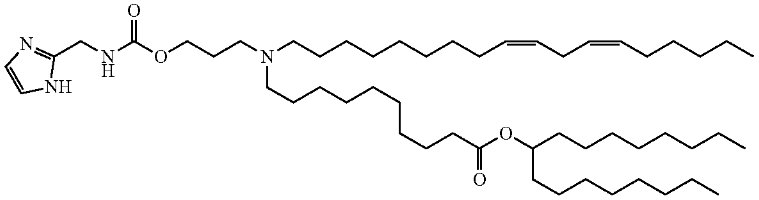 [SMILES: CCCCC/C=C\C/C=C\CCCCCCCCN(CCCCCCCCCC(=O)OC(CCCCCCCC)CCCCCCCC)CCCOC(=O)NCc1ncc[nH]1] | 855.4 |
| P71 | 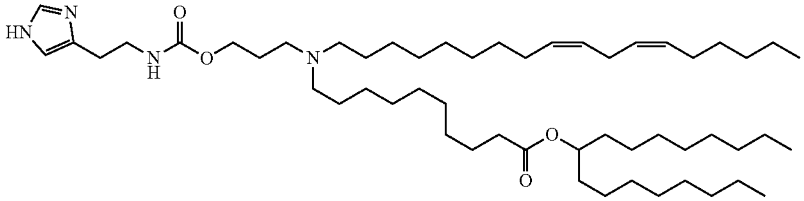 [SMILES: CCCCC/C=C\C/C=C\CCCCCCCCN(CCCCCCCCCC(=O)OC(CCCCCCCC)CCCCCCCC)CCCOC(=O)NCCc1c[nH]cn1] | 869.4 |
| P72 | 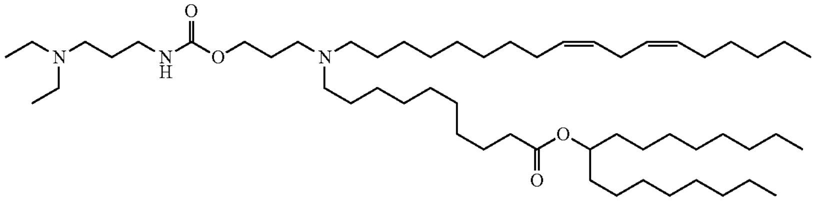 [SMILES: CCCCC/C=C\C/C=C\CCCCCCCCN(CCCCCCCCCC(=O)OC(CCCCCCCC)CCCCCCCC)CCCOC(=O)NCCCN(CC)CC] | 888.5 |
| P73 | 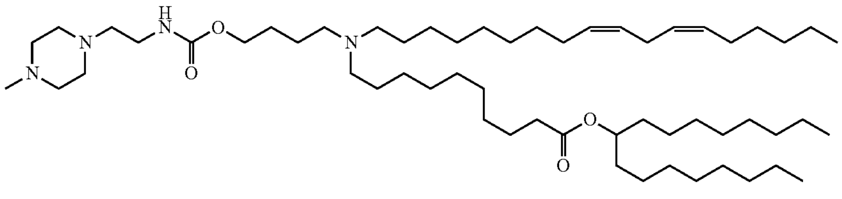 [SMILES: CCCCC/C=C\C/C=C\CCCCCCCCN(CCCCCCCCCC(=O)OC(CCCCCCCC)CCCCCCCC)CCCCOC(=O)NCCN1CCN(C)CC1] | 915.5 |
| P74 | 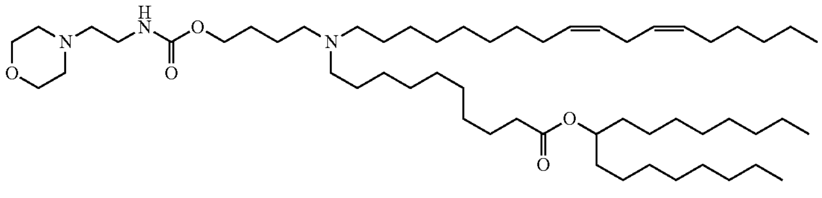 [SMILES: CCCCC/C=C\C/C=C\CCCCCCCCN(CCCCCCCCCC(=O)OC(CCCCCCCC)CCCCCCCC)CCCCOC(=O)NCCN1CCOCC1] | 902.5 |

TABLE P1-continued
| Lipid no | Structure | MW |
|---|---|---|
| P75 | 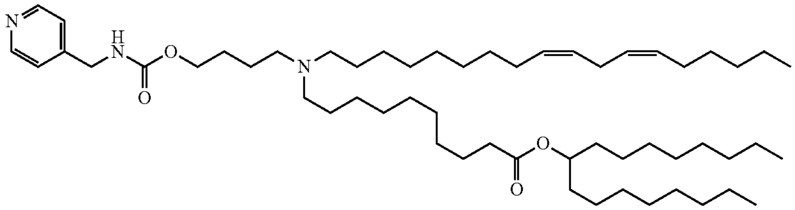 [SMILES: CCCCC/C=C\C/C=C\CCCCCCCCN(CCCCCCCCCC(=O)OC(CCCCCCCC)CCCCCCCC)CCCCOC(=O)NCc1ccncc1] | 880.4 |
| P76 | 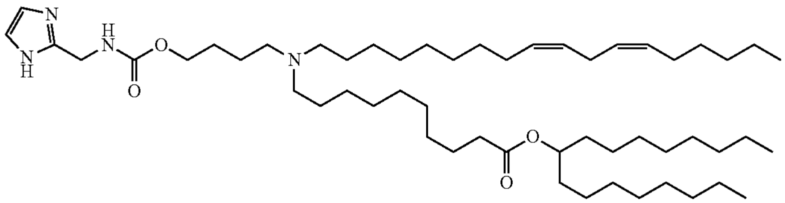 [SMILES: CCCCC/C=C\C/C=C\CCCCCCCCN(CCCCCCCCCC(=O)OC(CCCCCCCC)CCCCCCCC)CCCCOC(=O)NCc1ncc[nH]1] | 869.4 |
| P77 | 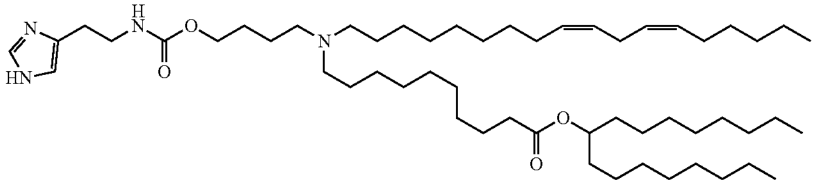 [SMILES: CCCCC/C=C\C/C=C\CCCCCCCCN(CCCCCCCCCC(=O)OC(CCCCCCCC)CCCCCCCC)CCCCOC(=O)NCCc1c[nH]cn1] | 883.4 |
| P78 | 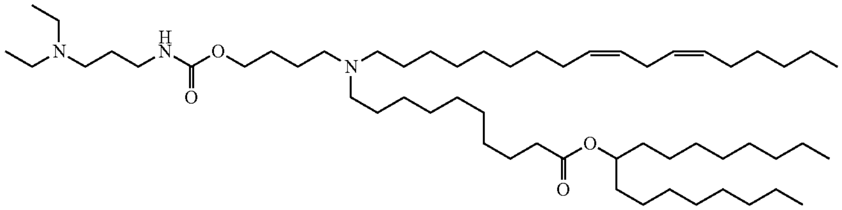 [SMILES: CCCCC/C=C\C/C=C\CCCCCCCCN(CCCCCCCCCC(=O)OC(CCCCCCCC)CCCCCCCC)CCCCOC(=O)NCCCN(CC)CC] | 902.5 |
| P79 | 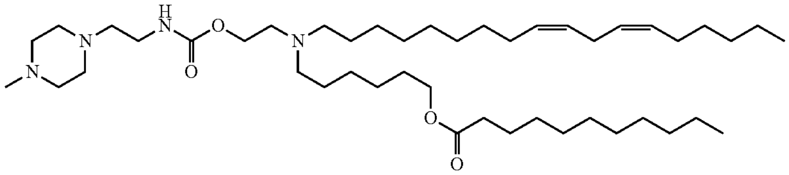 [SMILES: CCCCC/C=C\C/C=C\CCCCCCCCN(CCCCCCOC(=O)CCCCCCCCCC)CCOC(=O)NCCN1CCN(C)CC1] | 747.2 |
| P80 | 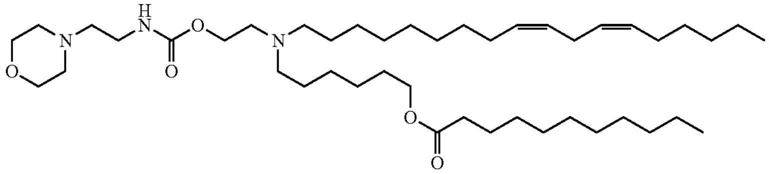 [SMILES: CCCCC/C=C\C/C=C\CCCCCCCCN(CCCCCCOC(=O)CCCCCCCCCC)CCOC(=O)NCCN1CCOCC1] | 734.2 |
| P81 | 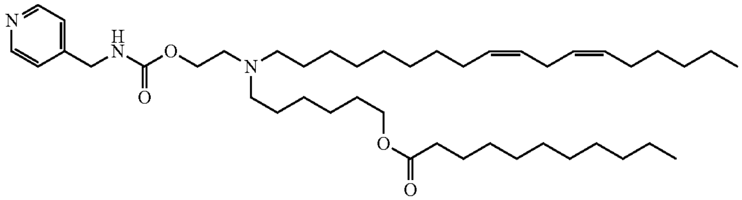 [SMILES: CCCCC/C=C\C/C=C\CCCCCCCCN(CCCCCCOC(=O)CCCCCCCCCC)CCOC(=O)NCc1ccncc1] | 712.1 |
| P82 | 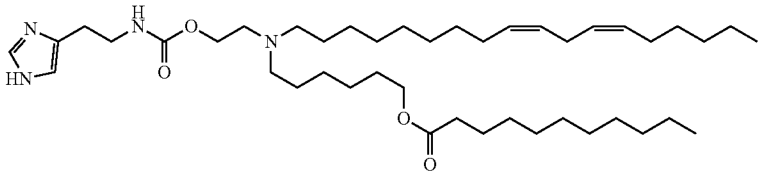 [SMILES: CCCCC/C=C\C/C=C\CCCCCCCCN(CCCCCCOC(=O)CCCCCCCCCC)CCOC(=O)NCCc1c[nH]cn1] | 715.1 |

TABLE P1-continued
| Lipid no | Structure | MW |
|---|---|---|
| P83 | 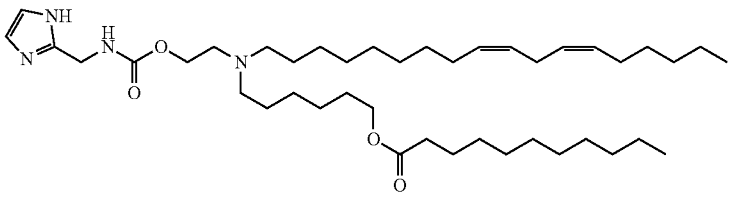 [SMILES: CCCCC/C=C\C/C=C\CCCCCCCCN(CCCCCCOC(=O)CCCCCCCCCC)CCOC(=O)NCc1ncc[nH]1] | 701.1 |
| P84 | 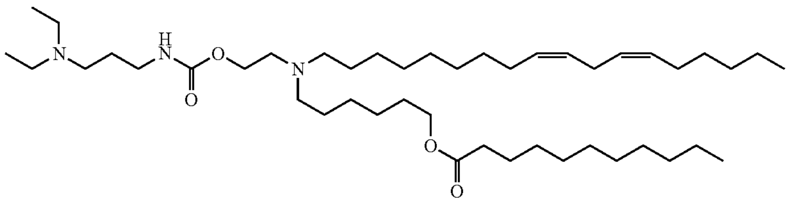 [SMILES: CCCCC/C=C\C/C=C\CCCCCCCCN(CCCCCCOC(=O)CCCCCCCCCC)CCOC(=O)NCCCN(CC)CC] | 734.2 |
| P85 | 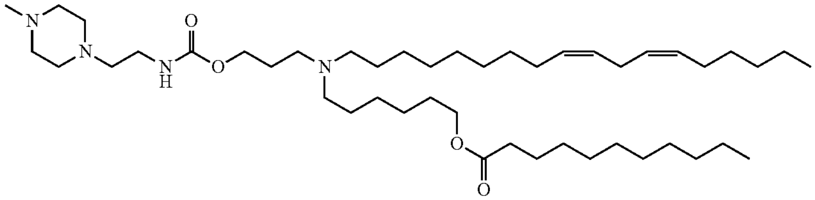 [SMILES: CCCCC/C=C\C/C=C\CCCCCCCCN(CCCCCCOC(=O)CCCCCCCCCC)CCCOC(=O)NCCN1CCN(C)CC1] | 761.2 |
| P86 | 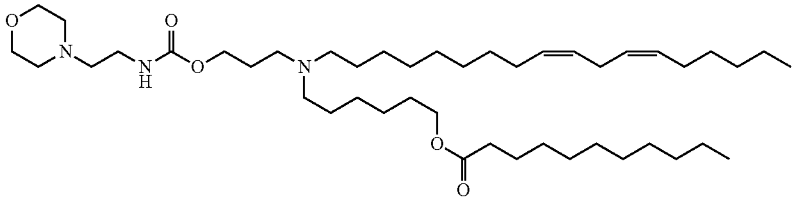 [SMILES: CCCCC/C=C\C/C=C\CCCCCCCCN(CCCCCCOC(=O)CCCCCCCCCC)CCCOC(=O)NCCN1CCOCC1] | 748.2 |
| P87 | 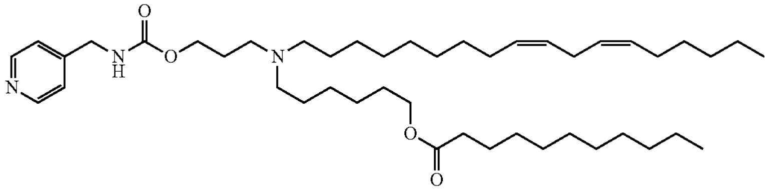 [SMILES: CCCCC/C=C\C/C=C\CCCCCCCCN(CCCCCCOC(=O)CCCCCCCCCC)CCCOC(=O)NCc1ccncc1] | 726.1 |
| P88 | 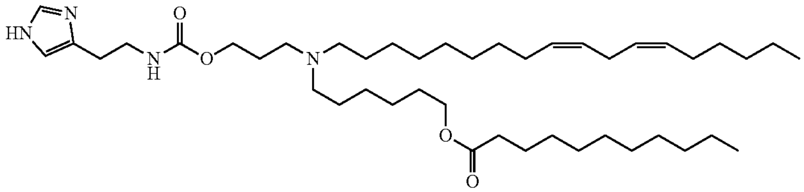 [SMILES: CCCCC/C=C\C/C=C\CCCCCCCCN(CCCCCCOC(=O)CCCCCCCCCC)CCCOC(=O)NCCc1c[nH]cn1] | 729.1 |
| P89 | 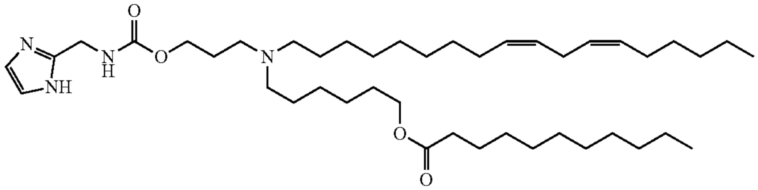 [SMILES: CCCCC/C=C\C/C=C\CCCCCCCCN(CCCCCCOC(=O)CCCCCCCCCC)CCCOC(=O)NCc1ncc[nH]1] | 715.1 |

TABLE P1-continued
| Lipid no | Structure | MW |
|---|---|---|
| P90 | 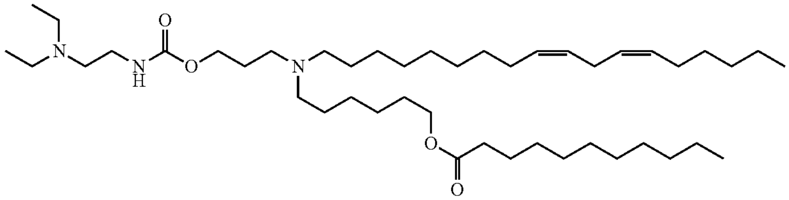 [SMILES: CCCCC/C=C\C/C=C\CCCCCCCCN(CCCCCCOC(=O)CCCCCCCCCC)CCCOC(=O)NCCN(CC)CC] | 734.2 |
| P91 | 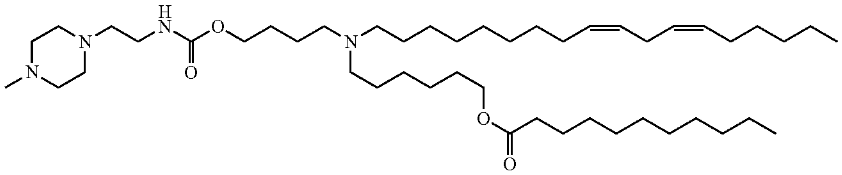 [SMILES: CCCCC/C=C\C/C=C\CCCCCCCCN(CCCCCCOC(=O)CCCCCCCCCC)CCCCOC(=O)NCCN1CCN(C)CC1] | 775.3 |
| P92 | 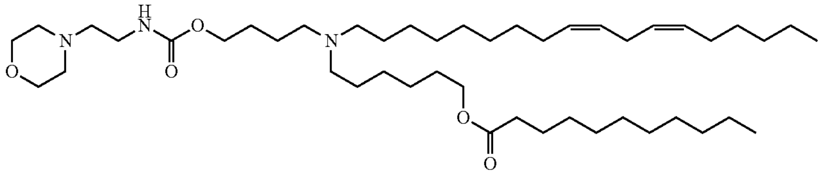 [SMILES: CCCCC/C=C\C/C=C\CCCCCCCCN(CCCCCCOC(=O)CCCCCCCCCC)CCCCOC(=O)NCCN1CCOCC1] | 762.2 |
| P93 | 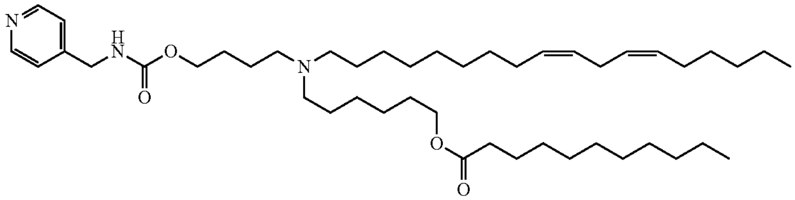 [SMILES: CCCCC/C=C\C/C=C\CCCCCCCCN(CCCCCCOC(=O)CCCCCCCCCC)CCCCOC(=O)NCc1ccncc1] | 740.2 |
| P94 | 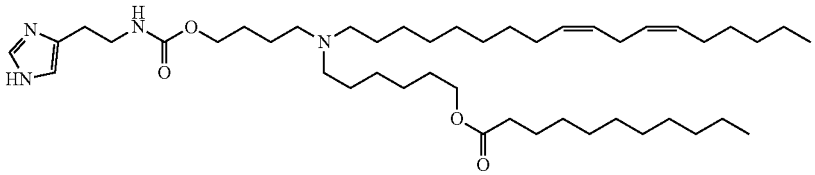 [SMILES: CCCCC/C=C\C/C=C\CCCCCCCCN(CCCCCCOC(=O)CCCCCCCCCC)CCCCOC(=O)NCCc1c[nH]cn1] | 743.2 |
| P95 | 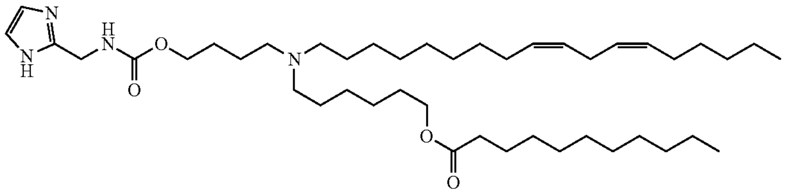 [SMILES: CCCCC/C=C\C/C=C\CCCCCCCCN(CCCCCCOC(=O)CCCCCCCCCC)CCCCOC(=O)NCc1ncc[nH]1] | 729.1 |
| P96 | 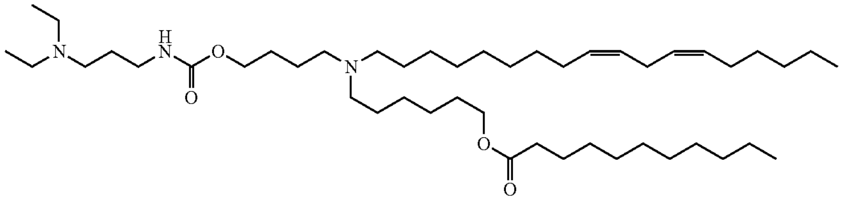 [SMILES: CCCCC/C=C\C/C=C\CCCCCCCCN(CCCCCCOC(=O)CCCCCCCCCC)CCCCOC(=O)NCCCN(CC)CC] | 762.3 |
| P97 | 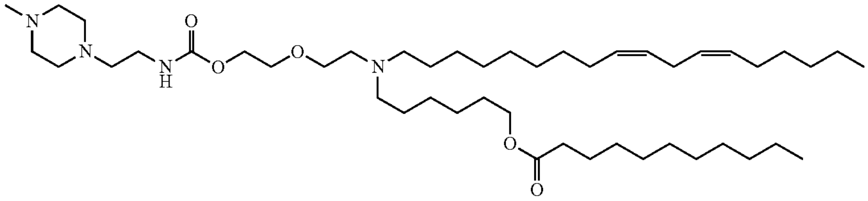 [SMILES: CCCCC/C=C\C/C=C\CCCCCCCCN(CCCCCCOC(=O)CCCCCCCCCC)CCOCCOC(=O)NCCN1CCN(C)CC1] | 791.3 |

TABLE P1-continued
| Lipid no | Structure | MW |
|---|---|---|
| P98 | 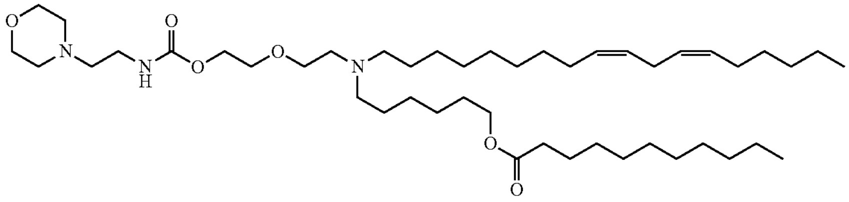 [SMILES: CCCCC/C=C\C/C=C\CCCCCCCCN(CCCCCCOC(=O)CCCCCCCCCC)CCOCCOC(=O)NCCN1CCOCC1] | 778.2 |
| P99 | 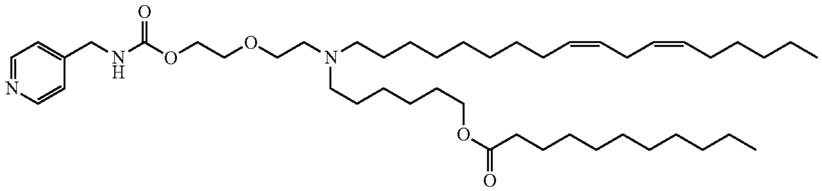 [SMILES: CCCCC/C=C\C/C=C\CCCCCCCCN(CCCCCCOC(=O)CCCCCCCCCC)CCOCCOC(=O)NCc1ccncc1] | 756.2 |
| P100 | 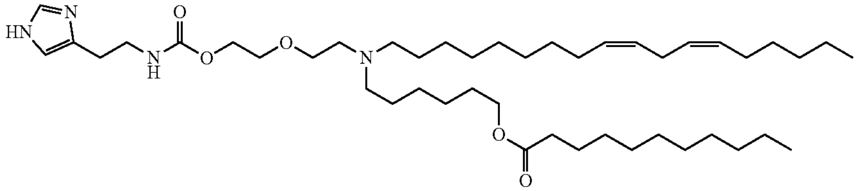 [SMILES: CCCCC/C=C\C/C=C\CCCCCCCCN(CCCCCCOC(=O)CCCCCCCCCC)CCOCCOC(=O)NCCc1c[nH]cn1] | 759.2 |
| P101 | 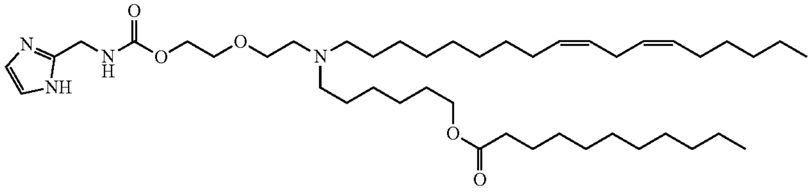 [SMILES: CCCCC/C=C\C/C=C\CCCCCCCCN(CCCCCCOC(=O)CCCCCCCCCC)CCOCCOC(=O)NCc1ncc[nH]1] | 745.2 |
| P102 | 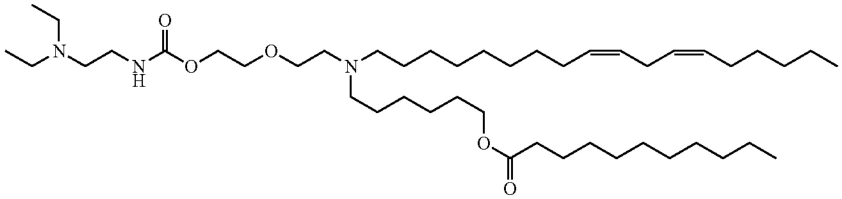 [SMILES: CCCCC/C=C\C/C=C\CCCCCCCCN(CCCCCCOC(=O)CCCCCCCCCC)CCOCCOC(=O)NCCN(CC)CC] | 764.2 |
| P103 | 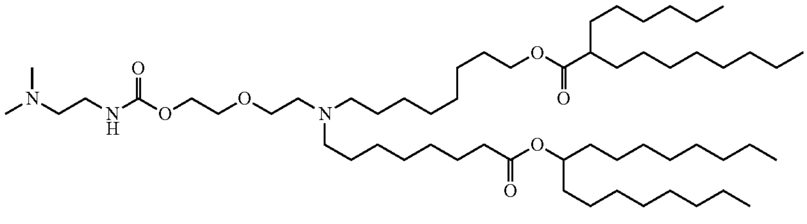 [SMILES: CCCCCCCCC(CCCCCCCC)OC(=O)CCCCCCCN(CCCCCCCCOC(=O)C(CCCCCC)CCCCCCCC)CCOCCOC(=O)NCCN(C)C] | 966.5 |
| P104 | 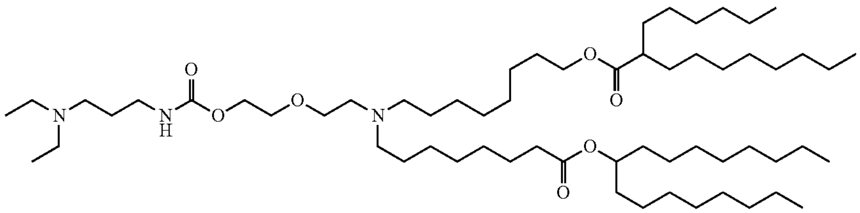 [SMILES: CCCCCCCCC(CCCCCCCC)OC(=O)CCCCCCCN(CCCCCCCCOC(=O)C(CCCCCC)CCCCCCCC)CCOCCOC(=O)NCCCN(CC)CC] | 1008.6 |

TABLE P1-continued
| Lipid no | Structure | MW |
|---|---|---|
| P105 | 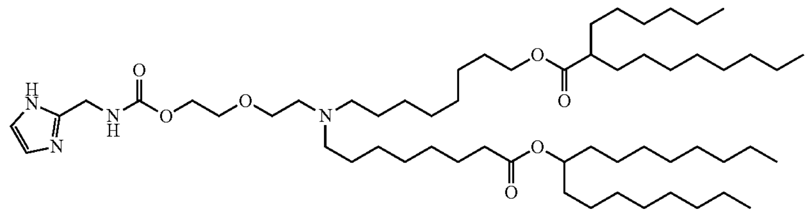 [SMILES: CCCCCCCCC(CCCCCCCC)OC(=O)CCCCCCCN(CCCCCCCCOC(=O)C(CCCCCC)CCCCCCCC)CCOCCOC(=O)NCc1ncc[nH]1] | 975.5 |
| P106 | 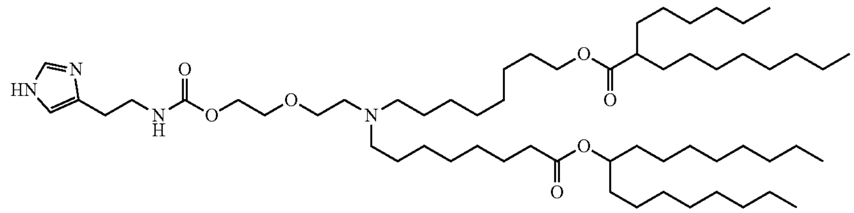 [SMILES: CCCCCCCCC(CCCCCCCC)OC(=O)CCCCCCCN(CCCCCCCCOC(=O)C(CCCCCC)CCCCCCCC)CCOCCOC(=O)NCCc1c[nH]cn1] | 989.5 |
| P107 | 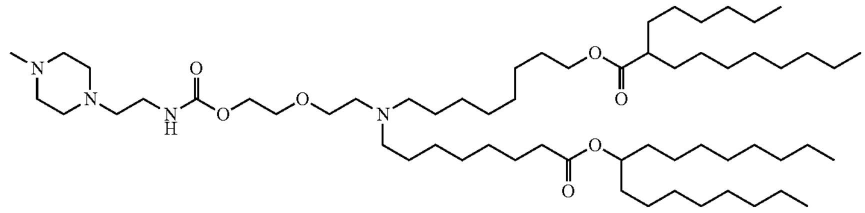 [SMILES: CCCCCCCCC(CCCCCCCC)OC(=O)CCCCCCCN(CCCCCCCCOC(=O)C(CCCCCC)CCCCCCCC)CCOCCOC(=O)NCCN1CCN(C)CC1] | 1021.6 |
| P108 | 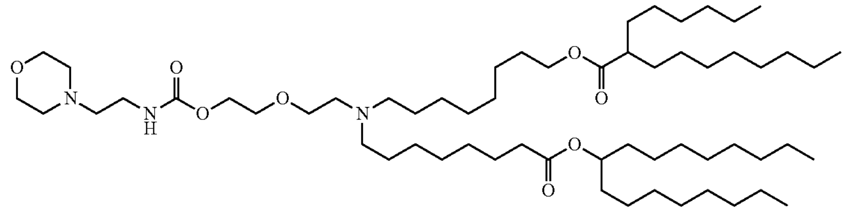 [SMILES: CCCCCCCCC(CCCCCCCC)OC(=O)CCCCCCCN(CCCCCCCCOC(=O)C(CCCCCC)CCCCCCCC)CCOCCOC(=O)NCCN1CCOCC1] | 1008.6 |
| P109 | 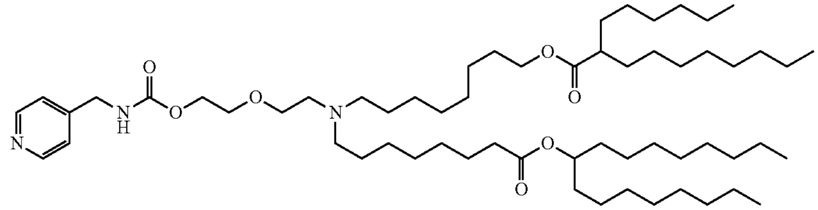 [SMILES: CCCCCCCCC(CCCCCCCC)OC(=O)CCCCCCCN(CCCCCCCCOC(=O)C(CCCCCC)CCCCCCCC)CCOCCOC(=O)NCc1ccncc1] | 986.5 |
| P110 | 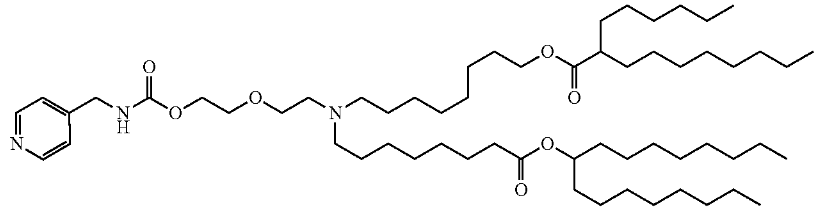 [SMILES: CCCCCCCCC(CCCCCCCC)OC(=O)CCCCCCCN(CCCCCCCCOC(=O)C(CCCCCC)CCCCCCCC)CCOCCOC(=O)NCc1ccncc1] | 1000.5 |
| P111 | 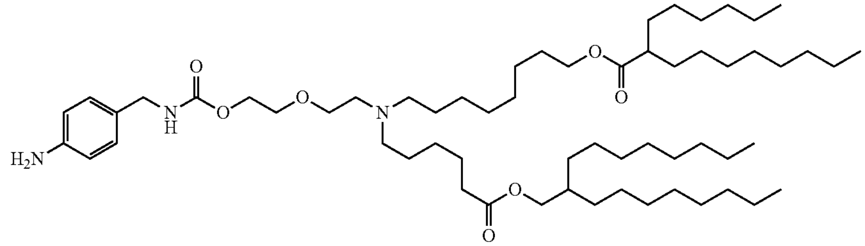 [SMILES: CCCCCCCCC(CCCCCCCC)COC(=O)CCCCCN(CCCCCCCCOC(=O)C(CCCCCC)CCCCCCCC)CCOCCOC(=O)NCc1ccc(N)cc1] | 986.6 |

TABLE P1-continued
| Lipid no | Structure | MW |
| --- | --- | --- |
| P112 | 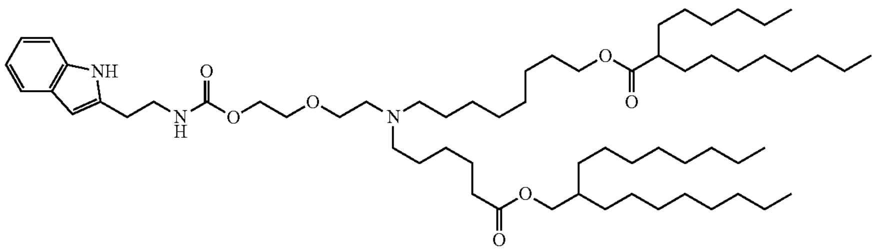 [SMILES: CCCCCCCCC(CCCCCCCC)COC(=O)CCCCCN(CCCCCCCCOC(=O)C(CCCCCC)CCCCCCCC)CCOCCOC(=O)NCCc1cc2ccccc2[nH]1] | 1024.6 |
| P113 | 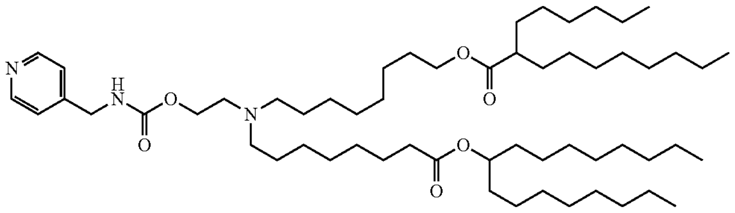 [SMILES: CCCCCCCCC(CCCCCCCC)OC(=O)CCCCCCCN(CCCCCCCCOC(=O)C(CCCCCC)CCCCCCCC)CCOC(=O)NCc1ccncc1] | 942.5 |
| P116 | 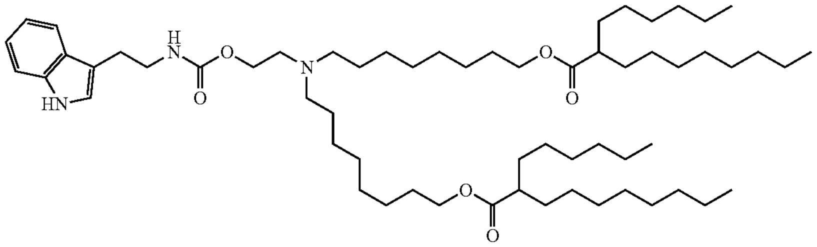 [SMILES: CCCCCCCCC(CCCCCC)C(=O)OCCCCCCCCN(CCCCCCCCOC(=O)C(CCCCCC)CCCCCCCC)CCOC(=O)NCCc1c[nH]c2ccccc12] | 980.6 |
| P117 | 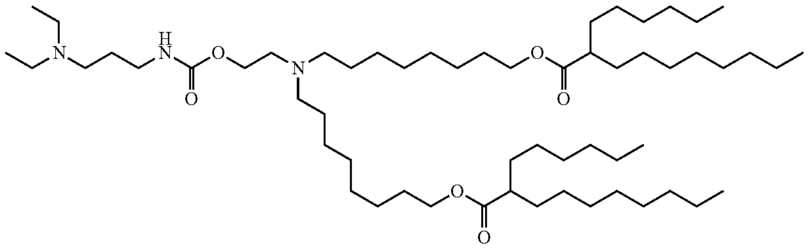 [SMILES: CCCCCCCCC(CCCCCC)C(=O)OCCCCCCCCN(CCCCCCCCOC(=O)C(CCCCCC)CCCCCCCC)CCOC(=O)NCCCN(CC)CC] | 950.6 |
| P118 | 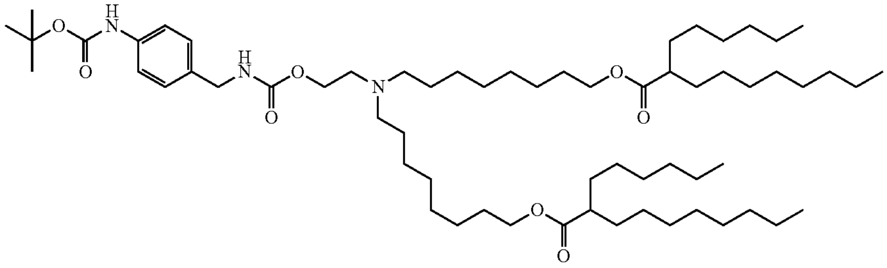 [SMILES: CCCCCCCCC(CCCCCC)C(=O)OCCCCCCCCN(CCCCCCCCOC(=O)C(CCCCCC)CCCCCCCC)CCOC(=O)NCc1ccc(NC(=O)OC(C)(C)C)cc1] | 1042.6 |
| P119 | 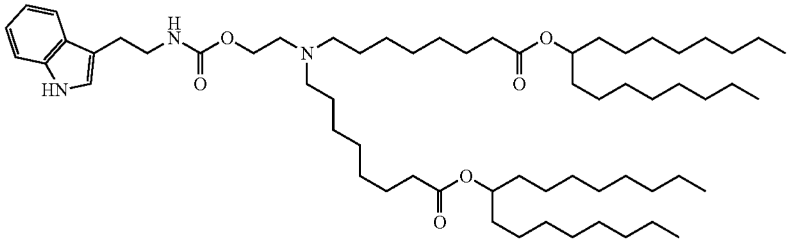 [SMILES: CCCCCCCCC(CCCCCCCC)OC(=O)CCCCCCCN(CCCCCCCC(=O)OC(CCCCCCCC)CCCCCCCC)CCOC(=O)NCCc1c[nH]c2ccccc12] | 1008.6 |

TABLE P1-continued
| Lipid no | Structure | MW |
|---|---|---|
| P120 | 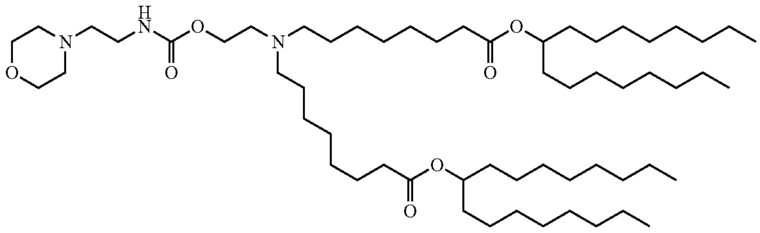 [SMILES: CCCCCCCCC(CCCCCCCC)OC(=O)CCCCCCCN(CCCCCCCC(=O)OC(CCCCCCCC)CCCCCCCC)CCOC(=O)NCCN1CCOCC1] | 978.6 |
| P121 | 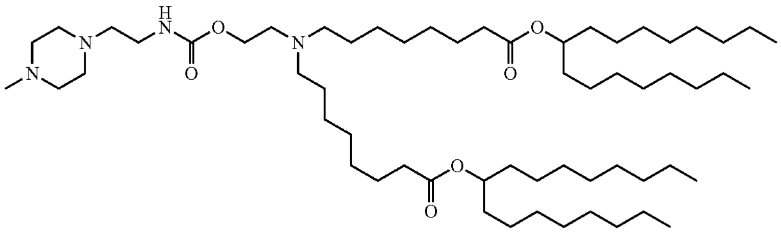 [SMILES: CCCCCCCCC(CCCCCCCC)OC(=O)CCCCCCCN(CCCCCCCC(=O)OC(CCCCCCCC)CCCCCCCC)CCOC(=O)NCCN1CCN(C)CC1] | 991.6 |
| P122 | 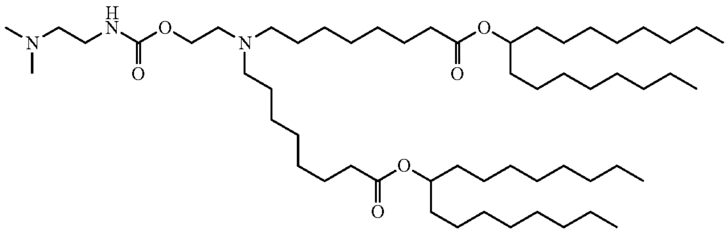 [SMILES: CCCCCCCCC(CCCCCCCC)OC(=O)CCCCCCCN(CCCCCCCC(=O)OC(CCCCCCCC)CCCCCCCC)CCOC(=O)NCCN(C)C] | 936.6 |
| P123 | 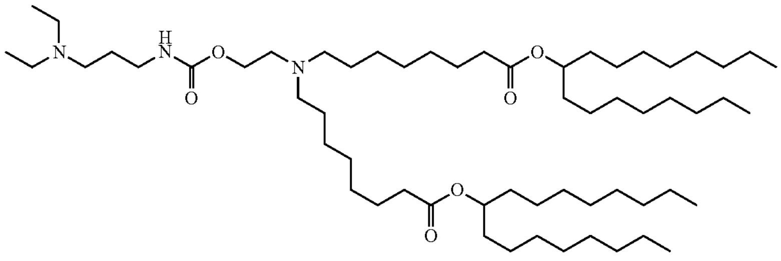 [SMILES: CCCCCCCCC(CCCCCCCC)OC(=O)CCCCCCCN(CCCCCCCC(=O)OC(CCCCCCCC)CCCCCCCC)CCOC(=O)NCCCN(CC)CC] | 978.6 |
| P124 | 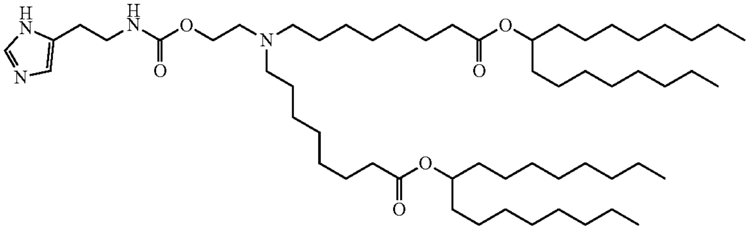 [SMILES: CCCCCCCCC(CCCCCCCC)OC(=O)CCCCCCCN(CCCCCCCC(=O)OC(CCCCCCCC)CCCCCCCC)CCOC(=O)NCCc1cnc[nH]1] | 959.5 |
| P125 | 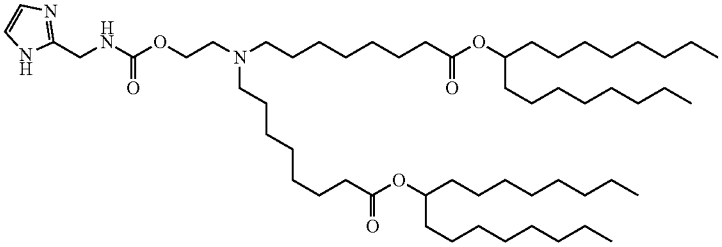 [SMILES: CCCCCCCCC(CCCCCCCC)OC(=O)CCCCCCCN(CCCCCCCC(=O)OC(CCCCCCCC)CCCCCCCC)CCOC(=O)NCc1ncc[nH]1] | 945.5 |

TABLE P1-continued
| Lipid no | Structure | MW |
|---|---|---|
| P126 | 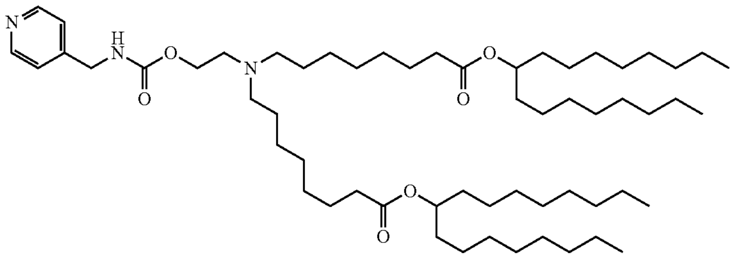 [SMILES: CCCCCCCCC(CCCCCCCC)OC(=O)CCCCCCCN(CCCCCCCC(=O)OC(CCCCCCCC)CCCCCCCC)CCOC(=O)NCc1ccncc1] | 956.5 |
| P127 | 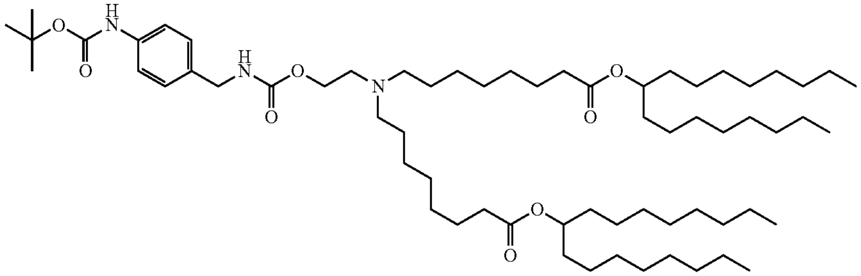 [SMILES: CCCCCCCCC(CCCCCCCC)OC(=O)CCCCCCCN(CCCCCCCC(=O)OC(CCCCCCCC)CCCCCCCC)CCOC(=O)NCc1ccc(NC(=O)OC(C)(C)C)cc1] | 1070.7 |
| P128 | 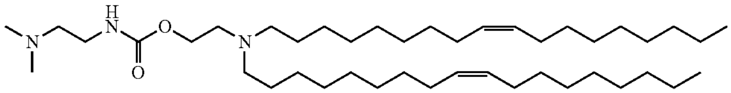 [SMILES: CCCCCCCC/C=C\CCCCCCCCN(CCCCCCCC/C=C\CCCCCCCC)CCOC(=O)NCCN(C)C] | 676.2 |
| P129 | 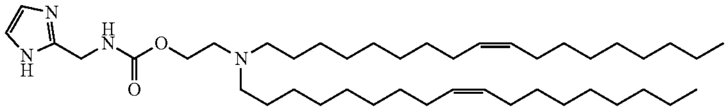 [SMILES: CCCCCCCC/C=C\CCCCCCCCN(CCCCCCCC/C=C\CCCCCCCC)CCOC(=O)NCc1ncc[nH]1] | 685.1 |
| P130 | 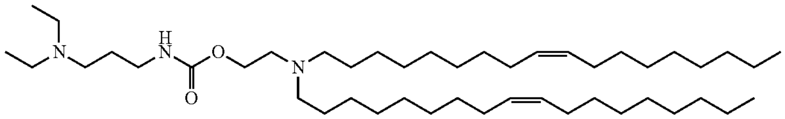 [SMILES: CCCCCCCC/C=C\CCCCCCCCN(CCCCCCCC/C=C\CCCCCCCC)CCOC(=O)NCCCN(CC)CC] | 718.3 |
| P131 | 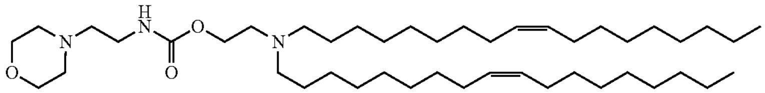 [SMILES: CCCCCCCC/C=C\CCCCCCCCN(CCCCCCCC/C=C\CCCCCCCC)CCOC(=O)NCCN1CCOCC1] | 718.2 |
| P132 | 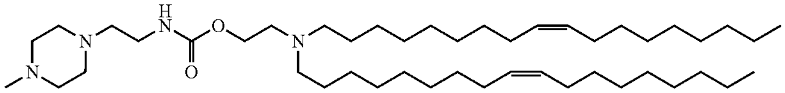 [SMILES: CCCCCCCC/C=C\CCCCCCCCN(CCCCCCCC/C=C\CCCCCCCC)CCOC(=O)NCCN1CCN(C)CC1] | 731.2 |
| P133 | 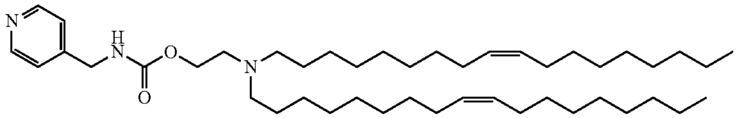 [SMILES: CCCCCCCC/C=C\CCCCCCCCN(CCCCCCCC/C=C\CCCCCCCC)CCOC(=O)NCc1ccncc1] | 696.2 |
| P134 | 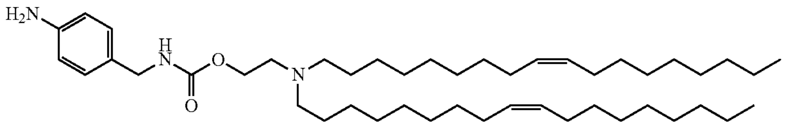 [SMILES: CCCCCCCC/C=C\CCCCCCCCN(CCCCCCCC/C=C\CCCCCCCC)CCOC(=O)NCc1ccc(N)cc1] | 710.2 |
| P135 | 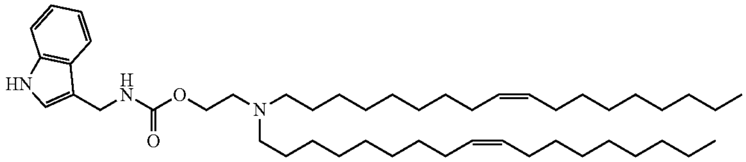 [SMILES: CCCCCCCC/C=C\CCCCCCCCN(CCCCCCCC/C=C\CCCCCCCC)CCOC(=O)NCc1c[nH]c2ccccc12] | 734.2 |

TABLE P1-continued
| Lipid no | Structure | MW |
|---|---|---|
| P136 | 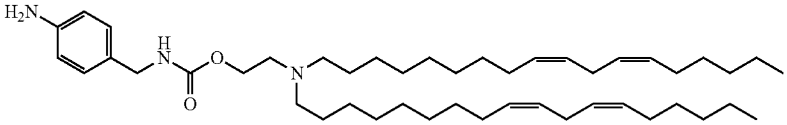 [SMILES: CCCCC/C=C\C/C=C\CCCCCCCCN(CCCCCCCC/C=C\C/C=C\CCCCC)CCOC(=O)NCc1ccc(N)cc1] | 706.2 |
| P137 | 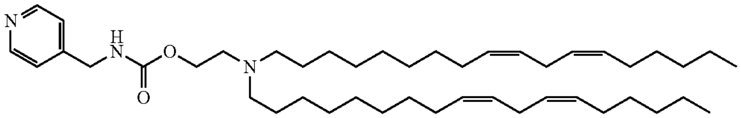 [SMILES: CCCCC/C=C\C/C=C\CCCCCCCCN(CCCCCCCC/C=C\C/C=C\CCCCC)CCOC(=O)NCc1ccncc1] | 692.1 |
| P138 | 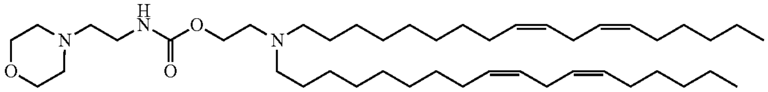 [SMILES: CCCCC/C=C\C/C=C\CCCCCCCCN(CCCCCCCC/C=C\C/C=C\CCCCC)CCOC(=O)NCCN1CCOCC1] | 714.2 |
| P139 | 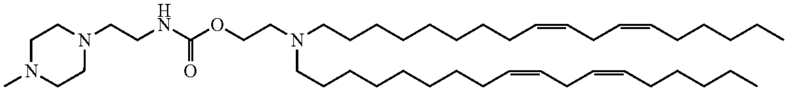 [SMILES: CCCCC/C=C\C/C=C\CCCCCCCCN(CCCCCCCC/C=C\C/C=C\CCCCC)CCOC(=O)NCCN1CCN(C)CC1] | 727.2 |
| P140 | 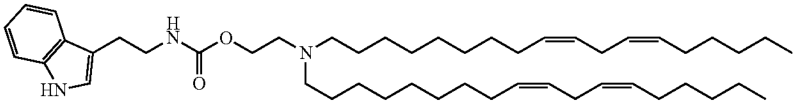 [SMILES: CCCCC/C=C\C/C=C\CCCCCCCCN(CCCCCCCC/C=C\C/C=C\CCCCC)CCOC(=O)NCCc1c[nH]c2ccccc12] | 744.2 |
| P141 | 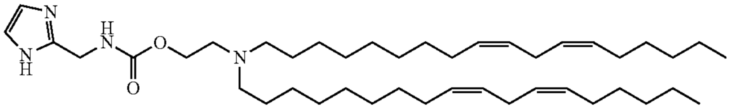 [SMILES: CCCCC/C=C\C/C=C\CCCCCCCCN(CCCCCCCC/C=C\C/C=C\CCCCC)CCOC(=O)NCc1ncc[nH]1] | 681.1 |
| P142 | 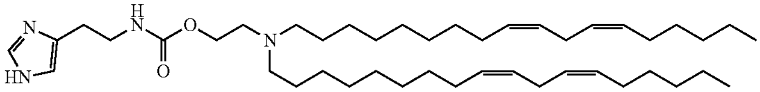 [SMILES: CCCCC/C=C\C/C=C\CCCCCCCCN(CCCCCCCC/C=C\C/C=C\CCCCC)CCOC(=O)NCCc1c[nH]cn1] | 695.1 |
| P143 | 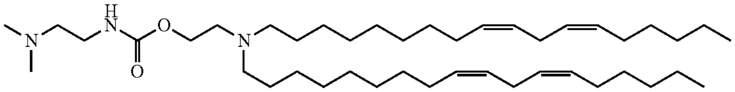 [SMILES: CCCCC/C=C\C/C=C\CCCCCCCCN(CCCCCCCC/C=C\C/C=C\CCCCC)CCOC(=O)NCCN(C)C] | 672.1 |
| P144 | 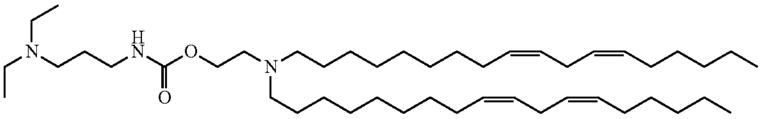 [SMILES: CCCCC/C=C\C/C=C\CCCCCCCCN(CCCCCCCC/C=C\C/C=C\CCCCC)CCOC(=O)NCCCN(CC)CC] | 714.2 |
| P145 | 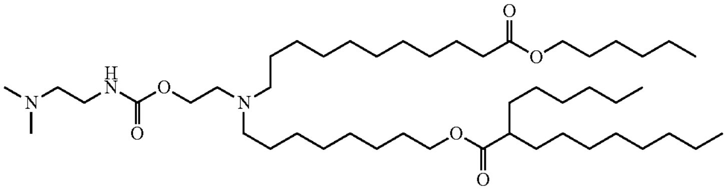 [SMILES: CCCCCCCCC(CCCCCC)C(=O)OCCCCCCCCN(CCCCCCCCCCC(=O)OCCCCCC)CCOC(=O)NCCN(C)C] | 810.3 |
| P146 | 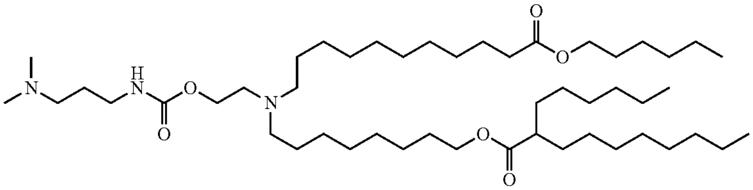 [SMILES: CCCCCCCCC(CCCCCC)C(=O)OCCCCCCCCN(CCCCCCCCCCC(=O)OCCCCCC)CCOC(=O)NCCCN(C)C] | 824.3 |

TABLE P1-continued
| Lipid no | Structure | MW |
| --- | --- | --- |
| P147 | 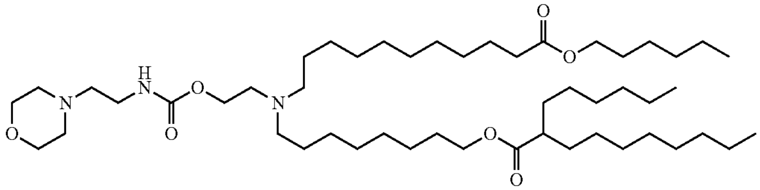 [SMILES: CCCCCCCCC(CCCCCC)C(=O)OCCCCCCCCN(CCCCCCCCCCC(=O)OCCCCCC)CCOC(=O)NCCN1CCOCC1] | 852.3 |
| P148 | 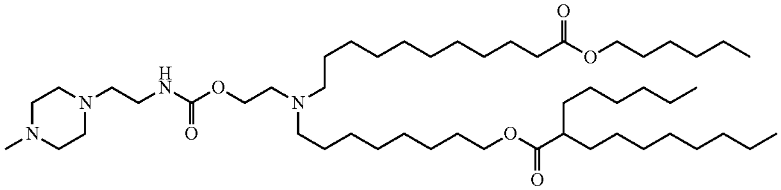 [SMILES: CCCCCCCCC(CCCCCC)C(=O)OCCCCCCCCN(CCCCCCCCCCC(=O)OCCCCCC)CCOC(=O)NCCN1CCN(C)CC1] | 865.4 |
| P149 | 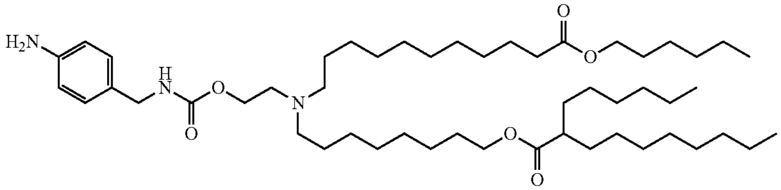 [SMILES: CCCCCCCCC(CCCCCC)C(=O)OCCCCCCCCN(CCCCCCCCCCC(=O)OCCCCCC)CCOC(=O)NCc1ccc(N)cc1] | 844.3 |
| P150 | 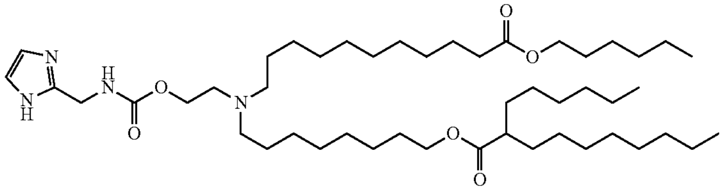 [SMILES: CCCCCCCCC(CCCCCC)C(=O)OCCCCCCCCN(CCCCCCCCCCC(=O)OCCCCCC)CCOC(=O)NCc1ncc[nH]1] | 819.2 |
| P151 | 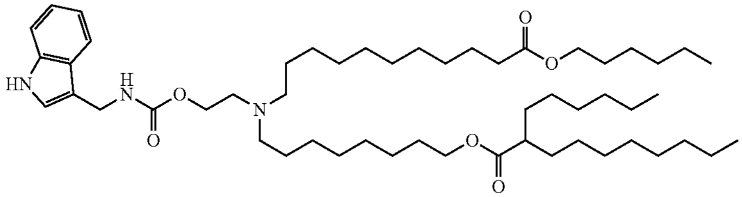 [SMILES: CCCCCCCCC(CCCCCC)C(=O)OCCCCCCCCN(CCCCCCCCCCC(=O)OCCCCCC)CCOC(=O)NCc1c[nH]c2ccccc12] | 868.3 |
| P152 | 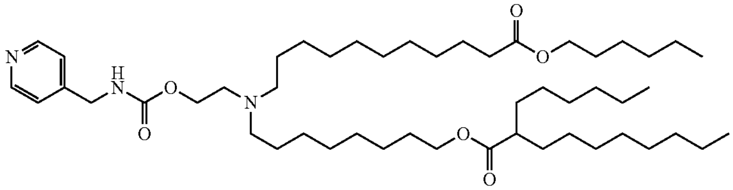 [SMILES: CCCCCCCCC(CCCCCC)C(=O)OCCCCCCCCN(CCCCCCCCCCC(=O)OCCCCCC)CCOC(=O)NCc1ccncc1] | 830.3 |
| P153 | 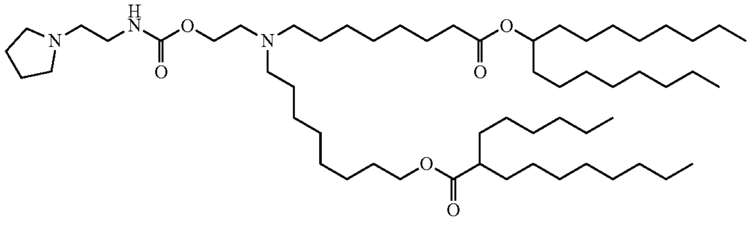 [SMILES: CCCCCCCCC(CCCCCCCC)OC(=O)CCCCCCCN(CCCCCCCCOC(=O)C(CCCCCC)CCCCCCCC)CCOC(=O)NCCN1CCCC1] | 948.6 |

TABLE P1-continued
| Lipid no | Structure | MW |
| --- | --- | --- |
| P154 | 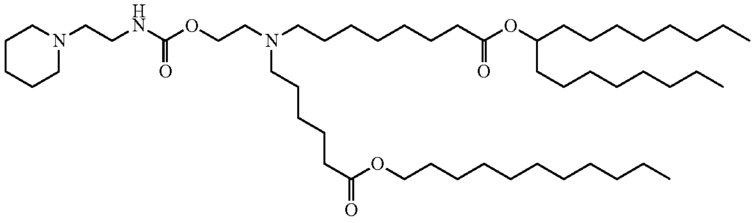 [SMILES: CCCCCCCCCCCOC(=O)CCCCCN(CCCCCCCC(=O)OC(CCCCCCCC)CCCCCCCC)CCOC(=O)NCCN1CCCCC1] | 864.4 |
| P155 | 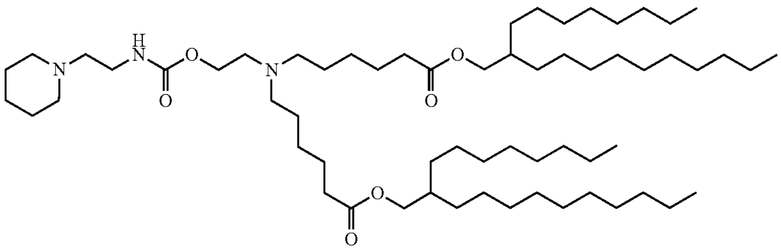 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCCC1] | 1004.7 |
| P156 | 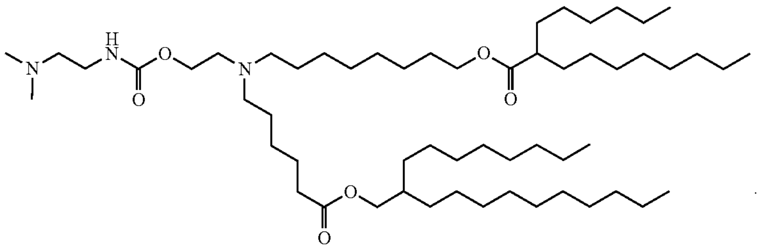 [SMILES: CCCCCCCCCCC(CCCCCCCC)COC(=O)CCCCCN(CCCCCCCCOC(=O)C(CCCCCC)CCCCCCCC)CCOC(=O)NCCN(C)C] | 936.5 |
| P157 | 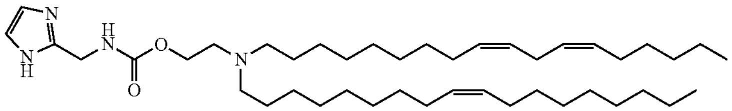 [SMILES: CCCCC/C=C\C/C=C\CCCCCCCCN(CCCCCCCC/C=C\CCCCCCCC)CCOC(=O)NCc1ncc[nH]1] | 683.1 |
| P158 | 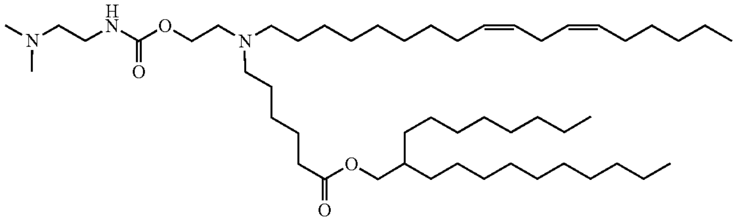 [SMILES: CCCCC/C=C\C/C=C\CCCCCCCCN(CCCCCC(=O)OCC(CCCCCCCC)CCCCCCCCCC)CCOC(=O)NCCN(C)C] | 818.4 |
| P159 | 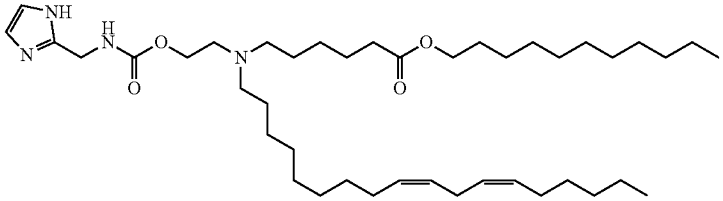 [SMILES: CCCCC/C=C\C/C=C\CCCCCCCCN(CCCCCC(=O)OCCCCCCCCCCC)CCOC(=O)NCc1ncc[nH]1] | 701.1 |
| P160 | 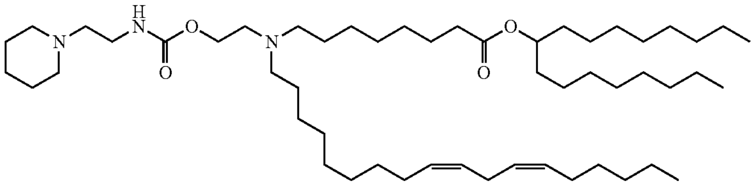 [SMILES: CCCCC/C=C\C/C=C\CCCCCCCCN(CCCCCCCC(=O)OC(CCCCCCCC)CCCCCCCC)CCOC(=O)NCCN1CCCCC1] | 844.4 |

TABLE P1-continued
| Lipid no | Structure | MW |
|---|---|---|
| P161 | 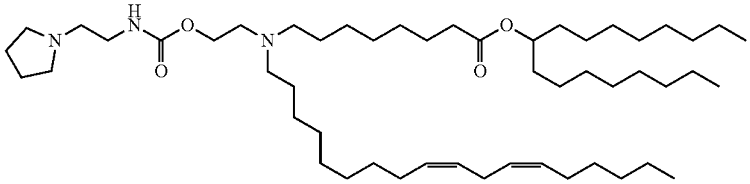 [SMILES: CCCCC/C=C\C/C=C\CCCCCCCCN(CCCCCCCC(=O)OC(CCCCCCCC)CCCCCCCC)CCOC(=O)NCCN1CCCC1] | 830.4 |
| P162 | 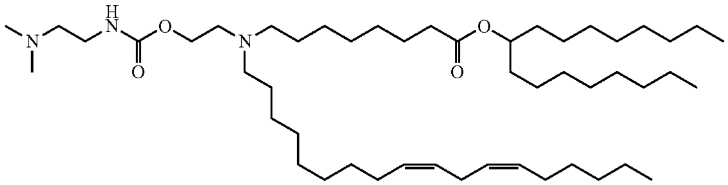 [SMILES: CCCCC/C=C\C/C=C\CCCCCCCCN(CCCCCCCC(=O)OC(CCCCCCCC)CCCCCCCC)CCOC(=O)NCCN(C)C] | 804.3 |
| P163 | 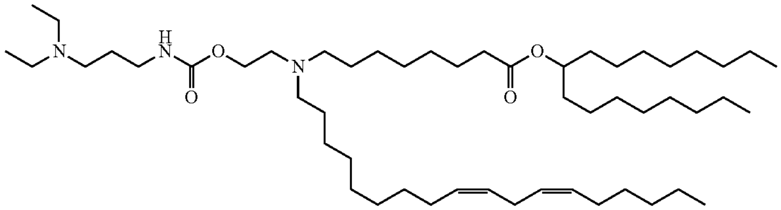 | 846.4 |
| P164 | 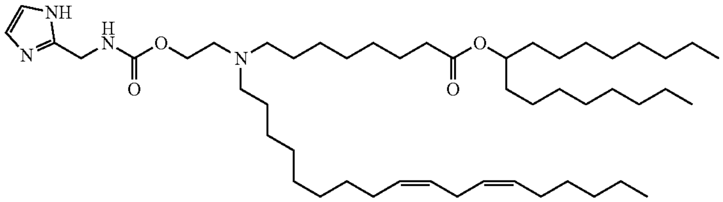 [SMILES: CCCCC/C=C\C/C=C\CCCCCCCCN(CCCCCCCC(=O)OC(CCCCCCCC)CCCCCCCC)CCOC(=O)NCc1ncc[nH]1] | 813.3 |
| P165 | 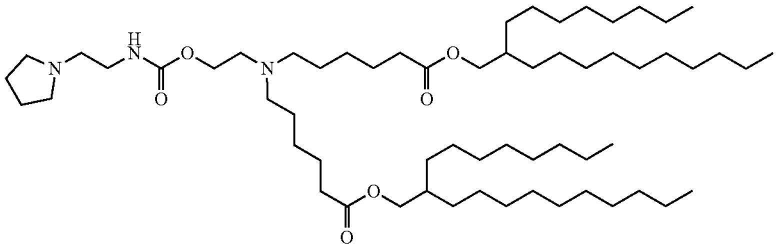 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCC1] | 990.6 |
| P166 | 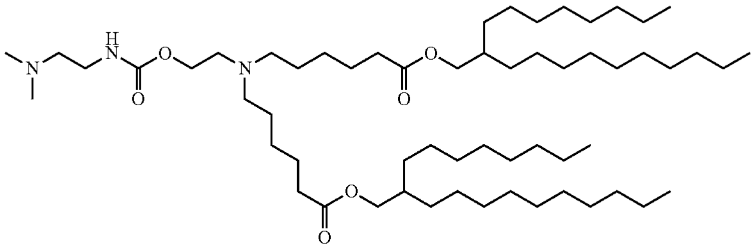 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C] | 964.6 |

In some aspects, the present invention provides an intermediate compound represented by the structure of formula (VI):
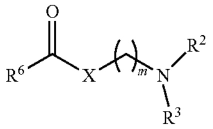
(VI)
wherein
$R^6$ is a leaving group, preferable is
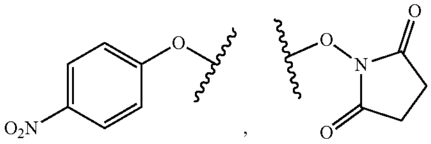
, , or
-continued
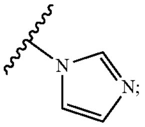
and
the remaining groups are as defined above.
In embodiments $R^6$ is
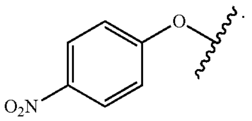 [SMILES: *Oc1ccc([N+](=O)[O-])cc1]
In embodiments, $R^2$ and $R^3$ are defined as above.
In embodiments, the intermediate compound is:
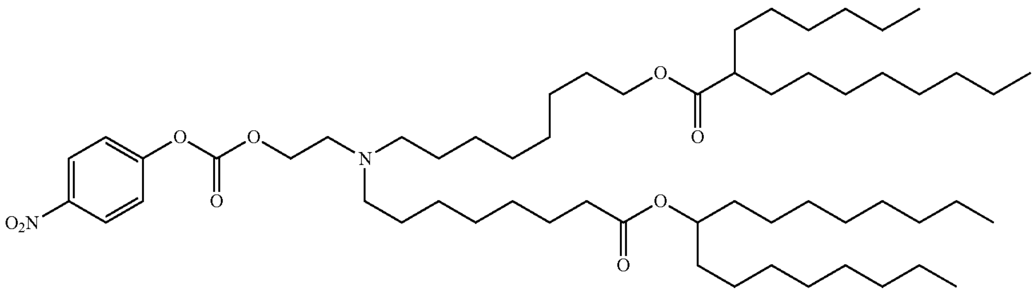
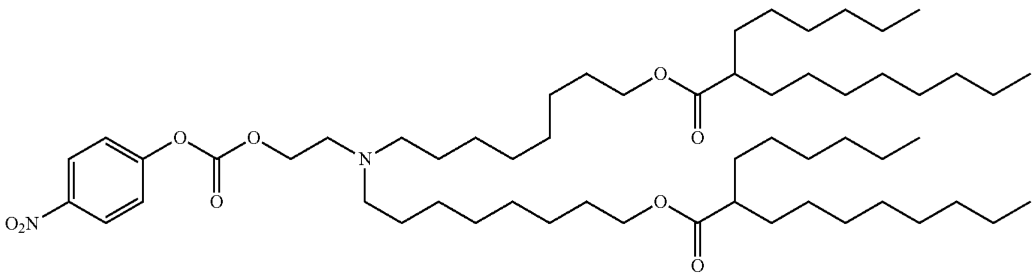
or
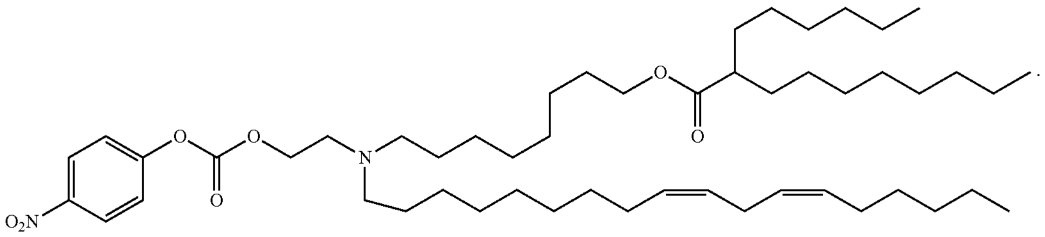

In some aspects, the present invention provides a method of preparing the cationic lipid of the invention, comprising a step of reacting a compound of formula (VI) with a compound of formula (VII), to afford the cationic lipid of formula (IA):

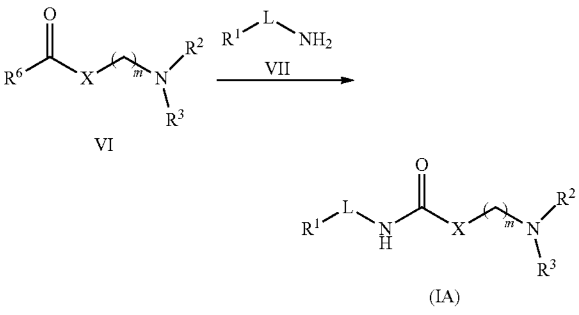

wherein each of the groups is as defined in aspects of the invention. In embodiments, the reaction is conducted in the presence of a base, e.g., TEA or DIPEA.

In some aspects, the present invention provides a nanoparticle composition, comprising a cationic lipid of the invention.

In some aspects, the present invention provides a nanoparticle composition, further comprising one or more selected from the group of a phospholipid, a PEG lipid and a structural lipid. In some aspects, the present invention provides a nanoparticle composition, further comprising a phospholipid, a PEG lipid and a structural lipid.

In some aspects, the present invention provides a pharmaceutical composition comprising a nanoparticle composition according to the present invention and a pharmaceutically acceptable carrier.

As used herein, "a therapeutic and/or prophylactic nucleic acid molecule" refers to a nucleic acid molecule encoding a therapeutic and/or prophylactic protein which can be translated in cells. Such a nucleic acid molecule can be any suitable forms of nucleic acid molecules, e.g. any linear RNA or any circular RNA.

In some aspects, the present invention provides a method of delivering a nucleic acid molecule to a cell, including the step of administering to a subject (i) the nanoparticle composition of the invention and (ii) said nucleic acid molecule, in which administering involves contacting the cell with the nanoparticle composition, whereby the nucleic acid molecule is delivered to the cell. In some aspects, the present invention provides a method of delivering a nucleic acid molecule to a cell, including the step of administering to a subject a composition including (i) the nanoparticle composition of the invention and (ii) said nucleic acid molecule, in which administering involves contacting the cell with the nanoparticle composition, whereby the nucleic acid molecule is delivered to the cell. In embodiments, said nucleic molecule is a protein-coding nucleic acid molecule. In embodiments, said nucleic molecule is a therapeutic and/or prophylactic nucleic acid molecule. In embodiments, the protein-coding molecule can be translated in vivo. n embodiments, the nucleic acid molecule is encapsulated in the nanoparticle composition of the present invention. In embodiments, the nucleic acid molecule is attached to the nanoparticle composition of the present invention. As used herein "attached to" refers to attaching the nucleic acid to the nanoparticle composition of the present invention via any physical or chemical means.

In some aspects, the present invention provides a method of delivering a therapeutic and/or prophylactic nucleic acid molecule to a cell, including the step of administering to a subject a pharmaceutical composition comprising (i) the nanoparticle composition of the invention and (ii) a therapeutic and/or prophylactic nucleic acid molecule, in which administering involves contacting the cell with the nanoparticle composition, whereby the therapeutic and/or prophylactic nucleic acid molecule is delivered to the cell. In embodiments, the nucleic acid molecule is encapsulated in the nanoparticle composition of the present invention. In embodiments, the nucleic acid molecule is attached to the nanoparticle composition of the present invention. As used herein "attached to" refers to attaching the nucleic acid to the nanoparticle composition of the present invention via any physical or chemical means.

In embodiments, the subject is a mammal. In embodiments, the mammal is a human.

In some aspects, the present invention provides a method of delivering a protein-coding nucleic acid molecule to a cell, including the step of administering to a subject (i) the nanoparticle composition of the invention and (ii) a protein-coding nucleic acid molecule, in which administering involves contacting the cell with the nanoparticle composition of the present invention, whereby the nucleic acid is delivered to the cell. In embodiments, the protein-coding nucleic acid molecule is encapsulated in the nanoparticle composition of the present invention. In embodiments, the protein-coding nucleic acid molecule is attached to the nanoparticle composition of the present invention. As used herein "attached to" refers to attaching the nucleic acid to the nanoparticle composition of the present invention via any physical or chemical means.

In some aspects, the present invention provides a method of providing a polypeptide of interest in a cell, including the step of contacting the cell with a nanoparticle composition of the invention and (ii) a nucleic acid molecule encoding the polypeptide of interest, whereby the nucleic acid molecule is capable of being translated in the cell to produce the polypeptide. In embodiments, the nucleic acid molecule is an mRNA molecule, a siRNA molecule, or a circular RNA molecule. In embodiments, the nucleic acid molecule is a linear RNA. In embodiments, the nucleic acid molecule is a circular RNA.

In some aspects, the present invention provides a nanoparticle composition for use in the manufacture of a medicament for the treatment of a disease or disorder in a subject or mammal in need thereof, wherein the nanoparticle composition includes (i) a lipid component including a phospholipid, a PEG lipid, a structural lipid, and a cationic lipid of the invention and (ii) a therapeutic and/or prophylactic nucleic acid molecule. In embodiments, the nucleic acid molecule is an mRNA, a siRNA or a circular RNA. In embodiments, the nucleic acid molecule is a linear RNA. In embodiments, the nucleic acid molecule is a circular RNA.

In some aspects, the present invention provides a nanoparticle composition for use in the manufacture of a medicament for the treatment of a disease or disorder in a subject or mammal in need thereof, wherein the nanoparticle composition includes (i) a cationic lipid of the invention and (ii) a nucleic acid molecule encoding a therapeutic and/or prophylactic protein. In embodiments, the nucleic acid molecule is an mRNA, a siRNA or a circular RNA. In embodiments, the nucleic acid molecule is a linear RNA. In embodiments, the nucleic acid molecule is a circular RNA.

In embodiments of the present invention, the subject is a mammal.

In embodiments of the present invention, the mammal is a human.

In some aspects, the present invention provides use of the cationic lipid of the invention, for the manufacture of a nanoparticle composition.

In some aspects, the present invention provides use of the cationic lipid of the invention or use of the nanoparticle composition of the invention for the manufacture of a medicament for the treatment of a disease or disorder in a subject in need thereof.

In embodiments, the subject is a mammal.

In embodiments, the mammal is a human.

In some aspects, the present invention provides a method of synthesizing a cationic lipid of Formula (I), (IA), (II), (III), (IV), or (V) and methods of making a nanoparticle composition including a lipid component comprising the cationic lipid of Formula (I), (IA), (II), (III), (IV), or (V).

Examples

The following examples are included to further illustrate the invention described herein and to demonstrate embodiments of the invention. It should be appreciated by those of skill in the art that the techniques disclosed in the examples which follow represent techniques discovered by the inventors to function well in the practice of the invention, and thus can be considered to constitute modes for its practice. However, those of skill in the art should, in light of the present disclosure, appreciate that many changes can be made in the specific embodiments which are disclosed and still obtain a like or similar result which are within the spirit and scope of the invention.

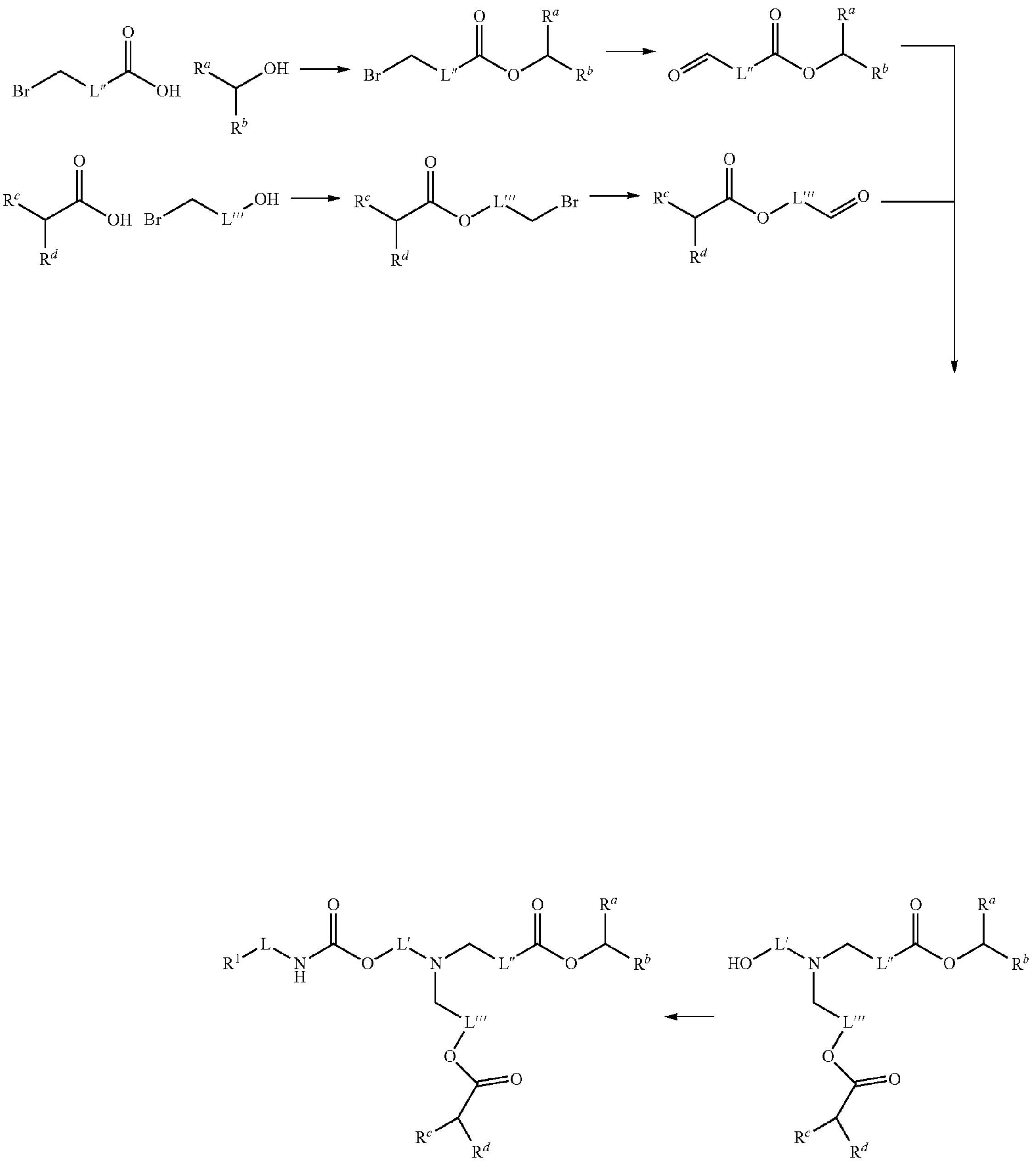

wherein

L" and L"' are each independently $C_3$-$C_{14}$ alkylene;

$R^a$, $R^b$, $R^c$ and $R^d$ are each independently $C_3$-$C_{21}$ alkyl or $C_3$-$C_{21}$ alkenyl, provided that $R^a$ and $R^b$ comprise 3-21 carbon atoms in total, and $R^c$ and $R^d$ comprise 3-21 carbon atoms in total; and the remaining groups are as defined herein.

The General scheme above depicts the synthetic strategy. In the first row Bromo-carboxylic acids are esterified with a given alcohol to yield a bromo bearing ester. The reaction is done by refluxing in toluene with catalytic amounts of p-toluenesulfonic acid. The ester subsequently oxidized into an aldehyde and used directly in the next reaction.

In the second row a carboxylic acid is esterified with a bromo-alcohol to form a bromo-bearing ester on the alcoholic acid (the reaction conditions are similar) which is subsequently oxidized to the corresponding aldehyde. In both cases Kornblum oxidation is carried out by heating the bromo bearing esters to 150° C. in DMSO and adding $NaHCO_3$. The aldehydes are then reacted in a sequential manner. The first reaction is done in methanol and the reduction is carried out by adding sodium borohydride. A short work up is done to remove excess of ethaolamine and the second aldehyde is added. The reaction takes place in DCM and Sodium triacetoxyborohydride is used as the reducing agent. Lastly, the carbamate is produced by reacting the resulting alcohol with p-Nitrophenylchloroformate followed by the addition of an amine.

Representative Synthetic Scheme 1
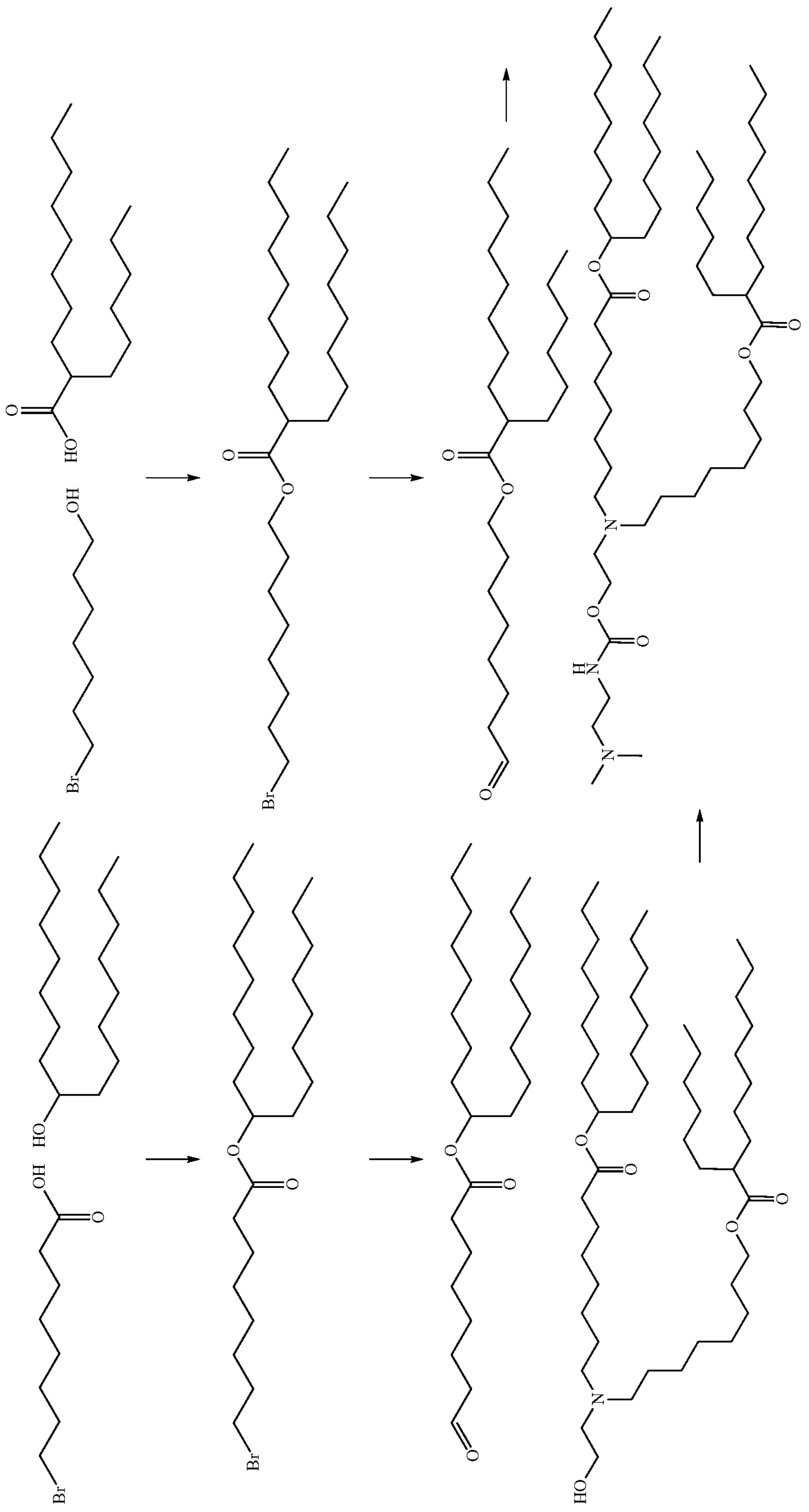

-continued
Representative Scheme 2
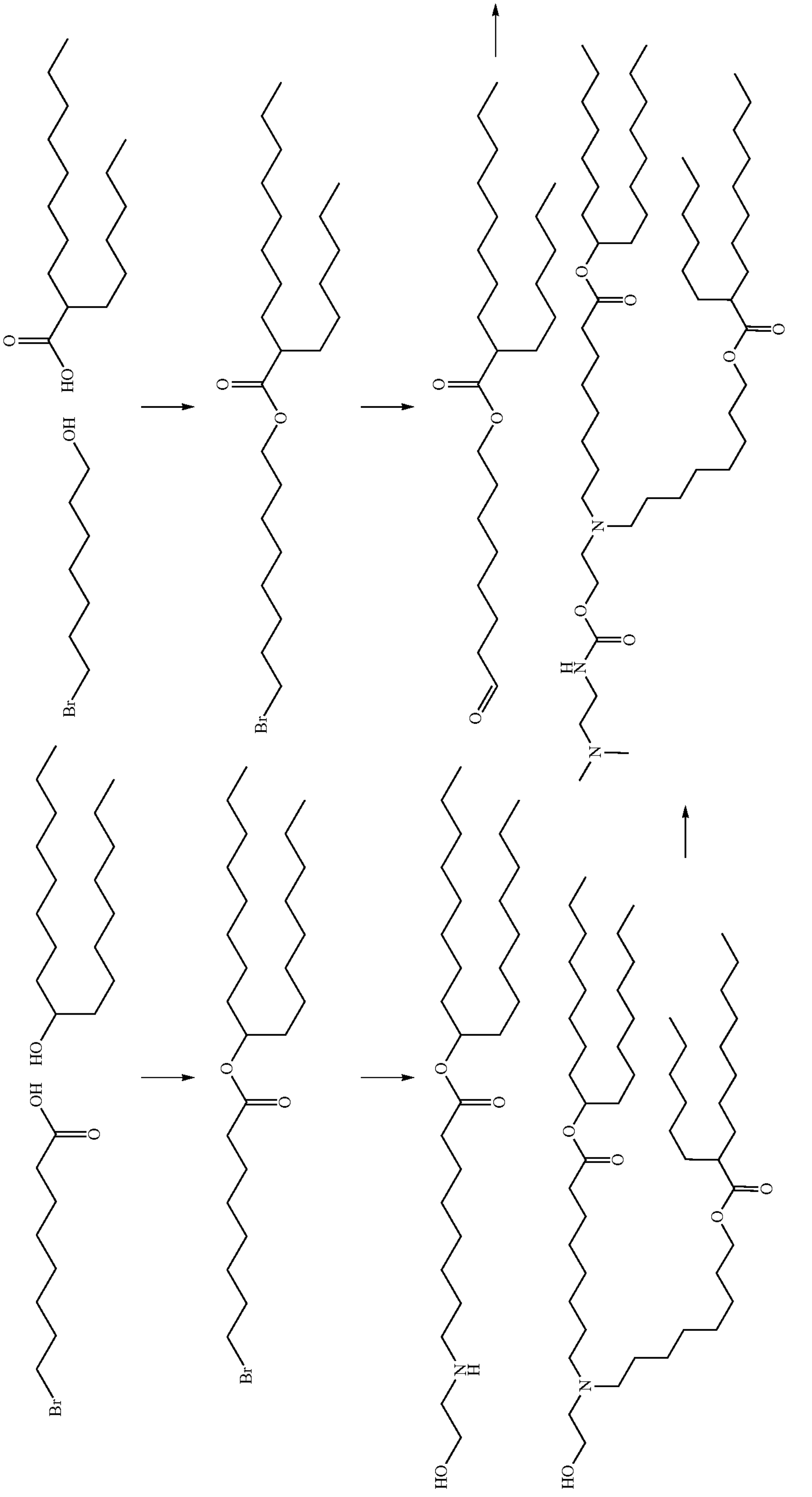

(Method 1)

Intermediate Example 1

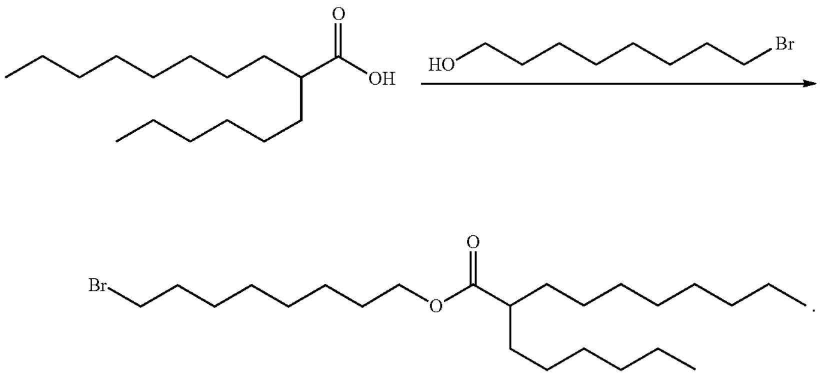

8-bromooctyl 2-hexyldecanoate 2-hexyldecanoic acid (5 g, 19.50 mmol), 8-bromooctan-1-ol (4.08 g, 19.50 mmol) and TsOH (0.185 g, 0.975 mmol) were dissolved in 80 mL Toluene dry. The reaction was left to stir at 125° C. O/N under Ar. The solvent was removed by evaporation and the crude material was purified by column chromatography (EtOAc 10% in Hexane) to afford the compound as a colorless oil (6.55 gr; 75%)$^1$H NMR (400 MHz, $CDCl_3$): δ 0.87 (6H, t, J=6.61 Hz), 1.25 (29H, m), 1.60 (5H, m), 1.85 (2H, quint, J=6.92 Hz), 2.31 (1H, m), 3.40 (2H, t, J=6.83 Hz), 4.06 (2H, t, J=6.60 Hz). MS [ESI]: m/z: [M+H] calc. 447.5 obs. 447.5.

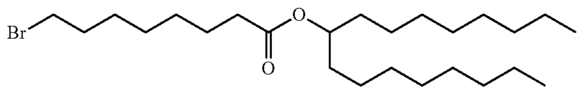 [SMILES: CCCCCCCCC(CCCCCCCC)OC(=O)CCCCCCCBr]

heptadecan-9-yl 8-bromooctanoate was synthesized according to method 1 from 8-bromooctanoic acid and heptadecan-9-ol to afford the compound as a yellow oil $^1$H NMR (400 MHz, CDCl3): δ 0.90 (6H, t, J=6.77 Hz), 1.28 (34H, m), 1.64 (2H, m), 1.86 (2H, quint, J=6.92 Hz), 2.30 (2H, t, J=7.44 Hz), 3.41 (2H, t, J=6.83 Hz), 4.89 (1H, quint, J=6.24 Hz).

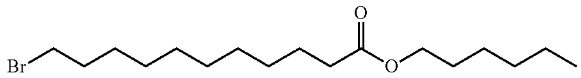 [SMILES: CCCCCCOC(=O)CCCCCCCCCCBr]

hexyl 11-bromoundecanoate was synthesized according to method 1 from 11-bromoundecanoic acid and hexan-1-ol to afford the compound as a colorless oil. $^1$H NMR (400 MHz, $CDCl_3$): δ 0.89 (3H, t, J=6.86 Hz), 1.28 (20H, m), 1.59 (5H, m), 1.76 (1H, t, J=7.35 Hz), 2.28 (2H, t, J=7.51 Hz), 3.40 (1H, t, J=6.86 Hz), 3.52 (1H, t, J=6.75 Hz), 4.05 (2H, t, J 6.72 Hz).

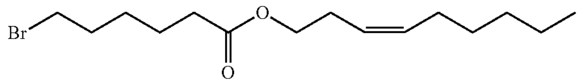 [SMILES: CCCCC/C=C\CCOC(=O)CCCCCBr]

(Z)-non-3-en-1-yl 6-bromohexanoate was synthesized according to method 1 from 6-bromohexanoic acid and (Z)-non-3-en-1-ol to afford the title compound as a colorless oil. $^1$H NMR (400 MHz, $CDCl_3$): δ 0.90 (3H, t, J=6.79 Hz), 1.32 (6H, m), 1.49 (2H, m), 1.68 (2H, m), 1.89 (2H, quint, J=6.89 Hz), 2.05 (2H, q, J=7.34 Hz), 2.30-2.44 (4H, 2.33 (t, J=7.42 Hz), 2.39 (q, J=7.07 Hz)), 3.42 (2H, t, J=6.76 Hz), 4.09 (2H, t, J=6.92 Hz), 5.36 (1H, m), 5.52 (1H, m).

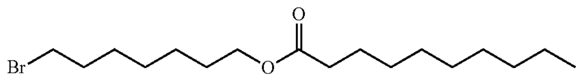 [SMILES: CCCCCCCCCC(=O)OCCCCCCCBr]

7-bromoheptyl decanoate was synthesized according to method 1 from decanoic acid and 7-bromoheptan-1-ol to afford the title compound as a colorless oil. $^1$H NMR (400 MHz, $CDCl_3$): δ 0.87 (3H, t, J=6.80 Hz), 1.20-1.48 (18H, 1.21 (m), 1.26 (m), 1.35 (m)), 1.62 (4H, m), 1.80-1.91 (2H, 1.85 (t, J=7.34 Hz), 1.88 (s)), 2.28 (2H, t, J=7.38 Hz), 3.39 (2H, t, J=6.66 Hz), 4.05 (2H, t, J=6.46 Hz).

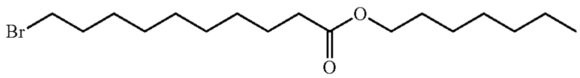 [SMILES: CCCCCCCOC(=O)CCCCCCCCCBr]

heptyl 10-bromodecanoate was synthesized according to method 1 from heptan-1-ol and 10-bromodecanoic acid to afford title compound as a colorless oil $^1$H NMR (400 MHz, $CDCl_3$): δ 0.87-0.93 (3H, 0.90 (t, J=6.93 Hz), 0.91 (s)), 1.31 (18H, m), 1.63 (4H, quint, J=6.97 Hz), 1.86 (2H, quint, J=6.93 Hz), 2.30 (2H, t, J=7.51 Hz), 3.41 (2H, t, J=6.86 Hz), 4.07 (2H, t, J=6.73 Hz).

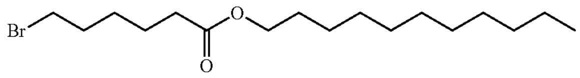 [SMILES: CCCCCCCCCCCOC(=O)CCCCCBr]

undecyl 6-bromohexanoate was synthesized according to method 1 from undecan-1-ol and 6-bromohexanoic acid to afford the title compound as a colorless oil $^1$H NMR (400 MHz, $CDCl_3$): δ 0.90 (3H, t, J=6.75 Hz), 1.28 (16H, m), 1.49 (2H, m), 1.58-1.73 (4H, m), 1.89 (2H, quint, J=6.89 Hz), 2.33 (2H, t, J=7.42 Hz), 3.42 (2H, t, J=6.76 Hz), 4.08 (2H, t, J=6.74 Hz).

Intermediate Example 2. (Method 2)

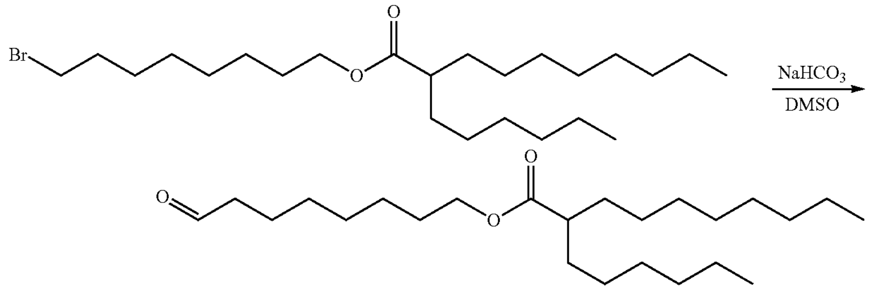

8-oxooctyl 2-hexyldecanoate $NaHCO_3$ (3.84 gr; 46.0 mmol) was dissolved in 18 mL DMSO and was heated to 150° C. 8-bromooctyl 2-hexyldecanoate compound (3.54 g, 9.20 mmol) was added in a single portion the reaction was left to stir at 150° C. until completion. 6 volumes of water were then added, and the mixture was extracted with hexane (60 mL×3). The organic phases were combined, dried over $Na_2SO_4$, filtered, and evaporated. The crude oil was purified on silica gel (10% EtOAc in Hexane) To acquire the title compound as a colorless oil. (1.6 gr; 44% yield) which was used directly in the next reaction. MS [ESI]: m/z: [M+H] calc. 383.6 obs. 383.5.

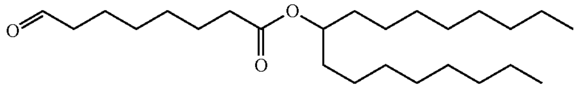 [SMILES: CCCCCCCCC(CCCCCCCC)OC(=O)CCCCCCC=O]

heptadecan-9-yl 8-oxooctanoate was synthesized according to method 2 from heptadecan-9-yl 8-bromooctanoate as a yellow oil which was used directly in the next reaction.

MS [ESI]: m/z: [M+Na] calc. 419.6 obs. 419.5.

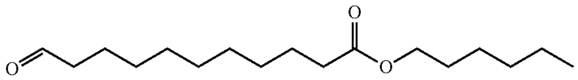 [SMILES: CCCCCCOC(=O)CCCCCCCCCC=O]

hexyl 11-oxoundecanoate was synthesized according to method 2 from hexyl 11-bromoundecanoate to afford the title compound as a yellow oil. MS [ESI]: m/z: [M+H] calc. 285.4 obs. 285.0.

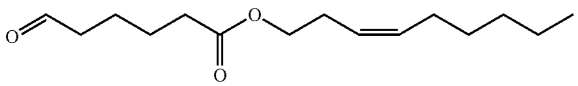 [SMILES: CCCCC/C=C\CCOC(=O)CCCCC=O]

(Z)-non-3-en-1-yl 6-oxohexanoate was synthesized according to method 2 from (Z)-non-3-en-1-yl 6-bromohexanoate to afford compound as a yellow oil MS [ESI]: m/z: [M+H] calc. 255.3 obs. 255.2.

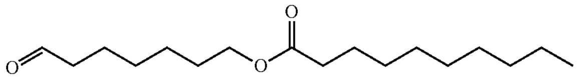 [SMILES: CCCCCCCCCC(=O)OCCCCCCC=O]

7-oxoheptyl decanoate was synthesized according to method 2 from 7-bromoheptyl decanoate to afford compound as a colorless oil MS [ESI]: m/z: [M+H] calc. 285.4 obs. 285.23.

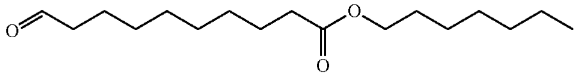 [SMILES: CCCCCCCOC(=O)CCCCCCCCC=O]

heptyl 10-oxodecanoate was synthesized according to method 2 from heptyl 10-bromodecanoate to afford compound as a colorless oil MS [ESI]: m/z: [M+H] calc. 285.4 obs. 285.6.

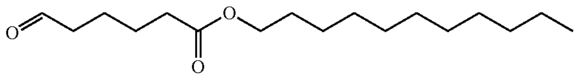 [SMILES: CCCCCCCCCCCOC(=O)CCCCC=O]

undecyl 6-oxohexanoate was synthesized according to method 2 from undecyl 6-bromohexanoate to afford compound as a colorless oil MS [ESI]: m/z: [M+H] calc. 285.4 obs. 285.1.

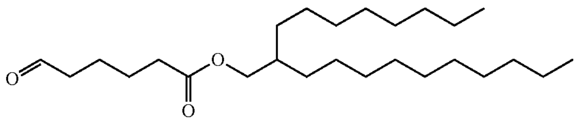 [SMILES: CCCCCCCCCCC(CCCCCCCC)COC(=O)CCCCC=O]

2-octyldodecyl 6-oxohexanoate was synthesized according to method 2 from 2-octyldodecyl 6-bromohexanoate to afford compound as a colorless oil MS [ESI]: m/z: [M+H] calc. 411.6 obs. 411.5.

Intermediate Example 5. (Method 3)

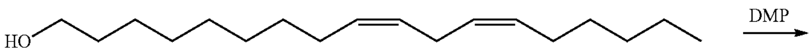

-continued

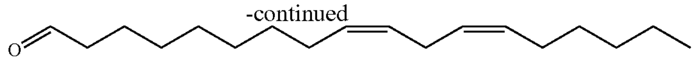

(9Z,12Z)-octadeca-9,12-dien-1-ol (3.5 g, 13.13 mmol) was dissolved in 100 mL DCM. sodium bicarbonate (11.03 g, 131 mmol) was then added and the solution was allowed to stir at RT dess-martinperiodinane (6.69 g, 15.76 mmol) was then added portion wise and the reaction was left to stir at RT under Argon. The reaction was monitored by TLC until full consumption of the starting material. The reaction was washed with 100 mL of water, 50 mL $NaHCO_3$sat. (x2), 50 mL Na2S2O2 10% and 50 mL Brine. The phases were separated, the organic phases were combined, dried over Na2SO4, filtered and evaporated. The resulting crude oil was purified via column chromatography (Hexane:EtOAc; 90:10) to yield the title compound as an oil with a yellowish tint (2.76 gr; 80% yield).

Intermediate Example 6. (Method 4)

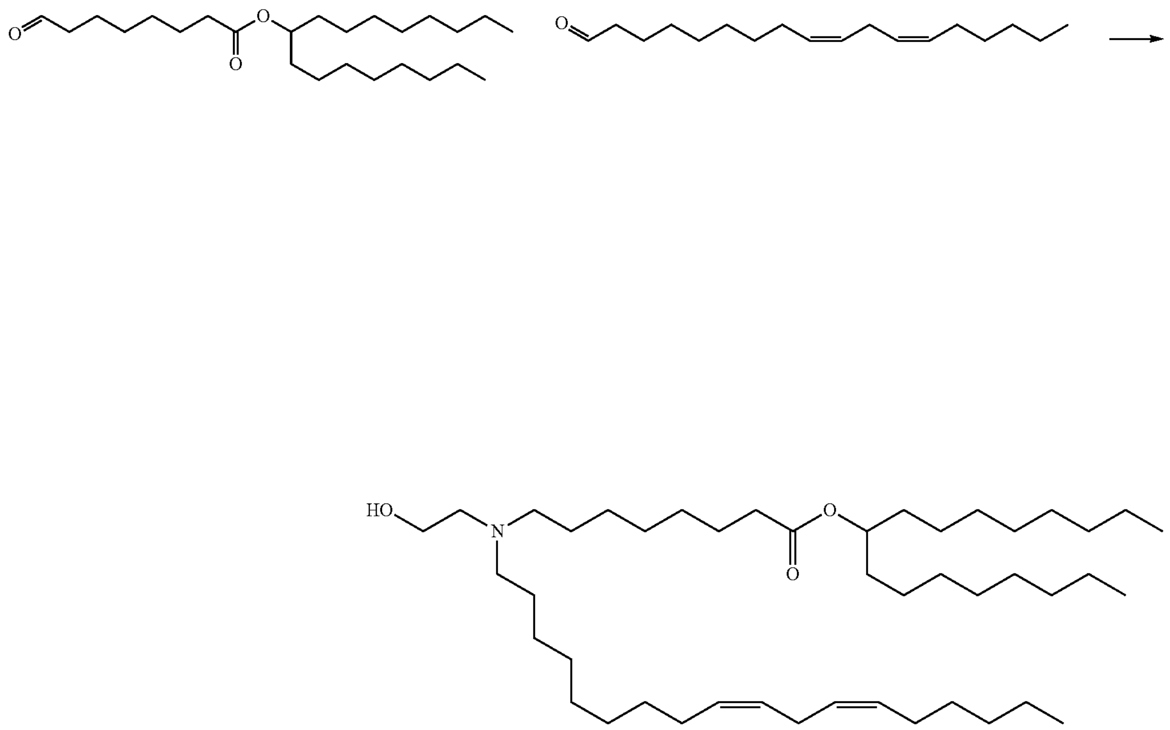

8-((8-(heptadecan-9-yloxy)-8-oxooctyl)(2-hydroxyethyl)amino)octyl 2-hexyldecanoate 8-oxooctyl 2-hexyldecanoate (1.3 g, 3.4 mmol, 1 equiv.) was dissolved in dry Methanol (10 mL) Ethanolamine (1.2 gr, 15.20 mmol, 5.0 equiv.) was added and the resulting solution was stirred for 3 hr. After which, the solution was cooled to 0° C. and Sodium borohydride (128 mg, 3.4 mmol, 1 equiv) was added the reaction was stirred for 20 mins the solvent was removed by evaporation and the crude was redissolved in 75 mL DCM. The organic phase was washed with $NaHCO_3$ sat. (30 mL×2), Brine (30 mL×1) dired over $Na_2SO_4$ filtered and evaporated. The crude material was re-dissolved in 25 mL DCM dry. (9Z,12Z)-octadeca-9,12-dienal (1.5 g, 4.0 mmol, 1 equiv.) was added and the solution was allowed to stir for 1 hr. at RT Sodium triacetoxyborohydride (1.4 g, 6.8 mmol, 2.0 equiv.) was added and the reaction was left to stir overnight under argon. The reaction was quenched with $NaHCO_3$ sat. solution and extracted with DCM (3 times). The organic portion was washed with brine solution and dried over anhydrous $Na_2SO_4$. The solvent was evaporated and the crude material was purified by column chromatography to acquire as a colorless oil (5.61 gr; 90% yield MS [ESI]: m/z: [M+H] calc. 691.2 obs. 690.9; $^1H$ NMR (500 MHz, $CDCl_3$): δ 0.88 (9H, m), 1.28 (47H, m), 1.50 (8H, m), 1.61 (2H, m), 2.05 (4H, q, J=7.59 Hz), 2.27 (2H, t, J=7.61 Hz), 2.55 (4H, m), 2.67 (2H, m), 2.77 (2H, t, J=6.73 Hz), 3.60 (2H, m), 4.86 (1H, i, J=6.79 Hz), 5.35 (4H, m).

Intermediate Example 6. (Method 5)

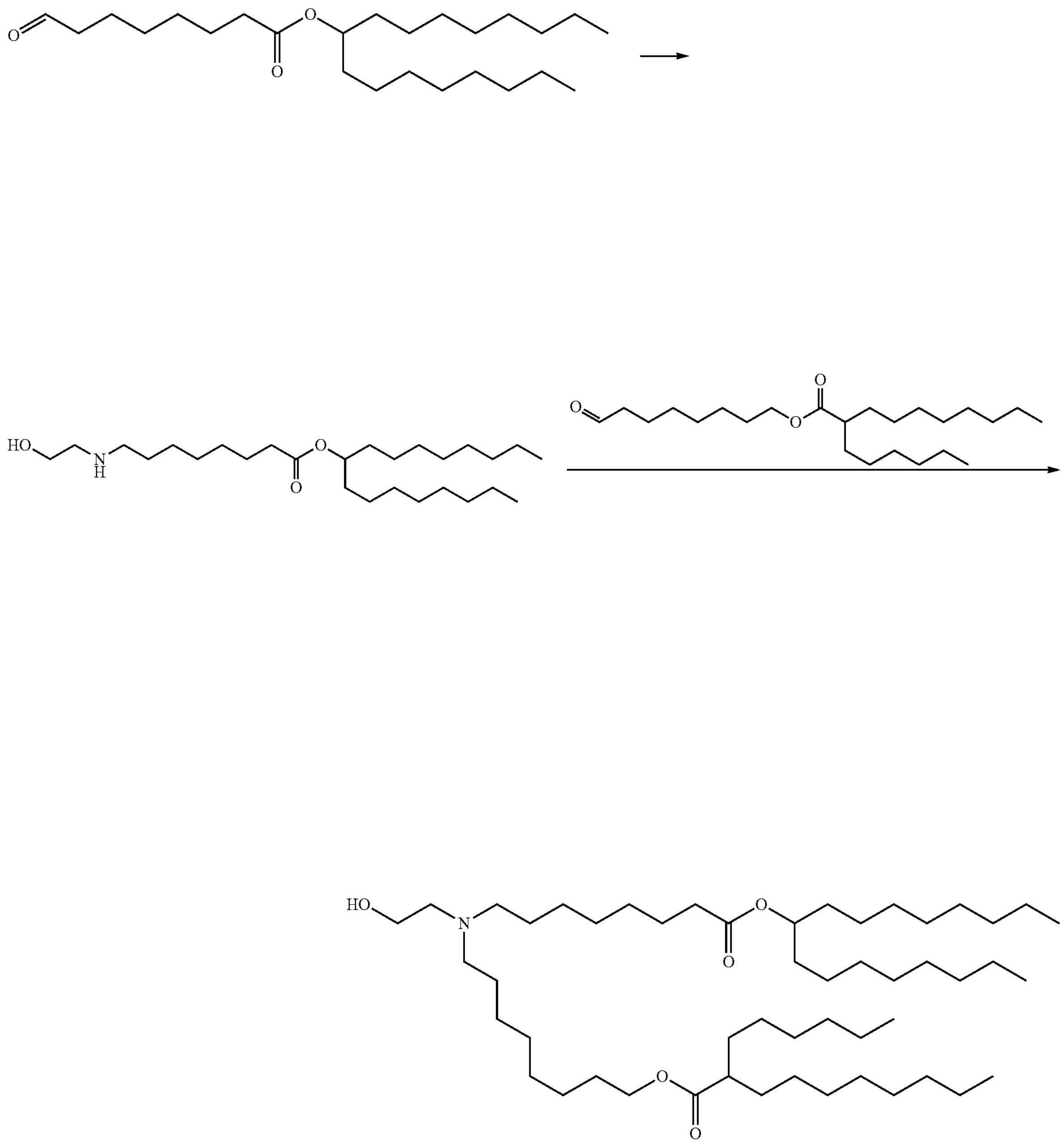

8-((8-(heptadecan-9-yloxy)-8-oxooctyl)(2-hydroxyethyl) amino)octyl 2-hexyldecanoate 8-oxooctyl 2-hexyldecanoate (1.3 g, 3.4 mmol, 1 equiv.) was dissolved in dry Methanol (10 mL) Ethanolamine (1.2 gr, 15.20 mmol, 5.0 equiv.) was added and the resulting solution was stirred for 3 hr. After which, the solution was cooled to 0° C. and Sodium borohydride (128 mg, 3.4 mmol, 1 equiv) was added the reaction was stirred for 20 mins the solvent was removed by evaporation and the crude was redissolved in 75 mL DCM. The organic phase was washed with $NaHCO_3$ sat. (30 mL×2), Brine (30 mL×1) dried over $Na_2SO_4$ filtered and evaporated. The crude material was re-dissolved in 25 mL DCM dry. heptadecan-9-yl 8-oxooctanoate (1.34 g, 4.0 mmol, 1 equiv.) was added and the solution was allowed to stir for 1 hr. at RT Sodium triacetoxyborohydride (1.4 g, 6.8 mmol, 2.0 equiv.) was added and the reaction was left to stir overnight under argon. The reaction was quenched with $NaHCO_3$ sat. solution and extracted with DCM (3 times). The organic portion was washed with brine solution and dried over anhydrous $Na_2SO_4$. The solvent was evaporated and the crude material was purified by column chromatography to acquire as a colorless oil (5.61 gr; 90% yield). MS [ESI]: m/z: [M+H] calc. 809.4 obs. 809.3 $^1H$ NMR (400 MHz, $CDCl_3$): δ ppm 4.86 (p, 1H); 4.06 (t, 2H); 3.53 (m, 2H); 2.58 (m, 2H); 2.44 (m, 4H); 2.27 (m+t, 3H), 1.61-1.28 (m, 74), 0.88 (m, 12H).

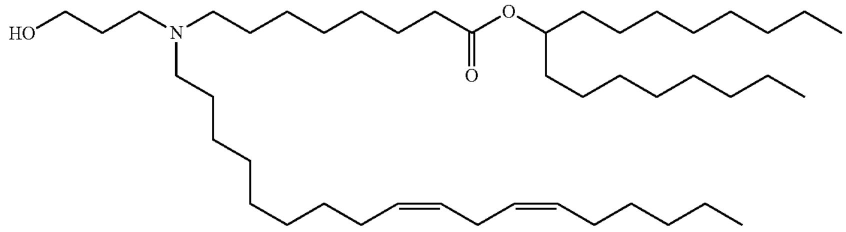 [SMILES: CCCCC/C=C\C/C=C\CCCCCCCCN(CCCO)CCCCCCCC(=O)OC(CCCCCCCC)CCCCCCCC]

Compound 1 heptadecan-9-yl 8-((3-hydroxypropyl)((9Z, 12Z)-octadeca-9,12-dien-1-yl)amino)octanoate was synthesized according to the general synthetic scheme and general methods. MS [ESI]: m/z: [M+H] calc. 704.7 obs. 704.7; $^1H$ NMR (400 MHz, $CDCl_3$): δ 0.88 (9H, m), 1.31 (54H, m), 1.64 (4H, m), 2.05 (4H, q, J=7.43 Hz), 2.27 (2H, t, J=7.51 Hz), 2.39 (4H, m), 2.62 (2H, t, J=5.54 Hz), 2.77 (2H, t, J=6.03 Hz), 3.79 (2H, t, J=5.81 Hz), 4.86 (1H, quint, J=6.21 Hz), 5.36 (4H, m).

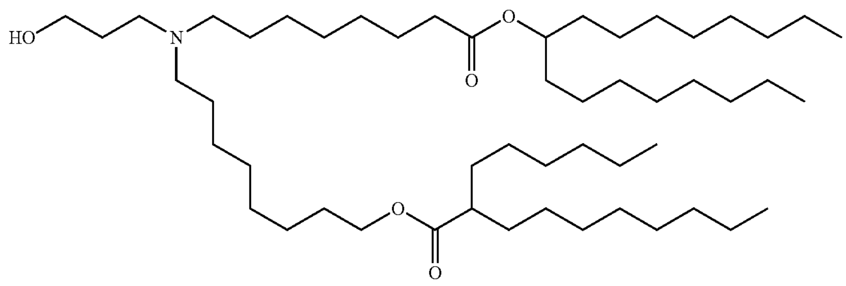 [SMILES: CCCCCCCCC(CCCCCCCC)OC(=O)CCCCCCCN(CCCO)CCCCCCCCOC(=O)C(CCCCCC)CCCCCCCC]

Compound 2 8-((8-(heptadecan-9-yloxy)-8-oxooctyl)(3-hydroxypropyl)amino)octyl 2-hexyldecanoate was synthesized according to the general synthetic scheme and general methods. MS [ESI]: m/z: [M+H] calc. 822.8 obs. 823.0; $^1$H NMR (500 MHz, $CDCl_3$): δ 0.87 (12H, m), 1.26 (75H, m), 2.27 (3H, m), 2.39 (4H, dd, J=9.08, 6.30 Hz), 2.63 (2H, dd, J=6.30, 4.49 Hz), 3.79 (2H, dd, J=5.77, 4.27 Hz), 4.06 (2H, t, J=6.52 Hz), 4.87 (1H, m), 5.66 (1H, m).

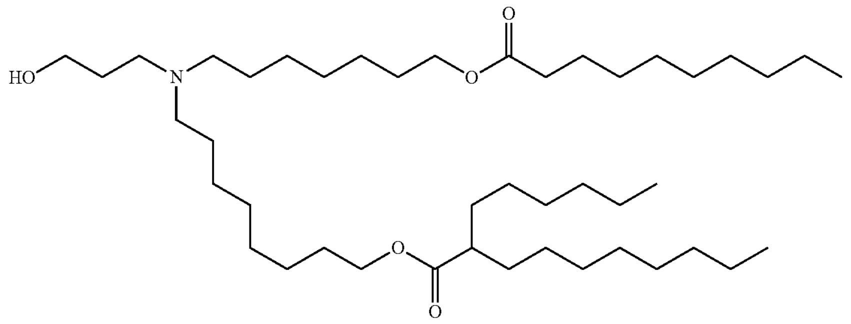 [SMILES: CCCCCCCCCC(=O)OCCCCCCCN(CCCO)CCCCCCCCOC(=O)C(CCCCCC)CCCCCCCC]

Compound 3 8-((7-(decanoyloxy)heptyl)(3-hydroxypropyl)amino)octyl 2-hexyldecanoate was synthesized according to the general synthetic scheme and general methods. MS [ESI]: m/z: [M+H] calc. 710.7 obs. 710.5; $^1$H NMR (500 MHz, $CDCl_3$): δ 0.87 (9H, m), 1.26 (46H, m), 1.61 (13H, m), 2.29 (4H, m), 2.40 (4H, m), 2.63 (2H, m), 3.64 (1H, m), 3.79 (2H, m), 4.06 (4H, m), 5.65 (1H, m).

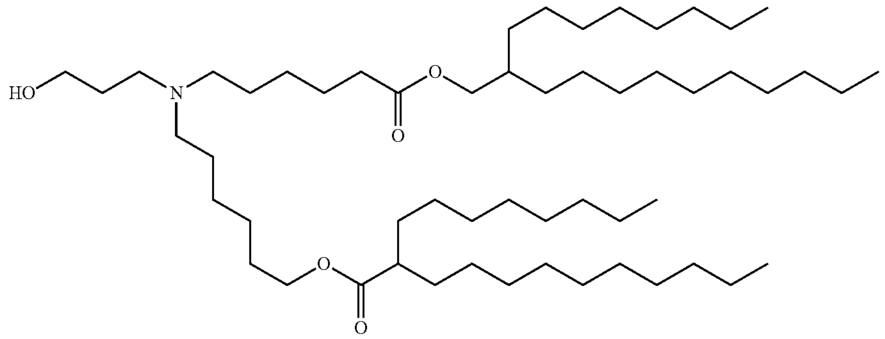 [SMILES: CCCCCCCCCCC(CCCCCCCC)COC(=O)CCCCCN(CCCO)CCCCCCOC(=O)C(CCCCCCCC)CCCCCCCCCC]

Compound 4 bis(2-octyldodecyl) 6,6'-((3-hydroxypropyl)azanediyl)dihexanoate was synthesized according to the general synthetic scheme and general methods. MS [ESI]: m/z: [M+H] calc. 864.8 obs. 864.9; $^1$H NMR (400 MHz, $CDCl_3$): δ 0.88 (12H, t, J=7.20 Hz), 1.27 (65H, m), 1.59 (14H, m), 2.30 (4H, t, J=7.68 Hz), 2.40 (4H, m), 2.62 (2H, t, J=5.89 Hz), 3.78 (2H, t, J=5.26 Hz), 3.97 (4H, d, J=5.79 Hz), 5.46 (1H, bs).

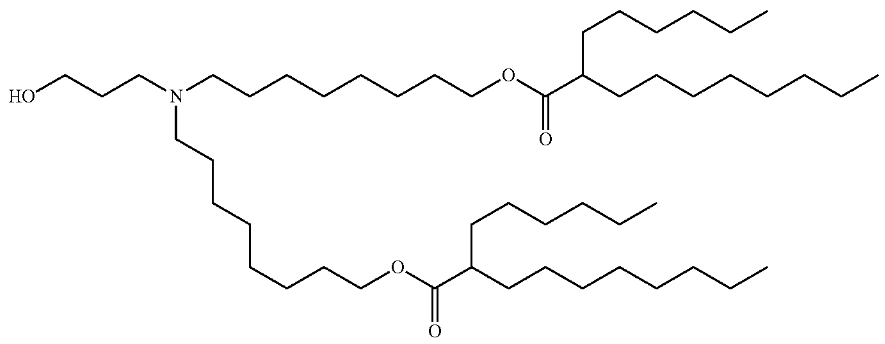 [SMILES: CCCCCCCCC(CCCCCC)C(=O)OCCCCCCCCN(CCCO)CCCCCCCCOC(=O)C(CCCCCC)CCCCCCCC]

Compound 5 ((3-hydroxypropyl)azanediyl)bis(octane-8,1-diyl) bis(2-hexyldecanoate) was synthesized according to the general synthetic scheme and general methods. MS [ESI]: m/z: [M+H] calc. 808.8 obs. 809.0; $^1$H NMR (400 MHz, $CDCl_3$): δ 0.88 (12H, t, J=6.70 Hz), 1.27 (52H, m), 1.44 (9H, m), 1.60 (12H, m), 2.31 (2H, tt, J=8.98, 5.31 Hz), 2.36-2.43 (4H, 2.40 (t, J=7.63 Hz), 2.39 (d, J=4.78 Hz)), 2.63 (2H, t, J=5.42 Hz), 3.79 (2H, t, J=5.06 Hz), 4.06 (4H, t, J=6.66 Hz), 5.65 (1H, m).

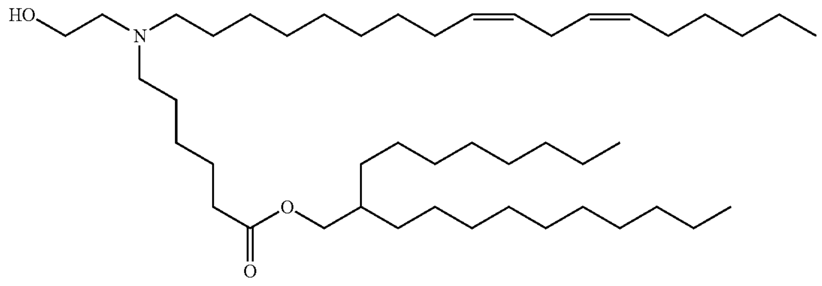 [SMILES: CCCCC/C=C\C/C=C\CCCCCCCCN(CCO)CCCCCC(=O)OCC(CCCCCCCC)CCCCCCCCCC]

Compound 7 2-octyldodecyl 6-((2-hydroxyethyl)((9Z,12Z)-octadeca-9,12-dien-1-yl)amino)hexanoate was synthesized according to the representative synthetic scheme 1 and method 4 MS [ESI]: m/z: [M+H] calc. 705.2 obs. 705.2 $^1$H NMR (400 MHz, $CDCl_3$): δ 0.90 (9H, m), 1.30 (53H, m), 1.68 (6H, m), 2.06 (4H, q, J=7.08 MHz), 2.33 (2H, t, J=7.31 MHz), 2.47 (1H, m), 2.79 (3H, m), 2.92 (3H, m), 3.86 (1H, m), 3.98 (2H, m), 5.37 (4H, m).

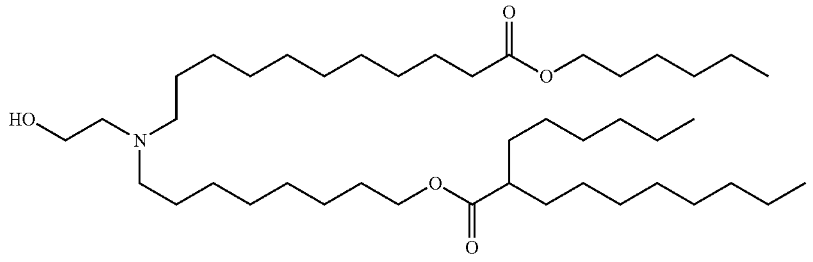 [SMILES: CCCCCCCCC(CCCCCC)C(=O)OCCCCCCCCN(CCO)CCCCCCCCCCC(=O)OCCCCCC]

Compound 8 hexyl 11-((8-((2-hexyldecanoyl)oxy)octyl)(2-hydroxyethyl)amino)undecanoate was synthesized according to the representative synthetic scheme and method 4 MS [ESI]: m/z: [M+H] calc 697.1 obs. 697.8 $^1$H NMR (400 MHz, $CDCl_3$): δ 0.89 (9H, m), 1.31 (52H, m), 1.64 (11H, m), 2.30 (3H, m), 2.93 (2H, m), 3.02 (1H, m), 3.89 (2H, m), 4.07 (4H, t, J=6.66 Hz).

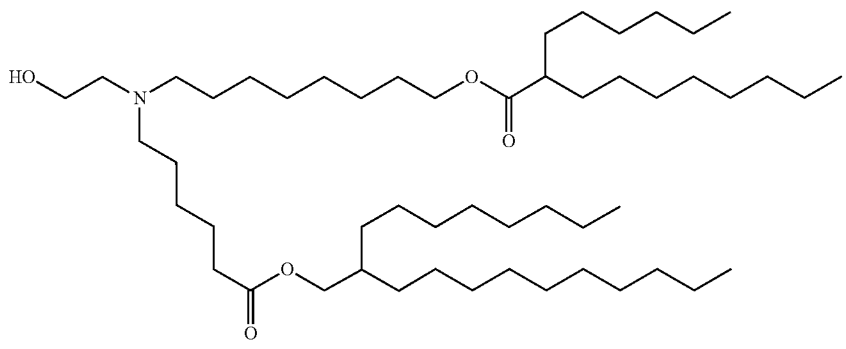 [SMILES: CCCCCCCCCCC(CCCCCCCC)COC(=O)CCCCCN(CCO)CCCCCCCCOC(=O)C(CCCCCC)CCCCCCCC]

Compound 9 8-((2-hydroxyethyl)(6-((2-octyldodecyl)oxy)-6-oxohexyl)amino)octyl 2-hexyldecanoate was synthesized according to the representative synthetic scheme and method 4. MS [ESI]: m/z: [M+H] calc 823.4 obs. 823.1 $^{1}H$ NMR (400 MHz, $CDCl_3$): δ 0.87 (12H, m), 1.27 (69H, m), 1.62 (10H, m), 2.31 (3H, m), 2.75 (2H, m), 2.86 (1H, m), 3.76 (1H, m), 3.96 (2H, d, J=5.77 Hz), 4.05 (2H, t, J=6.66 Hz).

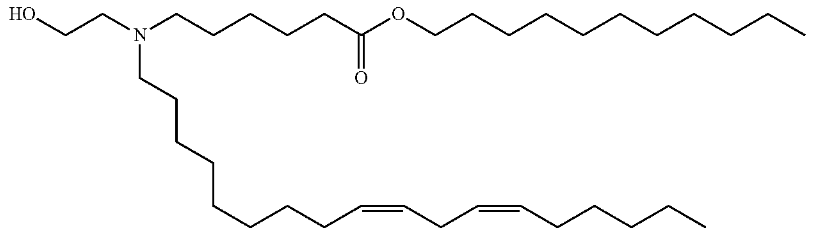 [SMILES: CCCCC/C=C\C/C=C\CCCCCCCCN(CCO)CCCCCC(=O)OCCCCCCCCCCC]

Compound 10 undecyl 2-methyl-10-((9Z,12Z)-octadeca-9,12-dien-1-yl)-6-oxo-7-oxa-2,5,10-triazahexadecan-16-oate was synthesized according to the representative synthetic scheme and method 4 MS [ESI]: m/z: [M+H] calc 578.9 obs. 578.9 $^{1}H$ NMR (400 MHz, $CDCl_3$): δ 0.90 (6H, h, J=4.22 Hz), 1.29 (40H, m), 1.64 (4H, m), 2.07 (4H, q, J=6.77 Hz), 2.32 (2H, t, J=7.48 Hz), 2.45 (4H, m), 2.58 (2H, t, J=5.38 Hz), 2.79 (2H, t, J=6.32 Hz), 3.53 (2H, t, J=5.37 Hz), 4.07 2H t, J=6.76 Hz), 5.38 (3H m).

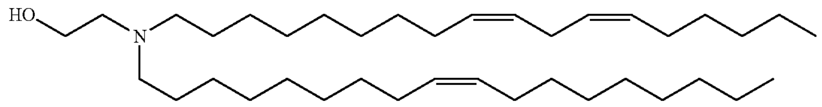 [SMILES: CCCCC/C=C\C/C=C\CCCCCCCCN(CCO)CCCCCCCC/C=C\CCCCCCCC]

Compound 11 2-(((Z)-octadec-9-en-1-yl)((9Z,12Z)-octadeca-9,12-dien-1-yl)amino)ethan-1-ol was synthesized according to the representative synthetic scheme and method 4. MS [ESI]: m/z: [M+H] calc 561.0 obs. 560.6 $^{1}H$ NMR (500 MHz, $CDCl_3$): δ 0.88 (6H, m), 1.29 (45H, m), 1.55 (2H, m), 2.05 (7H, m), 2.63 (2H, m), 2.76 (3H, m), 3.67 (1H, m),

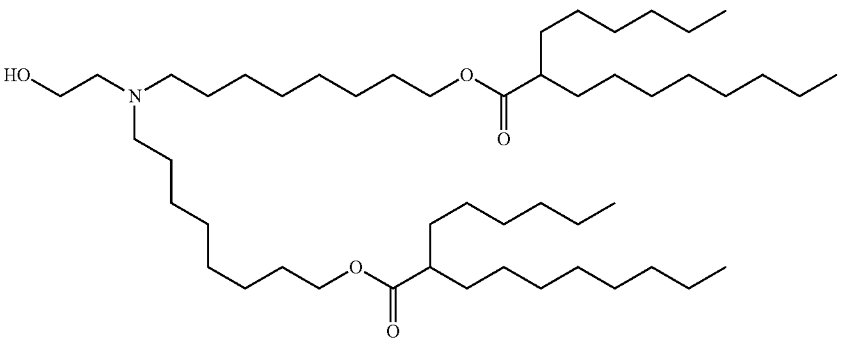 [SMILES: CCCCCCCCC(CCCCCC)C(=O)OCCCCCCCCN(CCO)CCCCCCCCOC(=O)C(CCCCCC)CCCCCCCC]

Compound 12 ((2-hydroxyethyl)azanediyl)bis(octane-8,1-diyl) bis(2-hexyldecanoate) was synthesized according to the representative synthetic scheme and method 4. MS [ESI]: m/z: [M+H] calc 794.8 obs. 795.0; 1H NMR (400 MHz, $CDCl_3$): δ 0.87 (12H, m), 1.25 (65H, m), 1.60 (10H, m), 2.30 (2H, m), 2.50 (3H, m), 2.62 (1H, m), 3.56 (1H, m), 4.06 (4H, t, J=6.66 Hz).

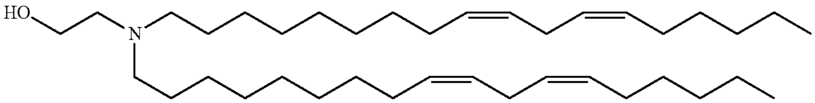 [SMILES: CCCCC/C=C\C/C=C\CCCCCCCCN(CCO)CCCCCCCC/C=C\C/C=C\CCCCC]

Compound 13 2-(di((9Z,12Z)-octadeca-9,12-dien-1-yl)amino)ethan-1-ol was synthesized according to the representative synthetic scheme and method 4. MS [ESI]: m/z: [M+H] calc 558.6 obs. 558.7; $^1$H NMR (400 MHz, $CDCl_3$): δ 0.90 (6H, m), 1.32 (34H, m), 1.58 (3H, in), 2.06 (8H, m 2.66 (3H, m) 2.78 (6H, 3.69 (2H, m), 5.37 (8H, m).

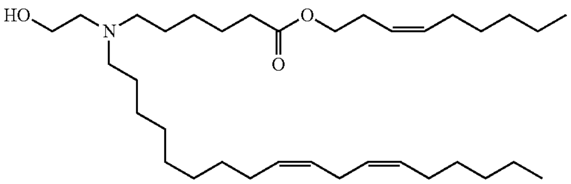 [SMILES: CCCCC/C=C\C/C=C\CCCCCCCCN(CCO)CCCCCC(=O)OCC/C=C\CCCCC]

Compound 14 (Z)-non-3-en-1-yl 6-((2-hydroxyethyl)((9Z,12Z)-octadeca-9,12-dien-1-yl)amino)hexanoate was synthesized according to the representative synthetic scheme and method 4. MS [ESI]: m/z: [M+H] calc 548.5 obs. 548.6; 1H NMR (500 MHz, $CDCl_3$): δ 0.88 (6H, t, J=7.23 Hz), 1.30 (25H, m), 1.51 (4H, m), 1.64 (2H, m), 2.04 (6H, m), 2.30 (2H, t, J=7.43 Hz), 2.37 (2H, q, J=6.98 Hz), 2.55 (4H, m), 2.67 (2H, m), 2.77 (2H, t, J=6.79 Hz), 3.60 (2H, m), 4.06 (2H, t, J=6.95 Hz), 5.35 (5H, m), 5.50 (1H, m).

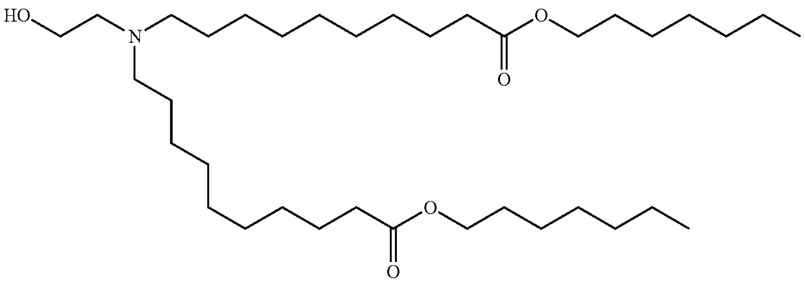 [SMILES: CCCCCCCOC(=O)CCCCCCCCCN(CCO)CCCCCCCCCC(=O)OCCCCCCC]

Compound 15 diheptyl 10,10'-((2-hydroxyethyl) azanediyl)bis(decanoate) was synthesized according to the representative synthetic scheme and method 4. MS [ESI]: m/z: [M+H] calc 598.5 obs. 598.6; 1H NMR (500 MHz, $CDCl_3$): δ 0.88 (6H, m), 1.29 (36H, m), 1.58 (12H, m), 2.28 (4H, t, J=7.77 Hz), 2.59 (4H, m), 2.71 (2H, m), 3.64 (2H, m), 4.05 (4H, t, J=6.73 Hz).

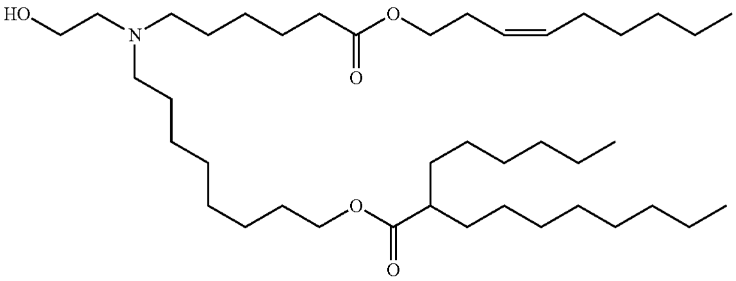 [SMILES: CCCCC/C=C\CCOC(=O)CCCCCN(CCO)CCCCCCCCOC(=O)C(CCCCCC)CCCCCCCC]

Compound 16 (Z)-8-((2-hydroxyethyl)(6-(non-3-en-1-yloxy)-6-oxohexyl)amino)octyl 2-hexyldecanoate was synthesized according to the representative synthetic scheme and method 4. MS [ESI]: m/z: [M+H] calc 666.6 obs. 666.7; $^{1}H$ NMR (400 MHz, $CDCl_3$): δ 0.88 (9H, m), 1.30 (42H, m), 1.61 (7H, m), 2.03 (2H, q, J=7.60 Hz), 2.37 (9H, m), 2.56 (2H, t, J=5.58 Hz), 3.51 (2H, t, J=5.49 Hz), 4.06 (4H, m), 5.34 (1H, m), 5.50 (1H, m).

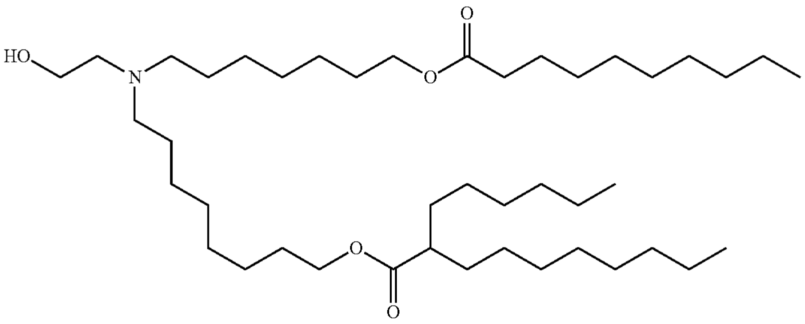 [SMILES: CCCCCCCCCC(=O)OCCCCCCCN(CCO)CCCCCCCCOC(=O)C(CCCCCC)CCCCCCCC]

Compound 17 8-((7-(decanoyloxy)heptyl)(2-hydroxyethyl)amino)octyl 2-hexyldecanoate was synthesized according to the representative synthetic scheme and method 4. MS [ESI]: m/z: [M+H] calc 696.7 obs. 697.0; 1H NMR (500 MHz, $CDCl_3$): δ 0.87 (9H, m), 1.29 (48H, m), 1.60 (12H, m), 2.28 (3H, m), 2.70 (4H, m), 2.82 (2H, m), 3.64 (1H, t, J=6.63 Hz), 3.72 (2H, m), 4.05 (4H, m).

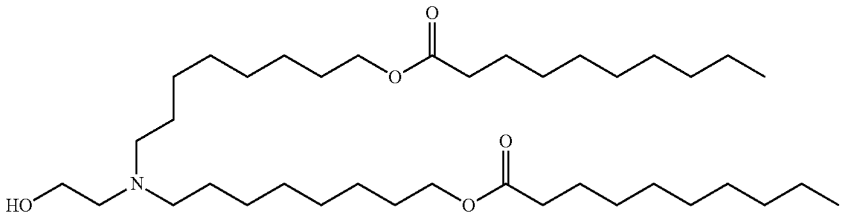 [SMILES: CCCCCCCCCC(=O)OCCCCCCCCN(CCO)CCCCCCCCOC(=O)CCCCCCCCC]

Compound 18 ((2-hydroxyethyl)azanediyl)bis(octane-8,1-diyl) bis(decanoate) was synthesized according to the representative synthetic scheme and method 4. MS [ESI]: m/z: [M+H] calc 626.6 obs. 626.7; $^1$H NMR (400 MHz, $CDCl_3$): δ 0.88 (6H, t, J=7.15 Hz), 1.30 (45H, m), 1.61 (8H, m), 2.28 (4H, t, J=7.68 Hz), 2.43 (4H, m), 2.57 (2H, t, J=5.37 Hz), 3.52 (2H, t, J=5.38 Hz), 4.05 (4H, t, J=6.73 Hz).

Intermediate Example P1.

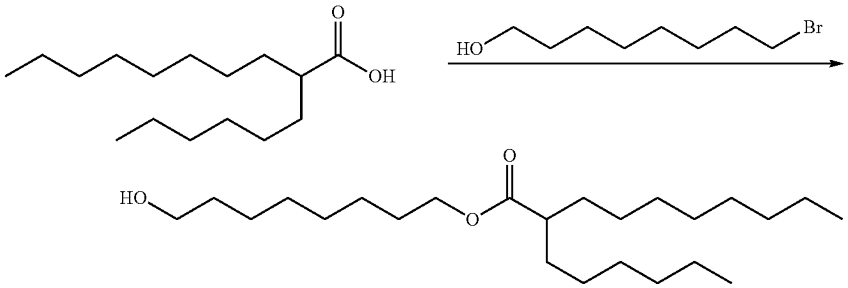

8-hydroxyoctyl 2-hexyldecanoate compound [001]8-bromooctan-1-ol (2.05 g, 9.80 mmol) and 2-hexyldecanoic acid (2.51 g, 9.80 mmol) were placed in a 100 mL RBF The flask was evacuated and purged with Argon (x2). 40 mL of dry DMF were then added followed by potassium carbonate (2.71 g, 19.61 mmol). The suspension was left to stir at 60° C. overnight. The reaction content was then poured into 120 mL of 1M HCl. The resulting solution was extracted with 60 mL hexane (x3). dried over $Na_2SO_4$, filtered and evacuated under vacuum. The crude material was purified via column chromatography Hexane 9:1 EtOAc to yield compound [001] as a slightly yellowish oil (3.54 gr; 9.2 mmol; 94% yield). $^1$H NMR (400 MHz, $CDCl_3$): δ 4.06 (2H, t, J=6.67 Hz); 3.62 (2H, t, J=6.62 Hz); 2.35-2.25 (1H, m); 1.66-1.48 (6H, m); 1.46-1.16 (30H, m); 0.86 (6H, t, J=6.87 Hz). MS [ESI]: m/z: [M+H] calc. 385.4 obs. 385.6 [M+Na] calc. 407.3 obs. 407.6

Intermediate Example P2.

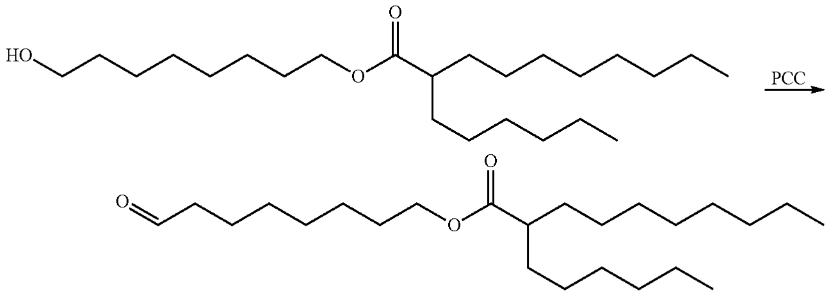

8-oxooctyl 2-hexyldecanoate compound [002]8-hydroxyoctyl 2-hexyldecanoate (3.54 g, 9.20 mmol) was dissolved in 100 mL DCM. PCC (2.98 g, 13.80 mmol) was added portionwise over 10 mins and the reaction was left to stir at RT after 2 hours the reaction mixture was passed through a silica plug (eluted with DCM). to afford compound 2 as a colorless oil. (3.1 gr; 88% yield) which was used directly in the next reaction.

Intermediate Example P3.

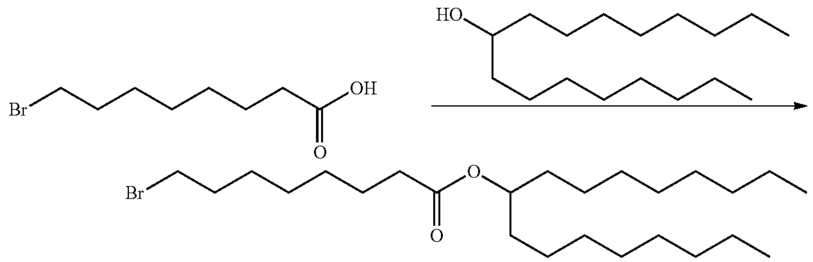

heptadecan-9-yl 8-bromooctanoate compound [003]8-bromooctanoic acid (4.70 g, 21.05 mmol) and heptadecan-9-ol (4.5 g, 17.55 mmol) were dissolved in 75 mL DCM dry. EDC (6.73 g, 35.1 mmol) and DMAP (0.429 g, 3.51 mmol) were added and the resulting solution was left to stir at RT overnight. The solvent was removed by evaporation and 60 mL hexane was added. The reaction solution was stirred vigorously, washed with brine (100 mL×2), dried over $Na_2SO_4$ filtered and evaporated. The crude material was then purified by column chromatography (EtOAc 5:95 Hexane) to afford compound [003] as an oil with a brownish tint (5.32 gr; 66% yield). $^1$H NMR (400 MHz, $CDCl_3$): δ ppm 4.89 (m, 1H); 3.42 (m, 2H); 2.31 (m, 2H); 1.89 (m, 2H); 1.73-1.18 (brm, 36H); 0.88 (m, 6H).

Intermediate Example P4.

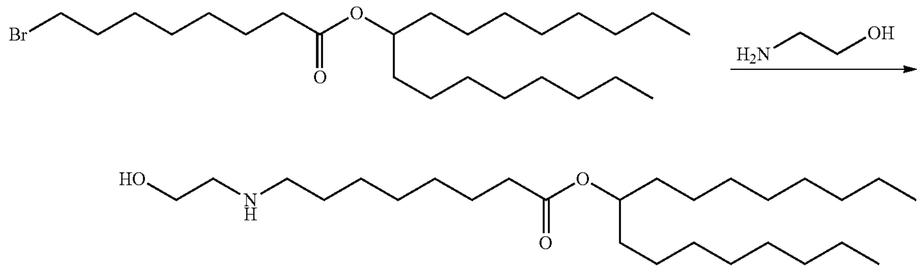

heptadecan-9-yl 8-((2-hydroxyethyl)amino)octanoate compound [004]heptadecan-9-yl 8-bromooctanoate (5.32 g, 11.53 mmol) was dissolved in 10 mL EtOH. Ethanolamine (20.91 ml, 346 mmol) was added and the resulting solution was allowed to stir at 65° C. overnight. the reaction mixture was evaporated in vacuo. and the crude material was dissolved in 40 mL EtOAc. The organic layer was washed with water 30 mL×2, dried over $Na_2SO_4$, filtered and evaporated. The crude oil was purified via column chromatography (0.10% TEAin 10% MeOH in DCM). to acquire compound [004] as a yellowish oil (3.84 gr 75% yield). $^1$H NMR (400 MHz, $CDCl_3$): δ ppm 4.86 (p. 1H); 3.67 (t, 2H); 2.83 (t, 2H) 2.67 (t, 2H); 2.32 (t, 2H) 1.96 (brm, 2H); 1.72-1.41 (m, 37H); 0.88 (m, 6H). MS [ESI]: m/z: [M+H] calc. 442.4 obs. 442.6

Intermediate Example P5.

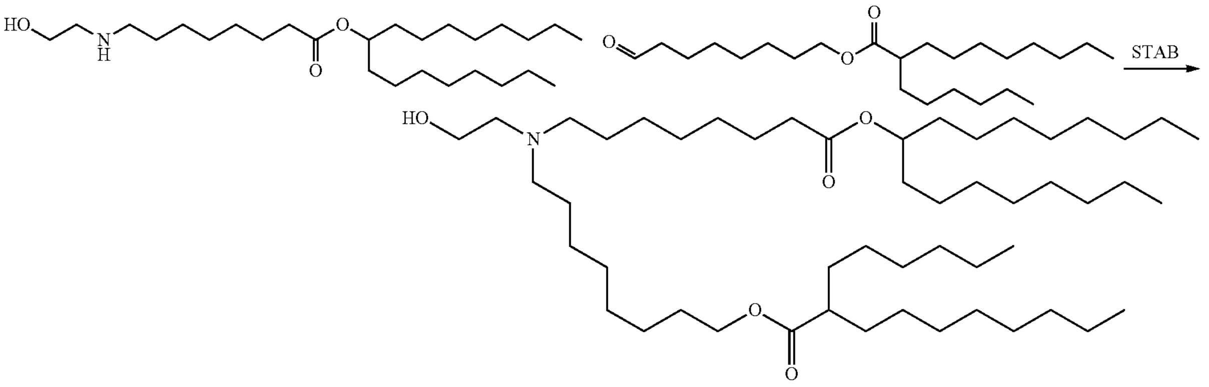

8-((8-(heptadecan-9-yloxy)-8-oxooctyl)(2-hydroxyethyl) amino)octyl 2-hexyldecanoate compound [005]8-oxooctyl 2-hexyldecanoate (3.09 g, 8.08 mmol) and heptadecan-9-yl 8-((2-hydroxyethyl)amino)octanoate (3.4 g, 7.70 mmol) were both dissolved in 120 mL DCM dry. The solution was allowed to stir at RT for 2 hrs. After which sodium triacetoxyborohydride (3.26 g, 15.39 mmol) was added and the resulting suspension was allowed to stir at RT O/N under argon. 40 mL of $NaHCO_3$ sat. were added and the phases were separated. The organic phase was washed with brine (40 mL) dried over $Na_2SO_4$ filtered and evaporated. the crude material was purified by column chromatography iPrOH 1-5% in $CHCl_3$ to acquire compound [005] as a colorless oil (5.61 gr; 90% yield). MS [ESI]: m/z: [M+H] calc. 809.4 obs. 809.3 $^1$H NMR (400 MHz, $CDCl_3$): δ ppm 4.86 (p, 1H); 4.06 (t, 2H); 3.53 (m, 2H); 2.58 (m, 2H); 2.44 (m, 4H); 2.27 (m+t, 3H), 1.61-1.28 (m, 74), 0.88 (m, 12H)

Intermediate Example P6.

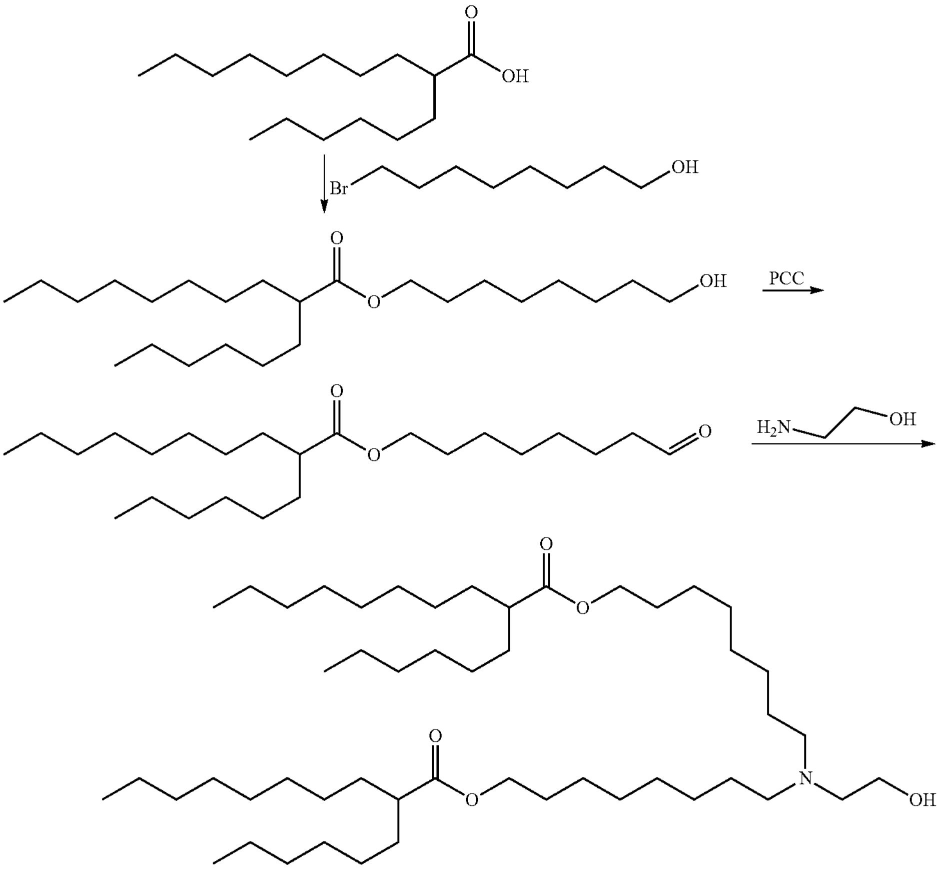

((2-hydroxyethyl)azanediyl)bis(octane-8,1-diyl) bis(2-hexyldecanoate) compound [006]8-oxooctyl 2-hexyldecanoate (1.391 g, 3.63 mmol) and ethanolamine (0.110 ml, 1.817 mmol) were dissolved in 25 mL DCM. The reaction mixture was left to stir at RT under argon for 2 hrs. sodium triacetoxyborohydride (1.155 g, 5.45 mmol) was then added portion wise over 10 mins and the reaction mixture was left to O/N. the reaction was then washed with 40 mL $NaHCO_3$ (40 mL) and brine (40 mL×2) the organic phase was then dried over $Na_2SO_4$, filtered and evaporated. The crude material was then purified via column chromatography (2% iPrOH in DCM) to acquire compound [006] as a colorless oil (1.095 gr; 76% yield). $^1H$ NMR (400 MHz, $CDCl_3$): δ ppm 4.05 (4H, t, J=6.67 Hz); 3.54 (2H, t, J=5.57 Hz) 2.59 (2H, t, J=5.57 Hz); 2.46 (4H, t, J=7.65 Hz); 2.34-2.24 (2H, m); 1.68-1.50 (8H, m); 1.48-1.36 (8H, m); 1.36-1.16 (56H, m); 0.86 (12H, t, J=6.87 Hz); MS [ESI]: m/z: [M+H] calc. 795.4 obs. 795.

Intermediate Example P7.

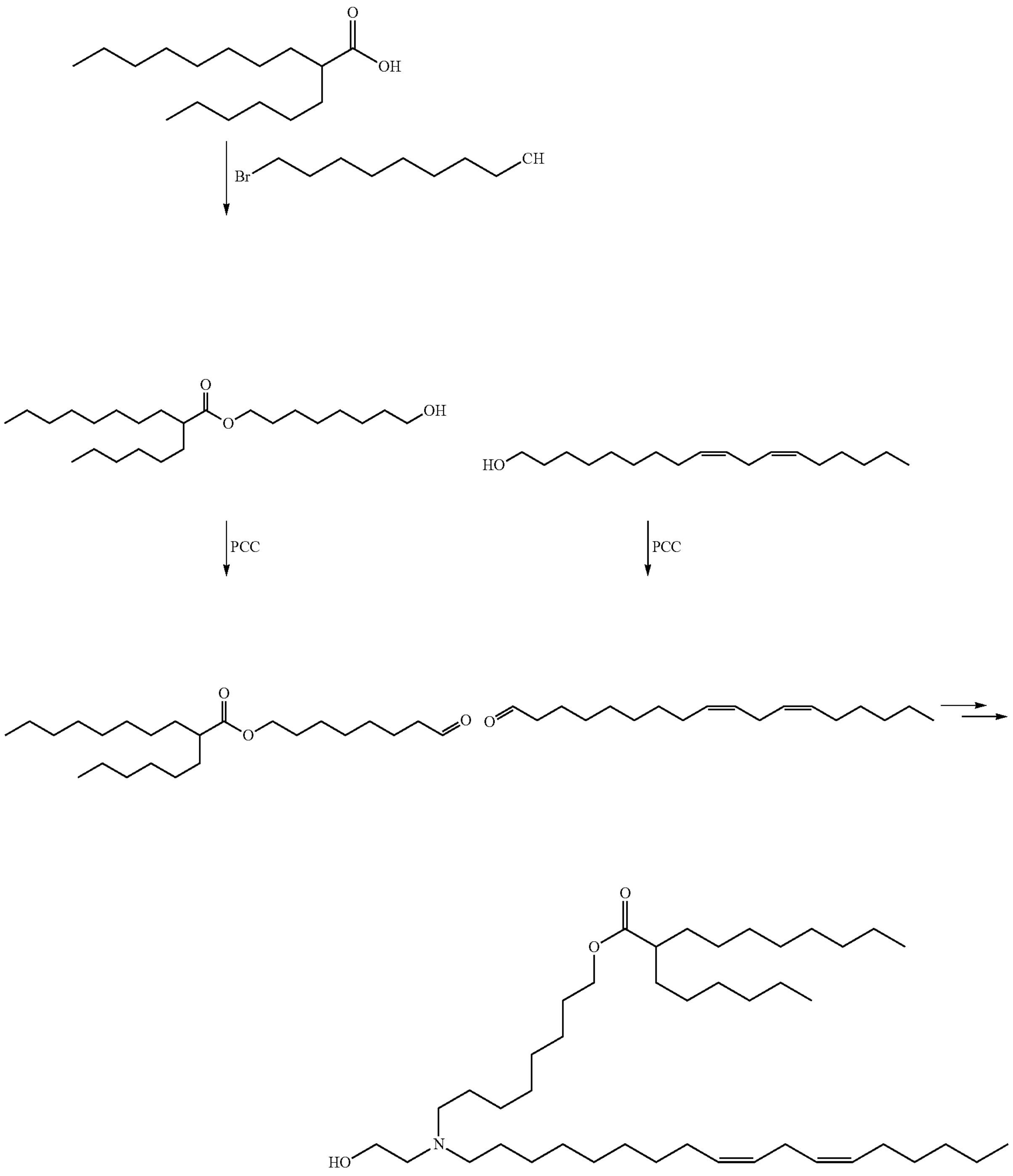

8-((2-hydroxyethyl)((9Z,12Z)-octadeca-9,12-dien-1-yl) amino)octyl 2-hexyldecanoate compound [007]8-oxooctyl 2-hexyldecanoate Compound [002](1.3 g, 3.4 mmol, 1 equiv.) was dissolved in dry Methanol (10 mL) Ethanolamine (1.2 gr, 15.20 mmol, 5.0 equiv.) was added and the resulting solution was stirred for 3 hr. After which, the solution was cooled to 0° C. and Sodium borohydride (128 mg, 3.4 mmol, 1 equiv) was added the reaction was stirred for 20 mins the solvent was removed by evaporation and the crude was redissolved in 75 mL DCM. The organic phase was washed with $NaHCO_3$ sat. (30 mL×2), Brine (30 mL×1) dired over $Na_2SO_4$ filtered and evaporated. The crude material was re-dissolved in 25 mL DCM dry. Linoleoyl aldehyde 2 (1.0 g, 4.0 mmol, 1.2 equiv.) was added and the solution was allowed to stir for 1 hr. at RT Sodium triacetoxyborohydride (1.4 g, 6.8 mmol, 2.0 equiv.) was added and the reaction was left to stir overnight under argon. The reaction was quenched with $NaHCO_3$ sat. solution and extracted with DCM (3 times). The organic portion was washed with brine solution and dried over anhydrous $Na_2SO_4$. The solvent was evaporated and the residue was purified by column chromatography to yield compound [007](1.7 g, 77%) as a pale yellow oil. MS [ESI]: m/z: [M+H] calc. 677.2 obs. 677.5.

Example 1 (Method 6)

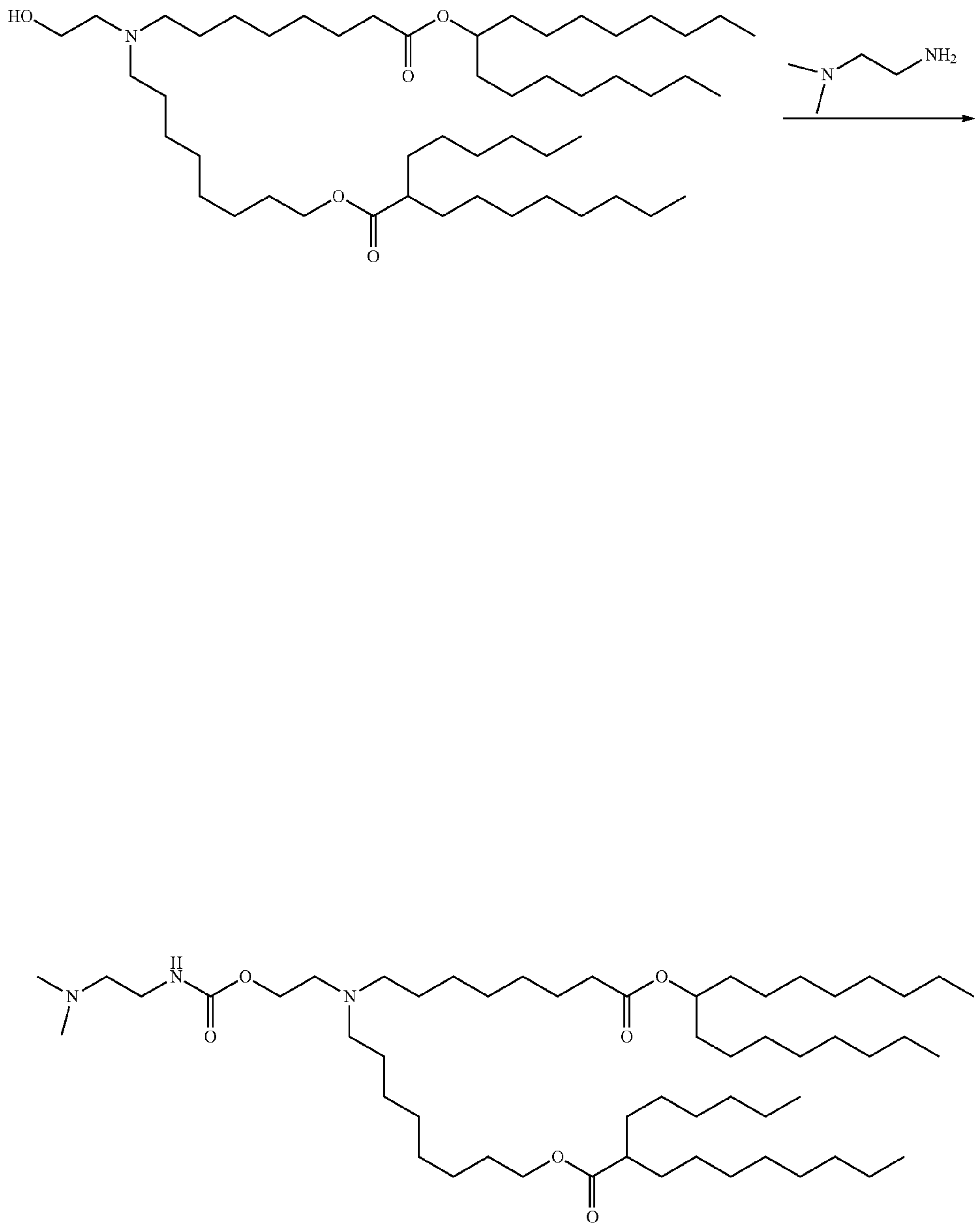

heptadecan-9-yl 10-(8-((2-hexyldecanoyl)oxy)octyl)-2-methyl-6-oxo-7-oxa-2,5,10-triazaoctadecan-18-oate Lipid 66 8-((8-(heptadecan-9-yloxy)-8-oxooctyl)(2-hydroxyethyl) amino)octyl 2-hexyldecanoate (0.3 g; 0.37 mmol) and 4-nitrophenyl chloroformate (0.090 g; 0.45 mmol) were dissolved in 10 mL dry DCM. TEA (0.103 ml; 0.742 mmol) was added and the reaction was left to stir at RT overnight. 2N1,N1-dimethylethane-1,2-diamine (0.083 g; 0.93 mmol) was then added and the reaction was left to stir at RT O/N. The reaction was then subjected directly to column chromatography (2%-10% iPrOH in DCM) to yield Lipid 66 as a yellowish oil (297 mg; 83%)-; MS [ESI]: m/z: [M+H] calc. 923.5 obs. 923.5.

$^1$H NMR (400 MHz, $CDCl_3$): δ 0.85 (12H, m), 1.23 (73H, m), 2.19 (6H, s), 2.22-2.30 (3H, 2.25 (t, J=7.54 Hz), 2.27 (m)), 2.34-2.45 (7H, 2.40 (m), 2.42 (t, J=7.58 Hz)), 2.64 (2H, t, J=5.96 Hz), 3.23 (2H, q, J=5.52 Hz), 4.03 (4H, m), 4.84 (1H, i, J=6.21 Hz), 5.19-5.25 (1H, in).

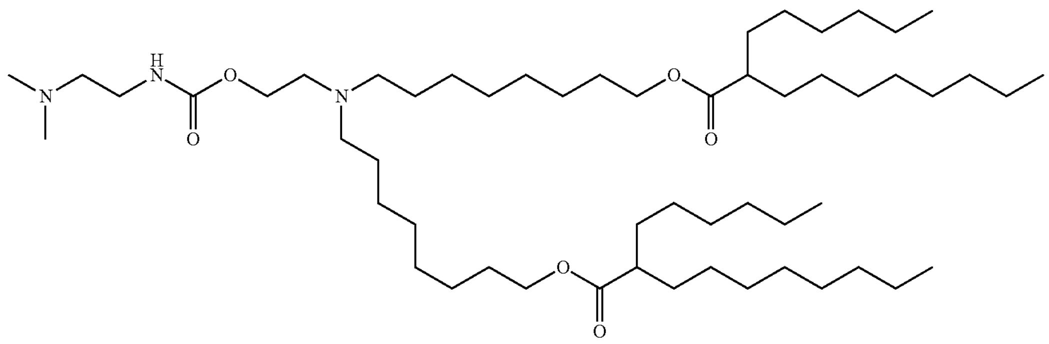 [SMILES: CCCCCCCCC(CCCCCC)C(=O)OCCCCCCCCN(CCCCCCCCOC(=O)C(CCCCCC)CCCCCCCC)CCOC(=O)NCCN(C)C]

Lipid 6 10-(8-((2-hexyldecanoyl)oxy)octyl)-2-methyl-6-oxo-7-oxa-2,5,10-triazaoctadecan-18-yl 2-hexyldecanoate was synthesized according to the general synthetic scheme and general methods. MS [ESI]: m/z: [M+H] calc 908.8 obs. 909.3; $^1$H NMR (500 MHz, $CDCl_3$): δ 0.87 (12H, t, J=6.84 Hz), 1.26 (55H, m), 1.42 (4H, m), 1.58 (12H, m), 2.30 (3H, m), 2.39 (5H, m), 2.65 (6H, m), 2.90 (3H, m), 3.35 (2H, m), 4.05 (4H, t, J=6.68 Hz), 4.24 (2H, m), 5.24 (1H, n).

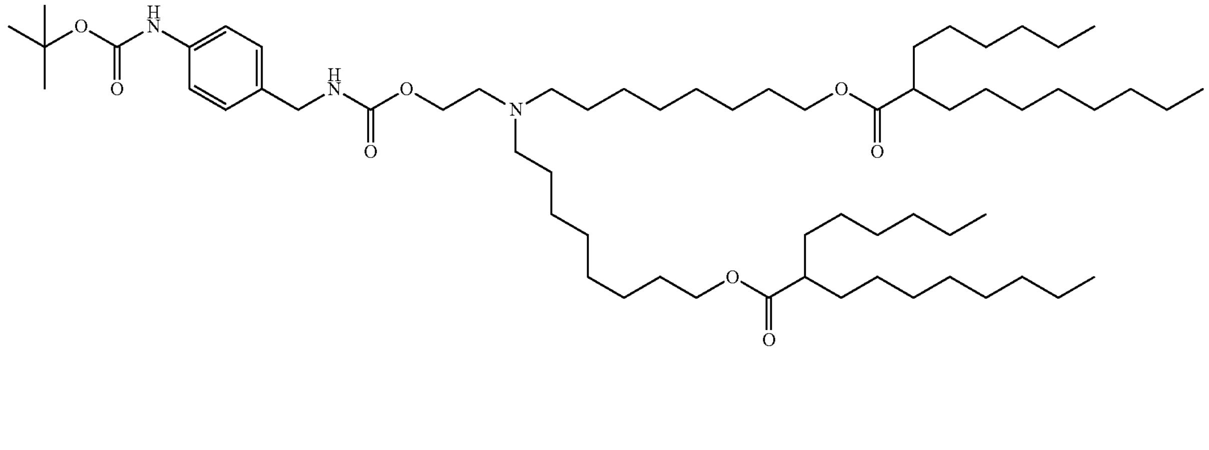 [SMILES: CCCCCCCCC(CCCCCC)C(=O)OCCCCCCCCN(CCCCCCCCOC(=O)C(CCCCCC)CCCCCCCC)CCOC(=O)NCc1ccc(NC(=O)OC(C)(C)C)cc1]

Lipid 8 ((2-(((4-((tert-butoxycarbonyl)amino)benzyl)carbamoyl)oxy)ethyl)azanediyl)bis(octane-8,1-diyl) bis(2-hexyldecanoate) was synthesized according to the general synthetic scheme and general methods. MS [ESI]: m/z: [M+H] calc 1043.6 obs. 1043.2 1H NMR (500 MHz, $CDCl_3$): δ 0.87 (12H, t, J=6.84 Hz), 1.27 (53H, m), 1.42 (5H, m), 1.51 (6H, s), 1.61 (14H, m), 2.30 (2H, m), 2.91 (6H, m), 3.21 (6H, m), 3.79 (1H, m), 4.05 (4H, t, J=6.94 Hz), 4.29 (2H, d, J=5.98 Hz), 4.41 (2H, m), 7.21 (2H, d, J=8.01 Hz), 7.32 (2H, d, J=8.01 Hz).

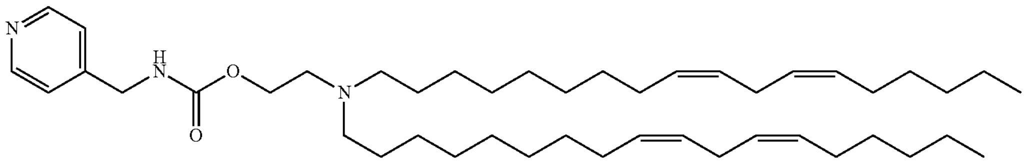 [SMILES: CCCCC/C=C\C/C=C\CCCCCCCCN(CCCCCCCC/C=C\C/C=C\CCCCC)CCOC(=O)NCc1ccncc1]

Lipid 35 2-(di((9Z,12Z)-octadeca-9,12-dien-1-yl)amino)ethyl (pyridin-4-ylmethyl)carbamate was synthesized according to the general synthetic scheme and general methods. MS [ESI]: m/z: [M+H] calc 693.1 obs. 692.6 $^1H$ NMR (400 MHz, CDCl3): δ 0.88 (6H, t, J=6.66 Hz), 1.29 (33H, m), 1.49 (4H, m), 2.04 (8H, m), 2.58 (3H, m), 2.77 (6H, m), 4.22 (2H, t, J=5.80 Hz), 4.37 (2H, d, J=6.15 Hz), 5.35 (8H, m), 5.59 (1H, m), 7.21 (2H, d, J=5.90 Hz), 8.54 (2H, d, J=5.90 Hz).

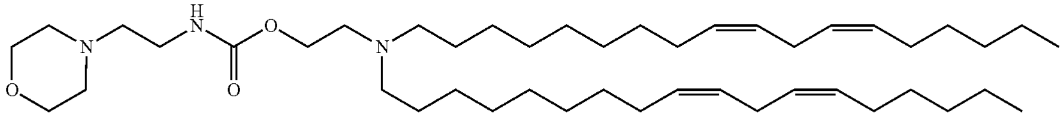 [SMILES: CCCCC/C=C\C/C=C\CCCCCCCCN(CCCCCCCC/C=C\C/C=C\CCCCC)CCOC(=O)NCCN1CCOCC1]

Lipid 36 2-(di((9Z,12Z)-octadeca-9,12-dien-1-yl)amino)ethyl (2-morpholinoethyl)carbamate was synthesized according to the general synthetic scheme and general methods. MS [ESI]: m/z: [M+H] calc 715.1 obs. 714.9 $^1H$ NMR (400 MHz, CDCl3): δ 0.89 (6H, t, J=6.75 Hz), 1.30 (31H, m), 1.49 (4H, m), 2.04 (8H, m), 2.45 (6H, m), 2.57 (5H, m), 2.77 (6H, m), 3.28 (2H, m), 3.69 (4H, m), 4.19 (2H, m), 5.35 (8H, m).

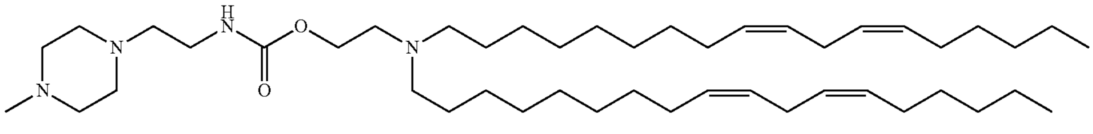 [SMILES: CCCCC/C=C\C/C=C\CCCCCCCCN(CCCCCCCC/C=C\C/C=C\CCCCC)CCOC(=O)NCCN1CCN(C)CC1]

Lipid 37 2-(di((9Z,12Z)-octadeca-9,12-dien-1-yl)amino)ethyl (2-(4-methylpiperazin-1-yl)ethyl)carbamate was synthesized according to the general synthetic scheme and general methods. MS [ESI]: m/z: [M+H] calc 728.7 obs. 727.9 $^1H$ NMR (400 MHz, CDCl3): δ 0.88 (6H, t, J=6.66 Hz), 1.29 (33H, m), 1.49 (4H, m), 2.04 (8H, m), 2.35 (3H, s), 2.55 (13H, m), 2.78 (6H, m), 3.27 (2H, m), 4.18 (2H, t, J=5.81 Hz), 5.35 (8H, m).

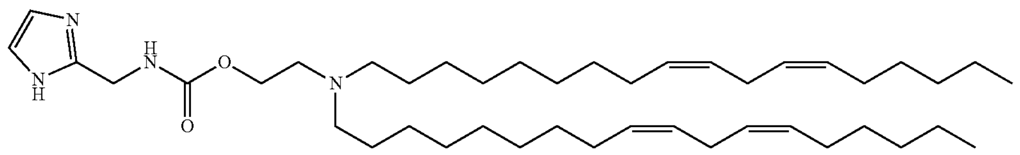 [SMILES: CCCCC/C=C\C/C=C\CCCCCCCCN(CCCCCCCC/C=C\C/C=C\CCCCC)CCOC(=O)NCc1ncc[nH]1]

Lipid 39 2-(di((9Z,12Z)-octadeca-9,12-dien-1-yl)amino)ethyl ((1H-imidazol-2-yl)methyl)carbamate was synthesized according to the general synthetic scheme and general methods. MS [ESI]: m/z: [M+H] calc 728.7 obs. 727.9 1H NMR (400 MHz, CDCl3): δ 0.88 (6H, t, J=6.75 Hz), 1.30 (32H, m), 1.56 (4H, m), 2.04 (8H, m), 2.67 (2H, m), 2.77 (6H, t, J=6.41 Hz), 2.88 (1H, m), 2.97 (1H, m), 4.29 (2H, m), 4.38 (1H, m), 4.47 (1H, d, J=6.15 Hz), 5.35 (8H, m), 6.01 (1H, m), 6.94 (2H, m).

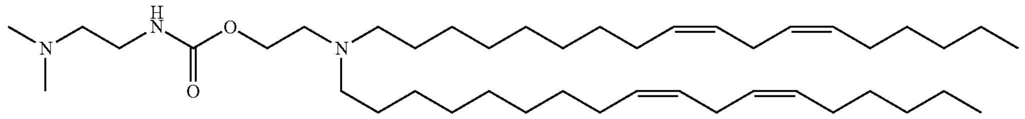

Lipid 41 2-(di((9Z,12Z)-octadeca-9,12-dien-1-yl)amino)ethyl (2-(dimethylamino)ethyl)carbamate was synthesized according to the general synthetic scheme and general methods. MS [ESI]: m/z: [M+H] calc 672.1 obs. 672.6; $^{1}H$ NMR (400 MHz, $CDCl_3$): δ 0.88 (6H, t, J=6.66 Hz), 1.30 (32H, m), 1.48 (4H, m), 2.04 (8H, m), 2.27 (6H, m), 2.47 (2H, m), 2.56 (4H, m), 2.77 (6H, m), 3.28 (2H, m), 4.18 (2H, t, J=6.06 Hz), 5.35 (8H, m), 5.47 (1H, m).

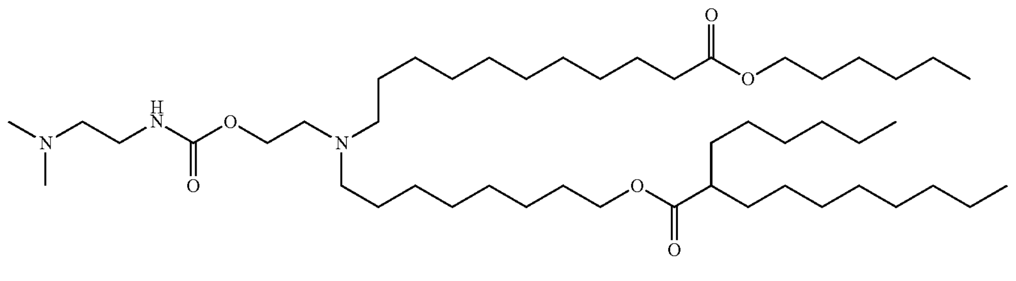 [SMILES: CCCCCCCCC(CCCCCC)C(=O)OCCCCCCCCN(CCCCCCCCCCC(=O)OCCCCCC)CCOC(=O)NCCN(C)C]

Lipid 43 hexyl 10-(8-((2-hexyldecanoyl)oxy)octyl)-2-methyl-6-oxo-7-oxa-2,5,10-triazahenicosan-21-oate was synthesized according to the general synthetic scheme and general methods. MS [ESI]: m/z: [M+H] calc 811.3 obs. 811.0; $^{1}H$ NMR (500 MHz, $CDCl_3$): δ 0.88 (9H, m), 1.24-1.35 (46H, m), 1.40-1.46 (3H, m), 1.53-1.63 (11H, m), 2.29 (2H, s), 2.40 (5H, s), 2.46 (1H, s), 2.59-2.64 (2H, m), 2.65-2.71 (4H, m), 2.89-2.93 (2H, m), 3.31-3.38 (3H, m), 4.05-4.08 (4H, 4.06 (s), 4.07 (s)), 4.21-4.26 (2H, m), 5.86-5.91 (1H, m).

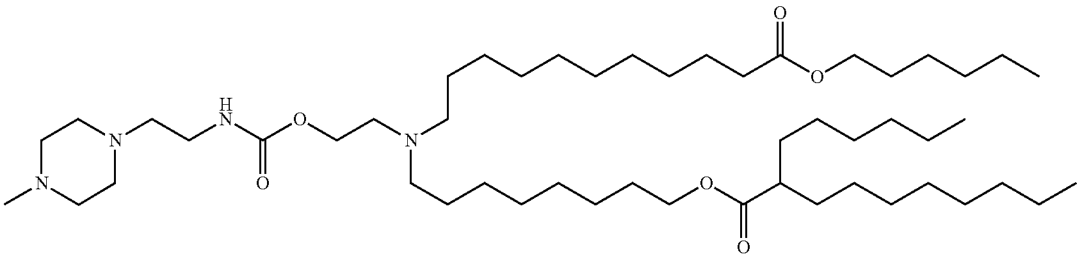 [SMILES: CCCCCCCCC(CCCCCC)C(=O)OCCCCCCCCN(CCCCCCCCCCC(=O)OCCCCCC)CCOC(=O)NCCN1CCN(C)CC1]

Lipid 46 hexyl 11-((8-((2-hexyldecanoyl)oxy)octyl)(2-(((2-(4-methylpiperazin-1-yl)ethyl)carbamoyl)oxy)ethyl)amino)undecanoate was synthesized according to the general synthetic scheme and general methods. MS [ESI]: m/z: [M+H] calc 866.4 obs. 866.0; $^1$H NMR $^1$H NMR (500 MHz, $CDCl_3$): δ 0.88 (9H, m), 1.25 (63H, m), 2.29 (3H, s), 2.39 (3H, m), 2.61 (12H, m), 2.84 (OH, m), 3.14 (1H, s), 3.25-3.30 (2H, m), 4.06 (5H, s), 4.19-4.22 (2H, m)

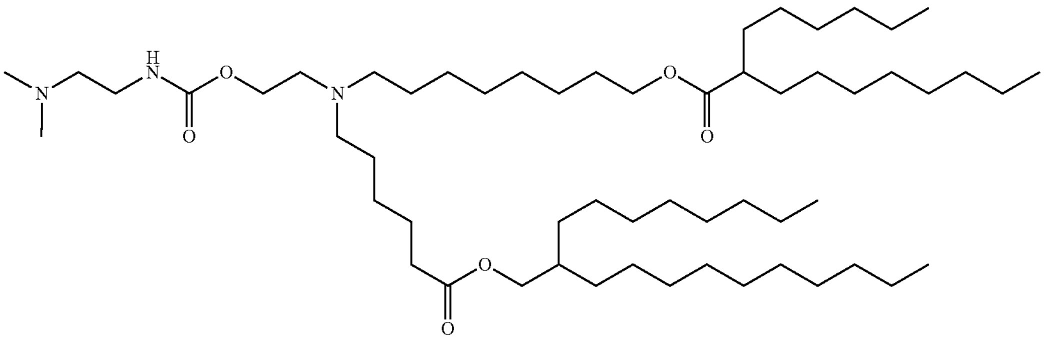 [SMILES: CCCCCCCCCCC(CCCCCCCC)COC(=O)CCCCCN(CCCCCCCCOC(=O)C(CCCCCC)CCCCCCCC)CCOC(=O)NCCN(C)C]

Lipid 51 2-octyldodecyl 10-(8-((2-hexyldecanoyl)oxy)octyl)-2-methyl-6-oxo-7-oxa-2,5,10-triazahexadecan-16-oate was synthesized according to the general synthetic scheme and general methods. MS [ESI]: m/z: [M+H] calc 937.5 obs. 937.2; $^1$H NMR (400 MHz, $CDCl_3$): δ 0.88 (12H, t, J=6.83 Hz), 1.26 (62H, s), 1.44 (4H, m), 1.63 (8H, m), 2.22 (6H, s), 2.30 (4H, t, J=7.53 Hz), 2.39 (2H, t, J=6.12 Hz), 2.42-2.47 (4H, m), 2.66 (2H, t, J=5.86 Hz), 3.20-3.27 (2H, m), 3.96 (4H, d, J=5.81 Hz), 4.09 (1H, m), 5.22-5.27 (1H, m).

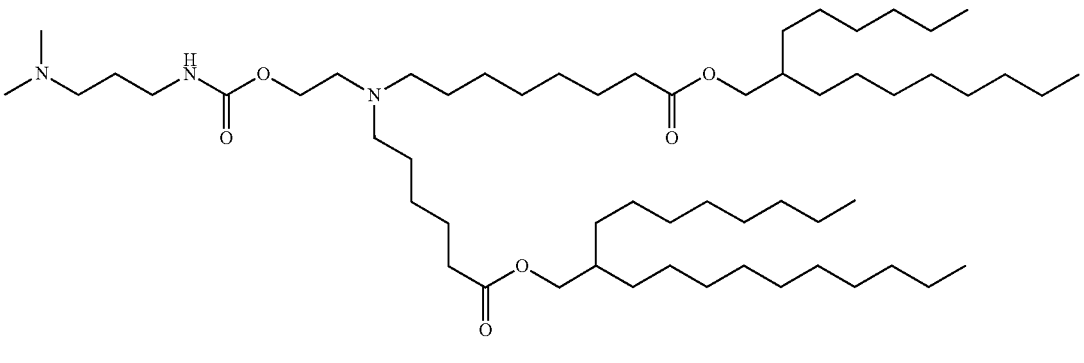 [SMILES: CCCCCCCCCCC(CCCCCCCC)COC(=O)CCCCCN(CCCCCCCC(=O)OCC(CCCCCC)CCCCCCCC)CCOC(=O)NCCCN(C)C]

Lipid 52 2-octyldodecyl 11-(8-((2-hexyldecanoyl)oxy)octyl)-2-methyl-7-oxo-8-oxa-2,6,11-triazaheptadecan-17-oate was synthesized according to the general synthetic scheme and general methods. MS [ESI]: m/z: [M+H] calc 950.6 obs. 950.8; 1H NMR (400 MHz, $CDCl_3$): δ 0.87 (12H, m), 1.26 (65H, m), 1.42 (3H, m), 1.58 (10H, m), 2.30 (4H, t, J=7.60 Hz), 2.37 (4H, t, J=1.62 Hz), 2.60 (4H, m), 2.82 (2H, m), 3.33 (2H, m), 3.57 (3H, m), 3.96 (2H, d, J=5.81 Hz), 4.05 (2H, t, J=6.75 Hz), 4.19 (2H, t, J=5.89 Hz).

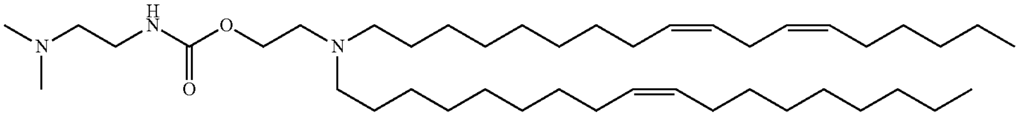 [SMILES: CCCCC/C=C\C/C=C\CCCCCCCCN(CCCCCCCC/C=C\CCCCCCCC)CCOC(=O)NCCN(C)C]

Lipid 67 2-(((Z)-octadec-9-en-1-yl)((9Z,12Z)-octadeca-9,12-dien-1-yl)amino)ethyl (2-(dimethylamino)ethyl)carbamate was synthesized according to the general synthetic scheme and general methods. MS [ESI]: m/z: [M+H] calc 674.2 obs. 674.9; $^1$H NMR (400 MHz): δ 0.88 (6H, td, J=6.70, 4.10 Hz), 1.22-1.55 (43H, 1.27 (m), 1.46 (br s)), 2.04 (8H, m), 2.24 (5H, s), 2.43 (2H, t, J=5.94 Hz), 2.48-2.55 (4H, 2.51 (t, J=7.67 Hz), 2.51 (d, J=4.44 Hz)), 2.76 (4H, m), 3.26 (2H, m), 4.15 (2H, t, J=5.97 Hz), 5.35 (7H, m).

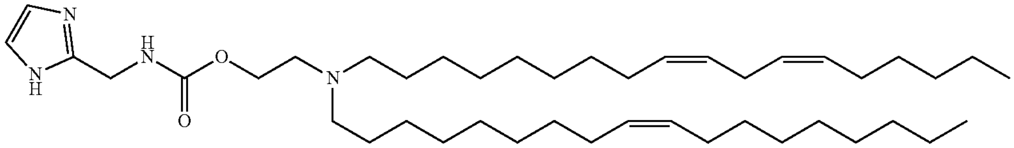 [SMILES: CCCCC/C=C\C/C=C\CCCCCCCCN(CCCCCCCC/C=C\CCCCCCCC)CCOC(=O)NCc1ncc[nH]1]

Lipid 68 2-(((Z)-octadec-9-en-1-yl)((9Z,12Z)-octadeca-9,12-dien-1-yl)amino)ethyl ((1H-imidazol-2-yl)methyl)carbamate was synthesized according to the general synthetic scheme and general methods. MS [ESI]: m/z: [M+H] calc 684.1 obs. 683.8; $^1$H NMR (500 MHz, $CDCl_3$): δ 0.88 (6H, m), 1.22-1.34 (39H, m), 1.47-1.56 (4H, m), 2.03 (8H, m), 2.59-2.68 (4H, m), 2.77 (2H, m), 2.85 (2H, m), 4.28 (2H, m), 4.35 (1H, m), 4.42 (1H, m), 5.34 (7H, m), 6.89-6.91 (1H, m), 6.96 (1H, s).

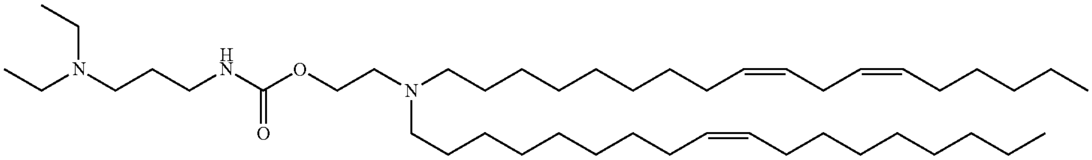

Lipid 69 2-(((Z)-octadec-9-en-1-yl)((9Z,12Z)-octadeca-9,12-dien-1-yl)amino)ethyl (3-(diethylamino)propyl)carbamate was synthesized according to the general synthetic scheme and general methods. MS [ESI]: m/z: [M+H] calc 716.2 obs. 716.9; $^1$H NMR (400 MHz, $CDCl_3$): δ 0.88 (6H, m), 1.28 (42H, m), 1.40-1.50 (4H, m), 2.04 (7H, m), 2.47-2.54 (4H, 2.51 (t, J=7.65 Hz), 2.51 (d, J=4.44 Hz)), 2.68-2.81 (9H, m), 4.13 (2H, m), 5.35 (6H, m), 1.77-1.85 (1H, m), 3.23-3.30 (2H, m), 1.15-1.20 (5H, m), 5.84-5.91 (1H, m).

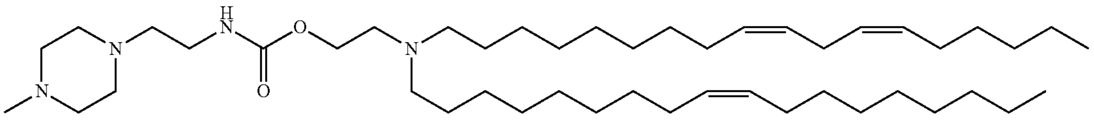 [SMILES: CCCCC/C=C\C/C=C\CCCCCCCCN(CCCCCCCC/C=C\CCCCCCCC)CCOC(=O)NCCN1CCN(C)CC1]

Lipid 70 2-(((Z)-octadec-9-en-1-yl)((9Z,12Z)-octadeca-9,12-dien-1-yl)amino)ethyl (2-(4-methylpiperazin-1-yl)ethyl) carbamate was synthesized according to the general synthetic scheme and general methods. MS [ESI]: m/z: [M+H] calc 729.2 obs 729.9:1H NMR (400 MHz, $CDCl_3$): δ 0.90 (6Hm), 1.31 (37H, m), 1.55 (4H, m), 2.04 (8H, m), 2.41 (3H, s), 2.53 (2H, m), 2.65 (9H, m), 2.79 (2H, t, J=6.32 Hz), 2.88 (2H, m), 3.15 (3H, s), 3.29 (2Hm), 4.23 (2H, m), 5.39 (7H, m).

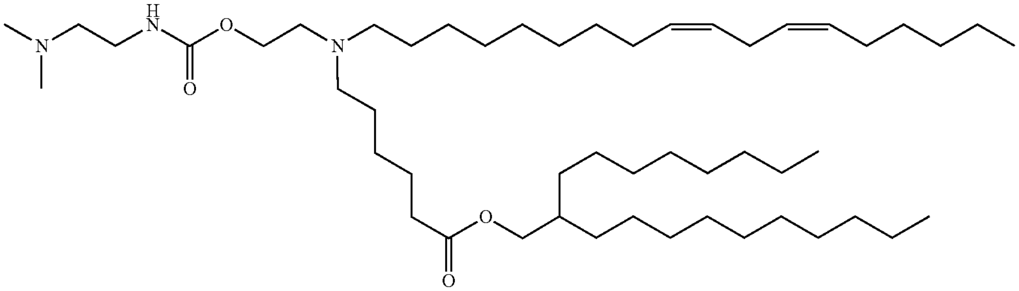 [SMILES: CCCCC/C=C\C/C=C\CCCCCCCCN(CCCCCC(=O)OCC(CCCCCCCC)CCCCCCCCCC)CCOC(=O)NCCN(C)C]

Lipid 75 2-octyldodecyl 2-methyl-10-((9Z,12Z)-octadeca-9,12-dien-1-yl)-6-oxo-7-oxa-2,5,10-triazahexadecan-16-oate was synthesized according to the general synthetic scheme and general methods. MS [ESI]: m/z: [M+H] calc 819.3 obs. 819.1; $^1$H NMR (400 MHz, $CDCl_3$): δ 0.89 (9H, m), 1.28 (52H, m), 1.43-1.54 (3H, m), 1.58-1.69 (3H, m), 2.06 (5H, q, J=7.08 Hz), 2.30 (8H, m), 2.43-2.58 (5H, m), 2.78 (3H, q, J=6.12 Hz), 3.31 (1H, m), 3.98 (2H, d, J=5.75 Hz), 4.13-4.19 (2H, m), 5.37 (4H, m), 5.48-5.54 (1H, m).

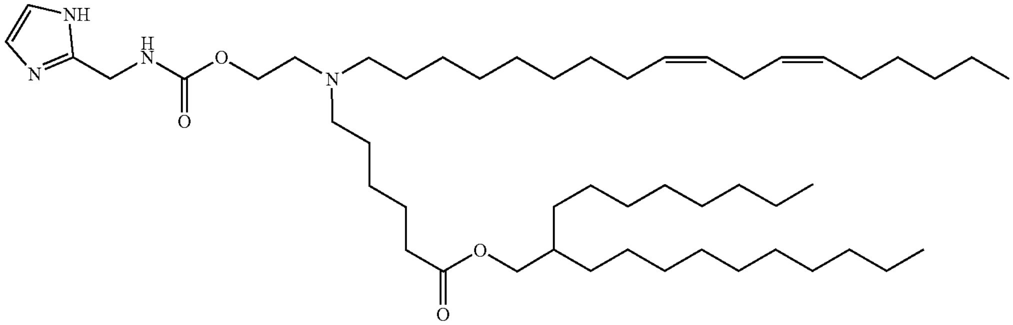 [SMILES: CCCCC/C=C\C/C=C\CCCCCCCCN(CCCCCC(=O)OCC(CCCCCCCC)CCCCCCCCCC)CCOC(=O)NCc1ncc[nH]1]

Lipid 76 2-octyldodecyl 6-((2-((((1H-imidazol-2-yl)methyl)carbamoyl)oxy)ethyl)((9Z,12Z)-octadeca-9,12-dien-1-yl)amino)hexanoate was synthesized according to the general synthetic scheme and general methods. MS [ESI]: m/z: [M+H] calc 827.3 obs. 827.1 $^1$H NMR (400 MHz, $CDCl_3$): δ 0.88 (9H, m), 1.26 (49H, m), 1.62 (7H, m), 2.02 (4H, m), 2.24-2.33 (2H, m), 2.76 (5H, m), 3.96 (2H, d, J=5.78 Hz), 4.30 (9H, m), 4.46 (2H, t, J=5.79 Hz), 5.31-5.39 (4H, m), 6.96 (2H, m), 2.89-2.99 (1H, m).

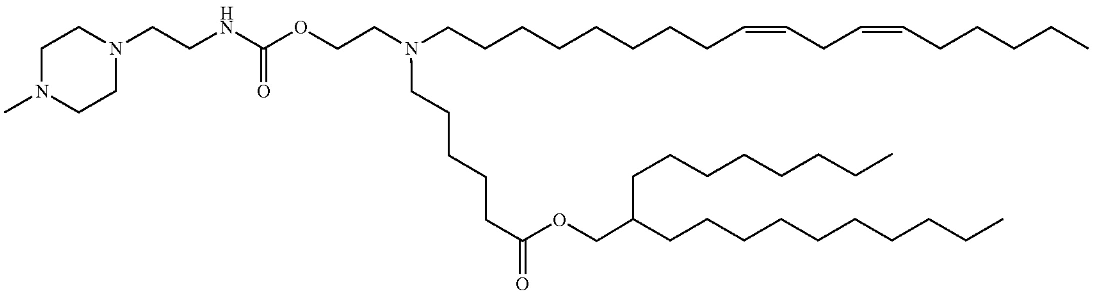 [SMILES: CCCCC/C=C\C/C=C\CCCCCCCCN(CCCCCC(=O)OCC(CCCCCCCC)CCCCCCCCCC)CCOC(=O)NCCN1CCN(C)CC1]

Lipid 78 2-octyldodecyl 6-((2-(((2-(4-methylpiperazin-1-yl)ethyl)carbamoyl)oxy)ethyl)((9Z,12Z)-octadeca-9,12-dien-1-yl)amino)hexanoate was synthesized according to the general synthetic scheme and general methods. MS [ESI]: m/z: [M+H] calc 873.5 obs. 873.0 $^1$H NMR (400 MHz, $CDCl_3$): $^1$H NMR (400 MHz): δ 0.88 (9H, m), 1.28 (46H, m), 1.46 (3H, sm), 1.62 (3H, m), 1.99 (4H, m), 2.04 (5H, m), 2.32 (11H, m), 2.51 (3H, m), 2.75 (4H, m), 3.26 (2H, m), 3.35 (4H, q, J=5.86 Hz), 3.52 (1H, m), 3.96 (2H, d, J=5.81 Hz), 4.13 (2H, t, J=6.15 Hz), 5.35 (4H, m), 6.11 (1H, m).

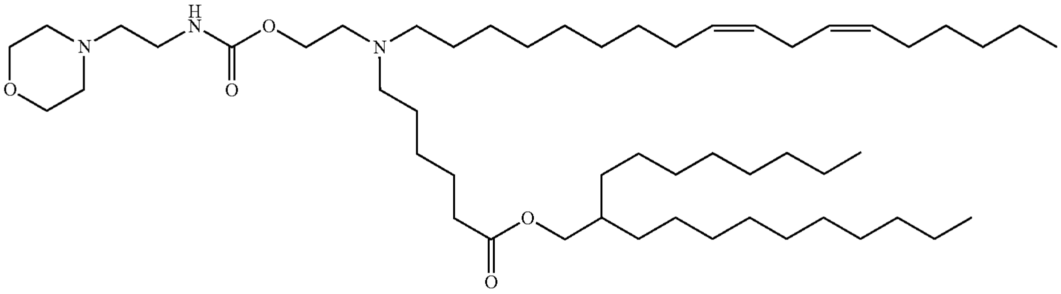 [SMILES: CCCCC/C=C\C/C=C\CCCCCCCCN(CCCCCC(=O)OCC(CCCCCCCC)CCCCCCCCCC)CCOC(=O)NCCN1CCOCC1]

Lipid 79 2-octyldodecyl 6-((2-(((2-morpholinoethyl)carbamoyl)oxy)ethyl)((9Z,12Z)-octadeca-9,12-dien-1-yl)amino)hexanoate was synthesized according to the general synthetic scheme and general methods. MS [ESI]: m/z: [M+H] calc 860.4 obs. 861.0; $^1$H NMR (400 MHz, $CDCl_3$): δ 0.88 (9H, m), 1.26 (51H, s), 1.52-1.67 (6H, m), 2.04 (5H, dtd, J=7.52, 6.58, 1.54 Hz), 2.31 (2H, t, J=7.39 Hz), 2.42-2.52 (7H, m), 2.76 (5H, m), 2.89-2.95 (1H, m), 3.24-3.32 (2H, m), 3.68-3.74 (5H, m), 3.96 (2H, d, J=5.79 Hz), 4.25-4.31 (1H, m), 5.30-5.38 (4H, m), 5.55-5.61 (1H, m).

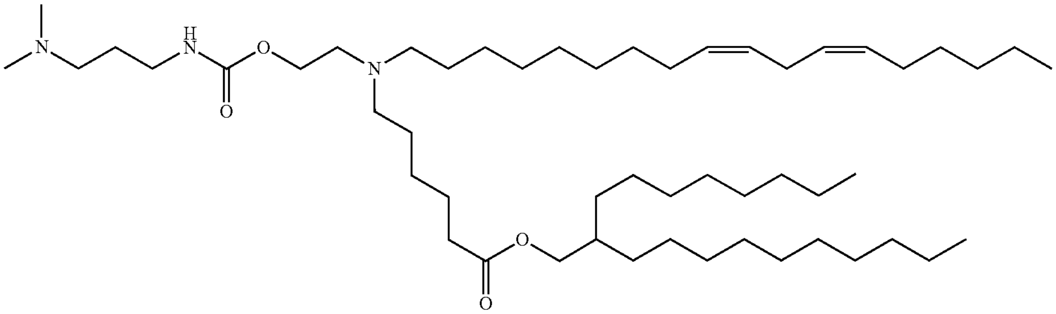 [SMILES: CCCCC/C=C\C/C=C\CCCCCCCCN(CCCCCC(=O)OCC(CCCCCCCC)CCCCCCCCCC)CCOC(=O)NCCCN(C)C]

Lipid 81 2-octyldodecyl 2-methyl-11-((9Z,12Z)-octadeca-9,12-dien-1-yl)-7-oxo-8-oxa-2,6,11-triazaheptadecan-17-oate was synthesized according to the general synthetic scheme and general methods. MS [ESI]: m/z: [M+H] calc 832.4 obs. 833.0; $^{1}H$ NMR (400 MHz, $CDCl_3$): δ 0.90 (9H, m), 1.28 (51H, m), 1.57-1.75 (7H, m), 2.07 (5H, m), 2.34 (1H, s), 2.70-2.73 (4H, 2.72 (s), 2.73 (s)), 2.76-2.80 (2H, 2.77 (s), 2.79 (d, J=2.56 Hz)), 2.83-2.90 (5H, m), 3.01-3.09 (8H, m), 3.30-3.37 (2H, m) 3.98 (2H, d, J=5.80 Hz), 4.27-4.33 (2H, m), 5.37 (2H, m), 6.23-6.30 (1H, br s).

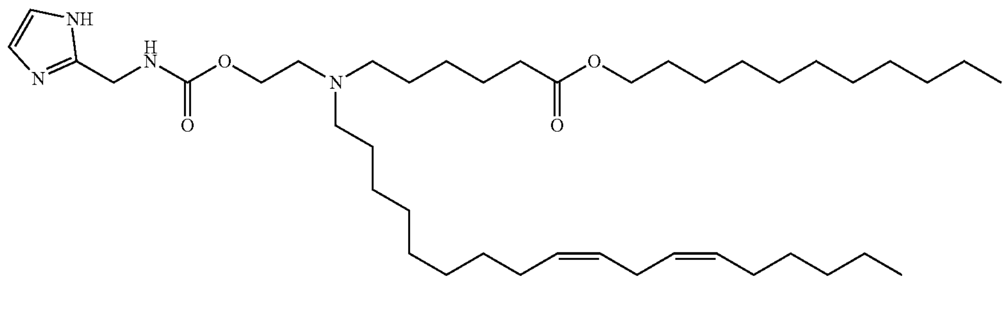 [SMILES: CCCCC/C=C\C/C=C\CCCCCCCCN(CCCCCC(=O)OCCCCCCCCCCC)CCOC(=O)NCc1ncc[nH]1]

Lipid 90 undecyl 6-((2-((((1H-imidazol-2-yl)methyl)carbamoyl)oxy)ethyl)((9Z,12Z)-octadeca-9,12-dien-1-yl) amino)hexanoate was synthesized according to the general synthetic scheme and general methods. MS [ESI]: m/z: [M+H] calc 702.1 obs. 701.9; $^{1}H$ NMR (400 MHz): δ 0.88 (6H, m), 1.26 (40H, m), 1.61 (4H, m), 2.04 (4H, q, J=5.89 Hz), 2.28 (2H, m), 2.44 (2H, m), 2.55-2.68 (3H, m) 2.77 (3H, m), 4.02-4.07 (2H, 4.04 (t, J=5.90 Hz), 4.05 (t, J=6.77 Hz)), 4.11-4.16 (1H, m), 4.25-4.28 (1H, m), 4.36 (2H, m), 5.35 (4H, m), 6.95 (2H, m).

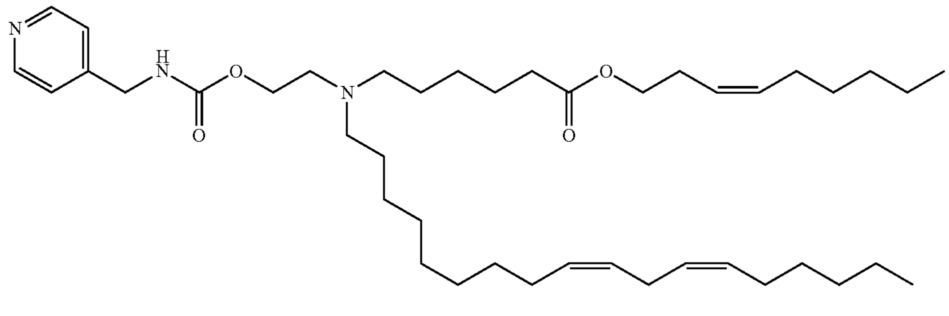 [SMILES: CCCCC/C=C\C/C=C\CCCCCCCCN(CCCCCC(=O)OCC/C=C\CCCCC)CCOC(=O)NCc1ccncc1]

Lipid 99 (Z)-non-3-en-1-yl 6-(((9Z,12Z)-octadeca-9,12-dien-1-yl)(2-(((pyridin-4-ylmethyl)carbamoyl)oxy)ethyl) amino)hexanoate was synthesized according to the general synthetic scheme and general methods. MS [ESI]: m/z: [M+H] calc 682.0 obs. 683.2; $^{1}H$ NMR (400 MHz, $CDCl_3$): δ 0.88 (6H, m), 1.27 (26H, m), 1.62 (3H, m), 2.04 (7H, m), 2.29 (2H, s), 2.36 (2H, q, J=6.78 Hz), 2.45 (4H, m), 2.68 (2H, t, J=5.72 Hz), 2.77 (2H, t, J=6.03 Hz), 4.03 (2H, t, J=6.93 Hz), 4.15 (2H, t, J=5.92 Hz), 4.38 (2H, d, J=6.20 Hz), 5.35 (6H, m), 5.49 (1H, m), 7.21 (2H, dd, J=4.26, 1.53 Hz), 8.55 (2H, dd, J=4.58, 1.42 Hz).

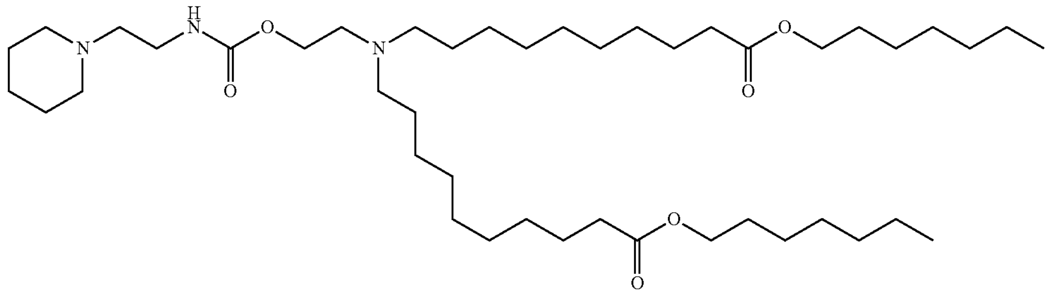 [SMILES: CCCCCCCOC(=O)CCCCCCCCCN(CCCCCCCCCC(=O)OCCCCCCC)CCOC(=O)NCCN1CCCCC1]

Lipid 118 diheptyl 10,10'-((2-(((2-(piperidin-1-yl)ethyl)carbamoyl)oxy)ethyl)azanediyl)bis(decanoate) was synthesized according to the general synthetic scheme and general methods. MS [ESI]: m/z: [M+H] calc 753.1 obs. 753.0. $^{1}$H NMR (400 MHz, $CDCl_3$): δ 0.88 (6H, t, J=6.85 Hz), 1.27 (43H, m), 1.53-1.64 (11H, m), 2.27 (4H, t, J=7.57 Hz), 2.67 (2H, t, J=6.35 Hz), 3.24 (2H, m), 4.05 (4H, t, J=6.75 Hz), 5.26 (1H, s), 2.42 (6H, m), 4.08-4.14 (2H, m), 2.31-2.36 (3H, m).

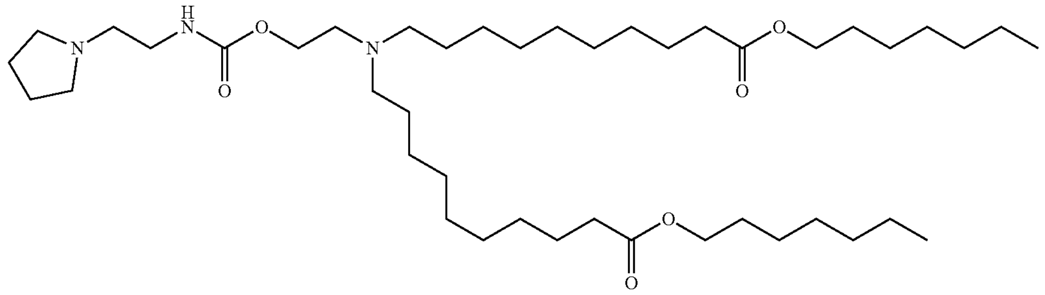 [SMILES: CCCCCCCOC(=O)CCCCCCCCCN(CCCCCCCCCC(=O)OCCCCCCC)CCOC(=O)NCCN1CCCC1]

Lipid 119 diheptyl 10,10'-((2-(((2-(pyrrolidin-1-yl)ethyl)carbamoyl)oxy)ethyl)azanediyl)bis(decanoate) was synthesized according to the general synthetic scheme and general methods. MS [ESI]: m/z: [M+H] calc 739.1, obs. 738.9.

$^{1}$H NMR (400 MHz, $CDCl_3$): δ 0.88 (6H, t, J=6.88 Hz), 1.28 (39H, m), 1.56-1.65 (8H, 1.60 (quint, J=7.24 Hz), 1.58 (s), 1.59 (s)), 1.75 (4H, quint, J=3.18 Hz), 2.28 (4H, t, J=7.54 Hz), 2.46 (11H, m), 2.67 (2H, t, J=5.97 Hz), 3.24-3.30 (2H, 3.27 (d, J=6.67 Hz), 3.25 (d, J=0.68 Hz)), 4.01-4.13 (7H, 4.10 (m), 4.05 (t, J=6.74 Hz)).

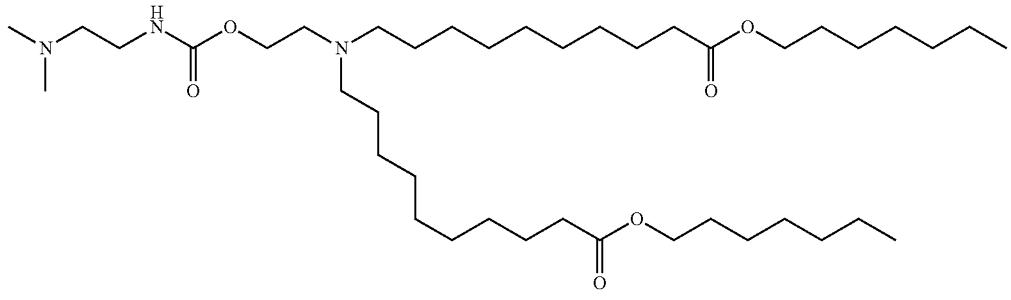 [SMILES: CCCCCCCOC(=O)CCCCCCCCCN(CCCCCCCCCC(=O)OCCCCCCC)CCOC(=O)NCCN(C)C]

Lipid 120 heptyl 10-(10-(heptyloxy)-10-oxodecyl)-2-methyl-6-oxo-7-oxa-2,5,10-triazaicosan-20-oate was synthesized according to the general synthetic scheme and general methods. MS [ESI]: m/z: [M+H] calc 713.1 obs. 712.9; $^1$H NMR (400 MHz, $CDCl_3$): $^1$H NMR (400 MHz): δ 0.88 (6H, t, J=6.87 Hz), 1.23-1.36 (37H, m), 1.39-1.44 (3H, m), 1.60 (8H, m), 2.20-2.22 (6H, 2.21 (s), 2.21 (s)), 2.28 (4H, t, J=7.53 Hz), 2.38 (2H, t, J=6.02 Hz), 2.41-2.47 (4H, 2.44 (t, J=7.62 Hz), 2.44 (d, J=4.44 Hz)), 2.67 (2H, t, J=6.00 Hz), 3.23 (2H, m), 4.02-4.13 (6H, 4.05 (t, J=6.74 Hz), 4.10 (t, J=5.99 Hz)).

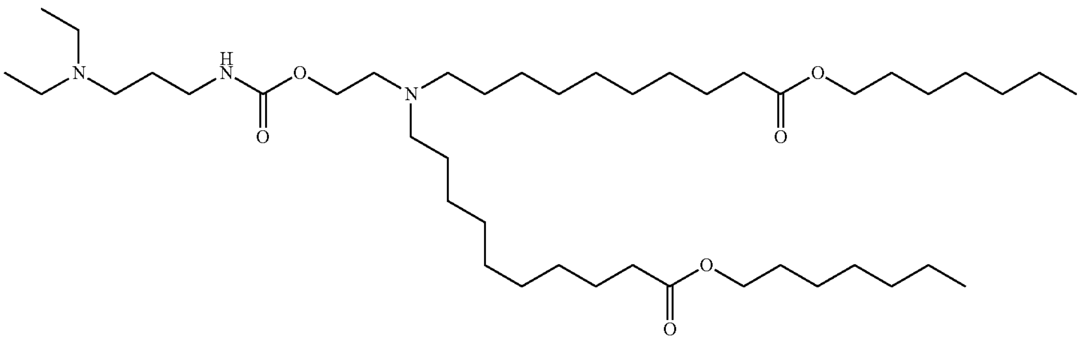 [SMILES: CCCCCCCOC(=O)CCCCCCCCCN(CCCCCCCCCC(=O)OCCCCCCC)CCOC(=O)NCCCN(CC)CC]

Lipid 122 heptyl 3-ethyl-12-(10-(heptyloxy)-10-oxodecyl)-8-oxo-9-oxa-3,7,12-triazadocosan-22-oate was synthesized according to the general synthetic scheme and general methods. MS [ESI]: m/z: [M+H] calc 755.2 obs. 754.9; 1H NMR (400 MHz, $CDCl_3$): δ 0.88 (6H, t, J=6.84 Hz), 1.02 (6H, t, J=7.14 Hz), 1.28 (40H, m), 1.61 (11H, m), 2.28 (4H, t, J=7.54 Hz), 2.48 (10H, m), 2.67 (2H, m), 3.24 (2H, m), 4.03-4.12 (6H, 4.05 (t, J=6.75 Hz), 4.09 (m)).

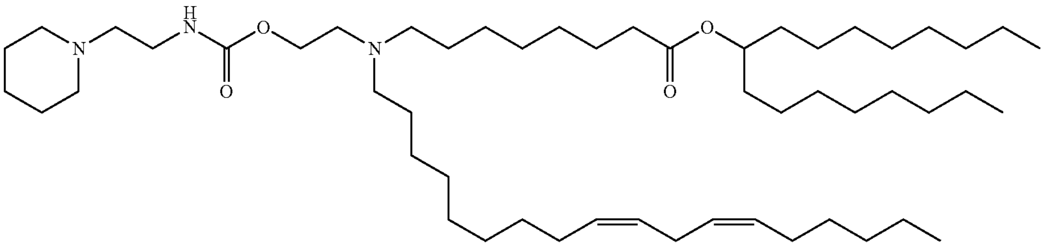 [SMILES: CCCCC/C=C\C/C=C\CCCCCCCCN(CCCCCCCC(=O)OC(CCCCCCCC)CCCCCCCC)CCOC(=O)NCCN1CCCCC1]

Lipid 127 heptadecan-9-yl 8-(((9Z,12Z)-octadeca-9,12-dien-1-yl)(2-(((2-(piperidin-1-yl)ethyl)carbamoyl)oxy)ethyl)amino)octanoate was synthesized according to the general synthetic scheme and general methods. MS [ESI]: m/z: [M+H] calc 845.4 obs. 844.8; $^1$H NMR (400 MHz, $CDCl_3$): δ 0.88 (9H, m), 1.14-1.64 (63H, 1.26 (m), 1.53 (m)), 2.05 (4H, q, J=6.52 Hz), 2.24-2.48 (12H, 2.27 (t, J=7.53 Hz), 2.42 (m)), 2.67 (2H, t, J=5.81 Hz), 2.77 (2H, m), 3.25 (2H, m), 4.10 (2H, t, J=6.01 Hz), 4.86 (1H, i, J=6.22 Hz), 5.35 (4H, m).

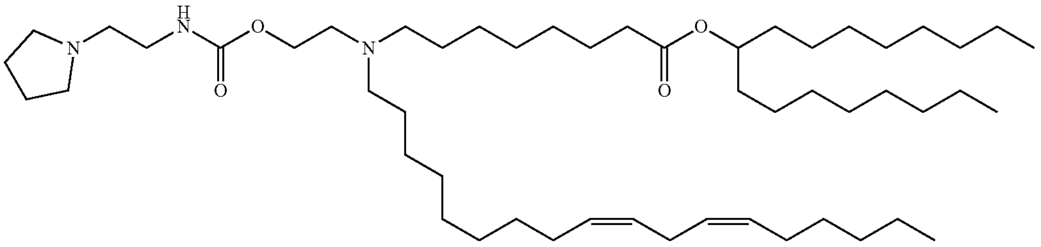 [SMILES: CCCCC/C=C\C/C=C\CCCCCCCCN(CCCCCCCC(=O)OC(CCCCCCCC)CCCCCCCC)CCOC(=O)NCCN1CCCC1]

Lipid 128 heptadecan-9-yl 8-(((9Z,12Z)-octadeca-9,12-dien-1-yl)(2-(((2-(pyrrolidin-1-yl)ethyl)carbamoyl)oxy) ethyl)amino)octanoate octanoate was synthesized according to the general synthetic scheme and general methods. MS [ESI]: m/z: [M+H] calc 831.3 obs. 833.1; $^1$H NMR (400 MHz, $CDCl_3$): δ 0.88 (9H, m), 1.26 (60H, m), 1.61 (2H, m), 1.76 (4H, i, J=3.16 Hz), 2.05 (4H, q, J=6.57 Hz), 2.27 (2H, t, J=7.53 Hz), 2.47 (8H, m), 2.57 (2H, t, J=6.11 Hz), 2.67 (2H, t, J=6.26 Hz), 2.77 (2H, t, J=5.92 Hz), 3.27 (2H, m), 4.10 (2H, t, J=6.23 Hz), 4.86 (1H, t, J=6.23 Hz), 5.35 (4H, m), 5.19-5.25 (1H, m)

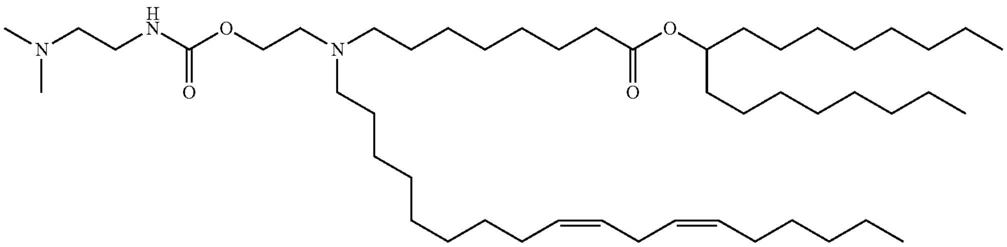 [SMILES: CCCCC/C=C\C/C=C\CCCCCCCCN(CCCCCCCC(=O)OC(CCCCCCCC)CCCCCCCC)CCOC(=O)NCCN(C)C]

Lipid 129 heptadecan-9-yl 2-methyl-10-((9Z,12Z)-octadeca-9,12-dien-1-yl)-6-oxo-7-oxa-2,5,10-triazaoctadecan-18-oate was synthesized according to the general synthetic scheme and general methods. MS [ESI]: m/z: [M+H] calc 805.3 obs. 805.1; $^1$H NMR (400 MHz, $CDCl_3$): δ 0.87 (9H, m), 1.25 (56H, m), 1.61 (2H, m), 2.05 (4H, q, J=6.79 Hz), 2.21 (5H, s), 2.27 (2H, t, J=7.53 Hz), 2.44 (6H, m), 2.67 (2H, t, J=6.92 Hz), 2.77 (2H, t, J=6.05 Hz), 3.24 (2H, m) i10 (2H, t, J=6.32 Hz), 4.86 (1H, q, J=6.20 Hz 5.35 4H, m).

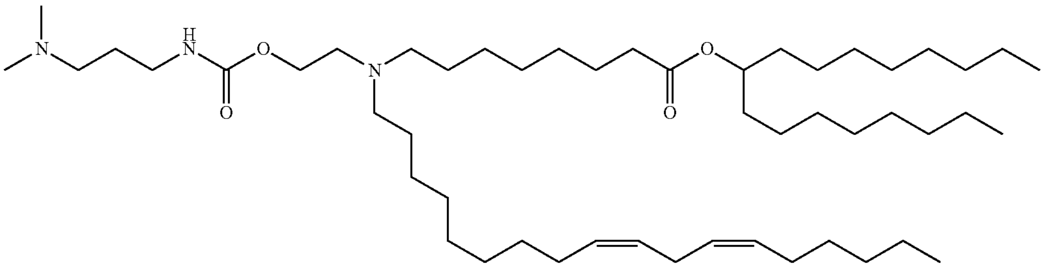

Lipid 130 heptadecan-9-yl 2-methyl-11-((9Z,12Z)-octadeca-9,12-dien-1-yl)-7-oxo-8-oxa-2,6,11-triazanonadecan-19-oate was synthesized according to the general synthetic scheme and general methods. MS [ESI]: m/z: [M+H] calc 819.3 obs. 819.1 $^1$H NMR (400 MHz, $CDCl_3$): δ 0.88 (9H, m), 1.30 (54H, m), 1.62 (4H, m), 2.04 (4H, q, J=7.52 Hz), 2.20 (6H, s), 2.30 (4H, m), 2.44 (4H, m), 2.67 (2H, t, J=6.32 Hz), 2.77 (2H, t, J=6.49 Hz), 3.23 (2H, m), 4.10 (2H, t, J=6.21 Hz), 4.86 (1H, i, J=6.49 Hz), 5.35 (4H, m), 5.49 (1H, m).

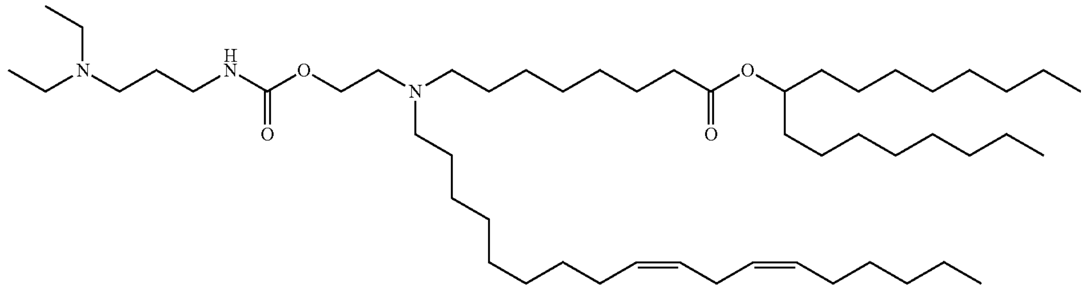 [SMILES: CCCCC/C=C\C/C=C\CCCCCCCCN(CCCCCCCC(=O)OC(CCCCCCCC)CCCCCCCC)CCOC(=O)NCCCN(CC)CC]

Lipid 131 heptadecan-9-yl 3-ethyl-12-((9Z,12Z)-octadeca-9,12-dien-1-yl)-8-oxo-9-oxa-3,7,12-triazaicosan-20-oate octanoate was synthesized according to the general synthetic scheme and general methods. MS [ESI]: m/z: [M+H] calc 847.4 obs. 847.1; $^1$H NMR (400 MHz, $CDCl_3$): δ 0.88 (9H, m), 1.02 (6H, t, J=7.14 Hz), 1.26 (53H, m), 1.62 (5H, h, J=6.40 Hz), 2.05 (4H, q, J=6.83 Hz), 2.27 (2H, t, J=7.52 Hz), 2.47 (10H, m), 2.66 (2H, m), 2.77 (2H, t, J=6.06 Hz), 3.24 (2H, m), 4.09 (2H, m), 4.86 (1H, q, J=6.22 Hz), 5.35 (4H, m).

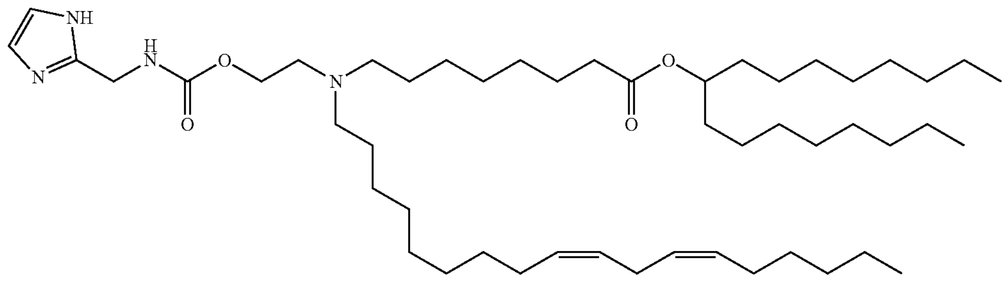

Lipid 132 heptadecan-9-yl 8-((2-((((1H-imidazol-2-yl)methyl)carbamoyl)oxy)ethyl)((9Z,12Z)-octadeca-9,12-dien-1-yl)amino)octanoate was synthesized according to the general synthetic scheme and general methods. MS [ESI]: m/z: [M+H] calc 814.3 obs. 814.1; $^1$H NMR (400 MHz, $CDCl_3$): δ 0.87 (9H, m), 1.25 (54H, m), 1.55-1.66 (3H, m), 2.04 (4H, q, J=7.58 Hz), 2.26 (2H, t, J=7.09 Hz), 2.43 (2H, m), 2.60 (2H, m), 2.77 (3H, m), 4.09-4.17 (1H, m), 4.27 (1H, m), 4.35 (2H, m), 4.86 (1H, br s), 5.22 (1H, m), 5.35 (4H, m), 6.95 (2H, s).

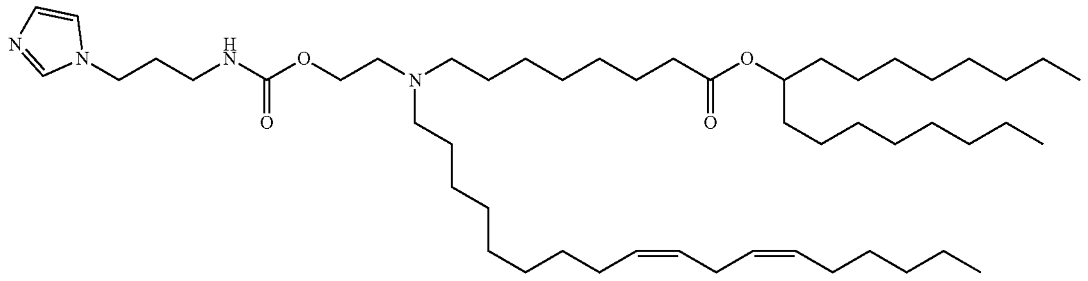 [SMILES: CCCCC/C=C\C/C=C\CCCCCCCCN(CCCCCCCC(=O)OC(CCCCCCCC)CCCCCCCC)CCOC(=O)NCCCn1ccnc1]

Lipid 133 heptadecan-9-yl 8-((2-(((3-(1H-imidazol-1-yl)propyl)carbamoyl)oxy)ethyl)((9Z,12Z)-octadeca-9,12-dien-1-yl)amino)octanoate was synthesized according to the general synthetic scheme and general methods. MS [ESI]: m/z: [M+H] calc 842.3 obs. 842.1; $^1$H NMR (400 MHz, $CDCl_3$): δ 0.87 (9H, m), 1.30 (53H, m), 1.60 (2H, m), 2.02 (6H, m), 2.27 (2H, t, J=7.69 Hz), 2.44 (4H, m), 2.66 (2H, t, J=6.05 Hz), 2.77 (2H, t, J=6.10 Hz), 3.18 (2H, q, J=6.47 Hz), 4.00 (2H, m), 4.11 (2H, t, J=6.06 Hz), 4.86 (2H, m), 5.35 (4H, m), 6.94 (1H, m), 7.06 (1H, m), 7.49 (1H, s).

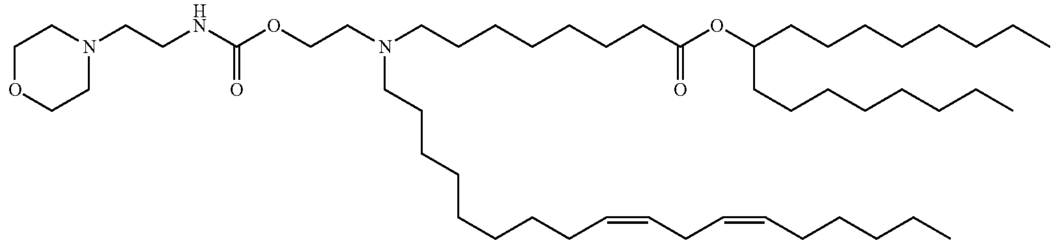 [SMILES: CCCCC/C=C\C/C=C\CCCCCCCCN(CCCCCCCC(=O)OC(CCCCCCCC)CCCCCCCC)CCOC(=O)NCCN1CCOCC1]

Lipid 134 heptadecan-9-yl 8-((2-(((2-morpholinoethyl)carbamoyl)oxy)ethyl)((9Z,12Z)-octadeca-9,12-dien-1-yl)amino)octanoate was synthesized according to the general synthetic scheme and general methods. MS [ESI]: m/z: [M+H] calc 846.3 obs. 847.1; $^1$H NMR (400 MHz, $CDCl_3$): δ 0.87 (9H, m), 1.30 (54H, m), 1.60 (2H, m), 2.04 (4H, q, J=7.52 Hz), 2.27 (2H, t, J=7.57 Hz), 2.44 (10H, m), 2.67 (2H, t, J=6.32 Hz), 2.77 (2H, t, J=6.41 Hz), 3.27 (2H, m), 3.69 (4H, m), 4.11 (2H, t, J=6.15 Hz), 4.86 (1H, i, J=6.28 Hz), 5.20 (1H, m), 5.35 (4H, m).

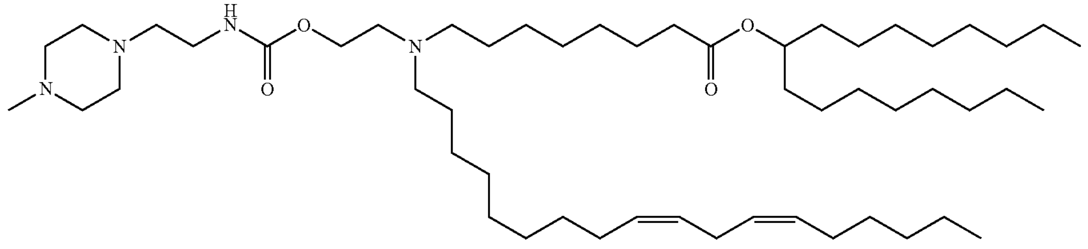 [SMILES: CCCCC/C=C\C/C=C\CCCCCCCCN(CCCCCCCC(=O)OC(CCCCCCCC)CCCCCCCC)CCOC(=O)NCCN1CCN(C)CC1]

Lipid 135 heptadecan-9-yl 8-((2-(((2-(4-methylpiperazin-1-yl)ethyl)carbamoyl)oxy)ethyl)((9Z,12Z)-octadeca-9,12-dien-1-yl)amino)octanoate was synthesized according to the general synthetic scheme and general methods. MS [ESI]: m/z: [M+H] calc 860.4 obs. 860.1 $^{1}$H NMR (400 MHz, $CDCl_3$): δ 0.88 (9H, m), 1.30 (54H, m), 1.61 (2H, m), 2.04 (4H, q, J=7.52 Hz), 2.28 (5H, m), 2.45 (13H, m), 2.68 (2H, t, J=6.23 Hz), 2.77 (2H, t, J=6.67 Hz), 3.26 (2H, m), 4.11 (2H, t, J=6.15 Hz), 4.86 (1H, i, J=6.24 Hz), 5.20 (1H, m), 5.35 (4H, m).

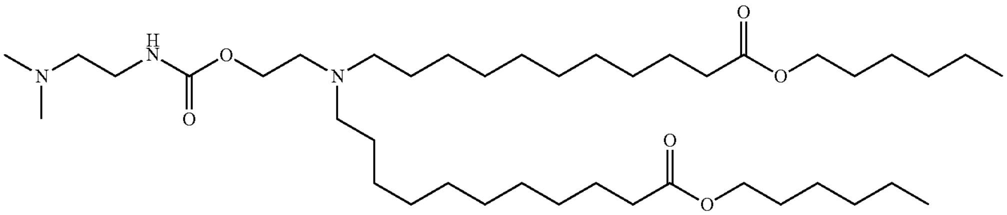 [SMILES: CCCCCCOC(=O)CCCCCCCCCCN(CCCCCCCCCCC(=O)OCCCCCC)CCOC(=O)NCCN(C)C]

Lipid 136 hexyl 10-(11-(hexyloxy)-11-oxoundecyl)-2-methyl-6-oxo-7-oxa-2,5,10-triazahenicosan-21-oate was synthesized according to the general synthetic scheme and general methods. MS [ESI]: m/z: [M+H] calc 713.1 obs. 712.8 $^{1}$H NMR (500 MHz, $CDCl_3$): δ 0.88 (6H, t, J=7.08 Hz), 1.29 (40H, m), 1.61 (8H, m), 2.21 (6H, s), 2.28 (4H, t, J=7.54 Hz), 2.38 (2H, t, J=5.96 Hz), 2.44 (4H, m), 2.67 (2H, t, J=6.52 Hz), 3.23 (2H, m), 4.05 (4H, t, J=6.73 Hz), 4.10 (2H, t, J=6.46 Hz), 5.18 (1H, m).

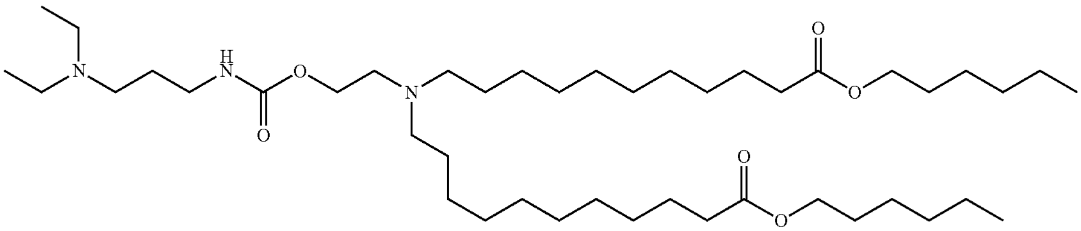 [SMILES: CCCCCCOC(=O)CCCCCCCCCCN(CCCCCCCCCCC(=O)OCCCCCC)CCOC(=O)NCCCN(CC)CC]

Lipid 137 hexyl 3-ethyl-12-(11-(hexyloxy)-11-oxoundecyl)-8-oxo-9-oxa-3,7,12-triazatricosan-23-oate was synthesized according to the general synthetic scheme and general methods. MS [ESI]: m/z: [M+H] calc 755.2 obs. 754.9 $^{1}$H NMR (500 MHz, $CDCl_3$): δ 0.89 (6H, t, J=6.79 Hz), 1.02 (6H, t, J=7.16 Hz), 1.29 (40H, m), 1.61 (8H, m), 2.28 (4H, t, J=7.84 Hz), 2.46 (10H, m), 2.67 (2H, m), 3.24 (4H, m), 4.07 (6H, m), 5.11 (1H, m).

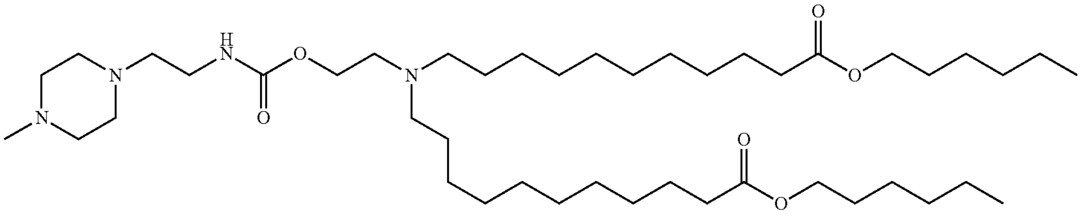 [SMILES: CCCCCCOC(=O)CCCCCCCCCCN(CCCCCCCCCCC(=O)OCCCCCC)CCOC(=O)NCCN1CCN(C)CC1]

Lipid 138 dihexyl 11,11'-((2-(((2-(4-methylpiperazin-1-yl)ethyl)carbamoyl)oxy)ethyl)azanediyl)diundecanoate was synthesized according to the general synthetic scheme and general methods. MS [ESI]: m/z: [M+H] calc 768.2 obs. 767.9 $^{1}$H NMR (500 MHz, $CDCl_3$): δ 0.88 (6H, t, J=6.73 Hz), 1.29 (40H, m), 1.60 (8H, m), 2.28 (7H, m), 2.45 (12H, m), 2.68 (2H, m), 3.26 (2H, m), 4.05 (4H, m), 4.11 (2H, m), 4.16 (1H, m), 5.21 (1H, m).

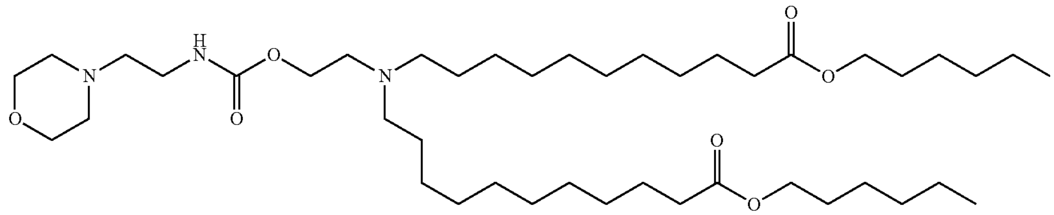 [SMILES: CCCCCCOC(=O)CCCCCCCCCCN(CCCCCCCCCCC(=O)OCCCCCC)CCOC(=O)NCCN1CCOCC1]

Lipid 139 dihexyl 11,11'-((2-(((2-morpholinoethyl)carbamoyl)oxy)ethyl)azanediyl)diundecanoate was synthesized according to the general synthetic scheme and general methods. MS [ESI]: m/z: [M+H] calc 755.2 obs. 755.0. $^{1}$H NMR (500 MHz, $CDCl_3$): δ 0.89 (6H, t, J=6.84 Hz), 1.26 (40H, m), 1.61 (8H, m), 2.28 (4H, t, J=7.54 Hz), 2.44 (10H, m), 2.68 (2H, m), 3.27 (2H, m), 3.69 (4H, m), 4.05 (7H, m).

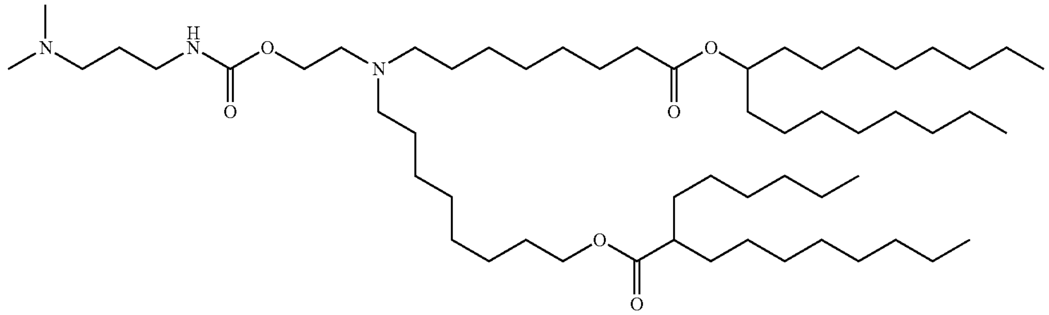 [SMILES: CCCCCCCCC(CCCCCCCC)OC(=O)CCCCCCCN(CCCCCCCCOC(=O)C(CCCCCC)CCCCCCCC)CCOC(=O)NCCCN(C)C]

Lipid 146 heptadecan-9-yl 11-(8-((2-hexyldecanoyl)oxy)octyl)-2-methyl-7-oxo-8-oxa-2,6,11-triazanonadecan-19-oate was synthesized according to the general synthetic scheme and general methods. MS [ESI]: m/z: [M+H] calc 937.5, obs. 937.0; $^{1}$H NMR (400 MHz, $CDCl_3$): δ 0.87 (12H, m), 1.25 (68H, m), 1.54-1.67 (10H, m), 2.21 (12H, m), 2.41-2.47 (3H, 2.44 (t, J=7.59 Hz), 2.44 (d, J=4.61 Hz)), 2.65-2.71 (1H, m), 3.21-3.25 (2H, m), 4.05 (4H, m), 4.5 (1H, i, J=6.09 Hz).

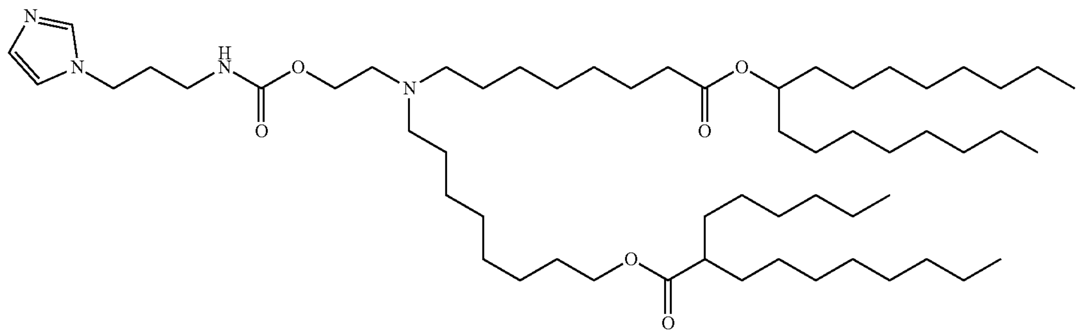 [SMILES: CCCCCCCCC(CCCCCCCC)OC(=O)CCCCCCCN(CCCCCCCCOC(=O)C(CCCCCC)CCCCCCCC)CCOC(=O)NCCCn1ccnc1]

Lipid 147 8-((2-(((3-(1H-imidazol-1-yl)propyl)carbamoyl)oxy)ethyl)(8-(heptadecan-9-yloxy)-8-oxooctyl)amino) octyl 2-hexyldecanoate was synthesized according to the general synthetic scheme and general methods. MS [ESI]: m/z: [M+H] calc 960.5, obs. 960.2 $^{1}$H NMR (400 MHz, $CDCl_3$): δ 0.87 (12H, m), 1.25 (63H, s), 1.49 (3H, m), 1.60 (7H, m), 2.00 (2H, m), 2.27 (3H, m), 2.41-2.47 (3H, 2.44 (t, J=7.58 Hz), 2.44 (d, J=4.10 Hz)), 2.66 (1H, t, J=6.07 Hz), 3.18 (2H, m), 4.03 (9H, m), 4.86 (1H, m), 6.94 (1H, s), 7.06 (1H, m), 7.49 (1H, s).

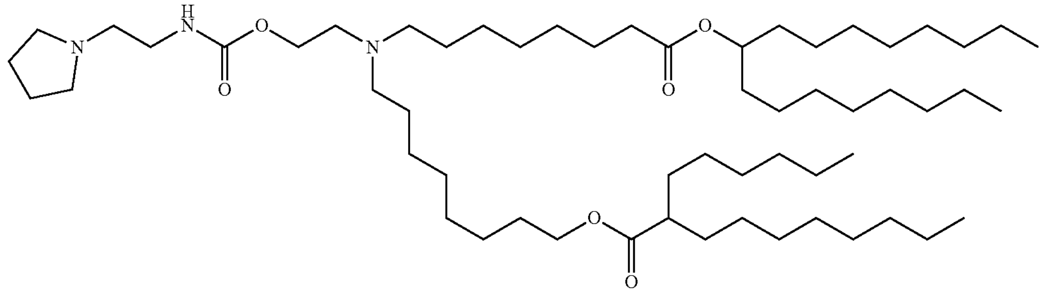 [SMILES: CCCCCCCCC(CCCCCCCC)OC(=O)CCCCCCCN(CCCCCCCCOC(=O)C(CCCCCC)CCCCCCCC)CCOC(=O)NCCN1CCCC1]

Lipid 148 8-((8-(heptadecan-9-yloxy)-8-oxooctyl)(2-(((2-(pyrrolidin-1-yl)ethyl)carbamoyl)oxy)ethyl)amino)octyl 2-hexyldecanoate hexyldecanoate was synthesized according to the general synthetic scheme and general methods. MS [ESI]: m/z: [M+H] calc 949.6, obs. 949.2 $^{1}$H NMR (400 MHz, $CDCl_3$): δ 0.87 (12H, m), 1.25 (76H, m), 1.76 (5H, m), 2.27 (3H, m), 2.50 (10H, m), 2.66 (1H, m), 3.28 (1H, m), 4.03-4.11 (4H, 4.06 (t, J=6.68 Hz), 4.10 (m), 4.85 (1H, i, J=6.38 Hz).

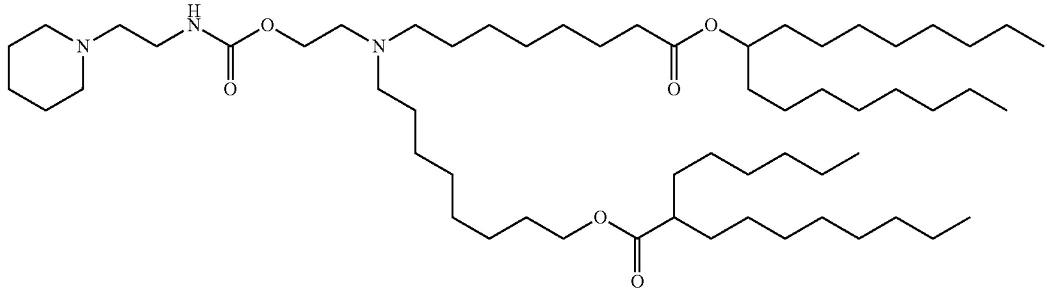 [SMILES: CCCCCCCCC(CCCCCCCC)OC(=O)CCCCCCCN(CCCCCCCCOC(=O)C(CCCCCC)CCCCCCCC)CCOC(=O)NCCN1CCCCC1]

Lipid 149 8-((8-(heptadecan-9-yloxy)-8-oxooctyl)(2-(((2-(piperidin-1-yl)ethyl)carbamoyl)oxy)ethyl)amino)octyl 2-hexyldecanoate was synthesized according to the general synthetic scheme and general methods. MS [ESI]: m/z: [M+H] calc 963.6 obs. 963.2 $^{1}$H NMR (400 MHz, $CDCl_3$): δ 0.87 (12H, m), 1.25 (56H, m), 1.37-1.46 (8H, m), 1.49-1.65 (15H, m), 2.40 (14H, m), 2.67 (1H, m), 3.22-3.29 (2H, m), 4.03-4.13 (5H, 4.06 (t, J=6.64 Hz), 4.10 (t, J=6.06 Hz)), 4.86 (1H, i, J=6.22 Hz).

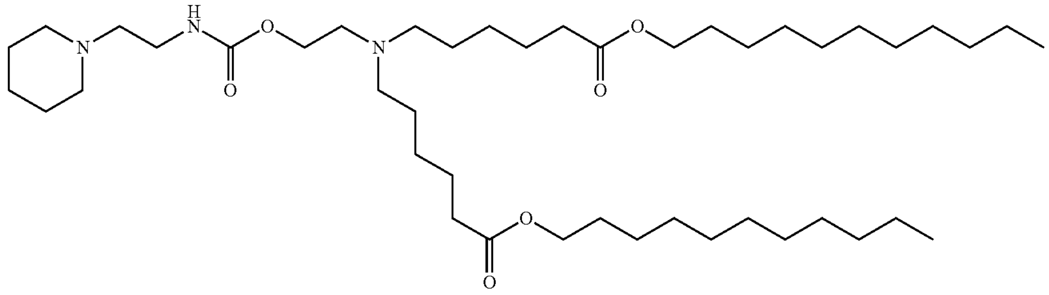 [SMILES: CCCCCCCCCCCOC(=O)CCCCCN(CCCCCC(=O)OCCCCCCCCCCC)CCOC(=O)NCCN1CCCCC1]

Lipid 150 diundecyl 6,6'-((2-(((2-(piperidin-1-yl)ethyl)carbamoyl)oxy)ethyl)azanediyl)dihexanoate was synthesized according to the general synthetic scheme and general methods. MS [ESI]: m/z: [M+H] calc 753.2 obs 753.0 $^1$H NMR (400 MHz, $CDCl_3$): δ 0.89 (6H, t, J=6.85 Hz), 1.28 (36H, m), 1.45 (6H, m), 1.61 (13H, m), 2.30 (4H, t, J=7.53 Hz), 2.42 (10H, m), 2.67 (2H, t, J=5.96 Hz), 3.27 (2H, d, J=5.38 Hz), 4.04-4.13 (6H, 4.06 (t, J=6.78 Hz), 4.11 (t, J=6.06 Hz)).

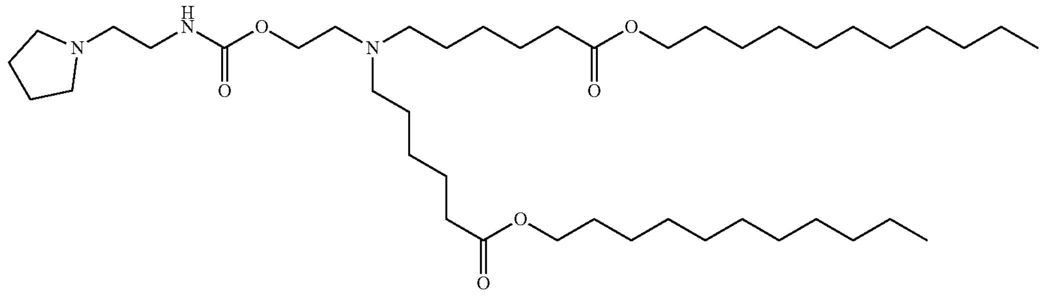 [SMILES: CCCCCCCCCCCOC(=O)CCCCCN(CCCCCC(=O)OCCCCCCCCCCC)CCOC(=O)NCCN1CCCC1]

Lipid 151 diundecyl 6,6'-((2-(((2-(pyrrolidin-1-yl)ethyl)carbamoyl)oxy)ethyl)azanediyl)dihexanoate was synthesized according to the general synthetic scheme and general methods. MS [ESI]: m/z: [M+H] calc 739.2 obs 738.9. $^1$H NMR (400 MHz, $CDCl_3$): δ 0.88 (6H, t, J=6.84 Hz), 1.26 (38H, m), 1.44 (5H, m), 1.62 (10H, m), 1.76 (5H, quint, J=3.14 Hz), 2.29 (4H, t, J=7.52 Hz), 2.45 (8H, m), 2.58 (2H, t, J=6.19 Hz), 2.65 (2H, m), 3.28 (2H, m), 4.03-4.11 (6H, 4.05 (t, J=6.78 Hz), 4.09 (t, J=5.86 Hz)).

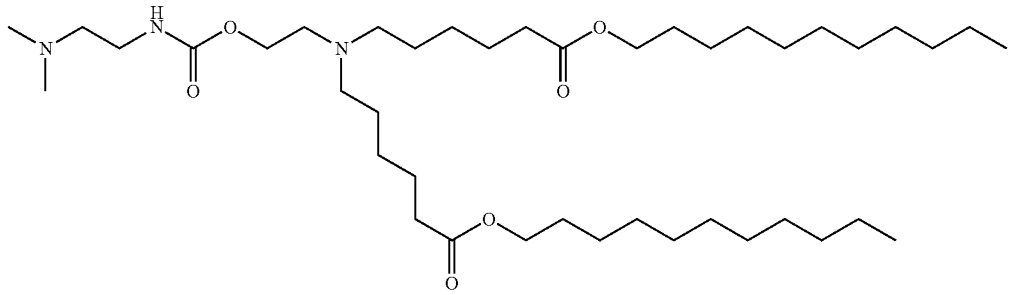 [SMILES: CCCCCCCCCCCOC(=O)CCCCCN(CCCCCC(=O)OCCCCCCCCCCC)CCOC(=O)NCCN(C)C]

Lipid 154 undecyl 2-methyl-6-oxo-10-(6-oxo-6-(undecyloxy)hexyl)-7-oxa-2,5,10-triazahexadecan-16-oate was synthesized according to the general synthetic scheme and general methods. MS [ESI]: m/z: [M+H] calc 713.1, obs. 712.95 $^1$H NMR (400 MHz, $CDCl_3$): δ 0.88 (6H, t, J=6.83 Hz), 1.26 (39H, s), 1.44 (4H, m), 1.61 (9H, m), 2.22 (5H, s), 2.29 (4H, t, J=7.52 Hz), 2.44 (7H, m), 2.67 (2H, m), 3.25 (2H, m), 4.02-4.12 (6H, 4.05 (t, J=6.78 Hz), 4.07 (m)).

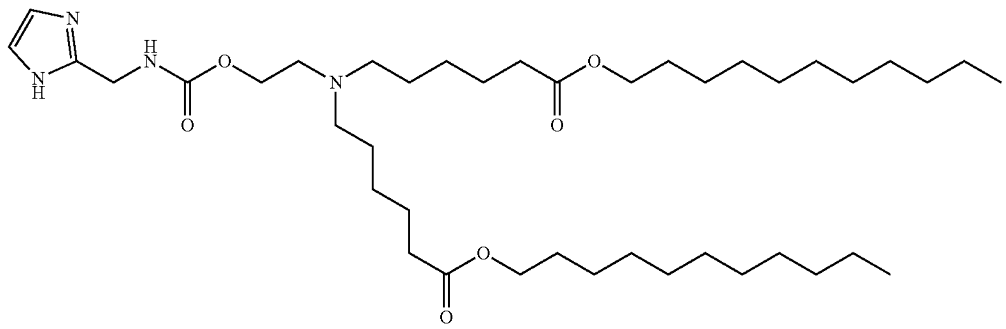 [SMILES: CCCCCCCCCCCOC(=O)CCCCCN(CCCCCC(=O)OCCCCCCCCCCC)CCOC(=O)NCc1ncc[nH]1]

Lipid 155 diundecyl 6,6'-((2-((((1H-imidazol-2-yl)methyl)carbamoyl)oxy)ethyl)azanediyl)dihexanoate was synthesized according to the general synthetic scheme and general methods. MS [ESI]: m/z: [M+H] calc 722.1, obs. 712.9$^1$H NMR (400 MHz, $CDCl_3$): δ 0.88 (6H, t, J=6.81 Hz), 1.26 (52H, m), 2.28 (4H, t, J=7.30 Hz), 2.43 (2H, m), 2.62 (2H, m), 4.05 (4H, t, J=6.78 Hz), 4.12 (1H, m), 4.37 (2H, m), 6.93 (2H, m).

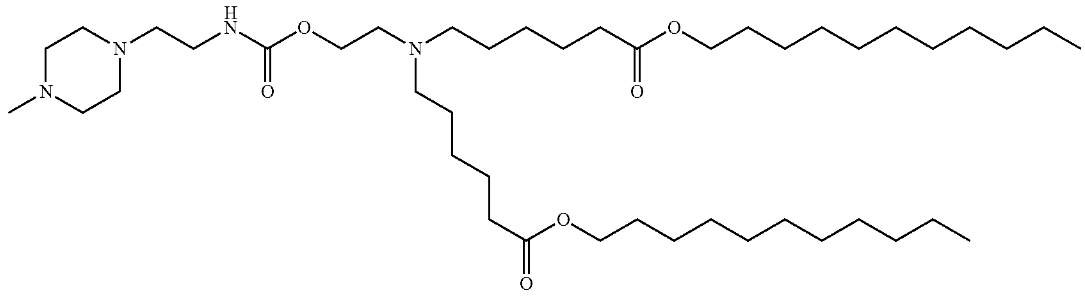 [SMILES: CCCCCCCCCCCOC(=O)CCCCCN(CCCCCC(=O)OCCCCCCCCCCC)CCOC(=O)NCCN1CCN(C)CC1]

Lipid 156 diundecyl 6,6'-((2-(((2-(4-methylpiperazin-1-yl)ethyl)carbamoyl)oxy)ethyl)azanediyl)dihexanoate was synthesized according to the general synthetic scheme and general methods. MS [ESI]: m/z: [M+H] calc 768.2 obs. 768.0. $^1$H NMR (400 MHz, $CDCl_3$): δ 0.88 (6H, m), 1.28 (36H, m), 1.46 (4H, m), 1.62 (8H, m), 2.31 (7H, m), 2.50 (13H, m), 2.69 (2H, t, J=6.06 Hz), 3.27 (2H, m), 4.05 (4H, t, J=6.77 Hz), 4.11 (2H, t, J=5.64 Hz), 5.31 (1H, m).

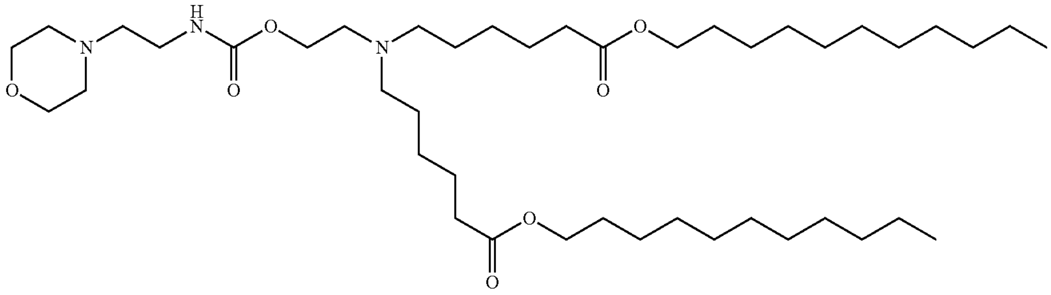 [SMILES: CCCCCCCCCCCOC(=O)CCCCCN(CCCCCC(=O)OCCCCCCCCCCC)CCOC(=O)NCCN1CCOCC1]

Lipid 157 diundecyl 6,6'-((2-(((2-morpholinoethyl)carbamoyl)oxy)ethyl)azanediyl)dihexanoate was synthesized according to the general synthetic scheme and general methods. MS [ESI]: m/z: [M+H] calc 755.2 obs. 754.9 $^1$H NMR (400 MHz, $CDCl_3$): δ 0.88 (6H, t, J=6.83 Hz), 1.26 (35H, s), 1.44 (5H, m), 1.62 (9H, m), 2.29 (4H, t, J=7.51 Hz), 2.45 (10H, m), 2.66 (2H, t, J=5.99 Hz), 3.27 (2H, m), 3.69 (4H, t, J=4.62 Hz), 4.02-4.13 (6H, 4.05 (t, J=6.78 Hz), 4.10 (t, J=5.96 Hz)).

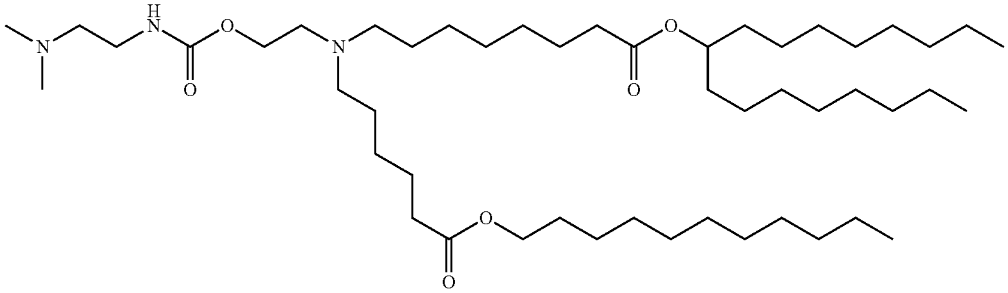 [SMILES: CCCCCCCCCCCOC(=O)CCCCCN(CCCCCCCC(=O)OC(CCCCCCCC)CCCCCCCC)CCOC(=O)NCCN(C)C]

Lipid 158 heptadecan-9-yl 2-methyl-6-oxo-10-(6-oxo-6-(undecyloxy)hexyl)-7-oxa-2,5,10-triazaoctadecan-18-oate was synthesized according to the general synthetic scheme and general methods. MS [ESI]: m/z: [M+H] calc 825.3 obs. 825.0 $^1$H NMR (400 MHz, $CDCl_3$): $^1$H NMR (400 MHz): δ 0.88 (9H, m), 1.26 (58H, m), 1.61 (6H, m), 2.28 (4H, q, J=7.49 Hz), 2.44 (6H, m), 2.66 (1H, s), 3.25 (1H, m), 4.05 (4H, m), 2.20-2.22 (6H, m), 4.86 (1H, i, J=6.15 Hz).

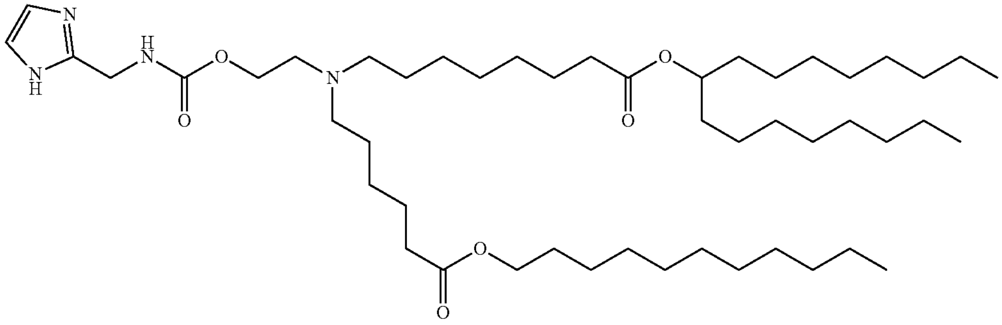 [SMILES: CCCCCCCCCCCOC(=O)CCCCCN(CCCCCCCC(=O)OC(CCCCCCCC)CCCCCCCC)CCOC(=O)NCc1ncc[nH]1]

Lipid 159 heptadecan-9-yl 8-((2-((((1H-imidazol-2-yl)methyl)carbamoyl)oxy)ethyl)(6-oxo-6-(undecyloxy)hexyl)amino)octanoate was synthesized according to the general synthetic scheme and general methods. MS [ESI]: m/z: [M+H] calc 833.7 obs. 834.0; $^1$H NMR (500 MHz, $CDCl_3$): δ 0.87 (9H, m), 1.30 (54H, m), 1.61 (7H, m), 2.27 (4H, m), 2.44 (3H, m), 2.63 (5H, m), 2.82 (2H, m), 4.05 (2H, m), 4.14 (2H, m), 4.86 (1H, m), 5.11 (1H, m), 6.93 (2H, m).

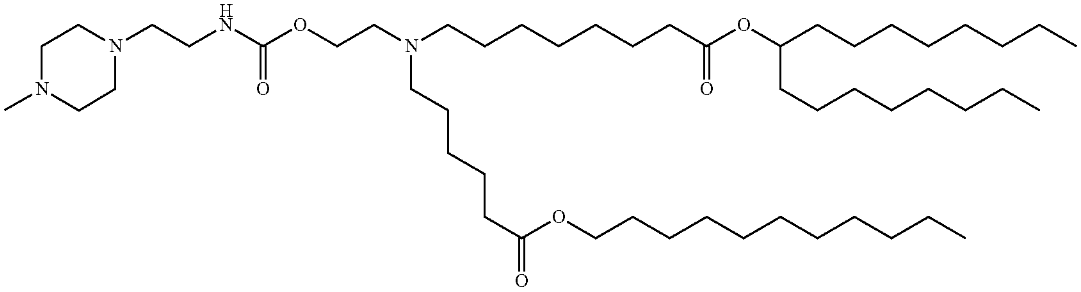 [SMILES: CCCCCCCCCCCOC(=O)CCCCCN(CCCCCCCC(=O)OC(CCCCCCCC)CCCCCCCC)CCOC(=O)NCCN1CCN(C)CC1]

Lipid 160 heptadecan-9-yl 8-((2-(((2-(4-methylpiperazin-1-yl)ethyl)carbamoyl)oxy)ethyl)(6-oxo-6-(undecyloxy)hexyl)amino)octanoate was synthesized according to the general synthetic scheme and general methods. MS [ESI]: m/z: [M+H] calc. 879.8 obs. 880.1; $^1$H NMR (400 MHz, $CDCl_3$): δ 0.88 (9H, m), 1.27 (45H, m), 1.54 (18H, m), 2.28 (7H, m), 2.46 (10H, m), 2.67 (2H, t, J=6.06 Hz), 3.27 (2H, m), 4.07 (5H, m), 4.86 (2H, m), 5.23 (1H, m).

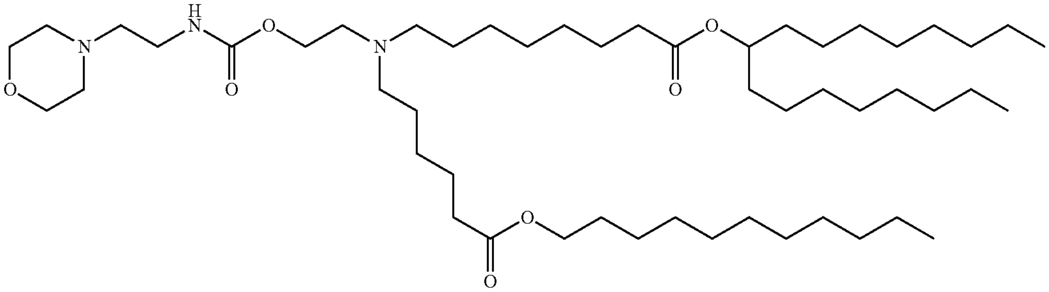 [SMILES: CCCCCCCCCCCOC(=O)CCCCCN(CCCCCCCC(=O)OC(CCCCCCCC)CCCCCCCC)CCOC(=O)NCCN1CCOCC1]

Lipid 161 heptadecan-9-yl 8-((2-(((2-morpholinoethyl)carbamoyl)oxy)ethyl)(6-oxo-6-(undecyloxy)hexyl)amino)octanoate was synthesized according to the general synthetic scheme and general methods. MS [ESI]: m/z: [M+H] calc. 866.8 obs. 867.1; $^1$H NMR (400 MHz, $CDCl_3$): δ 0.88 (9H, m), 1.27 (45H, m), 1.47 (10H, m), 1.62 (8H, m), 2.28 (4H, q, J=7.86 Hz), 2.44 (10H, m), 2.67 (2H, t, J=6.35 Hz), 3.28 (2H, m), 3.70 (4H, m), 4.07 (4H, m), 4.86 (1H, i, J=6.62 Hz), 5.22 (1H, m).

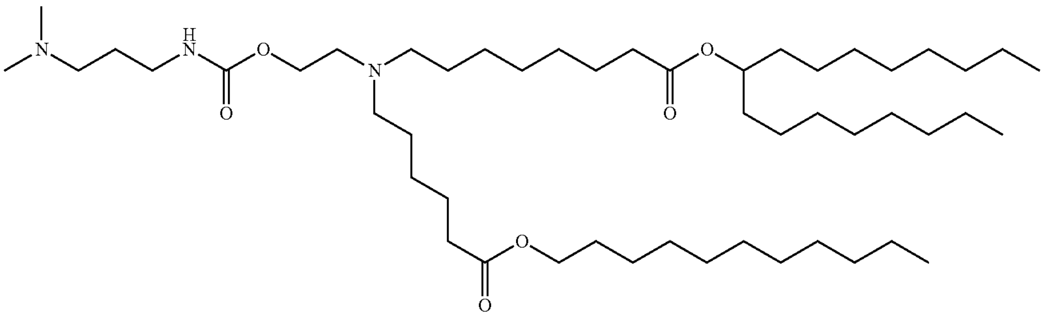 [SMILES: CCCCCCCCCCCOC(=O)CCCCCN(CCCCCCCC(=O)OC(CCCCCCCC)CCCCCCCC)CCOC(=O)NCCCN(C)C]

Lipid 162 heptadecan-9-yl 2-methyl-7-oxo-11-(6-oxo-6-(undecyloxy)hexyl)-8-oxa-2,6,11-triazanonadecan-19-oate was synthesized according to the general synthetic scheme and general methods. MS [ESI]: m/z: [M+H] calc. 838.8 obs. 839.1; $^1$H NMR (400 MHz, $CDCl_3$): δ 0.88 (9H, m), 1.27 (54H, s), 1.50 (4H, m), 1.62 (12H, m), 2.21-2.23 (6H, 2.21 (s), 2.22 (s)), 2.28 (3H, q, J=7.51 Hz), 2.33 (1H, t, J=6.95 Hz), 2.43 (2H, m), 4.03 (1H, s), 4.05 (1H, s), 4.86 (1H, i, J=6.10 Hz), 2.64-2.69 (2H, m), 3.21-3.27 (2H, m).

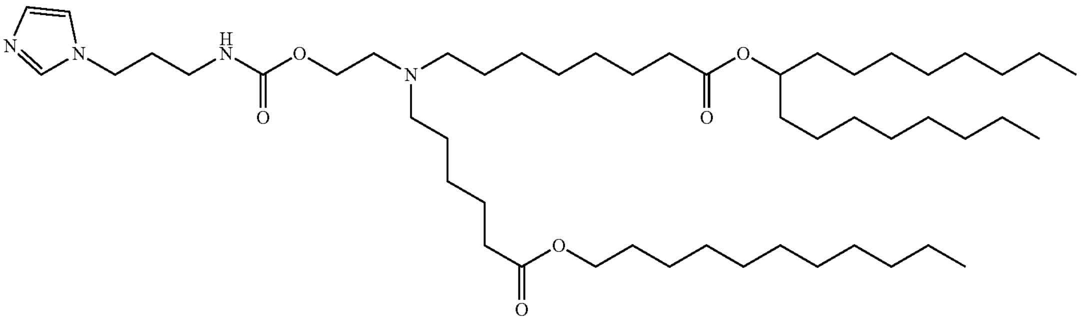 [SMILES: CCCCCCCCCCCOC(=O)CCCCCN(CCCCCCCC(=O)OC(CCCCCCCC)CCCCCCCC)CCOC(=O)NCCCn1ccnc1]

Lipid 163 heptadecan-9-yl 8-((2-(((3-(1H-imidazol-1-yl)propyl)carbamoyl)oxy)ethyl)(6-oxo-6-(undecyloxy)hexyl)amino)octanoate was synthesized according to the general synthetic scheme and general methods. MS [ESI]: m/z: [M+H] calc. 862.3 obs. 862.0; $^1$H NMR (400 MHz, $CDCl_3$): δ 0.88 (8H, m), 1.29 (61H, m), 1.58-1.66 (6H, m), 2.00 (2H, i, J=6.86 Hz), 2.28 (3H, m), 2.44 (3H, m), 2.66 (1H, m), 3.15-3.24 (2H, m), 4.02 (4H, m), 4.11 (1H, t, J=5.71 Hz), 4.86 (1H, i, J=6.10 Hz), 6.94 (1H, s), 7.06 (1H, s), 7.49 (1H, s),

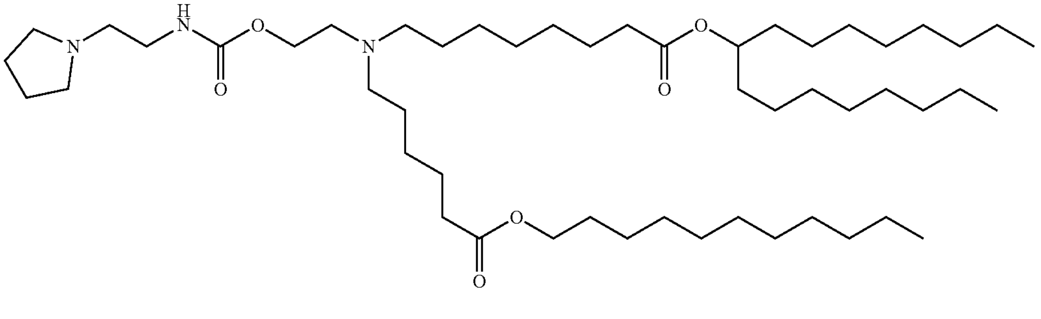 [SMILES: CCCCCCCCCCCOC(=O)CCCCCN(CCCCCCCC(=O)OC(CCCCCCCC)CCCCCCCC)CCOC(=O)NCCN1CCCC1]

Lipid 164 heptadecan-9-yl 8-((6-oxo-6-(undecyloxy) hexyl)(2-(((2-(pyrrolidin-1-yl)ethyl)carbamoyl)oxy)ethyl) amino)octanoate was synthesized according to the general synthetic scheme and general methods. MS [ESI]: m/z: [M+H] calc. 851.4 obs. 851.1; $^{1}$H NMR (400 MHz, $CDCl_3$): 0.88 (9H, m), 1.26 (54H, s), 1.51 (3H, m), 1.59-1.72 (9H, m), 2.25-2.36 (9H, 2.31 (dt, J=21.97, 7.46 Hz), 2.28 (s)), 2.98-3.07 (5H, m), 3.12-3.18 (3H, m), 3.20-3.28 (3H, m), 3.59-3.66 (2H, m), 4.05 (1H, s), 4.41-4.47 (2H, m), 4.82-4.89 (1H, m).

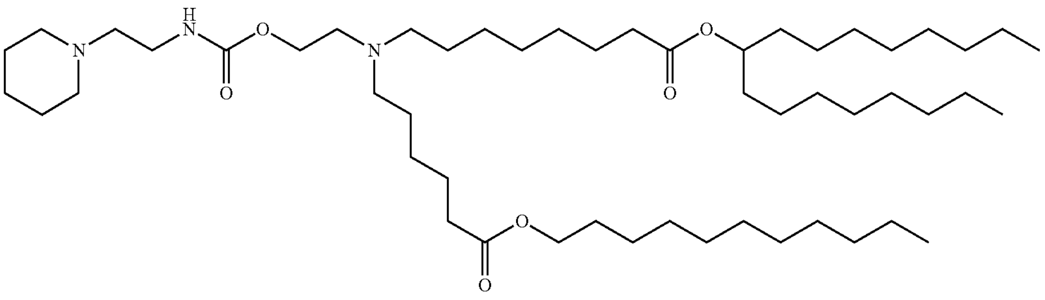 [SMILES: CCCCCCCCCCCOC(=O)CCCCCN(CCCCCCCC(=O)OC(CCCCCCCC)CCCCCCCC)CCOC(=O)NCCN1CCCCC1]

Lipid 165 heptadecan-9-yl 8-((6-oxo-6-(undecyloxy) hexyl)(2-(((2-(piperidin-1-yl)ethyl)carbamoyl)oxy)ethyl) amino)octanoate was synthesized according to the general synthetic scheme and general methods. MS [ESI]: m/z: [M+H] calc 864.8 obs. 865.1; $^{1}$H NMR (400 MHz, $CDCl_3$): δ 0.88 (9H, m), 1.26 (56H, s), 1.51 (3H, m), 1.59-1.72 (9H, m), 2.25-2.36 (9H, 2.31 (dt, J=21.97, 7.46 Hz), 2.28 (s)), 2.98-3.07 (5H, m), 3.12-3.18 (3H, m), 3.20-3.28 (3H, m), 3.59-3.66 (2H, m), 4.05 (1H, s), 4.41-4.47 (2H, m), 4.82-4.89 (1H, m).

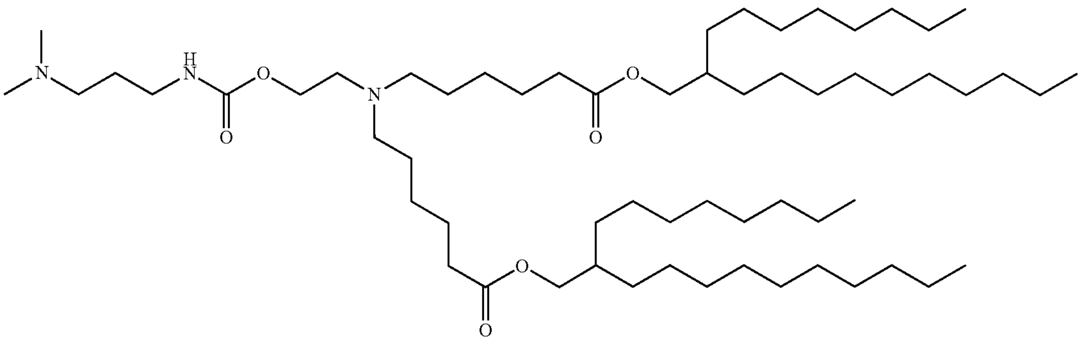 [SMILES: CCCCCCCCCCC(CCCCCCCC)COC(=O)CCCCCN(CCCCCC(=O)OCC(CCCCCCCC)CCCCCCCCCC)CCOC(=O)NCCCN(C)C]

Lipid 166 2-octyldodecyl 2-methyl-11-(6-((2-octyldodecyl)oxy)-6-oxohexyl)-7-oxo-8-oxa-2,6,11-triazaheptadecan-17-oate was synthesized according to the general synthetic scheme and general methods. MS [ESI]: m/z: [M+H] calc 979.3 obs. 979.3 $^{1}$H NMR (500 MHz, $CDCl_3$): δ 0.88 (12H, m), 1.27 (65H, m), 1.53 (4H, m), 1.64 (7H, m), 1.91 (2H, m), 2.04 (1H, m), 2.31 (4H, t, J=7.53 Hz), 2.57 (9H, m), 2.80 (4H, m), 3.29 (3H, m), 3.96 (4H, d, J=5.77 Hz), 4.07 (1H, m), 4.17 (2H, t, J=5.93 Hz), 5.89 (1H, m).

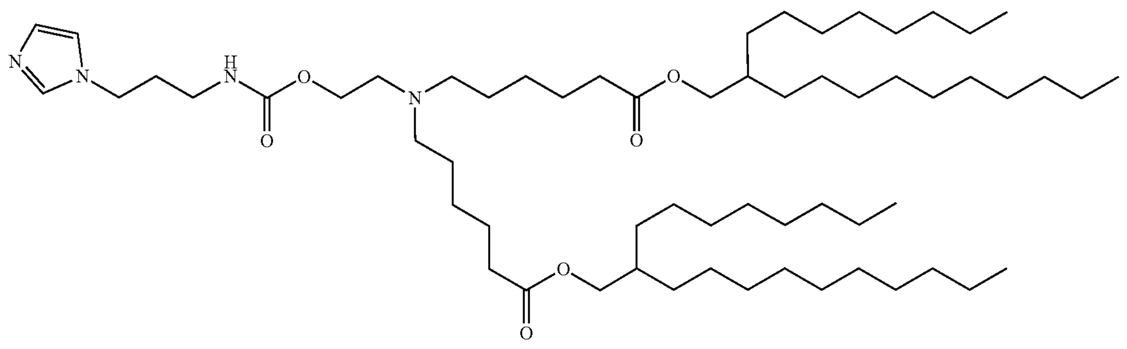 [SMILES: CCCCCCCCCCC(CCCCCCCC)COC(=O)CCCCCN(CCCCCC(=O)OCC(CCCCCCCC)CCCCCCCCCC)CCOC(=O)NCCCn1ccnc1]

Lipid 167 bis(2-octyldodecyl) 6,6'-((2-(((3-(1H-imidazol-1-yl)propyl)carbamoyl)oxy)ethyl)azanediyl)dihexanoate was synthesized according to the general synthetic scheme and general methods. MS [ESI]: m/z: [M+H] calc 1002.6 obs. 1002.4 $^{1}$H NMR (400 MHz, $CDCl_3$): $^{1}$H NMR (400 MHz): δ 0.88 (12H, t, J=6.81 Hz), 1.26 (74H, m), 1.62 (6H, m), 2.00 (2H, i, J=6.86 Hz), 2.30 (4H, t, J=7.44 Hz), 2.45 (4H, t, J=7.36 Hz), 2.65 (2H, t, J=5.73 Hz), 3.19 (2H, m), 3.96 (4H, d, J=5.72 Hz), 4.01 (3H, m), 4.08-4.14 (2H, m), 6.94 (1H, s), 7.49 (1H, s), 7.06 (1H, s).

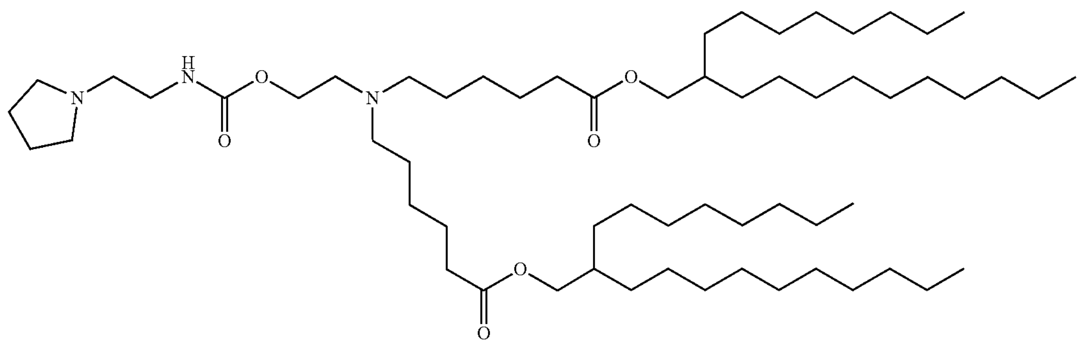 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCC1]

Lipid 168 bis(2-octyldodecyl) 6,6'-((2-(((2-(pyrrolidin-1-yl)ethyl)carbamoyl)oxy)ethyl)azanediyl)dihexanoate was synthesized according to the general synthetic scheme and general methods. MS [ESI]: m/z: [M+H] calc 990.9 obs. 991.3; $^{1}$H NMR (400 MHz, $CDCl_3$): δ 0.88 (12H, t, J=6.74 Hz), 1.26 (64H, m), 1.44 (4H, m), 1.63 (11H, quint, J=7.13 Hz), 1.76 (4H, m), 2.30 (4H, t, J=7.50 Hz), 2.46 (8H, m), 2.58 (2H, t, J=6.13 Hz), 2.66 (2H, m), 3.23-3.33 (2H, m), 3.96 (4H, d, J=5.77 Hz), 4.09 (2H, m).

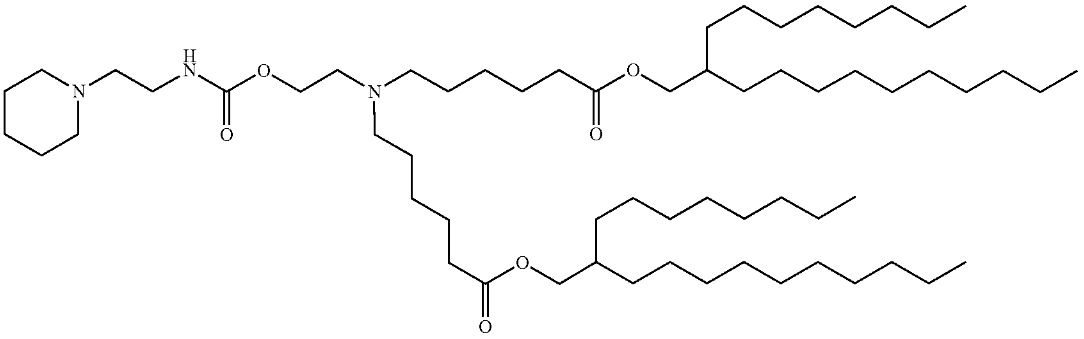 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCCCC1]

Lipid 169 bis(2-octyldodecyl) 6,6'-((2-(((2-(piperidin-1-yl)ethyl)carbamoyl)oxy)ethyl)azanediyl)dihexanoate was synthesized according to the general synthetic scheme and general methods. MS [ESI]: m/z: [M+H] calc 1004.9 obs. 1005.3; $^1$H NMR (400 MHz, $CDCl_3$): $^1$H NMR (400 MHz): δ 0.88 (12H, t, J=6.76 Hz), 1.28 (63H, m), 1.44 (6H, m), 1.60 (17H, m), 2.37 (15H, m), 2.67 (1H, m), 3.25 (1H, m), 3.96 (4H, d, J=5.77 Hz), 4.09 (2H, m).

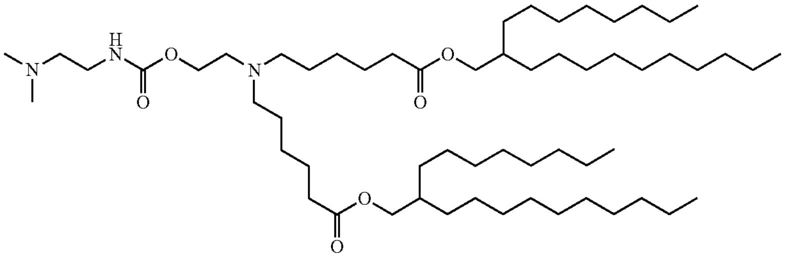 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C]

Lipid 170 2-octyldodecyl 2-methyl-10-(6-((2-octyldodecyl)oxy)-6-oxohexyl)-6-oxo-7-oxa-2,5,10-triazahexadecan-16-oate was synthesized according to the general synthetic scheme and general methods. MS [ESI]: m/z: [M+H] calc 964.9 obs. 965.4; $^1$H NMR (400 MHz, $CDCl_3$): $^1$H NMR (400 MHz): δ 0.88 (12H, t, J=6.83 Hz), 1.26 (70H, m), 1.44 (4H, m), 1.58-1.67 (8H, 1.63 (quint, J=7.57 Hz), 1.63 (d, J=8.20 Hz)), 2.21-2.23 (6H, 2.22 (s), 2.22 (s)), 2.30 (4H, t, J=7.53 Hz), 2.37-2.48 (6H, 2.39 (m), 2.45 (t, J=7.47 Hz)), 2.66 (2H, m), 3.96 (4H, d, J=5.81 Hz), 4.09 (1H, m), 3.21-3.27 (2H, m).

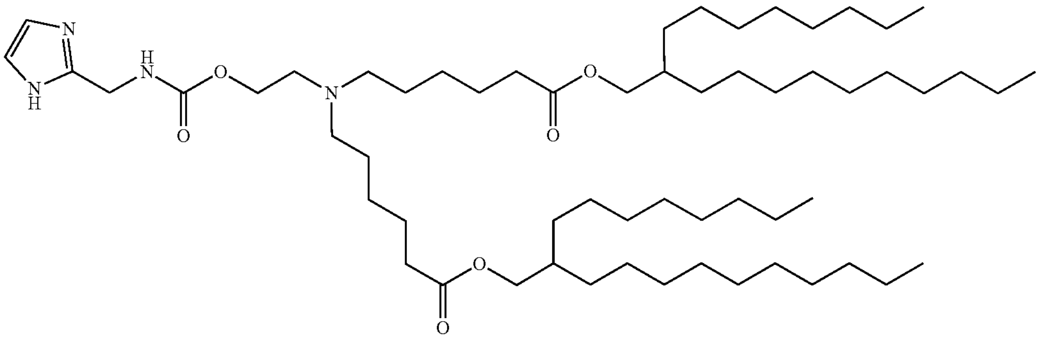 [SMILES: CCCCCCCCCCC(CCCCCCCC)COC(=O)CCCCCN(CCCCCC(=O)OCC(CCCCCCCC)CCCCCCCCCC)CCOC(=O)NCc1ncc[nH]1]

Lipid 171 bis(2-octyldodecyl) 6,6'-((2-((((1H-imidazol-2-yl)methyl)carbamoyl)oxy)ethyl)azanediyl)dihexanoate was synthesized according to the general synthetic scheme and general methods. MS [ESI]: m/z: [M+H] calc 974.6 obs. 974.2 $^1$H NMR (400 MHz, $CDCl_3$): $^1$H NMR (400 MHz): δ 0.90 (12H, t, J=6.83 Hz), 1.28 (79H, m), 2.31 (4H, t, J=7.09 Hz), 2.42-2.49 (2H, m), 2.59-2.68 (3H, m), 2.82-2.85 (1H, m), 3.98 (4H, d, J=5.72 Hz), 4.11-4.17 (1H, m), 4.25-4.30 (1H, m), 4.35-4.42 (2H, m), 5.71-5.79 (1H, m), 6.97 (2H, s),

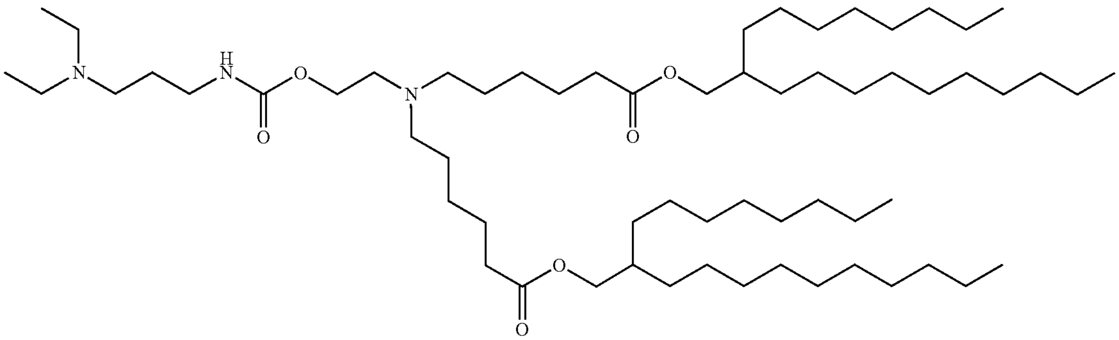 [SMILES: CCCCCCCCCCC(CCCCCCCC)COC(=O)CCCCCN(CCCCCC(=O)OCC(CCCCCCCC)CCCCCCCCCC)CCOC(=O)NCCCN(CC)CC]

Lipid 172 2-octyldodecyl 3-ethyl-12-(6-((2-octyldodecyl)oxy)-6-oxohexyl)-8-oxo-9-oxa-3,7,12-triazaoctadecan-18-oate was synthesized according to the general synthetic scheme and general methods. MS [ESI]: m/z: [M+H] calc. 1007.6 obs. 1007.2 $^1$H NMR (400 MHz, $CDCl_3$): δ 0.88 (12H, t, J=6.82 Hz), 1.02 (6H, t, J=7.14 Hz), 1.26 (68H, m), 1.43 (4H, m), 1.63 (9H, m), 2.29 (4H, t, J=7.53 Hz), 2.48 (10H, m), 2.65 (2H, m), 3.24 (2H, m), 3.96 (4H, d, J=5.80 Hz), 4.08 (2H, m).

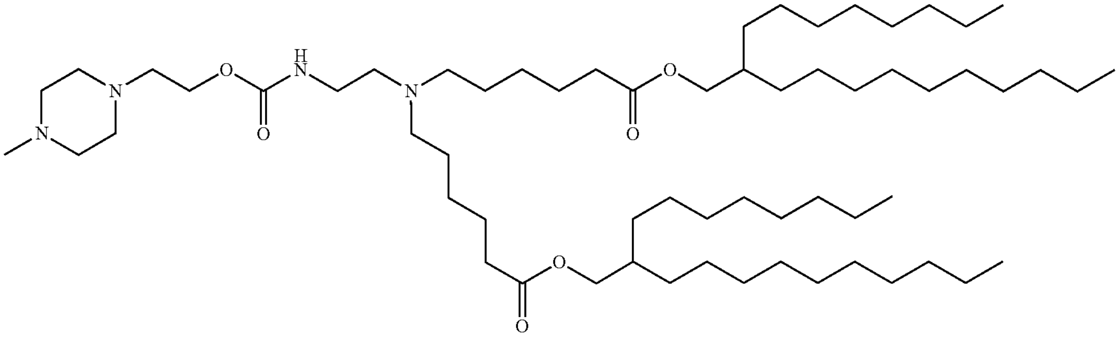 [SMILES: CCCCCCCCCCC(CCCCCCCC)COC(=O)CCCCCN(CCCCCC(=O)OCC(CCCCCCCC)CCCCCCCCCC)CCNC(=O)OCCN1CCN(C)CC1]

Lipid 173 bis(2-octyldodecyl) 6,6'-((2-(((2-(4-methylpiperazin-1-yl)ethyl)carbamoyl)oxy)ethyl)azanediyl)dihexanoate was synthesized according to the general synthetic scheme and general methods. MS [ESI]: m/z: [M+H] calc. 1020.7 obs. 1020.6 $^1$H NMR (400 MHz, $CDCl_3$): $^1$H NMR (400 MHz): δ 0.88 (12H, t, J=6.82 Hz), 1.26 (69H, m), 1.42-1.47 (4H, m), 1.59-1.66 (6H, m), 2.28 (9H, m), 2.46 (13H, m), 2.66 (2H, m), 3.96 (4H, d, J=5.80 Hz), 4.09 (2H, m), 3.23-3.29 (2H, m).

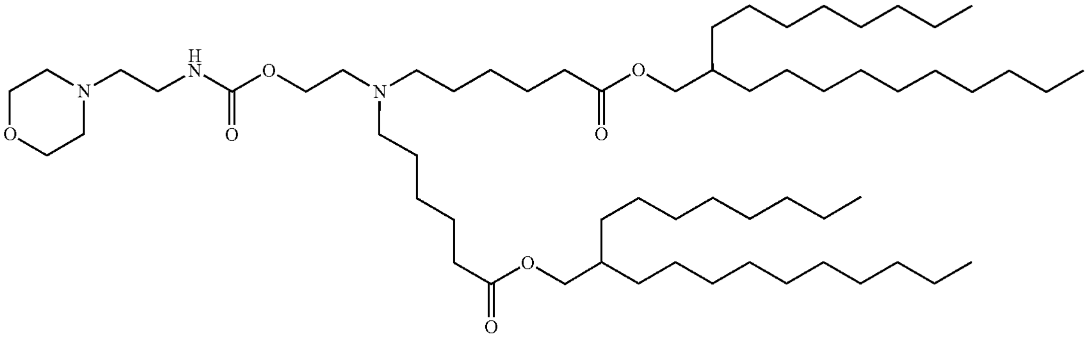 [SMILES: CCCCCCCCCCC(CCCCCCCC)COC(=O)CCCCCN(CCCCCC(=O)OCC(CCCCCCCC)CCCCCCCCCC)CCOC(=O)NCCN1CCOCC1]

Lipid 174 bis(2-octyldodecyl) 6,6'-((2-(((2-morpholinoethyl)carbamoyl)oxy)ethyl)azanediyl)dihexanoate was synthesized according to the general synthetic scheme and general methods. MS [ESI]: m/z: [M+H] calc. 1007.6 obs. 1007.2 $^1$H NMR (400 MHz, $CDCl_3$): δ 0.90 (12H, t, J=6.83 Hz), 1.29 (67H, m), 1.46 (4H, m), 1.65 (6H, m), 2.31 (4H, t, J=7.51 Hz), 2.47 (11H, m), 2.68 (2H, t, J=5.93 Hz), 3.30 (2H, m), 3.71 (4H, t, J=4.60 Hz), 3.98 (4H, d, J=5.81 Hz), 4.12 (2H, t, J=5.89 Hz), 5.31 (1H, m).

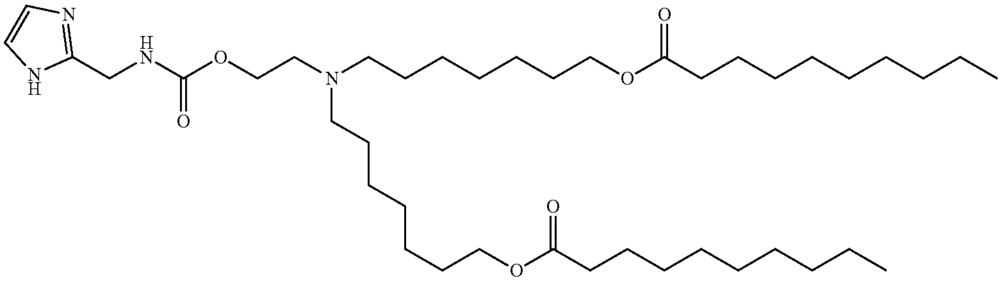 [SMILES: CCCCCCCCCC(=O)OCCCCCCCN(CCCCCCCOC(=O)CCCCCCCCC)CCOC(=O)NCc1ncc[nH]1]

Lipid 176 ((2-((((1H-imidazol-2-yl)methyl)carbamoyl)oxy)ethyl)azanediyl)bis(heptane-7,1-diyl) bis(decanoate) was synthesized according to the general synthetic scheme and general methods. MS [ESI]: m/z: [M+H] calc. 722.1 obs. 721.9 $^1$H NMR (400 MHz, $CDCl_3$): δ 0.88 (6H, t, J=6.83 Hz), 1.23-1.37 (39H, m), 1.60 (12H, m), 2.28 (4H, t, J=7.55 Hz), 2.69 (2H, m), 2.86-2.94 (2H, m), 4.05 (6H, m), 4.27 (1H, m), 4.35-4.40 (1H), 4.46 (1H, d, J=6.14 Hz), 6.93 (2H, m), m).

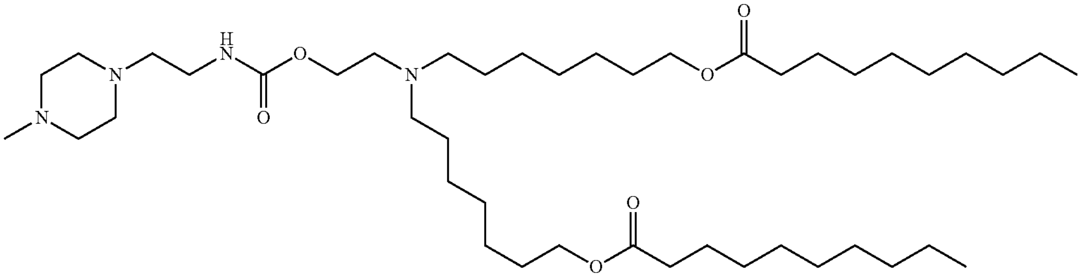 [SMILES: CCCCCCCCCC(=O)OCCCCCCCN(CCCCCCCOC(=O)CCCCCCCCC)CCOC(=O)NCCN1CCN(C)CC1]

Lipid 178 ((2-(((2-(4-methylpiperazin-1-yl)ethyl)carbamoyl)oxy)ethyl)azanediyl)bis(heptane-7,1-diyl) bis(decanoate) was synthesized according to the general synthetic scheme and general methods. MS [ESI]: m/z: [M+H] calc. 768.2 obs. 768.0 $^{1}$H NMR (400 MHz, $CDCl_3$): δ 0.87 (6H, m), 1.26 (43H, m), 2.28 (5H, m), 4.05 (5H, t, J=6.79 Hz), 1.61 (8H, m), 2.40-2.51 (13H, m), 2.64-2.69 (2H, m), 3.23-3.29 (2H, m), 4.09-4.13 (2H, m).

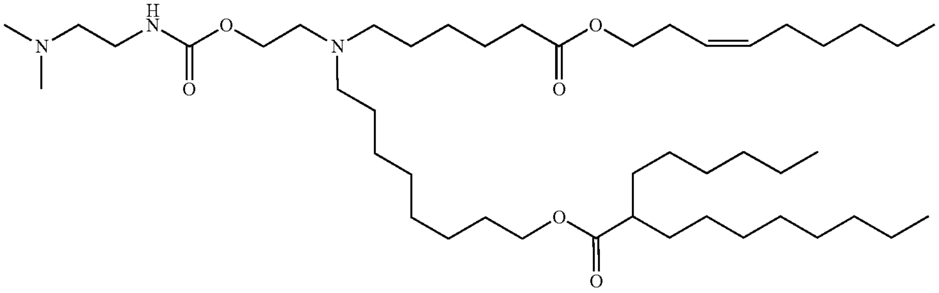 [SMILES: CCCCC/C=C\CCOC(=O)CCCCCN(CCCCCCCCOC(=O)C(CCCCCC)CCCCCCCC)CCOC(=O)NCCN(C)C]

Lipid 184 (Z)-non-3-en-1-yl 10-(8-((2-hexyldecanoyl)oxy)octyl)-2-methyl-6-oxo-7-oxa-2,5,10-triazahexadecan-16-oate was synthesized according to the general synthetic scheme and general methods. MS [ESI]: m/z: [M+H] calc.781.2 obs.781.1 $^{1}$H NMR (400 MHz, $CDCl_3$): δ 0.87 (9H, m), 1.25 (49H, m), 2.03 (2H, q, J=7.43 Hz), 2.21-2.22 (6H, 2.21 (s), 2.22 (s)), 2.37 (12H, m), 2.66 (2H, t, J=5.80 Hz), 3.24 (1H, q, J=2.18 Hz), 4.06 (7H, m), 5.31-5.37 (1H, m), 5.46-5.53 (1H, m).

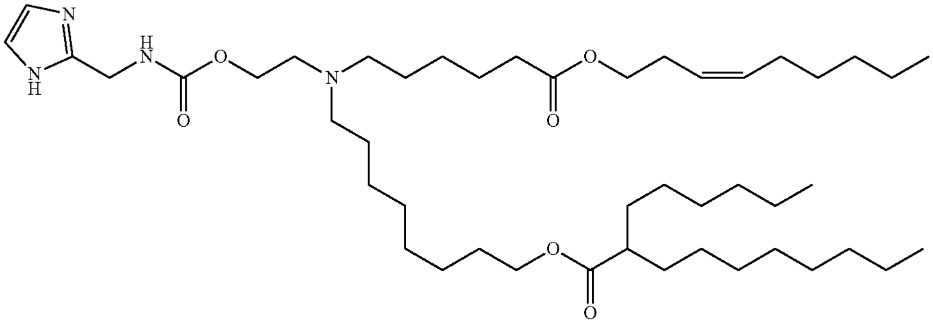 [SMILES: CCCCC/C=C\CCOC(=O)CCCCCN(CCCCCCCCOC(=O)C(CCCCCC)CCCCCCCC)CCOC(=O)NCc1ncc[nH]1]

Lipid 185 (Z)-8-((2-((((1H-imidazol-2-yl)methyl)carbamoyl)oxy)ethyl)(6-(non-3-en-1-yloxy)-6-oxohexyl)amino)octyl 2-hexyldecanoate was synthesized according to the general synthetic scheme and general methods. MS [ESI]: m/z: [M+H] calc. 790.2 obs. 789.9; $^{1}$H NMR (400 MHz, $CDCl_3$): $^{1}$H NMR (400 MHz): δ 0.87 (9H, m), 1.25 (54H, m), 2.00 (2H, q, J=7.02 Hz), 2.28 (7H, m), 2.61 (2H, m), 4.06 (4H, t, J=6.91 Hz), 4.36 (2H, m), 5.31-5.36 (1H, m), 5.46-5.54 (1H, m), 6.95 (2H, m).

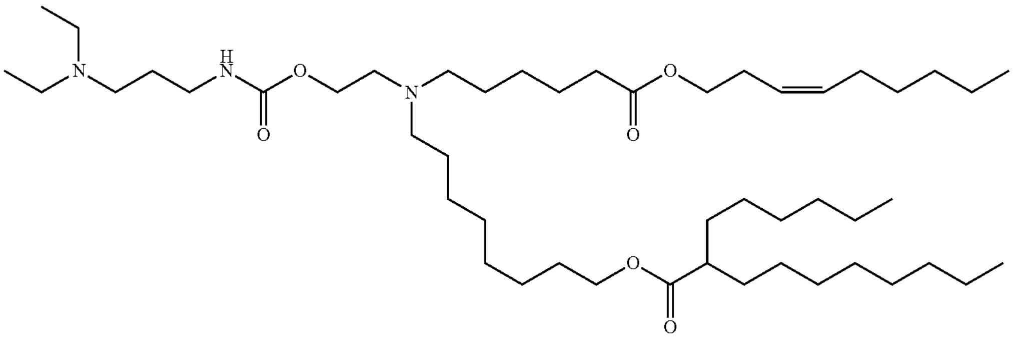 [SMILES: CCCCC/C=C\CCOC(=O)CCCCCN(CCCCCCCCOC(=O)C(CCCCCC)CCCCCCCC)CCOC(=O)NCCCN(CC)CC]

Lipid 186 (Z)-non-3-en-1-yl 3-ethyl-12-(8-((2-hexyldecanoyl)oxy)octyl)-8-oxo-9-oxa-3,7,12-triazaoctadecan-18-oate methyl)carbamoyl)oxy)ethyl)(6-(non-3-en-1-yloxy)-6-oxohexyl)amino)octyl 2-hexyldecanoate was synthesized according to the general synthetic scheme and general methods. MS [ESI]: m/z: [M+H] calc. 823.3 obs. 822.9 $^{1}$H NMR (400 MHz, $CDCl_3$): δ 0.88 (9H, m), 1.02 (6H, t, J=7.14 Hz), 1.26 (36H, m), 1.62 (15H, m), 2.03 (2H, q, J=7.86 Hz), 2.45 (16H, m), 2.66 (1H, m), 3.24 (2H, m), 4.06 (6H, t, J=6.56 Hz), 5.30-5.38 (1H, m), 5.50 (1H, m).

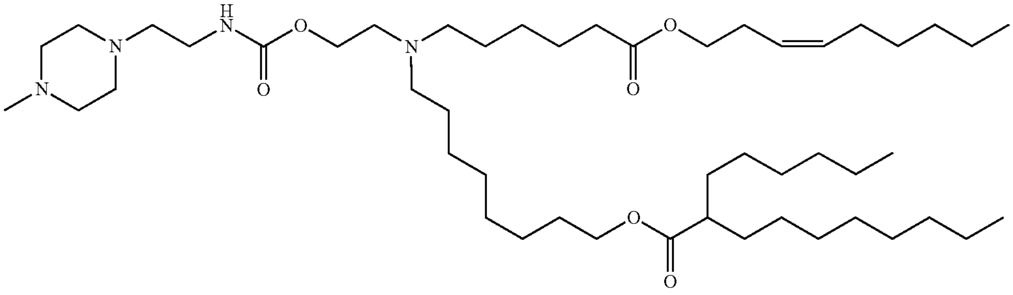 [SMILES: CCCCC/C=C\CCOC(=O)CCCCCN(CCCCCCCCOC(=O)C(CCCCCC)CCCCCCCC)CCOC(=O)NCCN1CCN(C)CC1]

Lipid 187 (Z)-8-((2-(((2-(4-methylpiperazin-1-yl)ethyl)carbamoyl)oxy)ethyl)(6-(non-3-en-1-yloxy)-6-oxohexyl)amino)octyl 2-hexyldecanoate was synthesized according to the general synthetic scheme and general methods. MS [ESI]: m/z: [M+H] calc. 836.3 obs. 836.1 $^{1}$H NMR (400 MHz, $CDCl_3$): δ 0.88 (9H, m), 1.26 (44H, m), 1.62 (6H, m), 2.04 (2H, q, J=7.42 Hz), 2.30 (20H, m), 2.68 (2H, t, J=5.98 Hz), 3.28 (2H, m), 4.07 (6H, m), 5.26 (1H, m), 5.35 (1H, m), 5.51 (1H, m).

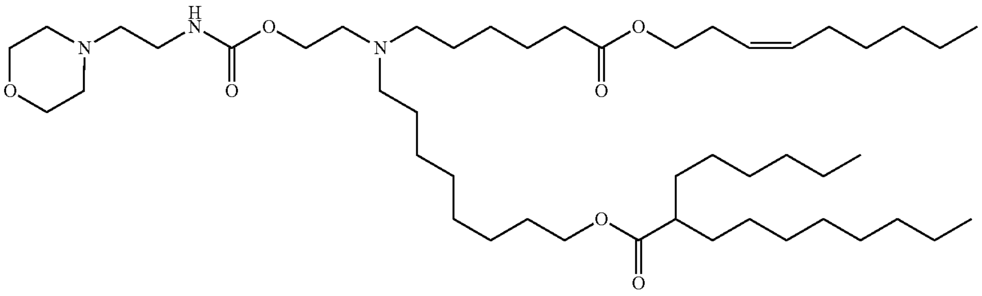 [SMILES: CCCCC/C=C\CCOC(=O)CCCCCN(CCCCCCCCOC(=O)C(CCCCCC)CCCCCCCC)CCOC(=O)NCCN1CCOCC1]

Lipid 188 (Z)-8-((2-(((2-morpholinoethyl)carbamoyl)oxy)ethyl)(6-(non-3-en-1-yloxy)-6-oxohexyl)amino)octyl 2-hexyldecanoate was synthesized according to the general synthetic scheme and general methods. MS [ESI]: m/z: [M+H] calc. 823.3 obs. 823.0 $^1$H NMR (400 MHz, $CDCl_3$): $^1$H NMR (400 MHz): δ 0.88 (9H, m), 1.25 (29H, m), 1.42-1.48 (4H, m), 1.61 (13H, m), 2.03 (2H, q, J=7.94 Hz), 2.45 (16H, m), 2.67 (2H, m), 3.28 (3H, m), 3.69 (5H, m), 4.06 (6H, m), 5.33 (1H, m), 5.49 (1H, m).

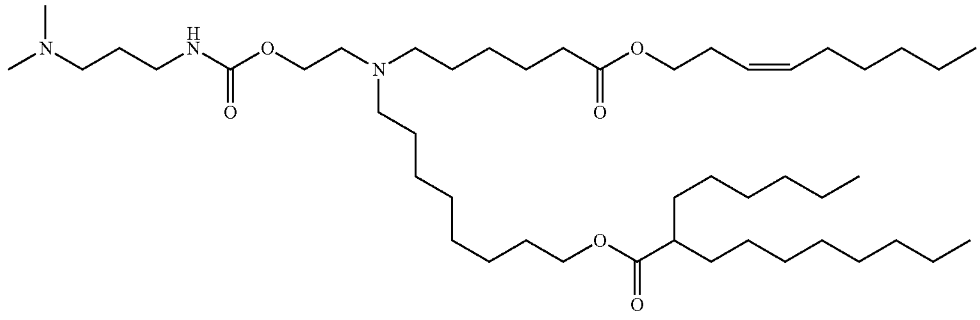 [SMILES: CCCCC/C=C\CCOC(=O)CCCCCN(CCCCCCCCOC(=O)C(CCCCCC)CCCCCCCC)CCOC(=O)NCCCN(C)C]

Lipid 189 (Z)-non-3-en-1-yl 11-(8-((2-hexyldecanoyl)oxy)octyl)-2-methyl-7-oxo-8-oxa-2,6,11-triazaheptadecan-17-oate was synthesized according to the general synthetic scheme and general methods. MS [ESI]: m/z: [M+H] calc. 795.3 obs. 795.1 $^1$H NMR (400 MHz, $CDCl_3$): δ 0.89 (9H, m), 1.31 (39H, m), 1.64 (8H, m), 2.05 (2H, m), 2.22-2.24 (6H, 2.23 (s), 2.24 (s)), 2.39 (14H, m), 2.68 (2H, m), 3.25 (2H, q, J=6.48 Hz), 4.08 (7H, m), 5.36 (1H, m), 5.52 (1H, m).

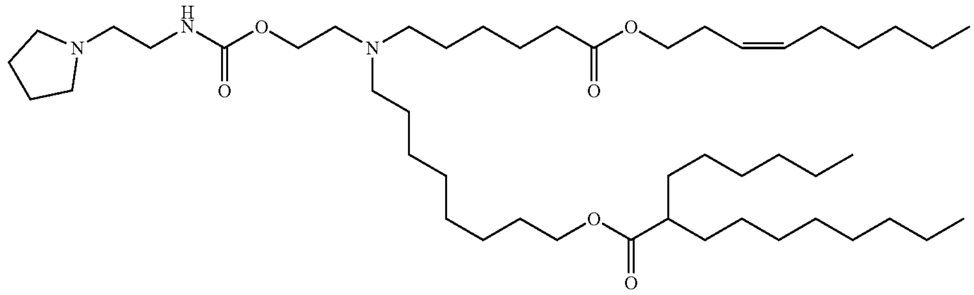 [SMILES: CCCCC/C=C\CCOC(=O)CCCCCN(CCCCCCCCOC(=O)C(CCCCCC)CCCCCCCC)CCOC(=O)NCCN1CCCC1]

Lipid 191 (Z)-8-((6-(non-3-en-1-yloxy)-6-oxohexyl)(2-(((2-(pyrrolidin-1-yl)ethyl)carbamoyl)oxy)ethyl)amino)octyl 2-hexyldecanoate was synthesized according to the general synthetic scheme and general methods. MS [ESI]: m/z: [M+H] calc. 807.3 obs. 807.1 $^1$H NMR (400 MHz, $CDCl_3$): δ 0.90 (9H, m), 1.31 (40H, m), 1.63 (7H, m), 1.78 (4H, m), 2.05 (2H, q, J=7.53 Hz), 2.49 (14H, m), 2.59 (2H, t, J=6.15 Hz), 2.68 (2H, t, J=6.00 Hz), 3.30 (2H, m), 4.08 (7H, m), 5.35 (1H, m), 5.51 (1H, m).

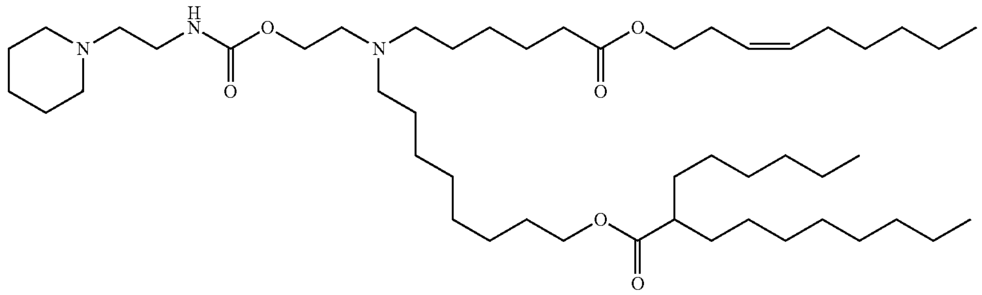 [SMILES: CCCCC/C=C\CCOC(=O)CCCCCN(CCCCCCCCOC(=O)C(CCCCCC)CCCCCCCC)CCOC(=O)NCCN1CCCCC1]

Lipid 192 (Z)-8-((6-(non-3-en-1-yloxy)-6-oxohexyl)(2-(((2-(piperidin-1-yl)ethyl)carbamoyl)oxy)ethyl)amino)octyl 2-hexyldecanoate was synthesized according to the general synthetic scheme and general methods. MS [ESI]: m/z: [M+H] calc. 821.3 obs. 821.2; $^1$H NMR (400 MHz, $CDCl_3$): $^1$H NMR (400 MHz): δ 0.88 (9H, m), 1.25 (43H, m), 1.61 (7H, m), 1.76 (4H, quint, J=3.18 Hz), 2.03 (2H, q, J=7.53 Hz), 2.43 (16H, m), 2.66 (2H, t, J=6.00 Hz), 3.28 (2H, m), 4.06 (7H, m), 5.34 (1H, m), 5.49 (1H, m).

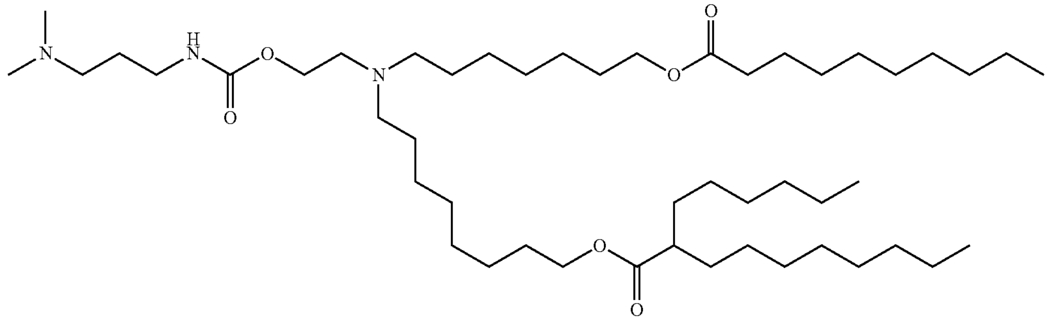 [SMILES: CCCCCCCCCC(=O)OCCCCCCCN(CCCCCCCCOC(=O)C(CCCCCC)CCCCCCCC)CCOC(=O)NCCCN(C)C]

Lipid 193 11-(7-(decanoyloxy)heptyl)-2-methyl-7-oxo-8-oxa-2,6,11-triazanonadecan-19-yl 2-hexyldecanoate hexyldecanoate was synthesized according to the general synthetic scheme and general methods. MS [ESI]: m/z: [M+H] calc. 825.3 obs. 825.0 $^1$H NMR (400 MHz, $CDCl_3$): δ 0.89 (9H, t, J=6.45 Hz), 1.31 (48H, m), 1.63 (11H, m), 2.22 (6H, s), 2.32 (6H, m), 2.46 (5H, m), 2.69 (2H, m), 3.25 (2H, m), 4.07 (8H, m).

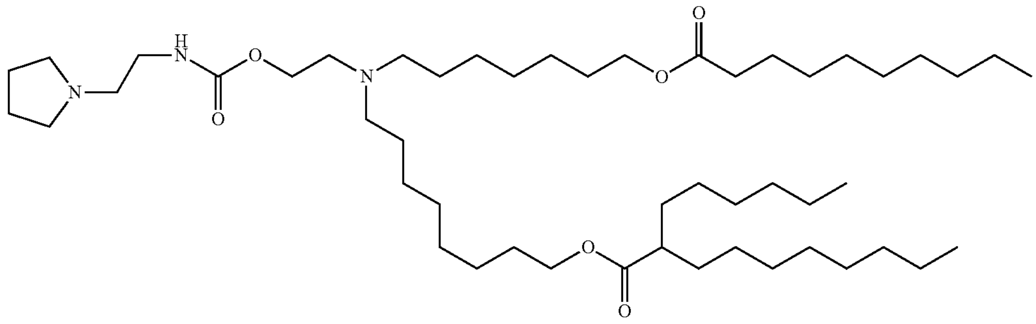 [SMILES: CCCCCCCCCC(=O)OCCCCCCCN(CCCCCCCCOC(=O)C(CCCCCC)CCCCCCCC)CCOC(=O)NCCN1CCCC1]

Lipid 195 8-((7-(decanoyloxy)heptyl)(2-(((2-(pyrrolidin-1-yl)ethyl)carbamoyl)oxy)ethyl)amino)octyl 2-hexyldecanoate was synthesized according to the general synthetic scheme and general methods. MS [ESI]: m/z: [M+H] calc 836.7 obs. 837.1; $^{1}$H NMR (400 MHz, $CDCl_3$): $^{1}$H NMR (400 MHz): δ 0.87 (9H, m), 1.25 (49H, m), 1.61 (9H, m), 1.76 (4H, m), 2.25-2.34 (3H, 2.28 (t, J=7.58 Hz), 2.29 (m)), 2.48 (10H, m), 2.66 (2H, m), 3.27 (2H, m), 4.05 (7H, m), 5.25 (1H, s).

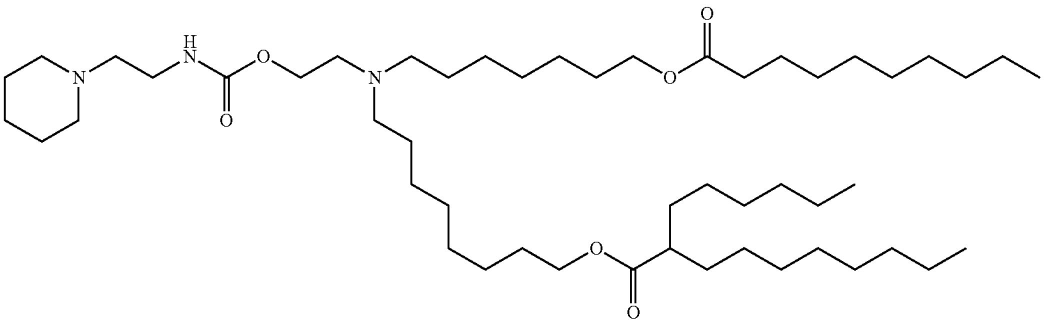 [SMILES: CCCCCCCCCC(=O)OCCCCCCCN(CCCCCCCCOC(=O)C(CCCCCC)CCCCCCCC)CCOC(=O)NCCN1CCCCC1]

Lipid 196 8-((7-(decanoyloxy)heptyl)(2-(((2-(piperidin-1-yl)ethyl)carbamoyl)oxy)ethyl)amino)octyl 2-hexyldecanoate was synthesized according to the general synthetic scheme and general methods. MS [ESI]: m/z: [M+H] calc 850.8 obs. 851.2; $^{1}$H NMR (400 MHz, $CDCl_3$): $^{1}$H NMR (400 MHz): δ 0.87 (9H, t, J=6.71 Hz), 1.25 (51H, m), 1.59 (15H, m), 2.37 (13H, m), 2.67 (2H, m), 3.24 (2H, m), 4.02-4.13 (6H, 4.05 (td, J=6.63, 3.50 Hz), 4.10 (t, J=6.40 Hz)), 5.26 (1H, m).

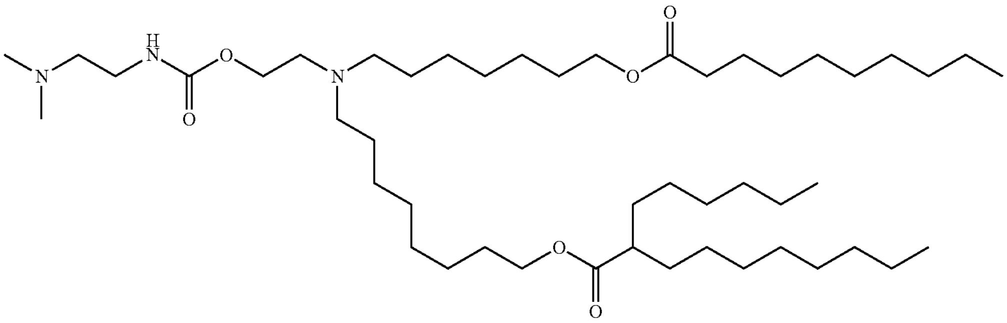 [SMILES: CCCCCCCCCC(=O)OCCCCCCCN(CCCCCCCCOC(=O)C(CCCCCC)CCCCCCCC)CCOC(=O)NCCN(C)C]

Lipid 197 10-(7-(decanoyloxy)heptyl)-2-methyl-6-oxo-7-oxa-2,5,10-triazaoctadecan-18-yl 2-hexyldecanoate was synthesized according to the general synthetic scheme and general methods. MS [ESI]: m/z: [M+H] calc 810.7 obs. 811.1; $^{1}$H NMR (400 MHz, $CDCl_3$): δ 0.87 (9H, t, J=6.44 Hz), 1.26 (46H, m), 1.62 (15H, m), 2.20-2.23 (6H, 2.21 (s), 2.22 (s)), 2.25-2.34 (3H, 2.29 (t, J=7.61 Hz), 2.29 (m)), 2.44 (6H, m), 2.66 (2H, m), 3.24 (2H, m), 4.02-4.12 (6H, 4.05 (td, J=6.72, 3.49 Hz), 4.10 (m)).

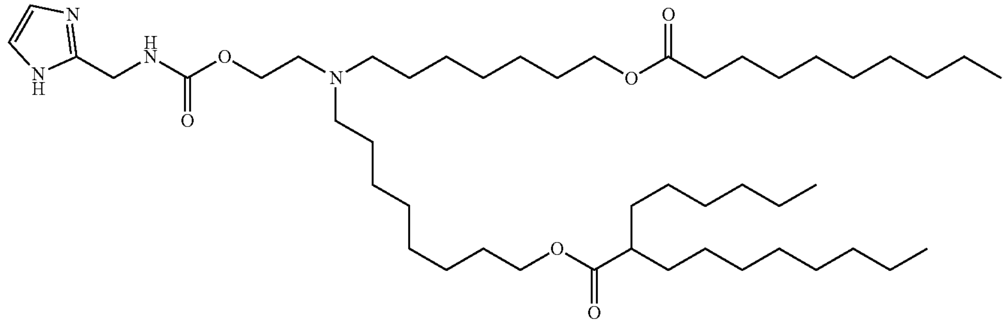 [SMILES: CCCCCCCCCC(=O)OCCCCCCCN(CCCCCCCCOC(=O)C(CCCCCC)CCCCCCCC)CCOC(=O)NCc1ncc[nH]1]

Lipid 198 8-((2-((((1H-imidazol-2-yl)methyl)carbamoyl)oxy)ethyl)(7-(decanoyloxy)heptyl)amino)octyl 2-hexyldecanoate was synthesized according to the general synthetic scheme and general methods. MS [ESI]: m/z: [M+H] calc. 820.3 obs. 820.0 $^{1}$H NMR (400 MHz, $CDCl_3$): δ 0.89 (9H, m), 1.27 (62H, m), 2.27-2.36 (3H, 2.30 (t, J=7.63 Hz), 2.31 (m)), 2.45 (2H, m), 2.62 (3H, m), 2.84 (1H, m), 4.06 (5H, m), 4.37 (3H, m), 6.98

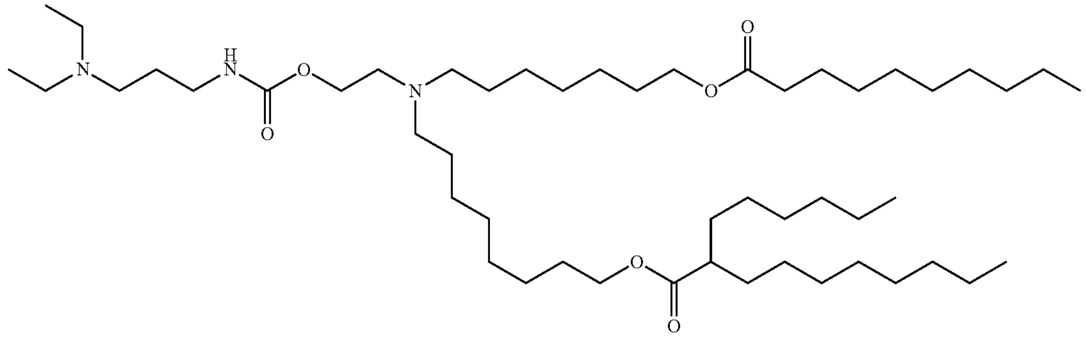 [SMILES: CCCCCCCCCC(=O)OCCCCCCCN(CCCCCCCCOC(=O)C(CCCCCC)CCCCCCCC)CCOC(=O)NCCCN(CC)CC]

Lipid 199 12-(7-(decanoyloxy)heptyl)-3-ethyl-8-oxo-9-oxa-3,7,12-triazaicosan-20-yl 2-hexyldecanoate was synthesized according to the general synthetic scheme and general methods. MS [ESI]: m/z: [M+H] calc. 853.4 obs. 853.2; $^{1}$H NMR (400 MHz, $CDCl_3$): δ 0.89 (9H, t, J=6.40 Hz), 1.04 (6H, t, J=7.12 Hz), 1.27 (50H, m), 1.63 (12H, m), 2.27-2.36 (3H, 2.30 (t, J=7.61 Hz), 2.32 (m)), 2.50 (10H, m), 2.68 (2H, m), 3.26 (2H, m), 4.07 (6H, m), 5.92 (1H, m).

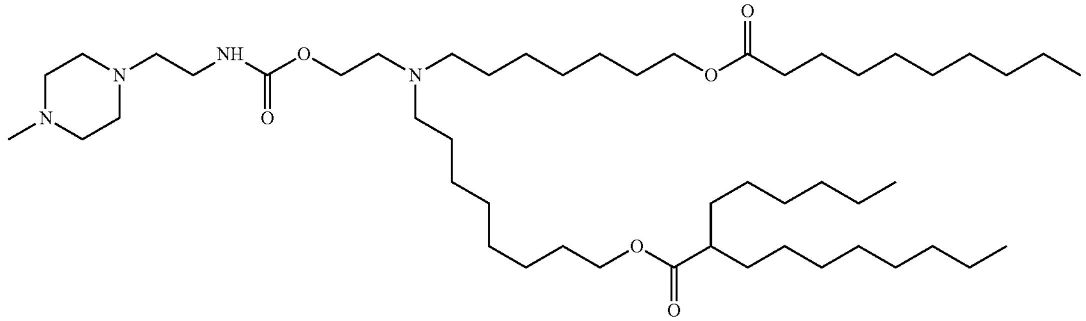 [SMILES: CCCCCCCCCC(=O)OCCCCCCCN(CCCCCCCCOC(=O)C(CCCCCC)CCCCCCCC)CCOC(=O)NCCN1CCN(C)CC1]

Lipid 200 8-((7-(decanoyloxy)heptyl)(2-(((2-(4-methylpiperazin-1-yl)ethyl)carbamoyl)oxy)ethyl)amino)octyl 2-hexyldecanoate was synthesized according to the general synthetic scheme and general methods. MS [ESI]: m/z: [M+H] calc. 866.4 obs. 866.1; $^1$H NMR (400 MHz, $CDCl_3$): δ 0.89 (9H, t, J=7.11 Hz), 1.28 (54H, m), 1.63 (8H, m), 2.31 (6H, m), 2.48 (12H, m), 2.70 (2H, m), 3.28 (2H, m), 4.04-4.16 (7H, 4.07 (td, J=6.70, 3.63 Hz), 4.13 (in)).

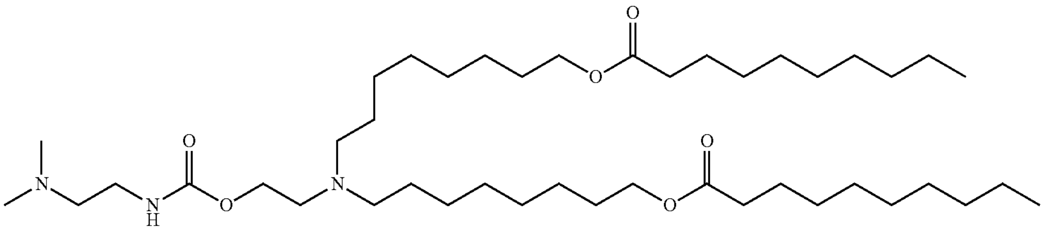 [SMILES: CCCCCCCCCC(=O)OCCCCCCCCN(CCCCCCCCOC(=O)CCCCCCCCC)CCOC(=O)NCCN(C)C]

Lipid 202 10-(8-(decanoyloxy)octyl)-2-methyl-6-oxo-7-oxa-2,5,10-triazaoctadecan-18-yl decanoate was synthesized according to the general synthetic scheme and general methods. MS [ESI]: m/z: [M+H] calc. 741.2 obs. 704.9; $^1$H NMR (400 MHz, $CDCl_3$): δ 0.89 (6H, t, J=6.53 Hz), 1.29 (45H, m), 1.63 (8H, m), 2.23 (6H, s), 2.30 (4H, t, J=7.36 Hz), 2.46 (6H, m), 2.69 (2H, m), 3.26 (2H, m), 4.07 (4H, t, J=6.66 Hz), 4.12 (2H, t, J=5.85 Hz).

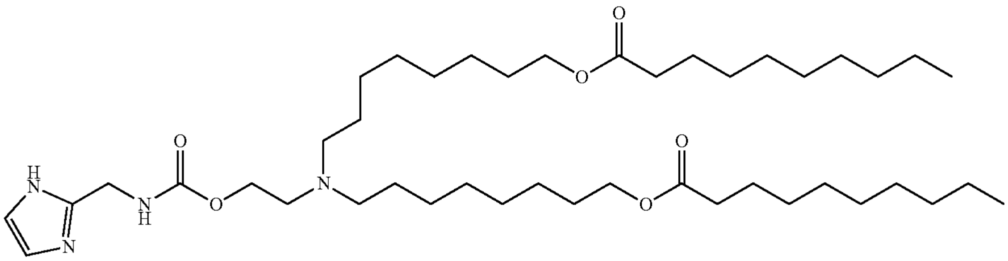 [SMILES: CCCCCCCCCC(=O)OCCCCCCCCN(CCCCCCCCOC(=O)CCCCCCCCC)CCOC(=O)NCc1ncc[nH]1]

Lipid 203 ((2-((((1H-imidazol-2-yl)methyl)carbamoyl)oxy)ethyl)azanediyl)bis(octane-8,1-diyl) bis(decanoate) was synthesized according to the general synthetic scheme and general methods. MS [ESI]: m/z: [M+H] calc. 750.1 obs. 749.9; $^1$H NMR (400 MHz, $CDCl_3$): δ 0.89 (6H, t, J=6.96 Hz), 1.29 (53H, m), 2.30 (4H, t, J=7.53 Hz), 2.45 (2H, m), 2.63 (3H, m), 2.83 (1H, m), 4.06 (5H, m), 4.16 (1H, m), 4.37 (3H, m), 6.94 (1H, m), 7.12 (1H, m).

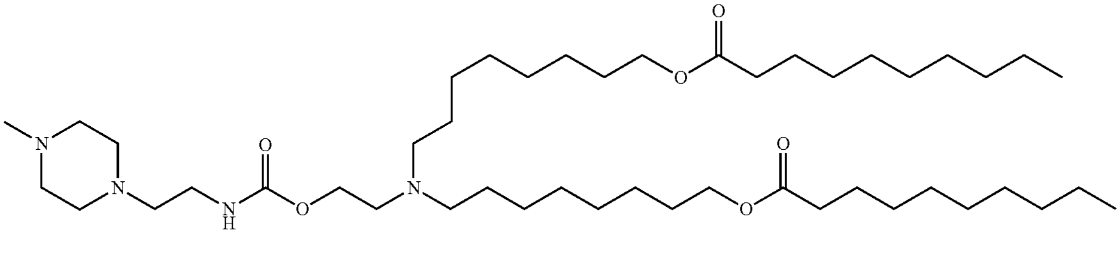 [SMILES: CCCCCCCCCC(=O)OCCCCCCCCN(CCCCCCCCOC(=O)CCCCCCCCC)CCOC(=O)NCCN1CCN(C)CC1]

Lipid 205 ((2-(((2-(4-methylpiperazin-1-yl)ethyl)carbamoyl)oxy)ethyl)azanediyl)bis(octane-8,1-diyl) bis(decanoate) was synthesized according to the general synthetic scheme and general methods. MS [ESI]: m/z: [M+H] calc. 795.7 obs. 796.0; 1H NMR (400 MHz, $CDCl_3$): δ 0.87 (6H, t, J=6.78 Hz), 1.28 (44H, m), 1.43 (4H, m), 1.61 (8H, m), 2.28 (7H, m), 2.46 (12H, m), 2.69 (2H, m), 3.27 (1H, m), 4.05 (4H, t, J=6.75 Hz), 4.11 (2H, m).

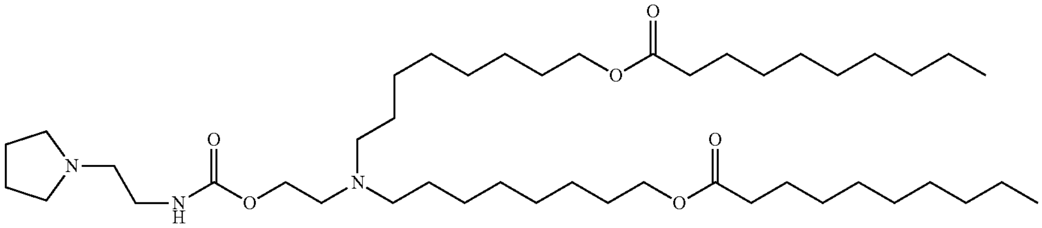 [SMILES: CCCCCCCCCC(=O)OCCCCCCCCN(CCCCCCCCOC(=O)CCCCCCCCC)CCOC(=O)NCCN1CCCC1]

Lipid 209 ((2-(((2-(pyrrolidin-1-yl)ethyl)carbamoyl)oxy)ethyl)azanediyl)bis(octane-8,1-diyl) bis(decanoate) was synthesized according to the general synthetic scheme and general methods. MS [ESI]: m/z: [M+H] calc. 766.7 obs. 767.0; 1H NMR (400 MHz, $CDCl_3$): δ 0.89 (6H, t, J=6.84 Hz), 1.29 (44H, m), 1.63 (8H, m), 1.78 (4H, m), 2.30 (4H, t, J=7.54 Hz), 2.49 (10H, m), 2.69 (2H, m), 3.30 (2H, m), 4.07 (4H, t, J=6.74 Hz), 4.12 (2H, m), 5.26 (1H, m).

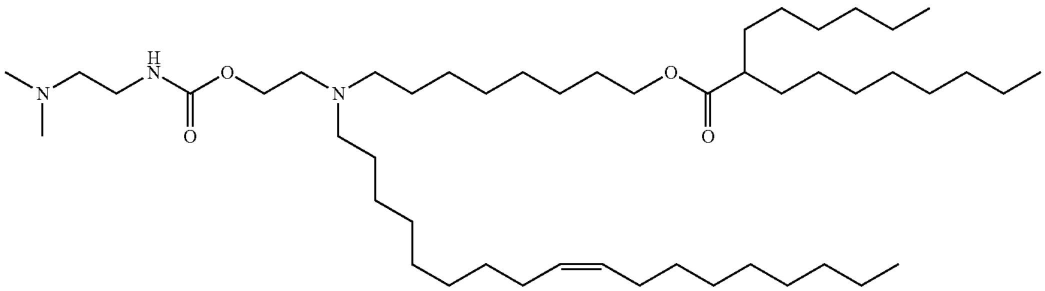 [SMILES: CCCCCCCC/C=C\CCCCCCCCN(CCCCCCCCOC(=O)C(CCCCCC)CCCCCCCC)CCOC(=O)NCCN(C)C]

Lipid 211 (Z)-2-methyl-10-(octadec-9-en-1-yl)-6-oxo-7-oxa-2,5,10-triazaoctadecan-18-yl 2-hexyldecanoate was synthesized according to the general synthetic scheme and general methods. MS [ESI]: m/z: [M+H] calc. 792.8 obs. 793.1; $^1$H NMR (400 MHz, $CDCl_3$): δ 0.89 (9H, t, J=1.44 Hz), 1.28 (57H, m), 1.61 (4H, m), 2.02 (4H, m), 2.23 (6H, s), 2.32 (1H, m), 2.46 (6H, m), 2.69 (2H, m), 3.26 (2H, m), 4.08 (4H, m), 5.36 (2H, m).

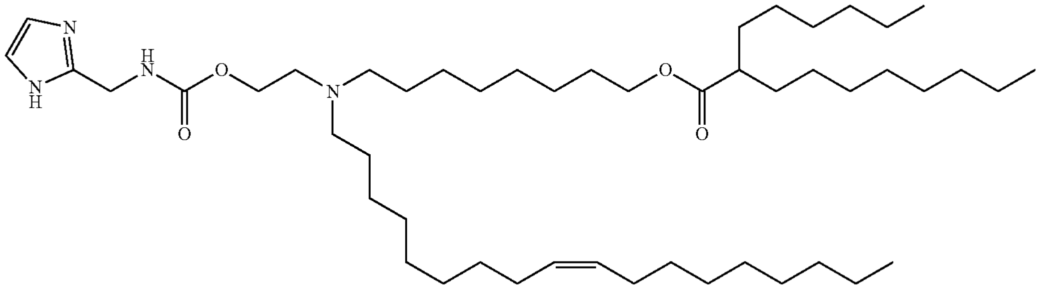 [SMILES: CCCCCCCC/C=C\CCCCCCCCN(CCCCCCCCOC(=O)C(CCCCCC)CCCCCCCC)CCOC(=O)NCc1ncc[nH]1]

Lipid 212 (Z)-8-((2-((((1H-imidazol-2-yl)methyl)carbamoyl)oxy)ethyl)(octadec-9-en-1-yl)amino)octyl 2-hexyldecanoate was synthesized according to the general synthetic scheme and general methods. MS [ESI]: m/z: [M+H] calc. 801.7 obs. 802.1; $^1$H NMR (400 MHz, $CDCl_3$): $^1$H NMR (400 MHz): δ 0.87 (9H, m), 1.25 (51H, m), 1.60 (4H, m), 1.74 (3H, m), 2.00 (3H, m), 2.43 (1H, m), 2.60 (2H, m), 4.02 (3H, m), 4.35 (3H, m), 5.34 (1H, m), 6.88-6.96 (2H, m).

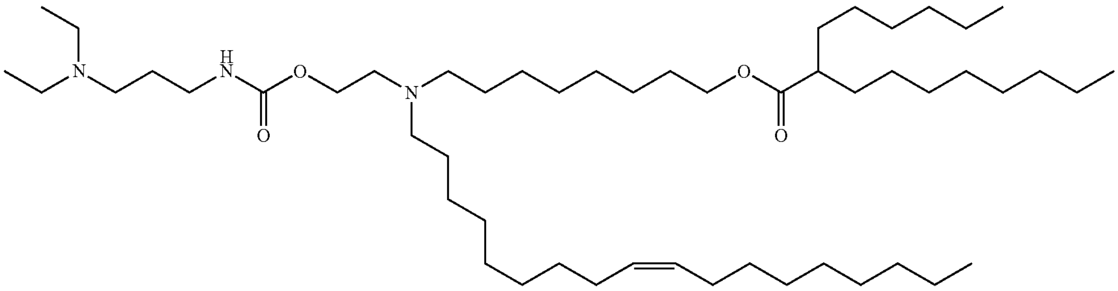 [SMILES: CCCCCCCC/C=C\CCCCCCCCN(CCCCCCCCOC(=O)C(CCCCCC)CCCCCCCC)CCOC(=O)NCCCN(CC)CC]

Lipid 213 (Z)-3-ethyl-12-(octadec-9-en-1-yl)-8-oxo-9-oxa-3,7,12-triazaicosan-20-yl 2-hexyldecanoate was synthesized according to the general synthetic scheme and general methods. MS [ESI]: m/z: [M+H] calc. 834.8 obs. 835.2; $^1$H NMR (400 MHz, $CDCl_3$): δ 0.88 (9H, m), 1.01 (6H, t, J=7.14 Hz), 1.25 (53H, m), 1.61 (8H, m), 2.00 (4H, m), 2.30 (1H, m), 2.47 (11H, m), 2.66 (2H, m), 3.24 (2H, m), 4.06 (4H, m), 5.34 (2H, m), 5.86-5.91 (1H, m).

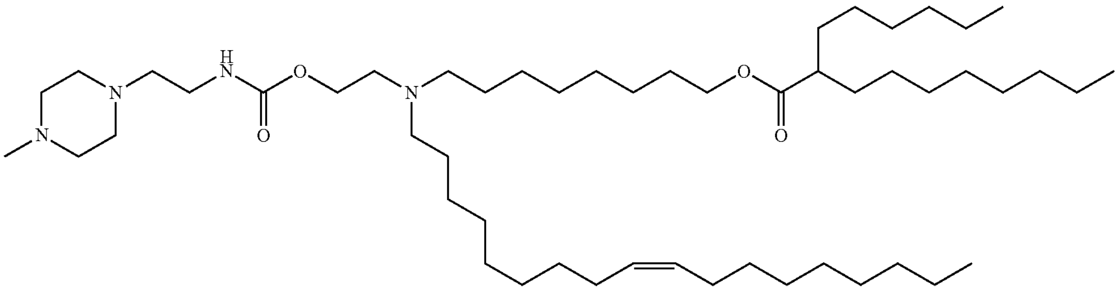 [SMILES: CCCCCCCC/C=C\CCCCCCCCN(CCCCCCCCOC(=O)C(CCCCCC)CCCCCCCC)CCOC(=O)NCCN1CCN(C)CC1]

Lipid 214 (Z)-8-((2-(((2-(4-methylpiperazin-1-yl)ethyl)carbamoyl)oxy)ethyl)(octadec-9-en-1-yl)amino)octyl 2-hexyldecanoate was synthesized according to the general synthetic scheme and general methods. MS [ESI]: m/z: [M+H] calc. 847.8 obs. 848.1; $^1$H NMR (400 MHz, $CDCl_3$): δ 0.88 (9H, m), 1.25 (61H, m), 1.51-1.65 (4H, m), 2.02 (4H, m), 2.29 (4H, s+m), 2.46 (11H, m), 2.67-2.73 (2H, m), 3.22-3.31 (2H, m), 4.06 (4H, m), 5.34 (2H, s), 5.19-5.23 (1H, m).

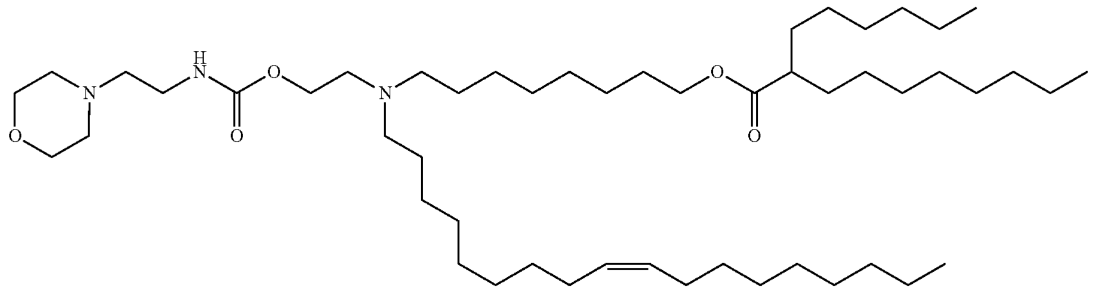 [SMILES: CCCCCCCC/C=C\CCCCCCCCN(CCCCCCCCOC(=O)C(CCCCCC)CCCCCCCC)CCOC(=O)NCCN1CCOCC1]

Lipid 215 (Z)-8-((2-(((2-morpholinoethyl)carbamoyl)oxy)ethyl)(octadec-9-en-1-yl)amino)octyl 2-hexyldecanoate was synthesized according to the general synthetic scheme and general methods. MS [ESI]: m/z: [M+H] calc. 834.8 obs. 835.2; $^1$H NMR (400 MHz, $CDCl_3$): δ 0.86-0.92 (9H, m), 1.31 (54H, m), 1.62 (6H, m), 2.03 (4H, m), 2.32 (1H, m), 2.47 (10H, m), 2.69 (2H, m), 3.30 (2H, m), 3.71 (4H, t, J=4.61 Hz), 4.08 (5H, m), 5.36 (2H, m).

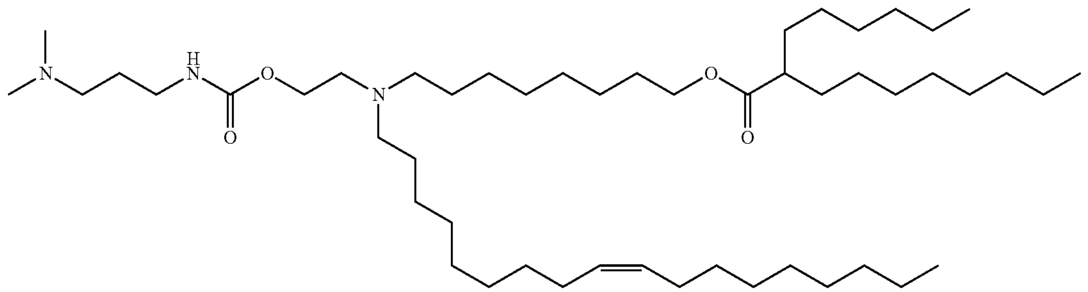 [SMILES: CCCCCCCC/C=C\CCCCCCCCN(CCCCCCCCOC(=O)C(CCCCCC)CCCCCCCC)CCOC(=O)NCCCN(C)C]

Lipid 216 (Z)-2-methyl-11-(octadec-9-en-1-yl)-7-oxo-8-oxa-2,6,11-triazanonadecan-19-yl 2-hexyldecanoate was synthesized according to the general synthetic scheme and general methods. MS [ESI]: m/z: [M+H] calc. 806.8 obs. 807.2; $^1$H NMR (400 MHz, $CDCl_3$): δ 0.86-0.92 (9H, m), 1.30 (58H, m), 1.63 (6H, m), 2.02 (3H, m), 2.22 (6H, s), 2.34 (3H, m), 2.46 (4H, m), 2.69 (2H, m), 3.25 (2H, m), 4.09 (4H, m), 5.36 (2H, m).

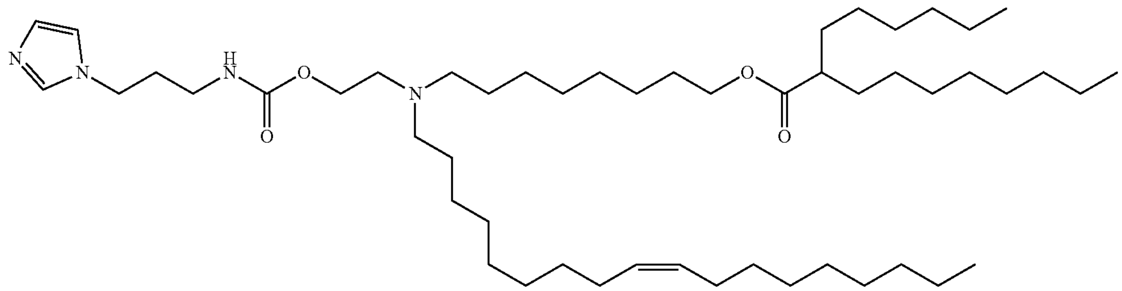 [SMILES: CCCCCCCC/C=C\CCCCCCCCN(CCCCCCCCOC(=O)C(CCCCCC)CCCCCCCC)CCOC(=O)NCCCn1ccnc1]

Lipid 217 (Z)-8-((2-(((3-(1H-imidazol-1-yl)propyl)carbamoyl)oxy)ethyl)(octadec-9-en-1-yl)amino)octyl 2-hexyldecanoate was synthesized according to the general synthetic scheme and general methods. MS [ESI]: m/z: [M+H] calc. 829.8 obs. 830.2; $^1$H NMR (400 MHz, $CDCl_3$): δ 0.83-0.90 (9H, m), 1.26 (57H, m), 1.59 (4H, m), 2.00 (6H, m), 2.30 (1H, m), 2.45 (4H, m), 2.67 (2H, t, J=6.35 Hz), 3.18 (2H, m), 4.00 (2H, t, J=7.00 Hz), 4.05 (2H, t, J=6.62 Hz), 4.11 (2H, t, J=5.94 Hz), 5.34 (2H, m), 6.94 (1H, s), 7.06 (1H, s), 7.49 (1H, s).

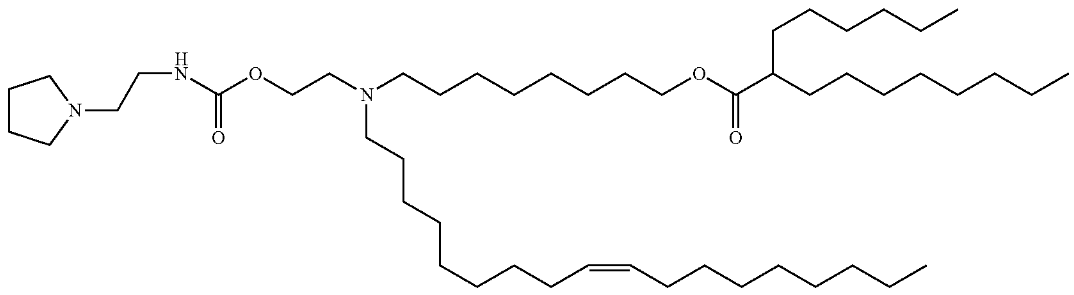

Lipid 218 (Z)-8-(octadec-9-en-1-yl(2-(((2-(pyrrolidin-1-yl)ethyl)carbamoyl)oxy)ethyl)amino)octyl 2-hexyldecanoate was synthesized according to the general synthetic scheme and general methods. MS [ESI]: m/z: [M+H] calc. 818.8 obs. 819.2; $^1$H NMR (400 MHz, $CDCl_3$): δ 0.88 (9H, m), 1.25 (51H, m), 1.63 (9H, m), 1.76 (4H, m), 2.02 (4H, m), 2.46 (8H, m), 2.57 (2H, t, J=6.12 Hz), 2.67 (2H, m), 3.25-3.32 (2H, m), 4.06 (4H, m), 5.35 (2H, m), 2.31 (1H, m), 5.20-5.26 (1H, m).

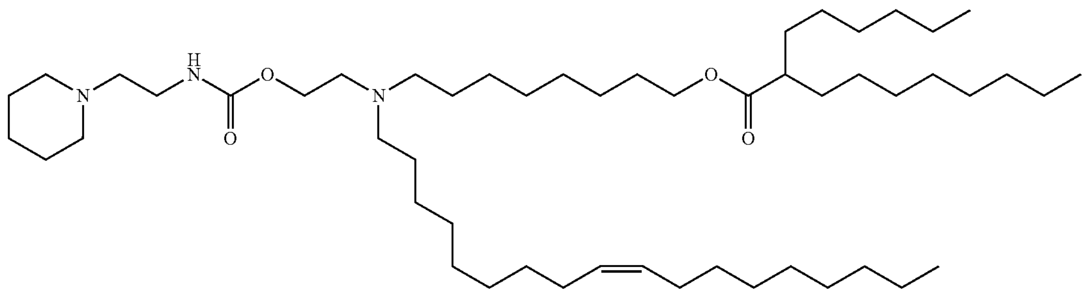 [SMILES: CCCCCCCC/C=C\CCCCCCCCN(CCCCCCCCOC(=O)C(CCCCCC)CCCCCCCC)CCOC(=O)NCCN1CCCCC1]

Lipid 219 (Z)-8-(octadec-9-en-1-yl(2-(((2-(piperidin-1-yl)ethyl)carbamoyl)oxy)ethyl)amino)octyl 2-hexyldecanoate was synthesized according to the general synthetic scheme and general methods. MS [ESI]: m/z: [M+H] calc. 832.8 obs. 833.2; $^1$H NMR (400 MHz, $CDCl_3$): δ 0.89 (9H, m), 1.28 (55H, m), 1.57 (12H, m), 2.03 (4H, m), 2.42 (11H, m), 2.69 (2H, m), 3.27 (2H, m), 4.08 (4H, m), 5.36 (2H, m).

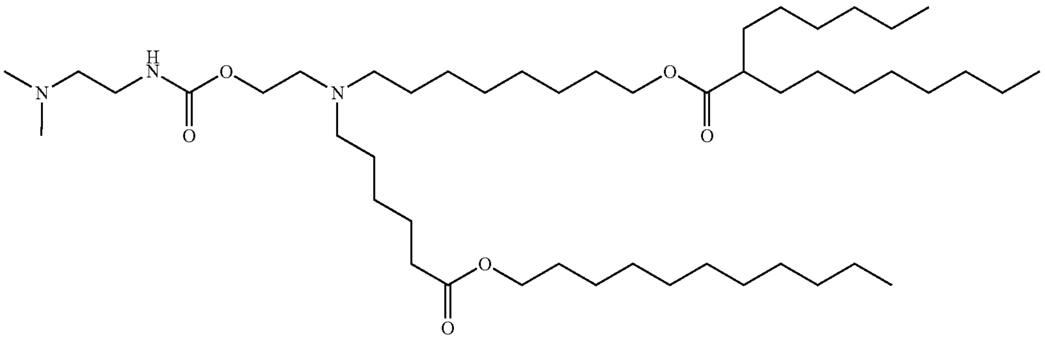 [SMILES: CCCCCCCCCCCOC(=O)CCCCCN(CCCCCCCCOC(=O)C(CCCCCC)CCCCCCCC)CCOC(=O)NCCN(C)C]

Lipid 220 undecyl 10-(8-((2-hexyldecanoyl)oxy)octyl)-2-methyl-6-oxo-7-oxa-2,5,10-triazahexadecan-16-oate was synthesized according to the general synthetic scheme and general methods. MS [ESI]: m/z: [M+H] calc. 810.7 obs. 811.1; $^1$H NMR (400 MHz, $CDCl_3$): δ 0.87 (9H, m), 1.27 (46H, m), 1.43 (6H, m), 1.61 (8H, m), 2.22 (6H, s), 2.29 (3H, t, J=7.07 Hz), 2.43 (6H, m), 2.67 (2H, m), 3.25 (2H, m), 4.05 (7H, m).

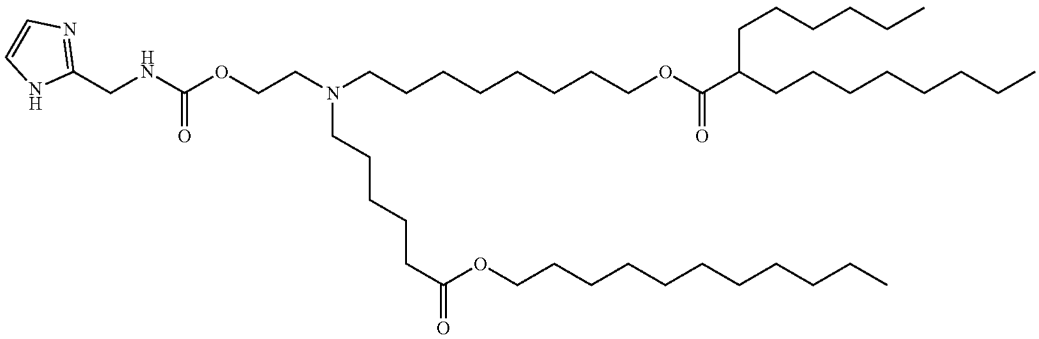 [SMILES: CCCCCCCCCCCOC(=O)CCCCCN(CCCCCCCCOC(=O)C(CCCCCC)CCCCCCCC)CCOC(=O)NCc1ncc[nH]1]

Lipid 221 8-((2-((((1H-imidazol-2-yl)methyl)carbamoyl)oxy)ethyl)(6-oxo-6-(undecyloxy)hexyl)amino)octyl 2-hexyldecanoate was synthesized according to the general synthetic scheme and general methods. MS [ESI]: m/z: [M+H] calc. 819.7 obs. 820.0; $^1$H NMR (400 MHz, $CDCl_3$): δ 0.88 (9H, m), 1.33 (63H, m), 2.29 (3H, m), 2.44 (2H, m), 2.62 (3H, m), 4.06 (5H, m), 4.34 (3H, m), 6.95 (2H, m).

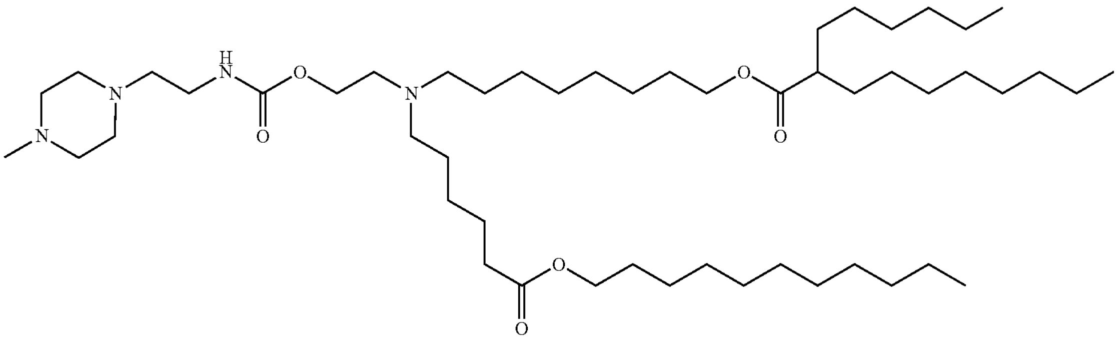 [SMILES: CCCCCCCCCCCOC(=O)CCCCCN(CCCCCCCCOC(=O)C(CCCCCC)CCCCCCCC)CCOC(=O)NCCN1CCN(C)CC1]

Lipid 222 8-((2-(((2-(4-methylpiperazin-1-yl)ethyl)carbamoyl)oxy)ethyl)(6-oxo-6-(undecyloxy)hexyl)amino)octyl 2-hexyldecanoate was synthesized according to the general synthetic scheme and general methods. MS [ESI]: m/z: [M+H] calc. 865.8 obs. 866.1; $^1$H NMR (400 MHz, $CDCl_3$): δ 0.89 (9H, m), 1.31 (53H, m), 1.63 (7H, m), 2.32 (7H, m), 2.49 (13H, m), 2.71 (2H, m), 3.29 (2H, m), 4.07 (7H, m).

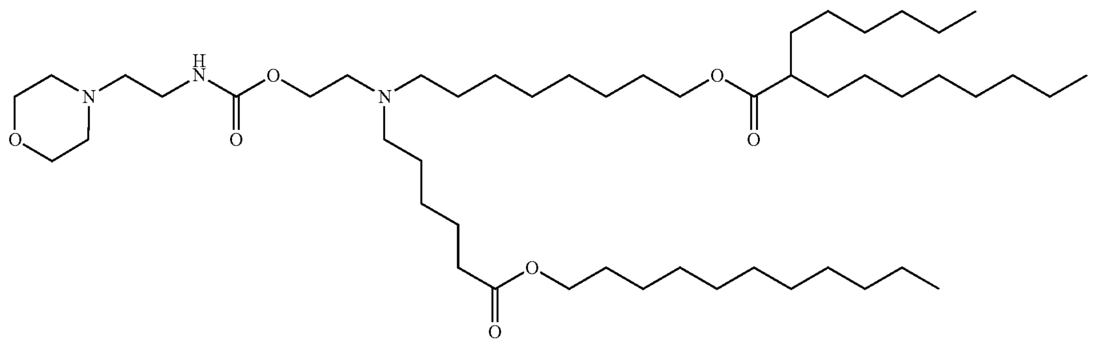 [SMILES: CCCCCCCCCCCOC(=O)CCCCCN(CCCCCCCCOC(=O)C(CCCCCC)CCCCCCCC)CCOC(=O)NCCN1CCOCC1]

Lipid 223 8-((2-(((2-morpholinoethyl)carbamoyl)oxy)ethyl)(6-oxo-6-(undecyloxy)hexyl)amino)octyl 2-hexyldecanoate was synthesized according to the general synthetic scheme and general methods. MS [ESI]: m/z: [M+H] calc. 852.7 obs. 853.1; $^1$H NMR (400 MHz, $CDCl_3$): δ 0.89 (9H, m), 1.30 (50H, m), 1.63 (8H, m), 2.31 (3H, m), 2.47 (11H, m), 2.70 (2H, m), 3.29 (2H, m), 3.71 (5H, m), 4.07 (7H, m).

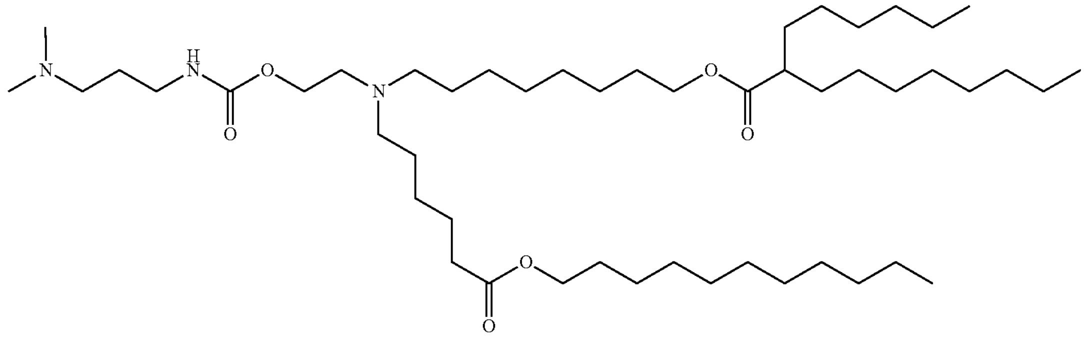 [SMILES: CCCCCCCCCCCOC(=O)CCCCCN(CCCCCCCCOC(=O)C(CCCCCC)CCCCCCCC)CCOC(=O)NCCCN(C)C]

Lipid 224 undecyl 11-(8-((2-hexyldecanoyl)oxy)octyl)-2-methyl-7-oxo-8-oxa-2,6,11-triazaheptadecan-17-oate was synthesized according to the general synthetic scheme and general methods. MS [ESI]: m/z: [M+H] calc. 824.7 obs. 825.0; $^1$H NMR (400 MHz, $CDCl_3$): δ 0.89 (9H, m), 1.30 (52H, m), 1.64 (14H, m), 2.22 (6H, s), 2.33 (6H, m), 2.46 (4H, m), 3.25 (1H, m), 4.09 (3H, m), 2.68 (2H, m).

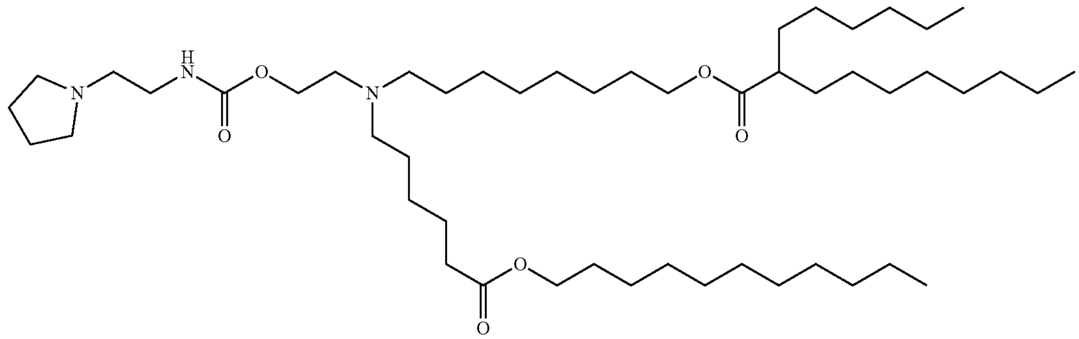 [SMILES: CCCCCCCCCCCOC(=O)CCCCCN(CCCCCCCCOC(=O)C(CCCCCC)CCCCCCCC)CCOC(=O)NCCN1CCCC1]

Lipid 226 8-((6-oxo-6-(undecyloxy)hexyl)(2-(((2-(pyrrolidin-1-yl)ethyl)carbamoyl)oxy)ethyl)amino)octyl 2-hexyldecanoate was synthesized according to the general synthetic scheme and general methods. MS [ESI]: m/z: [M+H] calc. 836.7 obs. 837.0; $^{1}H$ NMR (400 MHz, $CDCl_3$): $^{1}H$ NMR (400 MHz): δ 0.89 (9H, m), 1.26 (52H, m), 1.55-1.65 (8H, m), 2.26-2.34 (3H, 2.29 (t, J=7.43 Hz), 2.28 (m)), 2.47 (10H, m), 2.66 (1H, m), 3.23-3.29 (2H, m), 4.03-4.12 (6H, 4.05 (td, J=6.74, 3.08 Hz), 4.09 (m)), 5.24-5.28 (1H, m), 1.76 (5H, m).

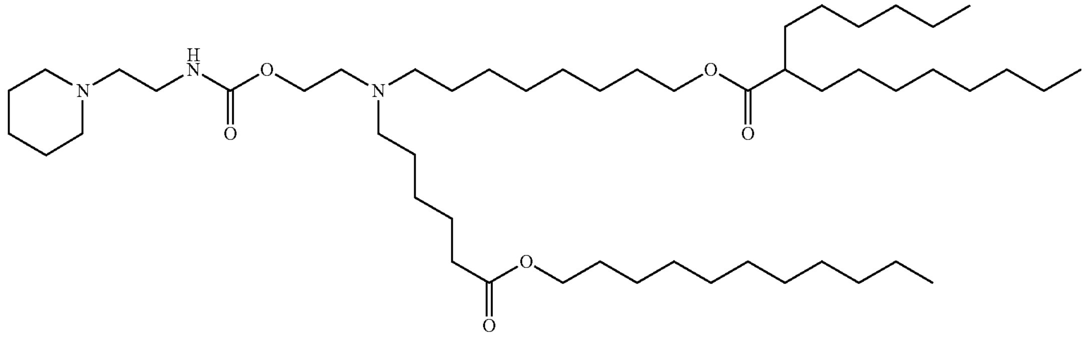 [SMILES: CCCCCCCCCCCOC(=O)CCCCCN(CCCCCCCCOC(=O)C(CCCCCC)CCCCCCCC)CCOC(=O)NCCN1CCCCC1]

Lipid 227 8-((6-oxo-6-(undecyloxy)hexyl)(2-(((2-(piperidin-1-yl)ethyl)carbamoyl)oxy) ethyl)amino)octyl 2-hexyldecanoate was synthesized according to the general synthetic scheme and general methods. MS [ESI]: m/z: [M+H] calc. 850.8 obs. 851.1; $^{1}H$ NMR (400 MHz, $CDCl_3$): δ 0.87 (9H, s), 1.29 (54H, m), 1.58 (12H, m), 2.38 (13H, m), 2.67 (2H, t, J=6.45 Hz), 3.25 (2H, m), 4.07 (6H, m), 5.29 (1H, m).

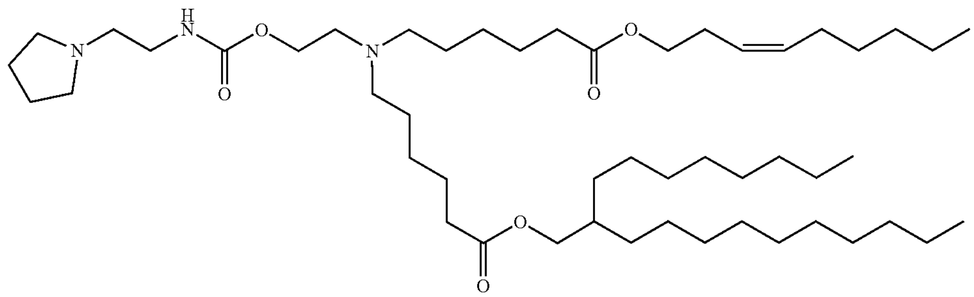

Lipid 244 (Z)-non-3-en-1-yl 6-((6-((2-octyldodecyl)oxy)-6-oxohexyl)(2-(((2-(pyrrolidin-1-yl)ethyl)carbamoyl)oxy)ethyl)amino)hexanoate was synthesized according to the general synthetic scheme and general methods. MS [ESI]: m/z: [M+H] calc. 834.7 obs. 835.0; $^1$H NMR (400 MHz, $CDCl_3$): δ 0.88 (9H, m), 1.28 (47H, m), 1.62 (5H, m), 1.76 (4H, m), 2.03 (2H, q, J=7.86 Hz), 2.29 (4H, tds, J=7.58, 2.51 Hz), 2.37 (2H, q, J=7.17 Hz), 2.47 (8H, m), 2.58 (2H, t, J=5.98 Hz), 2.66 (2H, t, J=6.75 Hz), 3.28 (2H, m), 3.96 (2H, d, J=5.72 Hz), 4.07 (4H, m), 5.33 (1H, m), 5.49 (1H, m).

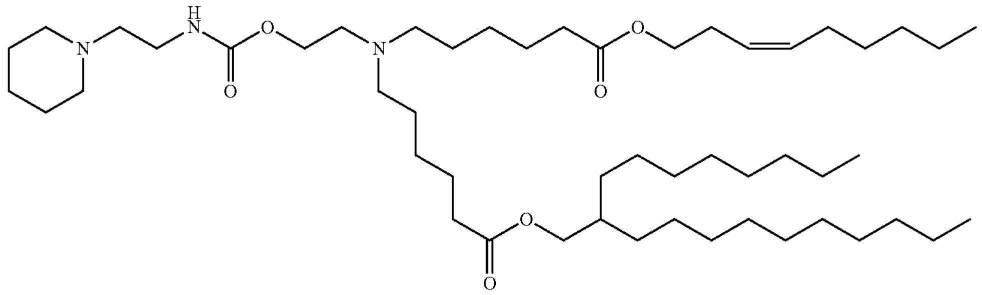 [SMILES: CCCCC/C=C\CCOC(=O)CCCCCN(CCCCCC(=O)OCC(CCCCCCCC)CCCCCCCCCC)CCOC(=O)NCCN1CCCCC1]

Lipid 245 (Z)-non-3-en-1-yl 6-((6-((2-octyldodecyl)oxy)-6-oxohexyl)(2-(((2-(piperidin-1-yl)ethyl)carbamoyl)oxy)ethyl)amino)hexanoate was synthesized according to the general synthetic scheme and general methods. MS [ESI]: m/z: [M+H] calc 848.7 obs. 848.9; $^1$H NMR (400 MHz, $CDCl_3$): δ 0.90 (9H, m), 1.28 (45H, m), 1.61 (13H, m), 2.05 (2H, q, J=7.34 Hz), 2.38 (16H, m), 2.68 (2H, t, J=7.26 Hz), 3.27 (2H, m), 3.98 (2H, d, J=5.80 Hz), 4.08 (4H, m), 5.33-5.37 (1H, m), 5.47-5.55 (1H, m).

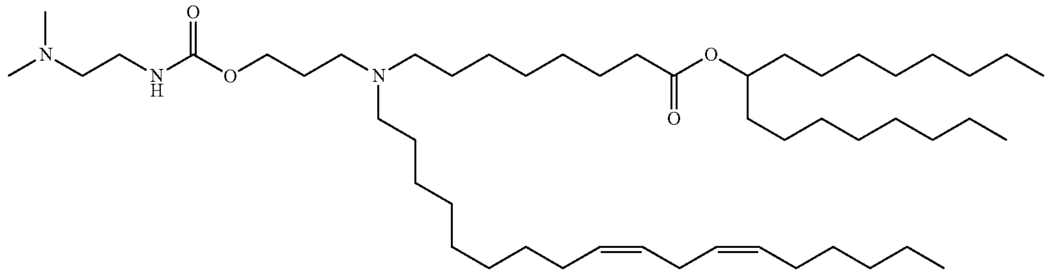 [SMILES: CCCCC/C=C\C/C=C\CCCCCCCCN(CCCCCCCC(=O)OC(CCCCCCCC)CCCCCCCC)CCCOC(=O)NCCN(C)C]

Lipid 270 heptadecan-9-yl 2-methyl-11-((9Z,12Z)-octadeca-9,12-dien-1-yl)-6-oxo-7-oxa-2,5,11-triazanonadecan-19-oate was synthesized according to the general synthetic scheme and general methods. MS [ESI]: m/z: [M+H] calc 818.8 obs. 819.1; $^1$H NMR (400 MHz, $CDCl_3$): δ 0.88 (9H, m), 1.26 (49H, m), 1.50 (4H, m), 1.61 (5H, m), 2.05 (4H, q, J=6.94 Hz), 2.22 (6H, s), 2.27 (2H, t, J=7.53 Hz), 2.38 (6H, m), 2.46 (1H, m), 2.76 (2H, t, J=6.57 Hz), 4.06-4.09 (1H, m), 5.36 (4H, m), 3.22-3.28 (2H, m), 1.69-1.76 (2H, m), 4.86 (1H, i, J=6.41 Hz), 5.08-5.15 (1H, m).

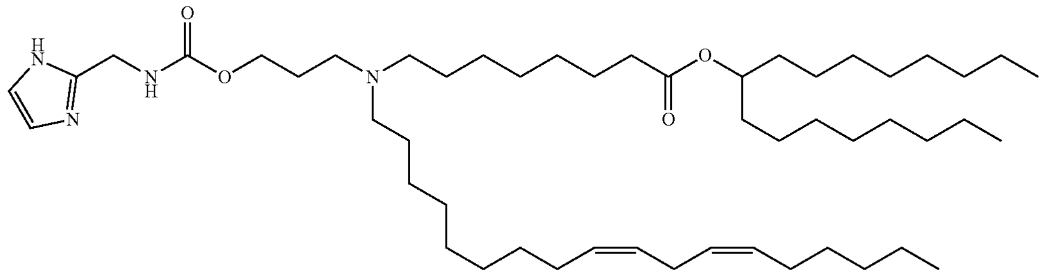 [SMILES: CCCCC/C=C\C/C=C\CCCCCCCCN(CCCCCCCC(=O)OC(CCCCCCCC)CCCCCCCC)CCCOC(=O)NCc1ncc[nH]1]

Lipid 271 heptadecan-9-yl 8-((3-((((1H-imidazol-2-yl)methyl)carbamoyl)oxy)propyl)((9Z,12Z)-octadeca-9,12-dien-1-yl)amino)octanoate was synthesized according to the general synthetic scheme and general methods. MS [ESI]: m/z: [M+H] calc 827.7 obs. 828.1; $^1$H NMR (400 MHz, $CDCl_3$): δ 0.90 (9H, m), 1.28 (56H, m), 1.62 (5H, m), 1.72-1.79 (1H, m), 2.07 (4H, q, J=6.77 Hz), 2.29 (2H, t, J=7.49 Hz), 2.37 (3H, m), 2.44-2.49 (2H, m), 2.78 (2H, t, J=6.52 Hz), 4.15 (1H, m), 4.37-4.40 (2H, 4.39 (d, J=6.13 Hz), 4.38 (s)), 4.88 (1H, i, J=5.95 Hz), 5.38 (4H, m), 6.98 (2H, s).

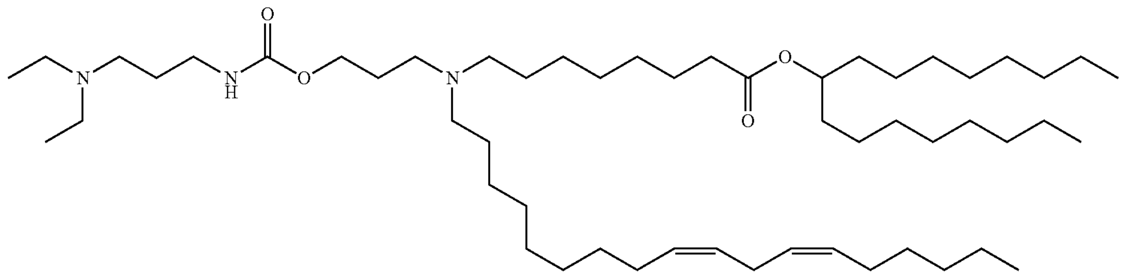 [SMILES: CCCCC/C=C\C/C=C\CCCCCCCCN(CCCCCCCC(=O)OC(CCCCCCCC)CCCCCCCC)CCCOC(=O)NCCCN(CC)CC]

Lipid 272 heptadecan-9-yl 3-ethyl-13-((9Z,12Z)-octadeca-9,12-dien-1-yl)-8-oxo-9-oxa-3,7,13-triazahenicosan-21-oate was synthesized according to the general synthetic scheme and general methods. MS [ESI]: m/z: [M+H] calc 860.8 obs. 861.1; $^1$H NMR (400 MHz, $CDCl_3$): δ 0.88 (9H, m), 1.02 (6H, t, J=7.13 Hz), 1.29 (49H, m), 1.50 (4H, m), 1.62 (5H, m), 1.73 (2H, m), 2.04 (4H, q, J=6.99 Hz), 2.27 (2H, t, J=7.43 Hz), 2.37 (4H, m), 2.48 (8H, m), 2.77 (2H, t, J=6.49 Hz), 3.24 (2H, m), 4.06 (2H, m), 4.86 (1H, quint, J=6.29 Hz), 5.35 (4H, m), 6.01 (1H, m).

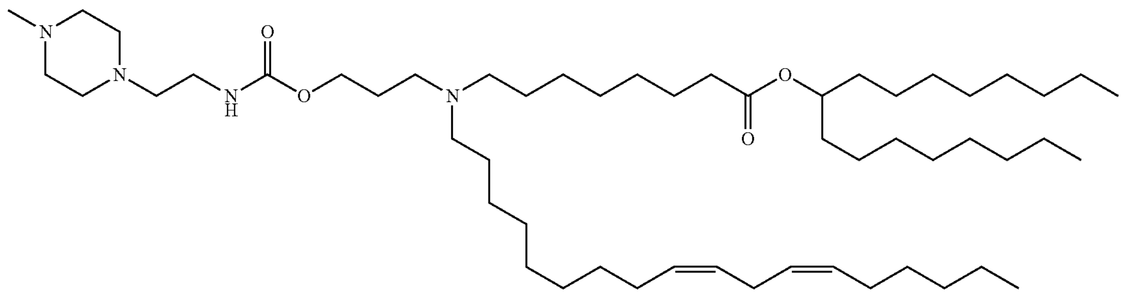 [SMILES: CCCCC/C=C\C/C=C\CCCCCCCCN(CCCCCCCC(=O)OC(CCCCCCCC)CCCCCCCC)CCCOC(=O)NCCN1CCN(C)CC1]

Lipid 273 heptadecan-9-yl 8-((3-(((2-(4-methylpiperazin-1-yl)ethyl)carbamoyl)oxy)propyl)((9Z,12Z)-octadeca-9,12-dien-1-yl)amino)octanoate was synthesized according to the general synthetic scheme and general methods. MS [ESI]: m/z: [M+H] calc 873.8 obs. 874.1; $^{1}H$ NMR (400 MHz, $CDCl_3$): δ 0.88 (9H, m), 1.27 (53H, m), 1.50 (3H, m), 1.61 (2H, m), 1.75 (2H, m), 2.04 (4H, q, J=7.39 Hz), 2.28 (5H, m), 2.44 (14H, m), 2.77 (2H, t, J=6.58 Hz), 3.26 (2H, m), 4.08 (2H, t, J=6.58 Hz), 4.86 (1H, quint, J=6.25 Hz), 5.11 (1H, m), 5.35 (4H, m).

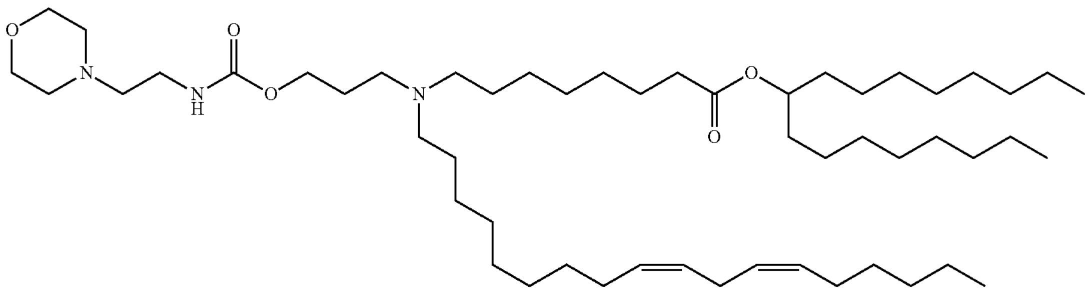 [SMILES: CCCCC/C=C\C/C=C\CCCCCCCCN(CCCCCCCC(=O)OC(CCCCCCCC)CCCCCCCC)CCCOC(=O)NCCN1CCOCC1]

Lipid 274 heptadecan-9-yl 8-((3-(((2-morpholinoethyl)carbamoyl)oxy)propyl)((9Z,12Z)-octadeca-9,12-dien-1-yl)amino)octanoate was synthesized according to the general synthetic scheme and general methods. MS [ESI]: m/z: [M+H] calc 860.8 obs. 861.0; $^{1}H$ NMR (400 MHz, $CDCl_3$): δ 0.88 (9H, m), 1.28 (50H, m), 1.50 (4H, m), 1.61 (2H, m), 1.75 (2H, m), 2.04 (4H, q, J=7.13 Hz), 2.27 (2H, t, J=7.50 Hz), 2.43 (12H, m), 2.77 (2H, t, J=6.41 Hz), 3.27 (2H, m), 3.70 (4H, m), 4.09 (2H, t, J=7.34 Hz), 4.86 (1H, guint, J=6.26 Hz) 5.11 (1H, m), 5.35 (4H, m).

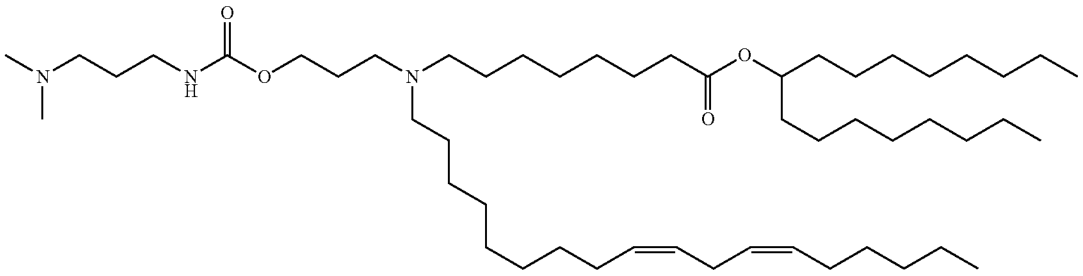 [SMILES: CCCCC/C=C\C/C=C\CCCCCCCCN(CCCCCCCC(=O)OC(CCCCCCCC)CCCCCCCC)CCCOC(=O)NCCCN(C)C]

Lipid 275 heptadecan-9-yl 2-methyl-12-((9Z,12Z)-octadeca-9,12-dien-1-yl)-7-oxo-8-oxa-2,6,12-triazaicosan-20-oate was synthesized according to the general synthetic scheme and general methods. MS [ESI]: m/z: [M+H] calc 832.8 obs. 833.1; $^{1}H$ NMR (400 MHz, $CDCl_3$): δ 0.88 (9H, m), 1.29 (48H, m), 1.50 (4H, m), 1.63 (5H, m), 1.74 (3H, m), 2.05 (4H, q, J=6.72 Hz), 2.21 (6H, s), 2.27 (2H, t, J=7.83 Hz), 2.36 (6H, m), 2.47 (2H, t, J=7.01 Hz), 2.77 (2H, t, J=6.49 Hz), 3.24 (2H, q, J=6.96 Hz), 4.07 (2H, t, J=6.83 Hz), 4.86 (1H, quint, J=6.75 Hz), 5.36 (4H, m), 5.47 (1H, m).

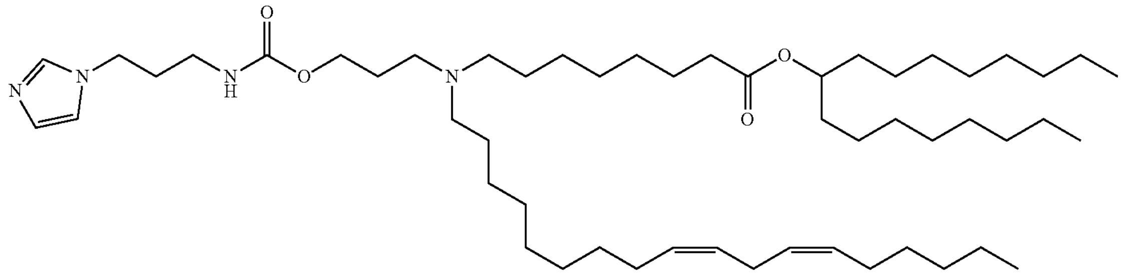 [SMILES: CCCCC/C=C\C/C=C\CCCCCCCCN(CCCCCCCC(=O)OC(CCCCCCCC)CCCCCCCC)CCCOC(=O)NCCCn1ccnc1]

Lipid 276 heptadecan-9-yl 8-((3-(((3-(1H-imidazol-1-yl)propyl)carbamoyl)oxy)propyl)((9Z,12Z)-octadeca-9,12-dien-1-yl)amino)octanoate was synthesized according to the general synthetic scheme and general methods. MS [ESI]: m/z: [M+H] calc 855.8 obs. 856.0; $^{1}$H NMR (400 MHz, $CDCl_3$): $^{1}$H NMR (400 MHz): δ 0.87 (9H, m), 1.25 (53H, m), 1.57-1.64 (2H, m), 1.73 (3H, m), 2.04 (6H, m), 2.27 (2H, t, J=7.50 Hz), 2.34-2.40 (4H, 2.37 (t, J=7.48 Hz), 2.37 (d, J=4.10 Hz)), 2.46 (2H, t, J=7.26 Hz), 2.77 (2H, t, J=6.17 Hz), 3.19 (2H, q, J=6.32 Hz), 4.00 (2H, t, J=7.01 Hz), 4.10 (2H, t, J=5.97 Hz), 4.86 (1H, i, J=6.24 Hz), 5.35 (4H, m), 6.93 (1H, s), 7.07 (1H, s), 7.49 (1H, s).

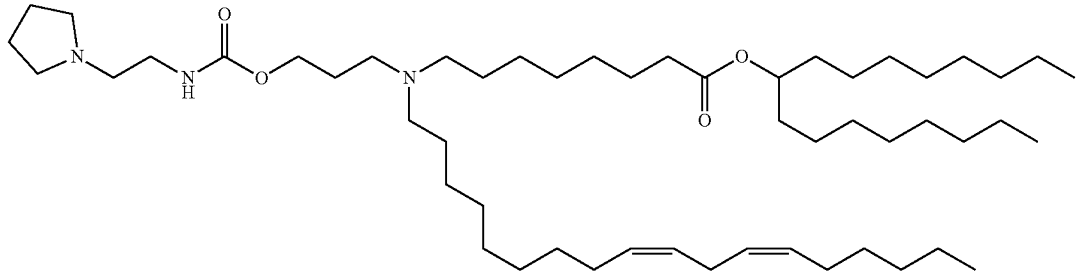 [SMILES: CCCCC/C=C\C/C=C\CCCCCCCCN(CCCCCCCC(=O)OC(CCCCCCCC)CCCCCCCC)CCCOC(=O)NCCN1CCCC1]

Lipid 277 heptadecan-9-yl 8-(((9Z,12Z)-octadeca-9,12-dien-1-yl)(3-(((2-(pyrrolidin-1-yl)ethyl)carbamoyl)oxy)propyl)amino)octanoate was synthesized according to the general synthetic scheme and general methods. MS [ESI]: m/z: [M+H] calc 844.8 obs. 844.9; $^{1}$H NMR (400 MHz, $CDCl_3$): δ 0.88 (9H, m), 1.30 (53H, m), 1.61 (3H, m), 1.76 (6H, m), 2.05 (4H, q, J=7.21 Hz), 2.27 (2H, t, J=7.67 Hz), 2.37 (4H, m), 2.49 (6H, m), 2.58 (2H, t, J=6.15 Hz), 2.77 (2H, t, J=6.41 Hz), 3.28 (2H, m), 4.08 (2H, t, J=6.88 Hz), 4.86 (1H, quint, J=6.26 Hz), 5.15 (1H, m), 5.35 (4H, m).

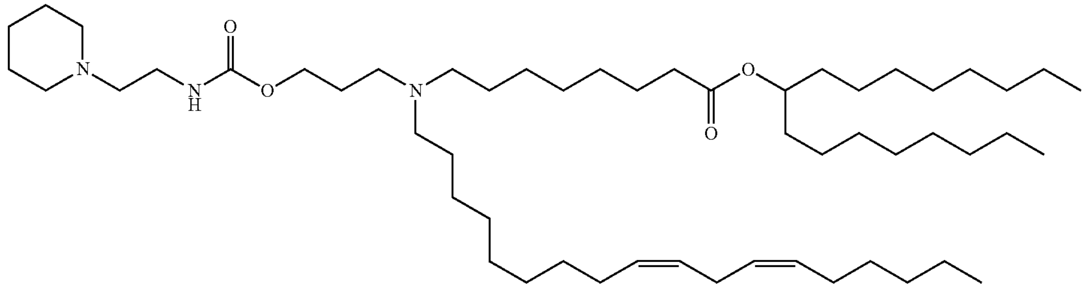 [SMILES: CCCCC/C=C\C/C=C\CCCCCCCCN(CCCCCCCC(=O)OC(CCCCCCCC)CCCCCCCC)CCCOC(=O)NCCN1CCCCC1]

Lipid 278 heptadecan-9-yl 8-(((9Z,12Z)-octadeca-9,12-dien-1-yl)(3-(((2-(piperidin-1-yl)ethyl)carbamoyl)oxy)propyl)amino)octanoate was synthesized according to the general synthetic scheme and general methods. MS [ESI]: m/z: [M+H] calc 858.8 obs. 859.0; $^{1}$H NMR (400 MHz, $CDCl_3$): δ 0.88 (9H, m), 1.34 (62H, m), 1.74 (2H, m), 2.05 (4H, q, J=6.80 Hz), 2.27 (2H, t, J=7.56 Hz), 2.37 (10H, m), 2.47 (2H, t, J=7.11 Hz), 2.77 (2H, t, J=6.41 Hz), 3.25 (2H, m), 4.08 (2H, t, J=6.28 Hz), 4.86 (1H, quint, J=6.27 Hz), 5.15 (1H, m), 5.36 (4H,

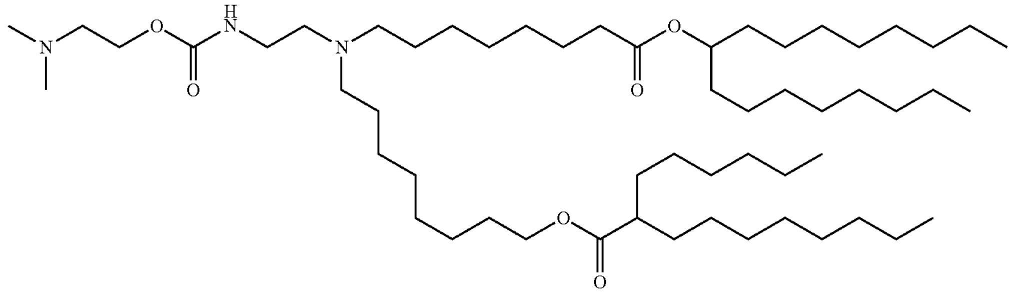 [SMILES: CCCCCCCCC(CCCCCCCC)OC(=O)CCCCCCCN(CCCCCCCCOC(=O)C(CCCCCC)CCCCCCCC)CCNC(=O)OCCN(C)C]

Lipid 279 heptadecan-9-yl 10-(8-((2-hexyldecanoyl)oxy)octyl)-2-methyl-6-oxo-5-oxa-2,7,10-triazaoctadecan-18-oate was synthesized according to the general synthetic scheme and general methods. MS [ESI]: m/z: [M+H] calc 922.9 obs. 923.2; $^{1}$H NMR (400 MHz, $CDCl_3$): δ 0.87 (12H, t, J=7.20 Hz), 1.32 (74H, m), 2.28 (9H, m), 2.37 (4H, m), 2.50 (2H, t, J=6.31 Hz), 2.55 (2H, t, J=6.06 Hz), 3.20 (2H, m), 4.06 (2H, t, J=6.81 Hz), 4.16 (2H, t, J=5.58 Hz), 4.86 (1H, i, J=5.68 Hz), 5.24 (1H, m).

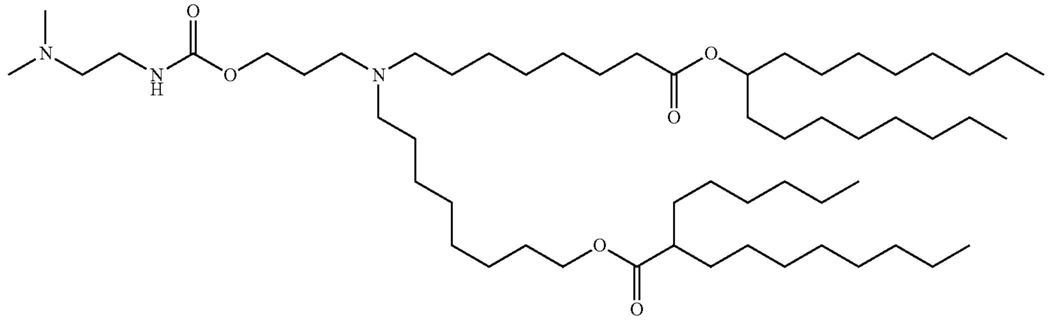 [SMILES: CCCCCCCCC(CCCCCCCC)OC(=O)CCCCCCCN(CCCCCCCCOC(=O)C(CCCCCC)CCCCCCCC)CCCOC(=O)NCCN(C)C]

Lipid 344 heptadecan-9-yl 11-(8-((2-hexyldecanoyl)oxy)octyl)-2-methyl-6-oxo-7-oxa-2,5,11-triazanonadecan-19-oate was synthesized according to the general synthetic scheme and general methods. MS [ESI]: m/z: [M+H] calc 936.9 obs. 937.2; $^{1}$H NMR (500 MHz, $CDCl_3$): δ 0.87 (12H, m), 1.25 (71H, m), 1.73 (2H, m), 2.22 (6H, m), 2.34 (10H, m), 2.46 (2H, m), 3.24 (2H, m), 4.06 (5H, m), 4.86 (2H, m), 5.12 (1H, m).

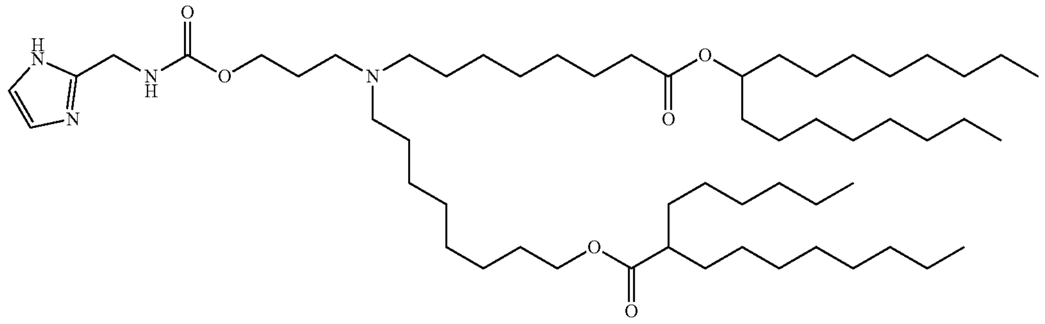 [SMILES: CCCCCCCCC(CCCCCCCC)OC(=O)CCCCCCCN(CCCCCCCCOC(=O)C(CCCCCC)CCCCCCCC)CCCOC(=O)NCc1ncc[nH]1]

Lipid 345 8-((3-((((1H-imidazol-2-yl)methyl)carbamoyl)oxy)propyl)(8-(heptadecan-9-yloxy)-8-oxooctyl)amino)octyl 2-hexyldecanoate was synthesized according to the general synthetic scheme and general methods. MS [ESI]: m/z: [M+H] calc 945.8 obs. 946.1; $^1$H NMR (500 MHz, $CDCl_3$): δ 0.88 (12H, m), 1.27 (62H, m), 1.50 (4H, m), 1.61 (8H, m), 1.73 (2H, m), 2.32 (7H, m), 2.44 (2H, t, J=6.92 Hz), 4.06 (2H, t, J=6.63 Hz), 4.13 (2H, t, J=6.41 Hz), 4.37 (2H, d, J=5.88 Hz), 4.86 (2H, quint, J=6.68 Hz), 5.47 (1H, m), 6.96 (2H, s).

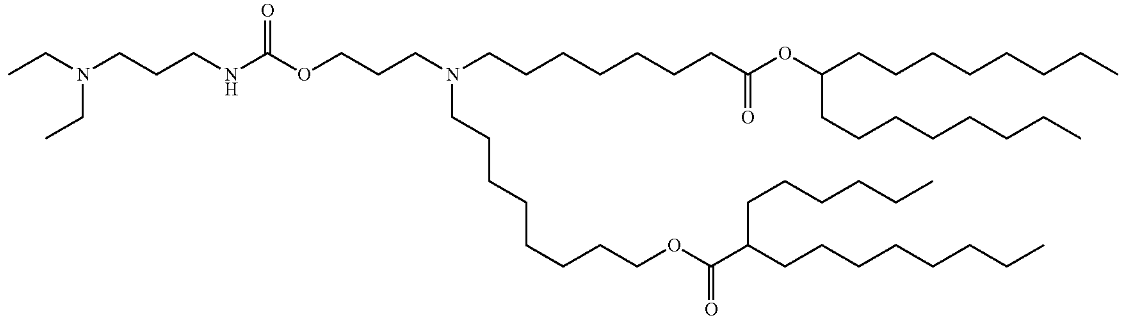 [SMILES: CCCCCCCCC(CCCCCCCC)OC(=O)CCCCCCCN(CCCCCCCCOC(=O)C(CCCCCC)CCCCCCCC)CCCOC(=O)NCCCN(CC)CC]

Lipid 346 heptadecan-9-yl 3-ethyl-13-(8-((2-hexyldecanoyl)oxy)octyl)-8-oxo-9-oxa-3,7,13-triazahenicosan-21-oate was synthesized according to the general synthetic scheme and general methods. MS [ESI]: m/z: [M+H] calc 978.9 obs. 979.3; $^1$H NMR (500 MHz, $CDCl_3$): δ 0.88 (12H, m), 1.02 (5H, t, J=7.14 Hz), 1.27 (56H, m), 1.40 (6H, m), 1.50 (4H, q, J=6.41 Hz), 1.60 (10H, m), 1.72 (2H, m), 2.28 (7H, m), 2.48 (8H, m), 3.24 (3H, m), 4.06 (4H, t, J=6.57 Hz), 4.86 (2H, m).

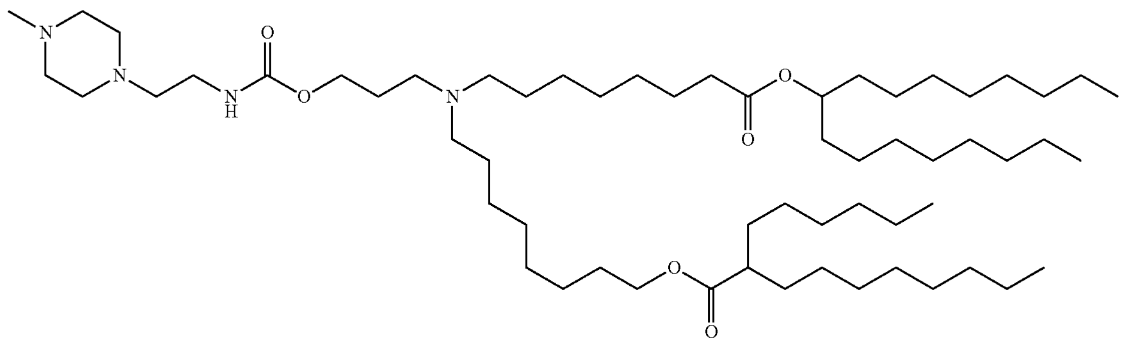 [SMILES: CCCCCCCCC(CCCCCCCC)OC(=O)CCCCCCCN(CCCCCCCCOC(=O)C(CCCCCC)CCCCCCCC)CCCOC(=O)NCCN1CCN(C)CC1]

Lipid 347 8-((8-(heptadecan-9-yloxy)-8-oxooctyl)(3-(((2-(4-methylpiperazin-1-yl)ethyl)carbamoyl)oxy)propyl)amino)octyl 2-hexyldecanoate was synthesized according to the general synthetic scheme and general methods. MS [ESI]: m/z: [M+H] calc 991.9 obs. 992.2; $^{1}H$ NMR (500 MHz, $CDCl_3$): δ 0.87 (12H, m), 1.25 (61H, m), 1.50 (5H, m), 1.61 (7H, m), 1.72 (3H, m), 2.39 (22H, m), 3.27 (2H, m), 4.07 (4H, m), 4.86 (1H, quint, J=6.84 Hz), 5.11 (1H, m).

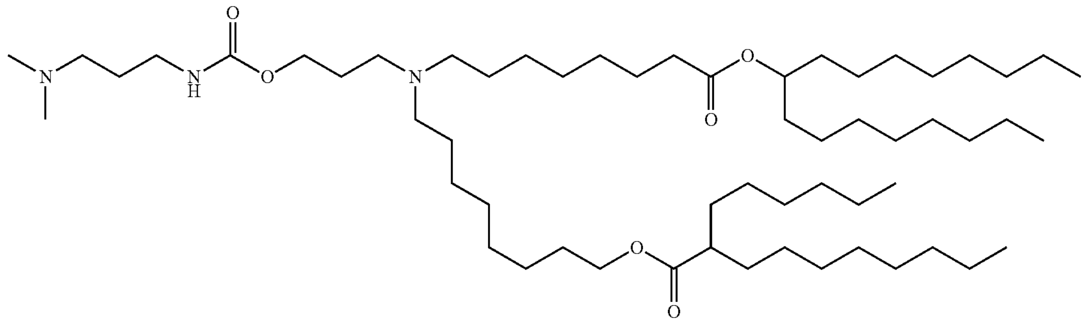 [SMILES: CCCCCCCCC(CCCCCCCC)OC(=O)CCCCCCCN(CCCCCCCCOC(=O)C(CCCCCC)CCCCCCCC)CCCOC(=O)NCCCN(C)C]

Lipid 348 heptadecan-9-yl 12-(8-((2-hexyldecanoyl)oxy)octyl)-2-methyl-7-oxo-8-oxa-2,6,12-triazaicosan-20-oate was synthesized according to the general synthetic scheme and general methods. MS [ESI]: m/z: [M+H] calc 950.9 obs. 951.2; $^{1}H$ NMR (500 MHz, $CDCl_3$): δ 0.87 (12H, m), 1.28 (61H, m), 1.50 (4H, m), 1.61 (9H, m), 1.73 (3H, m), 2.21 (6H, s), 2.33 (9H, m), 2.46 (2H, t, J=8.55 Hz), 3.23 (2H, m), 4.06 (4H, m), 4.86 (1H, m), 5.47 (1H, m).

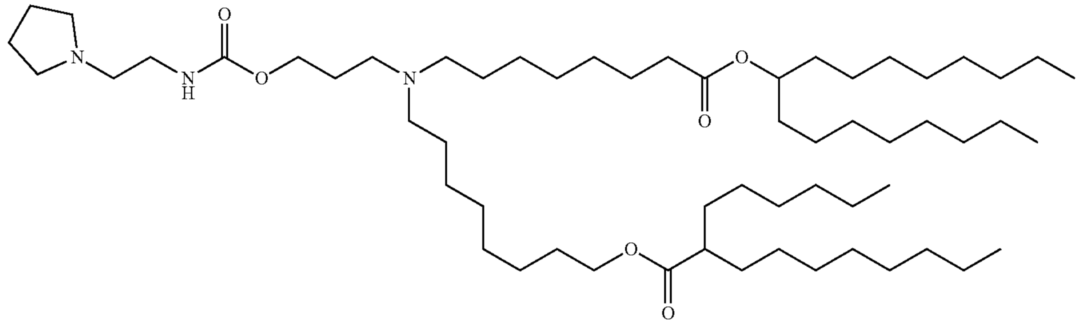 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCC1]

Lipid 349 8-((3-(((3-(1H-imidazol-1-yl)propyl)carbamoyl)oxy)propyl)(8-(heptadecan-9-yloxy)-8-oxooctyl)amino)octyl 2-hexyldecanoate was synthesized according to the general synthetic scheme and general methods. MS [ESI]: m/z: [M+H] calc 973.9 obs. 974.2; $^{1}H$ NMR (500 MHz, $CDCl_3$): δ 0.88 (12H, m), 1.25 (74H, m), 1.75 (1H, m), 2.00 (2H, m), 2.27 (3H, m), 2.40 (3H, m), 2.49 (2H, m), 3.19 (2H, m), 3.77 (1H, m), 4.00 (5H, m), 4.86 (2H, m), 6.94 (1H, m), 7.06 (1H, m), 7.49 (1H, d, J=1.60 Hz).

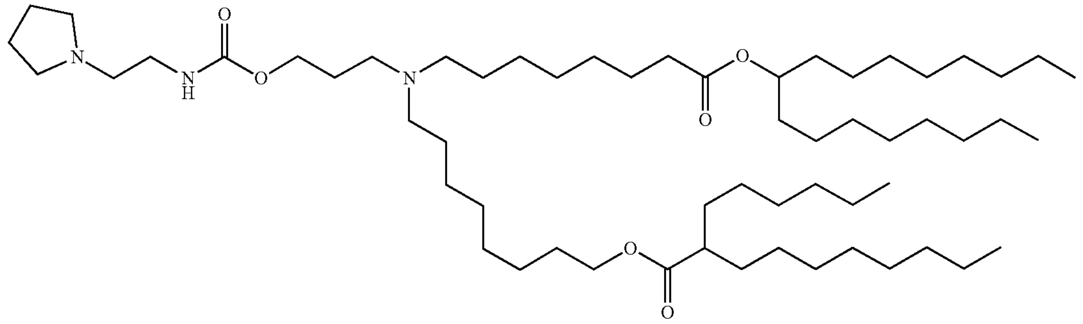 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCC1]

Lipid 350 8-((8-(heptadecan-9-yloxy)-8-oxooctyl)(3-(((2-(pyrrolidin-1-yl)ethyl)carbamoyl)oxy)propyl)amino)octyl 2-hexyldecanoate was synthesized according to the general synthetic scheme and general methods. MS [ESI]: m/z: [M+H] calc 962.9 obs. 963.2; $^{1}$H NMR (500 MHz, $CDCl_3$): δ 0.87 (12H, m), 1.31 (74H, m), 1.75 (6H, m), 2.33 (7H, m), 2.48 (6H, m), 2.57 (2H, t, J=6.19 Hz), 3.28 (2H, m), 4.07 (4H, m), 4.86 (1H, quint, J=6.77 Hz), 5.15 (1H, m).

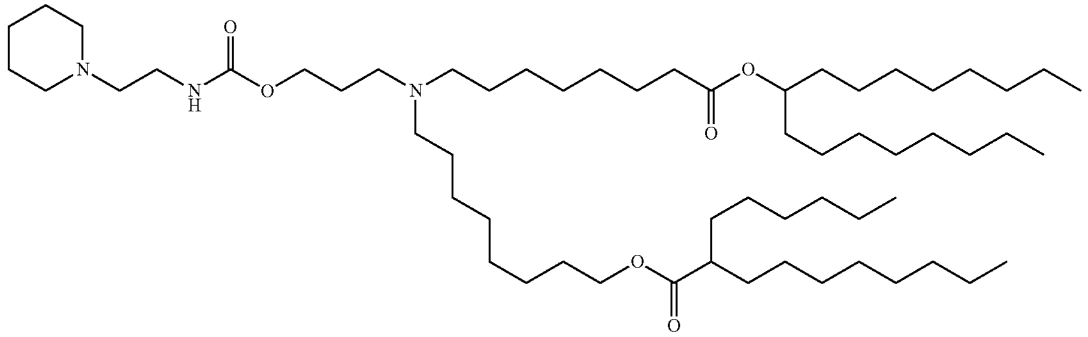 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCCC1]

Lipid 351 8-((8-(heptadecan-9-yloxy)-8-oxooctyl)(3-(((2-(piperidin-1-yl)ethyl)carbamoyl)oxy)propyl)amino)octyl 2-hexyldecanoate was synthesized according to the general synthetic scheme and general methods. MS [ESI]: m/z: [M+H] calc 976.9 obs. 977.2; $^{1}$H NMR (500 MHz, $CDCl_3$): δ 0.87 (12H, m), 1.33 (81H, m), 1.74 (2H, m), 2.37 (15H, m), 3.25 (2H, m), 4.07 (4H, m), 4.86 (1H, quint J=6.73 Hz), 5.16 (1H, m).

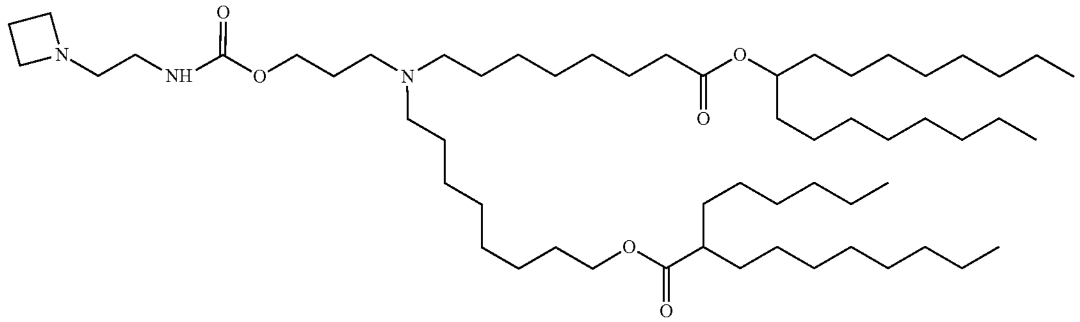 [SMILES: CCCCCCCCC(CCCCCCCC)OC(=O)CCCCCCCN(CCCCCCCCOC(=O)C(CCCCCC)CCCCCCCC)CCCOC(=O)NCCN1CCC1]

Lipid 353 8-((3-(((2-(azetidin-1-yl)ethyl)carbamoyl)oxy) propyl)(8-(heptadecan-9-yloxy)-8-oxooctyl)amino)octyl 2-hexyldecanoate was synthesized according to the general synthetic scheme and general methods. MS [ESI]: m/z: [M+H] calc 948.9 obs. 949.2; $^1$H NMR (500 MHz, $CDCl_3$): δ 0.87 (12H, m), 1.32 (72H, m), 1.72 (2H, m), 2.06 (2H, i, J=7.27 Hz), 2.33 (7H, m), 2.47 (4H, m), 3.12 (2H, m), 3.19 (4H, t, J=7.00 Hz), 4.06 (5H, m), 4.87 (2H, m), 5.03 (1H, m).

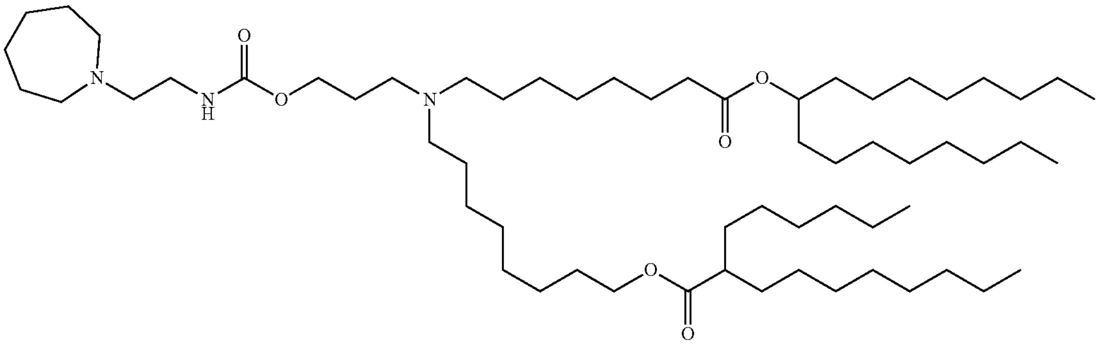 [SMILES: CCCCCCCCC(CCCCCCCC)OC(=O)CCCCCCCN(CCCCCCCCOC(=O)C(CCCCCC)CCCCCCCC)CCCOC(=O)NCCN1CCCCCC1]

Lipid 354 8-((3-(((2-(azepan-1-yl)ethyl)carbamoyl)oxy) propyl)(8-(heptadecan-9-yloxy)-8-oxooctyl)amino)octyl 2-hexyldecanoate was synthesized according to the general synthetic scheme and general methods. MS [ESI]: m/z: [M+H] calc 990.9 obs. 991.2; $^1$H NMR (500 MHz, $CDCl_3$): δ 0.87 (12H, m), 1.25 (83H, m), 1.74 (2H, m), 2.36 (6H, m), 2.46 (2H, m), 2.61 (5H, m), 3.21 (2H, m), 4.06 (4H, m), 4.86 (2H, ddt, J=6.95, 5.88, 2.08 Hz), 5.20 (1H, m).

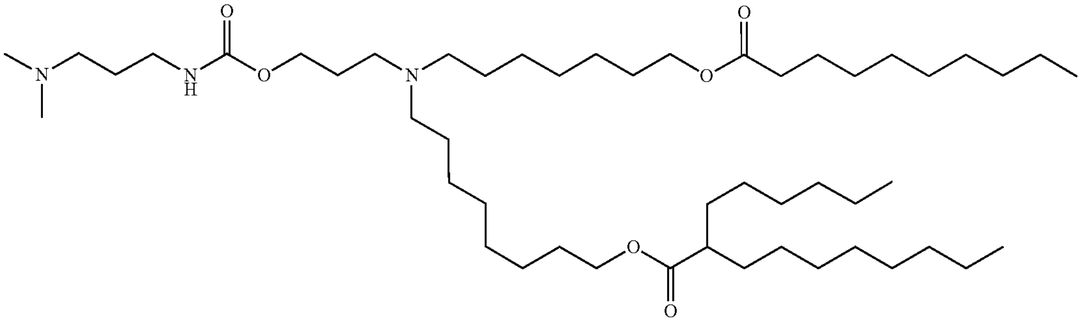 [SMILES: CCCCCCCCCC(=O)OCCCCCCCN(CCCCCCCCOC(=O)C(CCCCCC)CCCCCCCC)CCCOC(=O)NCCCN(C)C]

Lipid 355 12-(7-(decanoyloxy)heptyl)-2-methyl-7-oxo-8-oxa-2,6,12-triazaicosan-20-yl 2-hexyldecanoate was synthesized according to the general synthetic scheme and general methods. MS [ESI]: m/z: [M+H] calc 838.8 obs. 839.1; $^1$H NMR (400 MHz, $CDCl_3$): δ 0.88 (9H, t, J=0.95 Hz), 1.26 (50H, m), 1.61 (12H, m), 2.21 (6H, s), 2.29 (9H, m), 2.47 (2H, m), 3.23 (2H, m), 4.06 (6H, td, J=6.67, 3.04 Hz), 5.46 (1H, m).

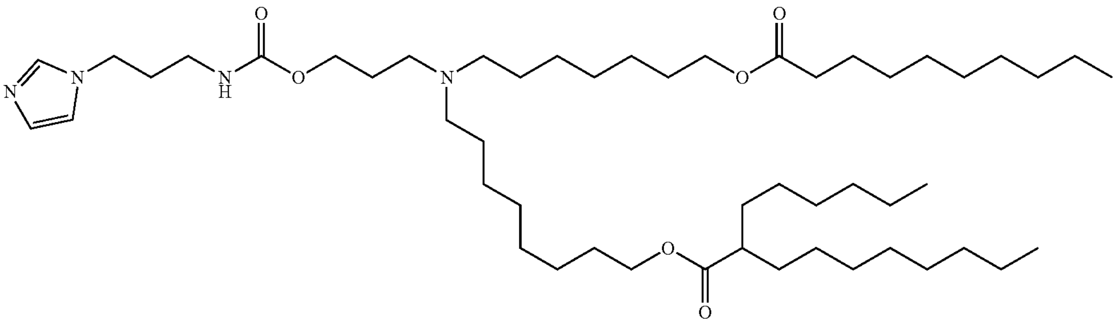 [SMILES: CCCCCCCCCC(=O)OCCCCCCCN(CCCCCCCCOC(=O)C(CCCCCC)CCCCCCCC)CCCOC(=O)NCCCn1ccnc1]

Lipid 356 8-((3-(((3-(1H-imidazol-1-yl)propyl)carbamoyl)oxy)propyl)(7-(decanoyloxy)heptyl)amino)octyl 2-hexyldecanoate was synthesized according to the general synthetic scheme and general methods. MS [ESI]: m/z: [M+H] calc 861.7 obs. 862.0; $^{1}$H NMR (400 MHz, $CDCl_3$): δ 0.87 (9H, t, J=0.96 Hz), 1.26 (53H, m), 1.61 (8H, m), 2.00 (2H, t, J=6.87 Hz), 2.28 (3H, t, J=7.58 Hz), 2.33-2.40 (4H, 2.34 (s), 2.36 (t, J=2.05 Hz), 2.38 (s)), 2.45 (2H, m), 3.19 (3H, m), 4.00 (2H, t, J=7.00 Hz), 4.06 (7H, m), 6.93 (1H, s), 7.06 (1H, s), 7.48 (1H, s).

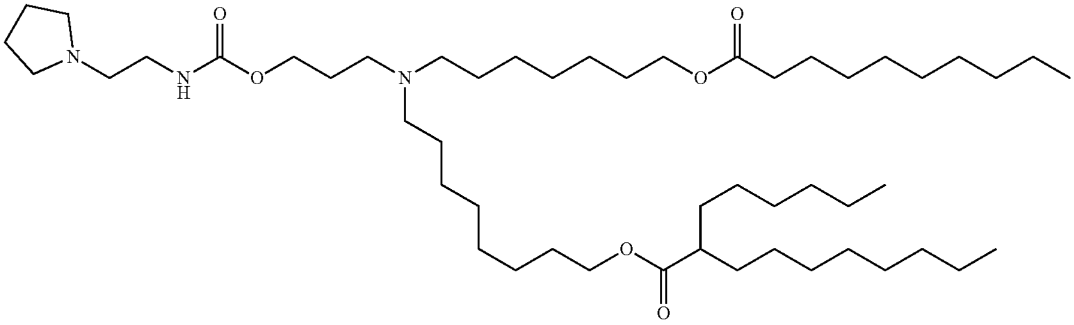 [SMILES: CCCCCCCCCC(=O)OCCCCCCCN(CCCCCCCCOC(=O)C(CCCCCC)CCCCCCCC)CCCOC(=O)NCCN1CCCC1]

Lipid 357 8-((7-(decanoyloxy)heptyl)(3-(((2-(pyrrolidin-1-yl)ethyl)carbamoyl)oxy)propyl)amino)octyl 2-hexyldecanoate was synthesized according to the general synthetic scheme and general methods. MS [ESI]: m/z: [M+H] calc 850.8 obs. 851.1; $^{1}$H NMR (400 MHz, $CDCl_3$): δ 0.87 (9H, m), 1.26 (56H, m), 1.61 (9H, m), 1.76 (5H, m), 2.28 (3H, t, J=7.59 Hz), 2.33-2.40 (4H, 2.36 (t, J=7.45 Hz), 2.36 (s)), 2.50 (6H, m), 2.58 (2H, t, J=6.12 Hz), 4.05 (5H, td, J=6.71, 3.12 Hz).

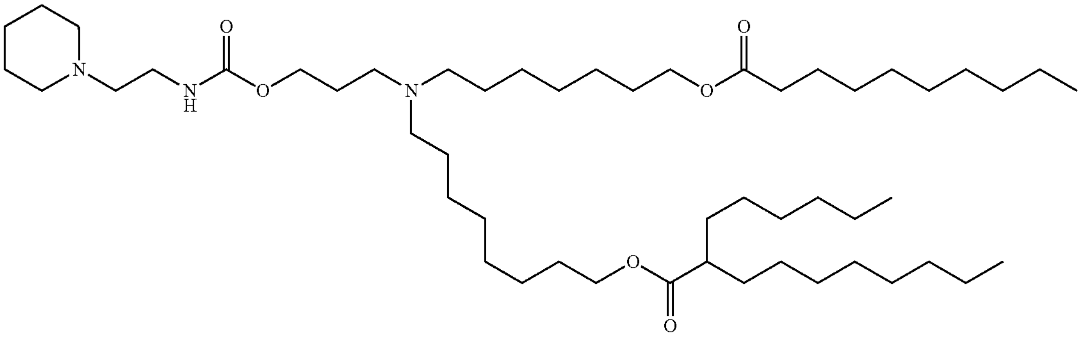 [SMILES: CCCCCCCCCC(=O)OCCCCCCCN(CCCCCCCCOC(=O)C(CCCCCC)CCCCCCCC)CCCOC(=O)NCCN1CCCCC1]

Lipid 358 8-((7-(decanoyloxy)heptyl)(3-(((2-(piperidin-1-yl)ethyl)carbamoyl)oxy)propyl)amino)octyl 2-hexyldecanoate was synthesized according to the general synthetic scheme and general methods. MS [ESI]: m/z: [M+H] calc 864.8 obs. 864.9; $^{1}H$ NMR (400 MHz, $CDCl_3$): δ 0.87 (9H, m), 1.26 (52H, m), 1.59 (13H, m), 1.74 (2H, m), 2.37 (16H, m), 3.26 (2H, m), 4.08 (6H, m), 5.16 (1H, m).

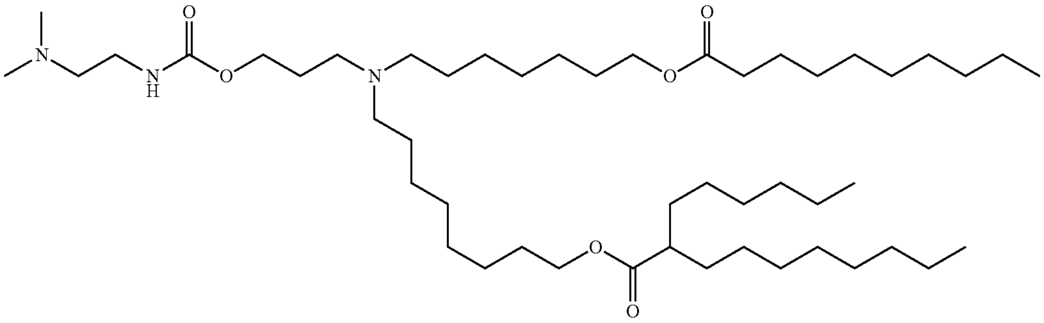 [SMILES: CCCCCCCCCC(=O)OCCCCCCCN(CCCCCCCCOC(=O)C(CCCCCC)CCCCCCCC)CCCOC(=O)NCCN(C)C]

Lipid 359 11-(7-(decanoyloxy)heptyl)-2-methyl-6-oxo-7-oxa-2,5,11-triazanonadecan-19-yl 2-hexyldecanoate was synthesized according to the general synthetic scheme and general methods. MS [ESI]: m/z: [M+H] calc 824.7 obs. 825.0; $^{1}H$ NMR (400 MHz, $CDCl_3$): δ 0.87 (9H, m), 1.29 (52H, m), 1.60 (9H, m), 1.73 (2H, m), 2.22 (6H, s), 2.28 (3H, t, J=7.59 Hz), 2.38 (6H, m), 2.46 (2H, t, J=7.40 Hz), 3.24 (2H, m), 4.06 (6H, m).

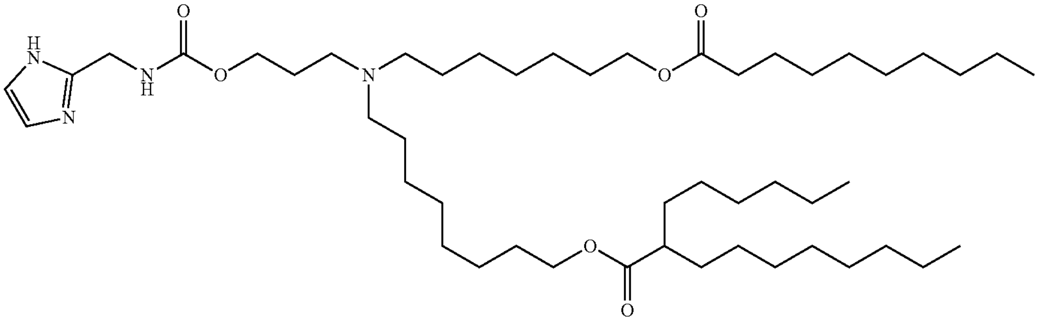 [SMILES: CCCCCCCCCC(=O)OCCCCCCCN(CCCCCCCCOC(=O)C(CCCCCC)CCCCCCCC)CCCOC(=O)NCc1ncc[nH]1]

Lipid 360 8-((3-((((1H-imidazol-2-yl)methyl)carbamoyl)oxy)propyl)(7-(decanoyloxy)heptyl)amino)octyl 2-hexyldecanoate was synthesized according to the general synthetic scheme and general methods. MS [ESI]: m/z: [M+H] calc 833.7 obs. 834.0; $^{1}H$ NMR (400 MHz, $CDCl_3$): δ 0.87 (9H, m), 1.26 (52H, m), 1.61 (9H, m), 1.73 (2H, m), 2.28 (7H, m), 2.44 (2H, m), 4.06 (4H, td, J=6.70, 3.24 Hz), 4.13 (2H, t, J=6.43 Hz), 4.37 (2H, d, J=6.08 Hz), 5.46 (1H, m), 6.96 (2H, s).

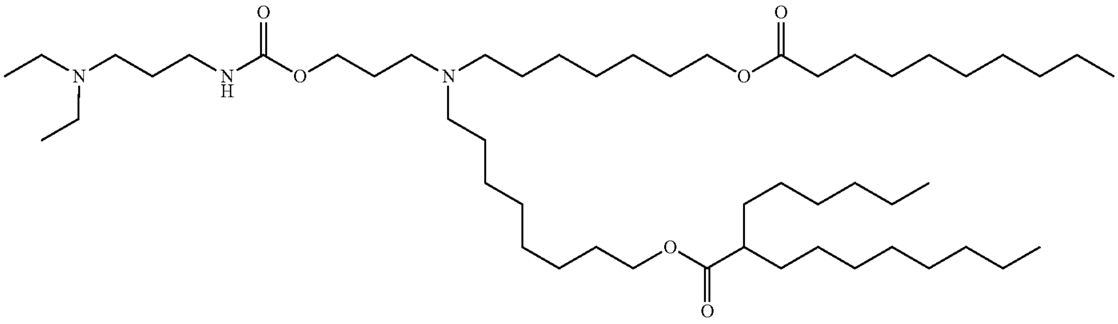 [SMILES: CCCCCCCCCC(=O)OCCCCCCCN(CCCCCCCCOC(=O)C(CCCCCC)CCCCCCCC)CCCOC(=O)NCCCN(CC)CC]

Lipid 361 13-(7-(decanoyloxy)heptyl)-3-ethyl-8-oxo-9-oxa-3,7,13-triazahenicosan-21-yl 2-hexyldecanoate was synthesized according to the general synthetic scheme and general methods. MS [ESI]: m/z: [M+H] calc 866.8 obs. 867.1; $^{1}H$ NMR (400 MHz, $CDCl_3$): δ 0.88 (9H, m), 1.02 (6H, t, J=7.14 Hz), 1.26 (53H, m), 1.61 (11H, quint, J=6.95 Hz), 1.72 (2H, m), 2.28 (3H, t, J=7.58 Hz), 2.36 (4H, t, J=7.46 Hz), 2.48 (8H, m), 3.24 (1H, s), 4.05 (6H, td, J=6.69, 3.37 Hz).

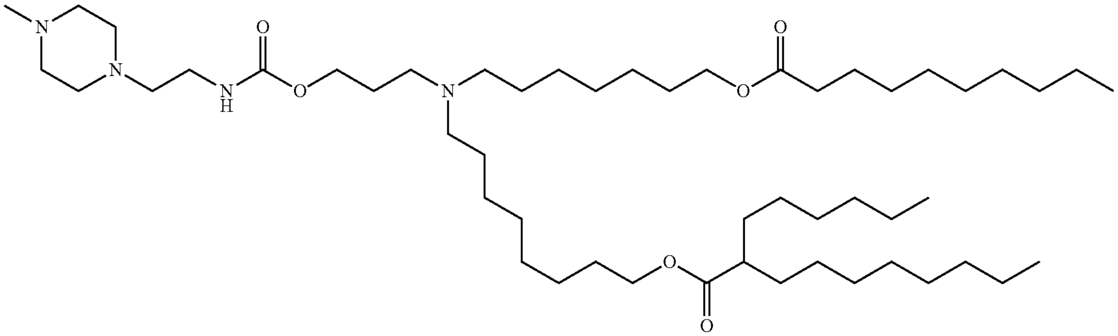 [SMILES: CCCCCCCCCC(=O)OCCCCCCCN(CCCCCCCCOC(=O)C(CCCCCC)CCCCCCCC)CCCOC(=O)NCCN1CCN(C)CC1]

Lipid 362 8-((7-(decanoyloxy)heptyl)(3-(((2-(4-methylpiperazin-1-yl)ethyl)carbamoyl)oxy)propyl)amino)octyl 2-hexyldecanoate was synthesized according to the general synthetic scheme and general methods. MS [ESI]: m/z: [M+H] calc 879.8 obs. 880.1; $^{1}H$ NMR (400 MHz, $CDCl_3$): δ 0.87 (9H, t, J=6.53 Hz), 1.26 (53H, m), 1.61 (8H, m), 1.74 (2H, m), 2.28 (7H m), 2.37 (5H, m), 2.46 (10H, m), 3.26 (2H, m), 4.06 (6H, m).

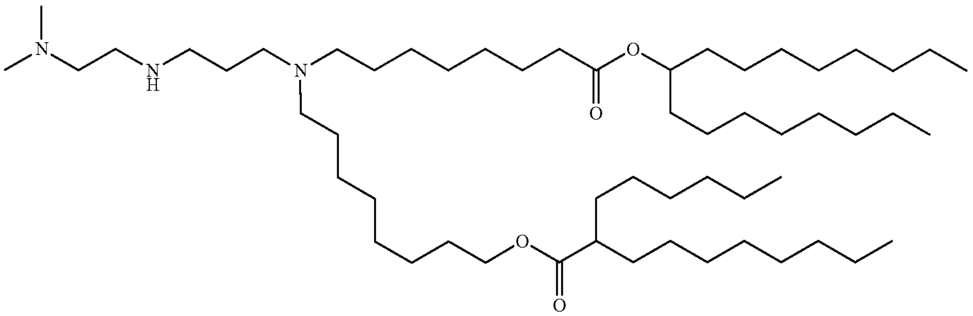 [SMILES: CCCCCCCCC(CCCCCCCC)OC(=O)CCCCCCCN(CCCCCCCCOC(=O)C(CCCCCC)CCCCCCCC)CCCNCCN(C)C]

Lipid 363 8-((3-((2-(dimethylamino)ethyl)amino)propyl)(8-(heptadecan-9-yloxy)-8-oxooctyl)amino)octyl 2-hexyldecanoate was synthesized according to the general synthetic scheme and general methods. MS [ESI]: m/z: [M+H] calc 892.9 obs. 893.0; $^1$H NMR (400 MHz, $CDCl_3$): δ 0.87 (12H, t, J=7.16 Hz), 1.27 (57H, m), 1.45 (10H, m), 1.61 (7H, m), 1.76 (3H, m), 2.25 (10H, m), 2.44 (9H, m), 2.74 (2H, m), 4.06 (2H, t, J=6.58 Hz), 4.86 (1H, quint, J=6.66 Hz).

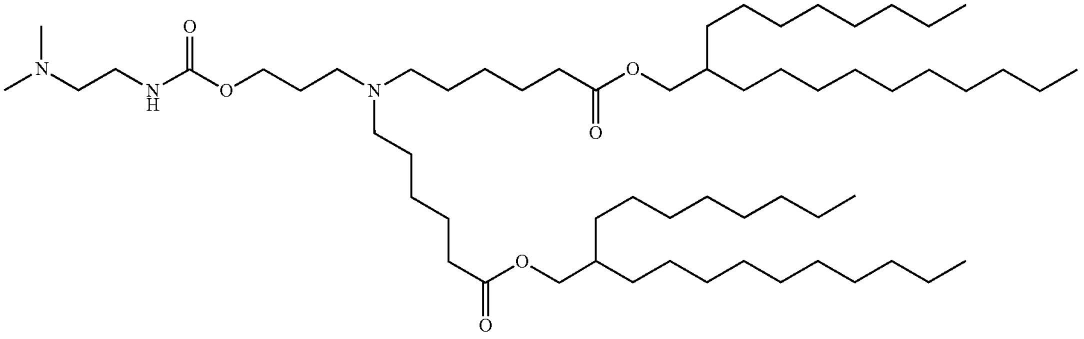 [SMILES: CCCCCCCCCCC(CCCCCCCC)COC(=O)CCCCCN(CCCCCC(=O)OCC(CCCCCCCC)CCCCCCCCCC)CCCOC(=O)NCCN(C)C]

Lipid 364 2-octyldodecyl 2-methyl-11-(6-((2-octyldodecyl)oxy)-6-oxohexyl)-6-oxo-7-oxa-2,5,11-triazaheptadecan-17-oate was synthesized according to the general synthetic scheme and general methods. MS [ESI]: m/z: [M+H] calc 978.9 obs. 979.3; $^1$H NMR (400 MHz, $CDCl_3$): δ 0.88 (12H, t, J=6.82 Hz), 1.26 (68H, m), 1.42 (4H, m), 1.63 (8H, quint, J=7.55 Hz), 1.72 (2H, m), 2.22 (5H, s), 2.30 (4H, t, J=7.53 Hz), 2.38 (7H, m), 3.24 (2H, m), 3.96 (4H, d, J=5.80 Hz), 4.07 (2H, m), 5.14 (1H, m).

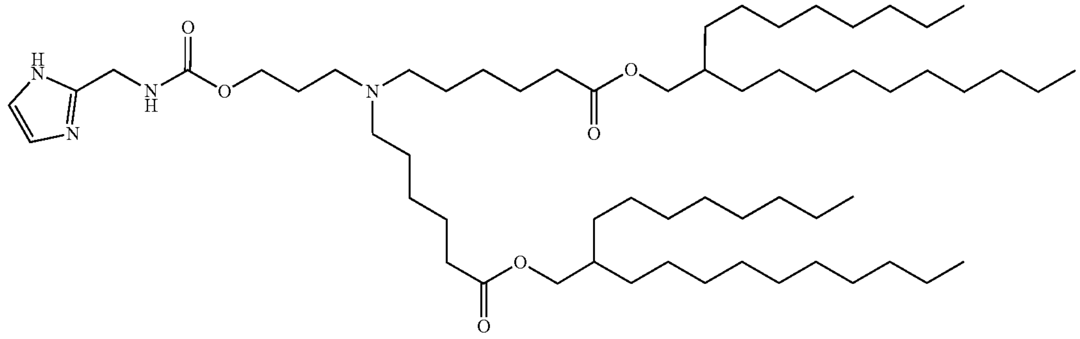 [SMILES: CCCCCCCCCCC(CCCCCCCC)COC(=O)CCCCCN(CCCCCC(=O)OCC(CCCCCCCC)CCCCCCCCCC)CCCOC(=O)NCc1ncc[nH]1]

Lipid 365 bis(2-octyldodecyl) 6,6'-((3-((((1H-imidazol-2-yl)methyl)carbamoyl)oxy)propyl)azanediyl)dihexanoate was synthesized according to the general synthetic scheme and general methods. MS [ESI]: m/z: [M+H] calc 987.9 obs. 988.2; $^1$H NMR (400 MHz, $CDCl_3$): δ 0.88 (12H, t, J=6.82 Hz), 1.26 (68H, m), 1.41 (3H, m), 1.61 (9H, m), 1.73 (1H, m), 2.30 (8H, m), 2.43 (2H, m), 3.96 (4H, d, J=5.80 Hz), 4.13 (2H, m), 4.37 (2H, d, J=6.05 Hz), 5.51 (1H, m), 6.96 (2H, s).

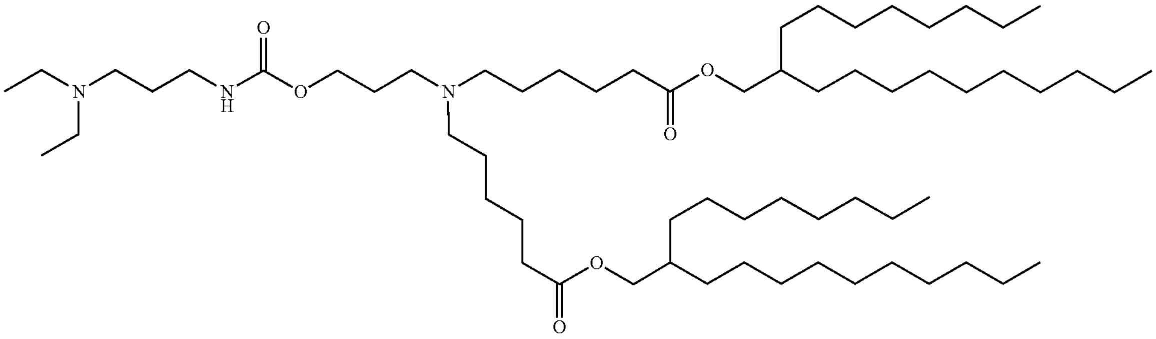 [SMILES: CCCCCCCCCCC(CCCCCCCC)COC(=O)CCCCCN(CCCCCC(=O)OCC(CCCCCCCC)CCCCCCCCCC)CCCOC(=O)NCCCN(CC)CC]

Lipid 366 2-octyldodecyl 3-ethyl-13-(6-((2-octyldodecyl) oxy)-6-oxohexyl)-8-oxo-9-oxa-3,7,13-triazanonadecan-19-oate was synthesized according to the general synthetic scheme and general methods. MS [ESI]: m/z: [M+H] calc 1021.0 obs. 1021.3; $^1$H NMR (400 MHz, $CDCl_3$): δ 0.88 (12H, t, J=7.20 Hz), 1.02 (6H, t, J=7.00 Hz), 1.26 (67H, m), 1.42 (4H, m), 1.64 (11H, m), 2.29 (4H, t, J=7.68 Hz), 2.37 (4H, m), 2.47 (8H, m), 3.24 (2H, m), 3.96 (4H, d, J=5.81 Hz), 4.06 (2H, t, J=6.58 Hz), 5.99 (1H, m).

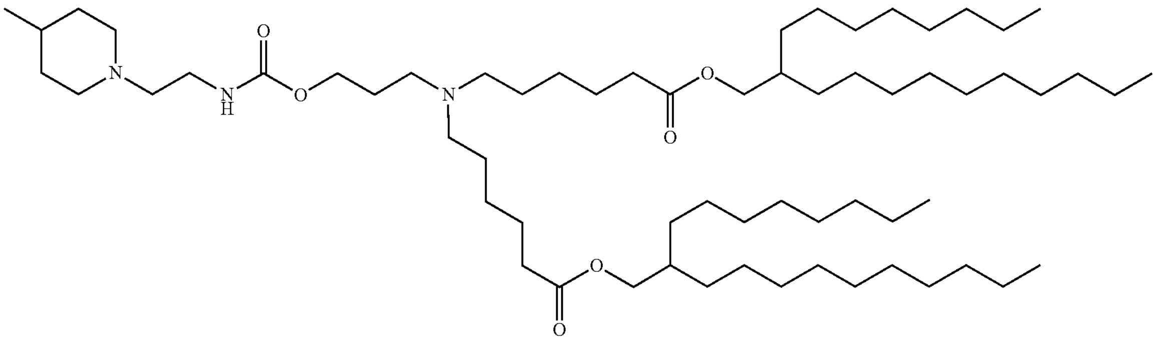 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCC(C)CC1]

Lipid 367 bis(2-octyldodecyl) 6,6'-((3-(((2-(4-methylpiperazin-1-yl)ethyl)carbamoyl)oxy)propyl)azanediyl)dihexanoate was synthesized according to the general synthetic scheme and general methods. MS [ESI]: m/z: [M+H] calc 1034.0 obs. 1034.3; $^1$H NMR (400 MHz, $CDCl_3$): δ 0.88 (12H, t, J=7.00 Hz), 1.27 (66H, m), 1.42 (4H, m), 1.62 (8H, m), 1.73 (2H, m), 2.39 (23H, m), 3.27 (2H, m), 3.96 (4H, d, J=5.80 Hz), 4.08 (2H, m), 5.12 (1H, m).

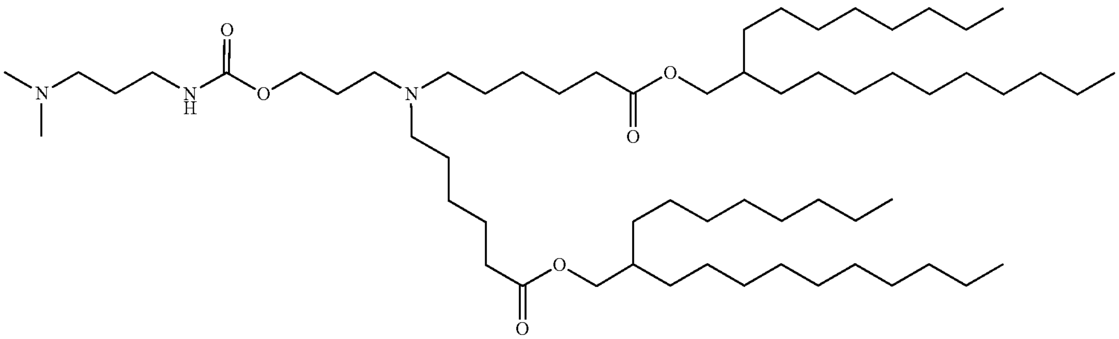 [SMILES: CCCCCCCCCCC(CCCCCCCC)COC(=O)CCCCCN(CCCCCC(=O)OCC(CCCCCCCC)CCCCCCCCCC)CCCOC(=O)NCCCN(C)C]

Lipid 368 2-octyldodecyl 2-methyl-12-(6-((2-octyldodecyl)oxy)-6-oxohexyl)-7-oxo-8-oxa-2,6,12-triazaoctadecan-18-oate was synthesized according to the general synthetic scheme and general methods. MS [ESI]: m/z: [M+H] calc 992.9 obs. 993.3; $^1$H NMR (400 MHz, $CDCl_3$): δ 0.88 (12H, t, J=7.07 Hz), 1.27 (66H, m), 1.42 (4H, m), 1.64 (12H, m), 2.21 (6H, s), 2.32 (10H, m), 2.46 (2H, t, J=7.25 Hz), 3.23 (2H, m), 3.96 (4H, d, J=5.81 Hz), 4.07 (2H, t, J=6.41 Hz), 5.48 (1H m).

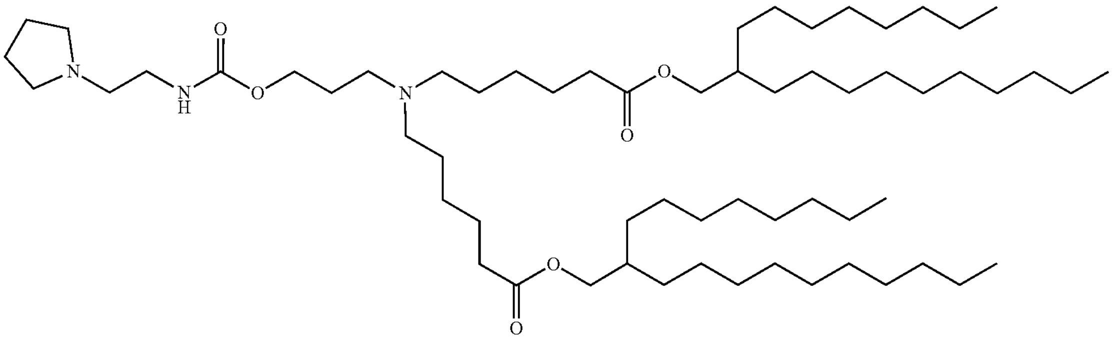 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCC1]

Lipid 369 bis(2-octyldodecyl) 6,6'-((3-(((2-(pyrrolidin-1-yl)ethyl)carbamoyl)oxy)propyl)azanediyl)dihexanoate was synthesized according to the general synthetic scheme and general methods. MS [ESI]: m/z: [M+H] calc 1004.9 obs. 1005.2; $^1$H NMR (400 MHz, $CDCl_3$): δ 0.88 (12H, t, J=7.09 Hz), 1.27 (66H, m), 1.42 (4H, m), 1.62 (8H, m), 1.75 (6H, m), 2.30 (4H, t, J=7.43 Hz), 2.37 (4H, m), 2.49 (6H, m), 2.58 (2H, t, J=6.30 Hz), 3.28 (2H, m), 3.96 (4H, d, J=5.81 Hz), 4.07 (2H, t, J=6.75 Hz), 5.17 (1H, m).

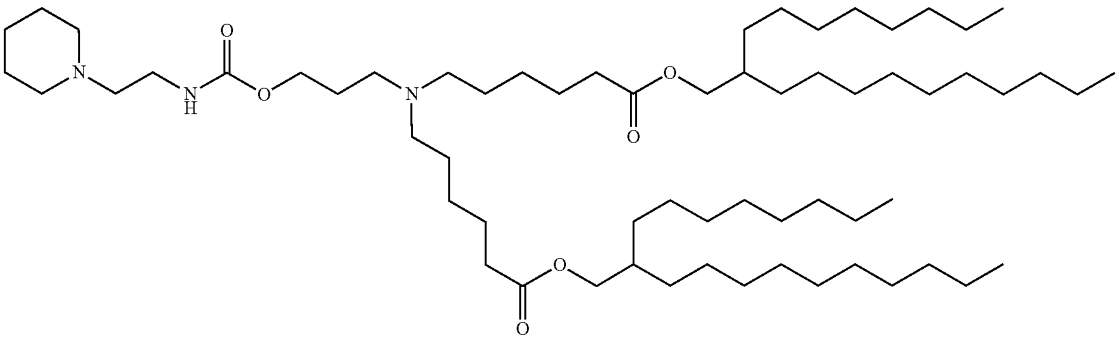 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCCC1]

Lipid 370 bis(2-octyldodecyl) 6,6'-((3-(((2-(piperidin-1-yl)ethyl)carbamoyl)oxy)propyl)azanediyl)dihexanoate was synthesized according to the general synthetic scheme and general methods. MS [ESI]: m/z: [M+H] calc 1018.9 obs. 1019.3; $^1$H NMR (400 MHz, $CDCl_3$): δ 0.88 (12H, t, J=7.13 Hz), 1.27 (67H, m), 1.42 (6H, m), 1.60 (12H, m), 1.73 (2H, m), 2.30 (4H, t, J=7.43 Hz), 2.39 (11H, m), 3.25 (2H, m), 3.96 (4H, d, J=5.64 Hz), 4.07 2H, m), 5.18 (1H, m).

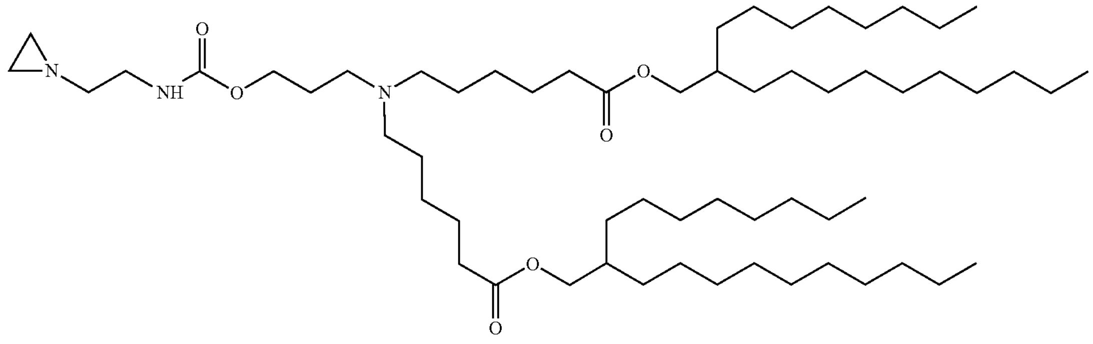 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CC1]

Lipid 371 bis(2-octyldodecyl) 6,6'-((3-(((2-(aziridin-1-yl)ethyl)carbamoyl)oxy)propyl)azanediyl)dihexanoate was synthesized according to the general synthetic scheme and general methods. MS [ESI]: m/z: [M+H] calc 976.9 obs. 977.2; $^{1}$H NMR (400 MHz, $CDCl_3$): δ 0.88 (12H, t, J=7.05 Hz), 1.15 (2H, m), 1.26 (66H, m), 1.42 (4H, m), 1.65 (12H, m), 2.33 (10H, m), 2.45 (2H, t, J=7.42 Hz), 3.34 (2H, m), 3.96 (4H, d, J=5.81 Hz), 4.08 (2H, t, J=6.92 Hz), 5.17 (1H, m).

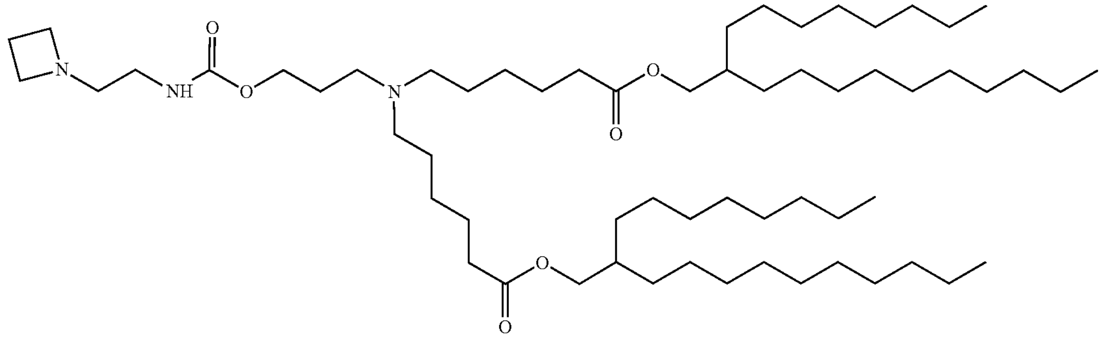 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCC1]

Lipid 372 bis(2-octyldodecyl) 6,6'-((3-(((2-(azetidin-1-yl)ethyl)carbamoyl)oxy)propyl)azanediyl)dihexanoate was synthesized according to the general synthetic scheme and general methods. MS [ESI]: m/z: [M+H] calc 990.9 obs. 991.2; $^{1}$H NMR (400 MHz, $CDCl_3$): δ 0.88 (12H, t, J=6.81 Hz), 1.26 (65H, m), 1.42 (4H, m), 1.61 (9H, m), 1.71 (2H, dt, J=6.41, 1.67 Hz), 2.06 (2H, t, J=7.00 Hz), 2.30 (4H, t, J=7.53 Hz), 2.37 (4H, t, J=7.38 Hz), 2.47 (4H, m), 3.12 (2H, m), 3.19 (4H, t, J=6.99 Hz), 3.96 (4H, d, J=5.80 Hz), 4.06 (2H, m), 5.06 (1H, m).

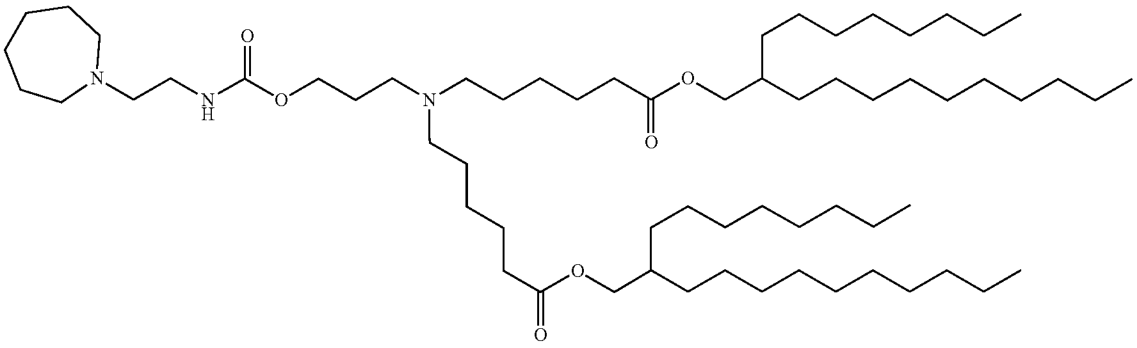 [SMILES: CCCCCCCCCCC(CCCCCCCC)COC(=O)CCCCCN(CCCCCC(=O)OCC(CCCCCCCC)CCCCCCCCCC)CCCOC(=O)NCCN1CCCCCC1]

Lipid 373 bis(2-octyldodecyl) 6,6'-((3-(((2-(azepan-1-yl)ethyl)carbamoyl)oxy)propyl)azanediyl)dihexanoate was synthesized according to the general synthetic scheme and general methods. MS [ESI]: m/z: [M+H] calc 1033.0 obs. 1033.3; $^1$H NMR (400 MHz, $CDCl_3$): δ 0.88 (12H, t, J=6.95 Hz), 1.27 (64H, m), 1.43 (4H, m), 1.61 (20H, m), 2.30 (4H, t, J=7.58 Hz), 2.37 (4H, m), 2.46 (2H, t, J=7.33 Hz), 2.61 (6H, m), 3.21 (2H, m), 3.96 (4H, d, J=5.64 Hz), 4.08 (2H, t, J=6.41 Hz), 5.20 (1H, m).

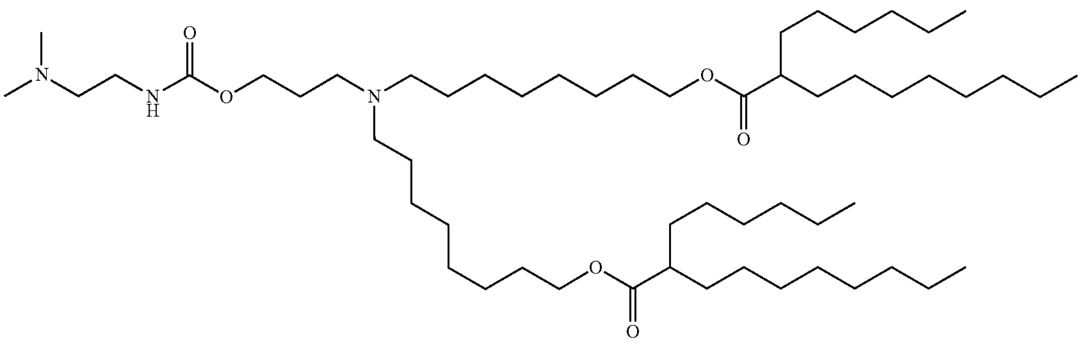 [SMILES: CCCCCCCCC(CCCCCC)C(=O)OCCCCCCCCN(CCCCCCCCOC(=O)C(CCCCCC)CCCCCCCC)CCCOC(=O)NCCN(C)C]

Lipid 374 11-(8-((2-hexyldecanoyl)oxy)octyl)-2-methyl-6-oxo-7-oxa-2,5,11-triazanonadecan-19-yl 2-hexyldecanoate was synthesized according to the general synthetic scheme and general methods. MS [ESI]: m/z: [M+H] calc 922.9 obs. 923.2; $^1$H NMR (500 MHz): δ 0.87 (12H, m), 1.28 (62H, m), 1.60 (10H, m), 1.73 (2H, m), 2.22 (6H, s), 2.36 (8H, m), 2.46 (2H, t, J=7.24 Hz), 3.25 (2H, m), 4.06 (6H, m), 5.12 (1H, m).

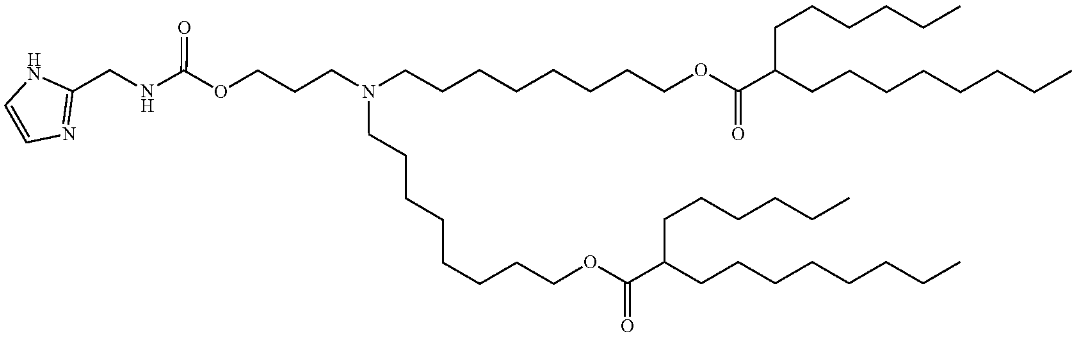 [SMILES: CCCCCCCCC(CCCCCC)C(=O)OCCCCCCCCN(CCCCCCCCOC(=O)C(CCCCCC)CCCCCCCC)CCCOC(=O)NCc1ncc[nH]1]

Lipid 375 ((3-((((1H-imidazol-2-yl)methyl)carbamoyl)oxy)propyl)azanediyl)bis(octane-8,1-diyl) bis(2-hexyldecanoate) was synthesized according to the general synthetic scheme and general methods. MS [ESI]: m/z: [M+H] calc 931.8 obs. 932.2; $^1$H NMR (500 MHz, $CDCl_3$): δ 0.87 (12H, m), 1.25 (62H, m), 1.60 (9H, m), 1.74 (2H, m), 2.31 (6H, m), 2.44 (2H, m), 4.06 (8H, m), 4.37 (2H, m), 5.44 (1H, m), 6.96 (2H, s).

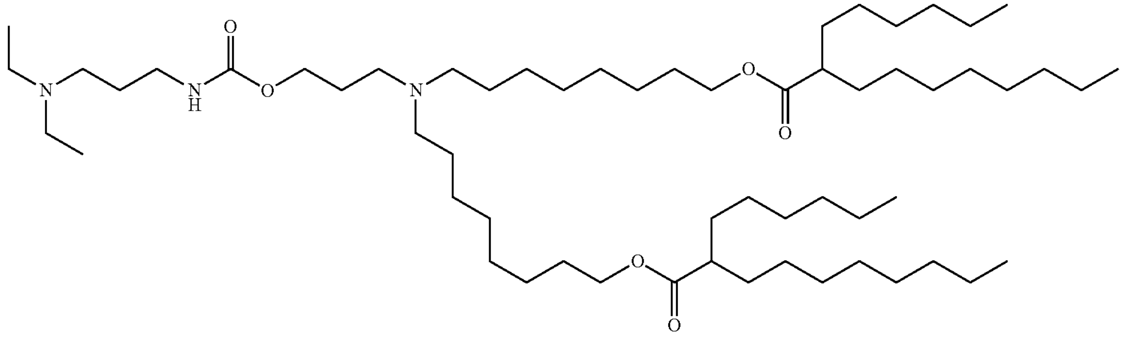 [SMILES: CCCCCCCCC(CCCCCC)C(=O)OCCCCCCCCN(CCCCCCCCOC(=O)C(CCCCCC)CCCCCCCC)CCCOC(=O)NCCCN(CC)CC]

Lipid 376 3-ethyl-13-(8-((2-hexyldecanoyl)oxy)octyl)-8-oxo-9-oxa-3,7,13-triazahenicosan-21-yl 2-hexyldecanoate was synthesized according to the general synthetic scheme and general methods. MS [ESI]: m/z: [M+H] calc 964.9 obs. 965.3; $^1$H NMR (500 MHz, $CDCl_3$): δ 0.87 (12H, m), 1.02 (6H, m), 1.25 (63H, m), 1.60 (10H, m), 1.73 (2H, m), 2.36 (6H, m), 2.48 (8H, m), 3.24 (2H, m), 4.06 (7H, m), 6.01 (1H, m).

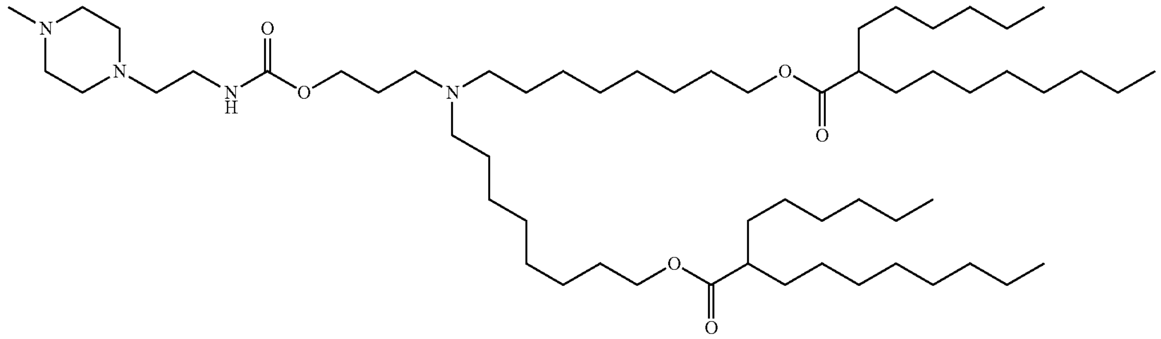 [SMILES: CCCCCCCCC(CCCCCC)C(=O)OCCCCCCCCN(CCCCCCCCOC(=O)C(CCCCCC)CCCCCCCC)CCCOC(=O)NCCN1CCN(C)CC1]

Lipid 377 ((3-(((2-(4-methylpiperazin-1-yl)ethyl)carbamoyl)oxy)propyl)azanediyl)bis(octane-8,1-diyl) bis(2-hexyldecanoate) was synthesized according to the general synthetic scheme and general methods. MS [ESI]: m/z: [M+H] calc 977.9 obs. 978.2; $^1$H NMR (500 MHz, $CDCl_3$): δ 0.87 (12H, m), 1.25 (63H, m), 1.60 (9H, m), 1.74 (2H, m), 2.40 (21H, m), 3.27 (2H, m), 4.06 (6H, m), 5.11 (1H, m).

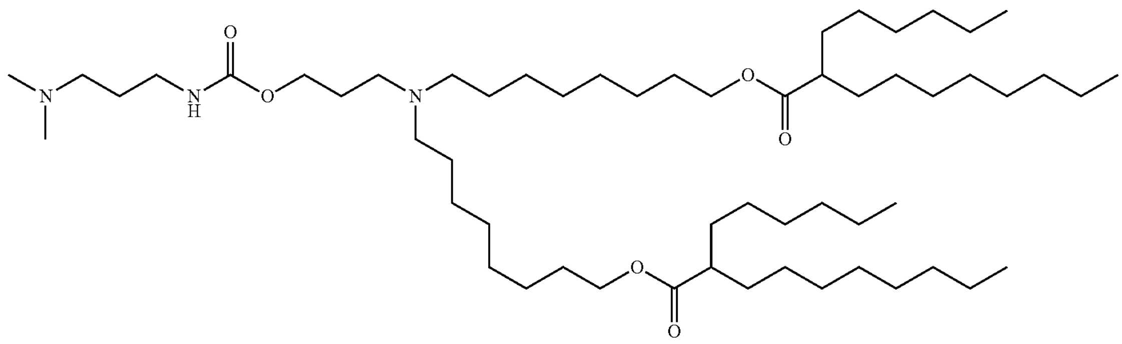 [SMILES: CCCCCCCCC(CCCCCC)C(=O)OCCCCCCCCN(CCCCCCCCOC(=O)C(CCCCCC)CCCCCCCC)CCCOC(=O)NCCCN(C)C]

Lipid 378 12-(8-((2-hexyldecanoyl)oxy)octyl)-2-methyl-7-oxo-8-oxa-2,6,12-triazaicosan-20-yl 2-hexyldecanoate was synthesized according to the general synthetic scheme and general methods. MS [ESI]: m/z: [M+H] calc 936.9 obs. 937.2; $^{1}H$ NMR (400 MHz, $CDCl_3$): δ 0.87 (12H, m), 1.25 (63H, m), 1.61 (12H, m), 1.73 (2H), 2.21 (5H, s), 2.34 (8H, m), 2.46 (2H, m), 3.23 (2H, m), 4.06 (6H, t, J=6.65 Hz), 5.46 (1H, m).

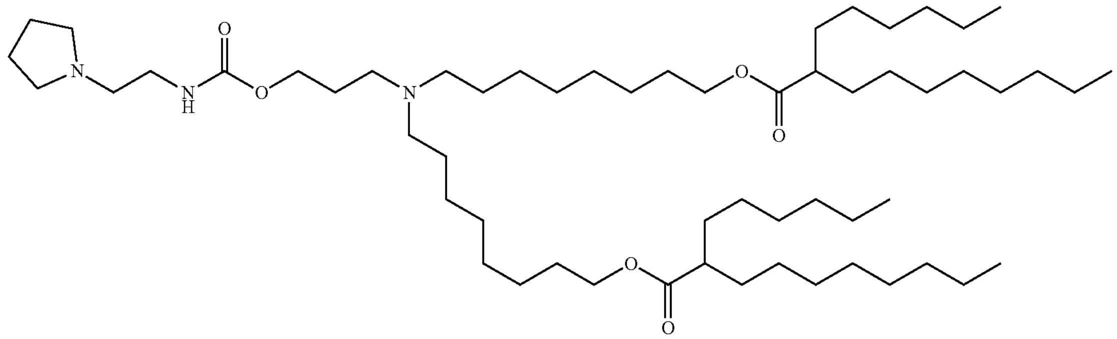 [SMILES: CCCCCCCCC(CCCCCC)C(=O)OCCCCCCCCN(CCCCCCCCOC(=O)C(CCCCCC)CCCCCCCC)CCCOC(=O)NCCN1CCCC1]

Lipid 379 ((3-(((2-(pyrrolidin-1-yl)ethyl)carbamoyl)oxy)propyl)azanediyl)bis(octane-8,1-diyl) bis(2-hexyldecanoate) was synthesized according to the general synthetic scheme and general methods. MS [ESI]: m/z: [M+H] calc 948.9 obs. 949.2; $^{1}H$ NMR (500 MHz, $CDCl_3$): δ 0.87 (12H, m), 1.25 (63H, m), 1.61 (9H, m), 1.76 (6H, m), 2.37 (6H, m), 2.50 (6H, m), 2.58 (2H, m), 3.28 (2H, m), 4.06 (6H, m), 5.15 (1H, m).

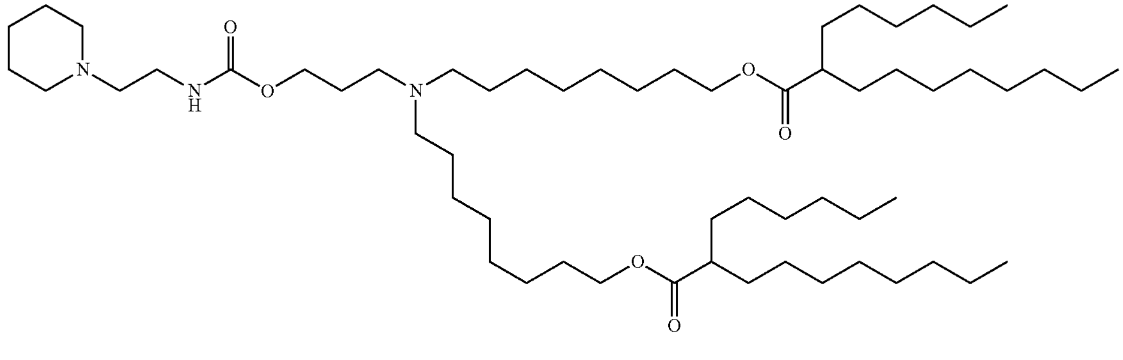 [SMILES: CCCCCCCCC(CCCCCC)C(=O)OCCCCCCCCN(CCCCCCCCOC(=O)C(CCCCCC)CCCCCCCC)CCCOC(=O)NCCN1CCCCC1]

Lipid 380 ((3-(((2-(piperidin-1-yl)ethyl)carbamoyl)oxy) propyl)azanediyl)bis(octane-8,1-diyl) bis(2-hexyldecanoate) was synthesized according to the general synthetic scheme and general methods. MS [ESI]: m/z: [M+H] calc 962.9 obs. 963.1; $^1$H NMR (500 MHz, $CDCl_3$): δ 0.87 (12H, m), 1.29 (64H, m), 1.58 (14H, m), 1.74 (2H, m), 2.36 (12H, m), 2.47 (2H, t, J=7.48 Hz), 325 (2H, m), 4.06 (6H, m), 5.16 (1H, m).

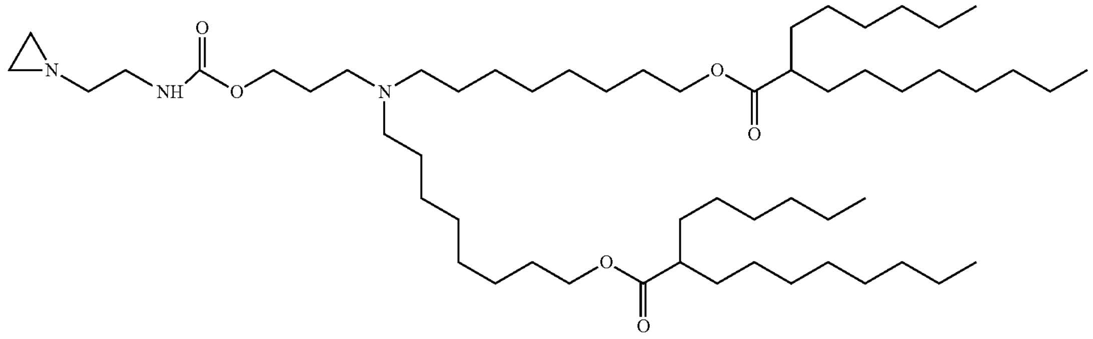 [SMILES: CCCCCCCCC(CCCCCC)C(=O)OCCCCCCCCN(CCCCCCCCOC(=O)C(CCCCCC)CCCCCCCC)CCCOC(=O)NCCN1CC1]

Lipid 381 ((3-(((2-(aziridin-1-yl)ethyl)carbamoyl)oxy) propyl)azanediyl)bis(octane-8,1-diyl) bis(2-hexyldecanoate) was synthesized according to the general synthetic scheme and general methods. MS [ESI]: m/z: [M+H] calc 920.8 obs. 921.1; $^1$H NMR (500 MHz, $CDCl_3$): δ 0.87 (12H, m), 1.16 (2H, m), 1.26 (62H, m), 1.61 (8H, m), 1.74 (4H, m), 2.21 (1H, m), 2.34 (8H, m), 2.46 (2H, m), 3.00 (1H, m), 3.34 (2H, m), 4.06 (6H, m), 5.14 (1H, m).

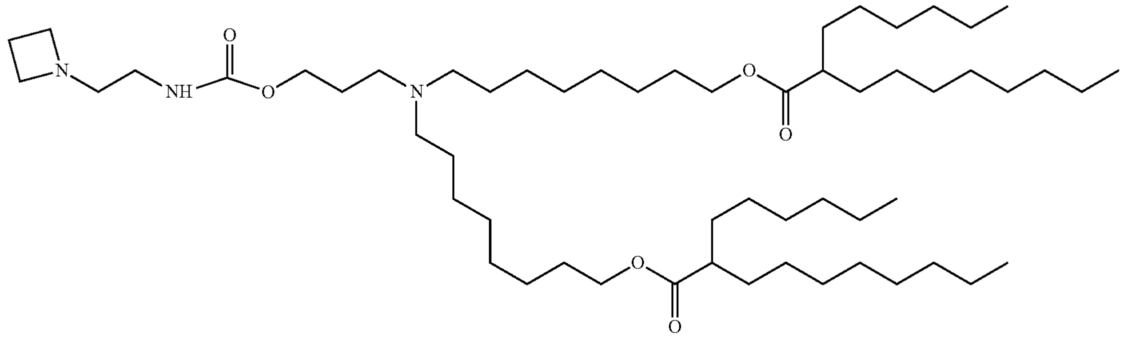 [SMILES: CCCCCCCCC(CCCCCC)C(=O)OCCCCCCCCN(CCCCCCCCOC(=O)C(CCCCCC)CCCCCCCC)CCCOC(=O)NCCN1CCC1]

Lipid 382 ((3-(((2-(azetidin-1-yl)ethyl)carbamoyl)oxy) propyl)azanediyl)bis(octane-8,1-diyl) bis(2-hexyldecanoate) was synthesized according to the general synthetic scheme and general methods. MS [ESI]: m/z: [M+H] calc 934.9 obs. 935.1; $^1$H NMR (500 MHz, $CDCl_3$): δ 0.87 (12H, m), 1.25 (61H, m), 1.60 (9H, m), 1.72 (2H, m), 2.06 (2H, m), 2.36 (6H, m), 2.48 (4H, m)_3.12 (3H, m), 3.19 (5H, t, J=6.95 Hz), 4.06 (6H, m), 5.03 (1H, m).

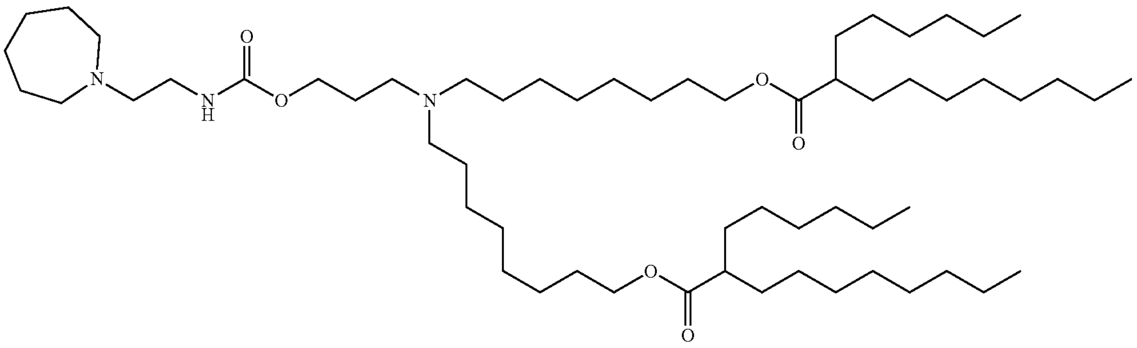 [SMILES: CCCCCCCCC(CCCCCC)C(=O)OCCCCCCCCN(CCCCCCCCOC(=O)C(CCCCCC)CCCCCCCC)CCCOC(=O)NCCN1CCCCCC1]

Lipid 383 ((3-(((2-(azepan-1-yl)ethyl)carbamoyl)oxy)propyl)azanediyl)bis(octane-8,1-diyl) bis(2-hexyldecanoate) was synthesized according to the general synthetic scheme and general methods. MS [ESI]: m/z: [M+H] calc 976.9 obs. 977.2; $^{1}$H NMR (500 MHz, $CDCl_3$): δ 0.87 (12H, m), 1.28 (61H, m), 1.59 (19H, m), 1.74 (2H, m), 2.35 (6H, m), 2.47 (2H, t, J=6.75 Hz), 2.60 (6H, m), 3.21 (2H, m), 4.07 (6H, m), 5.19 (1H, m).

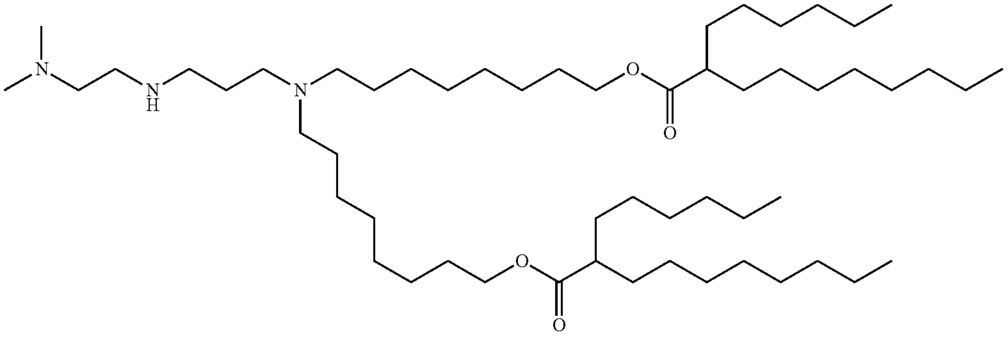 [SMILES: CCCCCCCCC(CCCCCC)C(=O)OCCCCCCCCN(CCCCCCCCOC(=O)C(CCCCCC)CCCCCCCC)CCCNCCN(C)C]

Lipid 384 ((3-((2-(dimethylamino)ethyl)amino)propyl)azanediyl)bis(octane-8,1-diyl) bis(2-hexyldecanoate) was synthesized according to the general synthetic scheme and general methods. MS [ESI]: m/z: [M+H] calc 878.9 obs. 879.1; $^{1}$H NMR (400 MHz, $CDCl_3$): δ 0.87 (12H, d, J=6.62 Hz), 1.28 (62H, m), 1.59 (13H, m), 2.22 (6H, s), 2.37 (10H, m), 2.62 (2H, t, J=7.13 Hz), 2.67 (2H, t, J=6.24 Hz), 4.06 (4H, t, J=6.65 Hz).

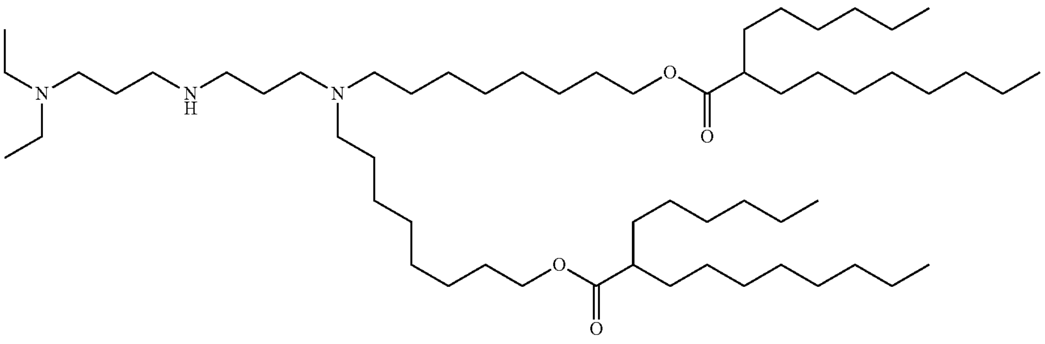 [SMILES: CCCCCCCCC(CCCCCC)C(=O)OCCCCCCCCN(CCCCCCCCOC(=O)C(CCCCCC)CCCCCCCC)CCCNCCCN(CC)CC]

Lipid 385 ((3-((3-(diethylamino)propyl)amino)propyl)azanediyl)bis(octane-8,1-diyl) bis(2-hexyldecanoate) was synthesized according to the general synthetic scheme and general methods. MS [ESI]: m/z: [M+H] calc 920.9 obs. 921.1; $^1$H NMR (400 MHz, $CDCl_3$): δ 0.87 (12H, m), 1.01 (6H, t, J=7.14 Hz), 1.27 (55H, m), 1.42 (1H, m), 1.58 (16H, m), 2.22 (1H, s), 2.41 (13H, m), 2.61 (2H, m), 4.06 (4H, t, J=6.66 Hz).

Example P1

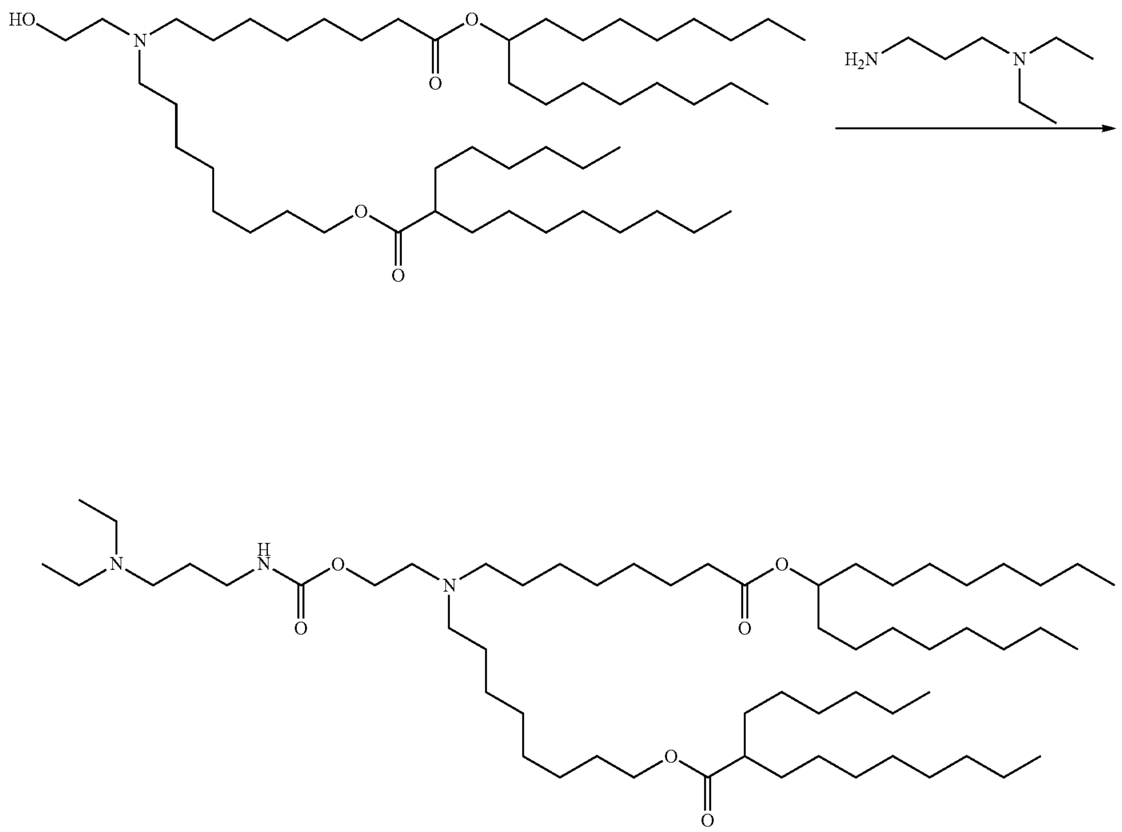

heptadecan-9-yl 3-ethyl-12-(8-((2-hexyldecanoyl)oxy)octyl)-8-oxo-9-oxa-3,7,12-triazaicosan-20-oate Lipid [006] 8-((8-(heptadecan-9-yloxy)-8-oxooctyl)(2-hydroxyethyl)amino)octyl 2-hexyldecanoate (0.3 g; 0.37 mmol) and 4-nitrophenyl chloroformate (0.090 g; 0.45 mmol) were dissolved in 10 mL dry DCM. TEA (0.103 ml; 0.742 mmol) was added and the reaction was left to stir at RT overnight. N1,N1-diethylpropane-1,3-diamine (0.121 g; 0.93 mmol) was then added and the reaction was left to stir at RT O/N. The reaction was then subjected directly to column chromatography (2%-10% iPrOH in DCM) to yield Lipid [006] as a yellowish oil (297 mg; 83%)$^1$H NMR (400 MHz, $CDCl_3$): δ ppm 5.87 (br, 1H); 4.83 (p, 1H); 4.03 (m, 4H) 3.24 (m, 2H); 2.61 (m, 8); 2.43 (m, 4H); 2.25 (m, 3H); 1.72-1.43 (m, 19H); 1.22 (m, 59H); 1.08 (m, 6H); 0.85 (m, 12H); MS [ESI]: m/z: [M+H] calc. 965.6 obs. 965.5

Example P2

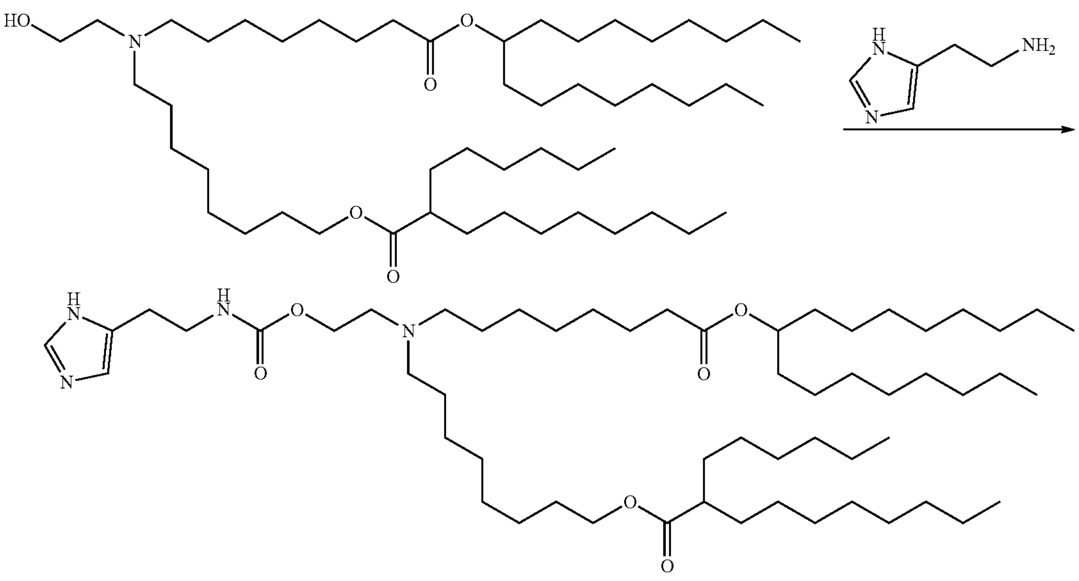

8-((2-(((2-(1H-imidazol-5-yl)ethyl)carbamoyl)oxy)ethyl)(8-(heptadecan-9-yloxy)-8-oxooctyl)amino)octyl 2-hexyldecanoate Lipid [007]8-((8-(heptadecan-9-yloxy)-8-oxooctyl)(2-hydroxyethyl)amino)octyl 2-hexyldecanoate (0.3 g, 0.37 mmol), 4-nitrophenyl chloroformate (0.090 g, 0.445 mmol) were dissolved in 10 mL DCM. TEA (0.103 ml, 0.742 mmol) was then added and the reaction was left to stir at RT O/N. 2-(1H-imidazol-5-yl)ethan-1-amine (0.041 g, 0.371 mmol) was then added and the reaction was left to stir at RT O/N. The reaction was then subjected directly to column chromatography (10% iPrOH in DCM with 0.1% TEA) to yield Lipid [007] as a yellowish oil (160 mg; 45%). $^1H$ NMR (400 MHz, $CDCl_3$): δ ppm 7.56 (s, 1H); 6.81 (s, 1H); 5.38 (brs, 1H); 4.86 (p, 1H); 4.17 (brm, 2H); 4.03 (m, 3H); 3.46 (m, 2H); 2.81 (m, 4H); 2.56 (brm, 4H); 2.27 (m, 4H); 1.60-1.19 (m, 73H); 0.87 (m, 12H); MS [ESI]: m/z: [M+H] calc. 946.5 obs. 946.3

Example P3

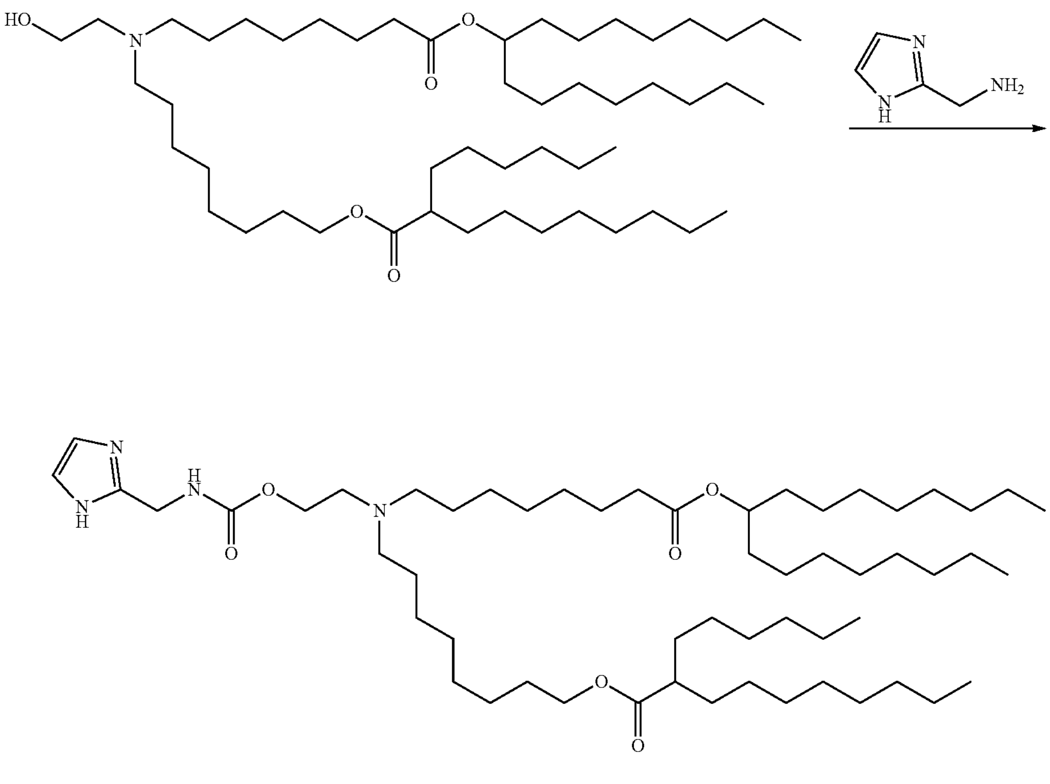

8-((2-((((1H-imidazol-2-yl)methyl)carbamoyl)oxy)ethyl)(8-(heptadecan-9-yloxy)-8-oxooctyl)amino)octyl 2-hexyldecanoate Lipid [008]8-((8-(heptadecan-9-yloxy)-8-oxooctyl)(2-hydroxyethyl)amino)octyl 2-hexyldecanoate (0.3 g, 0.371 mmol), 4-nitrophenyl chloroformate (0.090 g, 0.445 mmol) were dissolved in 10 mL DCM. TEA (0.103 ml, 0.742 mmol) was then added and the reaction was left to stir at RT O/N. (1H-imidazol-2-yl)methanamine (63 mg; 0.371) was dissolved in 5 mL DMF and TEA (0.103 ml, 0.742 mmol) was then added. The suspension was heated to form a clear solution and the resulting mixture was added to the reaction which was left to stir at RT O/N. The reaction was then subjected directly to column chromatography (10% iPrOH in DCM with 0.1% TEA) to yield Lipid [008] as a yellowish oil (160 mg; 45%) MS [ESI]: m/z: [M+H] calc. 932.5 obs. 932.3.

Experimental Example 1

Materials and Methods 1,2-distearoyl-sn-glycero-3-phosphocholine (DSPC), Cholesterol and 1,2-Dimyristoyl-rac-glycero-3-methoxy-polyethylene glycol-2000 (DMG-PEG 2000) were from Avanti Lipids. The Quant-it™ RiboGreen RNA Assay Kit was from ThermoFisher Scientific. The in-vitro Luciferase Assay System, CellTiter-Glo@Luminescent Cell Viability Assay and lysis buffers were from Promega. Reference lipids, i.e. Lipids A, B and C having the following structures were prepared according to the methods described in U.S. Ser. No. 11/851,389 B2.

stability test of the lipids of the present invention in Ethanol and PBS pH=7.4 which simulate the LNP synthesis conditions.

Lipid Nanoparticles (LNPs) Preparations

Ionizable lipid, DSPC, Cholesterol and DMG-PEG 2000 were mixed at a molar ratio of 50:10:38.5:1.5 in absolute ethanol. Circular RNA and linear mRNA payloads were suspended in 25 mM Acetate Buffer (pH 4.5). To form LNPs, three volumes of luciferase encoding RNA, in the form of cirRNA (SEQ ID NO:1) and mRNA (SEQ ID NO:2) respectively, were mixed with one volume of lipids in ethanol solution by microfluidic mixing with the Nanoassemblr Ignite (Precision Nanosystems) at a flow rate of 12 ml/min. The molar ratio of ionizable lipid to ribonucleotide was 15 or 6. The final lipid concentration in solution ranged from 1.5 mM to 6 mM. After encapsulation, the particles were dialyzed twice against PBS.

cirRNA:

SEQ ID NO: 1

AACTTTTAGTTATCCCACAGCAAGAATGCCATCATCTGTCCTCACCCCC

AATTTTCCCTTTTCTTCCCCTGCAACCATTACGCTTACTCGCATGTGCA

TTGAGTGGTGCATGTGTTGAACAAACAGCTACACTCACATGGGGGCGGG

TTTTCCCGCCCTACGGCCTCTCGCGAGGCCCACCCCTTCCCTCCCCTTA

TAACTACAGTGCTTTGGTAGGTAAGCATCCTGATCCCCCGCGGAAGCTG

CTCACGTGGCAACTGTGGGGACCCAGACAGGTTATCAAAGGCACCCGGT

Lipid A

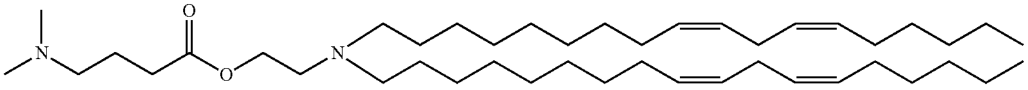

Lipid B

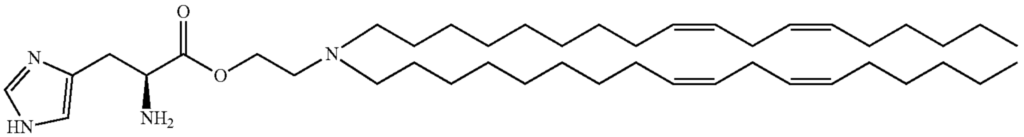

Lipid C

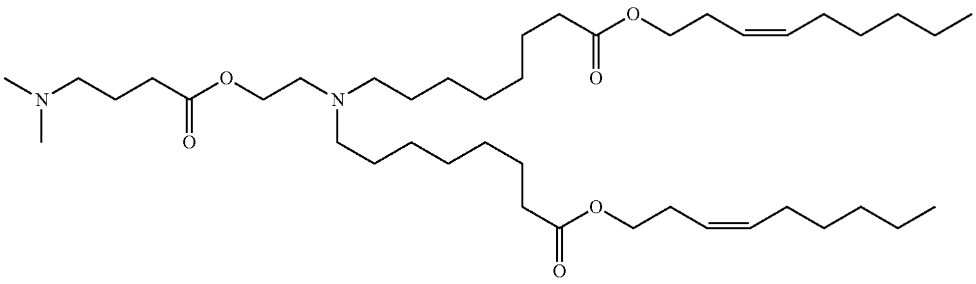

Long Term Stability Analysis

Figure 2:
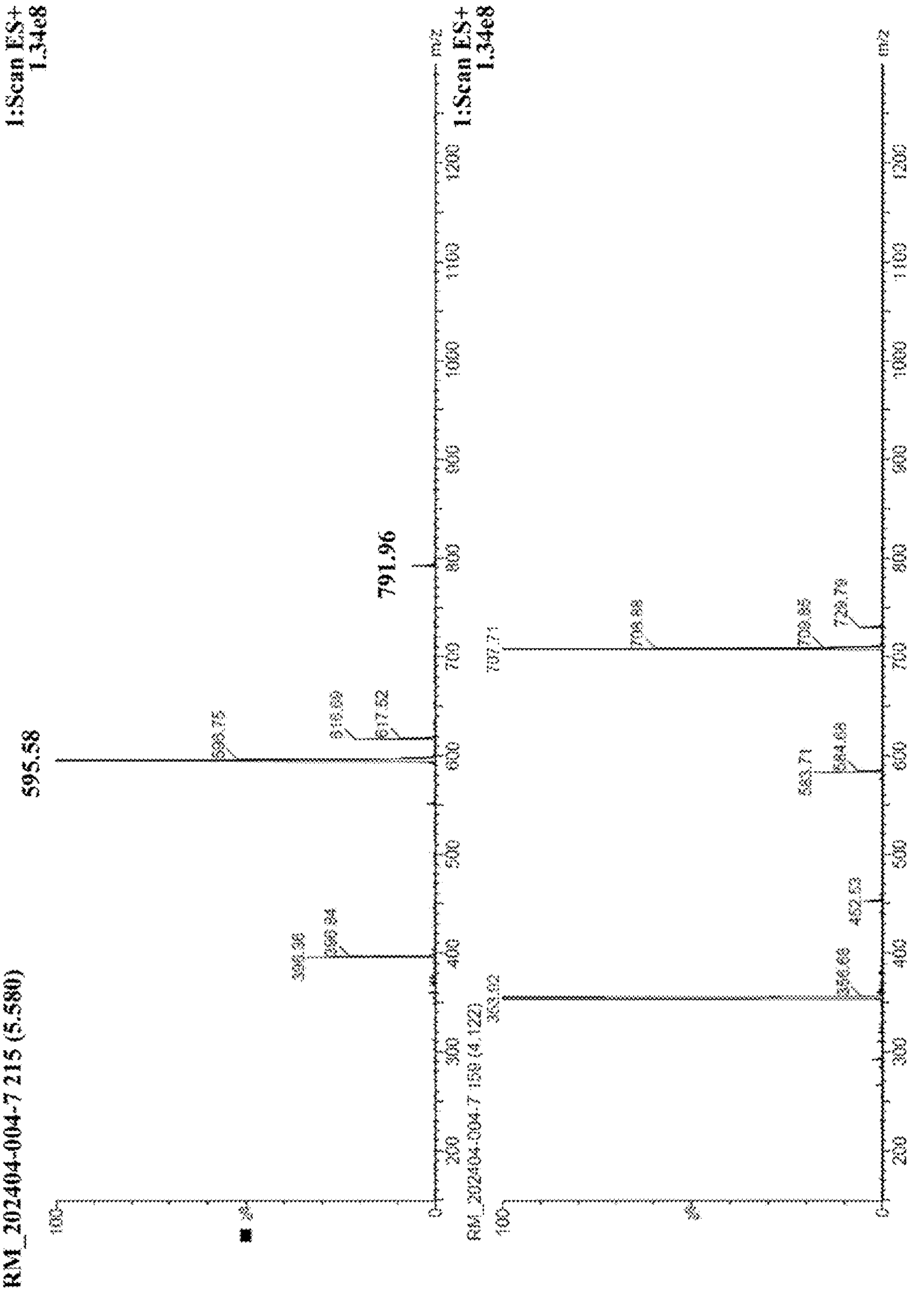
FIG. 2. Mass spectrograms of Lipid C and the hydrolyzed product.
Figure 3:
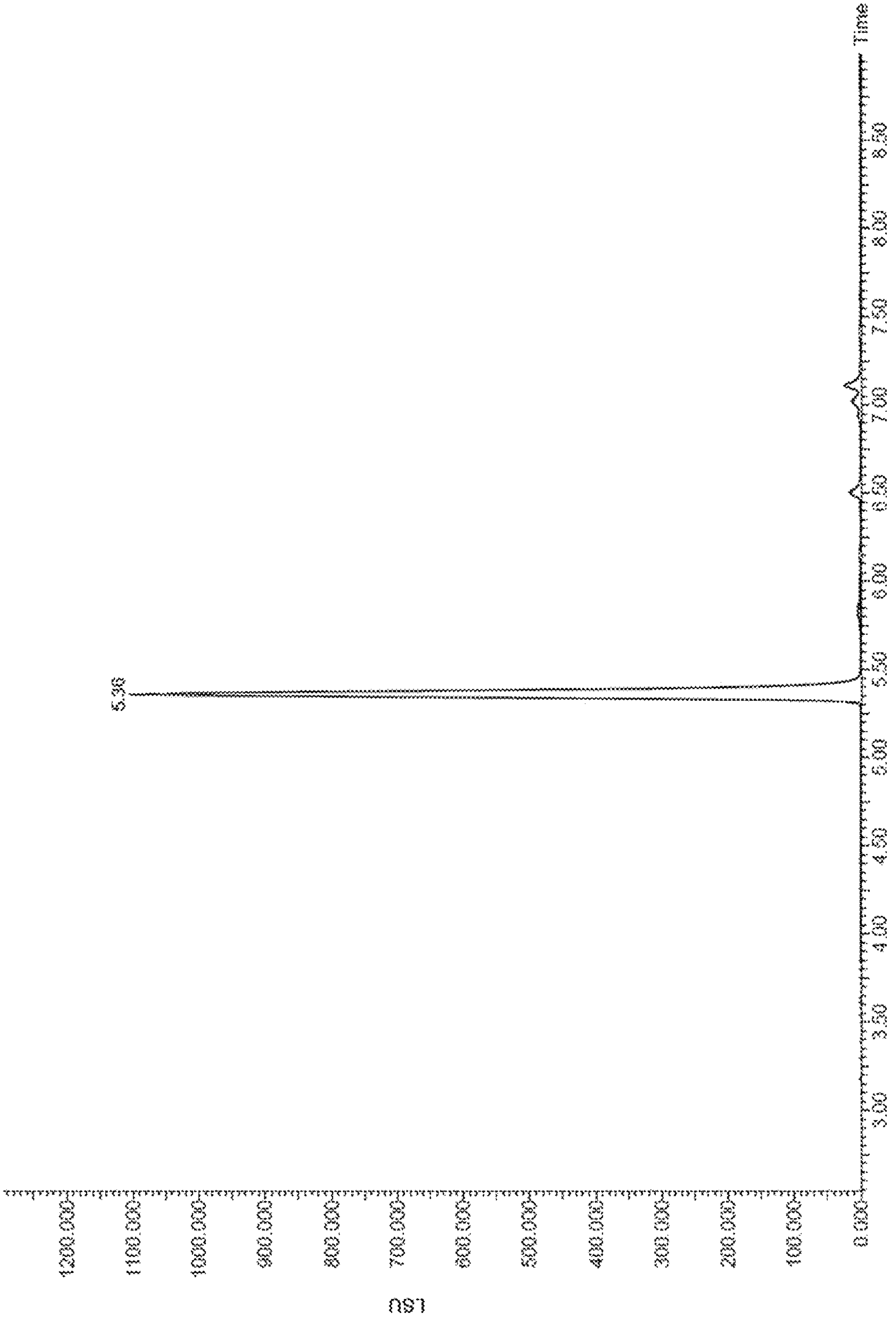
FIG. 3. Chromatogram overlay of t=0 and t=24 hr in EtOH PBS pH=7.4 of lipid 196.
Figure 4:
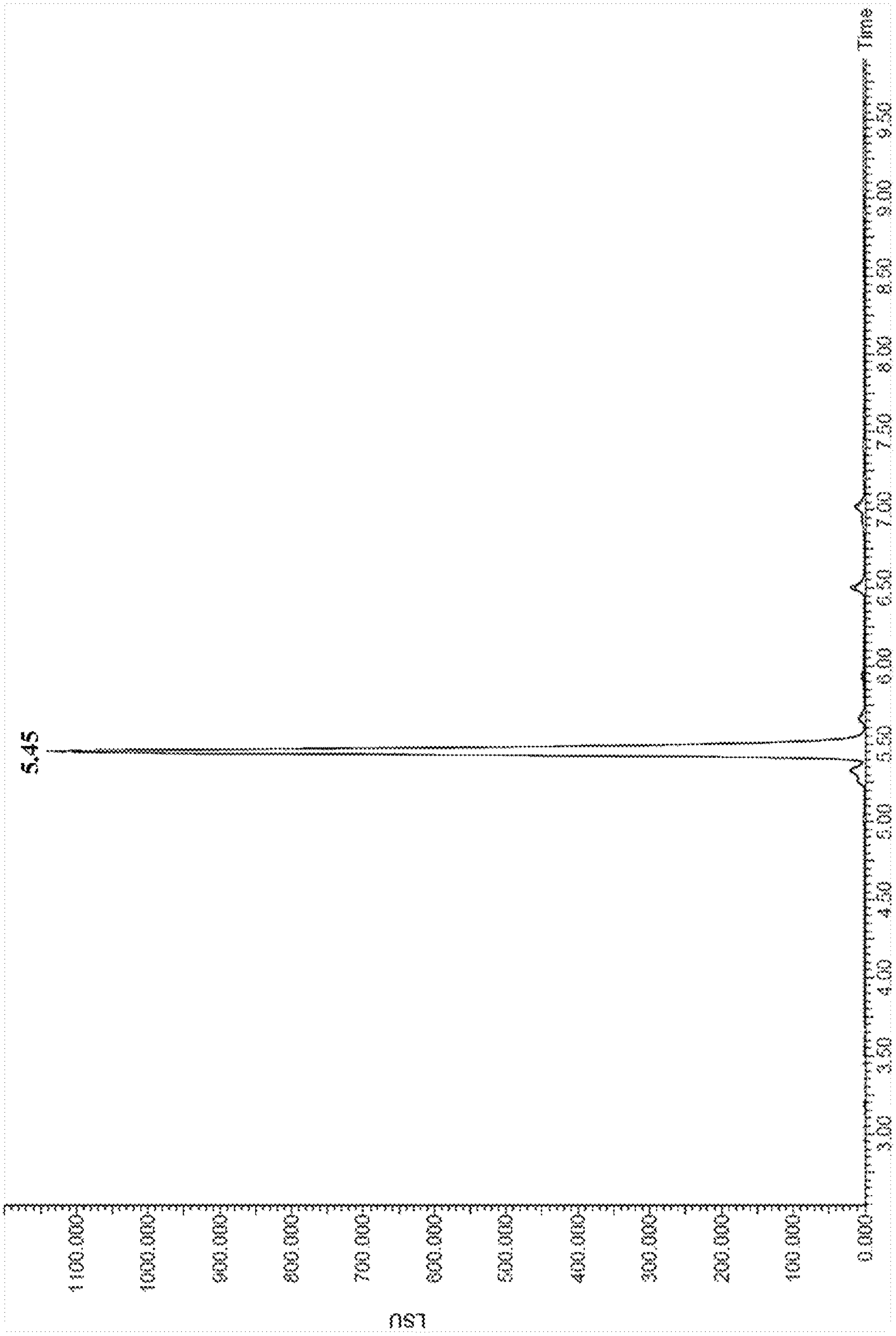
FIG. 4. Chromatogram overlay of t=0 and t=24 hr in EtOH PBS pH=7.4 of lipid 68.
Figure 5:
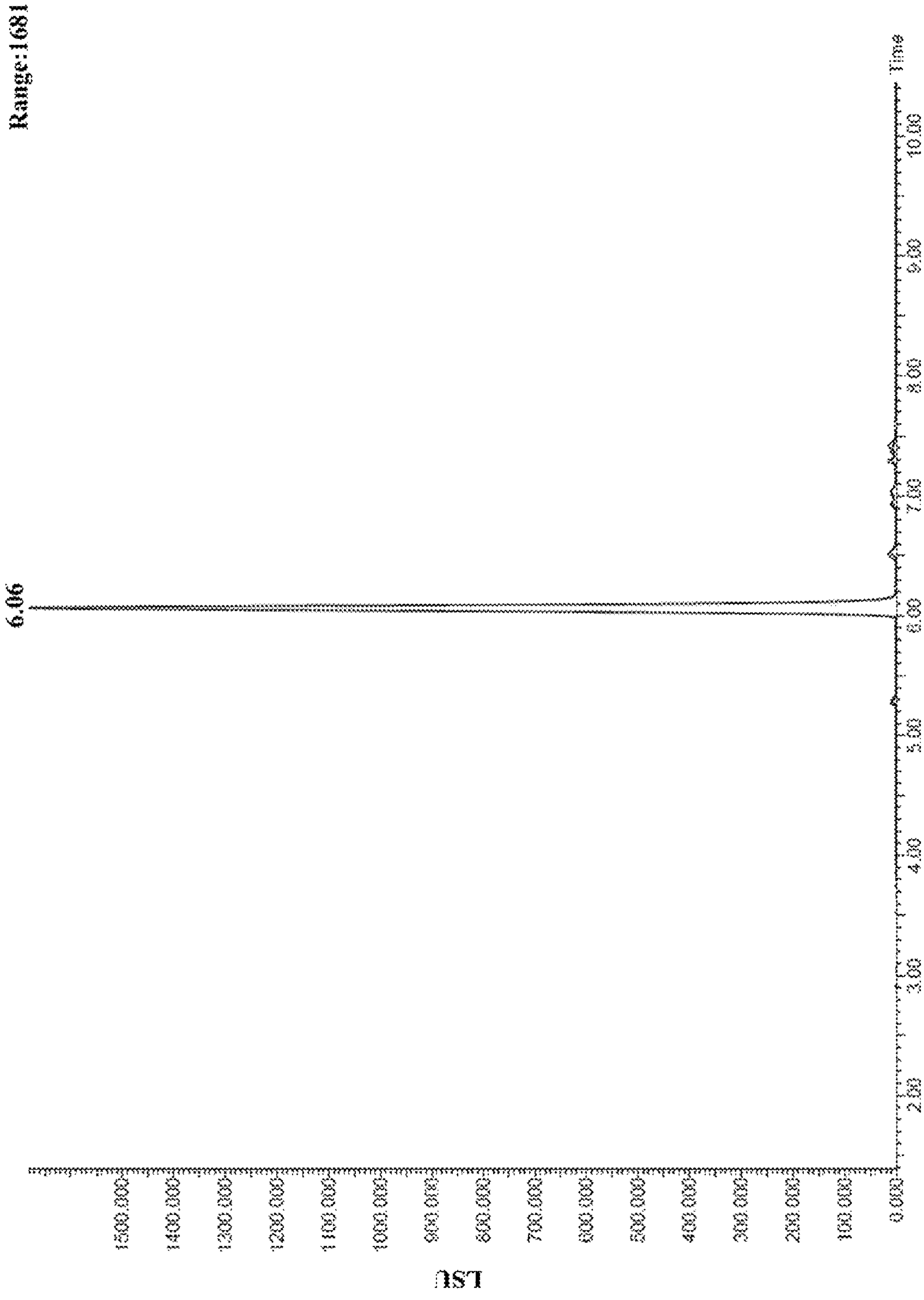
FIG. 5. Chromatogram overlay of t=0 and t=24 hr in EtOH PBS pH=7.4 of lipid 132.
Figure 6:
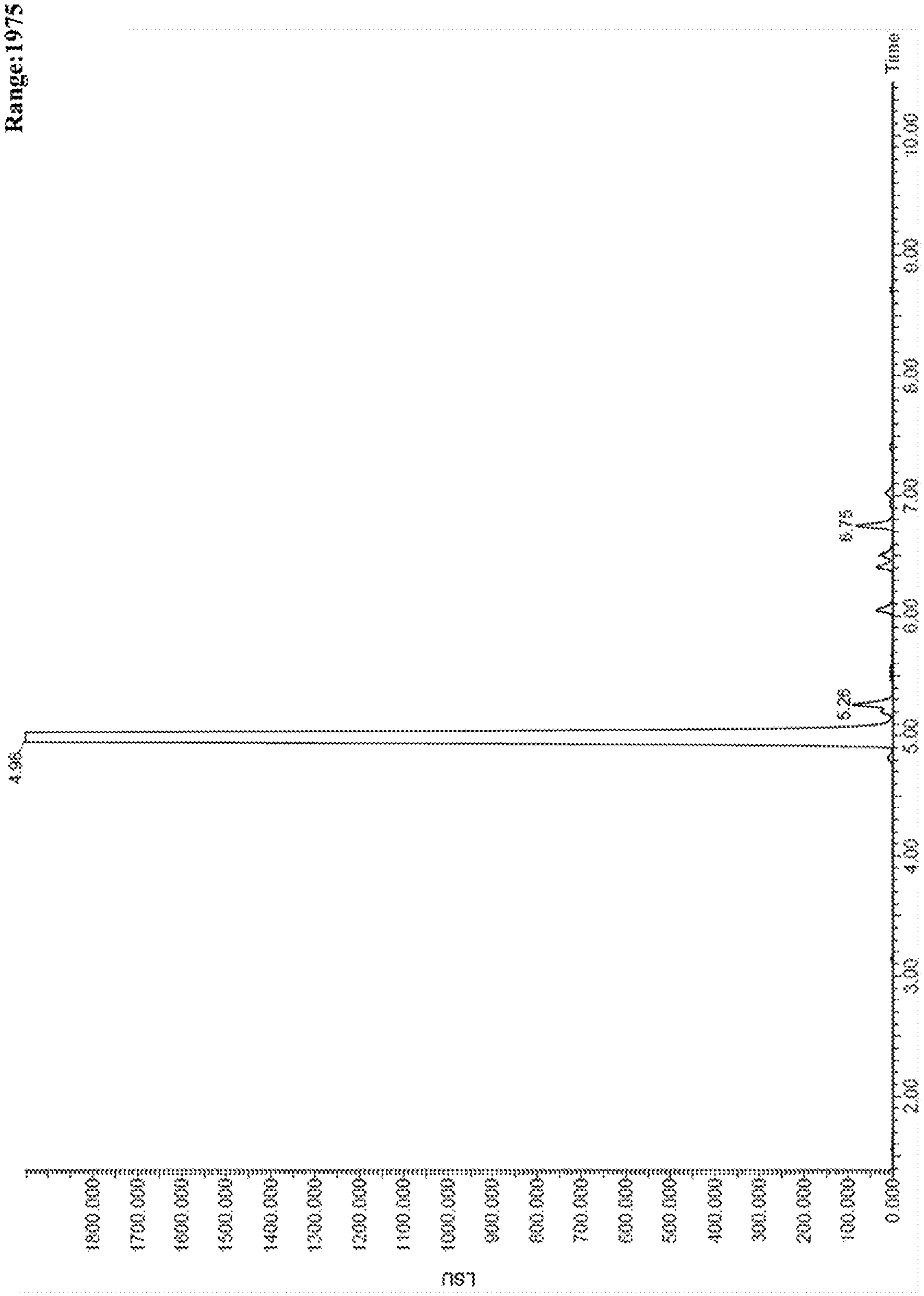
FIG. 6. Chromatogram overlay of t=0 and t=24 hr in EtOH PBS pH=7.4 of lipid 90.

Lipids of the present invention are compared to the Reference Lipids, and it was found that the lipids of the present invention have improved stability. The purity of the lipids was tested, after they were incorporated into lipid nanoparticles, only to find that the Reference Lipids were cleaved under LNP synthesis conditions, either via transesterification or hydrolysis. Long term stability studies also showed the formation of degradation products over time. The FIGS. 1-6 depict an example of the extensive hydrolysis of the ester moiety on the Reference Lipid C and also a -continued

CTTTCCGCCTTCAGGAGTATCCCTACTAGTGAATTCTAGCGGGGCTCTG

CTTGGTGCCAACCTCCCCCAAATGCGCGCTGCGGGAGTGCTCTTCCCCA

ACTCACCCTAGTATCCTCTCATGTGTGTGCTTGGTCAGCATATCTGAGA

CGATGTTCCGCTGTCCCAGACCAGTCCAGTAATGGACGGGCCAGTGCGT

GTAGTCGTCTTCCGGCTTGTCCGGGGCATGTTTGGTGAACCGGTGGGGT

-continued

AAGGTTGGTGTGCCCAACGCCCGTACTTTGGTGACACCTCAAGACCACC

CAGGAATGCCAGGGAGGTACCCCACCTCACGGTGGGATCTGACCCTGGG

CTAATTGTCTACGGTGGTTCTTCTTGCTTCCACTTCTTTCTTCTGTTCA

CGGCCACCATGGAGGACGCCAAGAACATCAAGAAGGGCCCGGCGCCCTT

CTACCCGCTGGAGGACGGGACCGCCGGCGAGCAGCTCCACAAGGCCATG

AAGCGGTACGCCCTGGTGCCGGGCACGATCGCCTTCACCGACGCCCACA

TCGAGGTCGACATCACCTACGCGGAGTACTTCGAGATGAGCGTGCGCCT

GGCCGAGGCCATGAAGCGGTACGGCCTGAACACCAACCACCGGATCGTG

GTGTGCTCGGAGAACAGCCTGCAGTTCTTCATGCCGGTGCTGGGCGCCC

TCTTCATCGGCGTGGCCGTCGCCCCGGCGAACGACATCTACAACGAGCG

GGAGCTGCTGAACAGCATGGGGATCAGCCAGCCGACCGTGGTGTTCGTG

AGCAAGAAGGGCCTGCAGAAGATCCTGAACGTGCAGAAGAAGCTGCCCA

TCATCCAGAAGATCATCATCATGGACAGCAAGACCGACTACCAGGGCTT

CCAGTCGATGTACACGTTCGTGACCAGCCACCTCCCGCCGGGCTTCAAC

GAGTACGACTTCGTCCCGGAGAGCTTCGACCGGGACAAGACCATCGCCC

TGATCATGAACAGCAGCGGCAGCACCGGCCTGCCGAAGGGGGTGGCCCT

GCCGCACCGGACCGCCTGCGTGCGCTTCTCGCACGCCCGGGACCCCATC

TTCGGCAACCAGATCATCCCGGACACCGCCATCCTGAGCGTGGTGCCGT

TCCACCACGGCTTCGGCATGTTCACGACCCTGGGCTACCTCATCTGCGG

CTTCCGGGTGGTCCTGATGTACCGGTTCGAGGAGGAGCTGTTCCTGCGG

AGCCTGCAGGACTACAAGATCCAGAGCGCGCTGCTCGTGCCGACCCTGT

TCAGCTTCTTCGCCAAGAGCACCCTGATCGACAAGTACGACCTGTCGAA

CCTGCACGAGATCGCCAGCGGGGGCGCCCCGCTGAGCAAGGAGGTGGGC

GAGGCCGTGGCCAAGCGGTTCCACCTCCCGGGCATCCGCCAGGGCTACG

GCCTGACCGAGACCACGAGCGCGATCCTGATCACCCCCGAGGGGGACGA

CAAGCCGGGCGCCGTGGGCAAGGTGGTCCCGTTCTTCGAGGCCAAGGTG

GTGGACCTGGACACCGGCAAGACCCTGGGCGTGAACCAGCGGGGCGAGC

TGTGCGTGCGGGGGCCGATGATCATGAGCGGCTACGTGAACAACCCGGA

GGCCACCAACGCCCTCATCGACAAGGACGGCTGGCTGCACAGCGGCGAC

ATCGCCTACTGGGACGAGGACGAGCACTTCTTCATCGTCGACCGGCTGA

AGTCGCTGATCAAGTACAAGGGCTACCAGGTGGCGCCGGCCGAGCTGGA

GAGCATCCTGCTCCAGCACCCCAACATCTTCGACGCCGGCGTGGCCGGG

CTGCCGGACGACGACGCCGGCGAGCTGCCGGCCGCGGTGGTGGTGCTGG

AGCACGGCAAGACCATGACGGAGAAGGAGATCGTCGACTACGTGGCCAG

CCAGGTGACCACCGCCAAGAAGCTGCGGGGCGGCGTGGTGTTCGTGGAC

GAGGTCCCGAAGGGCCTGACCGGGAAGCTCGACGCCCGGAAGATCCGCG

AGATCCTGATCAAGGCCAAGAAGGGCGGCAAGATCGCCGTGAGCTGATA

AACTACTGAAAGCAT mRNA

SEQ ID NO: 2

AAATAAGAGAGAAAAGAAGAGTAAGAAGAAATATAAGAGCCACCATGGA

GGACGCCAAGAACATCAAGAAGGGCCCGGCGCCCTTCTACCCGCTGGAG

GACGGGACCGCCGGCGAGCAGCTCCACAAGGCCATGAAGCGGTACGCCC

TGGTGCCGGGCACGATCGCCTTCACCGACGCCCACATCGAGGTCGACAT

CACCTACGCGGAGTACTTCGAGATGAGCGTGCGCCTGGCCGAGGCCATG

AAGCGGTACGGCCTGAACACCAACCACCGGATCGTGGTGTGCTCGGAGA

ACAGCCTGCAGTTCTTCATGCCGGTGCTGGGCGCCCTCTTCATCGGCGT

GGCCGTCGCCCCGGCGAACGACATCTACAACGAGCGGGAGCTGCTGAAC

AGCATGGGGATCAGCCAGCCGACCGTGGTGTTCGTGAGCAAGAAGGGCC

TGCAGAAGATCCTGAACGTGCAGAAGAAGCTGCCCATCATCCAGAAGAT

CATCATCATGGACAGCAAGACCGACTACCAGGGCTTCCAGTCGATGTAC

ACGTTCGTGACCAGCCACCTCCCGCCGGGCTTCAACGAGTACGACTTCG

TCCCGGAGAGCTTCGACCGGGACAAGACCATCGCCCTGATCATGAACAG

CAGCGGCAGCACCGGCCTGCCGAAGGGGGTGGCCCTGCCGCACCGGACC

GCCTGCGTGCGCTTCTCGCACGCCCGGGACCCCATCTTCGGCAACCAGA

TCATCCCGGACACCGCCATCCTGAGCGTGGTGCCGTTCCACCACGGCTT

CGGCATGTTCACGACCCTGGGCTACCTCATCTGCGGCTTCCGGGTGGTC

CTGATGTACCGGTTCGAGGAGGAGCTGTTCCTGCGGAGCCTGCAGGACT

ACAAGATCCAGAGCGCGCTGCTCGTGCCGACCCTGTTCAGCTTCTTCGC

CAAGAGCACCCTGATCGACAAGTACGACCTGTCGAACCTGCACGAGATC

GCCAGCGGGGGCGCCCCGCTGAGCAAGGAGGTGGGCGAGGCCGTGGCCA

AGCGGTTCCACCTCCCGGGCATCCGCCAGGGCTACGGCCTGACCGAGAC

CACGAGCGCGATCCTGATCACCCCCGAGGGGGACGACAAGCCGGGCGCC

GTGGGCAAGGTGGTCCCGTTCTTCGAGGCCAAGGTGGTGGACCTGGACA

CCGGCAAGACCCTGGGCGTGAACCAGCGGGGCGAGCTGTGCGTGCGGGG

GCCGATGATCATGAGCGGCTACGTGAACAACCCGGAGGCCACCAACGCC

CTCATCGACAAGGACGGCTGGCTGCACAGCGGCGACATCGCCTACTGGG

ACGAGGACGAGCACTTCTTCATCGTCGACCGGCTGAAGTCGCTGATCAA

GTACAAGGGCTACCAGGTGGCGCCGGCCGAGCTGGAGAGCATCCTGCTC

CAGCACCCCAACATCTTCGACGCCGGCGTGGCCGGGCTGCCGGACGACG

ACGCCGGCGAGCTGCCGGCCGCGGTGGTGGTGCTGGAGCACGGCAAGAC

-continued

```
CATGACGGAGAAGGAGATCGTCGACTACGTGGCCAGCCAGGTGACCACC

GCCAAGAAGCTGCGGGGCGGCGTGGTGTTCGTGGACGAGGTCCCGAAGG

GCCTGACCGGGAAGCTCGACGCCCGGAAGATCCGCGAGATCCTGATCAA

GGCCAAGAAGGGCGGCAAGATCGCCGTGAGCTAAGCTGCCTTCTGCGGG

GCTTGCCTTCTGGCCATGCCCTTCTTCTCTCCCTTGCACCTGTACCTCT

TGGTCTTTGAATAAAGCCTGAGTAGGAAGTATCCCAATGGCGCGCCGAG

CTTGGCAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAAAAA
```

Lipid Nanoparticles (LNPs) Physicochemical Characterization

The LNP size and polydispersity index (PDI), determined by dynamic light scattering (DLS), and zeta potential were measured by a Zetasizer machine (Malvern). RNA concentration and encapsulation efficacy were analyzed by the Quant-IT Ribogreen kit by calculating the percentage encapsulation at 100%−(RNA-LNPs/RNA-LNPs with Triton X-100).

In Vitro Expression

RAW 264.7 and Hep G2 cells were transfected with 100 ng/mL of RNA-LNPs encoding for firefly-luciferase. At 72 hours post transfection, the cells were washed and lysed. The luciferase expression was determined in the cell lysates with the luciferase assay reagent kit (Promega), according to the kit protocol, luciferase activity was measured by a luminometer.

In Vitro Toxicity

RAW 264.7 and Hep G2 cells were transfected with 1 μg/mL RNA-LNPs. At 72 hours post transfection, cell viability was determined with the CellTiter-Glo® reagent kit, according to the kit protocol, measured by a luminometer.

The cell viability was calculated according to the following formula:

$$\frac{\text{transfected cells luminescence signal}}{\text{untreated cells luminescence signal}} \times 100\%$$

In Vivo Expression 6-8 week old, female BALB/C mice were injected with 0.05 mg*kg-1 of RNA-LNPs encoding for firefly-luciferase by intravenous injection. At 6 hours post injection, animals were intraperitoneally injected with 15 mg/ml of Luciferin substrate and whole-body luminescence was determined by a bioluminescent in vivo imaging system (IVIS).

MCP-I Cytokine Elevation in Serum 6-8 week old, female BALB/C mice were injected with 0.5 mg*kg-1 of RNA LNPs by intravenous injection. At 2 and 24 hours post injection, animals were bled and sera concentrations of MCP-I were determined by an immunoassay (Luminex).

Liver Enzyme Elevation in Serum 6-8 week old, female BALB/C mice were injected with 0.5 mg*kg-1 of RNA LNPs by intravenous injection. At 2 and 24 hours post injection, animals were bled and sera concentrations of Alanine Aminotransferase (ALT) and Aspartate Aminotransferase (AST) were determined by a blood chemistry analyzer. PBS control data for mice are as follows:

| 1. PBS control | | | | | |
|---|---|---|---|---|---|
| ALT in Sera (IU/L) 2 hours After 0.5 MPK Injection | ALT in Sera (IU/L) 24 hours After 0.5 MPK Injection | AST in Sera (IU/L) 2 hours After 0.5 MPK Injection | AST in Sera (IU/L) 24 hours After 0.5 MPK Injection | MCP-I in Sera 2 hours After 0.5 MPK Injection (pg/ml) | MCP-I in Sera 24 hours After 0.5 MPK Injection (pg/ml) |
| 93 | 136.33 | 143 | 127.67 | 55.56333333 | 30.14 |

Local Tolerance Determination by Footpad Injection 6-8 week old, female BALB/C mice were injected with 0.175 mg*kg-1 RNA LNPs by subcutaneous injection into the footpad. Prior to, and 24 hours post injections, injected footpad thickness was determined by a caliper. Results in Table D showed slightly increase of footpad thickness.

The test results are shown in Table A1, Table A2, Table B1, Table B2, Table C and Table D.

TABLE A1

| | cirRNA (SEQ ID NO: 1) | | | |
|---|---|---|---|---|
| Lipid no. | Size | PDI | Zeta (mV) | Encapsulation Efficiency % |
| 43 | 91.2 | 0.04 | 1.26 | 95% |
| 51 | 89.19 | 0.04 | −0.71 | 97% |
| 68 | 57.94 | 0.12 | −0.647 | 92% |
| 75 | 91.13 | 0.13 | 1.59 | 97% |
| 90 | 67.68 | 0.06 | 1.34 | 87% |
| 127 | 71.42 | 0.04 | −3.13 | 95% |
| 128 | 93.54 | 0.1 | 0.282 | 94% |
| 129 | 88.9 | 0.08 | 0.417 | 96% |
| 131 | 74.78 | 0.22 | 5.61 | 96% |
| 132 | 91.78 | 0.072 | −0.7024 | 97% |
| 148 | 93.46 | 0.03 | −2.35 | 95% |
| 165 | 90.53 | 0.05 | −1.76 | 91% |
| 168 | 93.98 | 0.06 | −0.573 | 97% |
| 169 | 73.59 | 0.003 | −2.92 | 95% |
| 170 | 96.82 | 0.08 | −0.455 | 97% |
| 195 | 94.75 | 0.2474 | 6.123 | 94% |
| 196 | 89.57 | 0.0364 | 0.4256 | 93% |
| 197 | 82.64 | 0.14 | 5.5 | 96% |
| 245 | 99.5 | 0.12 | −5.02 | 86% |
| 66 | 86.66 | 0.05 | −2.1 | 96% |
| 6 | 87.2 | 0.06 | −2.24 | 96% |
| 8 | 80.1 | 0.162 | −20.4 | 84% |
| 35 | 116.3 | 0.115 | −6.298 | 71% |
| 36 | 125.4 | 0.138 | −3.556 | 96% |
| 37 | 145.8 | 0.138 | 4.079 | 95% |
| 39 | 169.5 | 0.07 | −3.335 | 91% |
| 41 | 186 | 0.163 | 5.74 | 91% |
| 46 | 137.6 | 0.088 | 3.255 | 100% |
| 52 | 120.9 | 0.09551 | 4.79 | 100% |
| 67 | 142.9 | 0.087 | 8.392 | 99% |
| 69 | 161.1 | 0.205 | 16.31 | 95% |
| 70 | 83.09 | 0.115 | 11.22 | 97% |
| 76 | 137.8 | 0.1484 | 0.03131 | 96% |
| 78 | 110 | 0.0918 | 9.83 | 100% |
| 79 | 99.18 | 0.2181 | −2.908 | 93% |
| 85 | 81.48 | 0.1671 | 4.031 | 91% |
| 119 | 142.1 | 0.064 | 9.53 | 96% |
| 120 | 143.8 | 0.09314 | 9.34 | 96% |
| 122 | 134.6 | 0.187 | 10.84 | 96% |
| 130 | 145.8 | 0.1685 | 11.37 | 99% |
| 133 | 92.91 | 0.0973 | 2.957 | 95% |
| 134 | 89.71 | 0.043 | −8.698 | 90% |
| 135 | 150.9 | 0.1211 | 8.469 | 100% |
| 136 | 143.7 | 0.146 | 16.11 | 95% |
| 137 | 224.1 | 0.1423 | 19.29 | 92% |
| 138 | 130.8 | 0.1821 | 15.82 | 96% |
| 146 | 59.34 | 0.2699 | 20.28 | 87% |
| 147 | 53.54 | 0.07303 | 4.888 | 86% |
| 149 | 71.14 | 0.02962 | 9.196 | 88% |
| 150 | 91.37 | 0.05565 | 17.84 | 79% |

TABLE A1-continued

| Lipid no. | cirRNA (SEQ ID NO: 1) Size | PDI | Zeta (mV) | Encapsulation Efficiency % |
|---|---|---|---|---|
| 151 | 98.37 | 0.1693 | 20.18 | 89% |
| 153 | 71.11 | 0.09308 | 18.95 | 89% |
| 154 | 75.25 | 0.1144 | 25.23 | 90% |
| 155 | 92.39 | 0.1182 | 15.16 | 76% |
| 158 | 97.72 | 0.2315 | 6.058 | 72% |
| 159 | 57.86 | 0.1754 | −5.631 | 84% |
| 161 | 58.97 | 0.08727 | −10.23 | 75% |
| 162 | 86.23 | 0.3875 | 14.91 | 76% |
| 163 | 61.87 | 0.1586 | −3.271 | 79% |
| 164 | 76.41 | 0.2218 | 3.42 | 75% |
| 166 | 71.24 | 0.2013 | 4.157 | 78% |
| 167 | 61.26 | 0.0668 | −3.412 | 82% |
| 171 | 55.9 | 0.1297 | −5.824 | 77% |
| 172 | 67.53 | 0.2521 | 1.36 | 83% |
| 173 | 73.65 | 0.3423 | −0.5735 | 82% |
| 174 | 57.29 | 0.0911 | −4.35 | 89% |
| 178 | 61.85 | 0.1534 | 16.19 | 95% |
| 185 | 69.89 | 0.102 | −1.137 | 88% |
| 186 | 122.7 | 0.4618 | 14.31 | 90% |
| 187 | 65.71 | 0.277 | 8.983 | 92% |
| 188 | 73.74 | 0.07877 | −9.419 | 88% |
| 189 | 84.04 | 0.4058 | 18.88 | 95% |
| 191 | 79.79 | 0.2327 | 12.32 | 91% |
| 192 | 76.52 | 0.1344 | −7.77 | 92% |
| 193 | 66.71 | 0.3634 | 15.29 | 94% |
| 198 | 64.1 | 0.2199 | −3.471 | 94% |
| 199 | 97.91 | 0.436 | 13.62 | 94% |
| 200 | 82.06 | 0.2967 | 7.27 | 95% |
| 202 | 60.75 | 0.1932 | 16.36 | 93% |
| 203 | 98.65 | 0.08783 | −0.09389 | 73% |
| 205 | 61.16 | 0.1521 | 18.81 | 94% |
| 209 | 86.68 | 0.1886 | 13.53 | 93% |
| 211 | 97.77 | 0.2243 | 7.113 | 94% |
| 212 | 65.77 | 0.1853 | −3.175 | 93% |
| 213 | 114.2 | 0.2952 | 13.22 | 94% |
| 214 | 76.43 | 0.304 | 5.906 | 96% |
| 215 | 62.22 | 0.05226 | −3.755 | 96% |
| 216 | 75.92 | 0.4093 | 11.61 | 96% |
| 217 | 60.05 | 0.1439 | 1.061 | 94% |
| 218 | 96.36 | 0.3124 | 5.94 | 96% |
| 219 | 76.57 | 0.1125 | 0.7668 | 93% |
| 220 | 112.7 | 0.304 | 10.78 | 96% |
| 221 | 65.7 | 0.1852 | −1.368 | 91% |
| 222 | 98.73 | 0.4109 | 26.75 | 97% |
| 223 | 60.01 | 0.08837 | −2.046 | 92% |
| 224 | 86.14 | 0.4284 | 27.23 | 97% |
| 226 | 115.7 | 0.298 | 14.86 | 95% |
| 227 | 79.97 | 0.1088 | 4.217 | 92% |
| 244 | 87.4 | 0.3577 | −0.164 | 96% |
| 279 | 87.32 | 0.2722 | −0.06404 | 95% |
| 270 | 66.18 | 0.258 | 3.201 | 95% |
| 271 | 98.73 | 0.2068 | 0.345 | 93% |
| 272 | 74.91 | 0.3463 | 5.434 | 95% |
| 273 | 88.34 | 0.257 | 1.543 | 95% |
| 274 | 50.6 | 0.112 | −2.714 | 94% |
| 275 | 60 | 0.2727 | 6.337 | 95% |
| 276 | 64.42 | 0.1464 | −0.02248 | 96% |
| 277 | 76.75 | 0.2188 | −0.6853 | 92% |
| 278 | 91.92 | 0.1471 | 0.06032 | 96% |
| 344 | 98.08 | 0.1332 | 2.343 | 97% |
| 345 | 70.01 | 0.1901 | −2.69 | 92% |
| 346 | 111.1 | 0.264 | −0.00452 | 95% |
| 347 | 90.56 | 0.2462 | −0.6677 | 94% |
| 348 | 100.8 | 0.2546 | 1.734 | 98% |
| 349 | 75.85 | 0.1452 | 0.02482 | 97% |
| 350 | 112.8 | 0.1717 | 6.91 | 97% |
| 351 | 99.16 | 0.1705 | −0.1951 | 95% |
| 353 | 116.6 | 0.2483 | 4.334 | 95% |
| 354 | 98.03 | 0.1505 | −2.263 | 96% |
| 355 | 64.55 | 0.2834 | 8.299 | 90% |
| 356 | 336.5 | 0.423 | −0.5834 | 77% |
| 357 | 104.3 | 0.3136 | 6.34 | 87% |
| 358 | 81.33 | 0.1606 | 1.109 | 87% |
| 359 | 113.9 | 0.337 | 6.547 | 89% |
| 360 | 82.84 | 0.2143 | −2.27 | 85% |

TABLE A1-continued

| Lipid no. | cirRNA (SEQ ID NO: 1) Size | PDI | Zeta (mV) | Encapsulation Efficiency % |
|---|---|---|---|---|
| 361 | 91.91 | 0.438 | 8.107 | 88% |
| 362 | 88.25 | 0.3944 | 11.87 | 89% |
| 363 | 130.7 | 0.2547 | 5.356 | 92% |
| 364 | 113.5 | 0.2481 | 0.2395 | 89% |
| 365 | 72.69 | 0.1303 | −2.341 | 92% |
| 366 | 118.4 | 0.2572 | −0.4163 | 92% |
| 367 | 131.6 | 0.2544 | 0.7313 | 91% |
| 368 | 130.2 | 0.2875 | 3.421 | 92% |
| 369 | 93.14 | 0.1084 | 4.427 | 97% |
| 370 | 90.63 | 0.08162 | 0.1617 | 97% |
| 372 | 118.2 | 0.2663 | 4.685 | 92% |
| 373 | 92.65 | 0.2353 | −3.695 | 92% |
| 374 | 105.2 | 0.1683 | 3.631 | 96% |
| 375 | 92.54 | 0.2011 | −1.253 | 89% |
| 376 | 102 | 0.1398 | 9.074 | 97% |
| 377 | 112.8 | 0.2338 | 2.594 | 93% |
| 378 | 130.6 | 0.2637 | 6.729 | 93% |
| 379 | 117.2 | 0.1919 | 3.38 | 92% |
| 380 | 112.8 | 0.1668 | −2.171 | 92% |
| 382 | 145.3 | 0.2452 | 4.75 | 94% |
| 383 | 90.41 | 0.1744 | −0.4606 | 95% |
| 384 | 135.9 | 0.2423 | 8.213 | 96% |
| 385 | 159 | 0.2458 | 11.28 | 94% |
| Lipid A | 145.2 | 0.2901 | 1.916 | 74% |
| Lipid B | 93.61 | 0.2623 | 3.811 | 88% |
| Lipid C | 118.3 | 0.1152 | −1.304 | 74% |

TABLE A2

| Lipid no. | mRNA (SEQ ID NO: 2) Size | PDI | Zeta (mV) | Encapsulation Efficiency |
|---|---|---|---|---|
| 43 | 67.1 | 0.09046 | 12.6 | 88% |
| 51 | 79.21 | 0.1368 | 3.197 | 89% |
| 68 | 61.9 | 0.1057 | 5.641 | 88% |
| 75 | 70.28 | 0.1903 | 13.66 | 89% |
| 90 | 65.54 | 0.06127 | 7.6 | 88% |
| 127 | 57.31 | 0.1822 | −1.439 | 87% |
| 128 | 75.38 | 0.1021 | 6.141 | 91% |
| 129 | 55.55 | 0.1768 | 0.5475 | 90% |
| 131 | 84.16 | 0.1606 | 15.29 | 90.68% |
| 132 | 56.12 | 0.2359 | −8.336 | 89.06% |
| 148 | 122.1 | 0.07065 | 3.769 | 93.50% |
| 165 | 98.24 | 0.1265 | −0.3264 | 86.43% |
| 168 | 68.36 | 0.101 | 0.8152 | 89.10% |
| 169 | 88.09 | 0.07881 | −0.8755 | 87.64% |
| 170 | 165.8 | 0.0744 | 3.233 | 86.13% |
| 195 | 114.3 | 0.1254 | 16.37 | 75.44% |
| 196 | 117.5 | 0.1806 | −2.076 | 91.87% |
| 197 | 113.7 | 0.07142 | 13.59 | 79.87% |
| 245 | 108.8 | 0.1109 | 2.004 | 85.53% |
| 66 | 75.46 | 0.09823 | 2.213 | 88.25% |
| 6 | 106.5 | 0.03302 | 4.201 | 93.16% |
| 270 | 101.7 | 0.1592 | 6.102 | 94.52% |
| 271 | 97.34 | 0.1219 | 0.8825 | 94.51% |
| 276 | 88.07 | 0.07602 | 0.8258 | 94.50% |
| 278 | 119 | 0.1831 | 0.3567 | 86.19% |
| 344 | 97.82 | 0.1063 | 1.967 | 93.45% |
| 348 | 101.8 | 0.1488 | 8.774 | 83.15% |
| 350 | 105.3 | 0.1151 | 0.9211 | 83.19% |
| 351 | 178.8 | 0.3512 | −4.142 | 66.39% |
| 354 | 128.6 | 0.2144 | −0.3781 | 71.30% |
| 369 | 120.9 | 0.1166 | 10 | 92.99% |
| 370 | 112.8 | 0.1494 | 0.9875 | 93.87% |
| 374 | 88.86 | 0.06656 | 3.895 | 85.44% |
| 375 | 75.13 | 0.008186 | −4.713 | 88.53% |
| 376 | 87.9 | 0.07745 | 5.722 | 90.28% |
| 380 | 88.83 | 0.02507 | −2.552 | 80.50% |
| 383 | 94.23 | 0.1802 | −13.05 | 86.72% |
| Lipid A | 118 | 0.2719 | 10.76 | 83.95% |

TABLE A2-continued

| | mRNA (SEQ ID NO: 2) | | | |
|---|---|---|---|---|
| Lipid no. | Size | PDI | Zeta (mV) | Encapsulation Efficiency |
| Lipid B | 80.28 | 0.2472 | 0.02157 | 86.87% |
| Lipid C | 139.5 | 0.08023 | 8.776 | 84.38% |

TABLE B1

| | cirRNA (SEQ ID NO: 1) | | | | |
|---|---|---|---|---|---|
| Lipid no. | In vitro Expression HepG2 | In vitro Expression RAW | In vitro Viability HepG2 | In vitro Viability RAW | In vivo Expression (Whole Body) |
| 43 | 1.75E+04 | 1.10E+05 | 97% | 97% | 6.22E+08 |
| 51 | 9.85E+05 | 8.74E+06 | 88% | 104% | 6.85E+08 |
| 68 | 2.63E+06 | 6.86E+05 | 99% | 67% | 1.34E+08 |
| 75 | 1.94E+06 | 2.08E+06 | 85% | 75% | 9.85E+08 |
| 90 | 1.27E+05 | 8.50E+04 | 95% | 24% | 8.80E+07 |
| 127 | 2.14E+06 | 4.87E+06 | 99% | 76% | 1.14E+09 |
| 128 | 4.01E+06 | 5.15E+06 | 103% | 59% | 5.46E+08 |
| 129 | 8.56E+06 | 8.78E+06 | 79% | 7% | 1.69E+09 |
| 131 | 4.49E+06 | 4.04E+06 | 83% | 77% | 2.27E+08 |
| 132 | 1.44E+05 | 4.24E+05 | 97% | 108% | 6.13E+08 |
| 148 | 2.35E+06 | 2.40E+05 | 47% | 21% | 5.07E+08 |
| 165 | 7.20E+05 | 5.29E+04 | 94% | 88% | 1.11E+08 |
| 168 | 1.03E+07 | 1.66E+06 | 55% | 79% | 4.82E+08 |
| 169 | 1.94E+06 | 5.36E+05 | 88% | 82% | 4.92E+08 |
| 170 | 2.91E+07 | 3.14E+06 | 31% | 92% | 3.35E+08 |
| 195 | 1.62E+05 | 9.03E+03 | 103% | 96% | 3.91E+07 |
| 196 | 5.54E+04 | 1.22E+04 | 103% | 91% | 1.86E+07 |
| 197 | 6.41E+05 | 1.87E+04 | 88% | 0% | 3.04E+07 |
| 245 | 7.24E+05 | 2.68E+05 | 88% | 94% | 2.99E+08 |
| 66 | 9.78E+07 | 9.90E+06 | 93% | 100% | 2.03E+09 |
| 6 | 1.82E+08 | 1.11E+07 | 89% | 100% | 1.21E+09 |
| 8 | 2.33E+01 | 6.90E+01 | 110% | 105% | 9.52E+04 |
| 35 | 2.82E+02 | 6.25E+03 | 103% | 108% | 1.16E+05 |
| 36 | 9.18E+04 | 2.03E+04 | 82% | 95% | 1.21E+05 |
| 37 | 5.96E+05 | 1.98E+04 | 87% | 92% | 1.16E+05 |
| 39 | 8.11E+02 | 2.58E+03 | 90% | 96% | 1.15E+04 |
| 41 | 2.77E+01 | 1.12E+05 | 89% | 70% | 4.69E+04 |
| 46 | 3.70E+01 | 3.51E+02 | 102% | 99% | 1.92E+06 |
| 52 | 2.08E+05 | 4.95E+03 | 73% | 94% | 3.60E+07 |
| 67 | 1.21E+05 | 5.99E+02 | 120% | 107% | 6.00E+07 |
| 69 | 4.62E+04 | 2.25E+02 | 86% | 102% | 2.17E+06 |
| 70 | 9.79E+04 | 2.29E+03 | 120% | 104% | 2.08E+05 |
| 76 | 1.22E+04 | 5.53E+02 | 121% | 86% | 2.55E+05 |
| 78 | 1.31E+05 | 7.80E+03 | 113% | 106% | 4.92E+05 |
| 79 | 3.94E+03 | 4.60E+01 | 104% | 104% | 4.70E+07 |
| 81 | 6.71E+04 | 1.56E+03 | 121% | 107% | 1.15E+04 |
| 85 | 2.85E+07 | 5.74E+05 | 78% | 105% | 1.96E+07 |
| 99 | 1.13E+04 | 1.01E+04 | 78% | 137% | 5.53E+07 |
| 118 | 1.43E+03 | 1.42E+04 | 19% | 8% | 7.90E+06 |
| 119 | 1.46E+03 | 1.47E+04 | 17% | 8% | 9.30E+05 |
| 120 | 2.13E+03 | 8.51E+03 | 100% | 81% | 3.33E+05 |
| 122 | 2.48E+03 | 2.24E+04 | 17% | 8% | 1.43E+05 |
| 130 | 5.31E+06 | 6.92E+05 | 91% | 90% | 1.08E+07 |
| 133 | 4.26E+04 | 8.30E+04 | 13% | 27% | 2.04E+08 |
| 134 | 3.17E+04 | 5.25E+04 | 13% | 84% | 8.93E+05 |
| 135 | 2.30E+06 | 9.80E+04 | 91% | 103% | 3.51E+07 |
| 136 | 2.15E+03 | 1.93E+02 | 20% | 8% | 6.14E+03 |
| 137 | 1.57E+03 | 1.21E+02 | 12% | 9% | 1.84E+05 |
| 138 | 6.75E+01 | 9.75E+01 | 12% | 10% | 1.30E+05 |
| 139 | 4.85E+01 | 1.64E+02 | 16% | 8% | 3.48E+06 |
| 146 | 9.18E+05 | 8.92E+04 | 41% | 99% | 4.74E+06 |
| 147 | 1.60E+04 | 7.92E+03 | 87% | 65% | 5.02E+07 |
| 149 | 2.08E+05 | 1.91E+04 | 123% | 100% | 6.07E+07 |
| 150 | 1.44E+04 | 6.81E+02 | 114% | 104% | 7.27E+05 |
| 151 | 8.79E+03 | 3.27E+01 | 110% | 99% | 1.18E+05 |
| 153 | 1.95E+04 | 2.44E+02 | 120% | 104% | 1.02E+05 |
| 154 | 2.59E+05 | 2.36E+03 | 106% | 101% | 1.01E+05 |
| 155 | 2.72E+04 | 5.98E+02 | 111% | 101% | 5.77E+07 |
| 156 | 2.86E+04 | 1.67E+03 | 84% | 93% | 4.92E+04 |
| 158 | 1.24E+06 | 1.37E+04 | 64% | 0% | 1.62E+07 |
| 159 | 8.41E+05 | 4.41E+04 | 92% | 90% | 1.95E+07 |

TABLE B1-continued

| | cirRNA (SEQ ID NO: 1) | | | | |
|---|---|---|---|---|---|
| Lipid no. | In vitro Expression HepG2 | In vitro Expression RAW | In vitro Viability HepG2 | In vitro Viability RAW | In vivo Expression (Whole Body) |
| 160 | 6.38E+05 | 1.94E+04 | 94% | 93% | 4.44E+05 |
| 161 | 4.62E+04 | 6.74E+03 | 95% | 81% | 1.88E+07 |
| 162 | 4.27E+05 | 3.76E+03 | 83% | 86% | 1.01E+06 |
| 163 | 5.77E+04 | 3.32E+03 | 92% | 88% | 7.96E+06 |
| 164 | 3.92E+06 | 9.56E+04 | 74% | 86% | 7.11E+07 |
| 166 | 2.17E+07 | 1.48E+06 | 22% | 12% | 6.43E+05 |
| 167 | 8.85E+04 | 2.79E+04 | 102% | 90% | 9.22E+06 |
| 171 | 3.04E+05 | 2.44E+05 | 97% | 88% | 5.09E+07 |
| 172 | 1.12E+07 | 5.83E+05 | 41% | 90% | 2.14E+07 |
| 173 | 3.32E+07 | 9.48E+05 | 57% | 90% | 3.45E+07 |
| 174 | 1.56E+05 | 1.30E+04 | 89% | 92% | 5.15E+07 |
| 176 | 6.28E+03 | 4.83E+04 | 88% | 93% | 1.31E+07 |
| 178 | 6.17E+04 | 1.31E+03 | 99% | 92% | 1.31E+06 |
| 184 | 9.87E+04 | 1.93E+03 | 91% | 88% | 5.28E+07 |
| 185 | 9.12E+03 | 5.29E+04 | 90% | 85% | 1.22E+08 |
| 186 | 1.51E+05 | 2.82E+02 | 88% | 0% | 2.96E+06 |
| 187 | 3.27E+05 | 7.47E+04 | 93% | 0% | 2.29E+06 |
| 188 | 1.12E+04 | 2.82E+03 | 96% | 87% | 2.17E+07 |
| 189 | 9.85E+04 | 2.71E+02 | 89% | 1% | 1.79E+06 |
| 191 | 4.43E+04 | 1.22E+03 | 92% | 4% | 1.02E+07 |
| 192 | 4.18E+04 | 8.42E+03 | 94% | 86% | 8.52E+07 |
| 193 | 5.28E+05 | 1.70E+03 | 94% | 3% | 1.00E+06 |
| 198 | 2.19E+04 | 8.39E+04 | 104% | 90% | 9.90E+06 |
| 199 | 3.74E+05 | 1.29E+03 | 87% | 0% | 3.44E+05 |
| 200 | 4.46E+05 | 4.45E+04 | 103% | 0% | 6.79E+05 |
| 202 | 2.49E+05 | 3.35E+02 | 94% | 92% | 2.33E+05 |
| 203 | 1.12E+04 | 7.82E+04 | 103% | 91% | 6.84E+06 |
| 205 | 5.81E+05 | 7.09E+03 | 94% | 95% | 6.61E+05 |
| 209 | 3.81E+04 | 1.08E+02 | 96% | 95% | 6.62E+05 |
| 211 | 1.14E+07 | 2.36E+05 | 90% | 91% | 1.09E+07 |
| 212 | 6.37E+04 | 1.44E+05 | 99% | 82% | 4.68E+06 |
| 213 | 6.40E+06 | 2.06E+04 | 74% | 90% | 2.11E+06 |
| 214 | 3.88E+06 | 1.20E+05 | 83% | 87% | 1.18E+06 |
| 215 | 5.62E+04 | 7.31E+03 | 85% | 86% | 1.61E+07 |
| 216 | 1.59E+07 | 3.31E+05 | 76% | 75% | 1.34E+06 |
| 217 | 2.45E+04 | 8.05E+03 | 82% | 90% | 7.35E+06 |
| 218 | 5.25E+06 | 9.16E+04 | 71% | 62% | 7.53E+07 |
| 219 | 7.09E+05 | 3.53E+04 | 58% | 80% | 1.34E+08 |
| 220 | 3.55E+06 | 1.52E+04 | 89% | 98% | 1.45E+07 |
| 221 | 2.82E+05 | 5.03E+05 | 87% | 83% | 1.79E+07 |
| 222 | 1.63E+06 | 8.85E+04 | 42% | 87% | 1.59E+06 |
| 223 | 6.42E+04 | 4.76E+04 | 92% | 76% | 5.53E+06 |
| 224 | 3.58E+05 | 6.89E+03 | 90% | 73% | 5.05E+05 |
| 226 | 7.79E+05 | 9.79E+03 | 91% | 108% | 2.20E+07 |
| 227 | 4.71E+05 | 1.99E+05 | 82% | 83% | 9.21E+07 |
| 244 | 3.62E+06 | 9.56E+02 | 94% | 90% | 3.95E+07 |
| 279 | 5.05E+06 | 1.62E+05 | 23% | 55% | 3.67E+07 |
| 270 | 9.88E+06 | 9.33E+06 | 95% | 120% | 9.90E+07 |
| 271 | 5.51E+06 | 1.59E+06 | 91% | 121% | 8.99E+07 |
| 272 | 1.01E+07 | 1.34E+06 | 97% | 121% | 6.35E+06 |
| 273 | 6.48E+06 | 1.35E+06 | 93% | 121% | 5.16E+06 |
| 274 | 4.11E+06 | 4.30E+05 | 97% | 127% | 2.06E+07 |
| 275 | 7.54E+06 | 4.30E+05 | 102% | 129% | 3.66E+06 |
| 276 | 9.80E+05 | 1.07E+06 | 95% | 117% | 1.88E+08 |
| 277 | 1.17E+07 | 8.13E+06 | 89% | 121% | 7.29E+07 |
| 278 | 2.22E+07 | 8.67E+06 | 91% | 132% | 1.19E+08 |
| 344 | 1.08E+07 | 1.97E+06 | 96% | 94% | 7.43E+07 |
| 345 | 2.57E+06 | 2.20E+05 | 99% | 102% | 2.49E+06 |
| 346 | 1.02E+06 | 1.46E+05 | 73% | 93% | 3.59E+06 |
| 347 | 1.04E+06 | 4.27E+04 | 92% | 96% | 7.61E+06 |
| 348 | 1.59E+06 | 2.47E+05 | 65% | 73% | 6.47E+07 |
| 349 | 2.42E+04 | 7.58E+03 | 90% | 87% | 1.01E+07 |
| 350 | 1.43E+07 | 3.38E+06 | 95% | 74% | 1.03E+08 |
| 351 | 1.87E+06 | 6.44E+05 | 96% | 98% | 1.35E+08 |
| 353 | 4.17E+04 | 3.38E+03 | 37% | 40% | 1.48E+06 |
| 354 | 1.63E+06 | 4.53E+05 | 119% | 45% | 6.08E+08 |
| 355 | 1.70E+03 | 9.80E+02 | 123% | 72% | 7.94E+05 |
| 356 | 1.96E+03 | 1.06E+04 | 112% | 84% | 5.24E+05 |
| 357 | 2.53E+05 | 7.92E+03 | 120% | 8% | 1.85E+06 |
| 358 | 1.88E+05 | 9.81E+03 | 121% | 83% | 2.29E+07 |
| 359 | 9.26E+04 | 2.38E+03 | 122% | 8% | 1.85E+06 |
| 360 | 1.22E+05 | 1.63E+05 | 113% | 86% | 7.50E+07 |
| 361 | 1.62E+05 | 2.97E+03 | 114% | 4% | 1.10E+06 |
| 362 | 3.82E+04 | 1.99E+03 | 106% | 0% | 1.68E+06 |

TABLE B1-continued

| | cirRNA (SEQ ID NO: 1) | | | | |
|---|---|---|---|---|---|
| Lipid no. | In vitro Expression HepG2 | In vitro Expression RAW | In vitro Viability HepG2 | In vitro Viability RAW | In vivo Expression (Whole Body) |
| 363 | 3.17E+05 | 9.15E+03 | 112% | 65% | 2.22E+06 |
| 364 | 1.11E+06 | 9.94E+04 | 81% | 64% | 4.73E+06 |
| 365 | 3.17E+05 | 3.87E+04 | 109% | 88% | 1.32E+08 |
| 366 | 3.39E+05 | 2.01E+04 | 84% | 99% | 3.26E+06 |
| 367 | 5.88E+05 | 2.48E+04 | 85% | 90% | 1.74E+06 |
| 368 | 1.22E+06 | 1.18E+05 | 68% | 67% | 4.18E+06 |
| 369 | 1.04E+06 | 1.84E+05 | 78% | 61% | 1.30E+07 |
| 370 | 2.65E+07 | 1.98E+06 | 93% | 96% | 3.68E+08 |
| 372 | 4.98E+03 | 3.30E+02 | 42% | 57% | 1.10E+06 |
| 373 | 5.98E+04 | 2.32E+04 | 63% | 91% | 5.62E+06 |
| 374 | 1.89E+07 | 2.34E+06 | 70% | 84% | 1.53E+08 |
| 375 | 1.10E+06 | 7.06E+05 | 100% | 90% | 3.46E+08 |
| 376 | 4.84E+06 | 1.00E+06 | 48% | 87% | 1.16E+08 |
| 377 | 2.55E+06 | 1.05E+05 | 71% | 85% | 8.84E+06 |
| 378 | 3.39E+06 | 6.58E+05 | 26% | 75% | 8.79E+06 |
| 379 | 1.16E+07 | 1.60E+06 | 45% | 72% | 2.86E+07 |
| 380 | 2.95E+07 | 2.22E+06 | 89% | 86% | 4.50E+08 |
| 382 | 3.97E+05 | 5.69E+04 | 42% | 84% | 4.22E+06 |
| 383 | 6.03E+06 | 2.93E+06 | 97% | 89% | 4.66E+08 |
| 384 | 2.57E+06 | 3.15E+05 | 81% | 88% | 1.15E+07 |
| 385 | 1.31E+05 | 1.37E+04 | 74% | 80% | 1.79E+06 |
| Lipid A | 1.90E+06 | Lipid A | 1.90E+06 | Lipid A | 1.90E+06 |
| Lipid B | 8.71E+05 | Lipid B | 8.71E+05 | Lipid B | 8.71E+05 |
| Lipid C | 8.20E+02 | Lipid C | 8.20E+02 | Lipid C | 8.20E+02 |

TABLE B2

| | mRNA (SEQ ID NO: 2) | | | | |
|---|---|---|---|---|---|
| Lipid no. | In vitro Expression HepG2 | In vitro Expression RAW | In vitro Viability HepG2 | In vitro Viability RAW | In vivo Expression (Whole Body) |
| 43 | 1.33E+06 | 9.60E+04 | 97% | 88% | 1.98E+08 |
| 51 | 4.66E+07 | 2.63E+06 | 83% | 80% | 1.78E+09 |
| 68 | 3.74E+03 | 5.58E+02 | 100% | 104% | 1.54E+08 |

TABLE B2-continued

| | mRNA (SEQ ID NO: 2) | | | | |
|---|---|---|---|---|---|
| Lipid no. | In vitro Expression HepG2 | In vitro Expression RAW | In vitro Viability HepG2 | In vitro Viability RAW | In vivo Expression (Whole Body) |
| 75 | 9.23E+06 | 2.18E+06 | 95% | 96% | 4.22E+08 |
| 90 | 2.16E+05 | 1.21E+05 | 85% | 96% | 2.73E+07 |
| 127 | 1.75E+06 | 5.53E+05 | 100% | 109% | 8.69E+07 |
| 128 | 2.16E+07 | 1.72E+06 | 94% | 92% | 6.98E+08 |
| 129 | 7.03E+06 | 1.11E+06 | 100% | 97% | 1.42E+08 |
| 131 | 5.66E+06 | 9.55E+05 | 89% | 96% | 4.52E+07 |
| 132 | 1.83E+05 | 1.27E+05 | 80% | 93% | 6.62E+08 |
| 148 | 6.39E+02 | 8.69E+05 | 128% | 102% | 1.69E+09 |
| 165 | 3.27E+06 | 6.06E+05 | 93% | 101% | 1.63E+08 |
| 168 | 1.80E+07 | 6.99E+05 | 70% | 75% | 5.89E+09 |
| 169 | 1.59E+07 | 2.87E+06 | 93% | 83% | 1.46E+09 |
| 170 | 2.23E+08 | 2.87E+02 | 124% | 82% | 1.02E+09 |
| 195 | 1.23E+07 | 1.67E+07 | 116% | 77% | 1.63E+08 |
| 196 | 1.58E+06 | 2.31E+06 | 91% | 110% | 1.41E+08 |
| 197 | 2.51E+07 | 1.19E+07 | 116% | 0% | 4.89E+08 |
| 245 | 4.35E+06 | 3.81E+06 | 118% | 89% | 1.18E+08 |
| 66 | 1.59E+08 | 6.79E+06 | 82% | 72% | 3.50E+09 |
| 6 | 2.28E+08 | 1.21E+07 | 113% | 77% | 1.91E+09 |
| 270 | 2.31E+07 | 3.27E+06 | 116% | 96% | 3.45E+08 |
| 271 | 3.69E+06 | 6.06E+06 | 117% | 85% | 8.51E+08 |
| 276 | 3.01E+05 | 8.16E+05 | 115% | 83% | 1.26E+07 |
| 278 | 3.75E+07 | 6.01E+06 | 100% | 83% | 2.18E+08 |
| 344 | 8.78E+07 | 1.59E+07 | 78% | 88% | 2.15E+09 |
| 348 | 1.45E+07 | 2.52E+03 | 60% | 77% | 1.87E+07 |
| 350 | 4.34E+07 | 5.78E+06 | 111% | 86% | 5.29E+08 |
| 351 | 1.00E+07 | 3.41E+06 | 87% | 94% | 1.71E+08 |
| 354 | 7.47E+06 | 1.10E+06 | 104% | 65% | 7.55E+08 |
| 369 | 7.28E+07 | 2.18E+07 | 94% | 90% | 6.54E+08 |
| 370 | 6.38E+07 | 3.26E+07 | 94% | 107% | 3.37E+08 |
| 374 | 3.70E+07 | 5.38E+05 | 57% | 84% | 4.07E+09 |
| 375 | 4.36E+05 | 2.13E+05 | 100% | 78% | 8.41E+08 |
| 376 | 5.32E+05 | 8.33E+04 | 53% | 100% | 1.56E+09 |
| 380 | 7.30E+07 | 1.45E+06 | 94% | 106% | 4.00E+08 |
| 383 | 3.97E+01 | 2.14E+06 | 94% | 94% | 2.01E+08 |
| Lipid A | 3.08E+07 | 5.86E+06 | 108% | 96% | 2.13E+08 |
| Lipid B | 4.21E+05 | 1.32E+05 | 97% | 92% | 3.42E+08 |
| Lipid C | 1.03E+04 | 4.63E+05 | 103% | 88% | 4.72E+05 |

TABLE C

| | cirRNA (SEQ ID NO: 1) | | | | | |
|---|---|---|---|---|---|---|
| Lipid no. | ALT in Sera (IU/L) 2 hours After 0.5 MPK Injection | ALT in Sera (IU/L) 24 hours After 0.5 MPK Injection | AST in Sera (IU/L) 2 hours After 0.5 MPK Injection | AST in Sera (IU/L) 24 hours After 0.5 MPK Injection | MCP-I in Sera 2 hours After 0.5 MPK Injection (pg/ml) | MCP-I in Sera 24 hours After 0.5 MPK Injection (pg/ml) |
| 43 | 57.07 | 41.53 | 135.60 | 88.97 | 5561.83 | 17.57 |
| 51 | 71.07 | 45.50 | 193.77 | 94.73 | 3296.20 | 562.40 |
| 68 | 40.77 | 33.37 | 81.27 | 60.20 | 129.34 | ND |
| 75 | 111.37 | 48.97 | 279.87 | 94.83 | 8335.00 | 93.14 |
| 90 | 40.57 | 37.87 | 77.50 | 64.70 | 153.05 | 33.08 |
| 127 | 74.17 | 54.90 | 161.17 | 91.53 | 301.91 | 128.65 |
| 128 | 58.17 | 56.00 | 195.53 | 131.30 | 6355.24 | 318.11 |
| 129 | 64.50 | 67.87 | 188.97 | 112.03 | 3830.40 | 272.54 |
| 131 | 51.17 | 44.57 | 161.27 | 83.17 | 5003.82 | 16.42 |
| 132 | 65.03 | 44.73 | 136.00 | 72.53 | 28.53 | 96.56 |
| 148 | 53.60 | 59.93 | 136.17 | 108.13 | 6709.61 | 69.59 |
| 165 | 63.90 | 61.47 | 128.43 | 99.03 | 127.19 | 113.67 |
| 168 | 72.80 | 57.60 | 218.63 | 139.13 | 4607.51 | 75.08 |
| 169 | 65.40 | 57.80 | 129.50 | 87.00 | 509.14 | 80.18 |
| 170 | 62.53 | 66.47 | 175.67 | 120.57 | 1322.04 | 922.24 |
| 195 | 109.00 | 35.00 | 264.00 | 84.67 | 2643.00 | 78.52 |
| 196 | 80.33 | 93.00 | 202.33 | 180.67 | 489.33 | 197.30 |
| 197 | 106.67 | 171.00 | 215.67 | 237.67 | 1958.67 | 122.47 |
| 245 | 136.50 | 107.33 | 387.00 | 187.67 | 2543.33 | 342.29 |
| 66 | 51.97 | 63.6 | 176.40 | 148.60 | 7911.52 | 448.43 |
| 6 | 99.33 | 181.67 | 316.00 | 411.00 | 7009.50 | 1653.42 |

TABLE C-continued cirRNA (SEQ ID NO: 1)

| Lipid no. | ALT in Sera (IU/L) 2 hours After 0.5 MPK Injection | ALT in Sera (IU/L) 24 hours After 0.5 MPK Injection | AST in Sera (IU/L) 2 hours After 0.5 MPK Injection | AST in Sera (IU/L) 24 hours After 0.5 MPK Injection | MCP-I in Sera 2 hours After 0.5 MPK Injection (pg/ml) | MCP-I in Sera 24 hours After 0.5 MPK Injection (pg/ml) |
|---|---|---|---|---|---|---|
| 270 | 253.00 | 79.00 | 477.67 | 220.00 | 4192.67 | 564.30 |
| 271 | 128.33 | 114.67 | 200.67 | 231.33 | 1986.67 | 522.62 |
| 276 | 247.67 | 52.00 | 247.33 | 89.67 | 1659.21 | 120.48 |
| 278 | 177.33 | 102.50 | 275.33 | 322.67 | 1815.67 | 1070.74 |
| 344 | 161.67 | 204.33 | 333.67 | 340.00 | 7150.00 | 946.87 |
| 348 | 82.33 | 96.33 | 307.00 | 148.00 | 1894.33 | 128.60 |
| 350 | 105.67 | 121.33 | 368.00 | 362.67 | 6084.33 | 2039.50 |
| 351 | 74.33 | 149.33 | 232.67 | 389.33 | 3172.67 | 1133.74 |
| 354 | 97.67 | 192.50 | 287.33 | 411.00 | 5469.33 | 1348.89 |
| 369 | 158.00 | 121.00 | 364.00 | 290.00 | 6463.00 | 1338.00 |
| 370 | 102.00 | 123.00 | 276.33 | 413.33 | 4872.33 | 1652.33 |
| 374 | 136.67 | 152.67 | 435.67 | 431.67 | 3843.00 | 1289.00 |
| 375 | 174.67 | 120.33 | 292.00 | 251.67 | 2740.67 | 396.29 |
| 376 | 117.33 | 141.33 | 434.67 | 293.67 | 6397.67 | 561.62 |
| 380 | 89.33 | 122.00 | 196.33 | 480.67 | 1168.73 | 1025.26 |
| 383 | 99.33 | 116.00 | 245.00 | 354.67 | 5759.00 | 2458.33 |

TABLE D cirRNA (SEQ ID NO: 1)

| Lipid no. | Footpad Thickness (24 h-0 h, mm) |
|---|---|
| 43 | 0.33 |
| 51 | 1.11 |
| 68 | 1.00 |
| 75 | 0.85 |
| 90 | 0.20 |
| 127 | 0.94 |
| 128 | 0.98 |
| 129 | 1.09 |
| 131 | 1.17 |
| 132 | 1.24 |
| 148 | 0.23 |
| 165 | 0.32 |
| 168 | 1.13 |
| 169 | 0.84 |
| 170 | 0.95 |
| 195 | 0.56 |
| 196 | 0.44 |
| 197 | 0.08 |
| 245 | 0.68 |

TABLE D-continued cirRNA (SEQ ID NO: 1)

| Lipid no. | Footpad Thickness (24 h-0 h, mm) |
|---|---|
| 66 | 1.43 |
| 6 | 0.44 |
| 270 | 0.65 |
| 271 | 0.40 |
| 276 | 0.51 |
| 278 | 0.63 |
| 344 | 0.53 |
| 348 | 0.78 |
| 350 | 0.55 |
| 351 | 0.68 |
| 354 | 0.80 |
| 369 | 0.57 |
| 370 | 0.50 |
| 374 | 0.63 |
| 375 | 0.27 |
| 376 | 0.89 |
| 380 | 0.25 |
| 383 | 0.60 |

What I claimed is:

1. A cationic lipid, or a salt, hydrate, solvate, polymorph, optical isomer, geometrical isomer, enantiomer, diastereomer, tautomer, isotope labeled compound or mixtures thereof, wherein the cationic lipid is represented by the structure of formula (IV):

(IV)

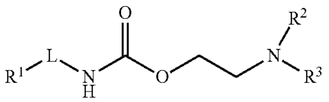

wherein $R^1$-L- is

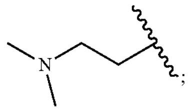 [SMILES: *CCN(C)C]

$R^2$ and $R^3$ are each independently $C_p$ alkylene-Z—$C_q$ alkyl;

Z, at each occurrence, is independently —O—C(═O)— or —C(═O)—O—;

p, at each occurrence, is independently an integer selected from 4, 5, 6, 7, 8, 9, or 10; and q, at each occurrence, is independently an integer selected from 10, 11, 12, 13, 14, 15, 16, 17, 18, 19, 20, 21 or 22.

2. The cationic lipid according to claim 1, or a salt, hydrate, solvate, polymorph, optical isomer, geometrical isomer, enantiomer, diastereomer, tautomer, isotope labeled compound or mixtures thereof, wherein said cationic lipid has the following structure:

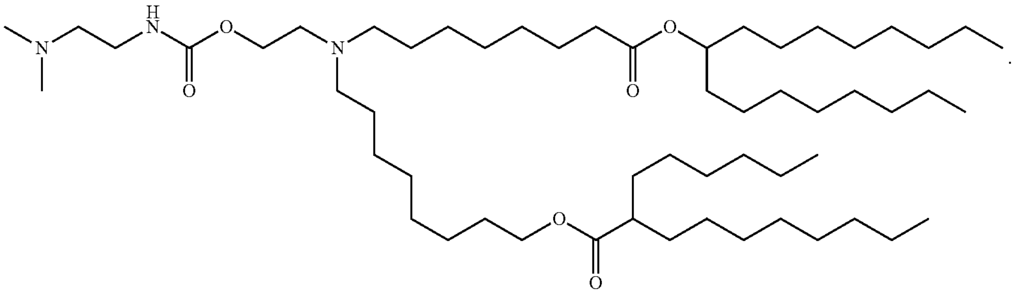 [SMILES: CCCCCCCCC(CCCCCCCC)OC(=O)CCCCCCCN(CCCCCCCCOC(=O)C(CCCCCC)CCCCCCCC)CCOC(=O)NCCN(C)C]

3. The cationic lipid according to claim 1, or a salt, hydrate, solvate, polymorph, optical isomer, geometrical isomer, enantiomer, diastereomer, tautomer, isotope labeled compound or mixtures thereof, wherein said cationic lipid has the following structure:

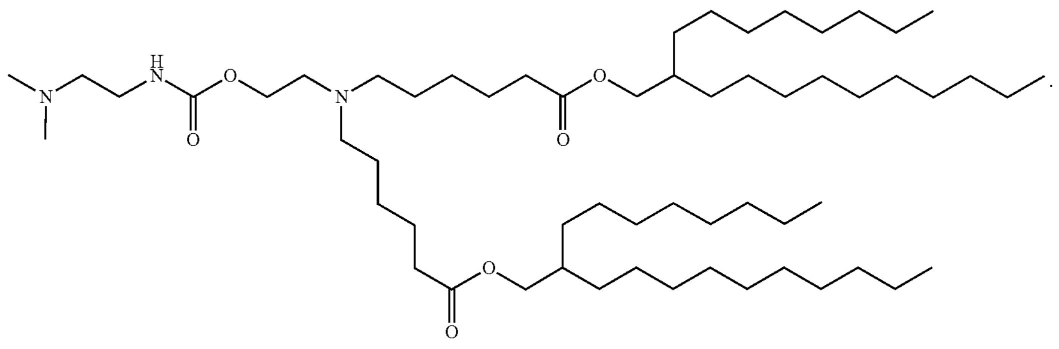 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C]

4. A nanoparticle composition, comprising the cationic lipid according to claim 1, or a salt, hydrate, solvate, polymorph, optical isomer, geometrical isomer, enantiomer, diastereomer, tautomer, isotope labeled compound or mixtures thereof.

5. The nanoparticle composition of claim 4, wherein said cationic lipid has the following structure:

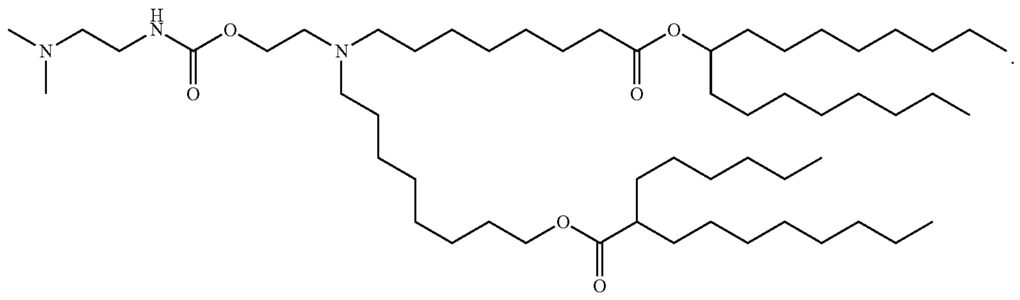 [SMILES: CCCCCCCCC(CCCCCCCC)OC(=O)CCCCCCCN(CCCCCCCCOC(=O)C(CCCCCC)CCCCCCCC)CCOC(=O)NCCN(C)C]

6. The nanoparticle composition of claim 4, wherein said cationic lipid has the following structure:

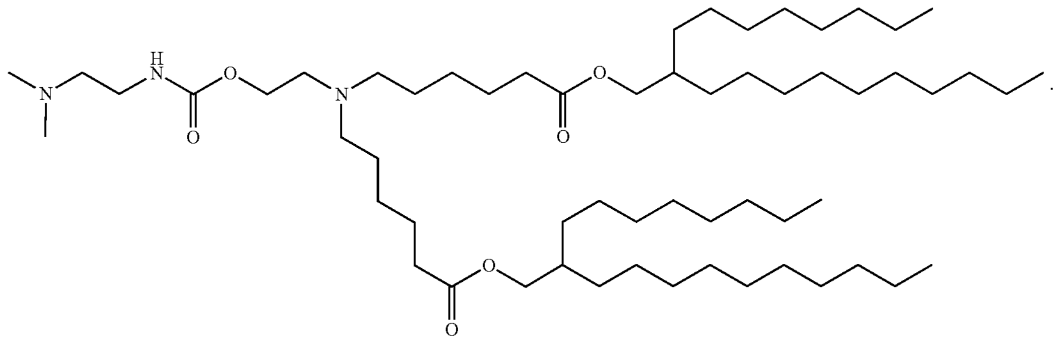 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C]

7. A pharmaceutical composition comprising the cationic lipid according to claim 1, or a salt, hydrate, solvate, polymorph, optical isomer, geometrical isomer, enantiomer, diastereomer, tautomer, isotope labeled compound or mixtures thereof, and a pharmaceutically acceptable carrier.

8. The pharmaceutical composition of claim 7, wherein said cationic lipid has the following structure:

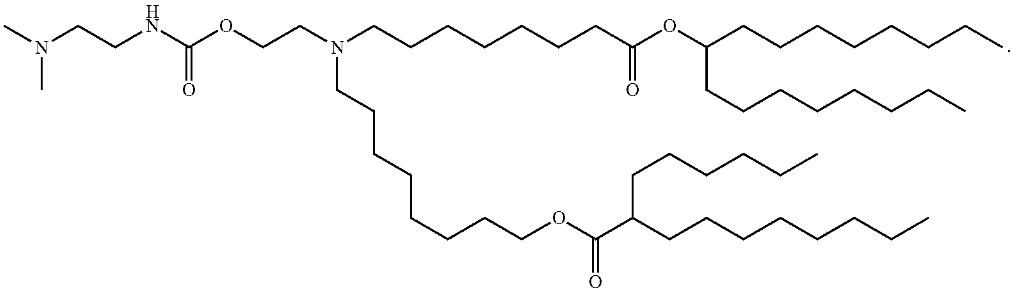 [SMILES: CCCCCCCCC(CCCCCCCC)OC(=O)CCCCCCCN(CCCCCCCCOC(=O)C(CCCCCC)CCCCCCCC)CCOC(=O)NCCN(C)C]

9. The pharmaceutical composition of claim 7, wherein said cationic lipid has the following structure:

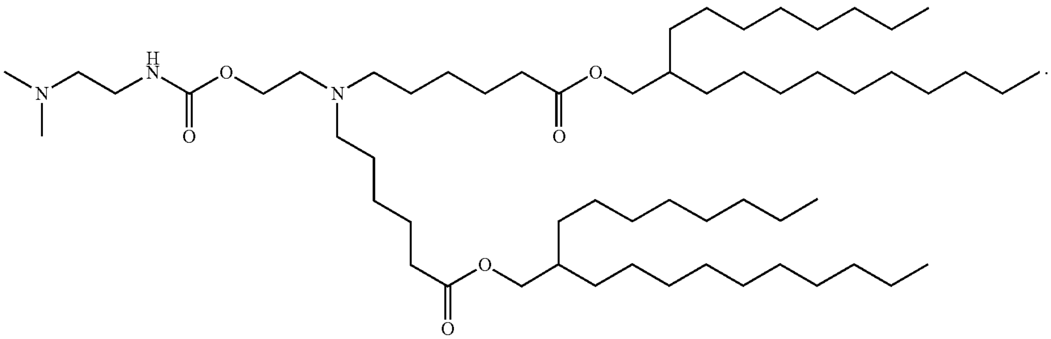 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C]

10. A pharmaceutical composition comprising the nanoparticle composition according to claim 4 and a pharmaceutically acceptable carrier.

11. The pharmaceutical composition of claim 10, wherein said cationic lipid has the following structure:

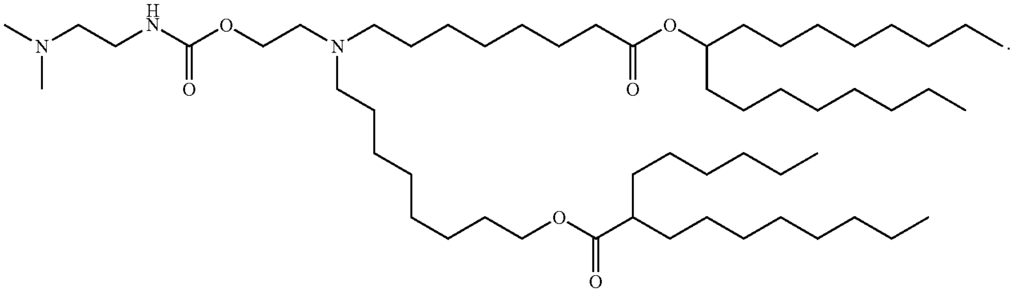 [SMILES: CCCCCCCCC(CCCCCCCC)OC(=O)CCCCCCCN(CCCCCCCCOC(=O)C(CCCCCC)CCCCCCCC)CCOC(=O)NCCN(C)C]

12. The pharmaceutical composition of claim 10, wherein said cationic lipid has the following structure:
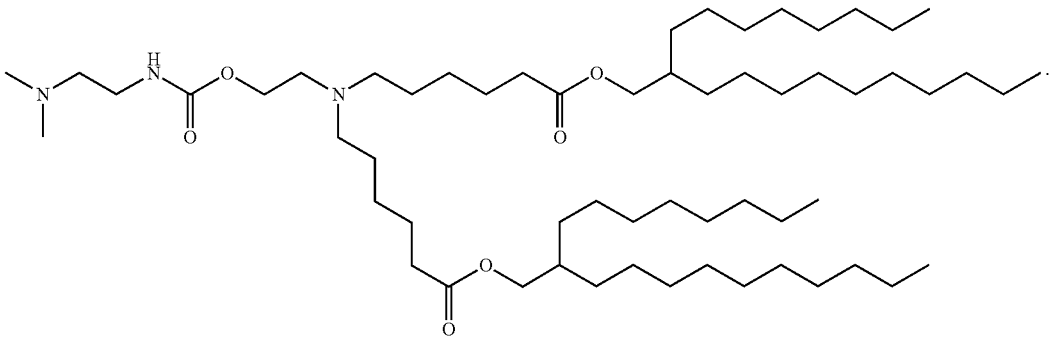 [SMILES: CCCCCCCCCCC(CCCCCCCC)COC(=O)CCCCCN(CCCCCC(=O)OCC(CCCCCCCC)CCCCCCCCCC)CCOC(=O)NCCN(C)C]
* * * * *